United States Patent
Lee et al.

(10) Patent No.: US 11,563,185 B2
(45) Date of Patent: Jan. 24, 2023

(54) HETEROCYCLIC COMPOUND AND ORGANIC LIGHT-EMITTING DEVICE COMPRISING SAME

(71) Applicant: LT MATERIALS CO., LTD., Gyeonggi-do (KR)

(72) Inventors: Nam-Jin Lee, Osan-si (KR); Min-Ji Park, Osan-si (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin (KR)

( * ) Notice: Subject to any disclaimer, the term of this patent is extended or adjusted under 35 U.S.C. 154(b) by 268 days.

(21) Appl. No.: 16/958,121

(22) PCT Filed: Dec. 24, 2018

(86) PCT No.: PCT/KR2018/016592
§ 371 (c)(1),
(2) Date: Jun. 25, 2020

(87) PCT Pub. No.: WO2019/132484
PCT Pub. Date: Jul. 4, 2019

(65) Prior Publication Data
US 2020/0343452 A1    Oct. 29, 2020

(30) Foreign Application Priority Data
Dec. 26, 2017  (KR) .................. 10-2017-0179859

(51) Int. Cl.
*H01L 51/00*   (2006.01)
*C07D 491/048*   (2006.01)
(Continued)

(52) U.S. Cl.
CPC ...... *H01L 51/0071* (2013.01); *C07D 491/048* (2013.01); *C07D 519/00* (2013.01);
(Continued)

(58) Field of Classification Search
None
See application file for complete search history.

(56) References Cited

U.S. PATENT DOCUMENTS 4,356,429 A    10/1982   Tang
10,446,765 B2  10/2019   Lee et al.
(Continued)

FOREIGN PATENT DOCUMENTS

JP     2010-270245 A    12/2010
KR     10-2016-0002408 A  1/2016
(Continued)

OTHER PUBLICATIONS

International Search Report for PCT/KR2018/016592 (PCT/ISA/210) dated Apr. 3, 2019.
(Continued)

*Primary Examiner* — Jay Yang
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

15 Claims, 3 Drawing Sheets

(51) Int. Cl.
    C09K 11/06    (2006.01)
    C07F 9/6561   (2006.01)
    C07D 519/00   (2006.01)
    H01L 51/52    (2006.01)
(52) U.S. Cl.
    CPC ............ *C07F 9/6561* (2013.01); *C09K 11/06* (2013.01); *H01L 51/0052* (2013.01); *H01L 51/0054* (2013.01); *H01L 51/0056* (2013.01); *H01L 51/0058* (2013.01); *H01L 51/0067* (2013.01); *H01L 51/0072* (2013.01); *H01L 51/0073* (2013.01); *H01L 51/0074* (2013.01); *C09K 2211/1018* (2013.01); *H01L 51/5278* (2013.01)

(56) References Cited

U.S. PATENT DOCUMENTS

2017/0133601 A1    5/2017   Sim et al.
2017/0133602 A1*   5/2017   Lee ..................... C07D 471/04

FOREIGN PATENT DOCUMENTS

| KR | 10-2016-0129781 A | 11/2016 |
| KR | 10-2017-0030291 A | 3/2017 |
| KR | 10-2017-0053759 A | 5/2017 |
| KR | 10-2017-0090139 A | 8/2017 |
| WO | WO 2016/064088 A2 | 4/2016 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Materials, 1994, 6, No. 9, pp. 677-679.

* cited by examiner

[FIG. 1]
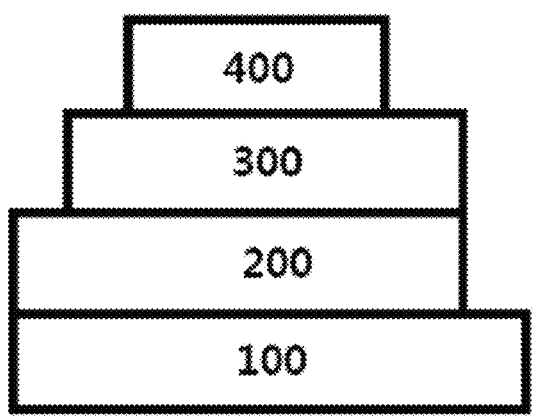
[FIG. 2]
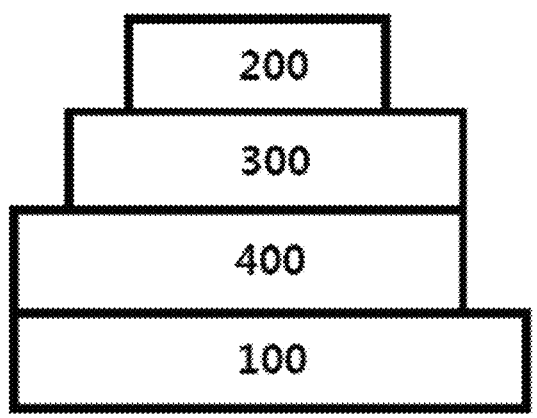

[FIG. 3]
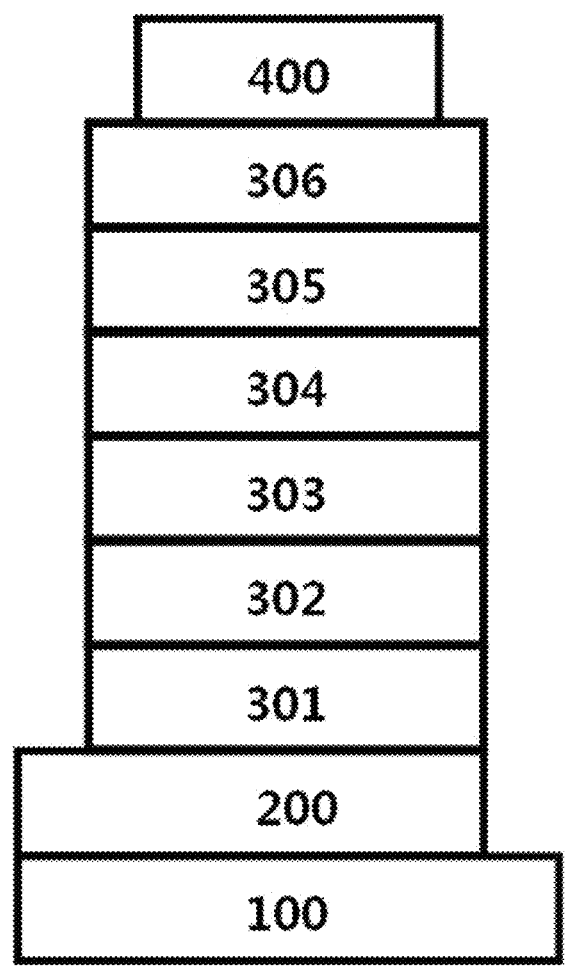

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT-EMITTING DEVICE COMPRISING SAME

TECHNICAL FIELD

This application claims priority to and the benefits of Korean Patent Application No. 10-2017-0179859, filed with the Korean Intellectual Property Office on Dec. 26, 2017, the entire contents of which are incorporated herein by reference.

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a novel heterocyclic compound and an organic light emitting device comprising the same.

Technical Solution

One embodiment of the present application provides a heterocyclic compound represented by the following Chemical Formula 1.

[Chemical Formula 1]

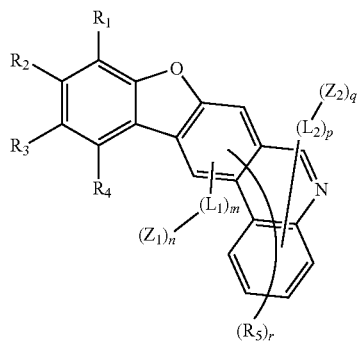

In Chemical Formula 1, $R_1$ to $R_4$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; SiRR'R''; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring, $R_5$ is hydrogen; a substituted or unsubstituted alkyl group; a substituted or unsubstituted aryl group; or a substituted or unsubstituted heteroaryl group, $L_1$ and $L_2$ are the same as or different from each other, and each independently a direct bond; a substituted or unsubstituted arylene group; or a substituted or unsubstituted heteroarylene group, $Z_1$ and $Z_2$ are the same as or different from each other, and each independently selected from the group consisting of deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; SiRR'R''; —P(=O)RR'; and an amine group unsubstituted or substituted with a substituted or unsubstituted alkyl group, a substituted or unsubstituted aryl group, or a substituted or unsubstituted heteroaryl group, R, R' and R'' are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, m and p are an integer of 1 to 4, n and q are an integer of 1 to 3, and r is an integer of 0 to 5.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to one embodiment of the present application.

Advantageous Effects

A compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the compound can be used as an electron transfer layer material, a hole blocking layer material or a charge generation layer material of the organic light emitting device.

Specifically, when using the compound represented by Chemical Formula 1 in the organic material layer, a driving voltage is lowered and light efficiency is enhanced in the device, and device lifetime properties can be enhanced by thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

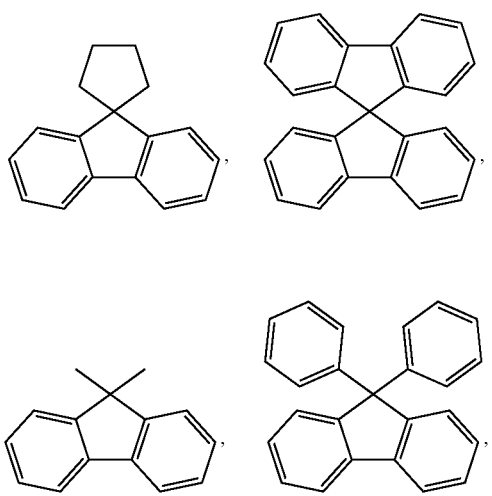

-continued

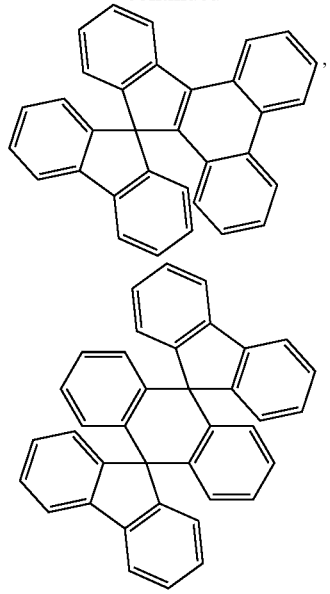

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, specific examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

Chemical Formula 1 has a core structure in which a quinoline group is fused to a dibenzofuran group, and when Chemical Formula 1 has a di-substituted structure while having the core structure, thermal stability is more superior compared to when mono-substituted, and structurally, substituents controlling hole transfer properties may be more diversely introduced compared to when mono-substituted, and structure properties may be excellently controlled.

In one embodiment of the present application, Chemical Formula 1 may be represented by the following Chemical Formula 2.

[Chemical Formula 2]

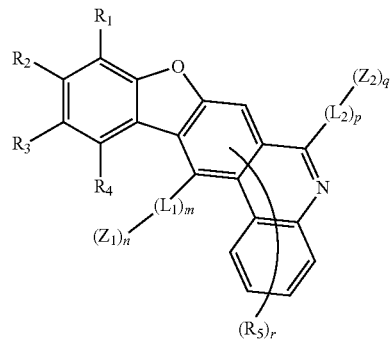

In Chemical Formula 2, each substituent has the same definition as the substituents of Chemical Formula 1.

In one embodiment of the present application, $R_1$ to $R_4$ of Chemical Formula 1 are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring.

In another embodiment, $R_1$ to $R_4$ of Chemical Formula 1 are the same as or different from each other, and may be each independently selected from the group consisting of hydrogen; a substituted or unsubstituted C1 to C60 aryl group; and a substituted or unsubstituted C2 to C60 heteroaryl group, or two or more groups adjacent to each other may bond to each other to form a substituted or unsubstituted aromatic hydrocarbon ring.

In another embodiment, $R_1$ to $R_4$ of Chemical Formula 1 are the same as or different from each other, and may be each independently selected from the group consisting of hydrogen; a substituted or unsubstituted C1 to C60 aryl group; and a substituted or unsubstituted C2 to C60 heteroaryl group.

In another embodiment, $R_1$ to $R_4$ of Chemical Formula 1 are the same as or different from each other, and may be each independently selected from the group consisting of hydrogen; a substituted or unsubstituted C1 to C40 aryl group; and a substituted or unsubstituted C2 to C40 heteroaryl group.

In another embodiment, $R_1$ to $R_4$ of Chemical Formula 1 may be hydrogen.

In one embodiment of the present application, $R_5$ of Chemical Formula 1 may be hydrogen; a substituted or unsubstituted alkyl group; a substituted or unsubstituted aryl group; or a substituted or unsubstituted heteroaryl group.

In another embodiment, $R_5$ of Chemical Formula 1 may be hydrogen; a substituted or unsubstituted C6 to C60 aryl group; or a substituted or unsubstituted C2 to C60 heteroaryl group.

In another embodiment, $R_5$ of Chemical Formula 1 may be hydrogen; a C6 to C40 aryl group; or a C2 to C40 heteroaryl group.

In another embodiment, $R_5$ of Chemical Formula 1 may be hydrogen.

In one embodiment of the present application, $L_1$ and $L_2$ are the same as or different from each other, and may be each independently a direct bond; a substituted or unsubstituted arylene group; or a substituted or unsubstituted heteroarylene group.

In another embodiment, $L_1$ and $L_2$ are the same as or different from each other, and may be each independently a direct bond; a substituted or unsubstituted C6 to C60 arylene group; or a substituted or unsubstituted C2 to C60 heteroarylene group.

In another embodiment, $L_1$ and $L_2$ are the same as or different from each other, and may be each independently a direct bond; a substituted or unsubstituted C6 to C40 arylene group; or a substituted or unsubstituted C2 to C40 heteroarylene group.

In another embodiment, $L_1$ and $L_2$ are the same as or different from each other, and may be each independently a direct bond; a substituted or unsubstituted C6 to C20 arylene group; or a substituted or unsubstituted C2 to C20 heteroarylene group.

In another embodiment, $L_1$ and $L_2$ are the same as or different from each other, and may be each independently a direct bond; a C6 to C20 arylene group; or a C2 to C20 heteroarylene group.

In another embodiment, $L_1$ and $L_2$ are the same as or different from each other, and may be each independently a direct bond; a phenylene group; a biphenylene group; a naphthalene group; a phenanthrenylene group; a divalent pyrimidine group; or a divalent triazine group.

In one embodiment of the present application, $Z_1$ and $Z_2$ are the same as or different from each other, and may be each independently selected from the group consisting of deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; SiRR'R''; —P(=O)RR'; and an amine group unsubstituted or substituted with a substituted or unsubstituted alkyl group, a substituted or unsubstituted aryl group, or a substituted or unsubstituted heteroaryl group.

In another embodiment, $Z_1$ and $Z_2$ are the same as or different from each other, and may be each independently deuterium; a substituted or unsubstituted aryl group; a substituted or unsubstituted heteroaryl group; or P(=O)RR'.

In another embodiment, $Z_1$ and $Z_2$ are the same as or different from each other, and may be each independently a substituted or unsubstituted C6 to C60 aryl group; a substituted or unsubstituted C2 to C60 heteroaryl group; or P(=O)RR'.

In another embodiment, $Z_1$ and $Z_2$ are the same as or different from each other, and may be each independently a substituted or unsubstituted C6 to C40 aryl group; a substituted or unsubstituted C2 to C40 heteroaryl group; or P(=O)RR'.

In another embodiment, $Z_1$ and $Z_2$ are the same as or different from each other, and may be each independently a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group and a C1 to C40 alkyl group; or P(=O)RR'.

In another embodiment, $Z_1$ and $Z_2$ are the same as or different from each other, and may be each independently P(=O)RR'; a phenyl group unsubstituted or substituted with one or more substituents selected from the group consisting of a methyl group, a phenyl group, a dibenzofuran group and a carbazole group; a biphenyl group; a naphthyl group; a triphenylenyl group; a terphenyl group; a spirobifluorenyl group; or a 9,9'-dimethylfluorenyl group.

In another embodiment, $Z_1$ and $Z_2$ are the same as or different from each other, and may be each independently P(=O)RR'; a carbazole group unsubstituted or substituted with a phenyl group; a dibenzofuran group; a dibenzothiophene group; a quinolone group; a quinazoline group unsubstituted or substituted with one or more substituents selected from the group consisting of a phenyl group and a biphenyl group; a benzothiazole group unsubstituted or substituted with a phenyl group; a benzimidazole group unsubstituted or substituted with one or more substituents selected from the group consisting of a methyl group, an ethyl group and a phenyl group; or a phenanthridine group unsubstituted or substituted with a phenyl group.

In one embodiment of the present application, m and p may be an integer of 1 to 4.

In one embodiment of the present application, n and q may be an integer of 1 to 3.

In one embodiment of the present application, r may be an integer of 0 to 5.

In one embodiment of the present application, R, R' and R'' are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R'' are the same as or different from each other, and may be each independently a substituted or unsubstituted aryl group.

In another embodiment, R, R' and R'' are the same as or different from each other, and may be each independently a substituted or unsubstituted C6 to C60 aryl group.

In another embodiment, R, R' and R'' are the same as or different from each other, and may be each independently a substituted or unsubstituted C6 to C40 aryl group.

In another embodiment, R, R' and R'' are the same as or different from each other, and may be each independently a C6 to C40 aryl group.

In another embodiment, R, R' and R'' are the same as or different from each other, and may be each independently a phenyl group.

In the heterocyclic compound provided in one embodiment of the present application, Chemical Formula 1 is represented by any one of the following Chemical Formulae 3 to 10.

[Chemical Formula 3]

[Chemical Formula 4]

[Chemical Formula 5]

[Chemical Formula 6]

[Chemical Formula 7]

[Chemical Formula 8]

[Chemical Formula 9]
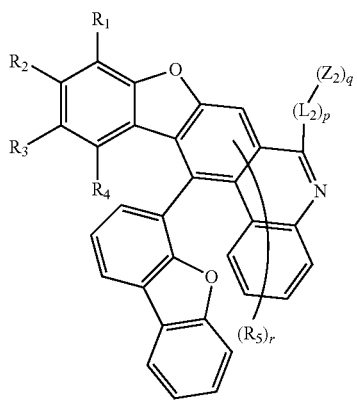
[Chemical Formula 10]
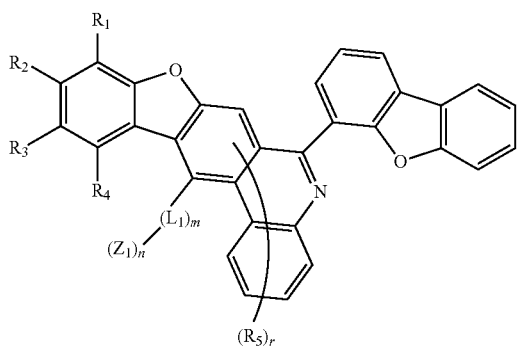
In Chemical Formulae 3 to 10,
$L_1$, $L_2$, $Z_1$, $Z_2$, m, n, p, q, r and $R_1$ to $R_5$ have the same definitions as in Chemical Formula 1.
In the heterocyclic compound provided in one embodiment of the present application, Chemical Formula 1 is represented by any one of the following compounds.
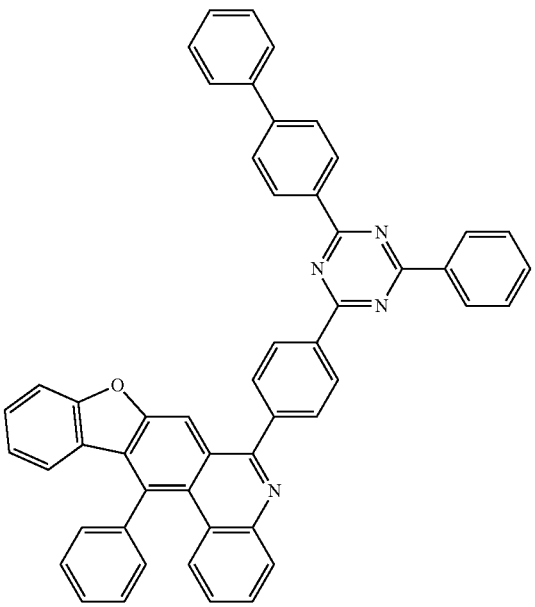
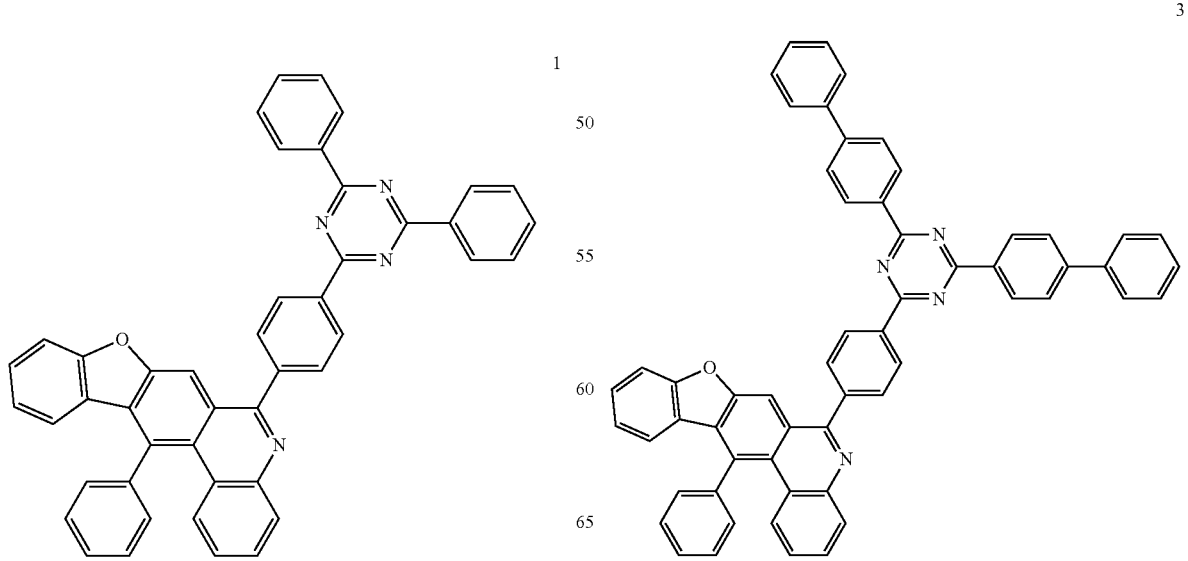

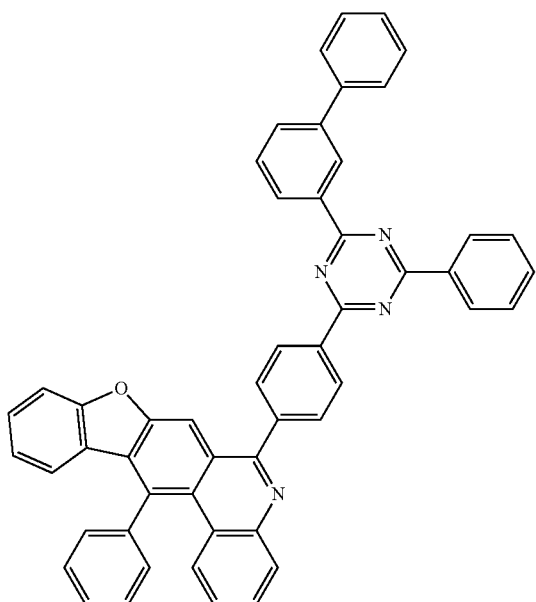
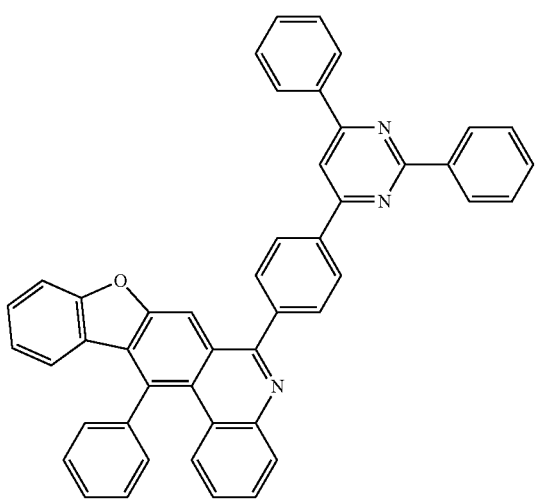 [SMILES: c1ccc(-c2nc(-c3ccccc3)nc(-c3ccc(-c4nc5ccccc5c5c(-c6ccccc6)c6c(cc45)oc4ccccc46)cc3)n2)cc1]

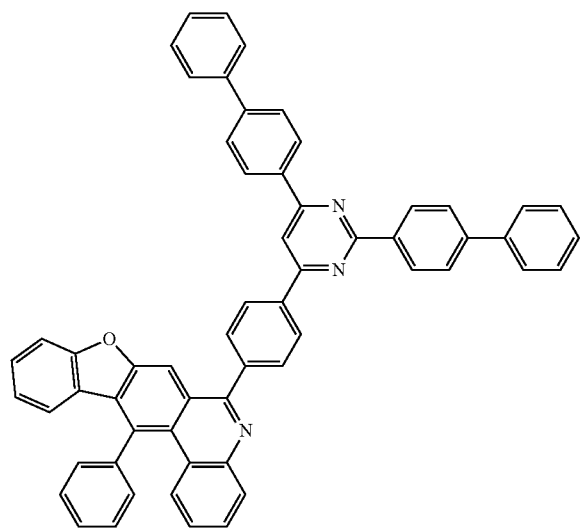
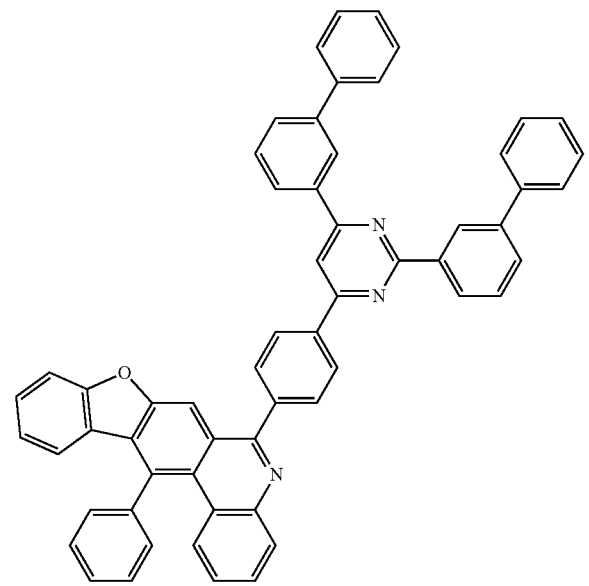
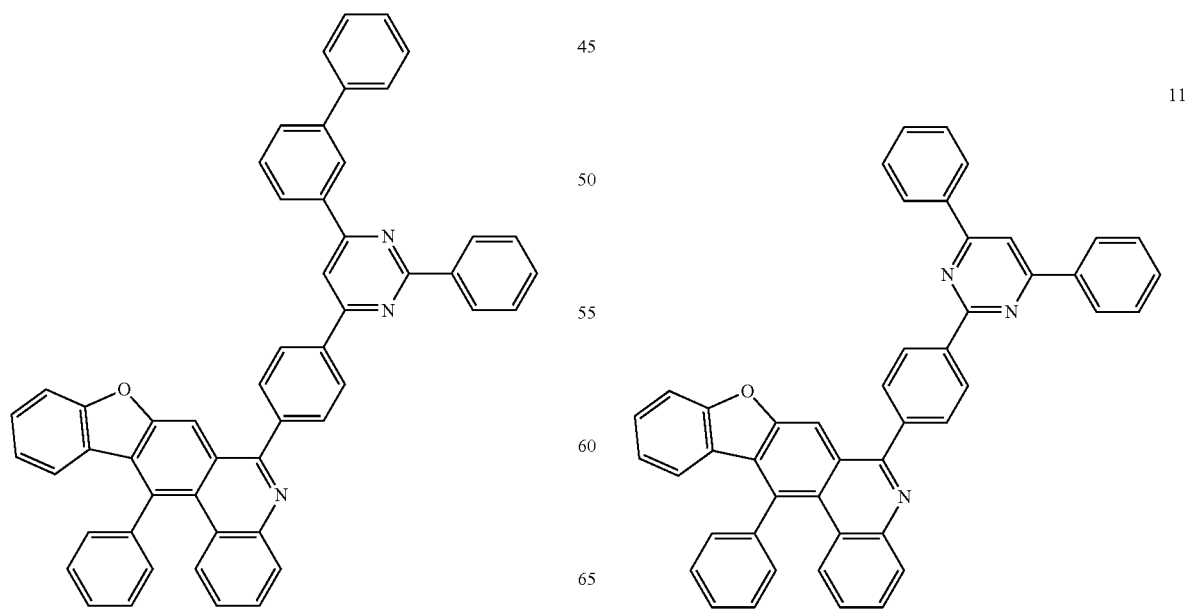

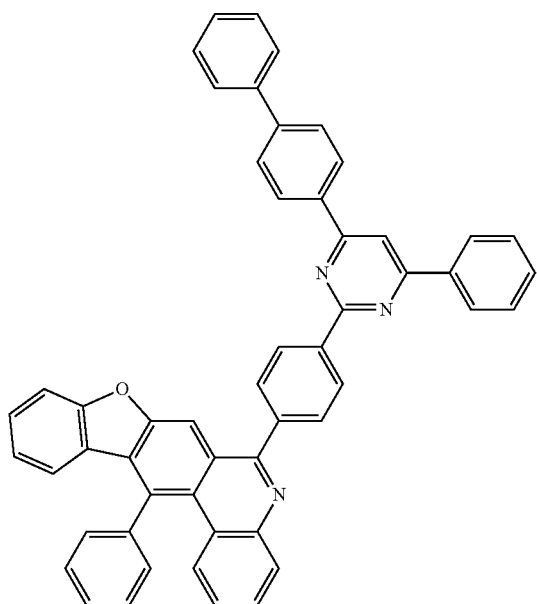
12
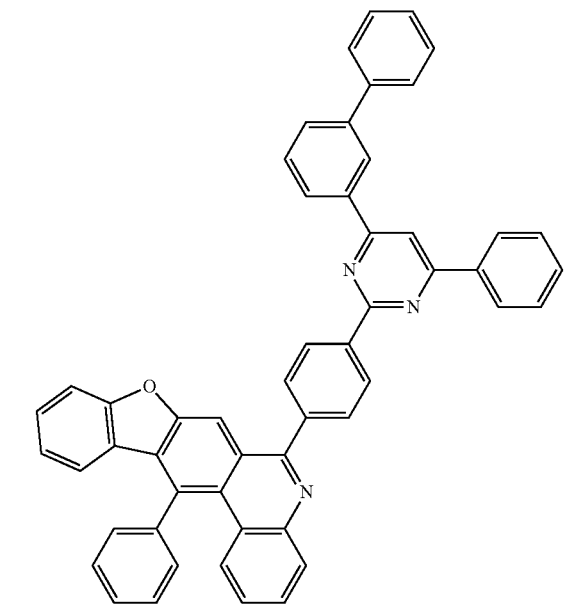
14
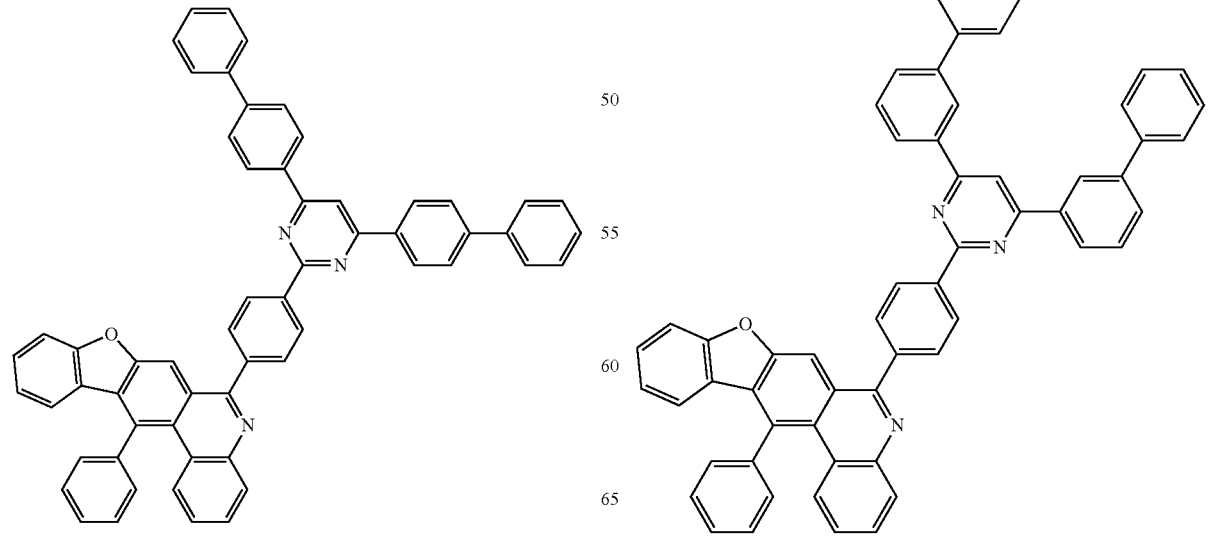

16
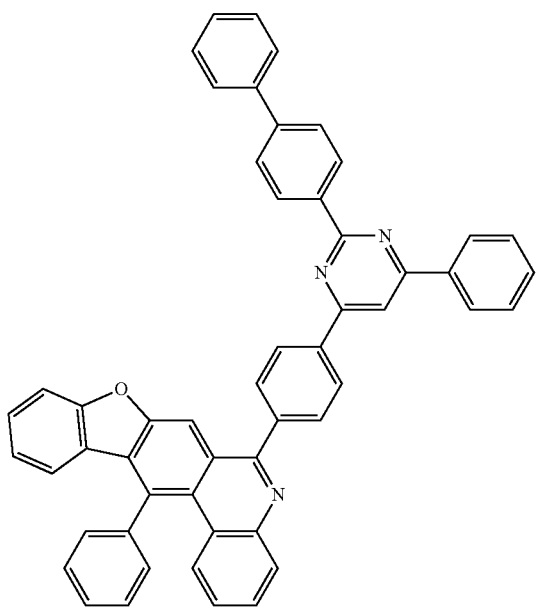 [SMILES: c1ccc(-c2ccc(-c3cc(-c4ccc(-c5nc6ccccc6c6c(-c7ccccc7)c7c(cc56)oc5ccccc57)cc4)nc(-c4ccccc4)n3)cc2)cc1]
17
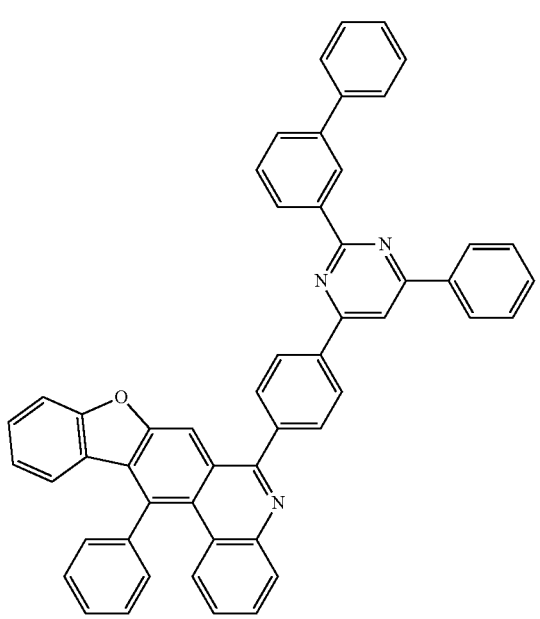 [SMILES: c1ccc(-c2cccc(-c3cc(-c4ccc(-c5nc6ccccc6c6c(-c7ccccc7)c7c(cc56)oc5ccccc57)cc4)nc(-c4ccccc4)n3)c2)cc1]
18
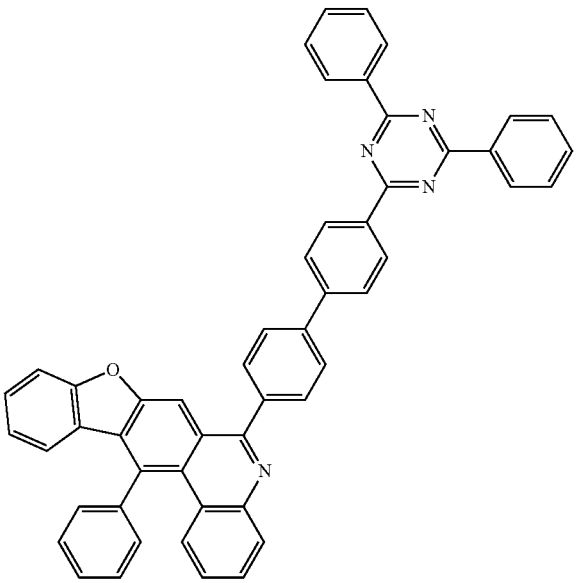 [SMILES: c1ccc(-c2nc(-c3ccccc3)nc(-c3ccc(-c4ccc(-c5nc6ccccc6c6c(-c7ccccc7)c7c(cc56)oc5ccccc57)cc4)cc3)n2)cc1]
19
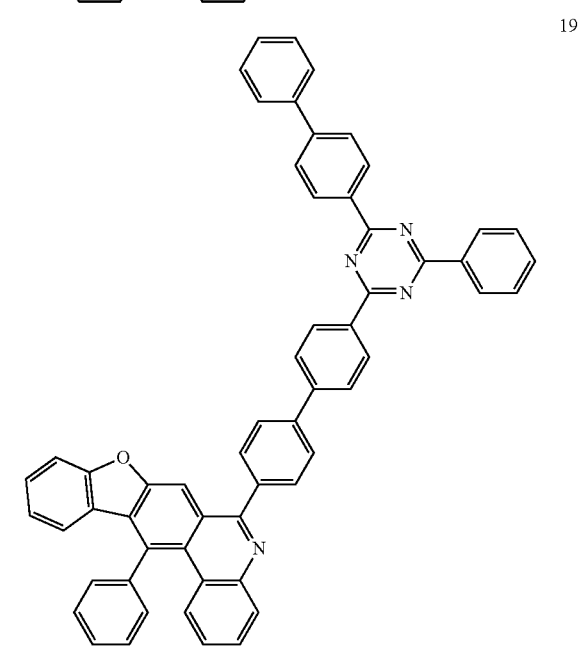
20
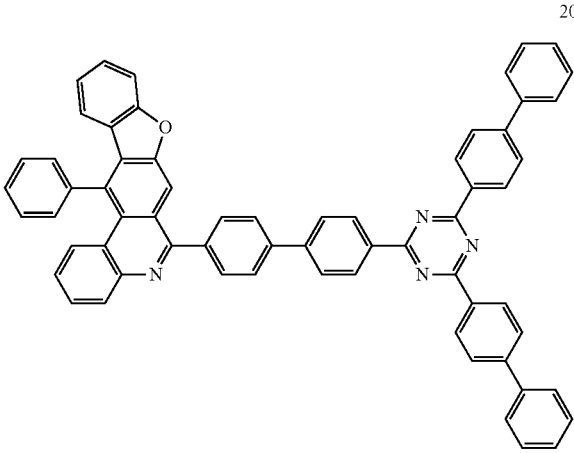

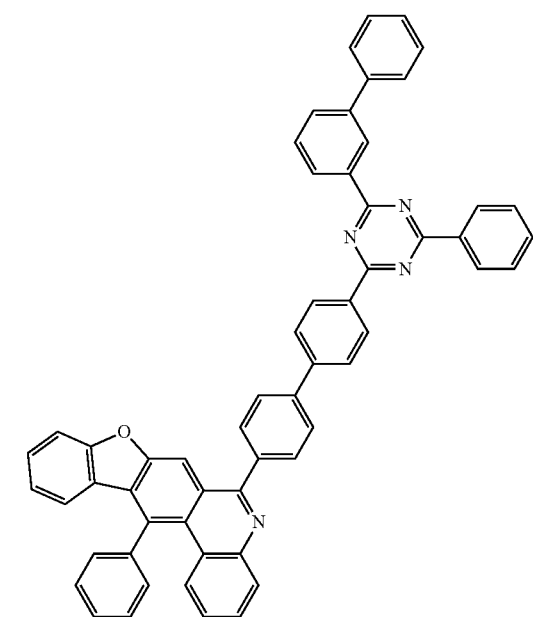
21
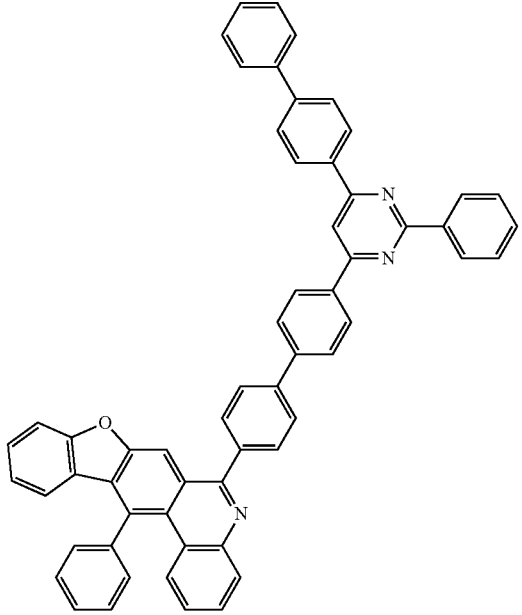
24
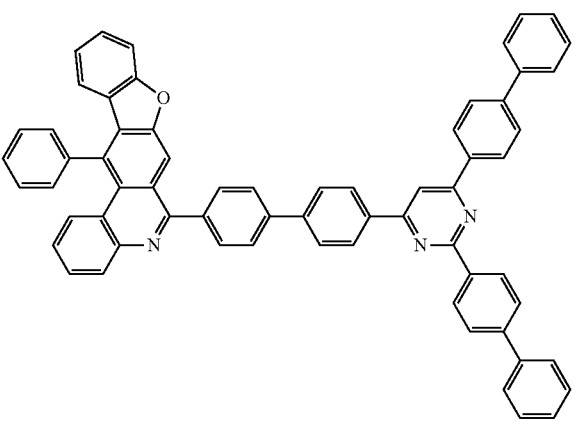 [SMILES: c1ccc(-c2ccc(-c3nc(-c4ccc(-c5ccccc5)cc4)nc(-c4ccc(-c5ccc(-c6nc7ccccc7c7c(-c8ccccc8)c8c(cc67)oc6ccccc68)cc5)cc4)n3)cc2)cc1]
22
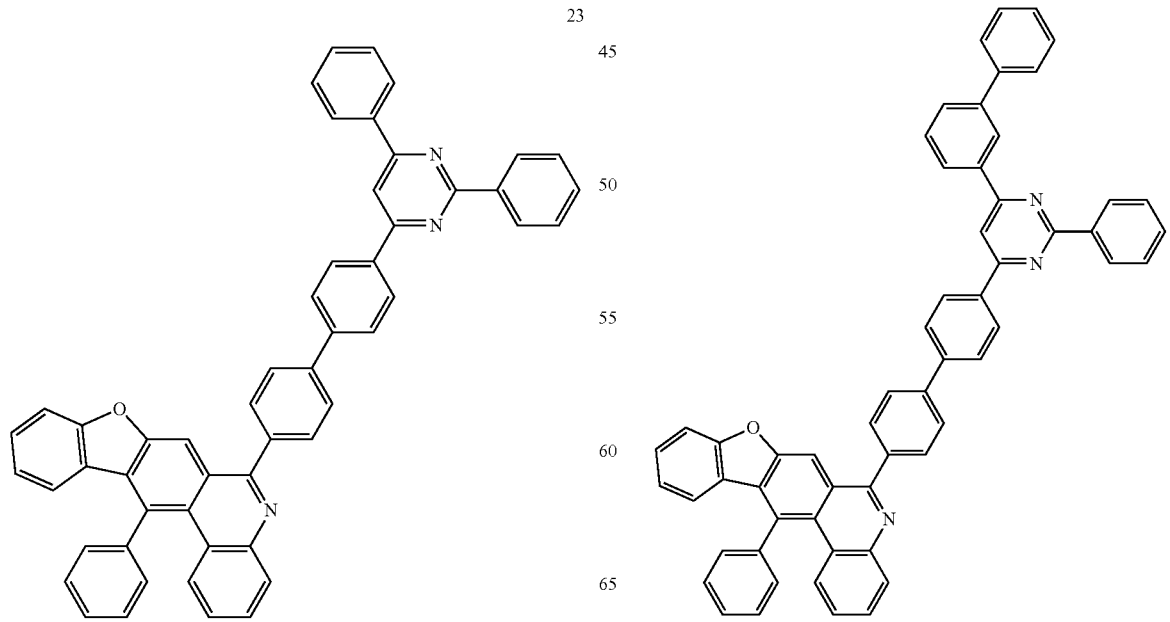

27
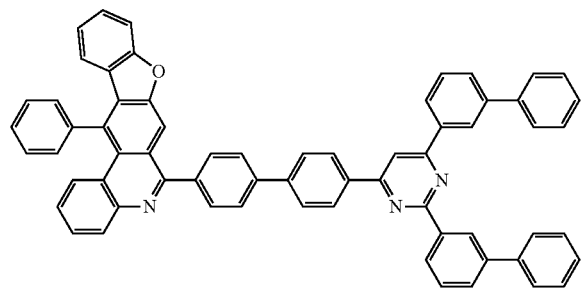
28
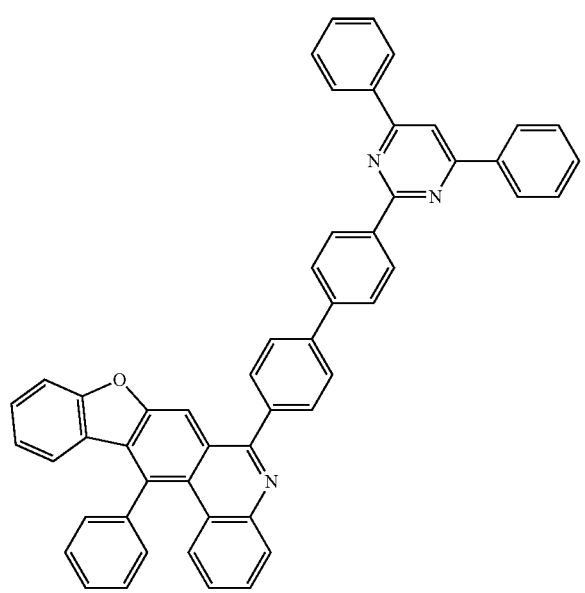
29
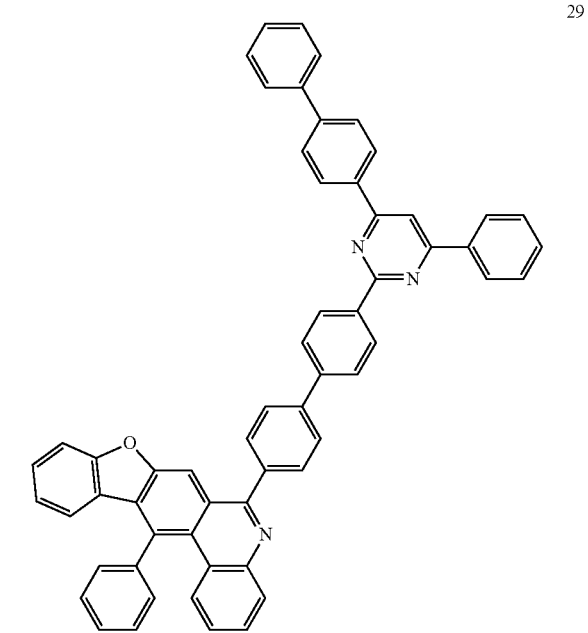
30
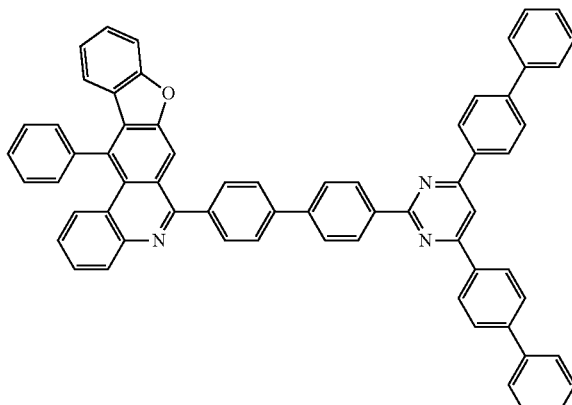
31
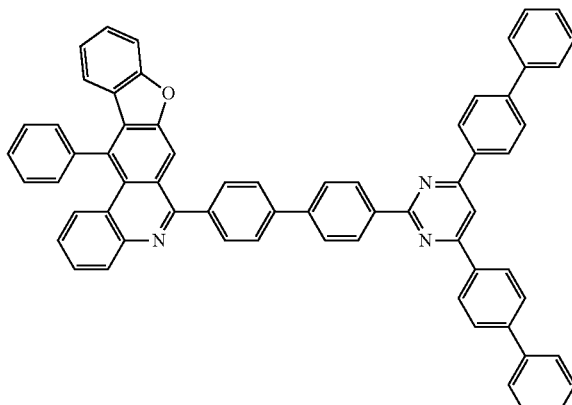
32

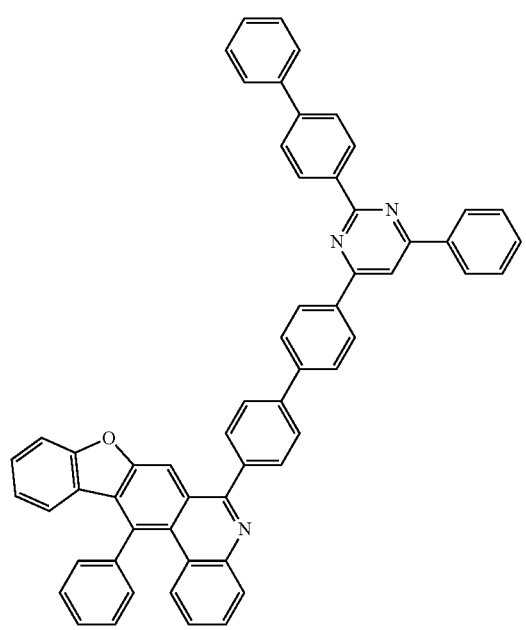 [SMILES: c1ccc(-c2ccc(-c3cc(-c4ccccc4)nc(-c4ccc(-c5ccc(-c6nc7ccccc7c7c(-c8ccccc8)c8c(cc67)oc6ccccc68)cc5)cc4)n3)cc2)cc1]
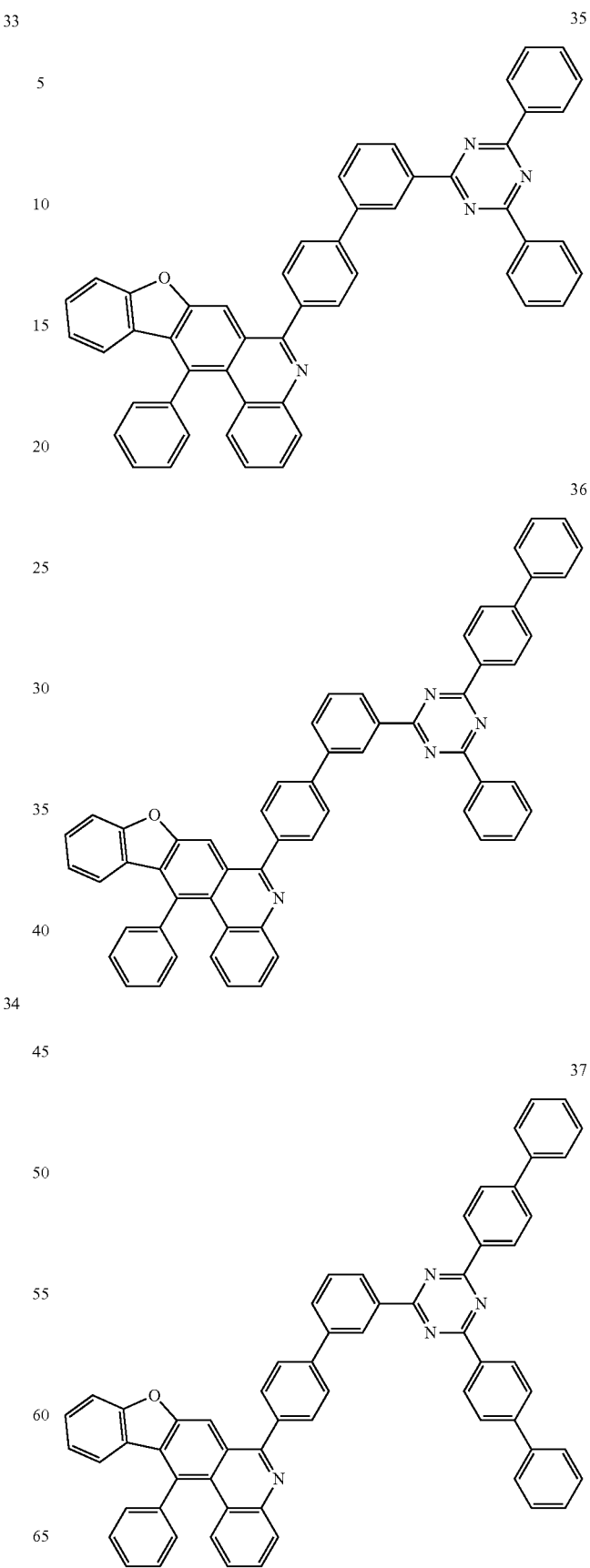

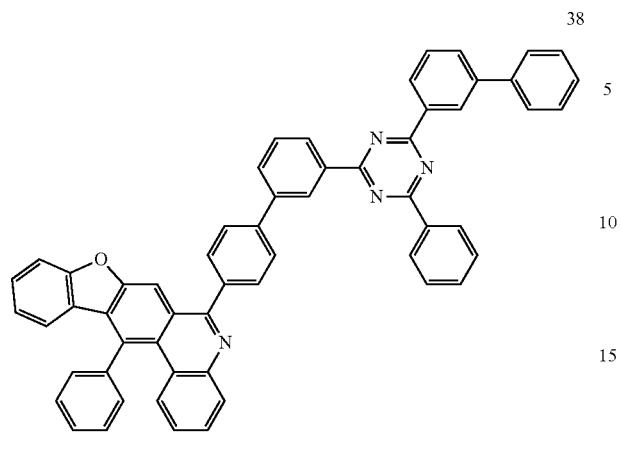
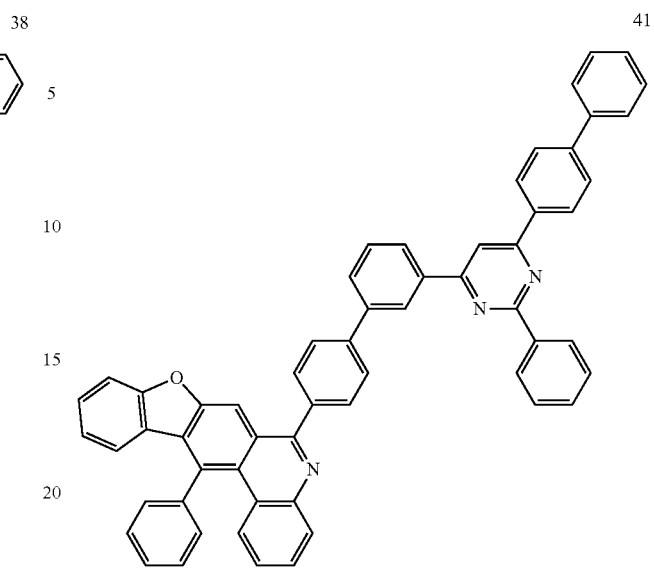
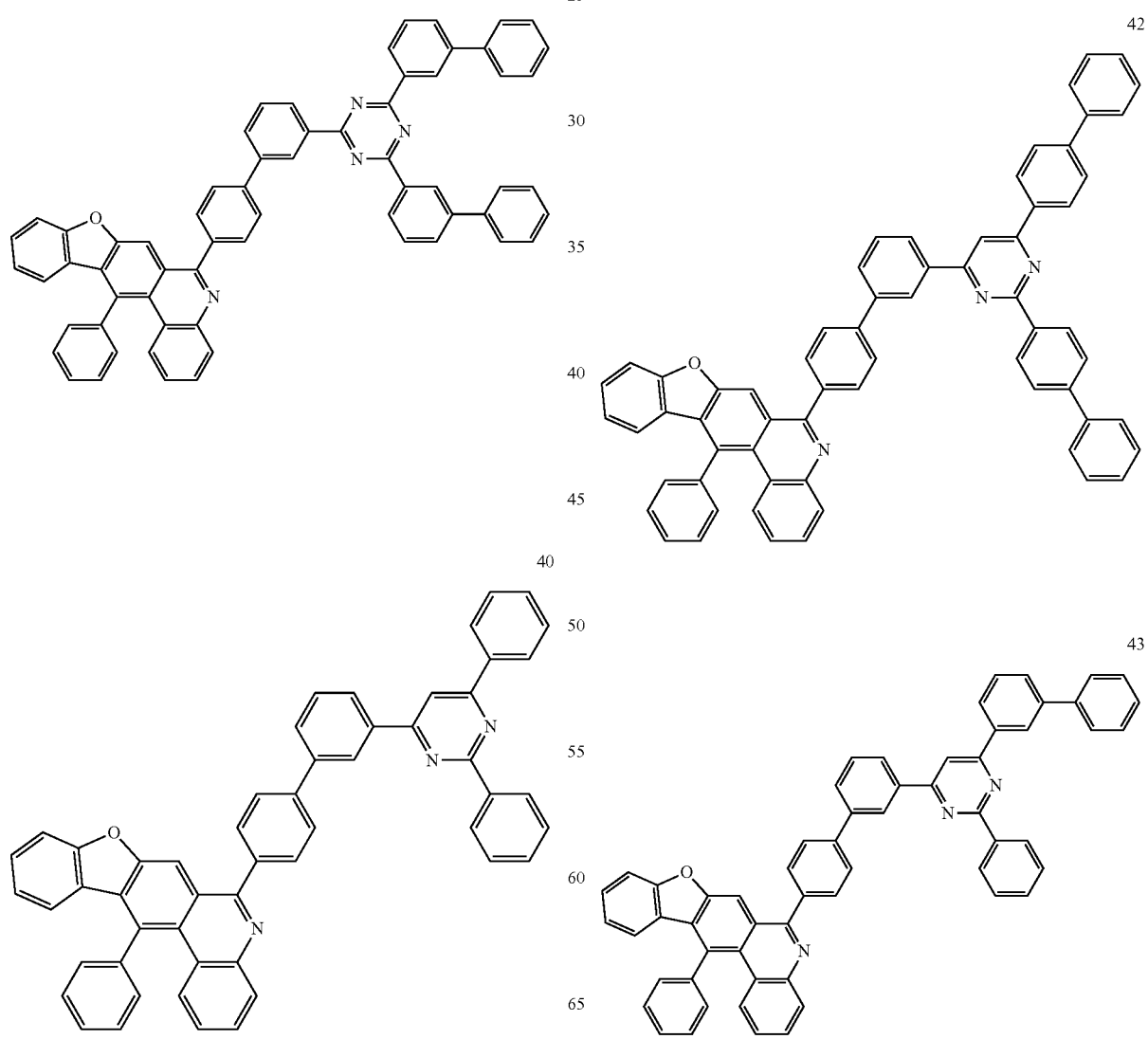

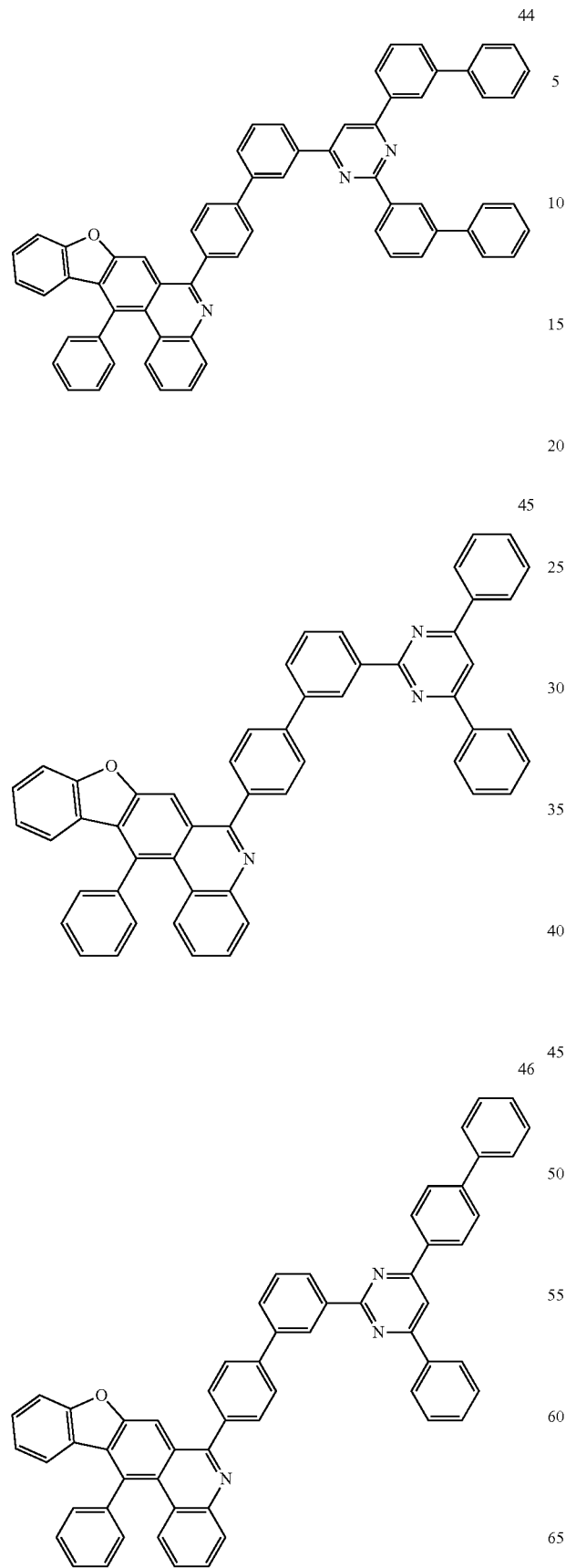
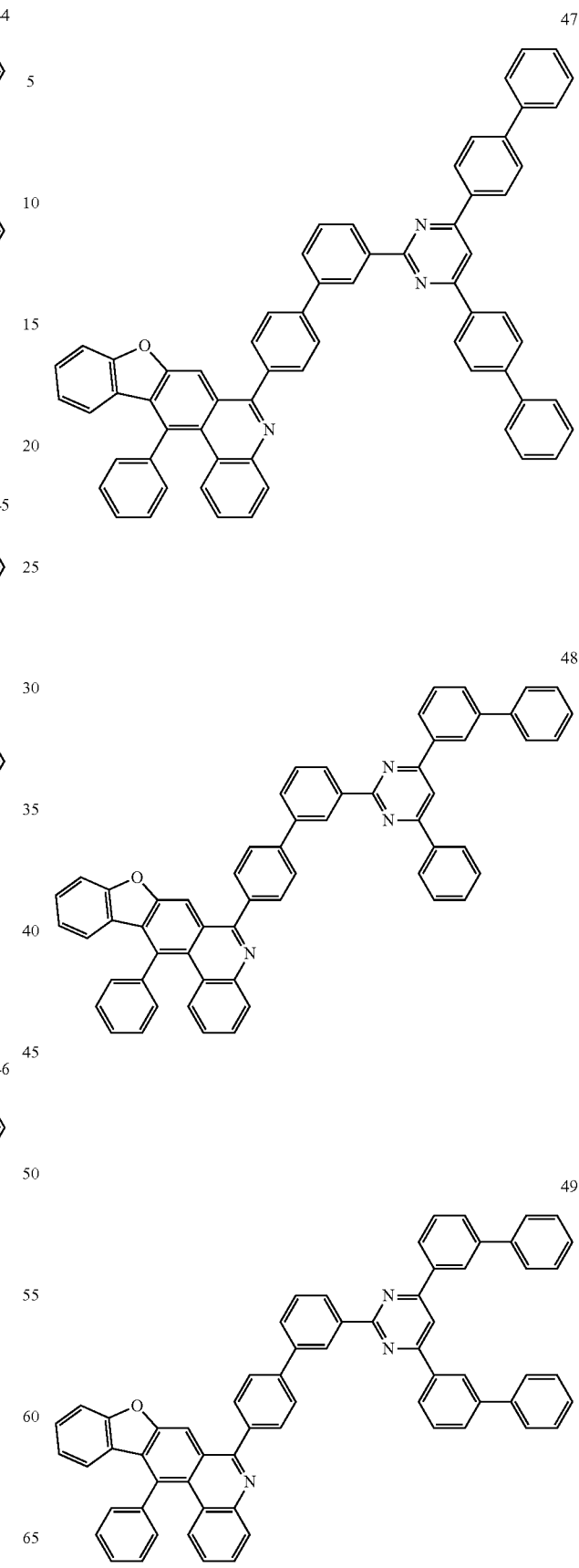

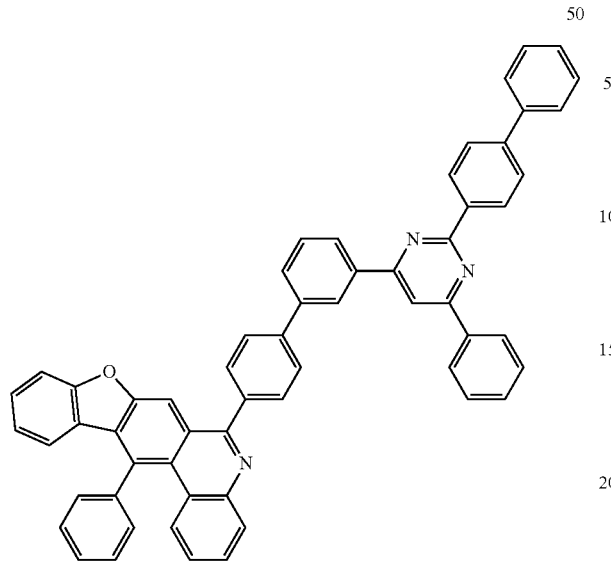
50
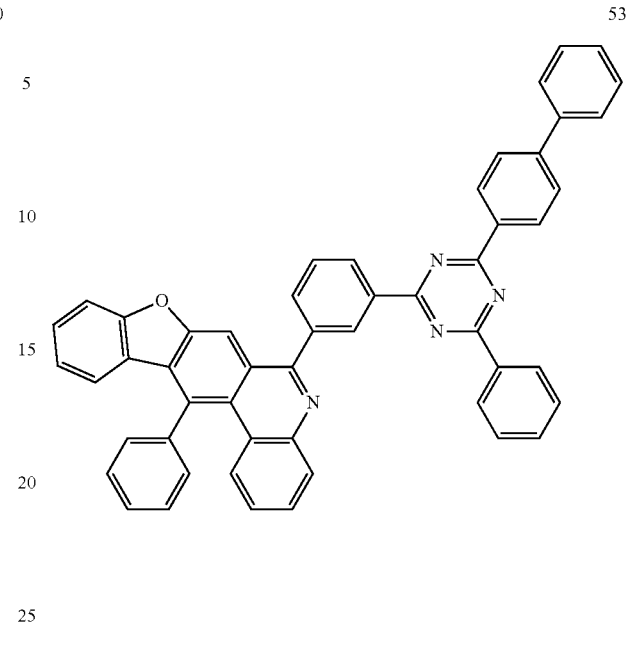
53
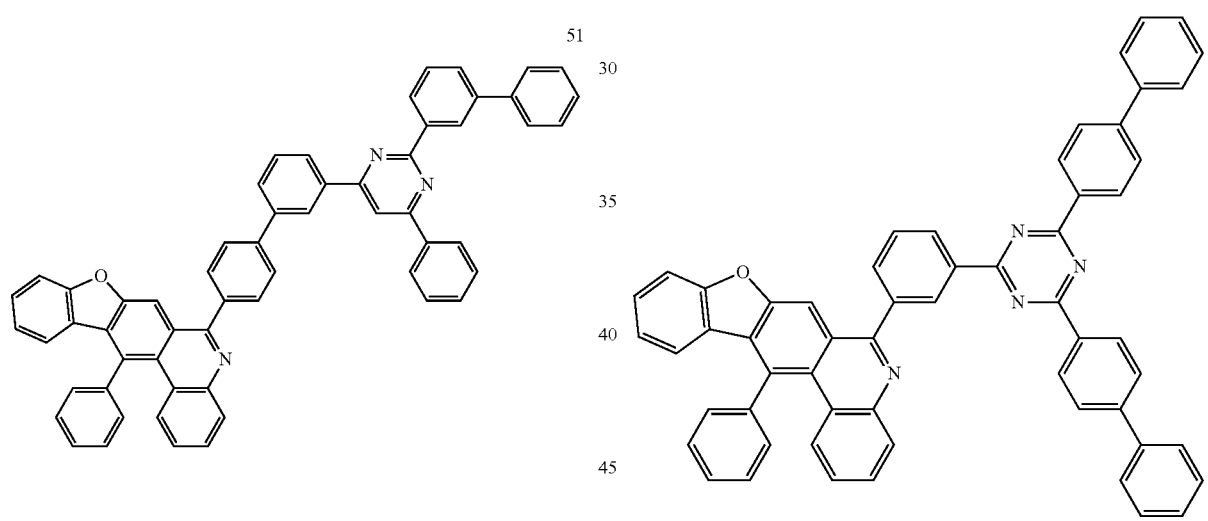
51
52
54
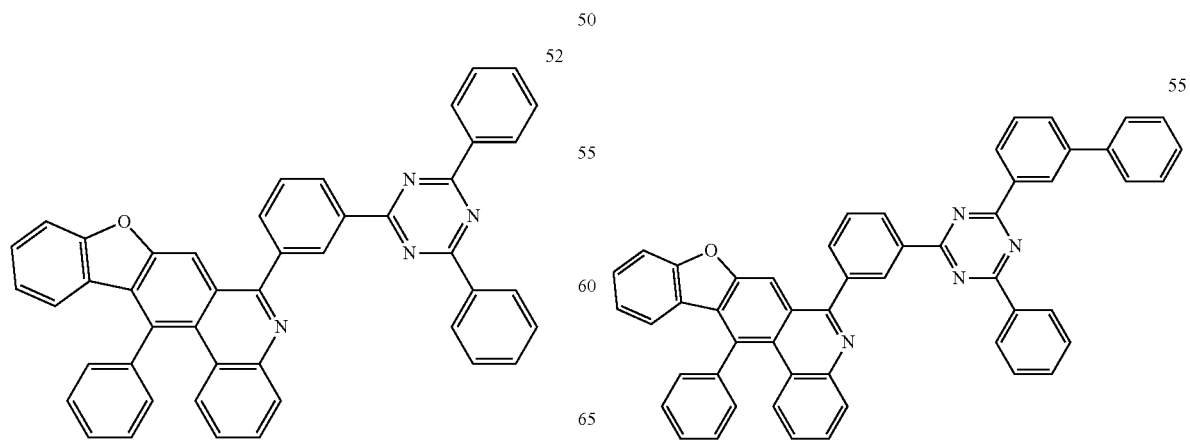
55

56
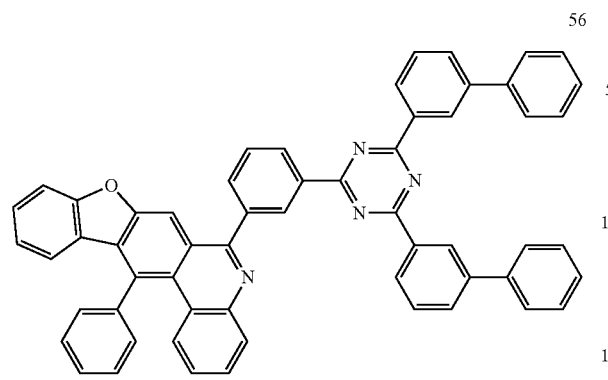
57
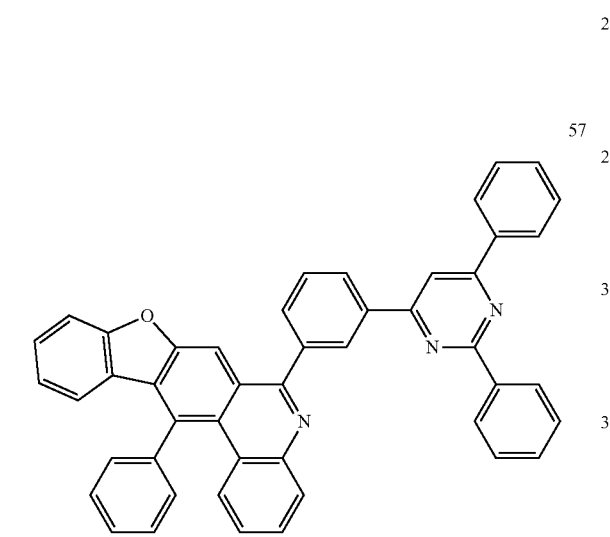
58
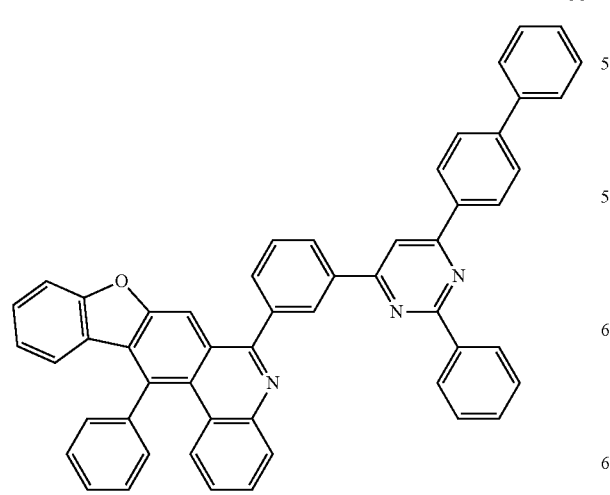
59
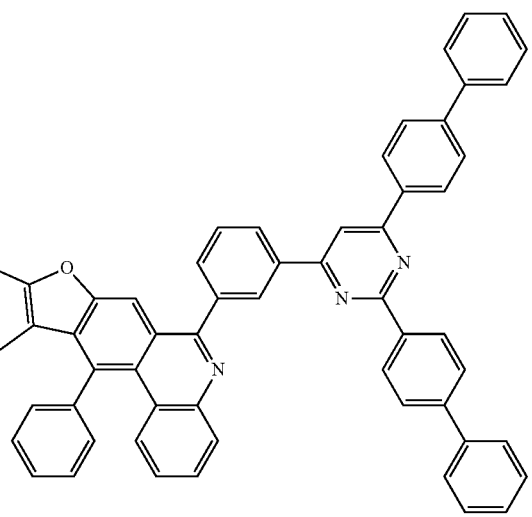
60
61
62

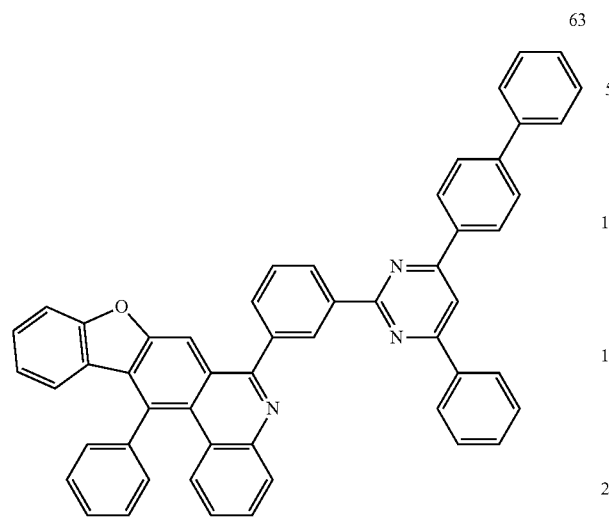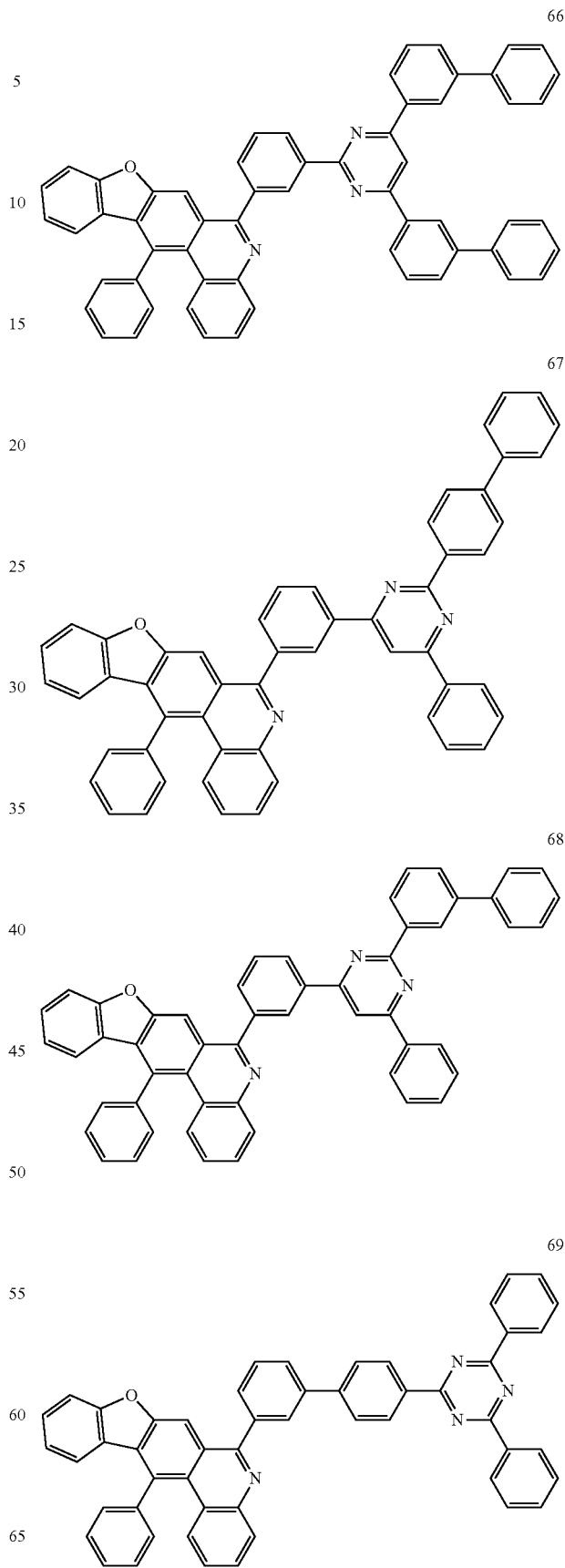

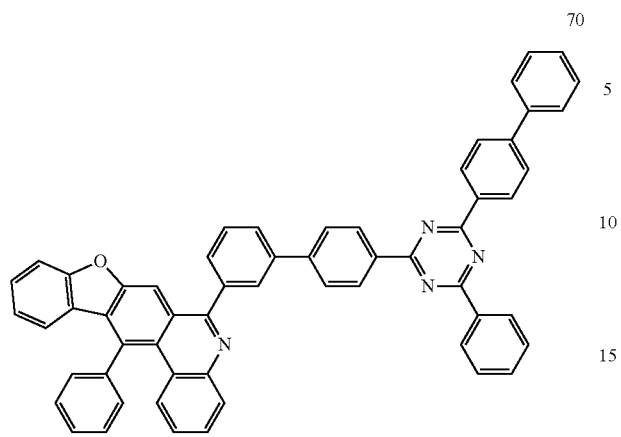
70
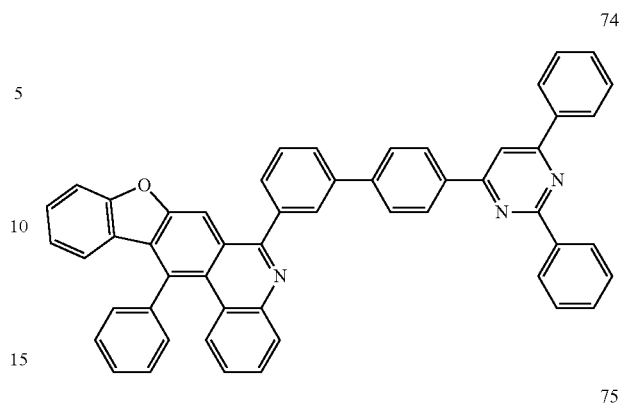
74
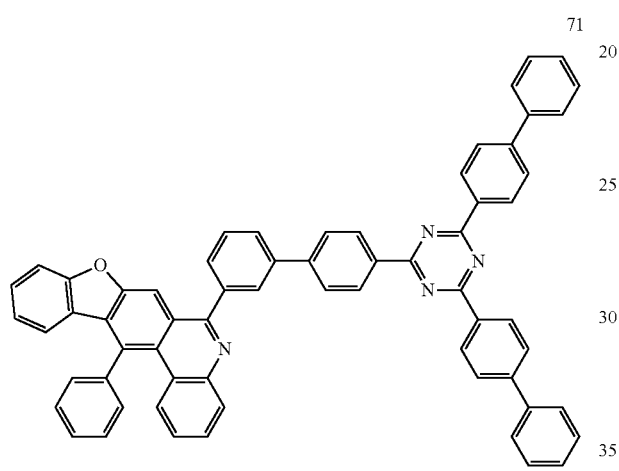
71
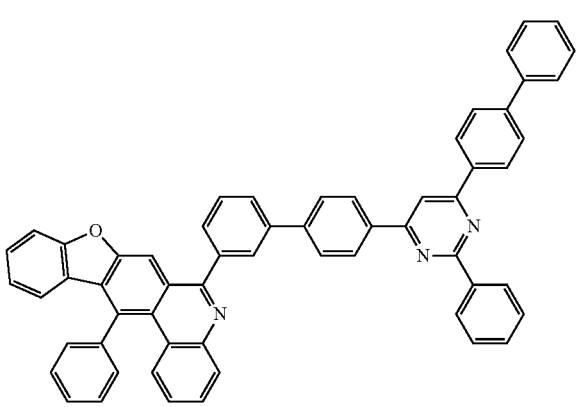 [SMILES: c1ccc(-c2ccc(-c3nc(-c4ccccc4)nc(-c4ccc(-c5cccc(-c6nc7ccccc7c7c(-c8ccccc8)c8c(cc67)oc6ccccc68)c5)cc4)n3)cc2)cc1]
75
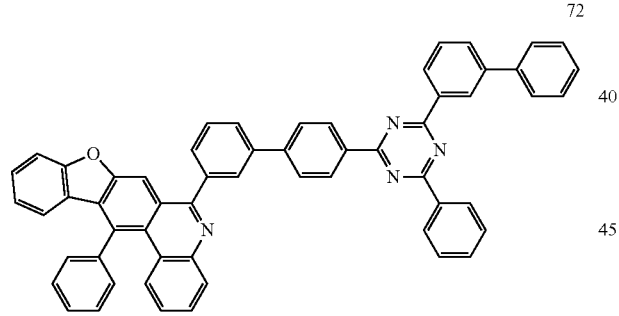
72
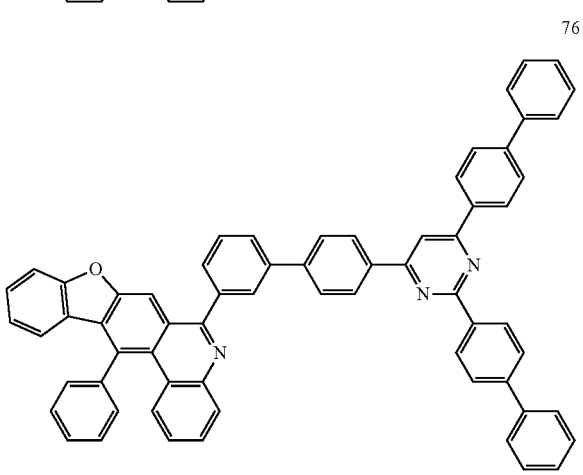
76
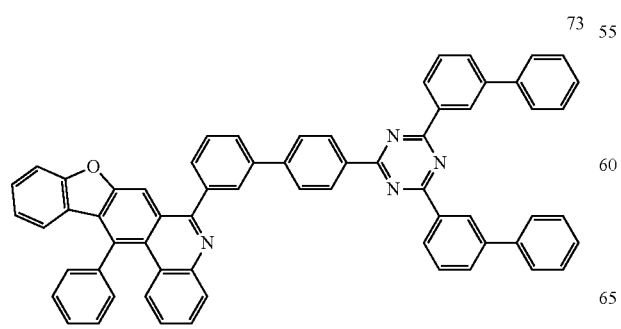
73
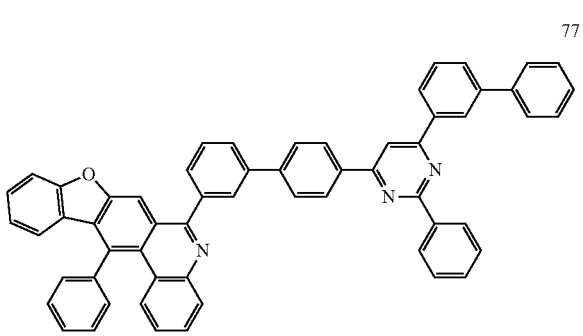
77

78
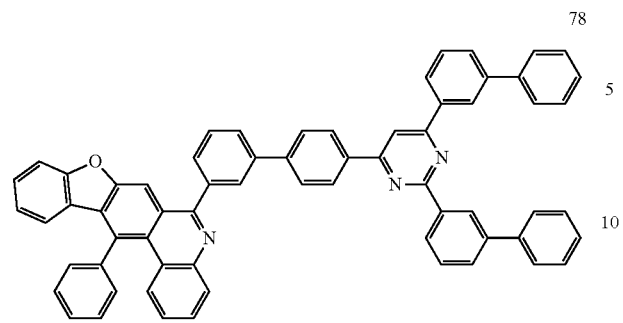
79
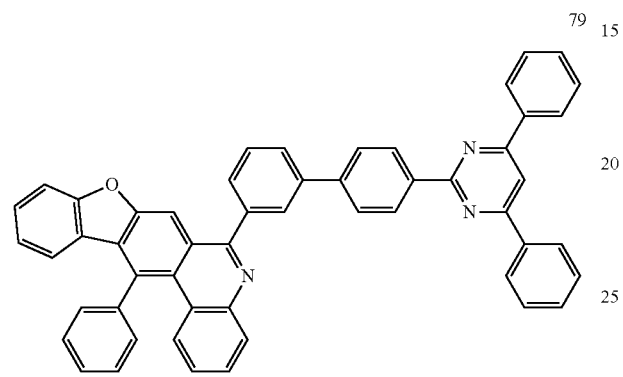
80
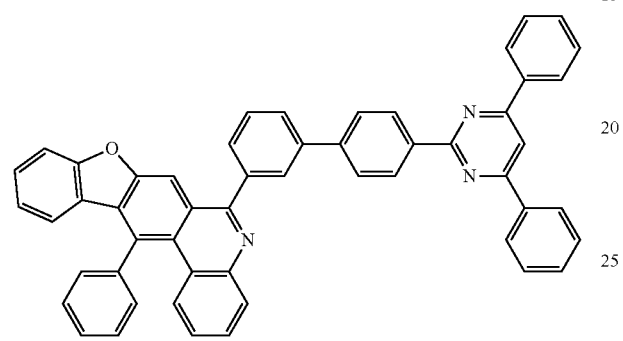
81
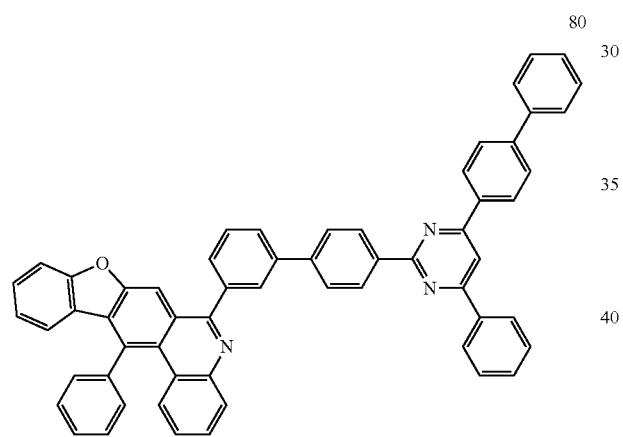
82
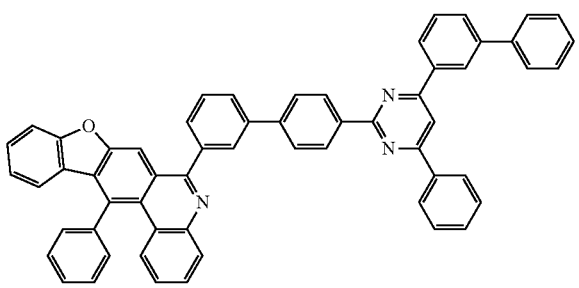
83
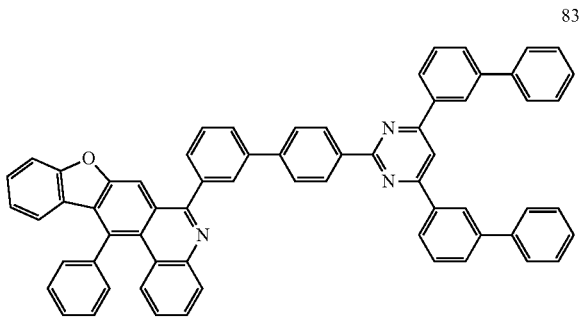
84
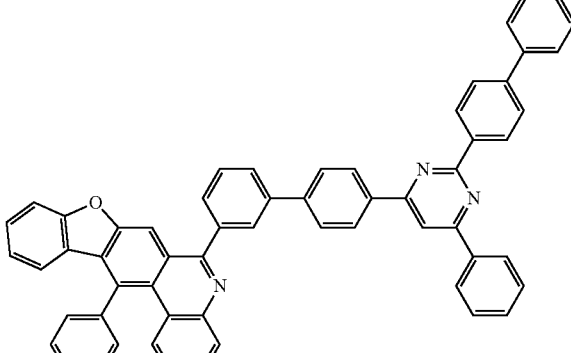
85
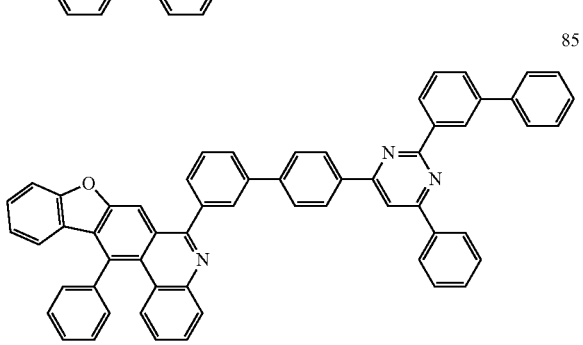
86
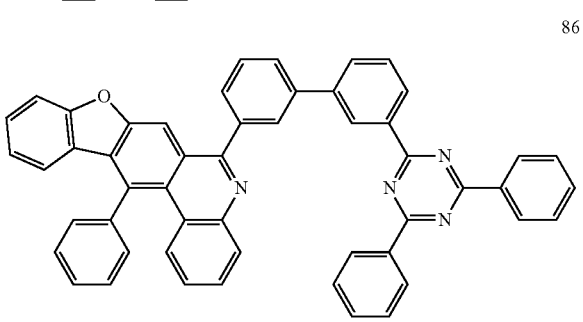

87
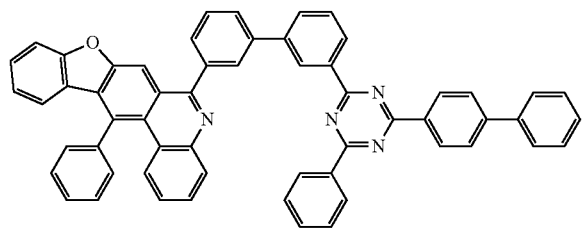
88
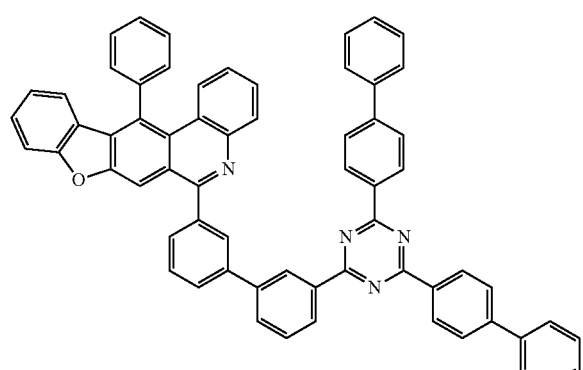
89
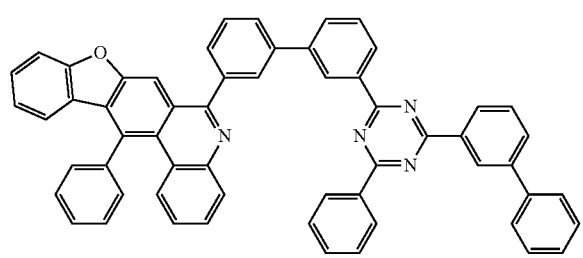
90
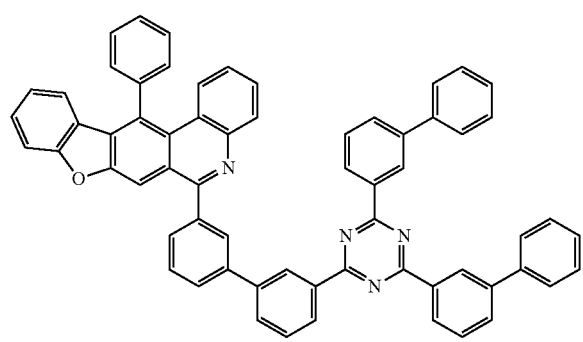
91
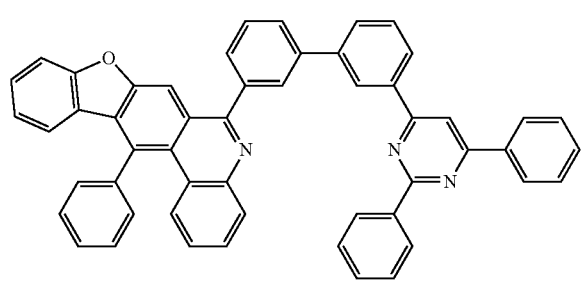
92
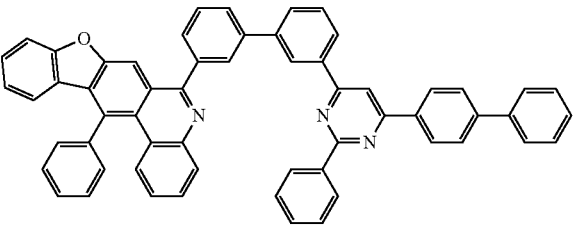
93
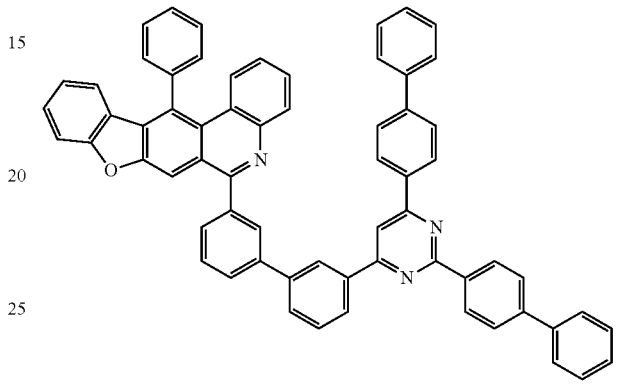
94
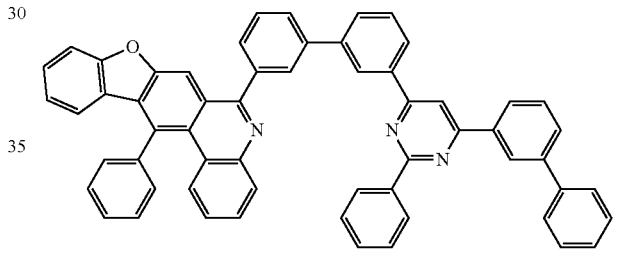
95
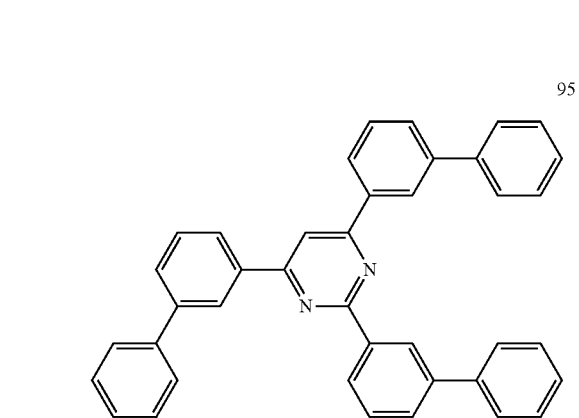
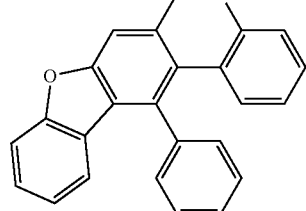

96
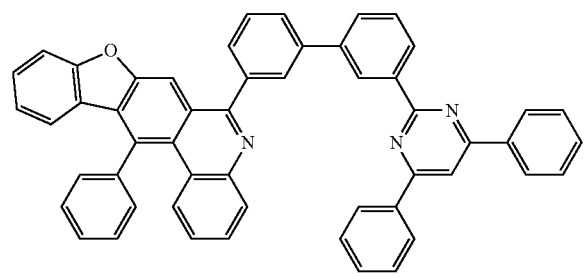 [SMILES: c1ccc(-c2nc(-c3ccccc3)nc(-c3cccc(-c4cccc(-c5nc6ccccc6c6c(-c7ccccc7)c7c(cc56)oc5ccccc57)c4)c3)n2)cc1]
97
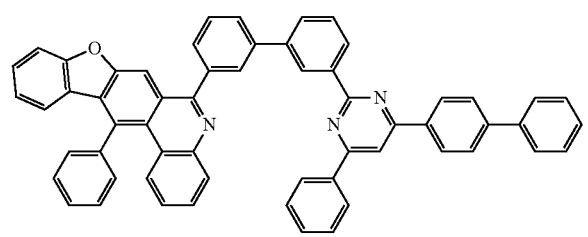
98
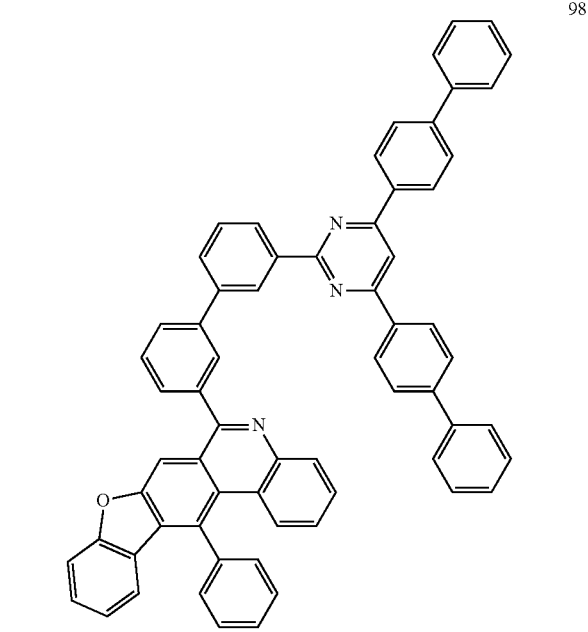
99
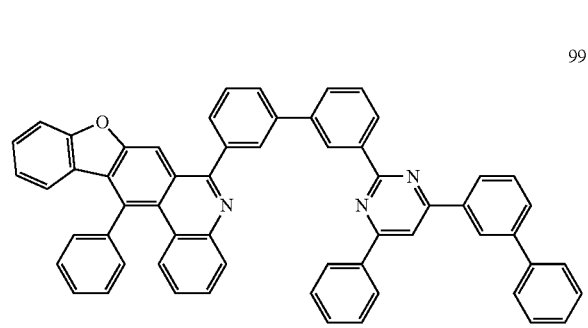
100
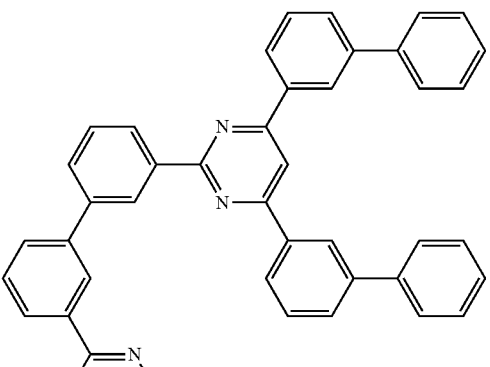
101
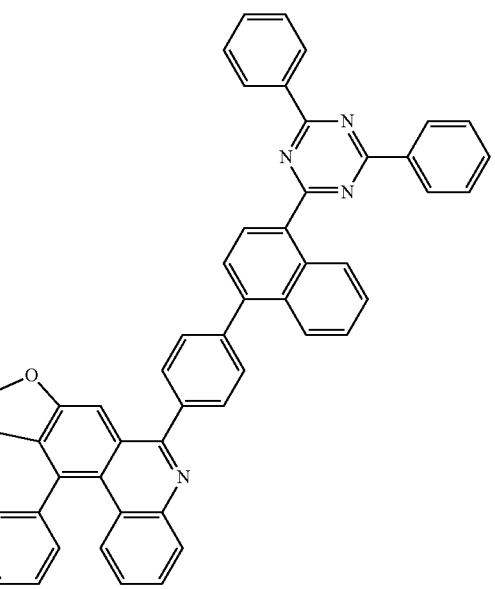
102
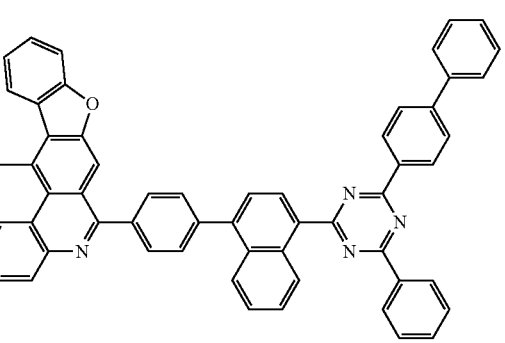

103
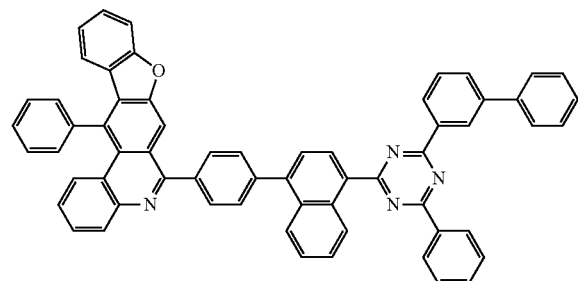
104
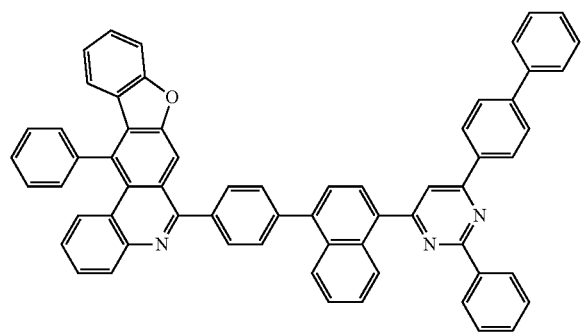 [SMILES: c1ccc(-c2ccc(-c3nc(-c4ccccc4)nc(-c4ccc(-c5ccc(-c6nc7ccccc7c7c(-c8ccccc8)c8c(cc67)oc6ccccc68)cc5)c5ccccc45)n3)cc2)cc1]
105
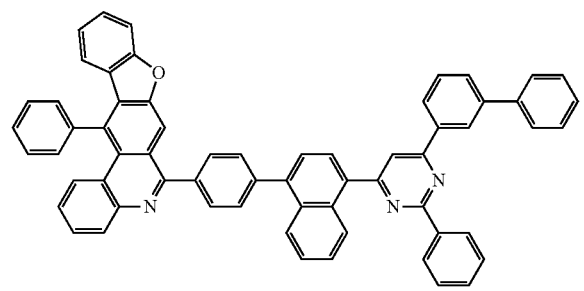 [SMILES: c1ccc(-c2cccc(-c3nc(-c4ccccc4)nc(-c4ccc(-c5ccc(-c6nc7ccccc7c7c(-c8ccccc8)c8c(cc67)oc6ccccc68)cc5)c5ccccc45)n3)c2)cc1]
106
107
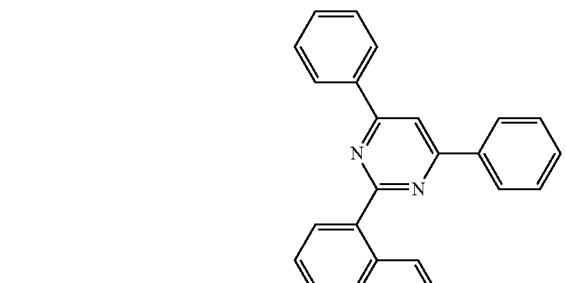
108
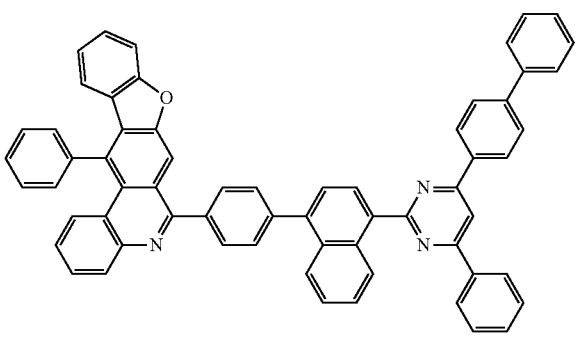
109
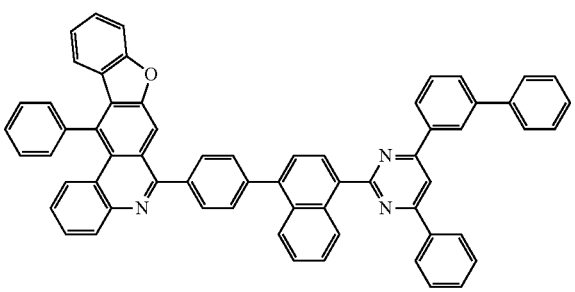
110
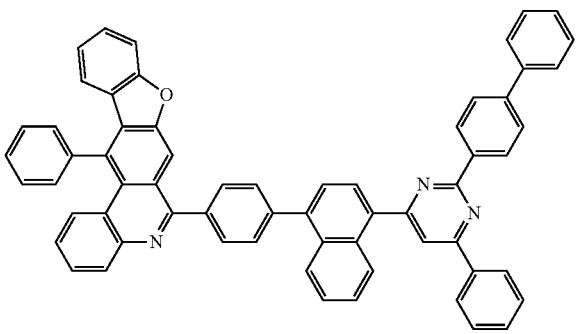

111
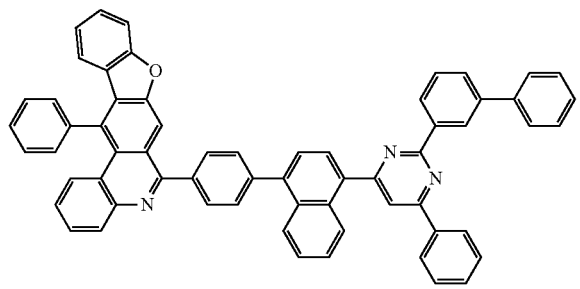 [SMILES: c1ccc(-c2cccc(-c3nc(-c4ccccc4)nc(-c4ccc(-c5ccc(-c6nc7ccccc7c7c(-c8ccccc8)c8c(cc67)oc6ccccc68)cc5)c5ccccc45)n3)c2)cc1]
112
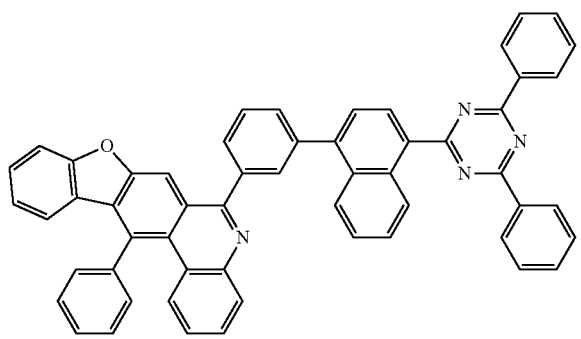 [SMILES: c1ccc(-c2nc(-c3ccccc3)nc(-c3ccc(-c4cccc(-c5nc6ccccc6c6c(-c7ccccc7)c7c(cc56)oc5ccccc57)c4)c4ccccc34)n2)cc1]
113
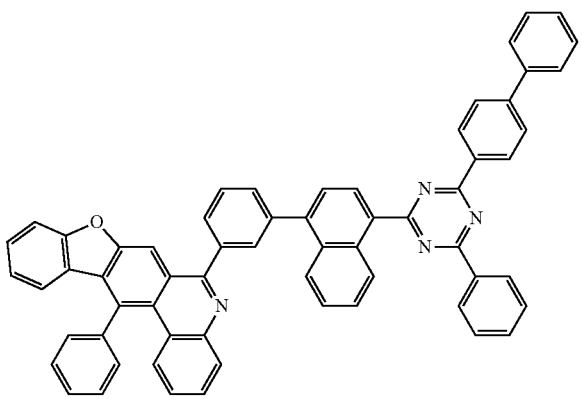 [SMILES: c1ccc(-c2ccc(-c3nc(-c4ccccc4)nc(-c4ccc(-c5cccc(-c6nc7ccccc7c7c(-c8ccccc8)c8c(cc67)oc6ccccc68)c5)c5ccccc45)n3)cc2)cc1]
114
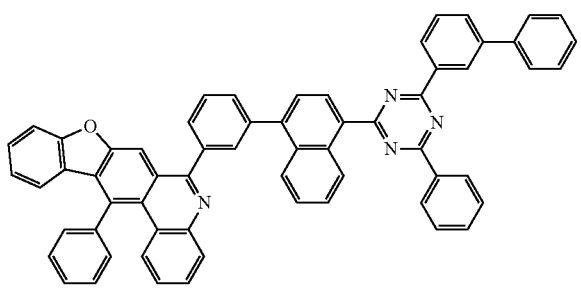
115
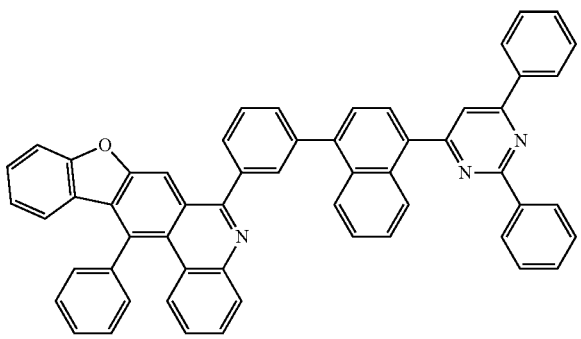 [SMILES: c1ccc(-c2cc(-c3ccc(-c4cccc(-c5nc6ccccc6c6c(-c7ccccc7)c7c(cc56)oc5ccccc57)c4)c4ccccc34)nc(-c3ccccc3)n2)cc1]
116
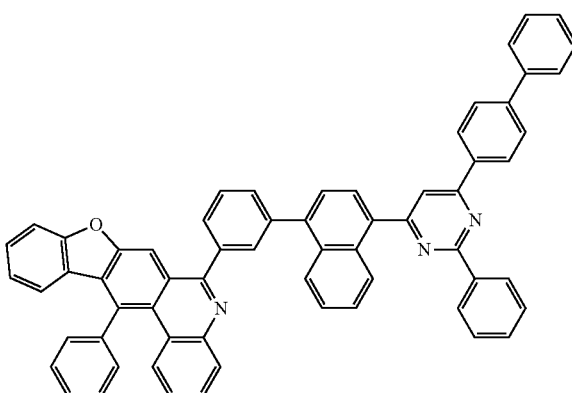
117
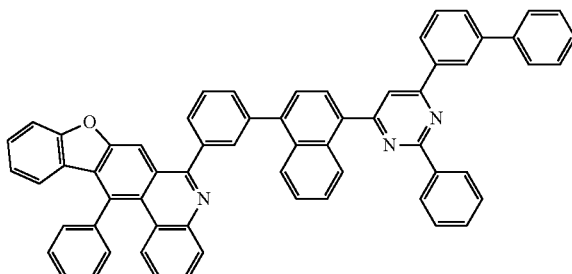
118
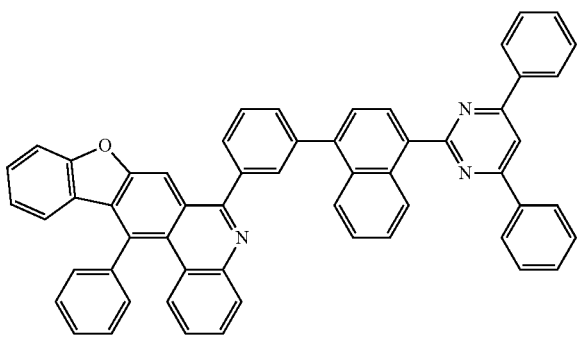

-continued
119
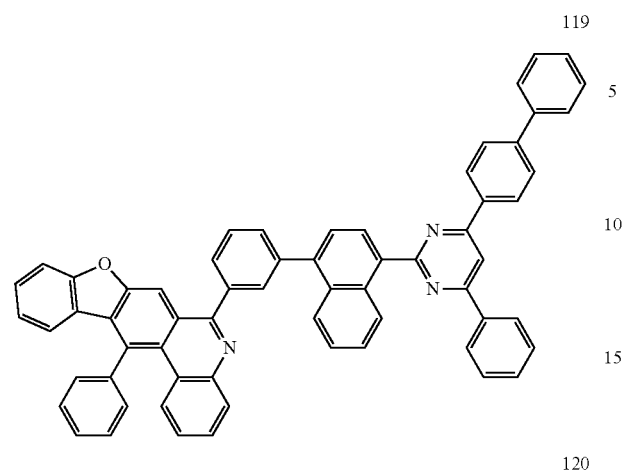
120
121
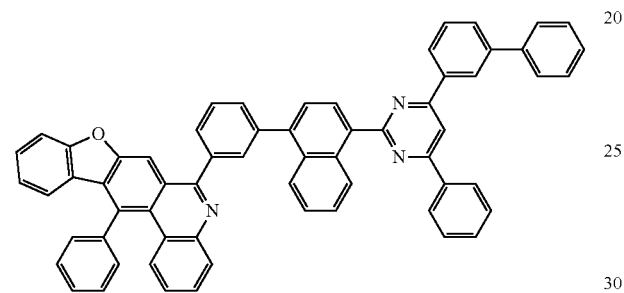
122
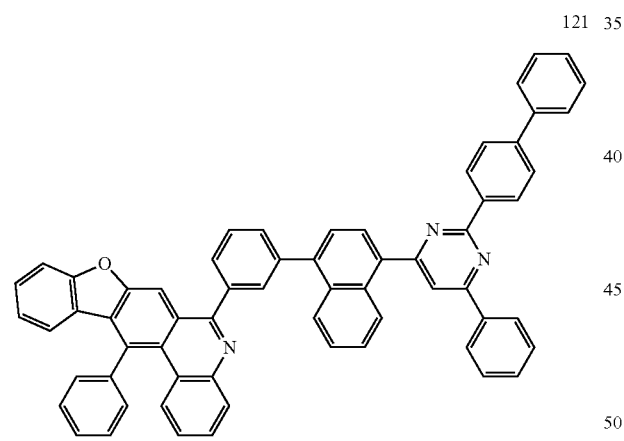
-continued
123
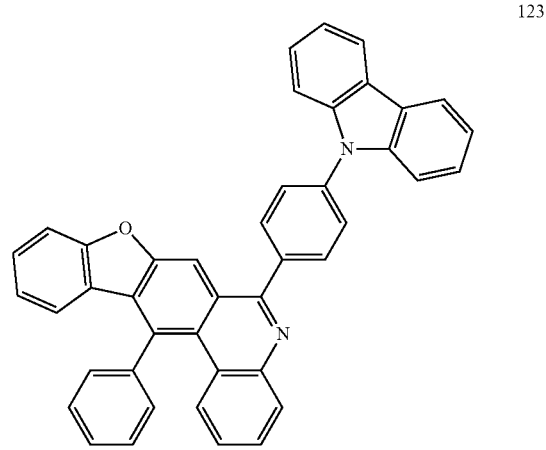
124
125
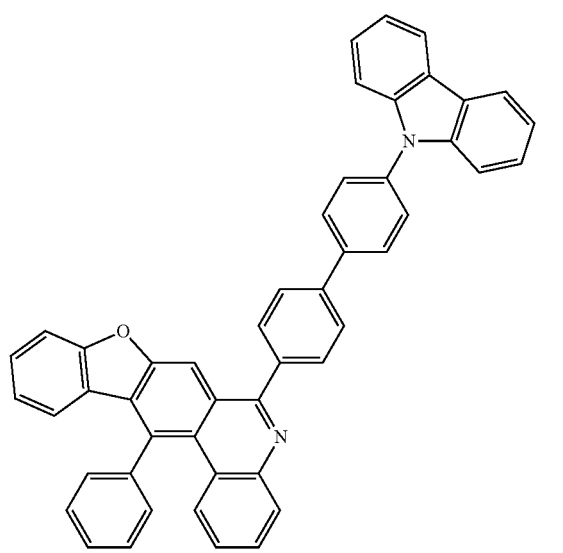 [SMILES: c1ccc(-c2c3c(cc4c(-c5ccc(-c6ccc(-n7c8ccccc8c8ccccc87)cc6)cc5)nc5ccccc5c24)oc2ccccc23)cc1]

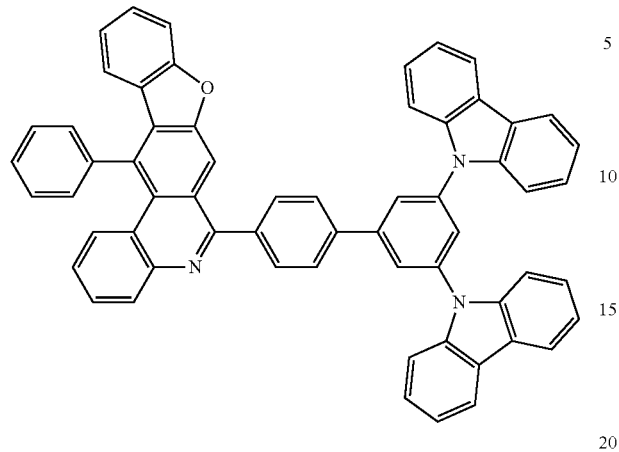
126
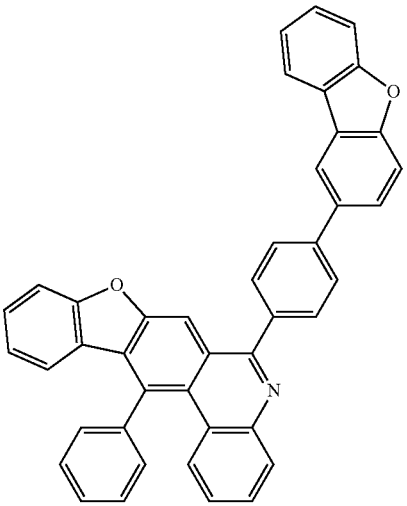
129
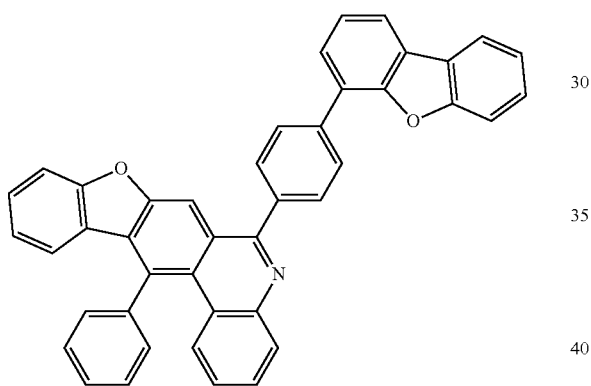
127
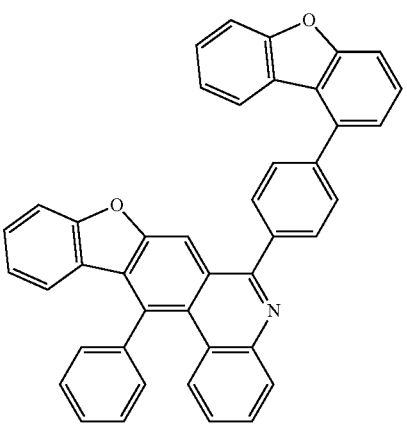
130
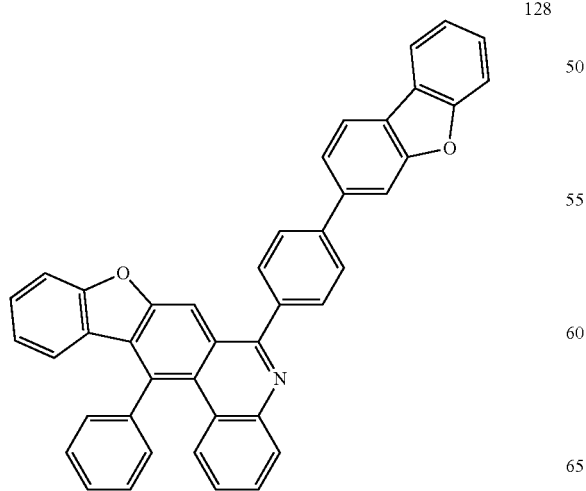
128
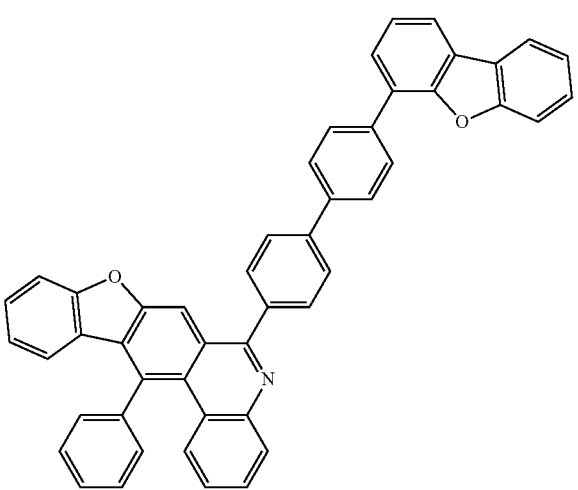 [SMILES: c1ccc(-c2c3c(cc4c(-c5ccc(-c6ccc(-c7cccc8c7oc7ccccc78)cc6)cc5)nc5ccccc5c24)oc2ccccc23)cc1]
131

132
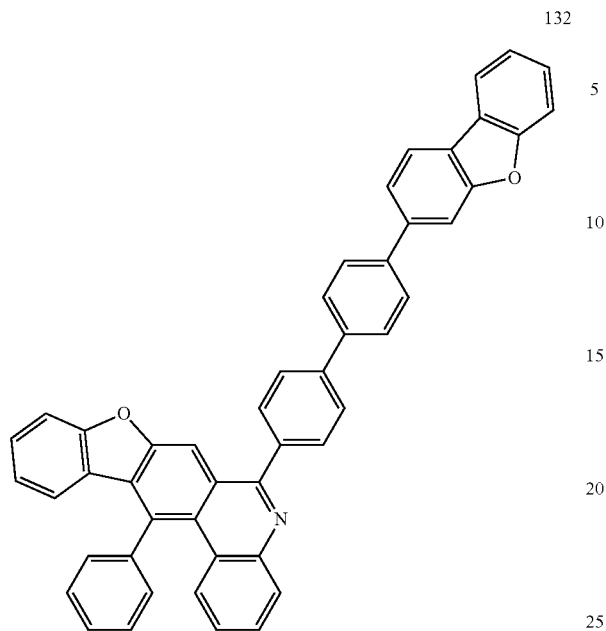
133
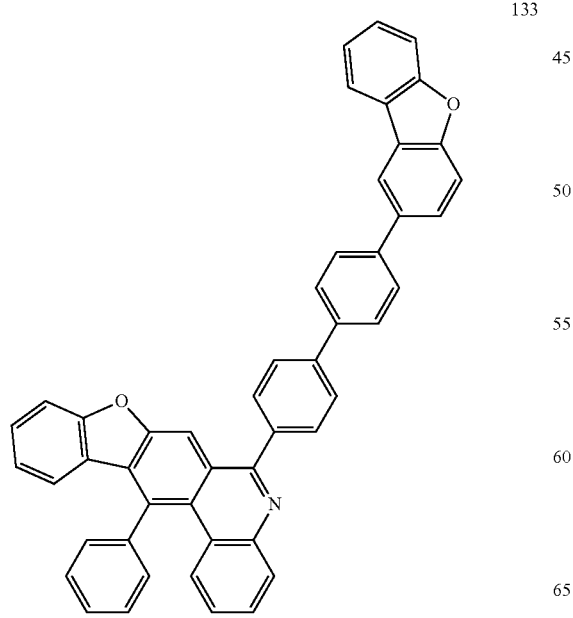
134
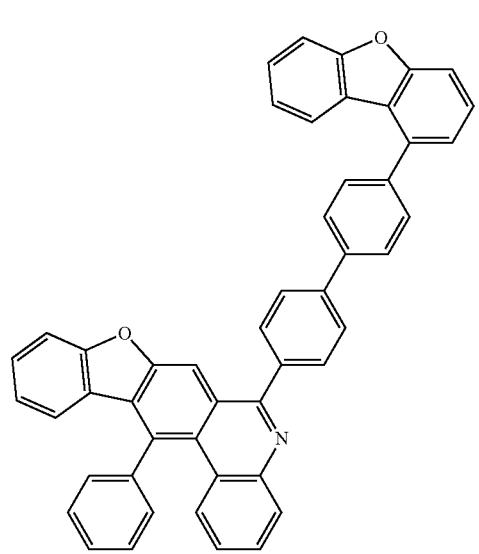
135
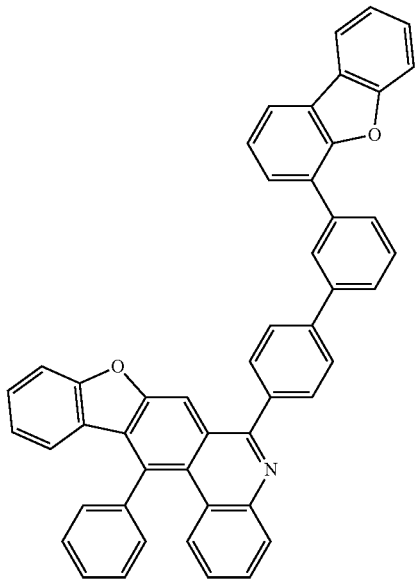

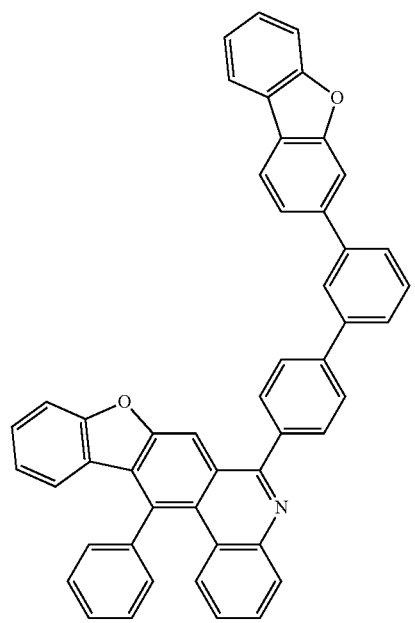 [SMILES: c1ccc(-c2c3c(cc4c(-c5ccc(-c6cccc(-c7ccc8c(c7)oc7ccccc78)c6)cc5)nc5ccccc5c24)oc2ccccc23)cc1]
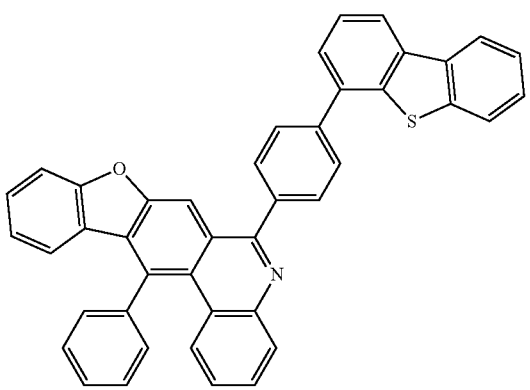 [SMILES: c1ccc(-c2c3c(cc4c(-c5ccc(-c6cccc7c6sc6ccccc67)cc5)nc5ccccc5c24)oc2ccccc23)cc1]
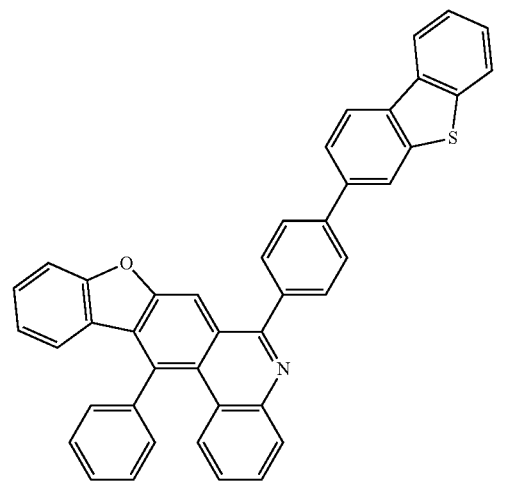
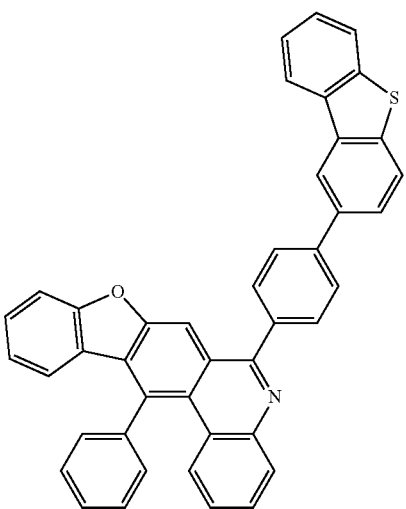 [SMILES: c1ccc(-c2c3c(cc4c(-c5ccc(-c6ccc7sc8ccccc8c7c6)cc5)nc5ccccc5c24)oc2ccccc23)cc1]

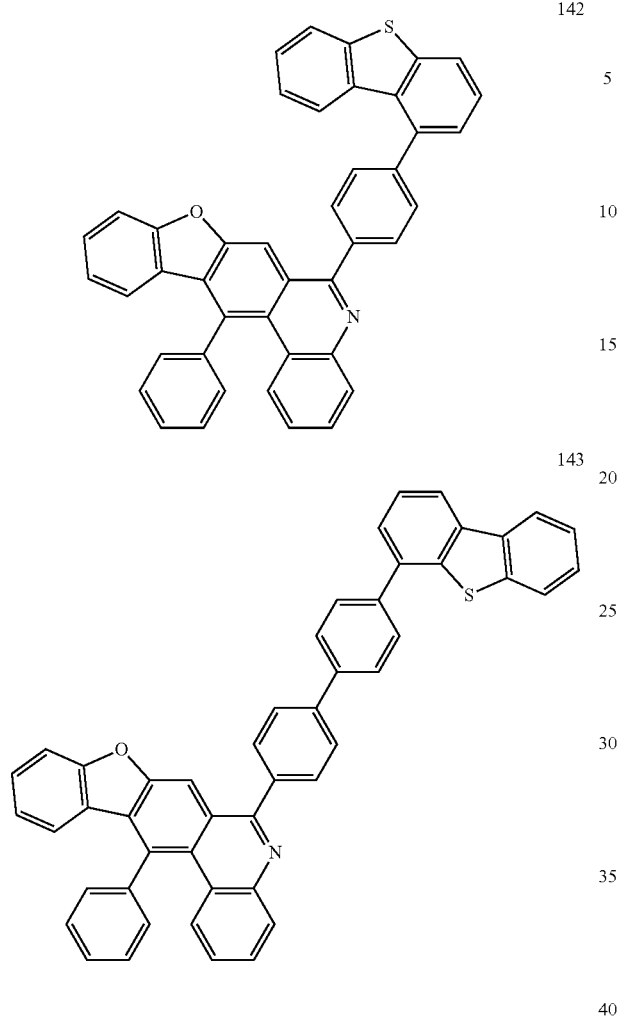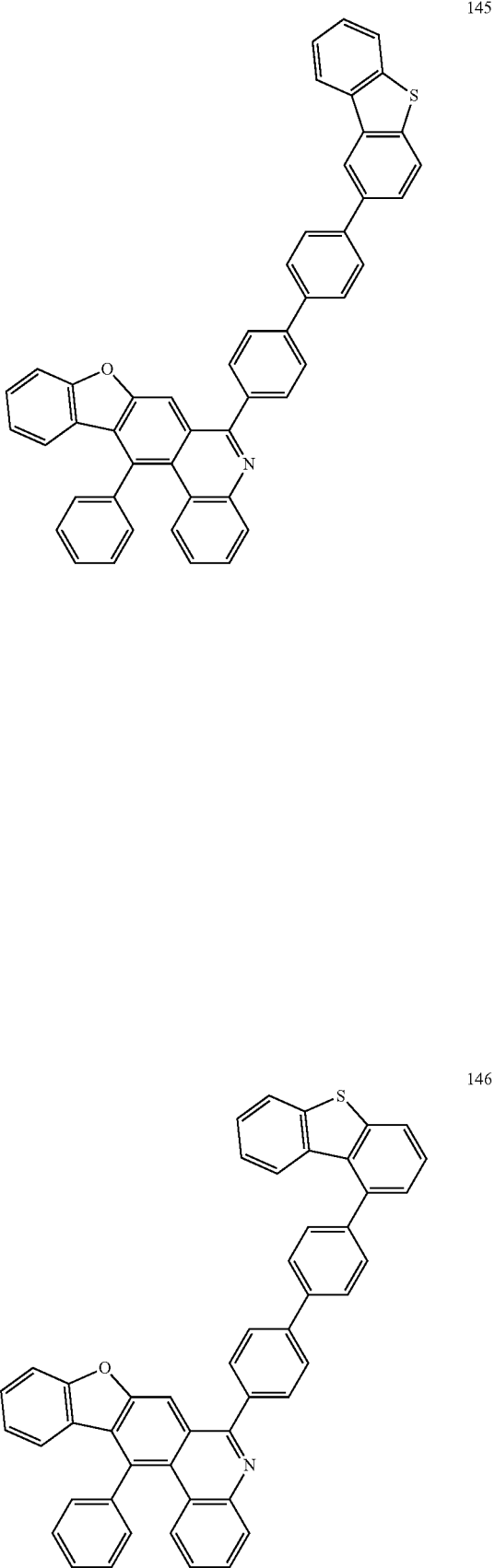

147
148
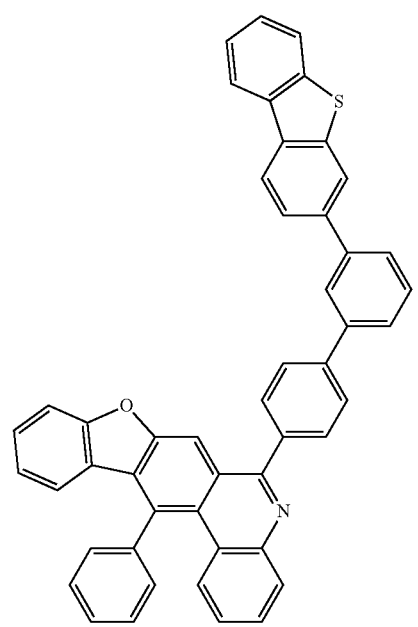
149
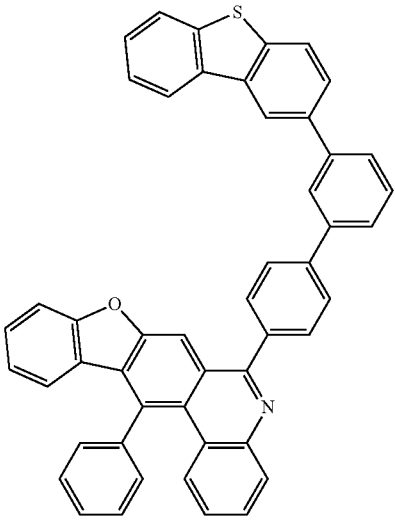
150
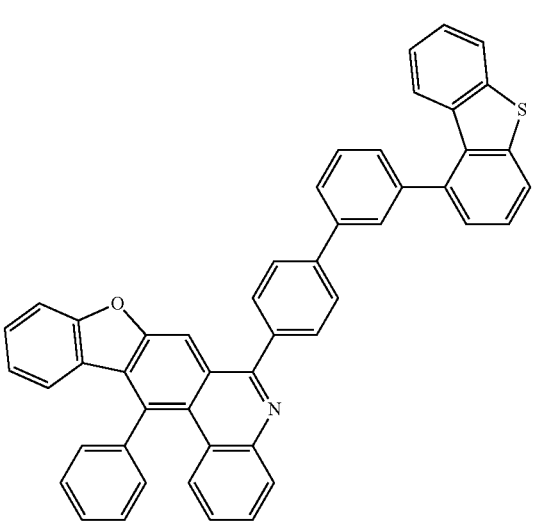
151
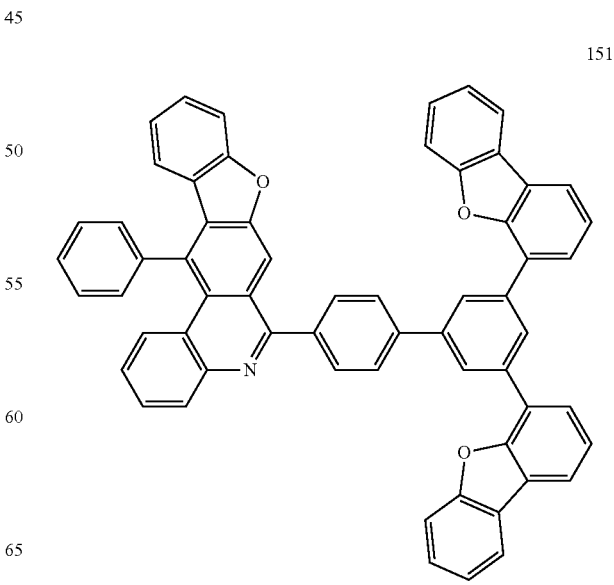

63
-continued
152
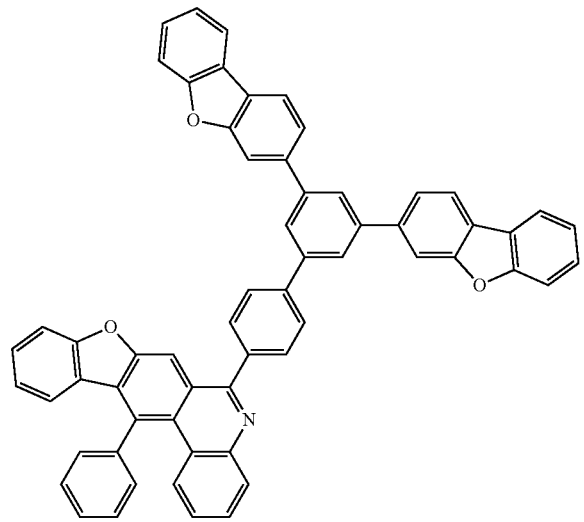
154
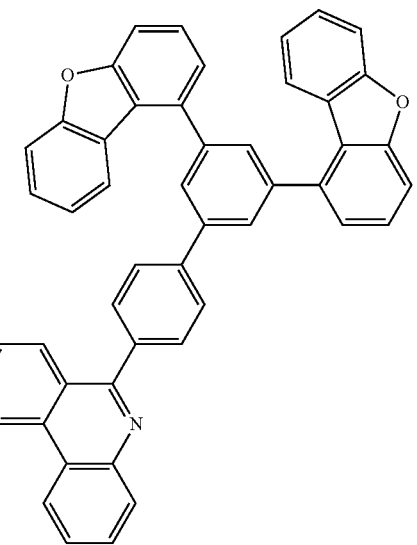
153
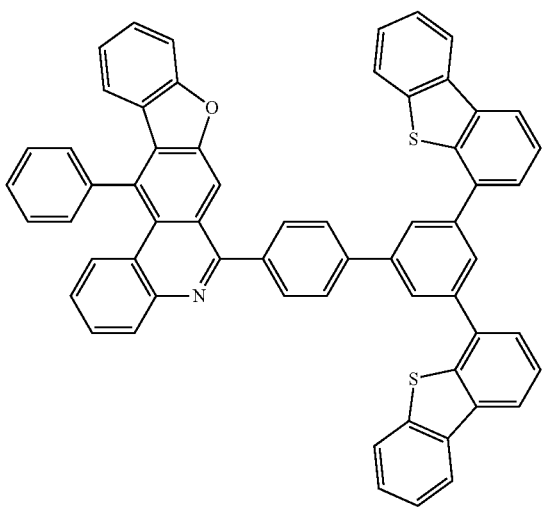 [SMILES: c1ccc(-c2c3c(cc4c(-c5ccc(-c6cc(-c7cccc8c7oc7ccccc78)cc(-c7cccc8c7oc7ccccc78)c6)cc5)nc5ccccc5c24)oc2ccccc23)cc1]
155
156
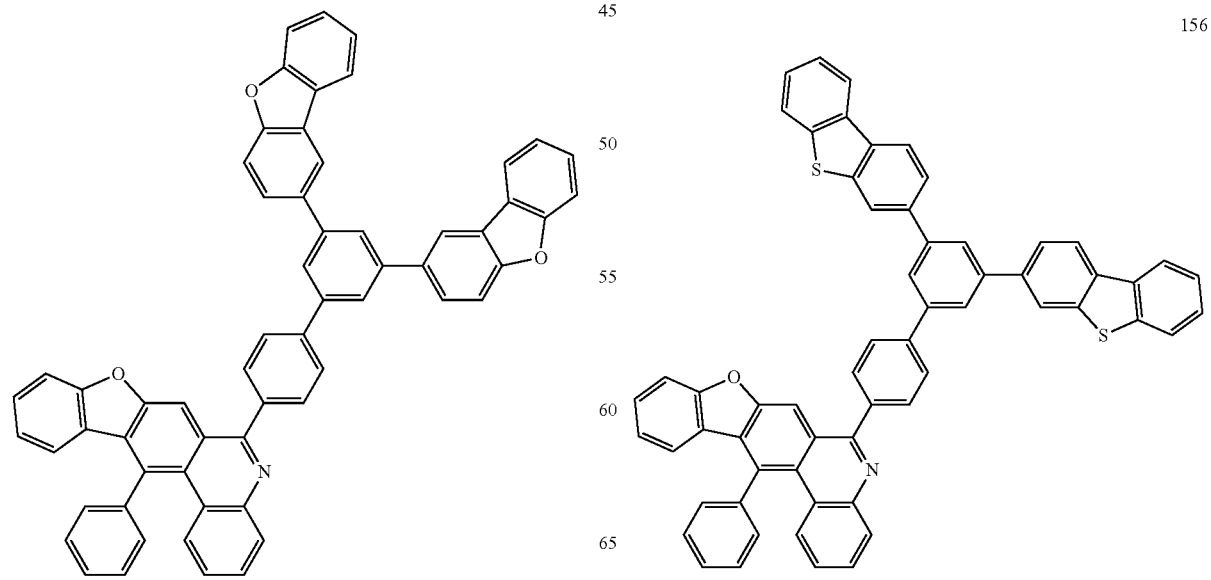

157
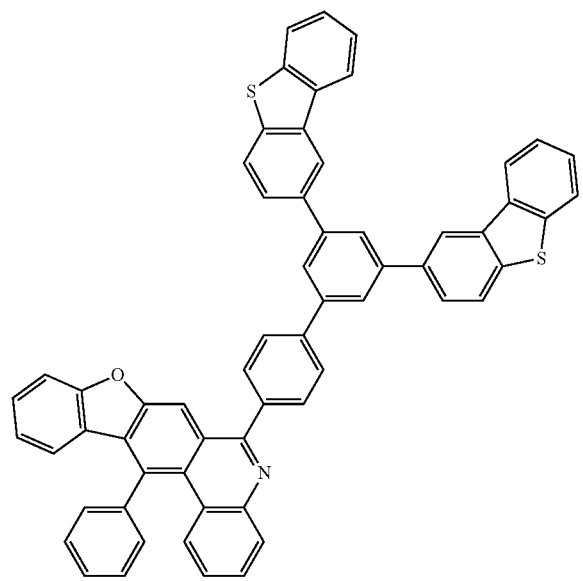
158
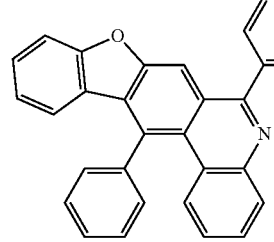
159
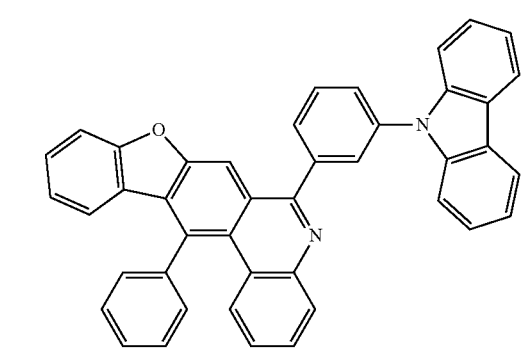
160
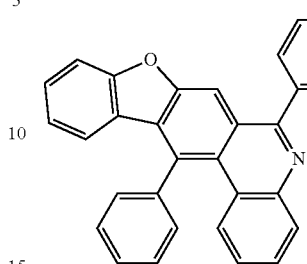
161
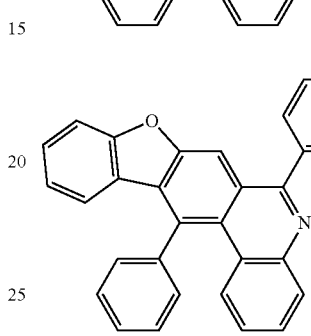
162
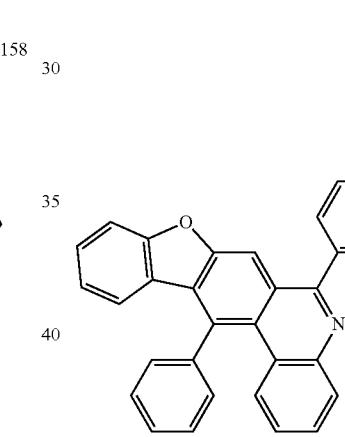
163
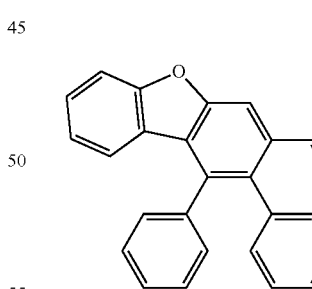
164
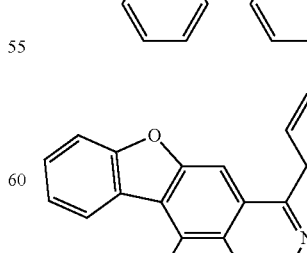

165
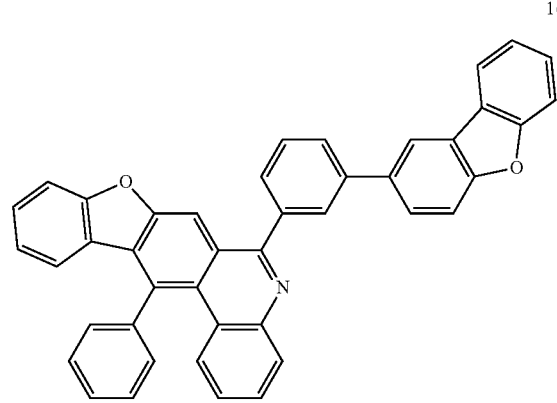
166

167
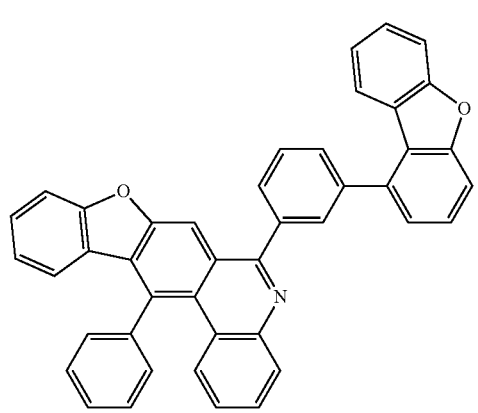
168
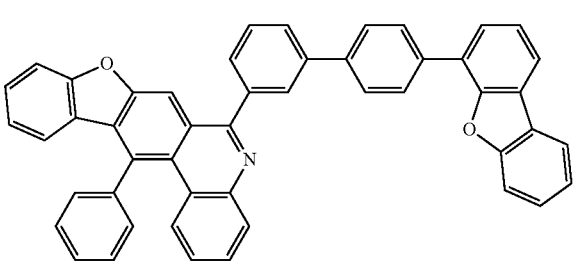
169
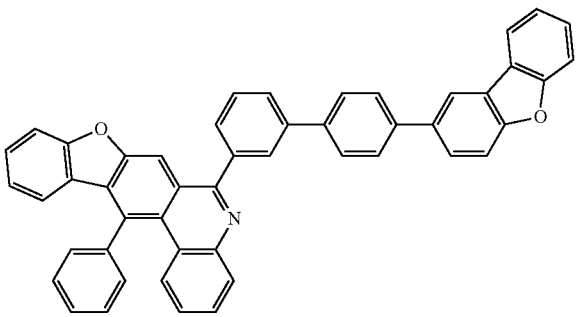
170
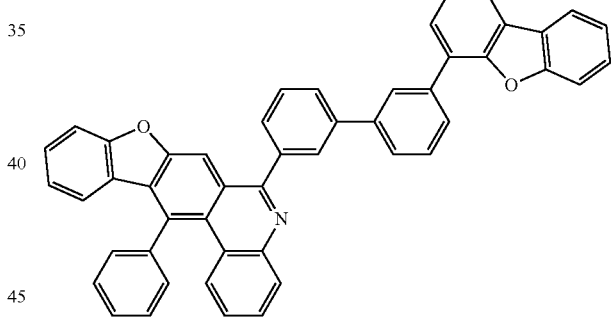
171
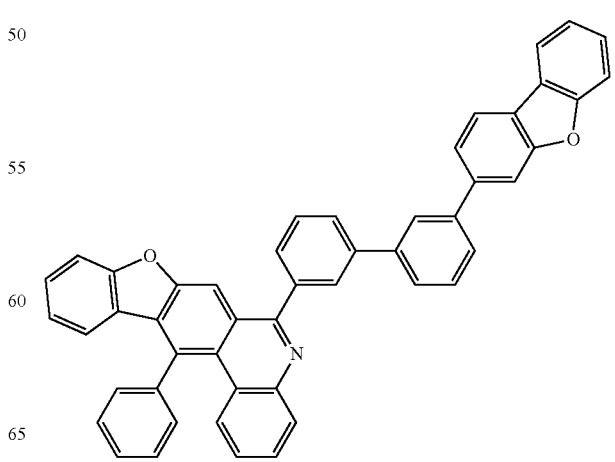
172
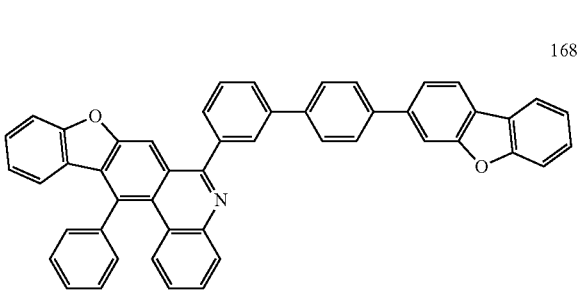

173
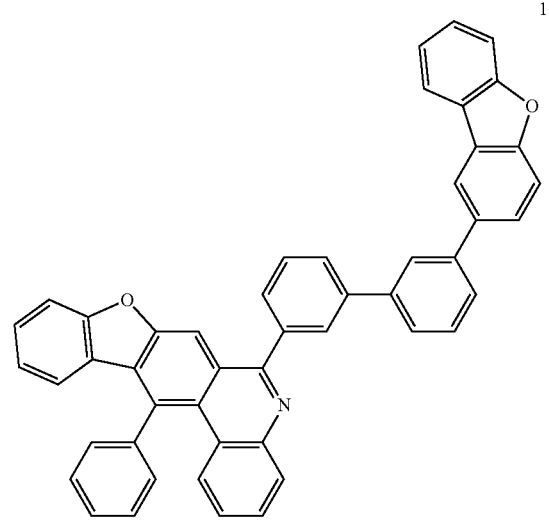
174
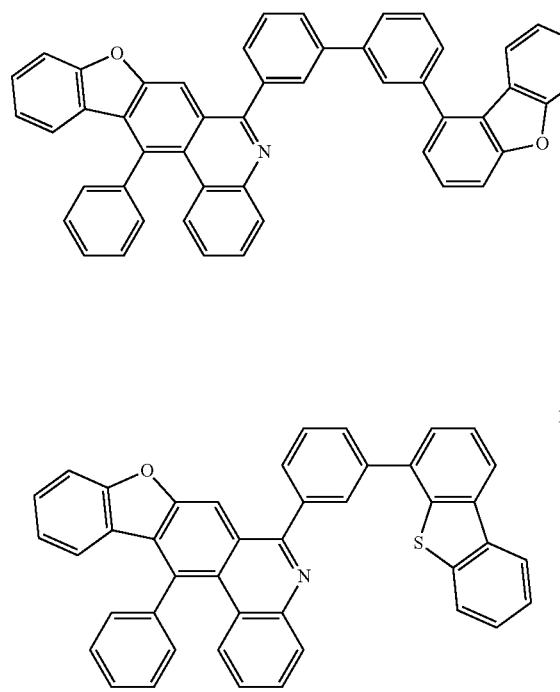
175
176
177
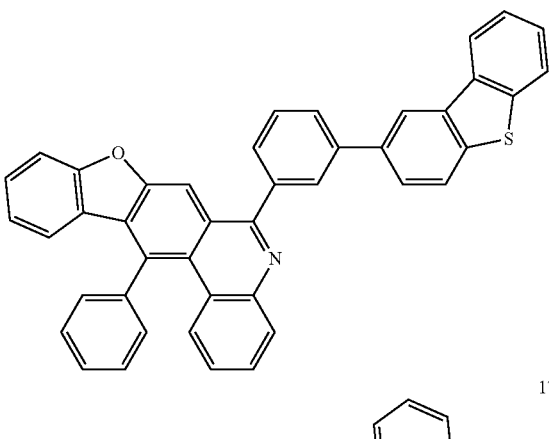
178
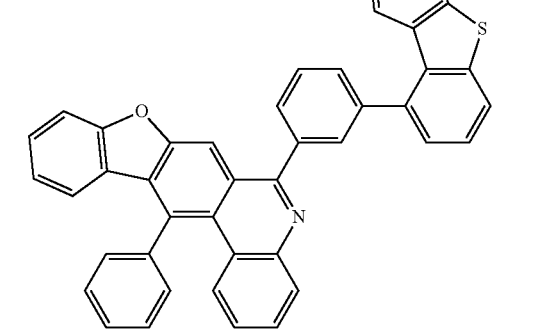
179
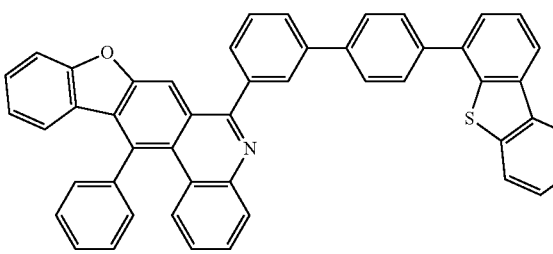
180
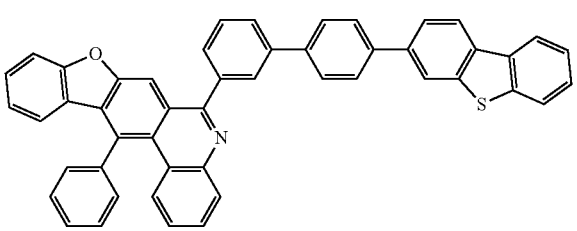
181
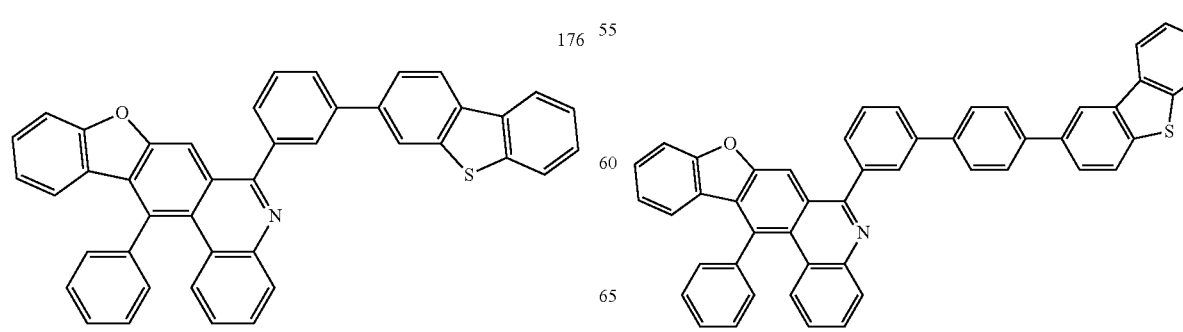

182
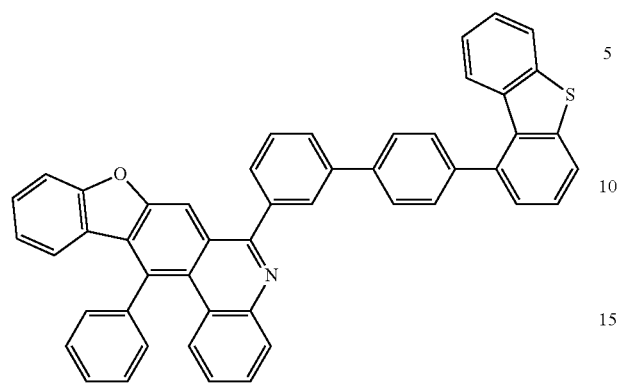
183
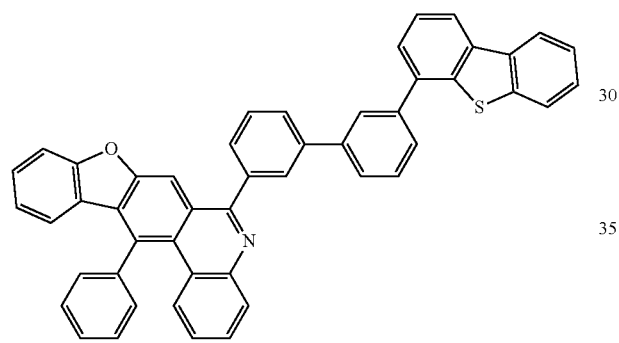
184
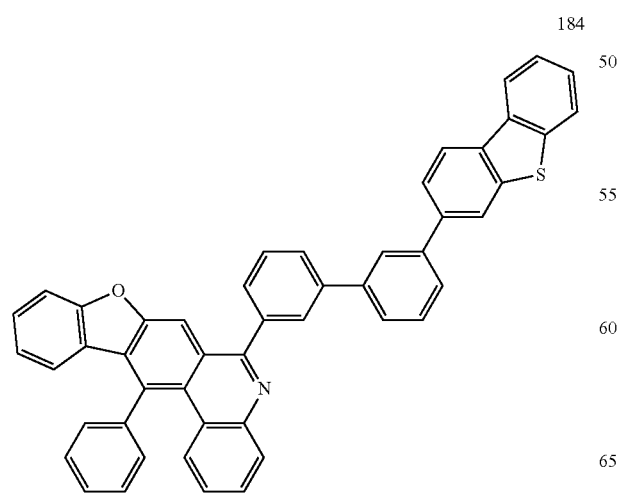
185
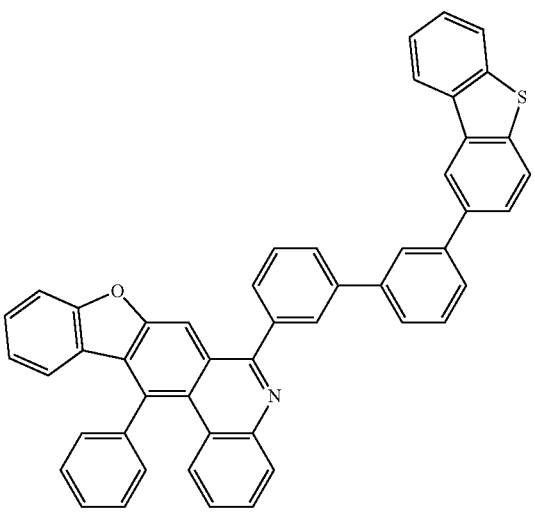
186
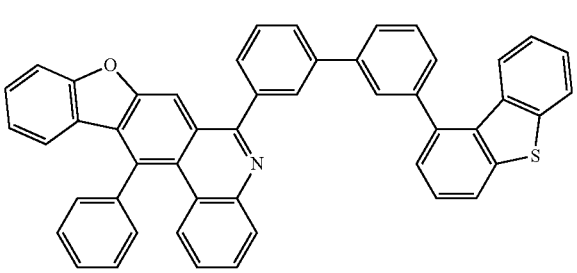 [SMILES: c1ccc(-c2c3c(cc4c(-c5cccc(-c6cccc(-c7cccc8sc9ccccc9c78)c6)c5)nc5ccccc5c24)oc2ccccc23)cc1]
187
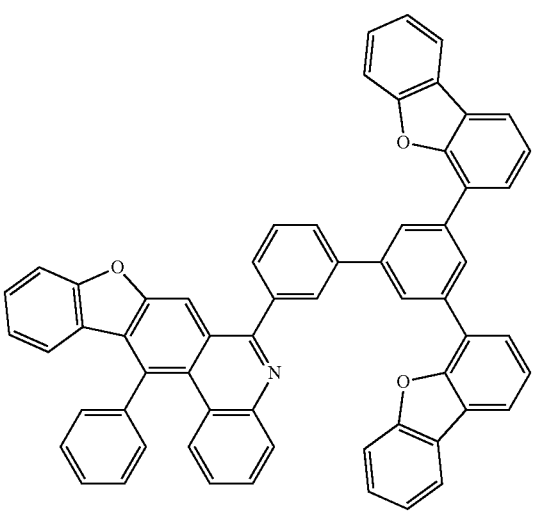

188
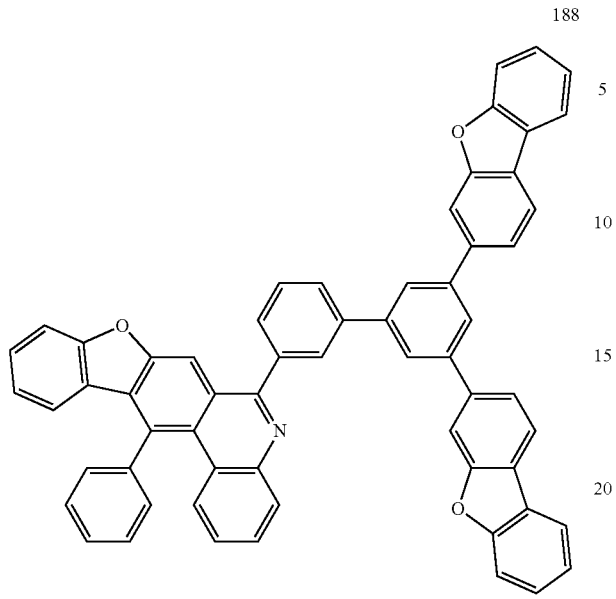
189
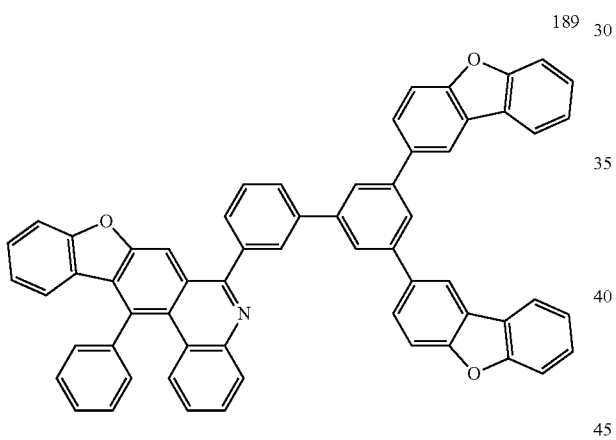
190
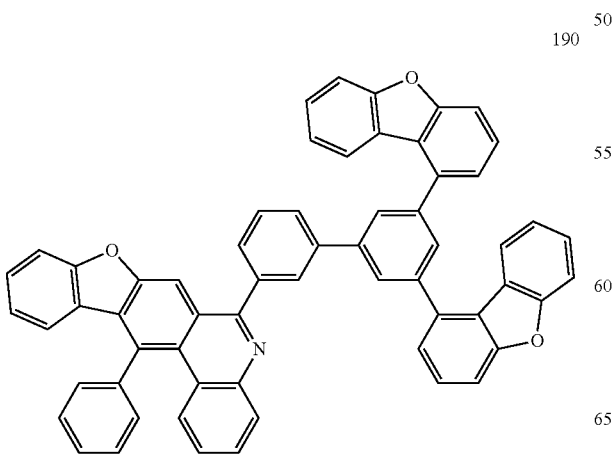
191
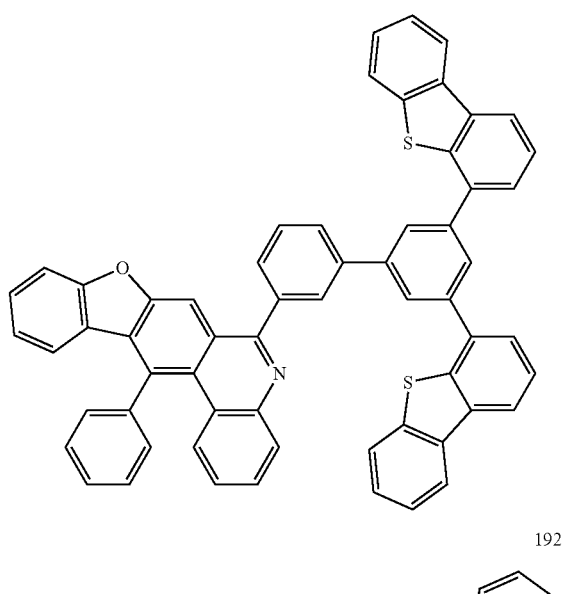
192
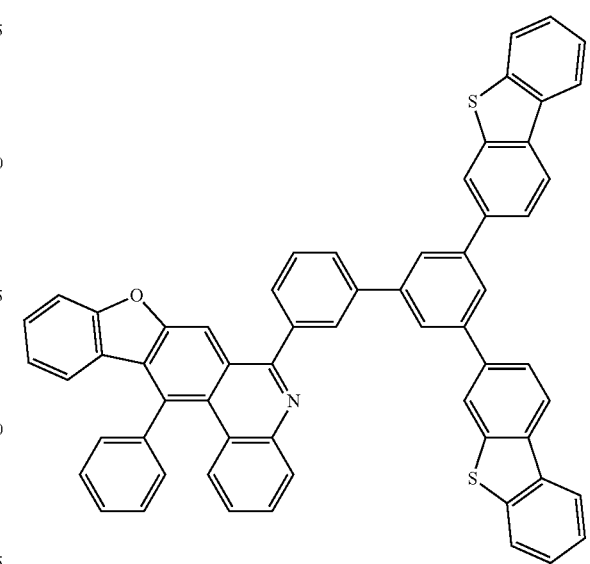
193
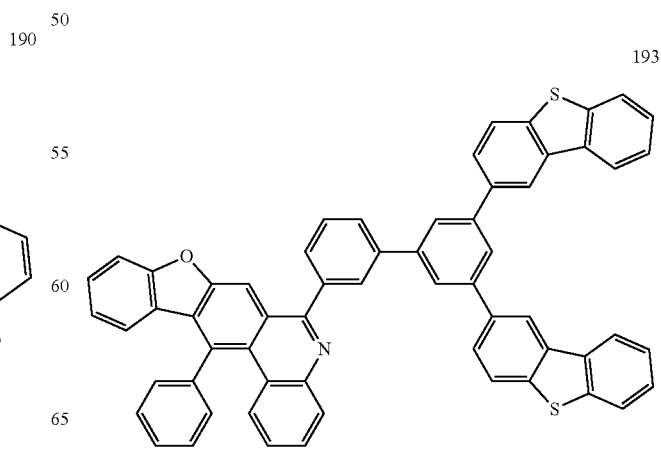

194
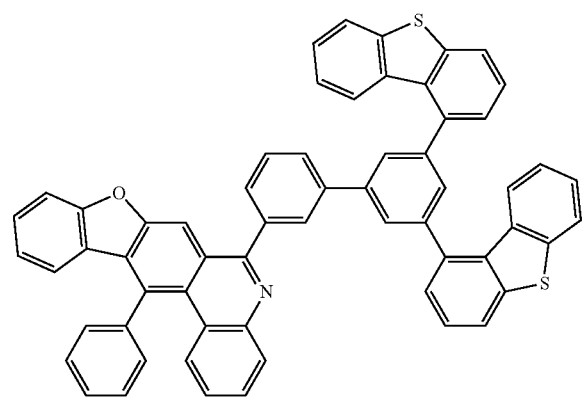 [SMILES: c1ccc(-c2c3c(cc4c(-c5cccc(-c6cc(-c7cccc8oc9ccccc9c78)cc(-c7cccc8oc9ccccc9c78)c6)c5)nc5ccccc5c24)oc2ccccc23)cc1]
195
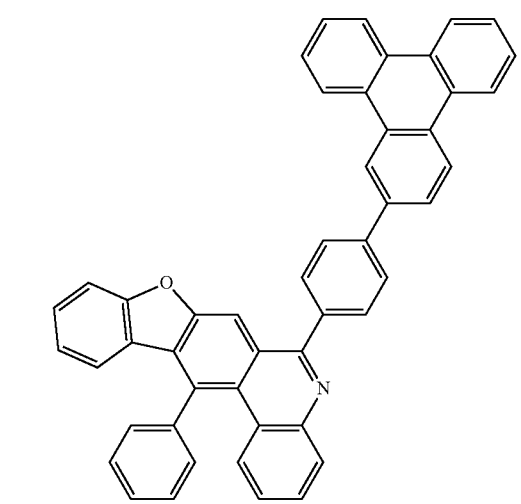 [SMILES: c1ccc(-c2c3c(cc4c(-c5ccc(-c6ccc7c8ccccc8c8ccccc8c7c6)cc5)nc5ccccc5c24)oc2ccccc23)cc1]
196
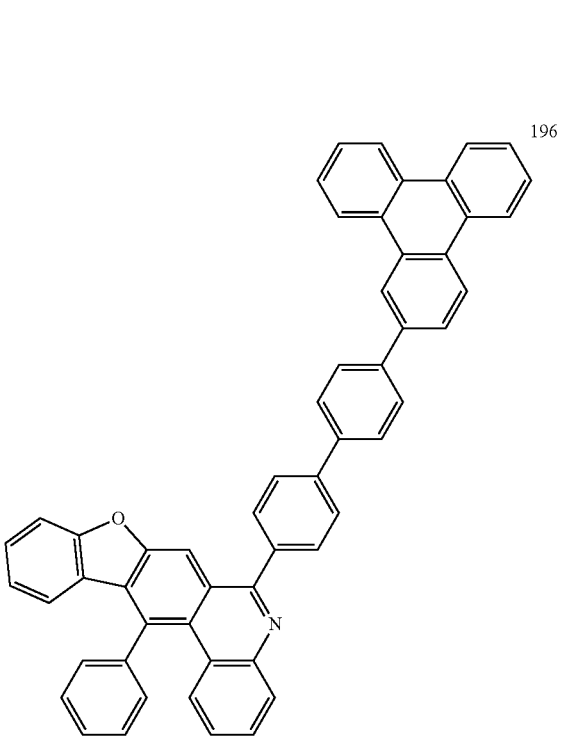
197
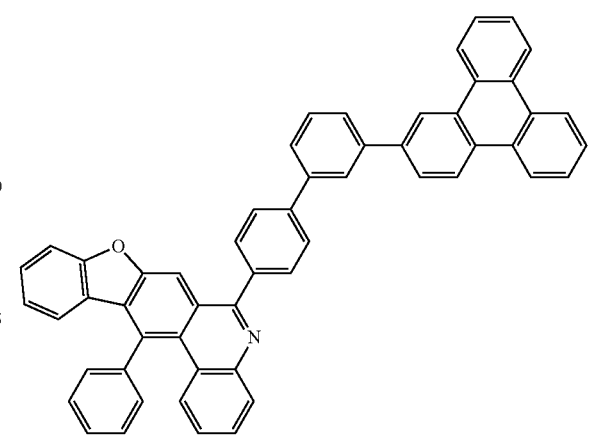
198
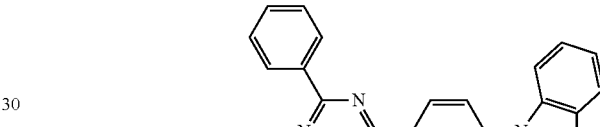
199
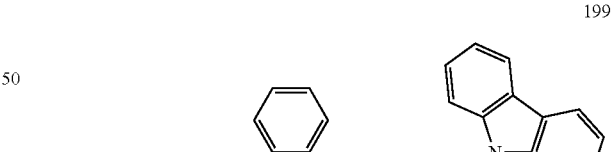

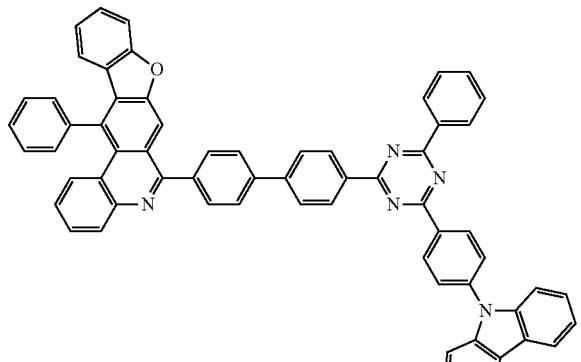
200
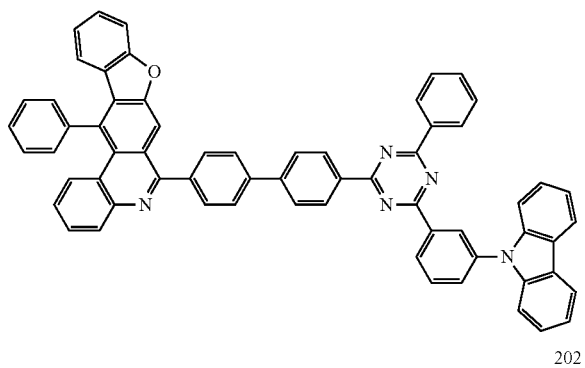
201
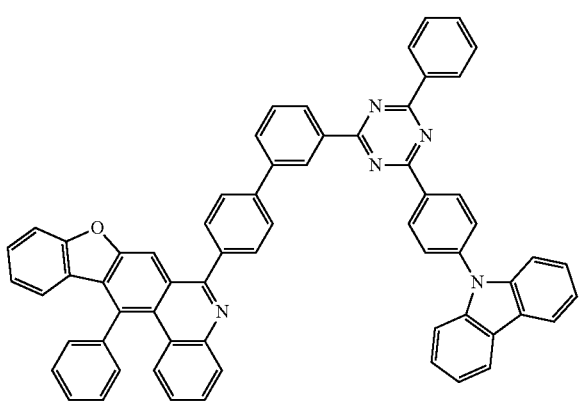
202
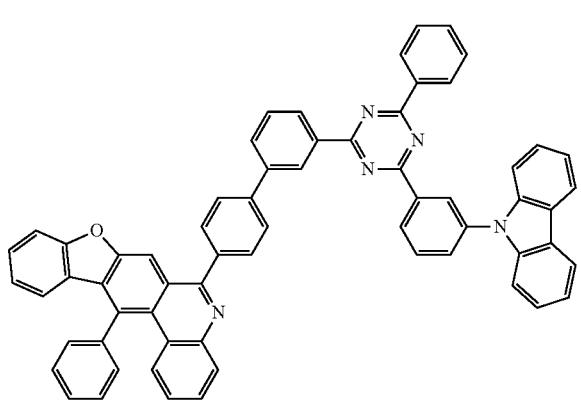
203
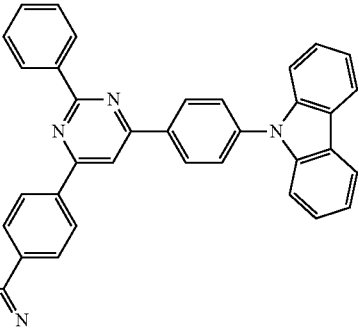
204
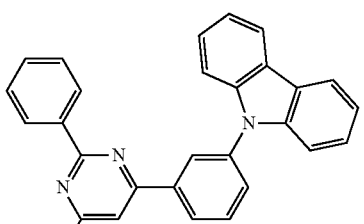
205
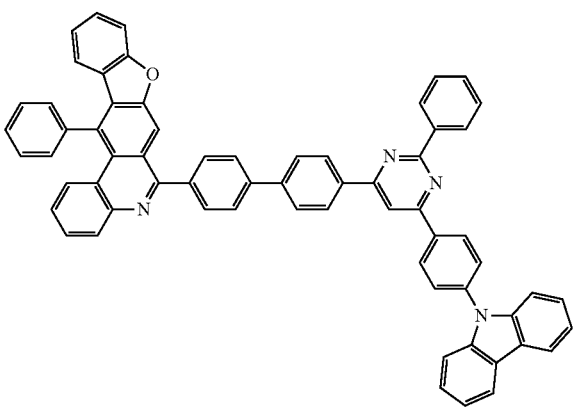
206

207

208

209

210

211

212

213

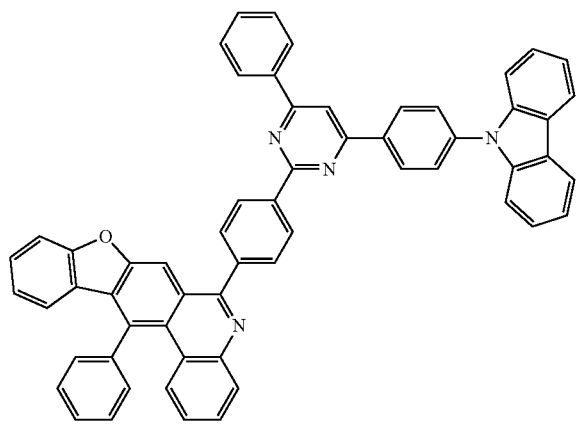 [SMILES: c1ccc(-c2nc(-c3ccc(-c4nc5ccccc5c5c(-c6ccccc6)c6c(cc45)oc4ccccc46)cc3)nc(-c3ccc(-n4c5ccccc5c5ccccc54)cc3)n2)cc1]
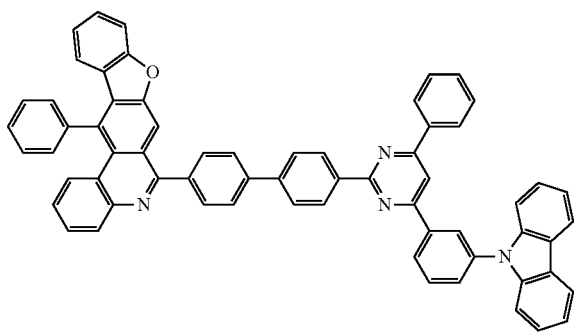 [SMILES: c1ccc(-c2nc(-c3ccc(-c4ccc(-c5nc6ccccc6c6c(-c7ccccc7)c7c(cc56)oc5ccccc57)cc4)cc3)nc(-c3cccc(-n4c5ccccc5c5ccccc54)c3)n2)cc1]
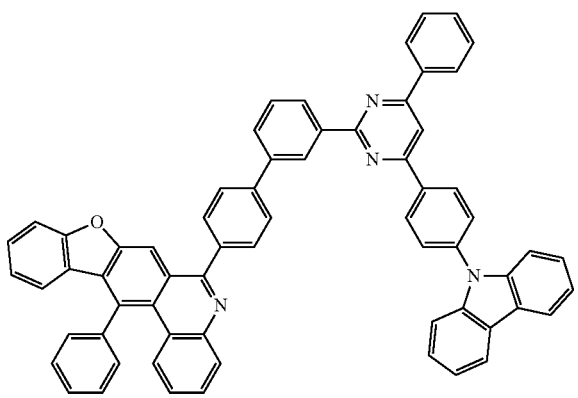 [SMILES: c1ccc(-c2nc(-c3ccc(-n4c5ccccc5c5ccccc54)cc3)nc(-c3cccc(-c4ccc(-c5nc6ccccc6c6c(-c7ccccc7)c7c(cc56)oc5ccccc57)cc4)c3)n2)cc1]
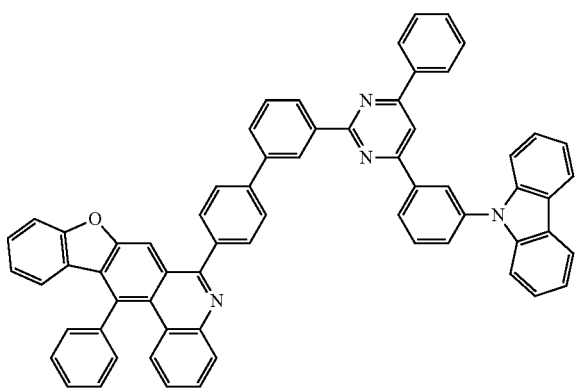 [SMILES: c1ccc(-c2nc(-c3cccc(-c4ccc(-c5nc6ccccc6c6c(-c7ccccc7)c7c(cc56)oc5ccccc57)cc4)c3)cc(-c3cccc(-n4c5ccccc5c5ccccc54)c3)n2)cc1]
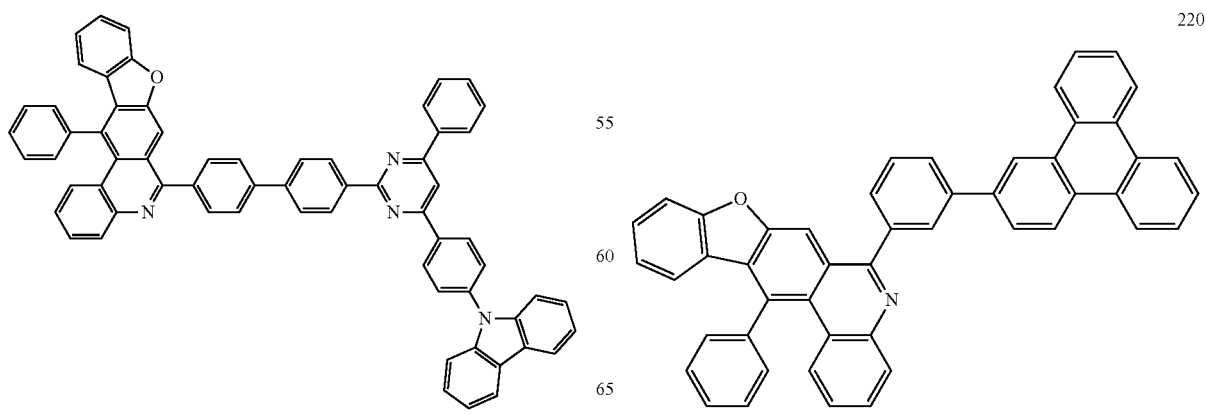

221
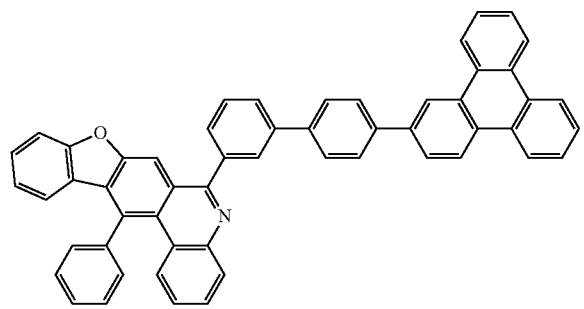 [SMILES: c1ccc(-c2c3c(cc4c(-c5cccc(-c6ccc(-c7ccc8c9ccccc9c9ccccc9c8c7)cc6)c5)nc5ccccc5c24)oc2ccccc23)cc1]
222
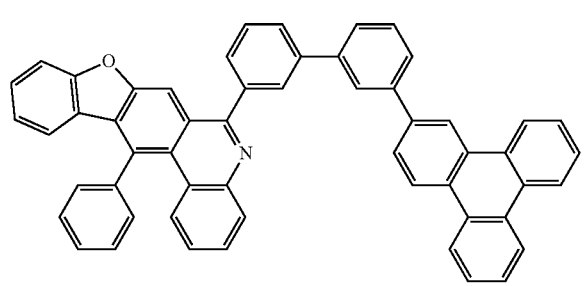
223
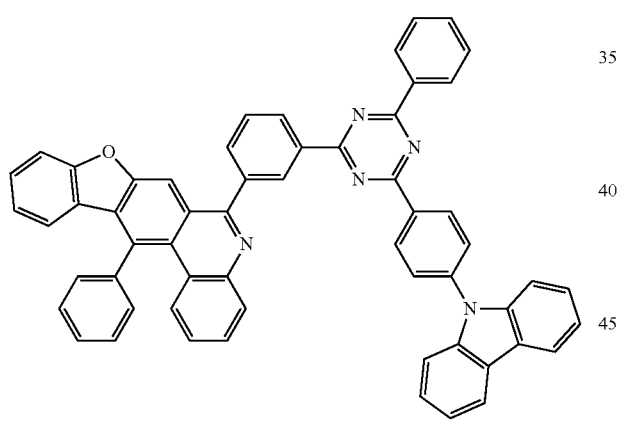
224
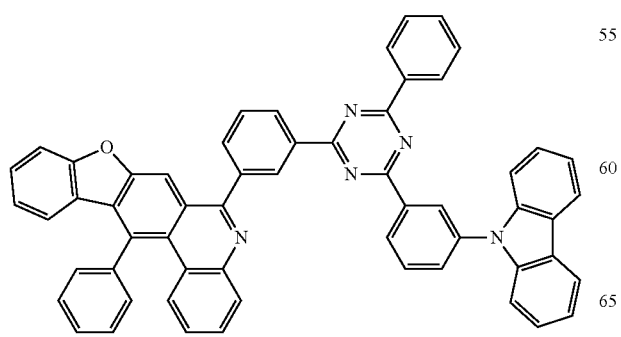
225
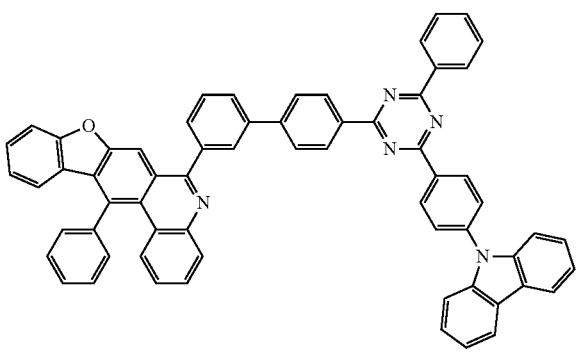
226
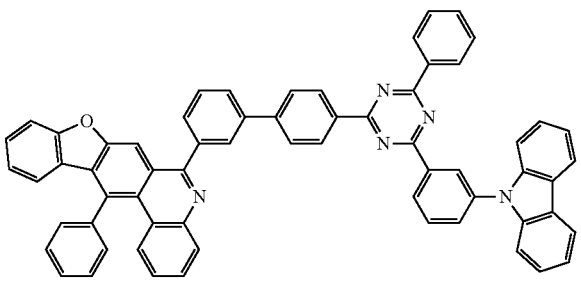 [SMILES: c1ccc(-c2nc(-c3ccc(-c4cccc(-c5nc6ccccc6c6c(-c7ccccc7)c7c(cc56)oc5ccccc57)c4)cc3)nc(-c3cccc(-n4c5ccccc5c5ccccc54)c3)n2)cc1]
227
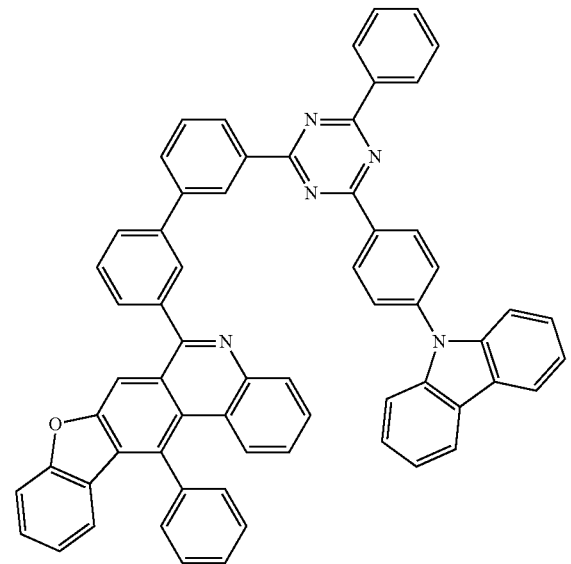

-continued
228
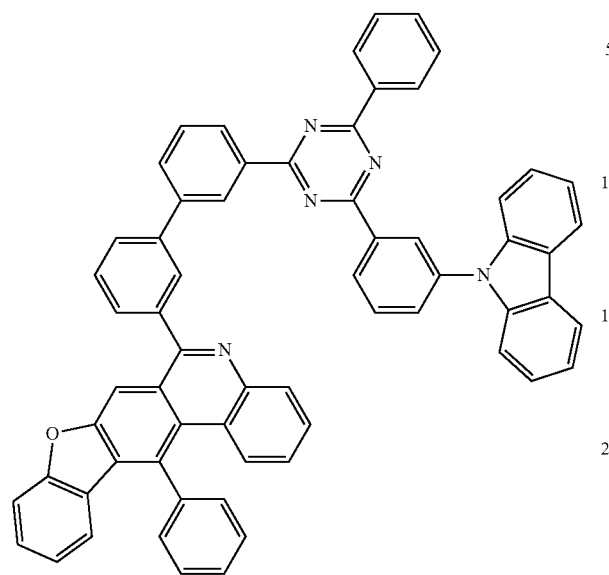
229
231
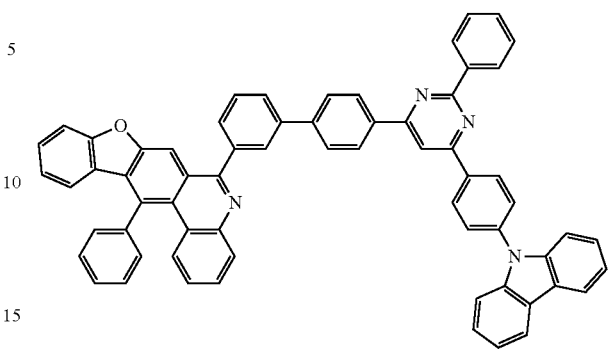
232
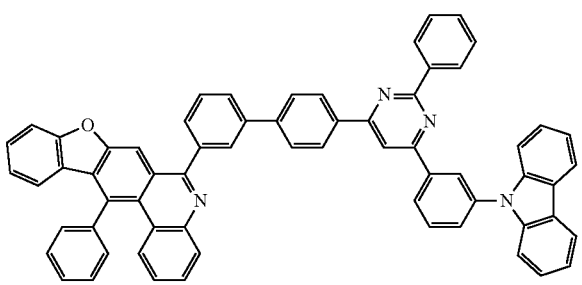
233
230
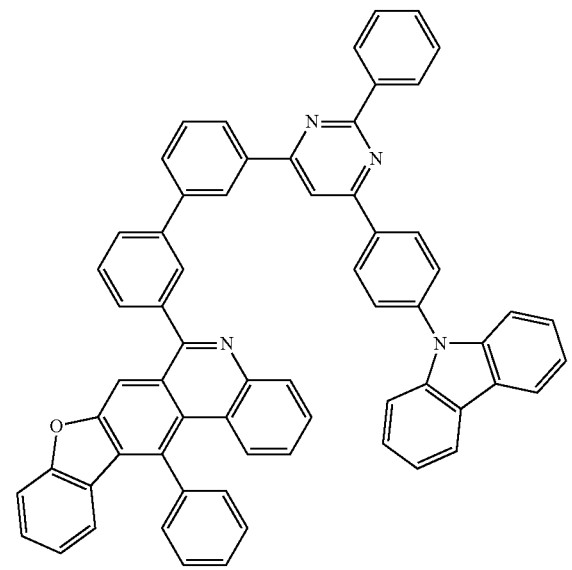

234
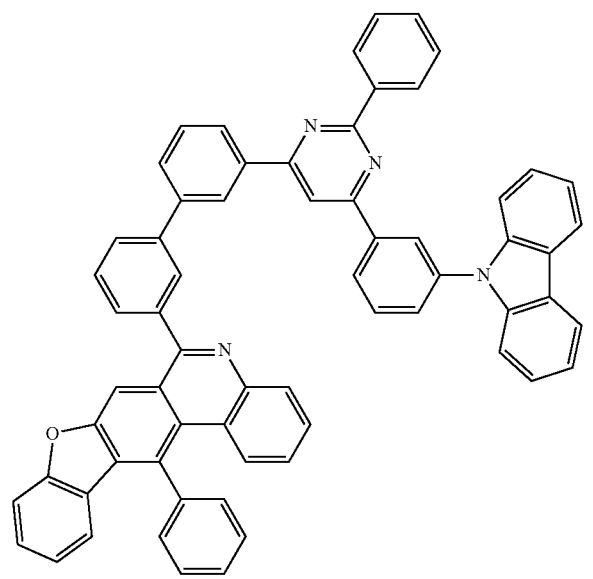
235
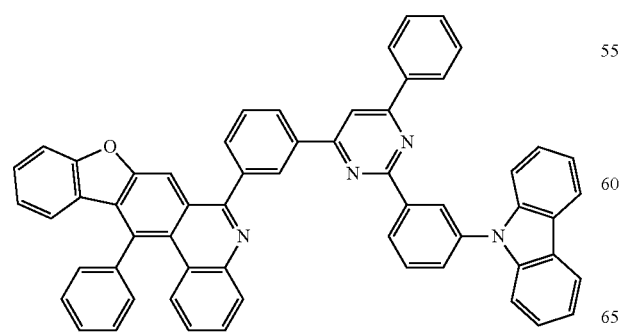
236
237
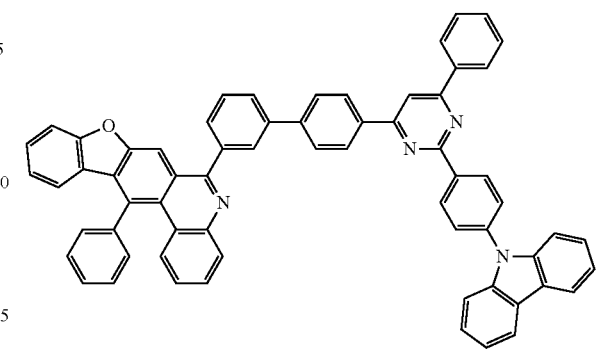
238
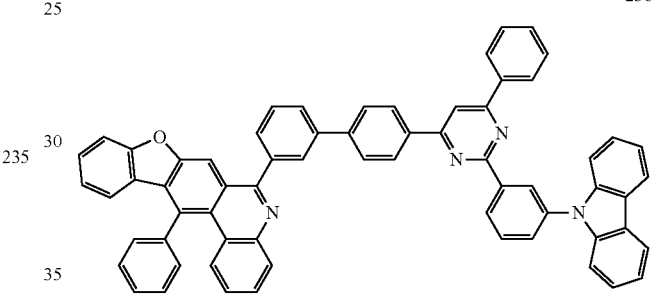
239
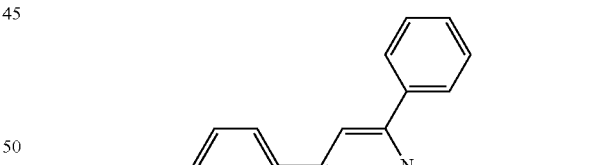

240
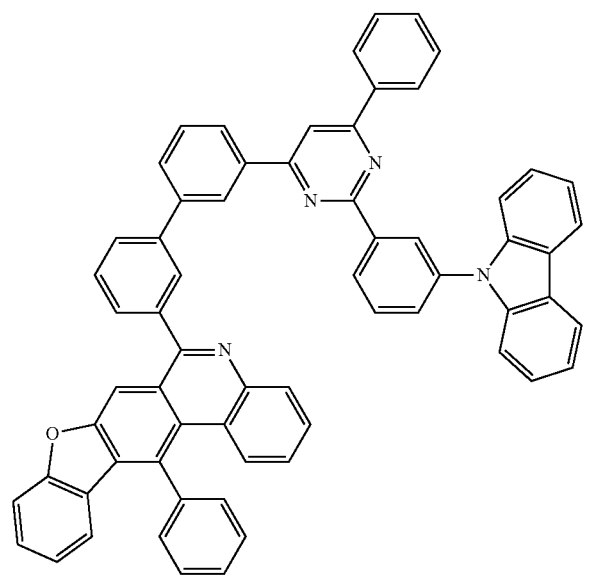 [SMILES: c1ccc(-c2cc(-c3cccc(-c4cccc(-c5nc6ccccc6c6c(-c7ccccc7)c7c(cc56)oc5ccccc57)c4)c3)nc(-c3cccc(-n4c5ccccc5c5ccccc54)c3)n2)cc1]
241
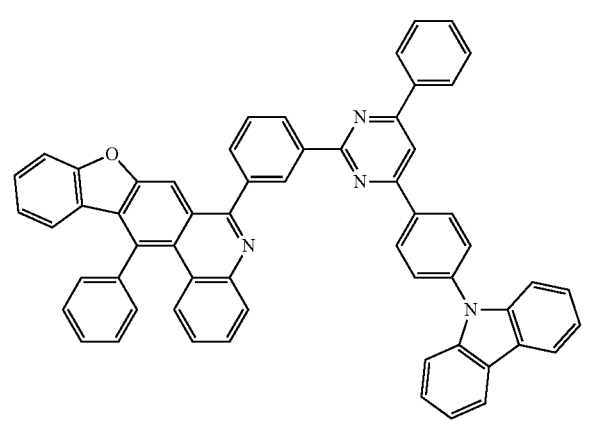
242
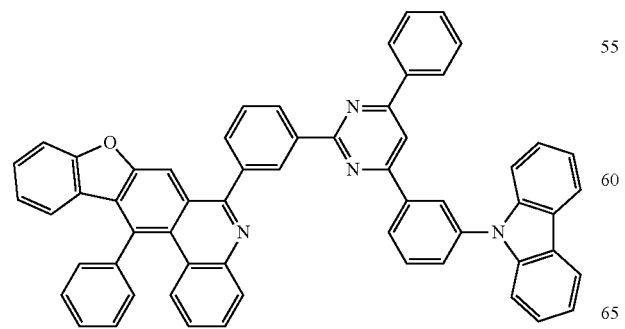
243
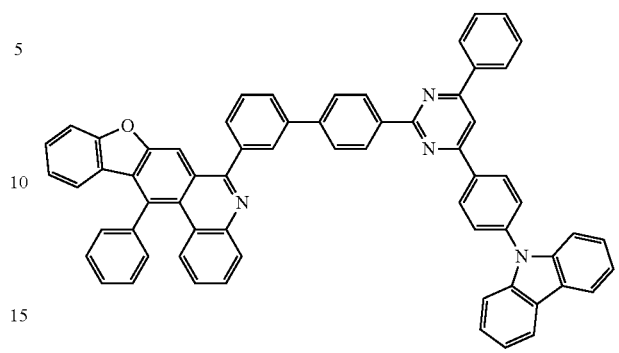
244
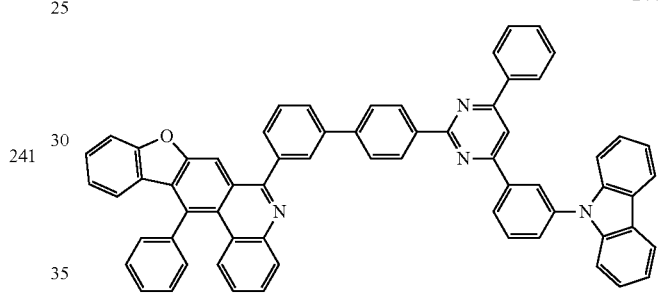
245
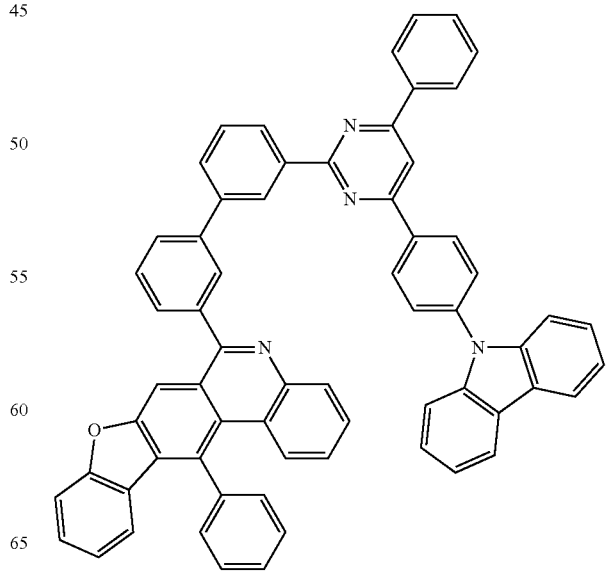

246
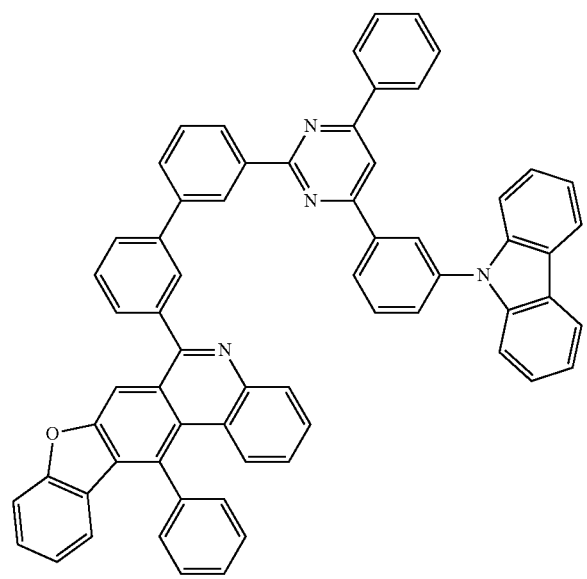
247
248
249
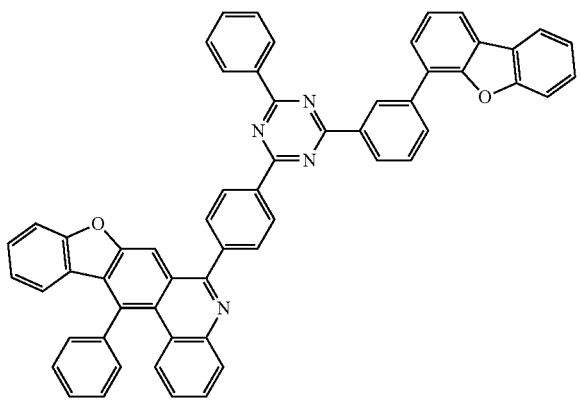 [SMILES: c1ccc(-c2nc(-c3ccc(-c4nc5ccccc5c5c(-c6ccccc6)c6c(cc45)oc4ccccc46)cc3)nc(-c3cccc(-c4cccc5c4oc4ccccc45)c3)n2)cc1]
250
251
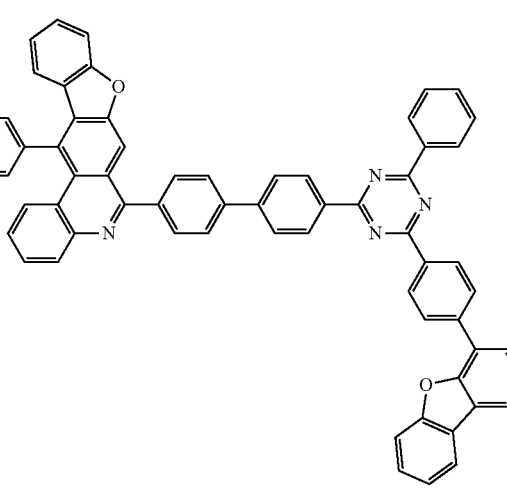
252
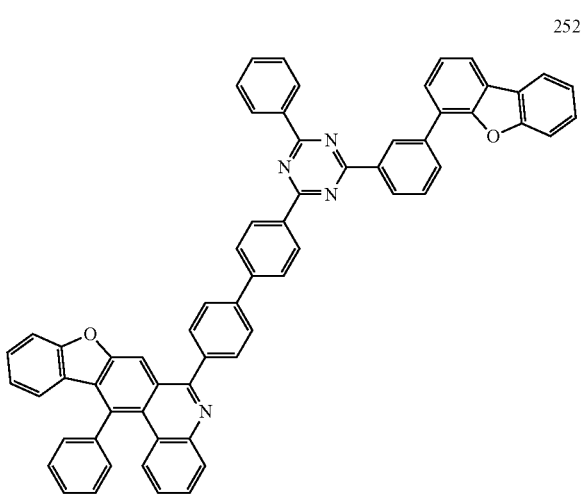

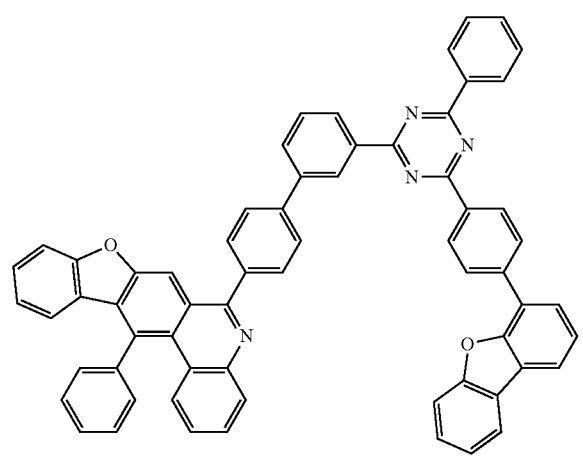
253
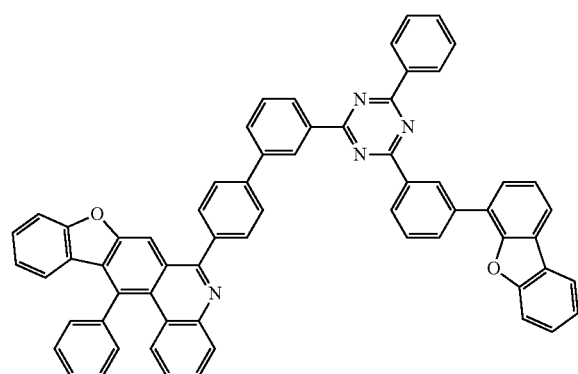
254
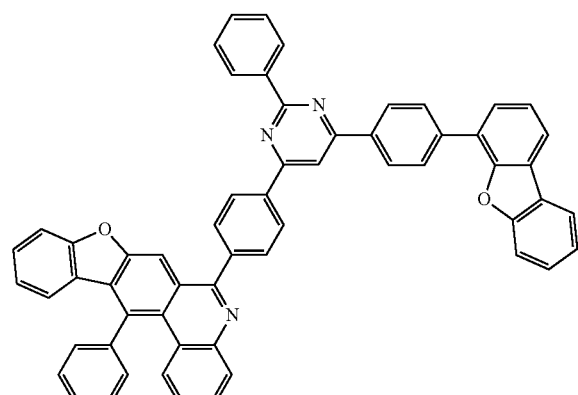
255
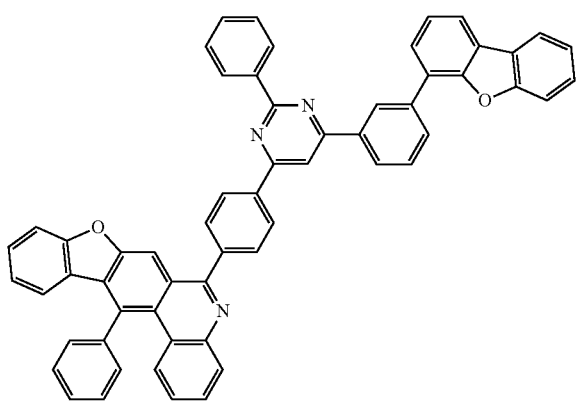
256
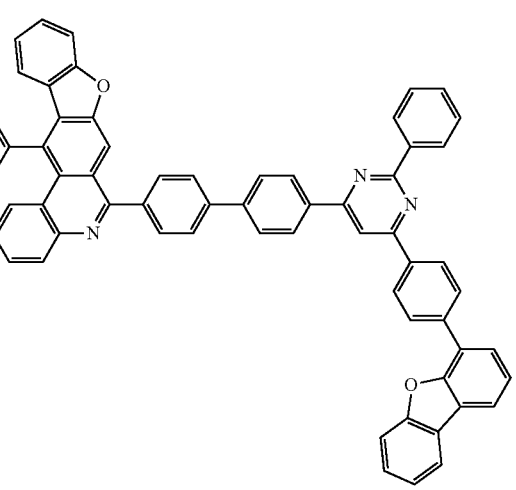
257
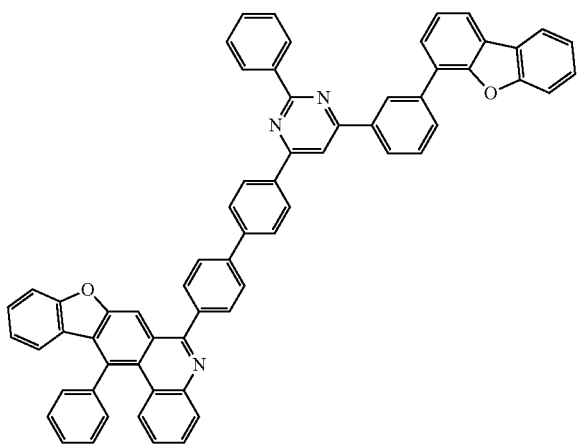
258

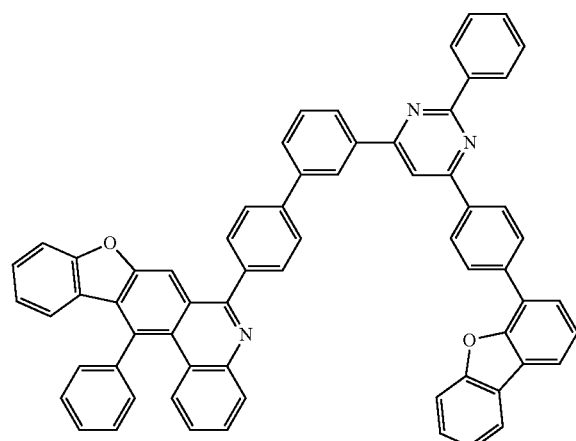
259
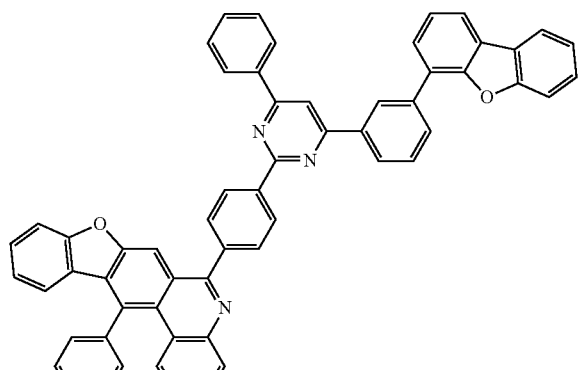
262
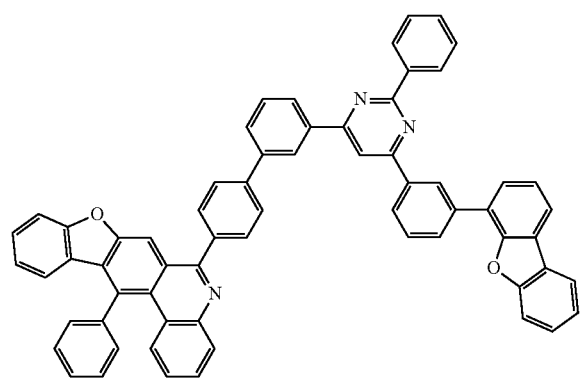
260
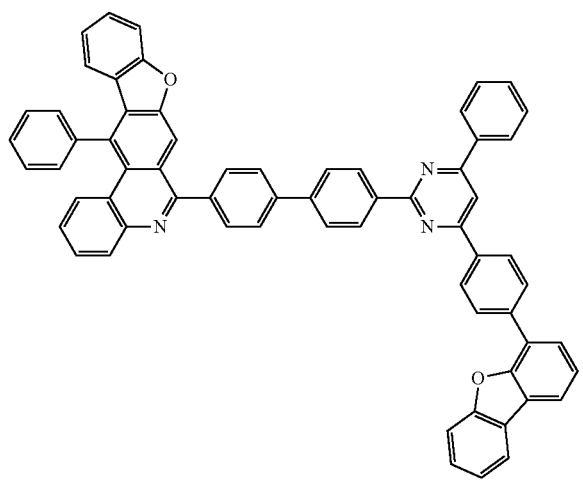 [SMILES: c1ccc(-c2nc(-c3ccc(-c4ccc(-c5nc6ccccc6c6c(-c7ccccc7)c7c(cc56)oc5ccccc57)cc4)cc3)nc(-c3ccc(-c4cccc5c4oc4ccccc45)cc3)n2)cc1]
263
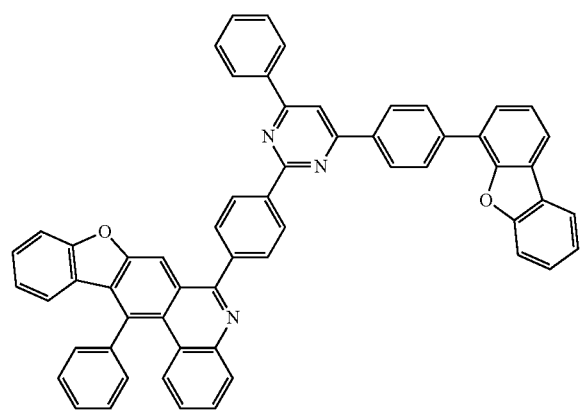 [SMILES: c1ccc(-c2nc(-c3ccc(-c4nc5ccccc5c5c(-c6ccccc6)c6c(cc45)oc4ccccc46)cc3)cc(-c3ccc(-c4cccc5c4oc4ccccc45)cc3)n2)cc1]
261
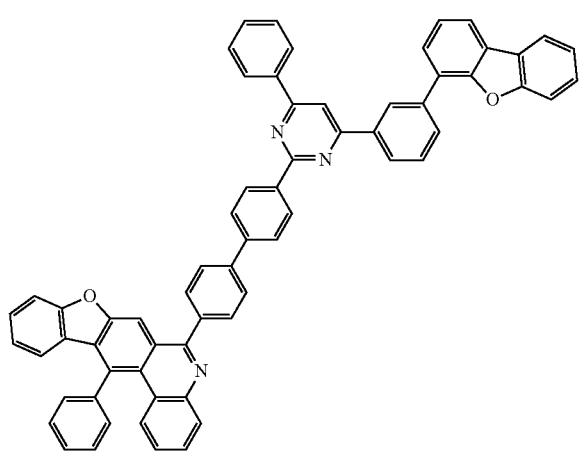
264

265
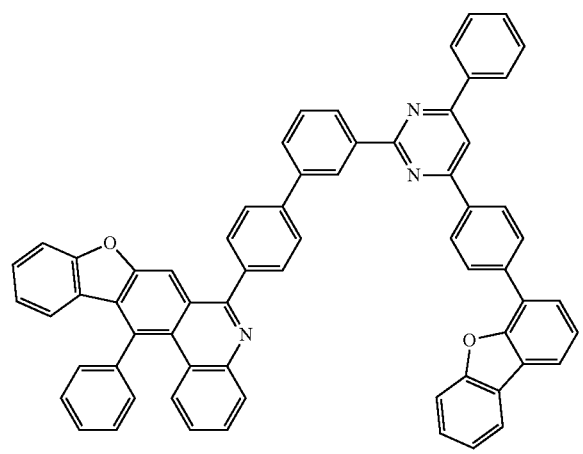 [SMILES: c1ccc(-c2nc(-c3ccc(-c4cccc5c4oc4ccccc45)cc3)cc(-c3cccc(-c4ccc(-c5nc6ccccc6c6c(-c7ccccc7)c7c(cc56)oc5ccccc57)cc4)c3)n2)cc1]
266
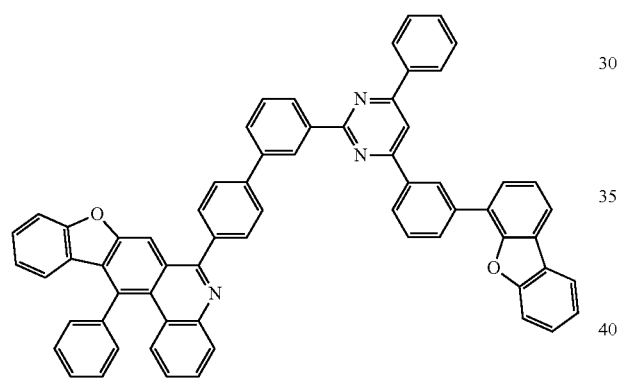
267
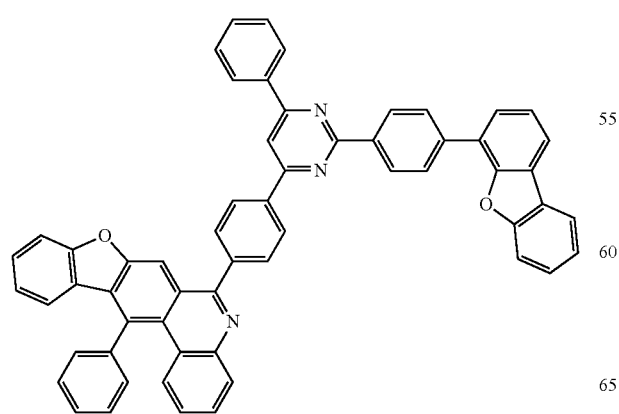
268
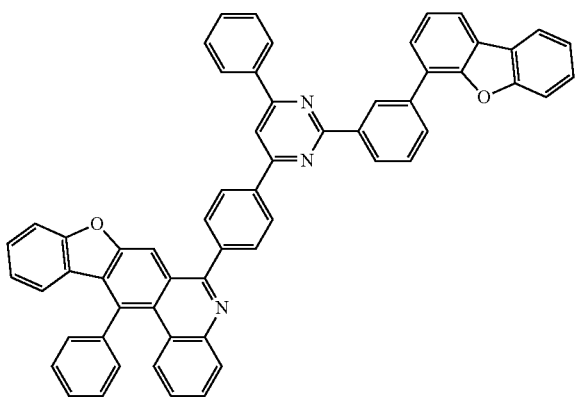
269
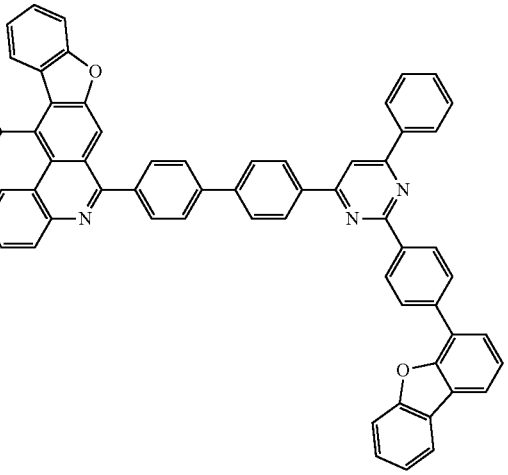
270
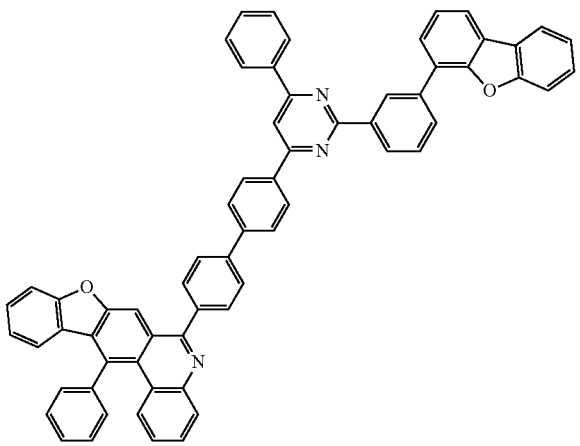

271
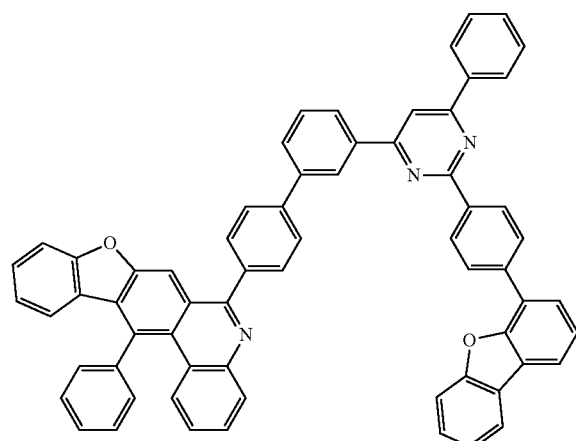
274
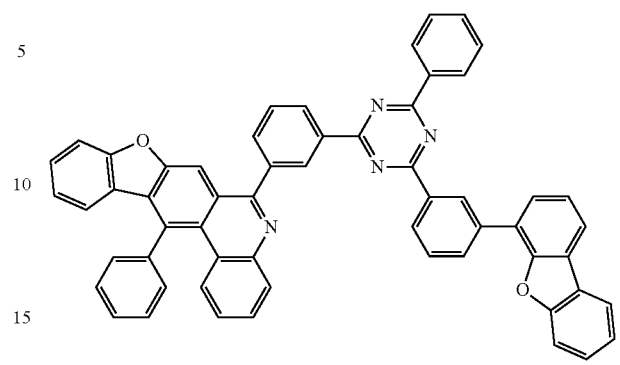
272
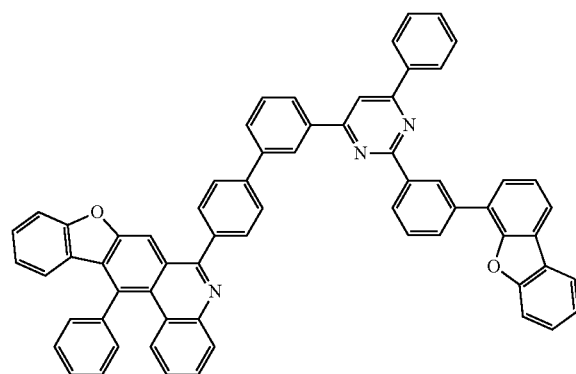
275
273
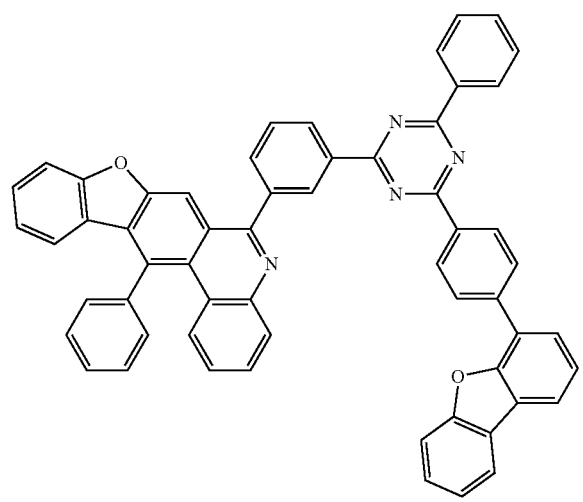
276
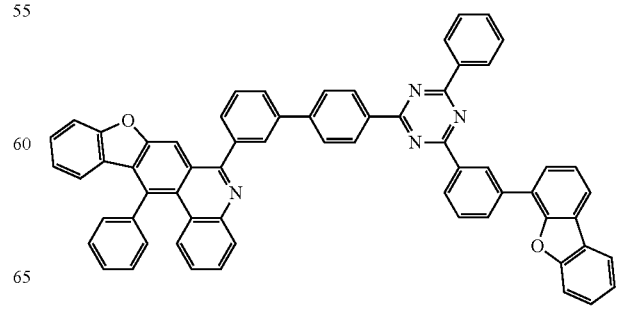

101
-continued
277
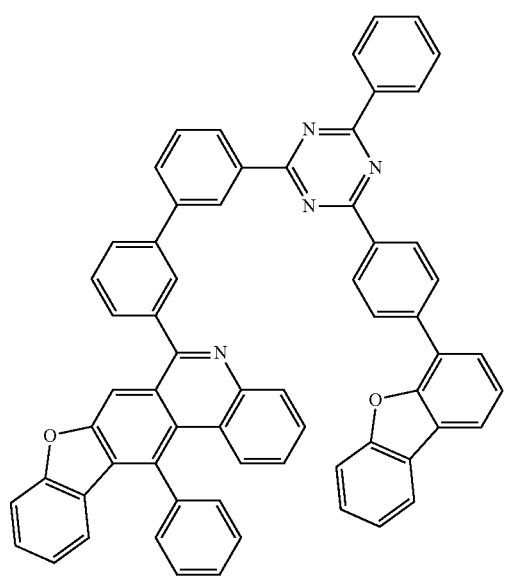
278
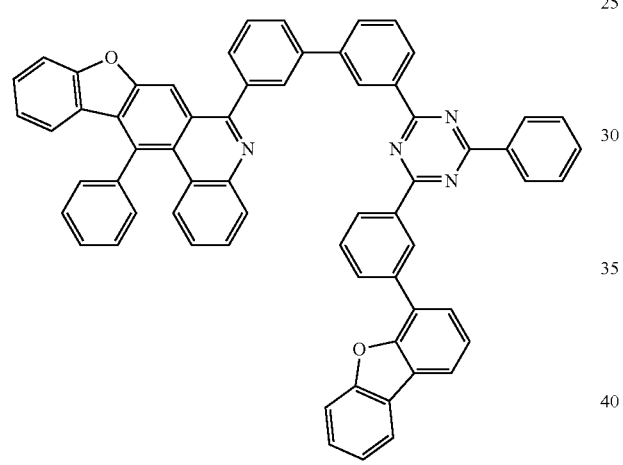
279
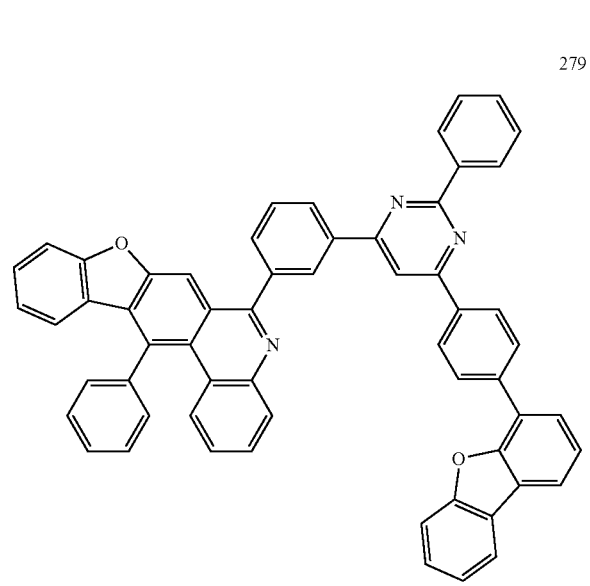
102
-continued
280
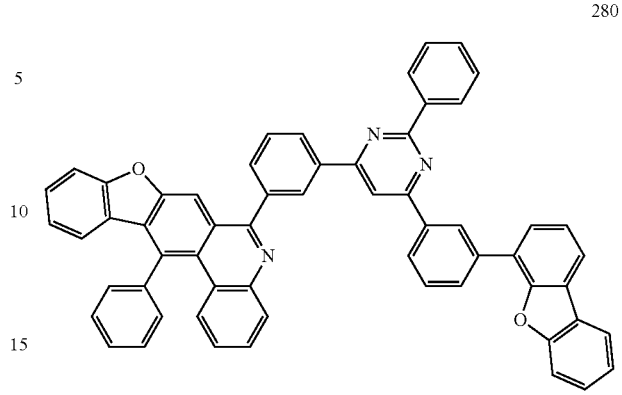
281
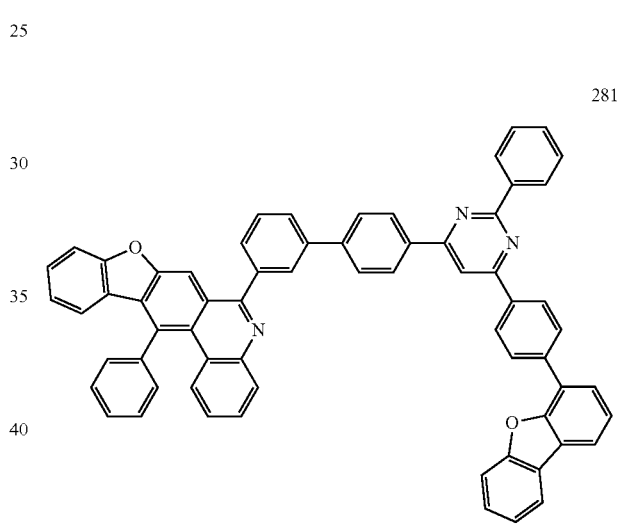
282
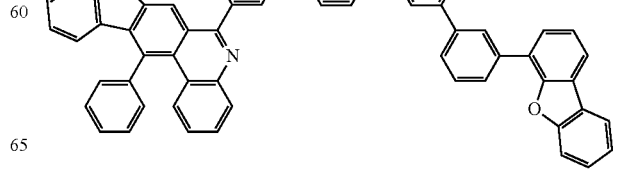

283
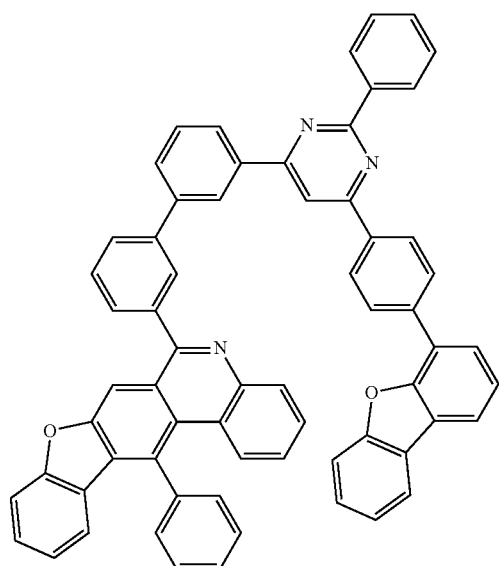
284
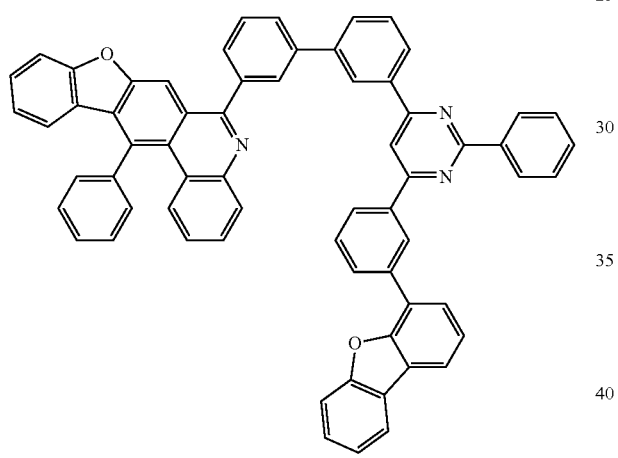
285
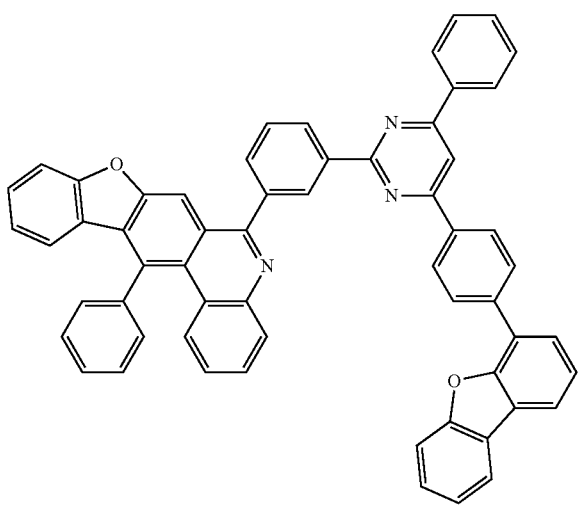 [SMILES: c1ccc(-c2nc(-c3ccc(-c4cccc5c4oc4ccccc45)cc3)cc(-c3cccc(-c4nc5ccccc5c5c(-c6ccccc6)c6c(cc45)oc4ccccc46)c3)n2)cc1]
286
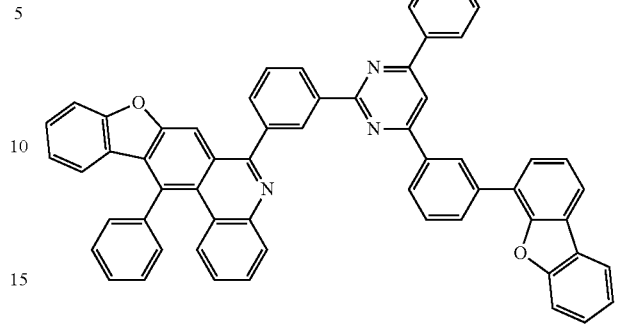
287
288
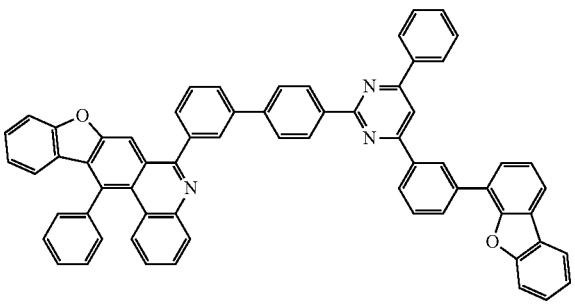

289
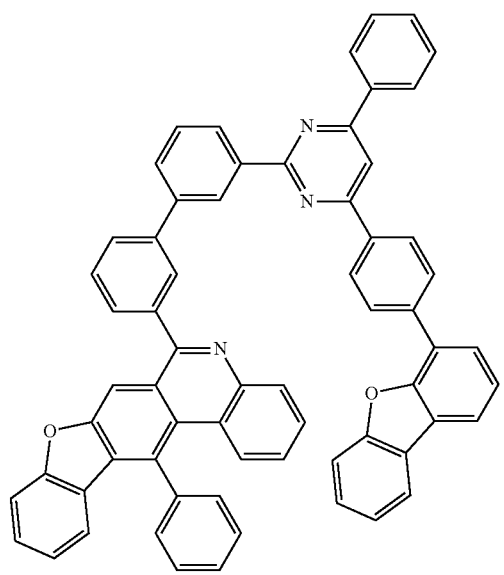
290
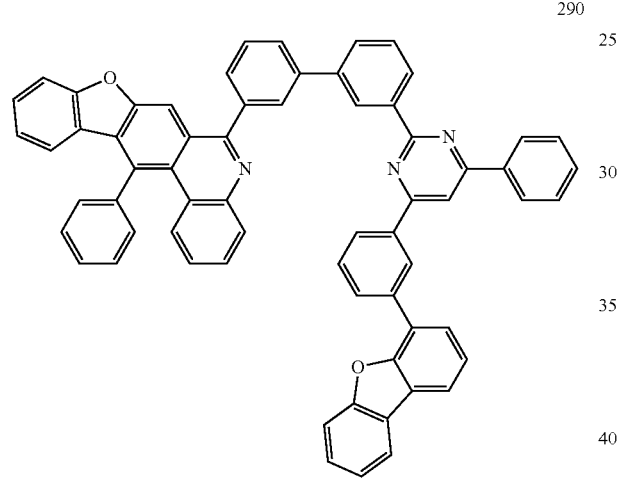
291
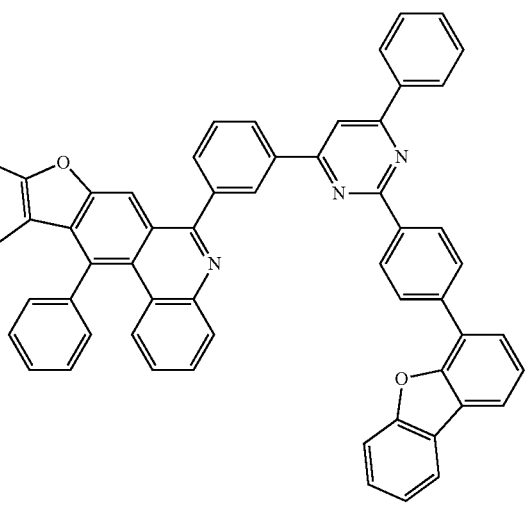
292
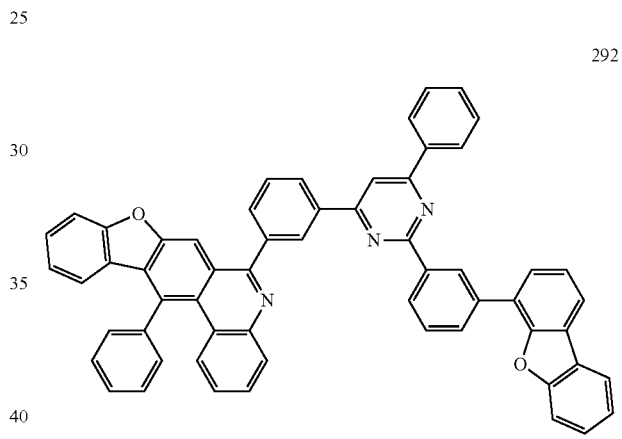
293
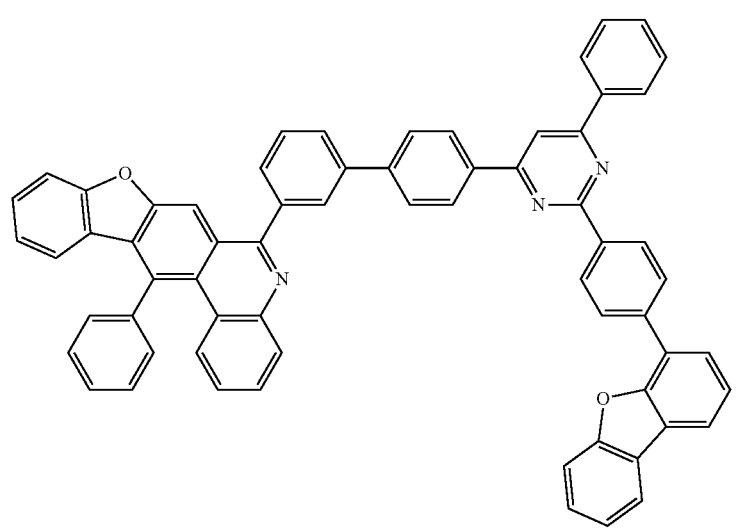 [SMILES: c1ccc(-c2nc(-c3ccc(-c4cccc(-c5nc6ccccc6c6c(-c7ccccc7)c7c(cc56)oc5ccccc57)c4)cc3)cc(-c3ccc(-c4cccc5c4oc4ccccc45)cc3)n2)cc1]

294
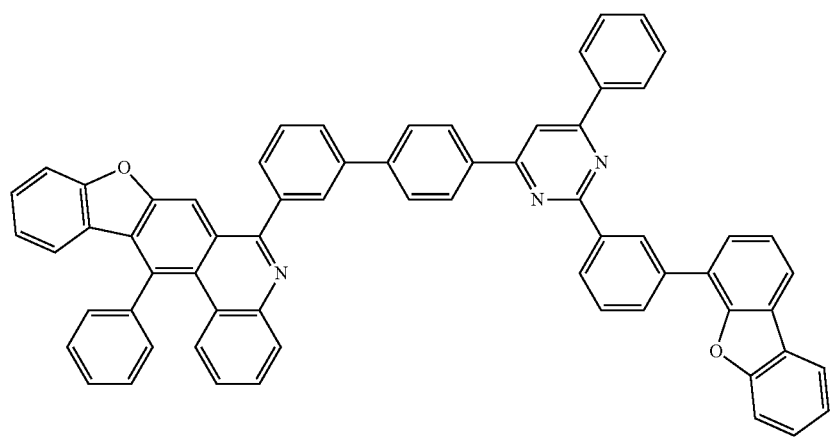
295
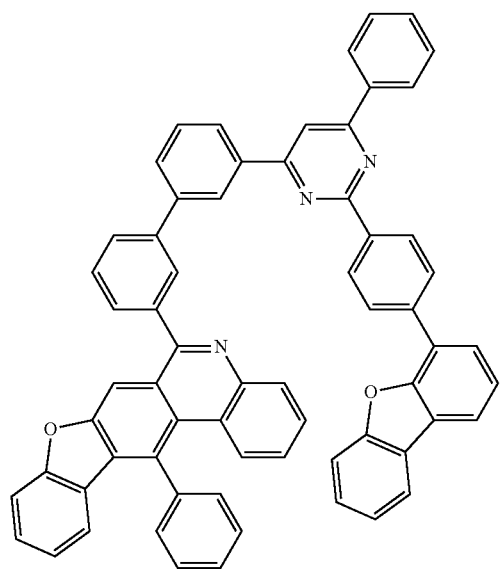
296
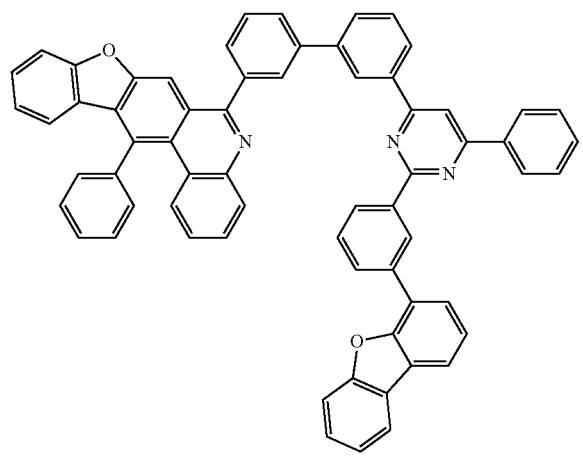
297
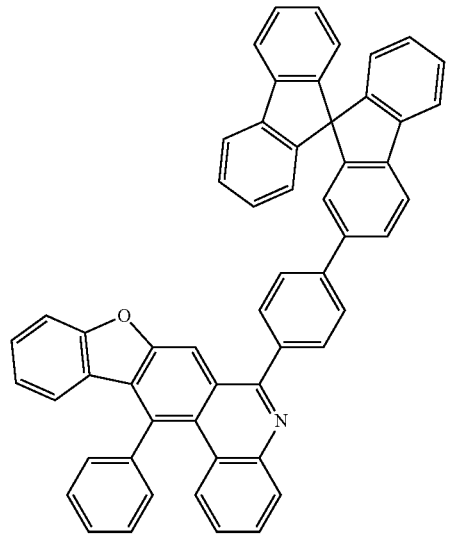 [SMILES: c1ccc(-c2c3c(cc4c(-c5ccc(-c6ccc7c(c6)C6(c8ccccc8-c8ccccc86)c6ccccc6-7)cc5)nc5ccccc5c24)oc2ccccc23)cc1]
298
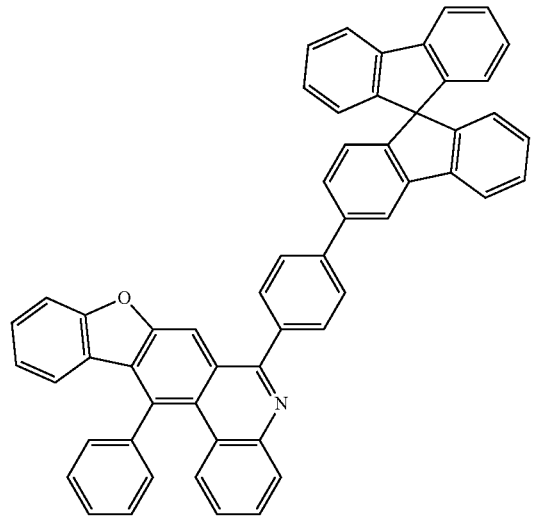 [SMILES: c1ccc(-c2c3c(cc4c(-c5ccc(-c6ccc7c(c6)-c6ccccc6C76c7ccccc7-c7ccccc76)cc5)nc5ccccc5c24)oc2ccccc23)cc1]

-continued
299
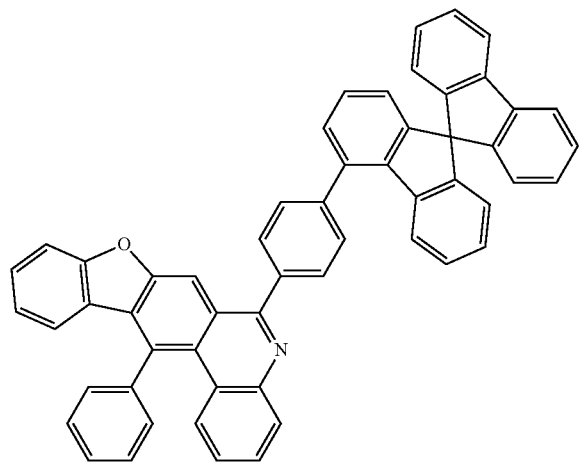 [SMILES: c1ccc(-c2c3c(cc4c(-c5ccc(-c6cccc7c6-c6ccccc6C76c7ccccc7-c7ccccc76)cc5)nc5ccccc5c24)oc2ccccc23)cc1]
300
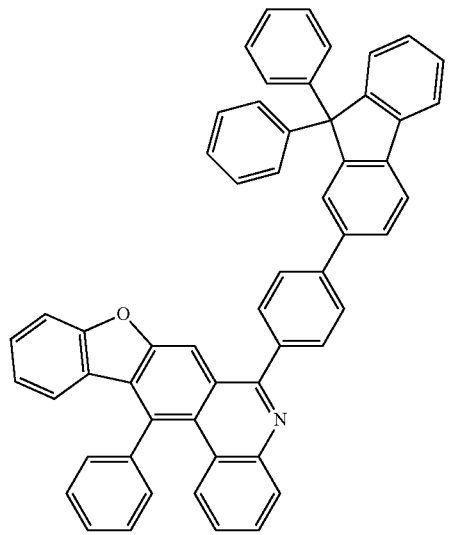
301
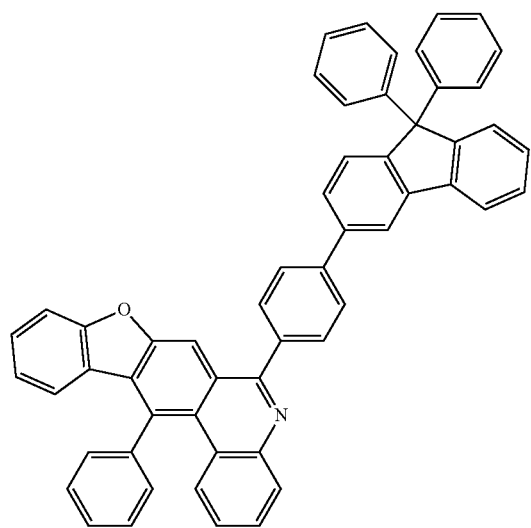
302
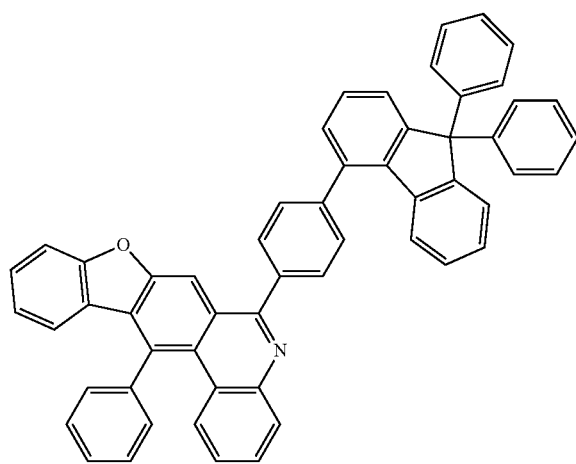

-continued
111
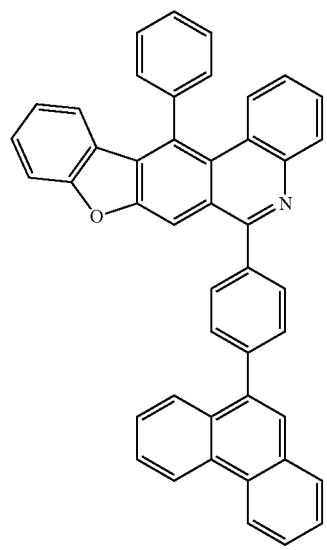 [SMILES: c1ccc(-c2c3c(cc4c(-c5ccc(-c6cc7ccccc7c7ccccc67)cc5)nc5ccccc5c24)oc2ccccc23)cc1]
303
112
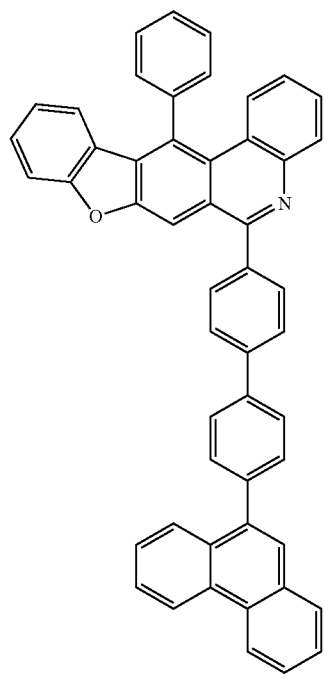
304
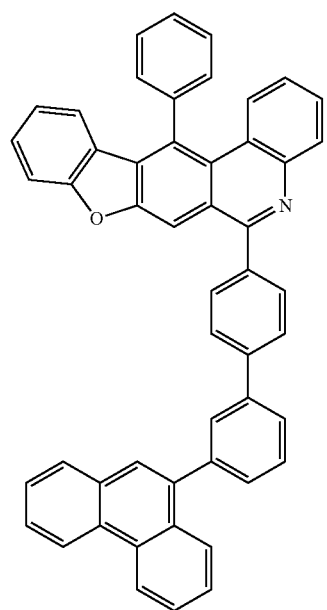
305
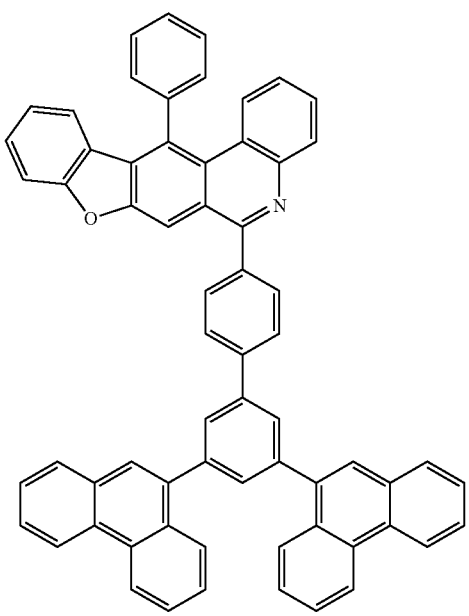
306

-continued
307
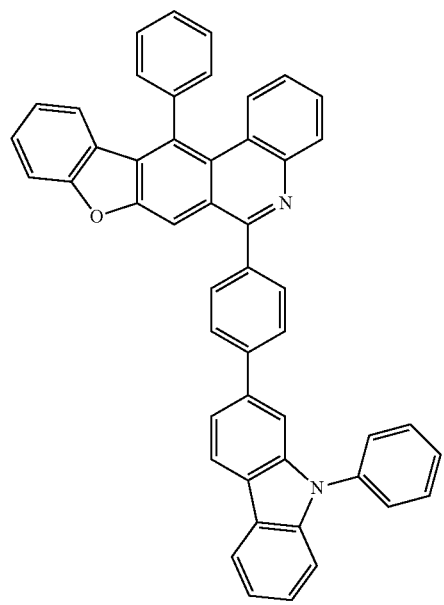
308
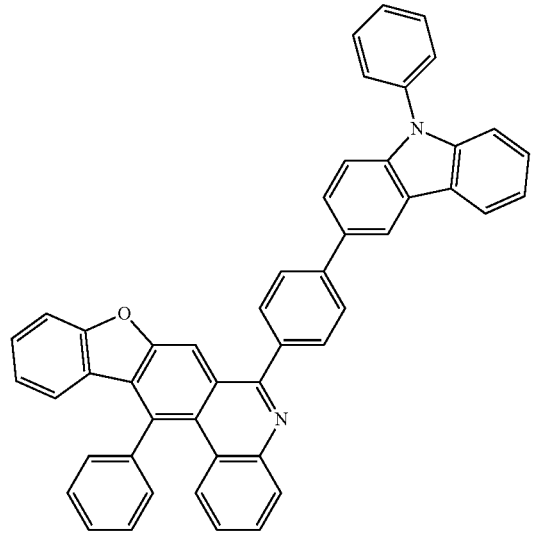 [SMILES: c1ccc(-c2c3c(cc4c(-c5ccc(-c6ccc7c(c6)c6ccccc6n7-c6ccccc6)cc5)nc5ccccc5c24)oc2ccccc23)cc1]
309
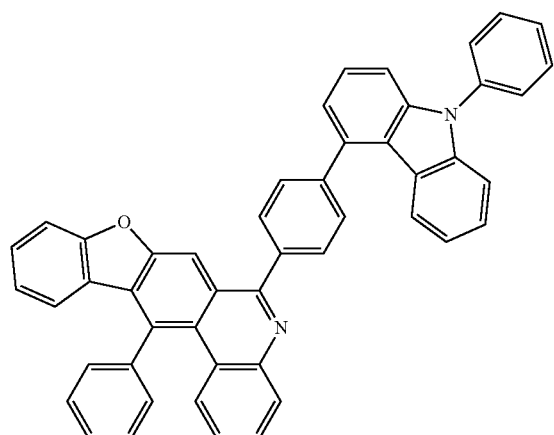 [SMILES: c1ccc(-c2c3c(cc4c(-c5ccc(-c6cccc7c6c6ccccc6n7-c6ccccc6)cc5)nc5ccccc5c24)oc2ccccc23)cc1]
310
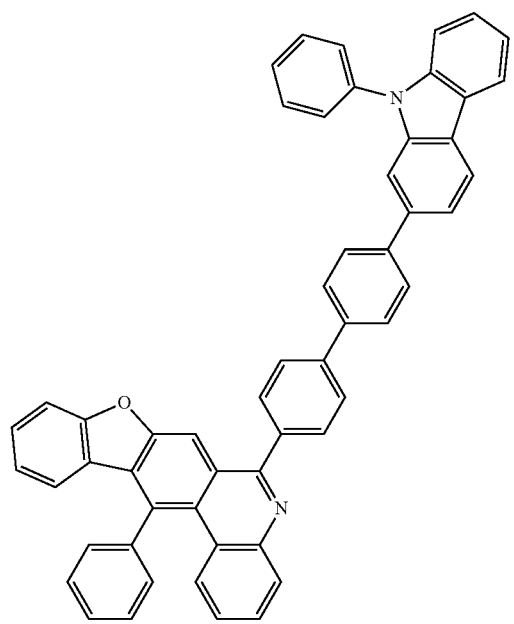

-continued
311
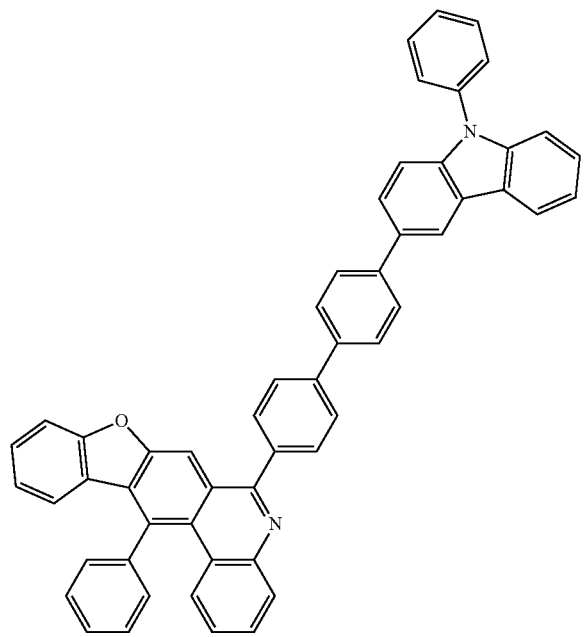
312
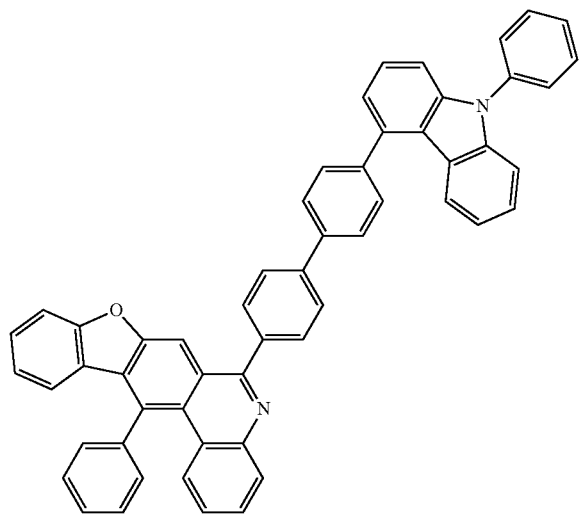
313
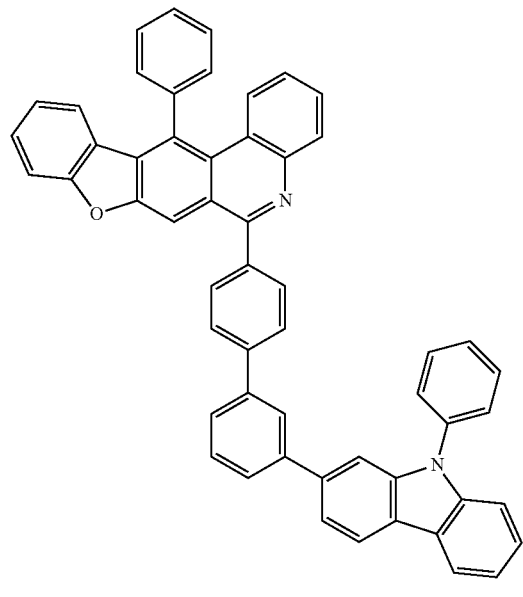
314
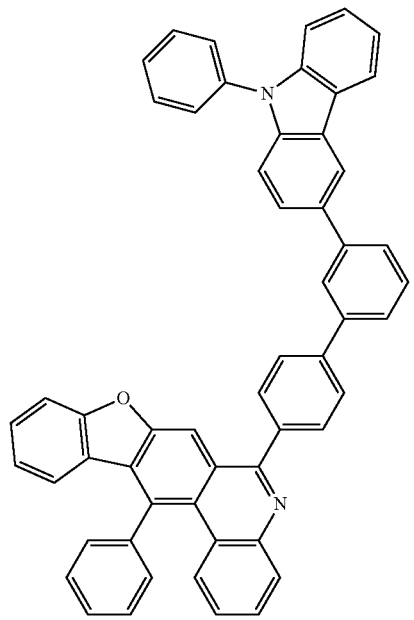

-continued
315
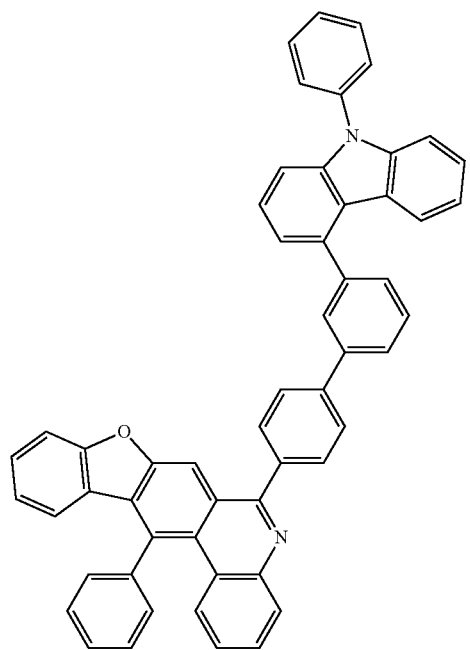
316
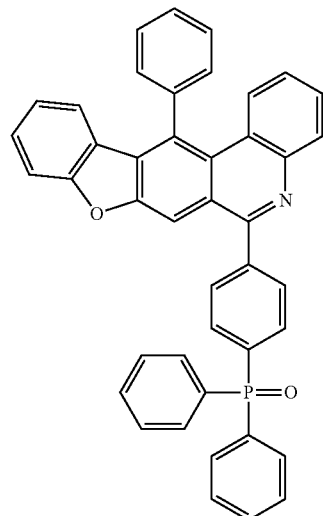
317
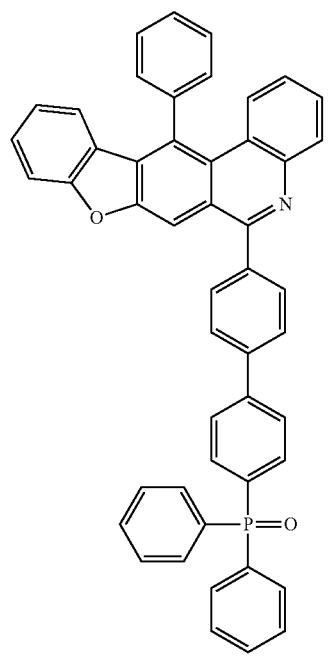 [SMILES: O=P(c1ccccc1)(c1ccccc1)c1ccc(-c2ccc(-c3nc4ccccc4c4c(-c5ccccc5)c5c(cc34)oc3ccccc35)cc2)cc1]
318
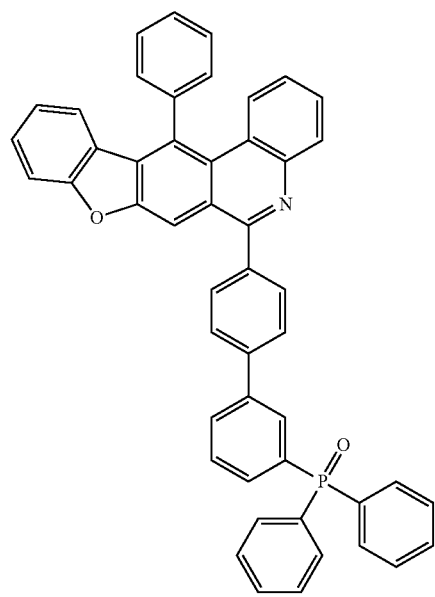

319
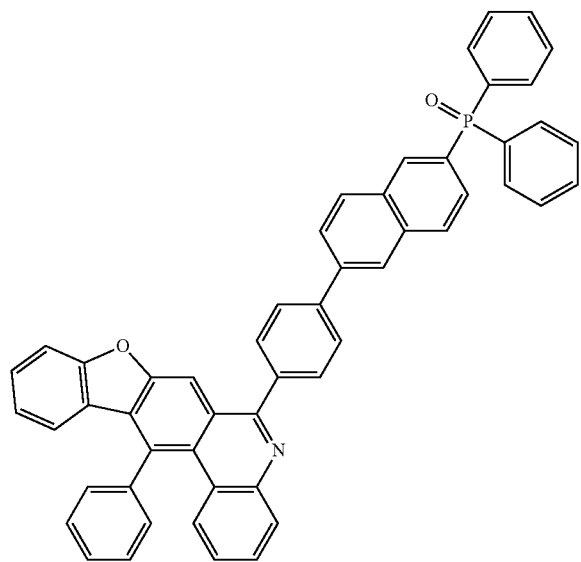 [SMILES: O=P(c1ccccc1)(c1ccccc1)c1ccc2cc(-c3ccc(-c4nc5ccccc5c5c(-c6ccccc6)c6c(cc45)oc4ccccc46)cc3)ccc2c1]
320
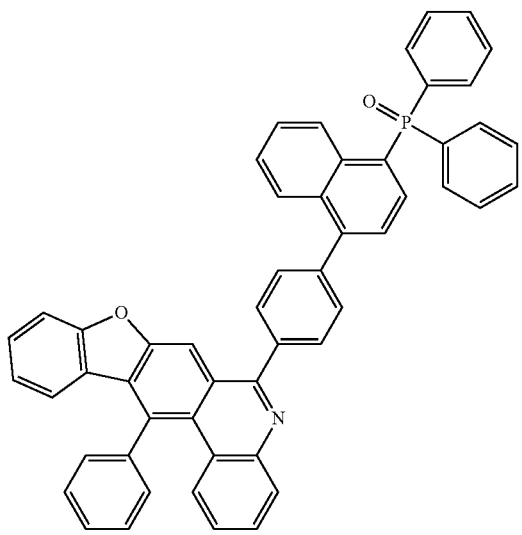 [SMILES: O=P(c1ccccc1)(c1ccccc1)c1ccc(-c2ccc(-c3nc4ccccc4c4c(-c5ccccc5)c5c(cc34)oc3ccccc35)cc2)c2ccccc12]
321
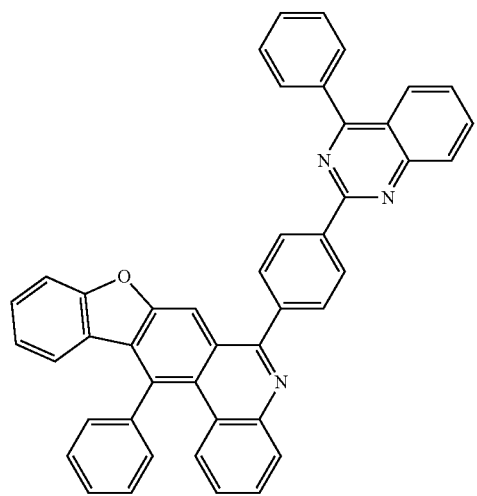 [SMILES: c1ccc(-c2nc(-c3ccc(-c4nc5ccccc5c5c(-c6ccccc6)c6c(cc45)oc4ccccc46)cc3)nc3ccccc23)cc1]
322
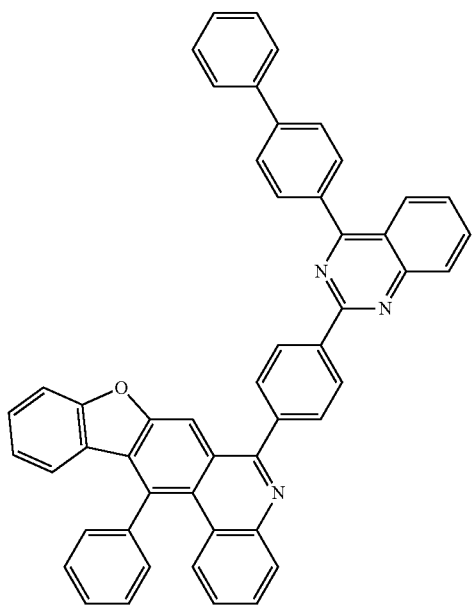

-continued
323
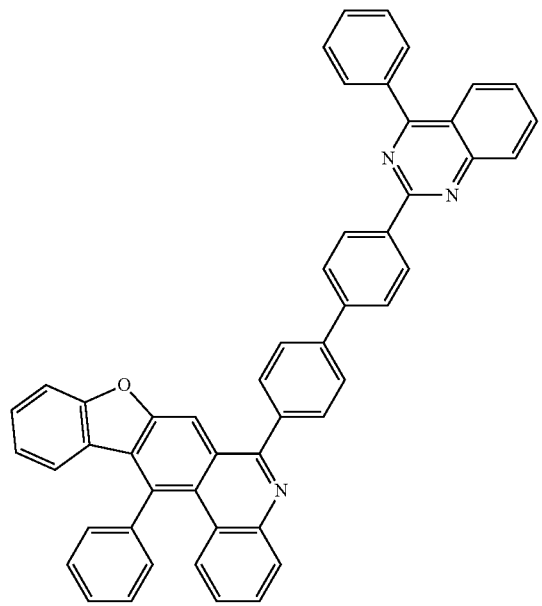
324
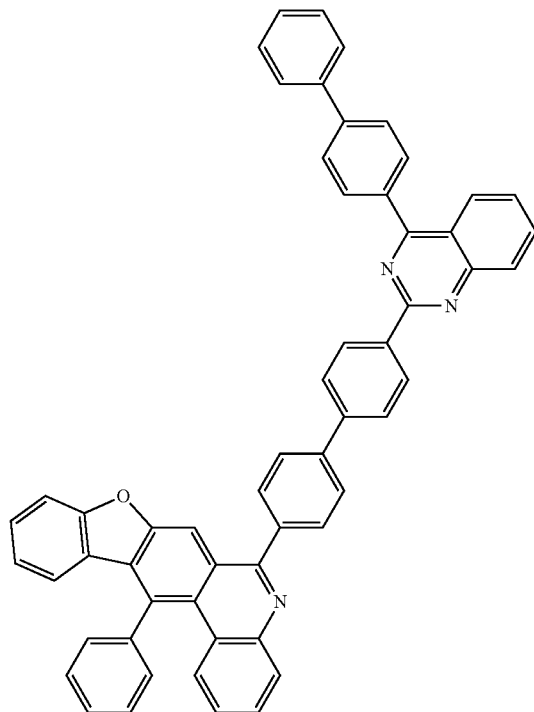 [SMILES: c1ccc(-c2ccc(-c3nc(-c4ccc(-c5ccc(-c6nc7ccccc7c7c(-c8ccccc8)c8c(cc67)oc6ccccc68)cc5)cc4)nc4ccccc34)cc2)cc1]
325
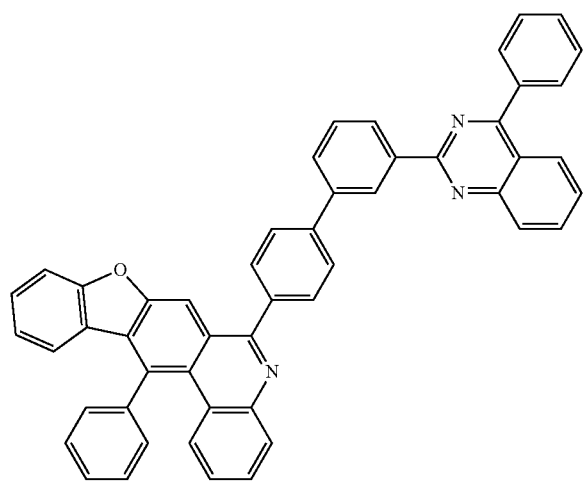
326
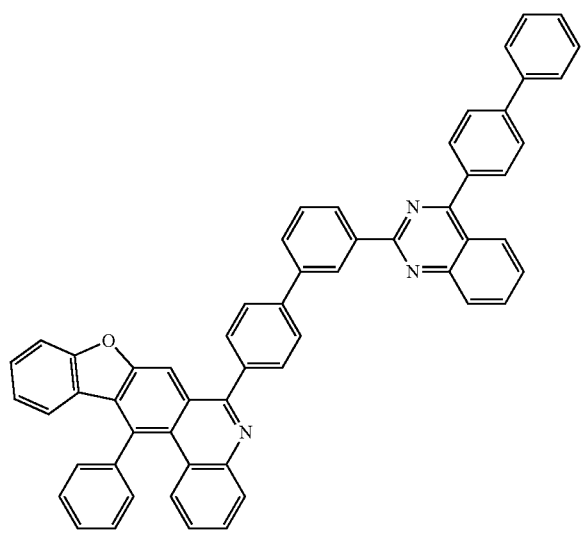 [SMILES: c1ccc(-c2ccc(-c3nc(-c4cccc(-c5ccc(-c6nc7ccccc7c7c(-c8ccccc8)c8c(cc67)oc6ccccc68)cc5)c4)nc4ccccc34)cc2)cc1]

-continued
327
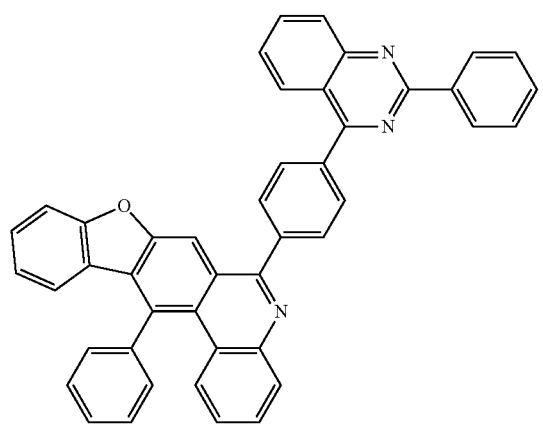 [SMILES: c1ccc(-c2nc(-c3ccc(-c4nc5ccccc5c5c(-c6ccccc6)c6c(cc45)oc4ccccc46)cc3)c3ccccc3n2)cc1]
328
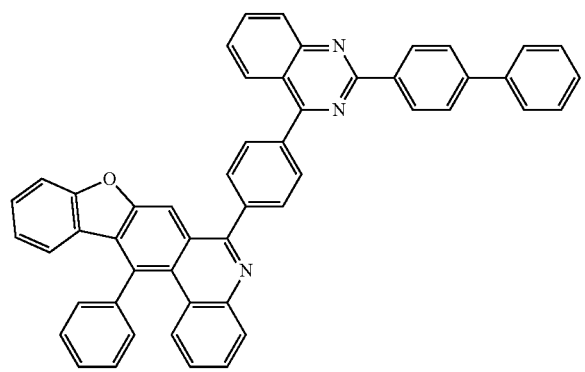
329
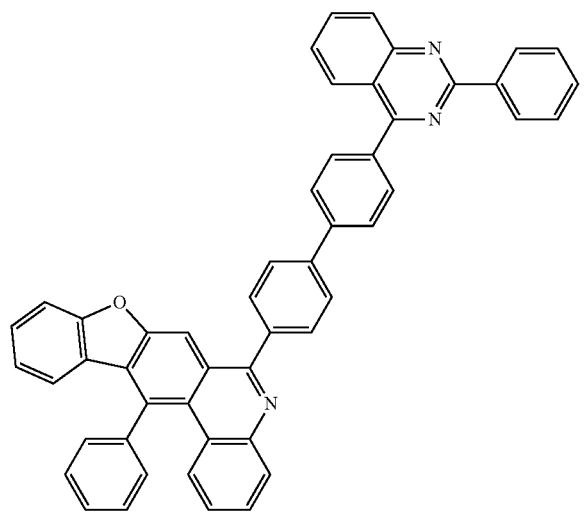
330
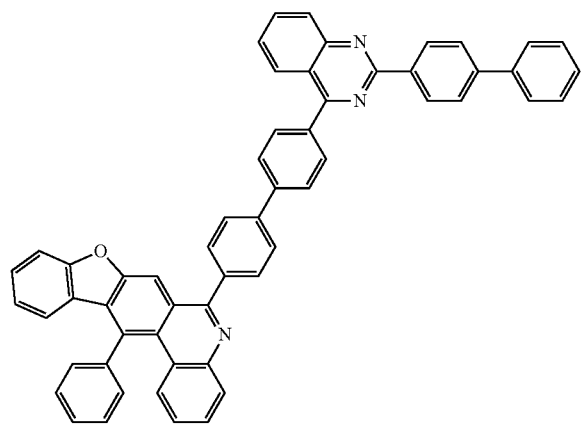

-continued
331
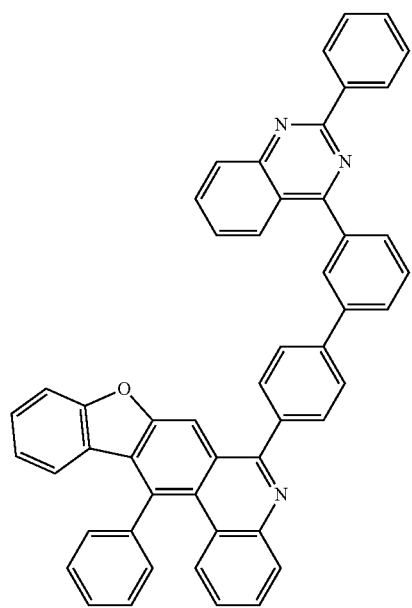
332
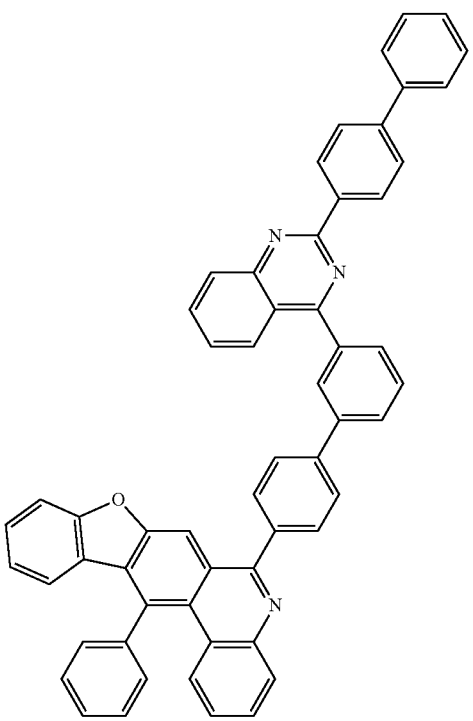
333
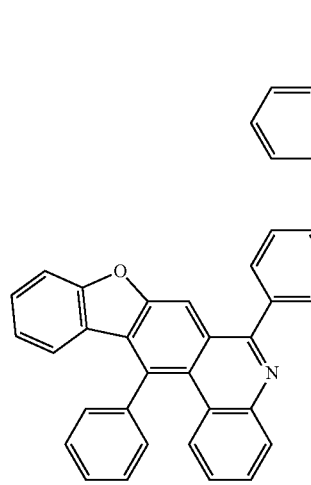
334
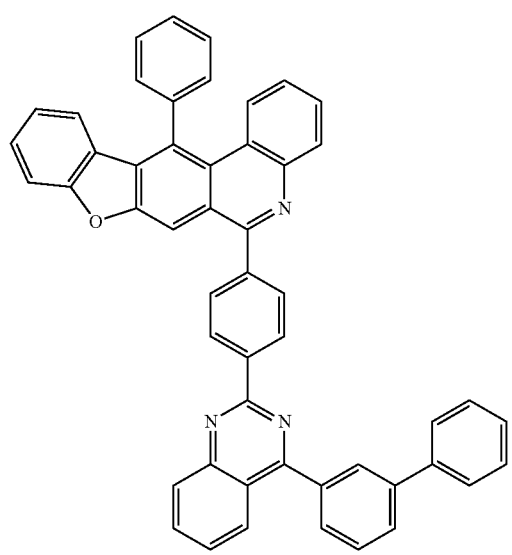 [SMILES: c1ccc(-c2cccc(-c3nc(-c4ccc(-c5nc6ccccc6c6c(-c7ccccc7)c7c(cc56)oc5ccccc57)cc4)nc4ccccc34)c2)cc1]

-continued
335
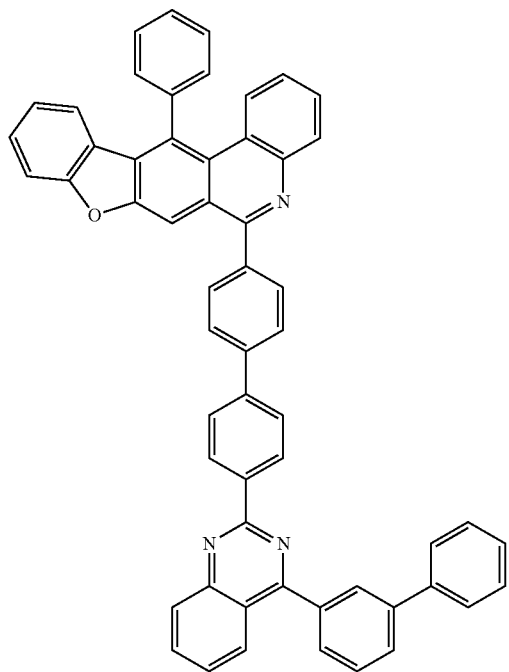
336
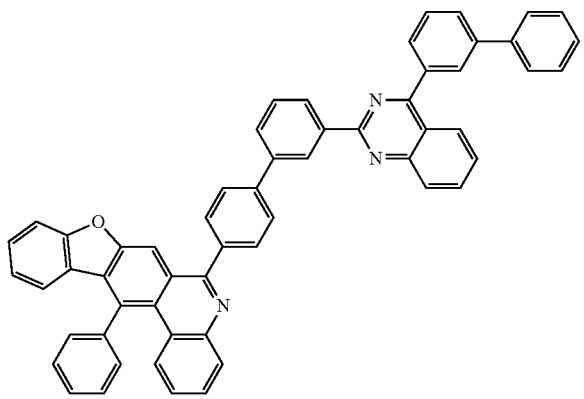
337
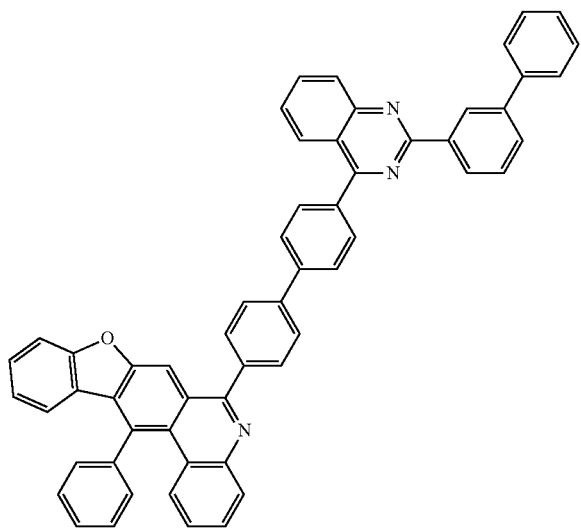
338
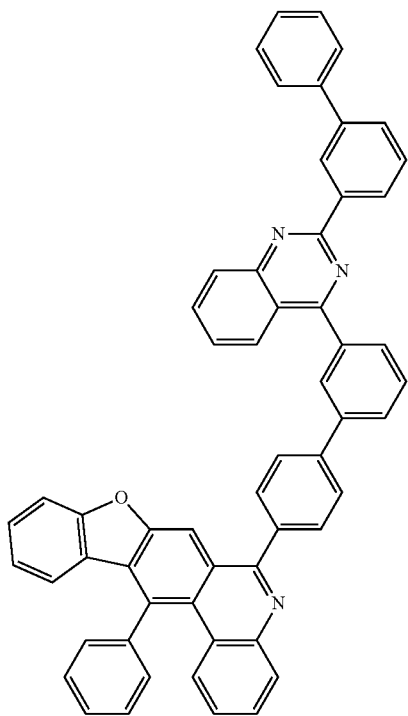

-continued
339
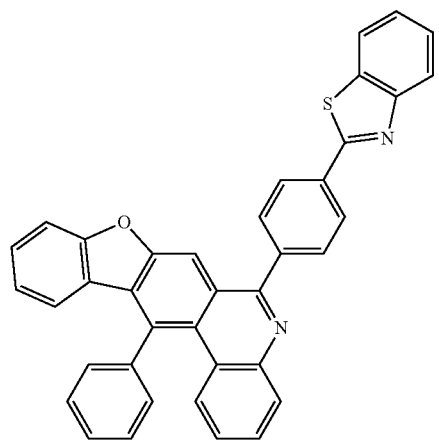 [SMILES: c1ccc(-c2c3c(cc4c(-c5ccc(-c6nc7ccccc7s6)cc5)nc5ccccc5c24)oc2ccccc23)cc1]
340
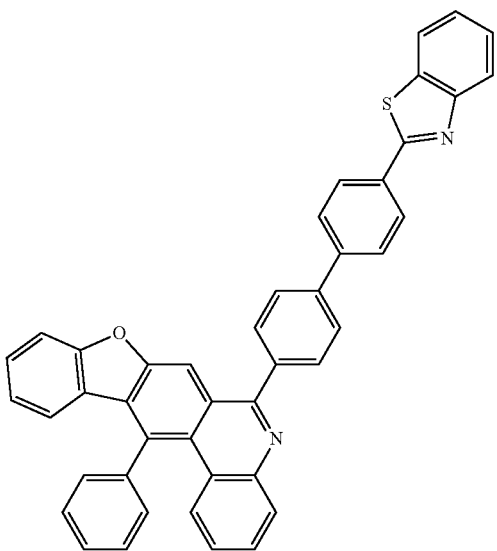
341
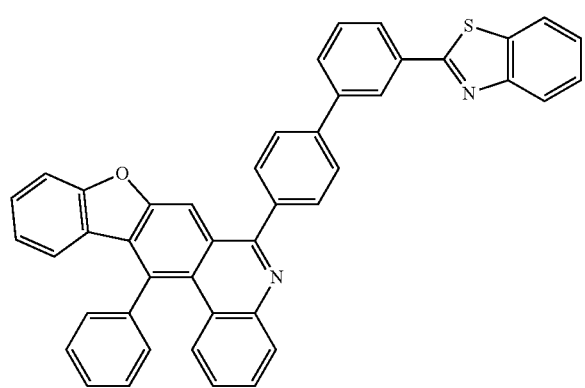
342
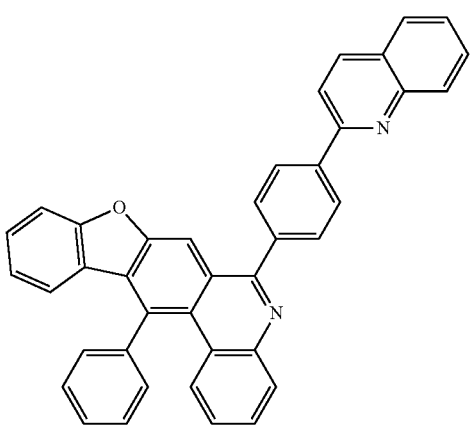 [SMILES: c1ccc(-c2c3c(cc4c(-c5ccc(-c6ccc7ccccc7n6)cc5)nc5ccccc5c24)oc2ccccc23)cc1]
343
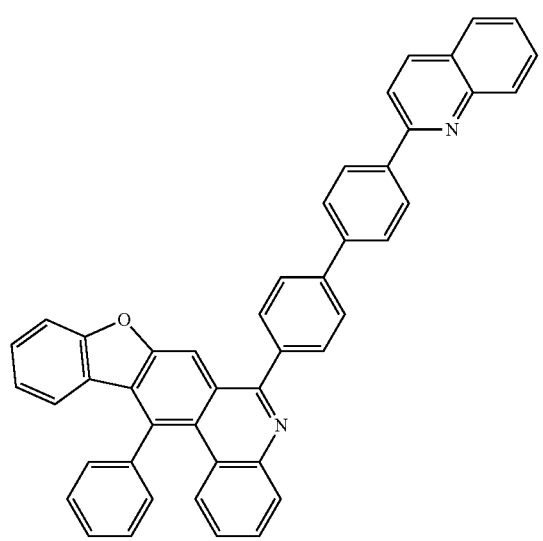
344
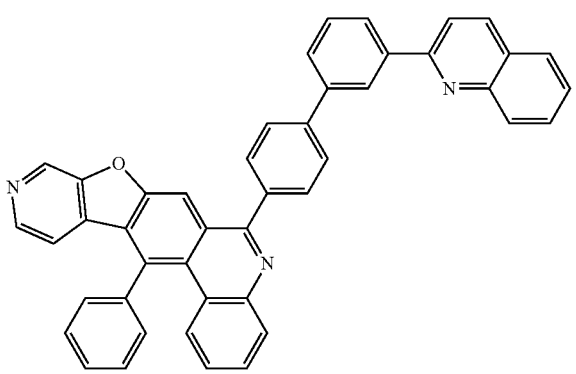

-continued
345
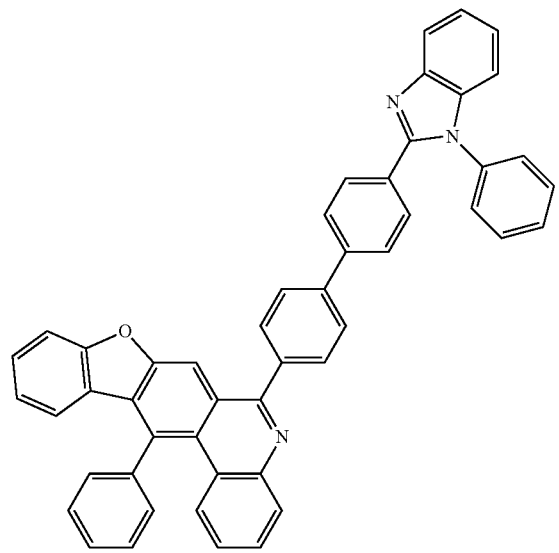
346
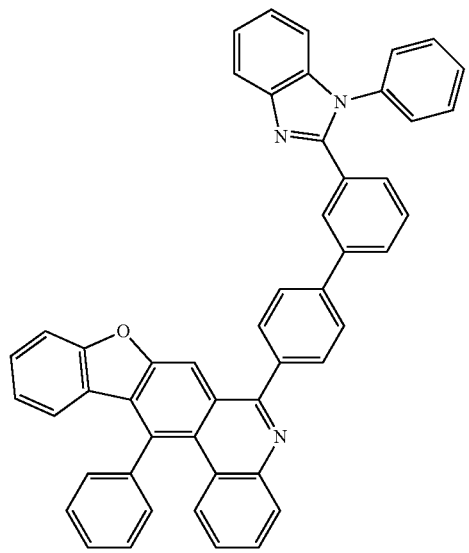
347
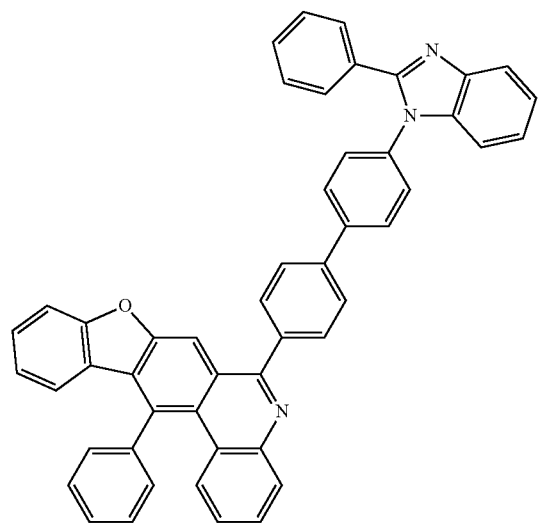 [SMILES: c1ccc(-c2c3c(cc4c(-c5ccc(-c6ccc(-n7c(-c8ccccc8)nc8ccccc87)cc6)cc5)nc5ccccc5c24)oc2ccccc23)cc1]
348
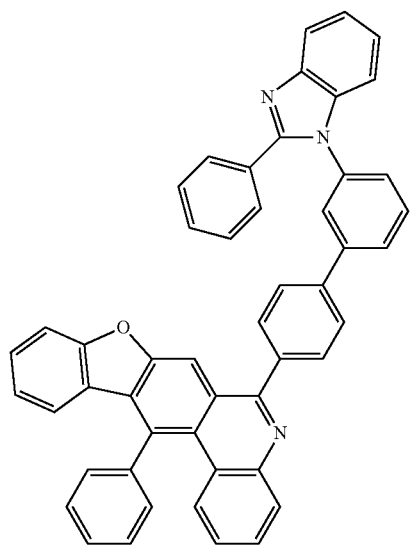

-continued
349
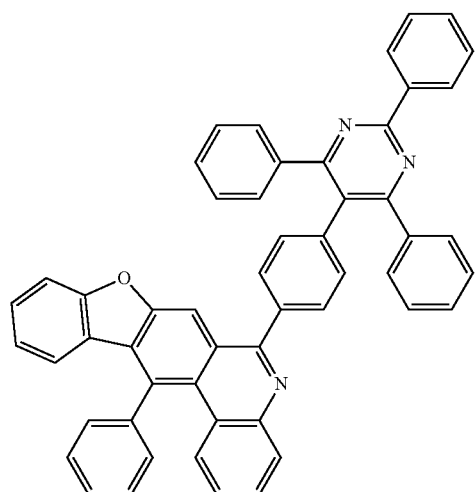
350
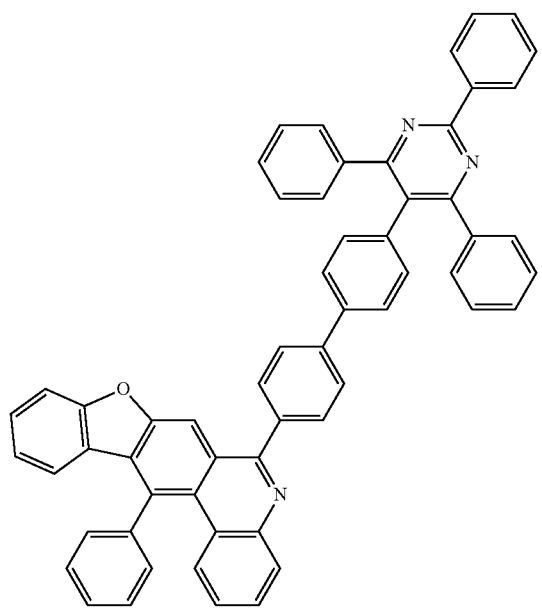
351
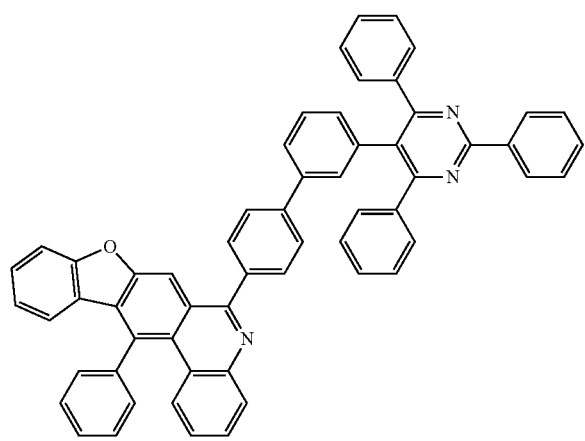
352
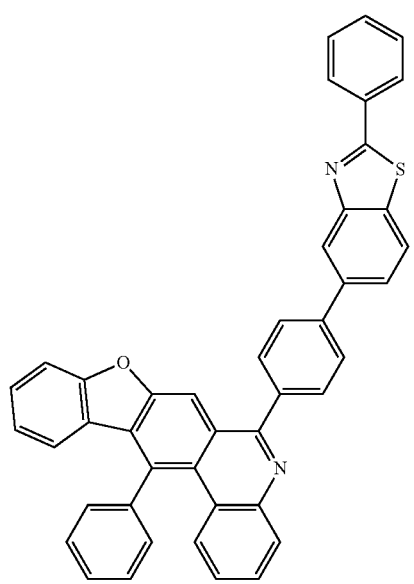

353
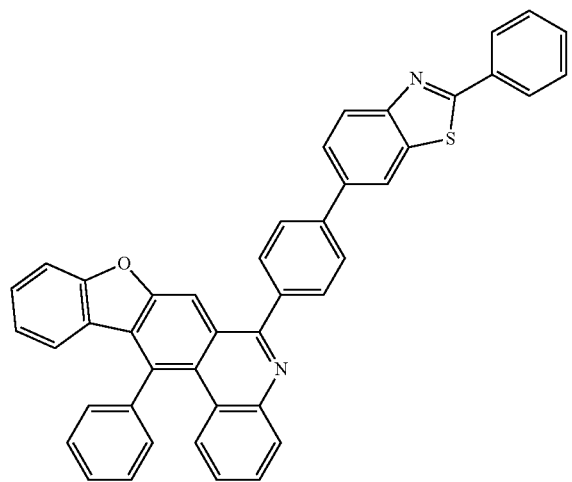
354
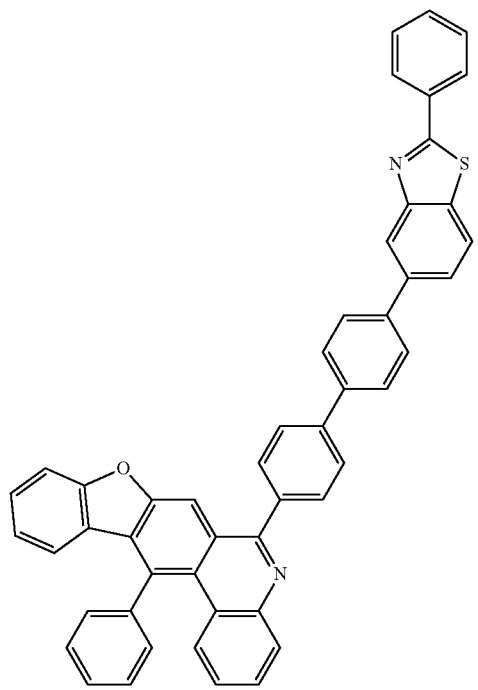
355
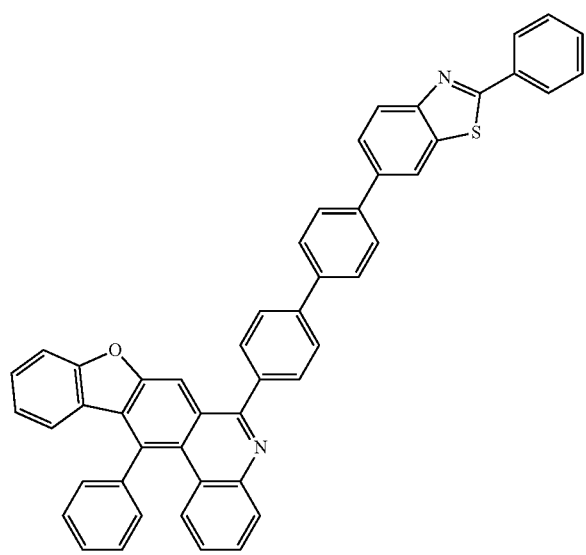
356
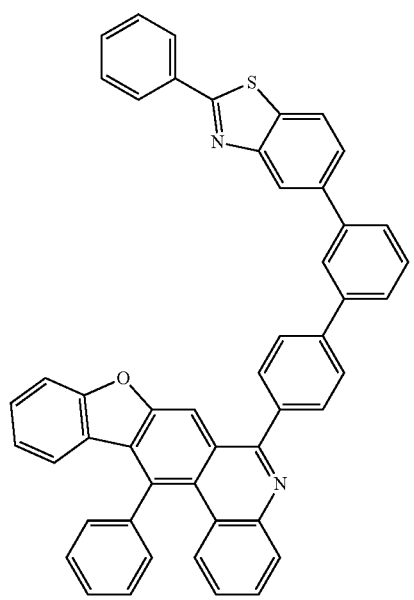

137 138
-continued
357 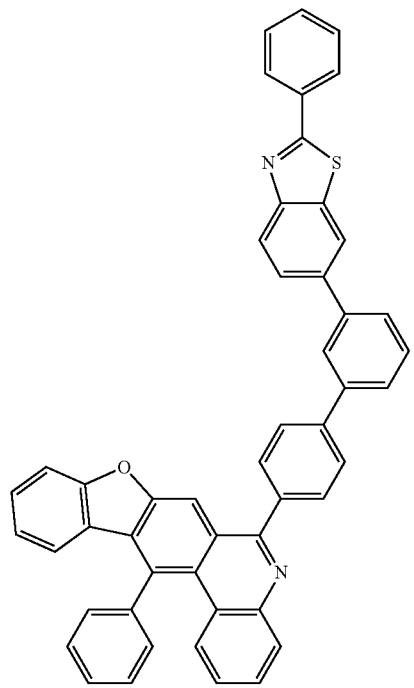
358 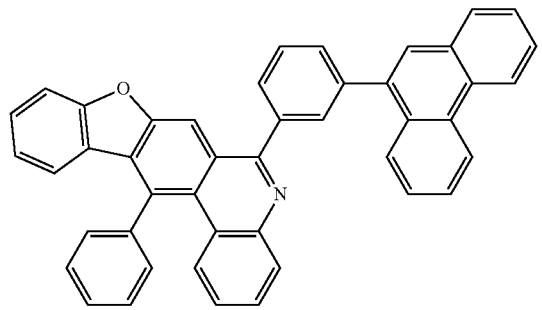
359 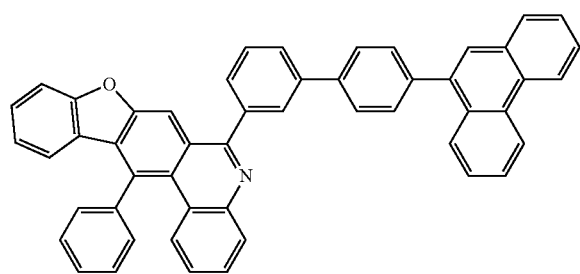
360 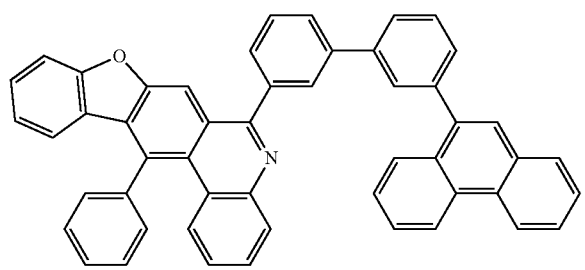
361 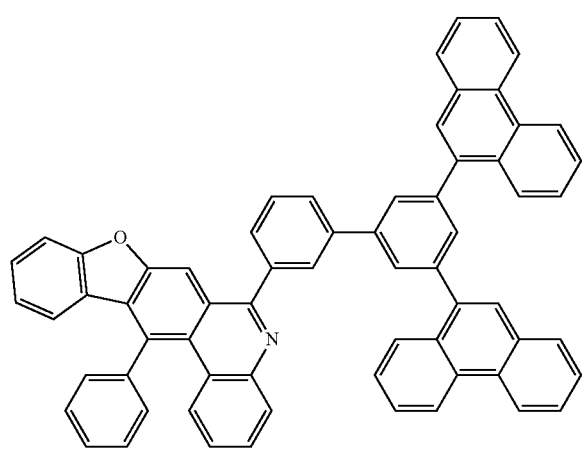
362 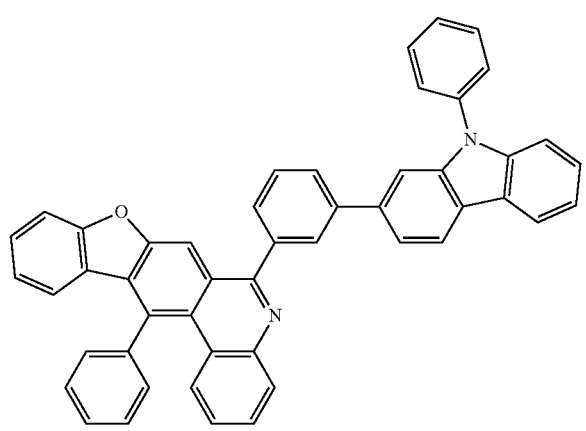

-continued
363
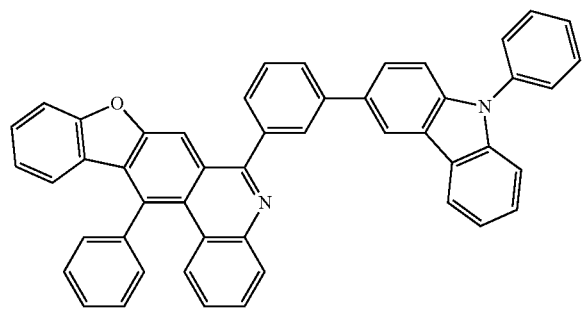
364
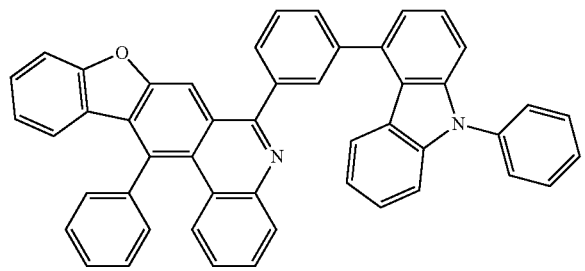
365
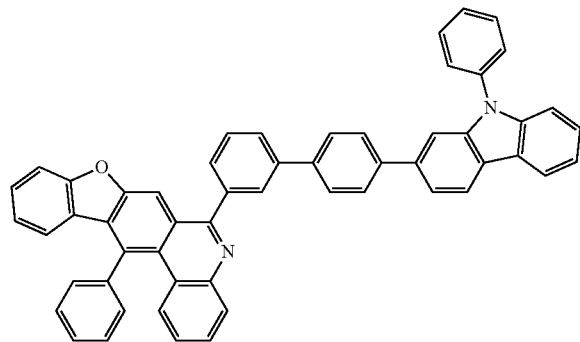
366
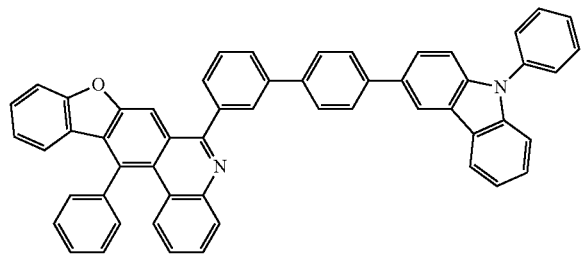
367
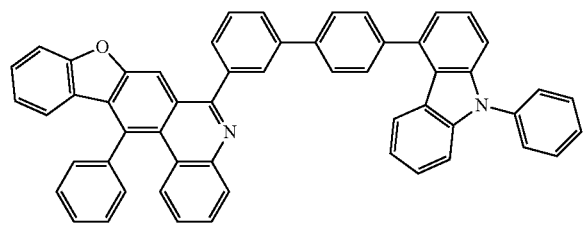
368
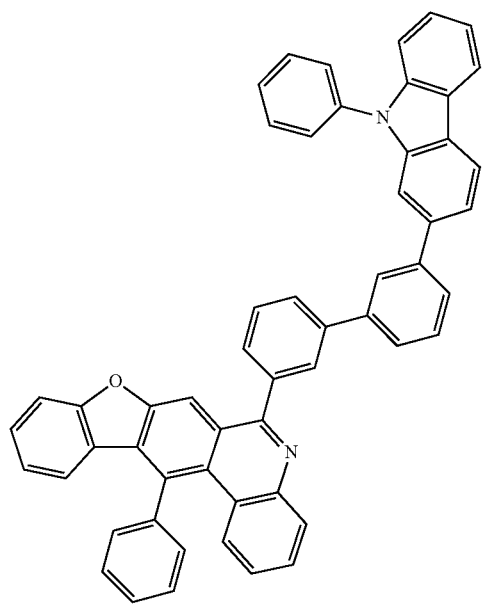

-continued
369
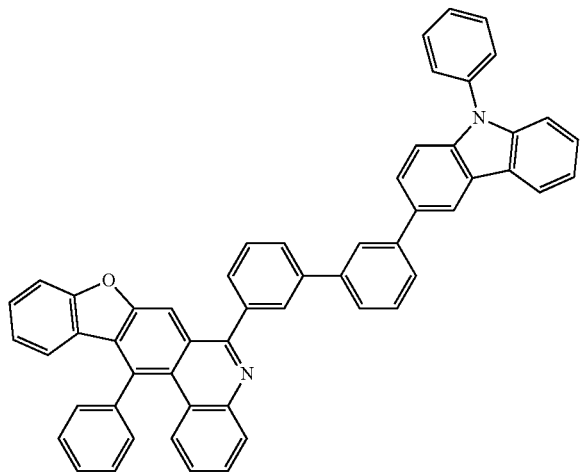
370
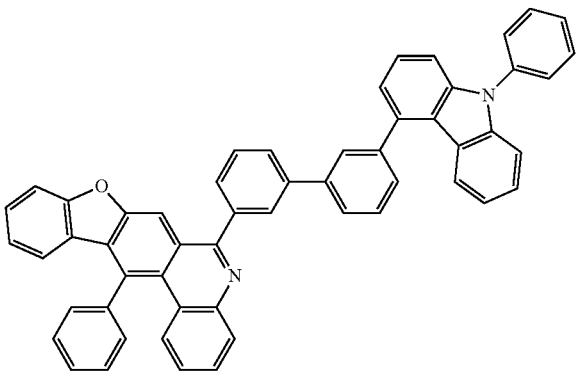
371
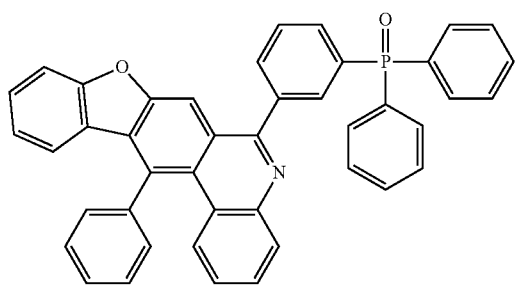
372
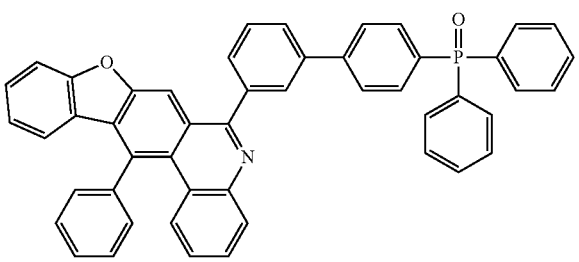
373
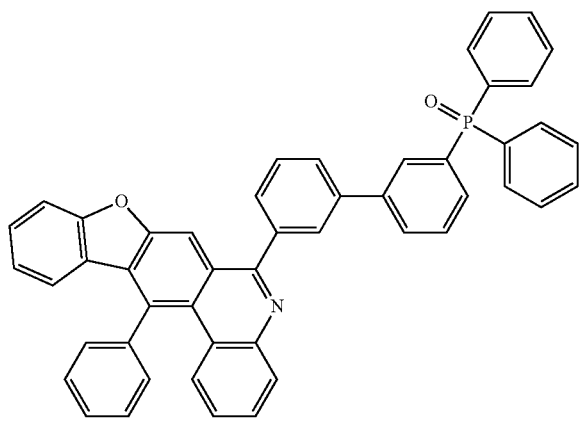
374
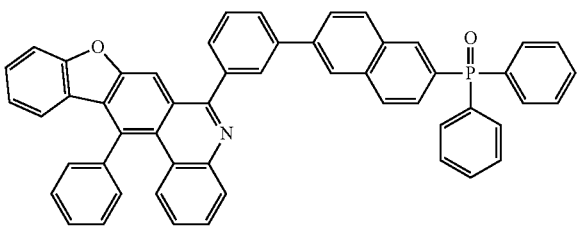
375
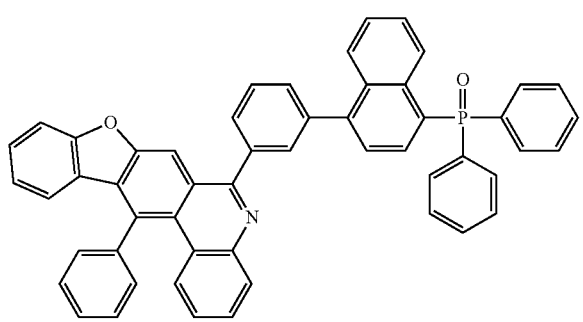 [SMILES: O=P(c1ccccc1)(c1ccccc1)c1ccc(-c2cccc(-c3nc4ccccc4c4c(-c5ccccc5)c5c(cc34)oc3ccccc35)c2)c2ccccc12]
376
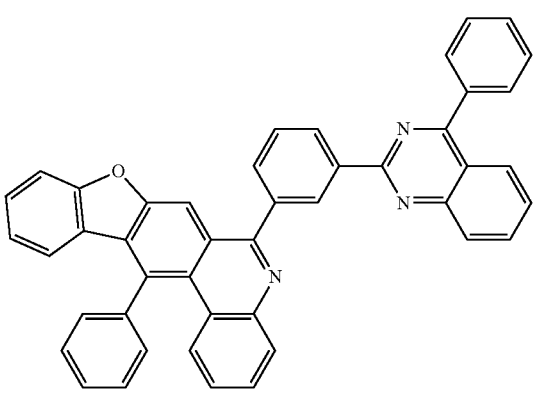 [SMILES: c1ccc(-c2nc(-c3cccc(-c4nc5ccccc5c5c(-c6ccccc6)c6c(cc45)oc4ccccc46)c3)nc3ccccc23)cc1]

-continued
377
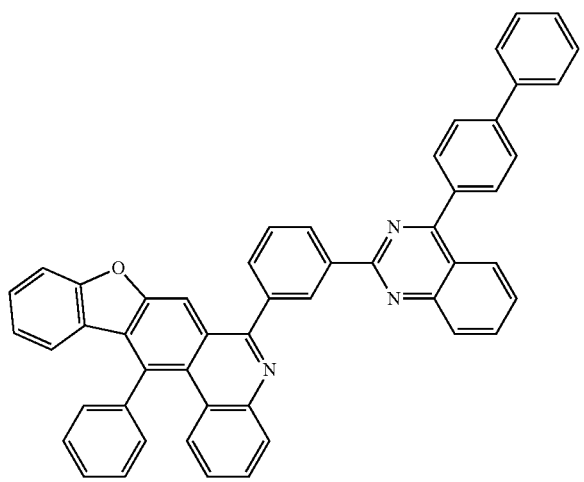
378
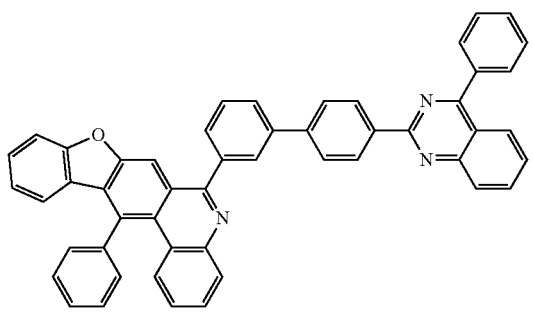
379
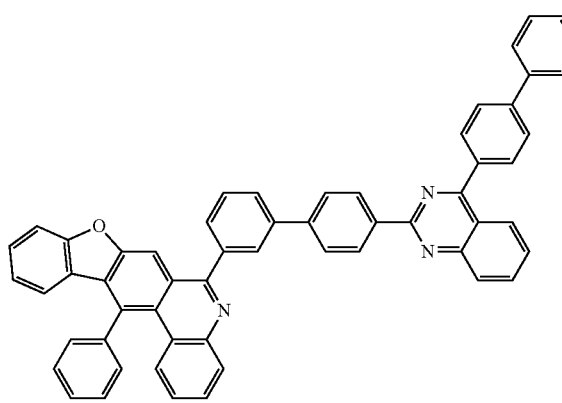
380
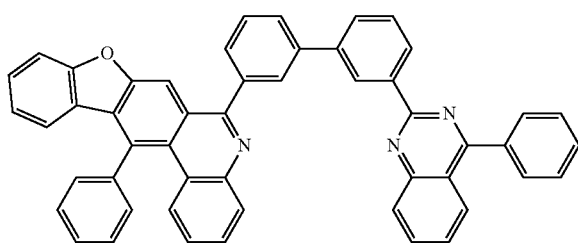
381
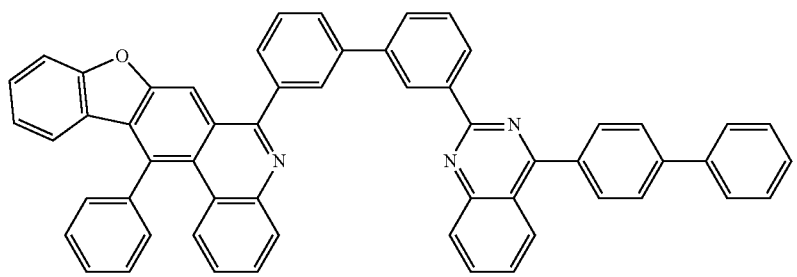
382
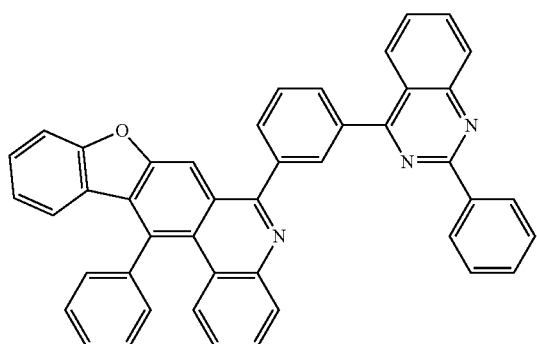
383
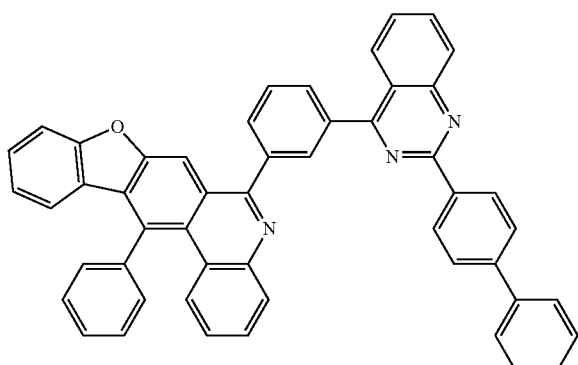

-continued
384
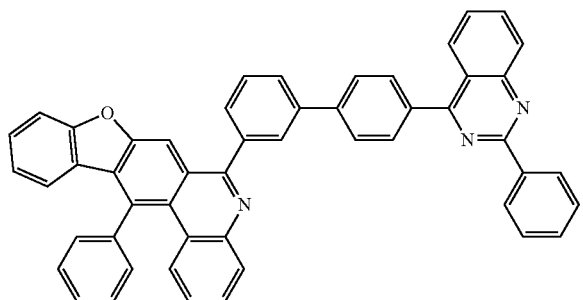
385
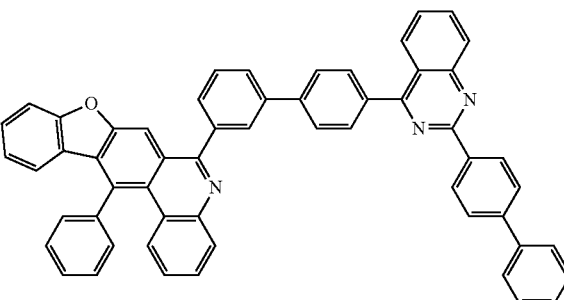
386
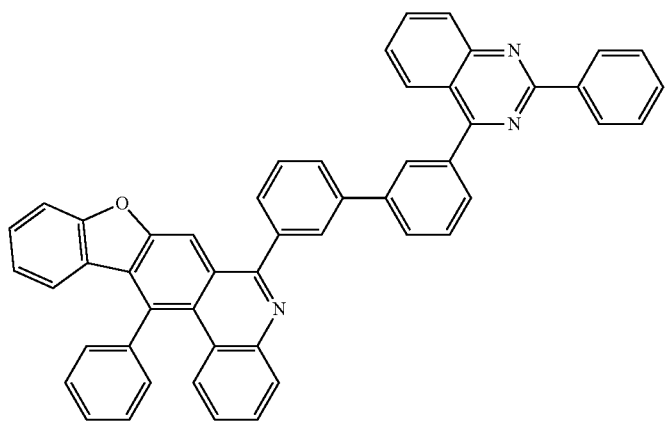
387
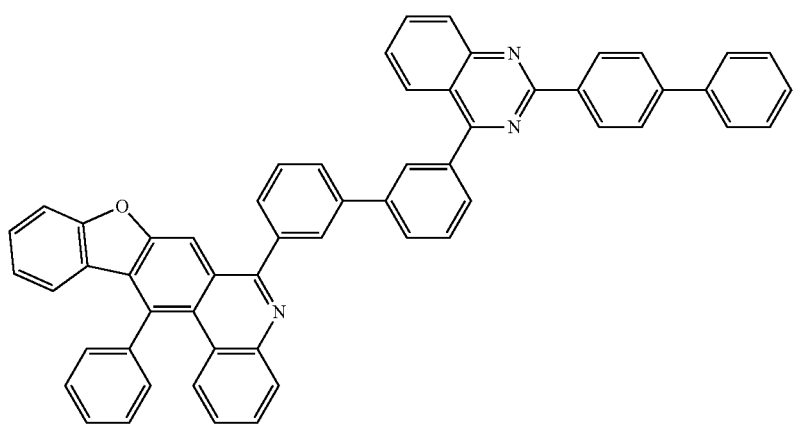
388
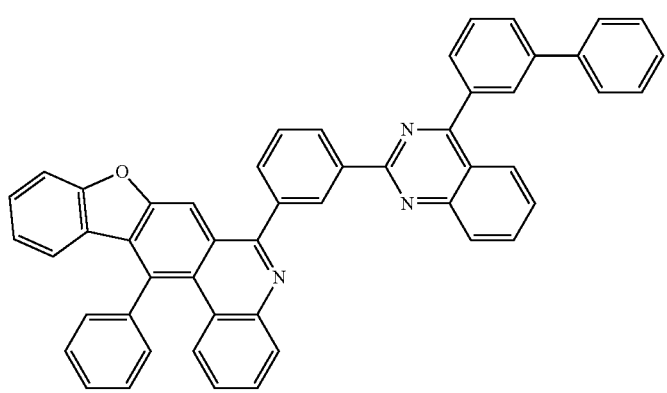

-continued
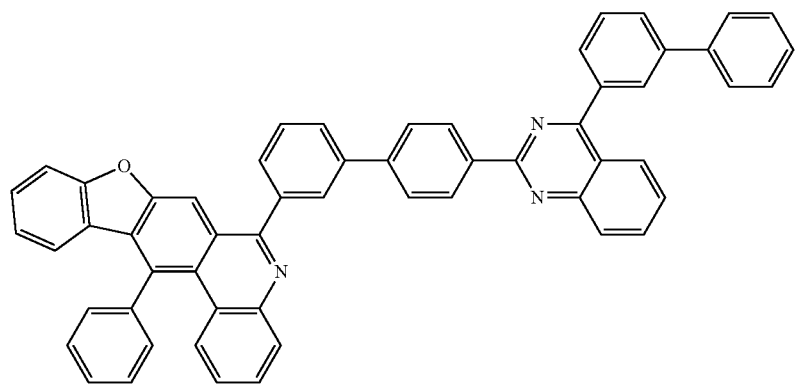
389
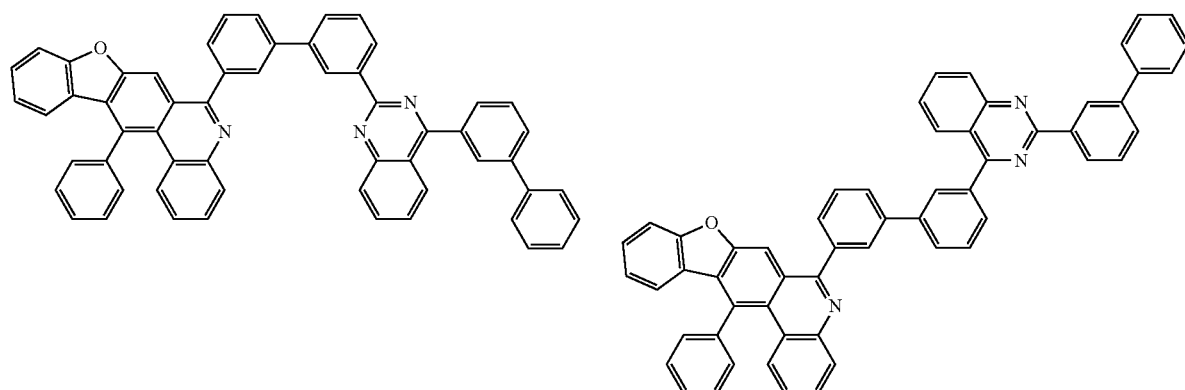
390 391
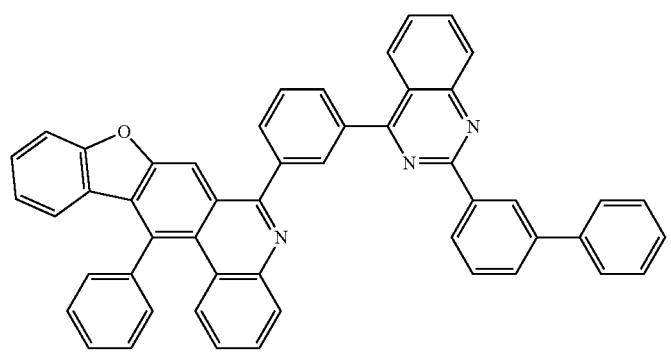
392
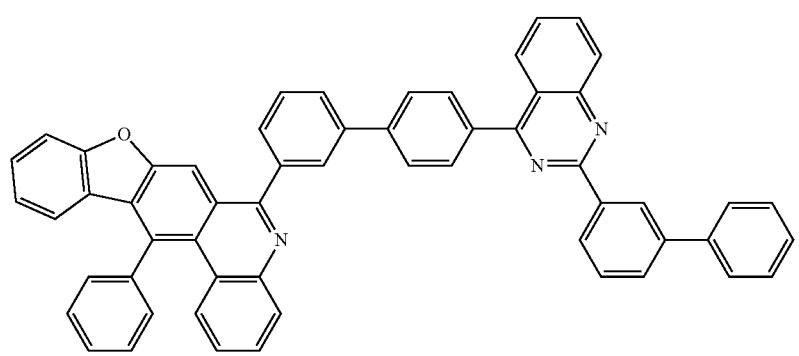
393

-continued
394
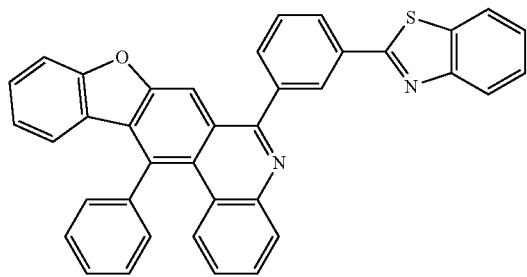
395
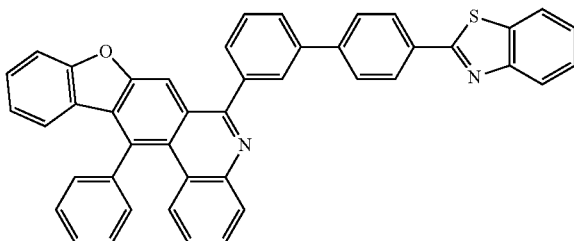
396
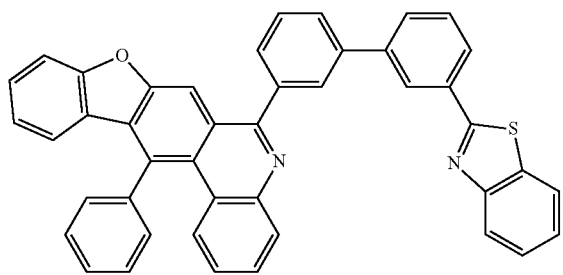
397
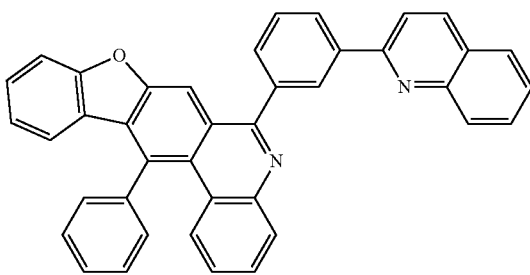
398
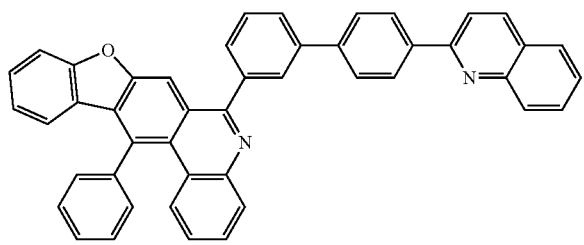
399
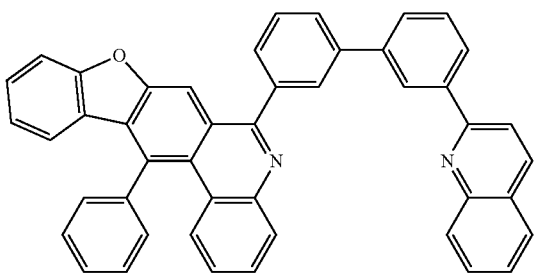
400
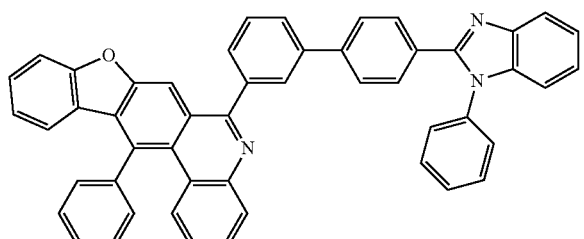
401
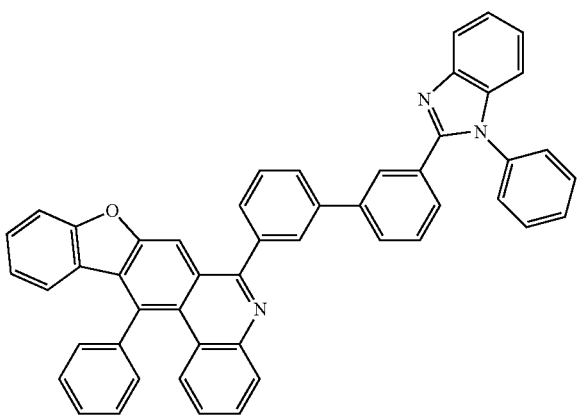

-continued
402
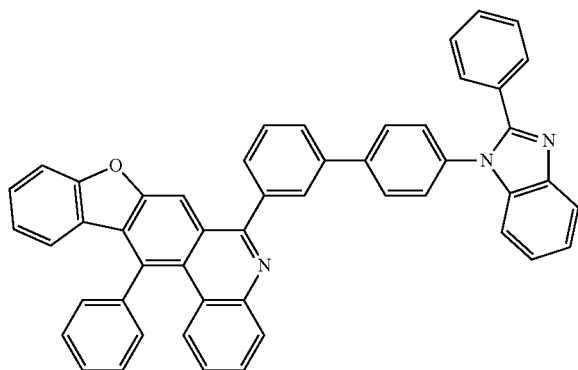
403
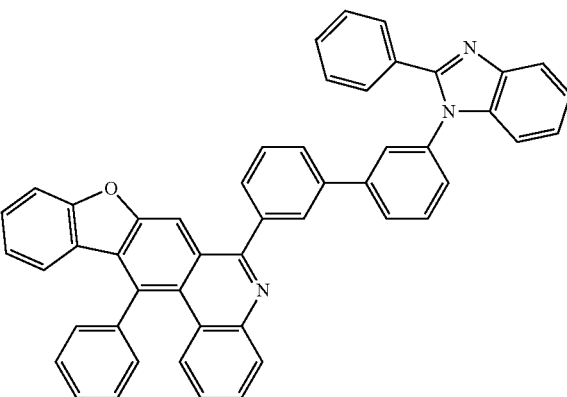
404
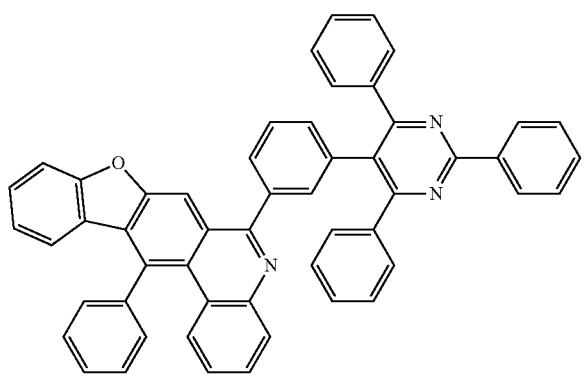
405
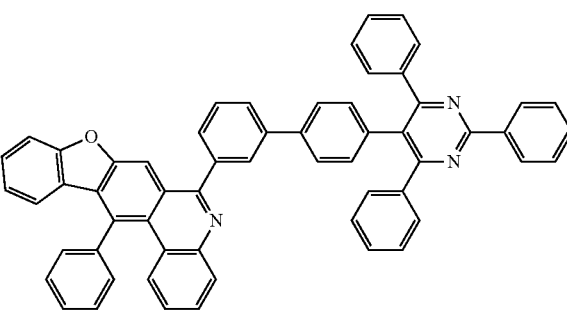
406
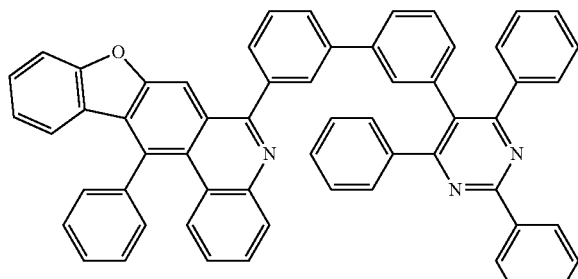
407
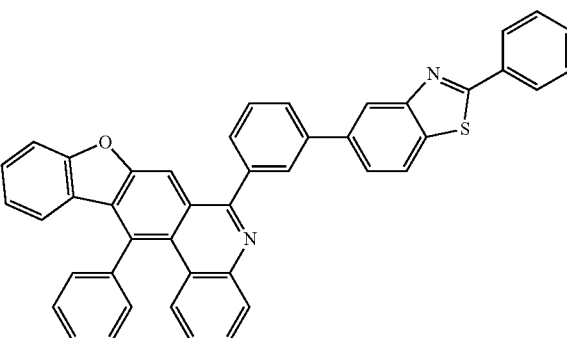
408
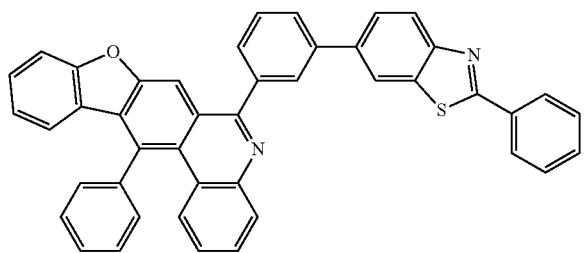
409
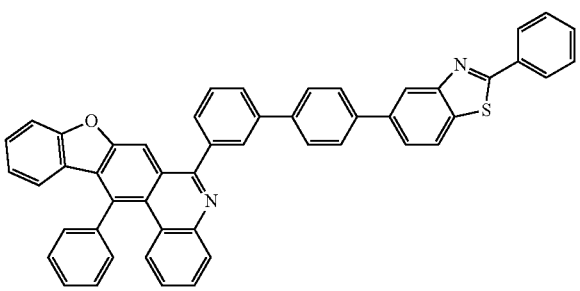

-continued
410
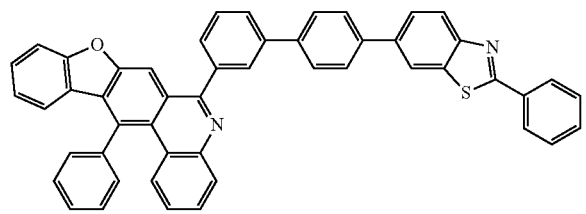
411
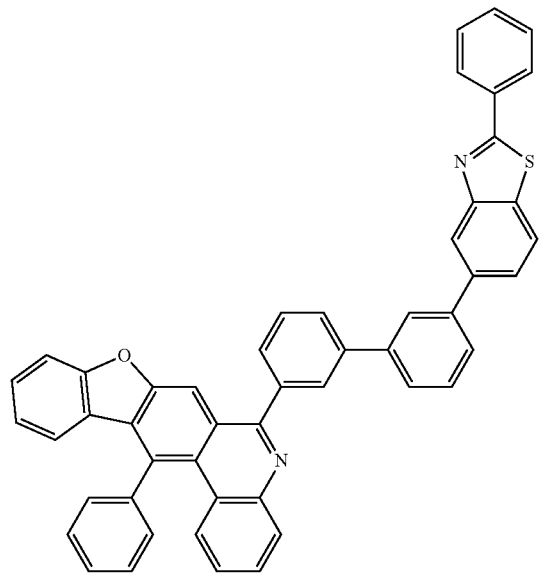
412
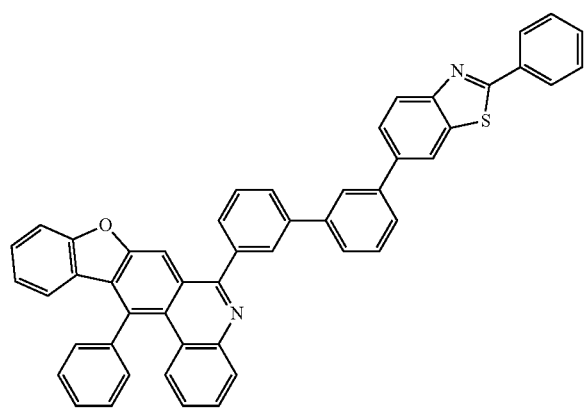
413
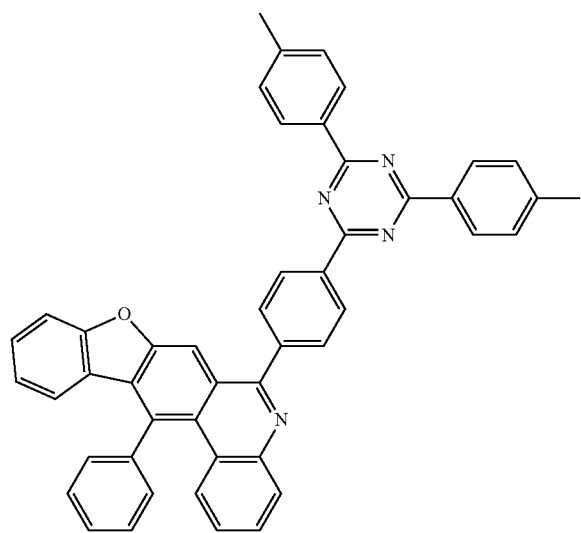 [SMILES: Cc1ccc(-c2nc(-c3ccc(C)cc3)nc(-c3ccc(-c4nc5ccccc5c5c(-c6ccccc6)c6c(cc45)oc4ccccc46)cc3)n2)cc1]

-continued
414
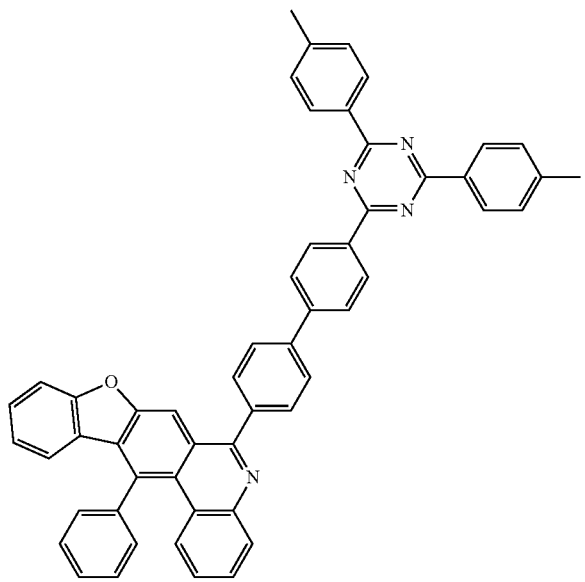
415
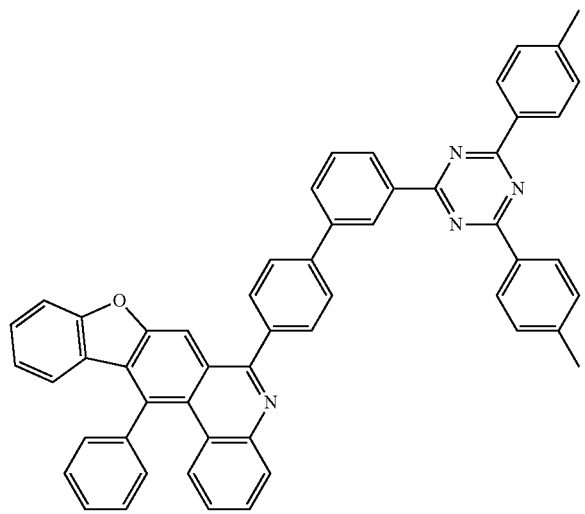 [SMILES: Cc1ccc(-c2nc(-c3ccc(C)cc3)nc(-c3cccc(-c4ccc(-c5nc6ccccc6c6c(-c7ccccc7)c7c(cc56)oc5ccccc57)cc4)c3)n2)cc1]
416
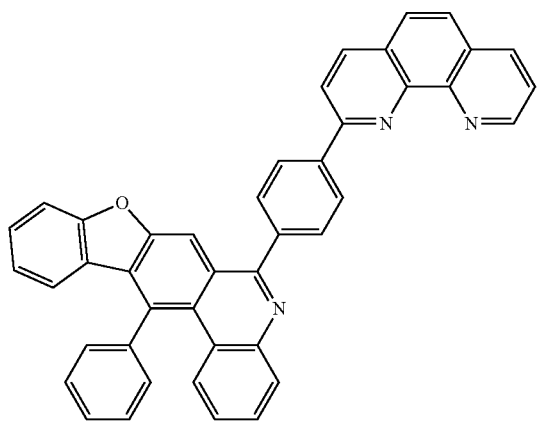
417
418
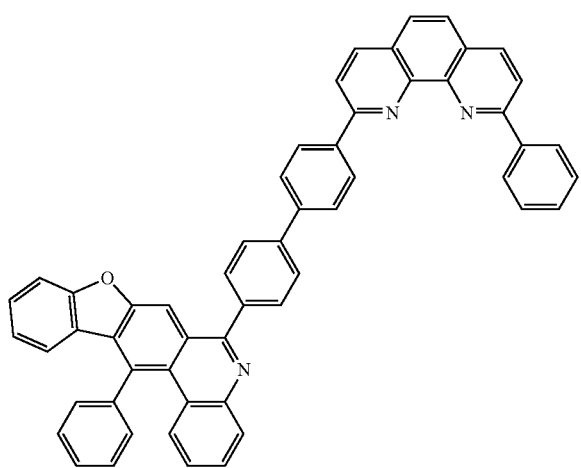 [SMILES: c1ccc(-c2ccc3ccc4ccc(-c5ccc(-c6ccc(-c7nc8ccccc8c8c(-c9ccccc9)c9c(cc78)oc7ccccc79)cc6)cc5)nc4c3n2)cc1]
419
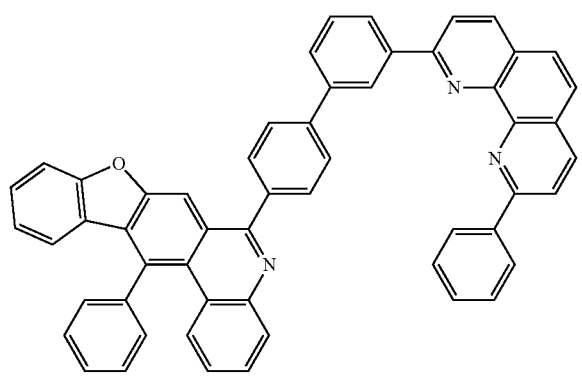 [SMILES: c1ccc(-c2ccc3ccc4ccc(-c5cccc(-c6ccc(-c7nc8ccccc8c8c(-c9ccccc9)c9c(cc78)oc7ccccc79)cc6)c5)nc4c3n2)cc1]

-continued
420
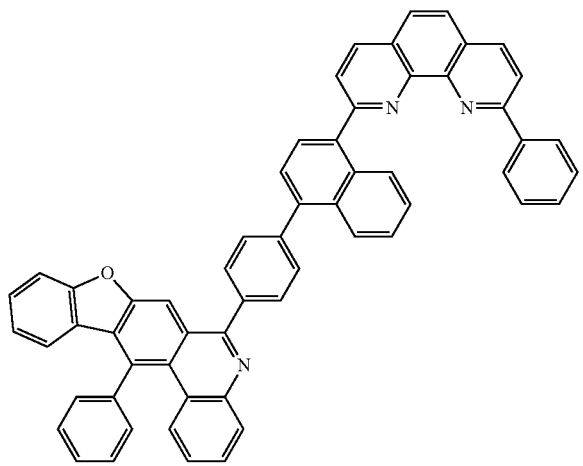 [SMILES: c1ccc(-c2ccc3ccc4ccc(-c5ccc(-c6ccc(-c7nc8ccccc8c8c(-c9ccccc9)c9c(cc78)oc7ccccc79)cc6)c6ccccc56)nc4c3c2)cc1]
421
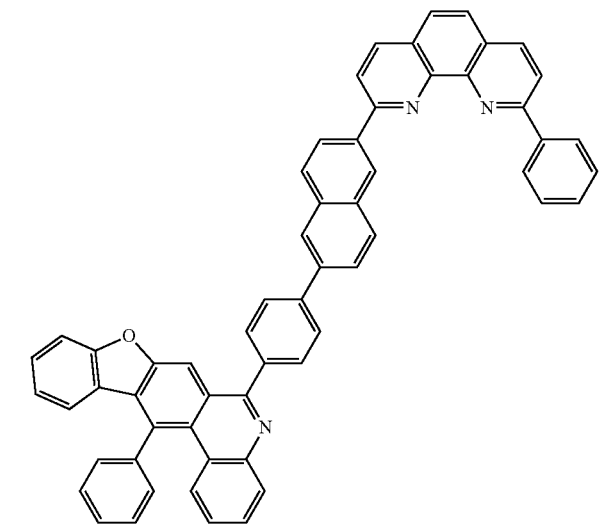
422
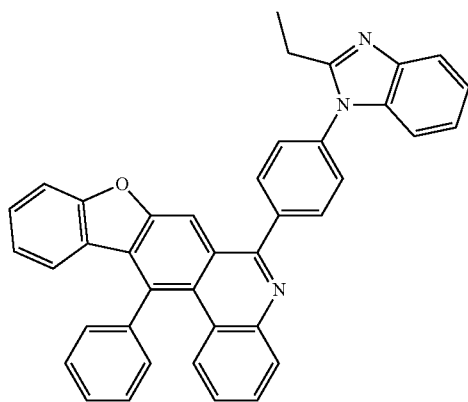
423
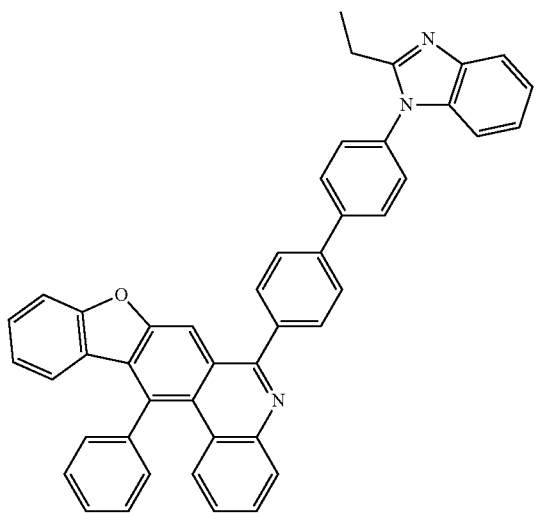
424
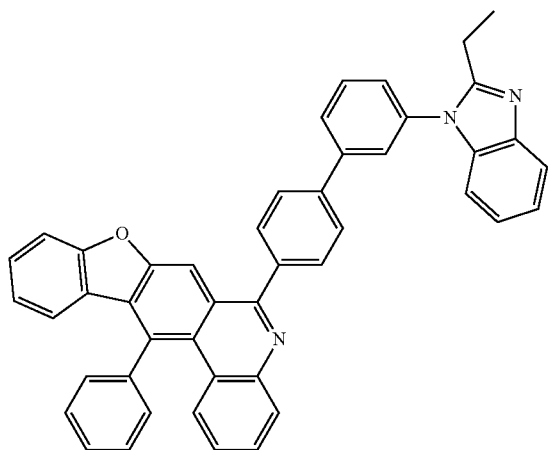
425
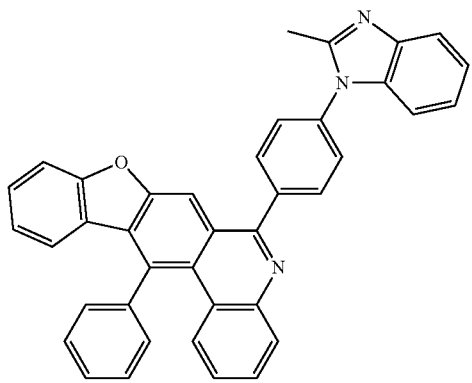

-continued
426
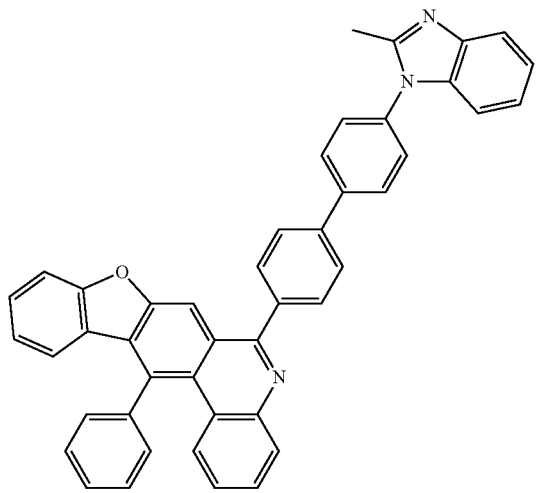
427
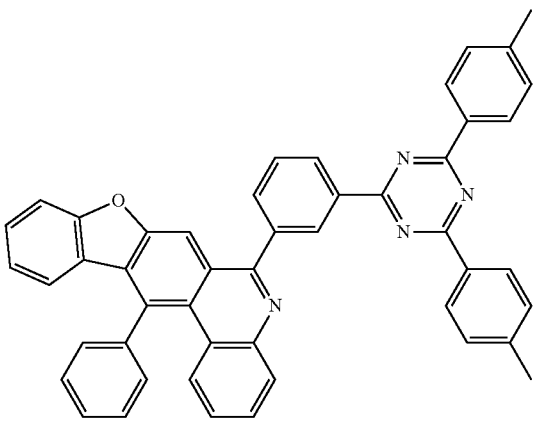 [SMILES: Cc1ccc(-c2nc(-c3ccc(C)cc3)nc(-c3cccc(-c4nc5ccccc5c5c(-c6ccccc6)c6c(cc45)oc4ccccc46)c3)n2)cc1]
428
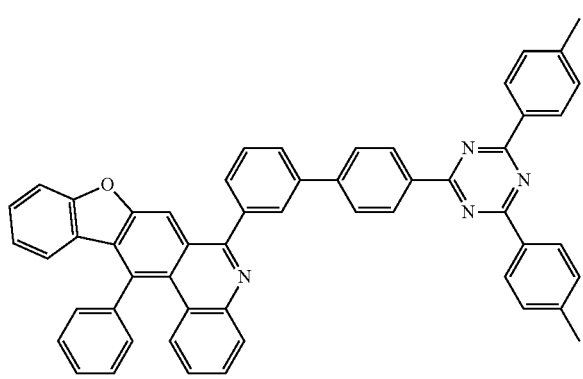
429
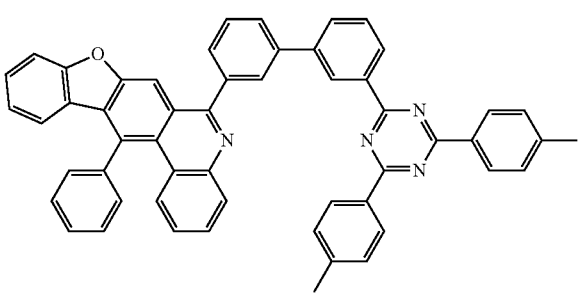
430
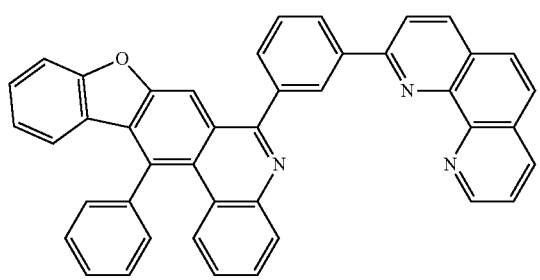 [SMILES: c1ccc(-c2c3c(cc4c(-c5cccc(-c6ccc7ccc8cccnc8c7n6)c5)nc5ccccc5c24)oc2ccccc23)cc1]
431
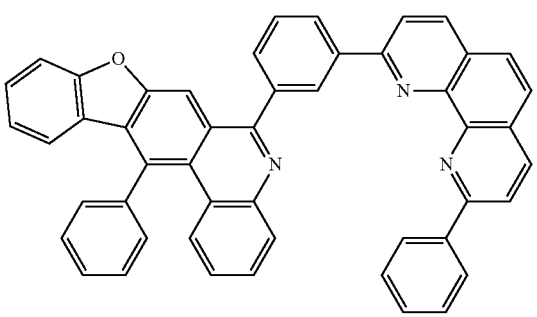 [SMILES: c1ccc(-c2ccc3ccc4ccc(-c5cccc(-c6nc7ccccc7c7c(-c8ccccc8)c8c(cc67)oc6ccccc68)c5)nc4c3n2)cc1]
432
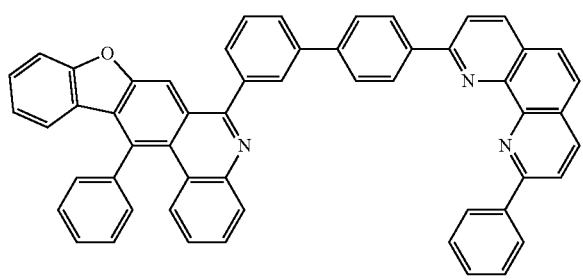 [SMILES: c1ccc(-c2ccc3ccc4ccc(-c5ccc(-c6cccc(-c7nc8ccccc8c8c(-c9ccccc9)c9c(cc78)oc7ccccc79)c6)cc5)nc4c3n2)cc1]
433
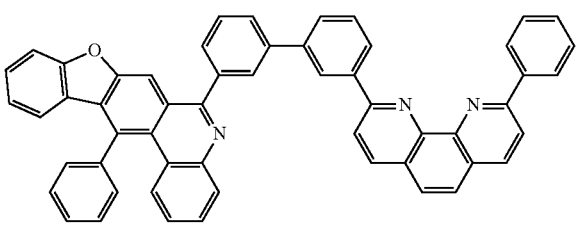

-continued
434
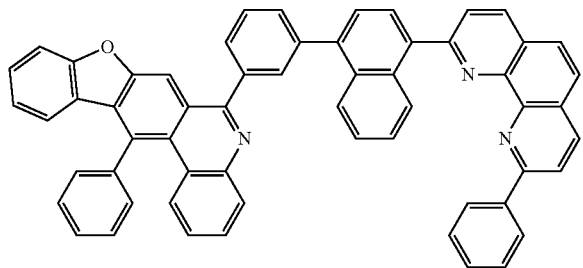
435
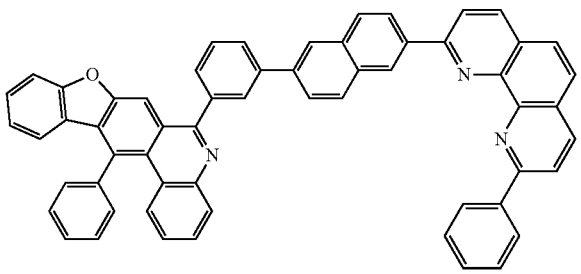
436
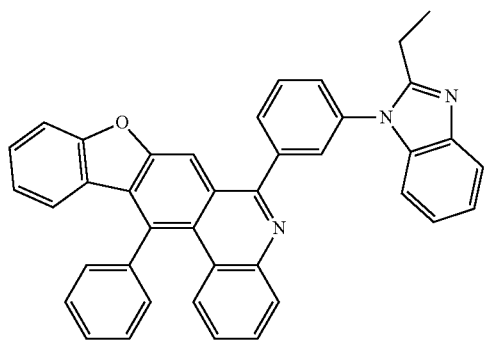
437
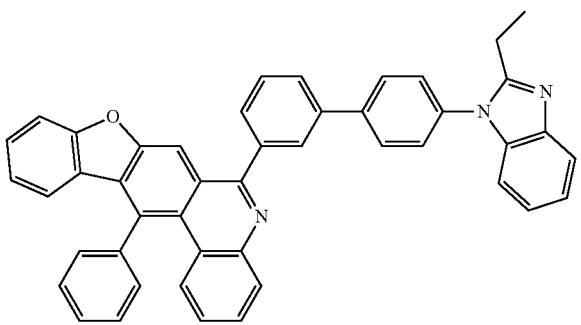
438
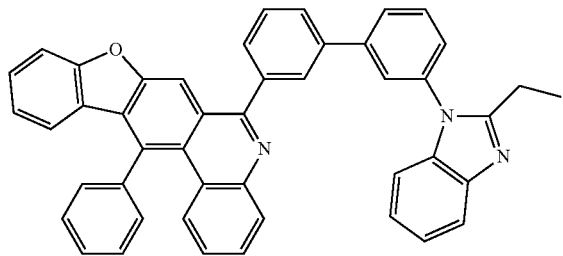
439
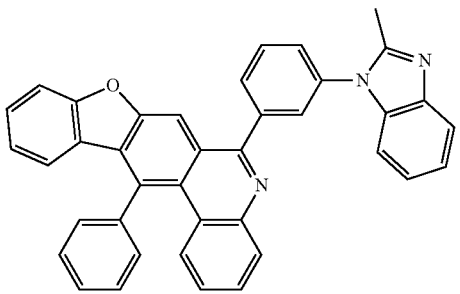
440
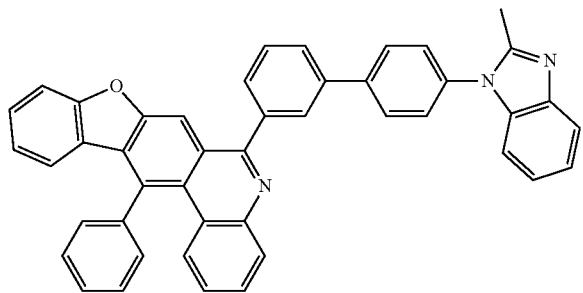
441
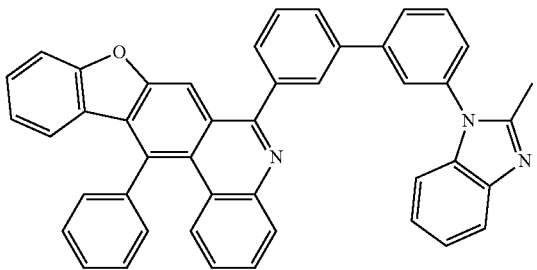

-continued
442
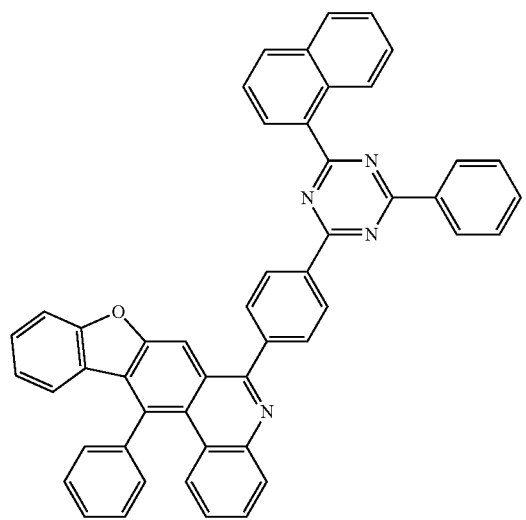
443
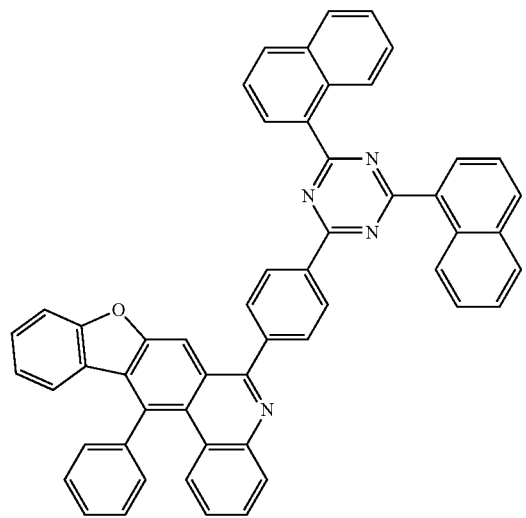
444
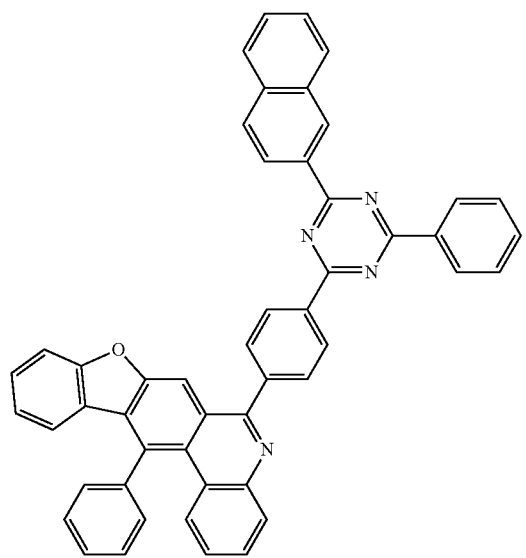
445
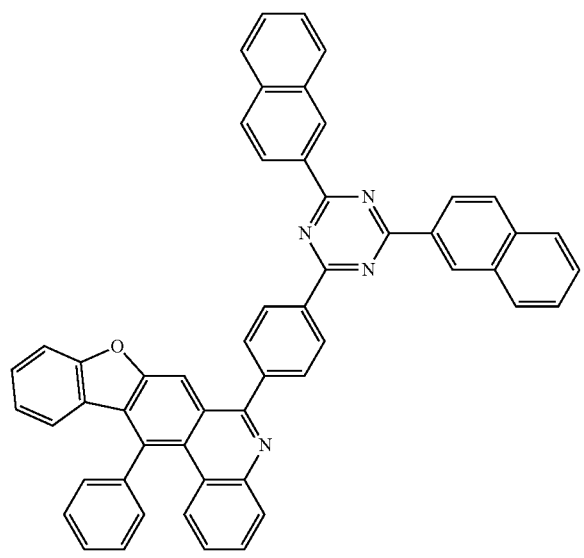

-continued
446
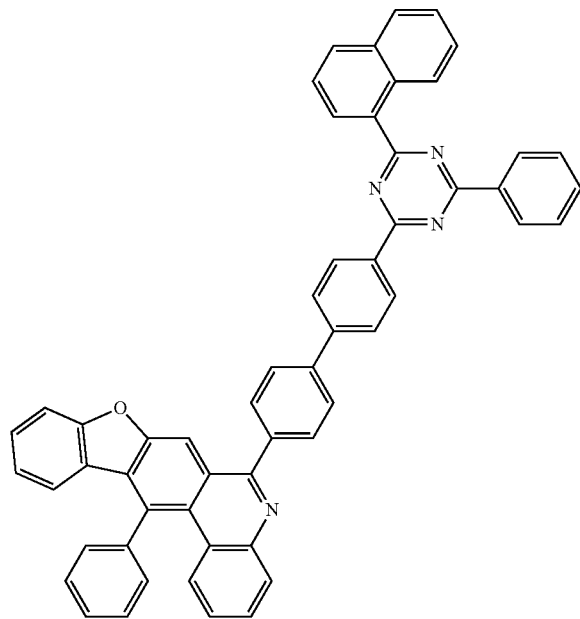 [SMILES: c1ccc(-c2nc(-c3ccc(-c4ccc(-c5nc6ccccc6c6c(-c7ccccc7)c7c(cc56)oc5ccccc57)cc4)cc3)nc(-c3cccc4ccccc34)n2)cc1]
447
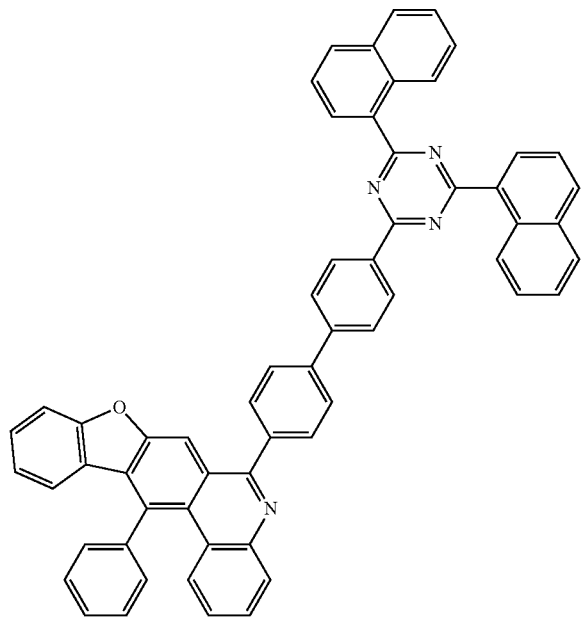 [SMILES: c1ccc(-c2c3c(cc4c(-c5ccc(-c6ccc(-c7nc(-c8cccc9ccccc89)nc(-c8cccc9ccccc89)n7)cc6)cc5)nc5ccccc5c24)oc2ccccc23)cc1]
448
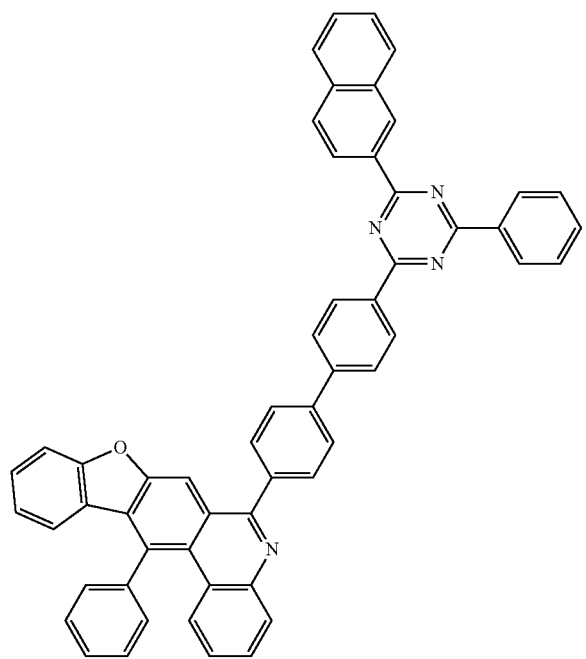
449
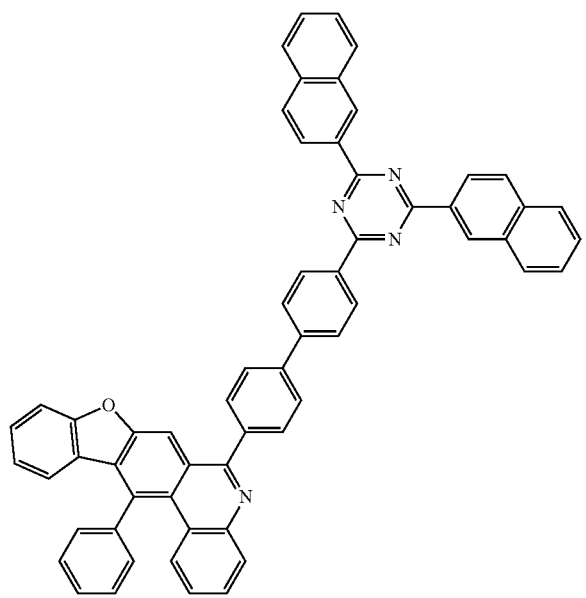

450
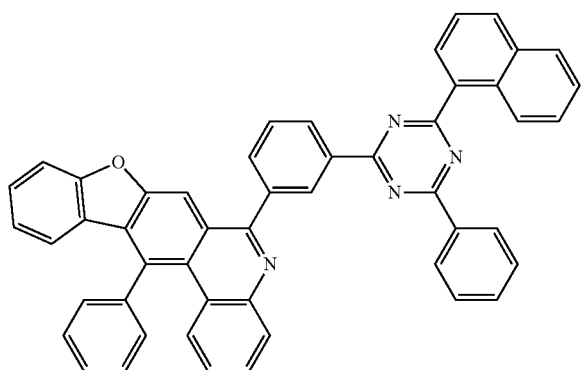
451
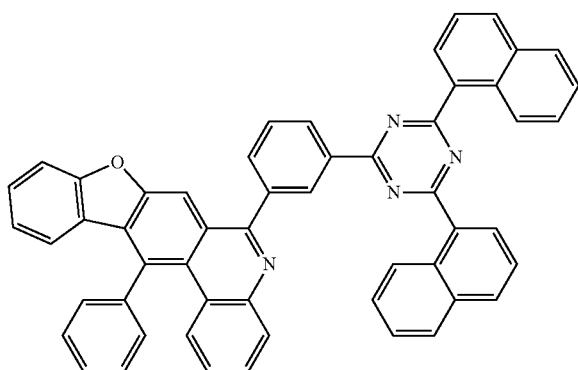
452
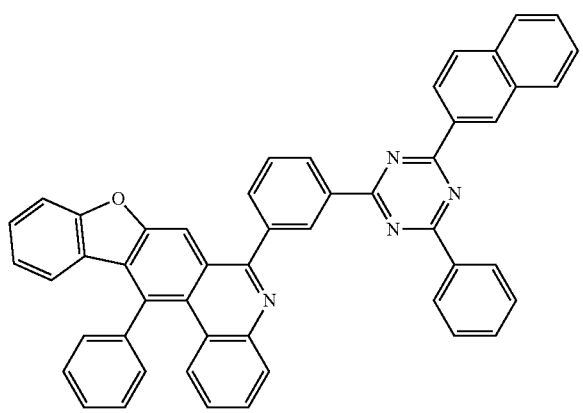
453
454
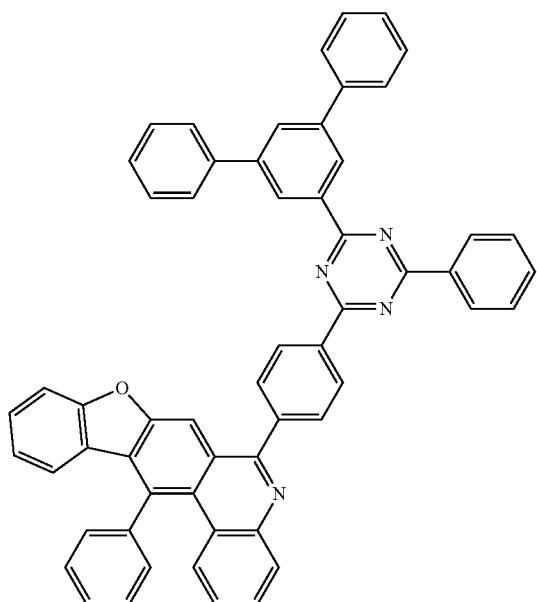
455
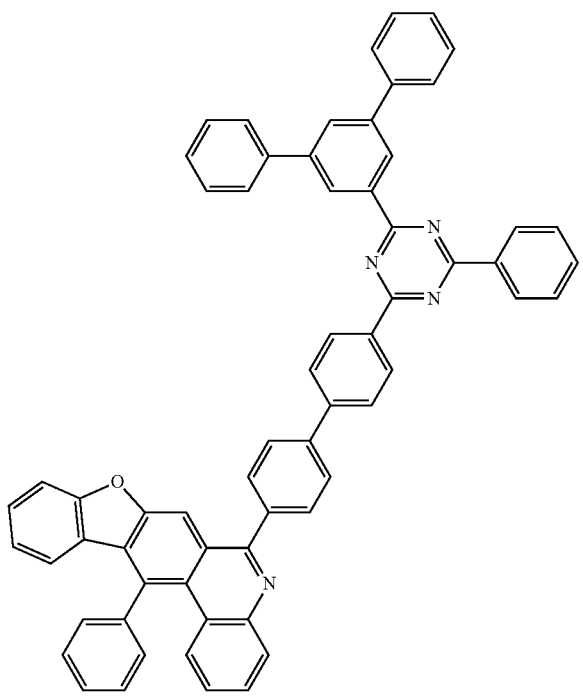

456
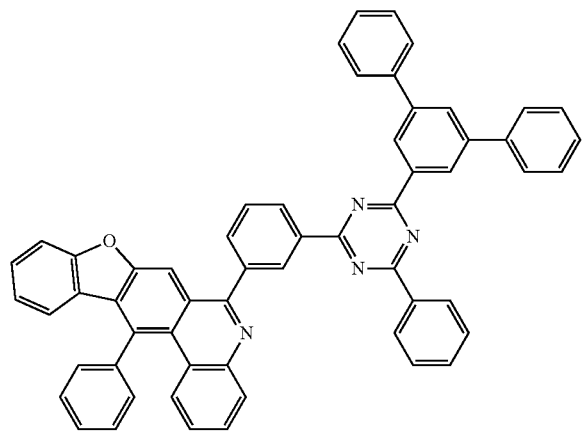 [SMILES: c1ccc(-c2cc(-c3ccccc3)cc(-c3nc(-c4ccccc4)nc(-c4cccc(-c5nc6ccccc6c6c(-c7ccccc7)c7c(cc56)oc5ccccc57)c4)n3)c2)cc1]
457
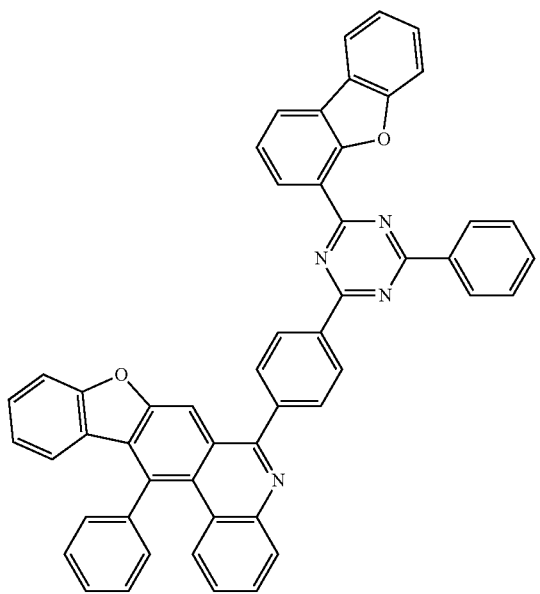 [SMILES: c1ccc(-c2nc(-c3ccc(-c4nc5ccccc5c5c(-c6ccccc6)c6c(cc45)oc4ccccc46)cc3)nc(-c3cccc4c3oc3ccccc34)n2)cc1]
458
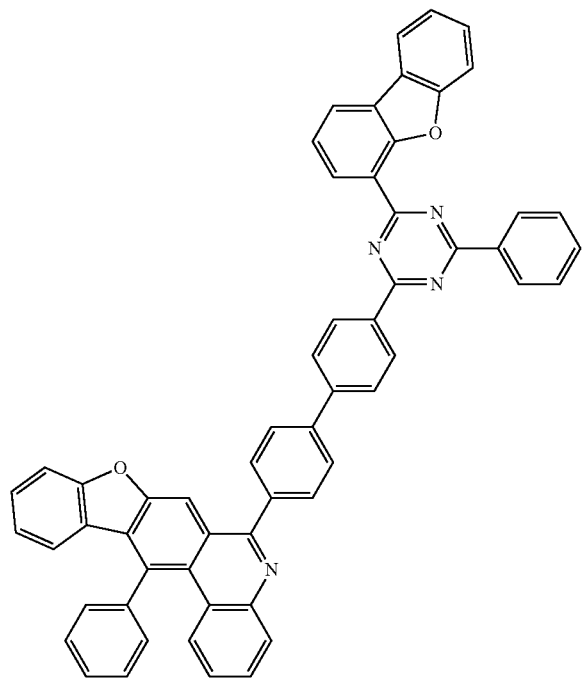
459
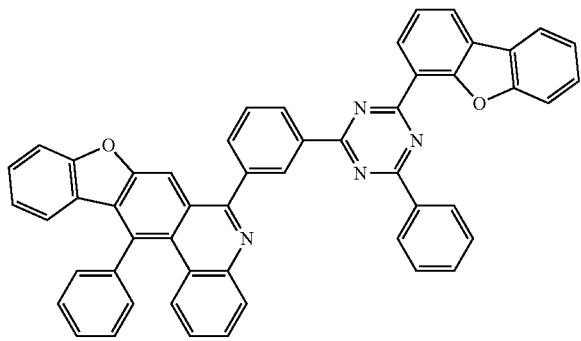 [SMILES: c1ccc(-c2nc(-c3cccc(-c4nc5ccccc5c5c(-c6ccccc6)c6c(cc45)oc4ccccc46)c3)nc(-c3cccc4c3oc3ccccc34)n2)cc1]

-continued
171
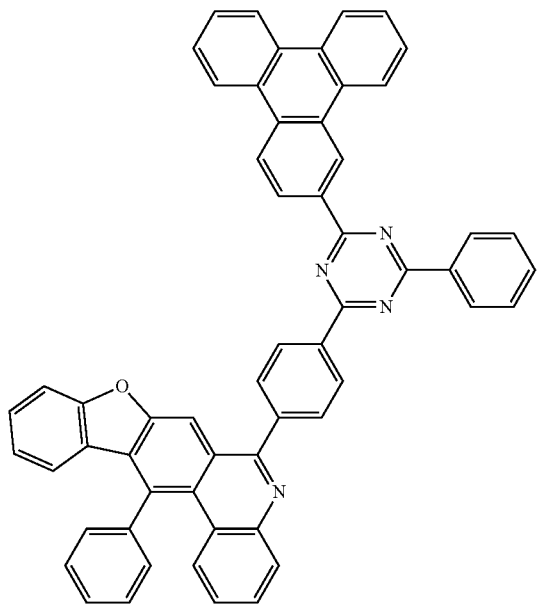 [SMILES: c1ccc(-c2nc(-c3ccc(-c4nc5ccccc5c5c(-c6ccccc6)c6c(cc45)oc4ccccc46)cc3)nc(-c3ccc4c5ccccc5c5ccccc5c4c3)n2)cc1]
460
172
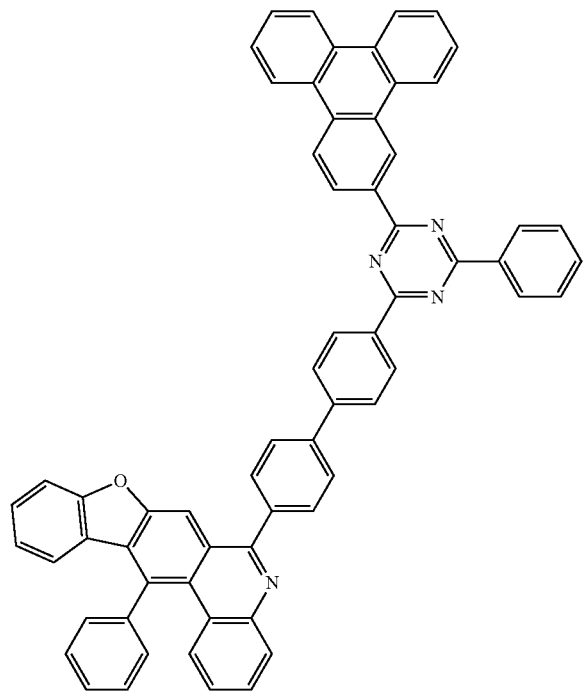
461
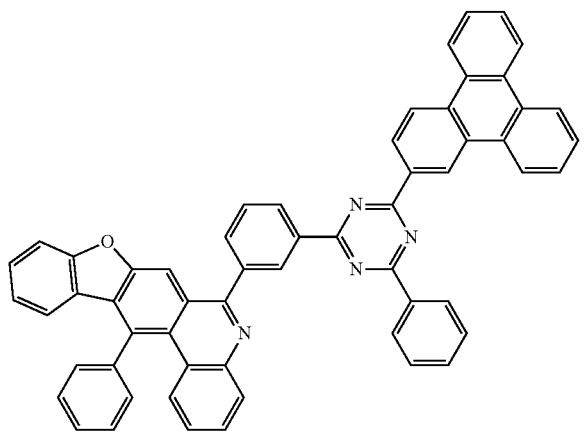 [SMILES: c1ccc(-c2nc(-c3cccc(-c4nc5ccccc5c5c(-c6ccccc6)c6c(cc45)oc4ccccc46)c3)nc(-c3ccc4c5ccccc5c5ccccc5c4c3)n2)cc1]
462
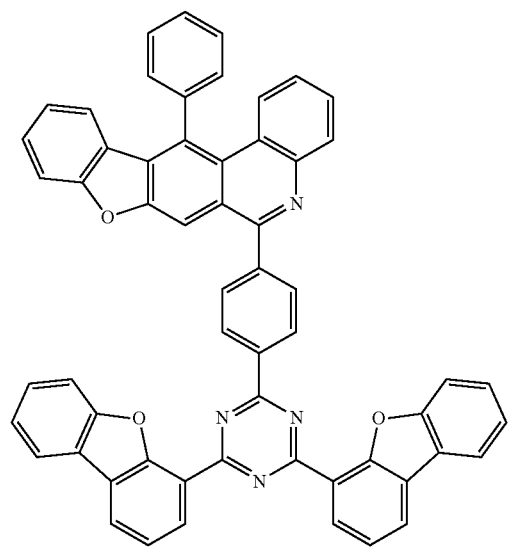 [SMILES: c1ccc(-c2c3c(cc4c(-c5ccc(-c6nc(-c7cccc8c7oc7ccccc78)nc(-c7cccc8c7oc7ccccc78)n6)cc5)nc5ccccc5c24)oc2ccccc23)cc1]
463

-continued
464
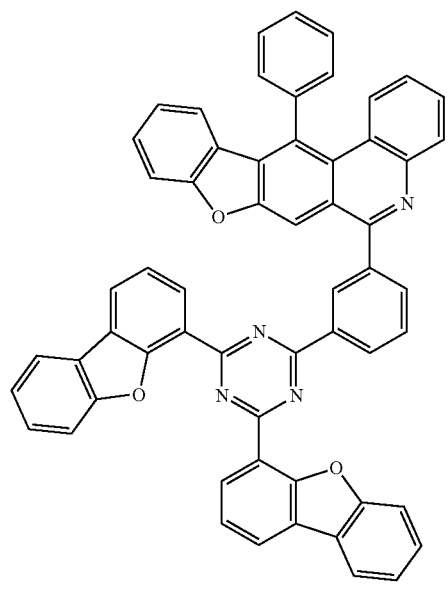
465
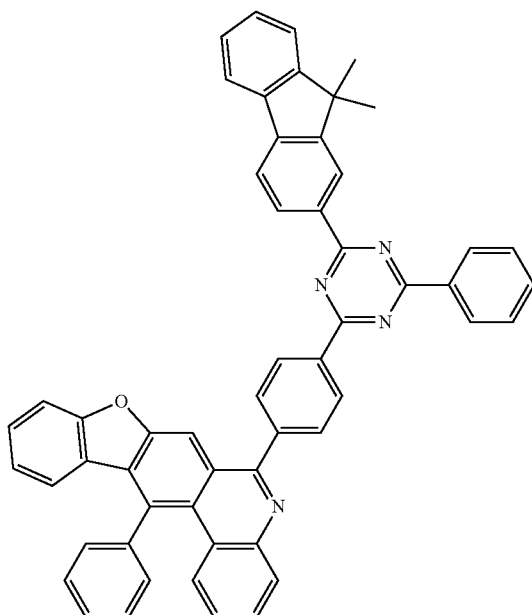 [SMILES: CC1(C)c2ccccc2-c2ccc(-c3nc(-c4ccccc4)nc(-c4ccc(-c5nc6ccccc6c6c(-c7ccccc7)c7c(cc56)oc5ccccc57)cc4)n3)cc21]
466
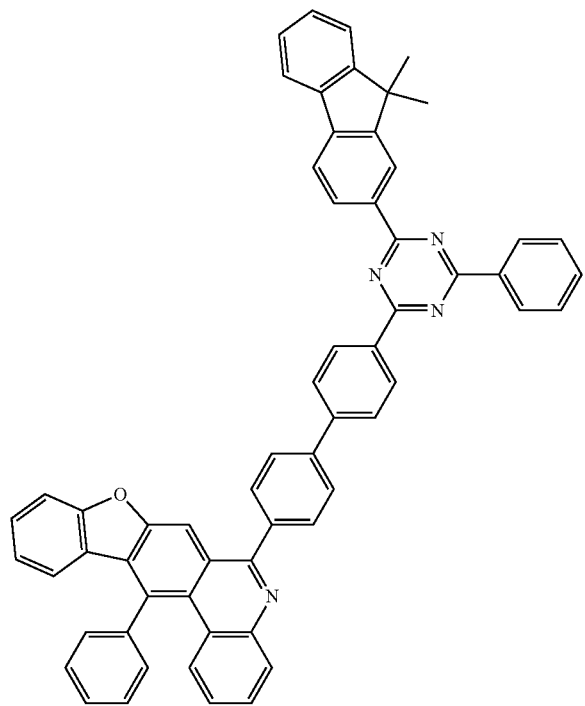
467
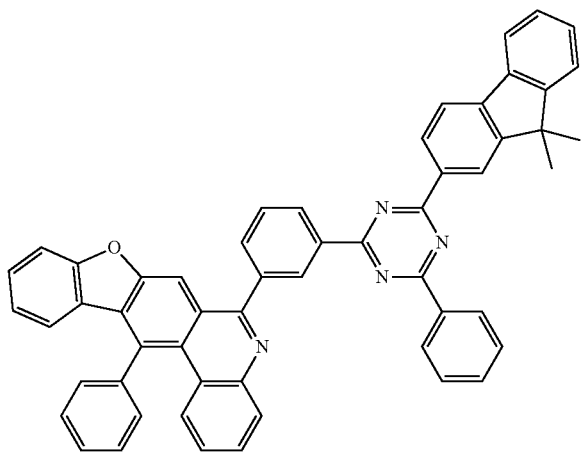

-continued
468
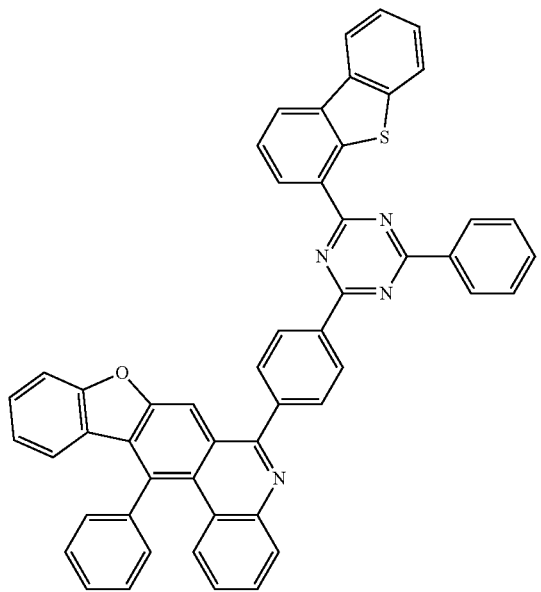
469
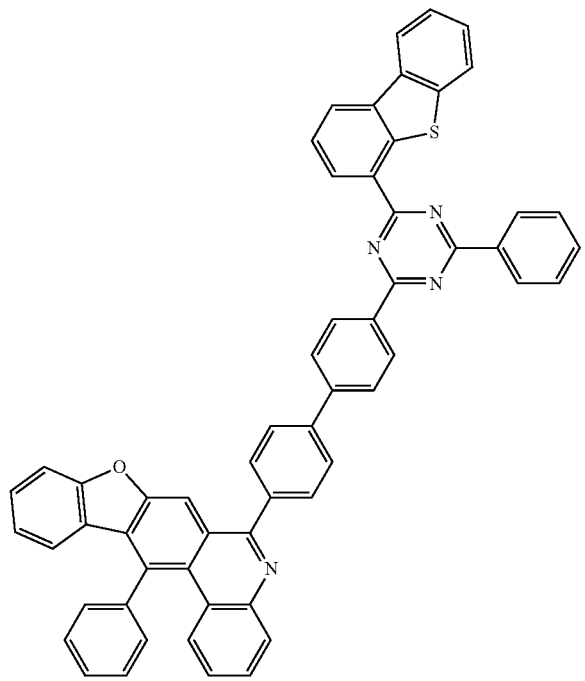
470
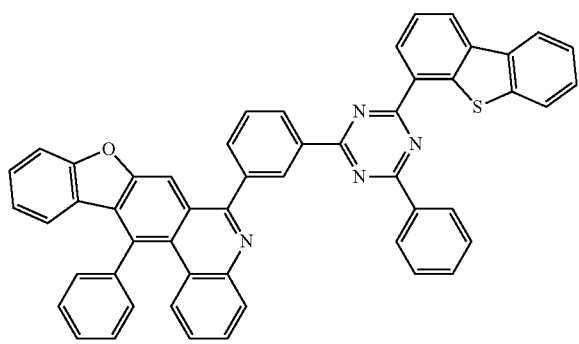
471
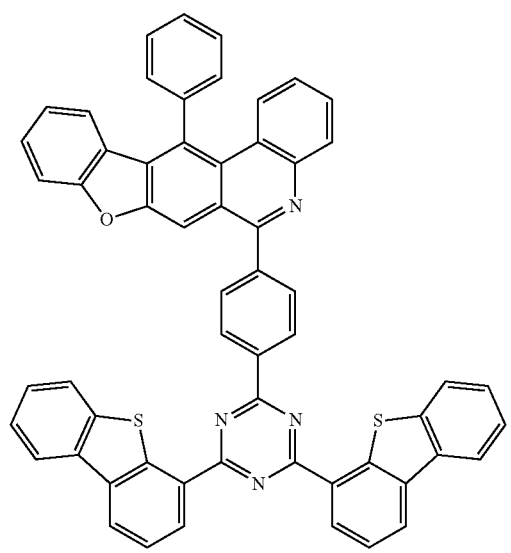 [SMILES: c1ccc(-c2c3c(cc4c(-c5ccc(-c6nc(-c7cccc8c7sc7ccccc78)nc(-c7cccc8c7sc7ccccc78)n6)cc5)nc5ccccc5c24)oc2ccccc23)cc1]

177
-continued
472
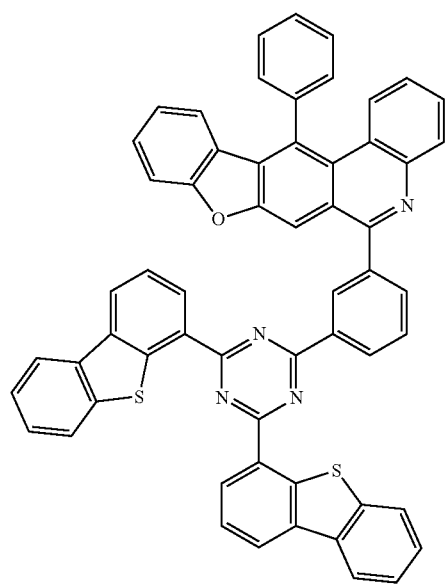
178
473
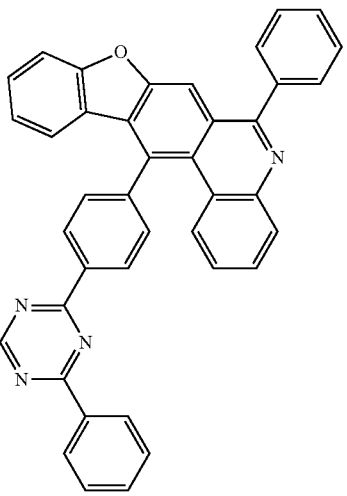
474
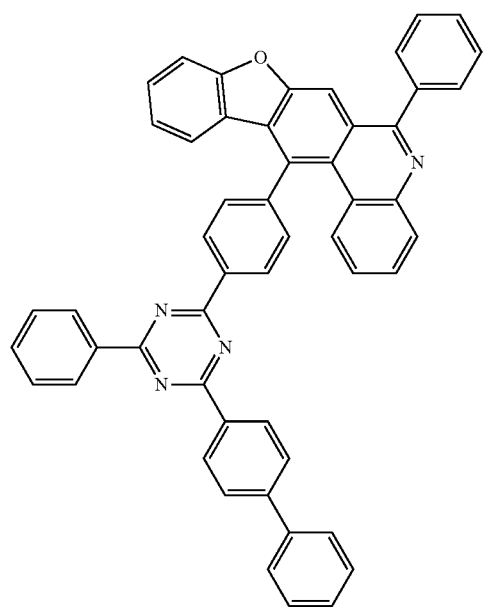
475
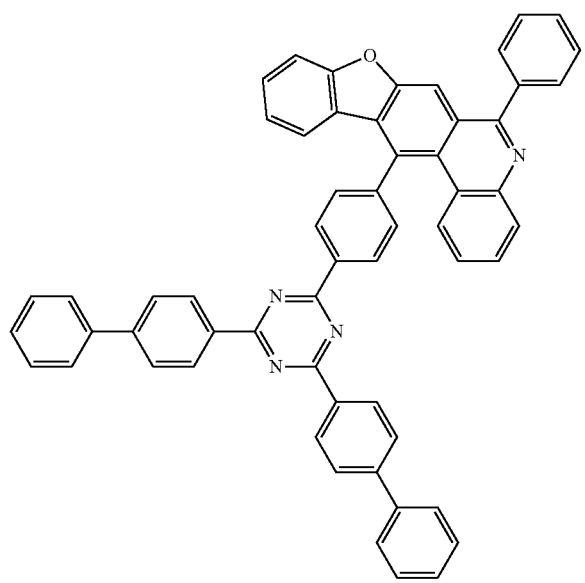

-continued
476
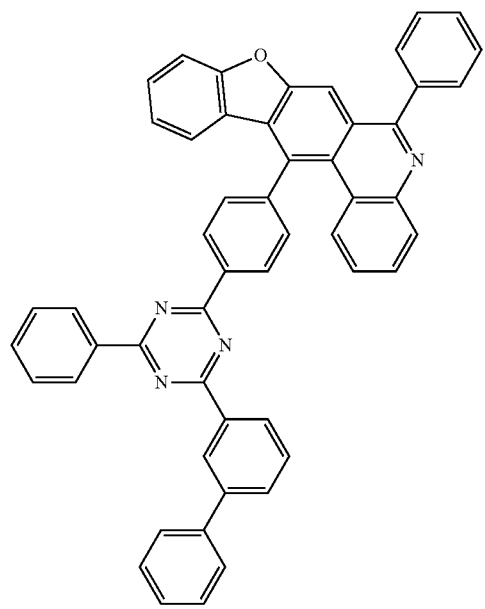
477
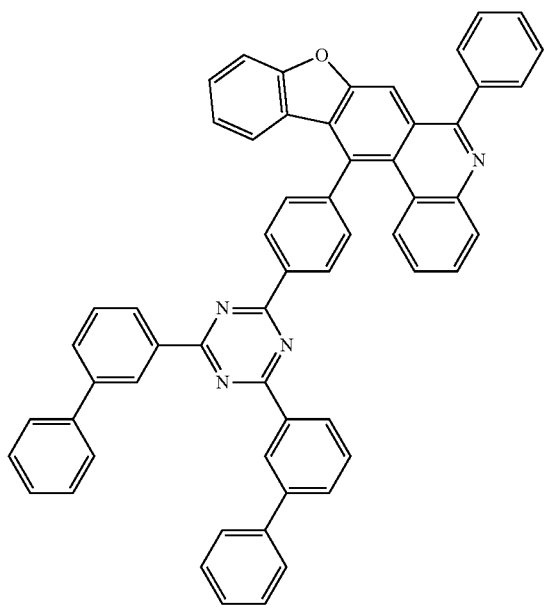
478
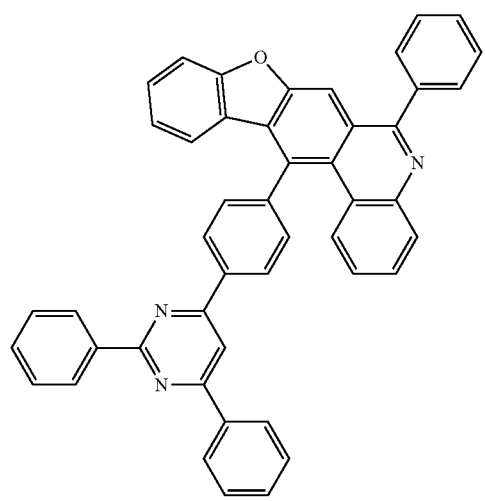
479
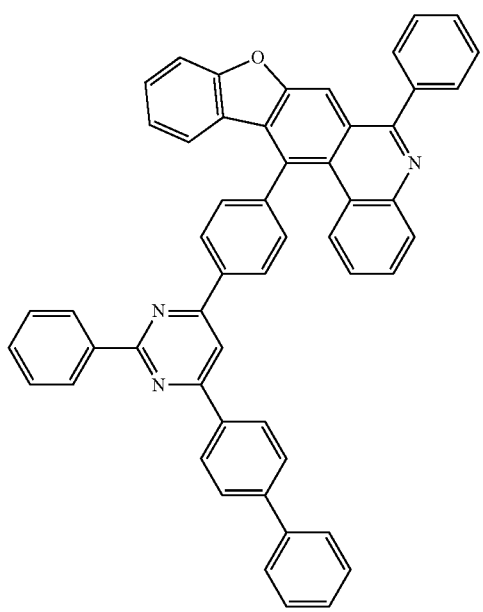

480
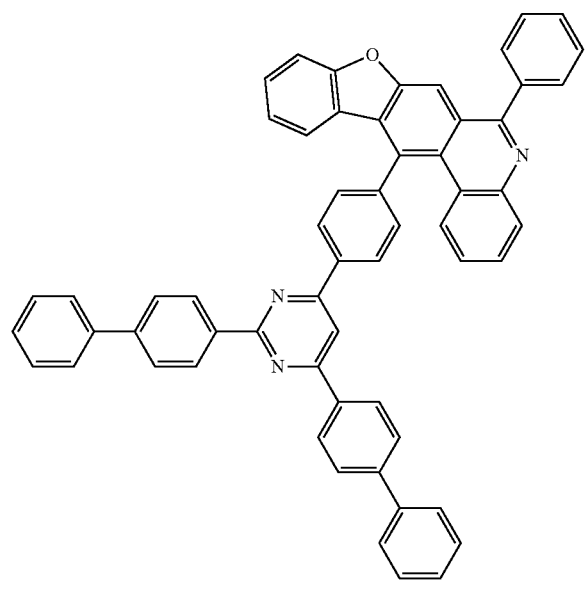
481
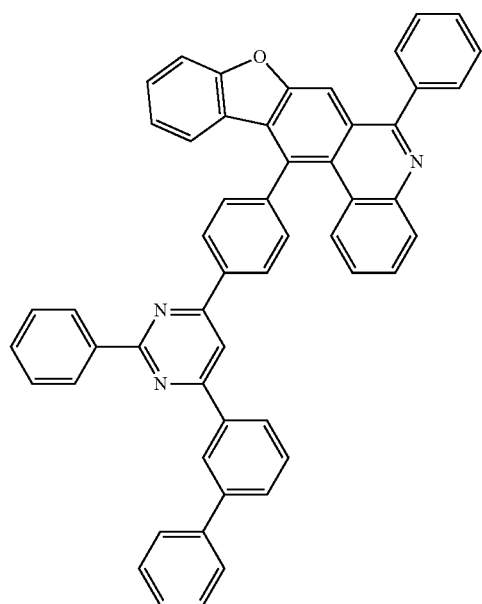
482
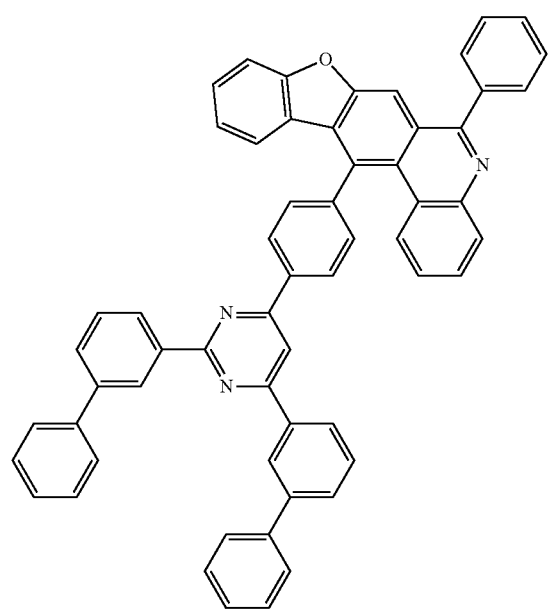
483
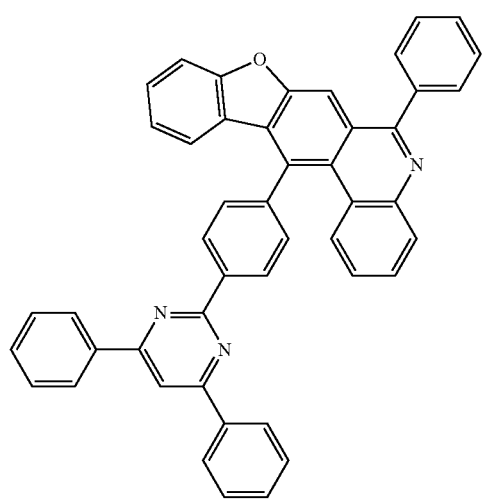 [SMILES: c1ccc(-c2nc(-c3ccccc3)nc(-c3ccc(-c4c5c(cc6c(-c7ccccc7)nc7ccccc7c46)oc4ccccc45)cc3)n2)cc1]

484
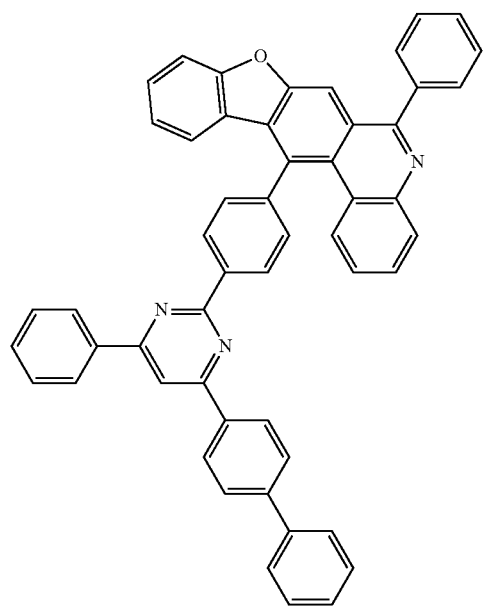
485
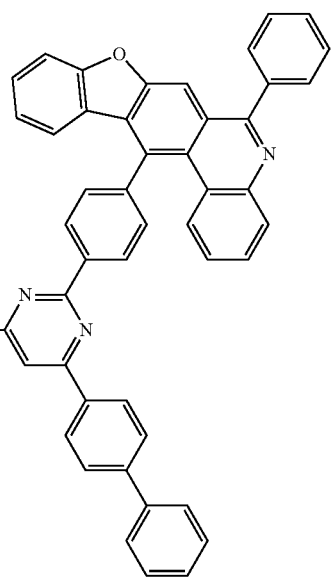
486
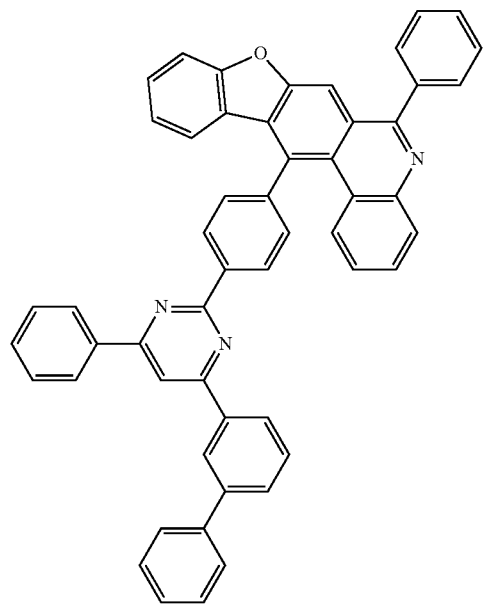 [SMILES: c1ccc(-c2cccc(-c3nc(-c4ccccc4)nc(-c4ccc(-c5c6c(cc7c(-c8ccccc8)nc8ccccc8c57)oc5ccccc56)cc4)n3)c2)cc1]
487
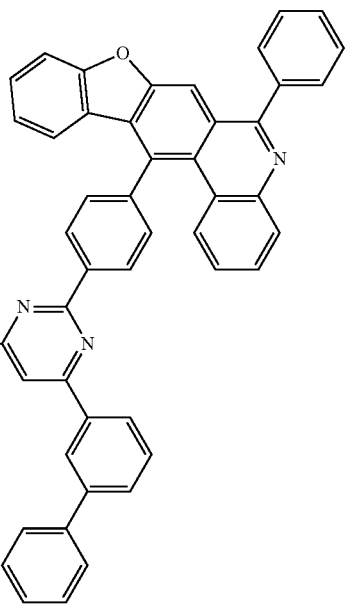

-continued
488
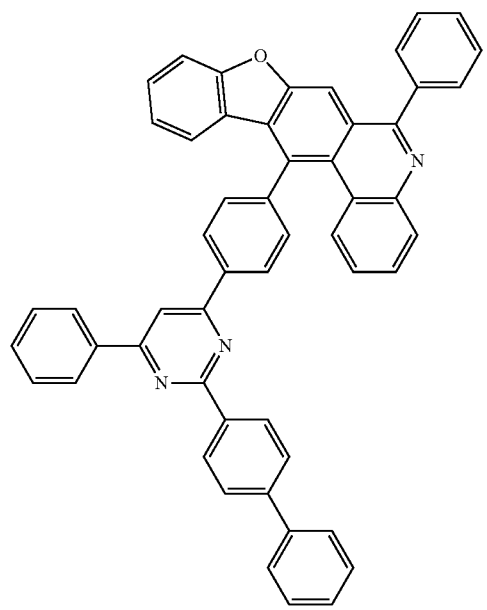 [SMILES: c1ccc(-c2ccc(-c3nc(-c4ccccc4)nc(-c4ccc(-c5c6c(cc7c(-c8ccccc8)nc8ccccc8c57)oc5ccccc56)cc4)n3)cc2)cc1]
489
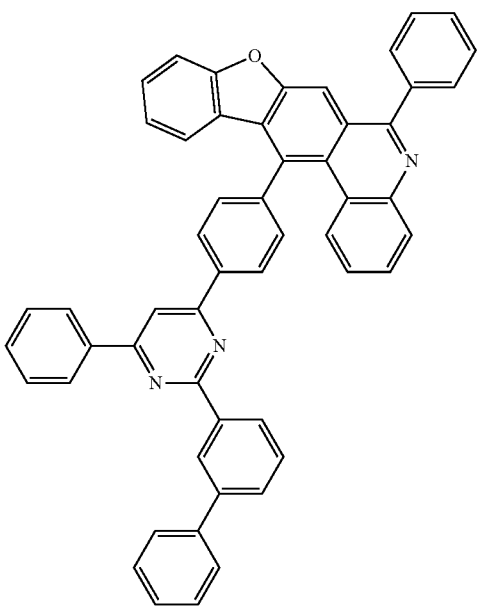
490
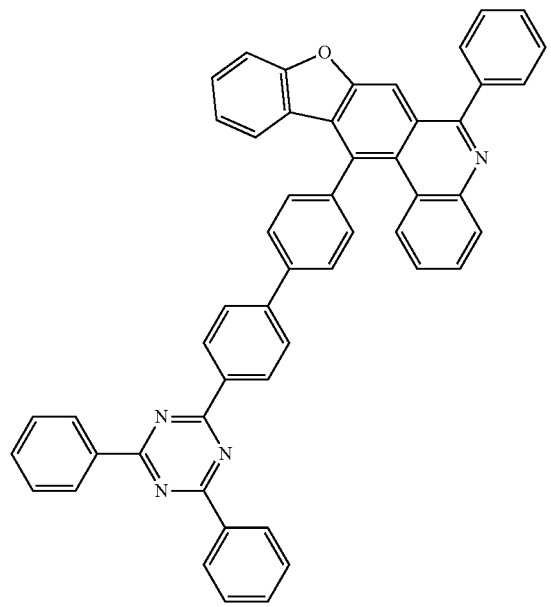
491
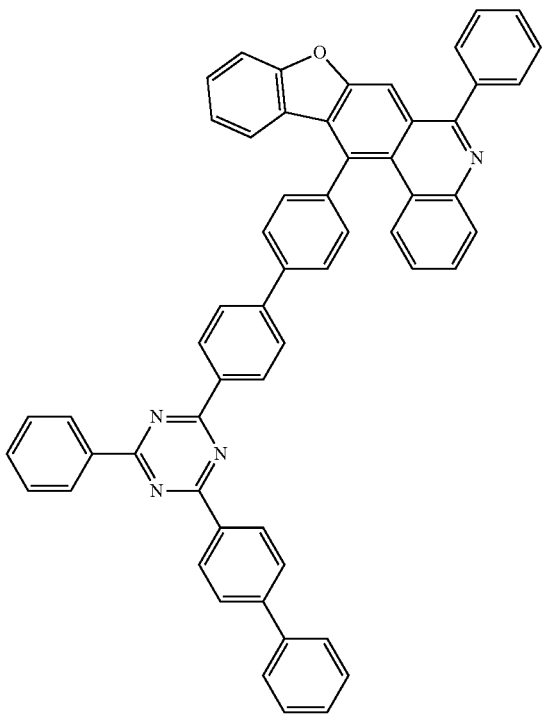

-continued
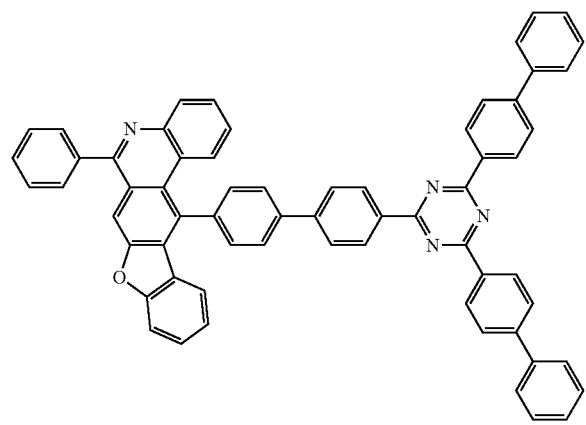
492
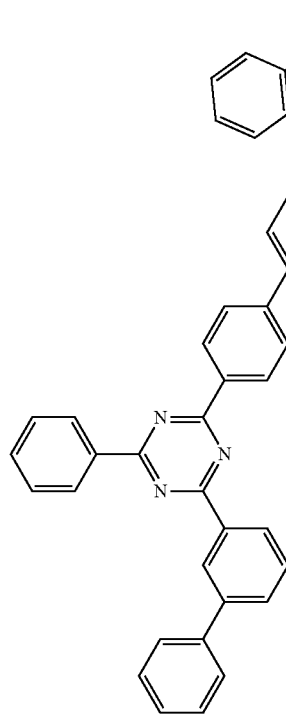
493
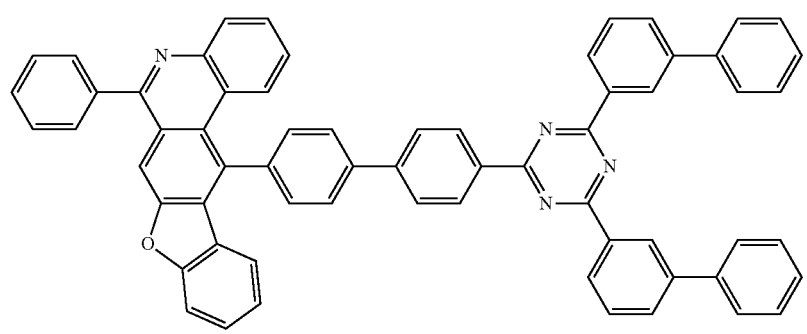 [SMILES: c1ccc(-c2cccc(-c3nc(-c4ccc(-c5ccc(-c6c7c(cc8c(-c9ccccc9)nc9ccccc9c68)oc6ccccc67)cc5)cc4)nc(-c4cccc(-c5ccccc5)c4)n3)c2)cc1]
494

-continued
495
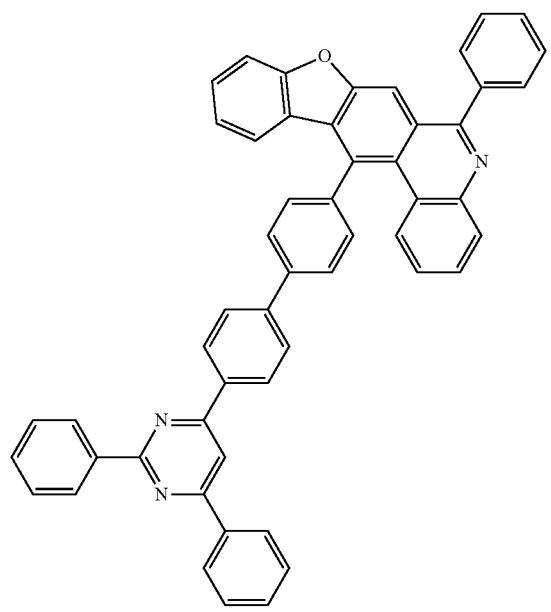
496
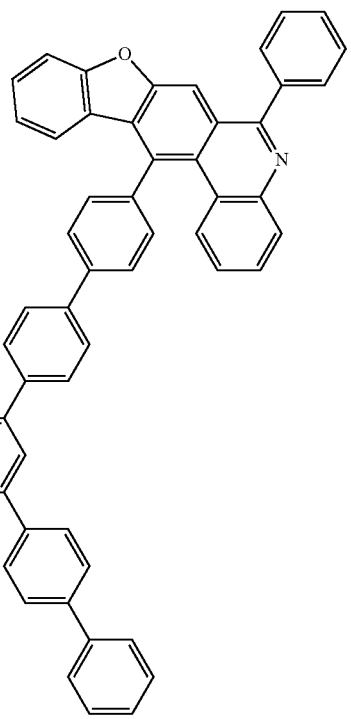
497
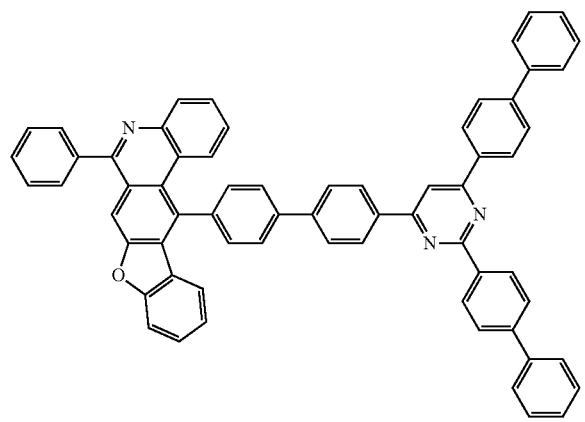
498
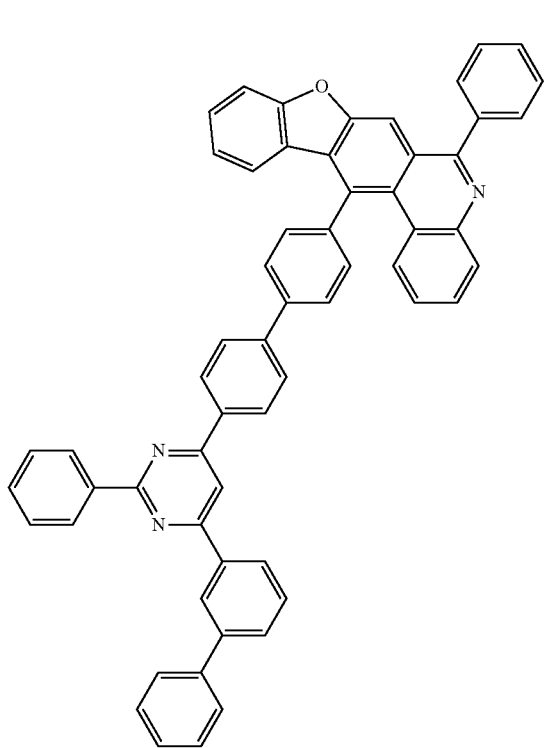

499
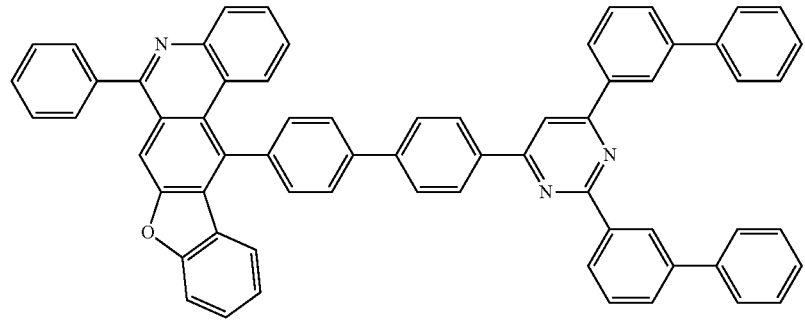
500
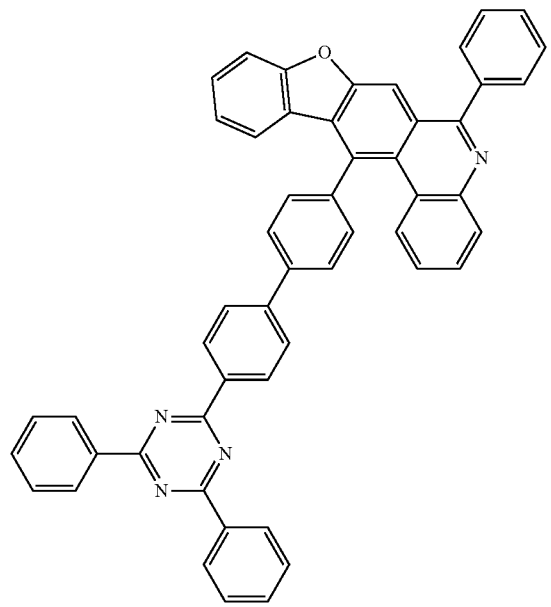
501
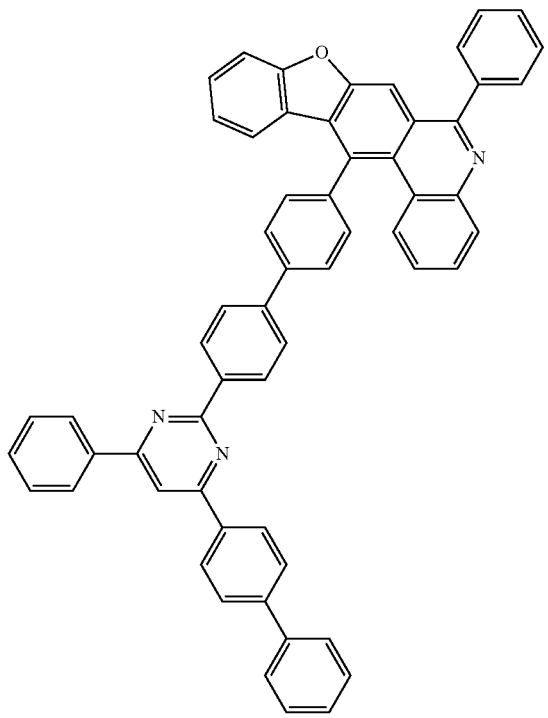

-continued
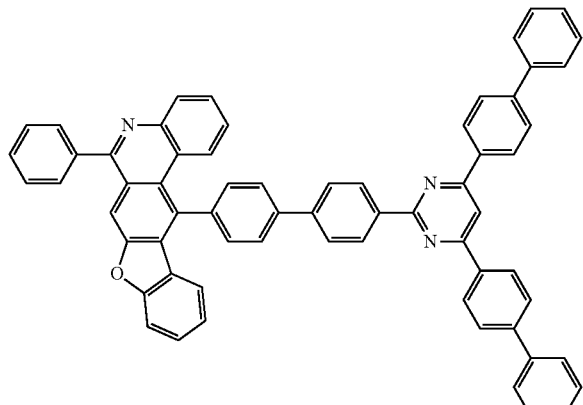
502
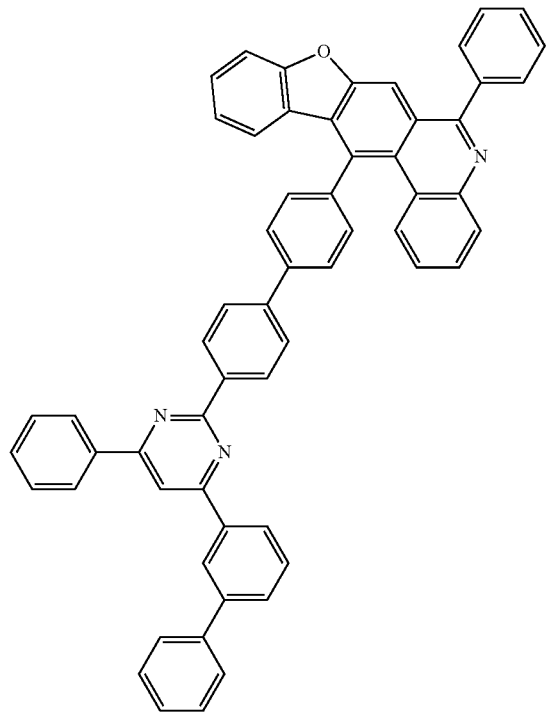
503
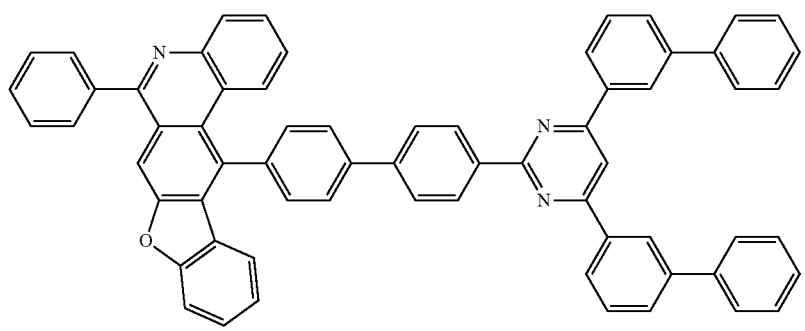
504

-continued
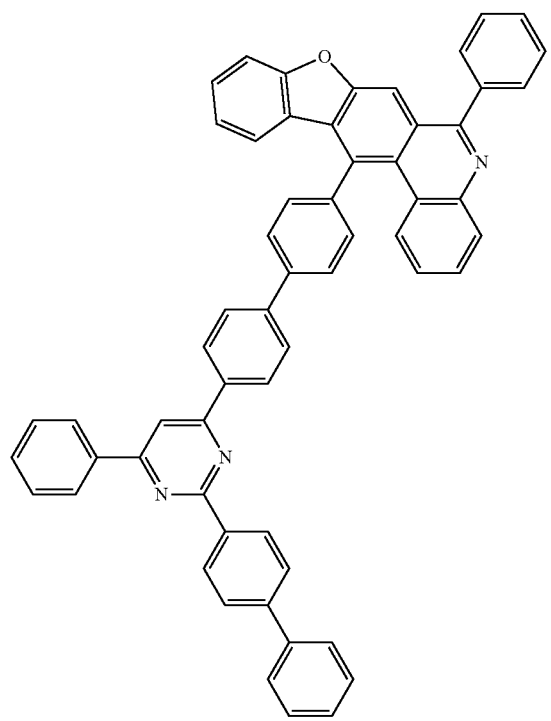
505
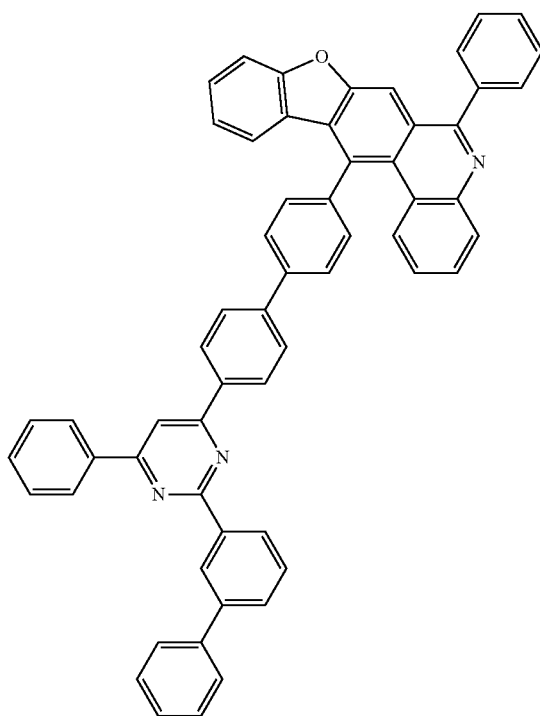
506
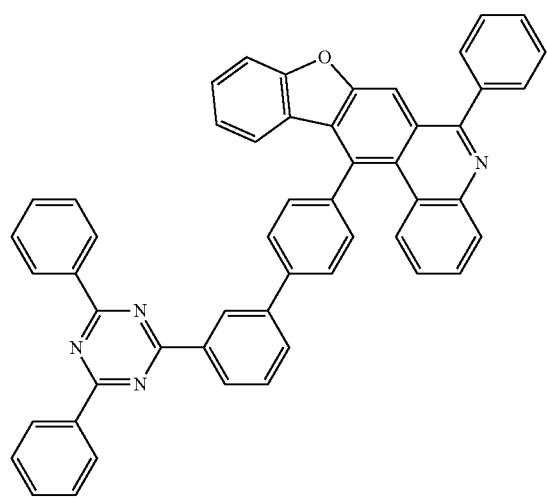
507
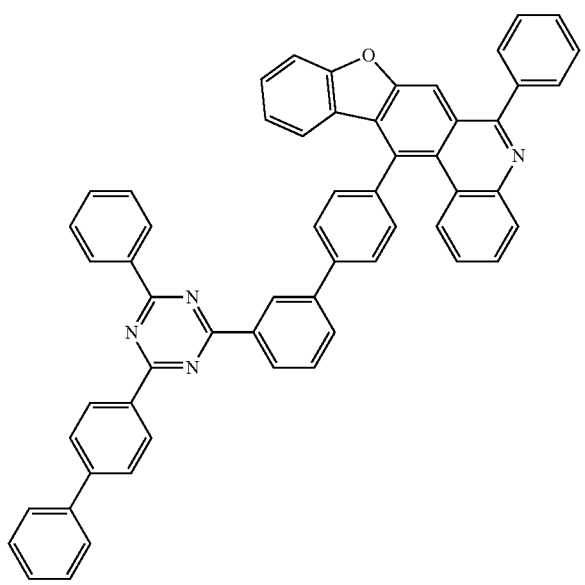
508

-continued
509
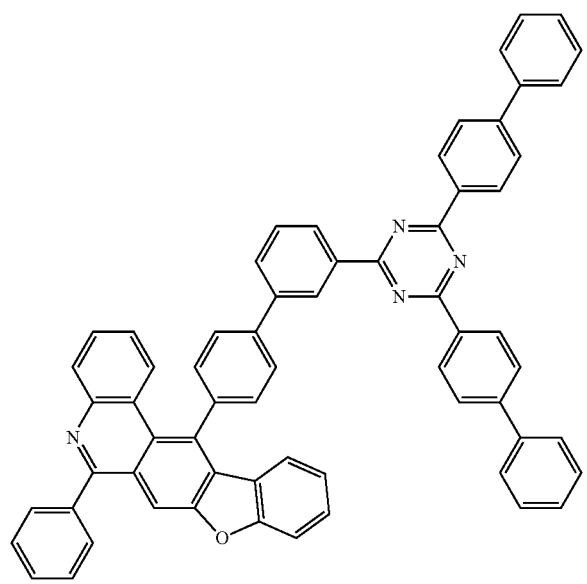
510
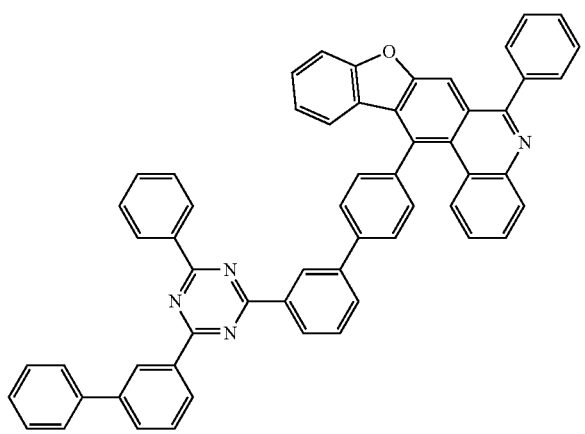
511
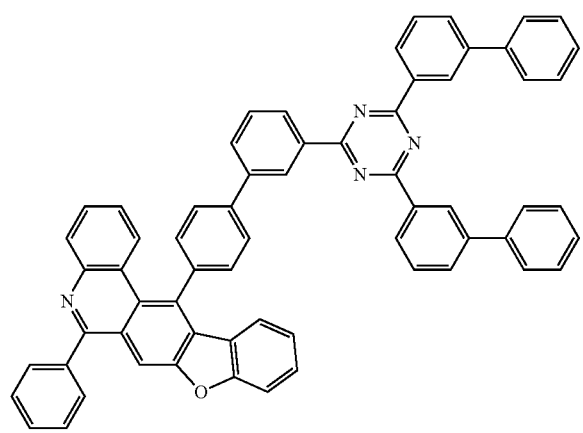
512
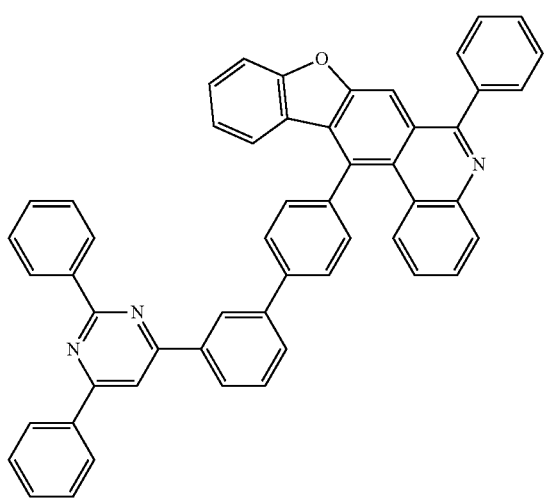

-continued
513
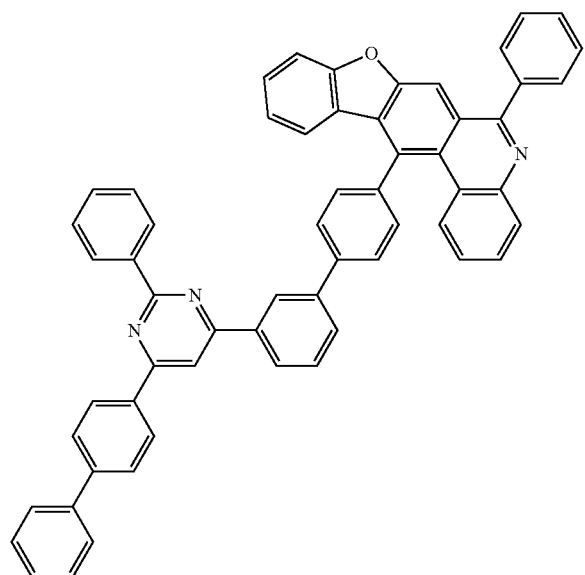
514
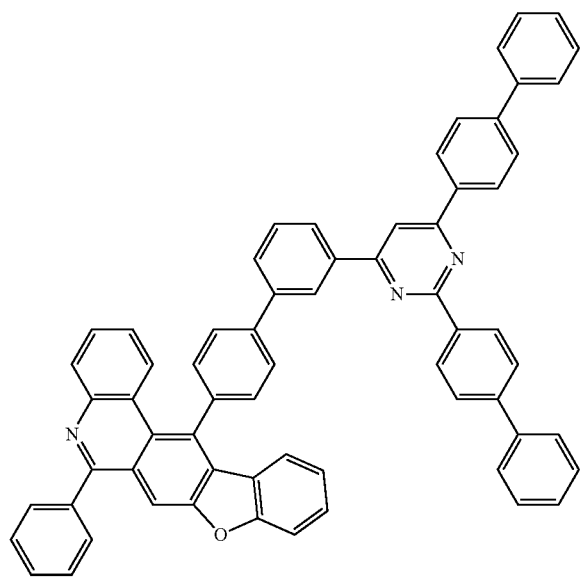
515
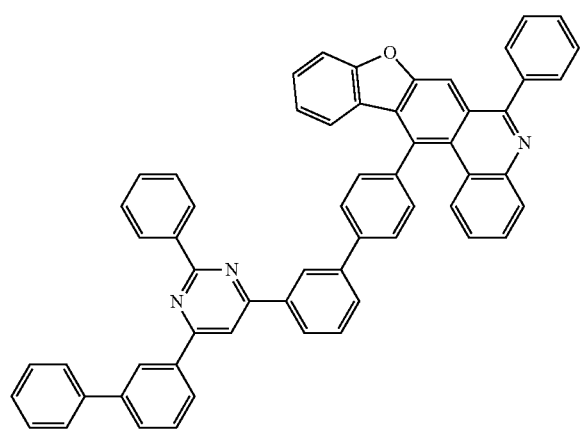
516
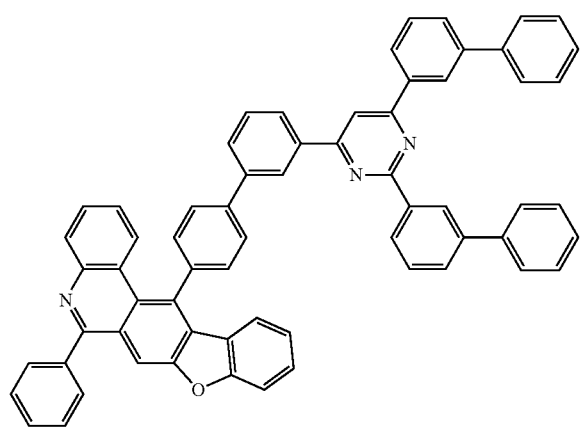
517
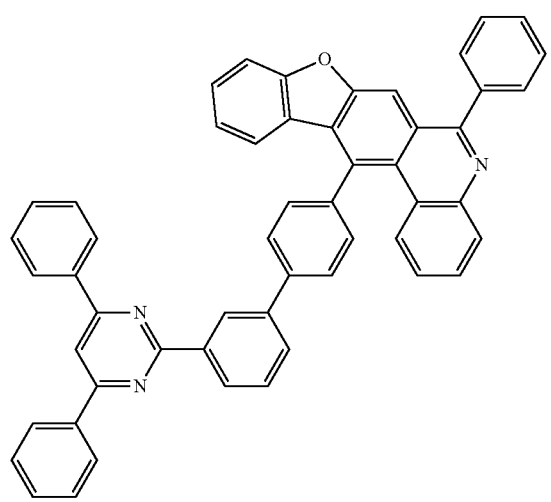
518
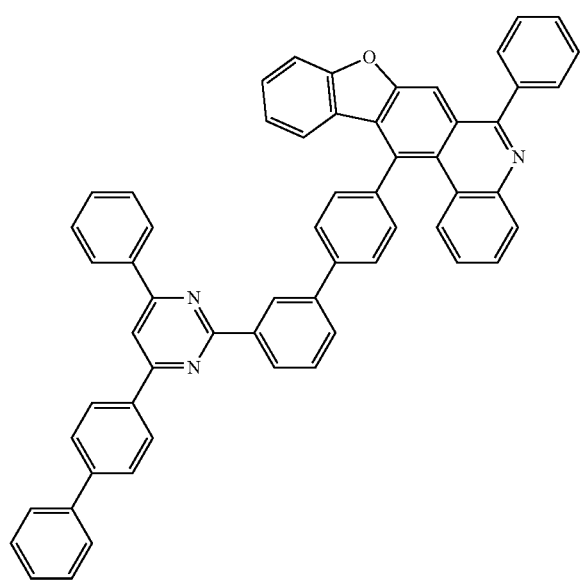

-continued
519
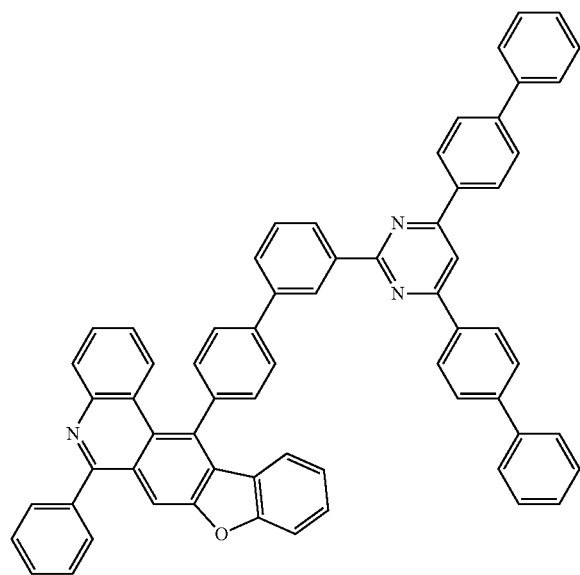
520
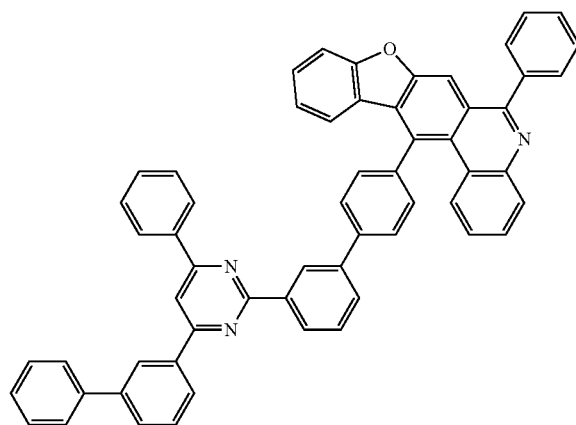
521
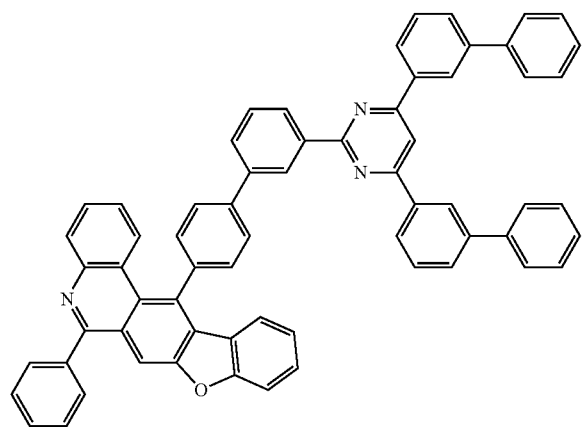
522
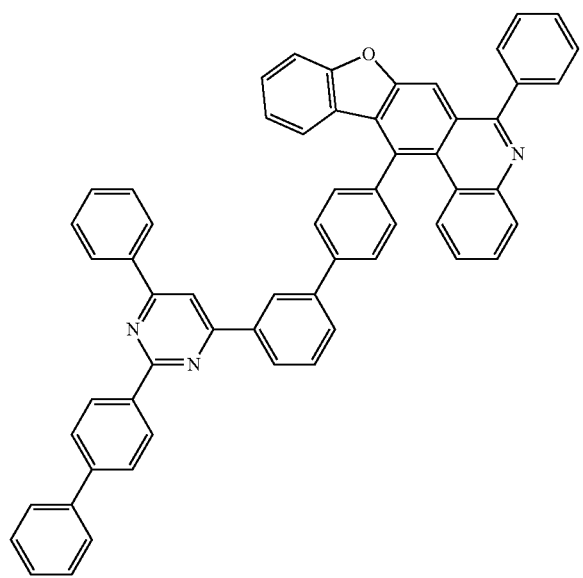

-continued
523
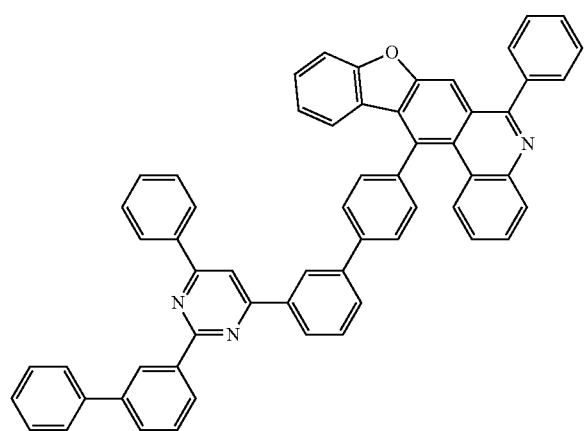
524
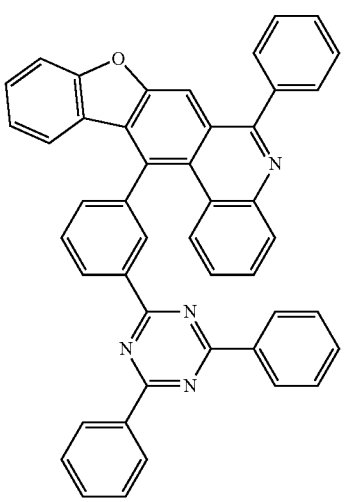 [SMILES: c1ccc(-c2cc(-c3cccc(-c4c5c(cc6c(-c7ccccc7)nc7ccccc7c46)oc4ccccc45)c3)nc(-c3ccccc3)n2)cc1]
525
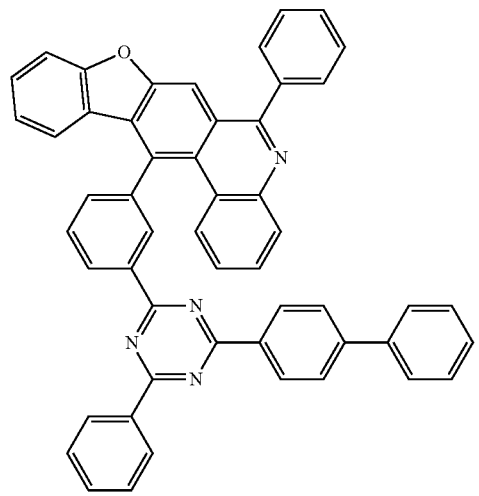
526
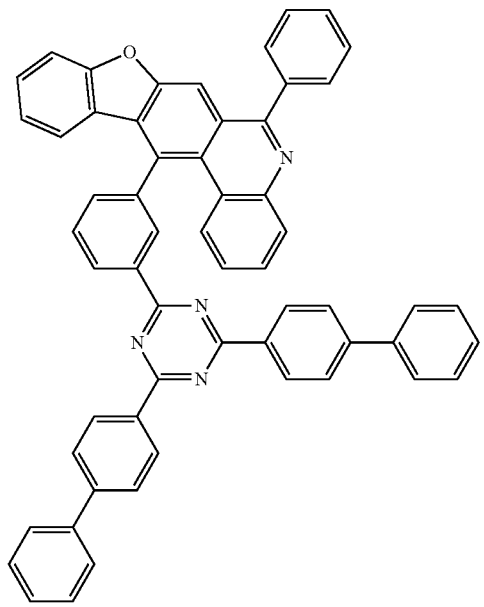

-continued
527
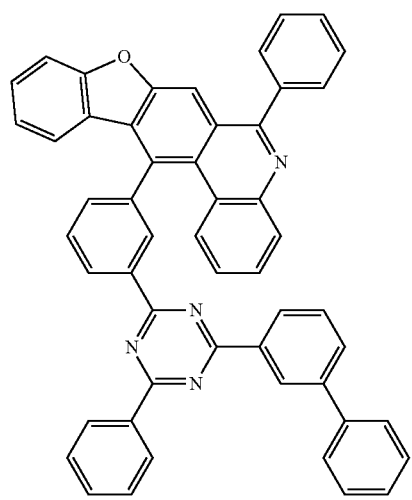
528
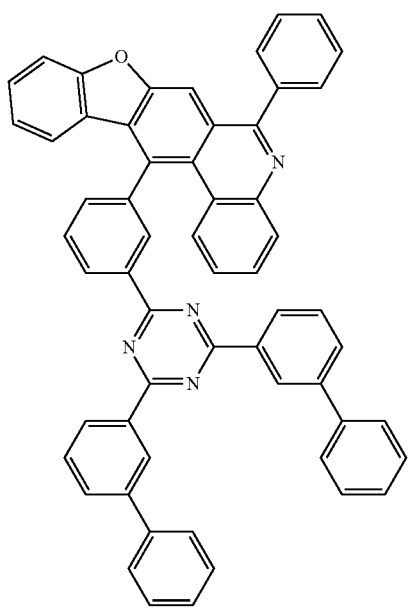
529
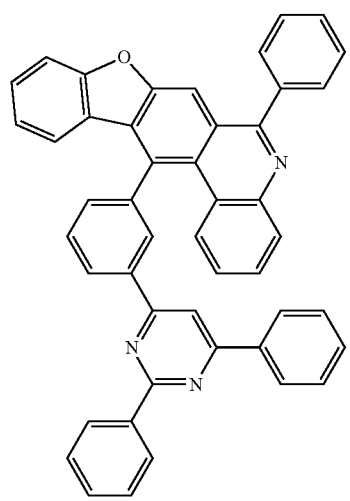
530
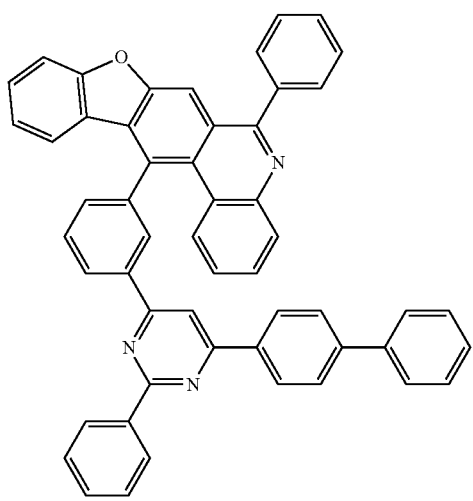

531
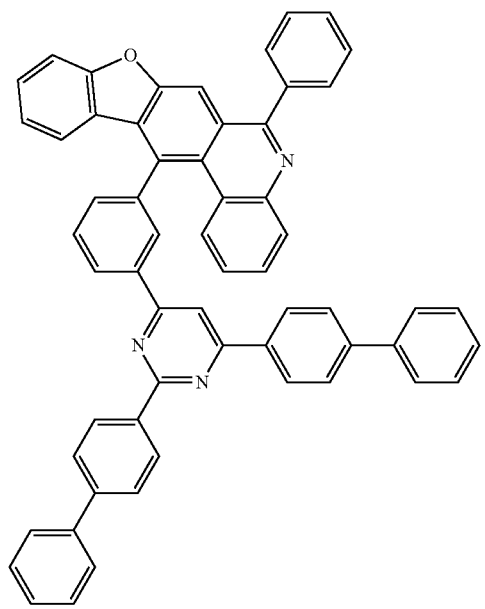
532
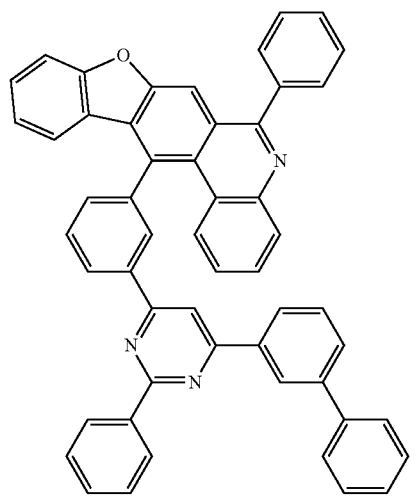
533
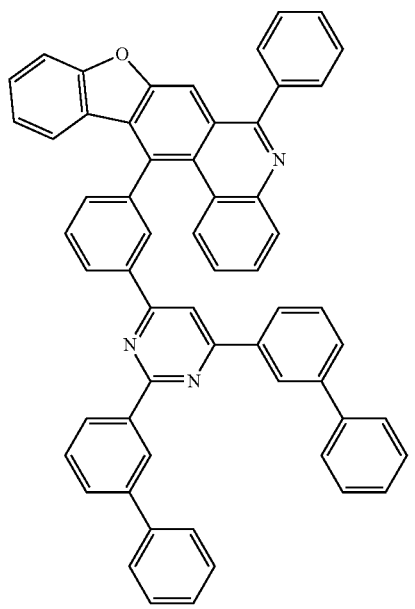
534

535
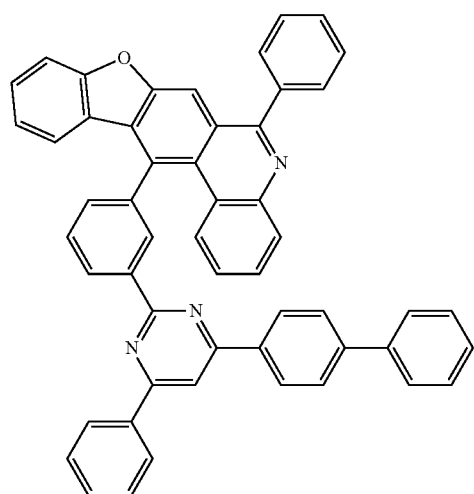
536
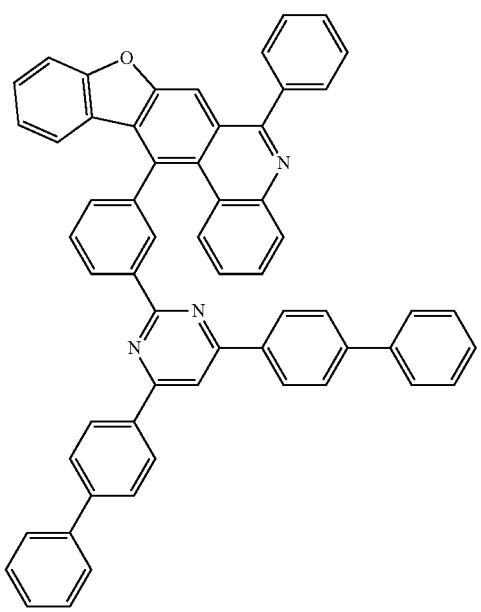
537
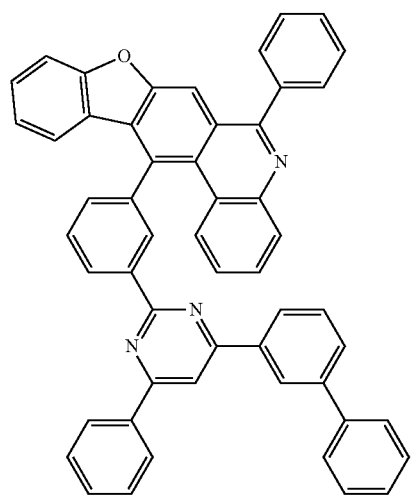
538
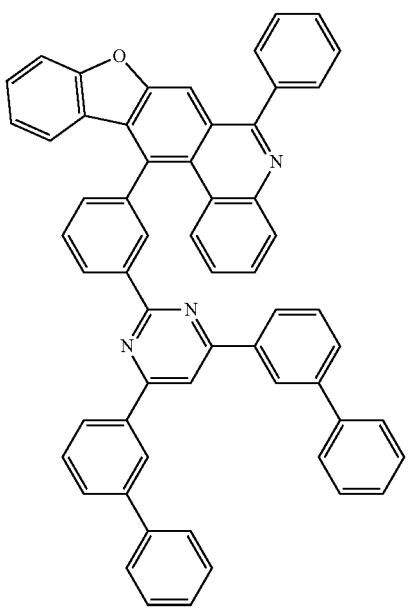

-continued
211
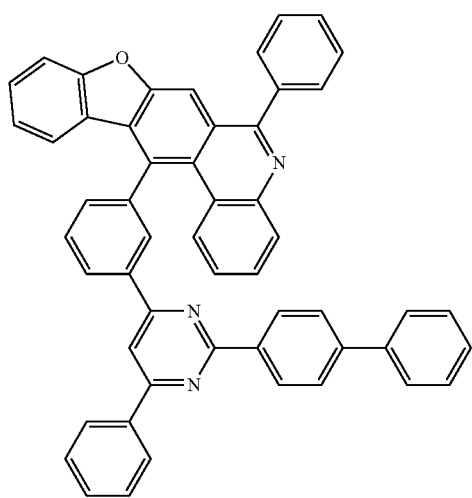
539
212
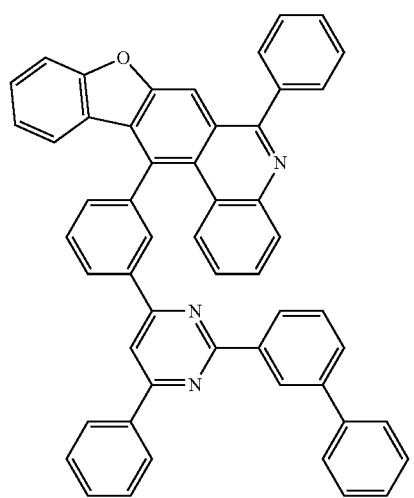
540
541
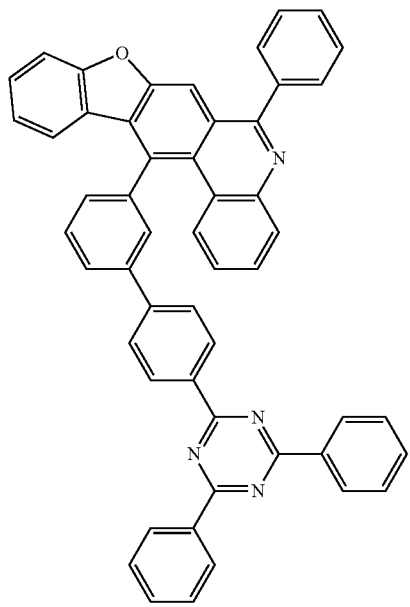
542
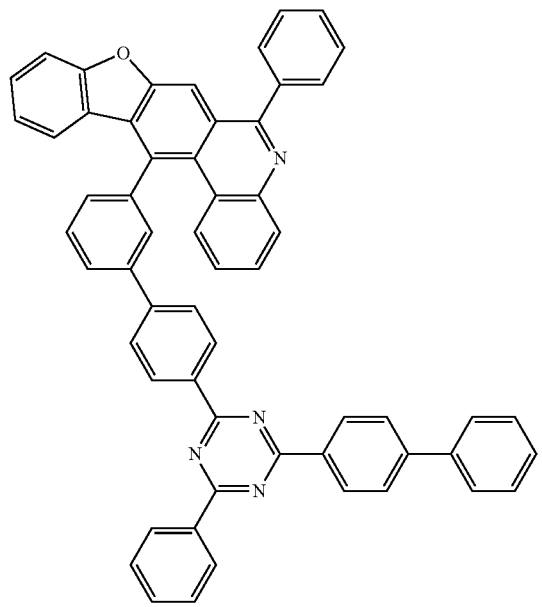

-continued
543
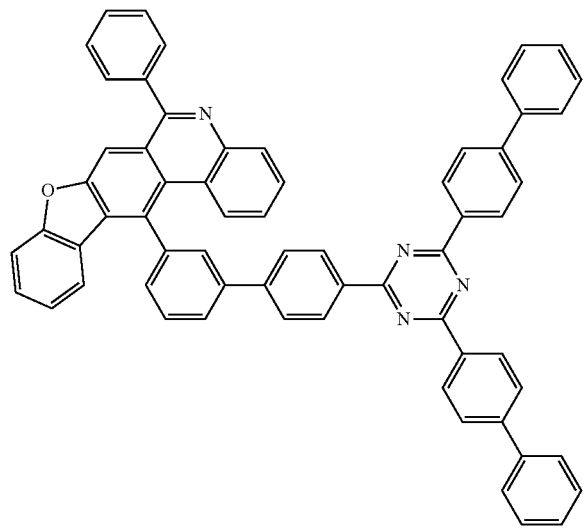
544
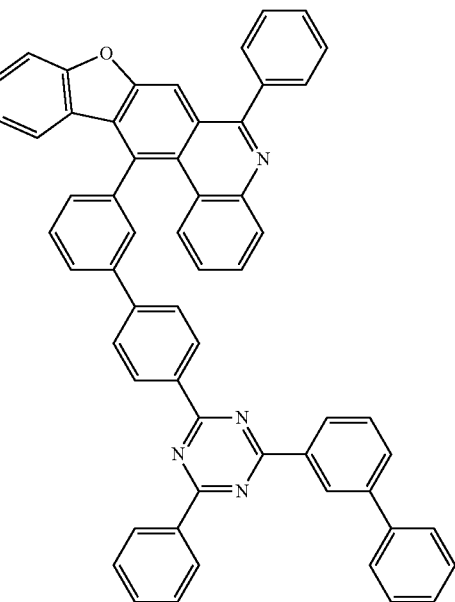
545
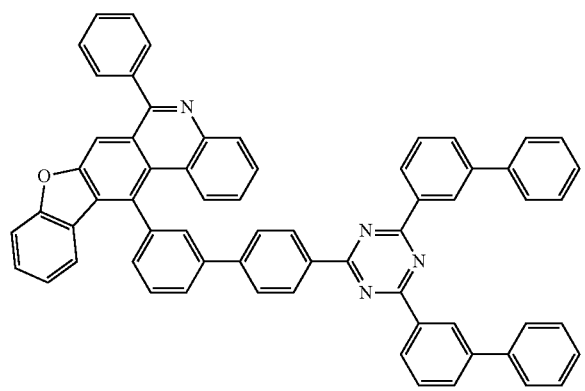
546
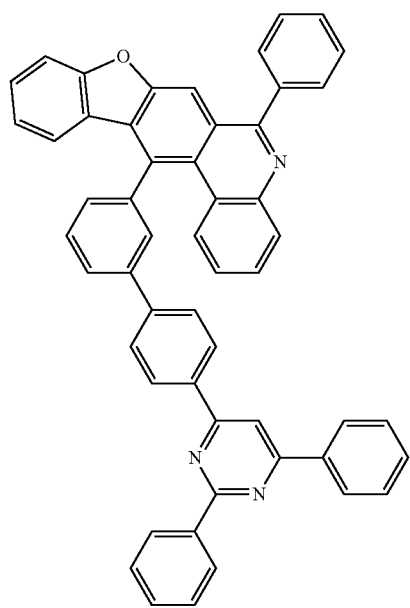

-continued
547
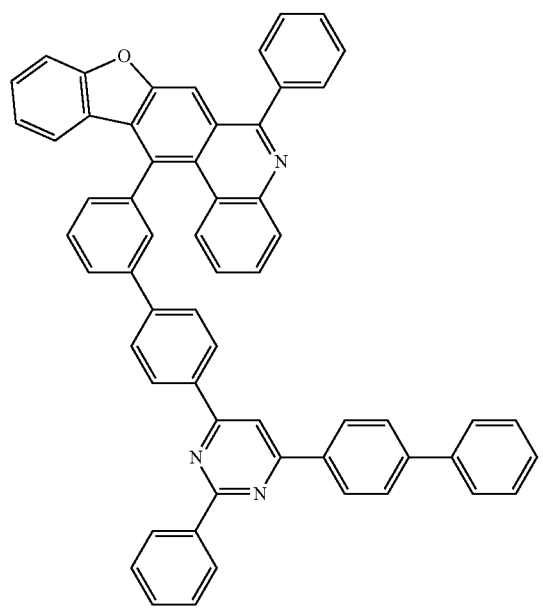
548
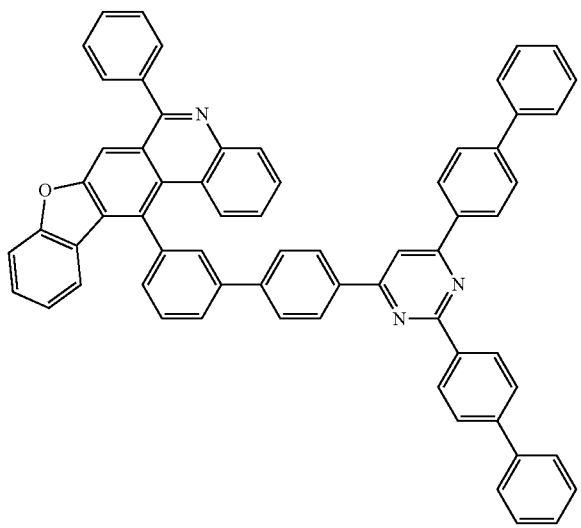
549
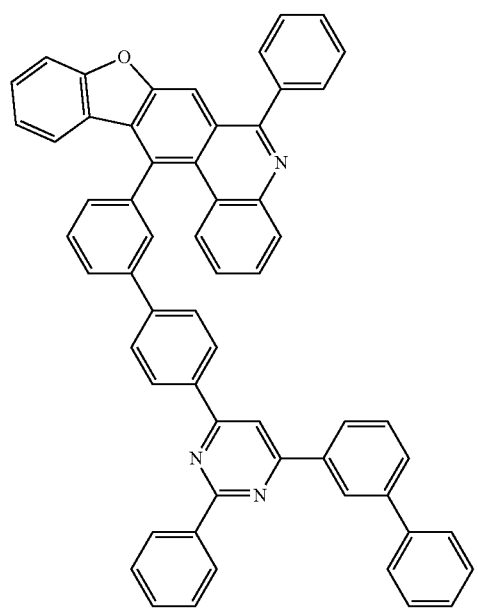
550
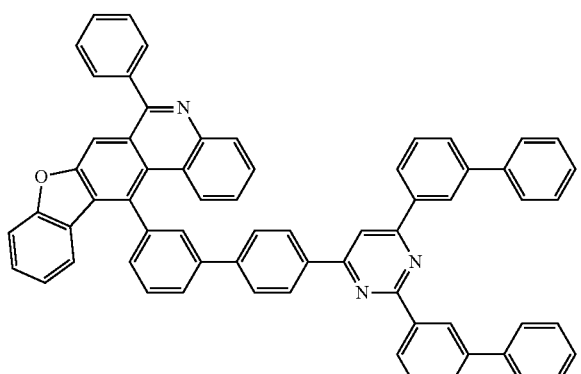

551 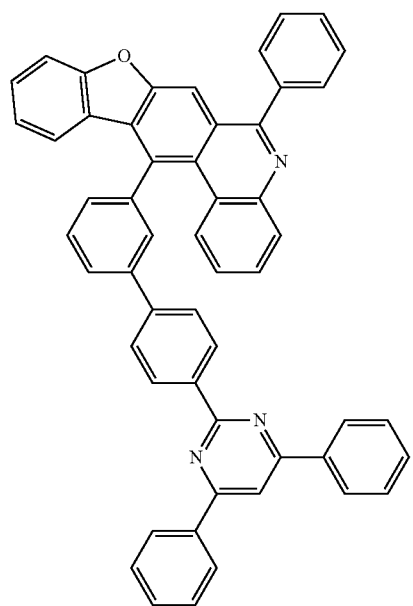
552 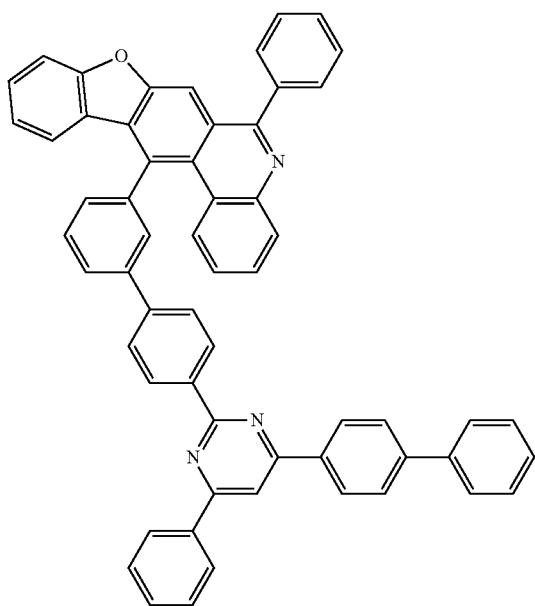
553 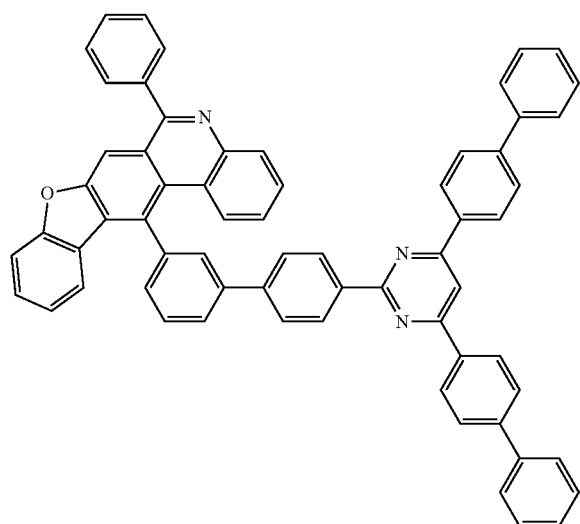
554 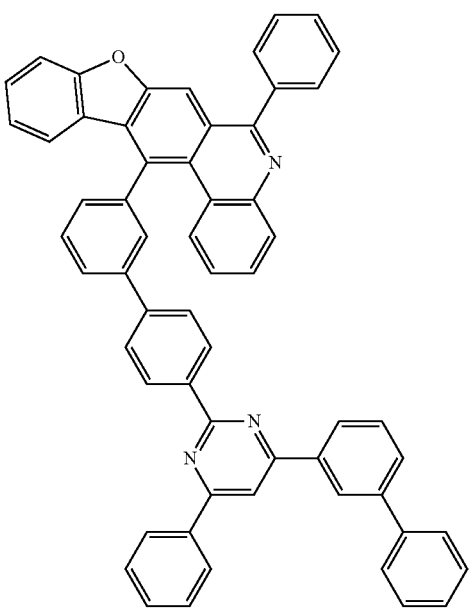

555
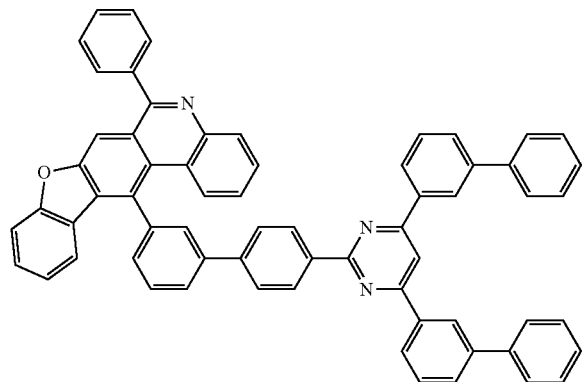
556
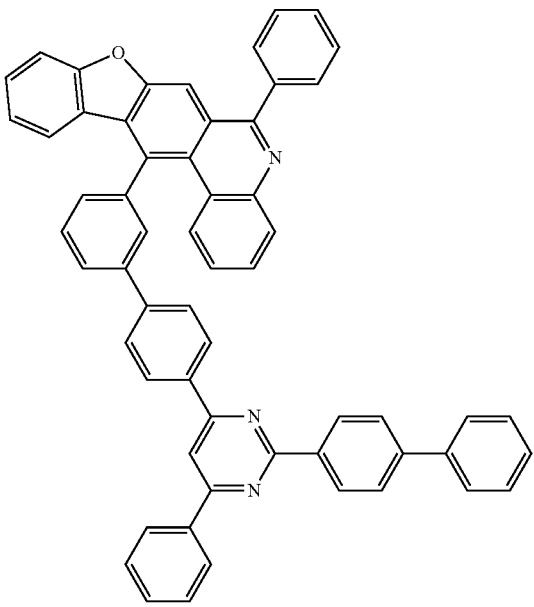
557
558

-continued
221
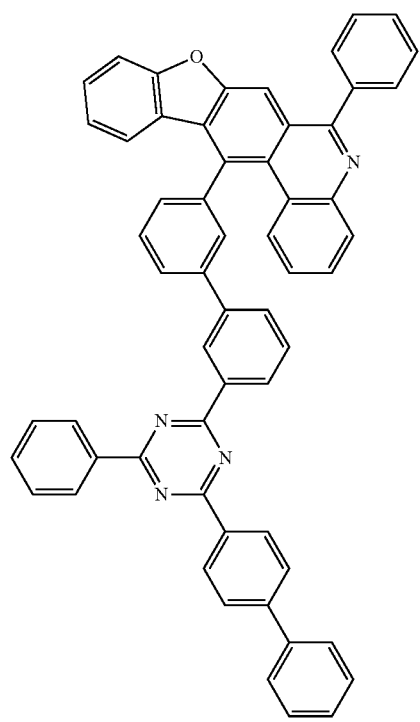
559
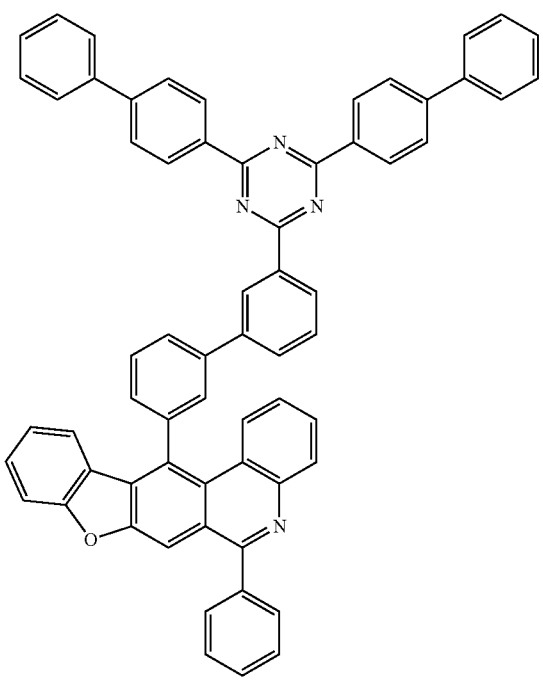
222
561
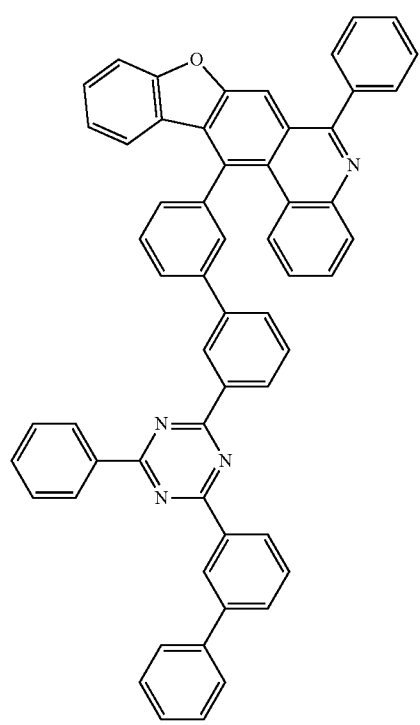
560
562
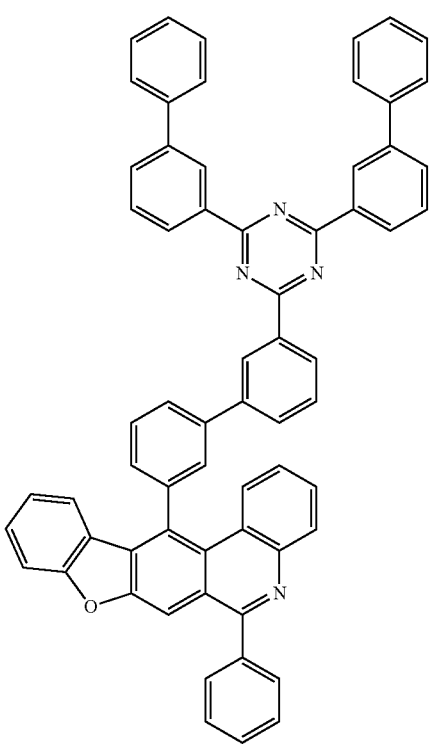

-continued
563
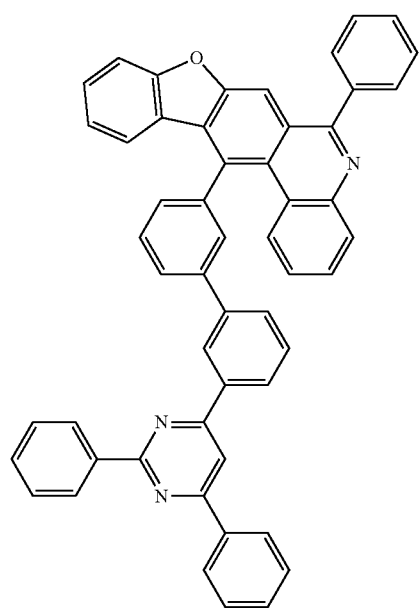
564
565
566

-continued
567
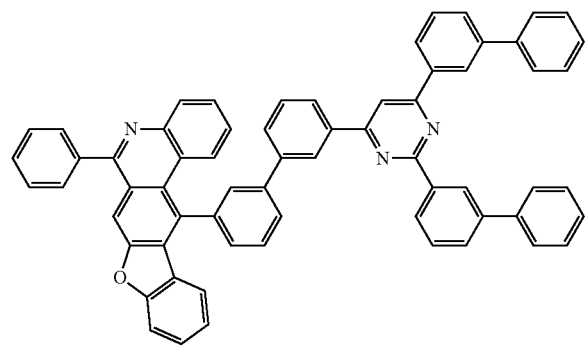
568
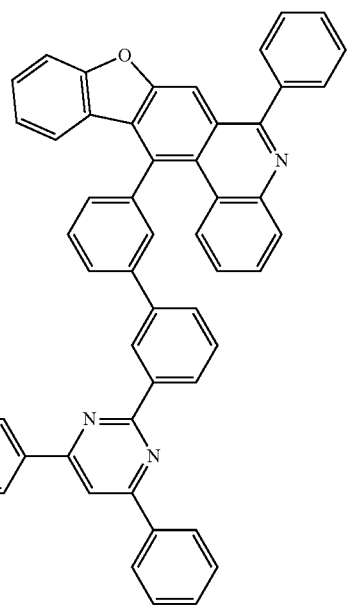
569
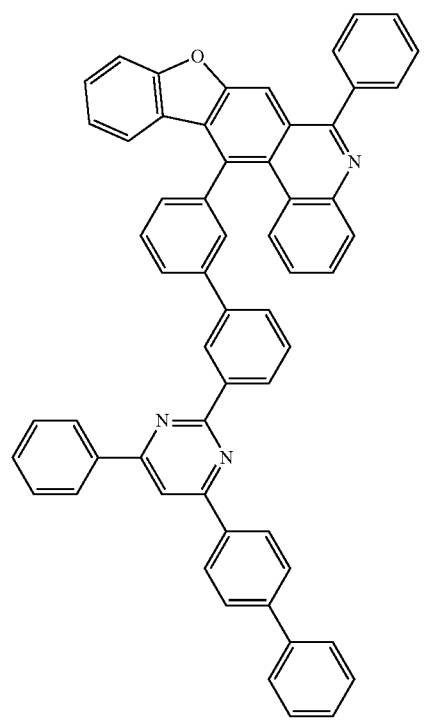
570
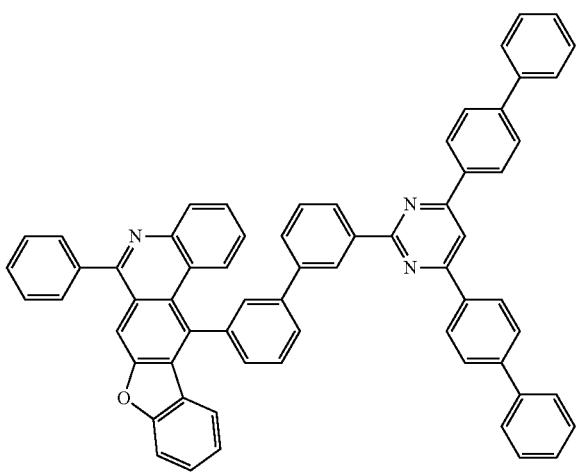

-continued
571 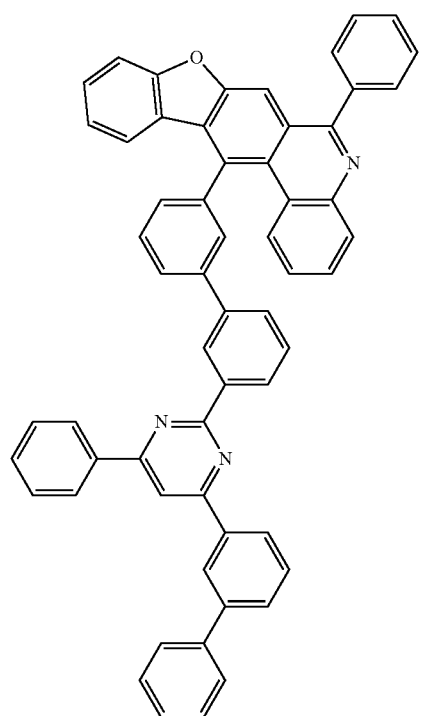
572 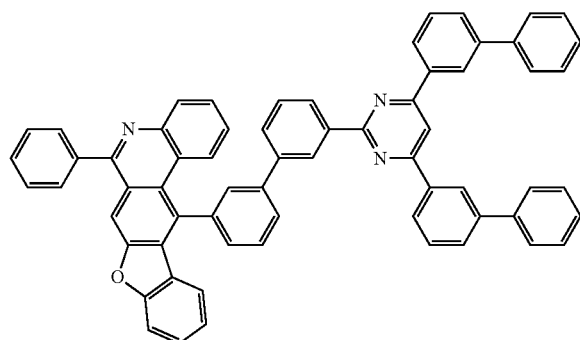
573 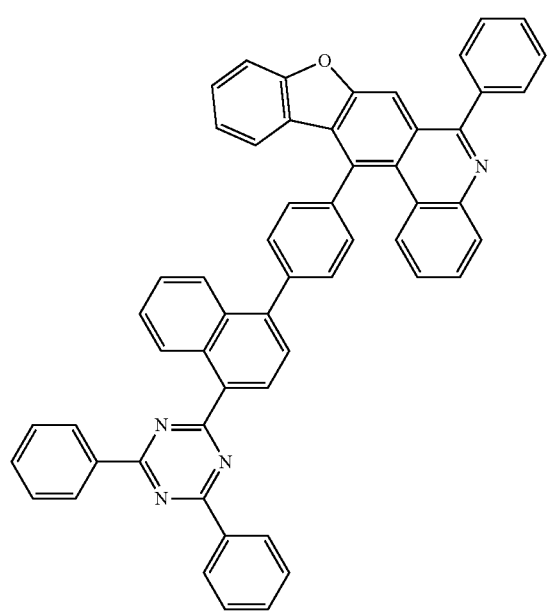 [SMILES: c1ccc(-c2nc(-c3ccccc3)nc(-c3ccc(-c4ccc(-c5c6c(cc7c(-c8ccccc8)nc8ccccc8c57)oc5ccccc56)cc4)c4ccccc34)n2)cc1]
574 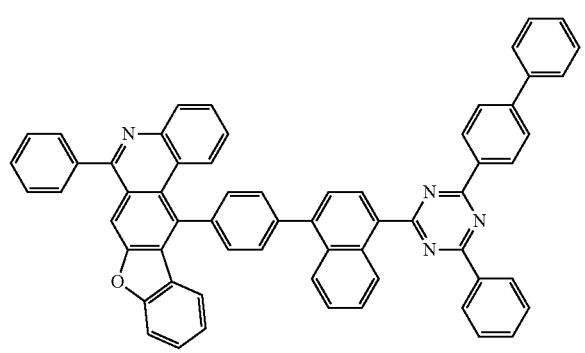

-continued
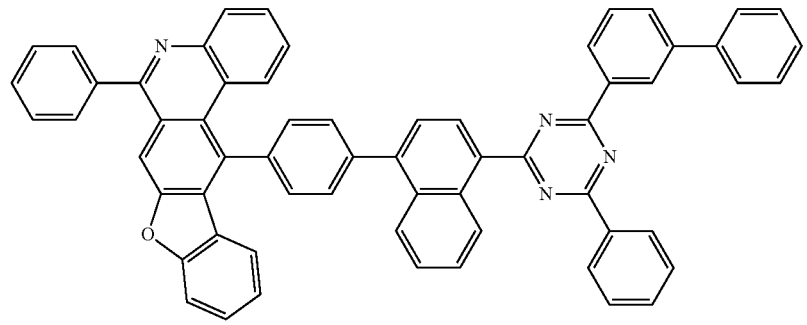 [SMILES: c1ccc(-c2cccc(-c3nc(-c4ccccc4)nc(-c4ccc(-c5ccc(-c6c7c(cc8c(-c9ccccc9)nc9ccccc9c68)oc6ccccc67)cc5)c5ccccc45)n3)c2)cc1]
575
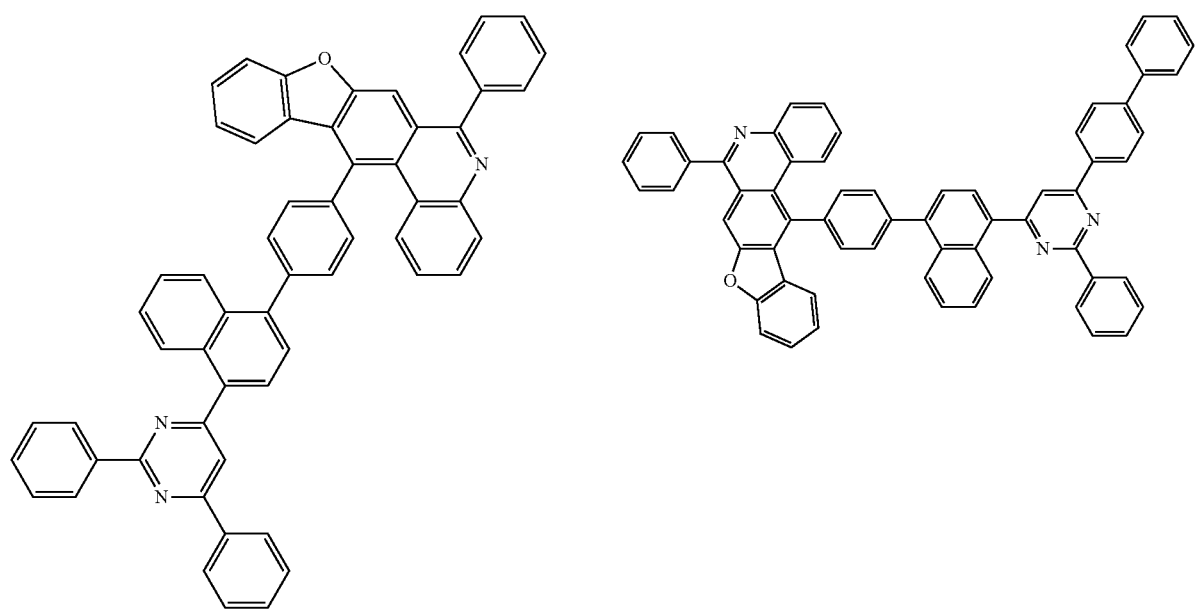
576
577
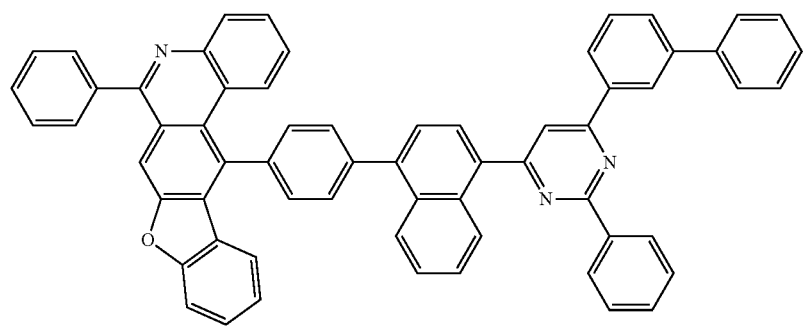
578

-continued
579
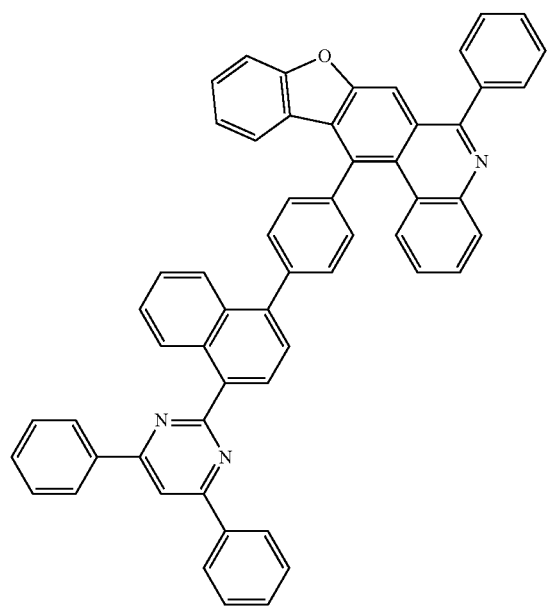
580
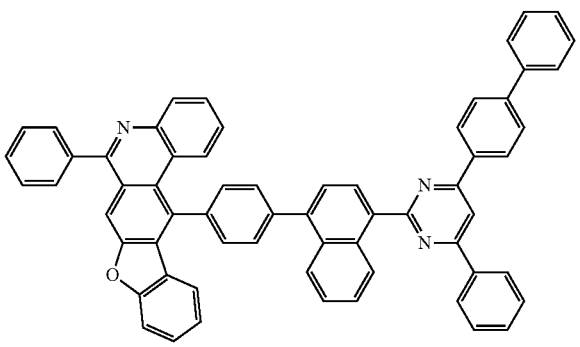
581
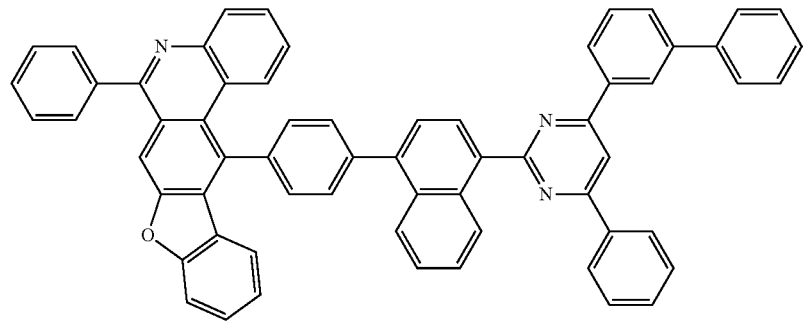
582
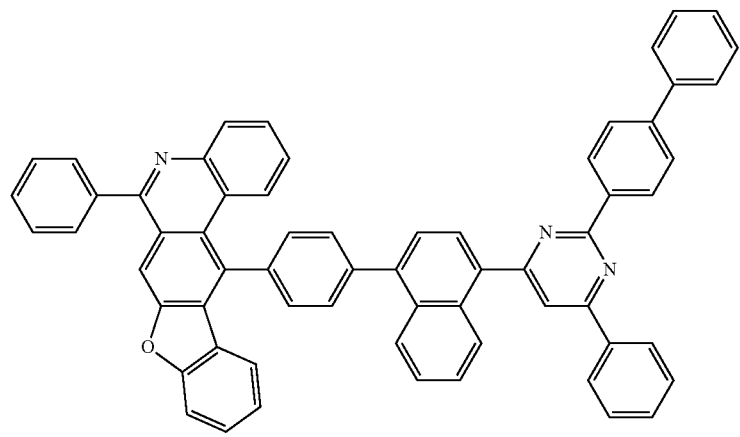

-continued
583
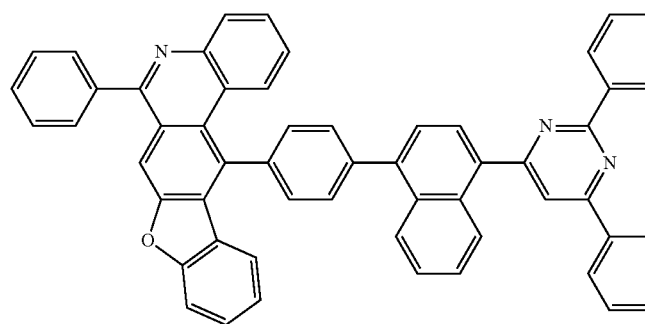
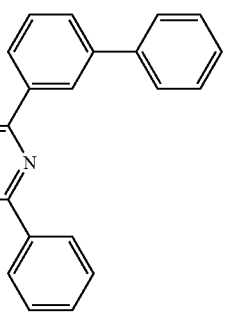
584
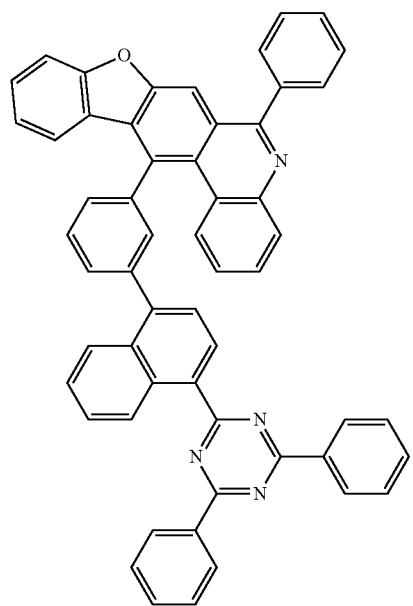
-continued
585
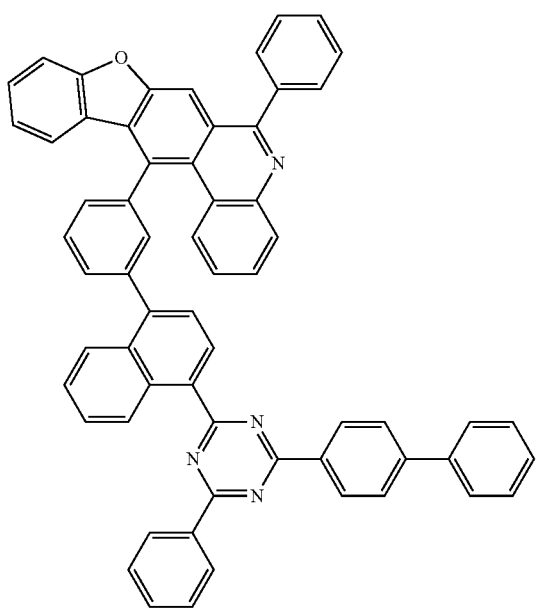
586
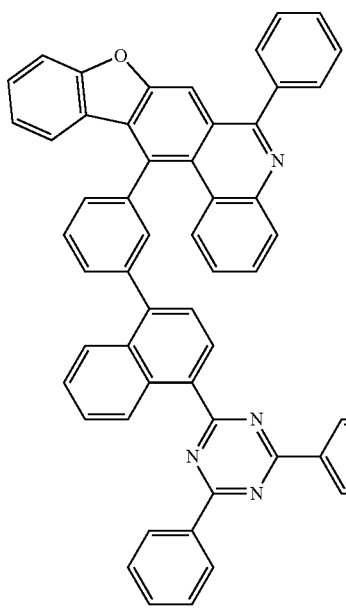

587
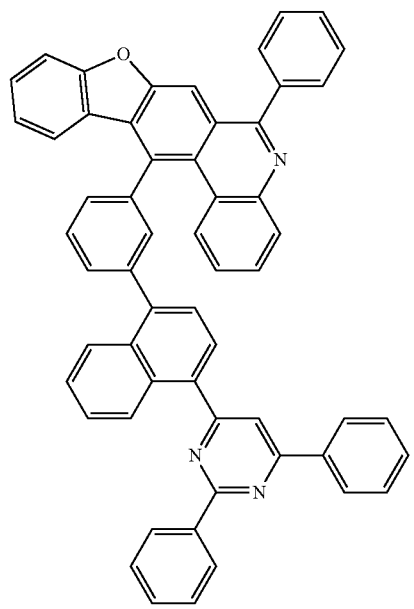
588
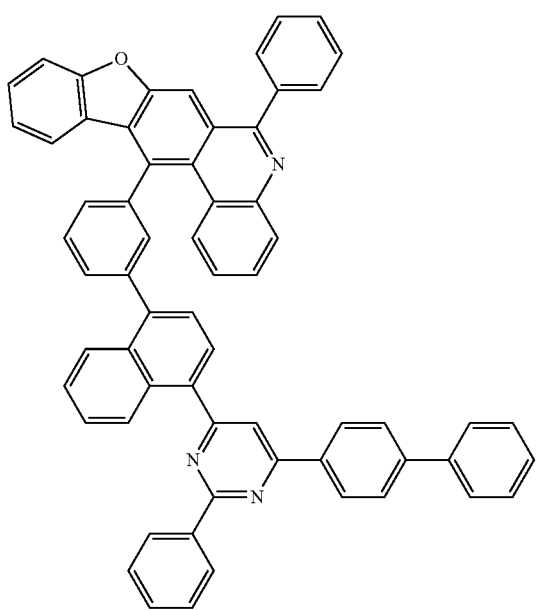
589
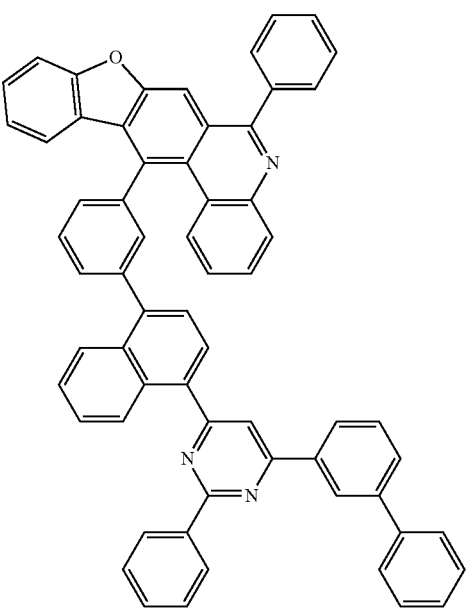
590
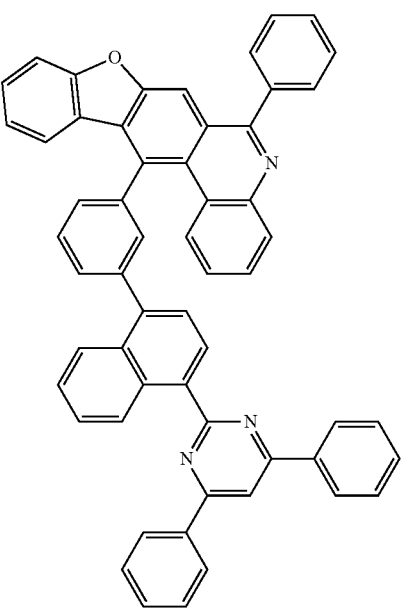

237
-continued
591
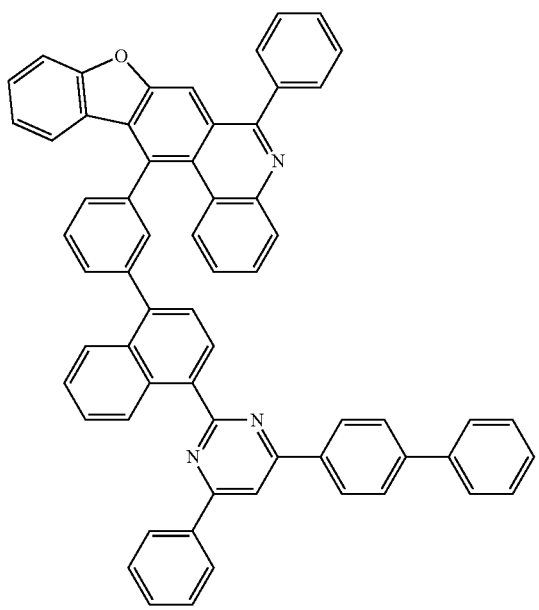
592
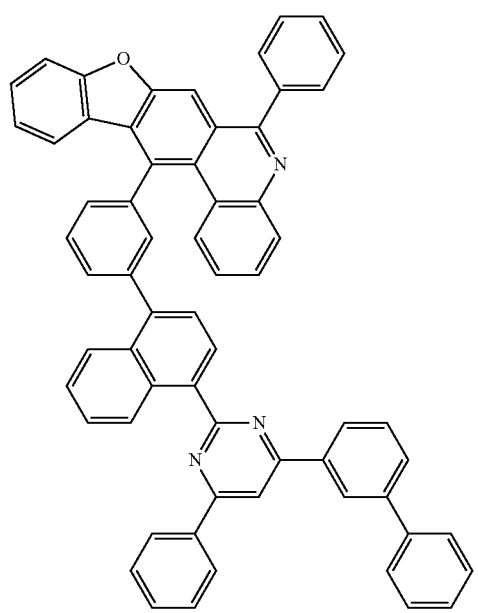
238
-continued
593
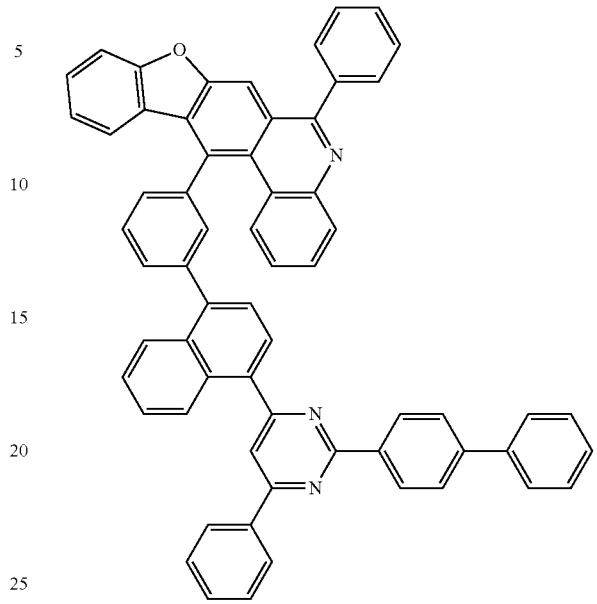
594
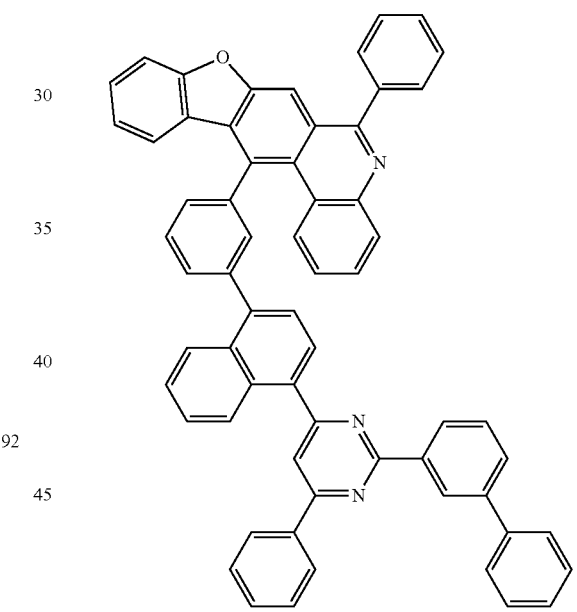
595
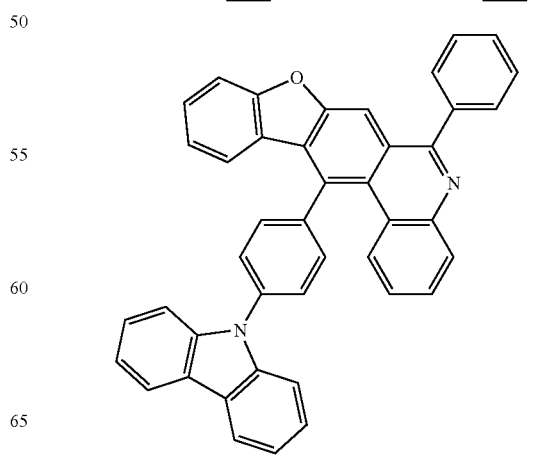

596
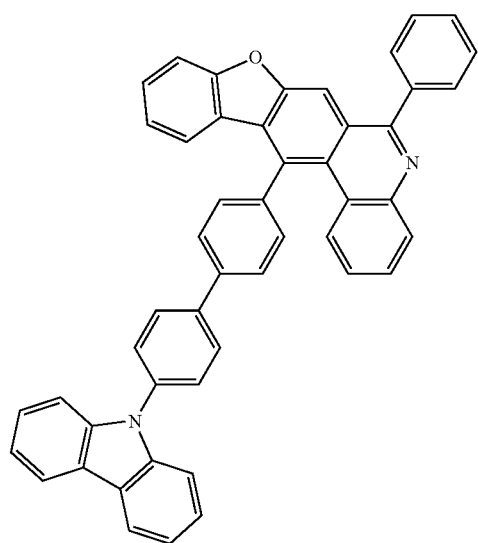
597
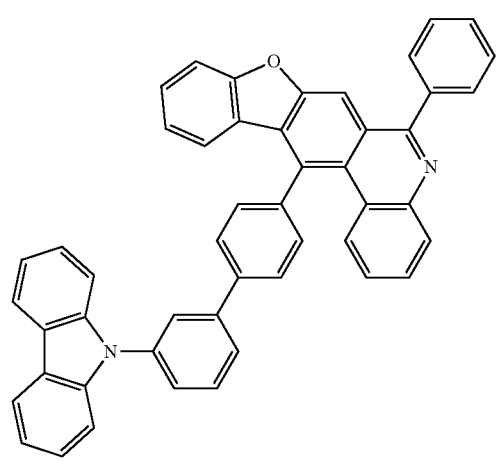
598
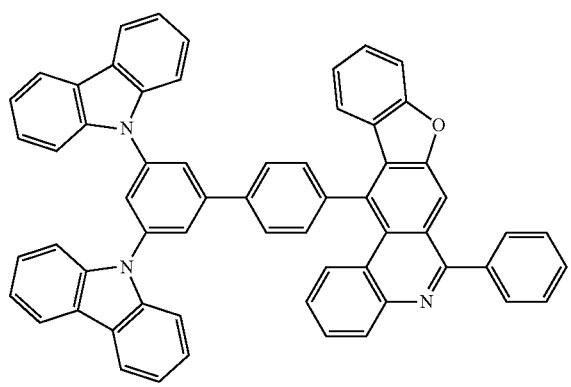
599
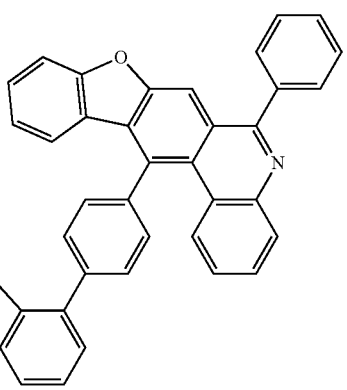
600
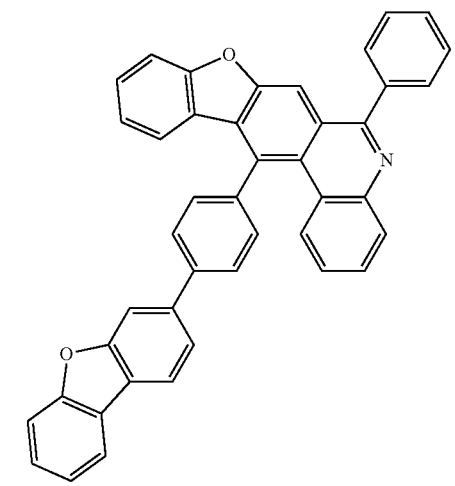
601
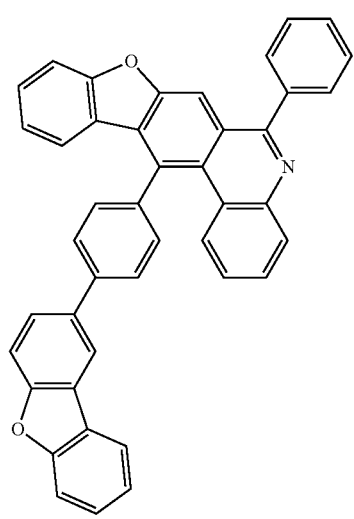

-continued
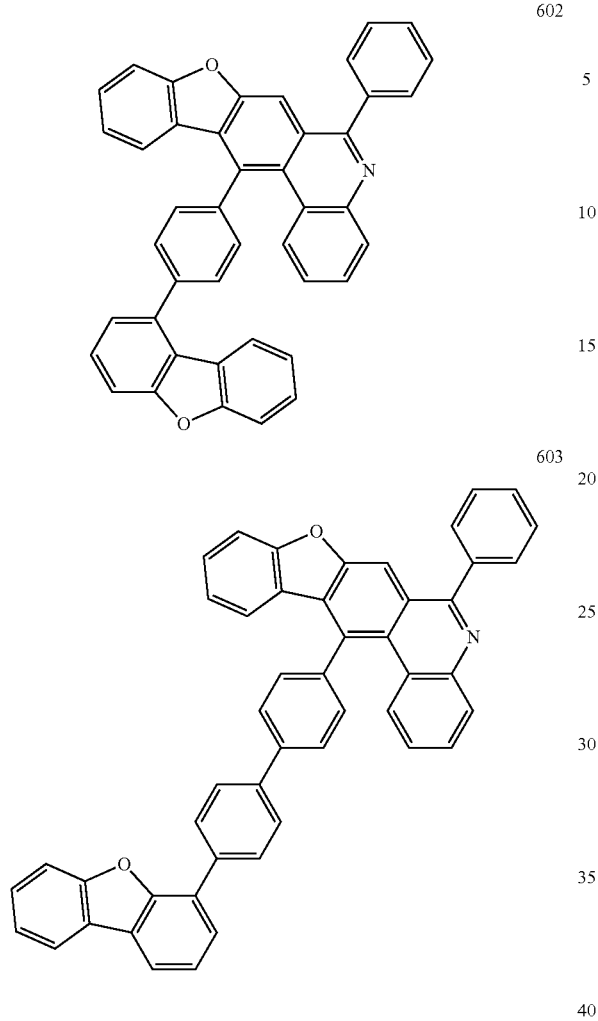
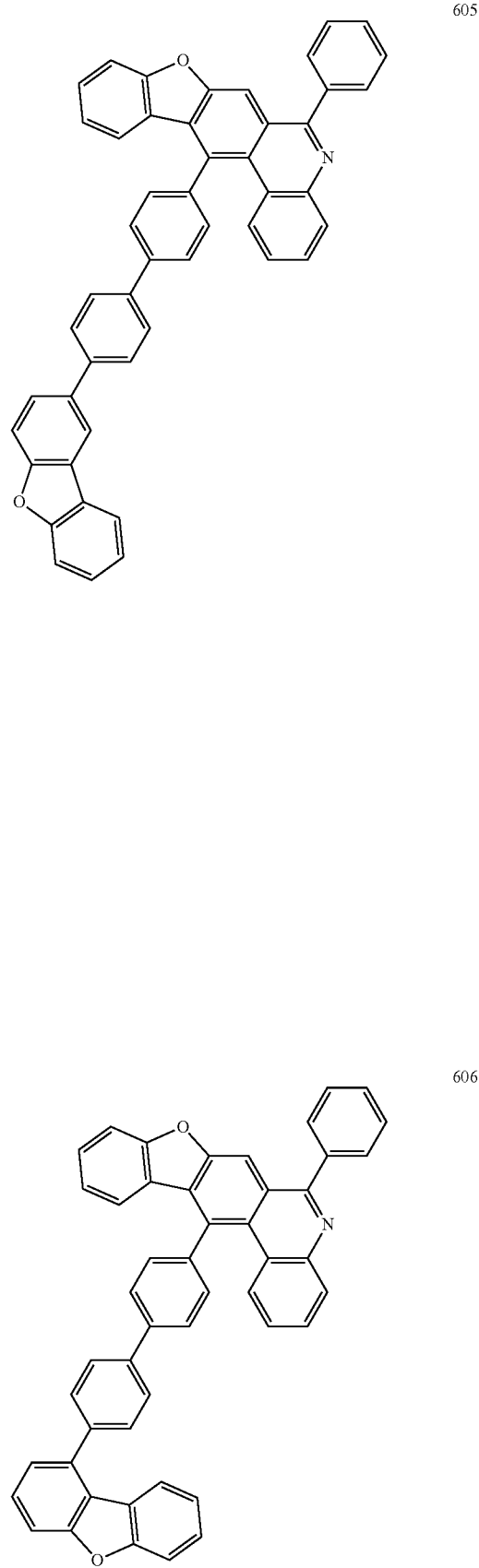

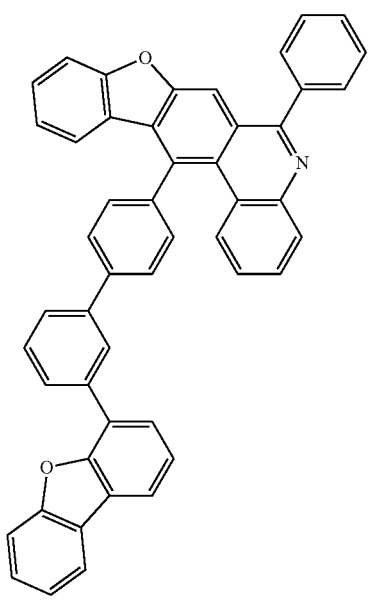
607
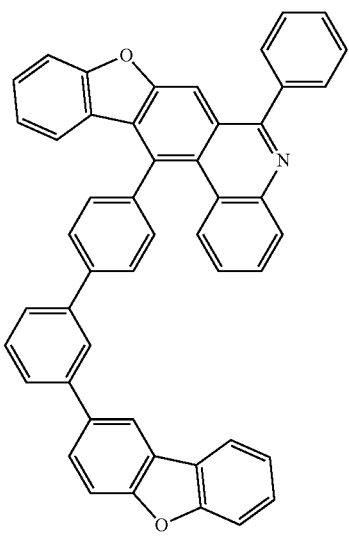
609
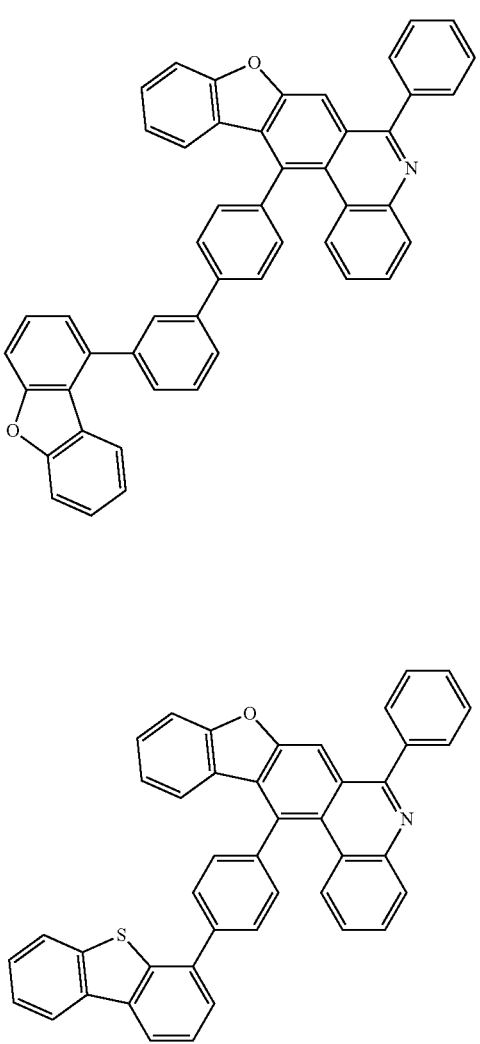
608
610
611

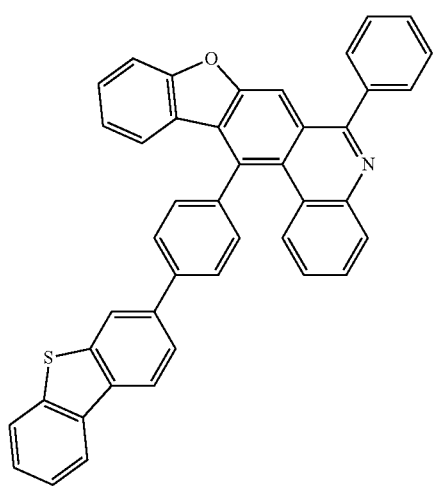
612
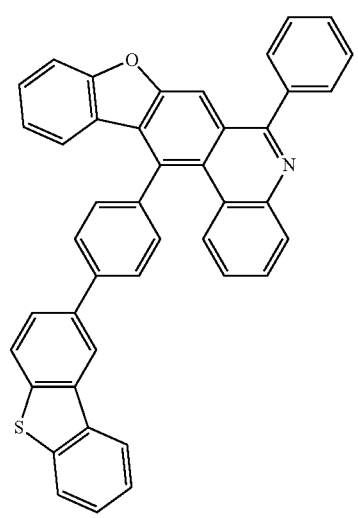
613
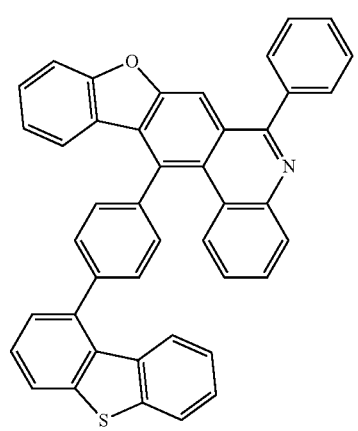 [SMILES: c1ccc(-c2nc3ccccc3c3c(-c4ccc(-c5cccc6oc7ccccc7c56)cc4)c4c(cc23)oc2ccccc24)cc1]
614
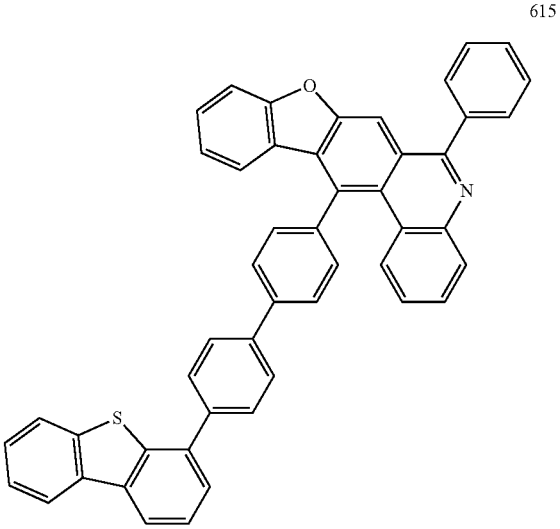
615
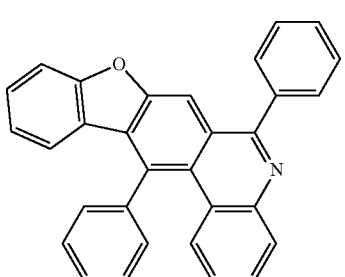
616

-continued
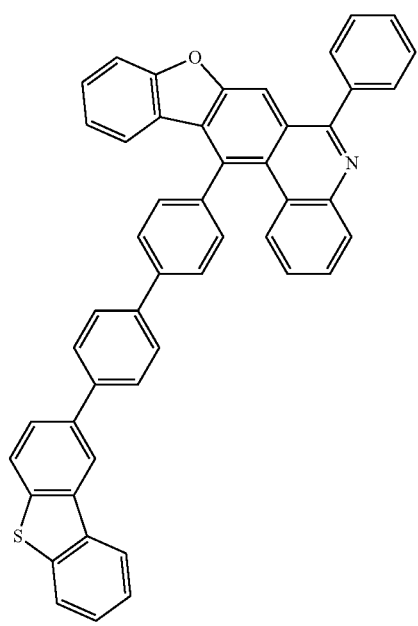
617
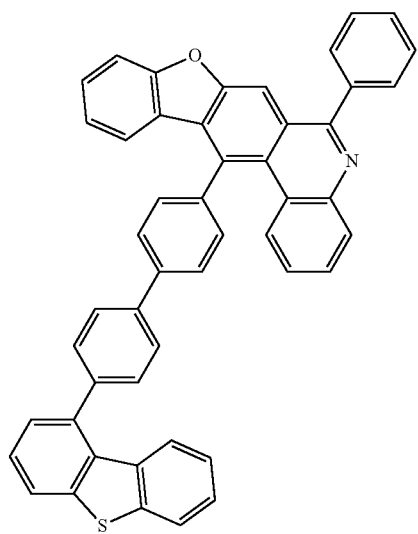 [SMILES: c1ccc(-c2nc3ccccc3c3c(-c4ccc(-c5ccc(-c6cccc7oc8ccccc8c67)cc5)cc4)c4c(cc23)oc2ccccc24)cc1]
618
-continued
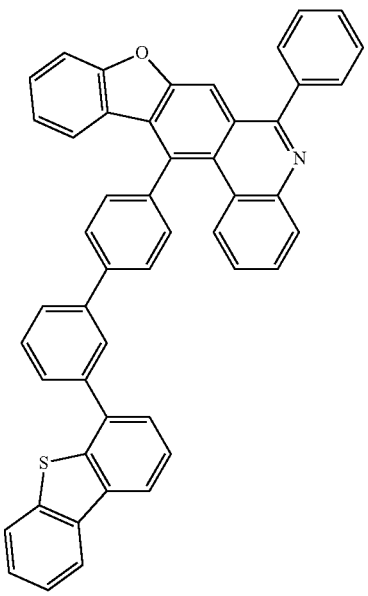
619
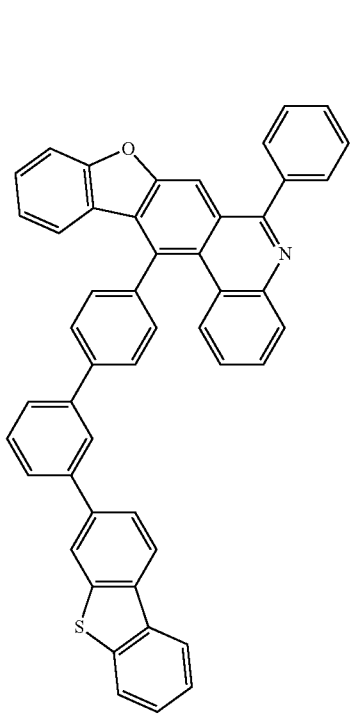
620

249
-continued
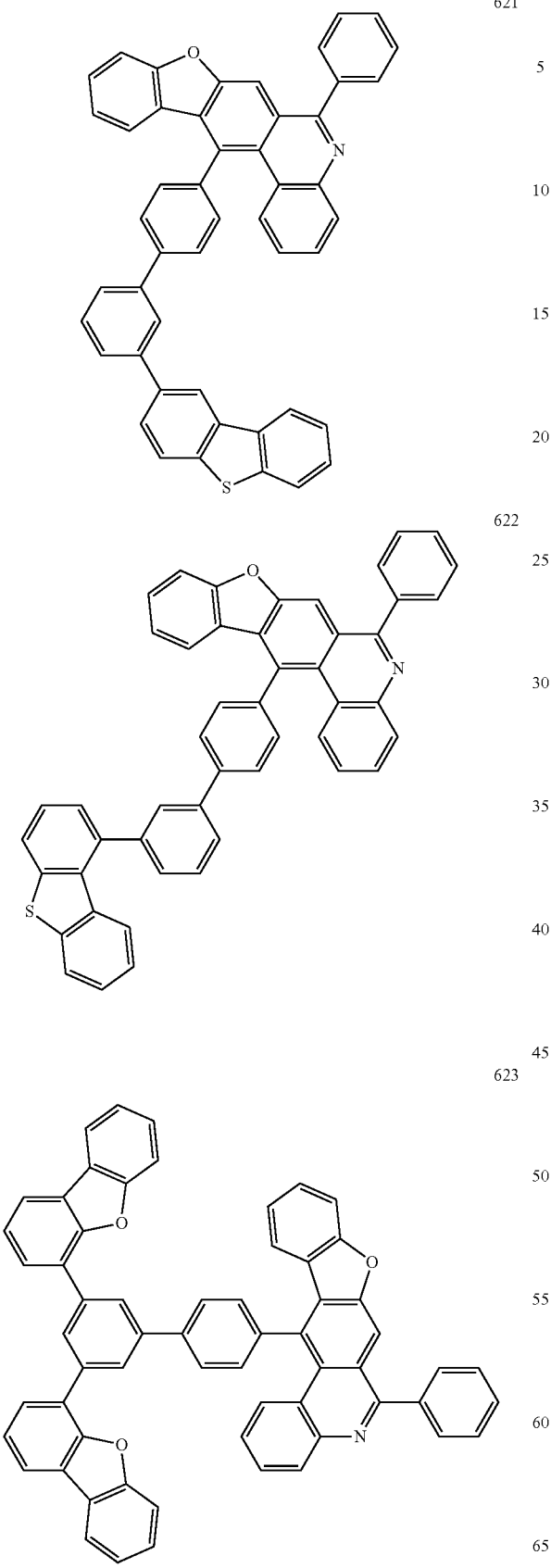
250
-continued
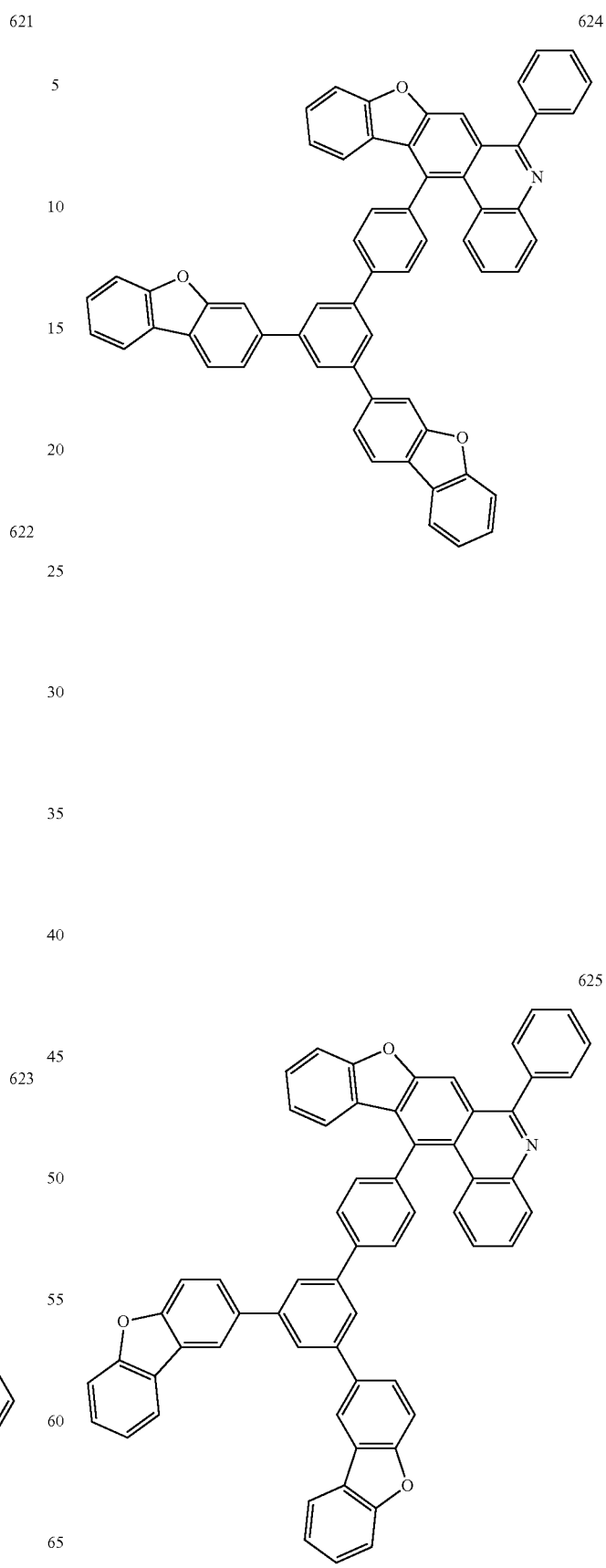

-continued
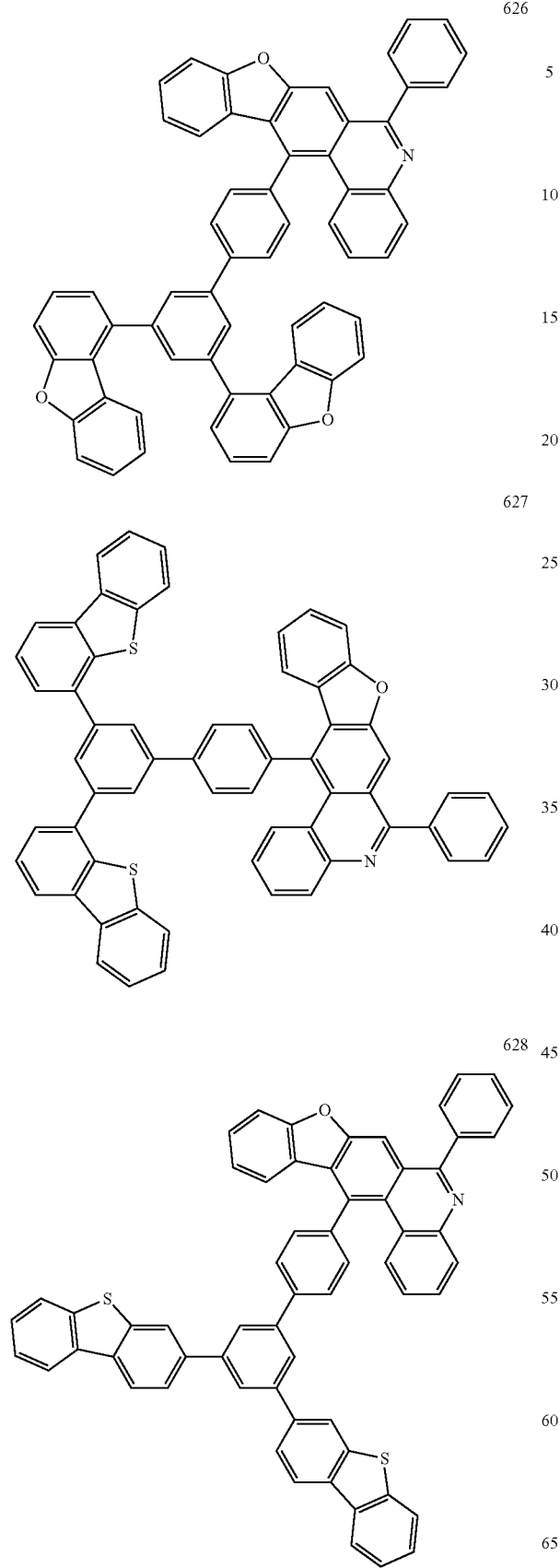
-continued

253
-continued
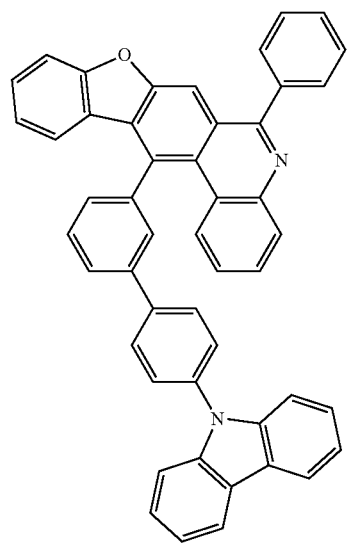
254
-continued
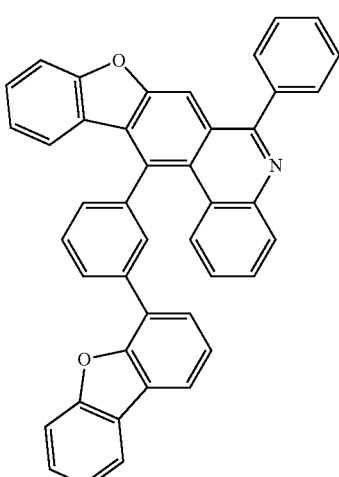

638
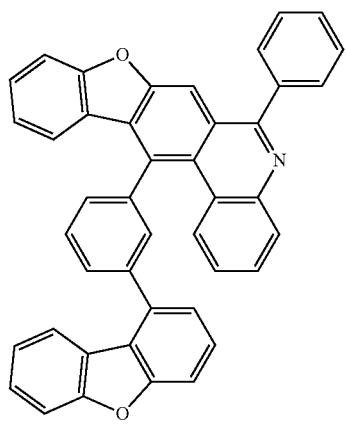
639
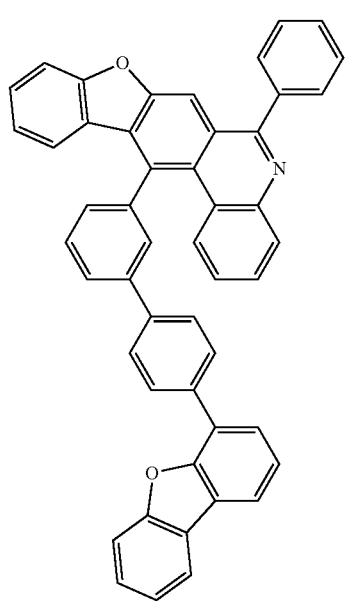
640
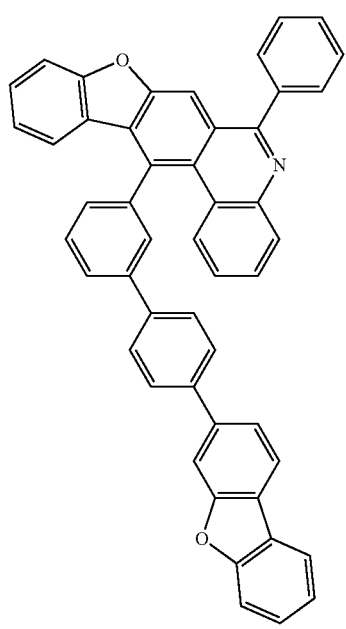
641
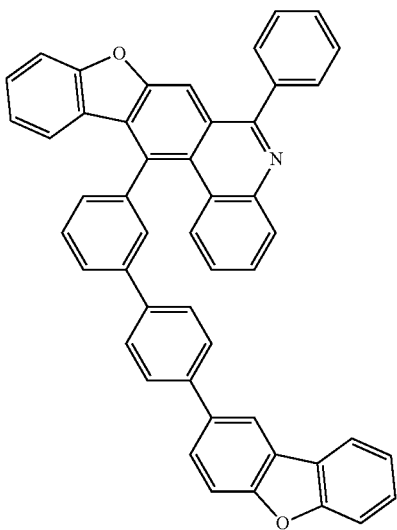
642
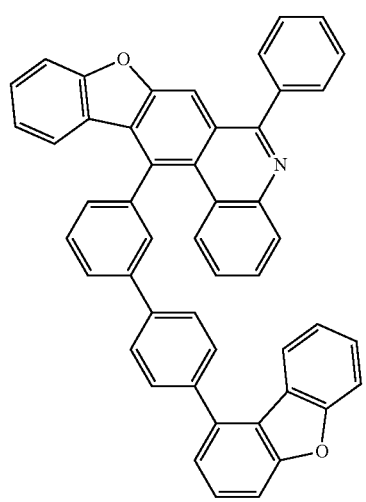
643
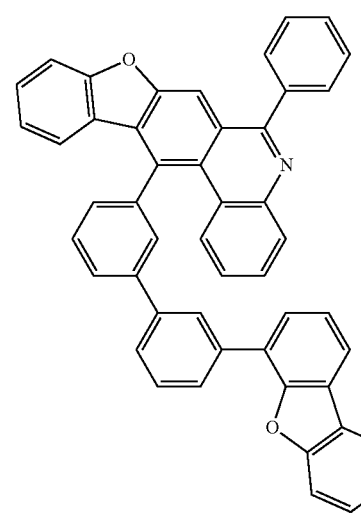

257
-continued
644
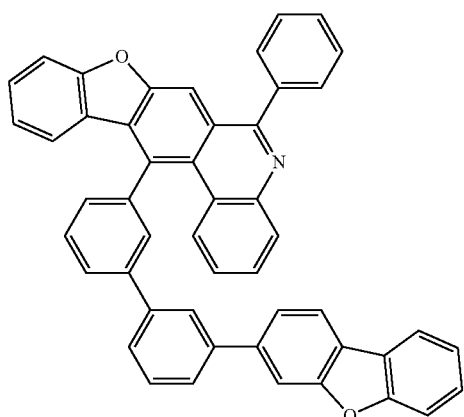
645
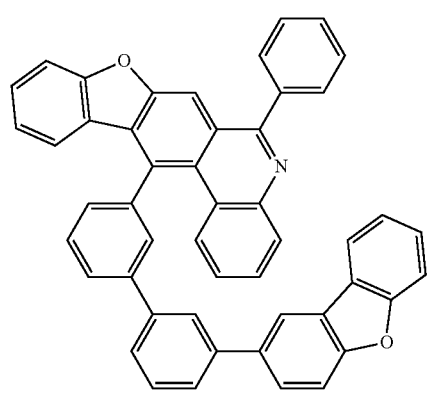
646
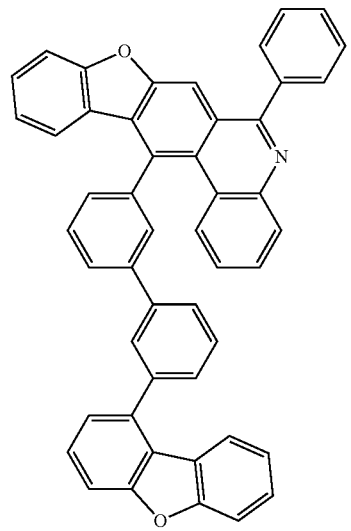
258
-continued
647
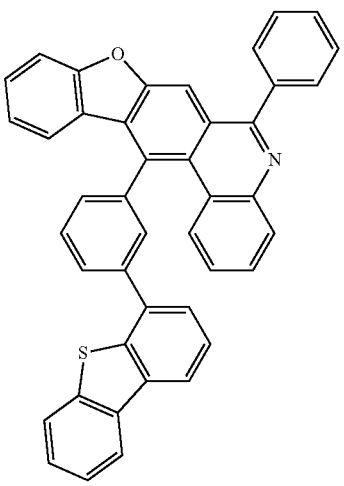
648
649
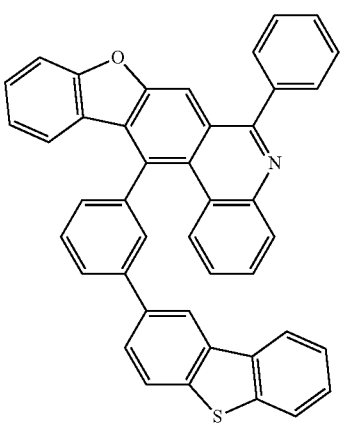

650
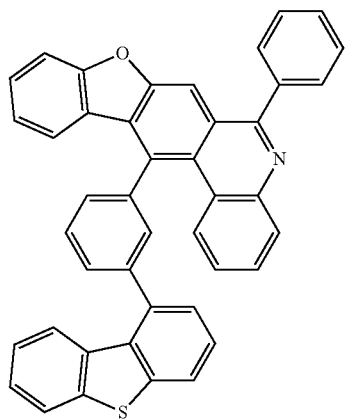
651
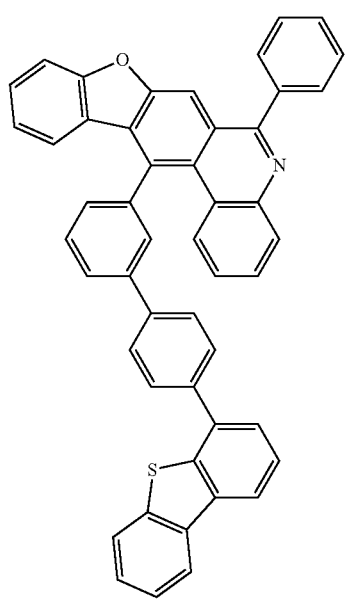
652
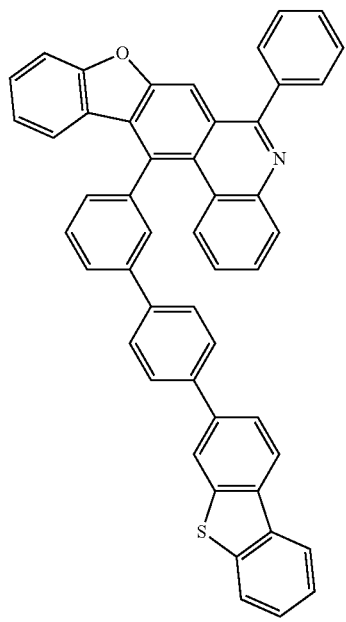
653
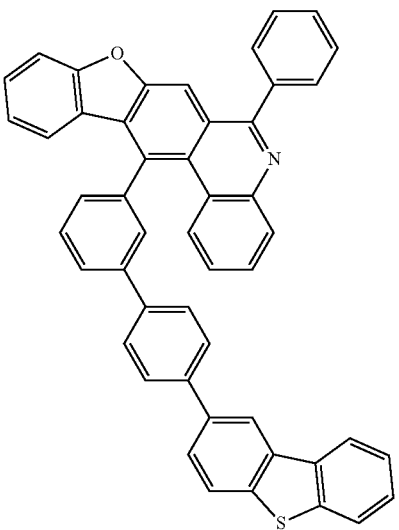
654
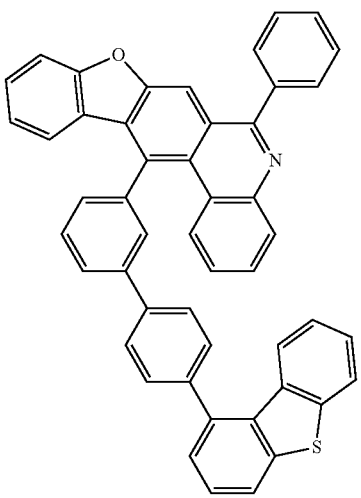
655
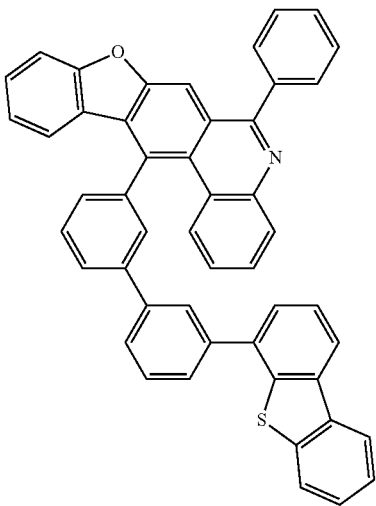

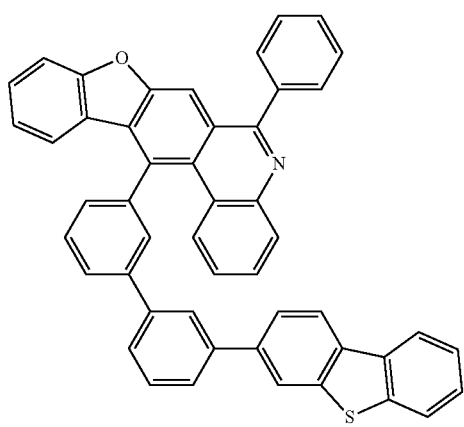
656
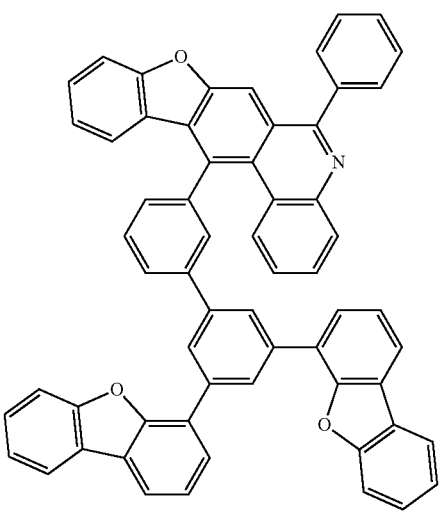 [SMILES: c1ccc(-c2nc3ccccc3c3c(-c4cccc(-c5cc(-c6cccc7c6sc6ccccc67)cc(-c6cccc7c6sc6ccccc67)c5)c4)c4c(cc23)oc2ccccc24)cc1]
659
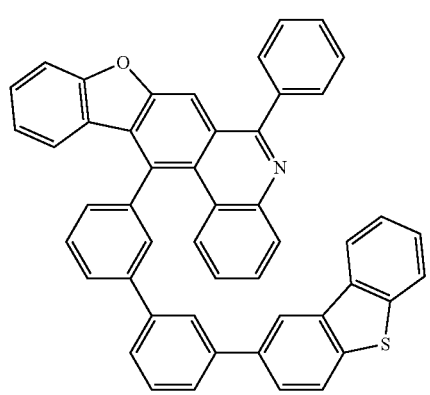
657
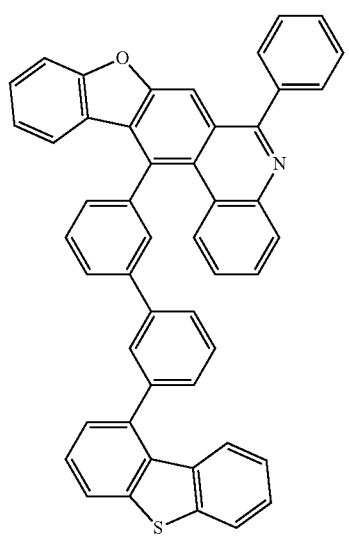
658
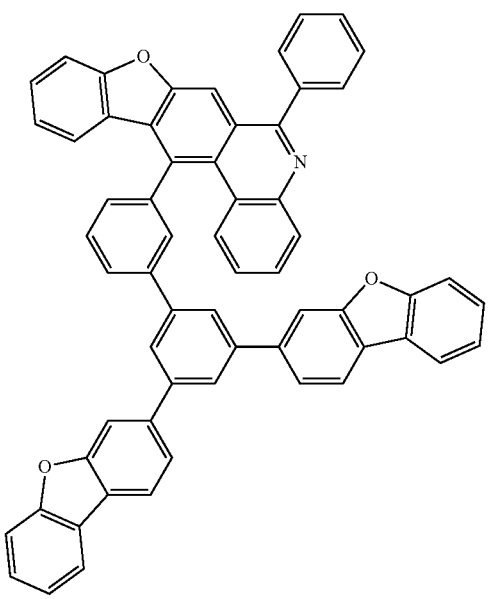
660

263
-continued
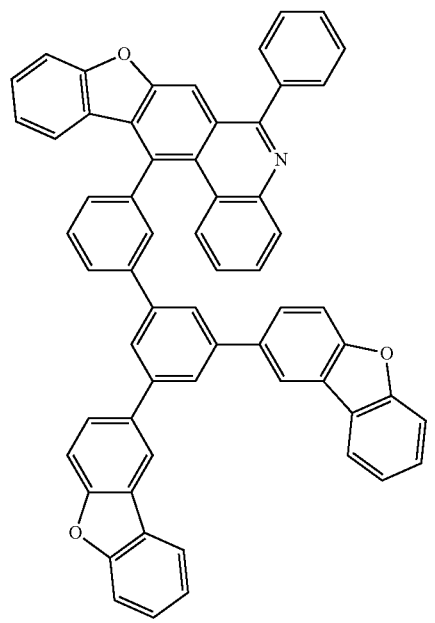
661
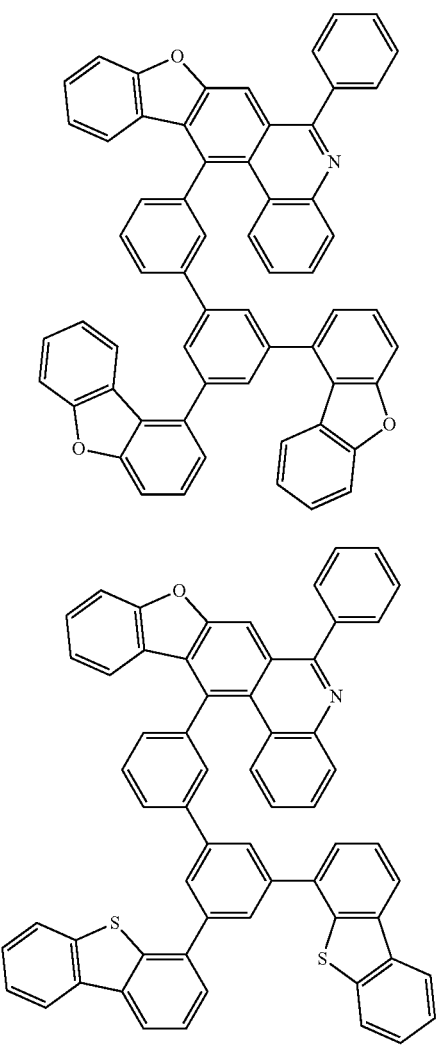
662
663
264
-continued
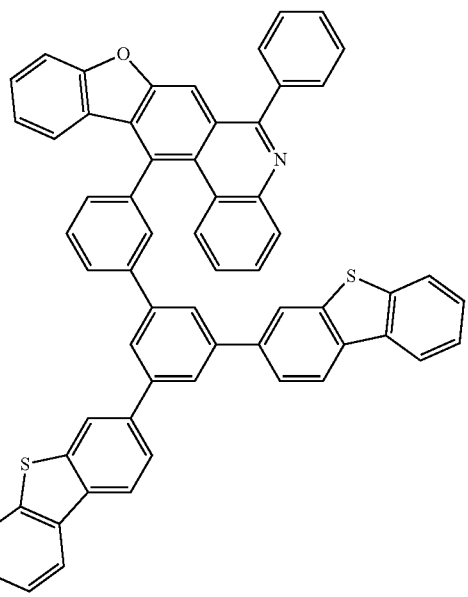
664
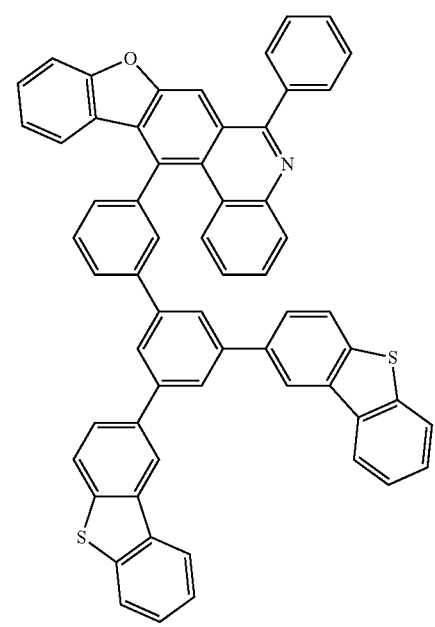
665

266  
-continued
669
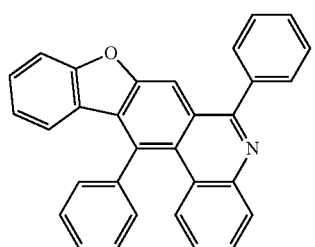
670
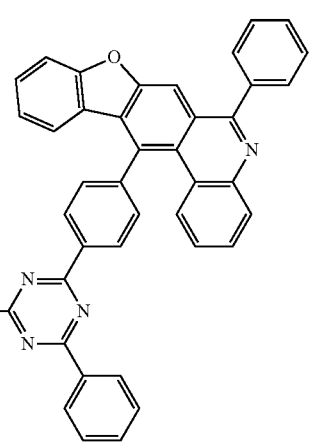
671
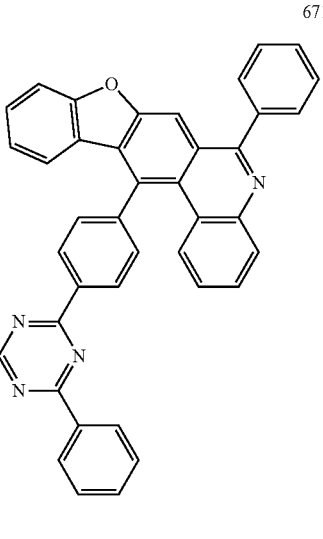
265  
-continued
666
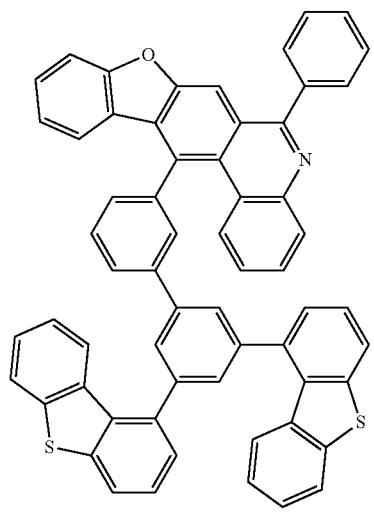
667
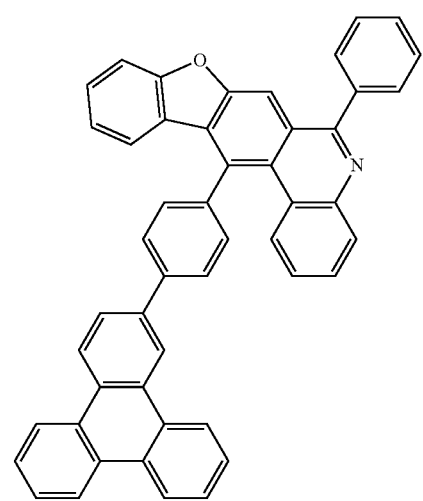 [SMILES: c1ccc(-c2nc3ccccc3c3c(-c4ccc(-c5ccc6c7ccccc7c7ccccc7c6c5)cc4)c4c(cc23)oc2ccccc24)cc1]
668
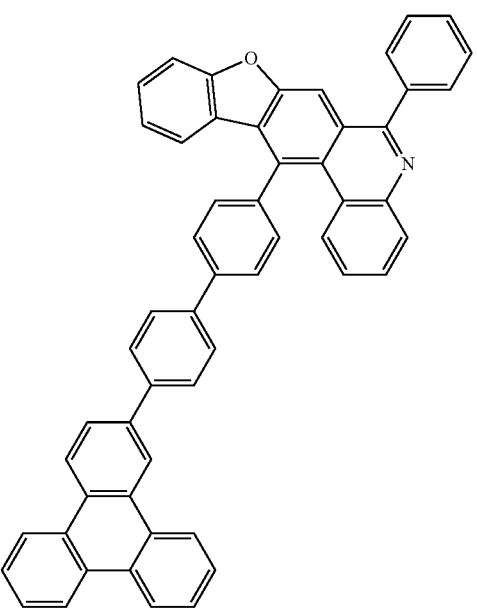 [SMILES: c1ccc(-c2nc3ccccc3c3c(-c4ccc(-c5ccc(-c6ccc7c8ccccc8c8ccccc8c7c6)cc5)cc4)c4c(cc23)oc2ccccc24)cc1]

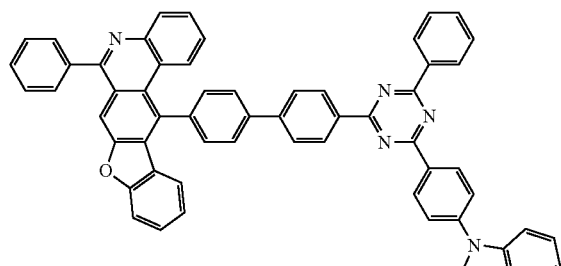
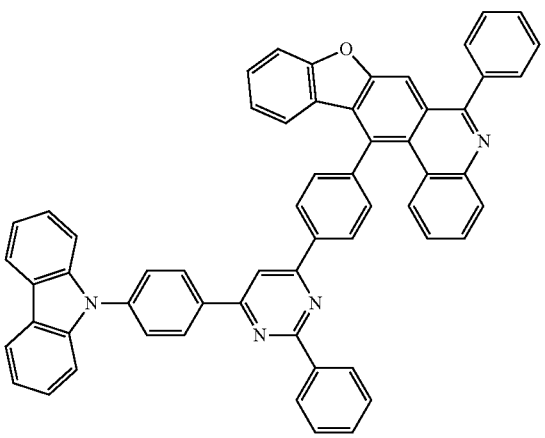
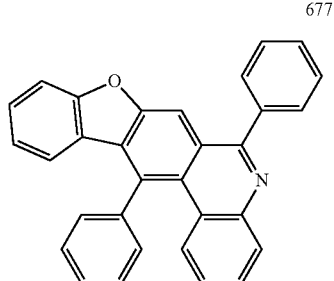
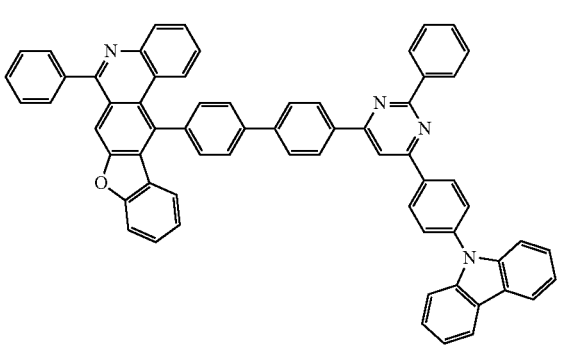
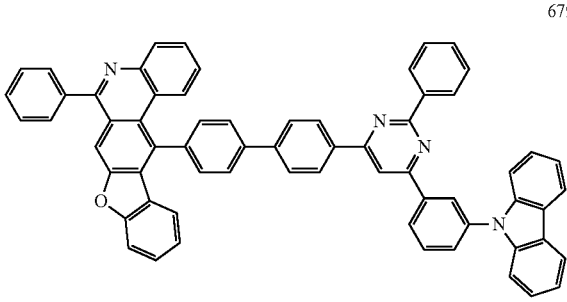

680
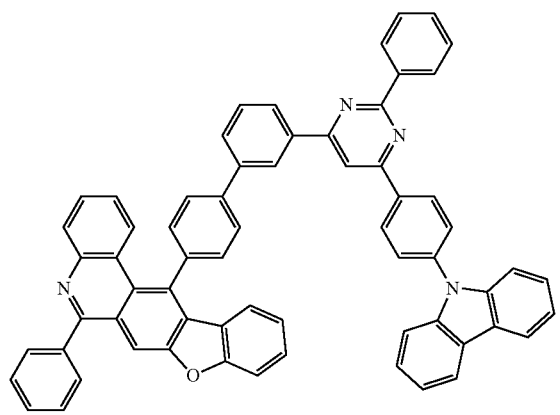
681
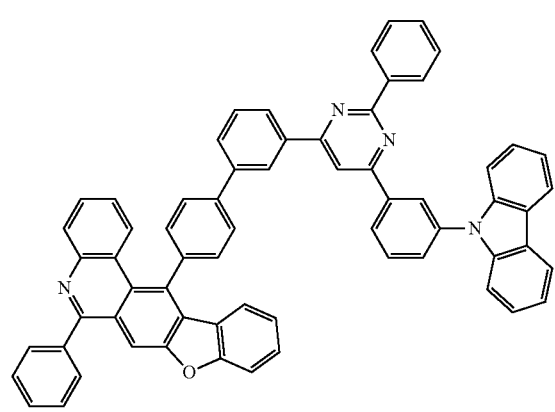
682
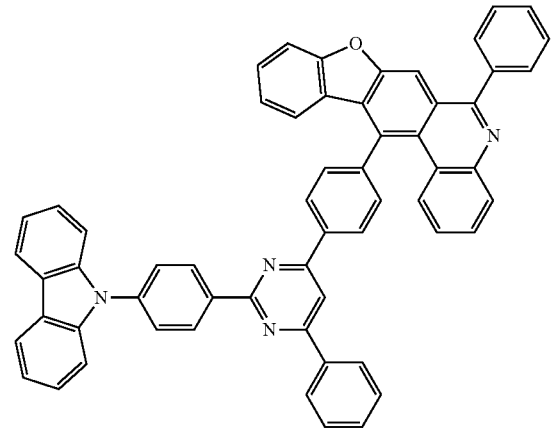 [SMILES: c1ccc(-c2cc(-c3ccc(-c4c5c(cc6c(-c7ccccc7)nc7ccccc7c46)oc4ccccc45)cc3)nc(-c3ccc(-n4c5ccccc5c5ccccc54)cc3)n2)cc1]
683
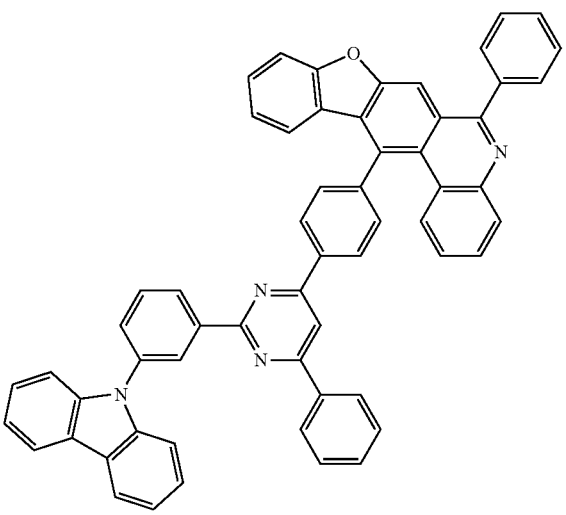
684
685
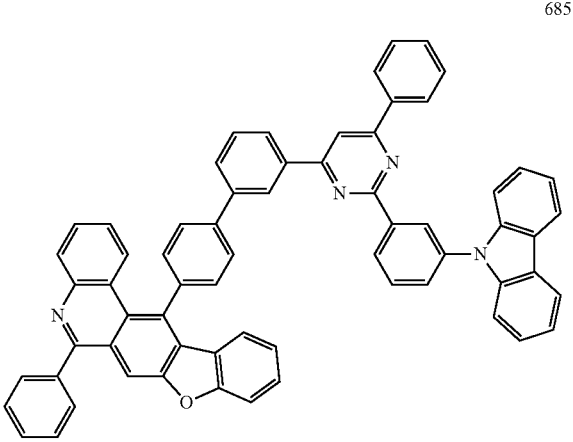

686
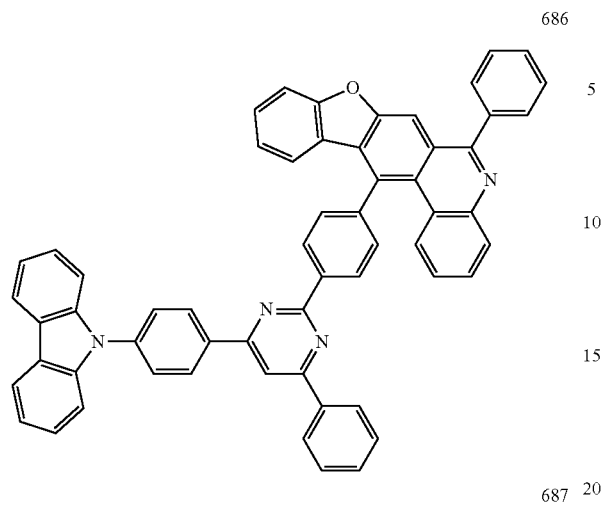
687
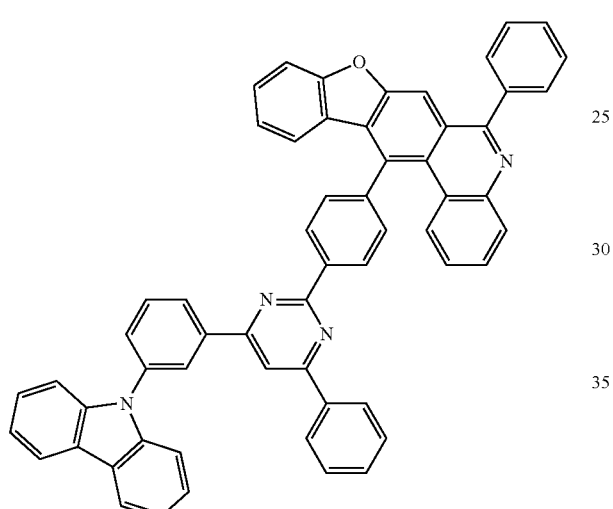
688
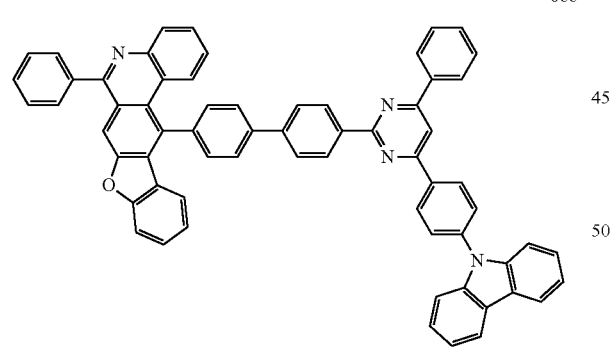
689
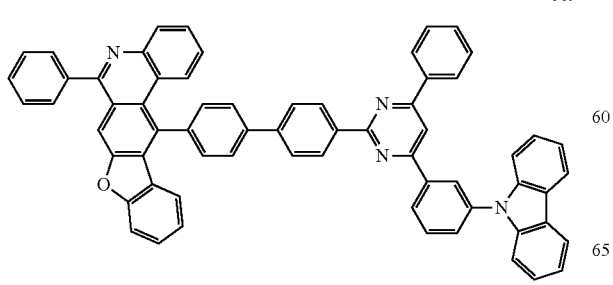
690
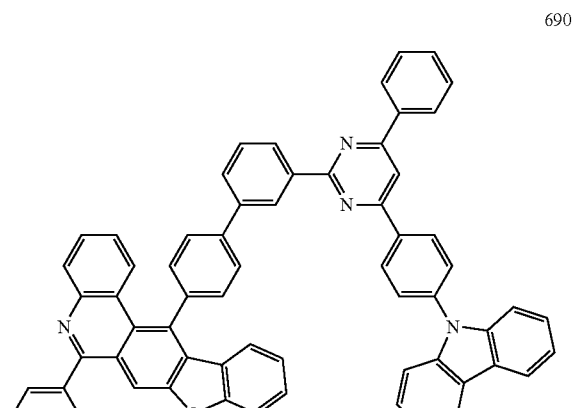
691
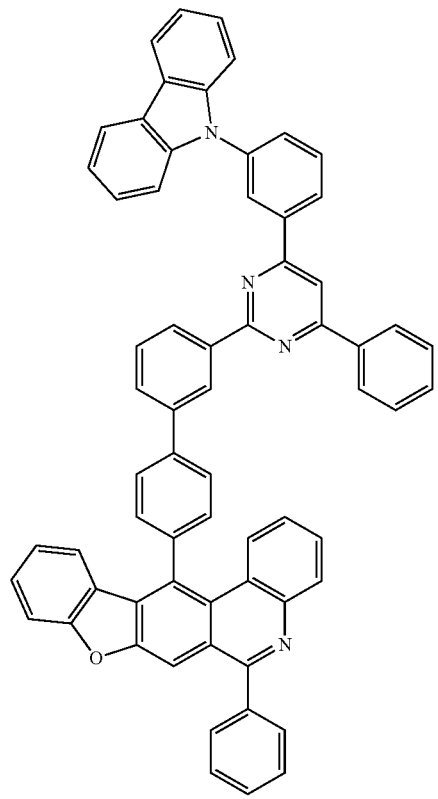

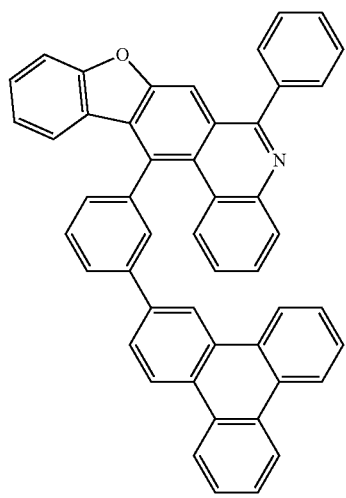
692
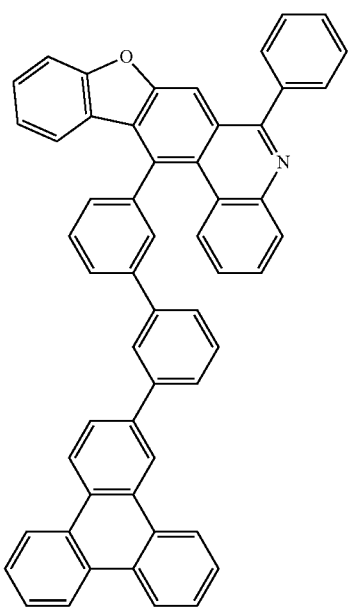
694
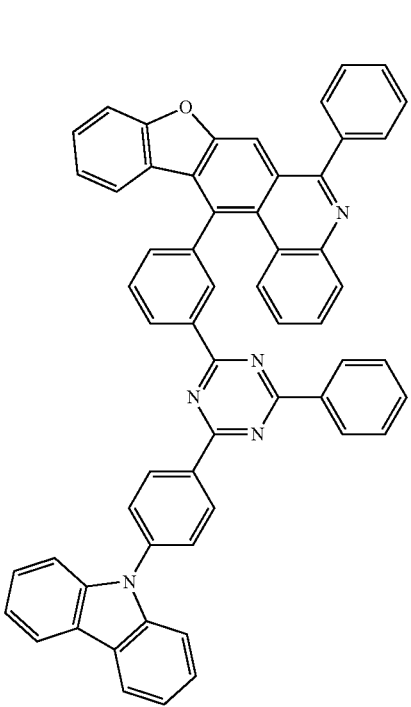
695

275
-continued
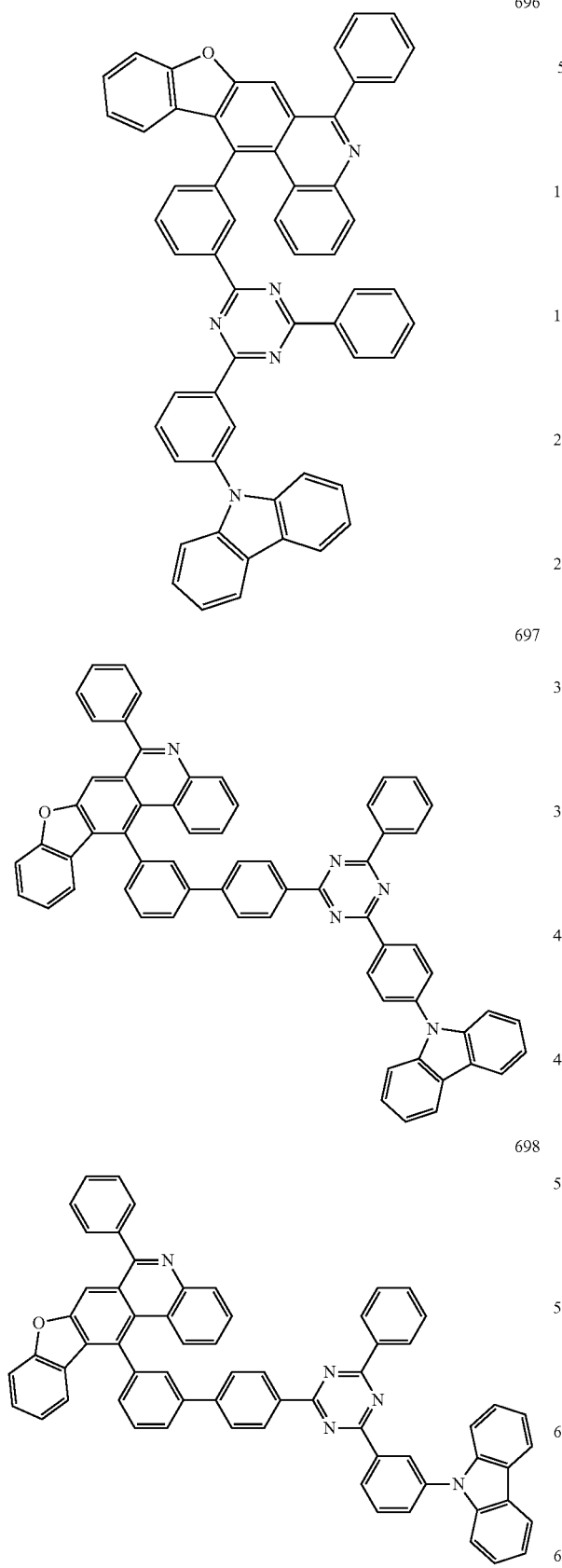
276
-continued
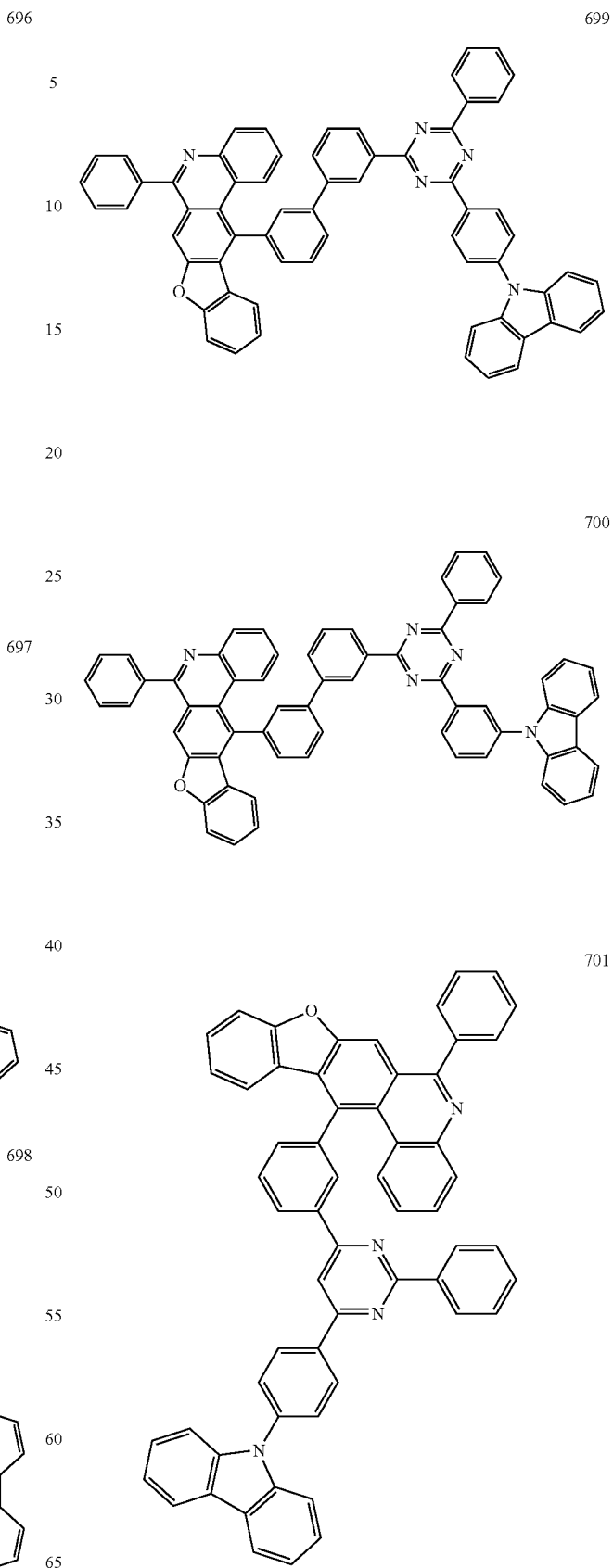

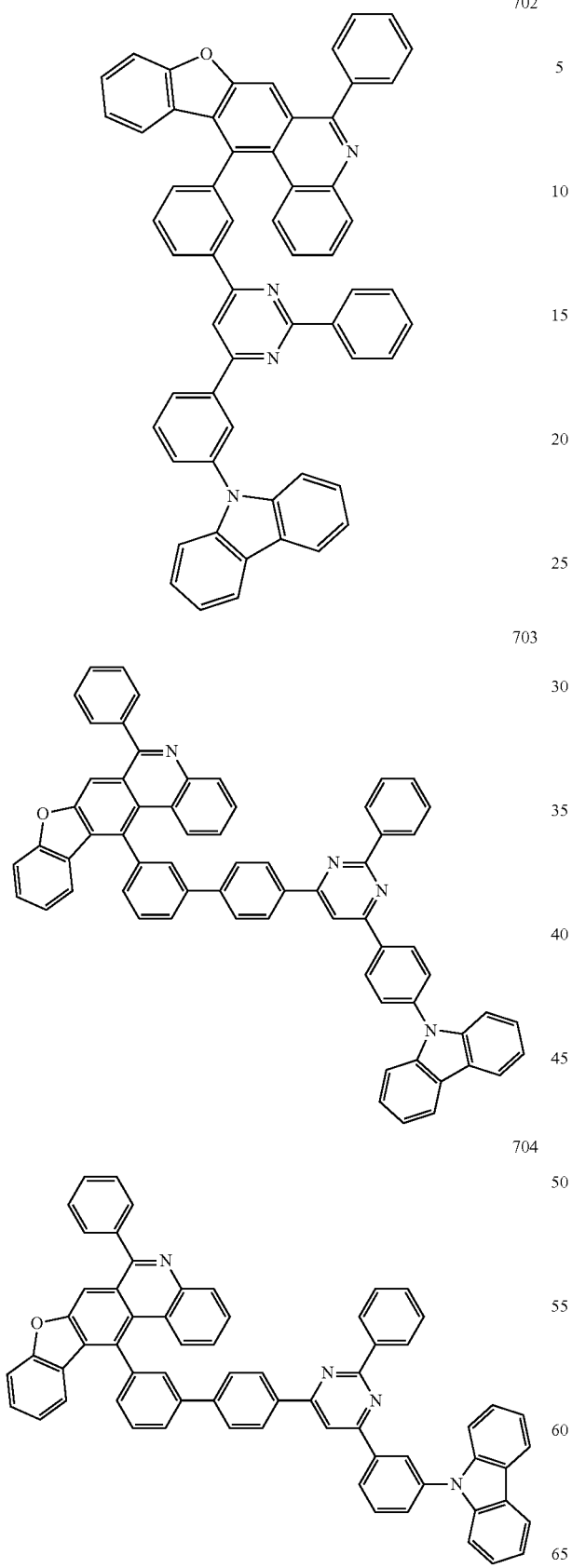
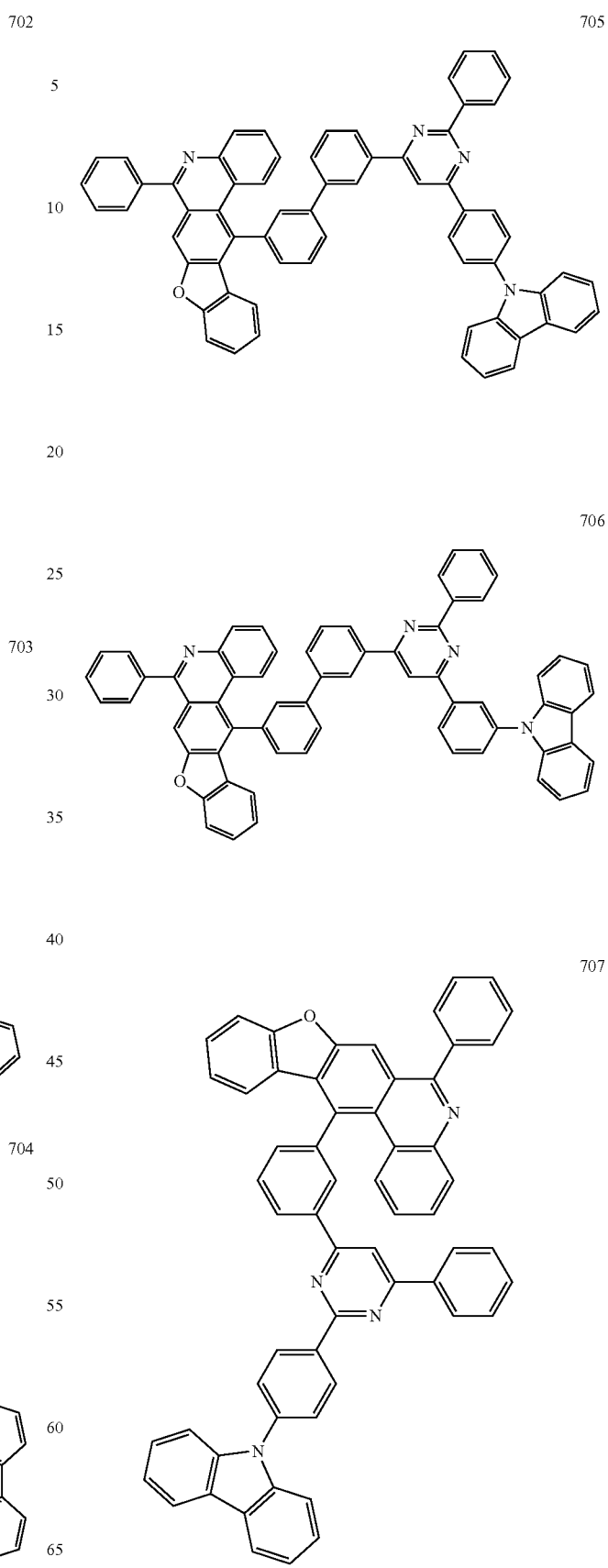

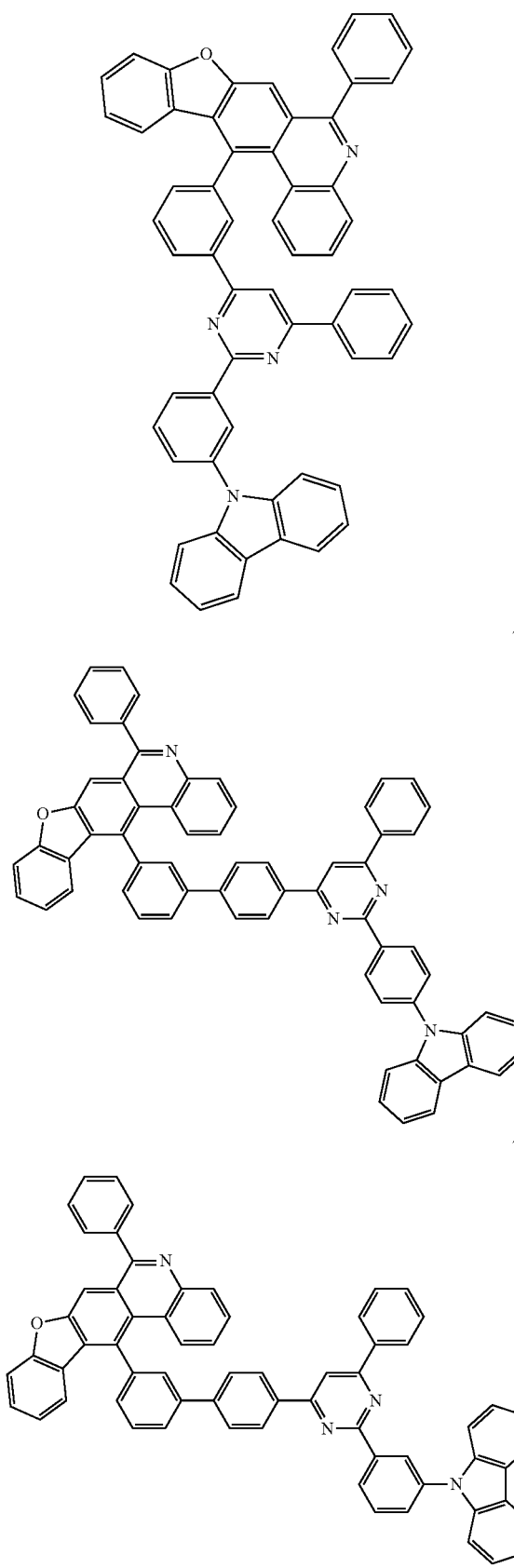
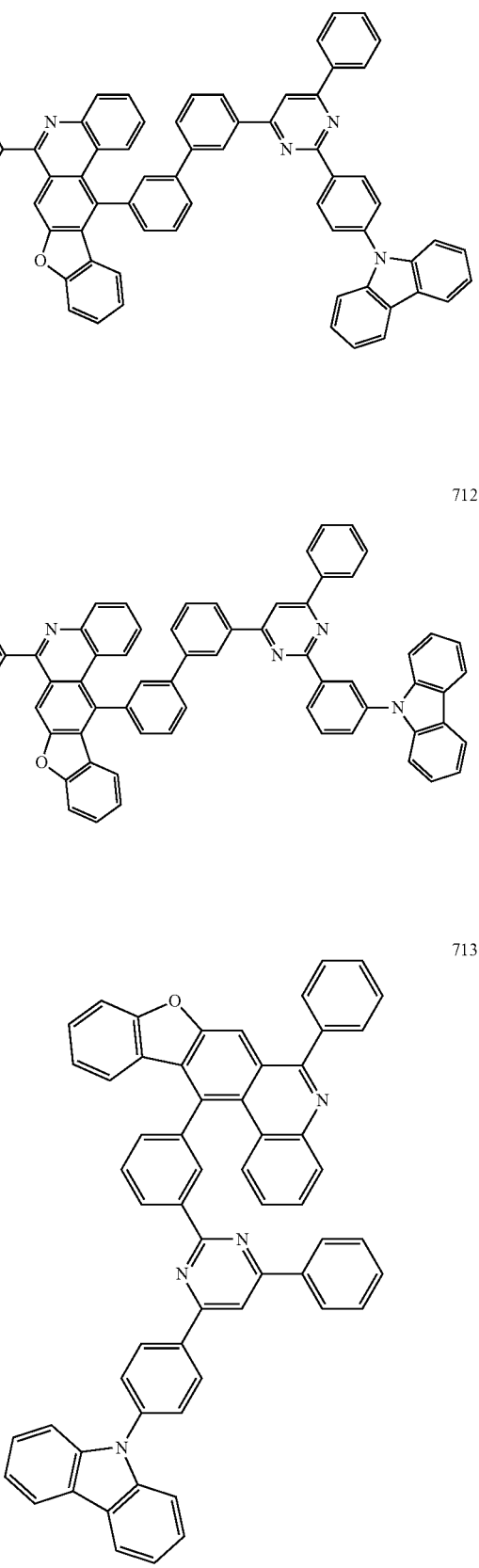

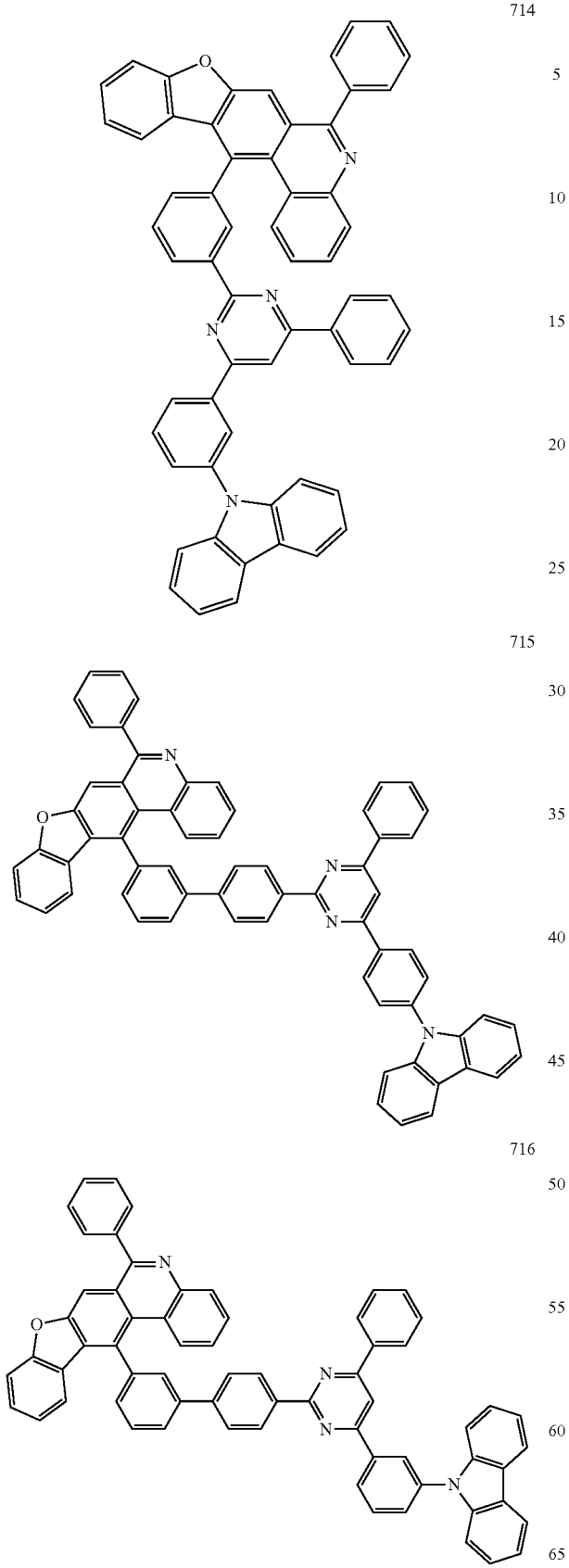
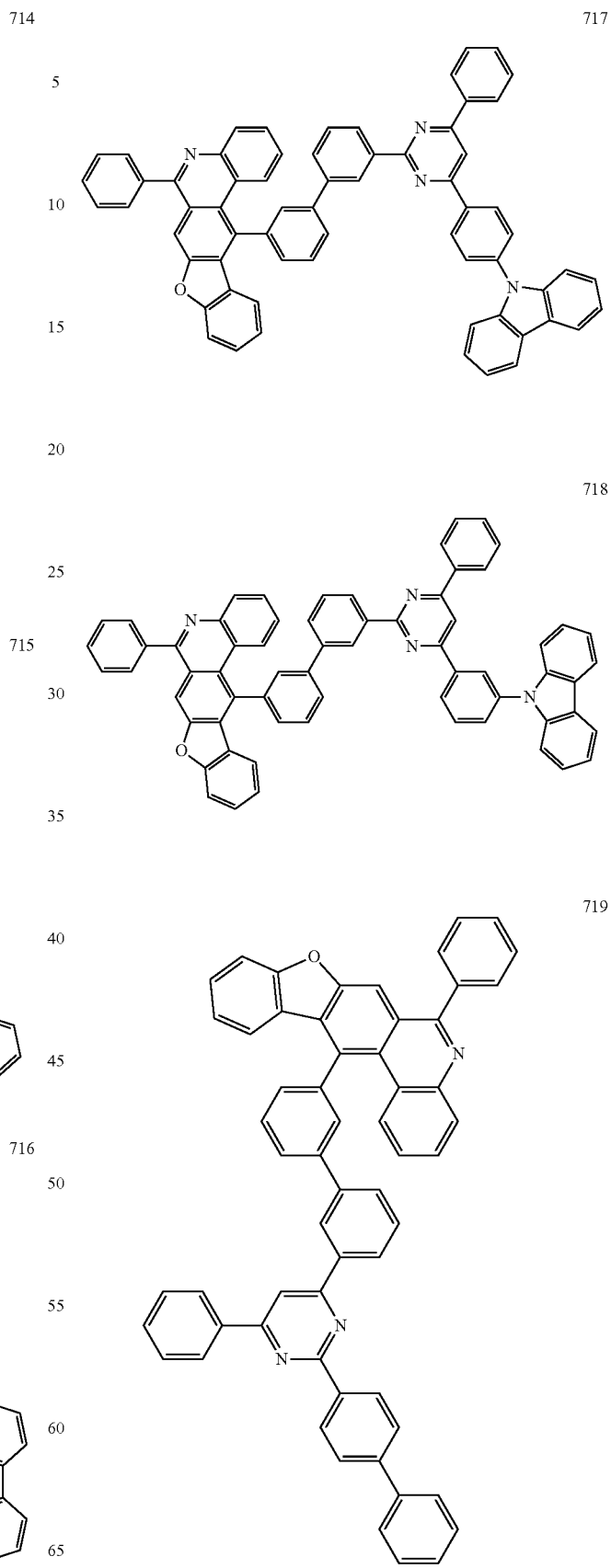

283
-continued
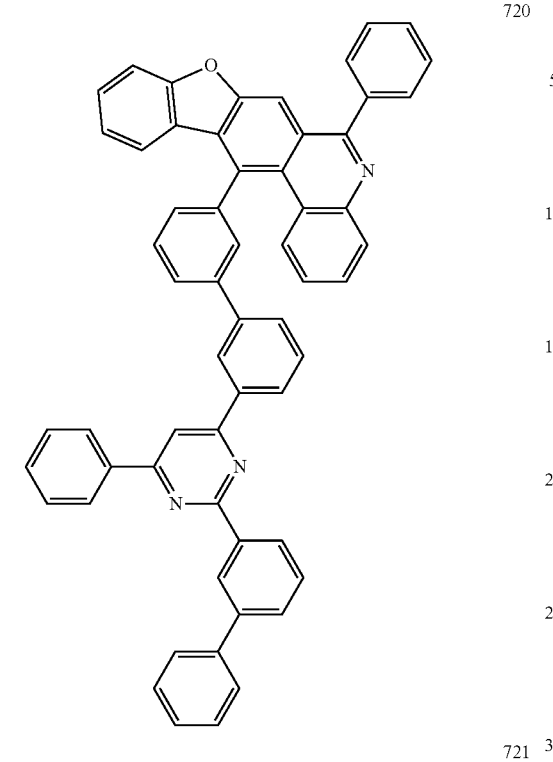
720
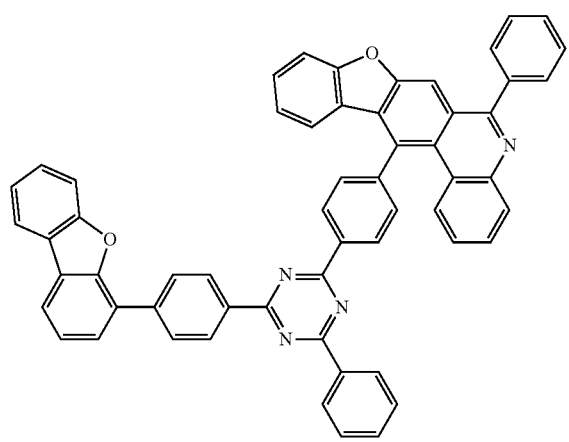
721
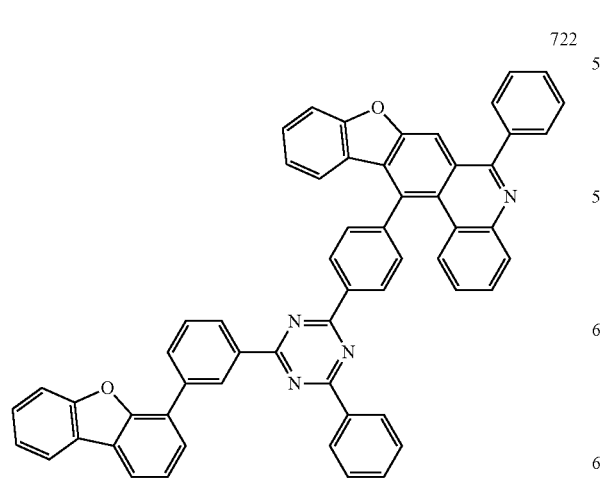
722
284
-continued
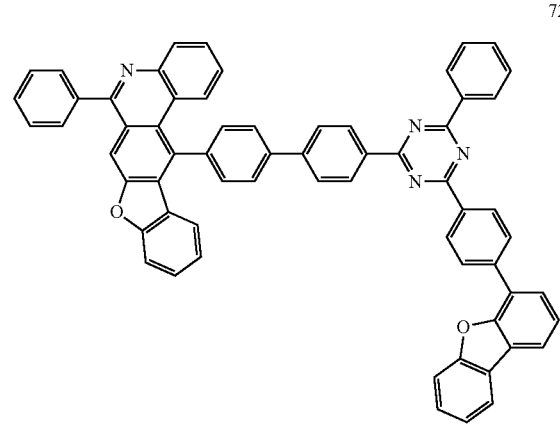
723
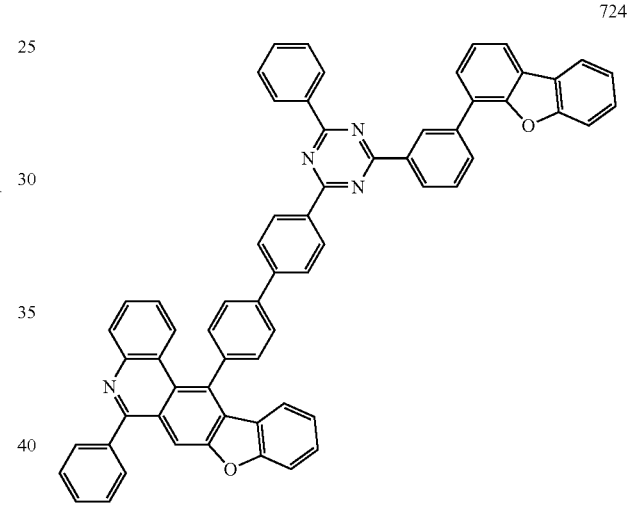
724
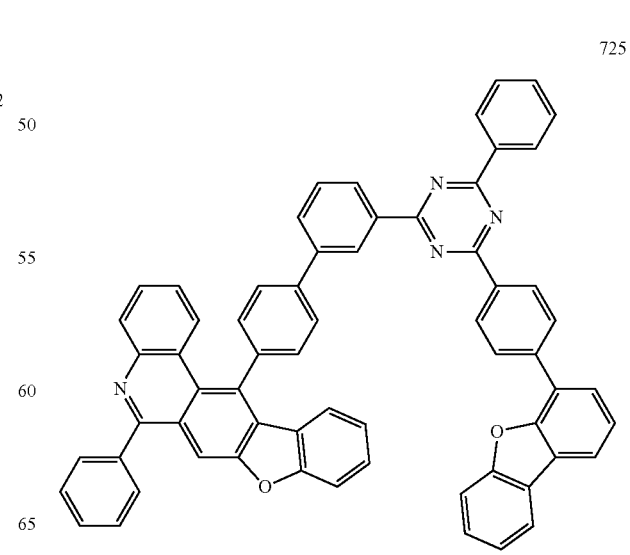
725

285
-continued
726
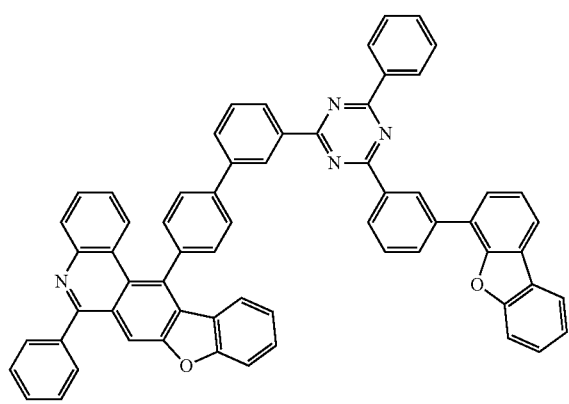
727
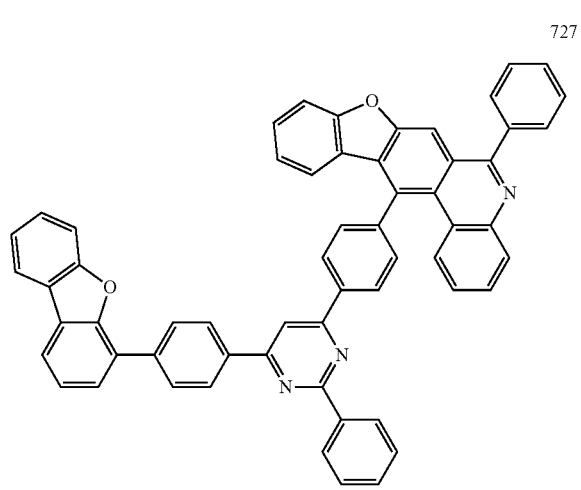
728
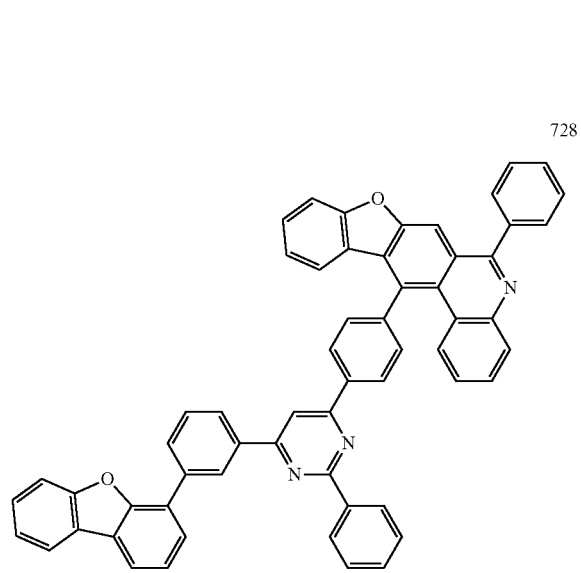
286
-continued
729
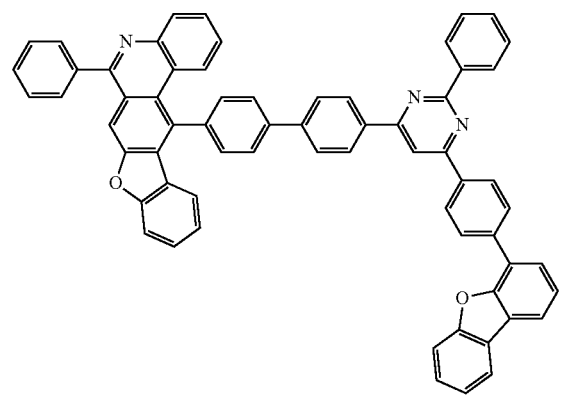 [SMILES: c1ccc(-c2nc(-c3ccc(-c4ccc(-c5c6c(cc7c(-c8ccccc8)nc8ccccc8c57)oc5ccccc56)cc4)cc3)nc(-c3ccc(-c4cccc5c4oc4ccccc45)cc3)n2)cc1]
730
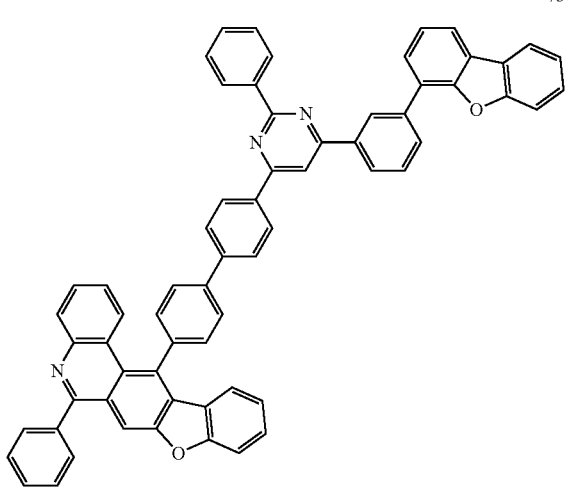
731
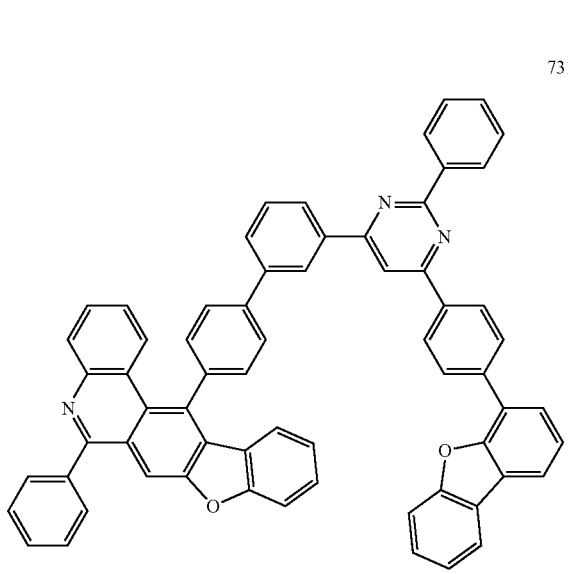

287
-continued
732
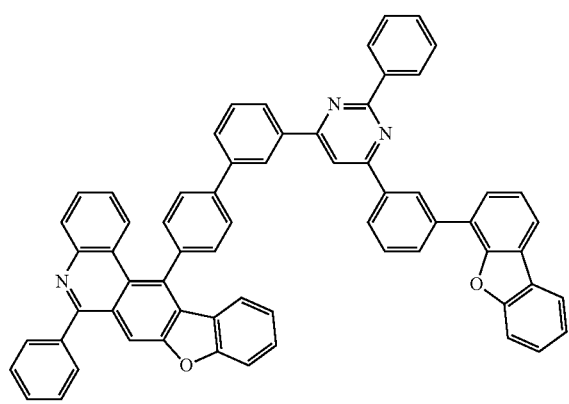
733
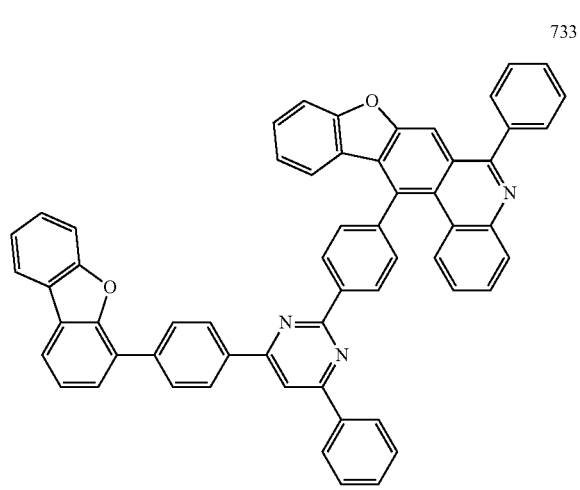
734
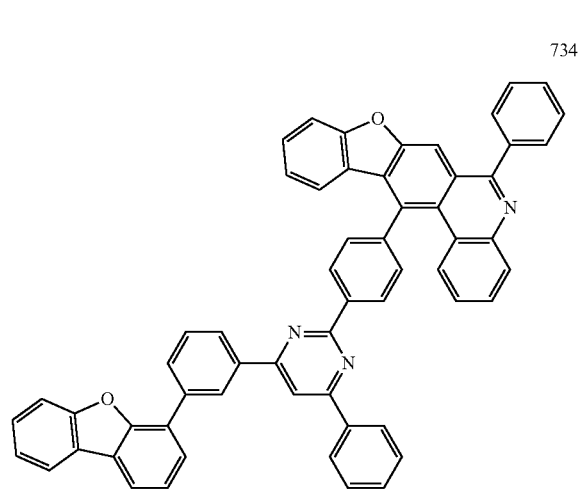
288
-continued
735
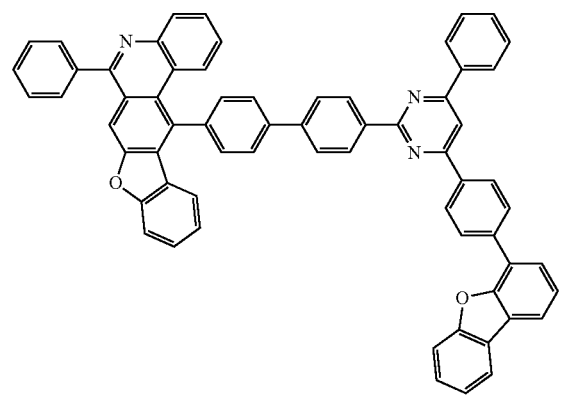
736
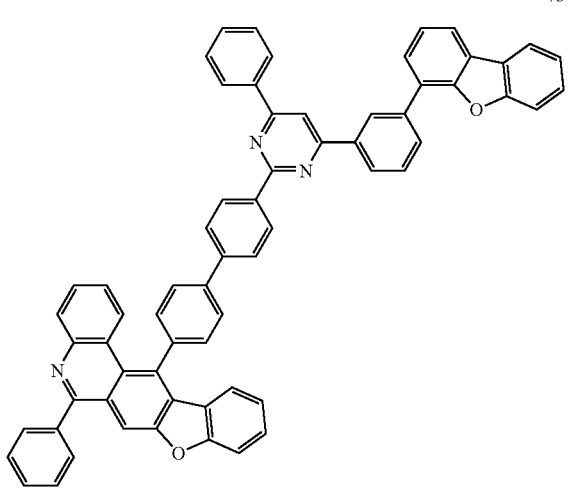
737
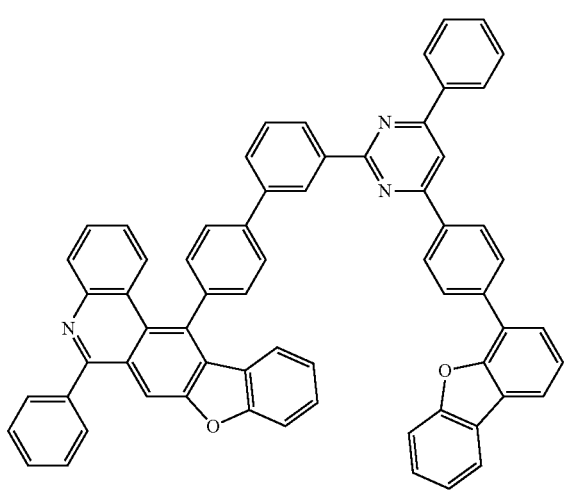

289
-continued
738
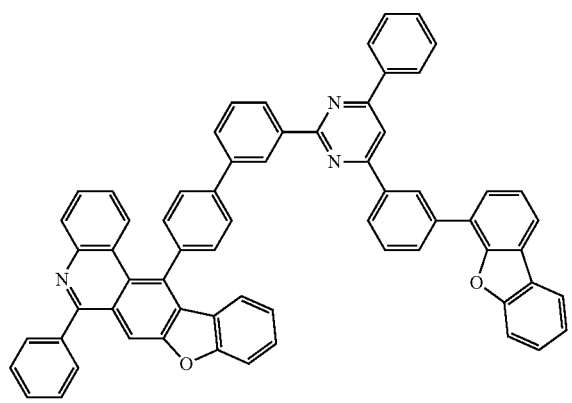
739
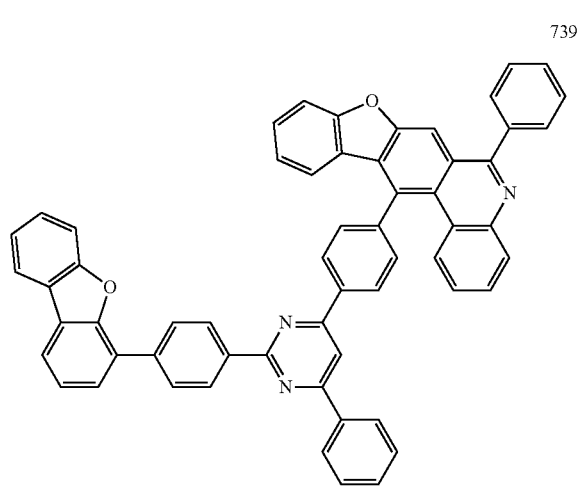
740
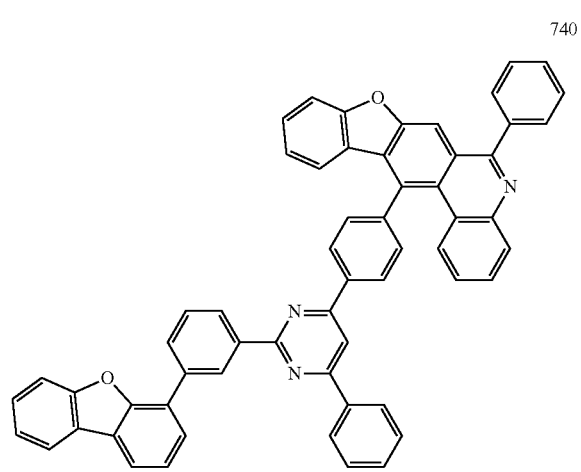
290
-continued
741
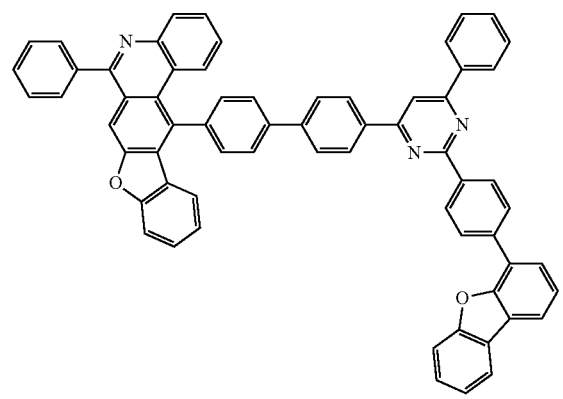 [SMILES: c1ccc(-c2cc(-c3ccc(-c4ccc(-c5c6c(cc7c(-c8ccccc8)nc8ccccc8c57)oc5ccccc56)cc4)cc3)nc(-c3ccc(-c4cccc5c4oc4ccccc45)cc3)n2)cc1]
742
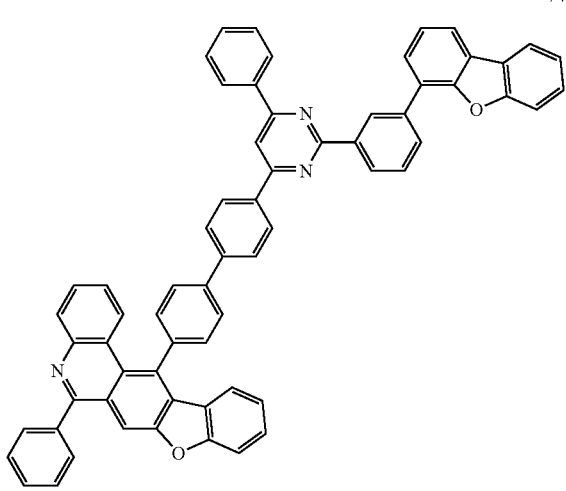
743
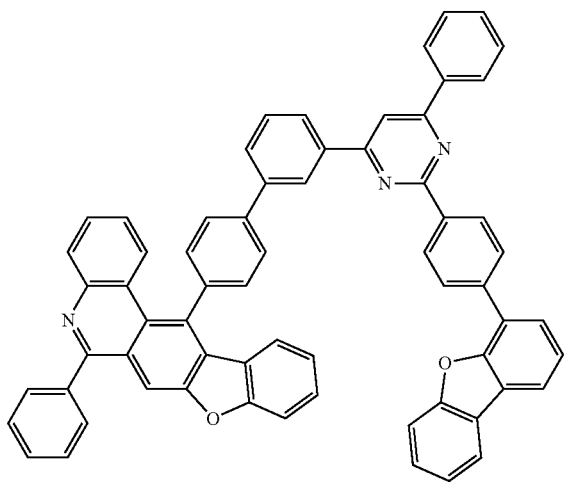

291
-continued
292
-continued
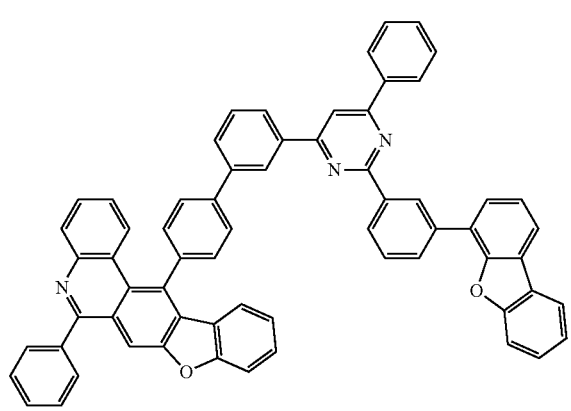
744
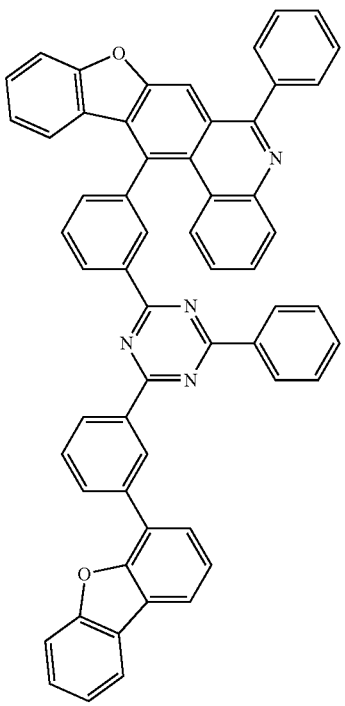
746
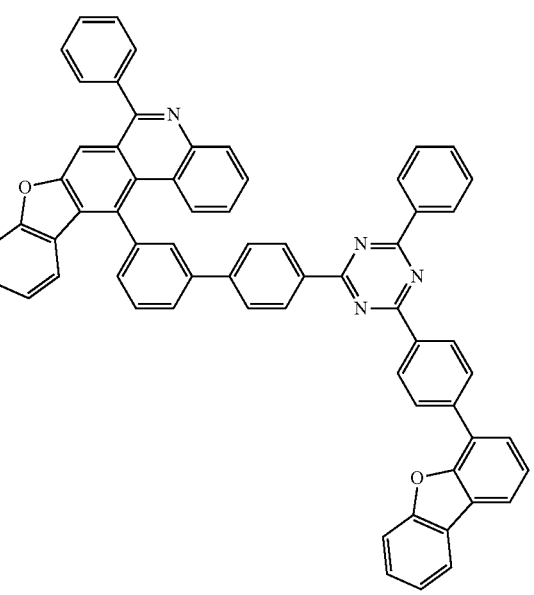
747
745

293
-continued
294
-continued
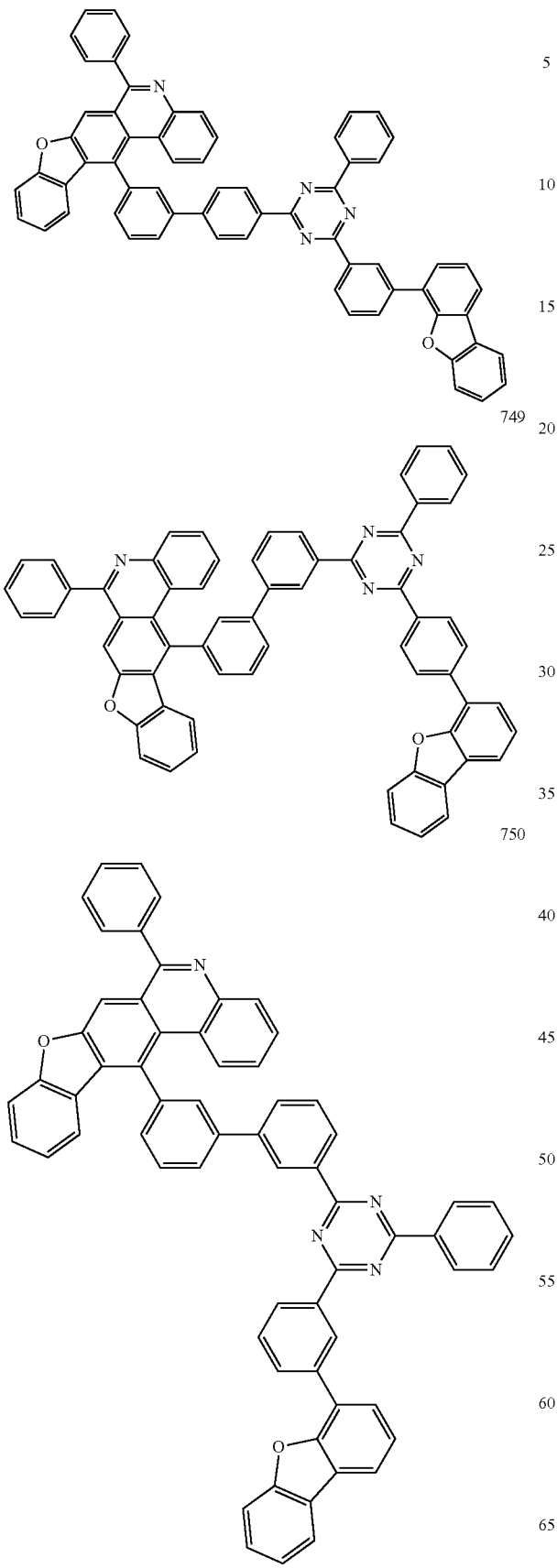
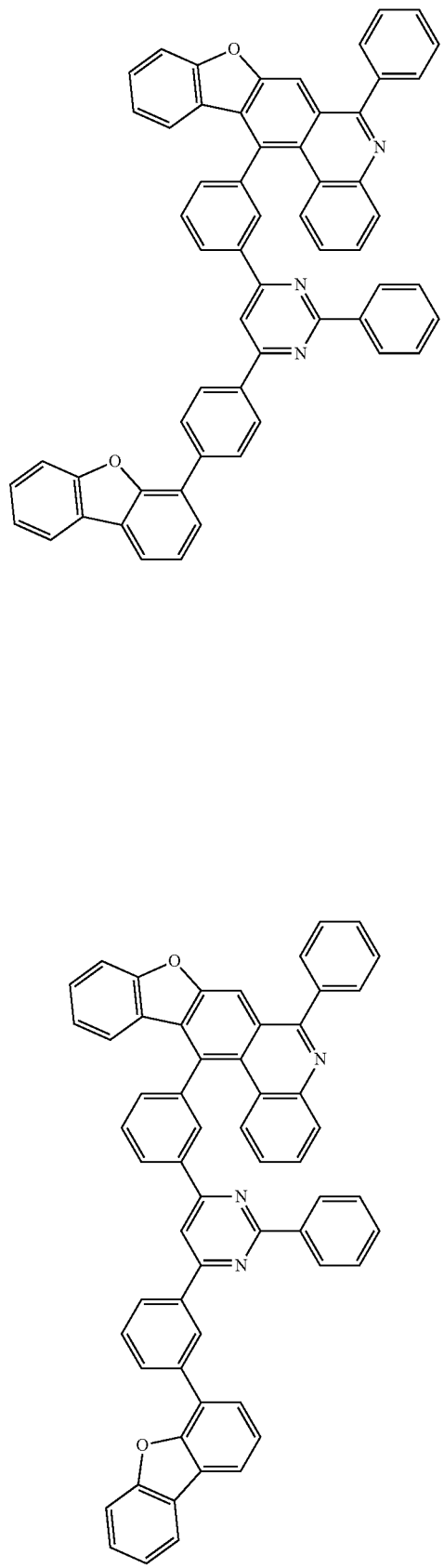

295
-continued
753
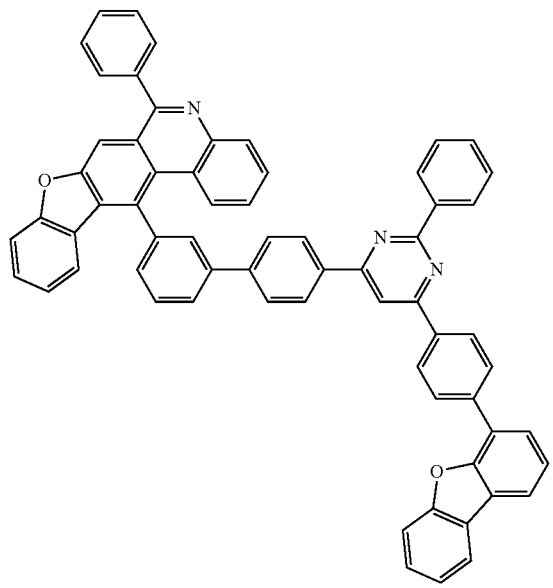
754
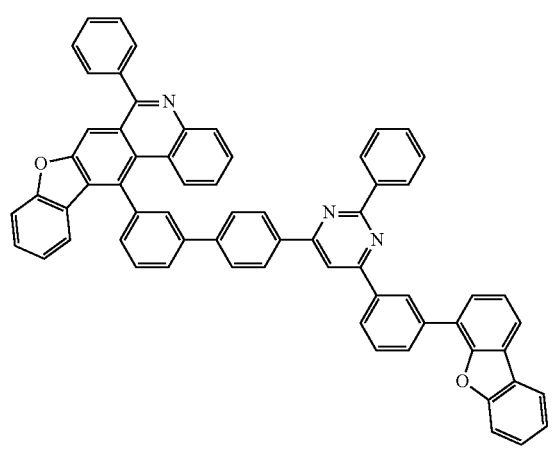
755
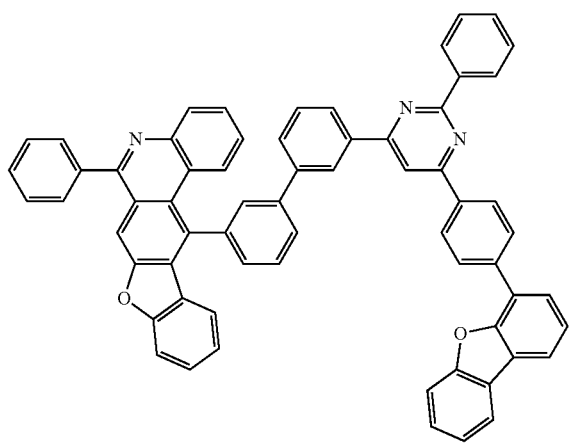
296
-continued
756
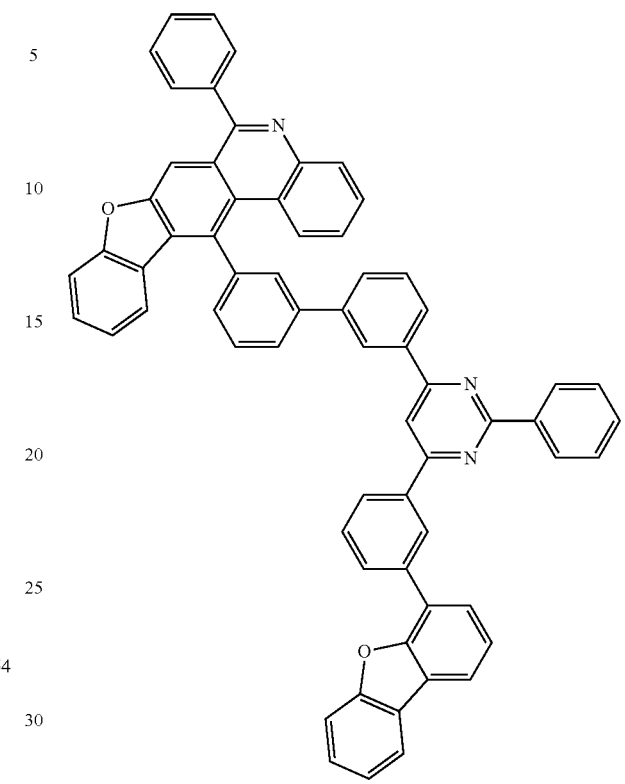
757
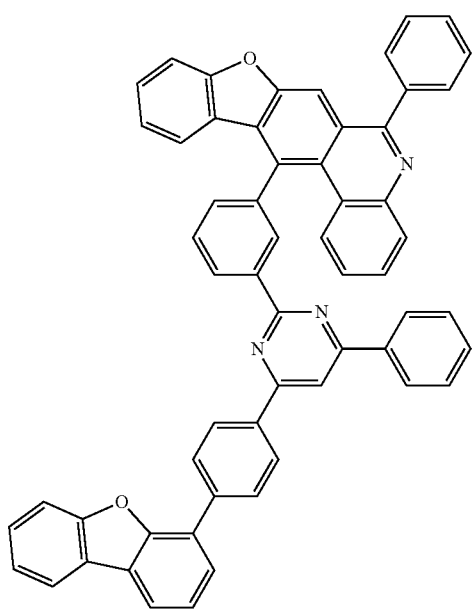 [SMILES: c1ccc(-c2nc(-c3ccc(-c4cccc5c4oc4ccccc45)cc3)nc(-c3cccc(-c4c5c(cc6c(-c7ccccc7)nc7ccccc7c46)oc4ccccc45)c3)n2)cc1]

297
-continued
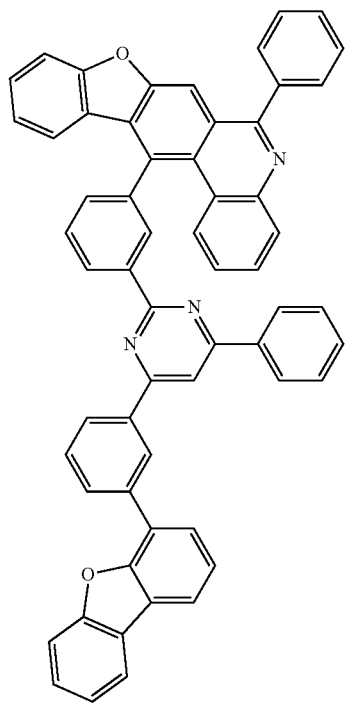
758
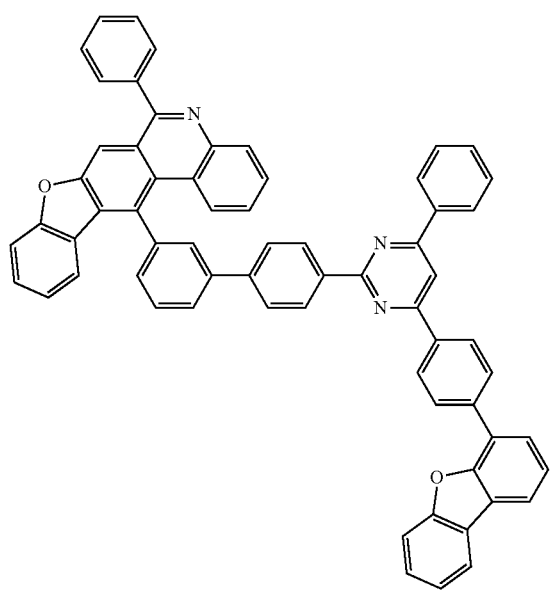
759
298
-continued
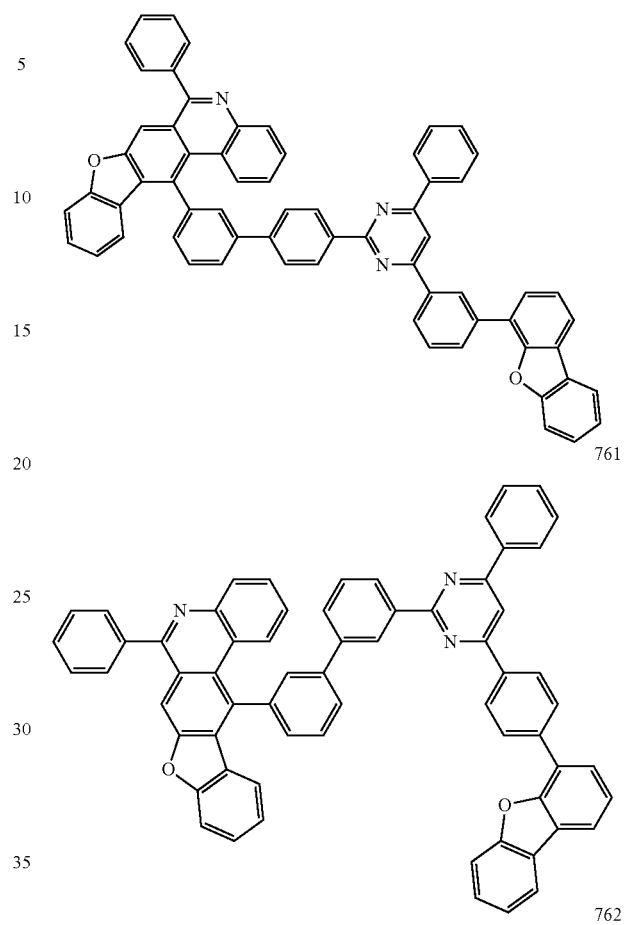
760
761
762

299
-continued
300
-continued
763
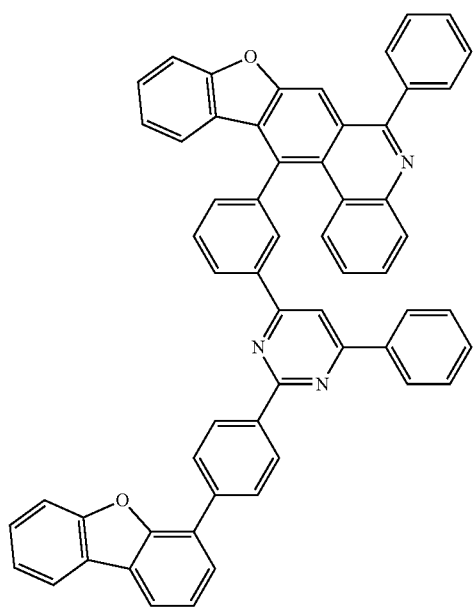
765
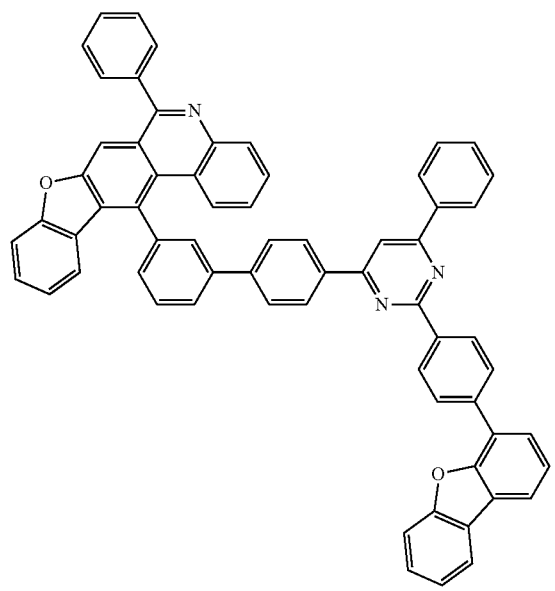
766
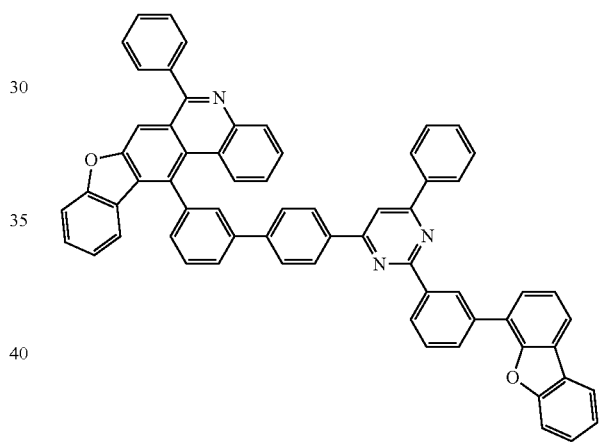
764
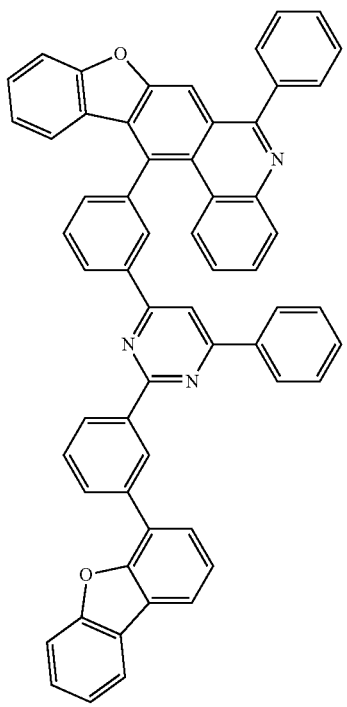
767
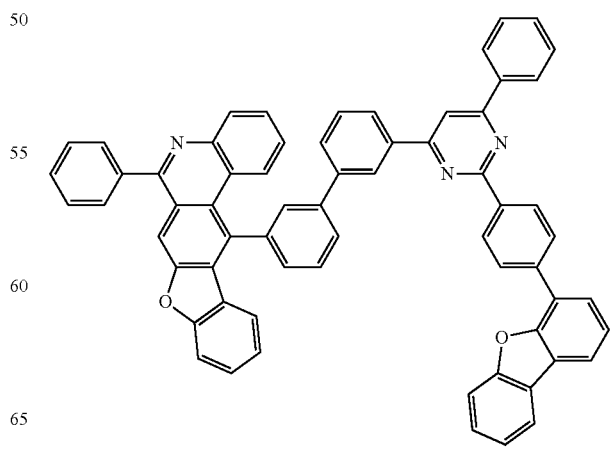

301
-continued
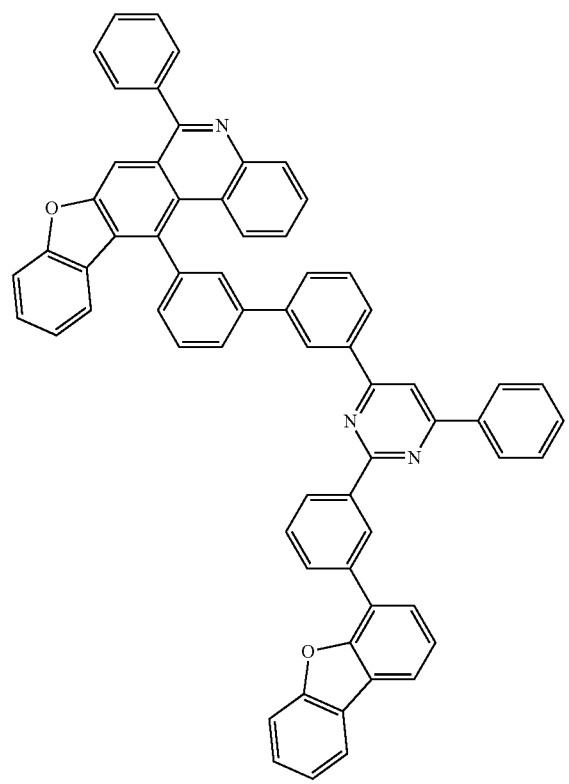
768
302
-continued
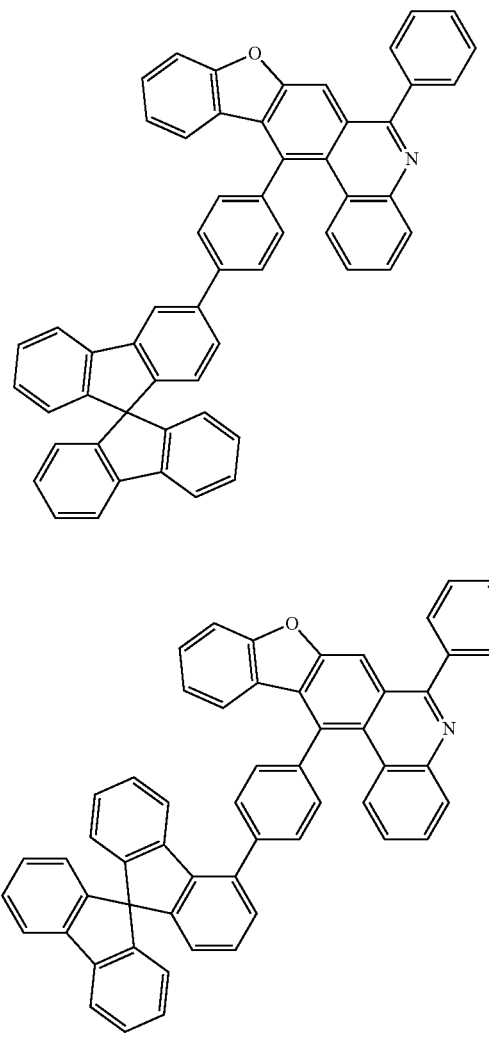
770
771
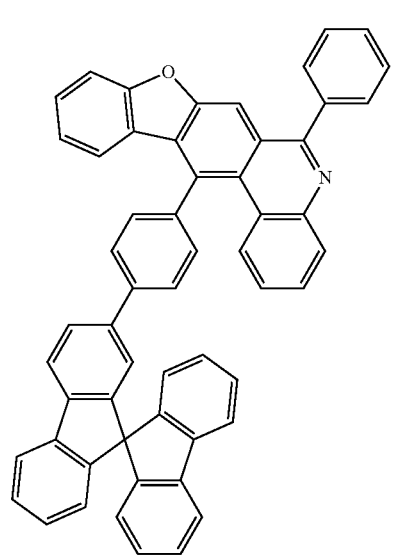
769
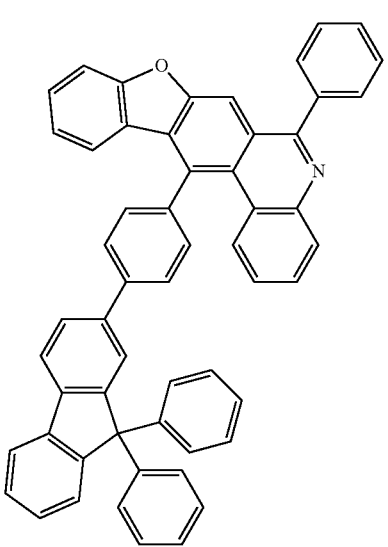
772

303
-continued
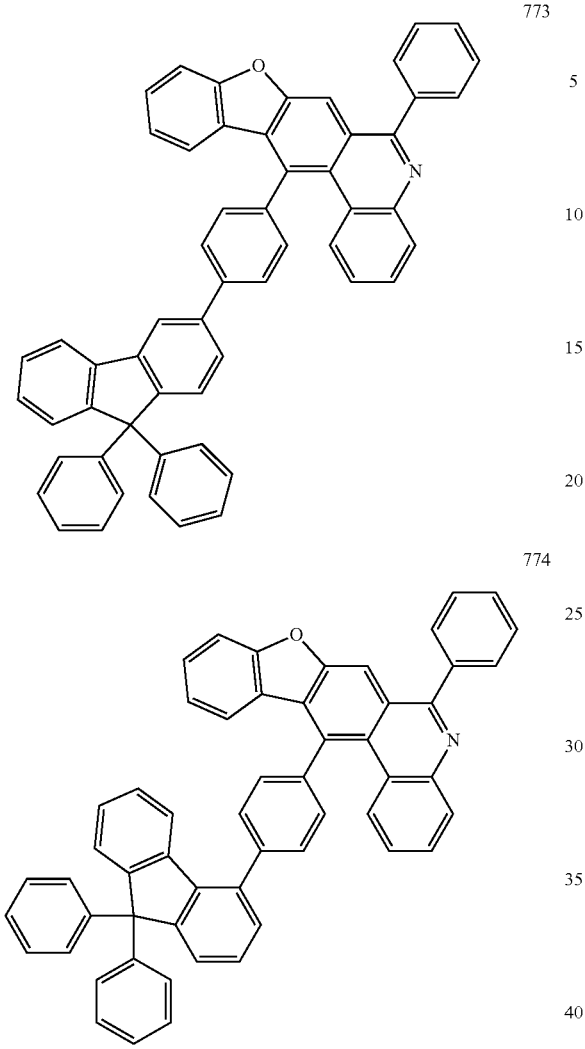
773
774
775
304
-continued
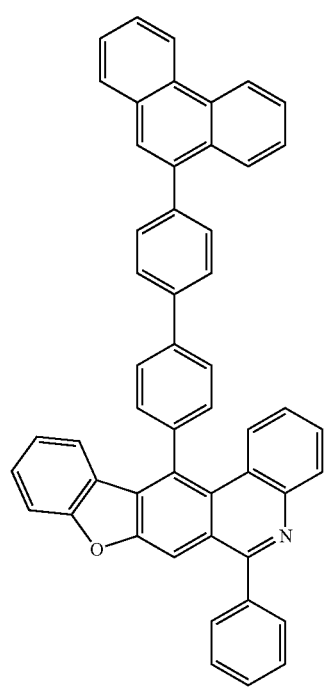
776
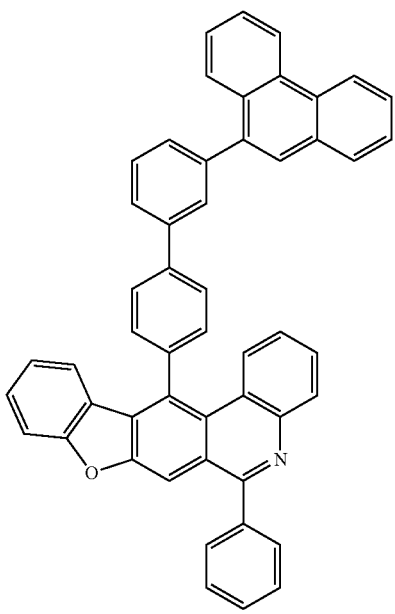
777
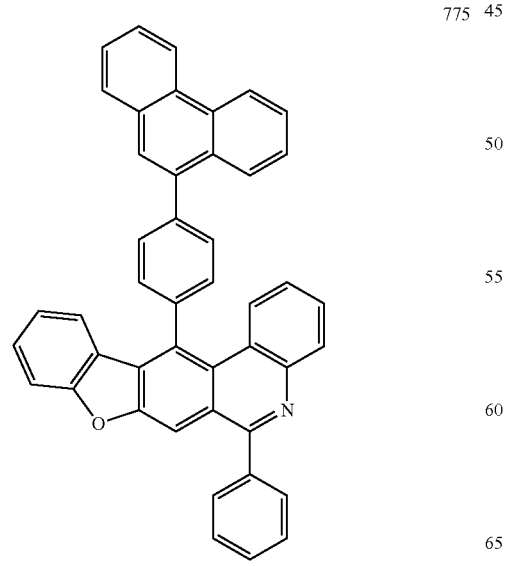

305
-continued
778
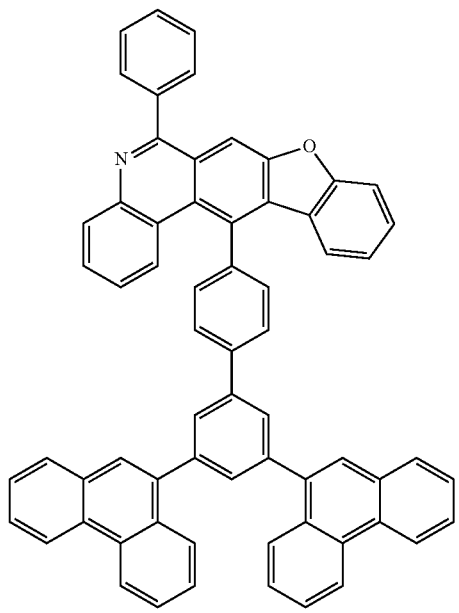
306
-continued
780
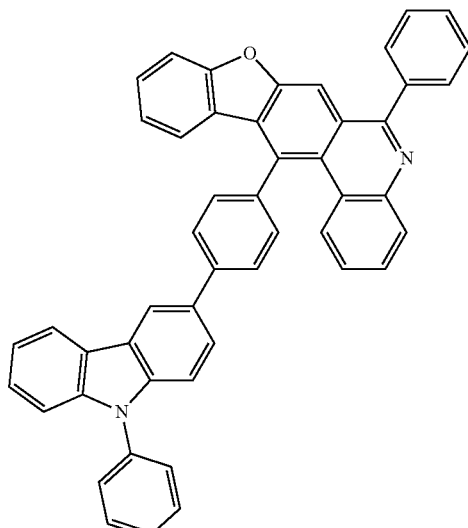
779
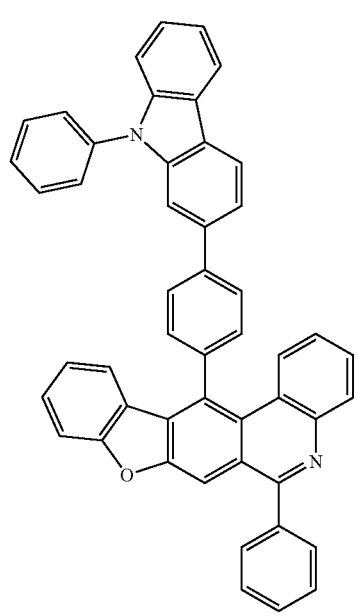
781
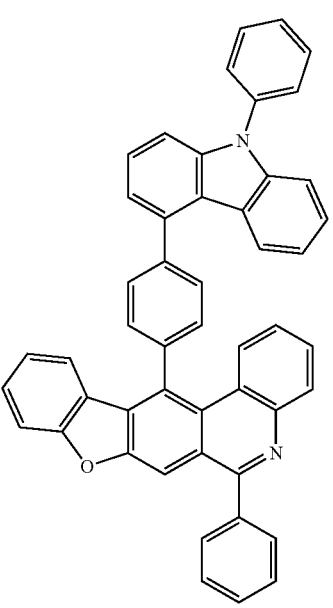

307
-continued
782
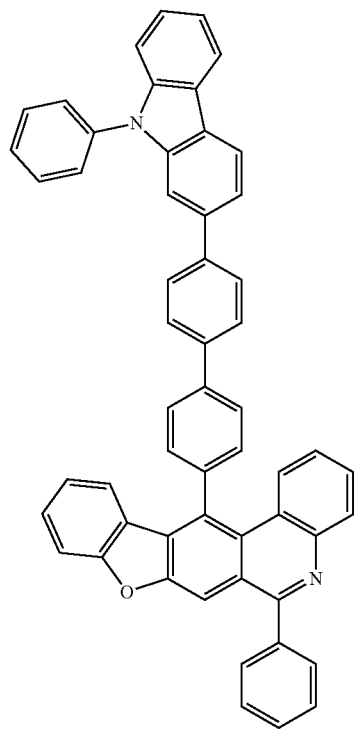
783
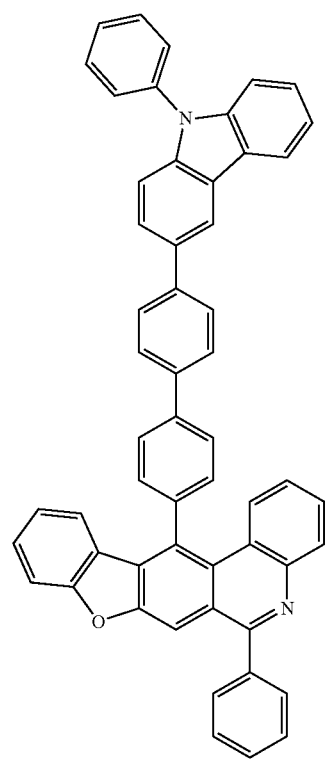
308
-continued
784
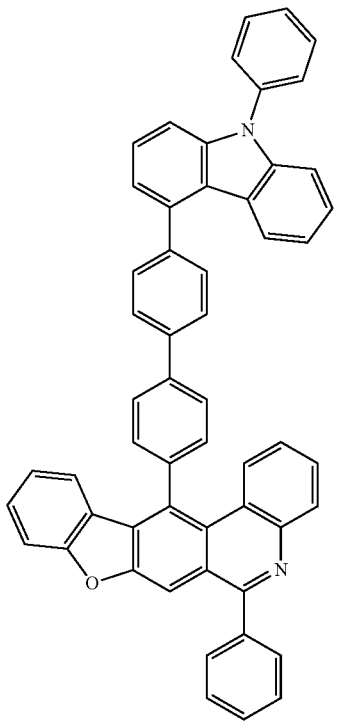
785
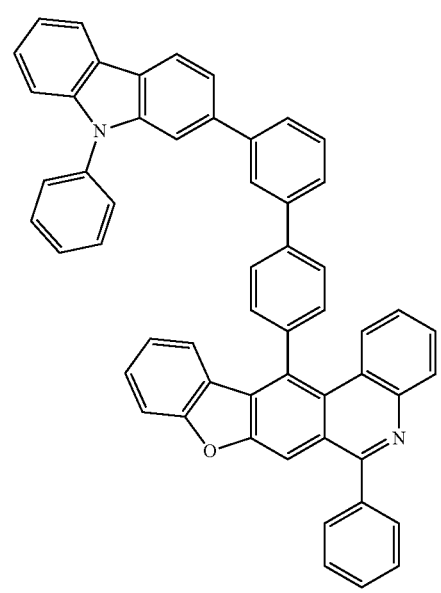

309
-continued
786
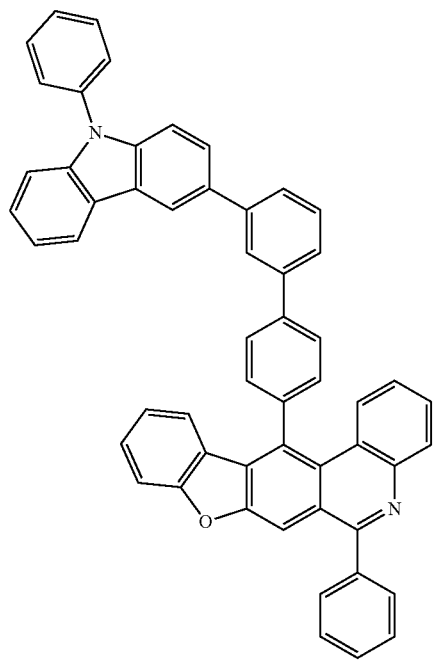
787
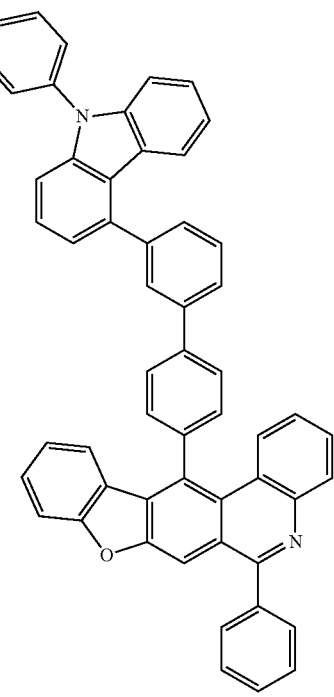
310
-continued
788
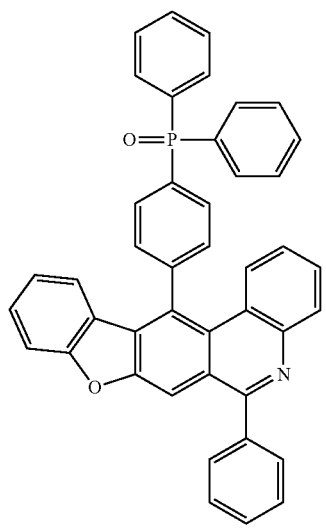
789
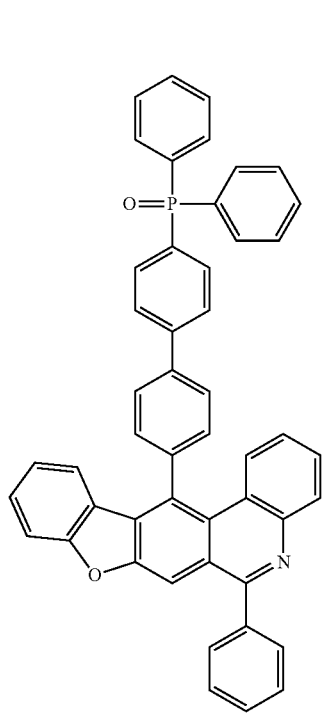 [SMILES: O=P(c1ccccc1)(c1ccccc1)c1ccc(-c2ccc(-c3c4c(cc5c(-c6ccccc6)nc6ccccc6c35)oc3ccccc34)cc2)cc1]

311
-continued
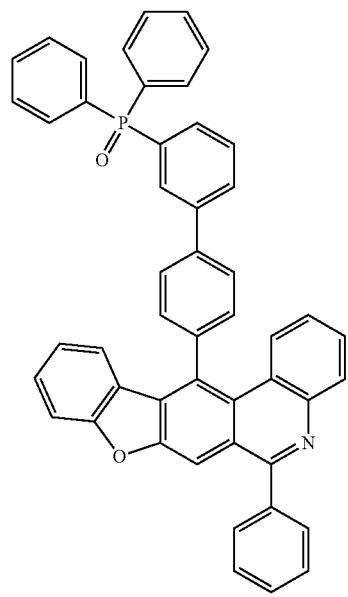
790
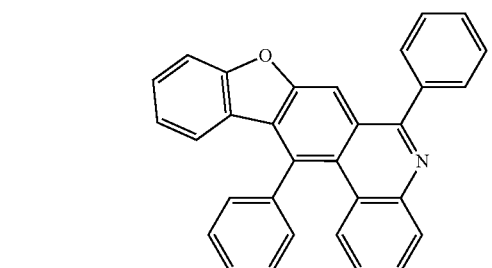
792
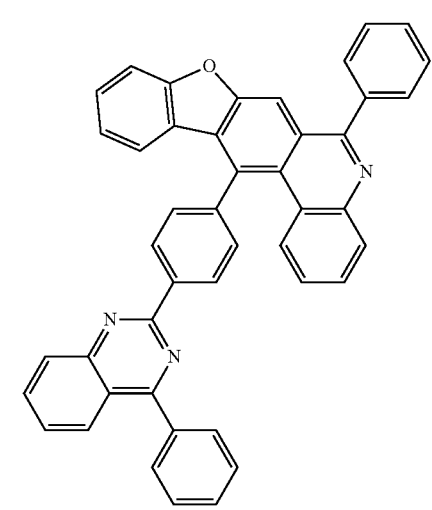
793
312
-continued
791
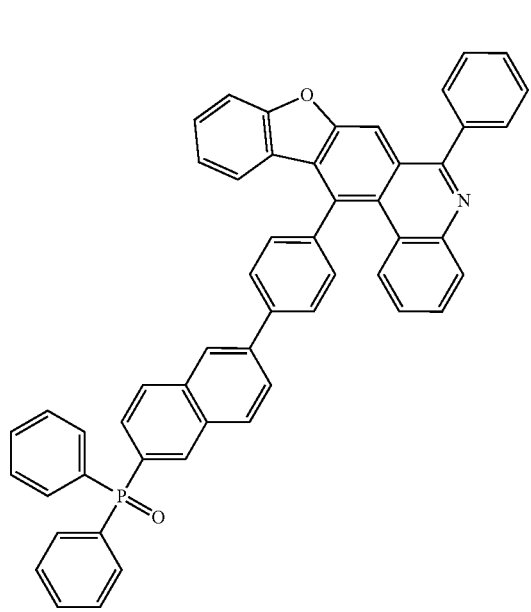
794
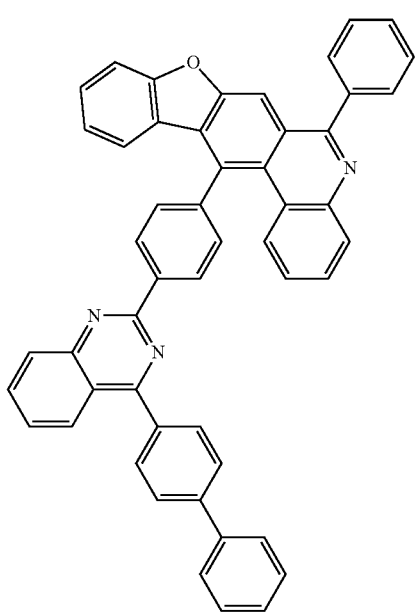

313
-continued
795
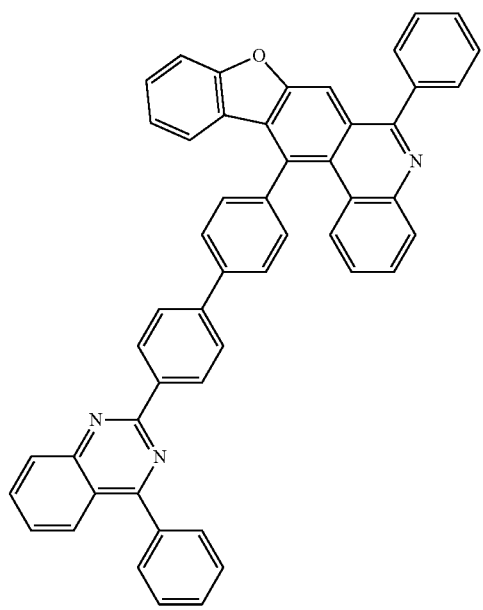
796
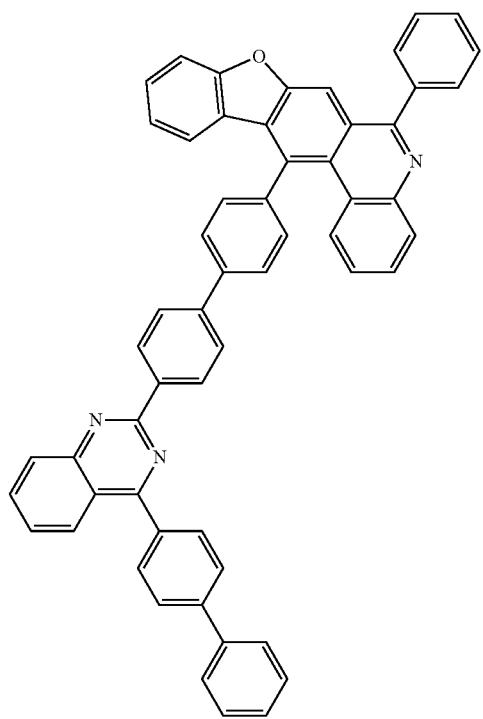
314
-continued
797
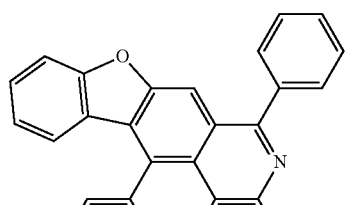
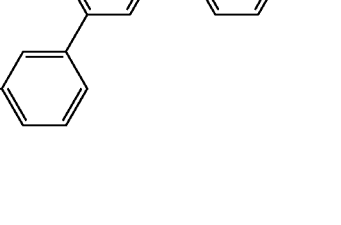
798
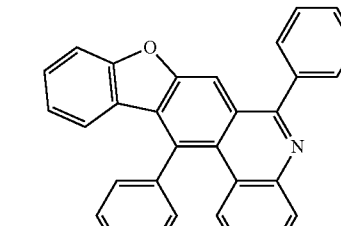
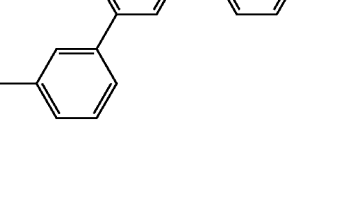
799

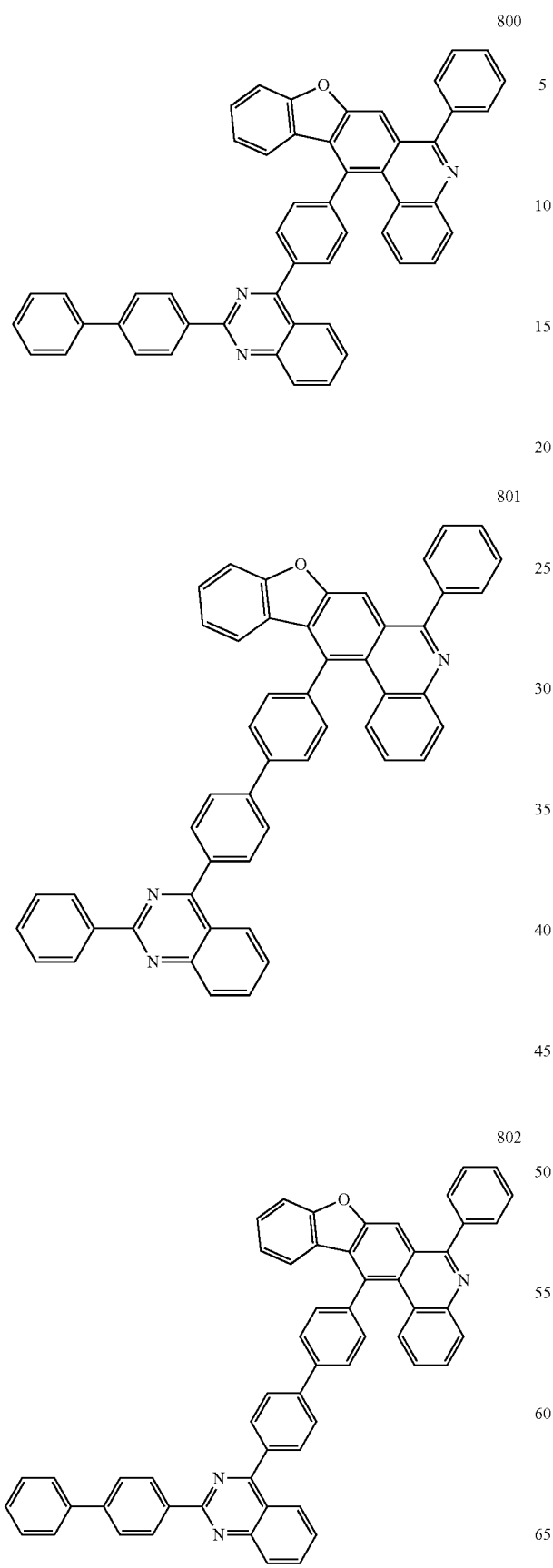
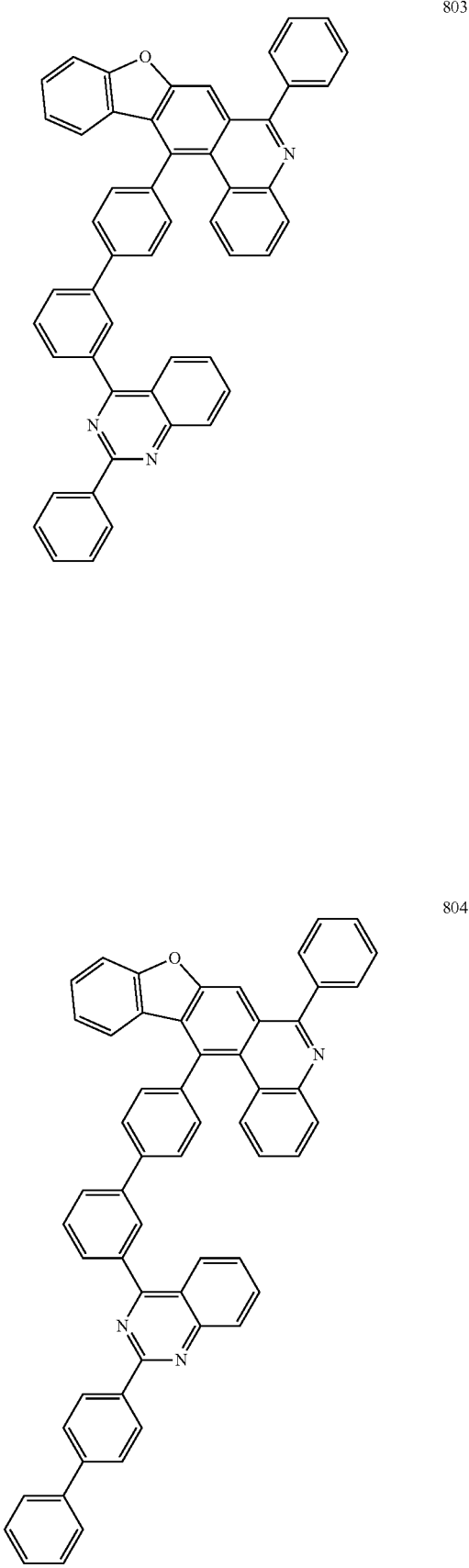

317
-continued
805
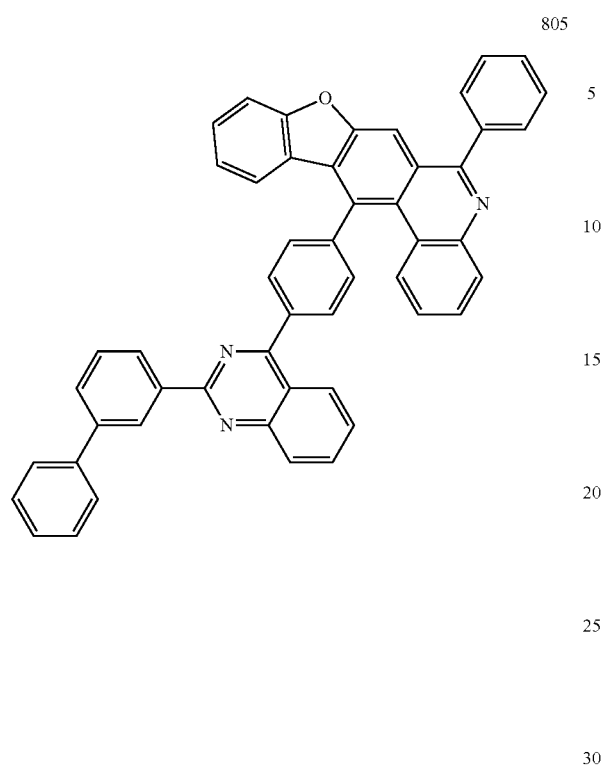
806
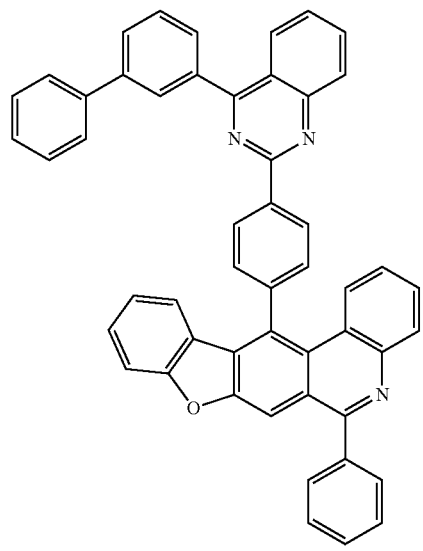
318
-continued
807
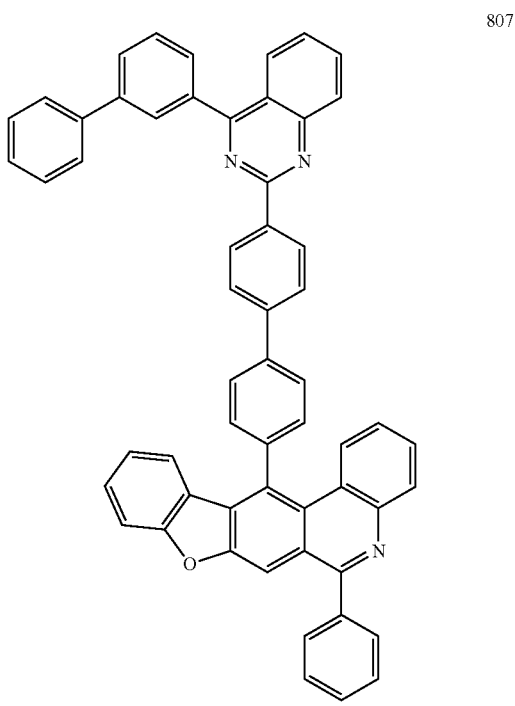
808
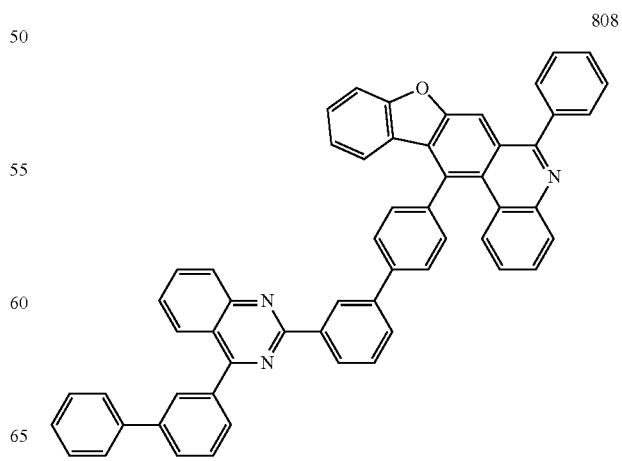

319
-continued
320
-continued
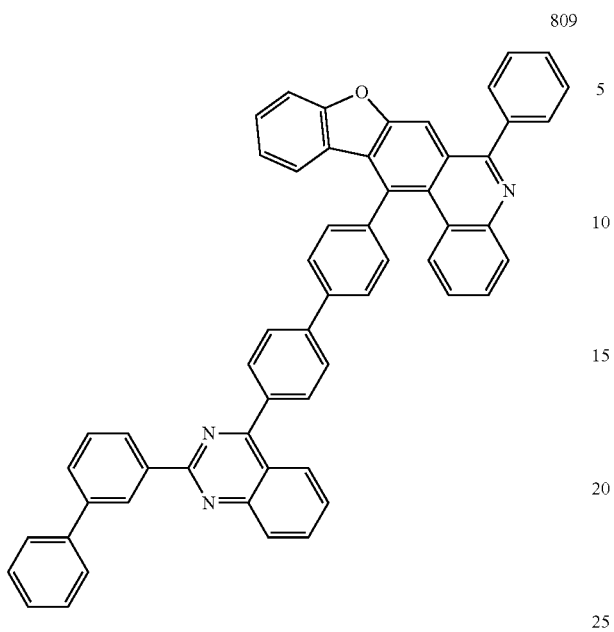
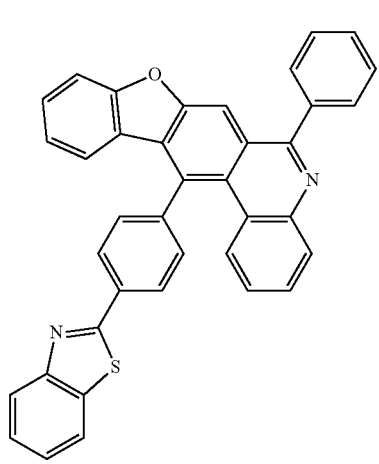
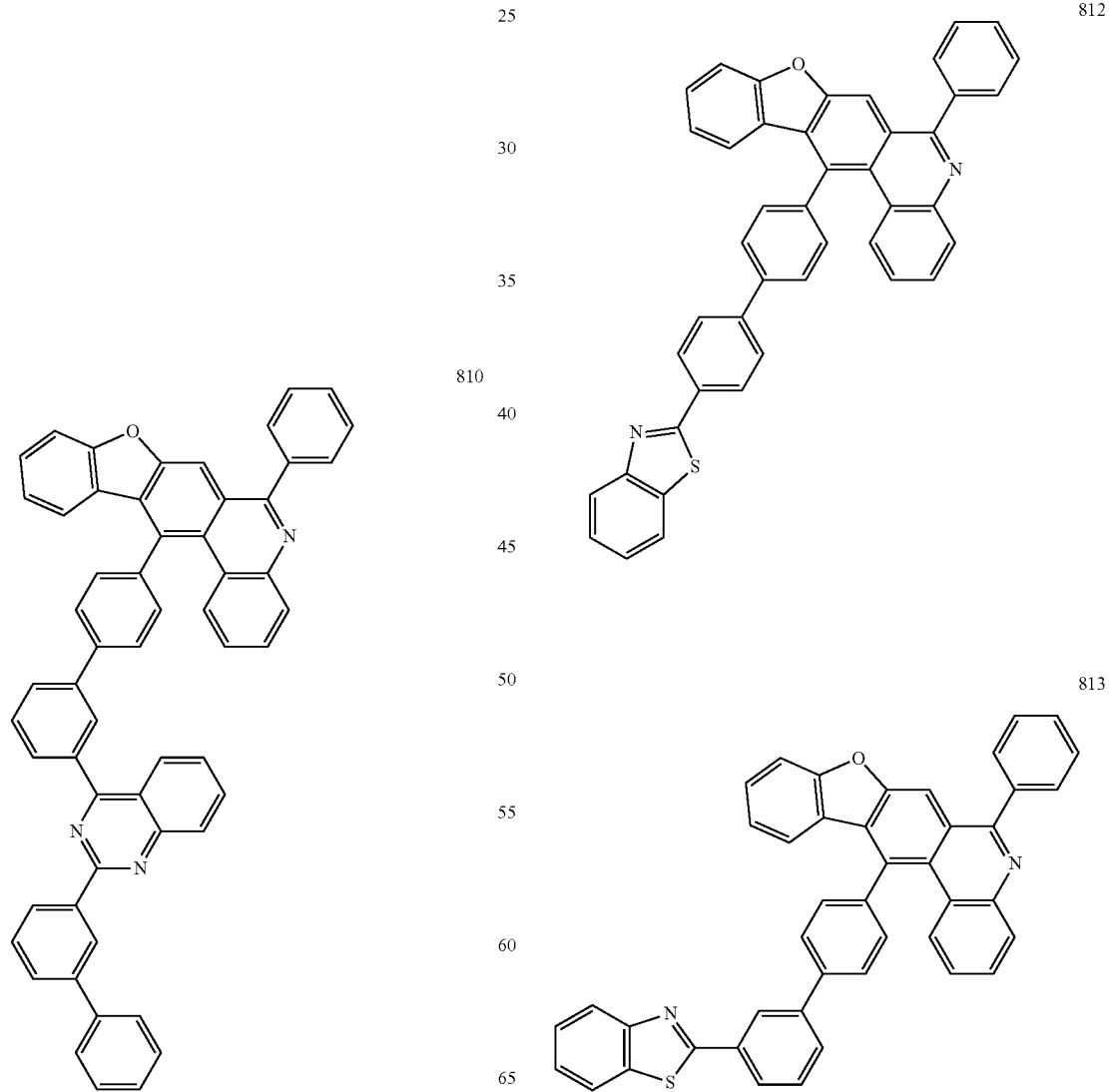

-continued
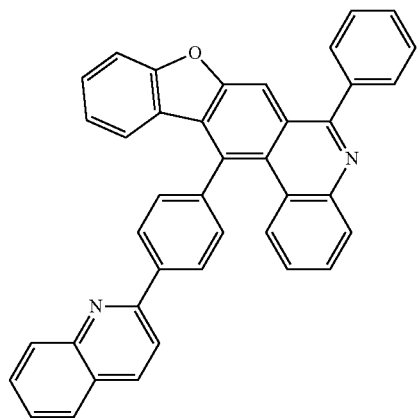
814
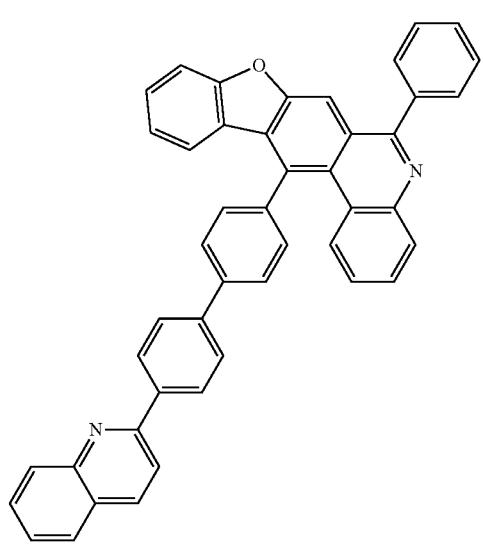 [SMILES: c1ccc(-c2nc3ccccc3c3c(-c4ccc(-c5ccc(-c6ccc7ccccc7n6)cc5)cc4)c4c(cc23)oc2ccccc24)cc1]
815
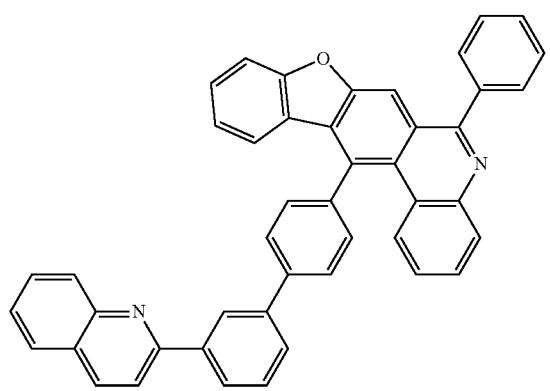
816
-continued
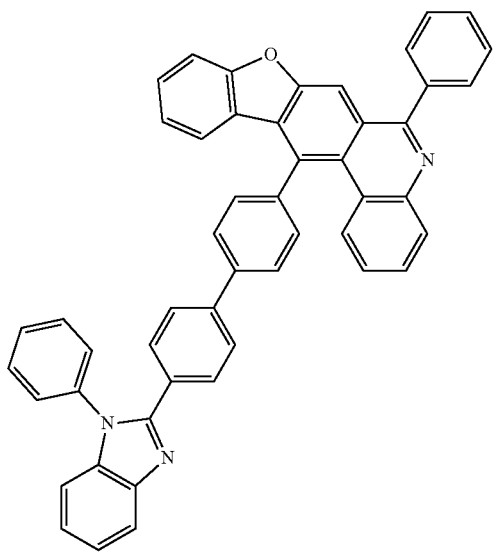
817
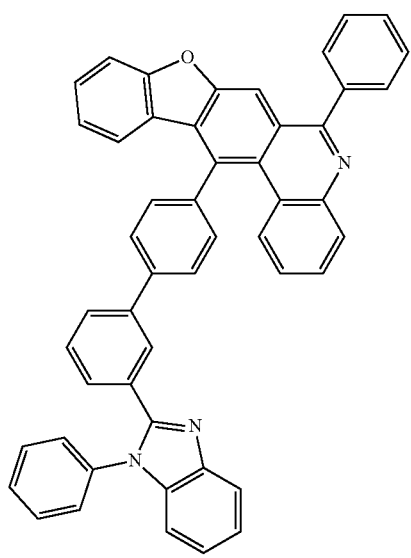
818
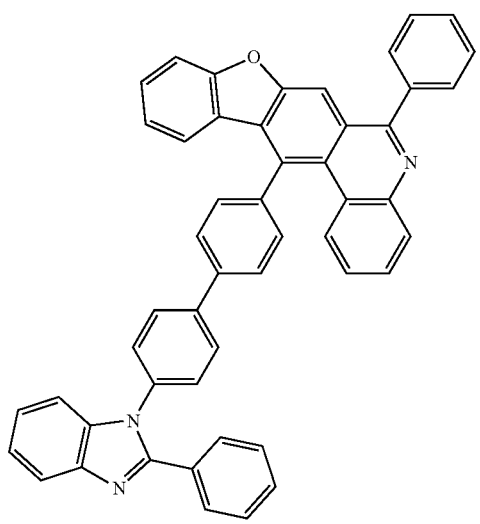
819

323
-continued
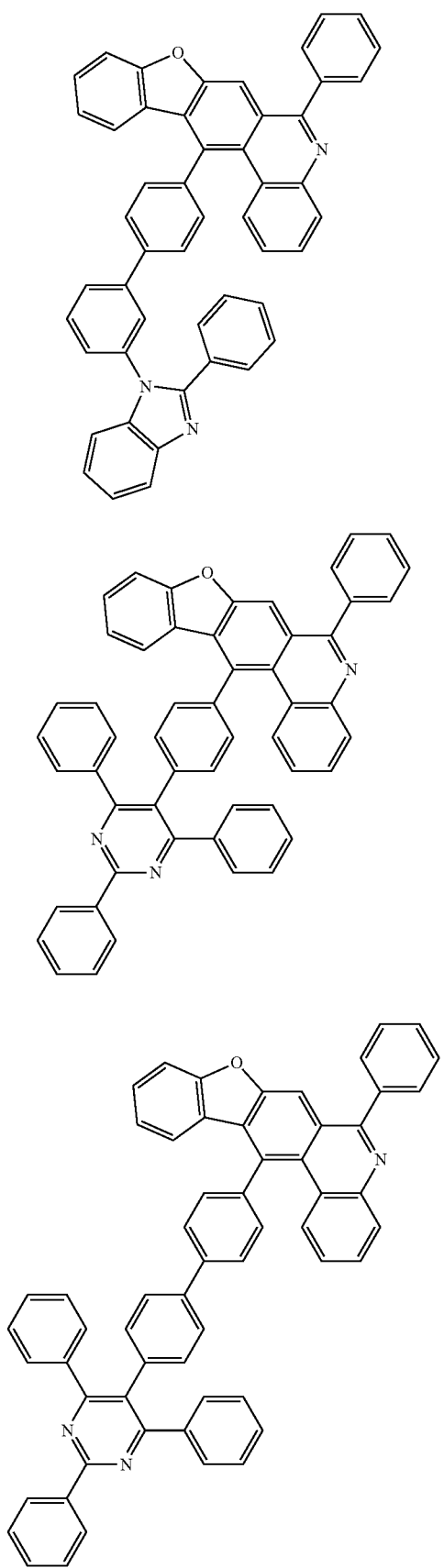
324
-continued
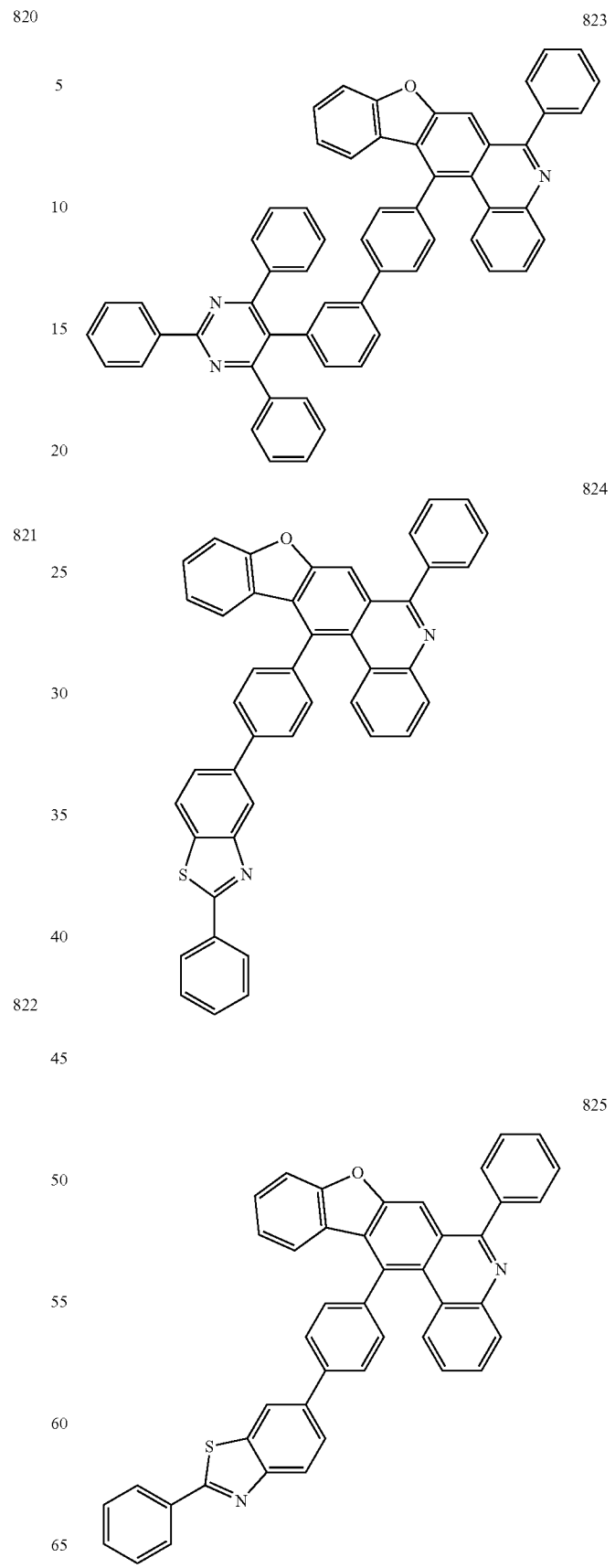

-continued
826
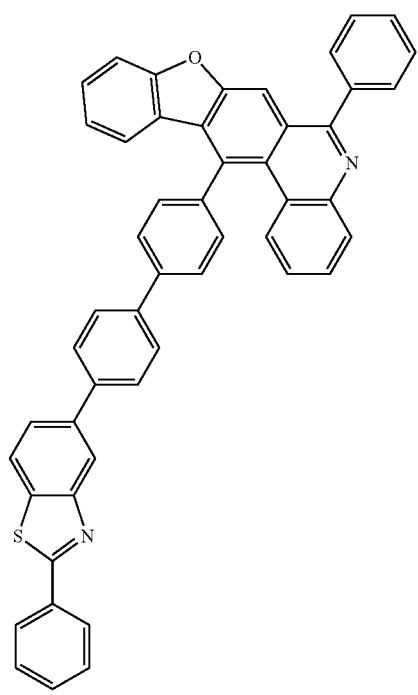
827
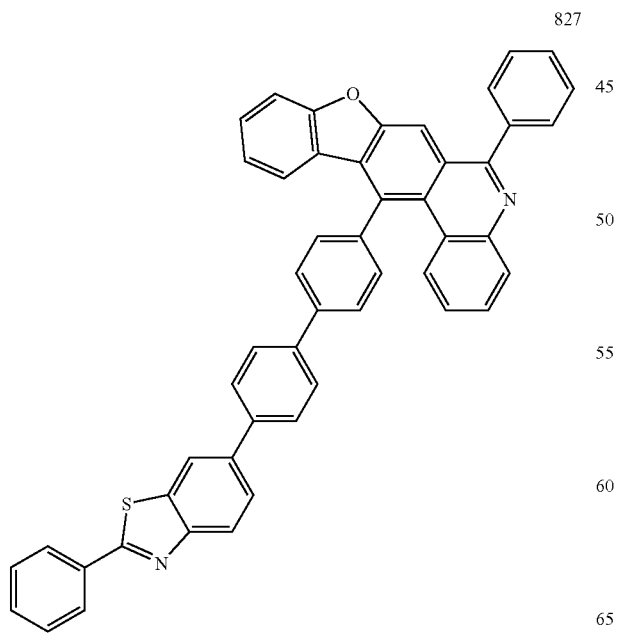
-continued
828
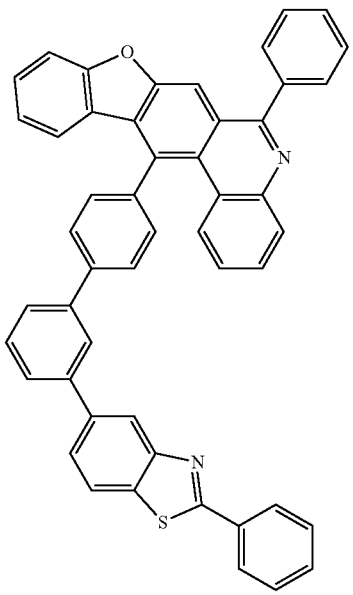
829
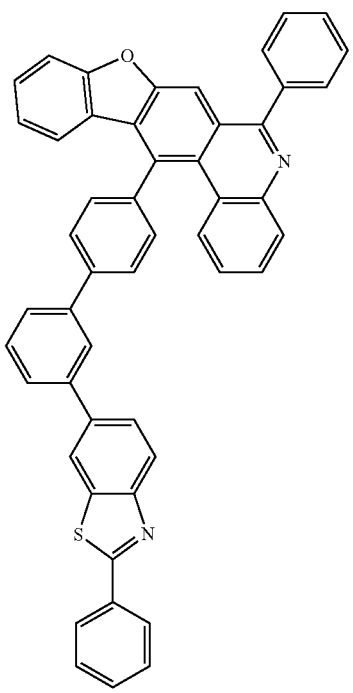

327
-continued
830
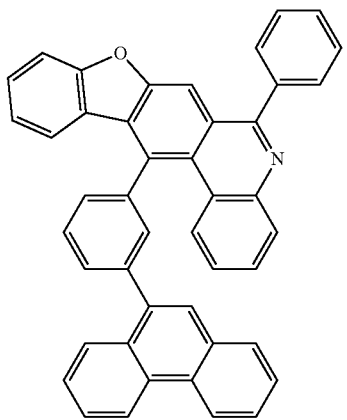
831
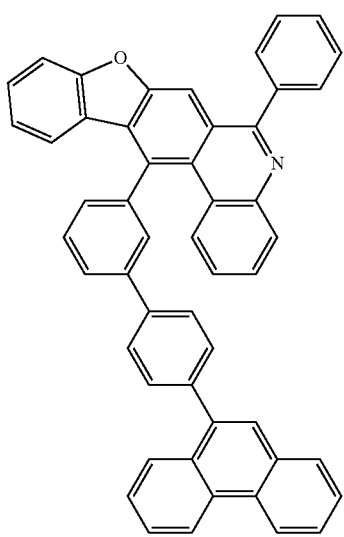
832
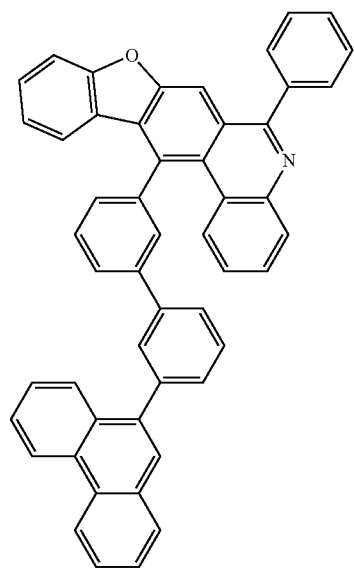
328
-continued
833
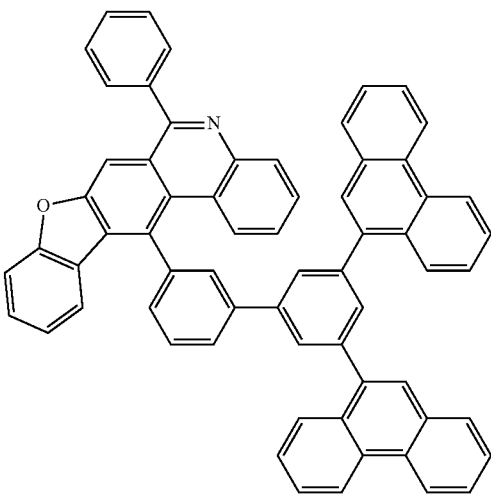
834
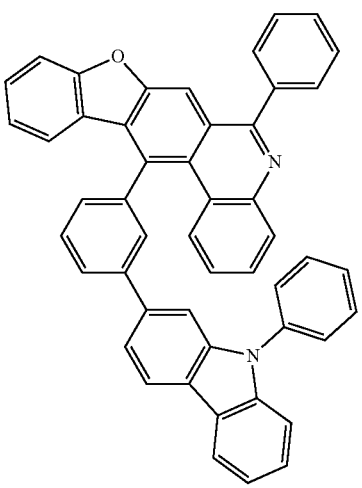
835

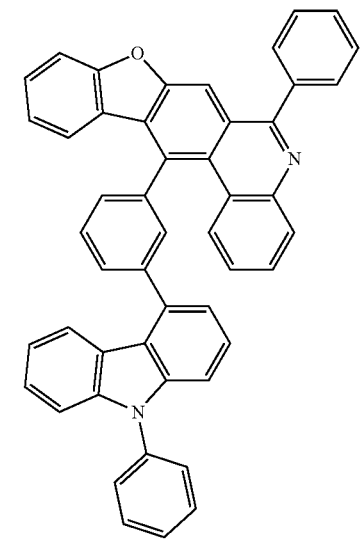 [SMILES: c1ccc(-c2nc3ccccc3c3c(-c4cccc(-c5cccc6c5c5ccccc5n6-c5ccccc5)c4)c4c(cc23)oc2ccccc24)cc1]
836
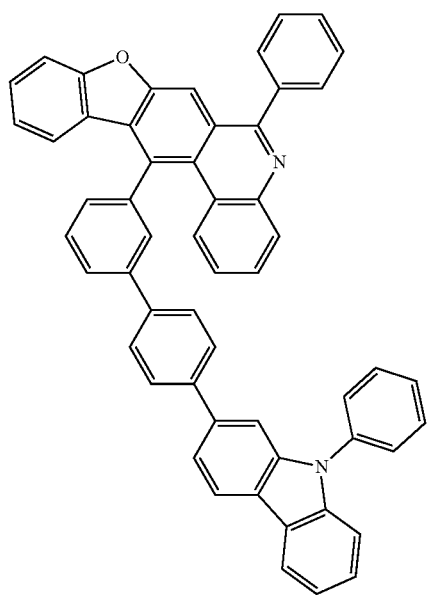
837
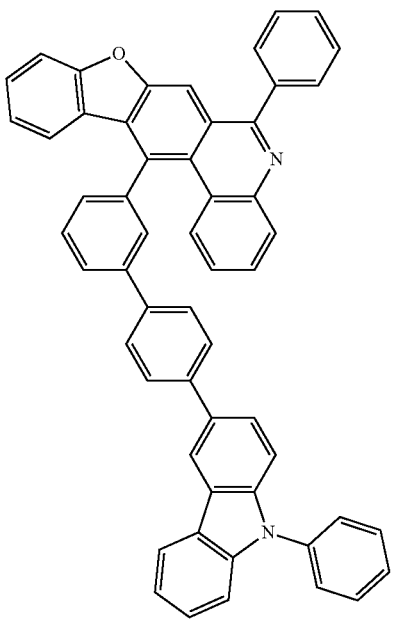
838
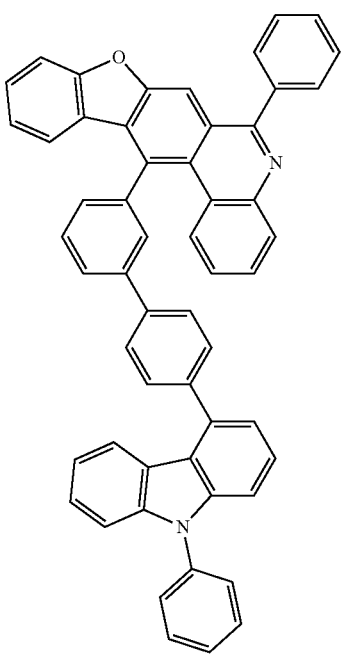
839
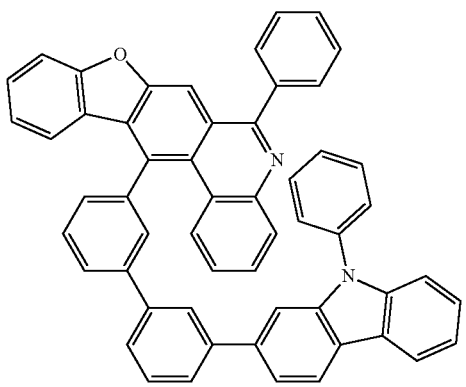
840

331
-continued
841
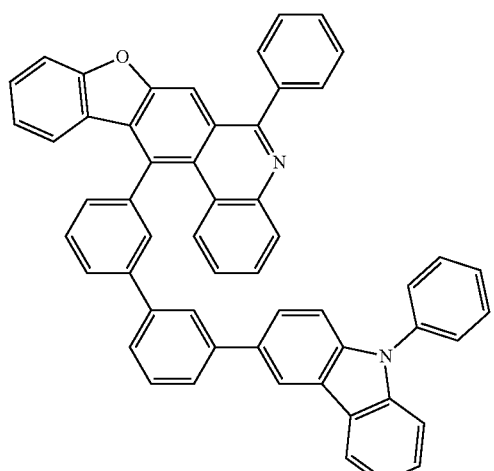
842
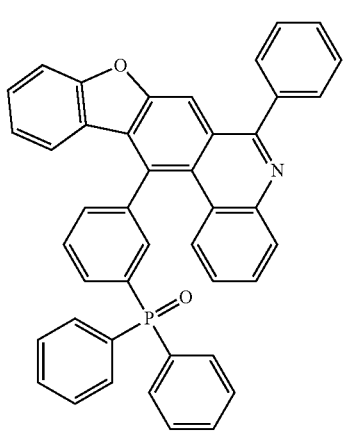
843
332
-continued
844
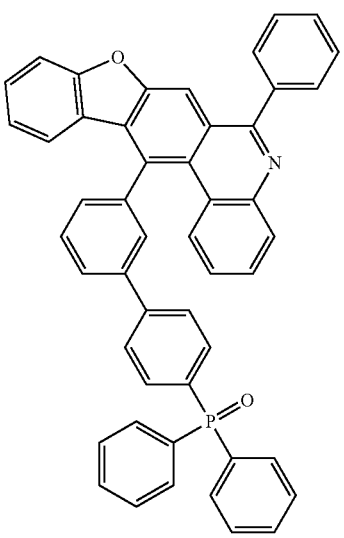
845
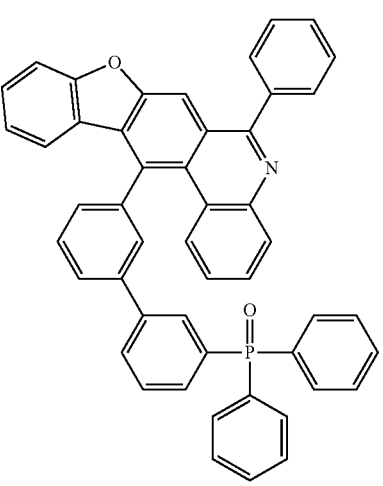
846

333
-continued
847
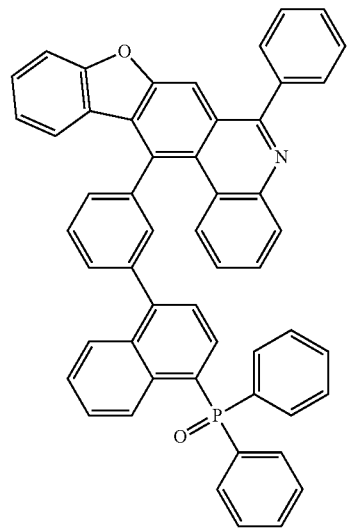 [SMILES: O=P(c1ccccc1)(c1ccccc1)c1ccc(-c2cccc(-c3c4c(cc5c(-c6ccccc6)nc6ccccc6c35)oc3ccccc34)c2)c2ccccc12]
848
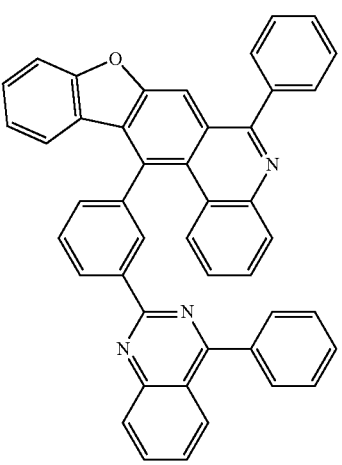 [SMILES: c1ccc(-c2nc(-c3cccc(-c4c5c(cc6c(-c7ccccc7)nc7ccccc7c46)oc4ccccc45)c3)nc3ccccc23)cc1]
849
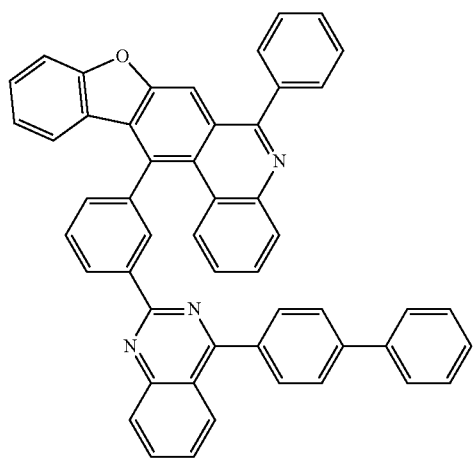
334
-continued
850
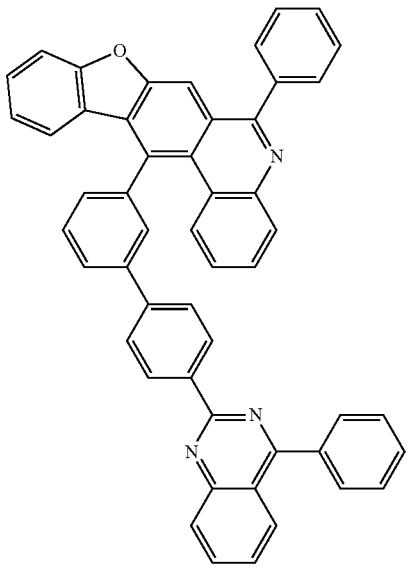
851
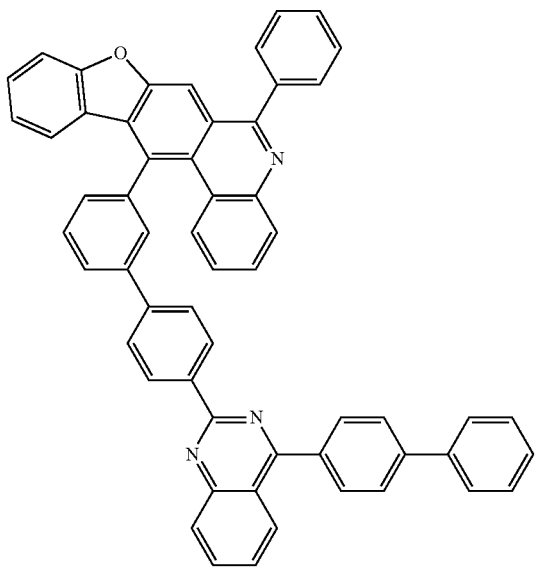

852
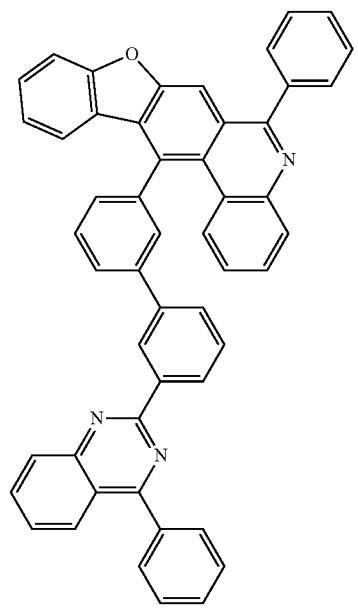
853
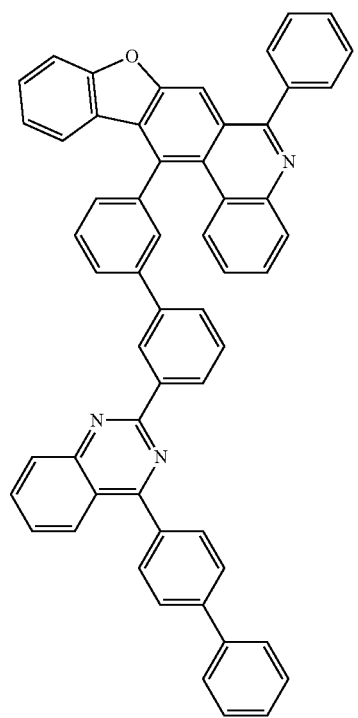
854
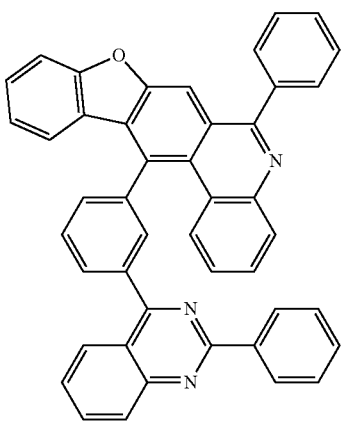
855
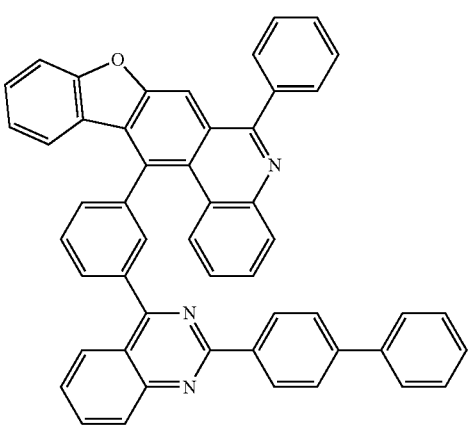 [SMILES: c1ccc(-c2ccc(-c3nc(-c4cccc(-c5c6c(cc7c(-c8ccccc8)nc8ccccc8c57)oc5ccccc56)c4)c4ccccc4n3)cc2)cc1]
856
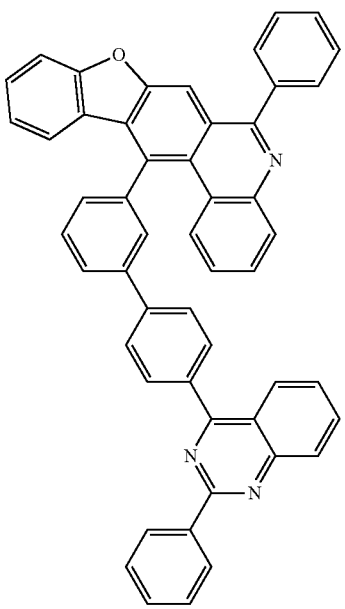

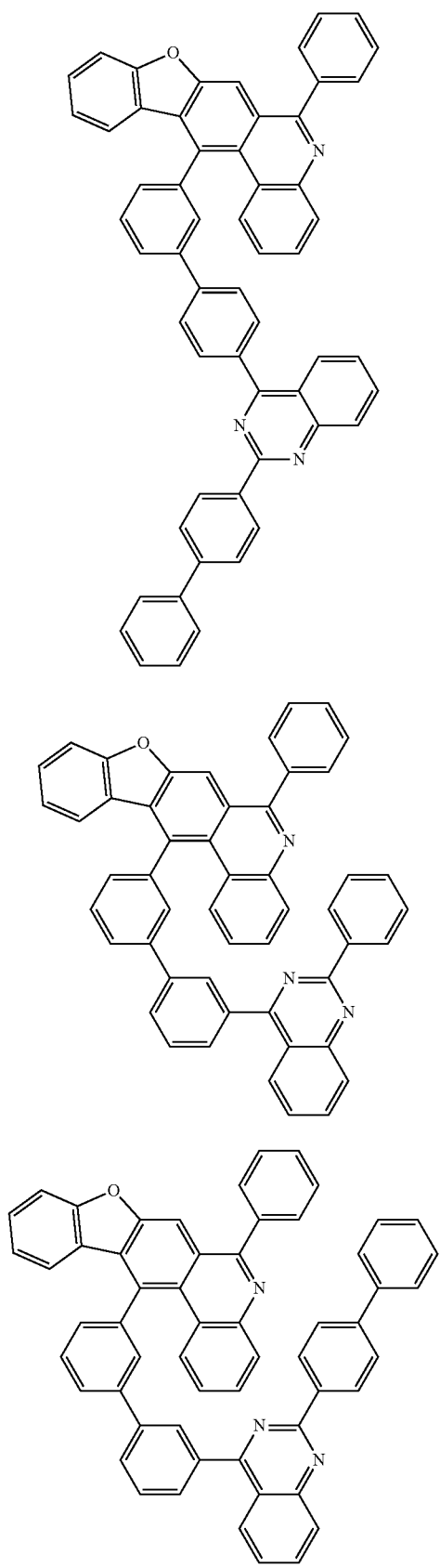
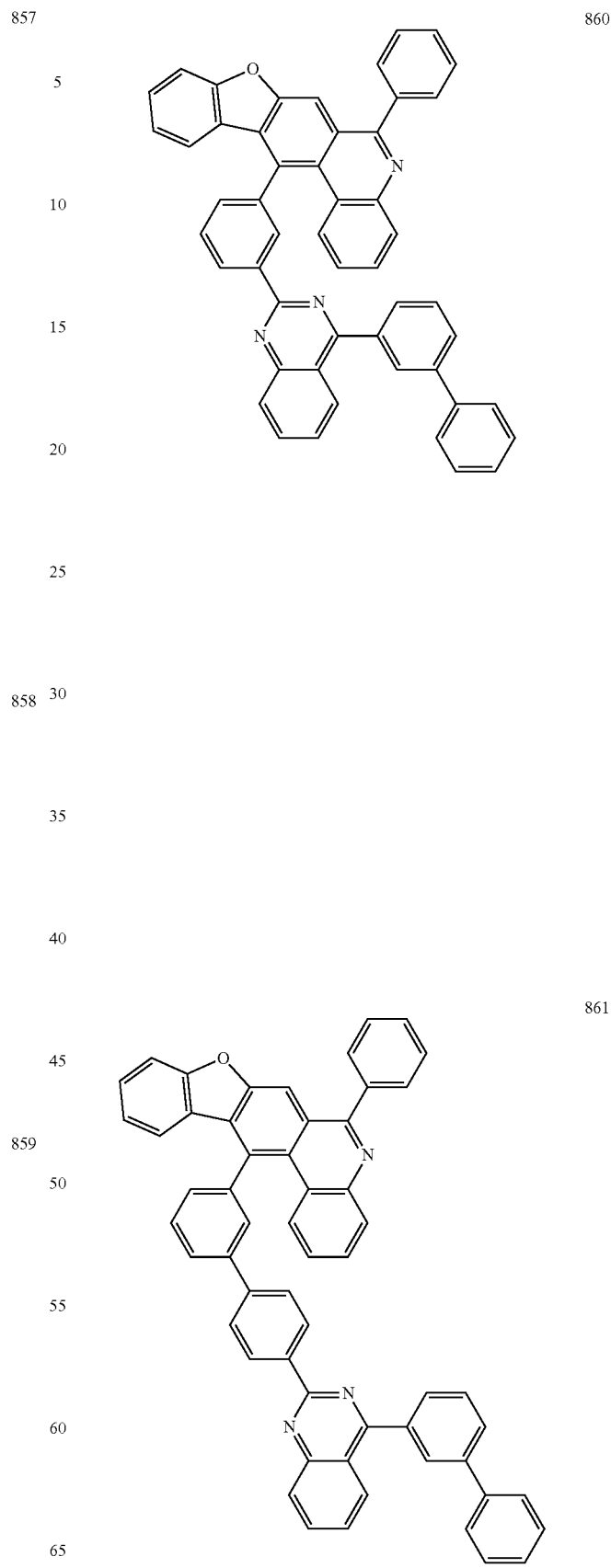

339
-continued
862
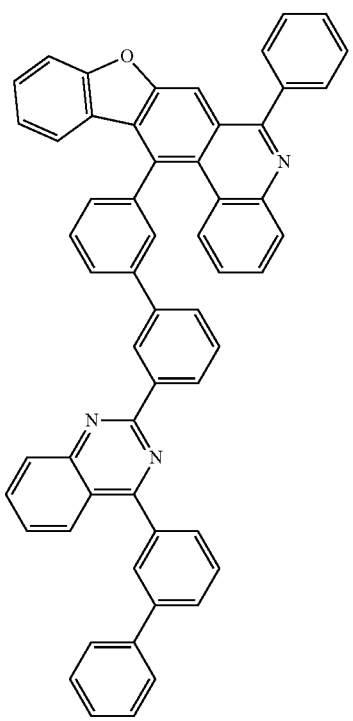
340
-continued
864
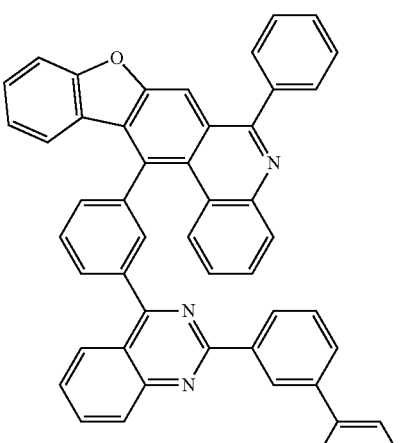
865
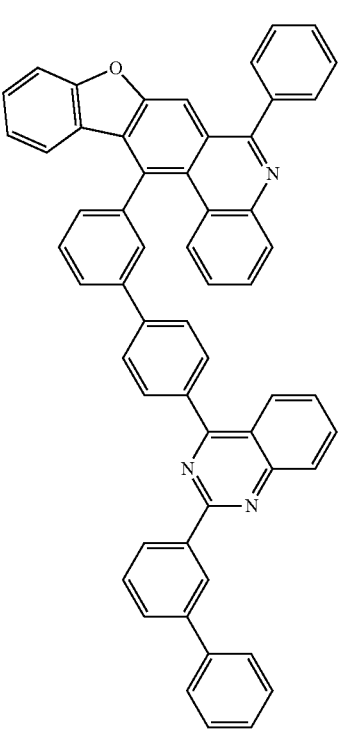
863
866
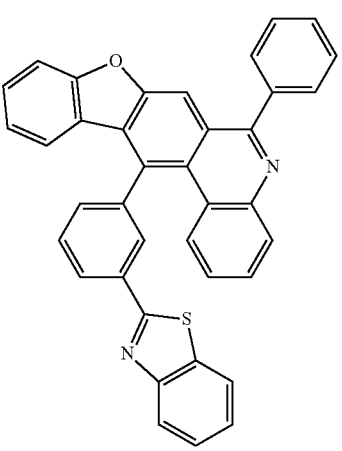

341
-continued
867
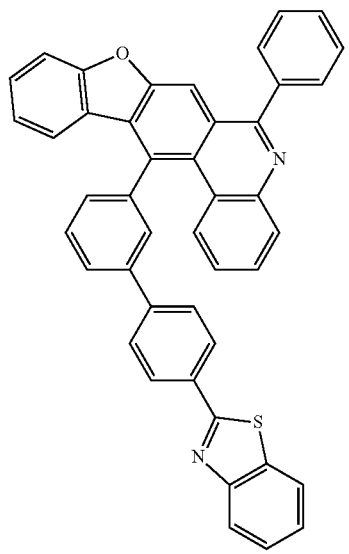
868
869
342
-continued
870
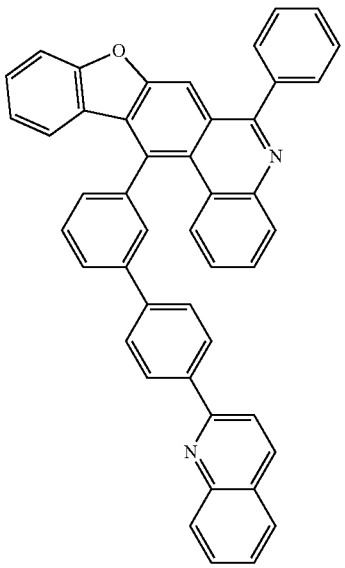
871
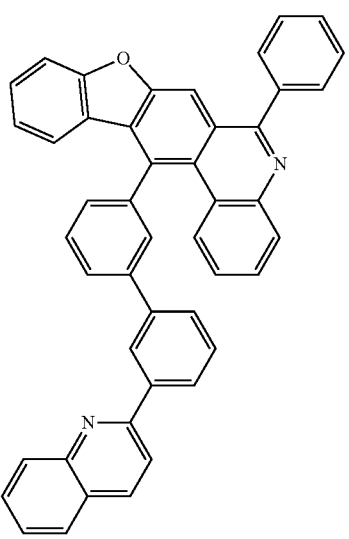
872
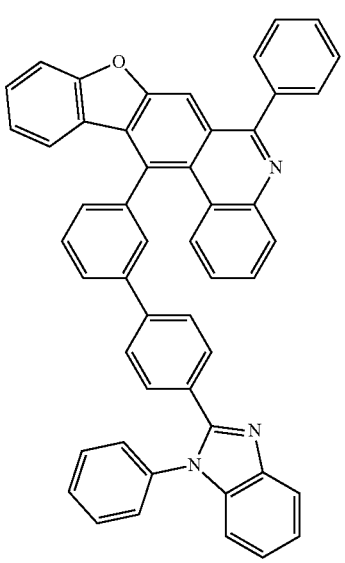

-continued
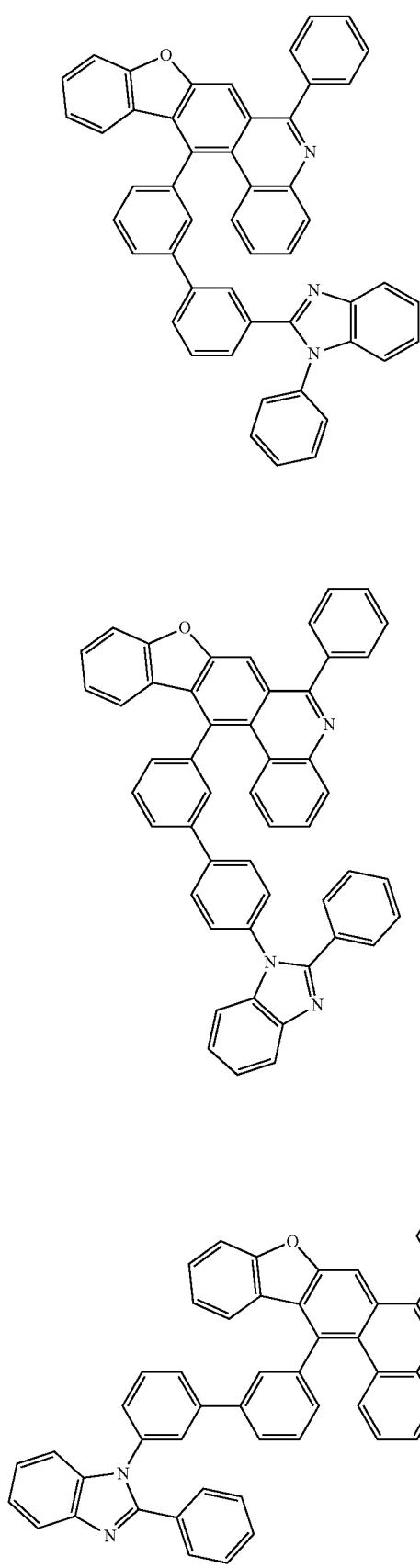
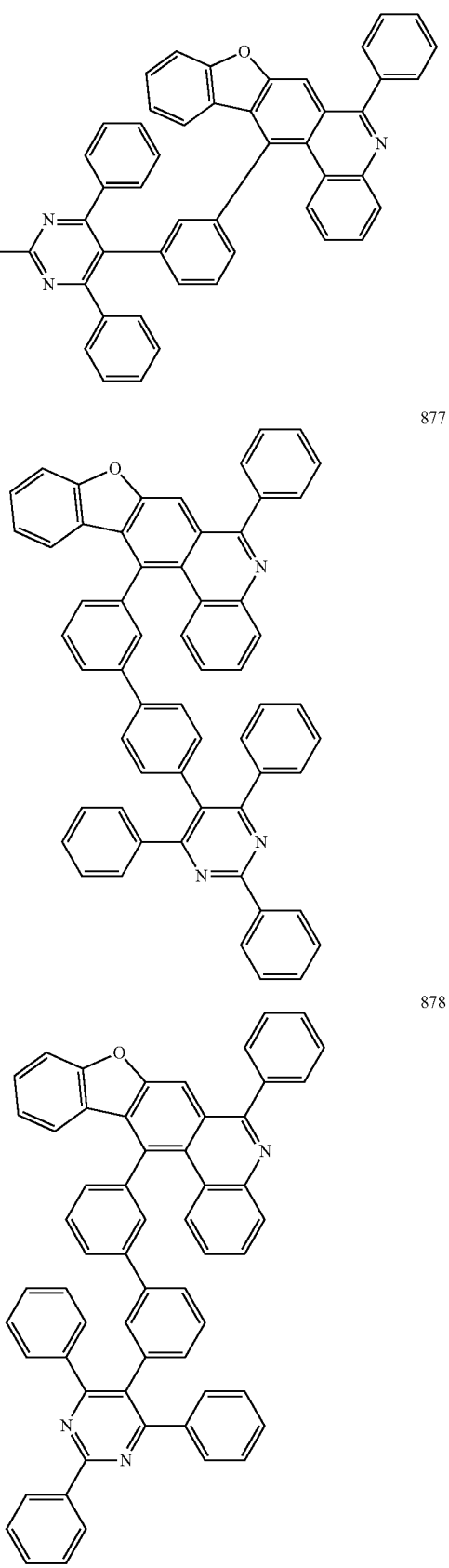

-continued
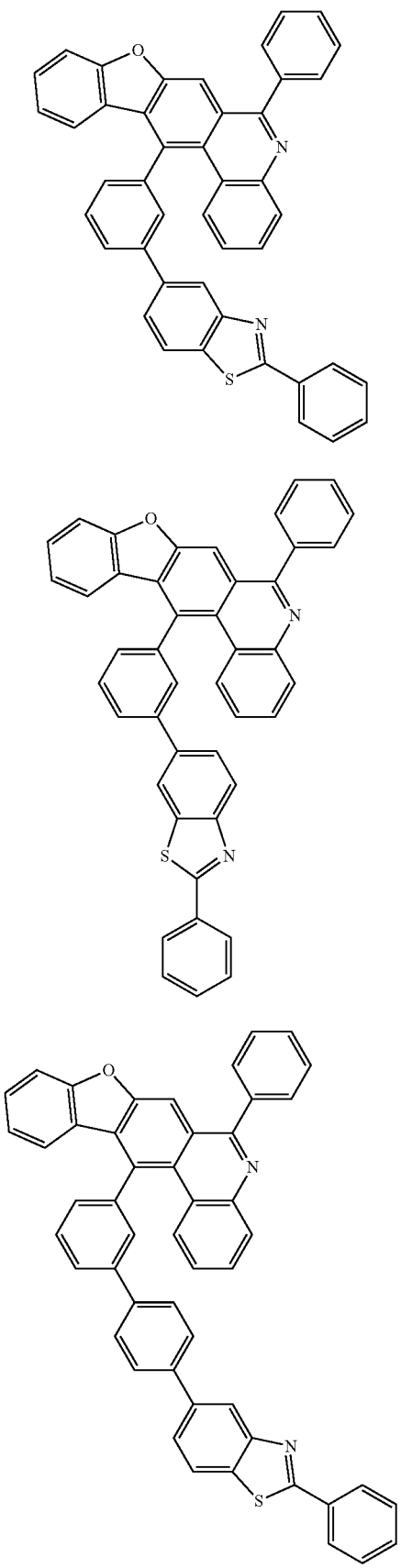
-continued
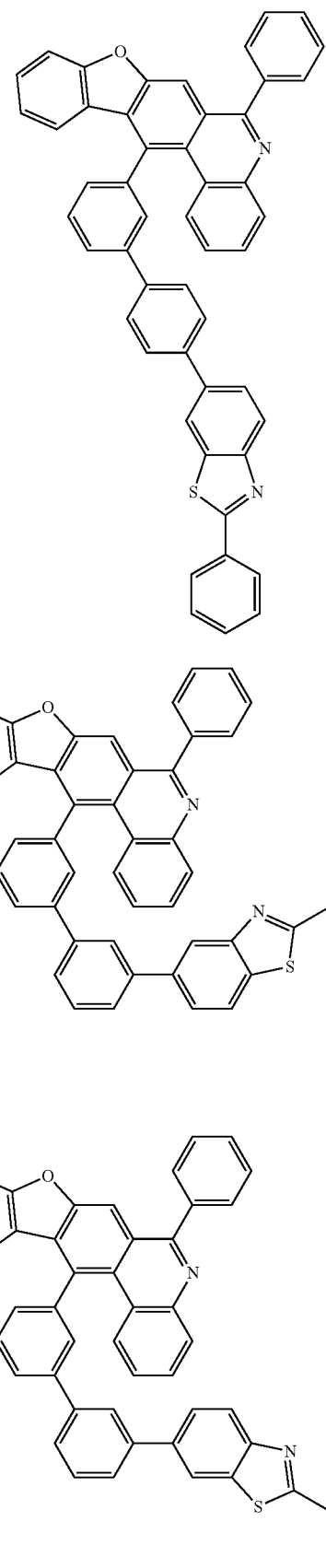

885
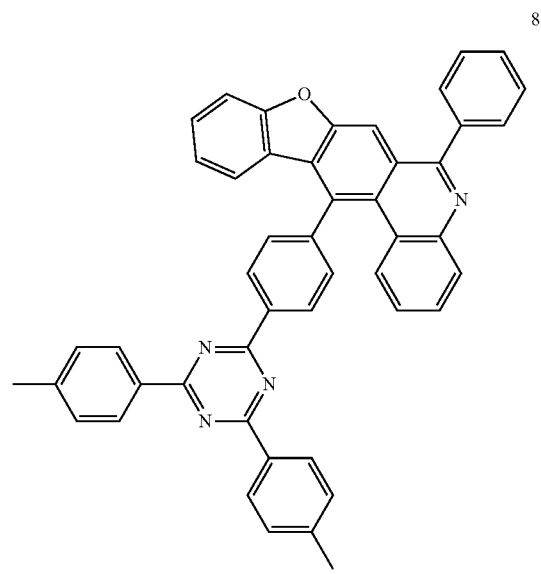
886
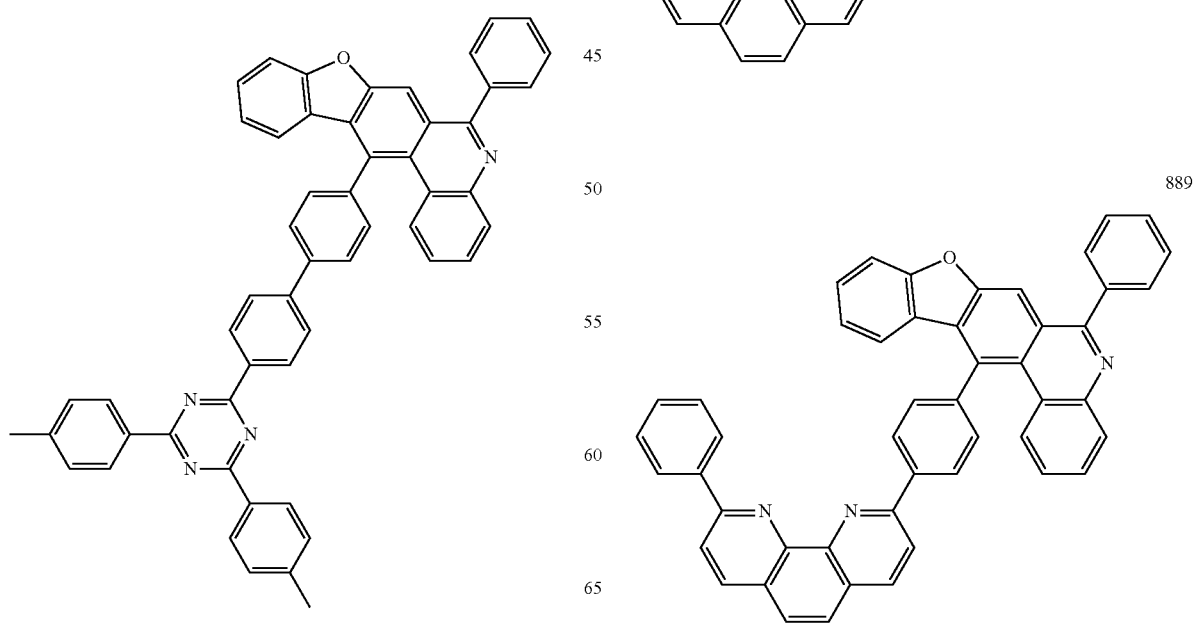
887
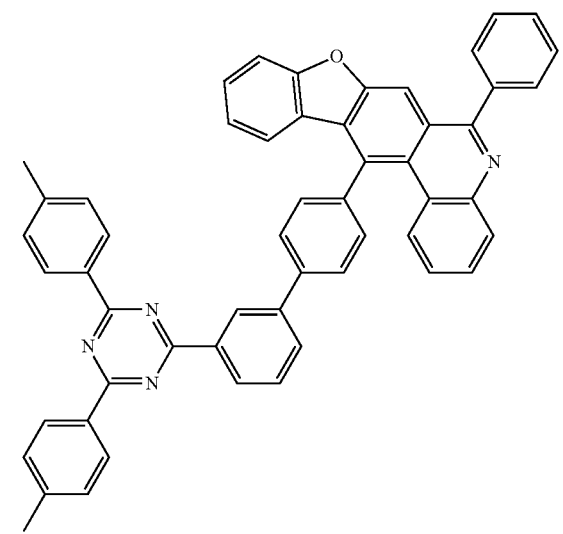
888
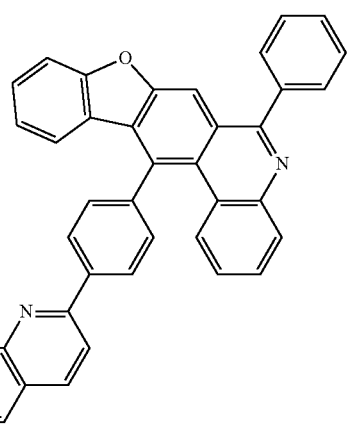
889

890
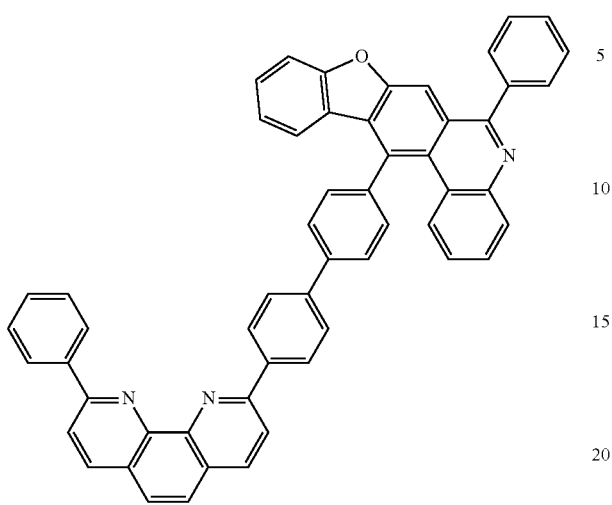
893
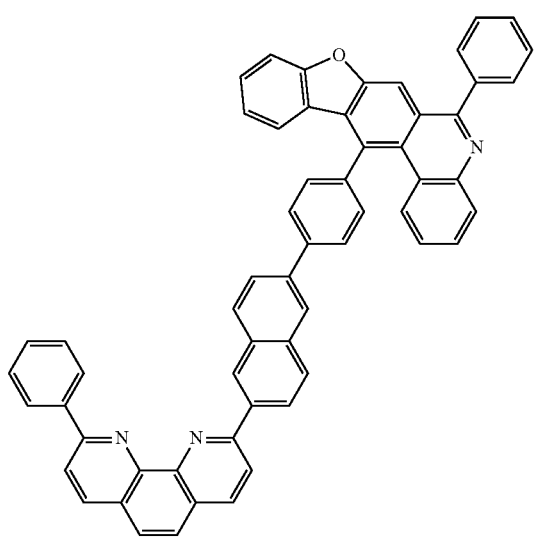
891
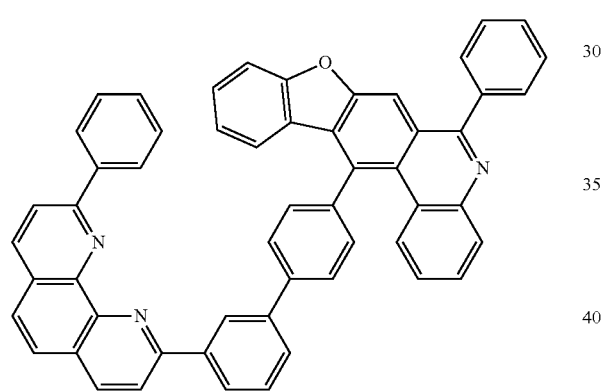
894
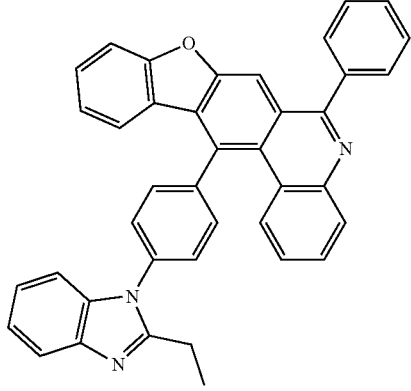
892
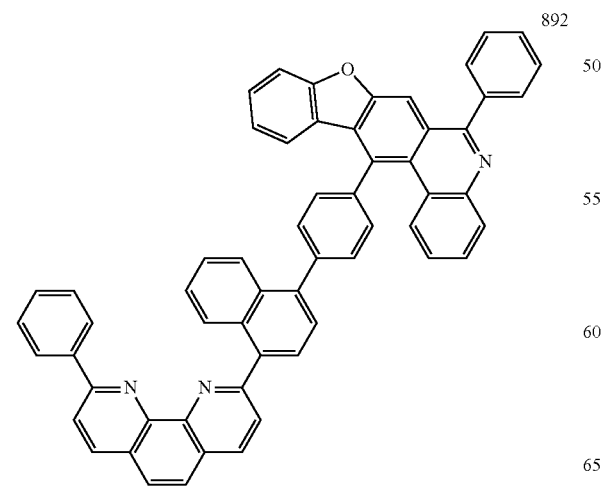
895
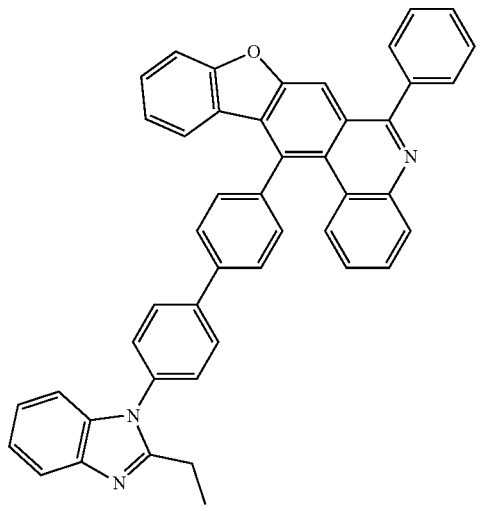

351
-continued
352
-continued
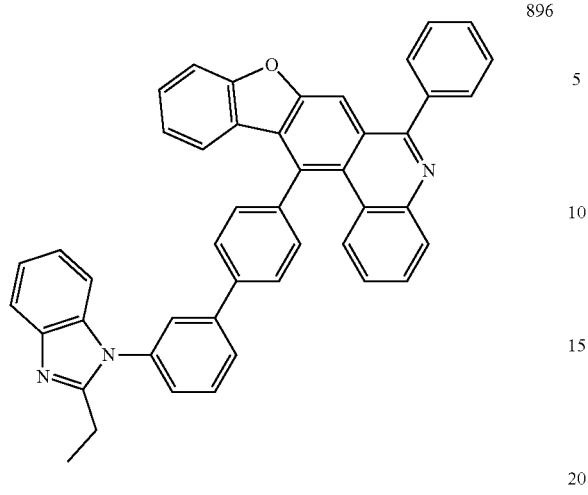
896
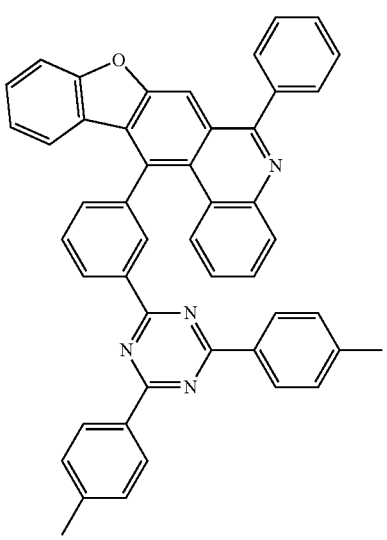
899
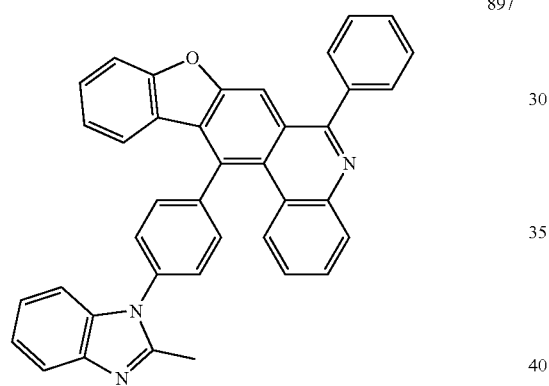
897
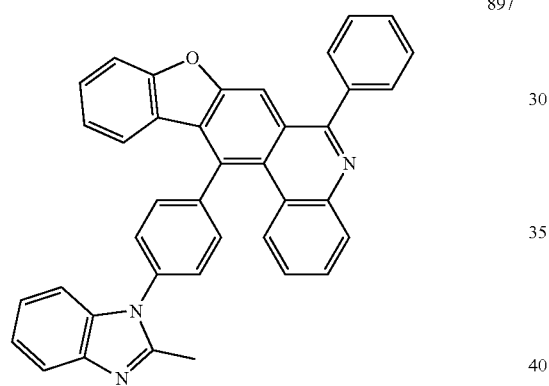
898
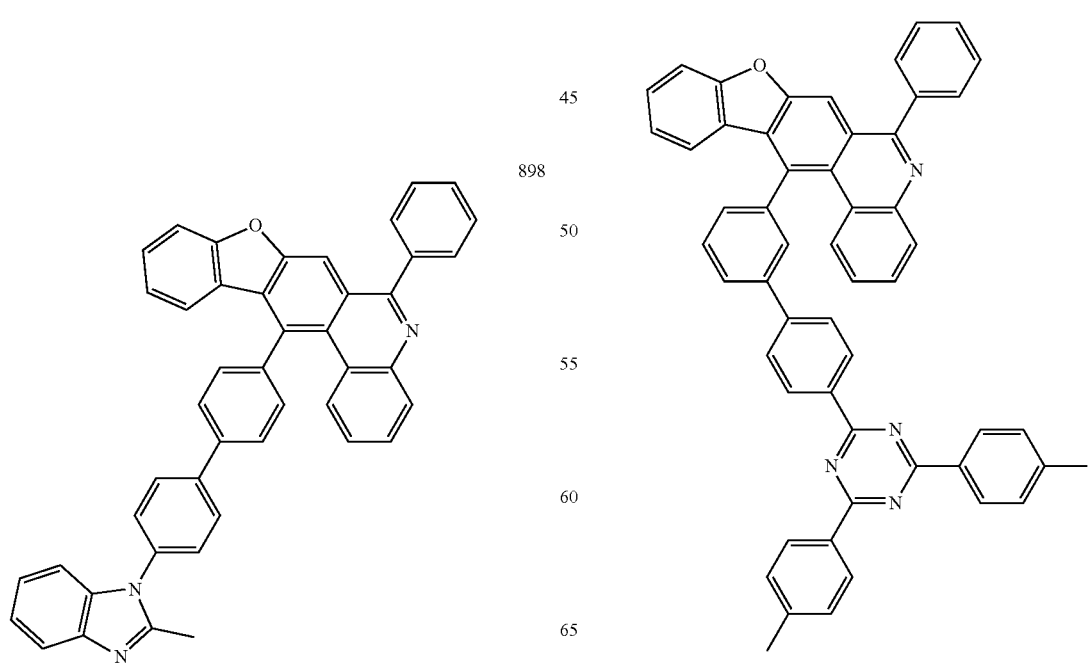
900

353
-continued
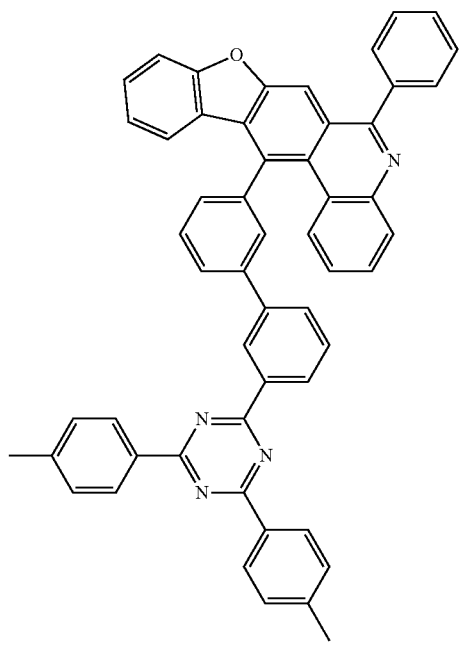
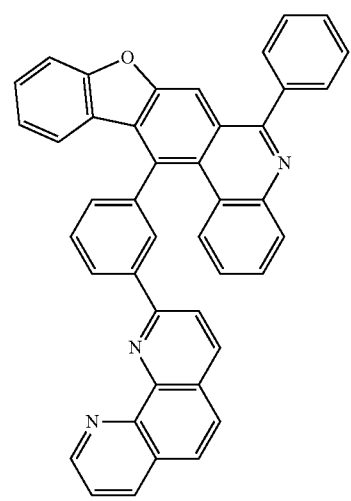
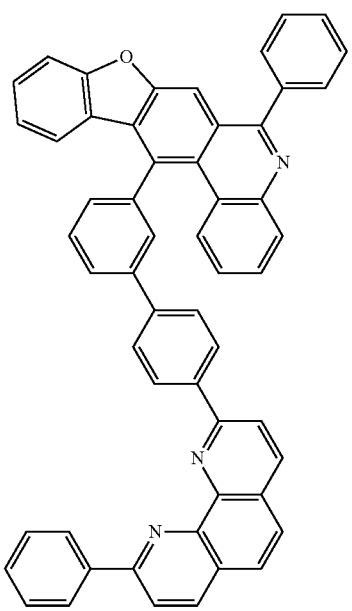
354
-continued
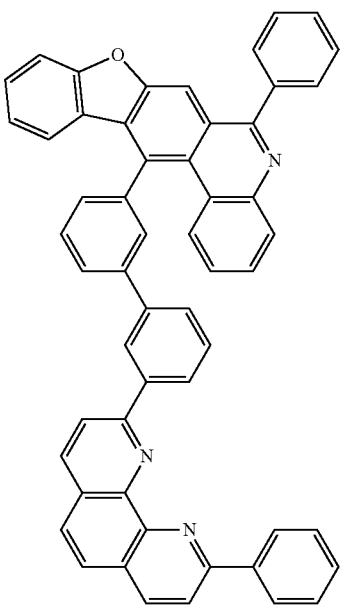

355
-continued
906
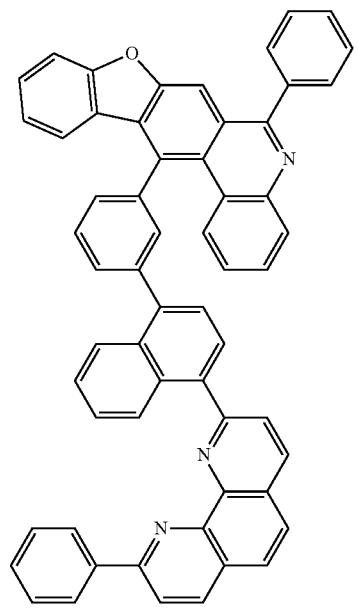 [SMILES: c1ccc(-c2ccc3ccc4ccc(-c5ccc(-c6cccc(-c7c8c(cc9c(-c%10ccccc%10)nc%10ccccc%10c79)oc7ccccc78)c6)c6ccccc56)nc4c3n2)cc1]
907
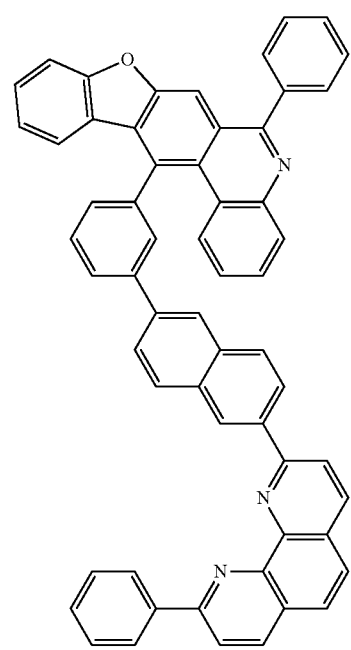
908
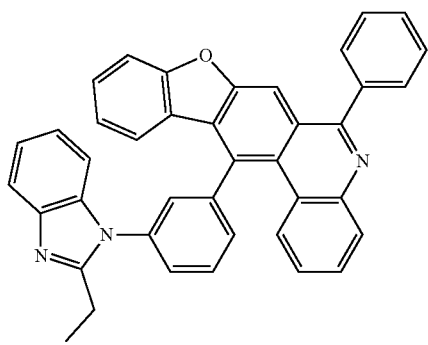
356
-continued
909
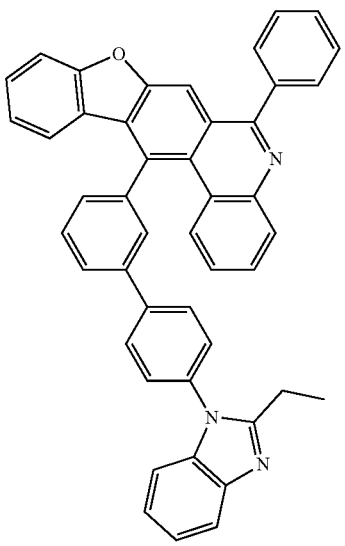
910
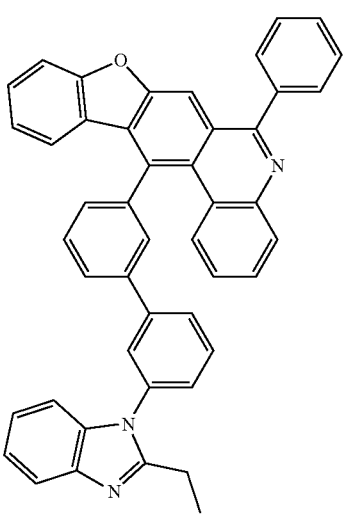
911
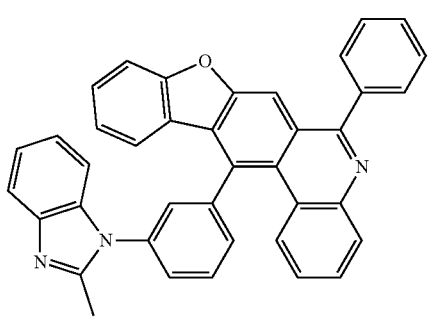

357
-continued
912
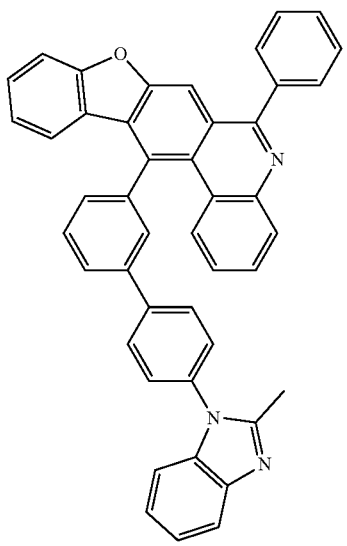
913
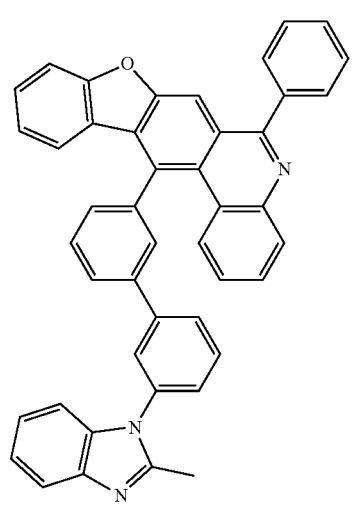
914
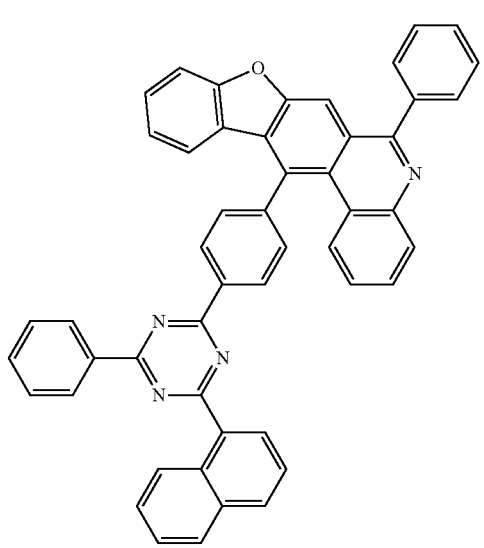 [SMILES: c1ccc(-c2nc(-c3ccc(-c4c5c(cc6c(-c7ccccc7)nc7ccccc7c46)oc4ccccc45)cc3)nc(-c3cccc4ccccc34)n2)cc1]
358
-continued
915
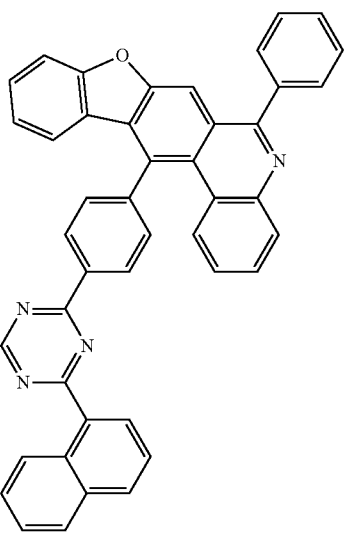
916
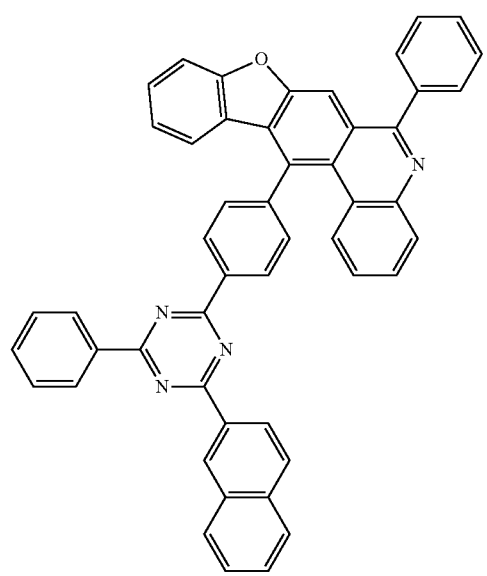

917
919
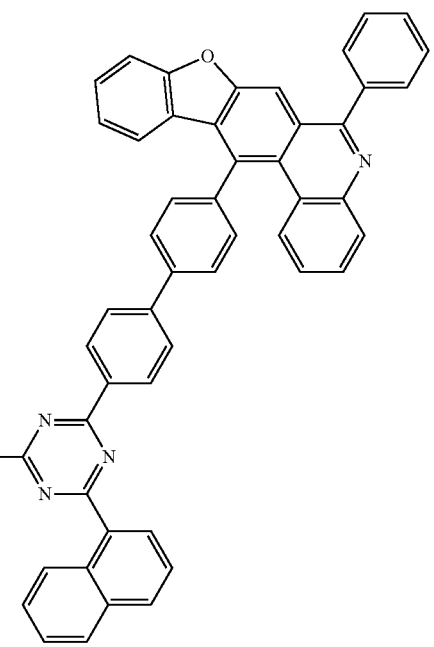
918
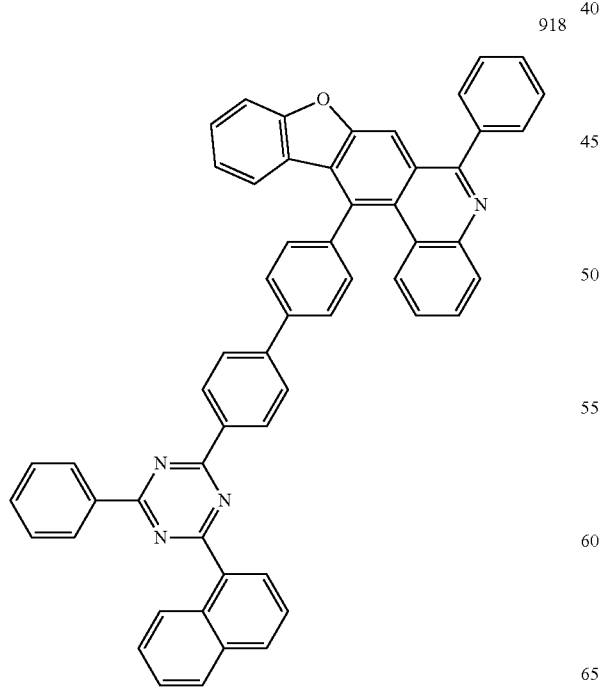
920

361
-continued
362
-continued
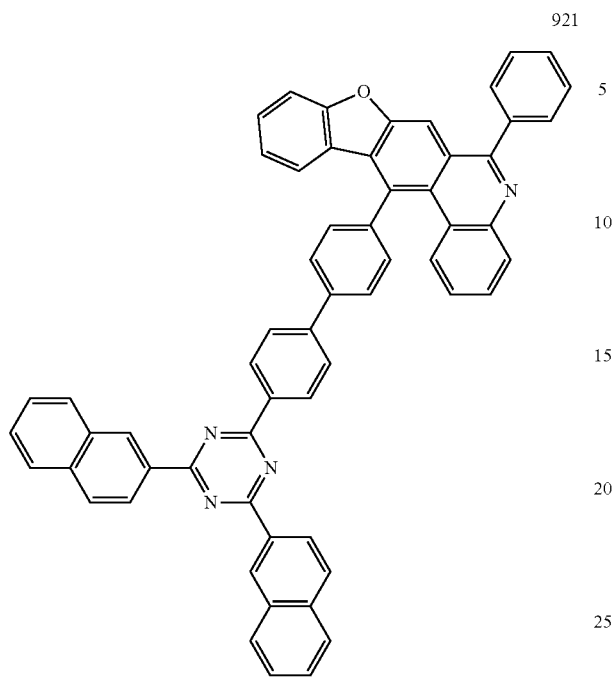
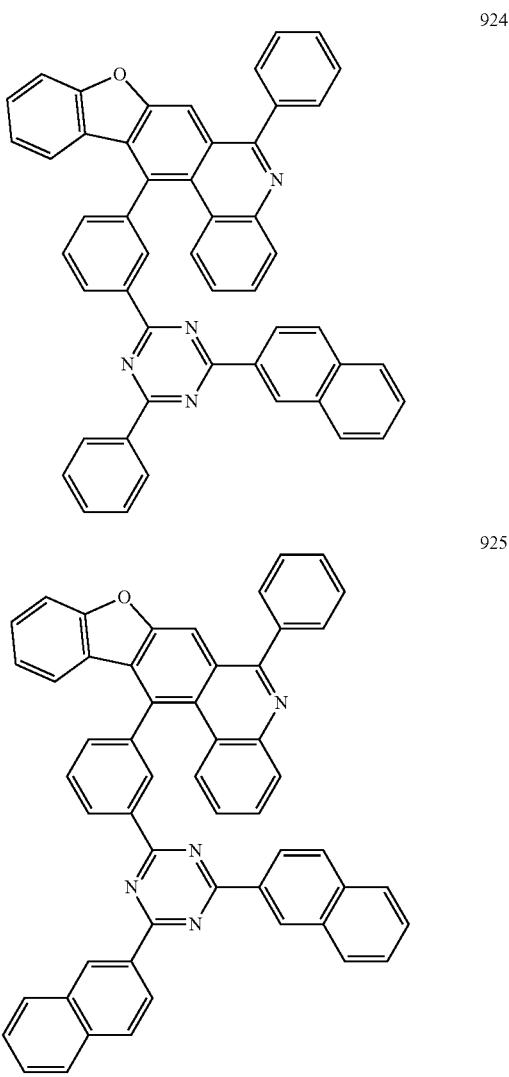
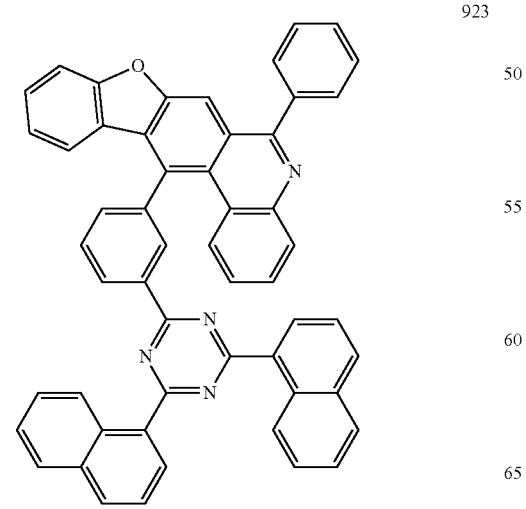

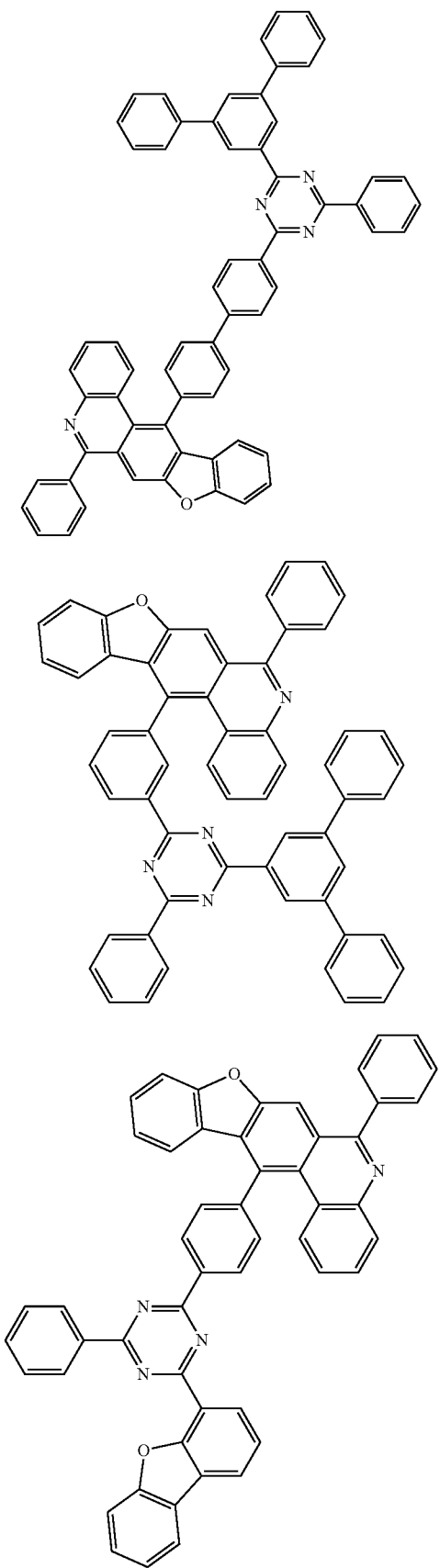
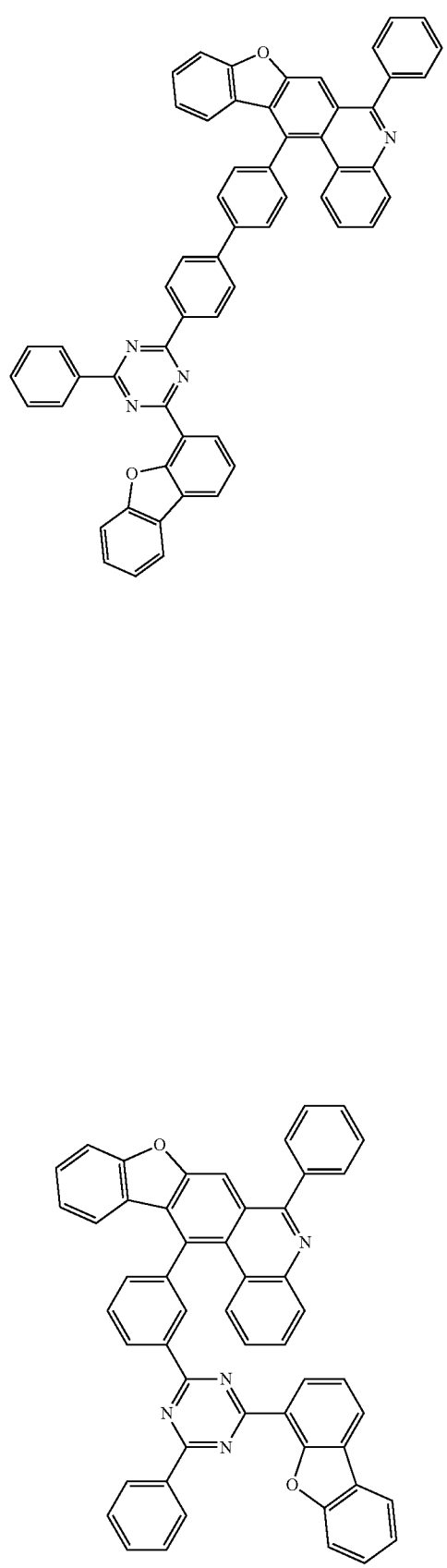

365
-continued
932
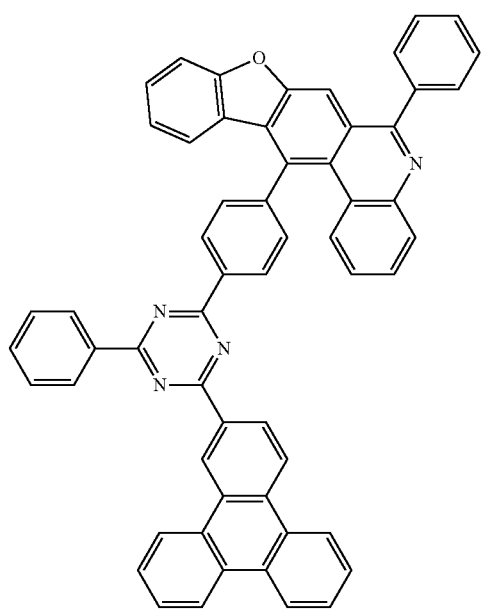
933
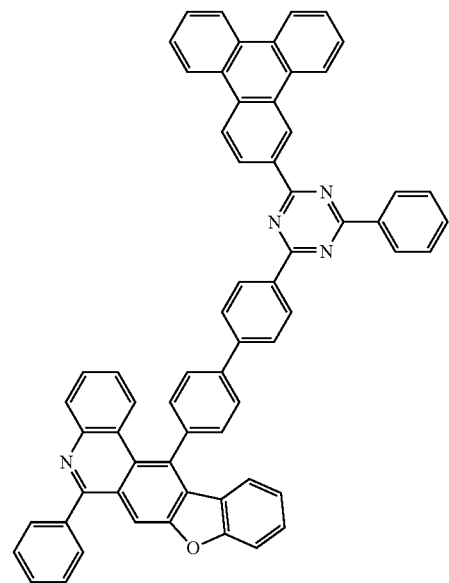 [SMILES: c1ccc(-c2nc(-c3ccc(-c4ccc(-c5c6c(cc7c(-c8ccccc8)nc8ccccc8c57)oc5ccccc56)cc4)cc3)nc(-c3ccc4c5ccccc5c5ccccc5c4c3)n2)cc1]
366
-continued
934
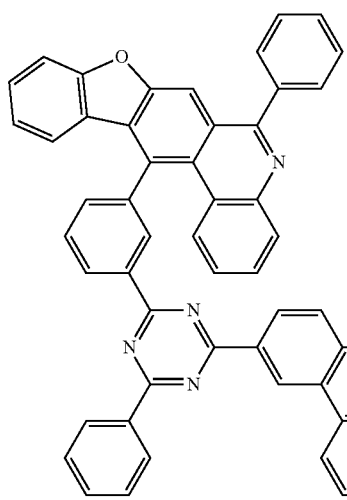
935
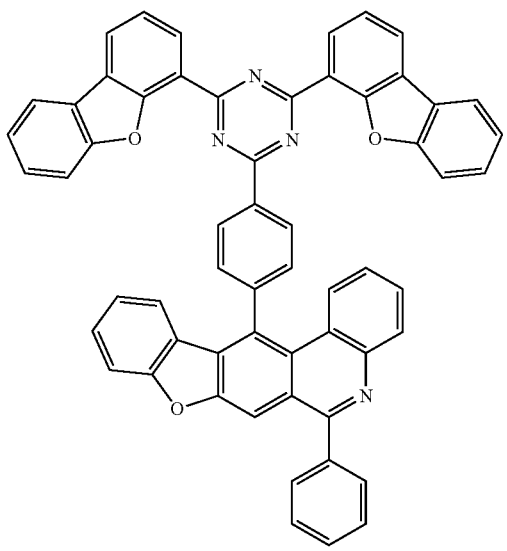
936
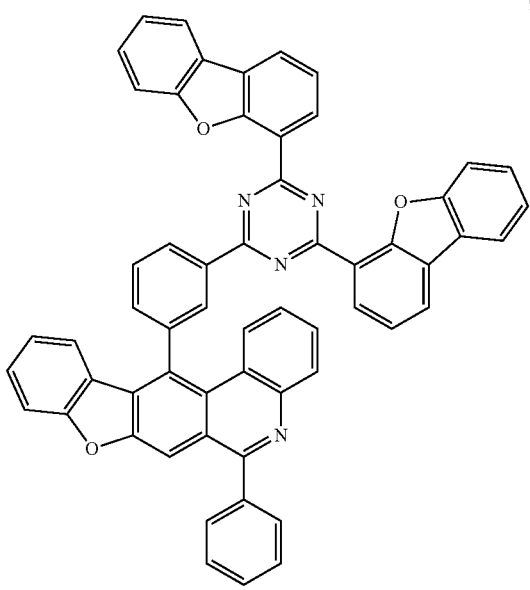

367
-continued
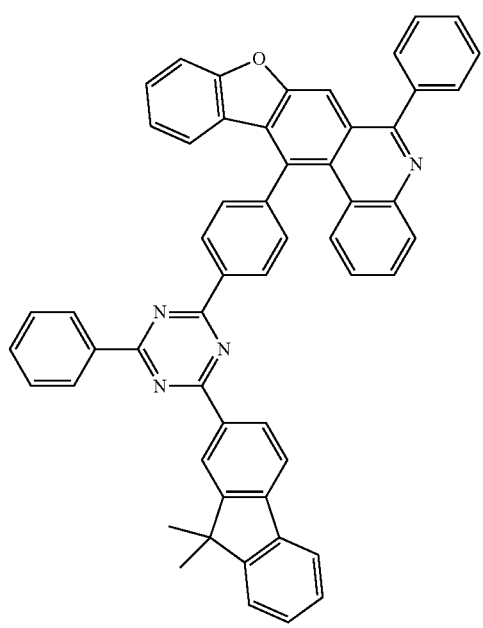 [SMILES: CC1(C)c2ccccc2-c2ccc(-c3nc(-c4ccccc4)nc(-c4ccc(-c5c6c(cc7c(-c8ccccc8)nc8ccccc8c57)oc5ccccc56)cc4)n3)cc21]
937
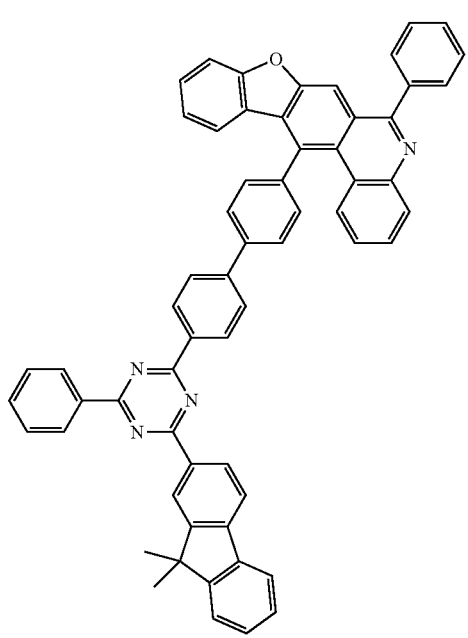
938
368
-continued
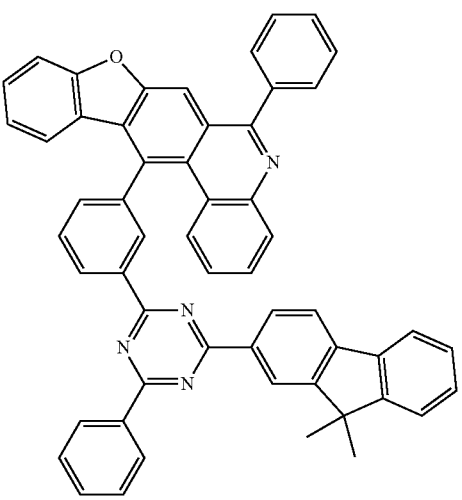
939
940

369
-continued
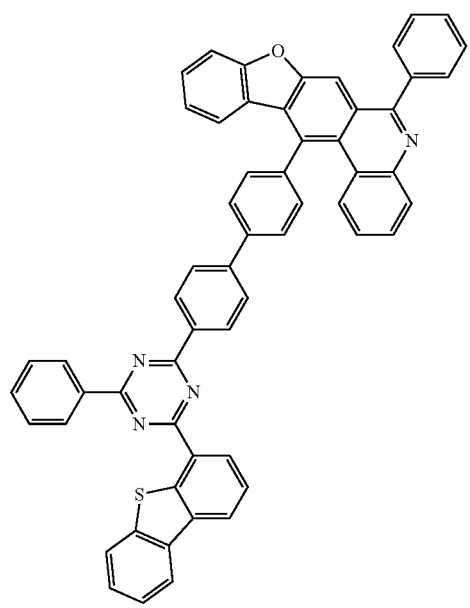
941
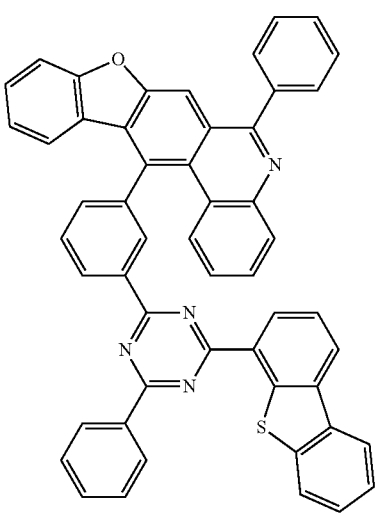
942
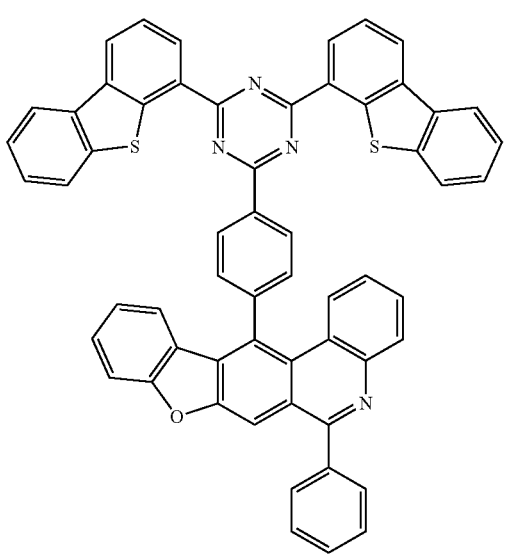 [SMILES: c1ccc(-c2nc3ccccc3c3c(-c4ccc(-c5nc(-c6cccc7c6sc6ccccc67)nc(-c6cccc7c6sc6ccccc67)n5)cc4)c4c(cc23)oc2ccccc24)cc1]
943
370
-continued
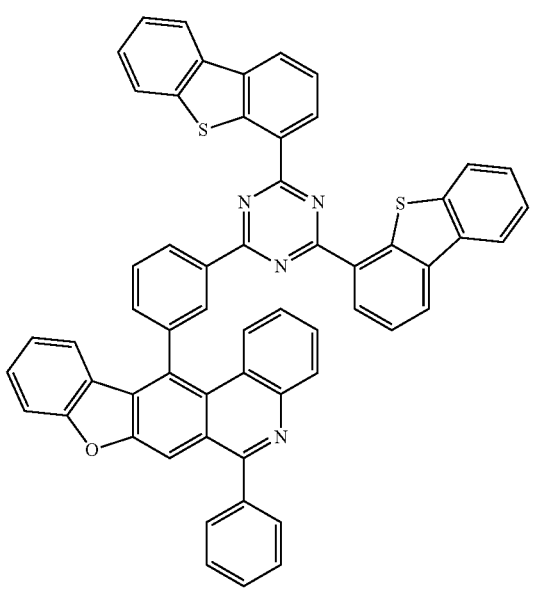
944
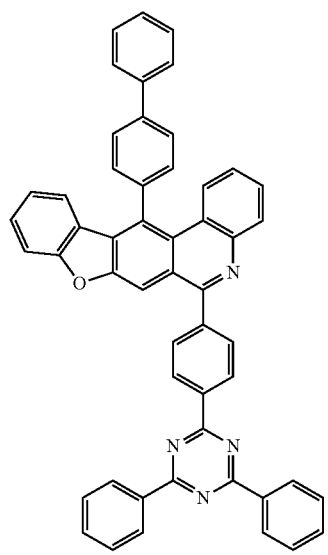 [SMILES: c1ccc(-c2ccc(-c3c4c(cc5c(-c6ccc(-c7nc(-c8ccccc8)nc(-c8ccccc8)n7)cc6)nc6ccccc6c35)oc3ccccc34)cc2)cc1]
945

371
-continued
946
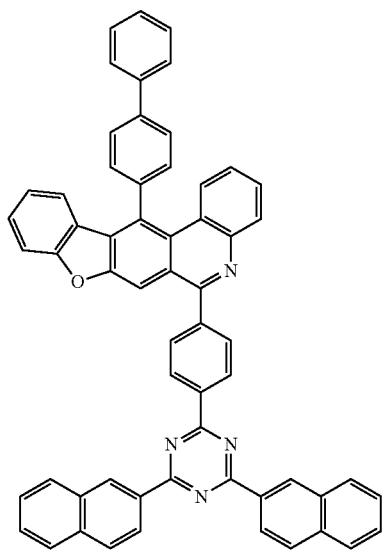 [SMILES: c1ccc(-c2ccc(-c3c4c(cc5c(-c6ccc(-c7nc(-c8ccc9ccccc9c8)nc(-c8ccc9ccccc9c8)n7)cc6)nc6ccccc6c35)oc3ccccc34)cc2)cc1]
372
-continued
948
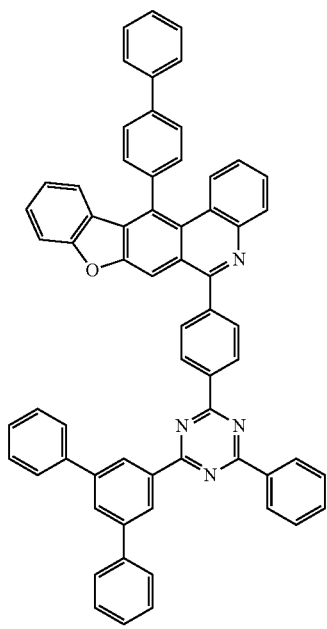 [SMILES: c1ccc(-c2ccc(-c3c4c(cc5c(-c6ccc(-c7nc(-c8ccccc8)nc(-c8cc(-c9ccccc9)cc(-c9ccccc9)c8)n7)cc6)nc6ccccc6c35)oc3ccccc34)cc2)cc1]
947
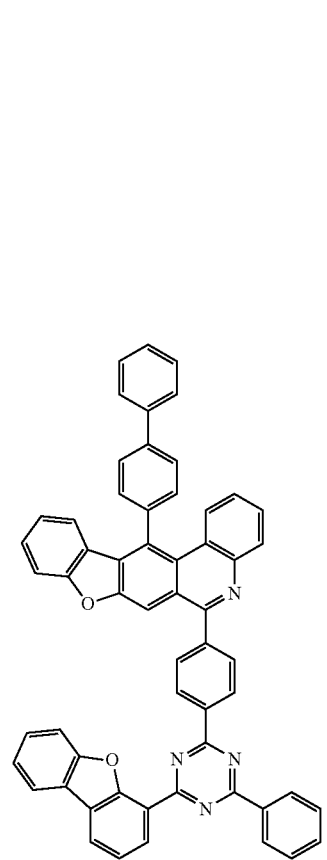 [SMILES: c1ccc(-c2ccc(-c3c4c(cc5c(-c6ccc(-c7nc(-c8ccccc8)nc(-c8cccc9c8oc8ccccc89)n7)cc6)nc6ccccc6c35)oc3ccccc34)cc2)cc1]
949

-continued
950
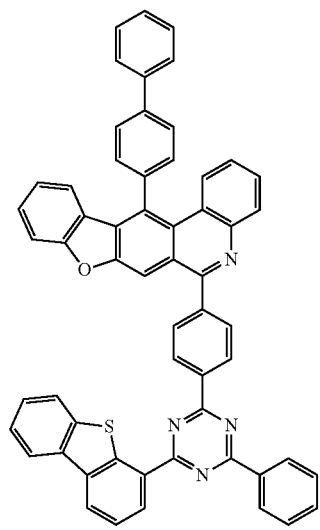 [SMILES: c1ccc(-c2ccc(-c3c4c(cc5c(-c6ccc(-c7nc(-c8ccccc8)nc(-c8cccc9c8sc8ccccc89)n7)cc6)nc6ccccc6c35)oc3ccccc34)cc2)cc1]
951
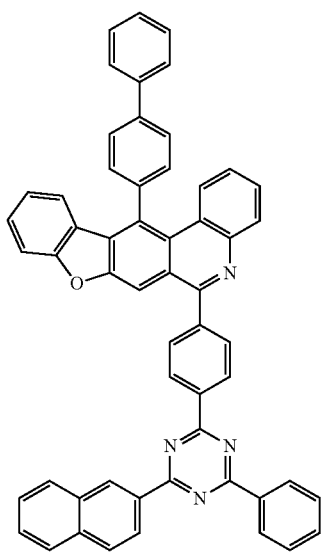
-continued
952
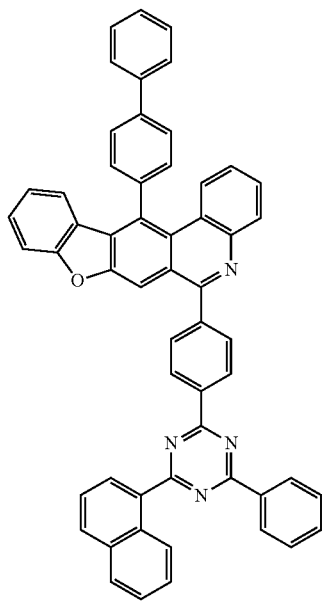
953
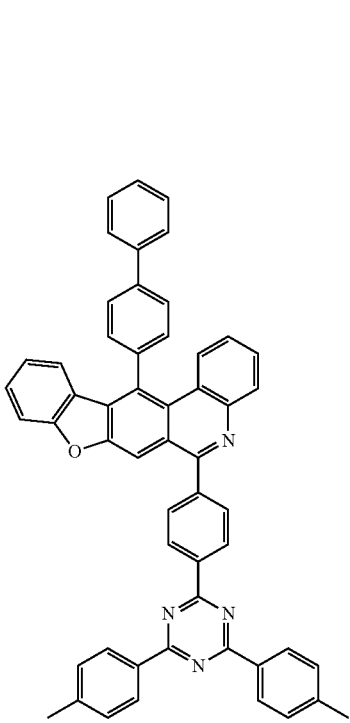 [SMILES: Cc1ccc(-c2nc(-c3ccc(C)cc3)nc(-c3ccc(-c4nc5ccccc5c5c(-c6ccc(-c7ccccc7)cc6)c6c(cc45)oc4ccccc46)cc3)n2)cc1]

375
-continued
954
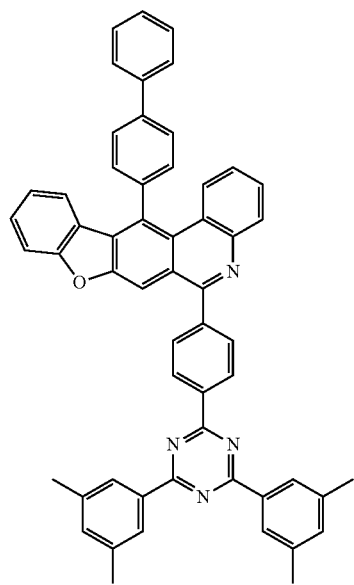
376
-continued
956
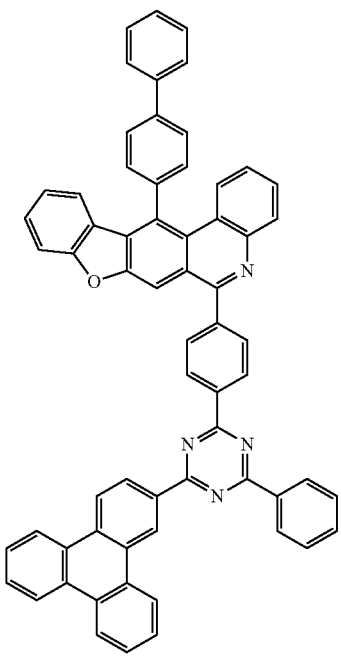 [SMILES: c1ccc(-c2ccc(-c3c4c(cc5c(-c6ccc(-c7nc(-c8ccccc8)nc(-c8ccc9c%10ccccc%10c%10ccccc%10c9c8)n7)cc6)nc6ccccc6c35)oc3ccccc34)cc2)cc1]
955
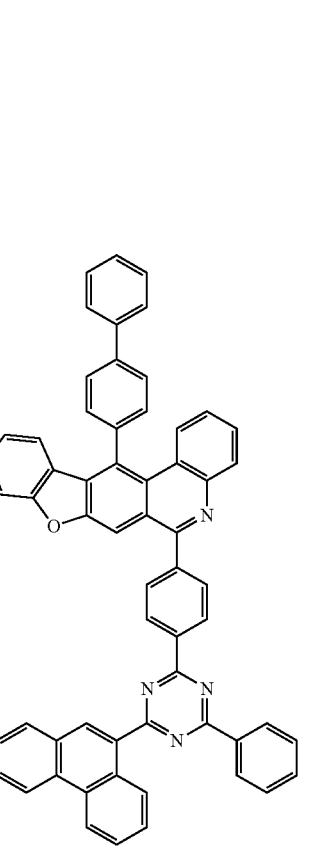
957
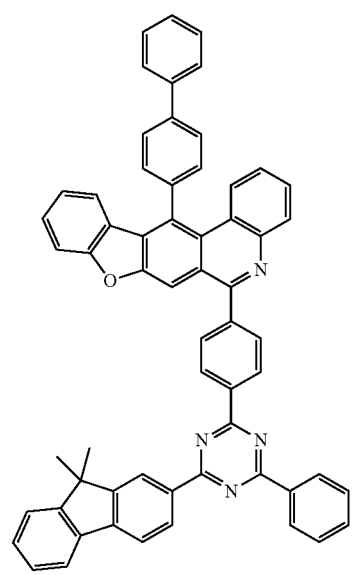 [SMILES: CC1(C)c2ccccc2-c2ccc(-c3nc(-c4ccccc4)nc(-c4ccc(-c5nc6ccccc6c6c(-c7ccc(-c8ccccc8)cc7)c7c(cc56)oc5ccccc57)cc4)n3)cc21]

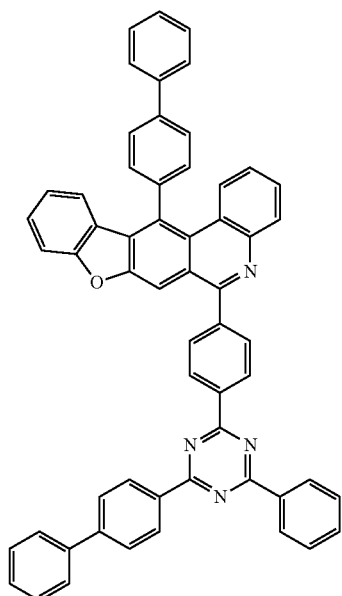
958
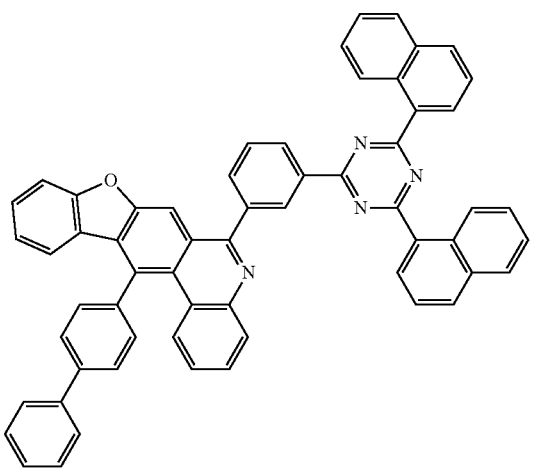
961
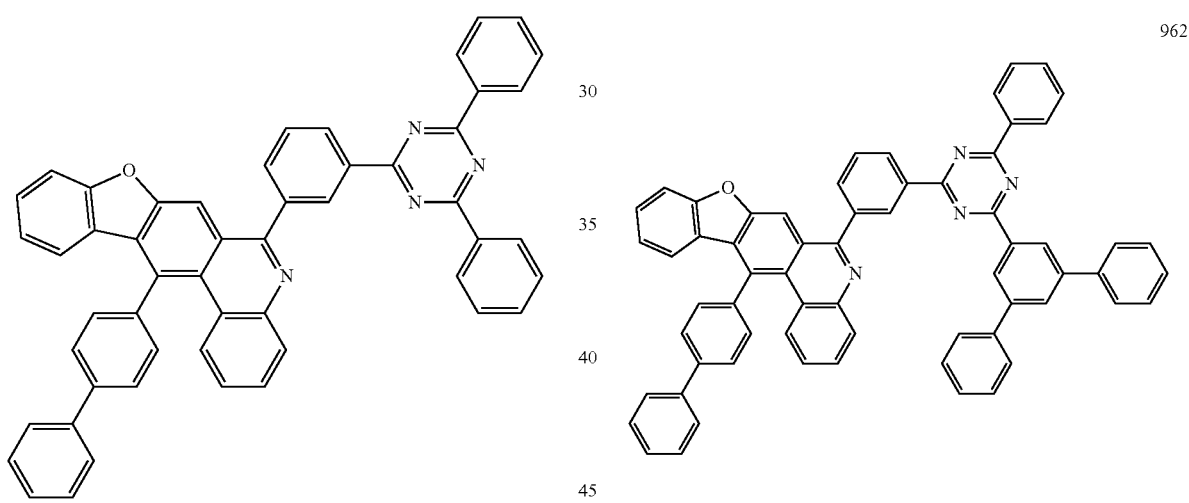
959
960
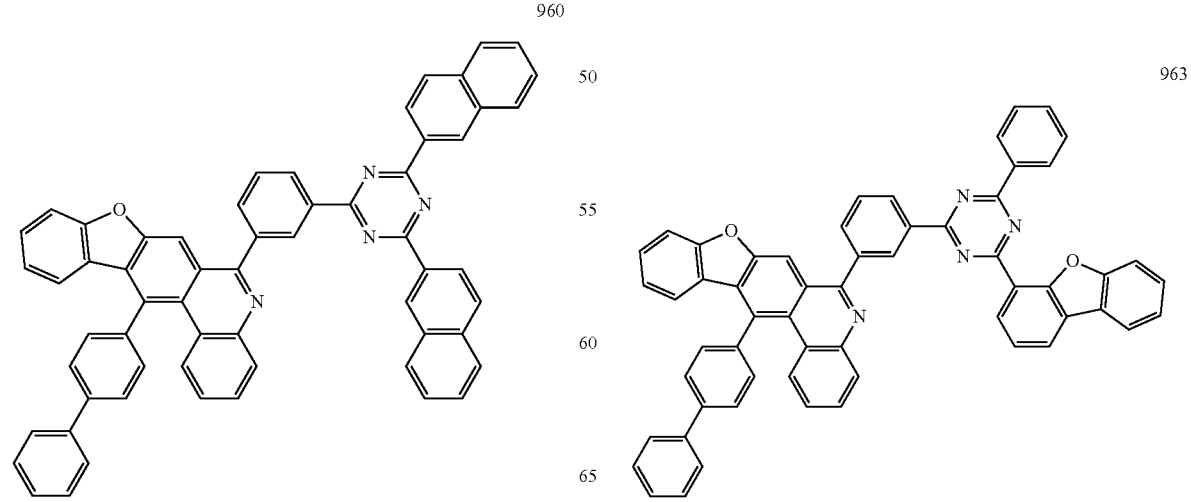
962
963

964
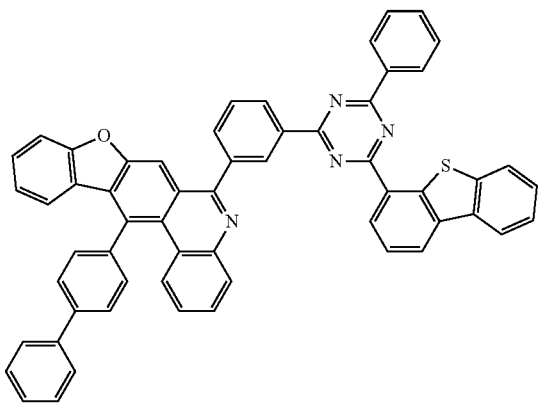
965
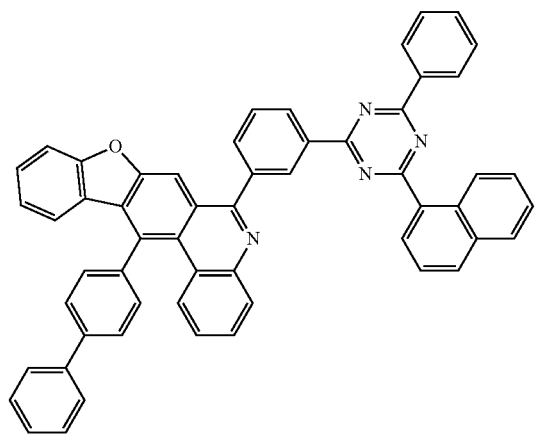
966
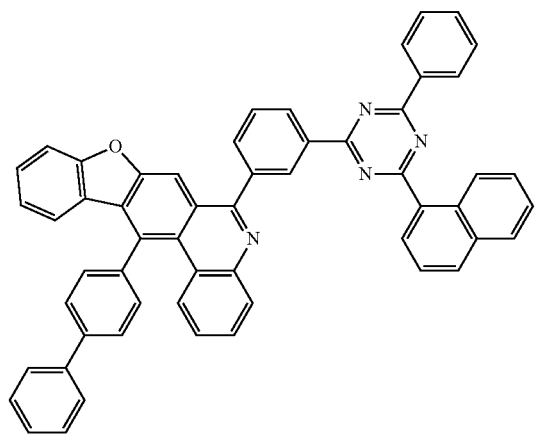
967
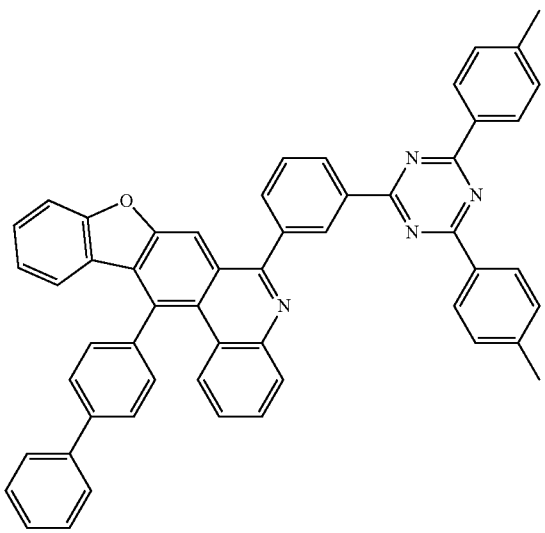
968
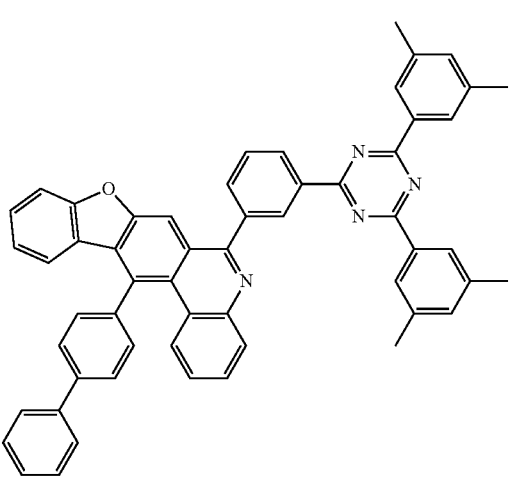
969
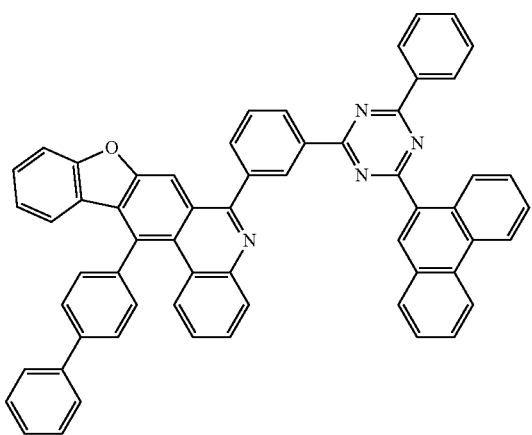

-continued
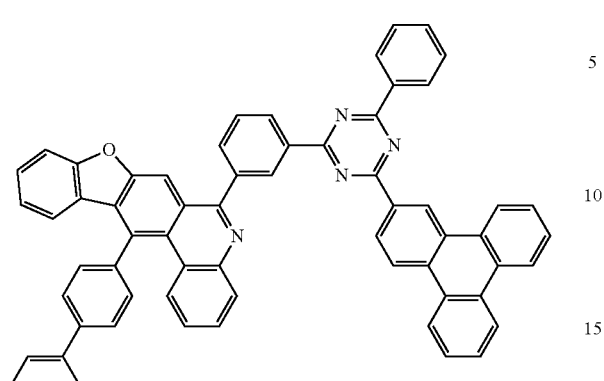
970
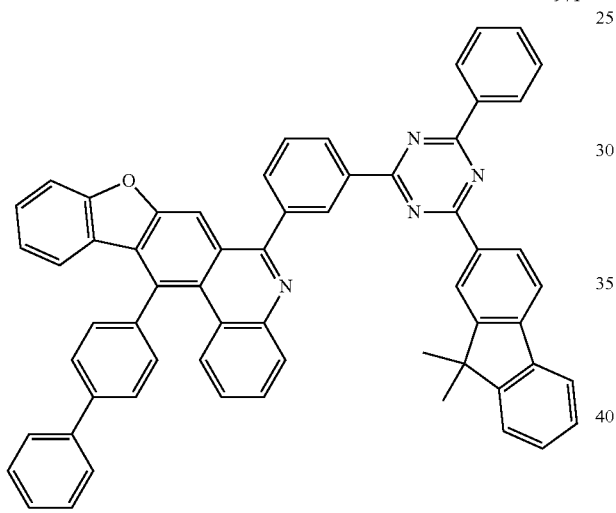
971
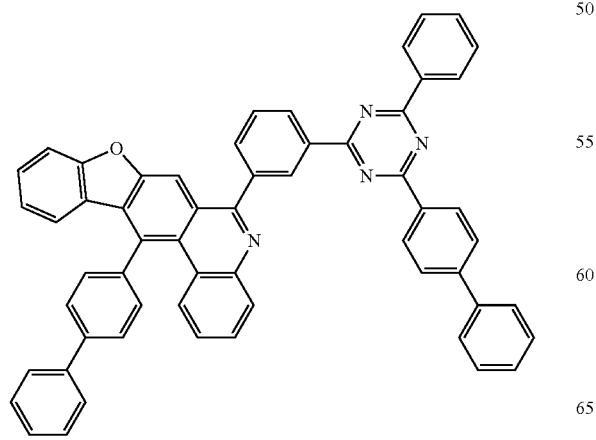
972
-continued
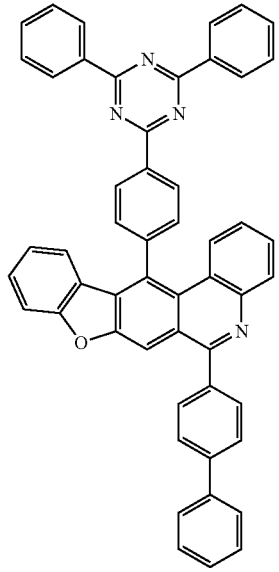 [SMILES: c1ccc(-c2ccc(-c3nc4ccccc4c4c(-c5ccc(-c6nc(-c7ccccc7)nc(-c7ccccc7)n6)cc5)c5c(cc34)oc3ccccc35)cc2)cc1]
973
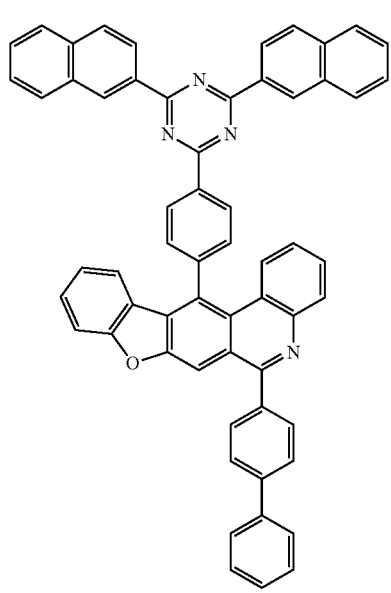 [SMILES: c1ccc(-c2ccc(-c3nc4ccccc4c4c(-c5ccc(-c6nc(-c7ccc8ccccc8c7)nc(-c7ccc8ccccc8c7)n6)cc5)c5c(cc34)oc3ccccc35)cc2)cc1]
974

383
-continued
975
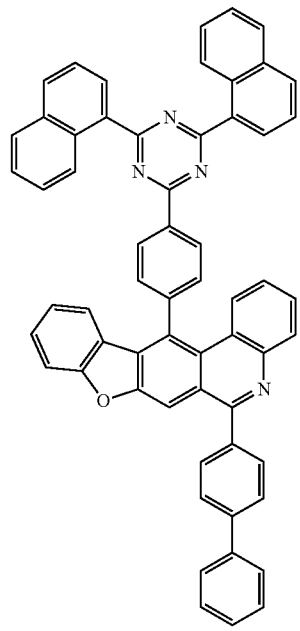 [SMILES: c1ccc(-c2ccc(-c3nc4ccccc4c4c(-c5ccc(-c6nc(-c7cccc8ccccc78)nc(-c7cccc8ccccc78)n6)cc5)c5c(cc34)oc3ccccc35)cc2)cc1]
976
384
-continued
977
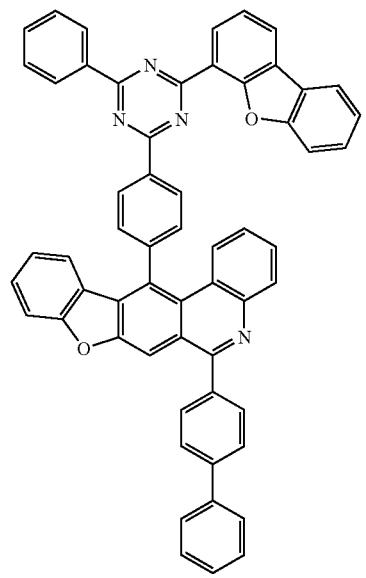 [SMILES: c1ccc(-c2ccc(-c3nc4ccccc4c4c(-c5ccc(-c6nc(-c7ccccc7)nc(-c7cccc8c7oc7ccccc78)n6)cc5)c5c(cc34)oc3ccccc35)cc2)cc1]
978
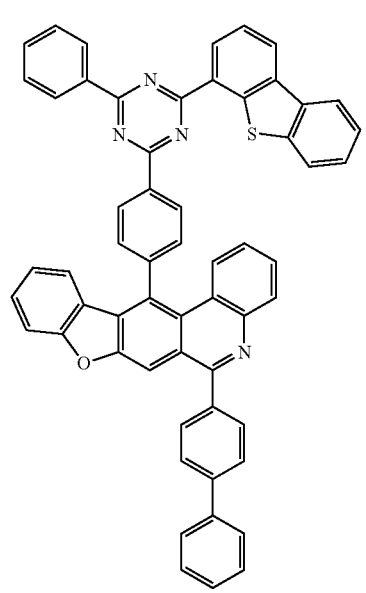 [SMILES: c1ccc(-c2ccc(-c3nc4ccccc4c4c(-c5ccc(-c6nc(-c7ccccc7)nc(-c7cccc8c7sc7ccccc78)n6)cc5)c5c(cc34)oc3ccccc35)cc2)cc1]

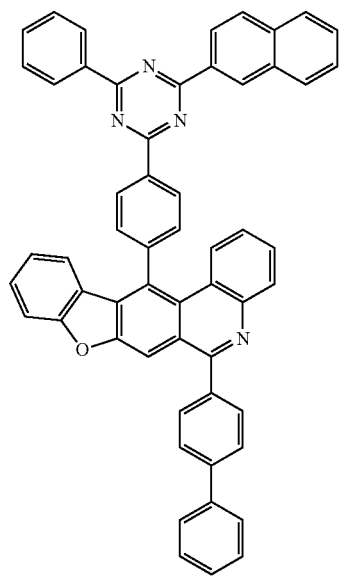
979
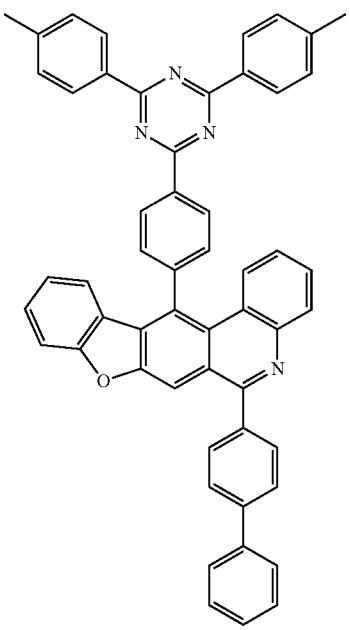
981
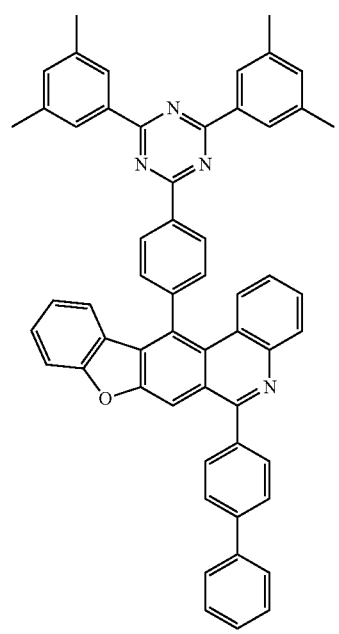
982

387
-continued
983
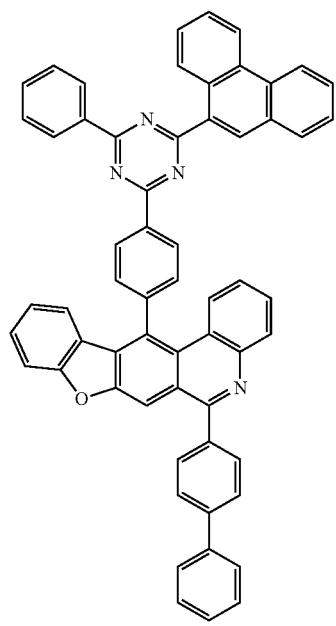
984
985
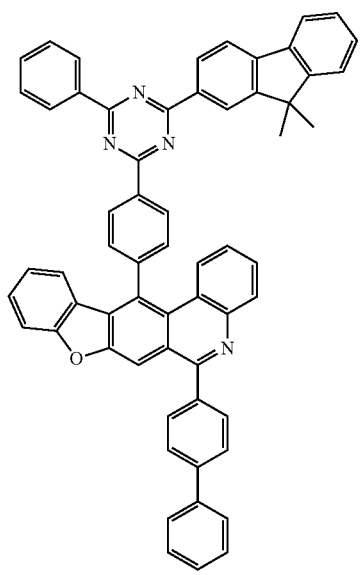 [SMILES: CC1(C)c2ccccc2-c2ccc(-c3nc(-c4ccccc4)nc(-c4ccc(-c5c6c(cc7c(-c8ccc(-c9ccccc9)cc8)nc8ccccc8c57)oc5ccccc56)cc4)n3)cc21]
986
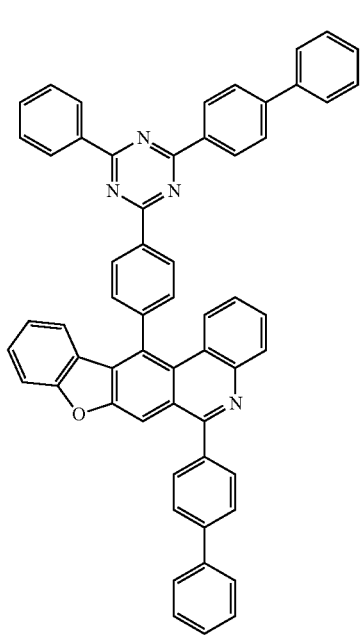
388
-continued 389
-continued
390
-continued
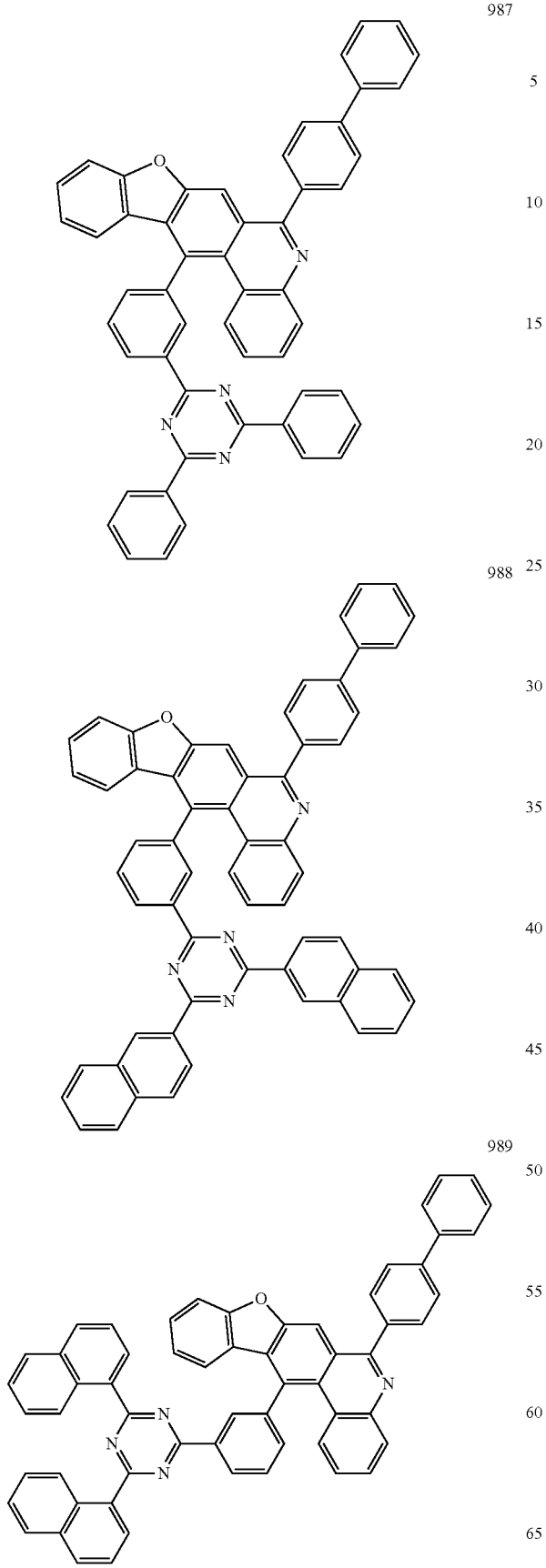
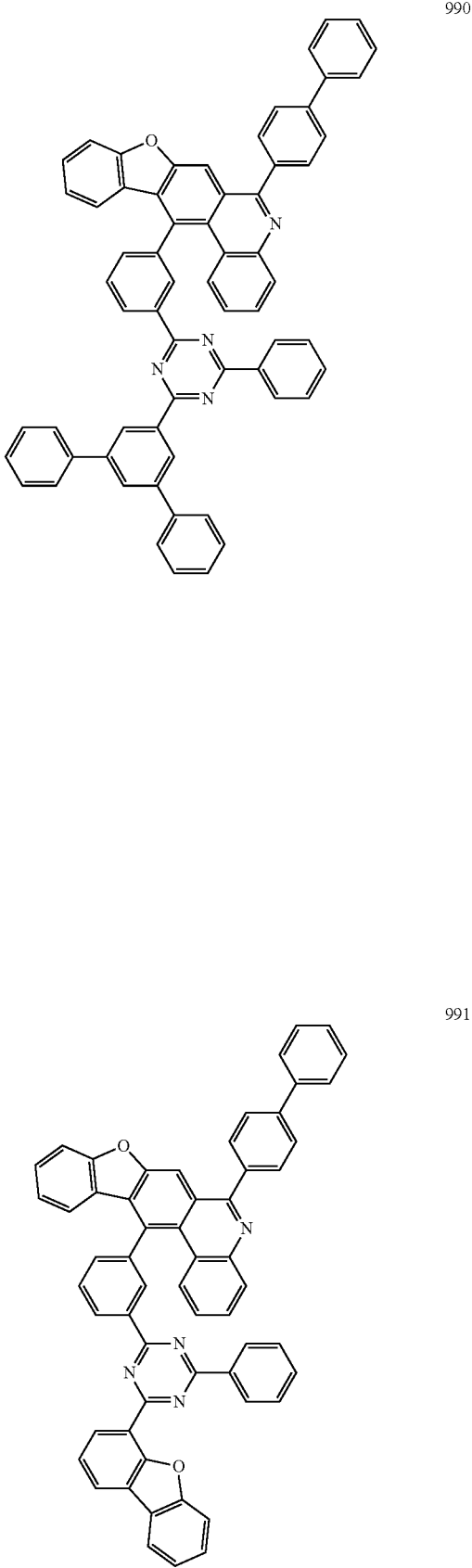

391
-continued
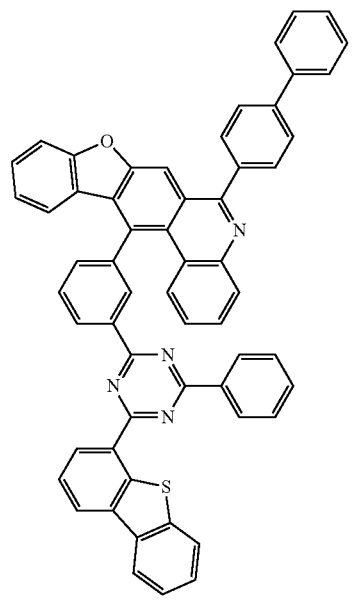
992
392
-continued
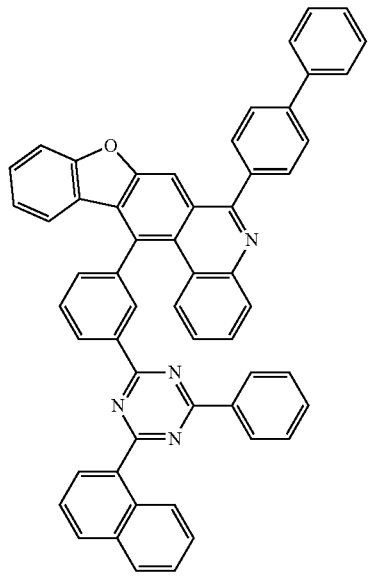
994
993
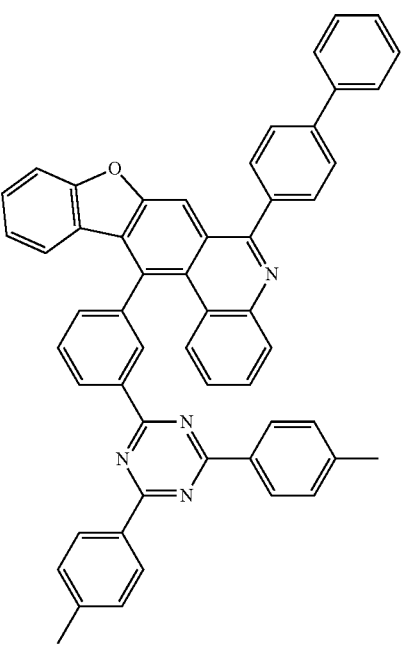
995

393
-continued
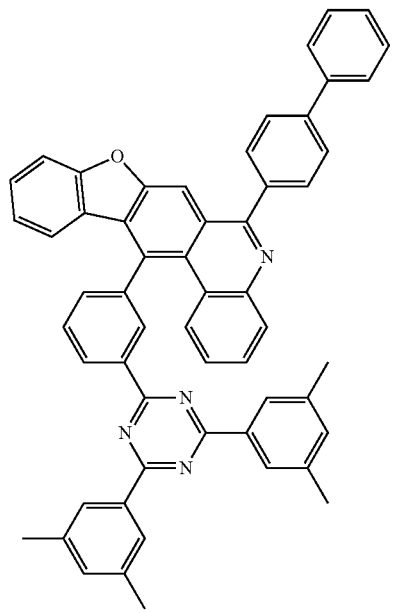
996
394
-continued
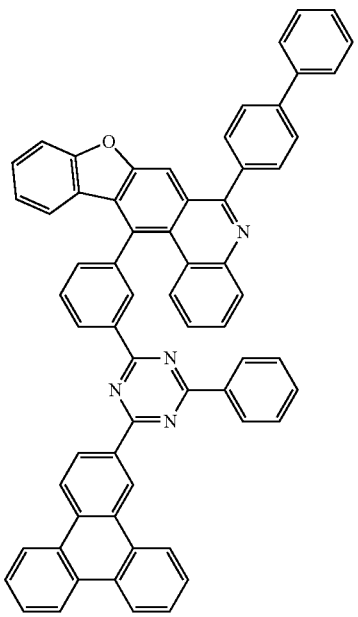
998
997
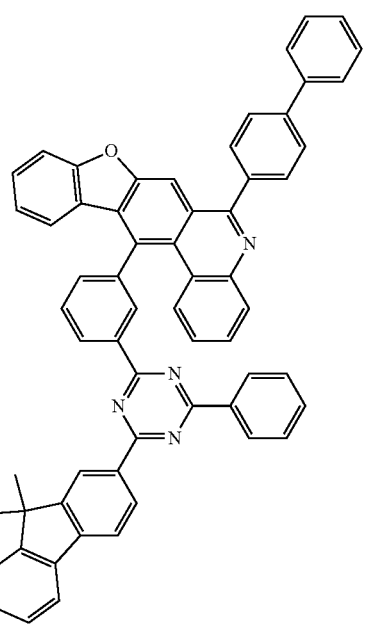
999

-continued
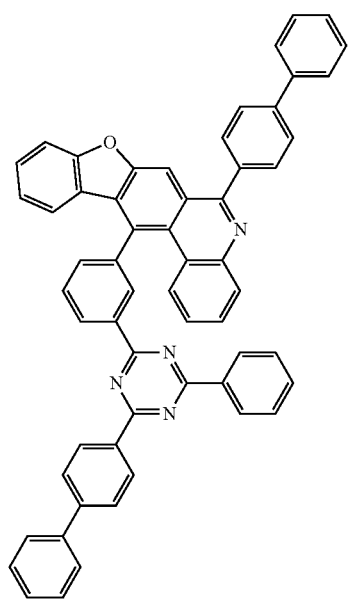
1000
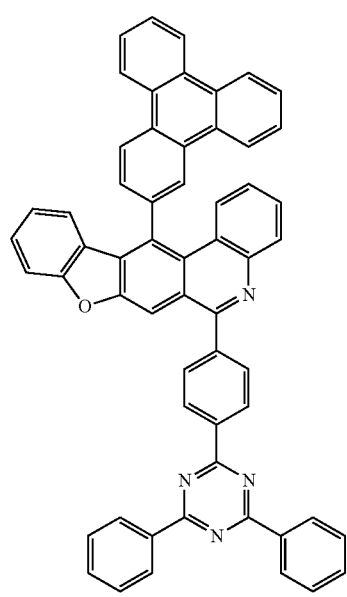
1001
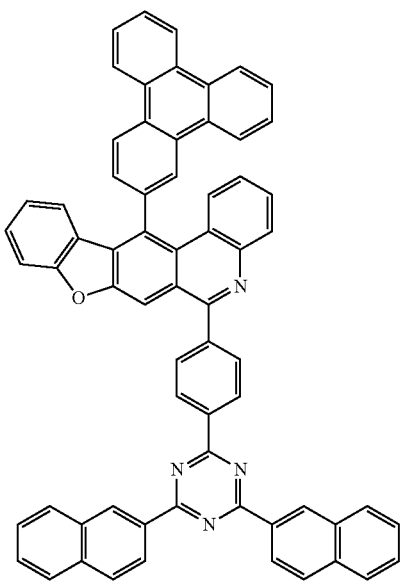
1002
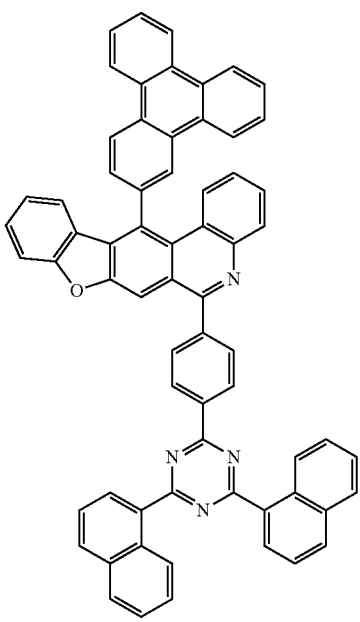
1003

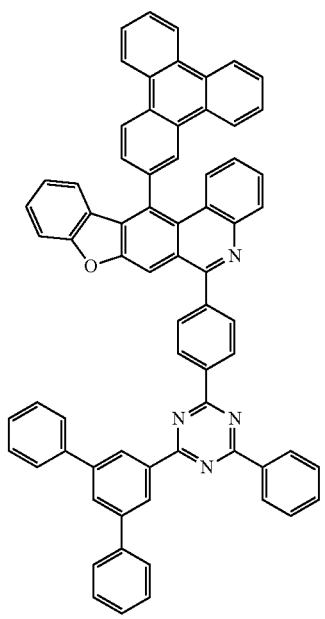
1004
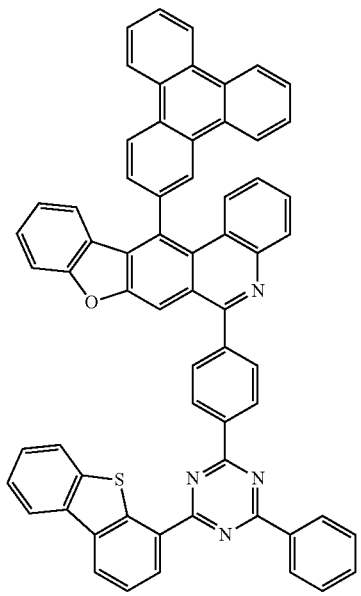
1006
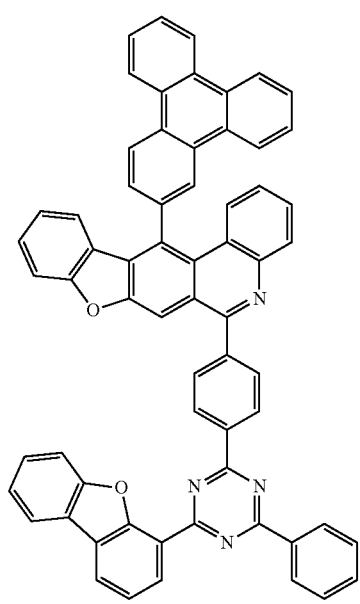
1005
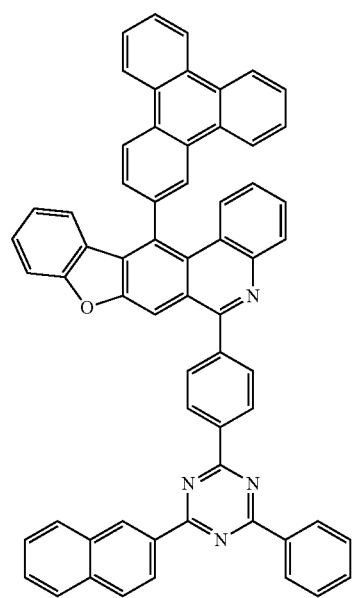
1007

399
-continued
400
-continued
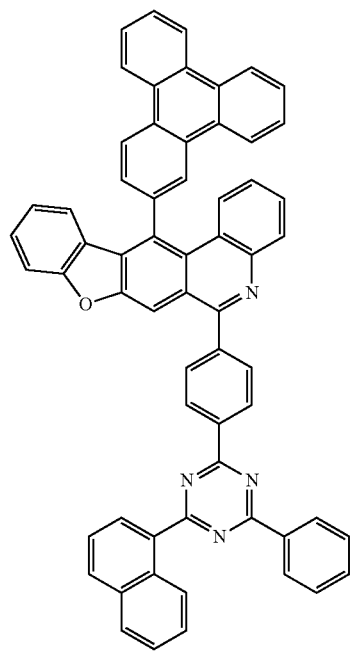
1008
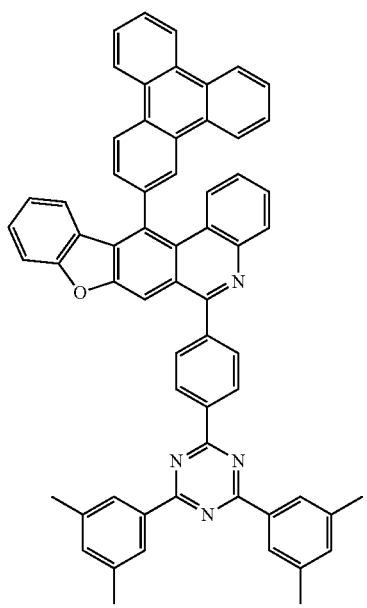
1010
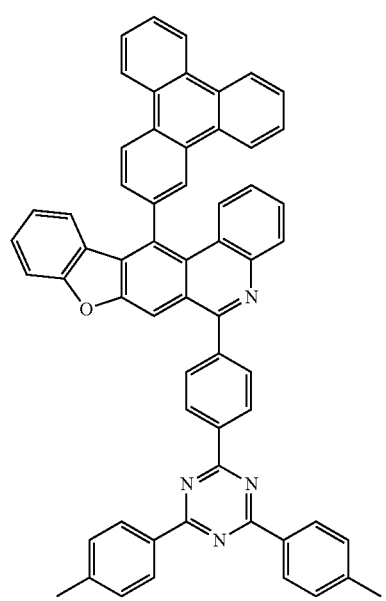
1009
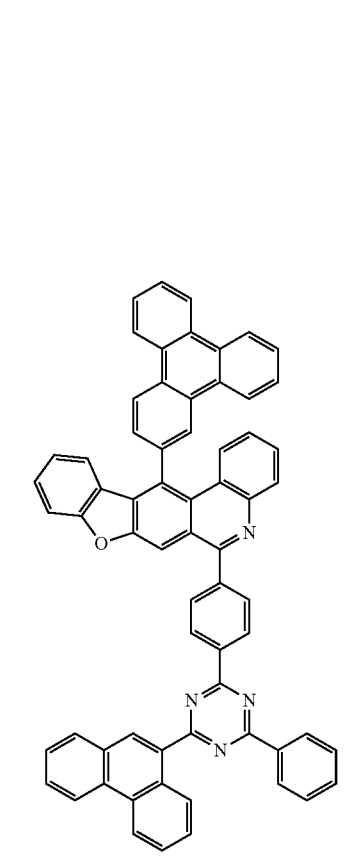
1011

401
-continued
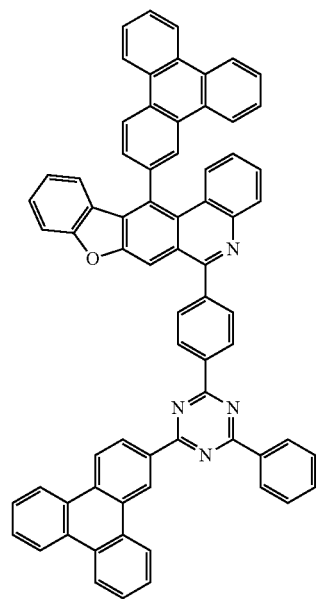
1012
402
-continued
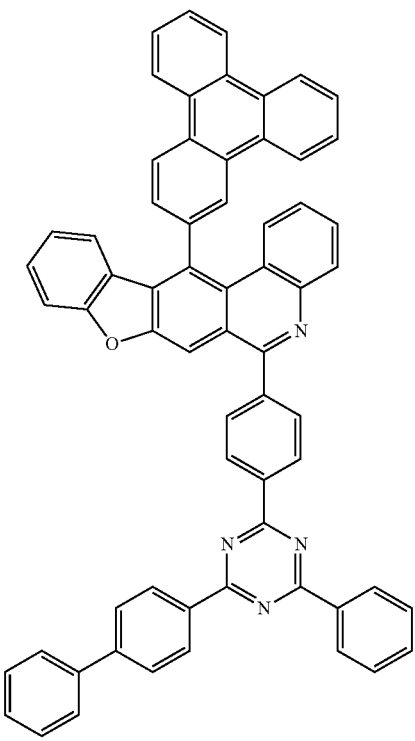
1014
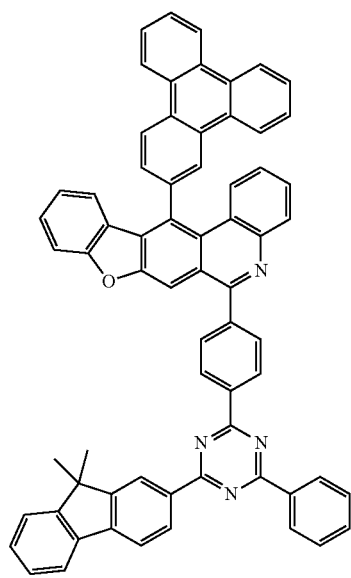
1013
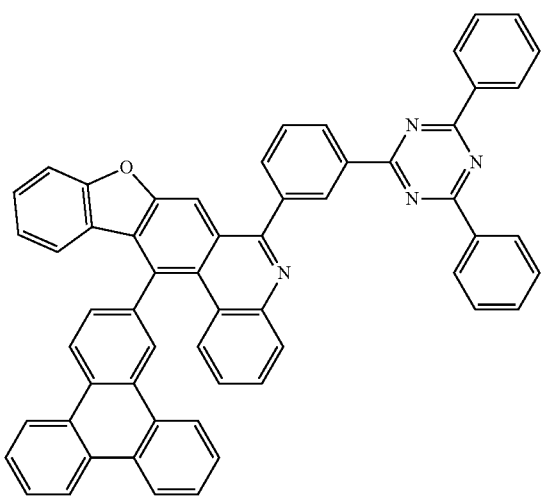 [SMILES: c1ccc(-c2nc(-c3ccccc3)nc(-c3cccc(-c4nc5ccccc5c5c(-c6ccc7c8ccccc8c8ccccc8c7c6)c6c(cc45)oc4ccccc46)c3)n2)cc1]
1015

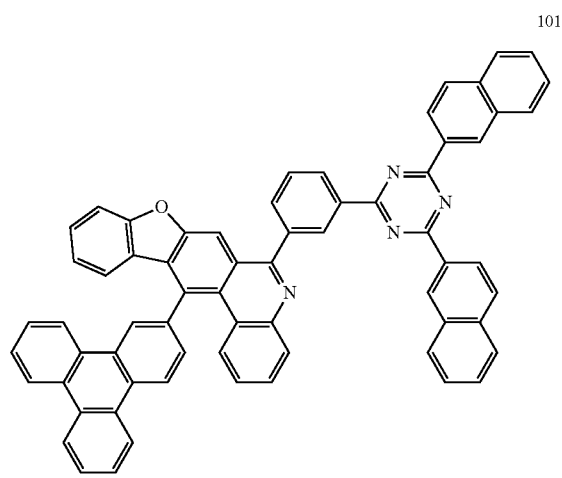
1016
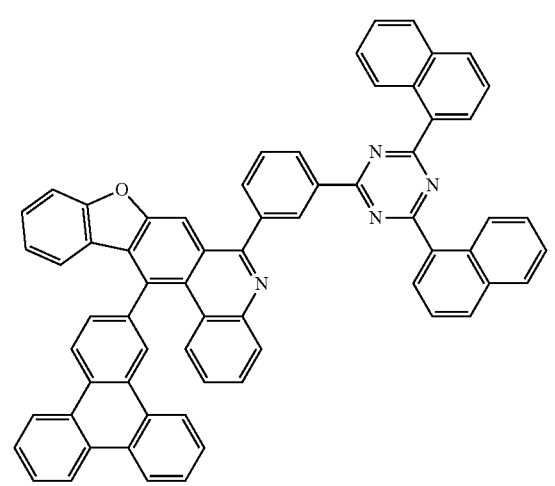 [SMILES: c1cc(-c2nc(-c3cccc4ccccc34)nc(-c3cccc4ccccc34)n2)cc(-c2nc3ccccc3c3c(-c4ccc5c6ccccc6c6ccccc6c5c4)c4c(cc23)oc2ccccc24)c1]
1017
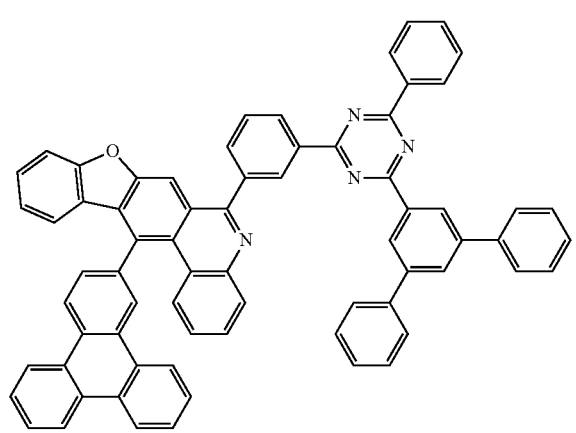 [SMILES: c1ccc(-c2cc(-c3ccccc3)cc(-c3nc(-c4ccccc4)nc(-c4cccc(-c5nc6ccccc6c6c(-c7ccc8c9ccccc9c9ccccc9c8c7)c7c(cc56)oc5ccccc57)c4)n3)c2)cc1]
1018
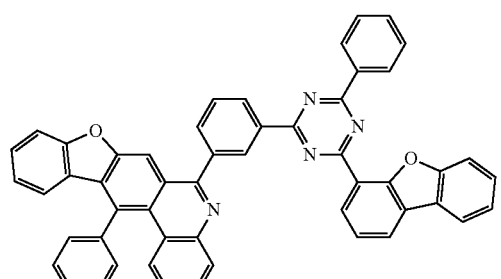
1019
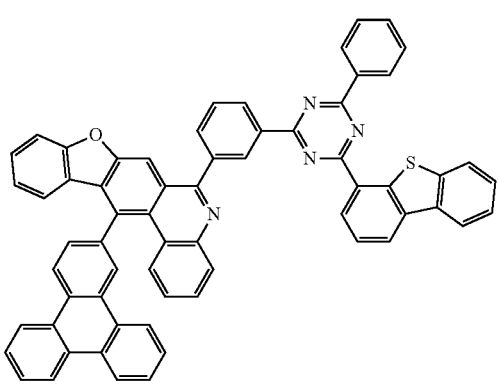
1020
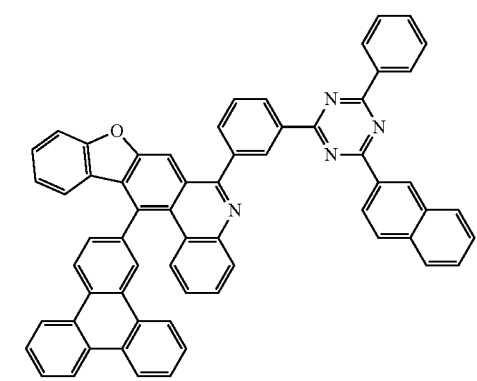
1021
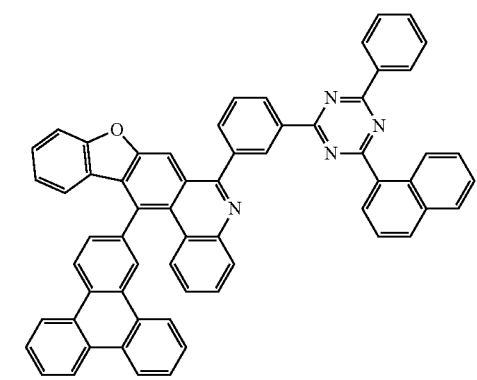
1022

405
-continued
1023
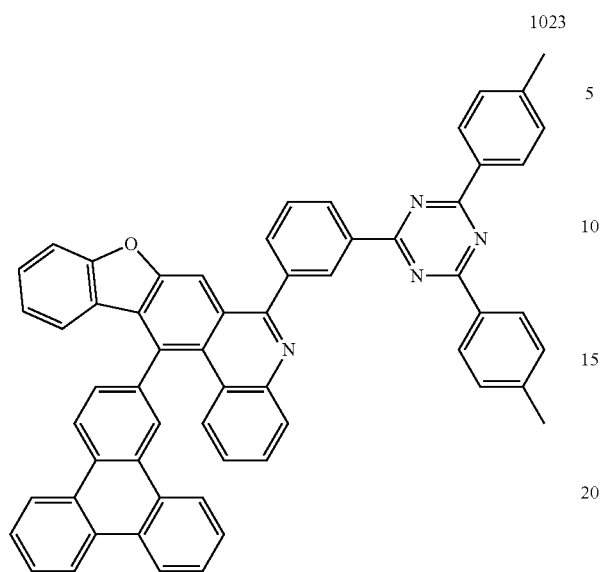
1024
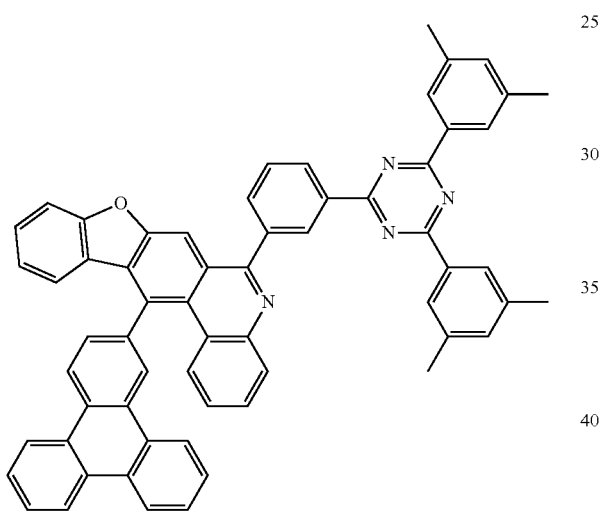
1025
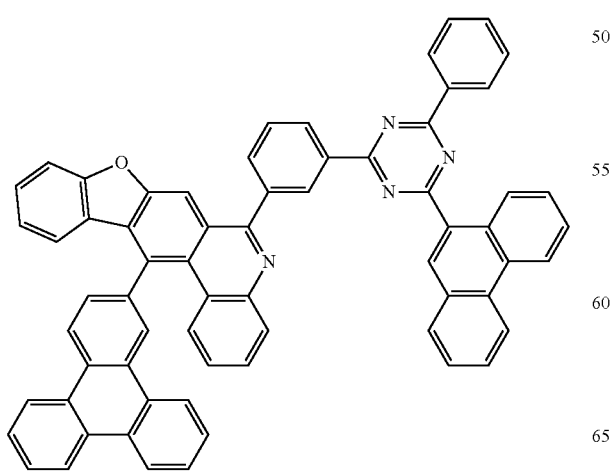
406
-continued
1026
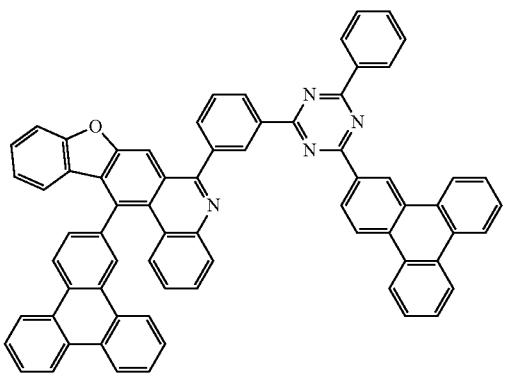 [SMILES: c1ccc(-c2nc(-c3cccc(-c4nc5ccccc5c5c(-c6ccc7c8ccccc8c8ccccc8c7c6)c6c(cc45)oc4ccccc46)c3)nc(-c3ccc4c5ccccc5c5ccccc5c4c3)n2)cc1]
1027
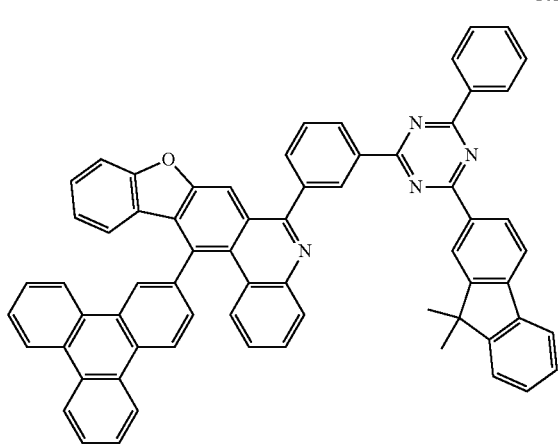
1028
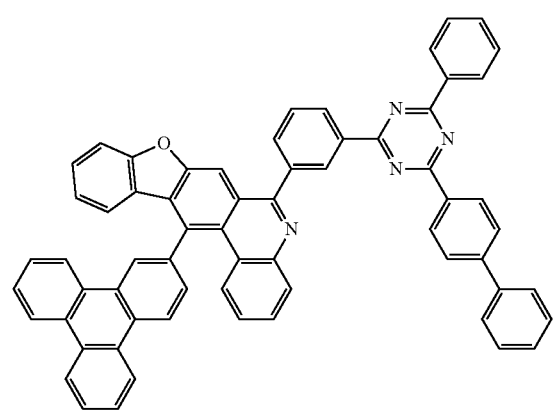

407
-continued
1029
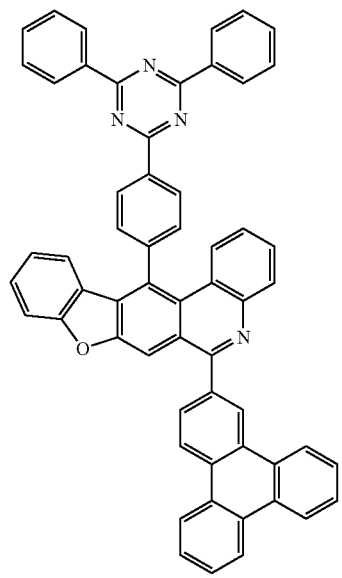
408
-continued
1031
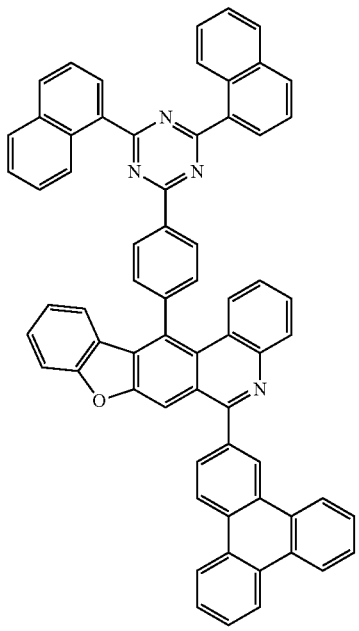
1030
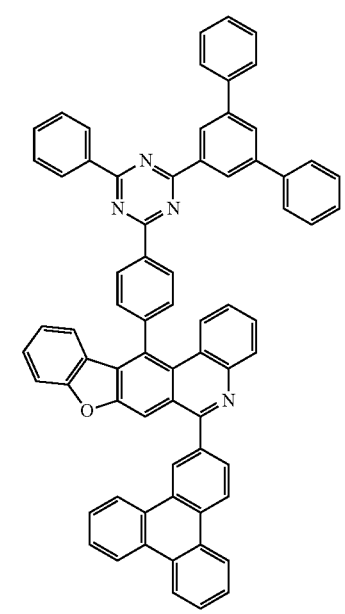
1032

409
-continued
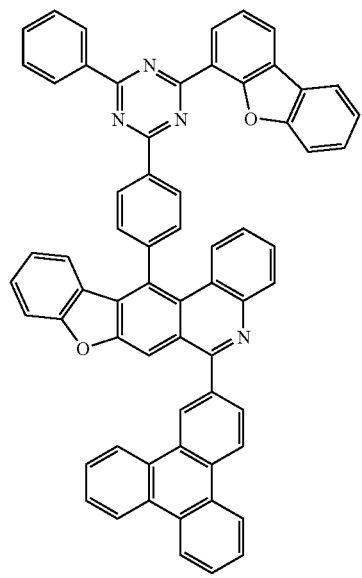
1033
410
-continued
1035
1034
1036
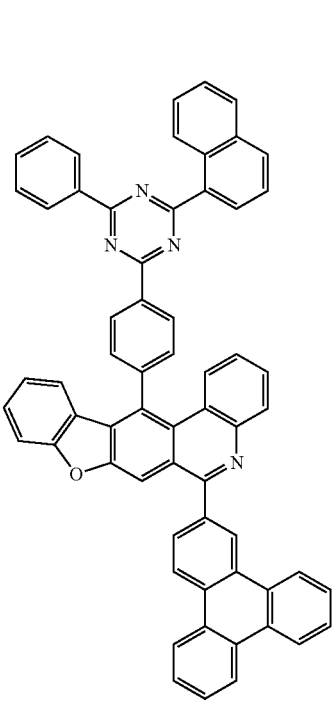

411
-continued
1037
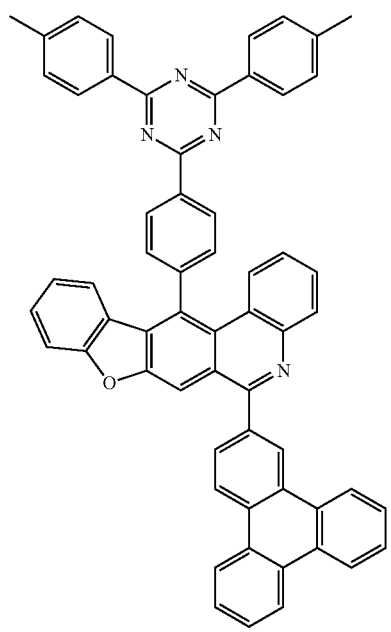
1038
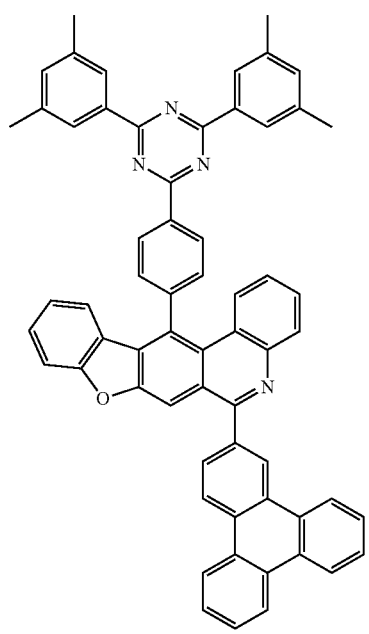
412
-continued
1039
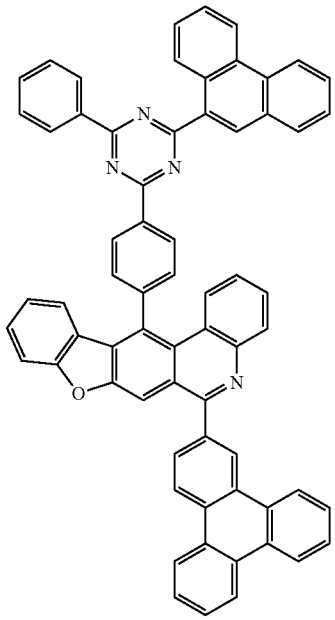
1040
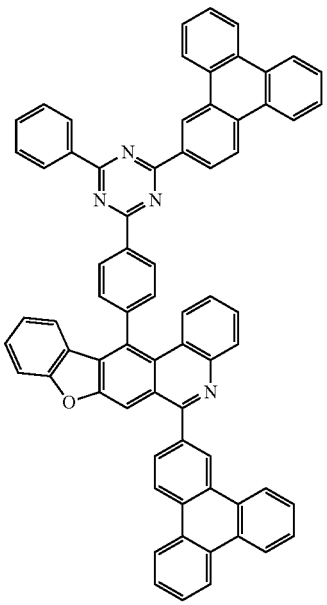

413
-continued
1041
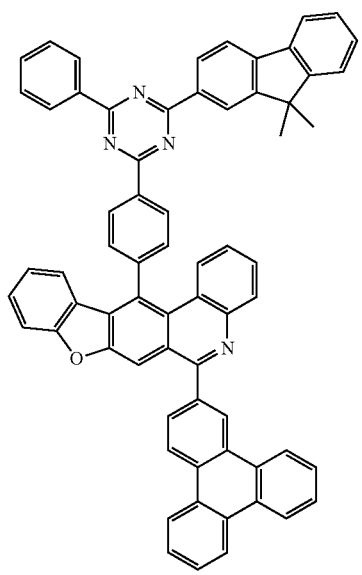
1042
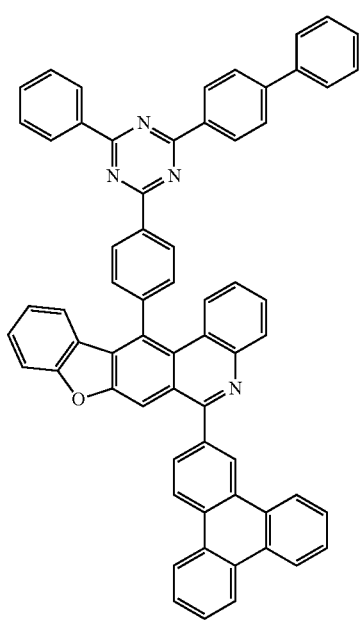
414
-continued
1043
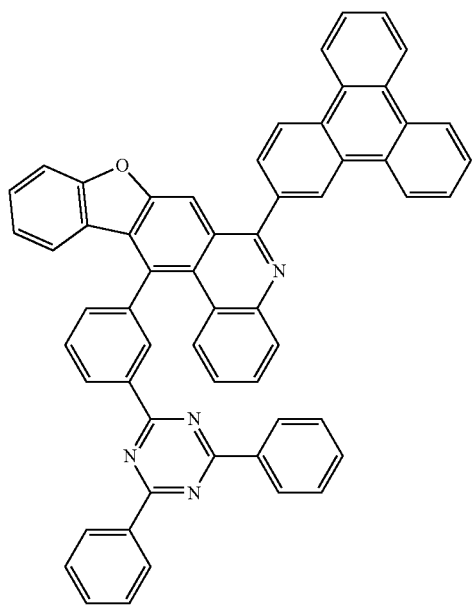 [SMILES: c1ccc(-c2nc(-c3ccccc3)nc(-c3cccc(-c4c5c(cc6c(-c7ccc8c9ccccc9c9ccccc9c8c7)nc7ccccc7c46)oc4ccccc45)c3)n2)cc1]
1044
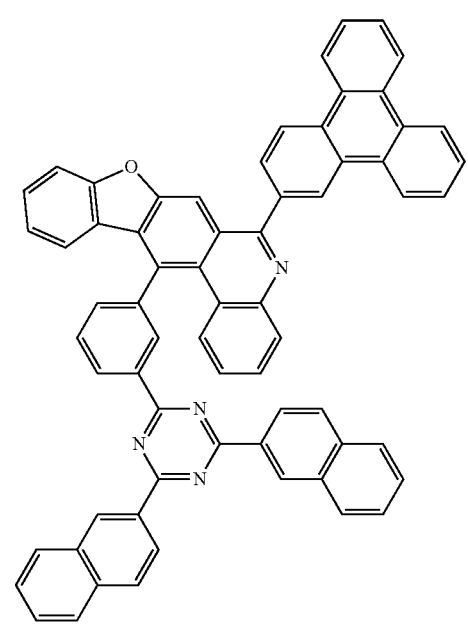 [SMILES: c1cc(-c2nc(-c3ccc4ccccc4c3)nc(-c3ccc4ccccc4c3)n2)cc(-c2c3c(cc4c(-c5ccc6c7ccccc7c7ccccc7c6c5)nc5ccccc5c24)oc2ccccc23)c1]

-continued
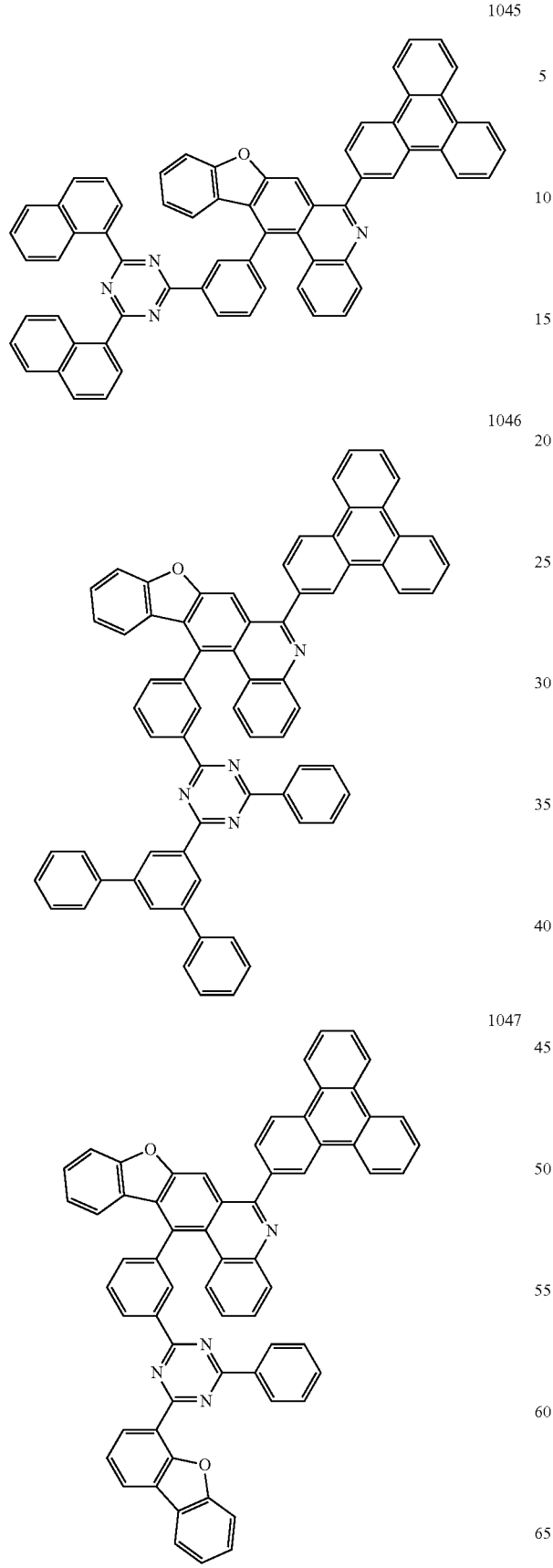
1045
1046
1047
-continued
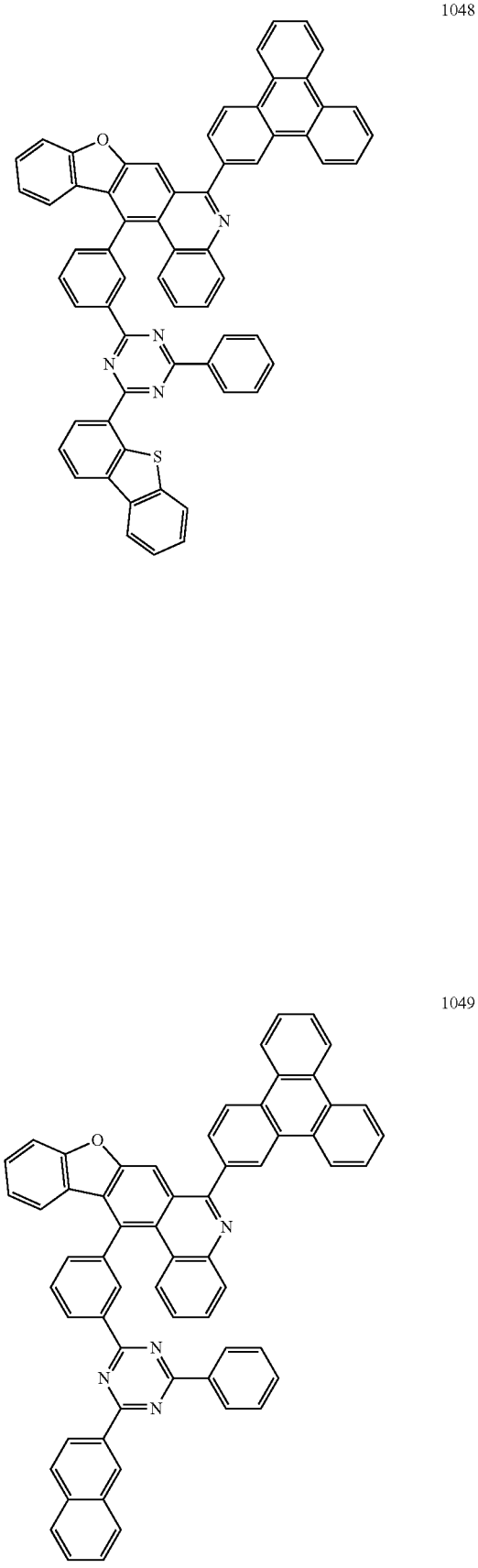
1048
1049

417
-continued
1050
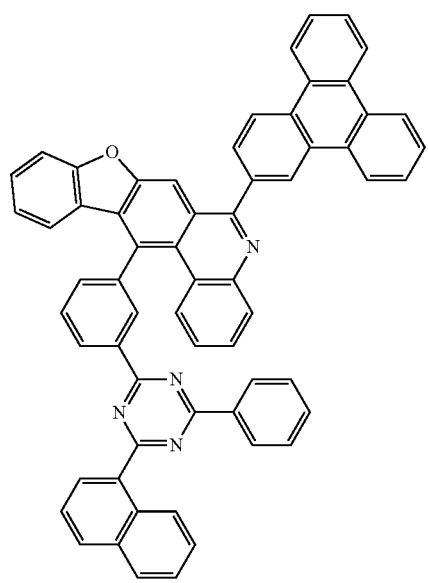
1051
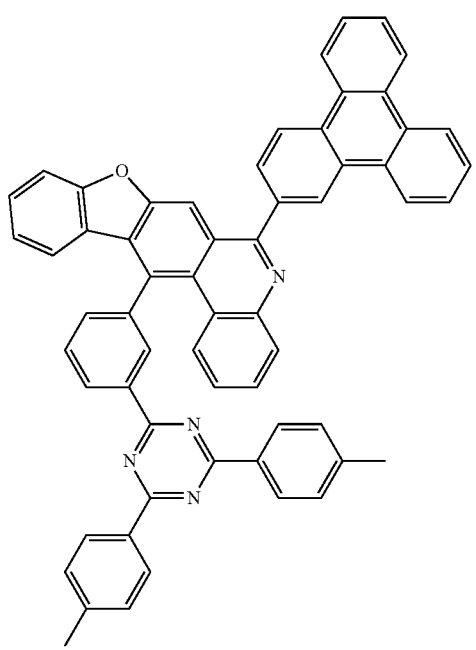
418
-continued
1052
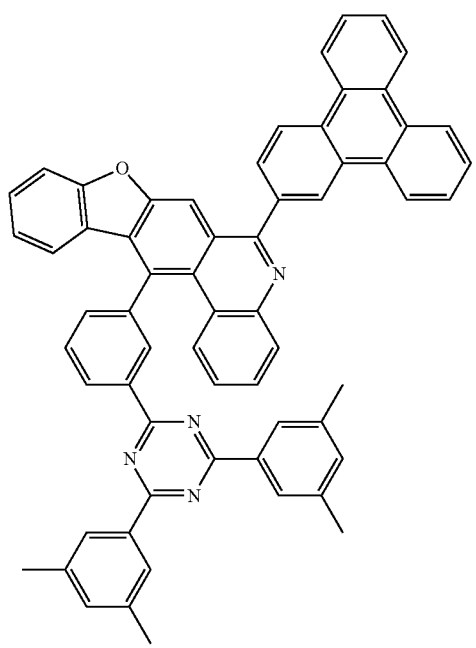
1053
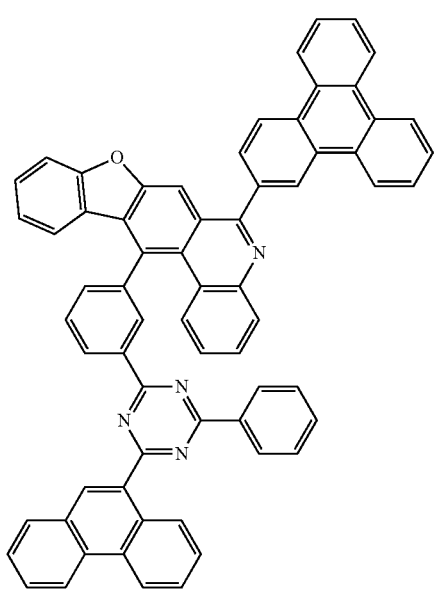

419
-continued
1054
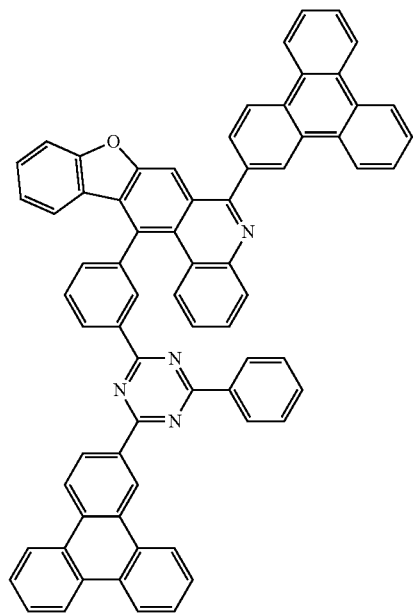
1055
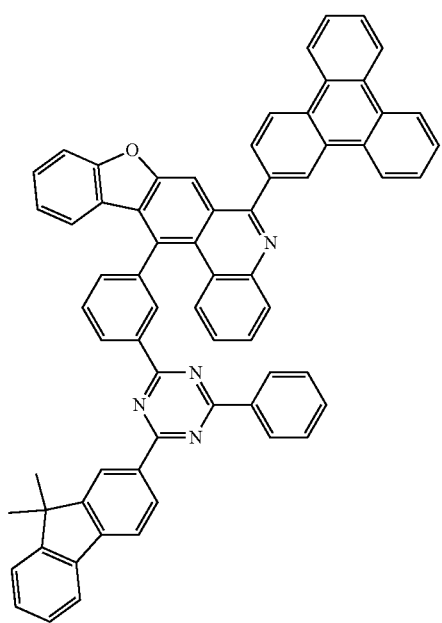
420
-continued
1056
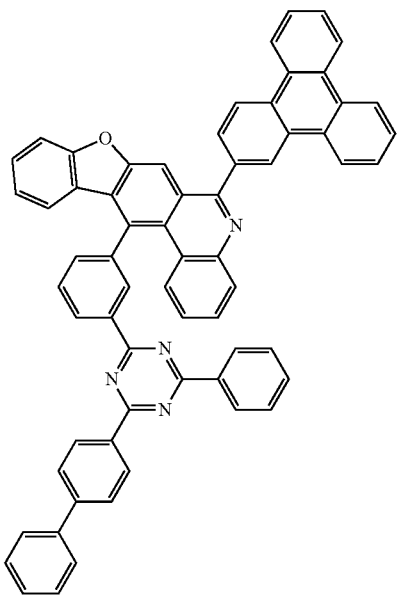
1057
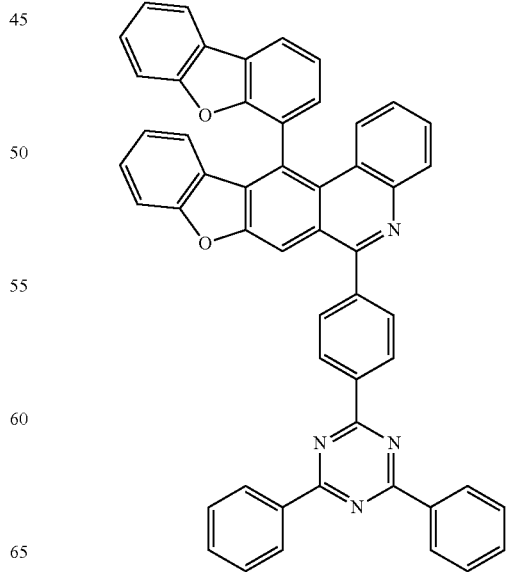

421
-continued
1058
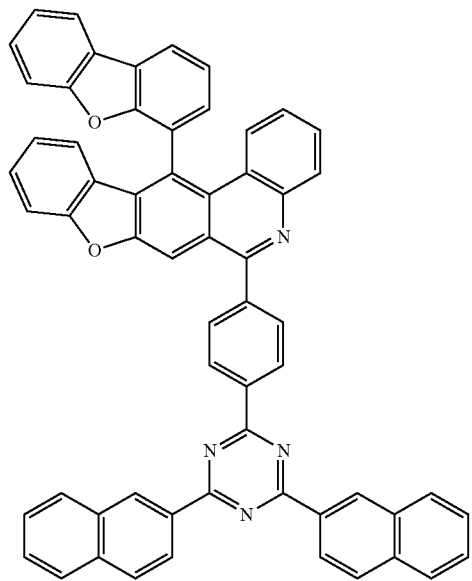
1059
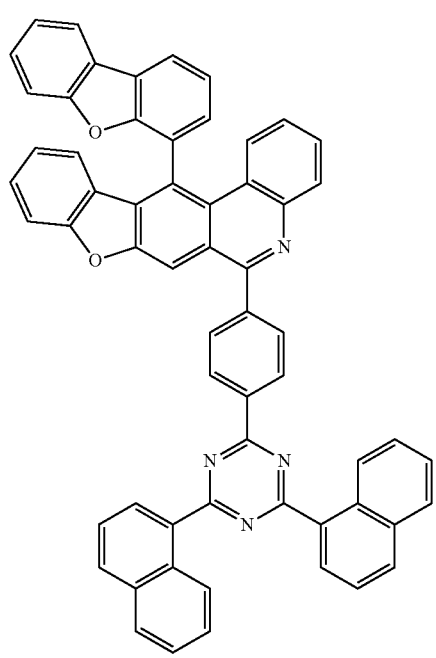
422
-continued
1060
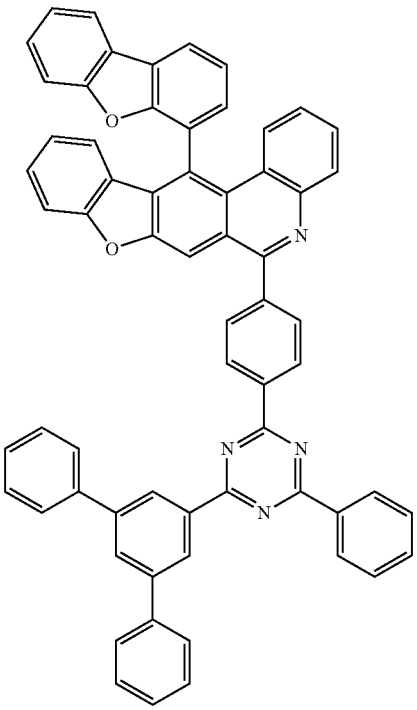
1061
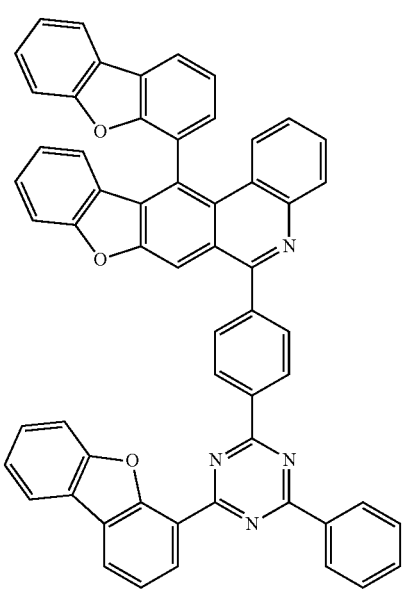

423
-continued
1062
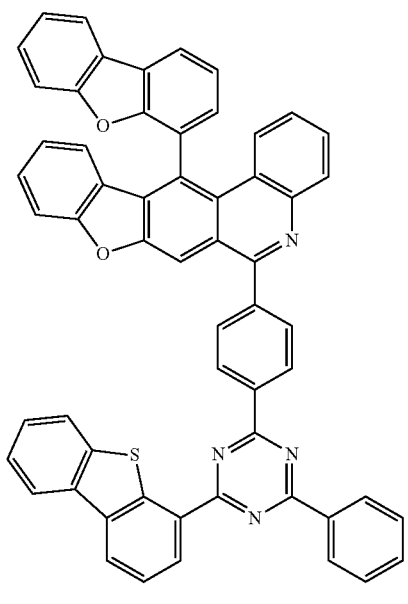
1063
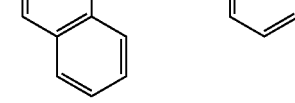
424
-continued
1064
1065
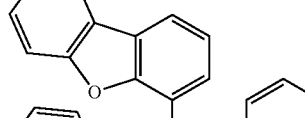

425
-continued
1066
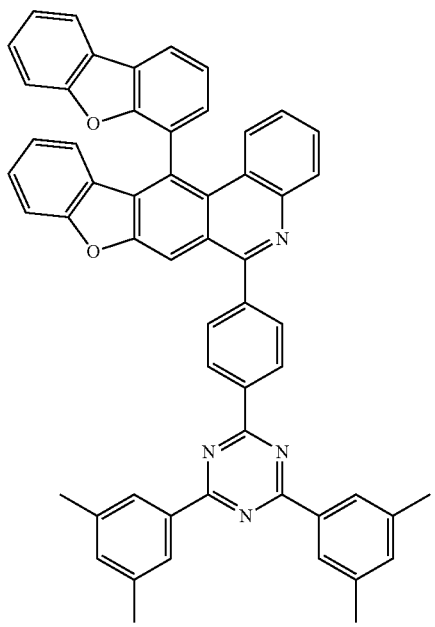
1067
426
-continued
1068
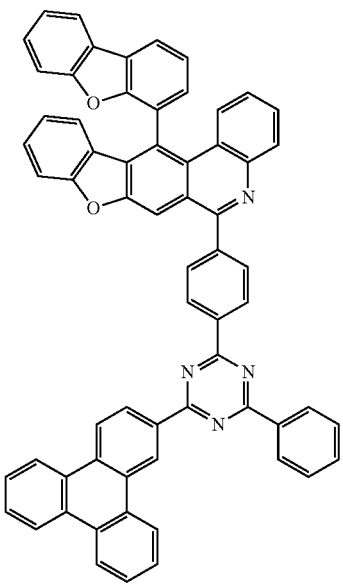
1069
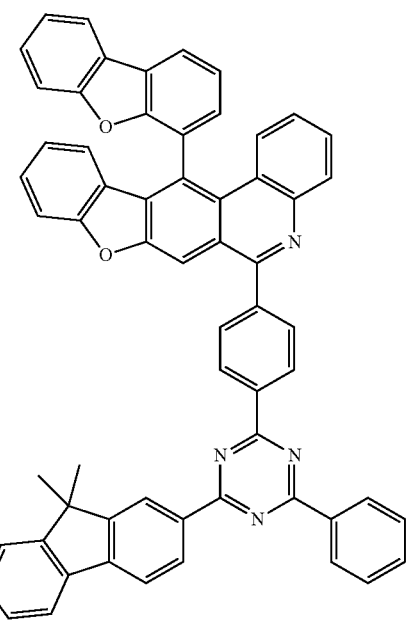

427
-continued
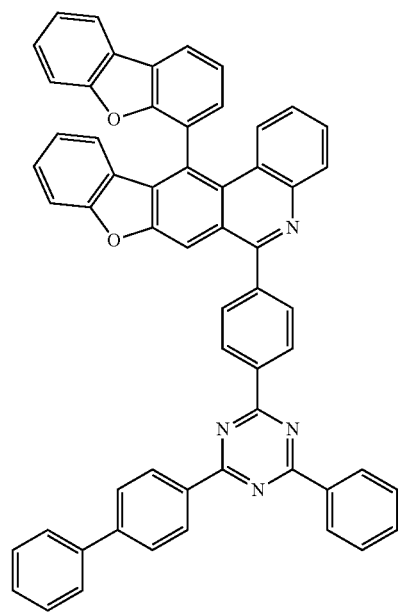
1071
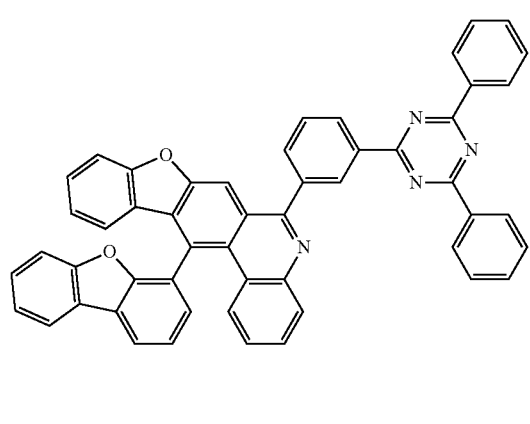
1072
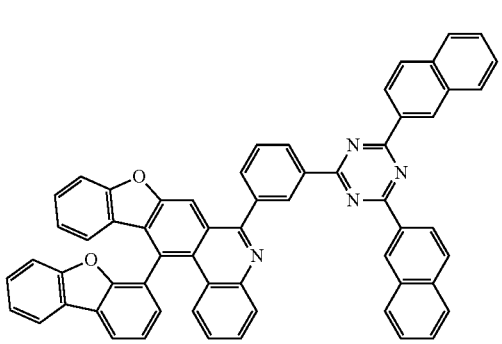
428
-continued
1070
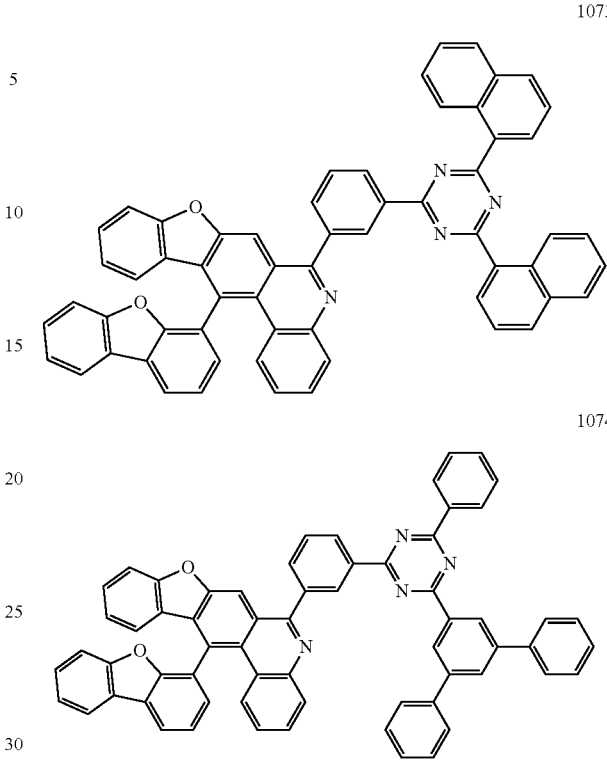
1073
1074
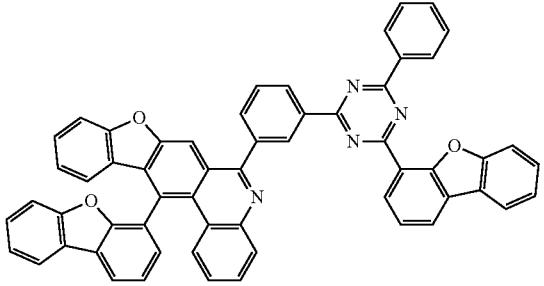
1075
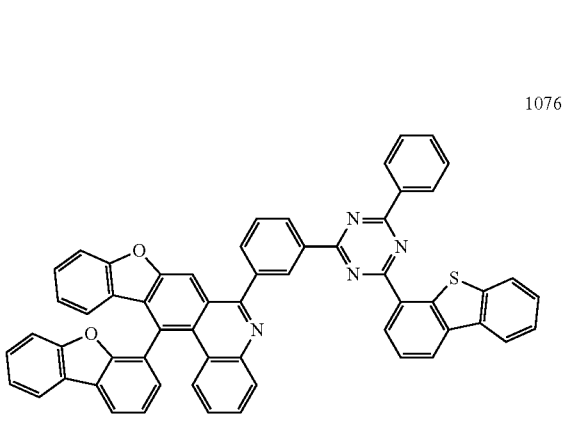
1076

1077
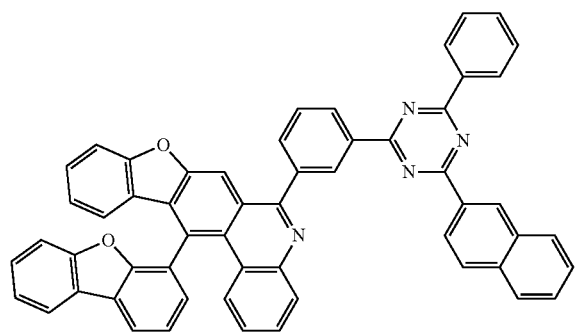
1078
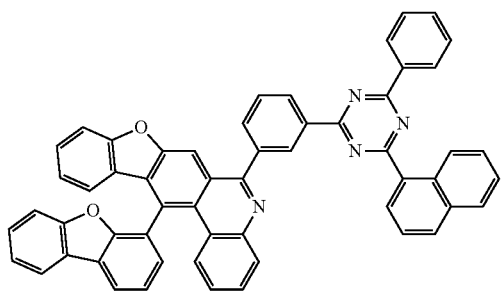
1079
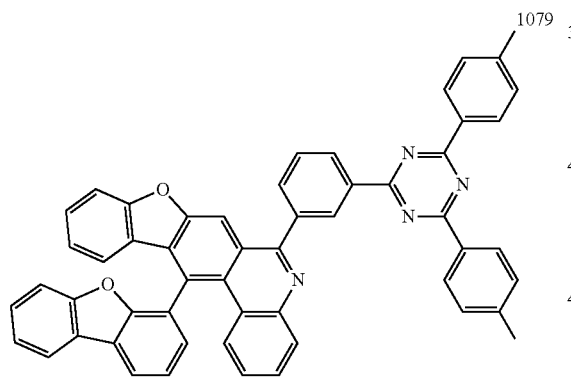
1080
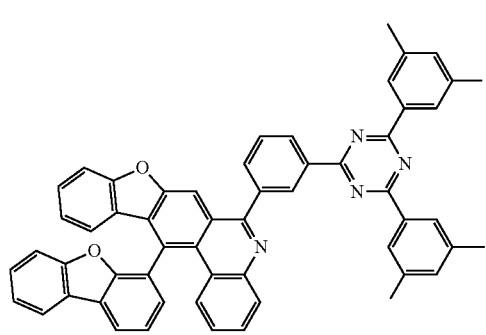
1081
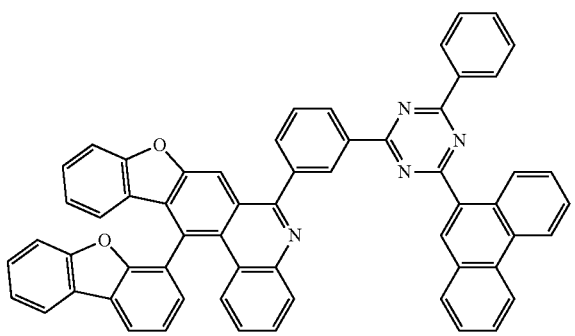
1082
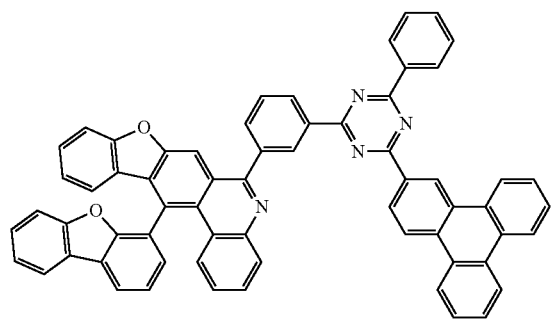
1083
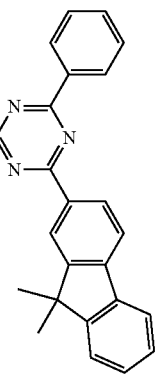
1084
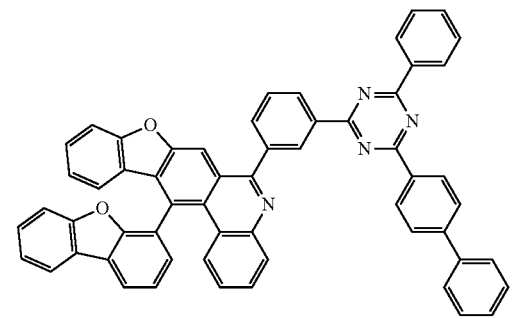

431
-continued
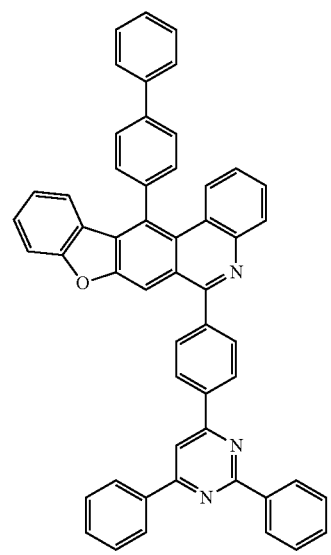
1085
432
-continued
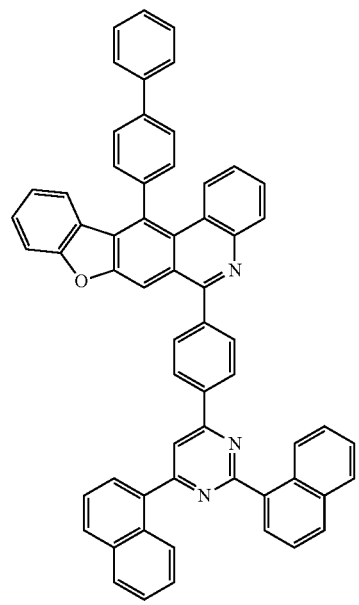
1087
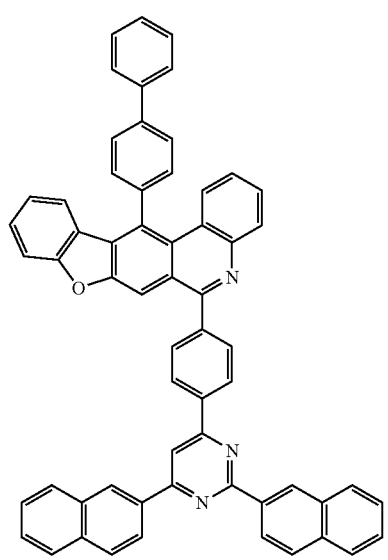
1086
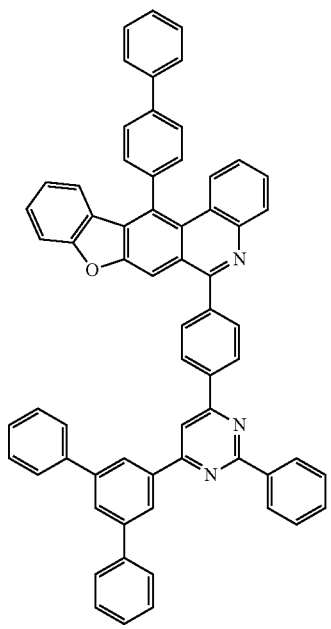
1088

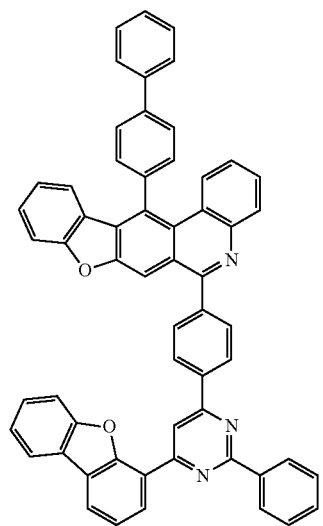
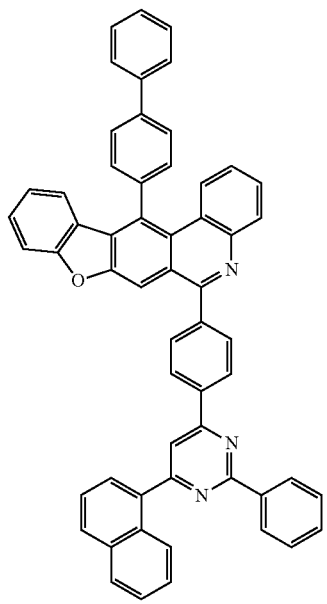
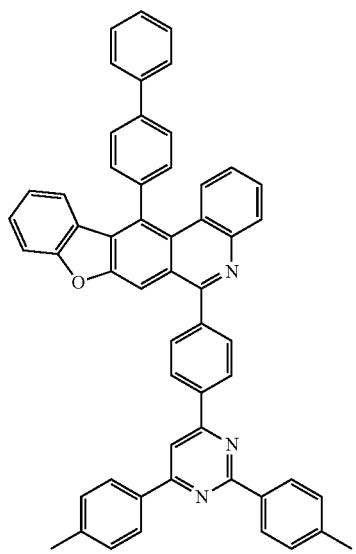

435
-continued
1094
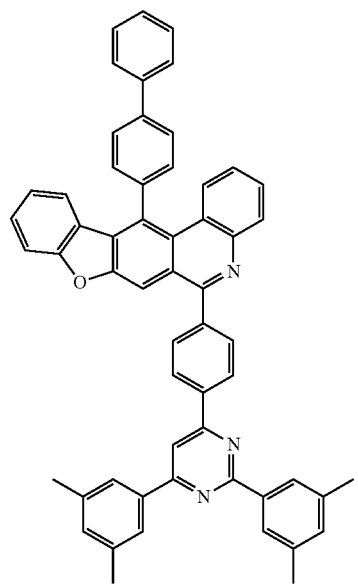
436
-continued
1096
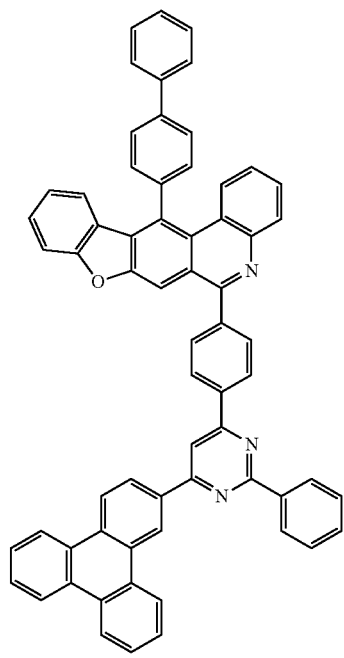
1095
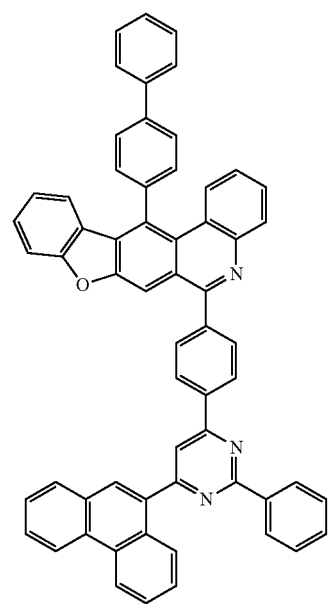
1097
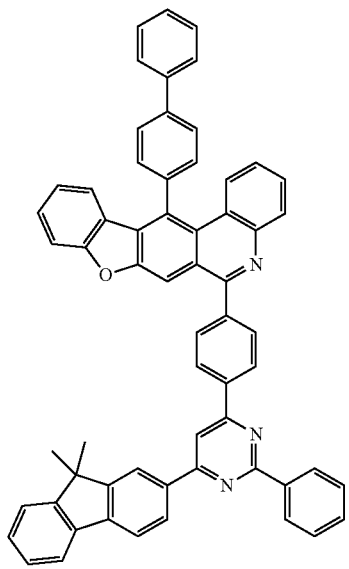

1098
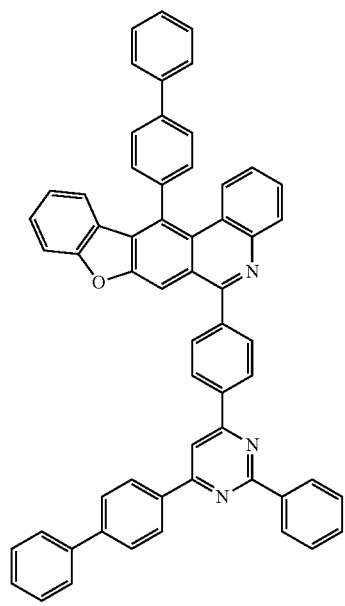
1099
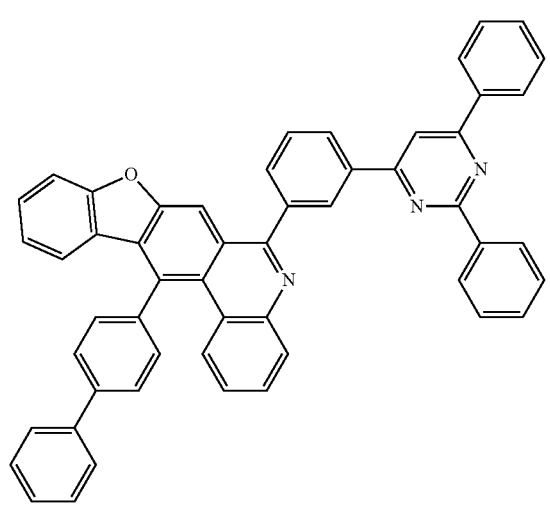
1100
1101
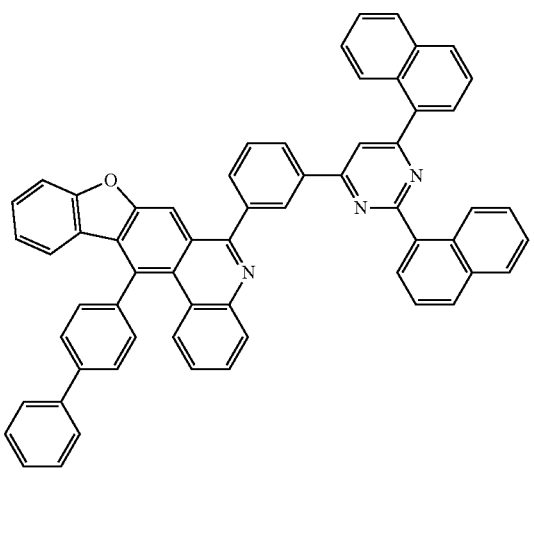
1102
1103
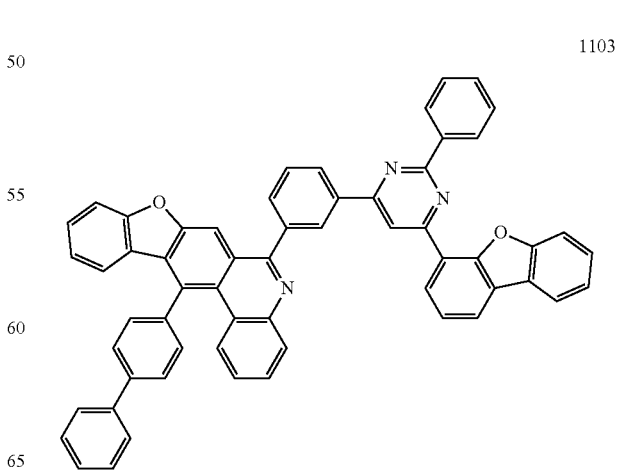

-continued
1104
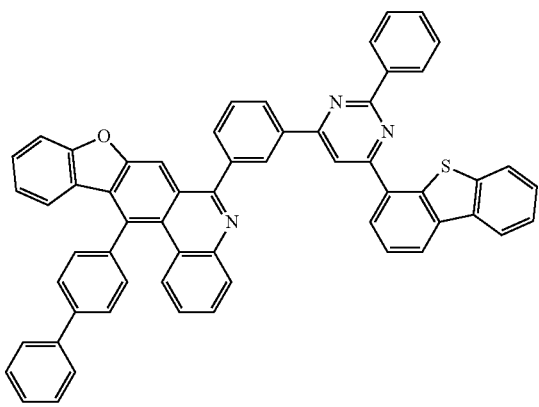
1105
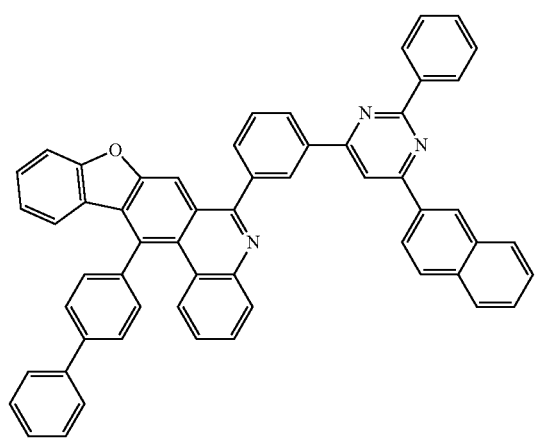
1106
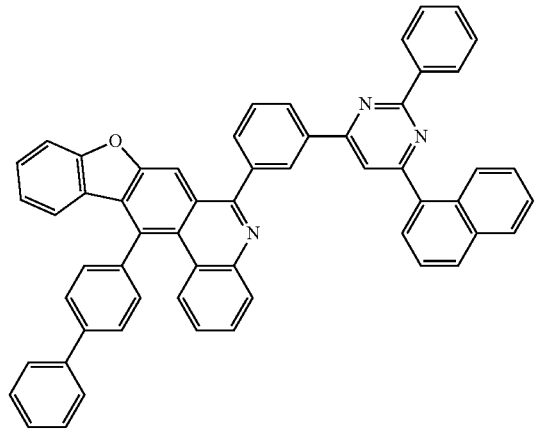
-continued
1107
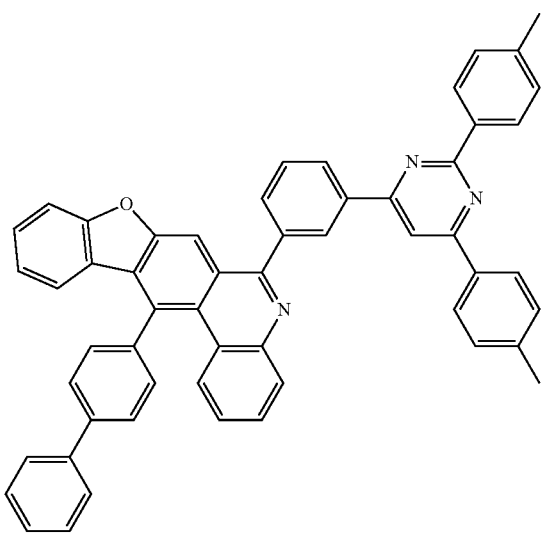
1108
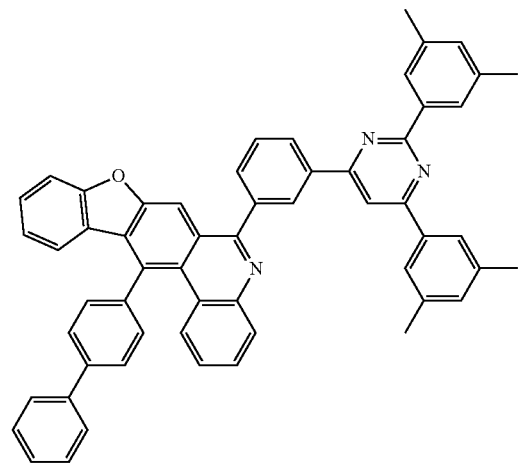
1109
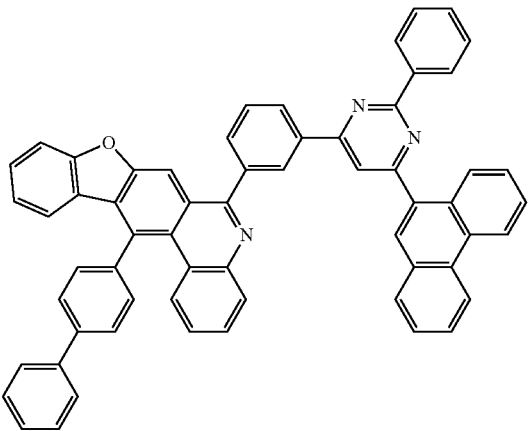

441
-continued
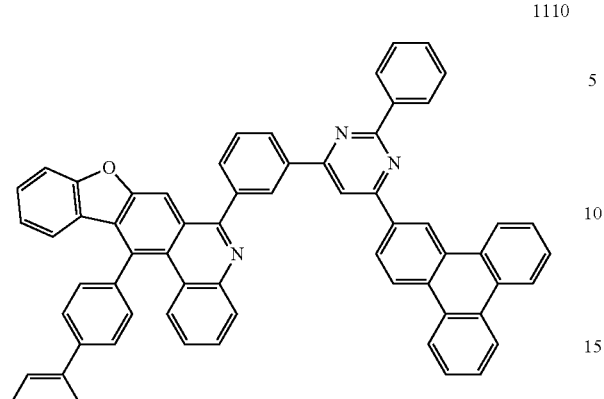
1110
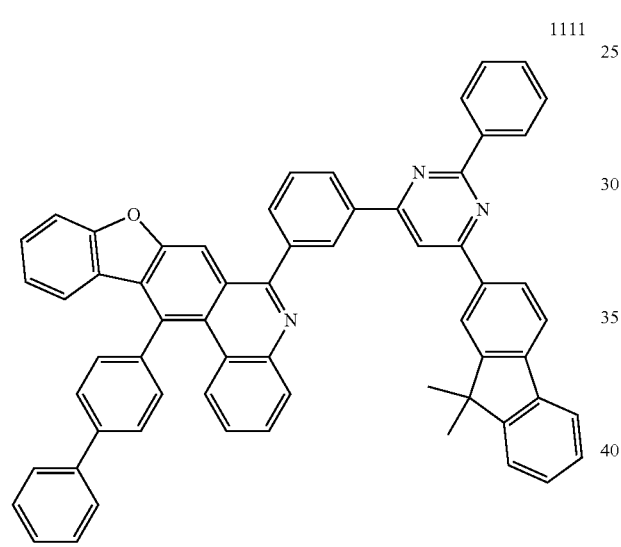
1111
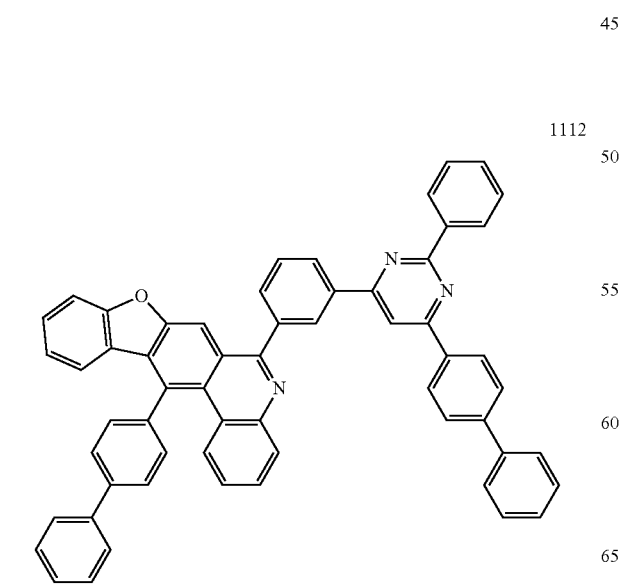
1112
442
-continued
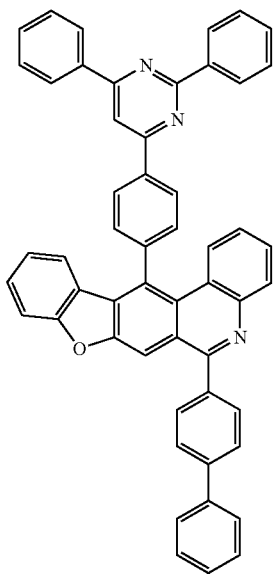
1113
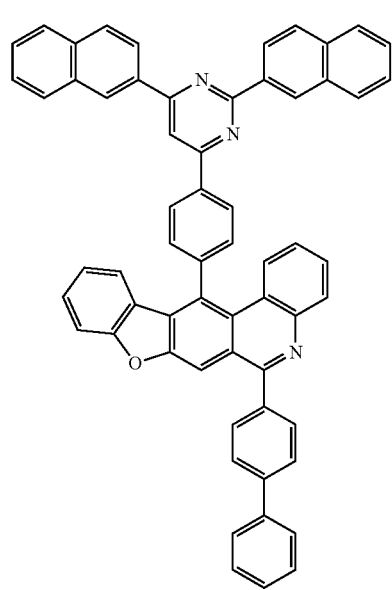
1114

443
-continued
1115
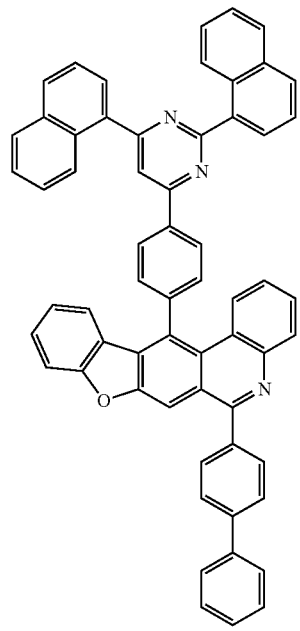
1116
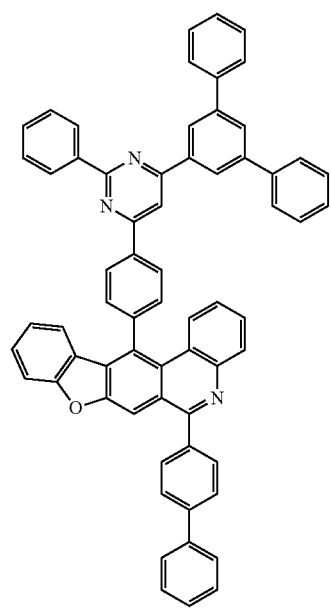
444
-continued
1117
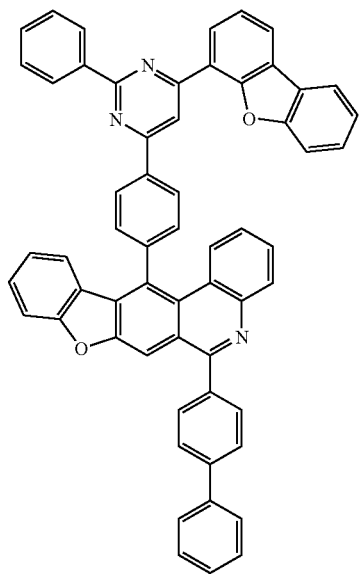
1118
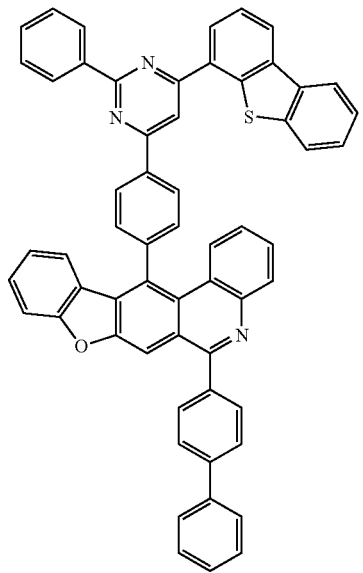

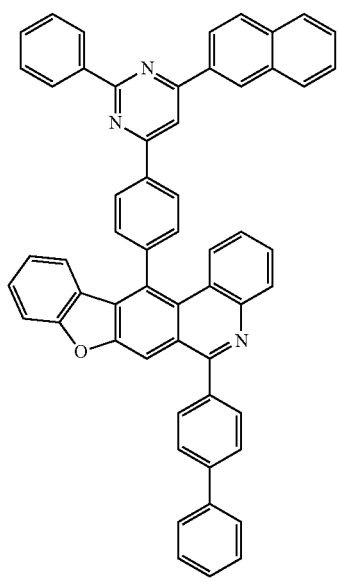
1119
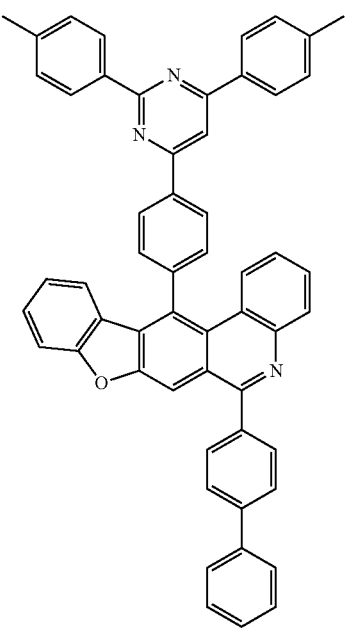
1121
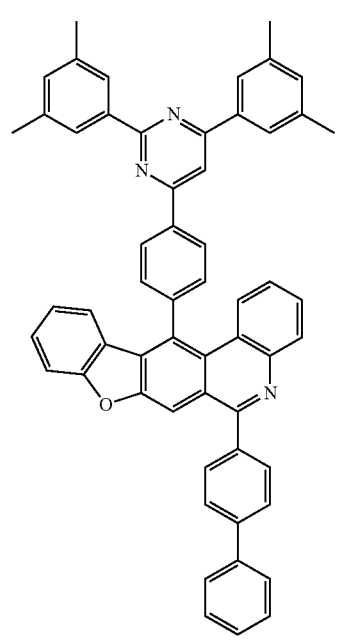
1122

447
-continued
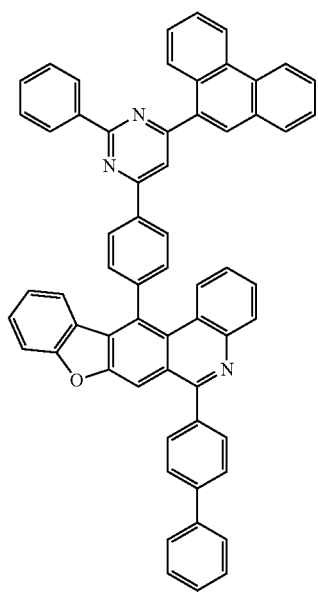
1123
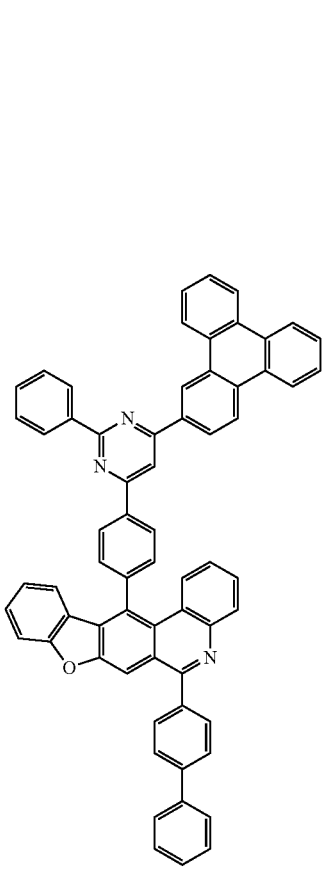
1124
448
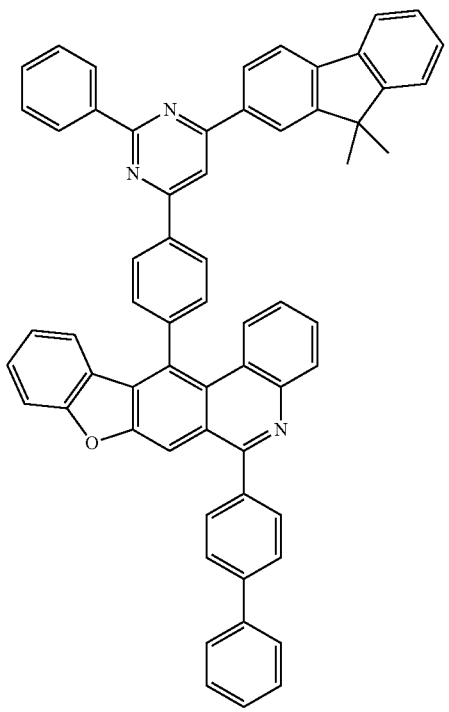
1125
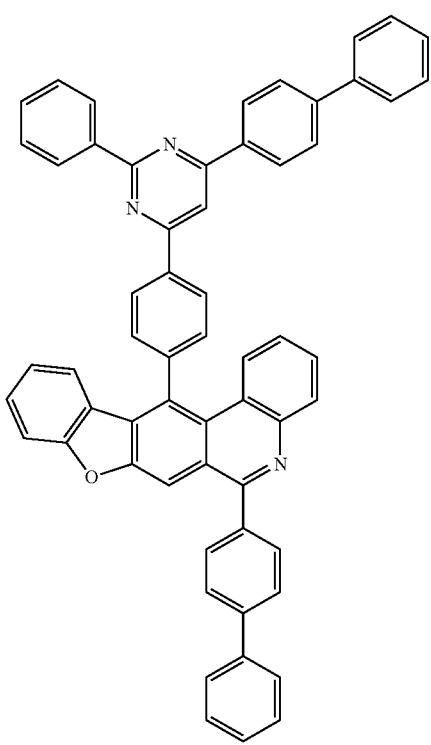
1126

1127
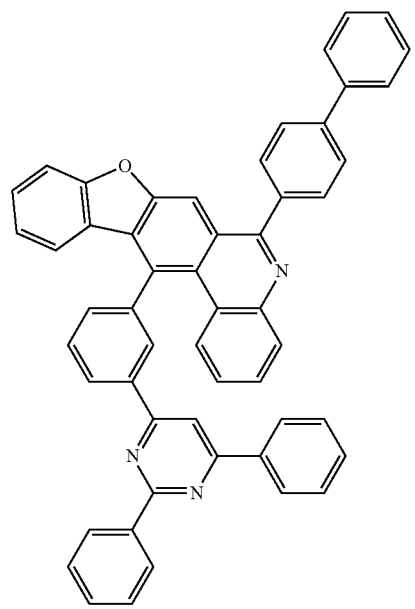
1128
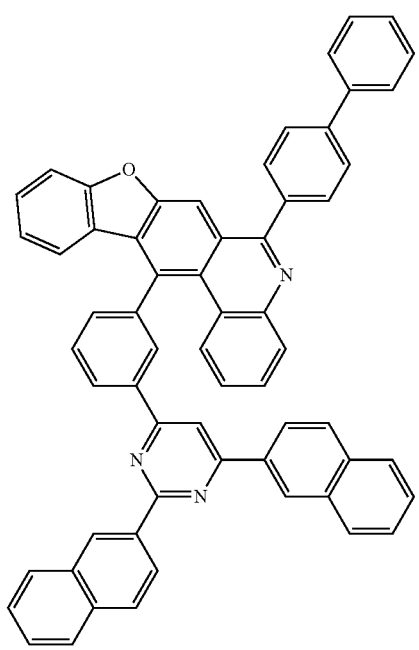
1129
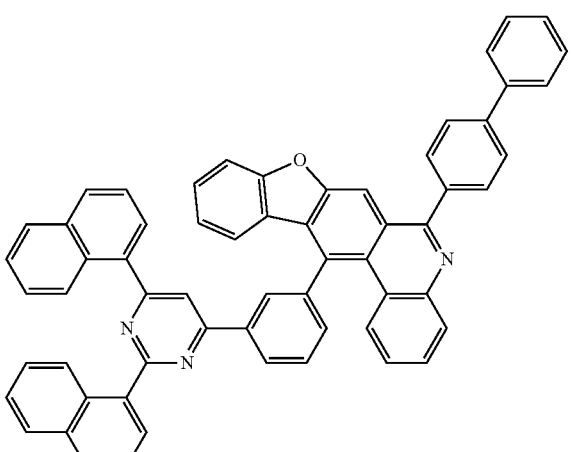
1130
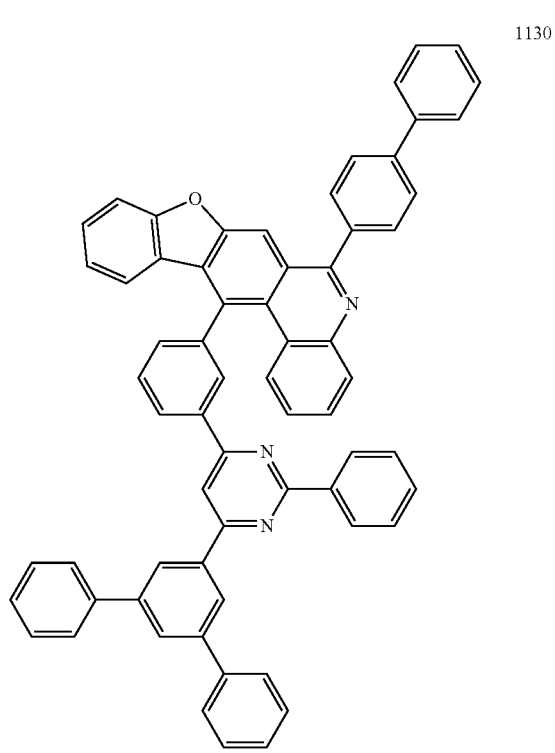

451
-continued
1131
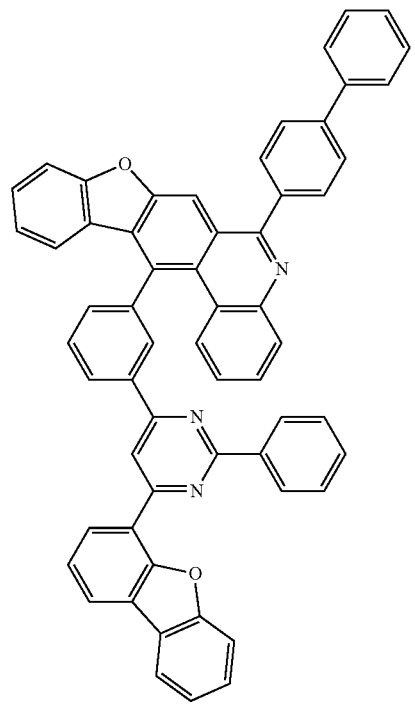
1132
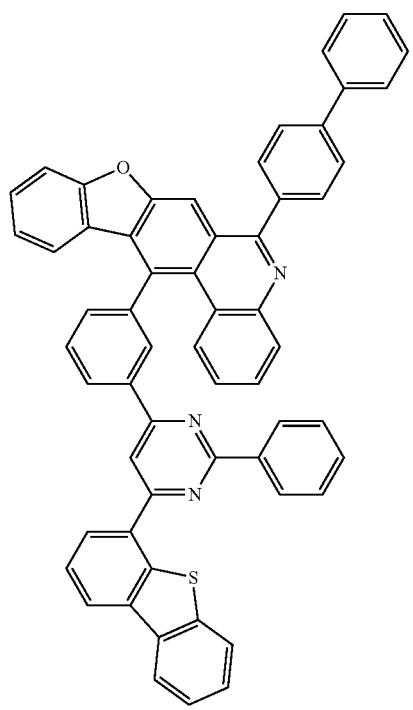
452
-continued
1133
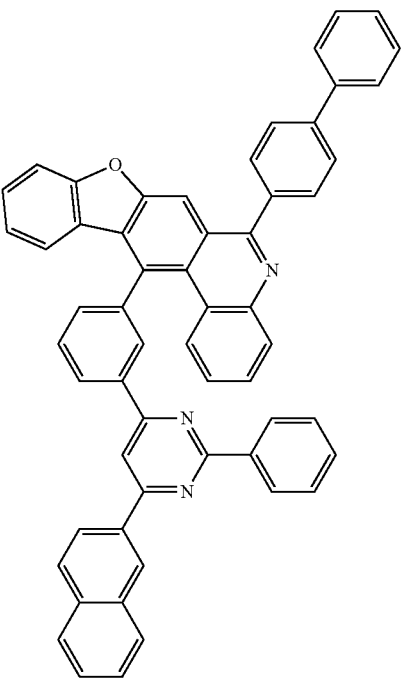
1134
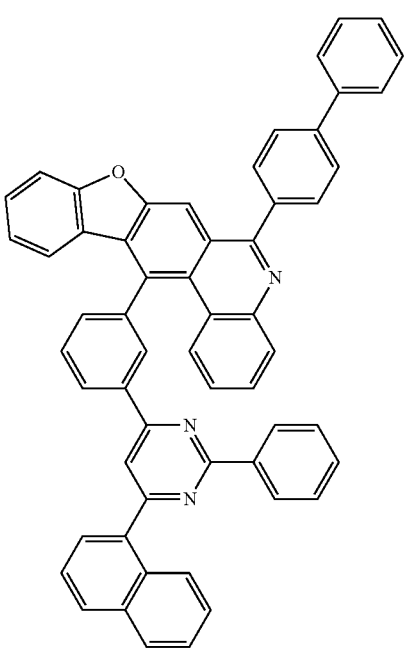

453
-continued
1135
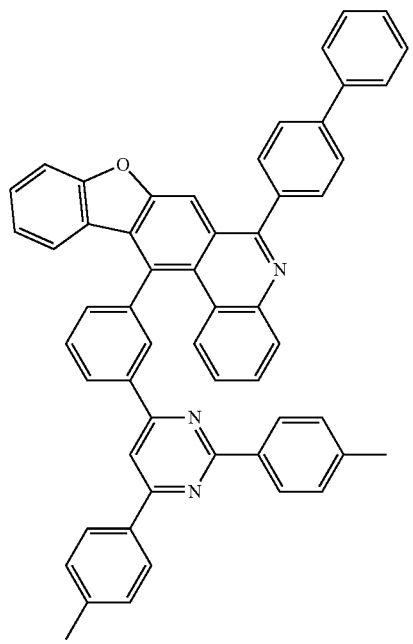
1136
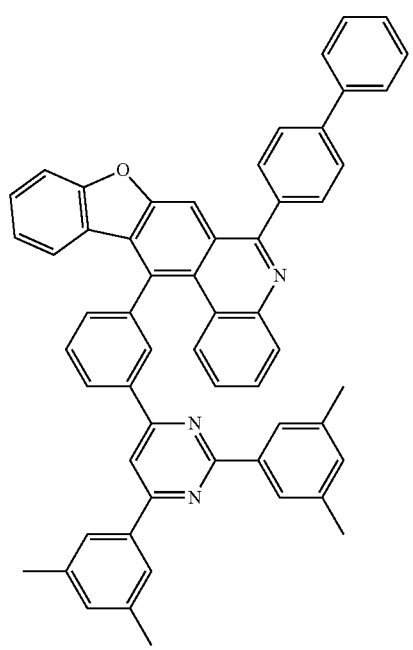
454
-continued
1137
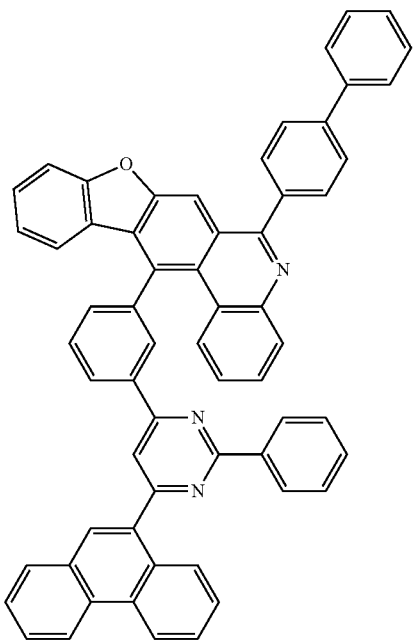
1138
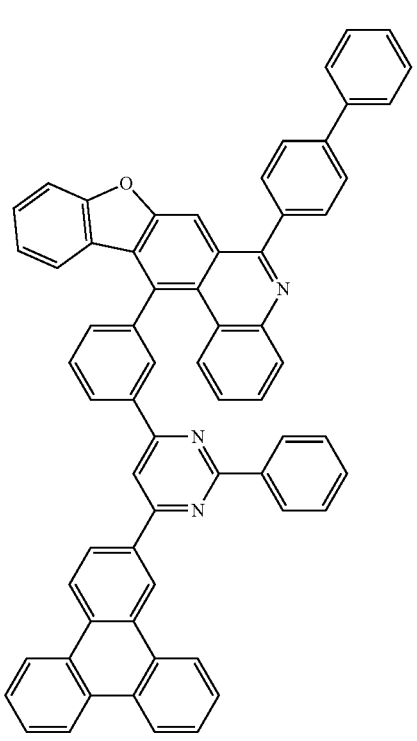

-continued

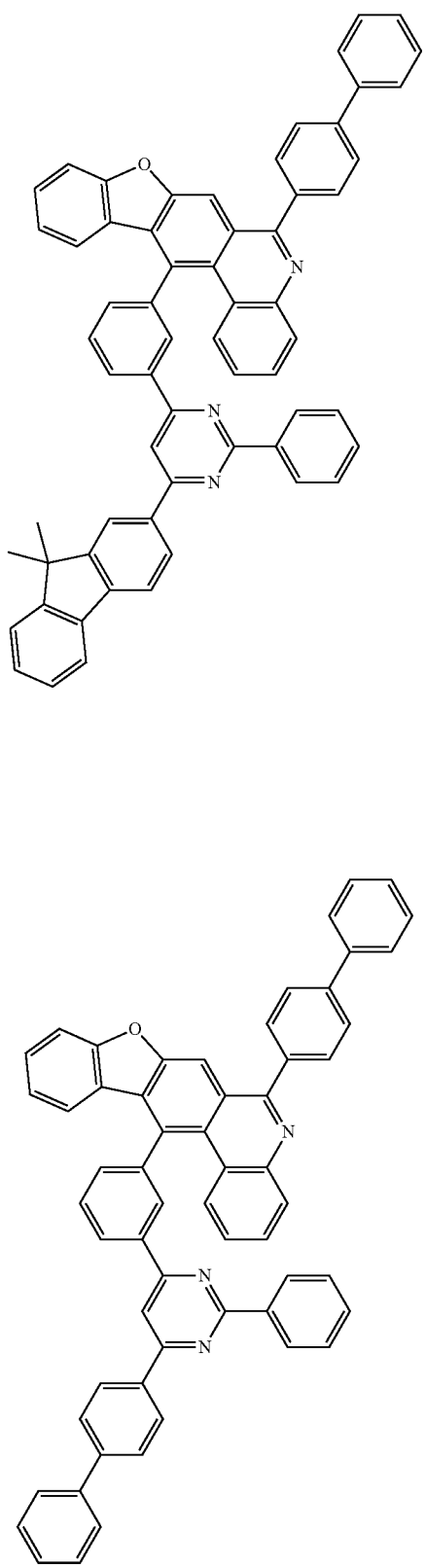

1139

1140

The compound according to one embodiment of the present application may be prepared according to the following General Formula 1.

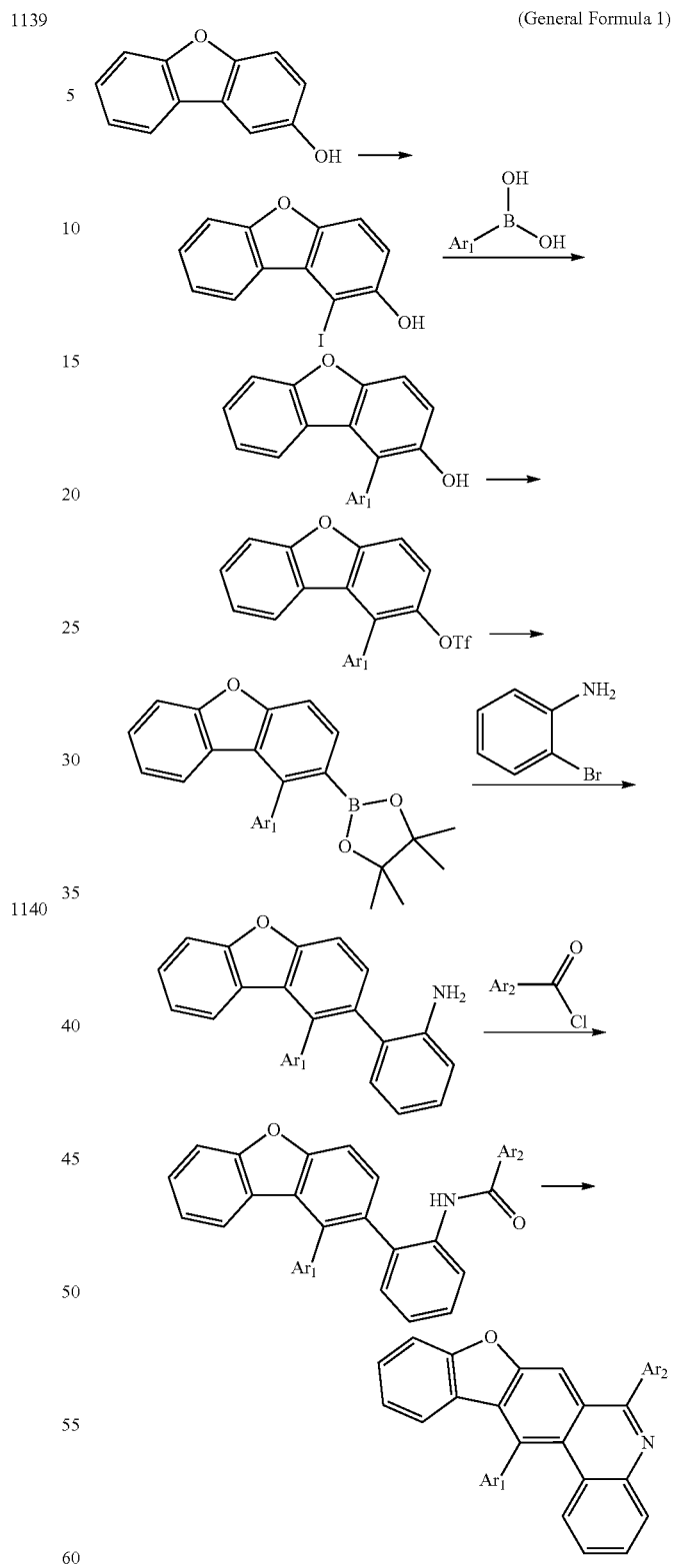

(General Formula 1)

In General Formula 1, $Ar_1$ or $Ar_2$ has the same definition as $-(L_1)_m-(Z_1)_n$ or $-(L_2)_p-(Z_2)_q$ of Chemical Formula 1.

In addition, by introducing various substituents to the structure of Chemical Formulae 1 to 10, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formulae 1 to 10, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

The heterocyclic compound according to one embodiment of the present application may be prepared through a multistep chemical reaction. Some intermediate compounds are prepared first, and the compound of Chemical Formula 1 may be prepared from the intermediate compounds. More specifically, the heterocyclic compound according to one embodiment of the present application may be prepared based on preparation examples to describe later.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in an electron transfer layer, a hole blocking layer or a charge generation layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in an electron transfer layer, a hole blocking layer or a charge generation layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in an electron transfer layer, a hole blocking layer or a charge generation layer of the red organic light emitting device.

Specific descriptions on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising Chemical Formulae 1 to 10 may further comprise other materials as necessary.

In addition, the organic light emitting device according to one embodiment of the present application comprises a first electrode, a second electrode, and two or more stacks provided between the first electrode and the second electrode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application may comprise a first electrode, a first stack provided on the first electrode and comprising a first light emitting layer, a charge generation layer provided on the first stack, a second stack provided on the charge generation layer and comprising a second light emitting layer, and a second electrode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer and the second hole blocking layer and the like described in FIG. 4 may not be included in some cases.

In the organic light emitting device according to one embodiment of the present application, materials other than the compounds of Chemical Formulae 1 to 10 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Intermediate C-1

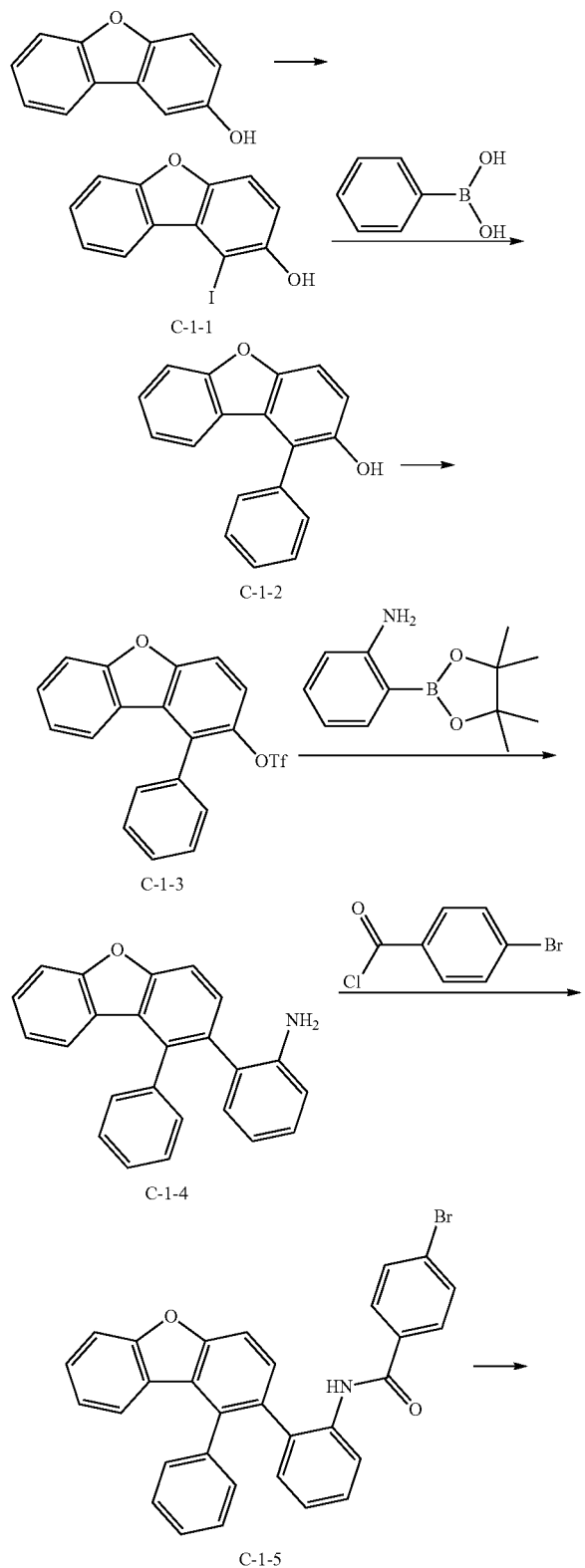

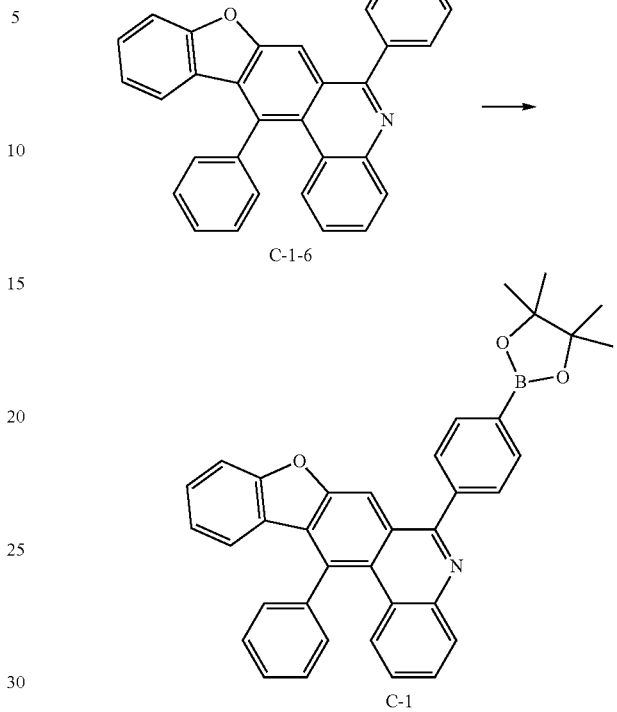

1) Preparation of Compound C-1-1

After dissolving dibenzo[b,d]furan-2-ol (150 g, 814.37 mmol) in acetic acid (900 ml), a mixed solution of iodine monochloride (132.22 g, 814.37 mmol), HCl (195 ml) and acetic acid (345 ml) was introduced thereto, and the result was stirred for 24 hours at room temperature. After the reaction was completed, water (3 L) was introduced to the reaction solution, and solids were filtered and then recrystallized with toluene to obtain Intermediate C-1-1 (155 g, 61%).

2) Preparation of Compound C-1-2

After dissolving Compound C-1-1 (118 g, 380.53 mmol) and phenylboronic acid (51.04 g, 418.58 mmol) in THF (1200 ml) and $H_2O$ (240 ml), ($N_2$ condition) Pd(PPh$_3$)$_4$ (13.19 g, 11.42 mmol) and $K_2CO_3$ (131.48 g, 951.33 mmol) were introduced thereto, and the result was stirred for 24 hours under reflux. After the reaction was completed, MC was introduced to the reaction solution for dissolution, and after extracting the result using distilled water, the organic layer was dried using anhydrous $MgSO_4$, the solvent was removed using a rotary evaporator, and with dichloromethane and hexane as a developing solvent, the result was purified using column chromatography to obtain Intermediate C-1-2 (98 g, 97%).

3) Preparation of Compound C-1-3

After dissolving Compound C-1-2 (98 g, 376.5 mmol) in methylene chloride (MC), $K_2CO_3$ (156.11 g, 1129.5 mmol) and pyridine (59.56 g, 753 mmol) were introduced thereto, and after slowly adding trifluoromethanesulfonic anhydride (138.09 g, 489.45 mmol) dropwise thereto at 0° C., the result was stirred for 1 hour. After the reaction was completed, the result was extracted with MC and distilled water, and after drying the organic layer with anhydrous $MgSO_4$, the solvent was removed using a rotary evaporator, and with dichloromethane and hexane as a developing solvent, the result was purified using column chromatography to obtain Intermediate C-1-3 (115 g, 80%).

4) Preparation of Compound C-1-4

After dissolving Compound C-1-3 (115 g, 293.11 mmol) and 2-(4,4,5,5-tetramethyl-1,3,2-dioxaborolan-2-yl)aniline (96.33 g, 439.67 mmol) in toluene (1150 ml), EtOH (230 ml) and H$_2$O (230 ml), (N$_2$ condition) Pd(PPh$_3$)$_4$ (10.16 g, 8.79 mmol) and NaHCO$_3$ (73.86 g, 879.33 mmol) were introduced thereto, and the result was stirred for 22 hours under reflux. After the reaction was completed, the result was extracted with MC and distilled water, and after drying the organic layer with anhydrous MgSO$_4$, the solvent was removed using a rotary evaporator, and with dichloromethane and hexane as a developing solvent, the result was purified using column chromatography to obtain Intermediate C-1-4 (42 g, 43%).

5) Preparation of Compound C-1-5

After dissolving Compound C-1-4 (36 g, 107.33 mmol) in MC, TEA (32.58 g, 321.99 mmol) was introduced thereto. The temperature was lowered from room temperature to 0° C., and 4-bromobenzoyl chloride (25.91 g, 118.06 mmol) dissolved in MC was slowly added dropwise thereto. After the reaction was completed, the result was extracted with MC and distilled water, and after drying the organic layer with anhydrous MgSO$_4$, the solvent was removed using a rotary evaporator, and with dichloromethane and hexane as a developing solvent, the result was purified using column chromatography to obtain Intermediate C-1-5 (54 g, 97%).

6) Preparation of Compound C-1-6

After dissolving Compound C-1-5 (54 g, 104.17 mmol) in nitrobenzene (500 ml), POCl$_3$ (23.96 g, 156.26 mmol) was slowly added dropwise thereto, and the result was stirred for 3 hours at 150° C. After the reaction was completed, the result was extracted with MC and distilled water, and after drying the organic layer with anhydrous MgSO$_4$, the solvent was removed using a rotary evaporator, and with dichloromethane and hexane as a developing solvent, the result was purified using column chromatography to obtain Intermediate C-1-6 (46 g, 88%).

7) Preparation of Intermediate C-1

After dissolving Compound C-1-6 (46 g, 91.93 mmol) and bis(pinacolato)diboron (30.35 g, 119.51 mmol) in 1,4-dioxane (500 ml), (N$_2$ condition) Pd(dppf)Cl$_2$ (3.36 g, 4.6 mmol) and KOAc (27.07 g, 275.79 mmol) were introduced thereto, and the result was stirred for 18 hours under reflux. After the reaction was completed, the result was extracted with MC and water, and after drying the organic layer with anhydrous MgSO$_4$, the result was silica gel filtered. The result was precipitated using MC/MeOH. The precipitates were filtered to obtain Intermediate C-1 (41 g, 81%).

Intermediate C of the following Table 1 was synthesized in the same manner as in the preparation of Preparation Example 1 except that Intermediate A of the following Table 1 was used instead of phenylboronic acid, and Intermediate B of the following Table 1 was used instead of 4-bromobenzoyl chloride.

TABLE 1

| Compound | Intermediate A | Intermediate B | Intermediate C | Yield |
| --- | --- | --- | --- | --- |
| Intermediate C-1 | phenylboronic acid | 4-bromobenzoyl chloride | [structure] | 81% |
| Intermediate C-2 | phenylboronic acid | 3-bromobenzoyl chloride | [structure] | 78% |

TABLE 1-continued

| Compound | Intermediate A | Intermediate B | Intermediate C | Yield |
|---|---|---|---|---|
| Intermediate C-3 | 4-bromophenylboronic acid | benzoyl chloride | (benzofuran-phenanthridine with phenyl and phenyl-Bpin substituents) | 72% |
| Intermediate C-4 | 3-bromophenylboronic acid | benzoyl chloride | (benzofuran-phenanthridine with phenyl and phenyl-Bpin substituents) | 79% |
| Intermediate C-5 | 4-biphenylboronic acid | 4-bromobenzoyl chloride | (benzofuran-phenanthridine with biphenyl and phenyl-Bpin substituents) | 79% |
| Intermediate C-6 | 4-bromophenylboronic acid | 4-biphenylcarbonyl chloride | (benzofuran-phenanthridine with biphenyl and phenyl-Bpin substituents) | 69% |

TABLE 1-continued

| Compound | Intermediate A | Intermediate B | Intermediate C | Yield |
|---|---|---|---|---|
| Intermediate C-7 | (triphenylene boronic acid) | (3-bromobenzoyl chloride) | (structure) | 82% |
| Intermediate C-8 | (3-bromophenyl boronic acid) | (triphenylene carbonyl chloride) | (structure) | 84% |
| Intermediate C-9 | (dibenzofuran-4-boronic acid) | (4-bromobenzoyl chloride) | (structure) | 78% |
| Intermediate C-10 | (dibenzofuran-4-boronic acid) | (3-bromobenzoyl chloride) | (structure) | 82% |
| Intermediate C-11 | (4-biphenyl boronic acid) | (3-bromobenzoyl chloride) | (structure) | 82% |

<Preparation Example 2> Preparation of Compound 1

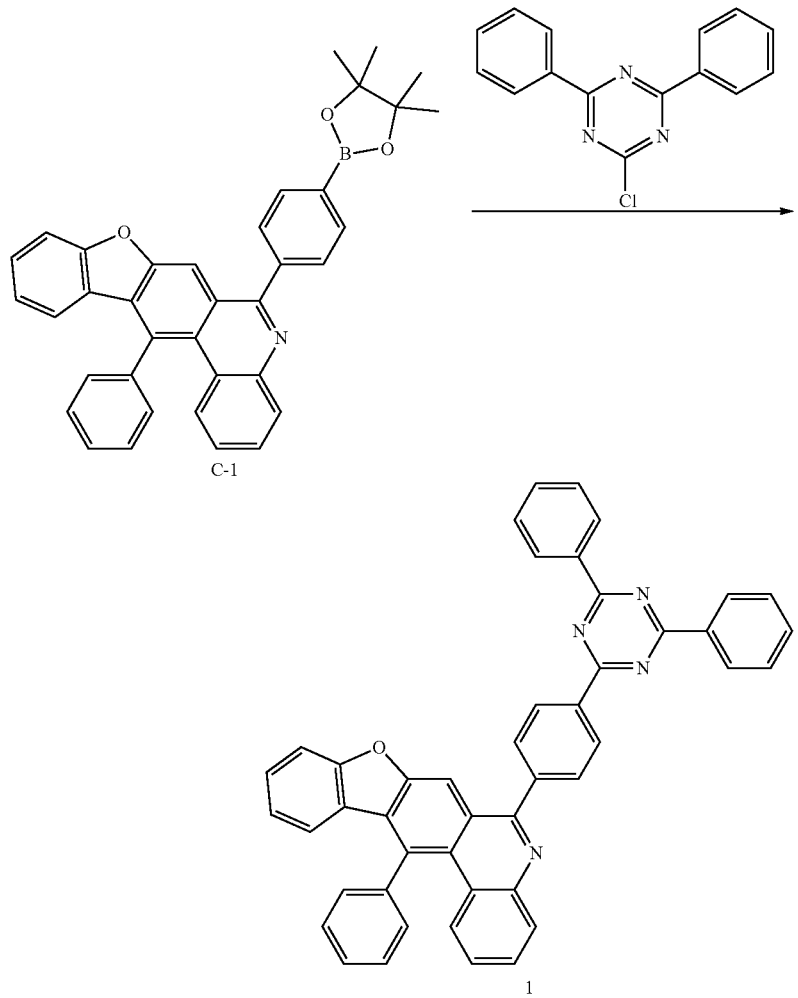

After dissolving Intermediate C-1 (7 g, 12.79 mmol) and 2-chloro-4,6-diphenyl-1,3,5-triazine (3.42 g, 12.79 mmol) in toluene (100 ml), EtOH (20 ml) and $H_2O$ (20 ml), ($N_2$ condition) Pd(PPh$_3$)$_4$ (0.74 g, 0.64 mmol) and $K_2CO_3$ (4.42 g, 31.98 mmol) were introduced thereto, and the result was stirred for 16 hours under reflux. After the reaction was completed, the result was cooled to room temperature, and produced solids were filtered and then washed with EA and MeOH. After that, the solids were all dissolved in excess dichloromethane and then filtered using silica gel to obtain Compound 1 (5.7 g, 69%).

Target compounds were synthesized in the same manner as in Preparation Example 2 except that Intermediate C of the following Table 2 was used instead of Intermediate C-1, and Intermediate D was used instead of 2-chloro-4,6-diphenyl-1,3,5-triazine.

TABLE 2

| Compound Number | Intermediate C | Intermediate D | Target Compound | Yield |
|---|---|---|---|---|
| 1 | | | | 69% |
| 2 | | | | 57% |

TABLE 2-continued

| Compound Number | Intermediate C | Intermediate D | Target Compound | Yield |
|---|---|---|---|---|
| 5 | | | | 66% |
| 7 | | | | 79% |

TABLE 2-continued

| Compound Number | Intermediate C | Intermediate D | Target Compound | Yield |
|---|---|---|---|---|
| 8 | | | | 59% |
| 9 | | | | 82% |

TABLE 2-continued

| Compound Number | Intermediate C | Intermediate D | Target Compound | Yield |
|---|---|---|---|---|
| 15 | [structure] | [structure] | [structure] | 87% |
| 18 | [structure] | [structure] | [structure] | 82% |

TABLE 2-continued
| Compound Number | Intermediate C | Intermediate D | Target Compound | Yield |
|---|---|---|---|---|
| 20 | 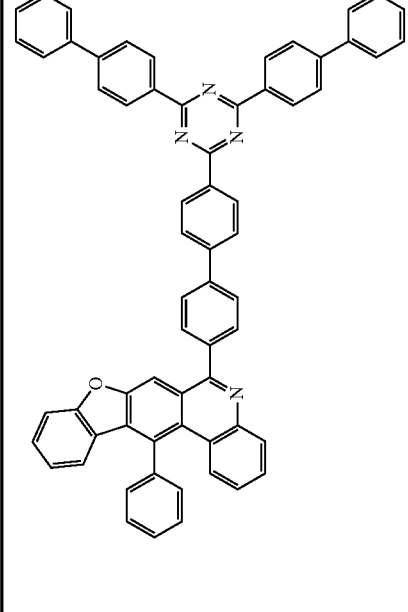 |  |  | 73% |
| 29 | 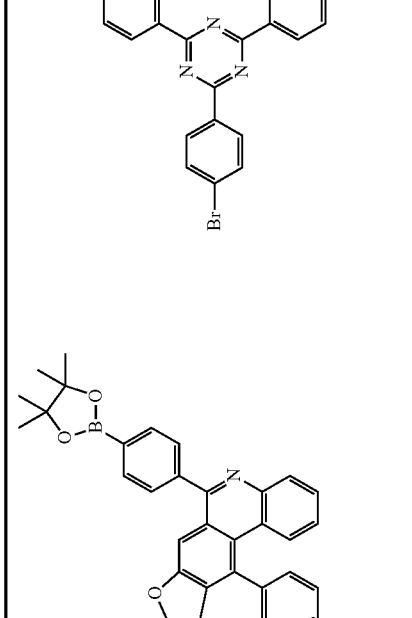 |  |  | 75% |

TABLE 2-continued

| Compound Number | Intermediate C | Intermediate D | Target Compound | Yield |
|---|---|---|---|---|
| 33 | | | | 67% |
| 35 | | | | 77% |

TABLE 2-continued

| Compound Number | Intermediate C | Intermediate D | Target Compound | Yield |
|---|---|---|---|---|
| 38 | | | | 83% |
| 40 | | | | 84% |

TABLE 2-continued

| Compound Number | Intermediate C | Intermediate D | Target Compound | Yield |
|---|---|---|---|---|
| 47 | | | | 79% |
| 49 | | | | 71% |

TABLE 2-continued

| Compound Number | Intermediate C | Intermediate D | Target Compound | Yield |
|---|---|---|---|---|
| 52 | | | | 65% |
| 53 | | | | 73% |
| 55 | | | | 72% |

TABLE 2-continued

| Compound Number | Intermediate C | Intermediate D | Target Compound | Yield |
|---|---|---|---|---|
| 57 | | | | 86% |
| 58 | | | | 61% |

TABLE 2-continued

| Compound Number | Intermediate C | Intermediate D | Target Compound | Yield |
|---|---|---|---|---|
| 70 | | | | 66% |
| 75 | | | | 69% |
| 86 | | | | 71% |

TABLE 2-continued

| Compound Number | Intermediate C | Intermediate D | Target Compound | Yield |
|---|---|---|---|---|
| 101 | | | | 69% |
| 102 | | | | 50% |

TABLE 2-continued

| Compound Number | Intermediate C | Intermediate D | Target Compound | Yield |
|---|---|---|---|---|
| 103 | | | | 63% |
| 104 | | | | 71% |

TABLE 2-continued

| Compound Number | Intermediate C | Intermediate D | Target Compound | Yield |
|---|---|---|---|---|
| 105 | | | | 74% |
| 112 | | | | 72% |
| 113 | | | | 74% |

TABLE 2-continued
| Compound Number | Intermediate C | Intermediate D | Target Compound | Yield |
|---|---|---|---|---|
| 115 | 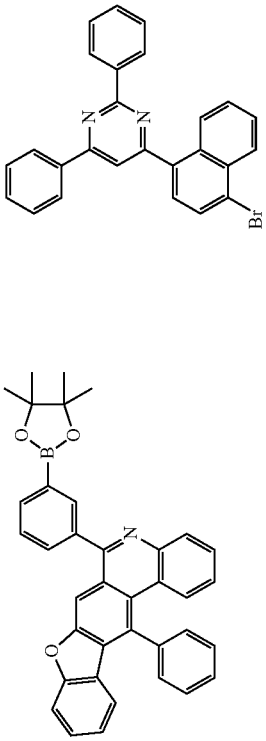 | 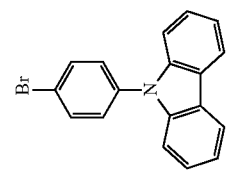 | 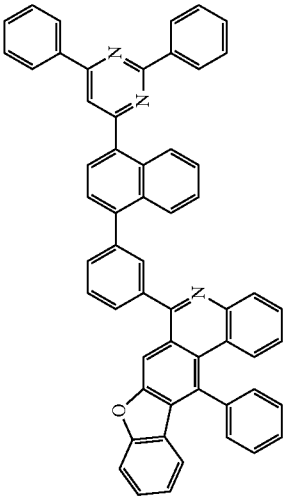 | 77% |
| 124 | 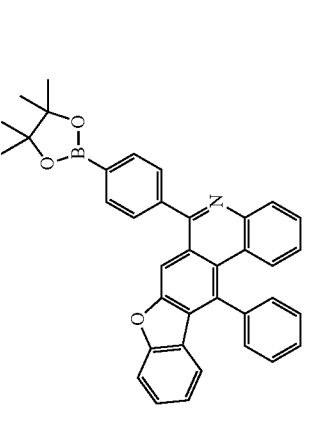 | 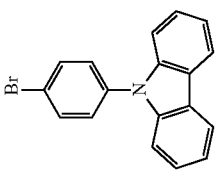 | 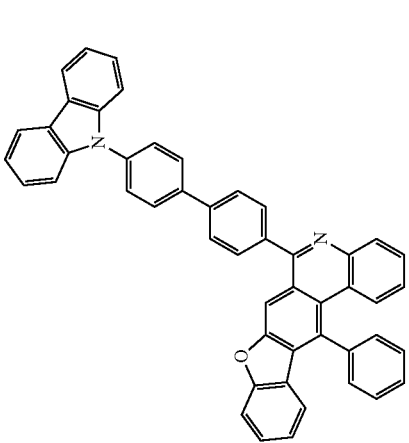 | 80% |

TABLE 2-continued

| Compound Number | Intermediate C | Intermediate D | Target Compound | Yield |
|---|---|---|---|---|
| 126 | | | | 76% |
| 127 | | | | 80% |
| 130 | | | | 71% |

TABLE 2-continued
| Compound Number | Intermediate C | Intermediate D | Target Compound | Yield |
|---|---|---|---|---|
| 131 | 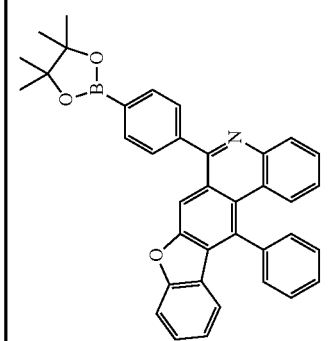 | 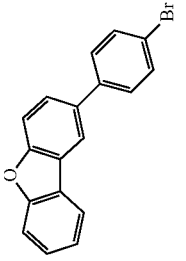 | 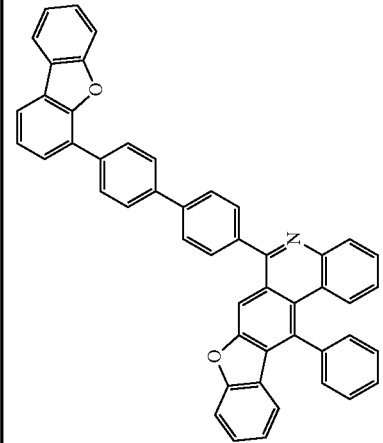 | 73% |
| 133 | 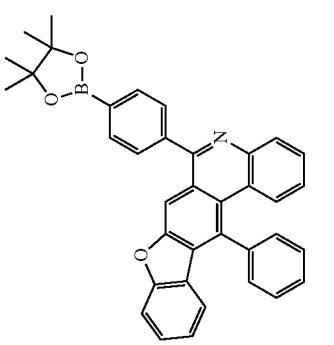 | 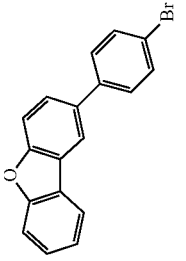 | 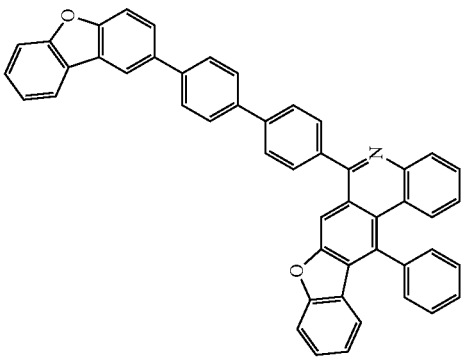 | 70% |

TABLE 2-continued

| Compound Number | Intermediate C | Intermediate D | Target Compound | Yield |
|---|---|---|---|---|
| 136 | | | | 69% |
| 139 | | | | 77% |

TABLE 2-continued

| Compound Number | Intermediate C | Intermediate D | Target Compound | Yield |
|---|---|---|---|---|
| 141 | | | | 83% |
| 142 | | | | 81% |

TABLE 2-continued
| Compound Number | Intermediate C | Intermediate D | Target Compound | Yield |
|---|---|---|---|---|
| 151 | 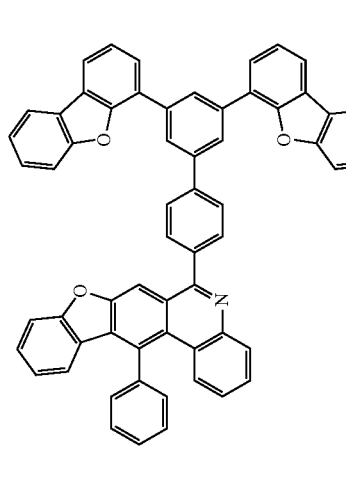 | 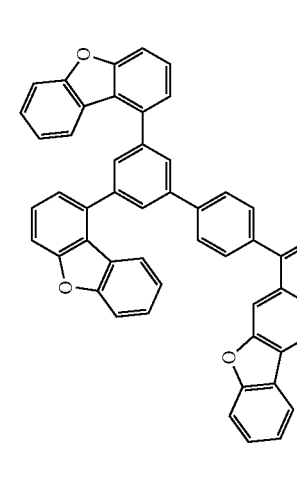 | 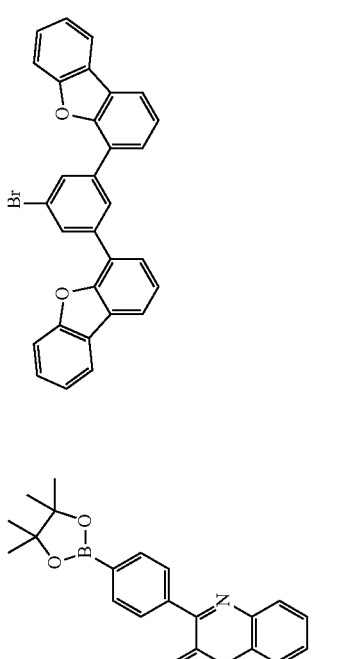 | 80% |
| 154 | 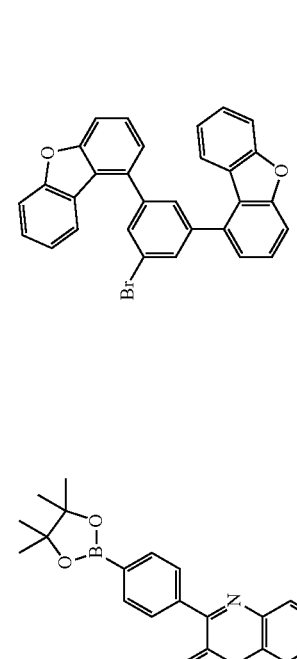 | 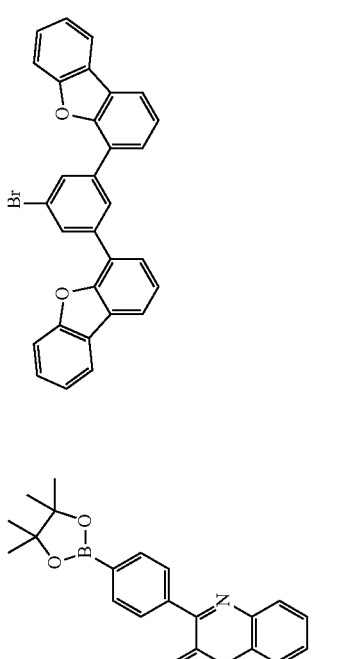 | 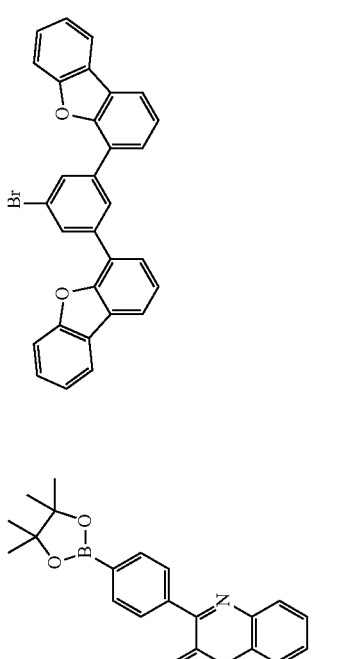 | 71% |

TABLE 2-continued

| Compound Number | Intermediate C | Intermediate D | Target Compound | Yield |
|---|---|---|---|---|
| 158 | | | | 69% |
| 160 | | | | 58% |
| 162 | | | | 81% |

TABLE 2-continued
| Compound Number | Intermediate C | Intermediate D | Target Compound | Yield |
|---|---|---|---|---|
| 175 | 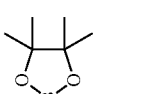 | 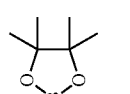 | 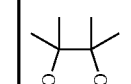 | 82% |
| 186 | 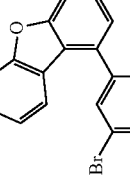 | 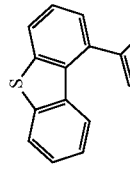 | 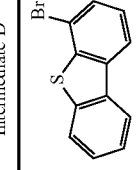 | 84% |
| 190 | 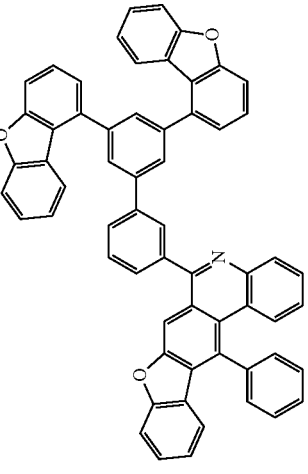 | 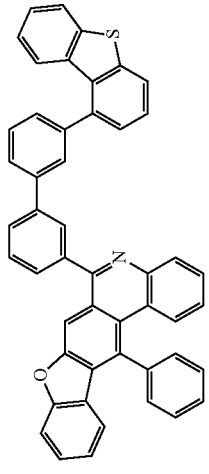 | 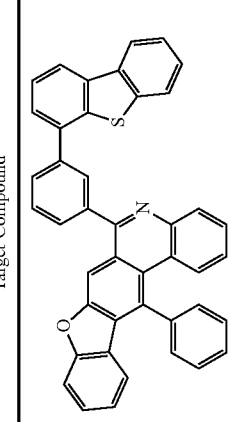 | 79% |

TABLE 2-continued

| Compound Number | Intermediate C | Intermediate D | Target Compound | Yield |
|---|---|---|---|---|
| 193 | | | | 71% |
| 195 | | | | 65% |

TABLE 2-continued

| Compound Number | Intermediate C | Intermediate D | Target Compound | Yield |
|---|---|---|---|---|
| 196 | | | | 73% |
| 198 | | | | 72% |

TABLE 2-continued
| Compound Number | Intermediate C | Intermediate D | Target Compound | Yield |
|---|---|---|---|---|
| 199 | 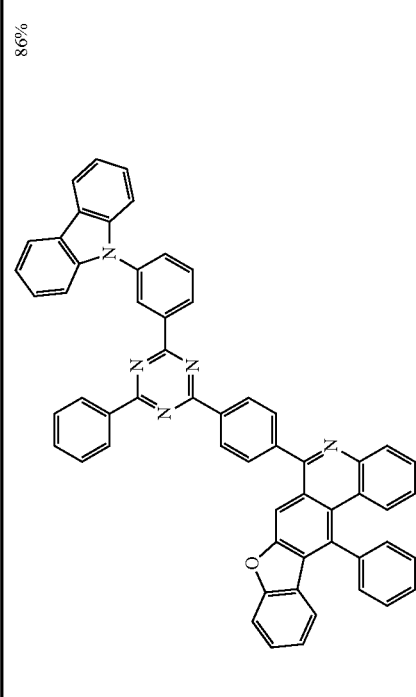 | 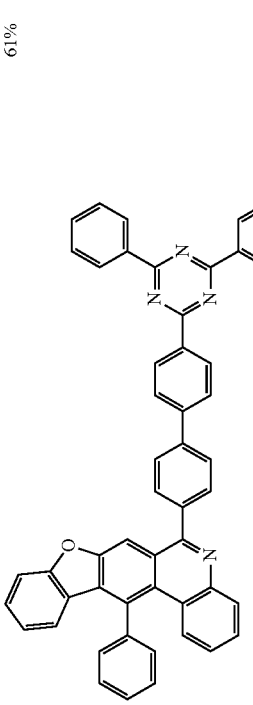 | 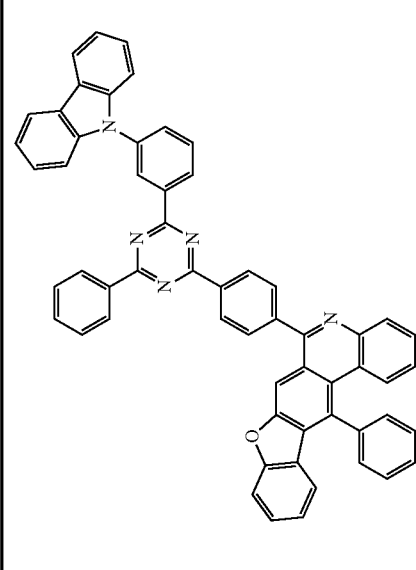 | 86% |
| 200 | 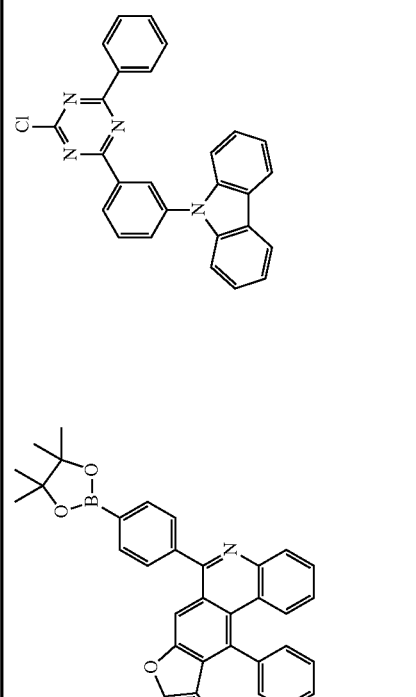 | 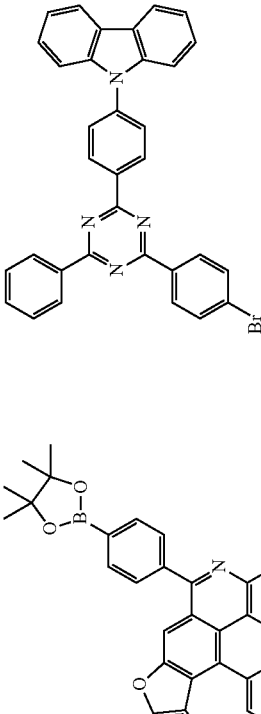 | 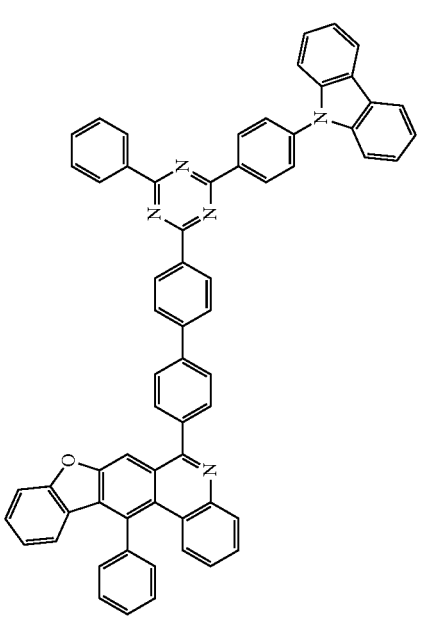 | 61% |

TABLE 2-continued

| Compound Number | Intermediate C | Intermediate D | Target Compound | Yield |
|---|---|---|---|---|
| 201 | | | | 66% |
| 202 | | | | 69% |

TABLE 2-continued

| Compound Number | Intermediate C | Intermediate D | Target Compound | Yield |
|---|---|---|---|---|
| 203 | | | | 71% |
| 204 | | | | 71% |

TABLE 2-continued

| Compound Number | Intermediate C | Intermediate D | Target Compound | Yield |
|---|---|---|---|---|
| 206 | | | | 72% |
| 209 | | | | 69% |

TABLE 2-continued

| Compound Number | Intermediate C | Intermediate D | Target Compound | Yield |
|---|---|---|---|---|
| 211 | | | | 50% |
| 221 | | | | 63% |

TABLE 2-continued

| Compound Number | Intermediate C | Intermediate D | Target Compound | Yield |
|---|---|---|---|---|
| 223 | | | | 71% |
| 224 | | | | 74% |
| 230 | | | | 72% |

TABLE 2-continued

| Compound Number | Intermediate C | Intermediate D | Target Compound | Yield |
|---|---|---|---|---|
| 232 | | | | 74% |
| 240 | | | | 77% |

TABLE 2-continued
| Compound Number | Intermediate C | Intermediate D | Target Compound | Yield |
|---|---|---|---|---|
| 242 |  |  | 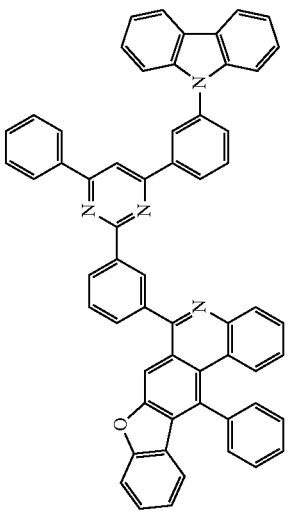 | 73% |
| 249 |  |  | 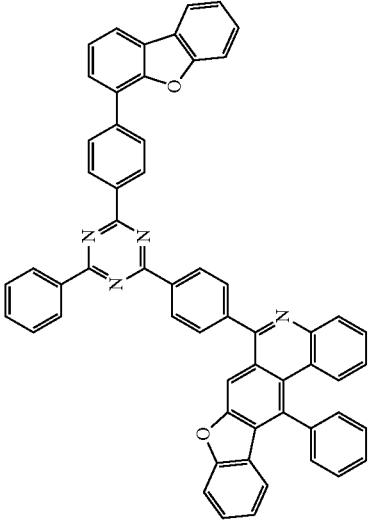 | 80% |

TABLE 2-continued

| Compound Number | Intermediate C | Intermediate D | Target Compound | Yield |
|---|---|---|---|---|
| 250 | | | | 76% |
| 251 | | | | 80% |

TABLE 2-continued

| Compound Number | Intermediate C | Intermediate D | Target Compound | Yield |
|---|---|---|---|---|
| 252 | | | | 71% |
| 255 | | | | 73% |

TABLE 2-continued
| Compound Number | Intermediate C | Intermediate D | Target Compound | Yield |
|---|---|---|---|---|
| 259 | 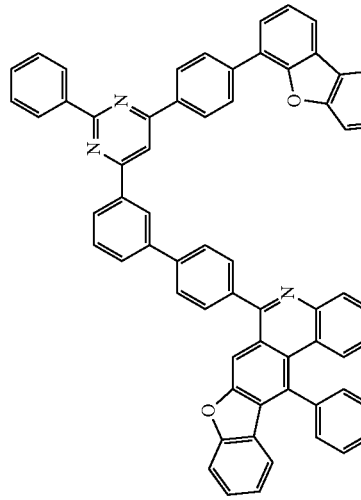 | 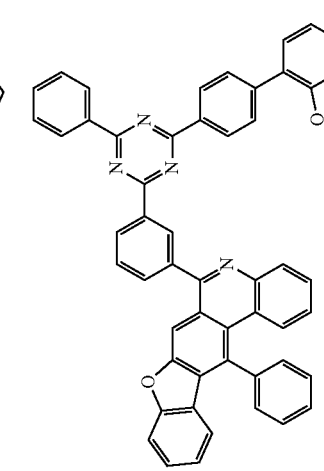 | 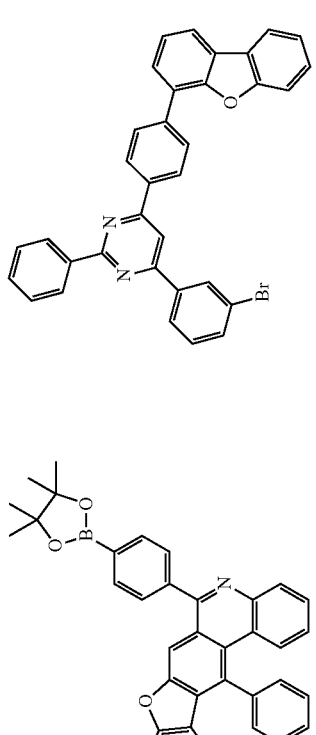 | 70% |
| 273 | | | | 69% |

| Compound Number | Intermediate C | Intermediate D | Target Compound | Yield |
|---|---|---|---|---|
| 274 | 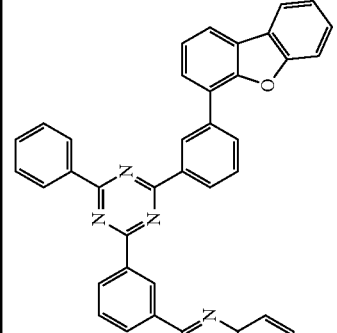 | 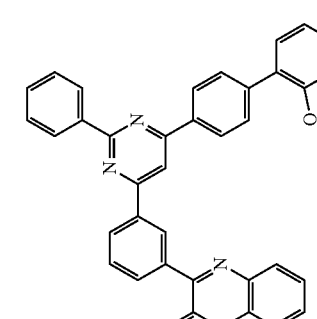 | 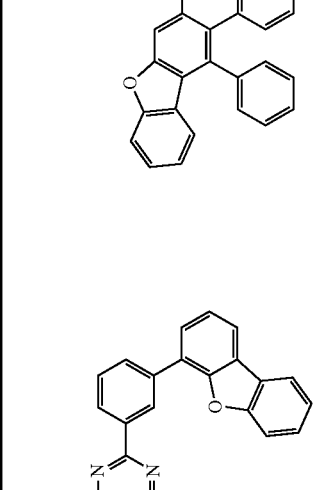 | 77% |
| 279 | 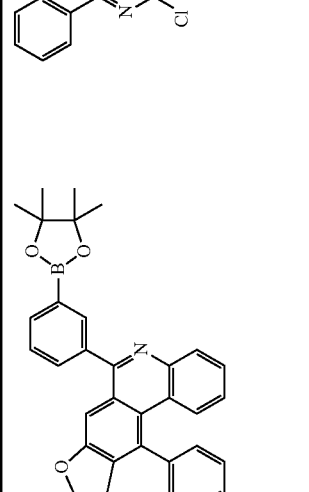 | 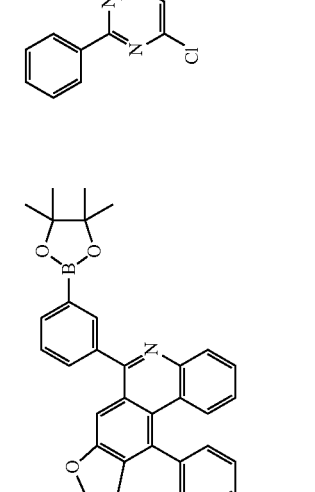 | 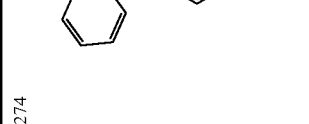 | 83% |

TABLE 2-continued

| Compound Number | Intermediate C | Intermediate D | Target Compound | Yield |
|---|---|---|---|---|
| 281 | | | | 81% |
| 297 | | | | 80% |

| Compound Number | Intermediate C | Intermediate D | Target Compound | Yield |
|---|---|---|---|---|
| 298 | 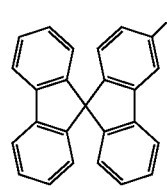 |  | 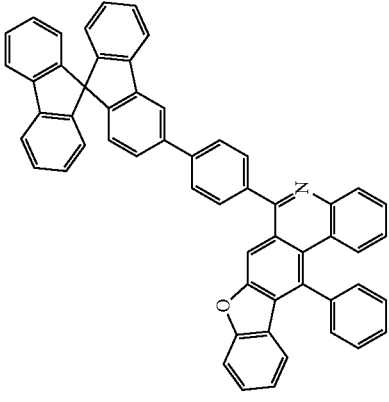 | 71% |
| 299 | 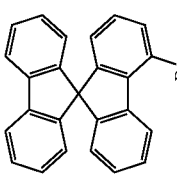 |  | 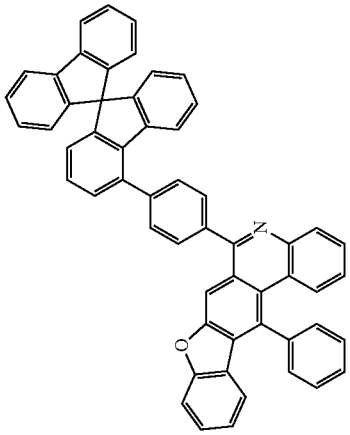 | 69% |

TABLE 2-continued
| Compound Number | Intermediate C | Intermediate D | Target Compound | Yield |
|---|---|---|---|---|
| 301 |  | 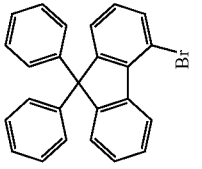 | 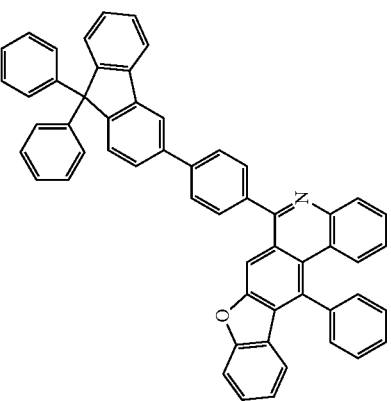 | 58% |
| 302 | 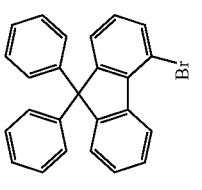 | 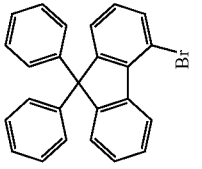 | 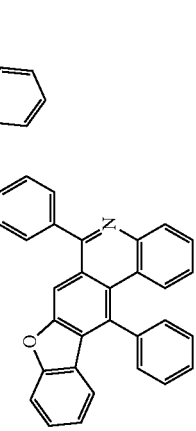 | 81% |

TABLE 2-continued
| Compound Number | Intermediate C | Intermediate D | Target Compound | Yield |
|---|---|---|---|---|
| 303 | 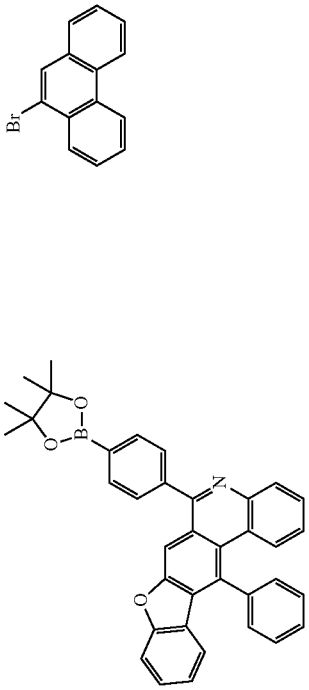 | 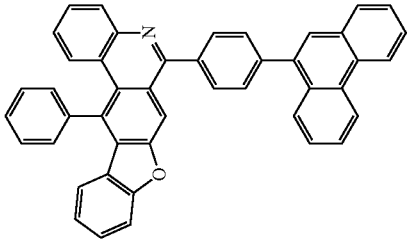 | 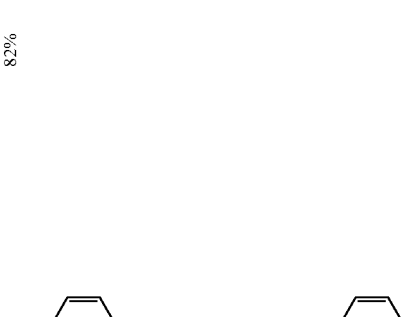 | 82% |
| 308 | 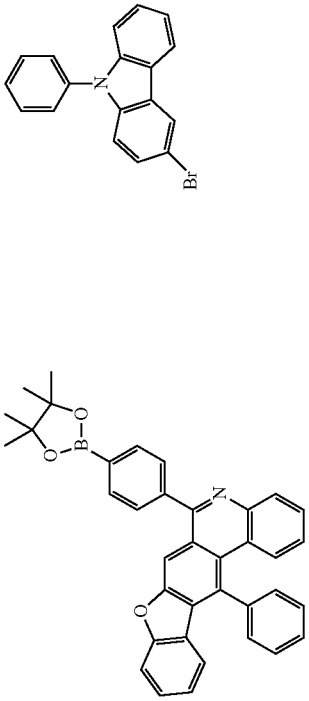 | 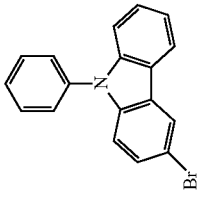 | 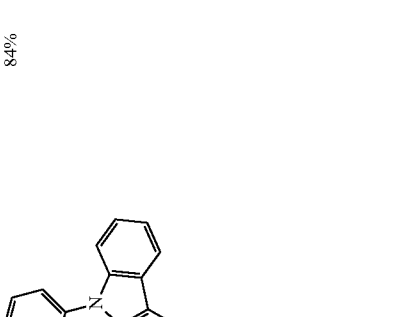 | 84% |

TABLE 2-continued

| Compound Number | Intermediate C | Intermediate D | Target Compound | Yield |
|---|---|---|---|---|
| 309 | | | | 79% |
| 317 | | | | 71% |

TABLE 2-continued
| Compound Number | Intermediate C | Intermediate D | Target Compound | Yield |
|---|---|---|---|---|
| 319 | 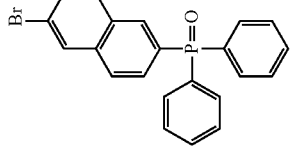 | 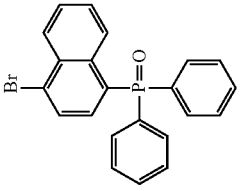 | 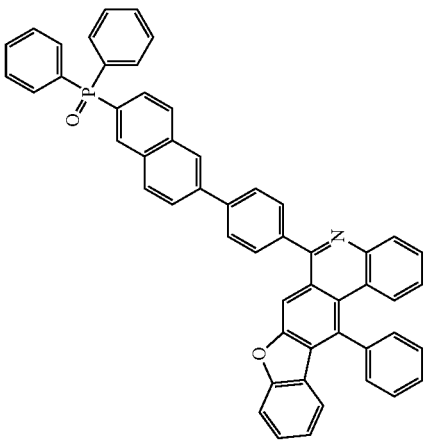 | 65% |
| 320 | 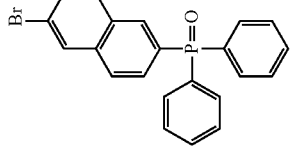 | 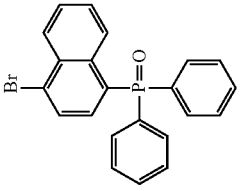 | 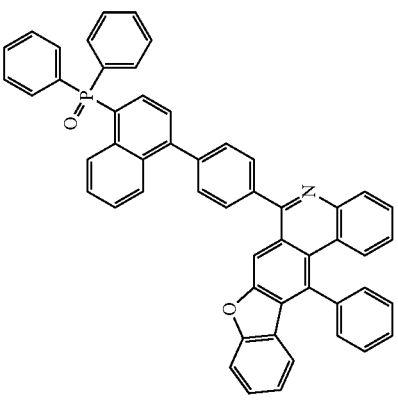 | 73% |

TABLE 2-continued
| Compound Number | Intermediate C | Intermediate D | Target Compound | Yield |
|---|---|---|---|---|
| 321 | 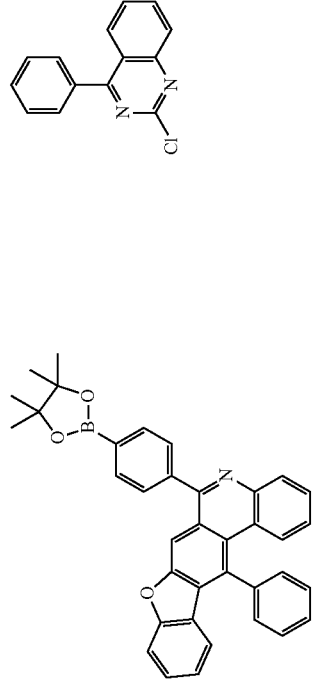 | 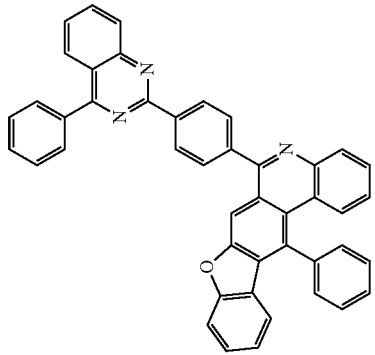 | 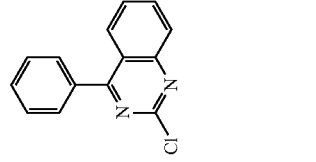 | 72% |
| 324 | 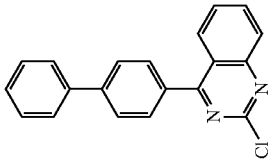 | 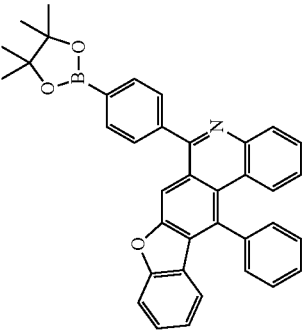 | 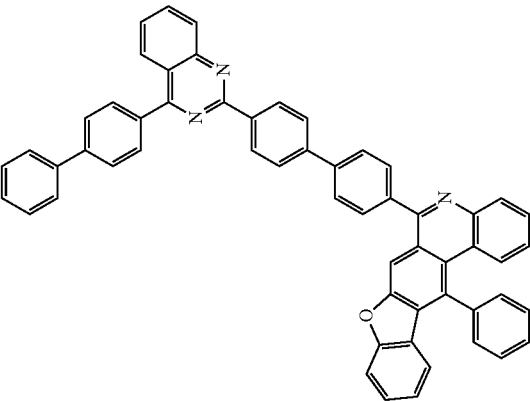 | 86% |

TABLE 2-continued
| Compound Number | Intermediate C | Intermediate D | Target Compound | Yield |
|---|---|---|---|---|
| 326 | 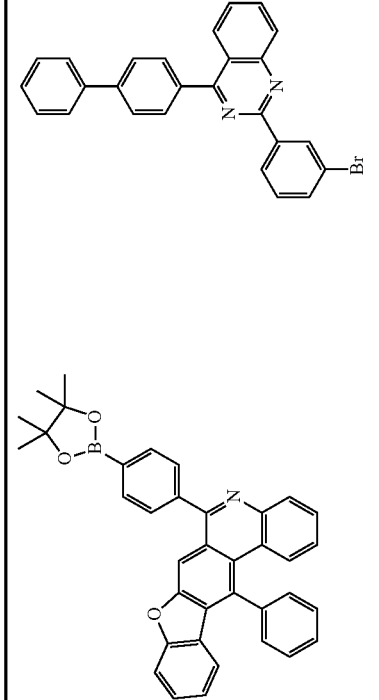 | 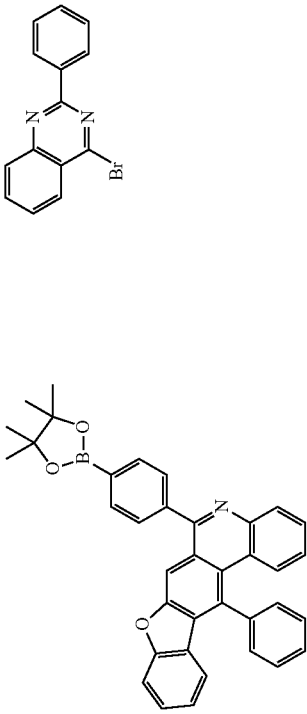 | 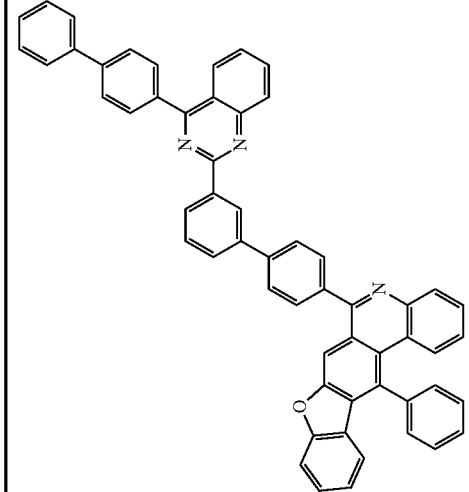 | 61% |
| 327 | 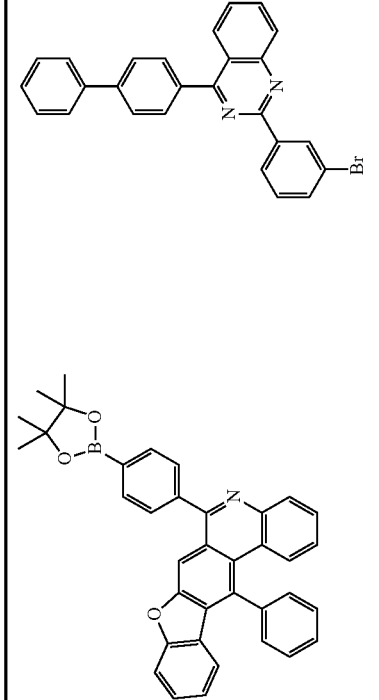 | 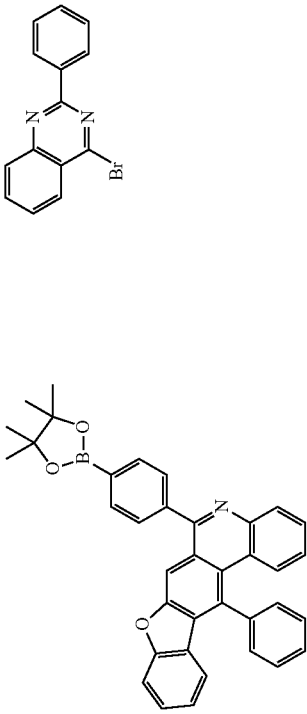 | 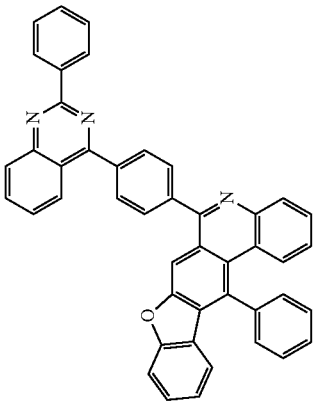 | 66% |

TABLE 2-continued

| Compound Number | Intermediate C | Intermediate D | Target Compound | Yield |
|---|---|---|---|---|
| 334 | [structure] | [structure] | [structure] | 69% |
| 339 | [structure] | [structure] | [structure] | 71% |

TABLE 2-continued
| Compound Number | Intermediate C | Intermediate D | Target Compound | Yield |
|---|---|---|---|---|
| 342 | 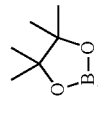 | 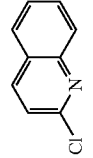 | 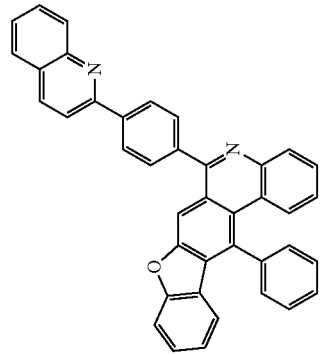 | 71% |
| 347 | 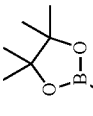 | 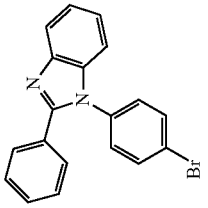 | 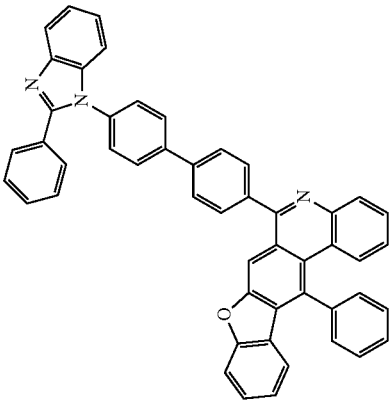 | 72% |

TABLE 2-continued
| Compound Number | Intermediate C | Intermediate D | Target Compound | Yield |
|---|---|---|---|---|
| 349 | 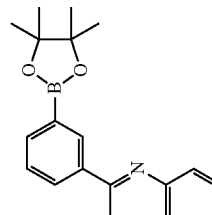 | 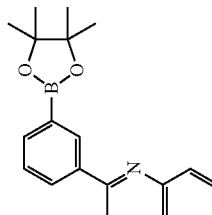 | 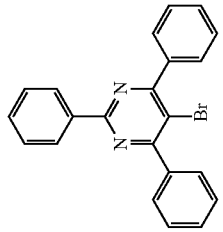 | 69% |
| 375 | 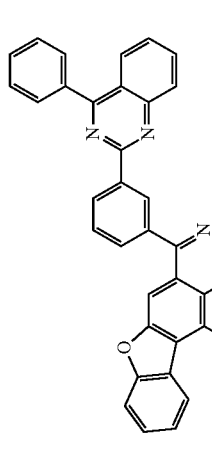 | 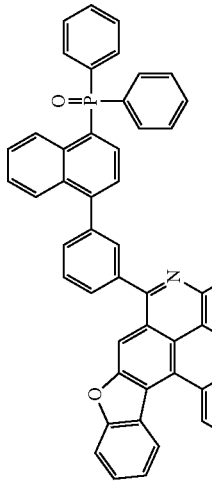 | 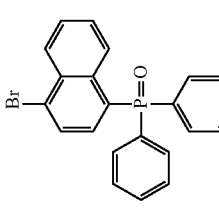 | 50% |
| 376 | 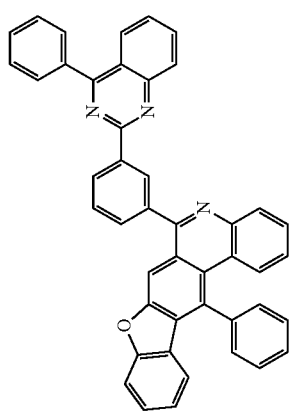 | 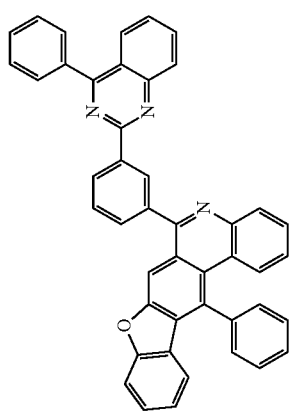 | 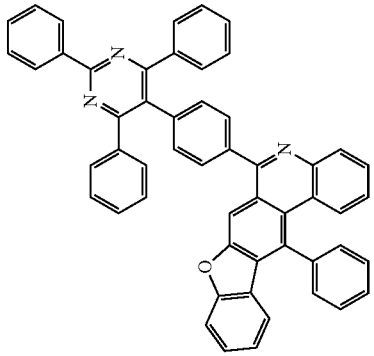 | 63% |

TABLE 2-continued

| Compound Number | Intermediate C | Intermediate D | Target Compound | Yield |
|---|---|---|---|---|
| 383 | | | | 71% |
| 413 | | | | 74% |

TABLE 2-continued

| Compound Number | Intermediate C | Intermediate D | Target Compound | Yield |
|---|---|---|---|---|
| 415 | | | | 72% |
| 417 | | | | 77% |

TABLE 2-continued
| Compound Number | Intermediate C | Intermediate D | Target Compound | Yield |
|---|---|---|---|---|
| 418 | 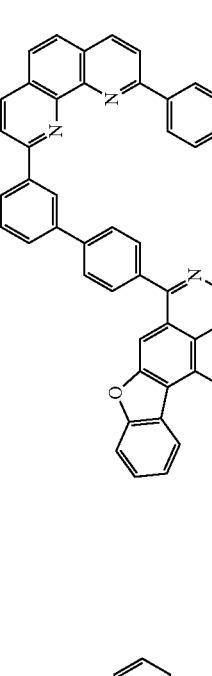 | 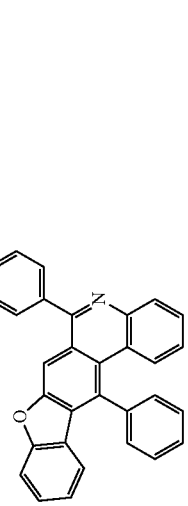 | 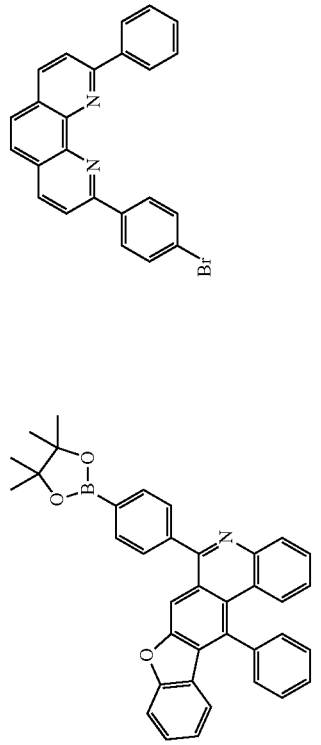 | 73% |
| 419 | 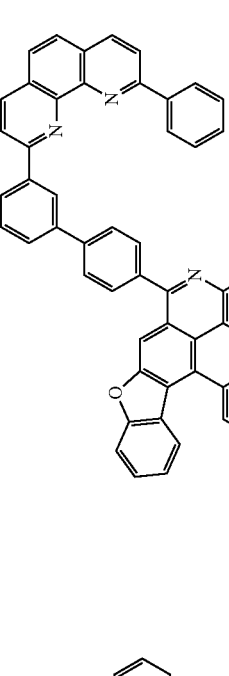 | 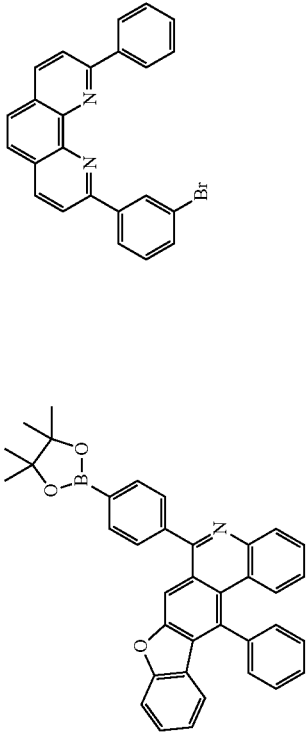 | 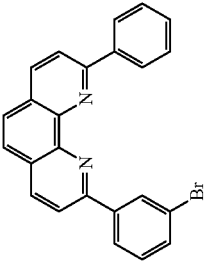 | 80% |

TABLE 2-continued

| Compound Number | Intermediate C | Intermediate D | Target Compound | Yield |
|---|---|---|---|---|
| 420 | | | | 76% |
| 427 | | | | 71% |
| 430 | | | | 73% |

TABLE 2-continued

| Compound Number | Intermediate C | Intermediate D | Target Compound | Yield |
|---|---|---|---|---|
| 431 | | | | 70% |
| 432 | | | | 69% |
| 437 | | | | 77% |

TABLE 2-continued

| Compound Number | Intermediate C | Intermediate D | Target Compound | Yield |
|---|---|---|---|---|
| 446 | | | | 81% |
| 447 | | | | 80% |

TABLE 2-continued

| Compound Number | Intermediate C | Intermediate D | Target Compound | Yield |
|---|---|---|---|---|
| 453 | | | | 69% |
| 454 | | | | 58% |

| Compound Number | Intermediate C | Intermediate D | Target Compound | Yield |
|---|---|---|---|---|
| 456 | | | | 81% |
| 457 | | | | 82% |

TABLE 2-continued

| Compound Number | Intermediate C | Intermediate D | Target Compound | Yield |
|---|---|---|---|---|
| 459 | | | | 84% |
| 460 | | | | 79% |

TABLE 2-continued

| Compound Number | Intermediate C | Intermediate D | Target Compound | Yield |
|---|---|---|---|---|
| 462 | | | | 71% |
| 463 | | | | 65% |

TABLE 2-continued

| Compound Number | Intermediate C | Intermediate D | Target Compound | Yield |
|---|---|---|---|---|
| 465 | | | | 73% |
| 468 | | | | 72% |

TABLE 2-continued

| Compound Number | Intermediate C | Intermediate D | Target Compound | Yield |
|---|---|---|---|---|
| 471 | | | | 86% |
| 473 | | | | 61% |

TABLE 2-continued

| Compound Number | Intermediate C | Intermediate D | Target Compound | Yield |
|---|---|---|---|---|
| 476 | | | | 66% |
| 479 | | | | 69% |

TABLE 2-continued

| Compound Number | Intermediate C | Intermediate D | Target Compound | Yield |
|---|---|---|---|---|
| 494 | | | | 71% |
| 529 | | | | 71% |

| Compound Number | Intermediate C | Intermediate D | Target Compound | Yield |
|---|---|---|---|---|
| 573 | 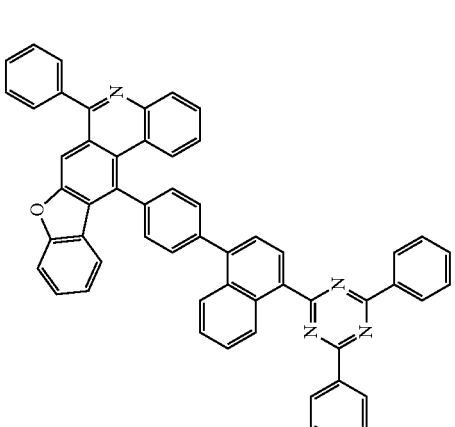 | 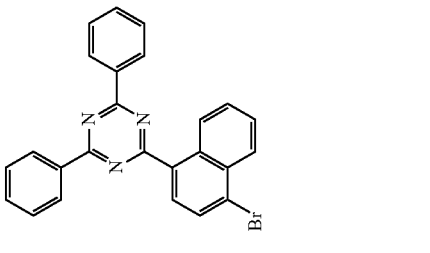 | 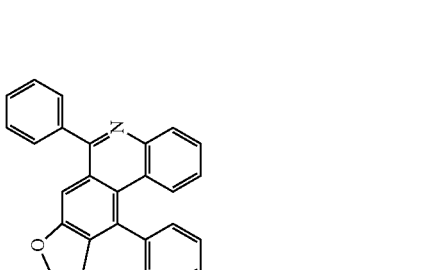 | 72% |
| 575 | 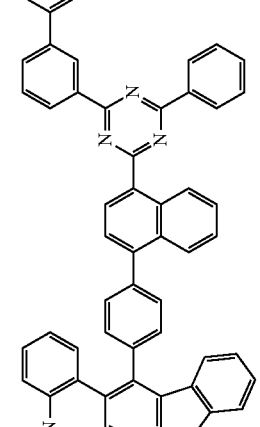 | 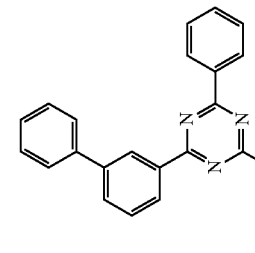 | 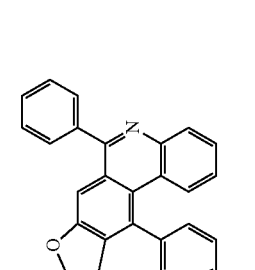 | 69% |

TABLE 2-continued

| Compound Number | Intermediate C | Intermediate D | Target Compound | Yield |
|---|---|---|---|---|
| 578 | | | | 50% |
| 584 | | | | 63% |

TABLE 2-continued

| Compound Number | Intermediate C | Intermediate D | Target Compound | Yield |
|---|---|---|---|---|
| 596 | | | | 71% |
| 598 | | | | 74% |

TABLE 2-continued

| Compound Number | Intermediate C | Intermediate D | Target Compound | Yield |
|---|---|---|---|---|
| 599 | | | | 72% |
| 602 | | | | 74% |
| 603 | | | | 77% |

TABLE 2-continued

| Compound Number | Intermediate C | Intermediate D | Target Compound | Yield |
|---|---|---|---|---|
| 606 | | | | 73% |
| 611 | | | | 80% |

TABLE 2-continued

| Compound Number | Intermediate C | Intermediate D | Target Compound | Yield |
|---|---|---|---|---|
| 623 | | | | 76% |
| 626 | | | | 80% |

TABLE 2-continued

| Compound Number | Intermediate C | Intermediate D | Target Compound | Yield |
|---|---|---|---|---|
| 663 | | | | 71% |
| 667 | | | | 73% |

TABLE 2-continued

| Compound Number | Intermediate C | Intermediate D | Target Compound | Yield |
|---|---|---|---|---|
| 668 | | | | 70% |
| 670 | | | | 69% |

TABLE 2-continued

| Compound Number | Intermediate C | Intermediate D | Target Compound | Yield |
|---|---|---|---|---|
| 671 | | | | 77% |
| 676 | | | | 83% |

TABLE 2-continued

| Compound Number | Intermediate C | Intermediate D | Target Compound | Yield |
|---|---|---|---|---|
| 679 | [structure] | [structure] | [structure] | 81% |
| 682 | [structure] | [structure] | [structure] | 80% |

TABLE 2-continued

| Compound Number | Intermediate C | Intermediate D | Target Compound | Yield |
|---|---|---|---|---|
| 695 | | | | 71% |
| 696 | | | | 69% |

TABLE 2-continued
| Compound Number | Intermediate C | Intermediate D | Target Compound | Yield |
|---|---|---|---|---|
| 721 | 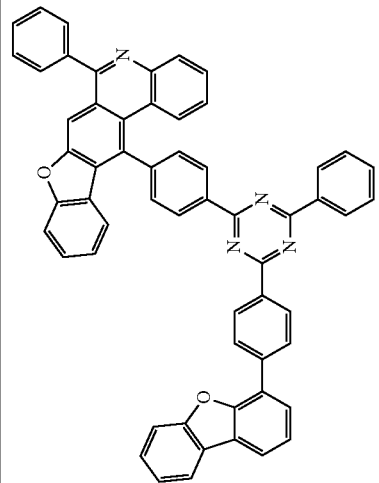 | | | 58% |
| 722 | | | | 81% |

TABLE 2-continued

| Compound Number | Intermediate C | Intermediate D | Target Compound | Yield |
|---|---|---|---|---|
| 723 | | | | 82% |
| 724 | | | | 84% |

TABLE 2-continued

| Compound Number | Intermediate C | Intermediate D | Target Compound | Yield |
|---|---|---|---|---|
| 727 | | | | 79% |
| 741 | | | | 71% |

TABLE 2-continued
| Compound Number | Intermediate C | Intermediate D | Target Compound | Yield |
|---|---|---|---|---|
| 745 | 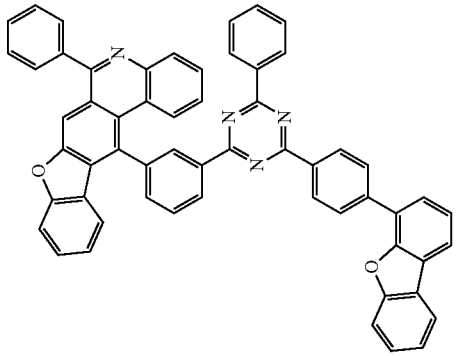 | 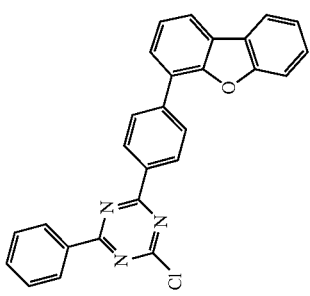 | 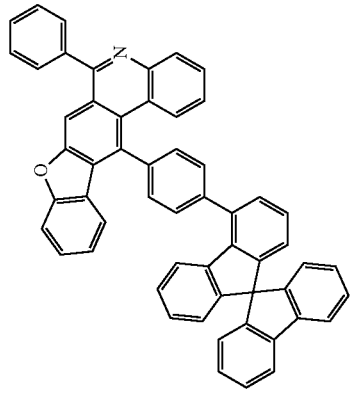 | 65% |
| 771 | 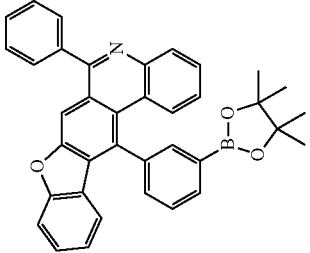 | 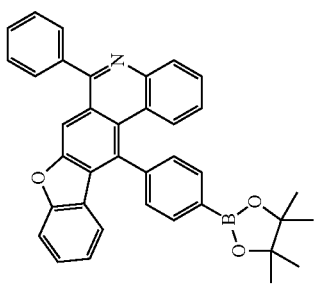 | 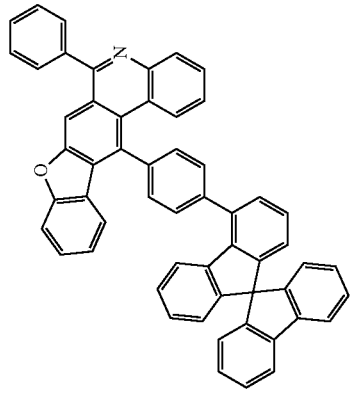 | 73% |

TABLE 2-continued
| Compound Number | Intermediate C | Intermediate D | Target Compound | Yield |
|---|---|---|---|---|
| 775 | 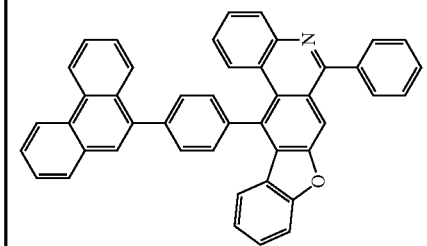 | 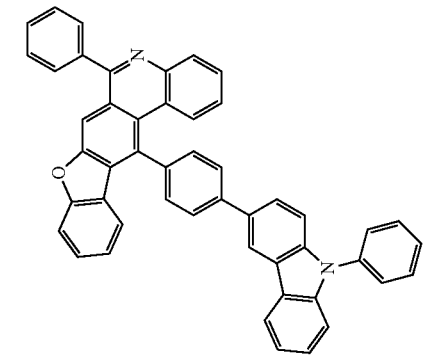 | 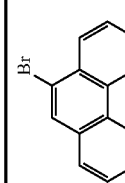 | 72% |
| 780 | 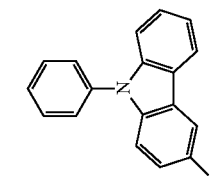 | | | 86% |

TABLE 2-continued

| Compound Number | Intermediate C | Intermediate D | Target Compound | Yield |
|---|---|---|---|---|
| 789 | | | | 61% |
| 792 | | | | 66% |

TABLE 2-continued

| Compound Number | Intermediate C | Intermediate D | Target Compound | Yield |
|---|---|---|---|---|
| 802 | | | | 69% |
| 804 | | | | 71% |

TABLE 2-continued

| Compound Number | Intermediate C | Intermediate D | Target Compound | Yield |
|---|---|---|---|---|
| 815 | | | | 71% |
| 822 | | | | 72% |

TABLE 2-continued

| Compound Number | Intermediate C | Intermediate D | Target Compound | Yield |
|---|---|---|---|---|
| 836 | | | | 69% |
| 847 | | | | 50% |

TABLE 2-continued
| Compound Number | Intermediate C | Intermediate D | Target Compound | Yield |
|---|---|---|---|---|
| 848 | 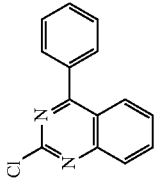 |  | 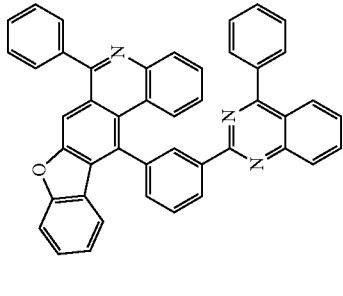 | 63% |
| 855 | 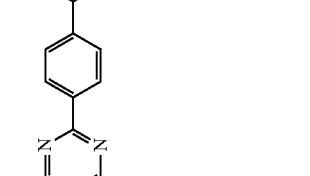 | 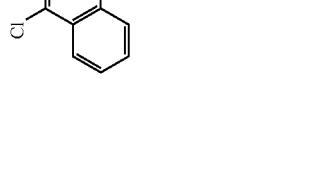 | 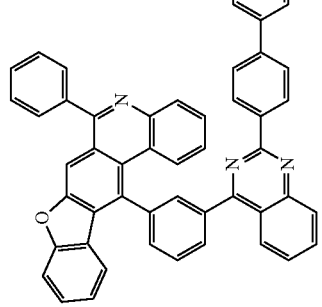 | 71% |

TABLE 2-continued

| Compound Number | Intermediate C | Intermediate D | Target Compound | Yield |
|---|---|---|---|---|
| 886 | | | | 74% |
| 889 | | | | 72% |

TABLE 2-continued

| Compound Number | Intermediate C | Intermediate D | Target Compound | Yield |
|---|---|---|---|---|
| 890 | | | | 74% |
| 892 | | | | 77% |

| Compound Number | Intermediate C | Intermediate D | Target Compound | Yield |
|---|---|---|---|---|
| 895 | | | | 73% |
| 906 | | | | 80% |

TABLE 2-continued

TABLE 2-continued
| Compound Number | Intermediate C | Intermediate D | Target Compound | Yield |
|---|---|---|---|---|
| 914 | 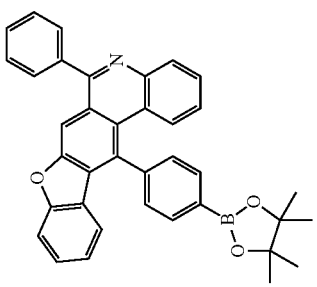 | 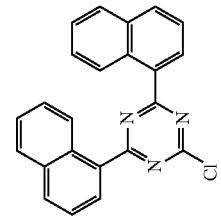 | 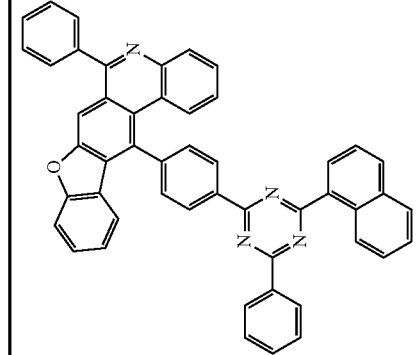 | 76% |
| 915 | 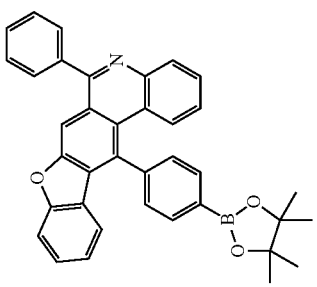 | 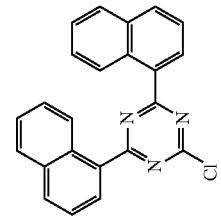 | 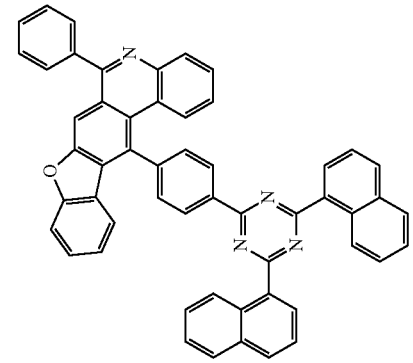 | 80% |

TABLE 2-continued
| Compound Number | Intermediate C | Intermediate D | Target Compound | Yield |
|---|---|---|---|---|
| 917 | 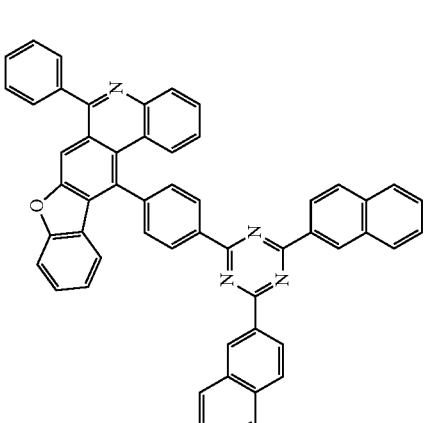 | 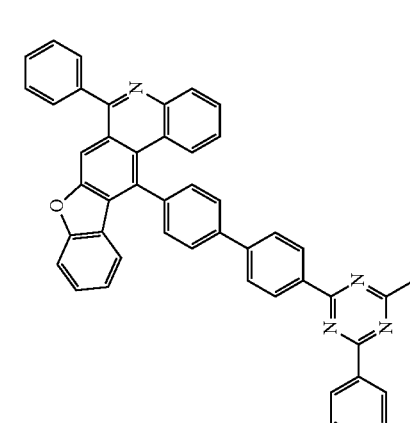 | 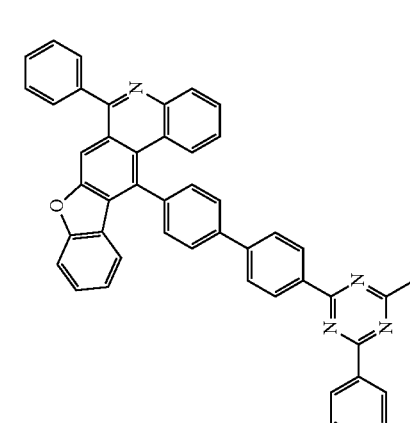 | 71% |
| 920 | 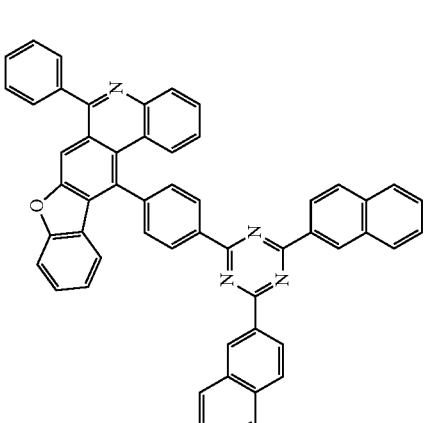 | 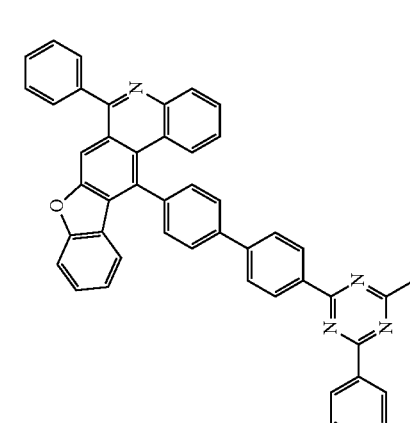 | 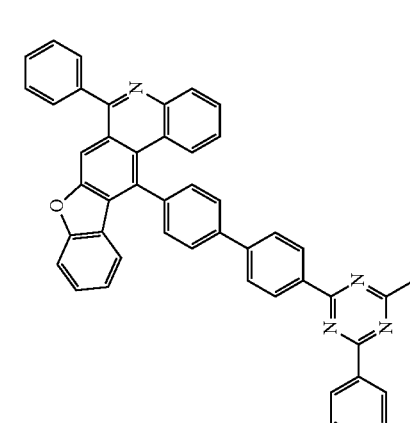 | 73% |

TABLE 2-continued

| Compound Number | Intermediate C | Intermediate D | Target Compound | Yield |
|---|---|---|---|---|
| 928 | | | | 70% |
| 933 | | | | 69% |

TABLE 2-continued

| Compound Number | Intermediate C | Intermediate D | Target Compound | Yield |
|---|---|---|---|---|
| 937 | | | | 77% |
| 943 | | | | 83% |

TABLE 2-continued
| Compound Number | Intermediate C | Intermediate D | Target Compound | Yield |
|---|---|---|---|---|
| 945 | 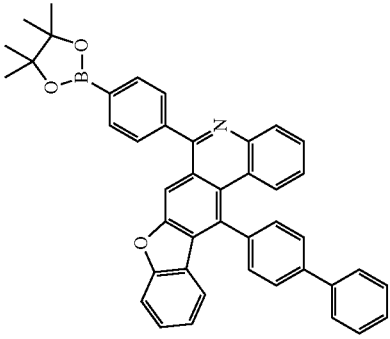 | 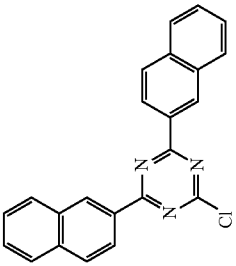 | 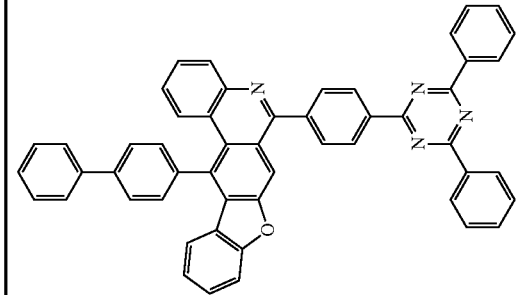 | 81% |
| 946 | 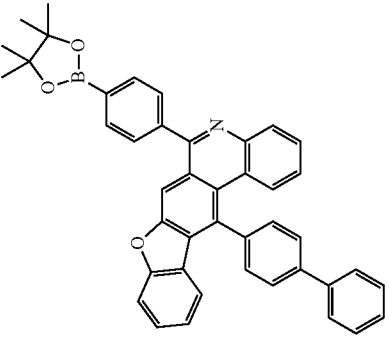 | 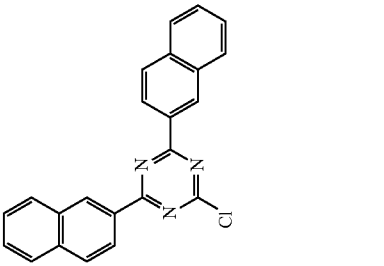 | 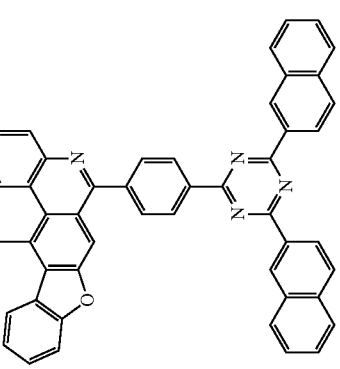 | 80% |

| Com- pound Number | Intermediate C | Intermediate D | Target Compound | Yield |
|---|---|---|---|---|
| 947 | 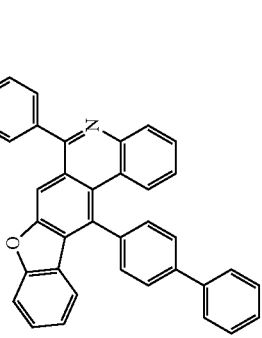 | 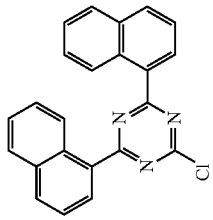 | 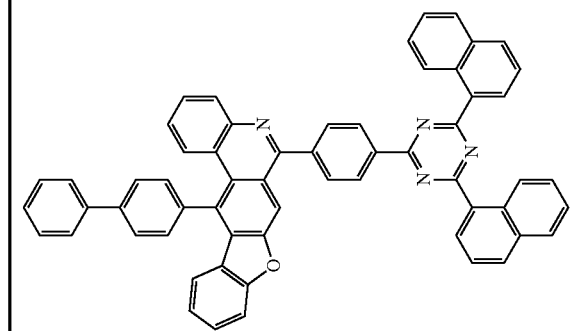 | 71% |

TABLE 2-continued
| Compound Number | Intermediate C | Intermediate D | Target Compound | Yield |
|---|---|---|---|---|
| 948 | 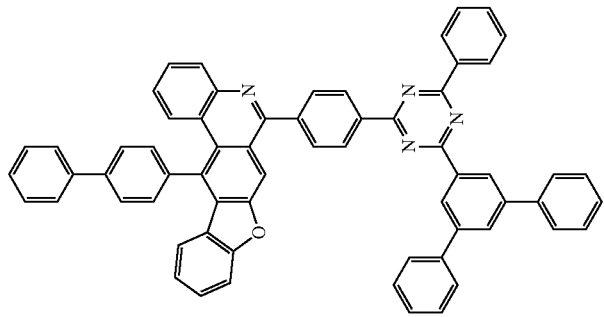 | 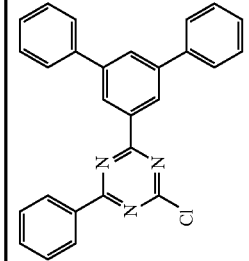 | 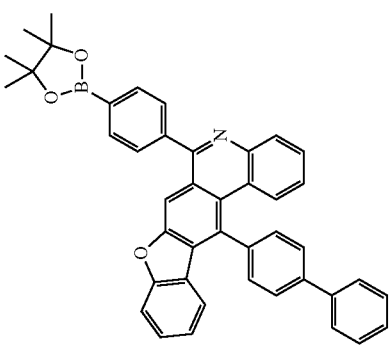 | 69% |

TABLE 2-continued
| Compound Number | Intermediate C | Intermediate D | Target Compound | Yield |
|---|---|---|---|---|
| 949 | 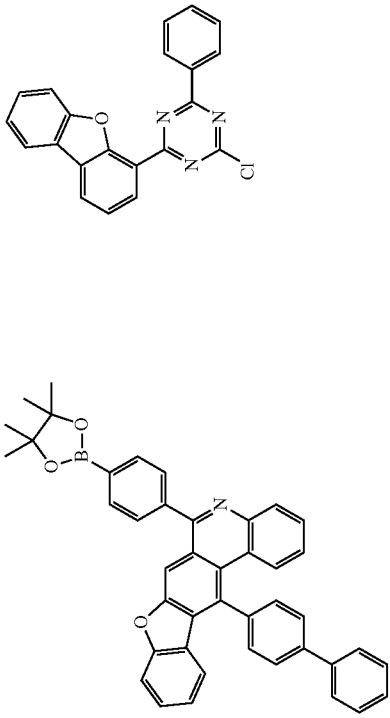 | 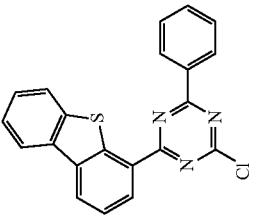 | 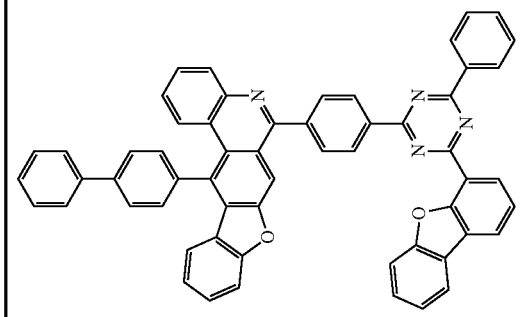 | 58% |
| 950 | 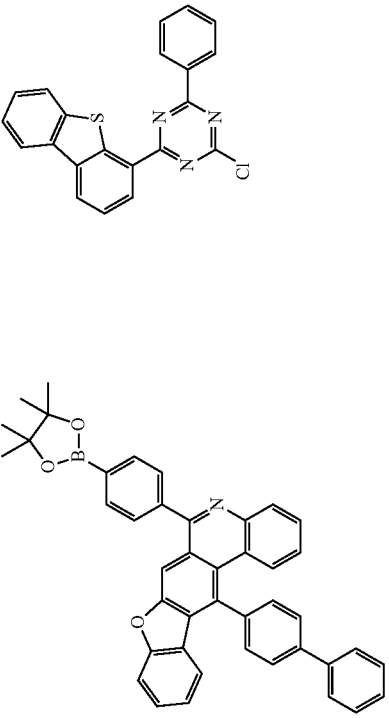 | 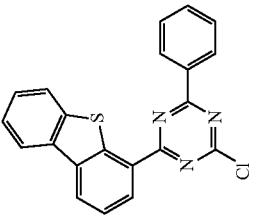 | 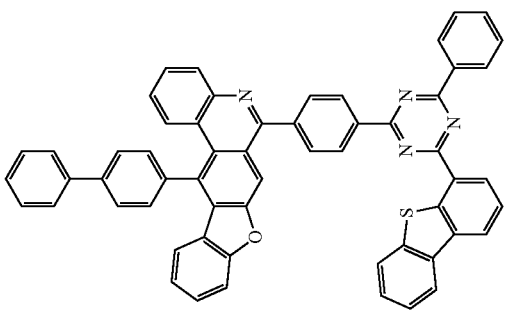 | 81% |

TABLE 2-continued

| Com-pound Number | Intermediate C | Intermediate D | Target Compound | Yield |
|---|---|---|---|---|
| 953 | | | | 82% |

TABLE 2-continued
| Compound Number | Intermediate C | Intermediate D | Target Compound | Yield |
|---|---|---|---|---|
| 956 | 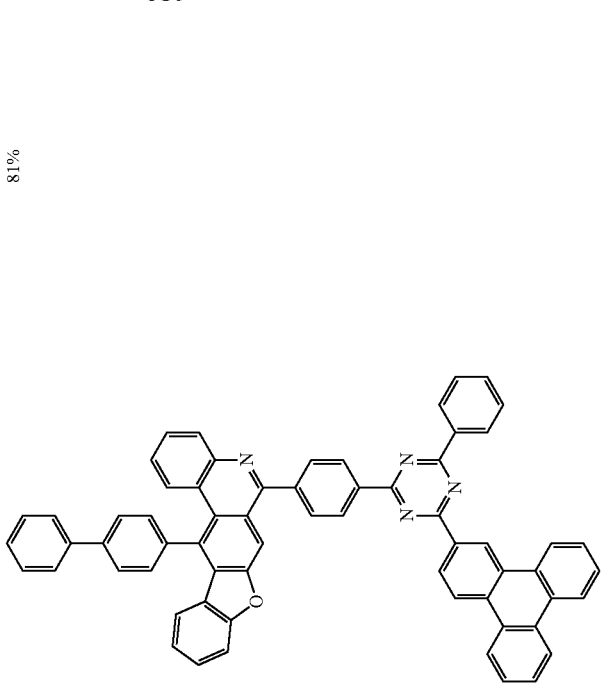 | 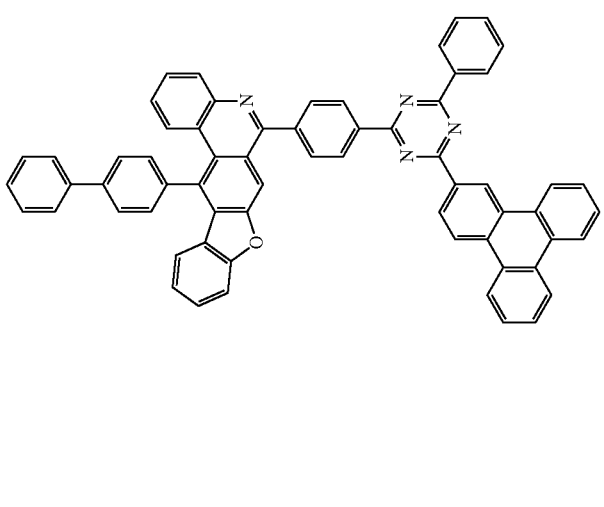 | 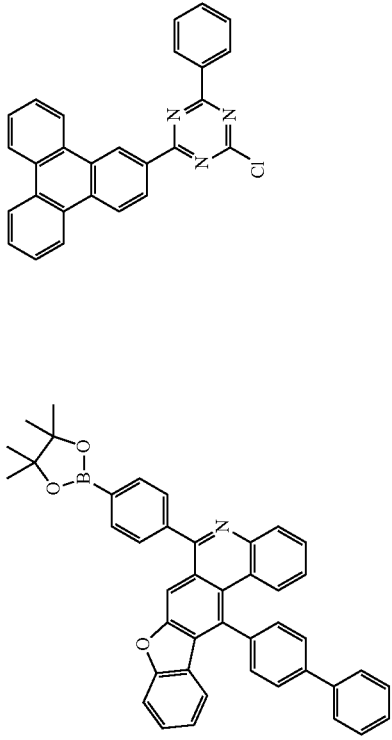 | 81% |

TABLE 2-continued
| Compound Number | Intermediate C | Intermediate D | Target Compound | Yield |
|---|---|---|---|---|
| 957 | 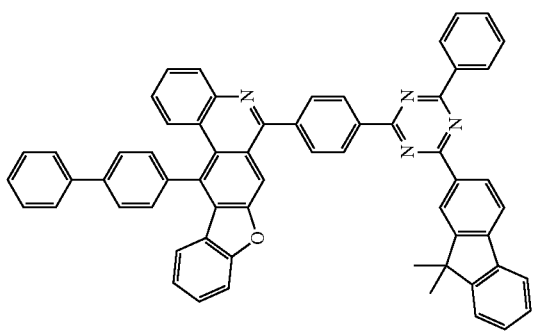 | 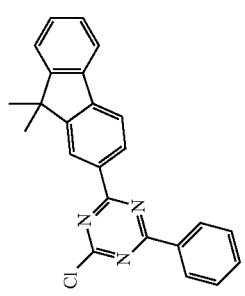 | 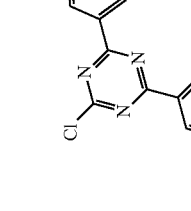 | 80% |

TABLE 2-continued

| Compound Number | Intermediate C | Intermediate D | Target Compound | Yield |
|---|---|---|---|---|
| 973 | | | | 71% |
| 974 | | | | 69% |

TABLE 2-continued

| Compound Number | Intermediate C | Intermediate D | Target Compound | Yield |
|---|---|---|---|---|
| 975 | | | | 58% |

TABLE 2-continued

| Compound Number | Intermediate C | Intermediate D | Target Compound | Yield |
|---|---|---|---|---|
| 976 | | | | 81% |

TABLE 2-continued
| Compound Number | Intermediate C | Intermediate D | Target Compound | Yield |
|---|---|---|---|---|
| 977 | 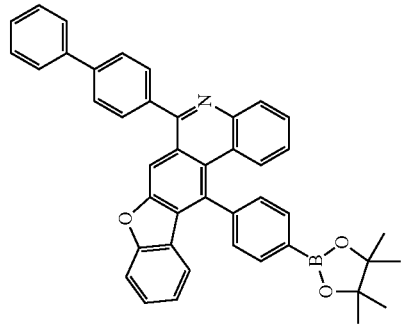 | 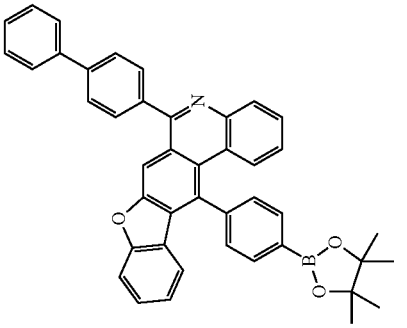 | 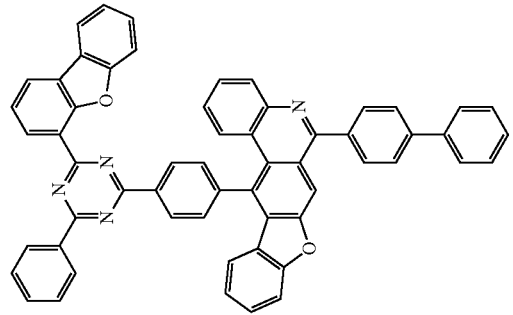 | 82% |
| 978 | 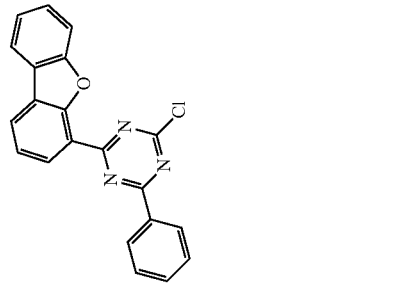 | 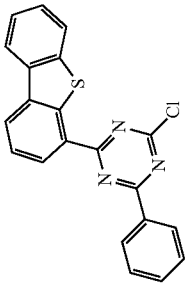 | 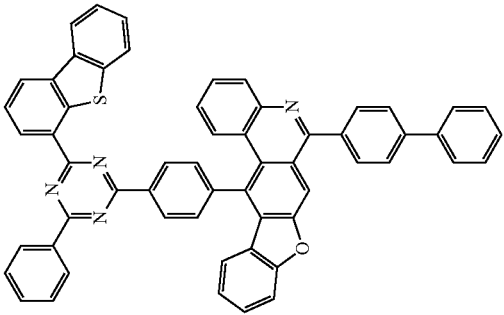 | 81% |

TABLE 2-continued

| Compound Number | Intermediate C | Intermediate D | Target Compound | Yield |
|---|---|---|---|---|
| 981 | | | | 80% |

TABLE 2-continued
| Compound Number | Intermediate C | Intermediate D | Target Compound | Yield |
|---|---|---|---|---|
| 984 | 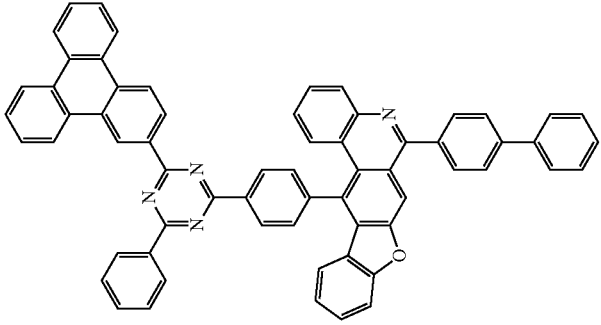 | 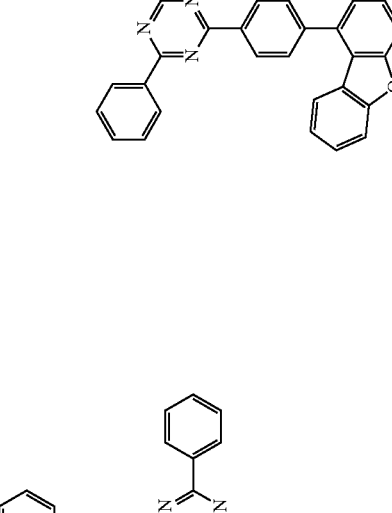 | 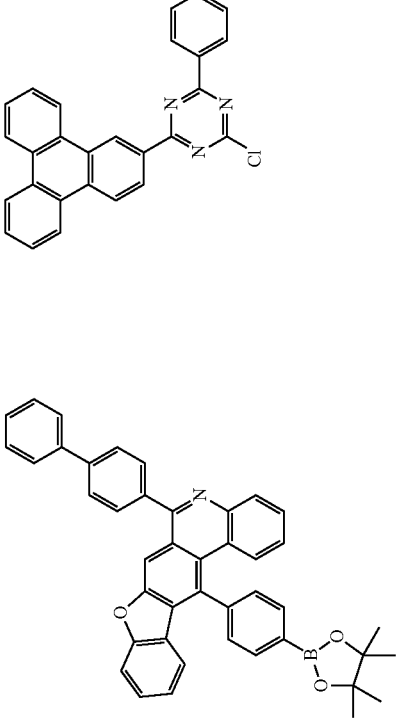 | 71% |

TABLE 2-continued

| Compound Number | Intermediate C | Intermediate D | Target Compound | Yield |
|---|---|---|---|---|
| 985 | | | | 69% |
| 1015 | | | | 58% |

TABLE 2-continued

| Compound Number | Intermediate C | Intermediate D | Target Compound | Yield |
|---|---|---|---|---|
| 1016 | | | | 81% |
| 1017 | | | | 82% |

TABLE 2-continued
| Compound Number | Intermediate C | Intermediate D | Target Compound | Yield |
|---|---|---|---|---|
| 1018 | 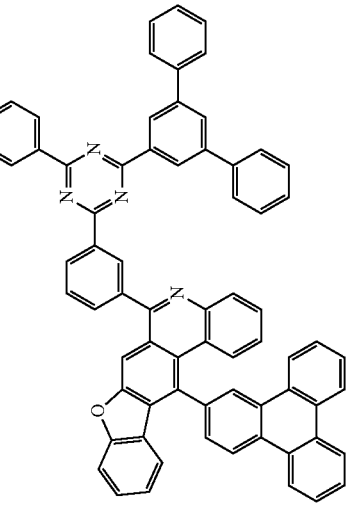 | 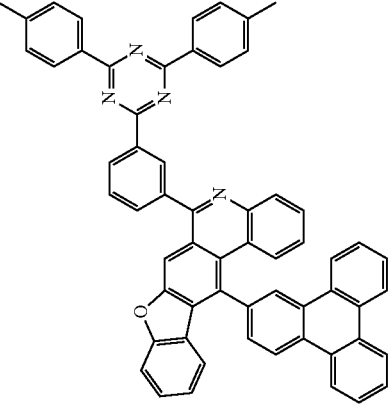 | 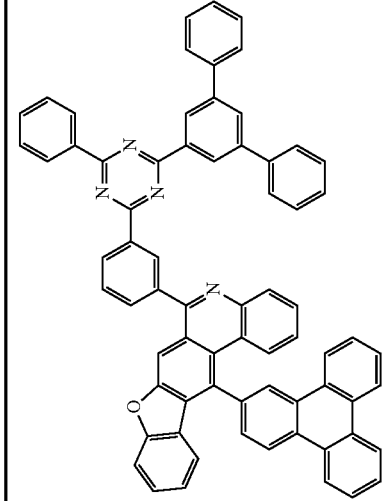 | 81% |
| 1023 | 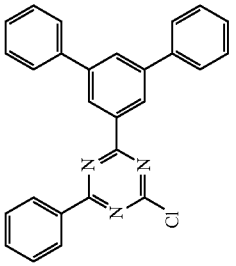 | 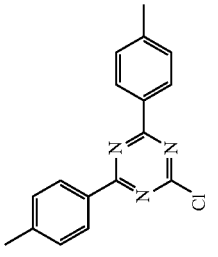 | 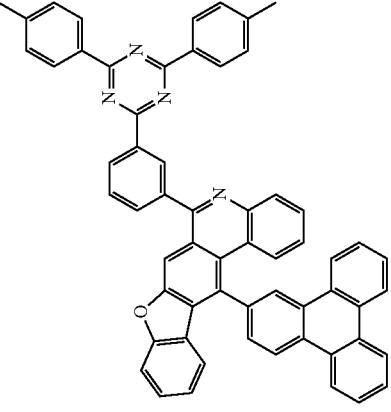 | 80% |

TABLE 2-continued

| Compound Number | Intermediate C | Intermediate D | Target Compound | Yield |
|---|---|---|---|---|
| 1026 | | | | 71% |
| 1027 | | | | 69% |

TABLE 2-continued

| Compound Number | Intermediate C | Intermediate D | Target Compound | Yield |
|---|---|---|---|---|
| 1043 | | | | 58% |
| 1044 | | | | 81% |

TABLE 2-continued

| Compound Number | Intermediate C | Intermediate D | Target Compound | Yield |
|---|---|---|---|---|
| 1045 | | | | 82% |
| 1046 | | | | 80% |

TABLE 2-continued

| Compound Number | Intermediate C | Intermediate D | Target Compound | Yield |
|---|---|---|---|---|
| 1051 | | | | 71% |
| 1054 | | | | 73% |

TABLE 2-continued

| Compound Number | Intermediate C | Intermediate D | Target Compound | Yield |
|---|---|---|---|---|
| 1055 | | | | 70% |

TABLE 2-continued

| Compound Number | Intermediate C | Intermediate D | Target Compound | Yield |
|---|---|---|---|---|
| 1056 | | | | 80% |
| 1057 | | | | 71% |

TABLE 2-continued

| Compound Number | Intermediate C | Intermediate D | Target Compound | Yield |
|---|---|---|---|---|
| 1058 | | | | 73% |
| 1060 | | | | 70% |

TABLE 2-continued

| Compound Number | Intermediate C | Intermediate D | Target Compound | Yield |
|---|---|---|---|---|
| 1068 | | | | 50% |
| 1075 | | | | 63% |

TABLE 2-continued
| Compound Number | Intermediate C | Intermediate D | Target Compound | Yield |
|---|---|---|---|---|
| 1079 | 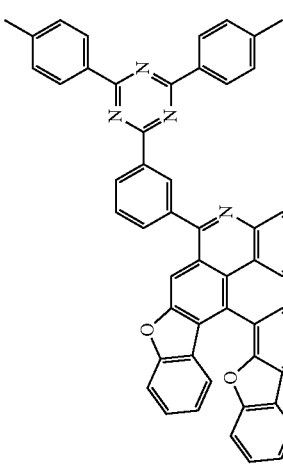 | 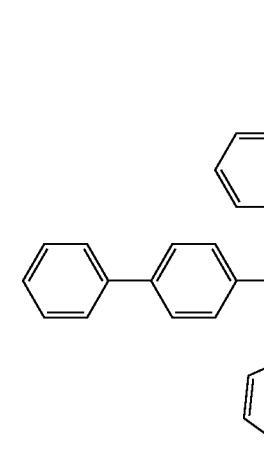 | 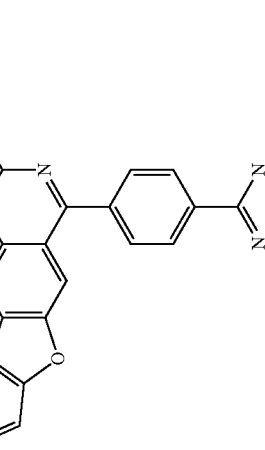 | 71% |
| 1085 | 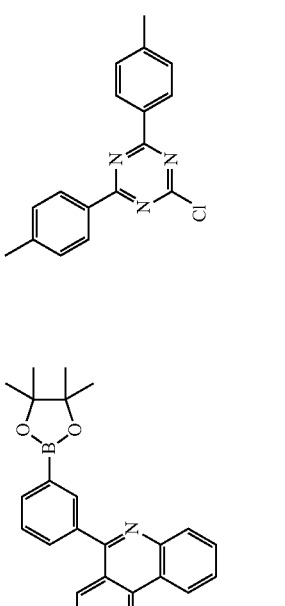 | 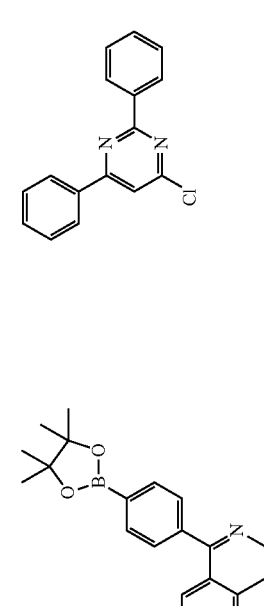 |  | 74% |

TABLE 2-continued
| Compound Number | Intermediate C | Intermediate D | Target Compound | Yield |
|---|---|---|---|---|
| 1086 | 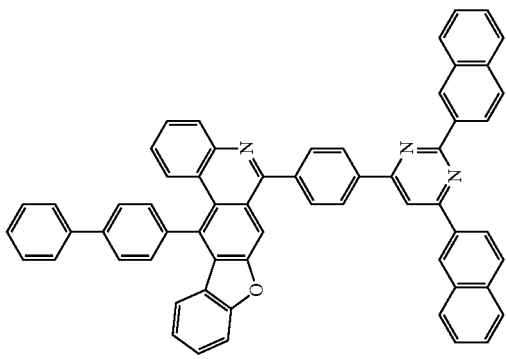 | 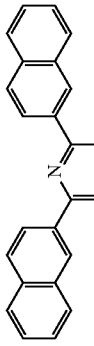 | 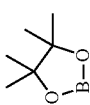 | 72% |

TABLE 2-continued
| Compound Number | Intermediate C | Intermediate D | Target Compound | Yield |
|---|---|---|---|---|
| 1088 | 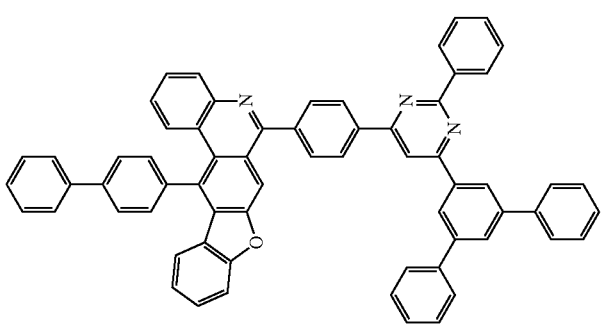 | 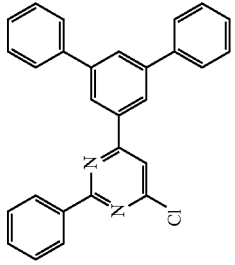 | 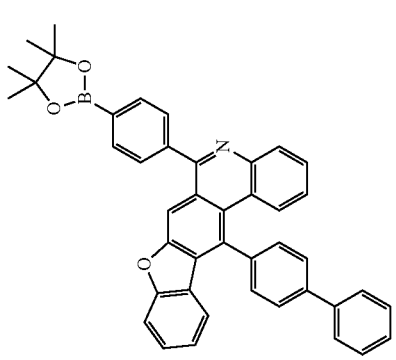 | 74% |

TABLE 2-continued

| Compound Number | Intermediate C | Intermediate D | Target Compound | Yield |
|---|---|---|---|---|
| 1096 | | | | 77% |
| 1099 | | | | 73% |

TABLE 2-continued
| Compound Number | Intermediate C | Intermediate D | Target Compound | Yield |
|---|---|---|---|---|
| 1103 | 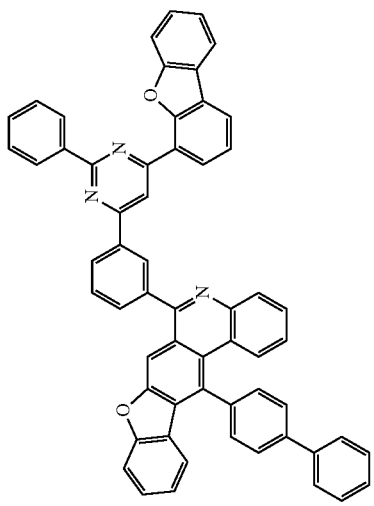 | 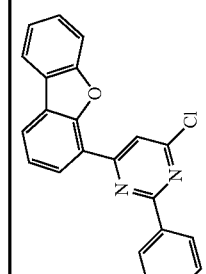 | 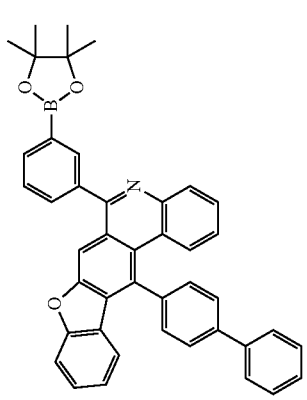 | 80% |

Compounds other than the compounds described in Table 2 were also prepared in the same manner as in the preparation examples described above.

The following Table 3 and Table 4 present ¹H NMR data and FD-MS data of the synthesized compounds, and through the following data, syntheses of target compounds may be identified.

TABLE 3

| NO | ¹H NMR (CDCl$_3$, 300 Mz) |
|---|---|
| 1 | δ = 8.81(t, 2H), 8.28(m, 4H), 7.52(m, 1H), 7.98(m, 1H), 7.89~7.78(m, 5H), 7.66~7.32(m, 15H) |
| 2 | δ = 8.81(t, 2H), 8.28(t, 2H), 7.52(m, 1H), 7.98(m, 1H), 7.89~7.83(m, 7H), 7.66~7.32(m, 18H) |
| 4 | δ = 8.81(t, 2H), 8.24~8.28(m, 3H), 7.52(m, 1H), 7.98(m, 1H), 7.89~7.83(m, 5H), 7.66~7.32(m, 20H) |
| 5 | δ = 8.81(t, 2H), 8.24(m, 2H), 7.52(m, 1H), 7.98(m, 1H), 7.89~7.78(m, 5H), 7.70~7.32(m, 25H) |
| 7 | δ = 8.81(t, 2H), 8.33~8.28(m, 7H), 8.06(m, 1H), 7.98(m, 1H), 7.89~7.78(m, 5H), 7.66~7.32(m, 17H) |
| 8 | δ = 8.81(t, 2H), 8.33~8.30(m, 4H), 8.06(m, 1H), 7.98(m, 1H), 7.89~7.85(m, 7H), 7.60~7.25(m, 21H) |
| 9 | δ = 8.81(t, 2H), 8.33~8.23(m, 5H), 8.06(m, 1H), 7.98(m, 1H), 7.89(m, 1H), 7.66~7.32(m, 23H) |
| 15 | δ = 8.81(t, 2H), 8.23(s, 1H), 8.06(m, 1H), 7.98(m, 1H), 7.89~7.32(m, 32H) |
| 18 | δ = 8.81(t, 2H), 8.28(m, 4H), 8.06(m, 1H), 7.98(m, 1H), 7.89~7.85(m, 7m) 7.66~7.41(m, 17H) |
| 20 | δ = 8.81(t, 2H), 8.28(m, 4H), 8.06(m, 1H), 7.89~7.83(m, 11H), 7.66~7.25(m, 25H) |
| 29 | δ = 8.81(t, 2H), 8.30(m, 2H), 8.23(m, 1H), 8.06(m, 1H), 7.98(m, 1H), 7.89~7.78(m, 11H), 7.66~7.32(m, 19H) |
| 33 | δ = 8.81(t, 2H), 8.30(m, 2H), 8.23(m, 1H), 8.06(m, 1H), 7.98(m, 1H), 7.89~7.78(m, 11H), 7.66~7.41(m, 19H) |
| 35 | δ = 8.81(t, 2H), 8.28~8.24(m, 5H), 8.06(m, 1H), 7.98(m, 1H), 7.89~7.78(m, 5H), 7.66~7.38(m, 18H) |
| 38 | δ = 8.81(t, 2H), 8.28~8.24(m, 4H), 8.06(m, 1H), 7.98(m, 1H), 7.88~7.78(m, 5H), 7.70~7.32(m, 23H) |
| 40 | δ = 8.81(t, 2H), 8.28~8.23(m, 3H), 8.06(m, 1H), 7.98(m, 1H), 7.89~7.32(m, 26H) |
| 47 | δ = 8.81(t, 2H), 8.30~8.23(m, 6H), 8.06(m, 1H), 7.98(m, 1H), 7.66~7.32(m, 22H) |
| 49 | δ = 8.81(t, 2H), 8.24~8.23(m, 2H), 8.06(m, 1H), 7.98(m, 1H), 7.88~7.32(m, 35H) |
| 52 | δ = 8.30~8.21(m, 7H), 8.06(m, 1H), 7.98(m, 1H), 7.83~7.78(m, 2H), 7.66~7.32(m, 16H) |
| 53 | δ = 8.30~8.21(m, 5H), 8.06(m, 1H), 7.98(m, 1H), 7.89~7.78(m, 5H), 7.66~7.32(m, 23H) |
| 55 | δ = 8.30~8.21 (m, 6H), 8.06(m, 1H), 7.98(m, 1H), 7.98(m, 1H), 7.83~7.78(m, 2H), 7.66~7.32(m, 21H) |
| 57 | δ = 8.28~8.21(m, 5H), 8.06(m, 1H), 7.98(m, 1H), 7.89(m, 1H), 7.83~7.78(m, 5H), 7.66~7.32(m, 16H) |
| 58 | δ = 8.30~8.21(m, 7H), 8.06(m, 1H), 7.98(m, 1H), 7.89~7.81(m, 6H), 7.66~7.32(m, 18H) |
| 70 | δ = 8.28~8.21(m, 4H), 8.06(m, 1H), 7.98(m, 1H), 7.89~7.78(m, 7H), 7.66~7.23(m, 23H) |
| 75 | δ = 8.30~8.21(m, 9H), 8.06(m, 1H), 7.98(m, 1H), 7.85~7.78(m, 7H), 7.66~7.32(m, 19H) |
| 86 | δ = 8.28~8.21(m, 7H), 8.06(m, 1H), 7.98(m, 1H), 7.89(m, 1H), 7.83~7.78(m, 2H), 7.70~7.32(m, 20H) |
| 87 | δ = 8.28~8.21(m, 5H), 8.06(m, 1H), 7.98(m, 1H), 7.89~7.83(m, 5H), 7.70~7.32(m, 24H) |
| 94 | δ = 8.28~8.21(m, 5H), 8.06(m, 1H), 7.98(m, 1H), 7.89(m, 1H), 7.83~7.32(m, 29H) |
| 101 | δ = 8.81(m, 2H), 8.55(t, 2H), 8.28(m, 4H), 8.06~7.98(m, 4H), 7.78~7.83(m, 2H), 7.66~7.28(m, 29H) |
| 102 | δ = 8.28(m, 2H), 8.06~7.98(m, 4H), 7.85~7.78(m, 4H), 7.66~7.25(m, 23H) |
| 103 | δ = 8.81(m, 2H), 8.55(m, 2H), 8.28~8.24(m, 3H), 8.06~7.98(m, 4H), 7.83~7.78(m, 2H), 7.66~7.28(m, 24H) |
| 104 | δ = 8.81(t, 2H), 8.55(t, 2H), 8.28~8.23(m, 3H), 8.06~7.98(m, 4H), 7.83~7.79(m, 4H), 7.66~7.28(m, 19H) |
| 105 | δ = 8.81(t, 2H), 8.55(t, 2H), 8.30~8.28(m, 5H), 8.06~7.98(m, 4H), 7.89~7.78(m, 5H), 7.66~7.32(m, 21H) |
| 112 | δ = 8.55(m, 2H), 8.28~8.21(m, 6H), 8.06~7.98(m, 4H), 7.83~7.78(m, 2H), 7.66~7.32(m, 19H) |
| 113 | δ = 8.55(m, 2H), 8.28~8.21(m, 4H), 8.06~7.98(m, 4H), 7.89~7.78(m, 5H), 7.66~7.25(m, 23H) |
| 115 | δ = 8.55(m, 2H), 8.28~8.21(m, 5H), 8.06~7.98(m, 4H), 7.89(m, 1H), 7.83~7.79(m, 4H), 7.66~7.32(m, 19H) |

TABLE 3-continued

| NO | $^1$H NMR (CDCl$_3$, 300 Mz) |
|---|---|
| 116 | δ = 8.55(m, 2H), 8.30~8.21(m, 7H), 8.06~7.98(m, 4H), 7.89~7.78(m, 5H), 7.66~7.32(m, 21H) |
| 124 | δ = 8.81(t, 2H), 8.55(d, 1H), 8.12~8.06(m, 2H), 7.98~7.79(m, 9H), 7.66~7.25(m, 16H) |
| 126 | δ = 8.81(t, 2H), 8.12~8.06(m, 5H), 7.98~7.83(m, 8H), 7.66~7.25(m, 21H) |
| 127 | δ = 8.81(t, 2H), 8.06(m, 1H), 7.98(m, 1H), 7.89~7.78(m, 6H), 7.66~7.28(m, 15H) |
| 130 | δ = 8.81(t, 2H), 8.06(m, 1H), 7.98(m, 1H), 7.89~7.75(m, 5H), 7.66~7.28(m, 16H) |
| 131 | δ = 8.81(t, 2H), 8.06(m, 1H), 7.98(m, 1H), 7.89~7.81(m, 8H), 7.66~7.32(m, 17H) |
| 133 | δ = 8.81(t, 2H), 8.06(m, 1H), 7.98(m, 1H), 7.89~7.32(m, 25H) |
| 136 | δ = 8.81(t, 2H), 8.06(m, 1H), 7.98~7.32(m, 26H) |
| 139 | δ = 8.81(t, 2H), 8.45~8.41(m, 2H), 8.20(m, 1H), 8.06(m, 1H), 7.98(m, 2H), 7.89~7.83(m, 3H), 7.66~7.32(m, 14H), |
| 141 | δ = 8.81(t, 2H), 8.45(m, 1H), 8.06~7.86(m, 5H), 7.89~7.78(m, 6H), 7.66~7.32(m, 11H) |
| 142 | δ = 8.81(t, 2H), 8.45(d, 1H), 8.06(m, 1H), 7.98~7.78(m, 7H), 7.66~7.32(m, 14H) |
| 151 | δ = 8.81(t, 2H), 8.06(m, 1H), 7.98(m, 1H), 7.89~7.78(m, 11H), 7.66~7.32(m, 20H) |
| 154 | δ = 8.81(t, 2H), 8.06(m, 1H), 7.98(m, 1H), 7.78~7.32(m, 31H) |
| 158 | δ = 8.81(t, 2H), 8.45(m, 2H), 8.06(m, 1H), 7.98~7.78(m, 12H), 7.66~7.32(m, 18H) |
| 160 | δ = 8.55(m, 1H), 8.26~8.21(m, 2H), 8.06~8.12(m, 2H), 7.98~7.78(m, 7H), 7.66~7.25(m, 18H) |
| 162 | δ = 8.55(t, 2H), 8.26~8.21(m, 2H), 8.12~8.06(m, 5H), 7.98~7.78(m, 5H), 7.66~7.25(m, 12H) |
| 175 | δ = 8.45~8.41(m, 2H), 8.26~8.21(m, 3H), 8.06(m, 1H), 7.98(m, 2H), 7.89(m, 1H), 7.78~7.83(m, 2H), 7.66~7.32(m, 14H) |
| 186 | δ = 8.45(d, 1H), 8.26~8.21(m, 2H), 8.06(m, 1H), 7.98~7.78(m, 7H), 7.66~7.32(m, 18H) |
| 190 | δ = 8.26~8.21(m, 2H), 8.06(m, 1H), 7.98(m, 1H), 7.89~7.75(m, 7H), 7.66~7.32(m, 24H) |
| 193 | δ = 8.45(t, 2H), 8.26~8.21(m, 2H), 8.06~7.98(m, 8H), 7.89~7.78(m, 5H), 7.66~7.32(m, 18H) |
| 195 | δ = 8.99~8.93(m, 3H), 8.81(m, 2H), 8.34(d, 2H), 8.12~8.06(m, 4H), 7.98(m, 1H), 7.89~7.78(m, 9H), 7.66~7.32(m, 9H) |
| 196 | δ = 8.99~8.93(m, 3H), 8.81(t, 2H), 8.34(d, 1H), 8.12~8.06(m, 4H), 7.98(m, 1H), 7.89~7.78(m, 9H), 7.66~7.25(m, 13H) |
| 198 | δ = 8.81(t, 2H), 8.55(m, 1H), 8.28(t, 2H), 8.12~8.06(m, 2H), 7.98~7.79(m, 9H), 7.68~7.32(m, 19H) |
| 199 | δ = 8.81(t, 2H), 8.55(d, 1H), 8.28(m, 3H), 8.12~8.06(m, 3H), 7.94~7.78(m, 7H), 7.66~7.25(m, 19H) |
| 200 | δ = 8.81(t, 2H), 8.55(d, 1H), 8.28(m, 2H), 8.12~8.06(m, 2H), 7.98~7.79(m, 11H), 7.68~7.25(m, 21H) |
| 201 | δ = 8.81(t, 2H), 8.55(d, 1H), 8.28(m, 3H), 8.12~8.06(m, 3H), 7.98~7.78(m, 9H), 7.66~7.32(m, 21H) |
| 202 | δ = 8.81(t, 2H), 8.55(d, 1H), 8.28~8.24(m, 3H), 8.12~8.06(m, 2H), 7.98~7.78(m, 9H), 7.70~7.32(m, 21H) |
| 203 | δ = 8.81(t, 2H), 8.55(m, 1H), 8.28~8.24(m, 4H), 8.12~8.06(m, 3H), 7.98~7.78(m, 7H), 7.70~7.25(m, 22H), |
| 204 | δ = 8.81(t, 2H), 8.55(d, 1H), 8.33~8.28(m, 5H), 8.12~8.06(m, 2H), 7.98~7.78(m, 7H), 7.66~7.25(m, 19H) |
| 205 | δ = 8.81(t, 2H), 8.55(d, 1H), 8.33~8.23(m, 5H), 8.12~8.06(m, 3H), 7.98~7.78(m, 6H), 7.66~7.25(m, 19H) |
| 206 | δ = 8.81(t, 2H), 8.55(d, 1H), 8.30~8.23(m, 5H), 8.12~8.06(m, 2H), 7.98~7.79(m, 11H), 7.68~7.25(m, 19H) |
| 209 | δ = 8.81(t, 2H), 8.55(d, 1H), 8.28~8.23(m, 3H), 8.12~8.06(m, 3H), 7.98~7.29(m, 24H) |
| 211 | δ = 8.81(t, 2H), 8.55(d, 1H), 8.33~8.23(m, 4H), 8.12~8.06(m, 3H), 7.98~7.78(m, 7H), 7.66~7.25(m, 19H) |
| 221 | δ = 8.99~8.93(m, 3H), 8.34(d, 1H), 8.26~8.21(m, 2H), 8.12~8.06(m, 4H), 7.98(m, 1H), 7.89~7.78(m, 7H), 7.66~7.25(m 15H) |
| 223 | δ = 8.55(m, 1H), 8.30~8.21(m, 5H), 8.12~8.06(m, 2H), 7.98~7.79(m, 7H), 7.68~7.25(m, 20H) |
| 224 | δ = 8.85(d, 1H), 8.30~8.21(m, 6H), 8.12~8.06(m, 3H), 7.98~7.89(m, 3H), 7.83~7.78(m, 2H), 7.66~7.25(m, 20H) |
| 230 | δ = 8.55(d, 1H), 8.28~8.21(m, 5H), 8.12~8.06(m, 3H), 7.98~7.78(m, 7H), 7.66~7.25(m, 20H) |
| 232 | δ = 8.55(m, 1H), 8.28~8.21(m, 7H), 8.12~8.06(m, 3H), 8.12~8.06(m, 3H), 7.98~7.78(m, 8H), 7.66~7.25(m, 21H) |
| 240 | δ = 8.55(d, 1H), 8.28~8.21(m, 4H), 8.12~8.06(m, 3H), 7.98~7.89(m, 3H), 7.75~7.25(m, 29H) |
| 242 | δ = 8.55(d, 1H), 8.30~8.21(m, 4H), 8.12~8.06(m, 3H), 7.98~7.79(m, 8H), 7.66~7.25(m, 20H) |
| 249 | δ = 8.81(t, 2H), 8.28(m, 2H), 8.06(m, 1H), 7.98(m, 1H), 7.89~7.78(m, 10H), 7.66~7.25(m, 18H) |

TABLE 3-continued

| NO | $^1$H NMR (CDCl$_3$, 300 Mz) |
|---|---|
| 250 | δ = 8.81(t, 2H), 8.24~8.28(m, 3H), 8.06(m, 1H), 7.98(m, 1H),, 7.89~7.78(m, 8H), 7.66~7.32(m, 19H) |
| 251 | δ = 8.81(t, 2H), 8.28(t, 2H), 8.06(m, 1H), 7.98(m, 1H), 7.89~7.78(m, 12H), 7.66~7.25(m, 20H) |
| 252 | δ = 8.81(t, 2H), 8.28~8.24(m, 3H), 8.06(m, 1H), 7.98(m, 1H), 7.89~7.78(m, 10H), 7.66~7.32(m, 21H) |
| 255 | δ = 8.81(t, 2H), 8.33~8.28(m, 7H), 8.06(m, 1H), 7.98(m, 1H), 7.89~7.78(m, 6H), 7.66~7.25(m, 18H) |
| 259 | δ = 8.81(t, 2H), 8.30~8.23(m, 5H), 8.06(m, 1H), 7.98(m, 1H), 7.89~7.25(m, 30H) |
| 273 | δ = 8.30~8.21(m, 5H), 8.06(m, 1H), 7.98(m, 1H), 7.89~7.73(m, 8H), 7.66~7.32(m, 19H) |
| 274 | δ = 8.30~8.21(m, 6H), 8.06(m, 1H), 7.98(m, 1H), 7.89~7.83(m, 6H), 7.70~7.32(m, 20H) |
| 279 | δ = 8.28~8.21(m, 7H), 8.06(m, 1H), 7.98(m, 1H), 7.89~7.78(m, 7H), 7.66~7.25(m, 19H) |
| 281 | δ = 8.30~8.21(m, 9H), 8.06(m, 1H), 7.98(m, 1H), 7.89~7.81(m, 8H), 7.66~7.25(m, 20H) |
| 297 | δ = 8.81(m, 2H), 8.06(m, 1H), 7.89~7.16(m, 30H) |
| 298 | δ = 8.81(m, 2H), 8.06(m, 2H), 7.98(m, 1H), 7.89~7.75(m, 8H), 7.66~7.19(m, 20H) |
| 299 | δ = 8.81(d, 2H), 8.06(m, 1H), 7.98(m, 1H), 7.89~7.75(m, 6H), 7.36~7.16(m, 23H) |
| 301 | δ = 8.81(d, 2H), 8.06(m, 2H), 7.98(m, 1H), 7.89~7.78(m, 6H), 7.66~7.26(m, 20H) |
| 302 | δ = 8.81(d, 2H), 8.06(m, 1H), 7.98(m, 1H), 7.89~7.87(m, 4H), 7.66~7.26(m, 23H), 7.11(m, 4H) |
| 303 | δ = 8.93(d, 2H), 8.81(d, 2H), 8.12~8.06(m, 3H), 7.98~7.82(m, 8H), 7.66~7.28(m, 11H,) |
| 308 | δ = 8.81(d, 2H), 8.55(m, 1H), 8.06(m, 1H), 7.98~7.78(m, 9H), 7.66~7.25(m, 17H) |
| 309 | δ = 8.81(d, 2H), 8.55(m, 1H), 8.06(m, 1H), 7.94~7.78(m, 6H), 7.59~7.25(m, 20H) |
| 317 | δ = 8.81(d, 2H), 8.06(m, 1H), 7.98(m, 1H), 7.89~7.77(m, 13H), 7.66~7.32(m, 15H) |
| 319 | δ = 8.81(d, 2H), 8.00~732(m, 31H) |
| 320 | δ = 8.81(d, 2H), 8.55(m, 1H), 8.08~8.06(m, 2H), 7.98~7.77(m, 9H), 7.66~7.32(m, 20H) |
| 321 | δ = 8.81(d, 2H), 8.16(m, 1H), 8.06(m, 1H), 7.98(m, 1H), 7.89~7.79(m, 9H), 7.66~7.32(m, 13H) |
| 324 | δ = 8.81(d, 2H), 8.30(d, 2H), 8.16(m, 1H), 8.06(m, 1H), 7.98(m, 1H), 7.89~7.78(m, 11H), 7.66~7.25(m, 17H) |
| 326 | δ = 8.81(d, 2H), 8.30~8.24(m, 3H), 8.16(m, 1H), 8.06(m, 1H), 7.98(m, 1H), 7.89~7.83(m, 9H), 7.70~7.32(m, 18H) |
| 327 | δ = 8.81(d, 2H), 8.33~8.28(m, 4H), 8.16(m, 1H), 8.06(m, 1H), 7.98(m, 1H), 7.89~7.78(m, 5H), 7.66~7.32(m, 13H) |
| 334 | δ = 8.81(d, 2H), 8.16(m, 1H), 8.06(m, 1H), 7.98(m, 1H),, 7.89~7.32(m, 26H) |
| 339 | δ = 8.81(d, 2H), 8.18(m, 1H), 8.06~7.98(m, 3H), 7.89~7.78(m, 5H), 7.66~7.32(m, 11H) |
| 342 | δ = 8.84(m, 4H), 8.10~7.98(m, 5H), 7.89~7.78(m, 4H), 7.66~7.35(m, 11H) |
| 347 | δ = 8.81(d, 2H), 8.56(m, 1H), 8.28(t, 2H), 8.06(m, 1H), 7.98(m, 1H), 7.89~7.78(m, 7H), 7.68~7.32(m, 15H), 7.22(m, 2H) |
| 349 | δ = 8.81(t, 2H), 8.28(m, 2H), 8.06(m, 1H), 7.98(m, 1H), 7.89(m, 1H), 7.83~7.79(m, 5H), 7.66~7.32(m, 20H) |
| 375 | δ = 8.55(m, 1H), 8.26~8.21(m, 2H), 8.08~8.06(m, 2H), 7.98~7.77(m, 9H), 7.66~7.32(m, 20H) |
| 376 | δ = 8.30~8.21(m, 4H), 8.06(m, 1H), 7.98(m, 1H), 7.89~7.79(m, 7H), 7.66~7.32(m, 14H) |
| 383 | δ = 8.26~8.16(m, 3H), 8.06(m, 1H), 7.98(m, 1H), 7.83~7.78(m, 8H), 7.66~7.25(m, 18H) |
| 413 | δ = 8.81(t, 2H), 8.52(m, 4H), 8.06(m, 1H), 7.98(m, 1H), 7.89~7.78(m, 5H), 7.66~7.29(m, 13H), |
| 415 | δ = 8.81(t, 2H), 8.52(m, 4H), 8.24(m, 1H), 8.06(m, 1H), 7.98(m, 1H), 7.89~7.78(m, 5H), 7.66~7.29(m, 16H) |
| 416 | δ = 8.84~8.83(m, 5H), 8.38(m, 1H), 8.10~8.06(m, 3H), 7.98(m, 1H), 7.89~7.78(m, 4H), 7.66~7.32(m, 11H) |
| 417 | δ = 8.84(d, 4H), 8.30(m, 2H), 8.10~8.06(m, 4H), 7.98(m, 1H), 7.89~7.78(m, 4H), 7.66~7.32(m, 14H) |
| 418 | δ = 8.81(m, 4H), 8.30(m, 2H), 8.10~8.06(m, 4H), 7.98(m, 1H), 7.89~7.78(m, 8H), 7.66~7.32(m, 14H) |
| 419 | δ = 8.81(t, 2H), 8.30~8.21(m, 4H), 8.10~8.06(m, 4H), 7.98(m, 1H), 7.88~7.78(m, 6H), 7.66~7.32(m, 16H) |
| 420 | δ = 8.81(t, 2H), 8.55~8.52(m, 3H), 8.30(m, 2H), 8.10~7.98(m, 6H), 7.89~7.78(m, 4H), 7.66~7.32(m, 18H) |
| 427 | δ = 8.52(m, 4H), 8.30~8.21(m, 3H), 8.06(m, 1H), 7.98(m, 1H), 7.83~7.78(m, 2H), 7.66~7.29(m, 14H) |
| 430 | δ = 8.83(m, 1H), 8.72(m, 1H), 8.38~8.32(m, 3H), 8.10~7.98(m, 3H), 7.89~7.78(m, 4H), 7.66~7.32(m, 12H) |

TABLE 3-continued

| NO | ¹H NMR (CDCl₃, 300 Mz) |
|---|---|
| 431 | δ = 8.72(m, 1H), 8.32~8.30(m, 4H), 8.10~8.06(m, 4H), 7.98(m, 1H), 7.89~7.83(m, 4H), 7.66~7.32(m, 15H) |
| 432 | δ = 8.81(t, 2H), 8.30~8.21(m, 4H), 8.10~8.06(m, 4H), 7.98(m, 1H), 7.89~7.81(m, 6H), 7.66~7.32(m, 16H) |
| 437 | δ = 8.56(m, 1H), 8.26~8.21(m, 2H), 8.06(m, 1H), 7.98(m, 1H), 7.89~7.78(m, 5H), 7.68~7.32(m, 14H), 7.22(m, 2H) |
| 445 | δ = 9.09(s, 2H), 8.81(d, 2H), 8.49(d, 2H), 8.00~7.78(m, 12H), 7.66~7.32(m, 13H) |
| 446 | δ = 8.81(d, 2H), 8.55(d, 1H), 8.28(d, 2H), 8.08~7.78(m, 12H), 7.66~7.32(m, 17H) |
| 447 | δ = 8.81(d, 2H), 8.55(d, 2H), 8.08~7.78(m, 15H), 7.66~7.25(m, 17H) |
| 449 | δ = 9.09(s, 2H), 8.81(d, 2H), 8.49(d, 2H), 8.00~7.78(m, 15H), 7.66~7.32(m, 15H) |
| 453 | δ = 9.09(s, 2H), 8.49(d, 2H), 8.30~8.21(m, 3H), 8.06~7.78(m, 11H), 7.66~7.32(m, 14H) |
| 454 | δ = 8.81(d, 2H), 8.28(d, 2H), 8.08(d, 1H), 7.98(d, 1H), 7.89~7.78(m, 5H), 7.66~7.32(m, 25H) |
| 456 | δ = 8.30~8.21(m, 5H), 8.08(d, 1H), 7.98(d, 1H), 7.89(d, 1H), 7.83~7.78(m, 2H), 7.66~7.32(m, 26H) |
| 457 | δ = 8.81(d, 2H), 8.28(d, 2H), 8.08(d, 1H), 7.98(d, 1H), 7.89~7.78(m, 8H), 7.66~7.32(m, 16H) |
| 459 | δ = 8.30~8.21(m, 5H), 8.08(d, 1H), 7.98(d, 1H), 7.89~7.78(m, 6H), 7.66~7.32(m, 17H) |
| 460 | δ = 9.15(s, 1H), 8.93(d, 2H), 8.81(d, 2H), 8.28(d, 2H), 8.18~7.98(m, 6H), 7.89~7.78(m, 9H), 7.66~7.32(m, 12H) |
| 462 | δ = 9.15(s, 1H), 8.93(d, 2H), 8.30~7.98(m, 11H), 7.89~7.78(m, 7H), 7.66~7.32(m, 13H) |
| 463 | δ = 8.81(d, 2H), 8.08(d, 1H), 7.98(d, 1H), 7.89~7.78(m, 11H), 7.66~7.32(m, 17H) |
| 465 | δ = 8.81(d, 2H), 8.28(d, 2H), 8.06(d, 1H), 7.98~7.78(m, 9H), 7.66~7.28(m, 16H), 1.72(s, 2H) |
| 468 | δ = 8.81(d, 2H), 8.45~8.41(m, 2H), 8.28(d, 2H), 8.08(d, 1H), 7.98(d, 1H), 7.89~7.78(m, 6H), 7.66~7.32(m, 15H) |
| 471 | δ = 8.81(d, 2H), 8.45~8.41(m, 4H), 8.06(m, 1H), 7.98(d, 2H), 7.89~7.78(m, 7H), 7.66~7.32(m, 15H) |
| 473 | δ = 8.30(m, 2H), 8.08(d, 1H), 7.98(d, 1H), 7.89~7.78(m, 5H), 7.66~7.32(m, 15H) |
| 476 | δ = 8.30~8.24(m, 5H), 8.08(d, 1H), 7.98(d, 1H), 7.89~7.78(m, 5H), 7.70~7.25(m, 20H) |
| 479 | δ = 8.30~8.28(m, 9H), 8.08(d, 1H), 7.98(d, 1H), 7.89~7.78(m, 5H), 7.66~7.32(m, 17H) |
| 494 | δ = 8.30~8.24(m, 4H), 8.08(d, 1H), 7.98(d, 1H), 7.89~7.78(m, 5H), 7.70~7.32(m, 29H) |
| 529 | δ = 8.30~8.28(m, 5H), 8.08(d, 1H), 7.98(d, 1H), 7.89~7.32(m, 22H) |
| 573 | δ = 8.55(m, 2H), 8.30~8.28(m, 6H), 8.06~7.98(m, 4H), 7.89~7.78(m, 3H), 7.66~7.32(m, 19H) |
| 575 | δ = 8.55(m, 2H), 8.30~8.24(m, 5H), 8.01~7.98(m, 4H), 7.89(m, 1H), 7.83~7.78(m, 2H), 7.66~7.25(m, 24H) |
| 578 | δ = 8.55(m, 2H), 8.30~8.23(m, 5H), 8.06~7.98(m, 4H), 7.89(m, 1H), 7.66~7.25(m, 27H) |
| 584 | δ = 8.55(d, 2H), 8.30~8.28(m, 6H), 8.06~7.98(m, 4H), 7.89~7.78(m, 3H), 7.66~7.32(m, 19H) |
| 596 | δ = 8.55(d, 1H), 8.30(d, 2H), 8.12~8.06(m, 2H), 7.98~7.79(m, 7H), 7.68~7.25(m, 18H) |
| 598 | δ = 8.55(d, 2H), 8.30(d, 2H), 8.12~8.06(m, 5H), 7.98~7.89(m, 4H), 7.83~7.78(m, 2H), 7.66~7.25(m, 22H) |
| 599 | δ = 8.30(d, 2H), 8.08(d, 1H), 7.98(d, 1H), 7.89~7.78(m, 6H), 7.66~7.32(m, 15H) |
| 602 | δ = 8.30(d, 2H), 8.08(d, 1H), 7.98(d, 1H), 7.89~7.75(m, 5H), 7.66~7.32(m, 16H) |
| 603 | δ = 8.30(d, 2H), 8.08(d, 1H), 7.98(d, 1H), 7.89~7.78(m, 6H), 7.66~7.25(m, 19H) |
| 606 | δ = 8.30(d, 2H), 8.08(d, 1H), 7.98(d, 1H), 7.89(d, 2H), 7.83~7.75(m, 3H), 7.66~7.25(m, 20H) |
| 611 | δ = 8.45~8.41(m, 2H), 8.30(d, 2H), 8.20(m, 1H), 8.06~7.98(m, 3H), 7.89~7.78(m, 3H), 7.66~7.25(m, 14H) |
| 623 | δ = 8.30(m, 2H), 8.06(d, 1H), 7.98(d, 1H), 7.89~7.78(m, 9H), 7.66~7.25(m, 22H) |
| 626 | δ = 8.30(m, 2H), 8.08(d, 1H), 7.98(d, 1H), 7.89~7.75(m, 7H), 7.66~7.25(m, 24H) |
| 663 | δ = 8.45~8.41(m, 4H), 8.30(d, 2H), 8.20~7.78(d, 2H), 7.98~7.70(m, 4H), 7.89~7.78(m, 3H), 7.66~7.32(m, 20H) |
| 667 | δ = 8.99~8.93(m, 3H), 8.34~8.30(m, 3H), 8.12~8.06(m, 4H), 7.98(m, 1H), 7.89~7.83(m, 7H), 7.66~7.25(m, 11H) |
| 668 | δ = 8.99~8.93(m, 3H), 8.30(m, 2H), 8.12~8.06(m, 4H), 7.98(m, 1H), 7.89~7.78(m, 7H), 7.66~7.25(m, 15H) |

TABLE 3-continued

| NO | ¹H NMR (CDCl₃, 300 Mz) |
|---|---|
| 670 | δ = 8.55(d, 1H), 8.30~8.28(m, 4H), 7.94~7.25(m, 30H) |
| 671 | δ = 8.55(d, 1H), 8.30~8.28(m, 5H), 8.12~8.06(m, 3H), 7.98~7.85(m, 7H), 7.66~7.25(m, 19H) |
| 676 | δ = 8.55(d, 1H), 8.30~8.23(m, 7H), 8.06(m, 1H), 7.98~7.79(m, 7H), 7.68~7.25(m, 19H) |
| 679 | δ = 8.55(m, 1H), 8.30~8.23(m, 7H), 8.12~8.06(m, 3H), 7.98~7.79(m, 8H), 7.60~7.25(m, 21H) |
| 682 | δ = 8.55(d, 1H), 8.30~8.23(m, 5H), 8.12~8.06(m, 2H), 7.98~7.79(m, 9H), 7.68~7.25(m, 19H) |
| 695 | δ = 8.55(d, 1H), 8.30~8.23(m, 4H), 8.12~8.06(m, 3H), 7.98~7.25(m, 32H) |
| 696 | δ = 8.28(m, 3H), 8.21(s, 1H), 8.13~8.07(m, 4H), 7.94~7.89(m, 2H), 7.66~7.63(m, 2H), 7.51~7.25(m, 17H), 6.56~6.49(m, 3H), 5.31(d, 1H), 5.24(d, 1H), 5.11(t, 2H), 4.99(t, 2H) |
| 721 | δ = 8.30~8.28(m, 4H), 8.06(d, 1H), 7.98(d, 1H), 7.89~7.78(m, 10H), 7.66~7.32(m, 18H) |
| 722 | δ = 8.30~8.24(m, 5H), 8.06(d, 1H), 7.98(d, 1H), 7.89~7.25(m, 27H) |
| 723 | δ = 8.30~8.28(m, 4H), 8.06(d, 1H), 7.98(d, 1H), 7.89~7.78(m, 10H), 7.66~7.25(m, 22H) |
| 724 | δ = 8.30~8.28(m, 5H), 8.06(d, 1H), 7.98(d, 1H), 7.89~7.78(m, 8H), 7.66~7.25(m, 23H) |
| 727 | δ = 8.30~8.28(m, 9H), 8.06(d, 1H), 7.98(d, 1H), 7.89~7.78(m, 6H), 7.66~7.25(m, 18H) |
| 741 | δ = 8.30(d, 4H), 8.23(s, 1H), 8.06(d, 1H), 7.98(d, 1H), 7.89~7.78(m, 12H), 7.66~7.25(m, 20H) |
| 745 | δ = 8.30~8.24(m, 5H), 8.06(d, 1H), 7.98(d, 1H), 7.85~7.25(m, 27H) |
| 771 | δ = 8.30(d, 2H), 8.06(d, 1H), 7.98(d, 1H), 7.89~7.75(m, 6H), 7.66~7.16(m, 23H) |
| 775 | δ = 8.93(d, 2H), 8.30(d, 2H), 8.12~8.06(m, 3H), 7.98~7.78(m, 9H), 7.66~7.25(m, 11H) |
| 780 | δ = 8.55(d. 1H), 8.30(d, 2H), 8.06(d, 1H), 7.98~7.77(m, 7H), 7.69~7.25(m, 19H) |
| 789 | δ = 8.30(d, 2H), 8.06(d, 1H), 7.98(d, 1H), 7.89~7.77(m, 11H), 7.66~7.25(m, 17H) |
| 792 | δ = 8.55(d, 1H), 8.30(m, 2H), 8.08~8.06(m, 2H), 7.98~7.77(m, 9H), 7.66~7.25(m, 20H) |
| 802 | δ = 8.30(d, 2H), 8.16(d, 1H), 8.06(d, 1H), 7.98(d, 1H), 7.89~7.78(m, 9H), 7.66~7.25(m, 19H) |
| 804 | δ = 8.30(d, 2H), 8.16(d, 2H), 8.06(d, 1H), 7.98(d, 1H), 7.70~7.25(m, 30H) |
| 815 | δ = 8.81(d, 2H), 8.30(d, 2H), 8.10~7.98(m, 5H), 7.89~7.78(m, 6H), 7.66~7.25(m, 13H) |
| 822 | δ = 8.30(d, 2H), 8.06(d, 1H), 7.98(d, 1H), 7.89(m, 1H), 7.83~7.78(m, 6H), 7.66~7.25(m, 24H) |
| 836 | δ = 8.55(d, 1H), 8.30(t, 2H), 8.06(m, 1H), 7.98~7.78(m, 6H), 7.66~7.25(m, 20H) |
| 847 | δ = 8.55(d, 1H), 8.30(d, 2H), 8.08~8.06(m, 2H), 7.98~7.89(m, 2H), 7.77~7.32(m, 26H) |
| 848 | δ = 8.30~8.24(m, 3H), 8.16(d, 1H), 8.06(d, 1H), 7.98(d, 1H), 7.79~7.32(m, 21H) |
| 855 | δ = 8.30(d, 2H), 8.16(d, 1H), 8.06(d, 1H), 7.98(d, 1H), 7.89~7.25(m, 26H) |
| 886 | δ = 8.30(d, 2H), 8.18(d, 1H), 8.06~7.98(m, 4H), 7.89~7.78(m, 3H), 7.66~7.32(m, 12H) |
| 889 | δ = 8.81(d, 2H), 8.30(d, 2H), 8.10~7.81(m, 5H), 7.89~7.78(m, 4H), 7.66~7.32(m, 14H) |
| 890 | δ = 8.81(t, 2H), 8.30(d, 4H), 8.10~7.98(m, 5H), 7.89~7.81(m, 6H), 7.66~7.25(m, 16H) |
| 892 | δ = 8.55~8.52(m, 3H), 8.30(d, 4H), 8.10~7.98(m, 6H), 7.89~7.78(m, 4H), 7.60~7.32(m, 18H) |
| 895 | δ = 8.56(d, 1H), 8.30(d, 2H), 8.06(d, 1H), 7.98(d, 1H), 7.89~7.79(m, 5H), 7.68~7.22(m, 16H), 2.85(m, 1H), 1.25(m, 1H) |
| 906 | δ = 8.55~8.52(m, 3H), 8.30(m, 4H), 8.10~7.98(m, 4H), 7.89~7.78(m, 4H), 7.66~7.32(m, 18H) |
| 914 | δ = 8.55(d, 1H), 8.30(m, 2H), 8.08~7.78(m, 9H), 7.66~7.32(m, 15H) |
| 915 | δ = 8.55(m, 2H), 8.30(m, 2H), 8.08~7.78(m, 13H), 7.66~7.32(m, 15H) |
| 917 | δ = 9.09(s, 1H), 8.49(d, 2H), 8.30(d, 2H), 8.00~7.78(m, 13H), 7.66~7.25(m, 13H) |
| 920 | δ = 8.55(m, 1H), 8.30~8.28(m, 4H), 8.08~7.78(m, 10H), 7.66~7.25(m, 19H) |
| 928 | δ = 8.30~8.24(m, 5H), 8.06(d, 1H), 7.98(d, 1H), 7.89(d, 1H), 7.83~7.66(m, 2H), 7.66~7.32(m, 26H) |
| 933 | δ = 9.15(s, 1H), 8.93(d, 2H), 8.30~8.28(m, 4H), 8.18~7.98(m, 6H), 7.88~7.78(m, 9H), 7.66~7.25(m, 16H) |
| 937 | δ = 8.30~8.28(m, 4H), 8.06(d, 1H), 7.98~7.78(m, 9H), 7.66~7.25(m, 16H) |
| 943 | δ = 8.45~8.41(m, 4H), 8.30(d, 2H), 8.06~7.98(m, 4H), 7.89~7.78(m, 7H), 7.66~7.25(m, 15H) |
| 945 | δ = 8.81(d, 2H), 8.28(d, 4H), 8.06(d, 1H), 7.98(d, 1H), 7.89~7.78(m, 5H), 7.66~7.25(m, 19H) |
| 946 | δ = 9.09(s, 2H), 8.81(d, 2H), 8.49(d, 2H), 7.92~7.78(m, 13H), 7.66~7.25(m, 17H) |

TABLE 3-continued

| NO | ¹H NMR (CDCl₃, 300 Mz) |
|---|---|
| 947 | δ = 8.81(d, 2H), 8.55(m, 2H), 8.08~7.78(m, 13H), 7.66~7.25(m, 19h) |
| 948 | δ = 8.28(m, 2H), 8.06(d, 1H), 7.98(d, 1H), 7.89~7.78(m, 5H), 7.66~7.25(m, 29H) |
| 949 | δ = 8.81(d, 2H), 8.28(d, 2H), 8.06(d, 1H), 7.98(d, 1H), 7.89~7.78(m, 8H), 7.66~7.25(m, 20H) |
| 950 | δ = 8.81(d, 2H), 8.45~8.41(m, 2H), 8.28(m, 2H), 8.06(d, 1H), 7.98(m, 2H), 7.89~7.78(m, 6H), 7.66~7.25(m, 19H) |
| 953 | δ = 8.81(d, 2H), 8.52(d, 4H), 8.06(d, 1H), 7.98(d, 1H), 7.89~7.78(m, 5H), 7.66~7.25(m, 17H) 2.34(s, 2H) |
| 956 | δ = 9.15(s, 1H), 8.93(d, 2H), 8.81(d, 2H), 8.28(d, 2H), 8.12~7.98(m, 6H), 7.89~7.78(m, 9H), 7.66~7.25(m, 16H) |
| 957 | δ = 8.28(d, 2H), 8.06(d, 1H), 7.98~7.78(m, 9H), 7.66~7.25(m, 20H), 1.72(s, 2H) |
| 973 | δ = 8.81(d, 2H), 8.28(d, 4H), 8.06(d, 1H), 7.98(d, 1H), 7.89~7.78(m, 7H), 7.66~7.32(m, 17H) |
| 974 | δ = 9.09(s, 2H), 8.81(d, 2H), 8.49(d, 2H), 8.00~7.78(m, 15H), 7.66~7.25(m, 15H) |
| 975 | δ = 8.81(d, 2H), 8.55(d, 2H), 8.08~7.79(m, 15H), 7.66~7.25(m, 17H) |
| 976 | δ = 8.81(d, 2H), 8.28(m, 2H), 8.06(d, 1H), 7.98(d, 1H), 7.88~7.79(m, 7H), 7.66~7.25(m, 27H) |
| 977 | δ = 8.81(d, 2H), 8.28(d, 2H), 8.06(d, 1H), 7.98(d, 1H), 7.89~7.78(m, 10H), 7.66~7.25(m, 18H) |
| 978 | δ = 8.81(d, 2H), 8.45~8.41(m, 2H), 8.28(d, 2H), 8.06(d, 1H), 7.98(m, 2H), 7.89~7.78(m, 8H), 7.66~7.25(m, 17H) |
| 981 | δ = 8.81(d, 2H), 8.52(d, 4H), 8.06(d, 1H), 7.98(d, 1H), 7.89~7.78(m, 7H), 7.66~7.25(m, 15H), 2.34(s, 2H) |
| 984 | δ = 9.15(s, 1H), 8.93(d, 2H), 8.81(d, 2H), 8.28(d, 2H), 8.12~8.04(m, 6H), 7.89~7.82(m, 11H), 7.66~7.32(m, 14H) |
| 985 | δ = 8.81(d, 2H), 8.28(d, 2H), 7.98~7.78(m, 11H), 7.66~7.25(m, 17H), 1.72(s, 2H) |
| 1015 | δ = 9.15(s, 1H), 8.93(d, 2H), 8.28~7.78(m, 13H), 7.89~7.78(m, 7H), 7.66~7.32(m, 11H) |
| 1016 | δ = 9.15~9.09(m, 3H), 8.93(d, 2H), 8.49(d, 2H), 8.00~7.78(m, 22H), 7.66~7.59(m, 7H), 7.38~7.32(m, 2H) |
| 1017 | δ = 9.15(s, 1H), 8.93(d, 2H), 8.55(d, 2H), 8.18~7.83(m, 22H), 7.66~7.55(m, 9H), 7.38~7.32(m, 2H) |
| 1018 | δ = 9.15(s, 1H), 8.93(d, 2H), 8.28~8.04(m, 11H), 7.89~7.78(m, 7H), 7.66~7.32(m, 21H) |
| 1023 | δ = 9.15(s, 1H), 8.93(d, 2H), 8.52(d, 4H), 8.30~8.12(m, 9H), 7.89~7.82(m, 7H), 7.66~7.60(m, 3H), 7.38~7.29(m, 6H), 2.34(s, 2H) |
| 1026 | δ = 9.15(s, 2H), 8.93(d, 3H), 8.28~7.88(m, 26H), 7.66~7.51(m, 5H), 7.41~7.32(m, 3H) |
| 1027 | δ = 9.15(s, 1H), 8.93(d, 2H), 8.30~7.78(m, 21H), 7.66~7.51(m, 7H), 7.41~7.28(m, 5H), 1.72(s, 2H) |
| 1043 | δ = 9.66(s, 1H), 8.93(d, 2H), 8.55(d, 1H), 8.28~8.21(m, 6H), 8.12~7.98(m, 4H), 7.89~7.32(m, 20H) |
| 1044 | δ = 9.66(s, 1H), 9.09(s, 2H), 8.93(d, 2H), 8.55~8.49(m, 3H), 8.24~8.21(m, 2H), 8.00~7.60(m, 25H), 7.48(m, 1H), 7.38~7.32(m, 2H) |
| 1045 | δ = 9.66(s, 1H), 8.93(d, 2H), 8.55(d, 3H), 8.24~8.21(m, 2H), 8.08~7.55(m, 27H), 7.95~7.67(m, 2H) |
| 1046 | δ = 9.66(s, 1H), 8.93(d, 2H), 8.55(d, 1H), 8.28~8.24(m, 4H), 8.12~8.06(m, 3H), 7.98(d, 1H), 7.89~7.82(m, 7H), 7.66~7.32 |
| 1051 | δ = 9.66(s, 1H), 8.93(d, 2H), 8.55~8.52(m, 5H), 8.24~8.21(m, 2H), 8.12~8.06(m, 3H), 7.98(m, 1H), 7.88~7.57(m, 11H), 7.48(1H), 7.38~7.29(m, 6H), 2.34(s, 2H) |
| 1054 | δ = 9.66(s, 1H), 9.15(s, 1H), 8.93(d, 4H), 8.55(d, 1H), 8.28~7.28(m, 33H) |
| 1055 | δ = 8.93(d, 2H), 8.55(d, 2H), 8.28~8.21(m, 4H), 8.12~8.06(m, 3H), 7.98~7.77(m, 10H), 7.66~7.28(m, 14H), 1.72(s, 2H) |
| 1057 | δ = 8.81(d, 2H), 8.28(m, 4H), 8.06(m, 1H), 7.98(d, 1H), 7.89~7.78(m, 8H), 7.66~7.32(m, 14H) |
| 1058 | δ = 9.09(s, 2H), 8.81(d, 2H), 8.49(m, 2H), 8.00~7.78(m, 16H), 7.66~7.59(m, 7H), 7.98~7.32(m, 5H) |
| 1060 | δ = 8.81(d, 2H), 8.28(d, 2H), 8.06(m, 1H), 7.98(d, 1H), 7.89~7.78(m, 7H), 7.66~7.32(m, 24H) |
| 1068 | δ = 9.15(s, 1H), 8.93(d, 2H), 8.81(d, 2H), 8.28(d, 2H), 8.18~7.98(m, 6H), 7.89~7.78(m, 11H), 7.66~7.51(m, 5H), 7.41~7.32(m, 6H) |
| 1075 | δ = 8.30~8.21(m, 5H), 8.06(d, 1H), 7.98(d, 1H), 7.89~7.81(m, 8H), 7.66~7.32(m, 16H) |
| 1079 | δ = 8.52(d, 4H), 8.30~8.21(m, 3H), 8.06(d, 1H), 7.98(d, 1H), 7.89~7.83(m, 6H), 7.66~7.60(m, 3H), 7.38~7.29(m, 9H), 2.34(s, 2H) |
| 1085 | δ = 8.81(d, 2H), 8.33~8.23(m, 5H), 8.06(d, 1H), 7.98(d, 1H), 7.83~7.79(m, 5H), 7.66~7.25(m, 19H) |
| 1086 | δ = 9.09(s, 1H), 8.81(d, 2H), 8.49(d, 1H), 8.34~8.33(m, 3H), 8.23(s, 1H), 8.00~7.78(m, 12H), 7.66~7.25(m, 17H) |
| 1088 | δ = 8.81(d, 2H), 8.33~8.28(m, 5H), 7.06(d, 1H), 7.98(d, 1H), 7.89(d, 1H), 7.83~7.78(m, 2H), 7.66~7.25(m, 29H) |
| 1096 | δ = 9.15(s, 1H), 8.93(d, 2H), 8.81(d, 2H), 8.33~7.98(m, 11H), 7.88~7.79(m, 7H), 7.66~7.25(m, 16H) |

TABLE 3-continued

| NO | $^1$H NMR (CDCl$_3$, 300 Mz) |
|---|---|
| 1099 | δ = 8.28~8.21(m, 5H), 8.06(d, 1H), 7.98(d, 1H), 7.89(d, 1H), 7.83~7.81(m, 2H), 7.66~7.25(m, 20H) |
| 1103 | δ = 8.28~8.23(m, 5H), 8.06(d, 1H), 7.98(d, 1H), 7.89~7.78(m, 6H), 7.66~7.25(m, 22H) |

TABLE 4

| Compound | FD-MS |
|---|---|
| 1 | m/z = 652.74 (C46H28N4O = 652.23) |
| 2 | m/z = 728.84 (C52H32N4O = 728.26) |
| 4 | m/z = 728.84 (C52H32N4O = 728.26) |
| 5 | m/z = 804.93 (C58H36N4O = 804.29) |
| 7 | m/z = 803.94 (C59H37N3O = 803.29) |
| 8 | m/z = 803.94 (C59H37N3O = 803.29) |
| 9 | m/z = 727.85 (C53H33N3O = 727.26) |
| 15 | m/z = 803.94 (C59H37N3O = 803.29) |
| 18 | m/z = 728.84 (C52H32N4O = 728.26) |
| 20 | m/z = 881.03 (C64H40N4O = 880.32) |
| 29 | m/z = 803.94 C59H37N3O = 803.29 |
| 33 | m/z = 803.94 (C59H37N3O = 803.29 |
| 35 | m/z = 728.84 (C52H32N4O = 728.26) |
| 38 | m/z = 804.93 (C58H36N4O = 804.29) |
| 40 | m/z = 727.85 (C53H33N3O = 727.26) |
| 47 | m/z = 880.04 (C65H41N3O = 879.32) |
| 49 | m/z = 880.04 (C65H41N3O = 879.32 |
| 52 | m/z = 728.84 (C52H32N4O = 728.26) |
| 53 | m/z = 652.74 (C46H28N4O = 652.23) |
| 55 | m/z = 728.84 (C52H32N4O = 728.26) |
| 57 | m/z = 651.75 (C47H29N3O = 651.23) |
| 58 | m/z = 727.85 (C53H33N3O = 727.26) |
| 70 | m/z = 804.93 (C58H36N4O = 804.29) |
| 75 | m/z = 803.94 (C59H37N3O = 803.29) |
| 86 | m/z = 728.84 (C52H32N4O = 728.26) |
| 87 | m/z = 804.93 (C58H36N4O = 804.29) |
| 94 | m/z = 803.94 (C59H37N3O = 803.29) |
| 101 | m/z = 778.90 (C56H34N4O = 778.27) |
| 102 | m/z = 854.99 (C62H38N4O = 854.30) |
| 103 | m/z = 854.99 (C62H38N4O = 854.30) |
| 104 | m/z = 777.91 (C57H35N3O = 777.28) |
| 105 | m/z = 854.00 (C63H39N3O = 853.31) |
| 112 | m/z = 778.90 (C56H34N4O = 778.27) |
| 113 | m/z = 854.99 (C62H38N4O = 854.30) |
| 115 | m/z = 777.91 (C57H35N3O = 777.28) |
| 116 | m/z = 854.00 (C63H39N3O = 853.31) |
| 124 | m/z = 662.78 (C49H30N2O = 662.24) |
| 126 | m/z = 689.80 (C61H37N3O = 827.29) |
| 127 | m/z = 587.66 (C43H25NO2 = 587.19) |
| 130 | m/z = 587.66 (C43H25NO2 = 587.19) |
| 131 | m/z = 663.76 (C49H29NO2 = 663.22) |
| 133 | m/z = 663.76 (C49H29NO2 = 663.22) |
| 136 | m/z = 663.76 (C49H29NO2 = 663.22) |
| 139 | m/z = 603.73 (C43H25NOS = 603.17) |
| 141 | m/z = 603.73 (C43H25NOS = 603.17) |
| 142 | m/z = 603.73 (C43H25NOS = 603.17) |
| 151 | m/z = 829.94 (C61H35NO3 = 829.26) |
| 154 | m/z = 829.94 (C61H35NO3 = 829.26) |
| 158 | m/z = 862.07 (C61H35NOS2 = 861.22) |
| 160 | m/z = 662.78 (C49H30N2O = 662.24) |
| 162 | m/z = 827.97 (C61H37N3O = 827.29) |
| 175 | m/z = 603.73 (C43H25NOS = 603.17) |
| 186 | m/z = 679.83 (C49H29NOS = 679.20) |
| 190 | m/z = 829.94 (C61H35NO3 = 829.26) |
| 193 | m/z = 862.07 (C61H35NOS2 = 861.22) |
| 195 | m/z = 647.76 (C49H29NO = 647.22) |
| 196 | m/z = 723.86 (C55H33NO = 723.26) |
| 198 | m/z = 817.93 (C58H35N5O = 817.28) |
| 199 | m/z = 817.93 (C58H35N5O = 817.28) |
| 200 | m/z = 894.03 (C64H39N5O = 893.32) |
| 201 | m/z = 894.03 (C64H39N5O = 893.32) |
| 202 | m/z = 894.03 (C64H39N5O = 893.32) |
| 203 | m/z = 894.03 (C64H39N5O = 893.32) |
| 204 | m/z = 816.94 (C59H36N4O = 816.29) |
| 205 | m/z = 816.94 (C59H36N4O = 816.29) |
| 206 | m/z = 893.04 (C65H40N4O = 892.32) |
| 209 | m/z = 893.04 (C65H40N4O = 892.32) |
| 211 | m/z = 816.94 (C59H36N4O = 816.29) |
| 221 | m/z = 723.86 (C55H33NO = 723.26) |
| 223 | m/z = 817.93 (C58H35N5O = 817.28) |
| 224 | m/z = 817.93 (C58H35N5O = 817.28) |
| 230 | m/z = 816.94 (C59H36N4O = 816.29) |
| 232 | m/z = 893.04 (C65H40N4O = 892.32) |
| 240 | m/z = 893.04 (C65H40N4O = 892.32) |
| 242 | m/z = 816.94 (C59H36N4O = 816.29) |
| 249 | m/z = 818.92 (C58H34N4O2 = 818.27) |
| 250 | m/z = 818.92 (C58H34N4O2 = 818.27) |
| 251 | m/z = 895.01 (C64H38N4O2 = 894.30) |
| 252 | m/z = 895.01 (C64H38N4O2 = 894.30) |
| 255 | m/z = 817.93 (C59H35N3O2 = 817.27) |
| 259 | m/z = 894.02 (C65H39N3O2 = 893.30) |
| 273 | m/z = 818.92 (C58H34N4O2 = 818.27) |
| 274 | m/z = 818.92 (C58H34N4O2 = 818.27) |
| 279 | m/z = 817.93 (C59H35N3O2 = 817.27) |
| 281 | m/z = 894.02 (C65H39N3O2 = 893.30) |
| 297 | m/z = 735.87 (C56H33NO = 735.26) |
| 298 | m/z = 735.87 (C56H33NO = 735.26) |
| 299 | m/z = 735.87 (C56H33NO = 735.26) |
| 301 | m/z = 737.88 (C56H35NO = 737.27) |
| 302 | m/z = 737.88 (C56H35NO = 737.27) |
| 303 | m/z = 597.70 (C45H27NO = 597.21) |
| 308 | m/z = 662.78 (C49H30N2O = 662.24) |
| 309 | m/z = 662.78 (C49H30N2O = 662.24) |
| 317 | m/z = 697.76 (C49H32NO2P = 697.22) |
| 319 | m/z = 747.82 (C53H34NO2P = 747.23) |
| 320 | m/z = 747.82 (C53H34NO2P = 747.23) |
| 321 | m/z = 625.72 (C45H27N3O = 625.22) |
| 324 | m/z = 777.91 (C57H35N3O = 777.28) |
| 326 | m/z = 777.91 (C57H35N3O = 777.28) |
| 327 | m/z = 625.72 (C45H27N3O = 625.22) |
| 334 | m/z = 701.81 (C51H31N3O = 701.25) |
| 339 | m/z = 554.66 (C38H22N2OS = 554.15) |
| 342 | m/z = 548.63 (C40H24N2O = 548.19) |
| 347 | m/z = 689.80 (C50H31N3O = 689.25) |
| 349 | m/z = 727.85 (C53H33N3O = 727.26) |
| 375 | m/z = 747.82 (C53H34NO2P = 747.23) |
| 376 | m/z = 625.72 (C45H27N3O = 625.22) |
| 383 | m/z = 701.81 (C51H31N3O = 701.25) |
| 413 | m/z = 680.79 (C48H32N4O = 680.26) |
| 415 | m/z = 756.89 (C54H36N4O = 756.29) |
| 416 | m/z = 599.68 (C43H25N3O = 599.20) |
| 417 | m/z = 675.77 (C49H29N3O = 675.23) |
| 418 | m/z = 751.87 (C55H33N3O = 751.26) |
| 419 | m/z = 751.87 (C55H33N3O = 751.26) |
| 420 | m/z = 801.93 (C59H35N3O = 801.28) |
| 427 | m/z = 680.79 (C48H32N4O = 680.26) |
| 430 | m/z = 599.68 (C43H25N3O = 599.20) |
| 431 | m/z = 675.77 (C49H29N3O = 675.23) |
| 432 | m/z = 751.87 (C55H33N3O = 751.26) |
| 437 | m/z = 641.76 (C46H31N3O = 641.25) |
| 445 | m/z = 778.90 (C56H34N4O = 778.27) |
| 446 | m/z = 778.90 (C56H34N4O = 778.27) |
| 447 | m/z = 828.95 (C60H36N4O = 828.29) |
| 449 | m/z = 828.95 (C60H36N4O = 828.29) |
| 453 | m/z = 752.86 (C54H32N4O = 752.26) |
| 454 | m/z = 804.93 (C58H36N4O = 804.29) |
| 456 | m/z = 804.93 (C58H36N4O = 804.29) |
| 457 | m/z = 742.82 (C52H30N4O2 = 742.24) |
| 459 | m/z = 742.82 (C52H30N4O2 = 742.24) |
| 460 | m/z = 802.92 (C58H34N4O = 802.27) |
| 462 | m/z = 802.92 (C58H34N4O = 802.27) |
| 463 | m/z = 832.90 (C58H32N4O3 = 832.25) |

TABLE 4-continued

| Compound | FD-MS |
|---|---|
| 465 | m/z = 768.90 (C55H36N4O = 768.29) |
| 468 | m/z = 758.89 (C52H30N4OS = 758.21) |
| 471 | m/z = 865.03 (C58H32N4OS2 = 864.20) |
| 473 | m/z = 652.74 (C46H28N4O = 652.23) |
| 476 | m/z = 728.84 (C52H32N4O = 728.26) |
| 479 | m/z = 727.85 (C53H33N3O = 727.26) |
| 494 | m/z = 881.03 (C64H40N4O = 880.32) |
| 529 | m/z = 651.75 (C47H29N3O = 651.23) |
| 573 | m/z = 778.90 (C56H34N4O = 778.27) |
| 575 | m/z = 854.99 (C62H38N4O = 854.30) |
| 578 | m/z = 854.00 (C63H39N3O = 853.31) |
| 584 | m/z = 778.90 (C56H34N4O = 778.27) |
| 596 | m/z = 662.78 (C49H30N2O = 662.24) |
| 598 | m/z = 827.97 (C61H37N3O = 827.29) |
| 599 | m/z = 587.66 (C43H25NO2 = 587.19) |
| 602 | m/z = 587.66 (C43H25NO2 = 587.19) |
| 603 | m/z = 663.76 (C49H29NO2 = 663.22) |
| 606 | m/z = 663.76 (C49H29NO2 = 663.22) |
| 611 | m/z = 603.73 (C43H25NOS = 603.17) |
| 623 | m/z = 829.94 (C61H35NO3 = 829.26) |
| 626 | m/z = 829.94 (C61H35NO3 = 829.26) |
| 663 | m/z = 862.07 (C61H35NOS2 = 861.22) |
| 667 | m/z = 647.76 (C49H29NO = 647.22) |
| 668 | m/z = 723.86 (C55H33NO = 723.26) |
| 670 | m/z = 817.93 C58H35N5O = 817.28 |
| 671 | m/z = 817.93 (C58H35N5O = 817.28) |
| 676 | m/z = 816.94 (C59H36N4O = 816.29) |
| 679 | m/z = 893.04 (C65H40N4O = 892.32) |
| 682 | m/z = 816.94 (C59H36N4O = 816.29) |
| 695 | m/z = 817.93 (C58H35N5O = 817.28) |
| 696 | m/z = 817.93 (C58H35N5O = 817.28) |
| 721 | m/z = 818.92 (C58H34N4O2 = 818.27) |
| 722 | m/z = 818.92 (C58H34N4O2 = 818.27) |
| 723 | m/z = 895.01 (C64H38N4O2 = 894.30) |
| 724 | m/z = 895.01 (C64H38N4O2 = 894.30) |
| 727 | m/z = 817.93 (C59H35N3O2 = 817.27) |
| 741 | m/z = 894.02 (C65H39N3O2 = 893.30) |
| 745 | m/z = 818.92 (C58H34N4O2 = 818.27) |
| 771 | m/z = 735.87 (C56H33NO = 735.26) |
| 775 | m/z = 597.70 (C45H27NO = 597.21) |
| 780 | m/z = 662.78 (C49H30N2O = 662.24) |
| 789 | m/z = 697.76 (C49H32NO2P = 697.22) |
| 792 | m/z = 747.82 (C53H34NO2P = 747.23) |
| 802 | m/z = 777.91 (C57H35N3O = 777.28) |
| 804 | m/z = 777.91 (C57H35N3O = 777.28) |
| 815 | m/z = 624.73 (C46H28N2O = 624.22) |
| 822 | m/z = 803.94 (C59H37N3O = 803.29) |
| 836 | m/z = 662.78 (C49H30N2O = 662.24) |
| 847 | m/z = 747.82 (C53H34NO2P = 747.23) |
| 848 | m/z = 625.72 (C45H27N3O = 625.22) |
| 855 | m/z = 701.81 (C51H31N3O = 701.25) |
| 886 | m/z = 756.89 (C54H36N4O = 756.29) |
| 889 | m/z = 675.77 (C49H29N3O = 675.23) |
| 890 | m/z = 751.87 (C55H33N3O = 751.26) |
| 892 | m/z = 801.93 (C59H35N3O = 801.28) |
| 895 | m/z = 641.76 (C46H31N3O = 641.25) |
| 906 | m/z = 801.93 (C59H35N3O = 801.28) |
| 914 | m/z = 702.80 (C50H30N4O = 702.24) |
| 915 | m/z = 752.86 (C54H32N4O = 752.26) |
| 917 | m/z = 752.86 (C54H32N4O = 752.26) |
| 920 | m/z = 778.90 (C56H34N4O = 778.27) |
| 928 | m/z = 804.93 (C58H36N4O = 804.29) |
| 933 | m/z = 879.01 (C64H38N4O = 878.30) |
| 937 | m/z = 768.90 (C55H36N4O = 768.29) |
| 943 | m/z = 865.03 (C58H32N4OS2 = 864.20) |
| 945 | m/z = 728.84 (C52H32N4O = 728.26) |
| 946 | m/z = 828.95 (C60H36N4O =: 828.29) |
| 947 | m/z = 828.95 (C60H36N4O = 828.29) |
| 948 | m/z = 881.03 (C64H40N4O = 880.32) |
| 949 | m/z = 818.92 (C58H34N4O2 = 818.27) |
| 950 | m/z = 834.98 (C58H34N4OS = 834.25) |
| 953 | m/z = 756.89 (C54H36N4O = 756.29) |
| 956 | m/z = 879.01 (C64H38N4O = 878.30) |
| 957 | m/z = 845.00 (C61H40N4O = 844.32) |
| 973 | m/z = 728.84 (C52H32N4O = 728.26) |
| 974 | m/z = 828.95 (C60H36N4O = 828.29) |
| 975 | m/z = 828.95 (C60H36N4O = 828.29) |
| 976 | m/z = 881.03 (C64H40N4O = 880.32) |
| 977 | m/z = 818.92 (C58H34N4O2 = 818.27) |
| 978 | m/z = 834.98 (C58H34N4OS = 834.25) |
| 981 | m/z = 756.89 (C54H36N4O = 756.29) |
| 984 | m/z = 879.01 (C64H38N4O = 878.30) |
| 985 | m/z = 845.00 (C61H40N4O = 844.32) |
| 1015 | m/z = 802.92 (C58H34N4O = 802.27) |
| 1016 | m/z = 903.03 (C66H38N4O = 902.30) |
| 1017 | m/z = 903.03 (C66H38N4O = 902.30) |
| 1018 | m/z = 955.11 (C66H38N4O = 902.30) |
| 1023 | m/z = 955.11 (C70H42N4O = 954.34) |
| 1026 | m/z = 953.09 (C70H40N4O = 952.32) |
| 1027 | m/z = 919.08 (C67H42N4O = 918.34) |
| 1043 | m/z = 802.92 (C58H34N4O = 802.27) |
| 1044 | m/z = 903.03 (C66H38N4O = 902.30) |
| 1045 | m/z = 903.03 (C66H38N4O = 902.30) |
| 1046 | m/z = 955.11 (C70H42N4O = 954.34) |
| 1051 | m/z = 830.97 (C60H38N4O = 830.30) |
| 1054 | m/z = 953.09 (C70H40N4O = 952.32) |
| 1055 | m/z = 919.08 (C67H42N4O = 918.34) |
| 1057 | m/z = 842.94 (C60H34N4O2 = 842.27) |
| 1058 | m/z = 742.82 (C52H30N4O2 = 742.24) |
| 1060 | m/z = 95.01 (C64H38N4O2 = 894.30) |
| 1068 | m/z = 893.00 (C64H36N4O2 = 892.28) |
| 1075 | m/z = 832.90 (C58H32N4O3 = 832.25) |
| 1079 | m/z = 770.87 (C54H34N4O2 = 770.27) |
| 1085 | m/z = 727.85 (C53H33N3O = 727.26) |
| 1086 | m/z = 827.97 (C61H37N3O = 827.29) |
| 1088 | m/z = 880.04 (C65H41N3O = 879.32) |
| 1096 | m/z = 878.02 (C65H39N3O = 877.31) |
| 1099 | m/z = 727.85 (C53H33N3O = 727.26) |
| 1103 | m/z = 817.93 (C59H35N3O2 = 817.27) |

<Experimental Example 1> Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was deposited on a cell in the vacuum deposition apparatus.

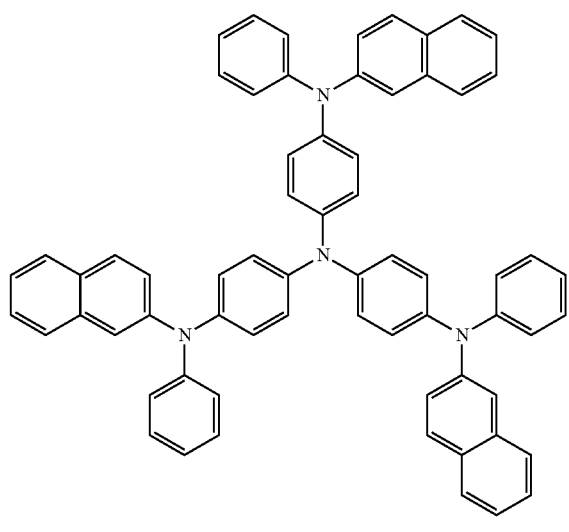

2-TNATA

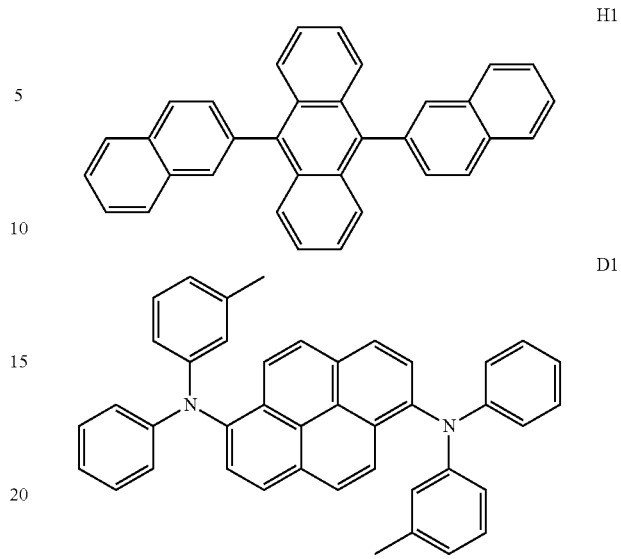

H1

D1

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

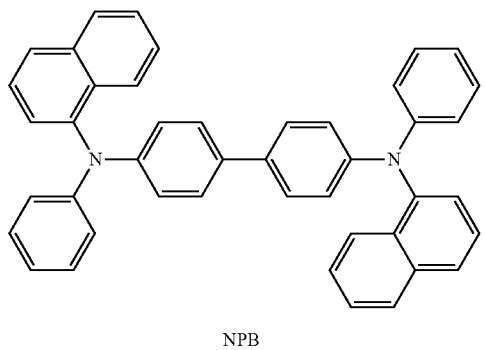

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

Subsequently, a compound of the following Table 5 was deposited to a thickness of 300 Å as an electron transfer layer.

As an electron injection layer, lithium fluoride (LiF) was deposited to a thickness of 10 Å, and an Al cathode was employed to a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

Results of measuring a driving voltage, light emission efficiency, a color coordinate (CIE) and a lifetime of the blue organic light emitting device manufactured according to the present disclosure are as shown in Table 5.

TABLE 5

| | Compound | Driving voltage (V) | Light Emission Efficiency (cd/A) | CIE (x, y) | Lifetime ($T_{95}$) |
|---|---|---|---|---|---|
| Comparative Example 1 | E1 | 5.56 | 5.31 | (0.134, 0.100) | 28 |
| Comparative Example 2 | E2 | 5.51 | 5.44 | (0.134, 0.101) | 38 |
| Comparative Example 3 | E3 | 5.53 | 5.48 | (0.134, 0.101) | 36 |
| Comparative Example 4 | E4 | 5.43 | 5.61 | (0.134, 0.100) | 32 |
| Example 1 | 2 | 5.23 | 6.67 | (0.134, 0.101) | 52 |
| Example 2 | 4 | 5.14 | 6.89 | (0.134, 0.102) | 54 |
| Example 3 | 5 | 5.34 | 6.58 | (0.134, 0.101) | 44 |
| Example 4 | 7 | 5.38 | 6.51 | (0.134, 0.103) | 47 |
| Example 5 | 8 | 5.11 | 6.75 | (0.134, 0.102) | 46 |
| Example 6 | 9 | 5.42 | 6.21 | (0.134, 0.101) | 54 |
| Example 7 | 15 | 5.13 | 6.63 | (0.134, 0.102) | 52 |
| Example 8 | 18 | 5.05 | 6.66 | (0.134, 0.101) | 49 |
| Example 9 | 20 | 5.42 | 6.13 | (0.134, 0.101) | 41 |

TABLE 5-continued

| | Compound | Driving voltage (V) | Light Emission Efficiency (cd/A) | CIE (x, y) | Lifetime ($T_{95}$) |
|---|---|---|---|---|---|
| Example 10 | 29 | 5.44 | 5.94 | (0.134, 0.100) | 43 |
| Example 11 | 33 | 5.27 | 6.17 | (0.134, 0.101) | 46 |
| Example 12 | 35 | 5.68 | 5.88 | (0.134, 0.102) | 45 |
| Example 13 | 38 | 5.54 | 5.86 | (0.134, 0.100) | 49 |
| Example 14 | 40 | 5.61 | 5.68 | (0.134, 0.100) | 50 |
| Example 15 | 47 | 5.44 | 5.56 | (0.134, 0.102) | 51 |
| Example 16 | 49 | 5.46 | 5.91 | (0.134, 0.101) | 50 |
| Example 17 | 52 | 5.48 | 5.92 | (0.134, 0.100) | 48 |
| Example 18 | 53 | 5.60 | 5.69 | (0.134, 0.101) | 49 |
| Example 19 | 55 | 4.96 | 5.77 | (0.134, 0.101) | 50 |
| Example 20 | 57 | 4.89 | 5.67 | (0.134, 0.102) | 52 |
| Example 21 | 58 | 5.55 | 5.69 | (0.134, 0.100) | 55 |
| Example 22 | 70 | 5.56 | 5.89 | (0.134, 0.101) | 47 |
| Example 23 | 75 | 5.23 | 5.72 | (0.134, 0.101) | 49 |
| Example 24 | 86 | 5.42 | 5.71 | (0.134, 0.101) | 48 |
| Example 25 | 87 | 5.32 | 5.61 | (0.134, 0.100) | 50 |
| Example 26 | 94 | 5.53 | 5.63 | (0.134, 0.102) | 52 |
| Example 27 | 101 | 5.01 | 5.59 | (0.134, 0.102) | 53 |
| Example 28 | 102 | 5.52 | 5.89 | (0.134, 0.102) | 48 |
| Example 29 | 103 | 5.21 | 5.77 | (0.134, 0.101) | 49 |
| Example 30 | 104 | 4.86 | 5.81 | (0.134, 0.102) | 50 |
| Example 31 | 105 | 5.42 | 5.86 | (0.134, 0.101) | 51 |
| Example 32 | 112 | 5.23 | 5.83 | (0.134, 0.101) | 50 |
| Example 33 | 113 | 5.12 | 5.96 | (0.134, 0.100) | 53 |
| Example 34 | 115 | 5.06 | 5.94 | (0.134, 0.102) | 49 |
| Example 35 | 116 | 5.23 | 5.91 | (0.134, 0.101) | 48 |
| Example 36 | 124 | 5.08 | 5.86 | (0.134, 0.100) | 50 |
| Example 37 | 126 | 5.13 | 5.87 | (0.134, 0.102) | 52 |
| Example 38 | 196 | 5.24 | 5.75 | (0.134, 0.101) | 48 |
| Example 39 | 198 | 5.12 | 5.56 | (0.134, 0.100) | 49 |
| Example 40 | 199 | 5.45 | 5.76 | (0.134, 0.101) | 38 |
| Example 41 | 200 | 5.44 | 5.68 | (0.134, 0.102) | 42 |
| Example 42 | 201 | 5.47 | 5.79 | (0.134, 0.101) | 46 |
| Example 43 | 202 | 4.77 | 5.72 | (0.134, 0.102) | 39 |
| Example 44 | 203 | 4.86 | 5.92 | (0.134, 0.101) | 40 |
| Example 45 | 204 | 5.48 | 5.91 | (0.134, 0.100) | 35 |
| Example 46 | 205 | 4.91 | 5.93 | (0.134, 0.102) | 37 |
| Example 47 | 206 | 4.63 | 5.78 | (0.134, 0.101) | 46 |
| Example 48 | 209 | 4.86 | 5.89 | (0.134, 0.102) | 48 |
| Example 49 | 211 | 5.50 | 5.76 | (0.134, 0.101) | 41 |
| Example 50 | 221 | 5.51 | 5.74 | (0.134, 0.101) | 51 |
| Example 51 | 223 | 5.41 | 5.70 | (0.134, 0.102) | 50 |
| Example 52 | 224 | 5.49 | 5.72 | (0.134, 0.100) | 52 |
| Example 53 | 230 | 5.46 | 5.89 | (0.134, 0.101) | 55 |
| Example 54 | 232 | 5.40 | 5.68 | (0.134, 0.101) | 48 |
| Example 55 | 240 | 5.48 | 5.69 | (0.134, 0.102) | 42 |
| Example 56 | 242 | 4.66 | 5.72 | (0.134, 0.100) | 49 |
| Example 57 | 249 | 5.49 | 5.89 | (0.134, 0.102) | 50 |
| Example 58 | 250 | 5.44 | 5.88 | (0.134, 0.101) | 57 |
| Example 59 | 251 | 5.45 | 5.92 | (0.134, 0.101) | 52 |
| Example 60 | 252 | 5.50 | 5.94 | (0.134, 0.102) | 54 |
| Example 61 | 255 | 5.47 | 5.96 | (0.134, 0.101) | 56 |
| Example 62 | 259 | 4.32 | 5.98 | (0.134, 0.100) | 49 |
| Example 63 | 273 | 4.62 | 5.97 | (0.134, 0.100) | 42 |
| Example 64 | 274 | 5.36 | 5.86 | (0.134, 0.100) | 39 |
| Example 65 | 279 | 5.25 | 5.97 | (0.134, 0.101) | 48 |
| Example 66 | 281 | 5.19 | 5.84 | (0.134, 0.101) | 51 |
| Example 67 | 299 | 5.28 | 5.82 | (0.134, 0.101) | 50 |
| Example 68 | 317 | 5.29 | 5.78 | (0.134, 0.101) | 47 |
| Example 69 | 319 | 5.61 | 5.66 | (0.134, 0.100) | 52 |
| Example 70 | 320 | 5.51 | 5.79 | (0.134, 0.101) | 54 |
| Example 71 | 321 | 5.48 | 5.77 | (0.134, 0.100) | 44 |
| Example 72 | 326 | 5.39 | 5.75 | (0.134, 0.101) | 47 |
| Example 73 | 327 | 5.49 | 5.68 | (0.134, 0.102) | 46 |
| Example 74 | 334 | 5.38 | 6.01 | (0.134, 0.101) | 54 |
| Example 75 | 339 | 4.99 | 5.72 | (0.134, 0.103) | 52 |
| Example 76 | 342 | 5.61 | 5.95 | (0.134, 0.102) | 49 |
| Example 77 | 347 | 5.42 | 5.68 | (0.134, 0.101) | 41 |
| Example 78 | 349 | 5.58 | 5.64 | (0.134, 0.102) | 43 |
| Example 79 | 375 | 5.52 | 5.71 | (0.134, 0.101) | 46 |
| Example 80 | 376 | 5.49 | 5.75 | (0.134, 0.101) | 45 |
| Example 81 | 383 | 5.41 | 5.55 | (0.134, 0.100) | 49 |
| Example 82 | 413 | 5.48 | 5.72 | (0.134, 0.101) | 50 |
| Example 83 | 415 | 5.45 | 5.82 | (0.134, 0.102) | 51 |

TABLE 5-continued

| | Compound | Driving voltage (V) | Light Emission Efficiency (cd/A) | CIE (x, y) | Lifetime (T$_{95}$) |
|---|---|---|---|---|---|
| Example 84 | 427 | 6.12 | 5.72 | (0.134, 0.100) | 50 |
| Example 85 | 437 | 6.08 | 5.91 | (0.134, 0.100) | 48 |
| Example 86 | 445 | 5.89 | 5.96 | (0.134, 0.102) | 49 |
| Example 87 | 446 | 5.49 | 5.88 | (0.134, 0.101) | 50 |
| Example 88 | 447 | 5.40 | 5.82 | (0.134, 0.100) | 52 |
| Example 89 | 449 | 5.36 | 5.83 | (0.134, 0.101) | 55 |
| Example 90 | 453 | 5.32 | 6.05 | (0.134, 0.101) | 47 |
| Example 91 | 454 | 5.26 | 5.92 | (0.134, 0.102) | 49 |
| Example 92 | 457 | 5.64 | 5.75 | (0.134, 0.100) | 48 |
| Example 93 | 459 | 5.29 | 5.86 | (0.134, 0.101) | 50 |
| Example 94 | 460 | 5.87 | 5.78 | (0.134, 0.101) | 52 |
| Example 95 | 462 | 5.78 | 5.71 | (0.134, 0.101) | 53 |
| Example 96 | 463 | 6.15 | 5.76 | (0.134, 0.100) | 48 |
| Example 97 | 465 | 5.48 | 5.79 | (0.134, 0.102) | 49 |
| Example 98 | 468 | 5.16 | 5.69 | (0.134, 0.102) | 50 |
| Example 99 | 471 | 4.98 | 5.88 | (0.134, 0.102) | 51 |
| Example 100 | 473 | 5.55 | 5.86 | (0.134, 0.101) | 50 |
| Example 101 | 476 | 5.84 | 5.76 | (0.134, 0.102) | 53 |
| Example 102 | 479 | 5.88 | 5.96 | (0.134, 0.101) | 49 |
| Example 103 | 494 | 5.78 | 5.72 | (0.134, 0.101) | 48 |
| Example 104 | 529 | 5.99 | 6.08 | (0.134, 0.100) | 50 |
| Example 105 | 573 | 5.08 | 6.02 | (0.134, 0.102) | 52 |
| Example 106 | 575 | 5.61 | 5.99 | (0.134, 0.101) | 48 |
| Example 107 | 578 | 5.78 | 5.78 | (0.134, 0.100) | 49 |
| Example 108 | 584 | 5.18 | 5.76 | (0.134, 0.102) | 38 |
| Example 109 | 670 | 5.45 | 5.78 | (0.134, 0.101) | 42 |
| Example 110 | 671 | 5.67 | 5.68 | (0.134, 0.100) | 46 |
| Example 111 | 676 | 5.52 | 5.69 | (0.134, 0.101) | 39 |
| Example 112 | 679 | 5.41 | 6.15 | (0.134, 0.102) | 40 |
| Example 113 | 682 | 5.79 | 5.86 | (0.134, 0.101) | 35 |
| Example 114 | 695 | 5.36 | 5.69 | (0.134, 0.102) | 37 |
| Example 115 | 696 | 6.23 | 5.72 | (0.134, 0.101) | 46 |
| Example 116 | 721 | 6.09 | 5.88 | (0.134, 0.100) | 48 |
| Example 117 | 722 | 5.39 | 5.96 | (0.134, 0.102) | 41 |
| Example 118 | 723 | 5.88 | 5.71 | (0.134, 0.101) | 51 |
| Example 119 | 724 | 5.62 | 5.75 | (0.134, 0.102) | 50 |
| Example 120 | 727 | 5.59 | 5.91 | (0.134, 0.101) | 52 |
| Example 121 | 741 | 5.45 | 5.86 | (0.134, 0.101) | 55 |
| Example 122 | 745 | 5.49 | 5.75 | (0.134, 0.102) | 48 |
| Example 123 | 771 | 5.37 | 5.72 | (0.134, 0.100) | 42 |
| Example 124 | 789 | 5.46 | 5.98 | (0.134, 0.101) | 49 |
| Example 125 | 792 | 5.49 | 5.78 | (0.134, 0.101) | 50 |
| Example 126 | 802 | 5.68 | 5.64 | (0.134, 0.102) | 57 |
| Example 127 | 804 | 5.94 | 5.62 | (0.134, 0.100) | 52 |
| Example 128 | 815 | 5.42 | 5.98 | (0.134, 0.102) | 54 |
| Example 129 | 822 | 5.52 | 6.01 | (0.134, 0.101) | 56 |
| Example 130 | 847 | 5.41 | 6.08 | (0.134, 0.101) | 49 |
| Example 131 | 848 | 5.89 | 5.69 | (0.134, 0.102) | 42 |
| Example 132 | 855 | 6.15 | 5.88 | (0.134, 0.101) | 39 |
| Example 133 | 886 | 6.08 | 5.85 | (0.134, 0.100) | 48 |
| Example 134 | 895 | 5.45 | 5.68 | (0.134, 0.100) | 51 |
| Example 135 | 914 | 5.46 | 5.79 | (0.134, 0.100) | 50 |
| Example 136 | 915 | 5.37 | 5.98 | (0.134, 0.101) | 47 |
| Example 137 | 917 | 5.66 | 5.95 | (0.134, 0.101) | 52 |
| Example 138 | 920 | 5.59 | 5.82 | (0.134, 0.101) | 54 |
| Example 139 | 928 | 5.68 | 5.80 | (0.134, 0.101) | 44 |
| Example 140 | 933 | 5.29 | 5.99 | (0.134, 0.100) | 47 |
| Example 141 | 937 | 5.33 | 5.79 | (0.134, 0.101) | 46 |
| Example 142 | 943 | 5.43 | 5.64 | (0.134, 0.100) | 54 |
| Example 143 | 945 | 5.23 | 6.00 | (0.134, 0.101) | 52 |
| Example 144 | 946 | 5.33 | 5.62 | (0.134, 0.102) | 49 |
| Example 145 | 947 | 5.49 | 5.59 | (0.134, 0.101) | 41 |
| Example 146 | 948 | 5.56 | 5.78 | (0.134, 0.103) | 43 |
| Example 147 | 949 | 5.40 | 6.09 | (0.134, 0.102) | 46 |
| Example 148 | 950 | 5.78 | 5.78 | (0.134, 0.101) | 45 |
| Example 149 | 953 | 5.79 | 5.69 | (0.134, 0.102) | 49 |
| Example 150 | 956 | 4.89 | 5.64 | (0.134, 0.101) | 50 |
| Example 151 | 957 | 5.86 | 6.05 | (0.134, 0.101) | 51 |
| Example 152 | 973 | 5.81 | 5.78 | (0.134, 0.100) | 50 |
| Example 153 | 974 | 5.67. | 5.85 | (0.134, 0.101) | 48 |
| Example 154 | 975 | 5.59 | 5.81 | (0.134, 0.102) | 49 |
| Example 155 | 976 | 5.38 | 5.86 | (0.134, 0.100) | 50 |
| Example 156 | 977 | 5.78 | 5.95 | (0.134, 0.100) | 52 |
| Example 157 | 978 | 5.39 | 5.92 | (0.134, 0.102) | 55 |

TABLE 5-continued
| | Compound | Driving voltage (V) | Light Emission Efficiency (cd/A) | CIE (x, y) | Lifetime ($T_{95}$) |
|---|---|---|---|---|---|
| Example 159 | 981 | 5.61 | 5.84 | (0.134, 0.101) | 47 |
| Example 160 | 984 | 5.77 | 5.78 | (0.134, 0.100) | 49 |
| Example 161 | 985 | 5.41 | 5.69 | (0.134, 0.101) | 48 |
| Example 162 | 1015 | 5.24 | 5.99 | (0.134, 0.101) | 50 |
| Example 163 | 1016 | 5.45 | 5.82 | (0.134, 0.102) | 52 |
| Example 164 | 1017 | 5.42 | 5.74 | (0.134, 0.100) | 53 |
| Example 165 | 1018 | 5.50 | 6.25 | (0.134, 0.101) | 48 |
| Example 166 | 1023 | 5.70 | 6.12 | (0.134, 0.101) | 49 |
| Example 167 | 1026 | 5.77 | 5.74 | (0.134, 0.101) | 50 |
| Example 168 | 1027 | 5.89 | 6.05 | (0.134, 0.100) | 51 |
| Example 169 | 1043 | 5.65 | 5.62 | (0.134, 0.102) | 50 |
| Example 170 | 1044 | 5.63 | 5.69 | (0.134, 0.102) | 53 |
| Example 171 | 1045 | 5.28 | 5.64 | (0.134, 0.102) | 49 |
| Example 172 | 1046 | 5.74 | 5.89 | (0.134, 0.101) | 48 |
| Example 173 | 1051 | 5.76 | 5.98 | (0.134, 0.102) | 50 |
| Example 174 | 1054 | 5.45 | 6.09 | (0.134, 0.101) | 52 |
| Example 175 | 1055 | 5.19 | 5.84 | (0.134, 0.101) | 48 |
| Example 176 | 1057 | 5.62 | 5.86 | (0.134, 0.100) | 49 |
| Example 177 | 1058 | 5.48 | 5.75 | (0.134, 0.102) | 38 |
| Example 178 | 1060 | 5.59 | 5.76 | (0.134, 0.101) | 42 |
| Example 179 | 1068 | 5.52 | 6.07 | (0.134, 0.100) | 46 |
| Example 180 | 1075 | 5.42 | 5.69 | (0.134, 0.102) | 39 |
| Example 181 | 1079 | 5.47 | 5.68 | (0.134, 0.101) | 40 |
| Example 182 | 1085 | 5.68 | 5.77 | (0.134, 0.100) | 35 |
| Example 183 | 1086 | 5.98 | 5.67 | (0.134, 0.101) | 37 |
| Example 184 | 1088 | 6.05 | 5.59 | (0.134, 0.102) | 46 |
| Example 185 | 11096 | 5.40 | 5.48 | (0.134, 0.101) | 48 |
| Example 186 | 1099 | 5.42 | 6.12 | (0.134, 0.102) | 41 |
| Example 187 | 1103 | 5.53 | 5.65 | (0.134, 0.101) | 51 |
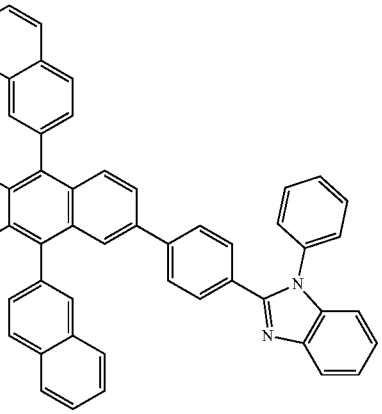
E1
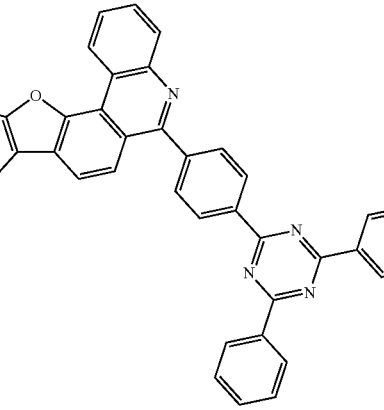
E2
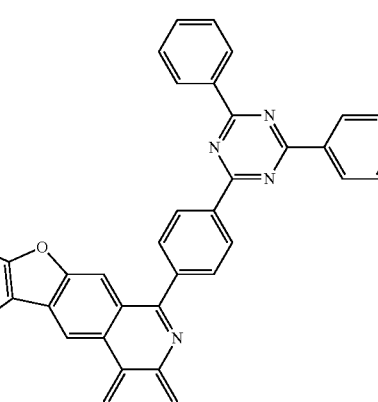
E3

TABLE 5-continued

| Compound | Driving voltage (V) | Light Emission Efficiency (cd/A) | CIE (x, y) | Lifetime ($T_{95}$) |
|---|---|---|---|---|

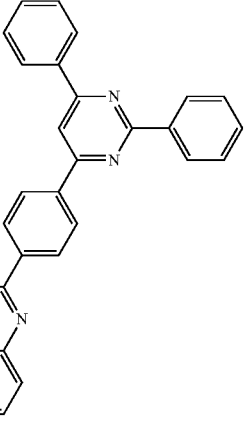

E4

As seen from the results of Table 5, the organic electroluminescent device using an electron transfer layer material of the blue organic electroluminescent device of the present disclosure had a lower driving voltage and significantly improved light emission efficiency and lifetime compared to Comparative Example 1. When comparing Comparative Examples 2 to 4 in which the core structure of the present application is mono-substituted and the material of the present disclosure in which the core structure is di-substituted as in the invention of the present application, compounds may be stabilized by, unlike when mono-ubstituted, introducing phenyl or acene-based compounds when di-substituted, and hole properties may be controlled as well, and as a result, injection rates of electrons and holes in the light emitting layer may be controlled. Due to such a reason, it was identified that di-substitution was superior compared to mono-substitution in all aspects of driving, efficiency and lifetime. Particularly, it was identified that Examples 19, 20, 30, 43, 44, 47, 48, 56, 62, 63, 75, 99 and 150 were superior in all aspects of driving, efficiency and lifetime.

Such a result is considered to be due to the fact that, when using the disclosed compound having proper length, strength and flat properties as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

<Experimental Example 2> Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was deposited on a cell in the vacuum deposition apparatus.

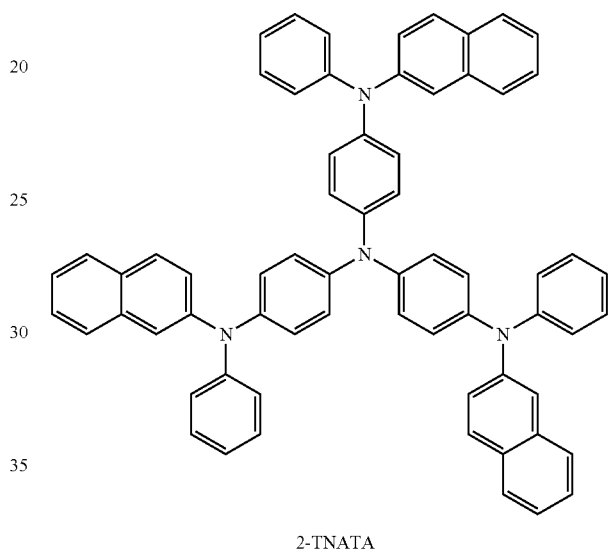

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

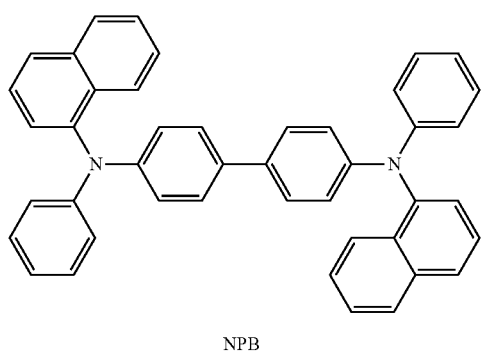

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

Subsequently, a compound of the following structural formula E1 was deposited to a thickness of 300 Å as an electron transfer layer.

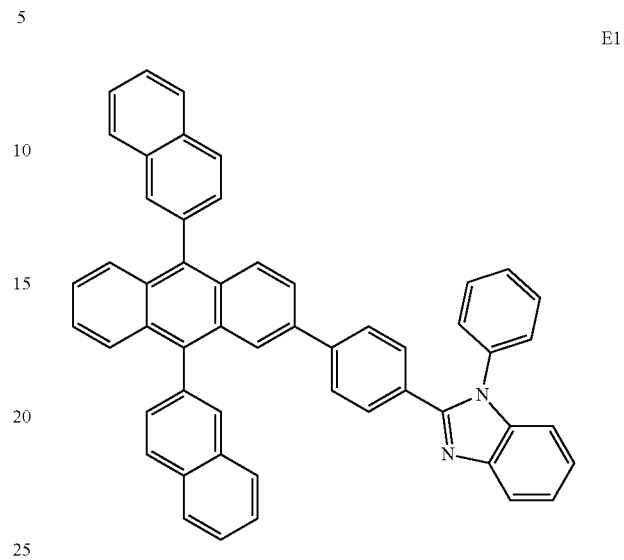

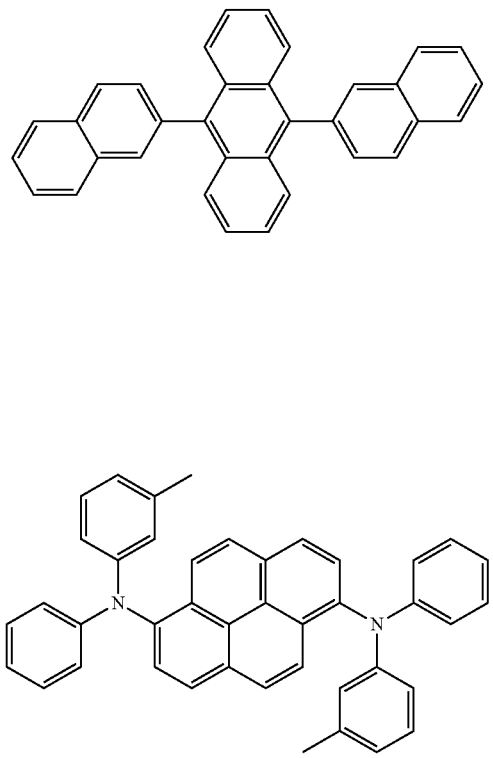

As an electron injection layer, lithium fluoride (LiF) was deposited to a thickness of 10 Å, and an Al cathode was employed to a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

An electroluminescent device was manufactured in the same manner as in Experimental Example 2 except that, after forming the electron transfer layer E1 to a thickness of 250 Å, a hole blocking layer was formed on the electron transfer layer using a compound presented in Table 6 to a thickness of 50 Å.

Results of measuring a driving voltage, light emission efficiency, a color coordinate (CIE) and a lifetime of the blue organic light emitting device manufactured according to the present disclosure are as shown in Table 6.

TABLE 6

|  | Compound | Driving voltage (V) | Light Emission Efficiency (cd/A) | CIE (x, y) | Lifetime ($T_{95}$) |
| --- | --- | --- | --- | --- | --- |
| Comparative Example 5 | — | 5.51 | 5.54 | (0.134, 0.100) | 31 |
| Example 188 | 124 | 5.23 | 6.17 | (0.134, 0.101) | 52 |
| Example 189 | 126 | 5.14 | 6.59 | (0.134, 0.102) | 54 |
| Example 190 | 127 | 5.34 | 5.58 | (0.134, 0.101) | 44 |
| Example 191 | 130 | 5.38 | 6.51 | (0.134, 0.103) | 47 |
| Example 192 | 131 | 5.11 | 5.75 | (0.134, 0.102) | 46 |
| Example 193 | 133 | 5.42 | 6.21 | (0.134, 0.101) | 54 |
| Example 194 | 136 | 5.13 | 5.63 | (0.134, 0.102) | 52 |
| Example 195 | 139 | 5.05 | 6.76 | (0.134, 0.101) | 49 |
| Example 196 | 141 | 5.42 | 6.13 | (0.134, 0.101) | 41 |
| Example 197 | 142 | 5.44 | 5.94 | (0.134, 0.100) | 43 |
| Example 198 | 151 | 5.27 | 6.17 | (0.134, 0.101) | 46 |
| Example 199 | 154 | 5.32 | 6.25 | (0.134, 0.101) | 55 |
| Example 200 | 158 | 5.14 | 6.46 | (0.134, 0.102) | 51 |
| Example 201 | 160 | 5.04 | 6.62 | (0.134, 0.101) | 55 |
| Example 202 | 162 | 5.22 | 6.34 | (0.134, 0.101) | 42 |
| Example 203 | 175 | 5.53 | 5.95 | (0.134, 0.100) | 48 |
| Example 204 | 186 | 5.33 | 6.47 | (0.134, 0.101) | 46 |
| Example 205 | 190 | 5.38 | 6.51 | (0.134, 0.103) | 47 |

TABLE 6-continued

| Compound | Driving voltage (V) | Light Emission Efficiency (cd/A) | CIE (x, y) | Lifetime ($T_{95}$) |
|---|---|---|---|---|
| Example 206 | 193 | 5.11 | 6.75 | (0.134, 0.102) | 46 |
| Example 207 | 195 | 5.42 | 6.21 | (0.134, 0.101) | 54 |
| Example 208 | 297 | 5.13 | 6.63 | (0.134, 0.102) | 52 |
| Example 209 | 298 | 5.05 | 5.66 | (0.134, 0.101) | 49 |
| Example 210 | 301 | 5.42 | 6.13 | (0.134, 0.101) | 41 |
| Example 211 | 302 | 5.54 | 5.94 | (0.134, 0.100) | 43 |
| Example 212 | 303 | 5.11 | 6.35 | (0.134, 0.102) | 46 |
| Example 213 | 308 | 5.42 | 6.21 | (0.134, 0.101) | 54 |
| Example 214 | 309 | 5.23 | 5.63 | (0.134, 0.102) | 52 |
| Example 215 | 317 | 5.05 | 6.26 | (0.134, 0.101) | 49 |
| Example 216 | 459 | 5.42 | 6.13 | (0.134, 0.101) | 41 |
| Example 217 | 468 | 5.43 | 5.94 | (0.134, 0.100) | 43 |
| Example 218 | 529 | 5.28 | 6.17 | (0.134, 0.101) | 46 |
| Example 219 | 596 | 5.32 | 6.25 | (0.134, 0.101) | 55 |
| Example 220 | 598 | 5.14 | 6.40 | (0.134, 0.102) | 51 |
| Example 221 | 599 | 5.04 | 6.22 | (0.134, 0.101) | 55 |
| Example 222 | 602 | 5.22 | 6.34 | (0.134, 0.101) | 42 |
| Example 223 | 603 | 5.53 | 5.95 | (0.134, 0.100) | 48 |
| Example 224 | 606 | 5.33 | 6.36 | (0.134, 0.101) | 46 |
| Example 225 | 611 | 5.38 | 6.11 | (0.134, 0.103) | 47 |
| Example 226 | 623 | 5.11 | 6.35 | (0.134, 0.102) | 46 |
| Example 227 | 626 | 5.42 | 6.21 | (0.134, 0.101) | 53 |
| Example 228 | 663 | 5.13 | 6.33 | (0.134, 0.102) | 52 |
| Example 229 | 667 | 5.05 | 6.16 | (0.134, 0.101) | 49 |
| Example 230 | 668 | 5.42 | 6.13 | (0.134, 0.101) | 41 |
| Example 231 | 771 | 5.44 | 5.94 | (0.134, 0.100) | 43 |
| Example 232 | 775 | 5.33 | 6.57 | (0.134, 0.101) | 52 |
| Example 233 | 780 | 5.14 | 5.69 | (0.134, 0.102) | 54 |
| Example 234 | 789 | 5.34 | 6.48 | (0.134, 0.101) | 44 |
| Example 235 | 836 | 5.38 | 6.51 | (0.134, 0.103) | 47 |
| Example 236 | 950 | 5.21 | 6.75 | (0.134, 0.102) | 46 |
| Example 237 | 957 | 5.42 | 6.21 | (0.134, 0.101) | 54 |
| Example 238 | 974 | 5.13 | 6.53 | (0.134, 0.102) | 55 |
| Example 239 | 985 | 5.05 | 5.36 | (0.134, 0.101) | 49 |
| Example 240 | 1015 | 5.42 | 6.13 | (0.134, 0.101) | 40 |
| Example 241 | 1026 | 5.44 | 5.94 | (0.134, 0.100) | 43 |
| Example 242 | 1045 | 5.27 | 6.17 | (0.134, 0.101) | 46 |
| Example 243 | 1055 | 5.32 | 6.25 | (0.134, 0.101) | 55 |
| Example 244 | 1060 | 5.14 | 5.46 | (0.134, 0.102) | 52 |

As seen from the results of Table 6, the organic electroluminescent device using the hole blocking layer material of the blue organic electroluminescent device of the present disclosure had a lower driving voltage and significantly improved light emission efficiency and lifetime compared to Comparative Example 5. Particularly, it was identified that Examples 189, 191, 195, 201, 205, 206, 208, 232, 235 and 236 were superior in all aspects of driving, efficiency and lifetime.

<Experimental Example 3> Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

On the transparent ITO electrode (anode), an organic material was formed in a 2 stack white organic light emitting device (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping FIrpic to TCzl, a host, by 8% as a blue phosphorescent dopant. After forming an electron transfer layer to 400 Å using TmPyPB, a charge generation layer was formed to 100 Å by doping $Cs_2CO_3$ to the compound listed in the following Table 7 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and then depositing TAPC to 300 Å. A light emitting layer was deposited thereon to 300 Å by doping $Ir(ppy)_3$, a green phosphorescent dopant, to TCzl, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED were vacuum sublimation purified under $10^{-6}$ torr to $10^{-8}$ torr by each material to be used in the OLED manufacture.

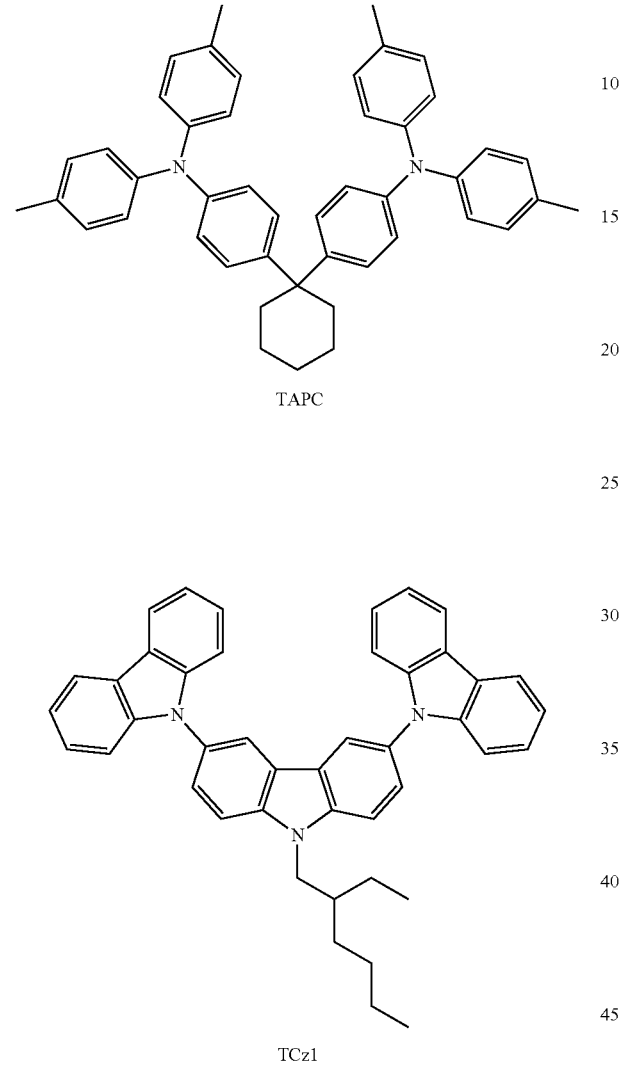

TAPC

TCz1

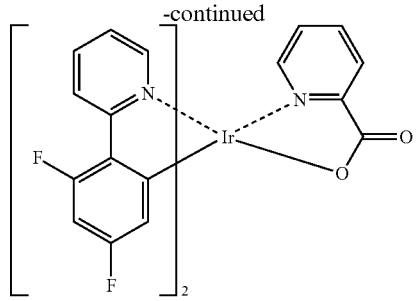

FIrpic

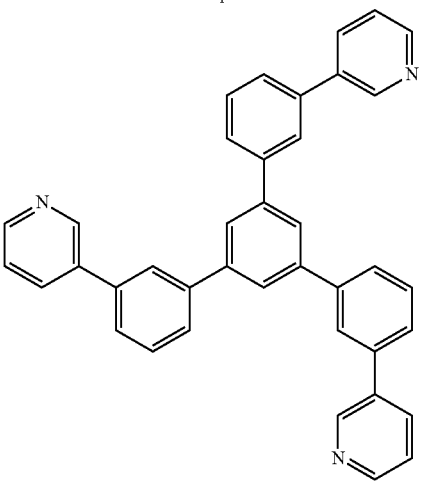

TmPyPB

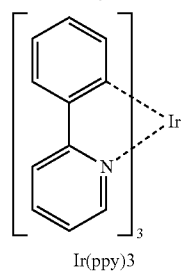

Ir(ppy)3

Results of measuring a driving voltage, light emission efficiency, a color coordinate (CIE) and a lifetime of the white organic light emitting device manufactured according to the present disclosure are as shown in Table 7.

TABLE 7

| | Compound | Driving voltage (V) | Light Emission Efficiency (cd/A) | CIE (x, y) | Lifetime ($T_{95}$) |
|---|---|---|---|---|---|
| Comparative Example6 | — | 8.54 | 54.23 | (0.213, 0.430) | 25 |
| Example 245 | 416 | 7.34 | 65.77 | (0.212, 0.421) | 40 |
| Example 246 | 417 | 7.44 | 65.32 | (0.211, 0.433) | 33 |
| Example 247 | 418 | 6.49 | 79.68 | (0.217, 0.439) | 50 |
| Example 248 | 419 | 6.47 | 79.99 | (0.212, 0.424) | 53 |
| Example 249 | 420 | 7.12 | 67.56 | (0.211, 0.435) | 34 |
| Example 250 | 430 | 8.03 | 62.27 | (0.215, 0.432) | 25 |
| Example 251 | 431 | 7.63 | 66.13 | (0.218, 0.430) | 32 |
| Example 252 | 432 | 7.00 | 69.92 | (0.221, 0.427) | 40 |
| Example 253 | 889 | 6.35 | 77.12 | (0.211, 0.435) | 52 |
| Example 254 | 890 | 7.62 | 69.33 | (0.214, 0.432) | 32 |

TABLE 7-continued

| | Compound | Driving voltage (V) | Light Emission Efficiency (cd/A) | CIE (x, y) | Lifetime ($T_{95}$) |
|---|---|---|---|---|---|
| Example 255 | 891 | 7.23 | 71.29 | (0.217, 0.431) | 38 |
| Example 256 | 892 | 7.67 | 73.78 | (0.214, 0.438) | 43 |
| Example 257 | 906 | 7.41 | 72.19 | (0.212, 0.427) | 38 |

As seen from the results of Table 7, the organic light emitting device using the charge generation layer material of the 2-stack white organic light emitting device of the present disclosure had a lower driving voltage and improved light emission efficiency compared to Comparative Example 6. Particularly, it was identified that Examples 247, 248 and 253 were significantly superior in all aspects of driving, efficiency and lifetime. Such a result is considered to be due to the fact that the compound of the present disclosure used as the N-type charge generation layer formed with the disclosed skeleton having proper length, strength and flat properties and a proper hetero-compound capable of binding with a metal forms a gap state in the N-type charge generation layer by doping an alkali metal or an alkaline earth metal, and electrons produced from the P-type charge generation layer are readily injected to the electron transfer layer through the gap state produced in the N-type charge generation layer. Accordingly, it is considered that the P-type charge generation layer favorably injects and transfers electrons to the N-type charge generation layer, and as a result, a driving voltage was lowered, and efficiency and lifetime were improved in the organic light emitting device.

The invention claimed is:
1. A heterocyclic compound represented by the following Chemical Formula 1:

[Chemical Formula 1]

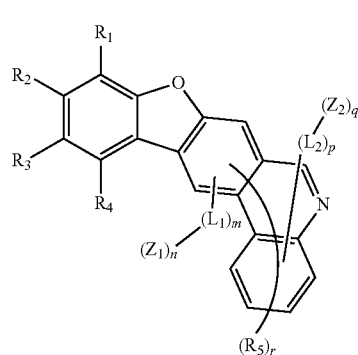

wherein, in Chemical Formula 1,
$R_1$ to $R_4$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring;
$R_5$ is hydrogen; a substituted or unsubstituted alkyl group; a substituted or unsubstituted aryl group; or a substituted or unsubstituted heteroaryl group;
$L_1$ and $L_2$ are the same as or different from each other, and each independently a direct bond; a substituted or unsubstituted arylene group; or a substituted or unsubstituted heteroarylene group;
$Z_1$ and $Z_2$ are the same as or different from each other, and each independently selected from the group consisting of deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group;
R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;
m and p are an integer of 1 to 4;
n and q are an integer of 1 to 3; and
r is an integer of 0 to 5.

2. The heterocyclic compound of claim 1, wherein the "substituted or unsubstituted" means being substituted with one or more substituents selected from the group consisting of C1 to C60 linear or branched alkyl; C2 to C60 linear alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and
R, R' and R" have the same definitions as in Chemical Formula 1.

3. The heterocyclic compound of claim 1, wherein $Z_1$ and $Z_2$ are the same as or different from each other, and each independently a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group and a C1 to C40 alkyl group; or P(=O)RR'; and R and R' have the same definitions as in Chemical Formula 1.

4. The heterocyclic compound of claim 1, wherein $L_1$ and $L_2$ are the same as or different from each other, and each independently a direct bond; a C6 to C20 arylene group; or a C2 to C20 heteroarylene group.

5. The heterocyclic compound of claim 1, wherein $R_1$ to $R_5$ are hydrogen.

6. The heterocyclic compound of claim 1, wherein Chemical Formula 1 is represented by any one of the following Chemical Formulae 3 to 10:

[Chemical Formula 3]

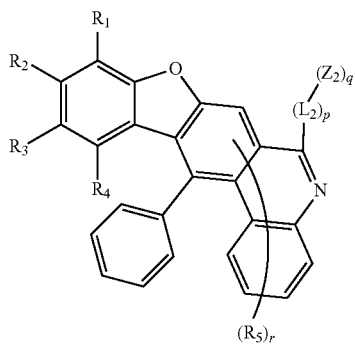

[Chemical Formula 4]

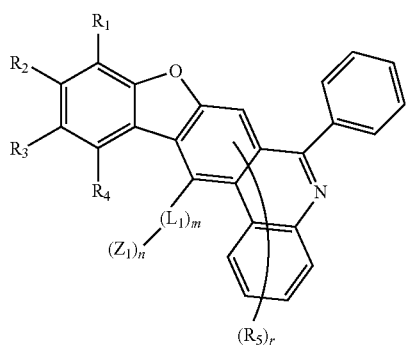

[Chemical Formula 5]

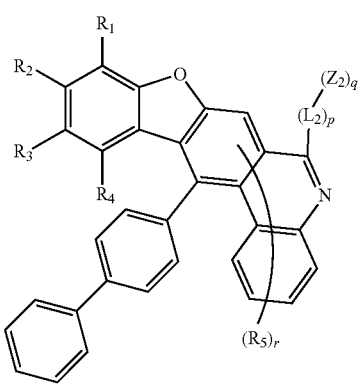

[Chemical Formula 6]

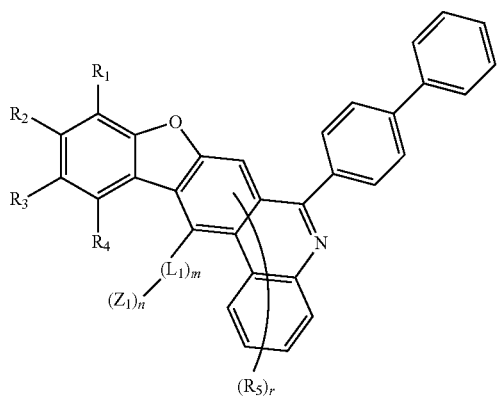

[Chemical Formula 7]

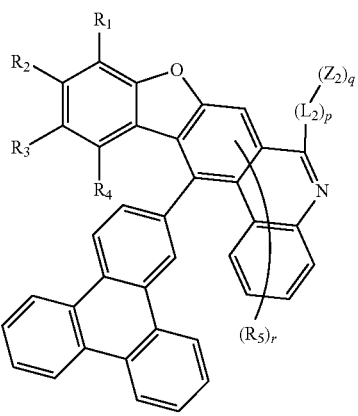

[Chemical Formula 8]

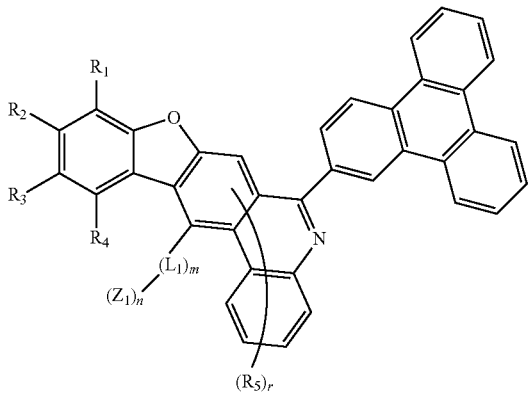

743
-continued
[Chemical Formula 9]
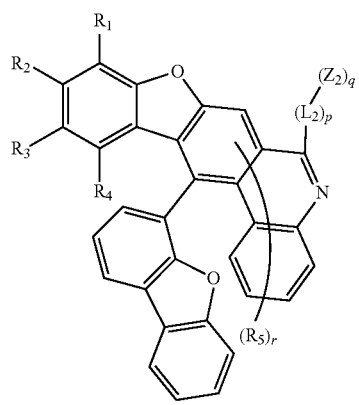
[Chemical Formula 10]
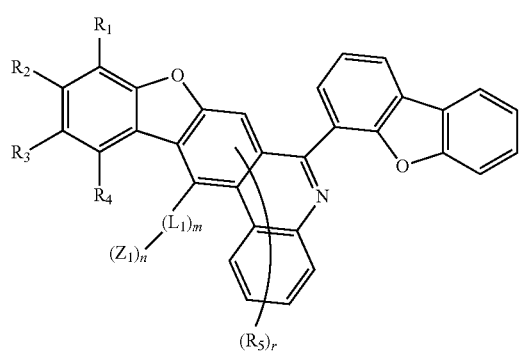
in Chemical Formulae 3 to 10,
$L_1$, $L_2$, $Z_1$, $Z_2$, m, n, p, q, r and $R_1$ to $R_5$ have the same definitions as in Chemical Formula 1.
7. The heterocyclic compound of claim 1, wherein Chemical Formula 1 is represented by any one of the following compounds:
744
-continued
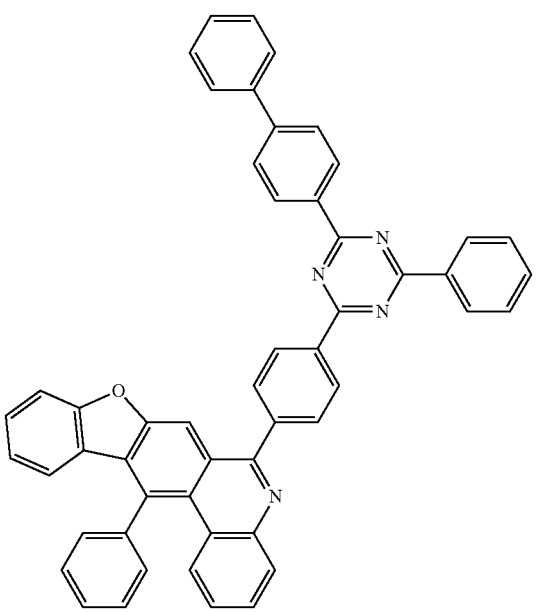
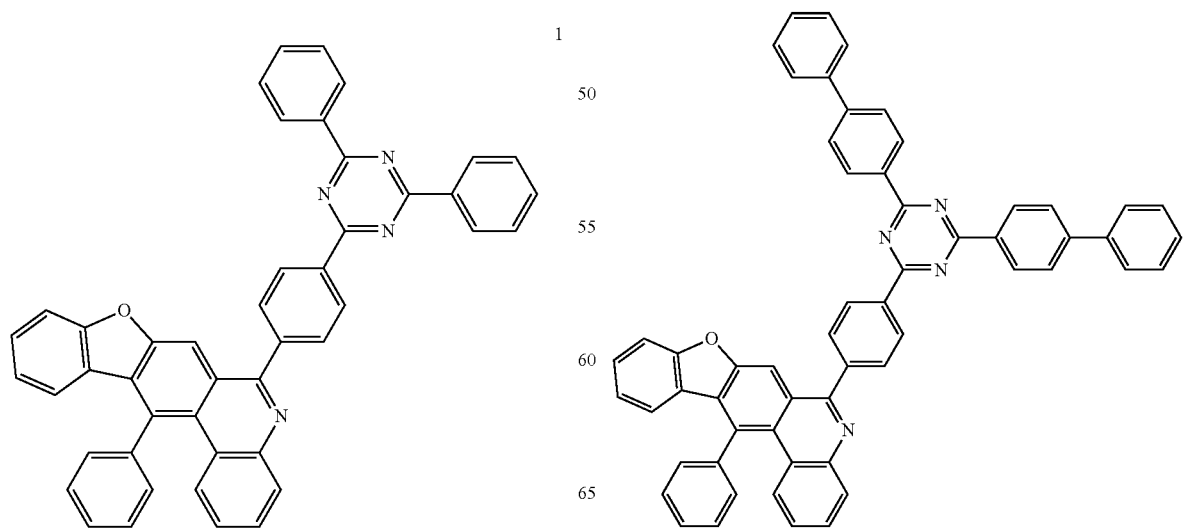

745
-continued
4
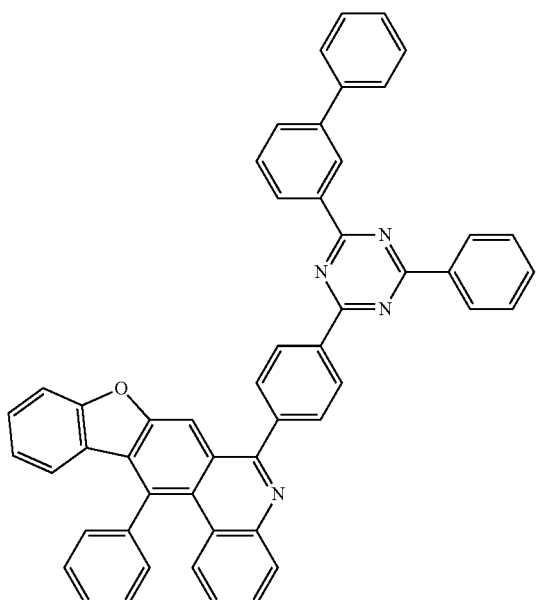
746
-continued
6
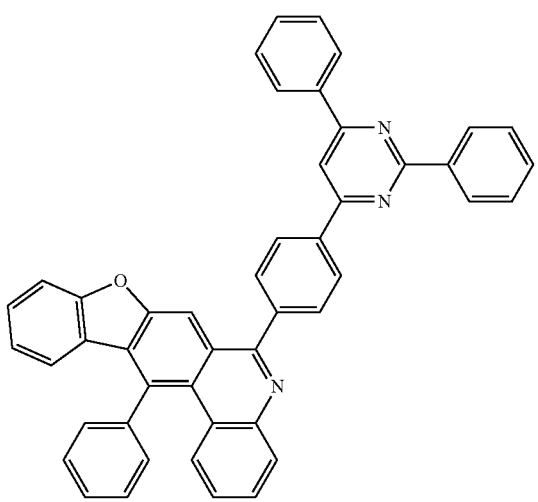
5
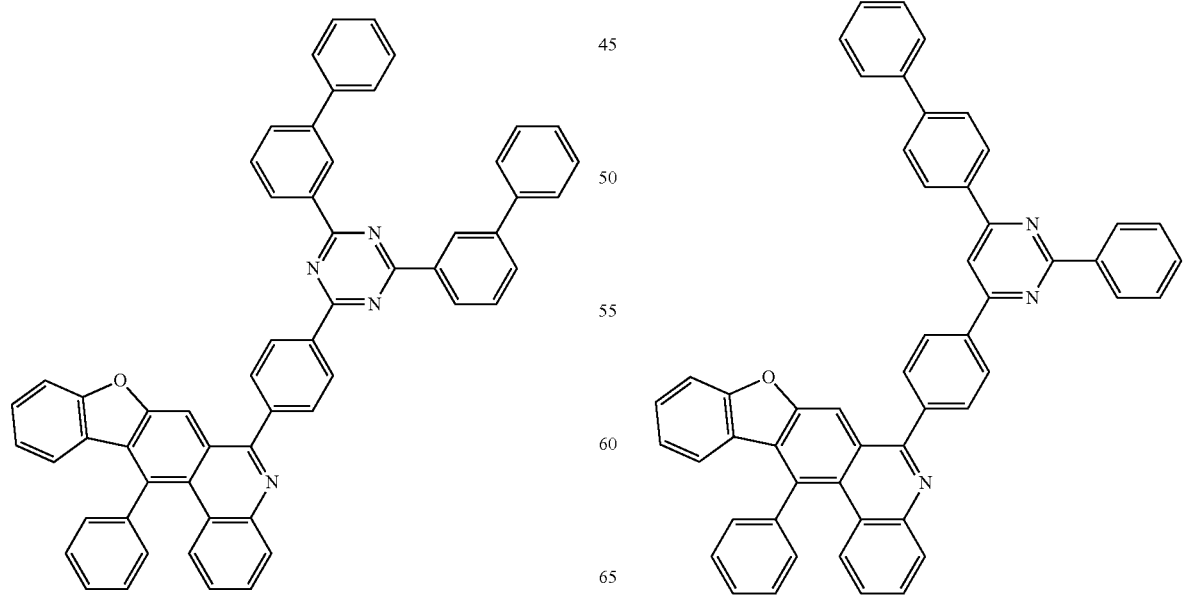
7

747
-continued
748
-continued
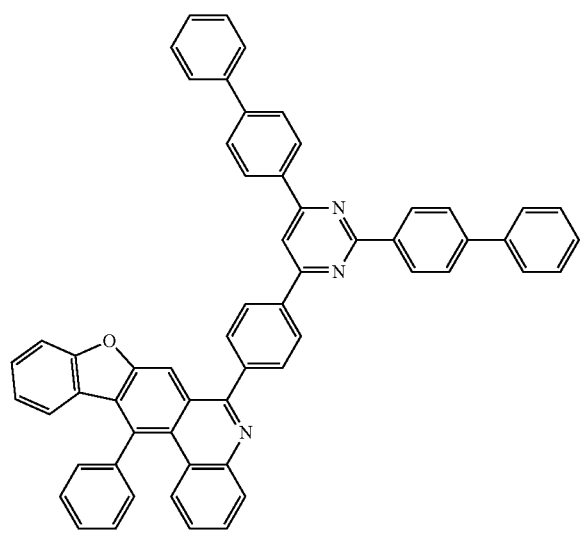
8
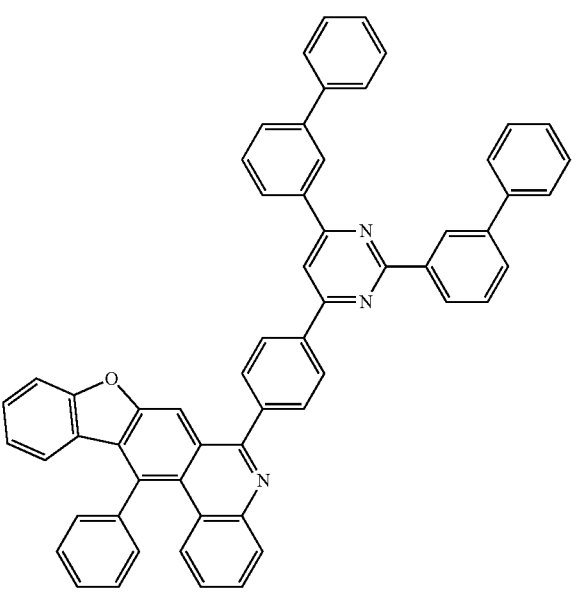
10
9
11

749
-continued
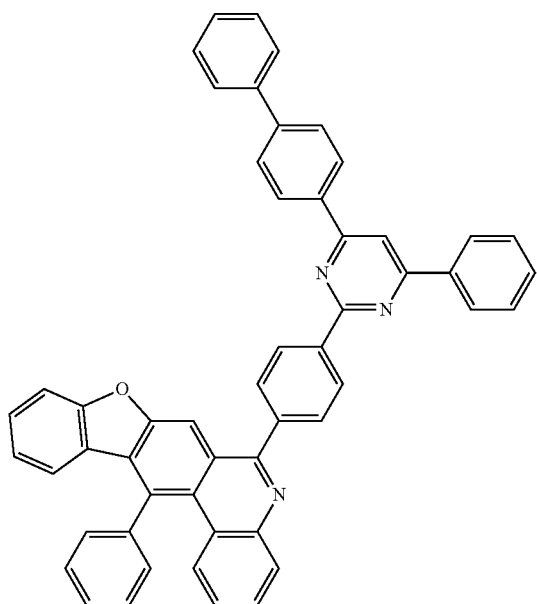
12
750
-continued
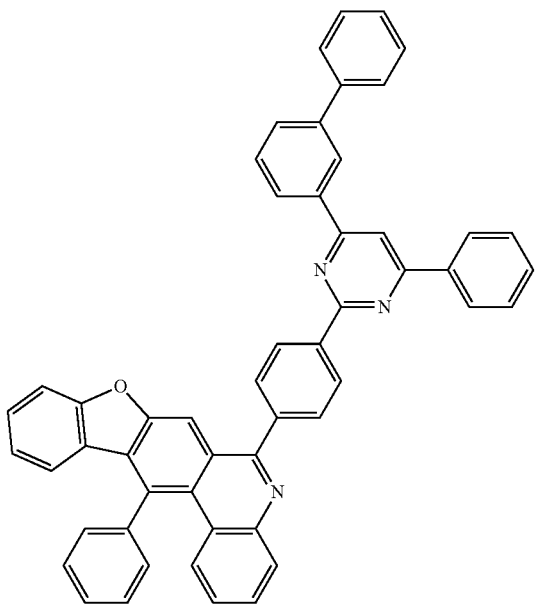
14
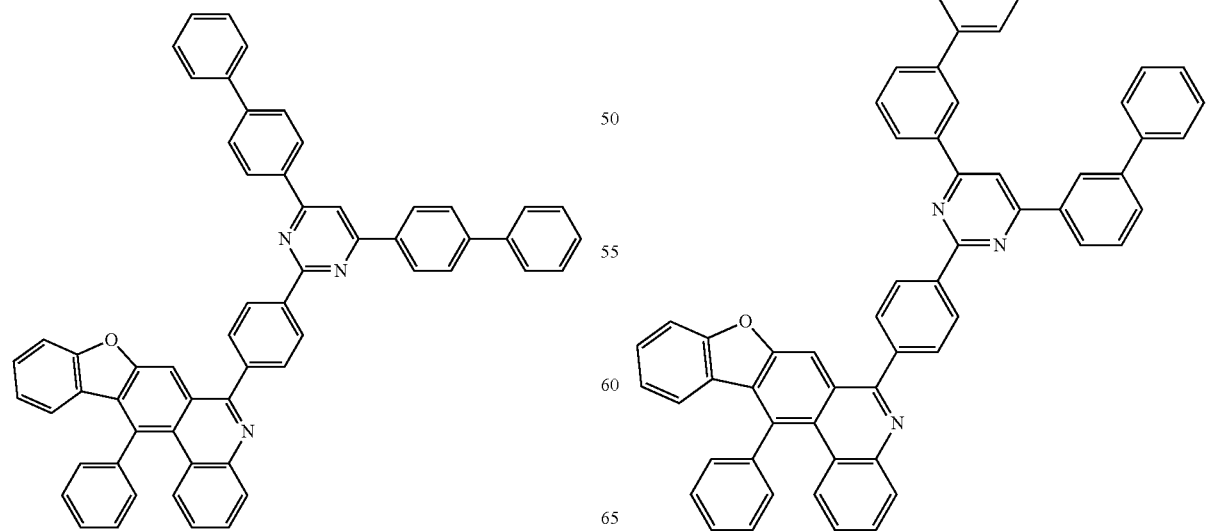

751
-continued
16
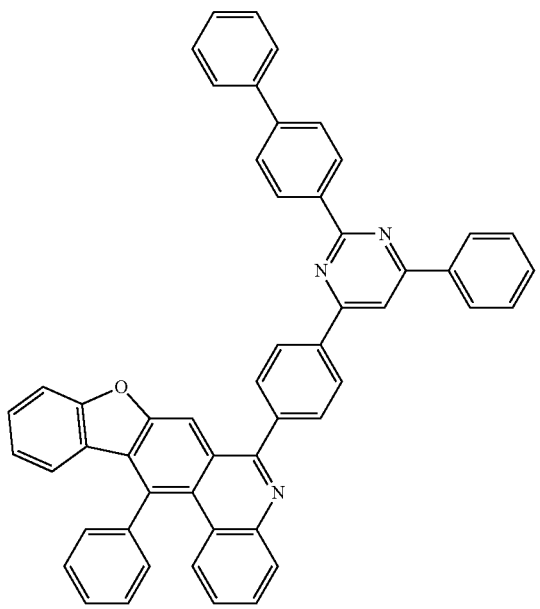
17
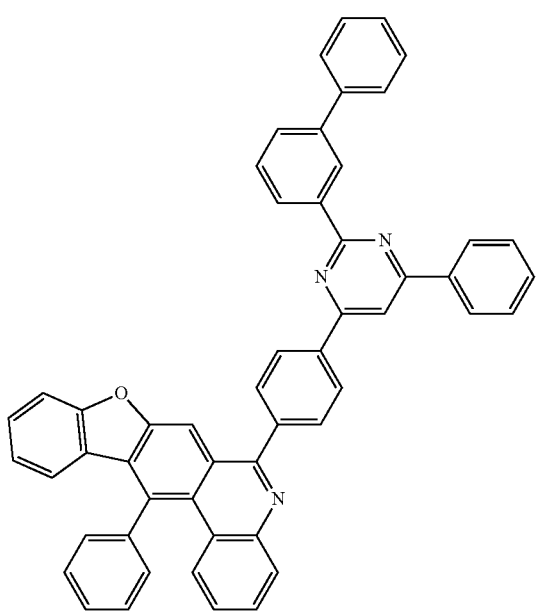
752
-continued
18
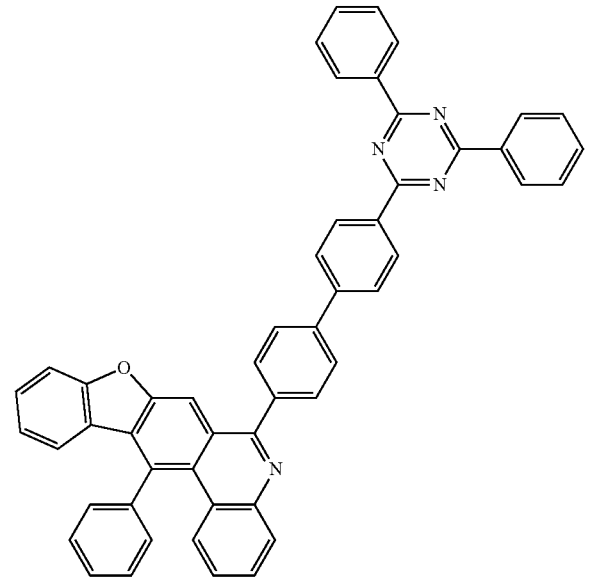
19
20
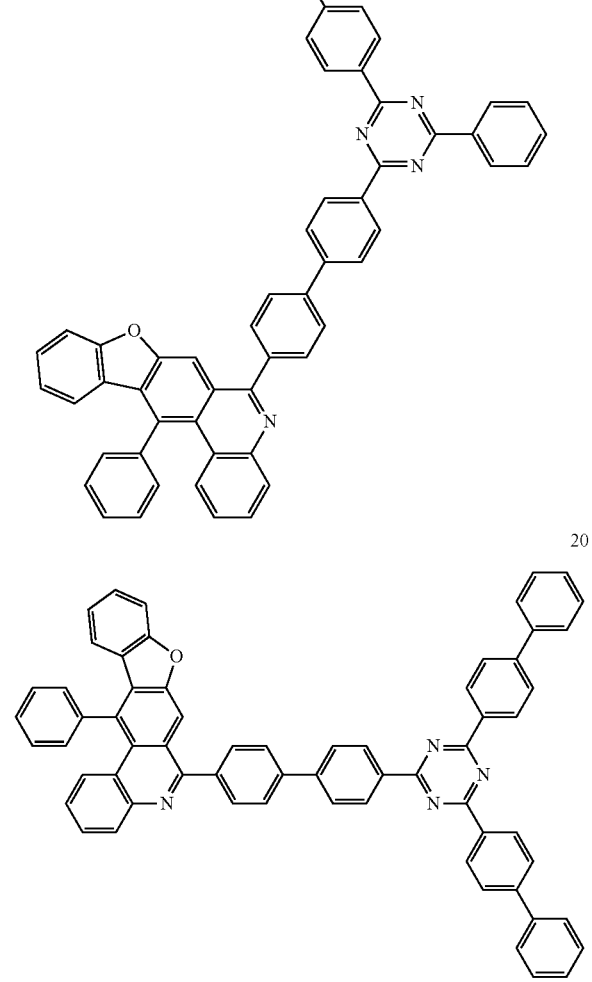

753
-continued
21
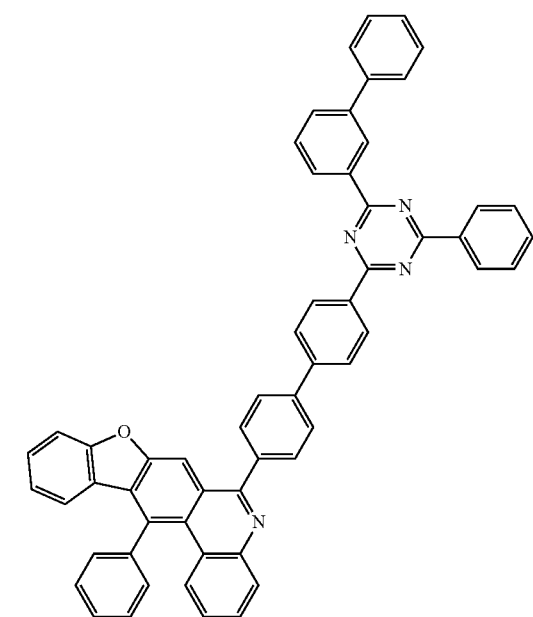
22
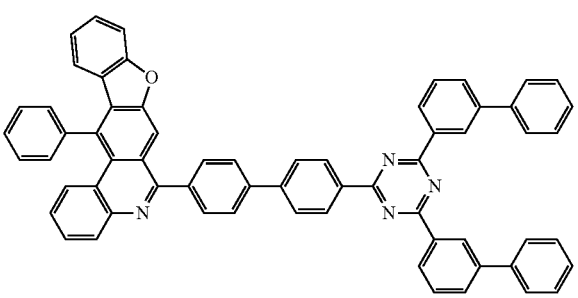
23
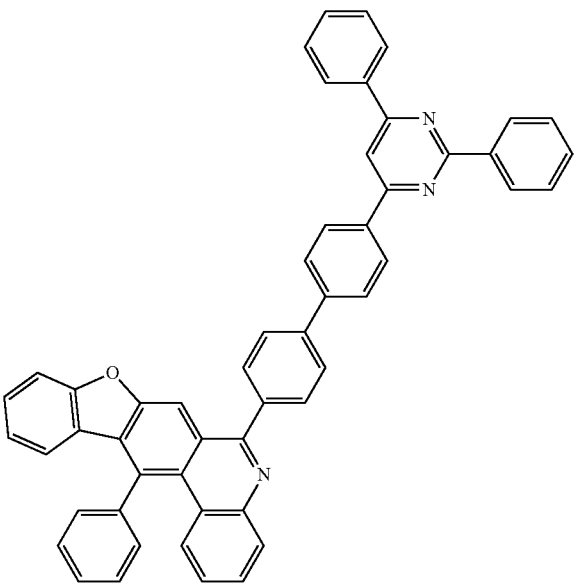
754
-continued
24
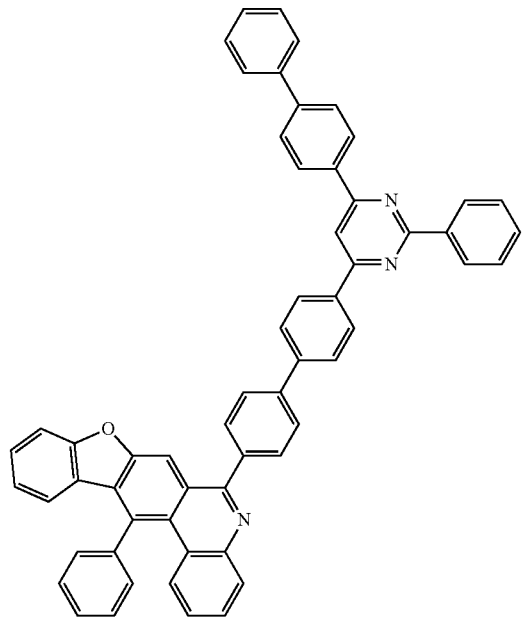
25
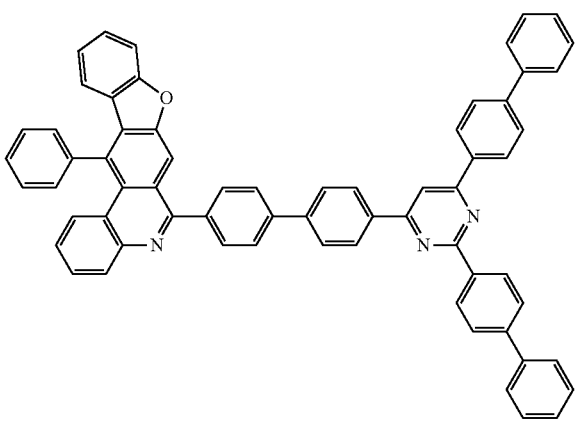
26
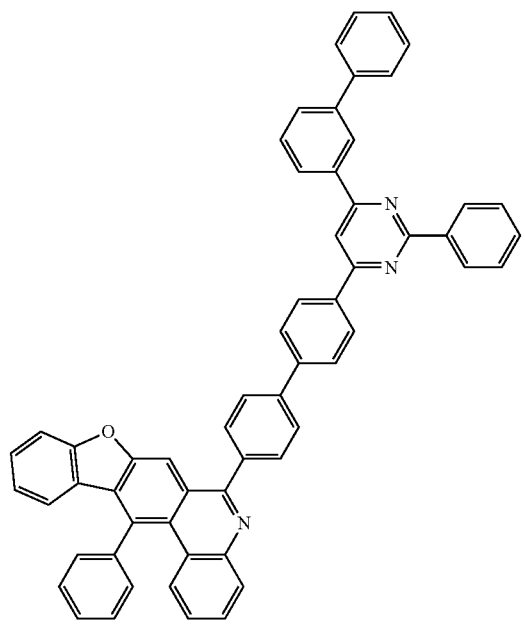

755
-continued
27
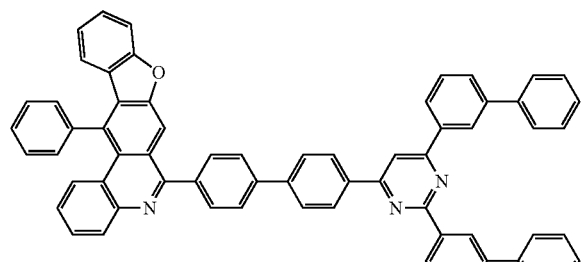
28

29
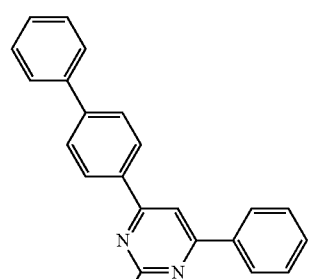
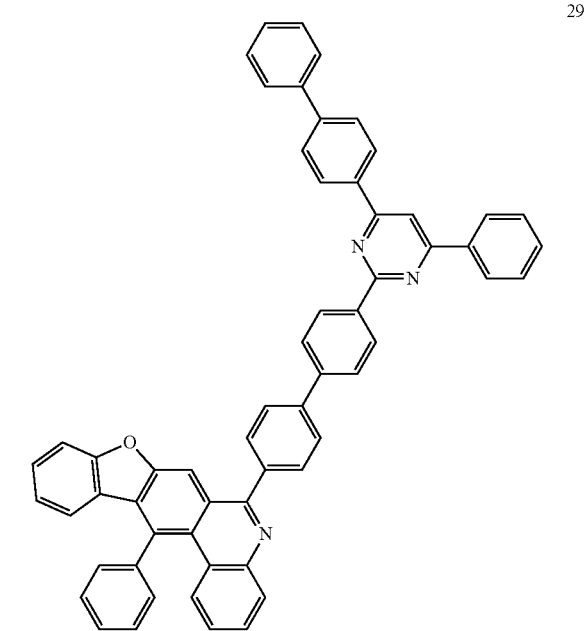
756
-continued
30
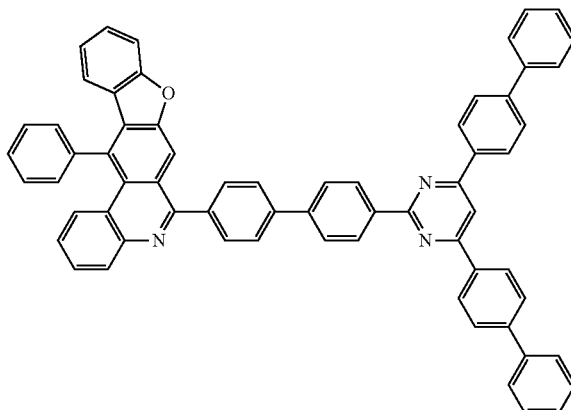
31

32
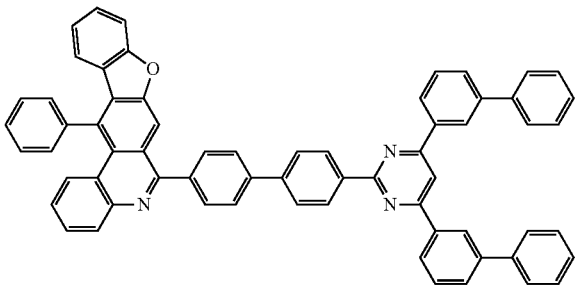

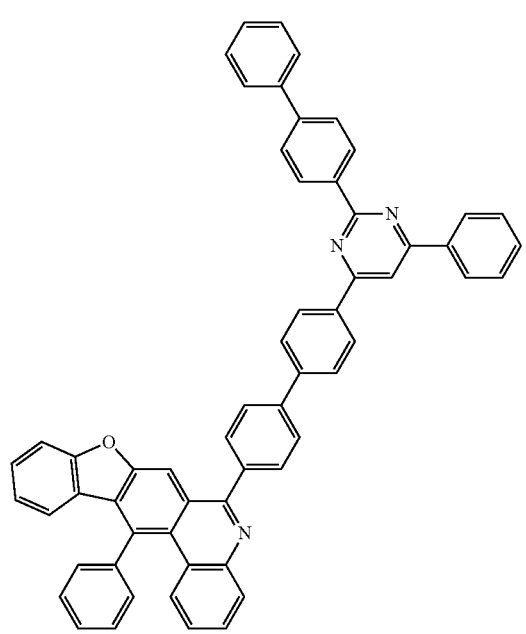
33
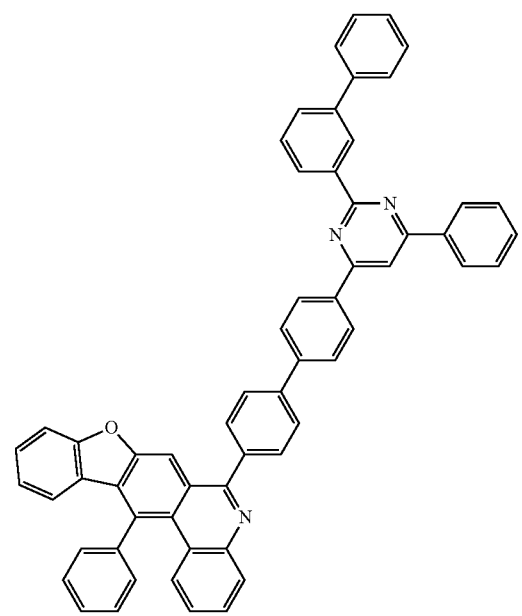
34
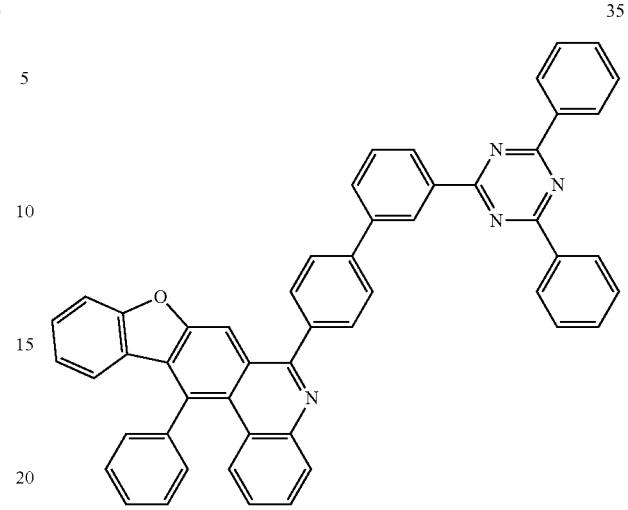
35
36
37

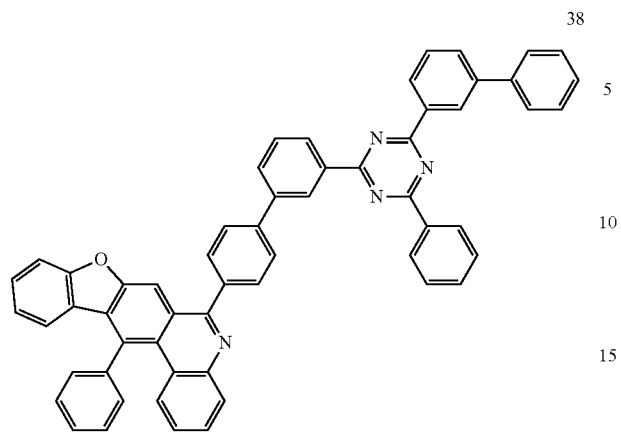
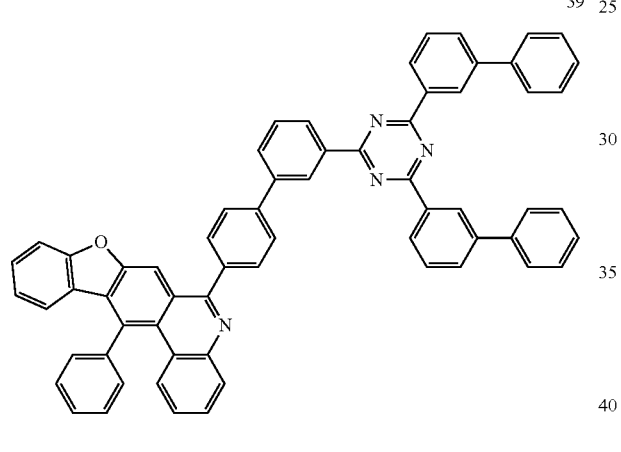
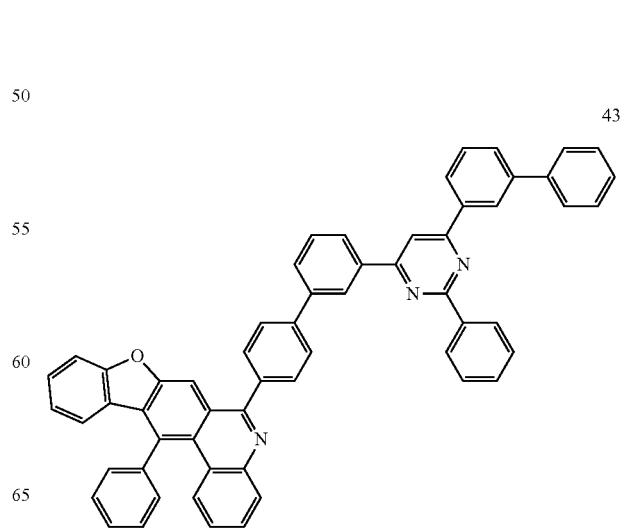

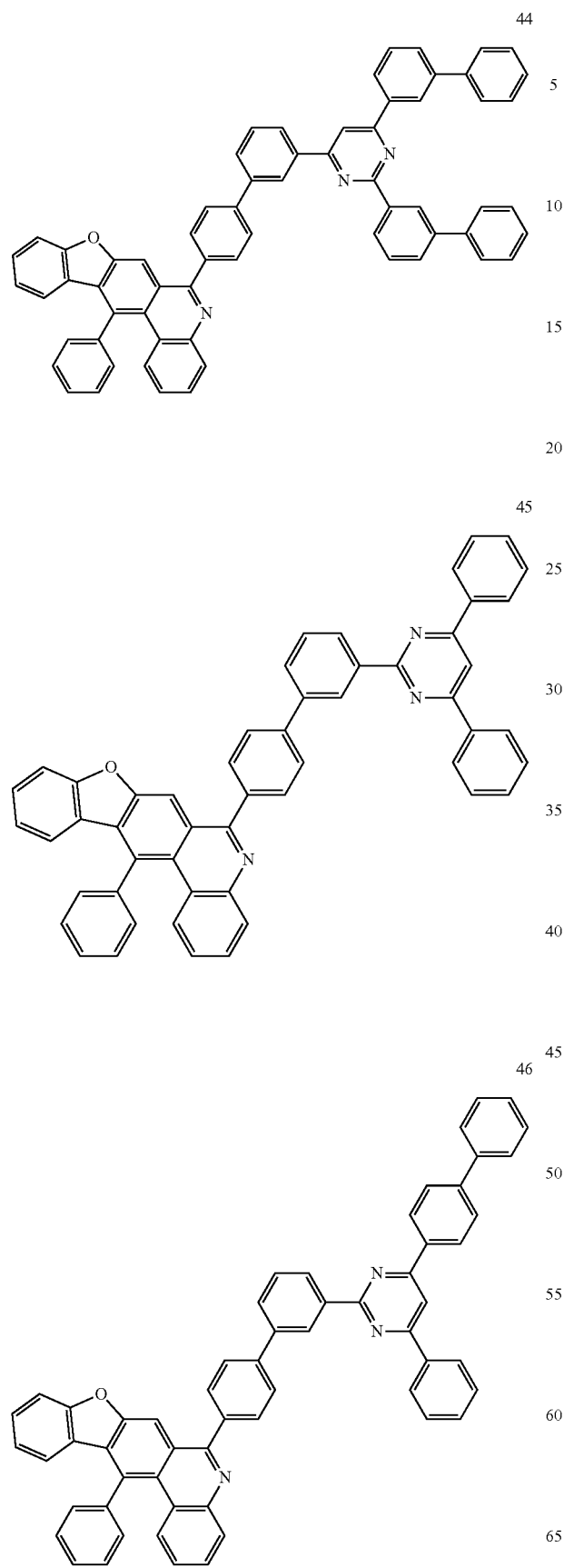
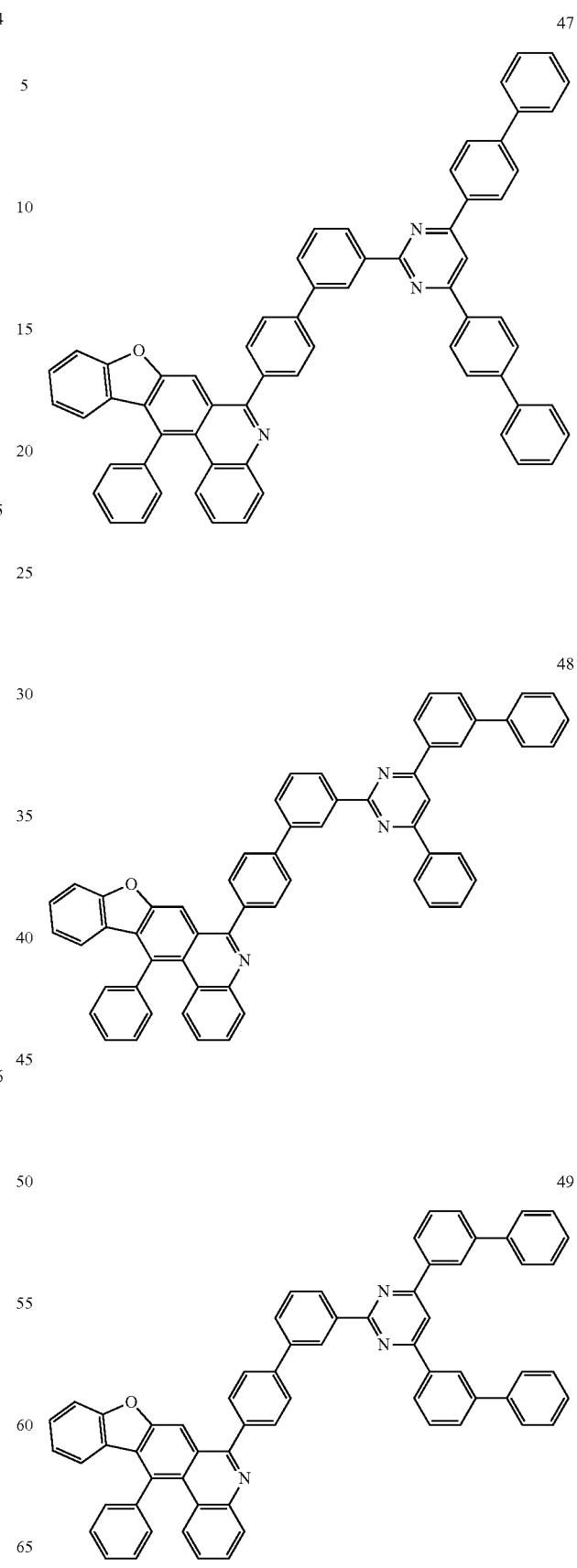

763
-continued
764
-continued
50
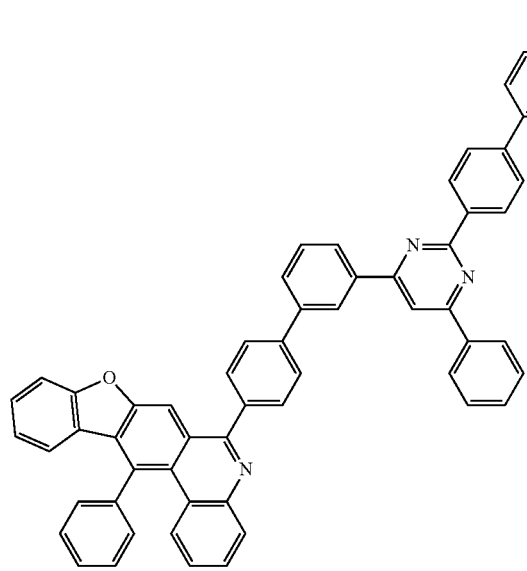
53
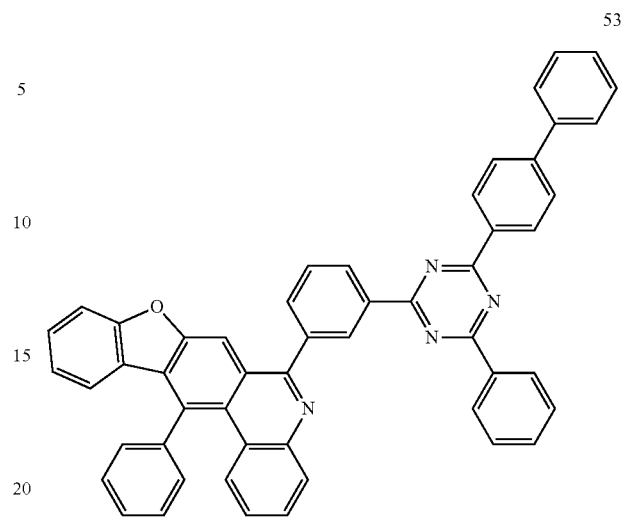
51
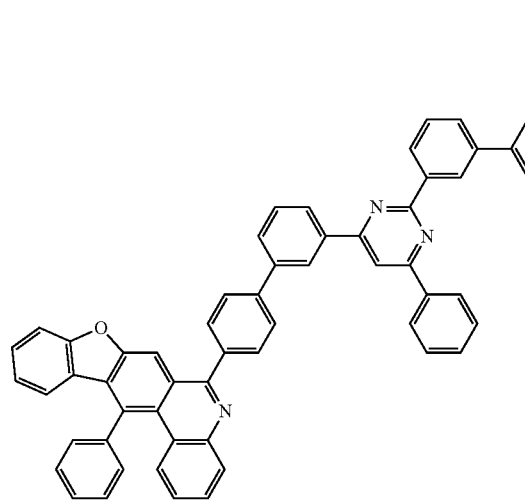
54
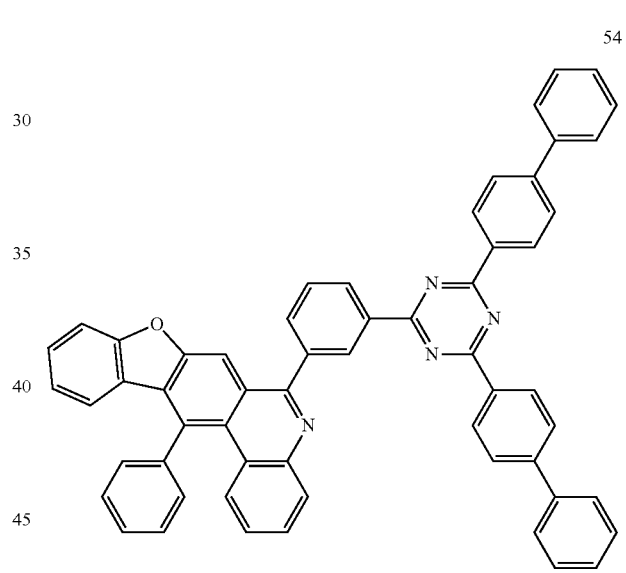
52
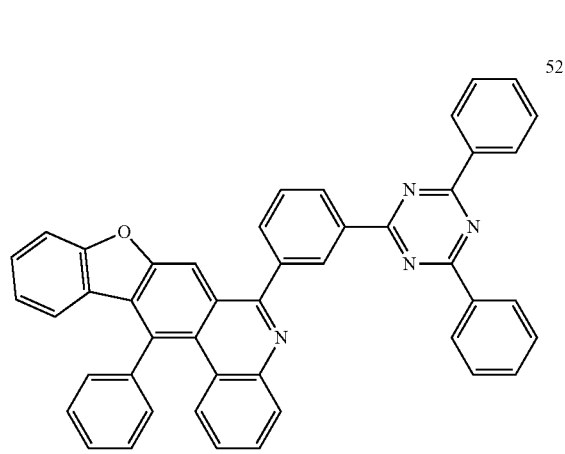
55
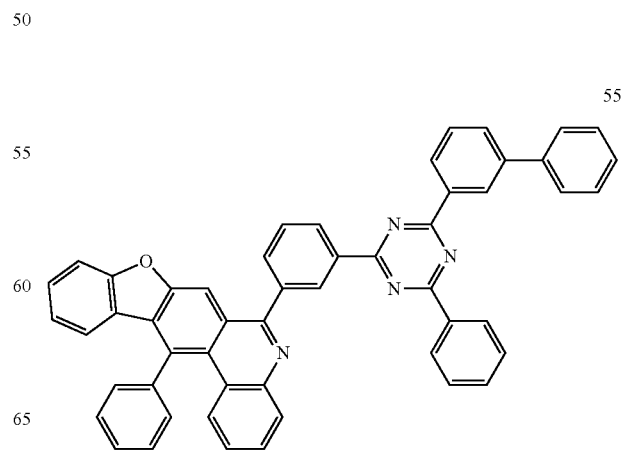

-continued
56
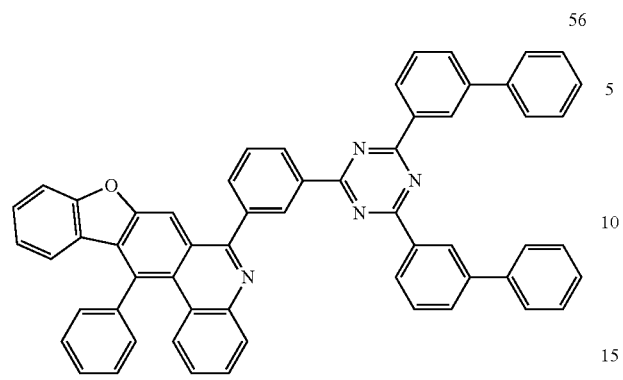
57
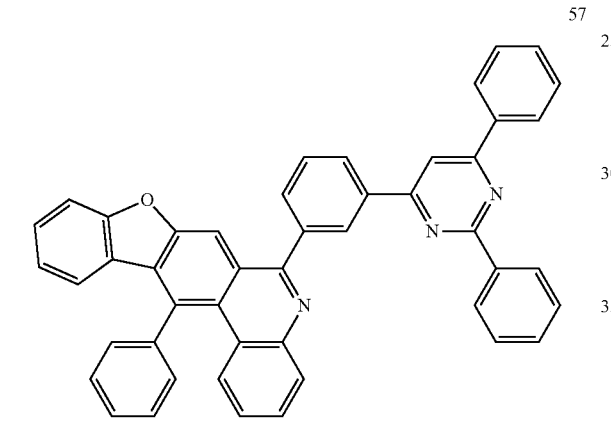
58
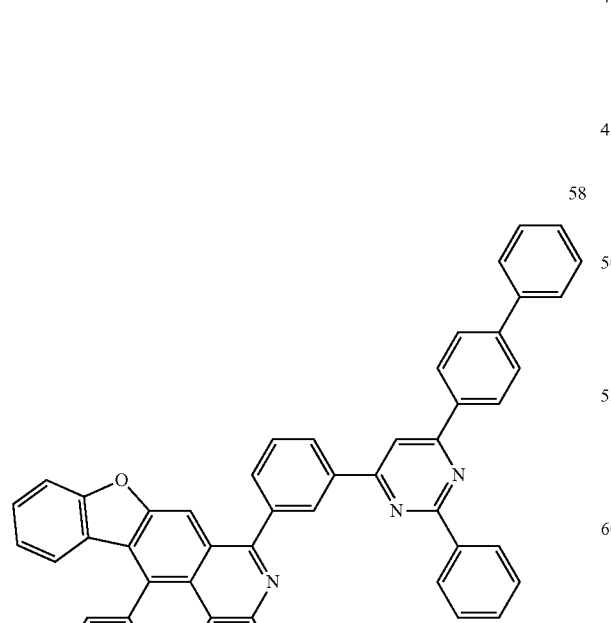
-continued
59
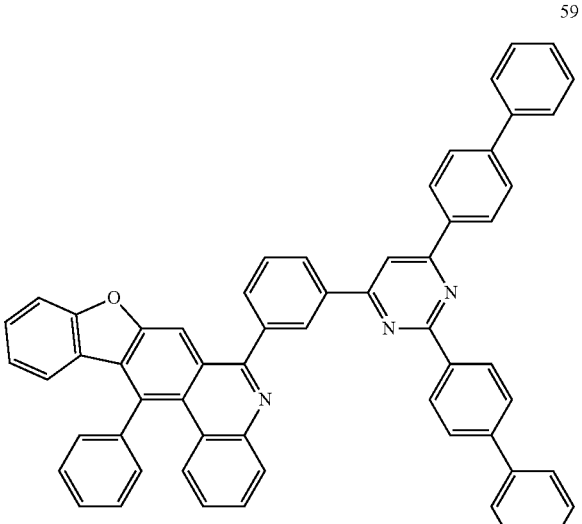
60
61
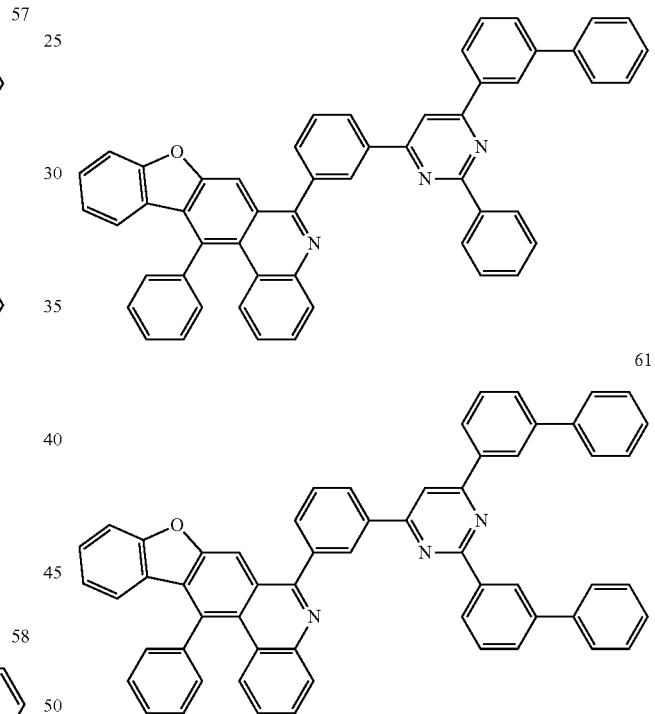
62
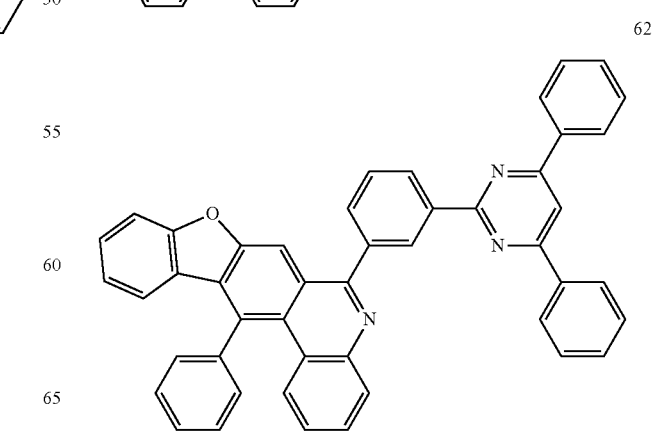

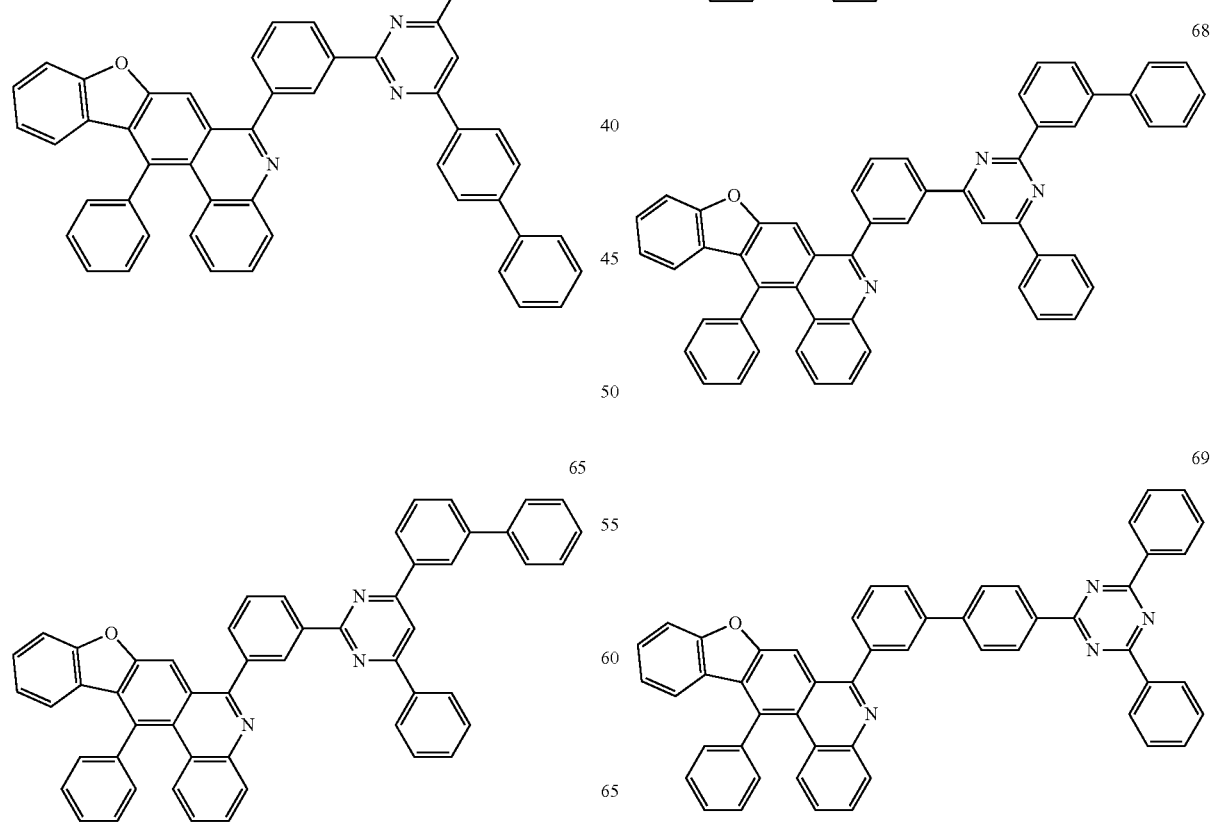

769
-continued
70
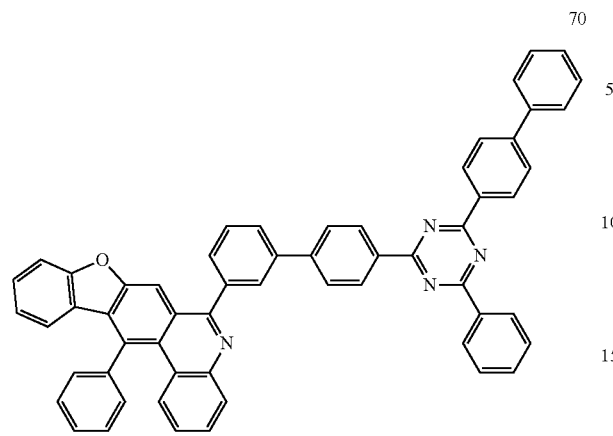
71
72
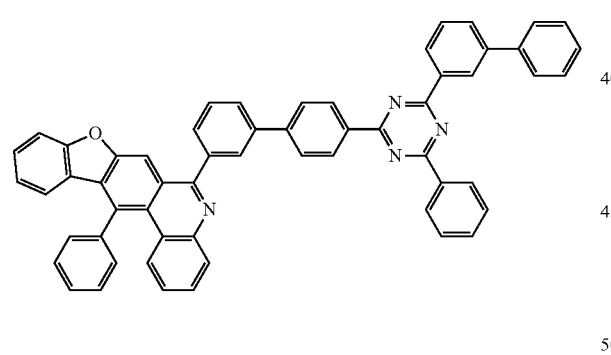
73
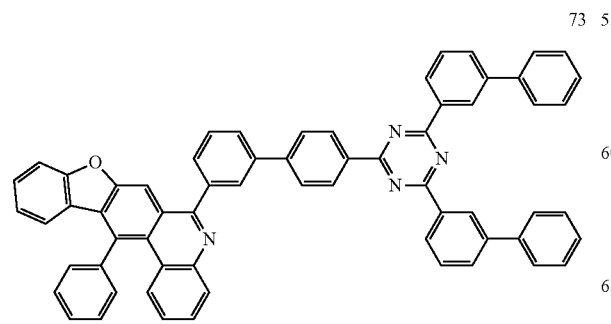
770
-continued
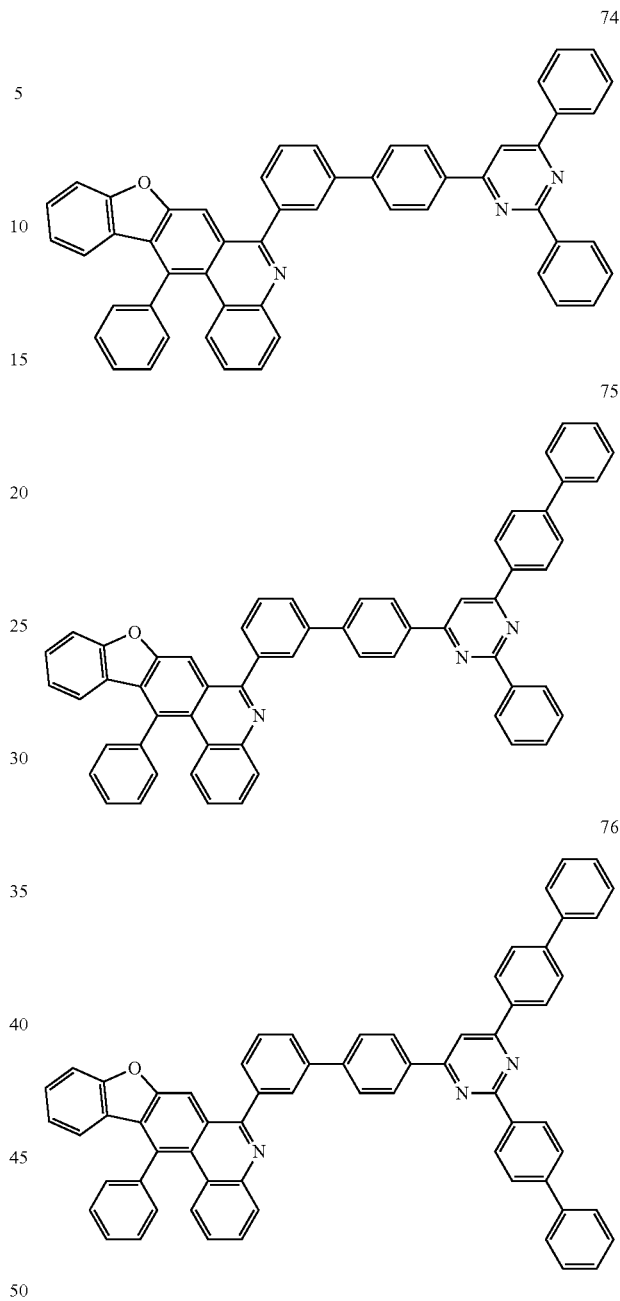
77
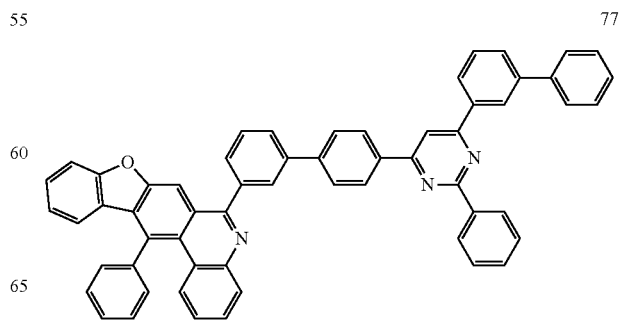

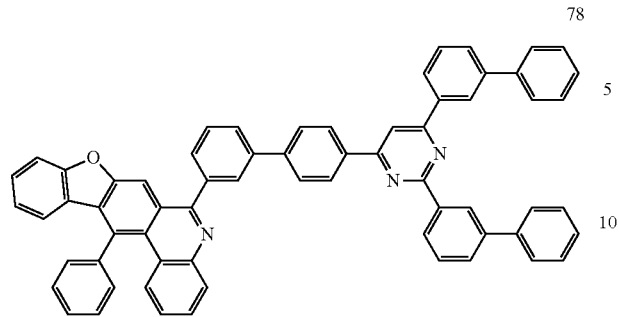
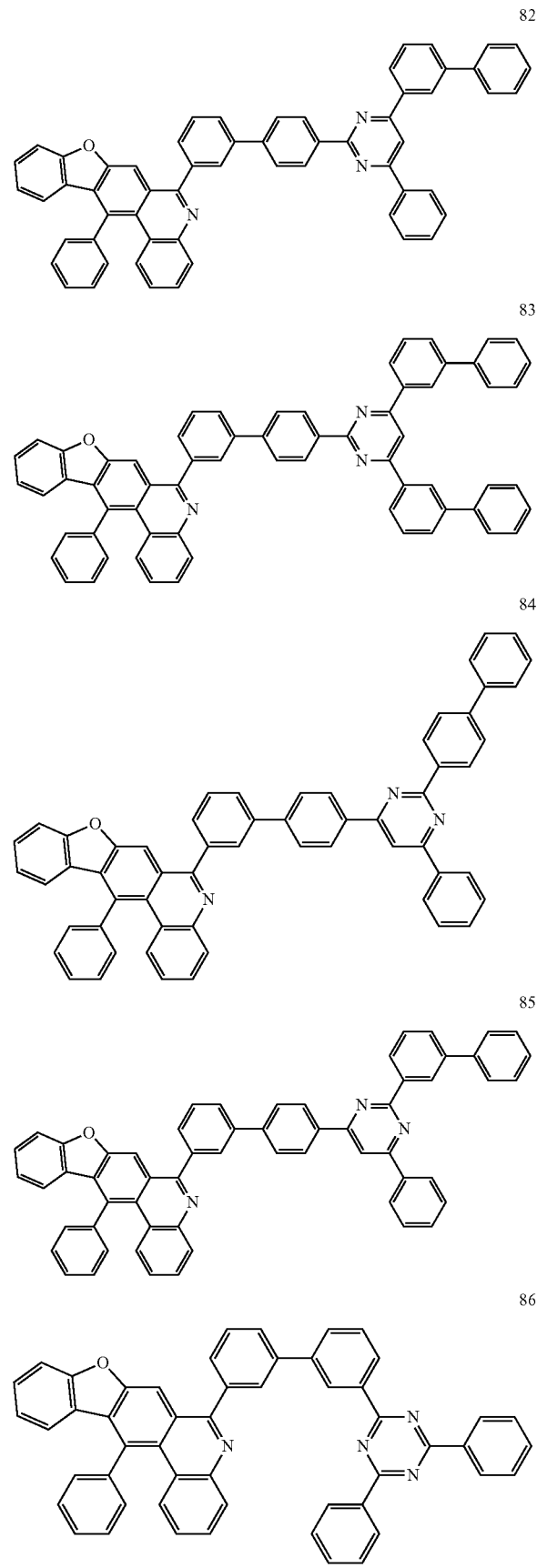

773
-continued
87
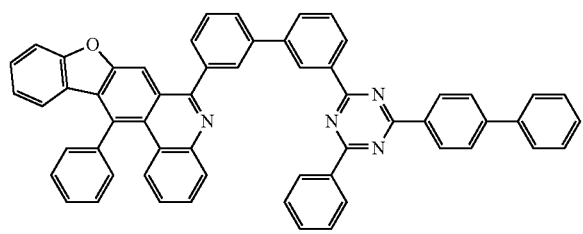
88
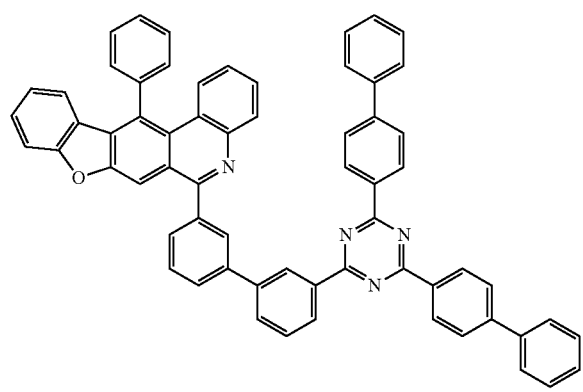
89
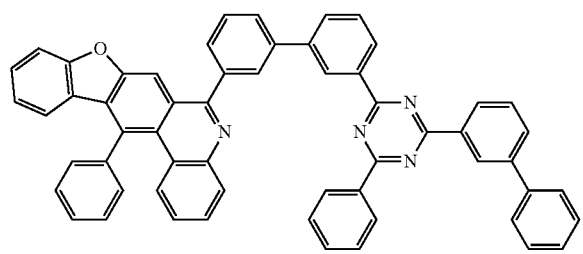
90
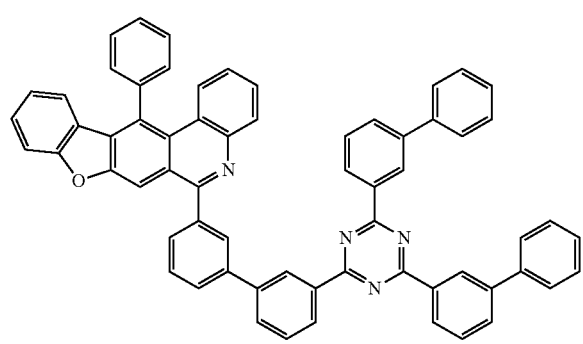
91
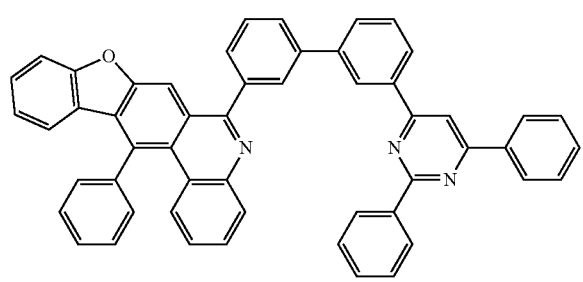
774
-continued
92
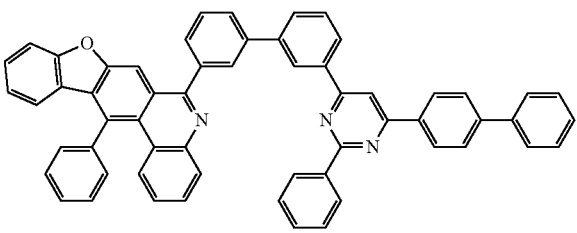
93
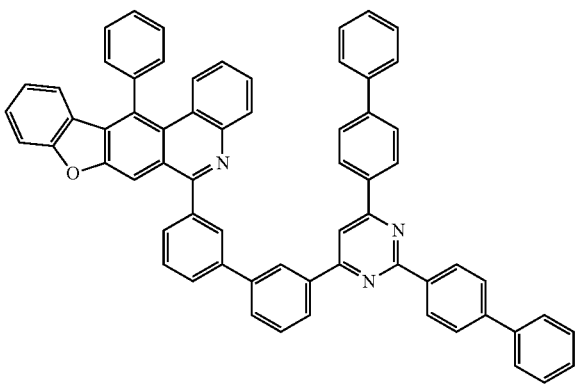
94
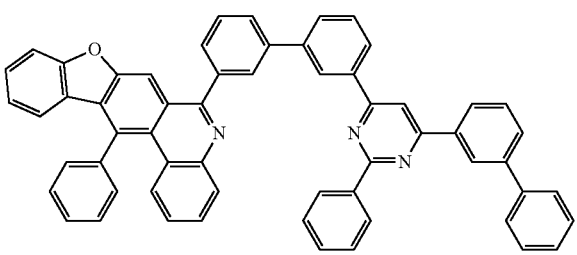
95
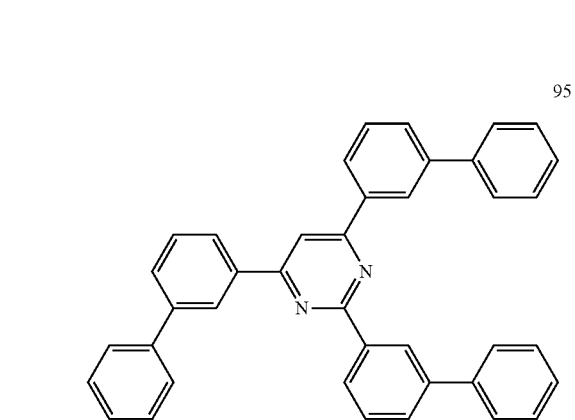
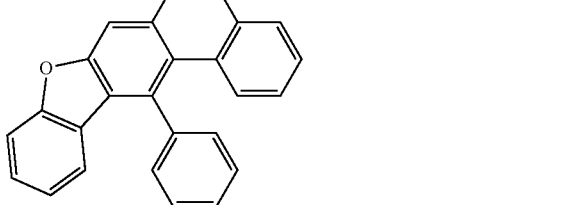

775
-continued
96
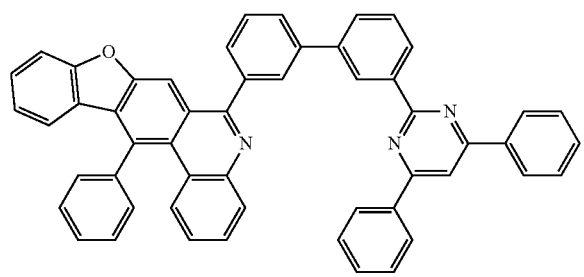
97
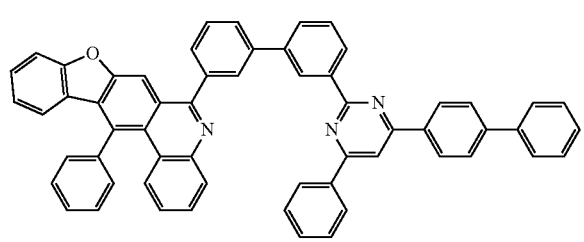
98
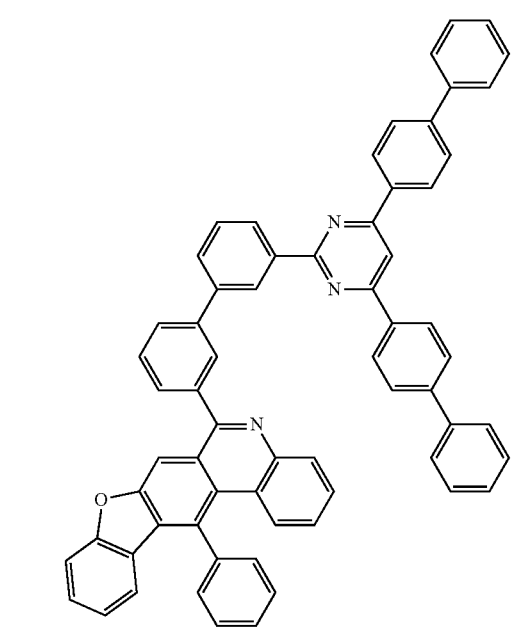
99
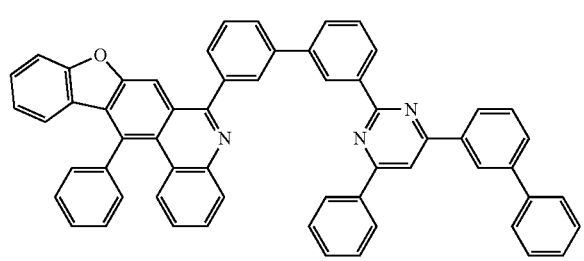
776
-continued
100
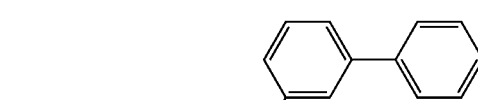
101
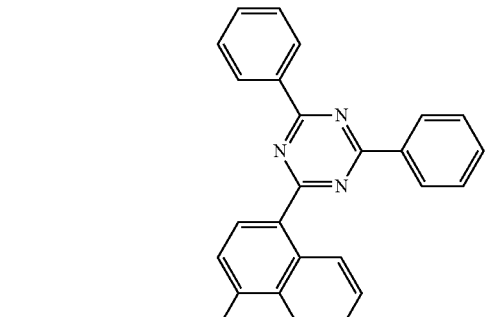
102
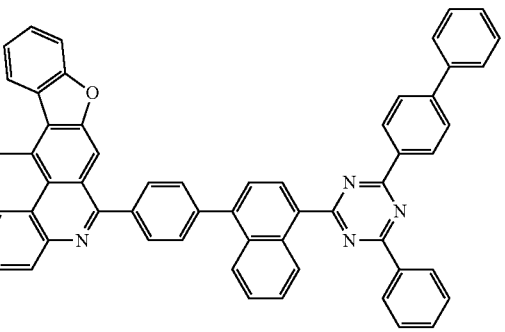

103
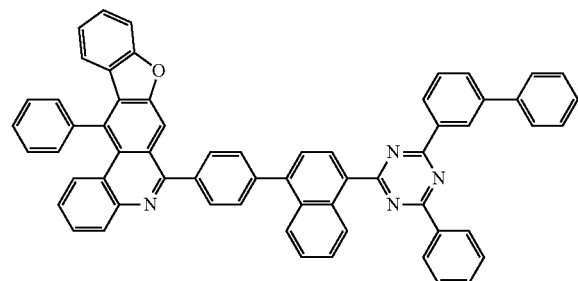
104
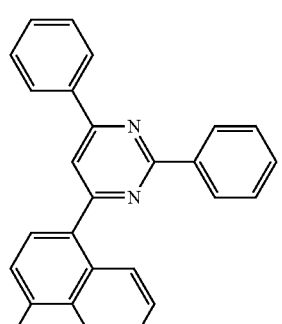
105
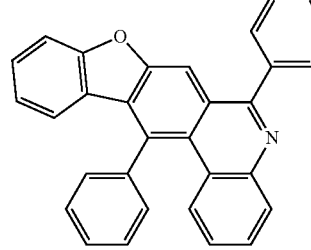
106
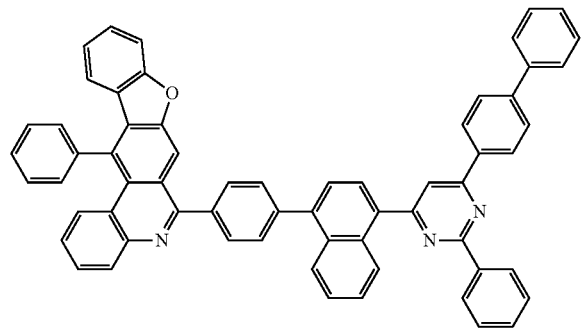
107
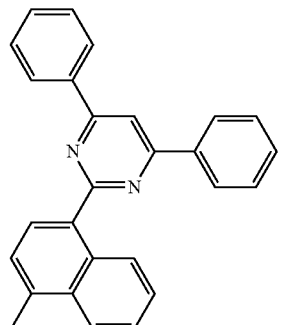
108
109
110
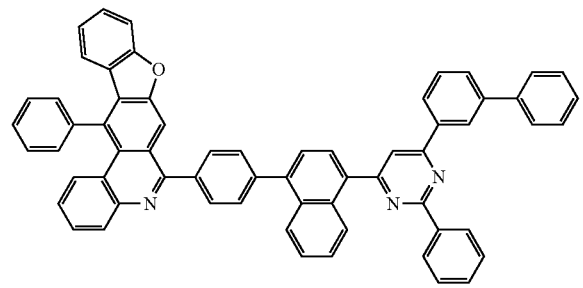
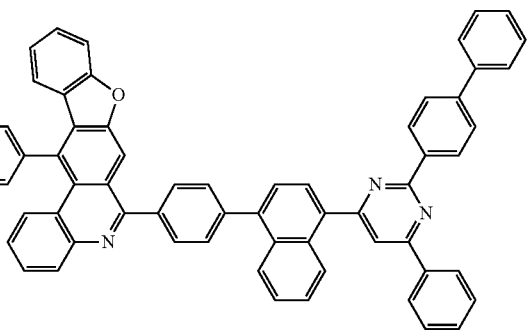

111
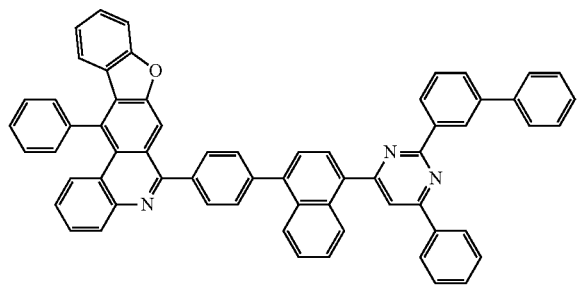
112
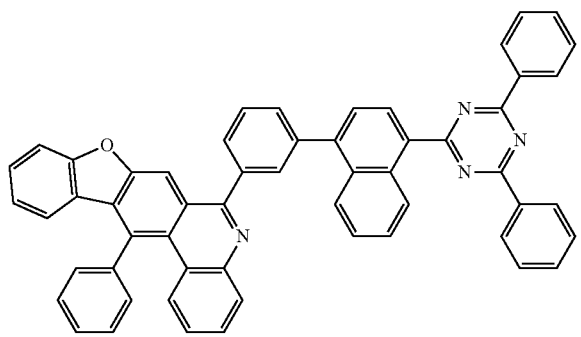
113
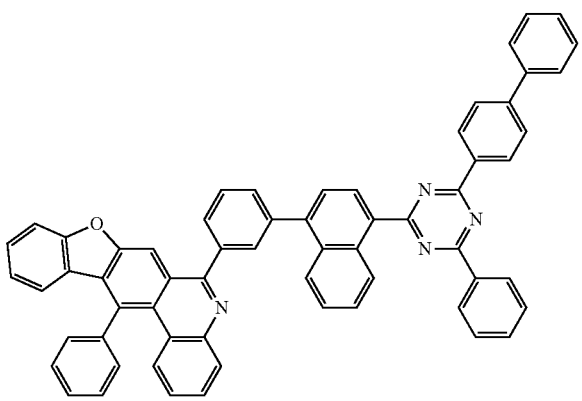
114
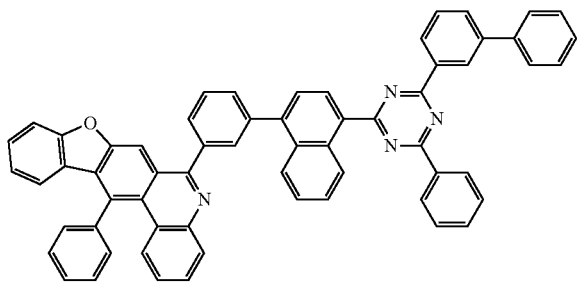
115
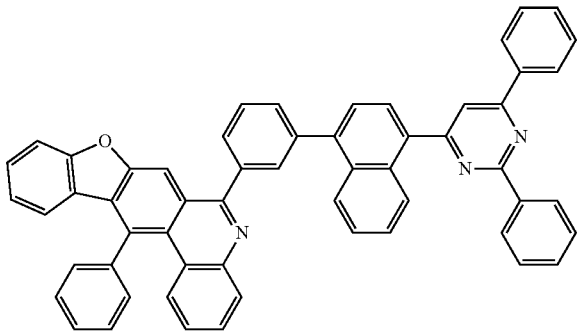
116
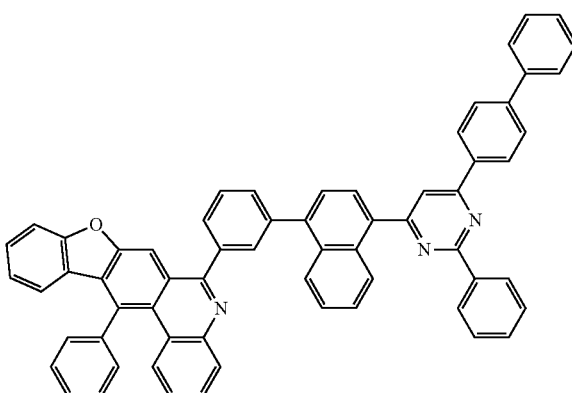
117
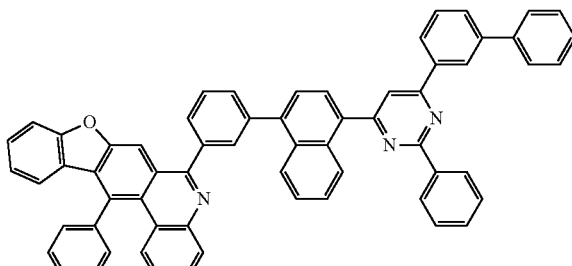
118
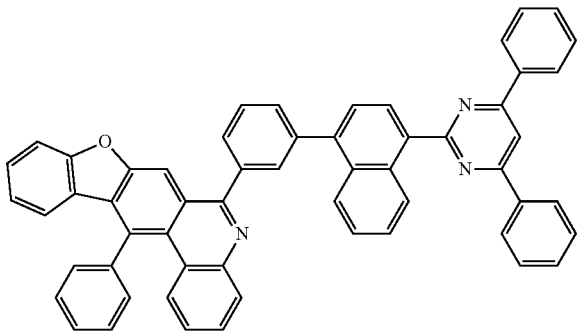

-continued
119
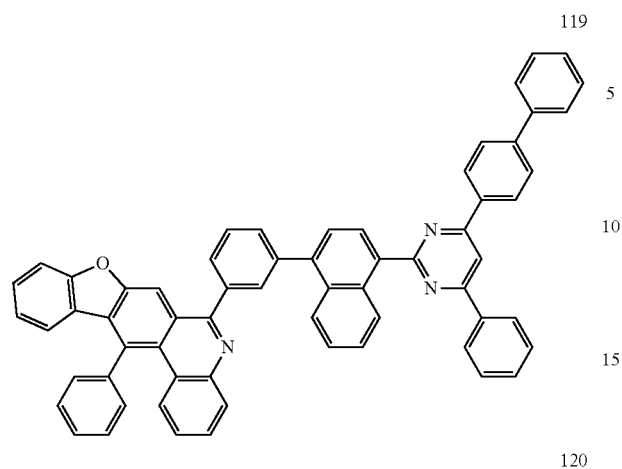
120
121
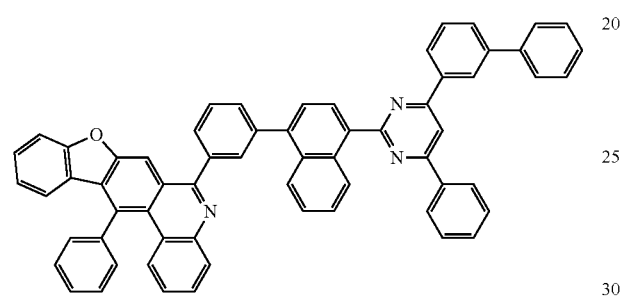
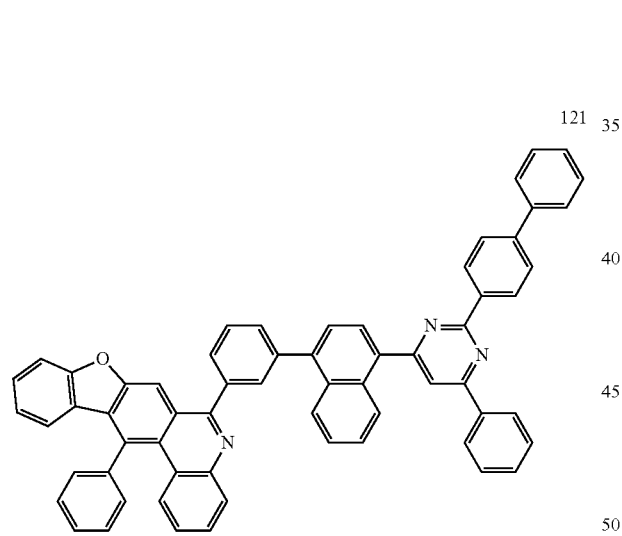
122
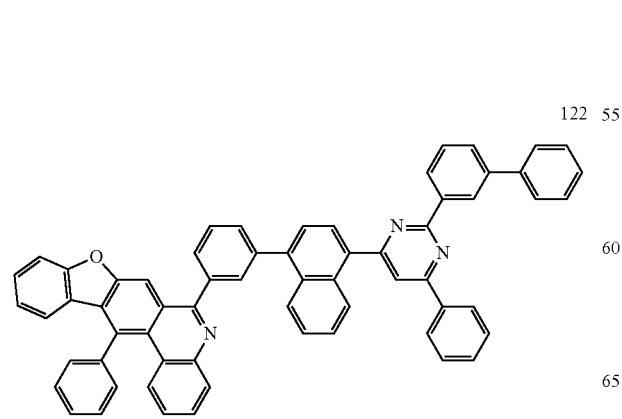
-continued
123
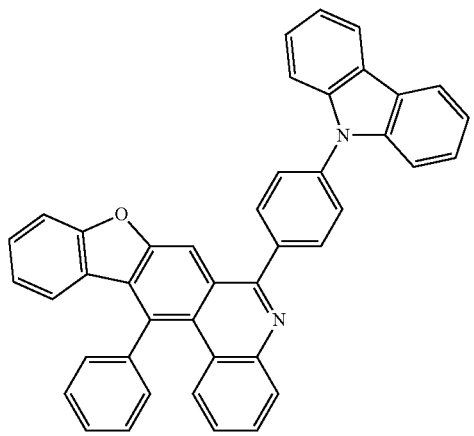
124
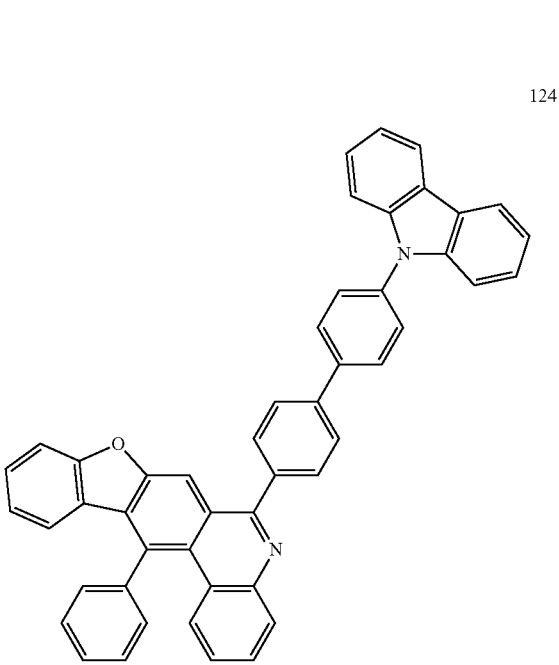
125
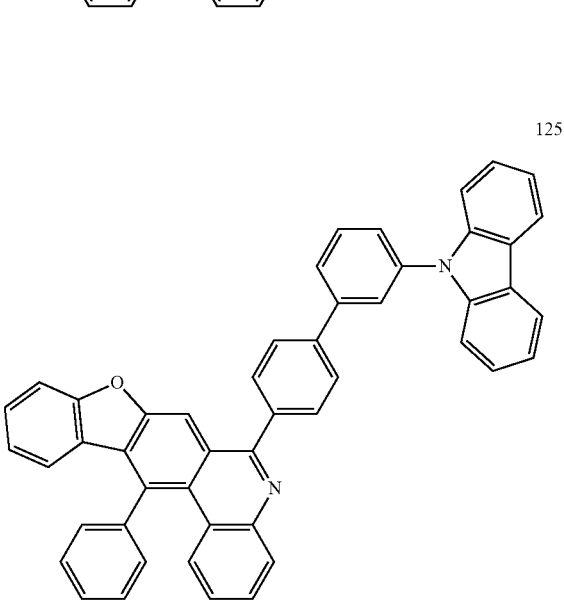

126
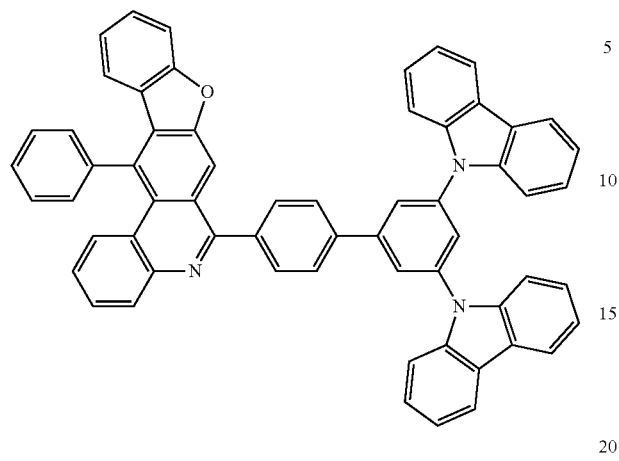
127
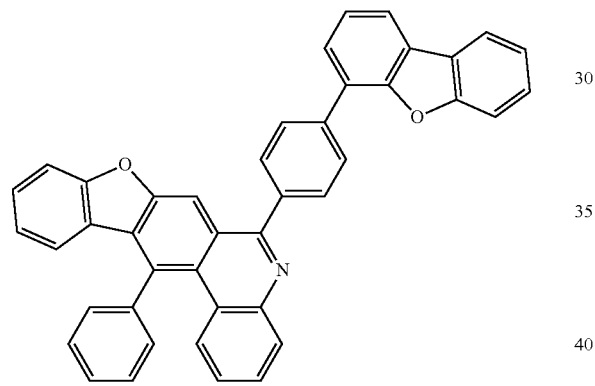
128
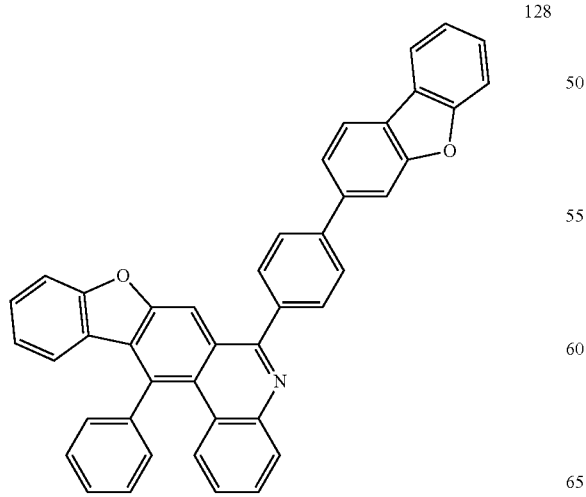
129
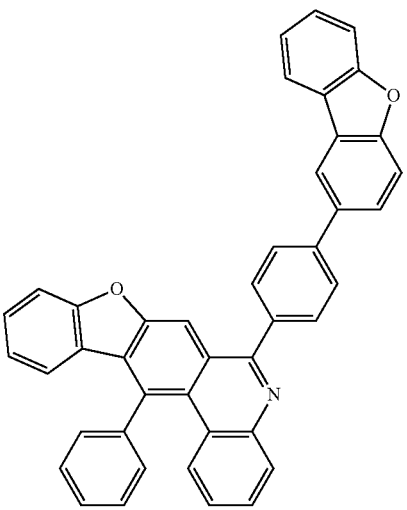
130
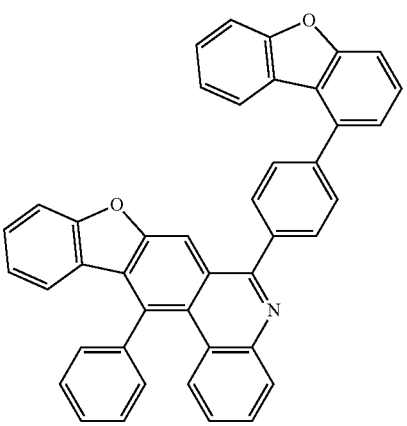
131
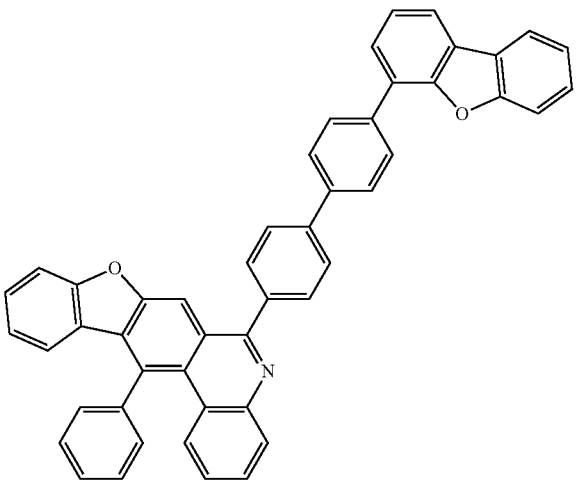

785
-continued
786
-continued
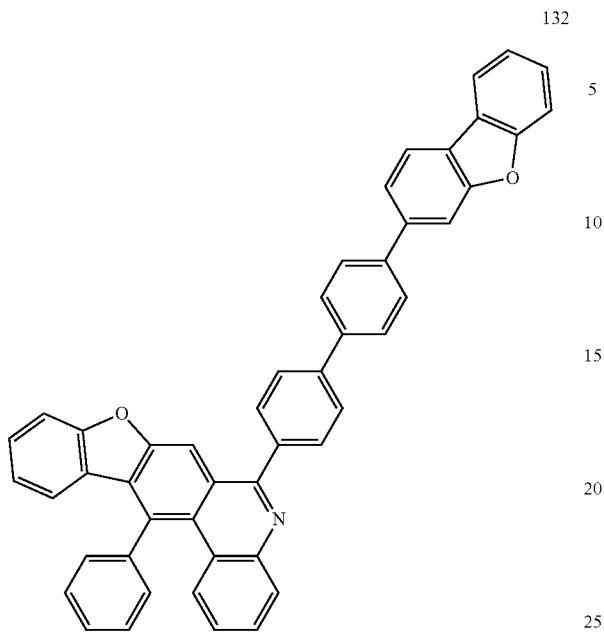
132
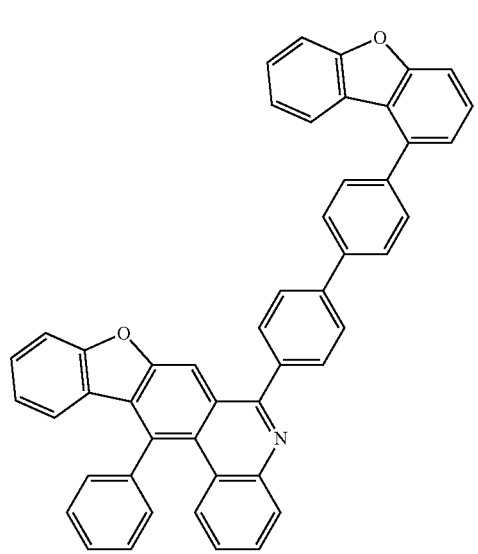
134
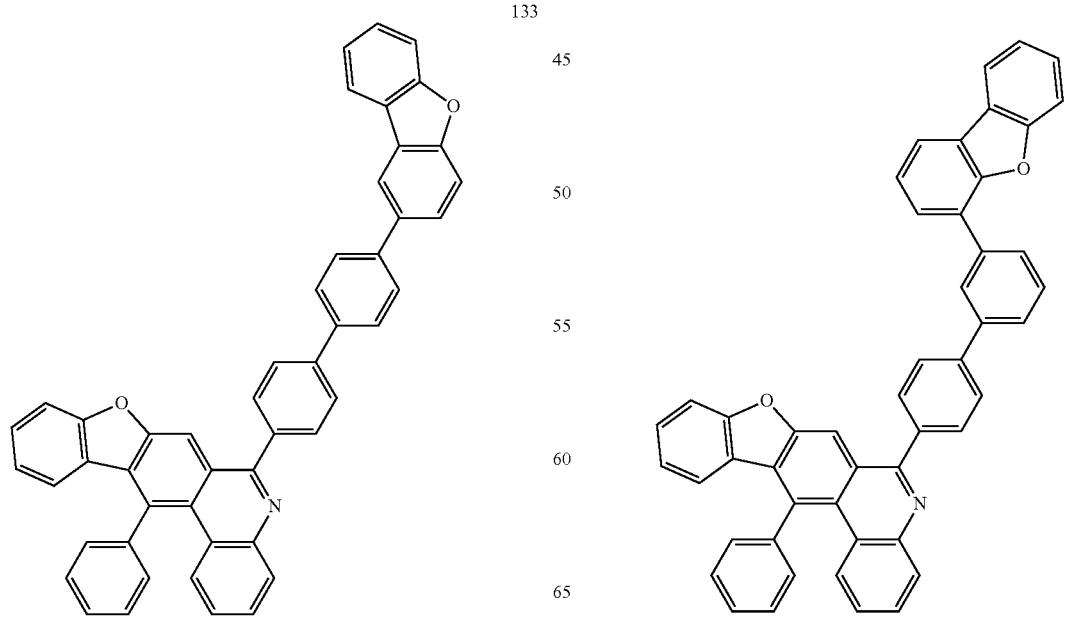
133
135

136
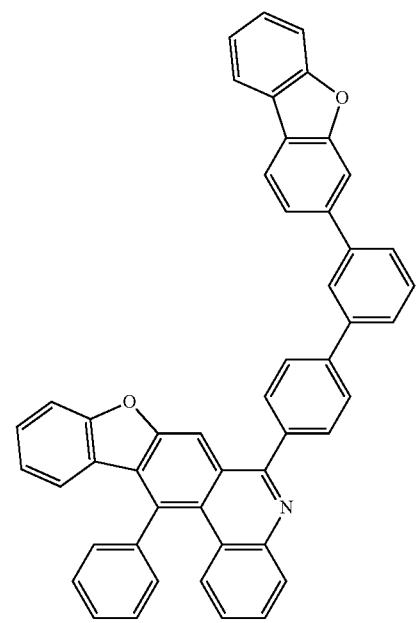
137
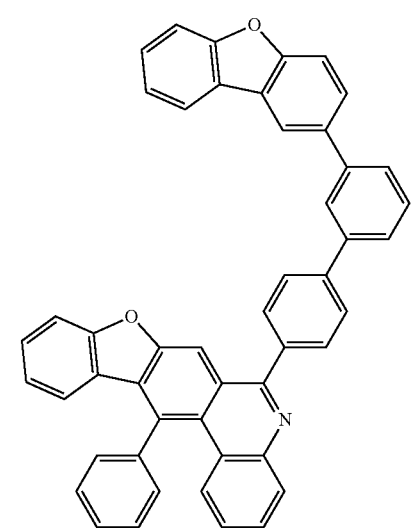
138
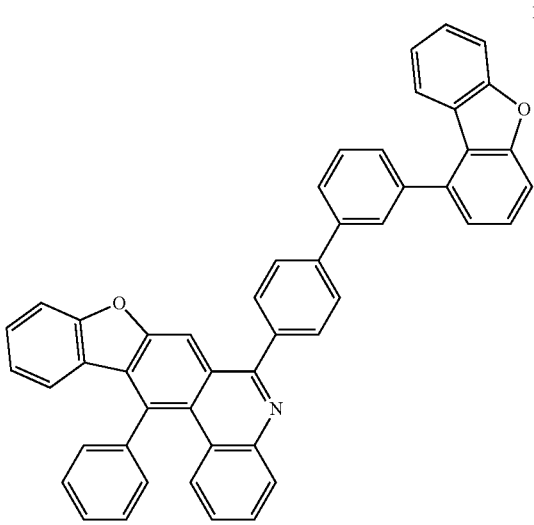
139
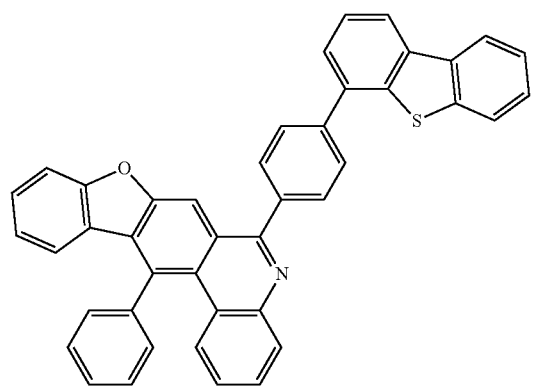
140
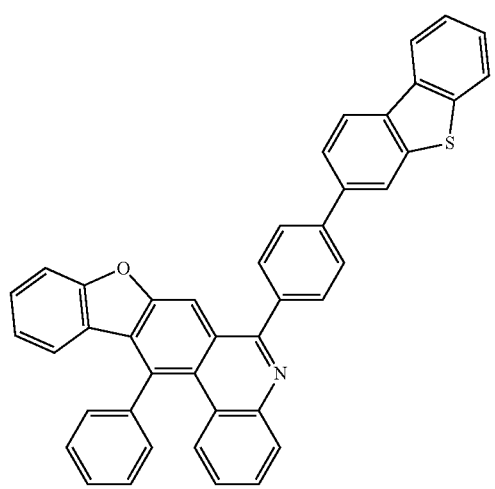
141
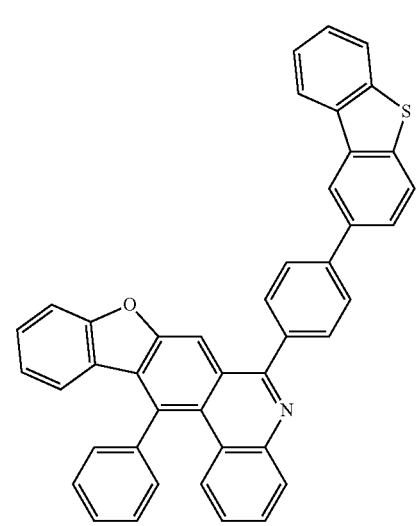

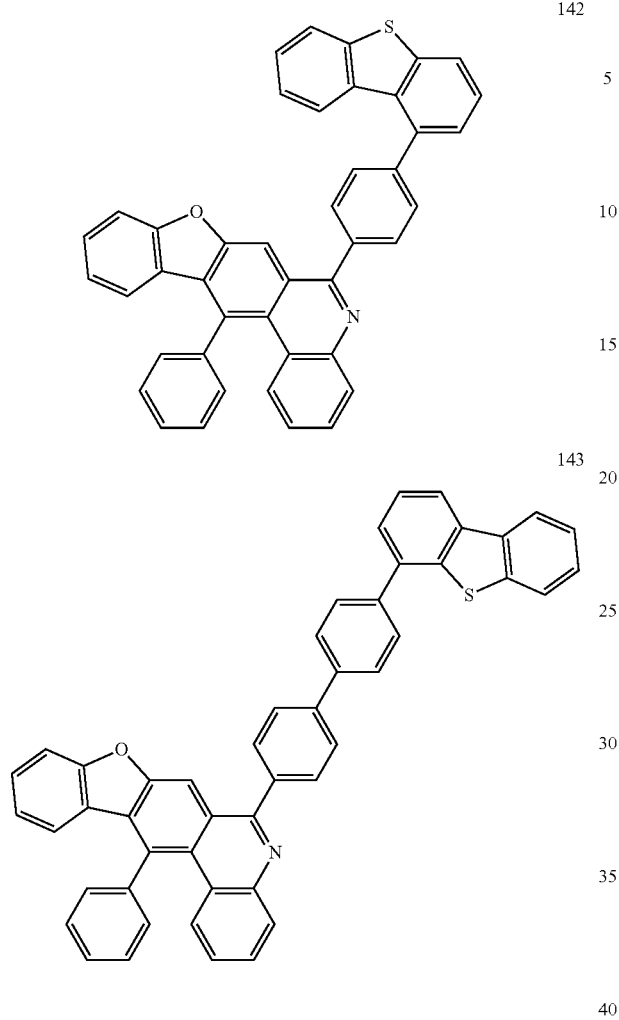
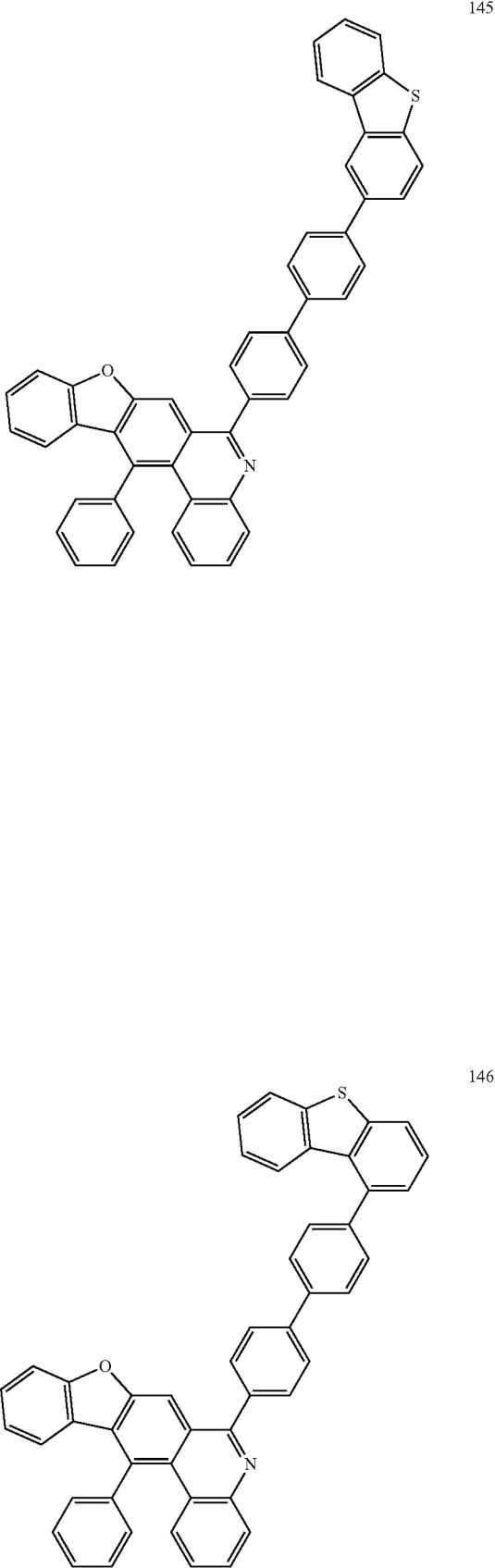

147
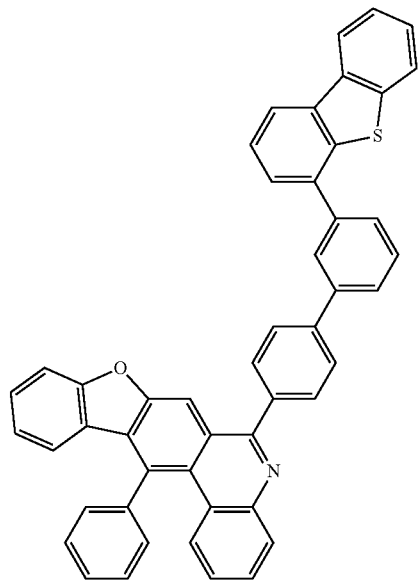
148
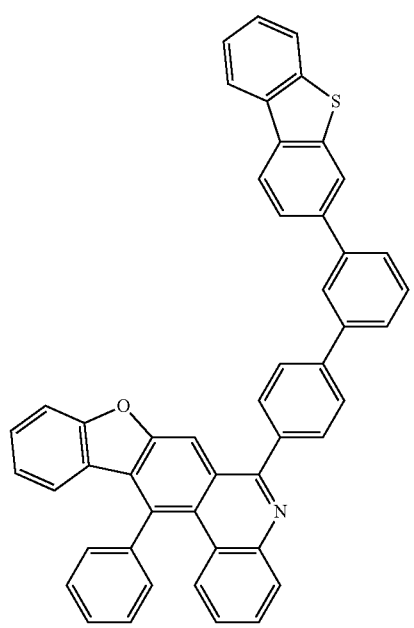
149
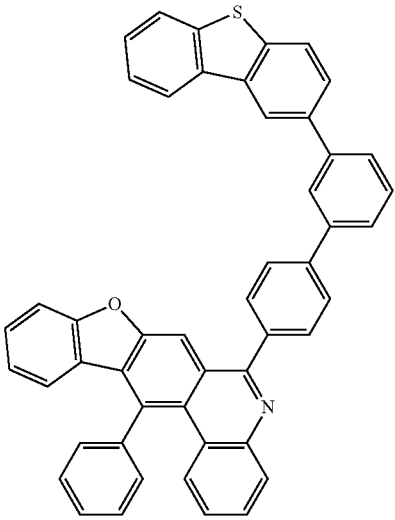
150
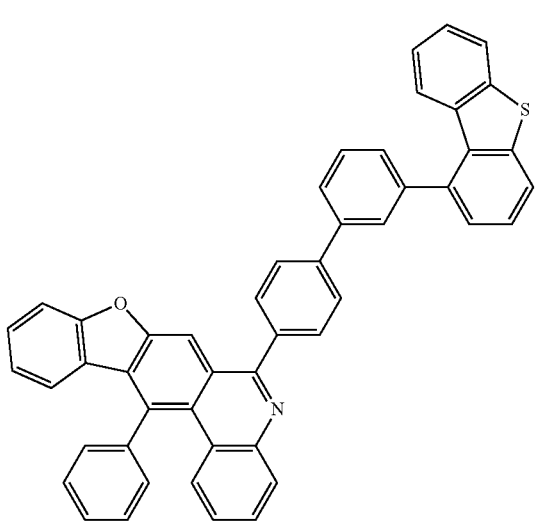
151
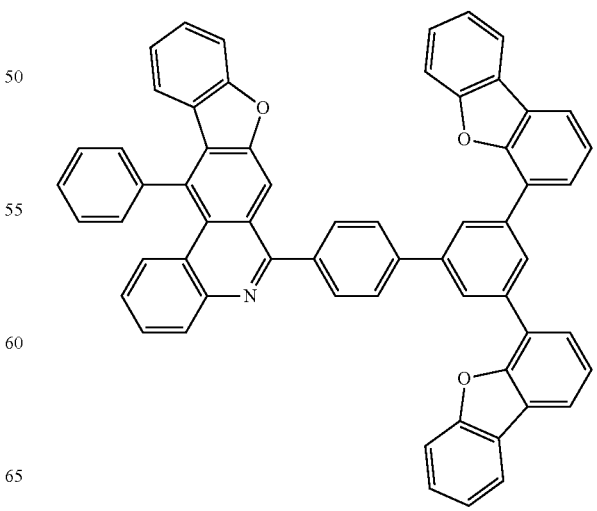

793
-continued
152
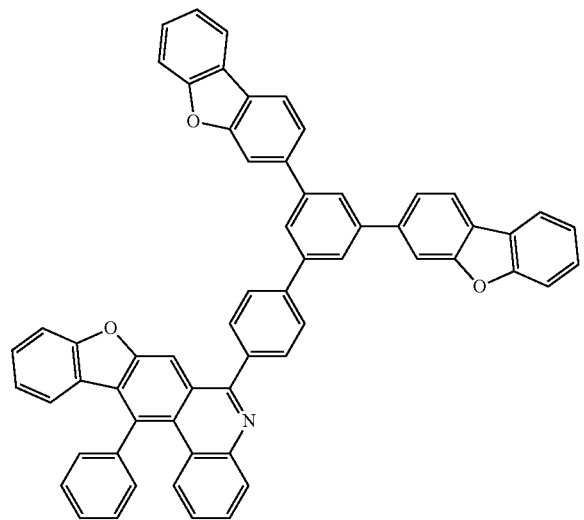
153
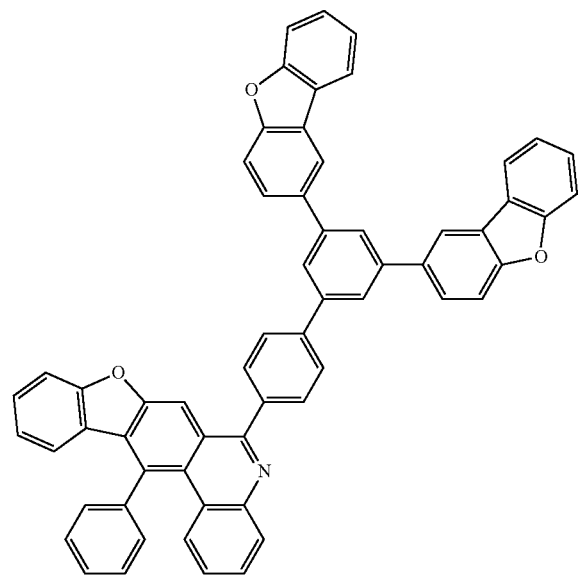
794
-continued
154
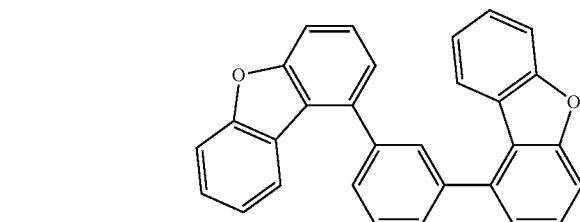
155
156
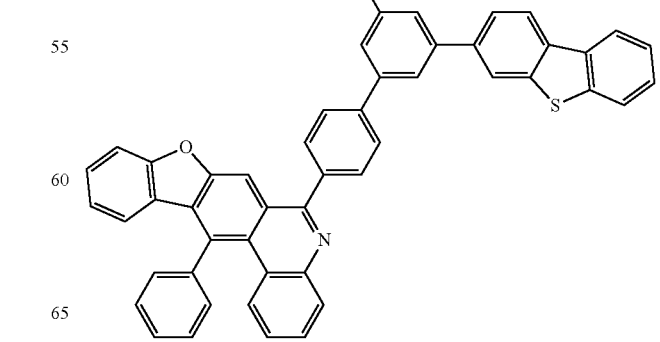

157
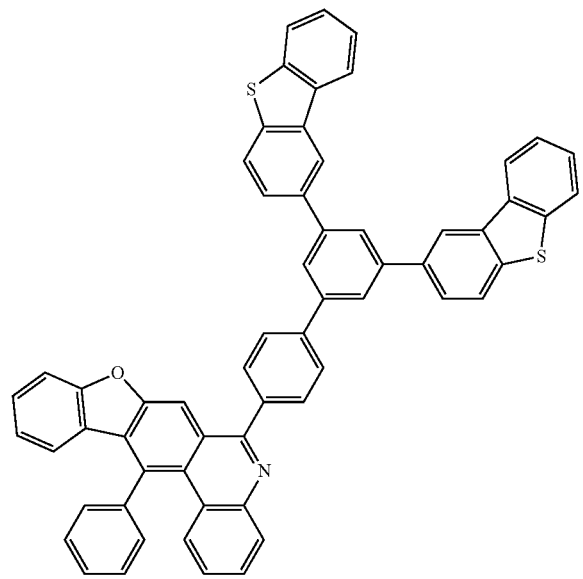
158
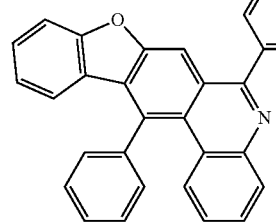
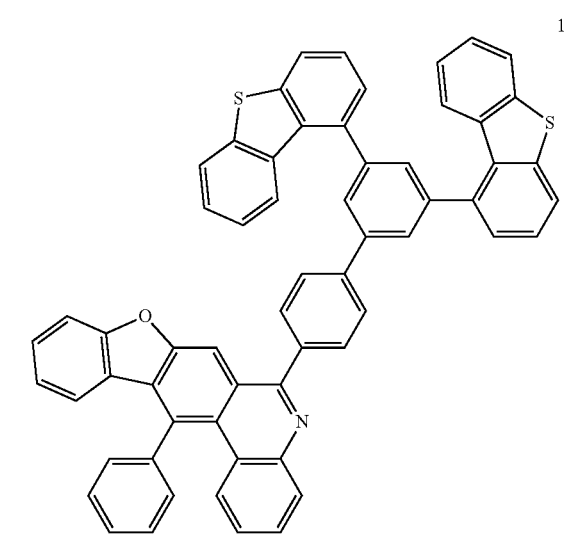
159
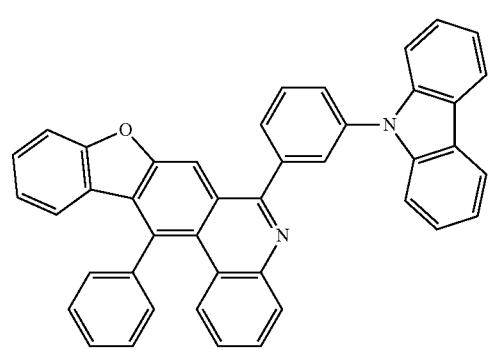
160
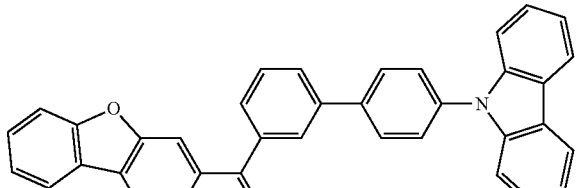
161
162
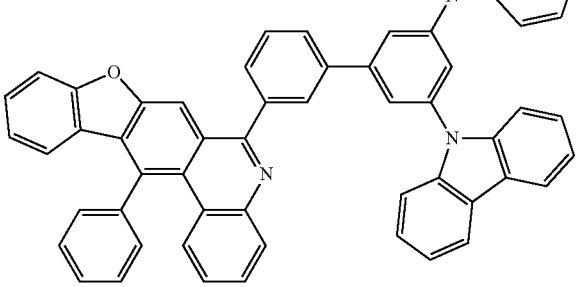
163
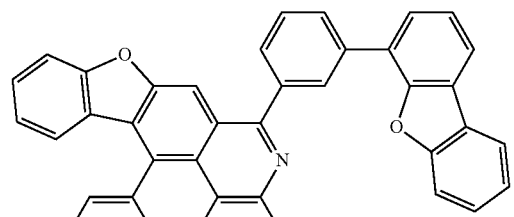
164
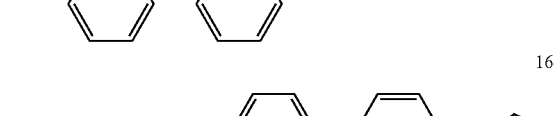
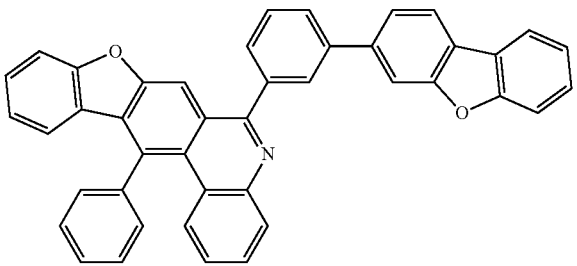

797
-continued
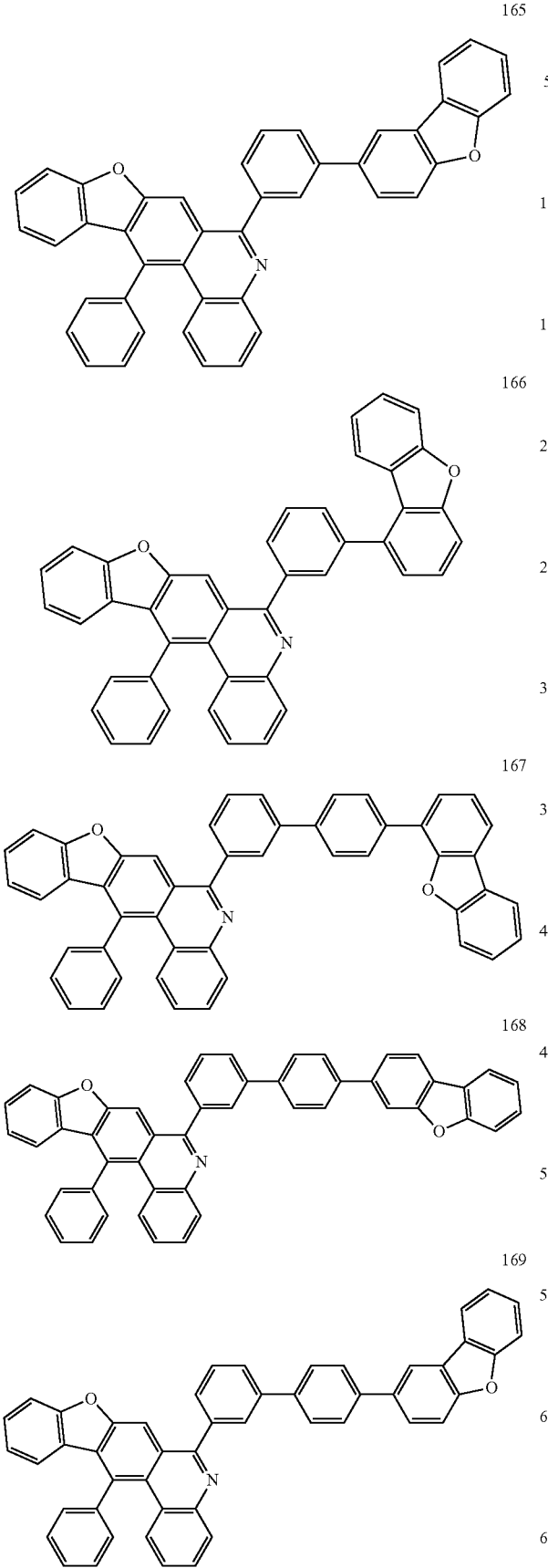
798
-continued
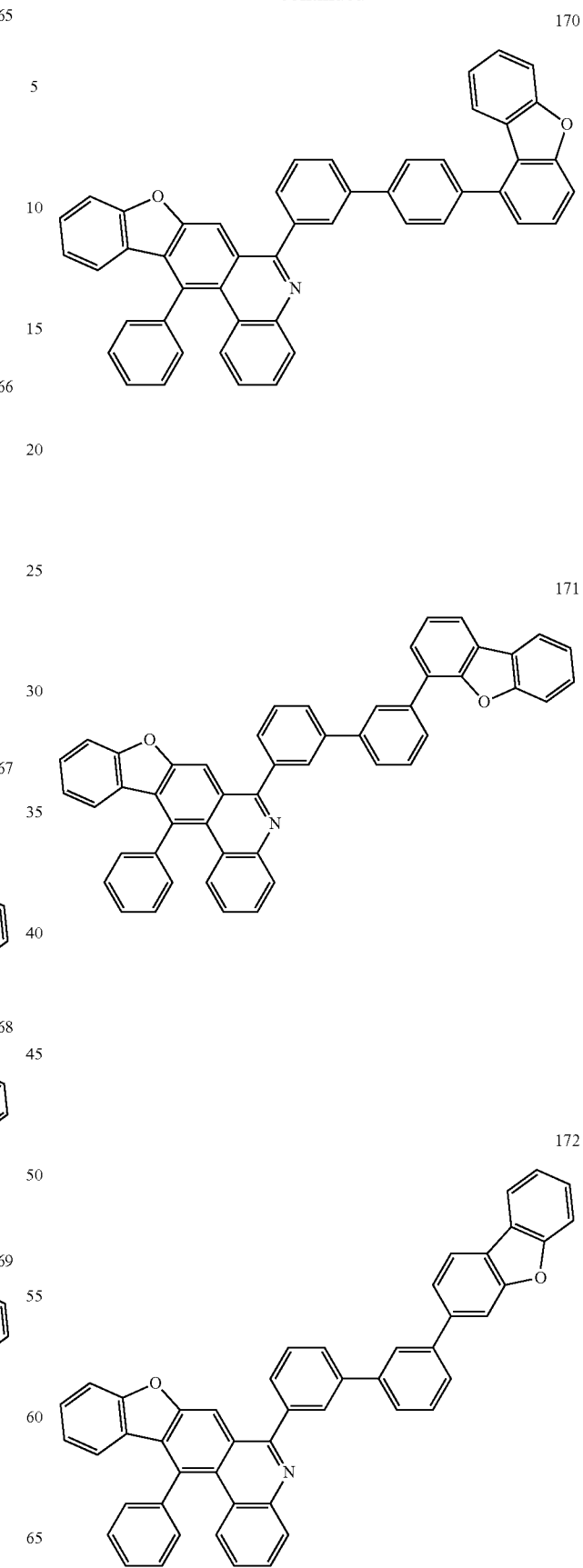

799
-continued
800
-continued
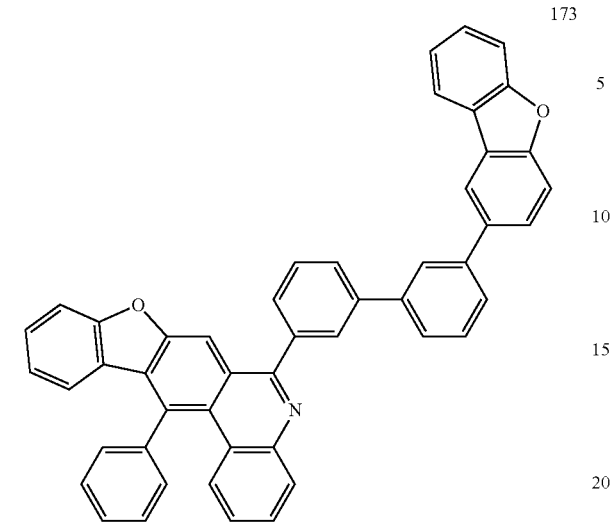
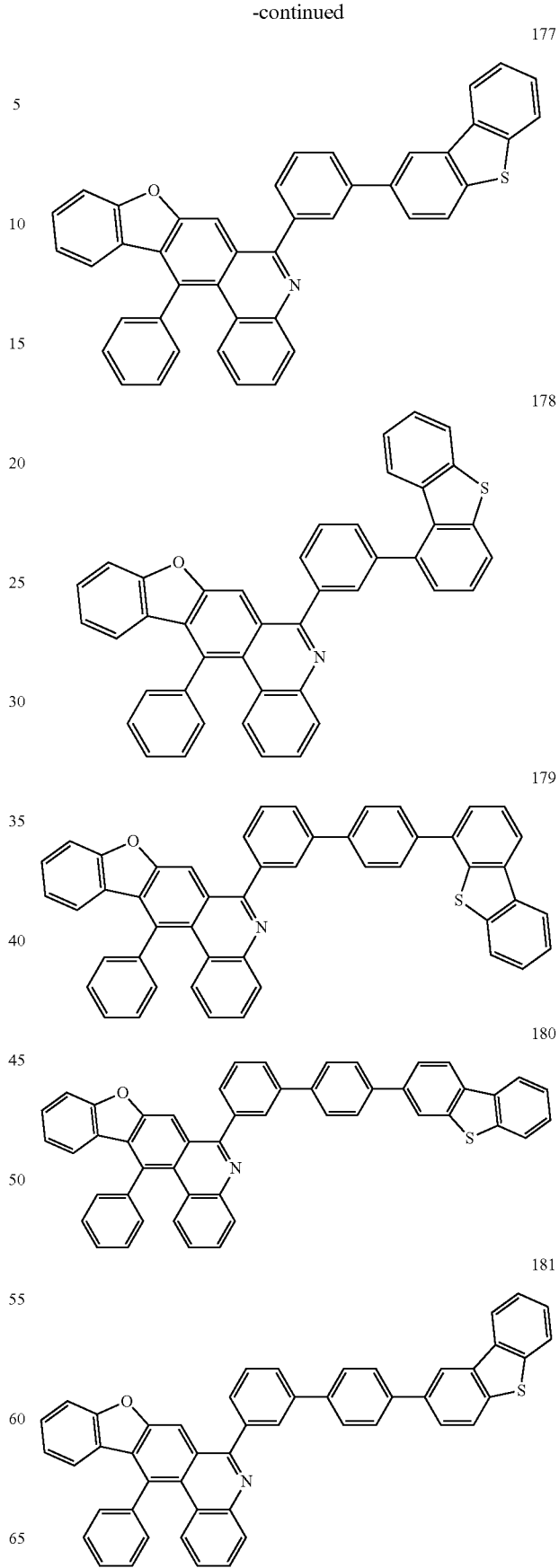

801
-continued
182
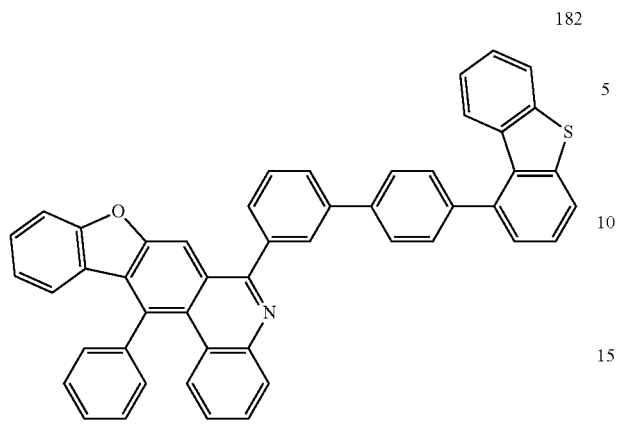
183
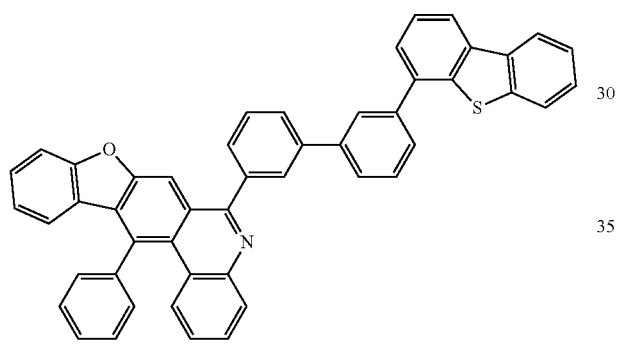
184
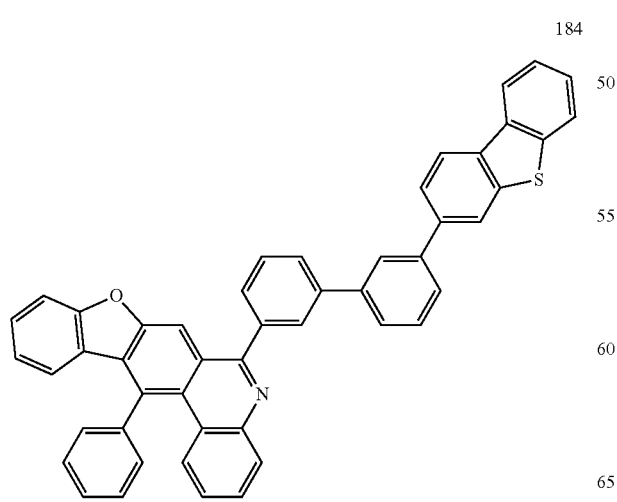
802
-continued
185
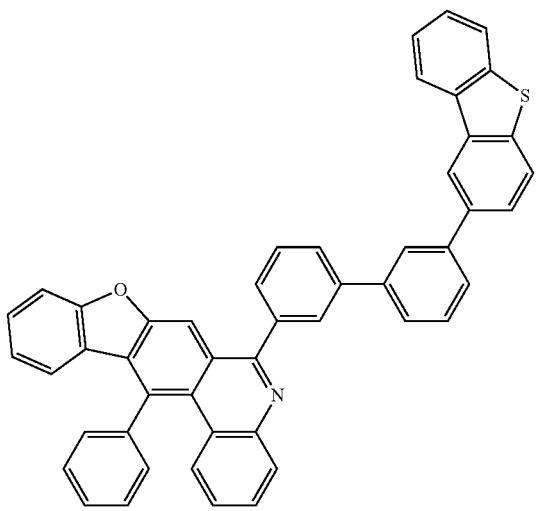
186
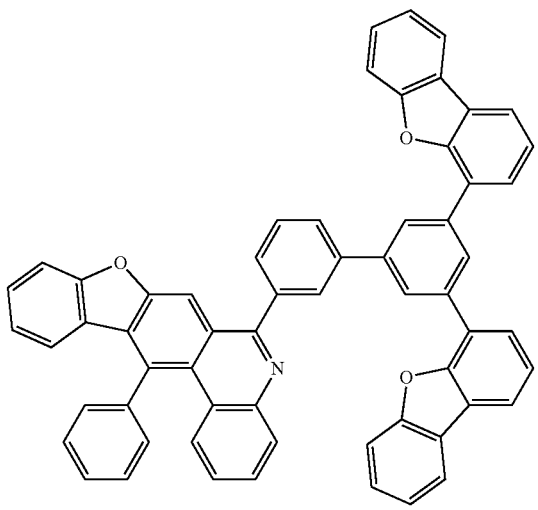
187

803
-continued
188
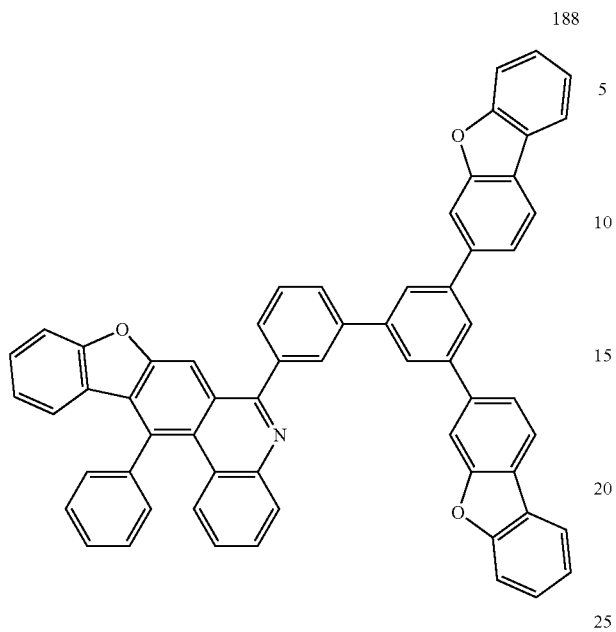
189
804
-continued
191
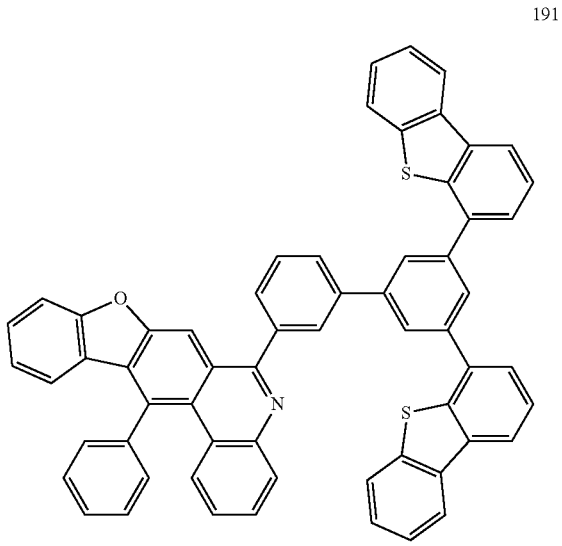
192
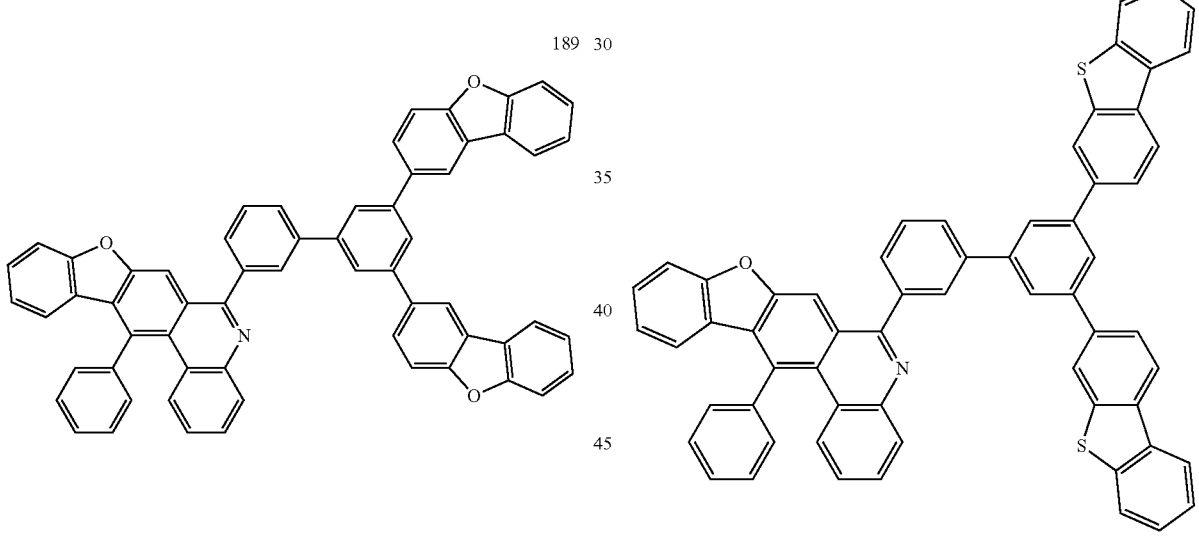
190
193
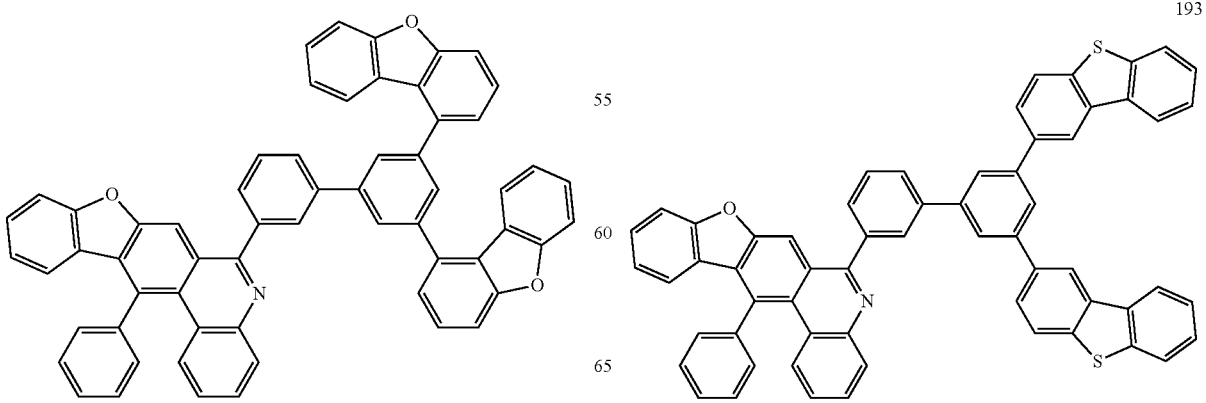

-continued
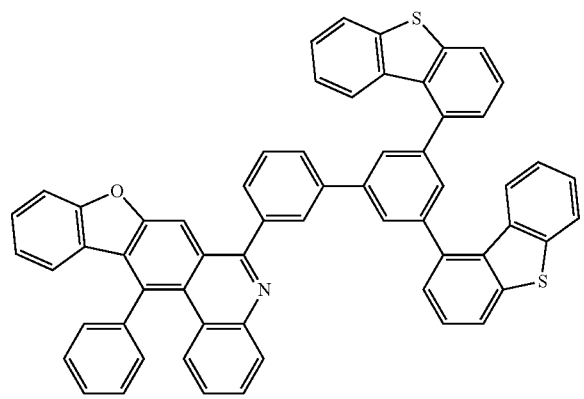
194
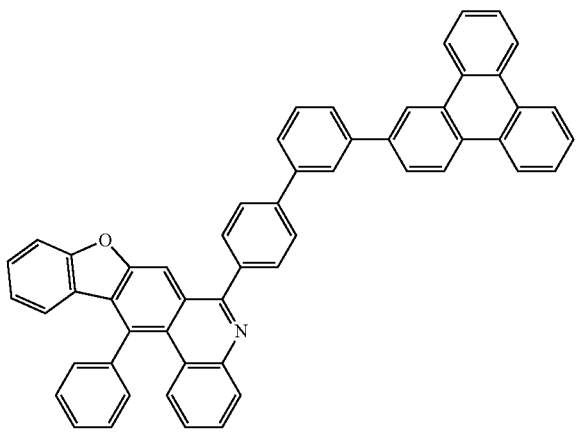
197
195
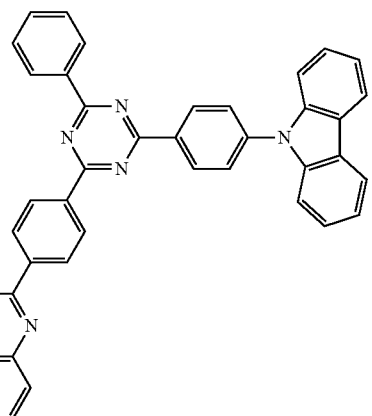
198
196
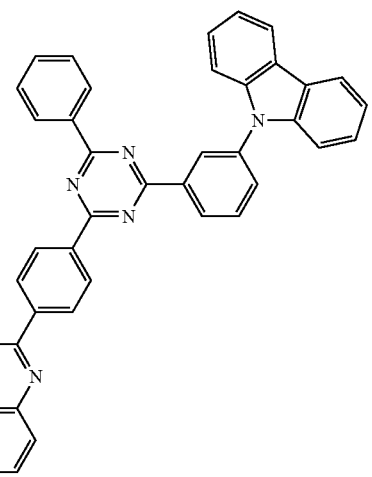
199

200
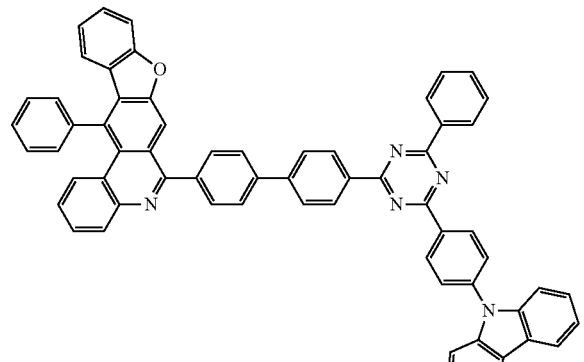
201
202
203
204
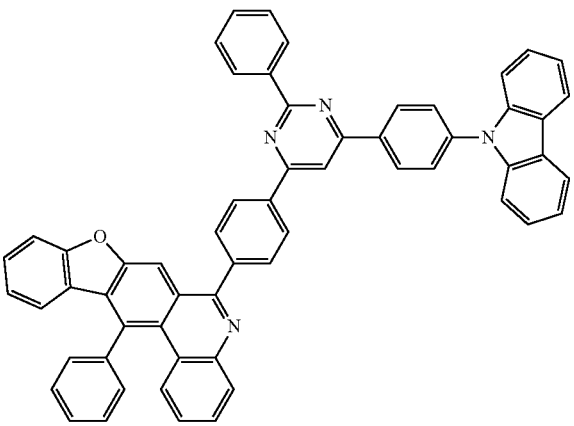
205
206

809
-continued
207
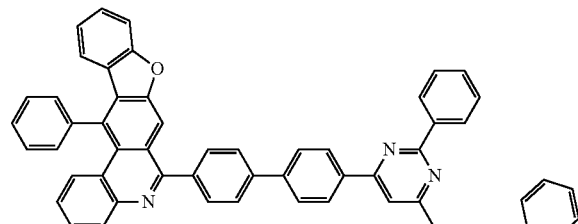
208
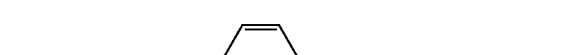
209
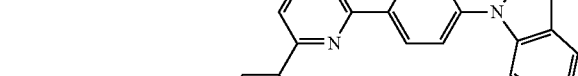
210
810
-continued
211
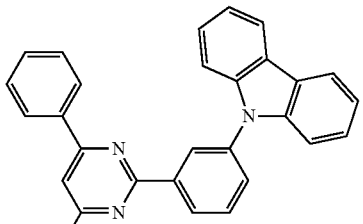
212
213
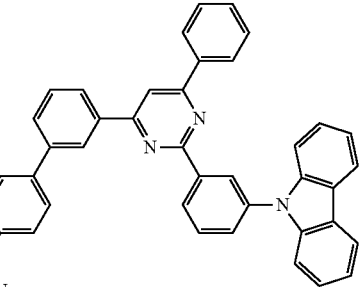

214
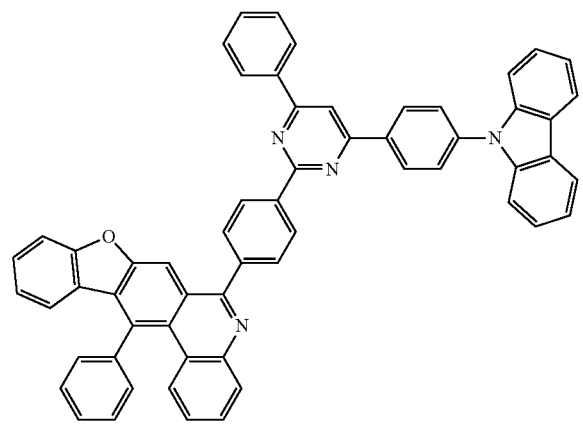
215
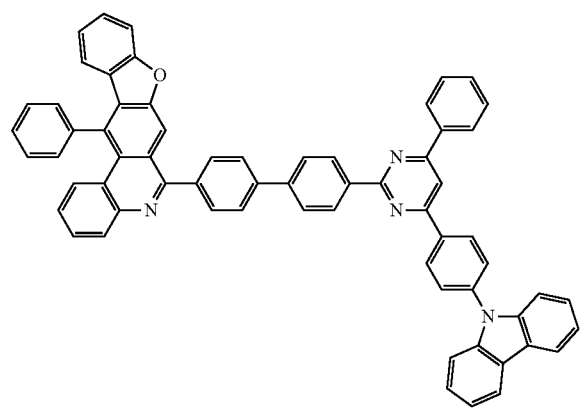
216
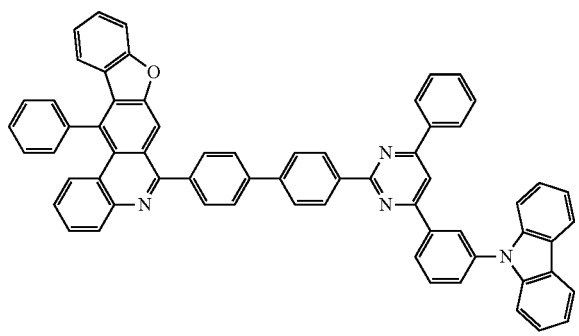
217
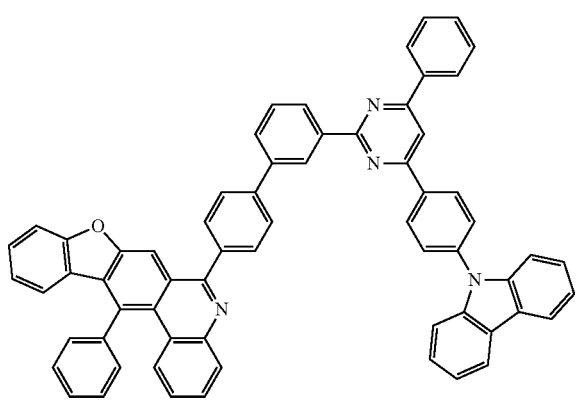
218
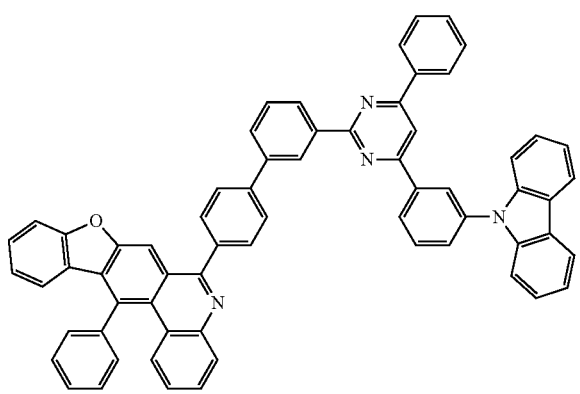
219
220
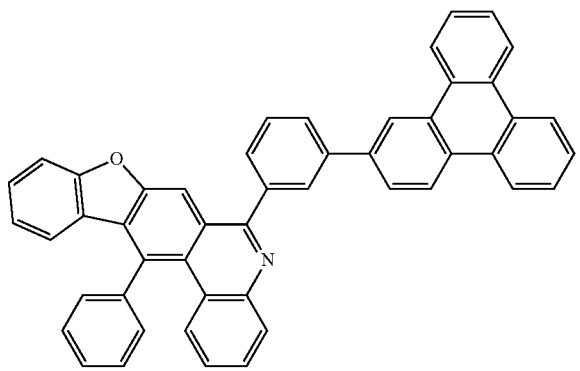

813
-continued
221
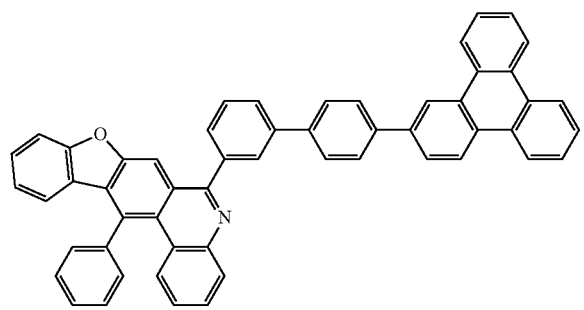
222
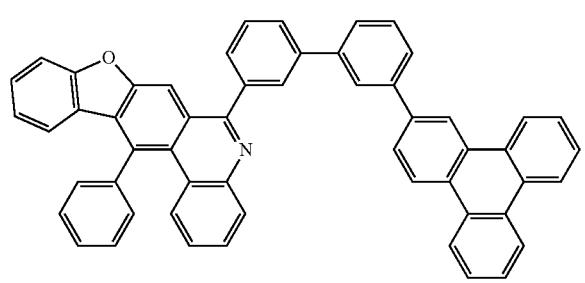
223
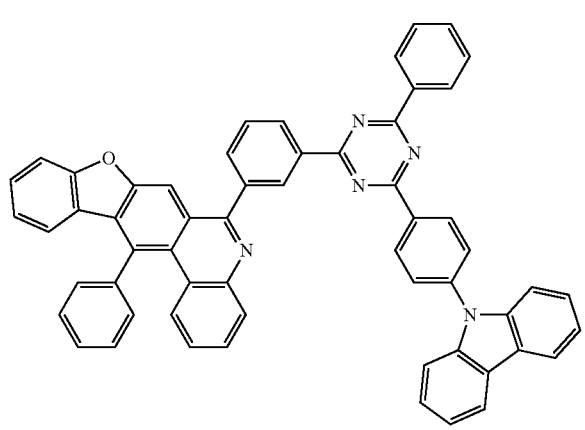
224
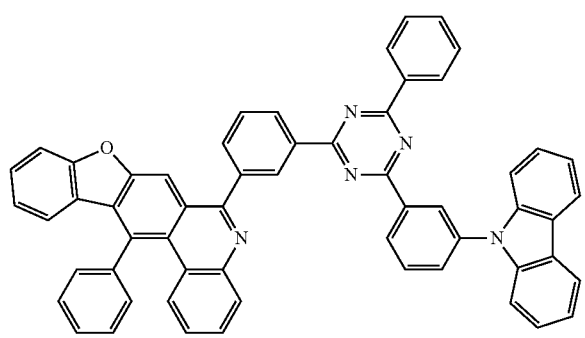
814
-continued
225
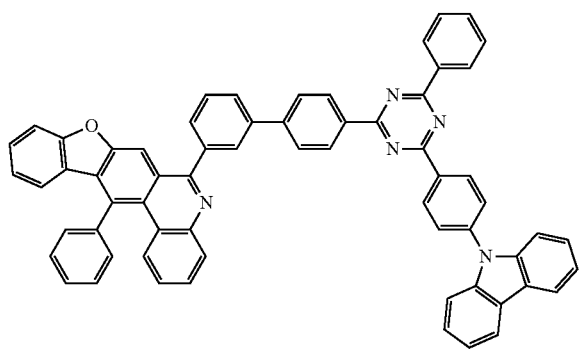
226
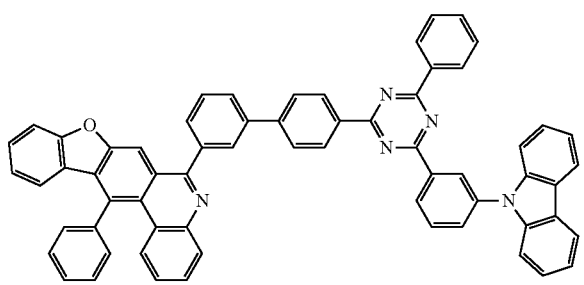
227
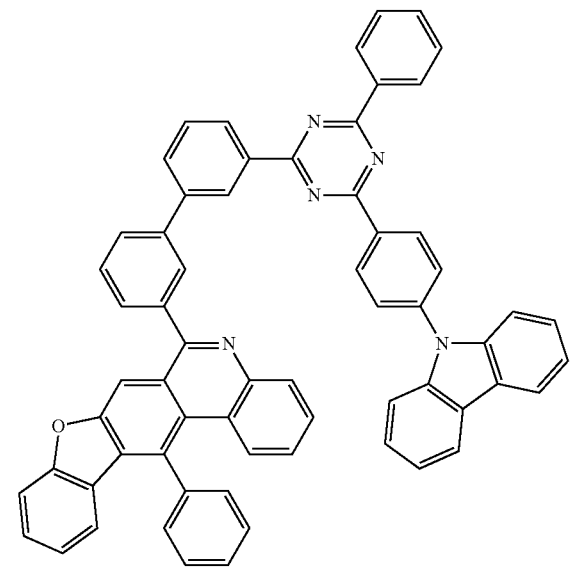

228
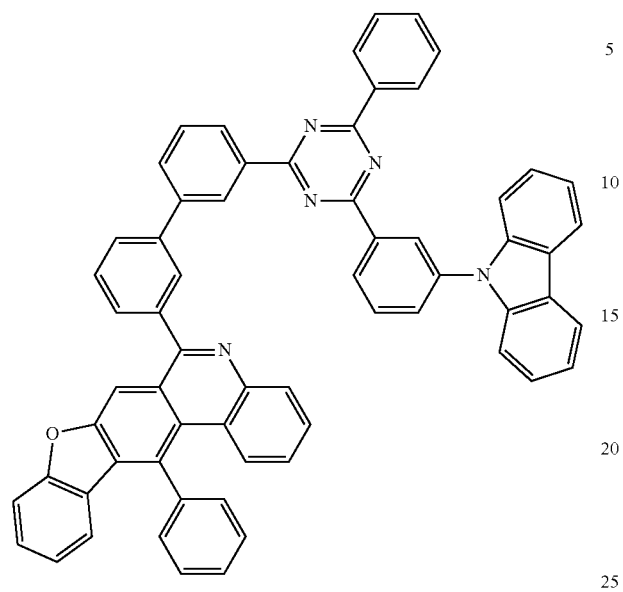
229
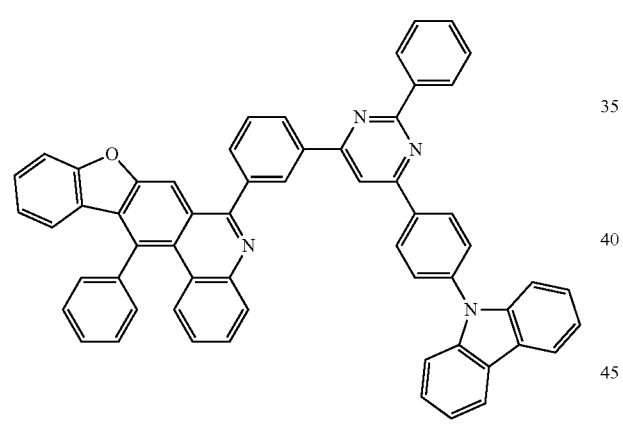
230
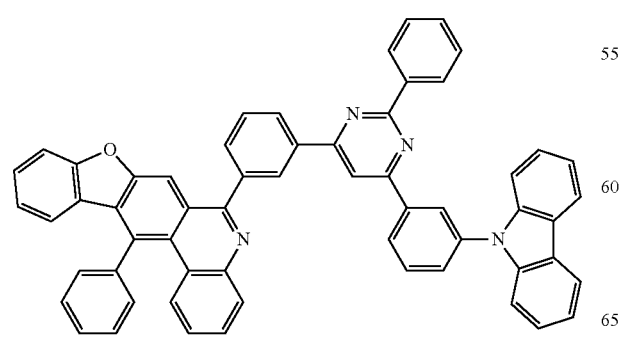
231
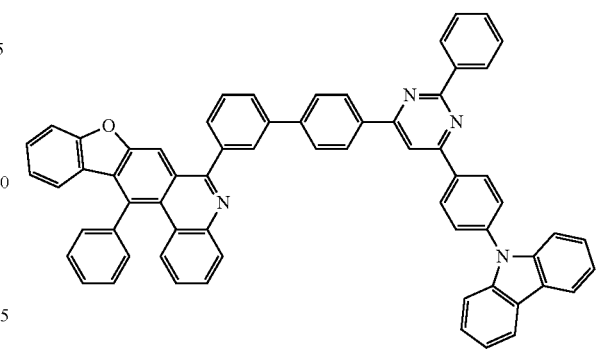
232
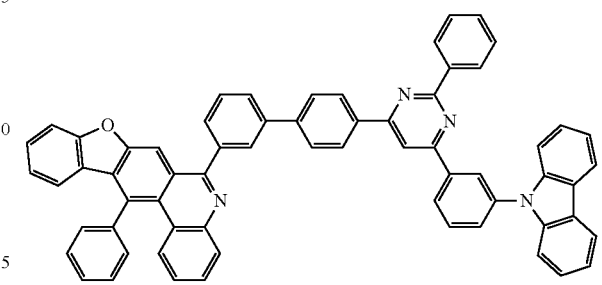
233
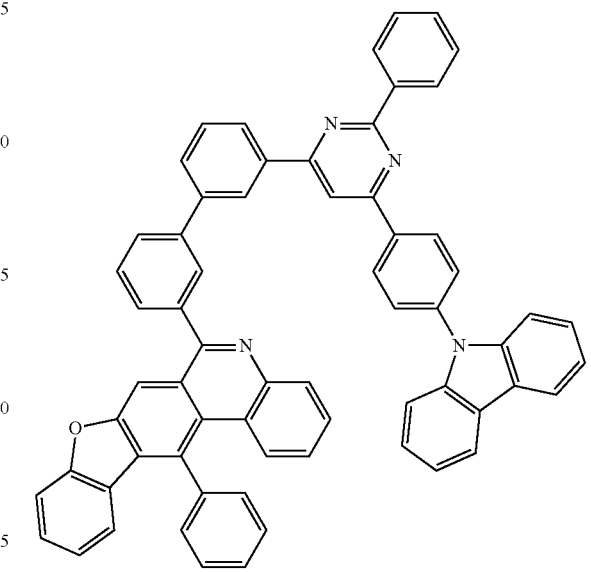

234
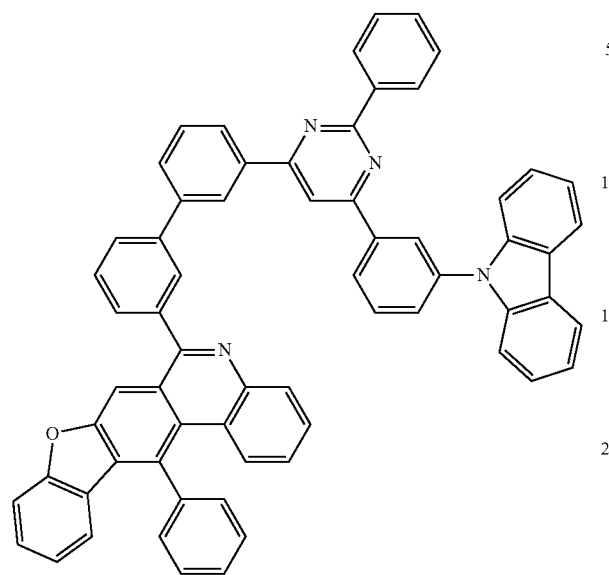
235

236
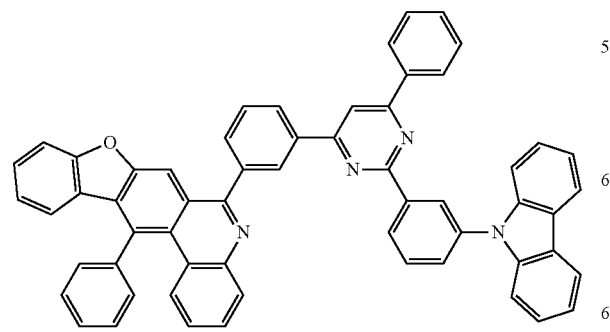
237
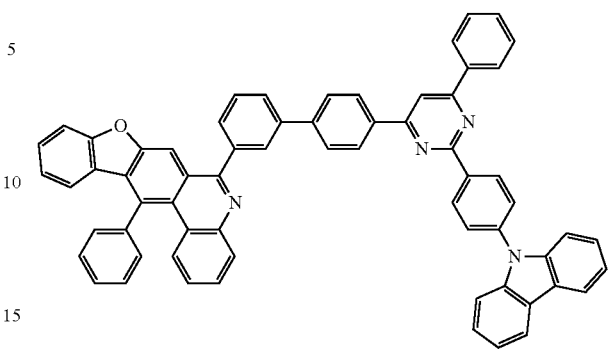
238
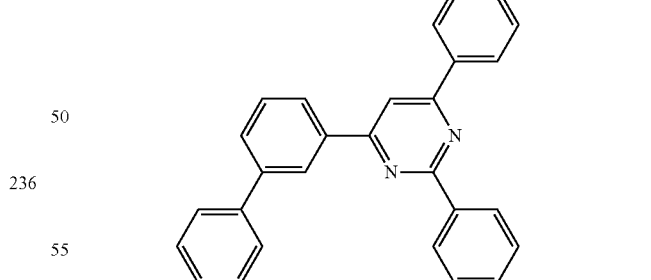
239
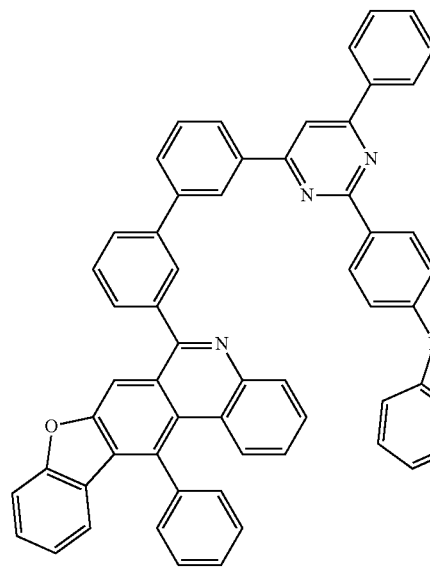

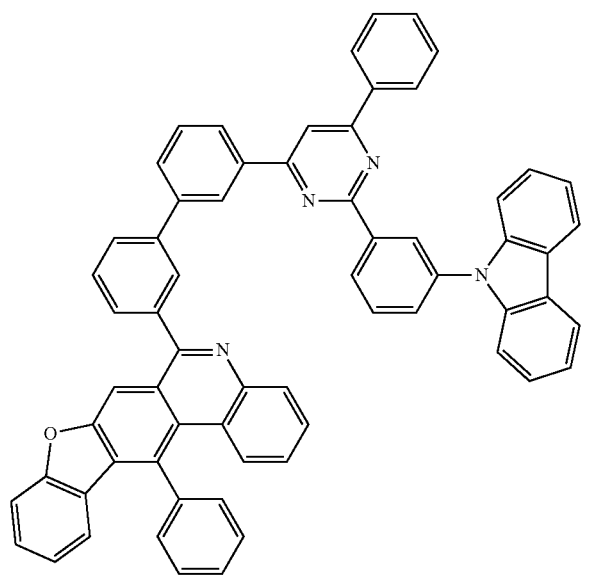
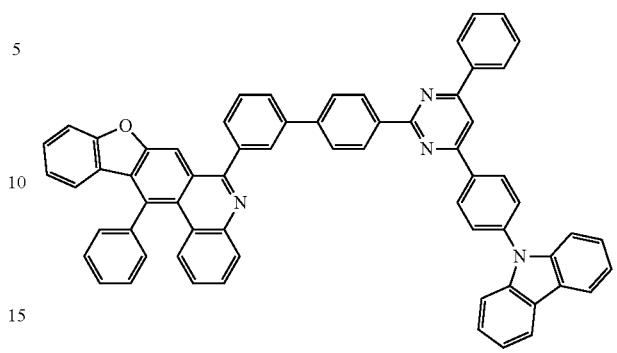
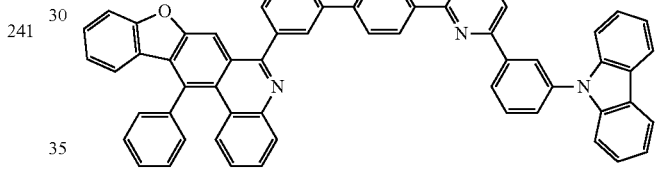
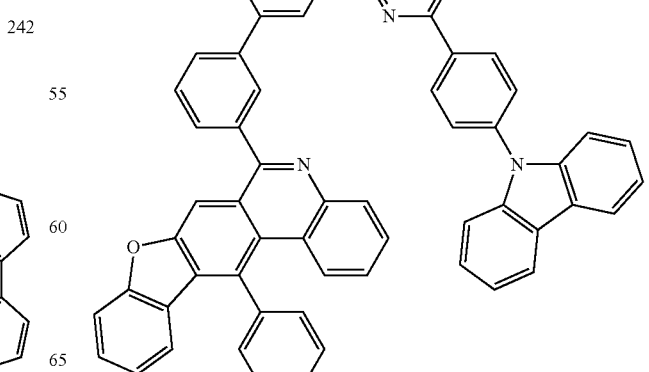

-continued
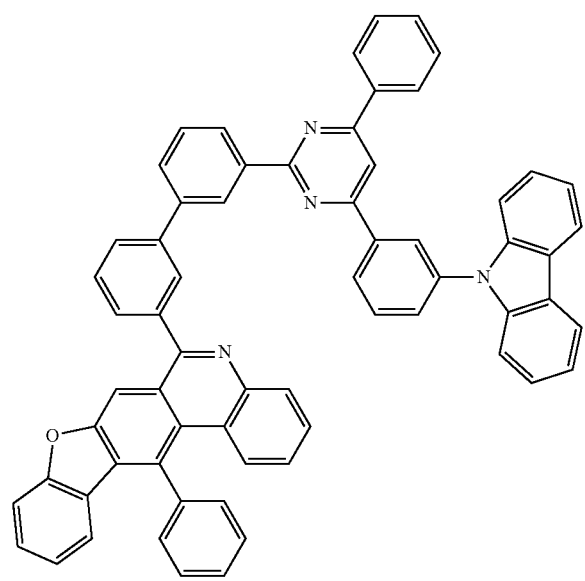
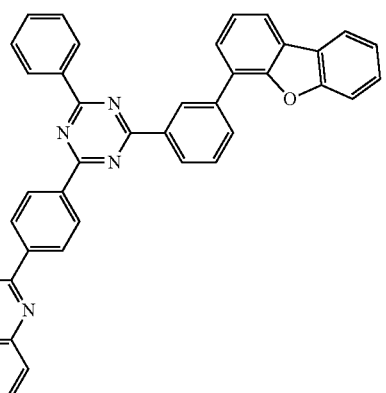
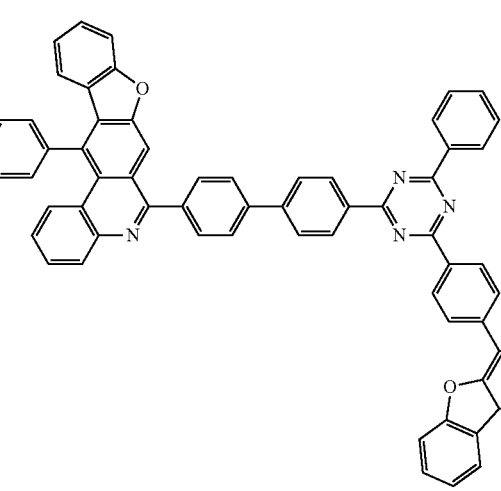
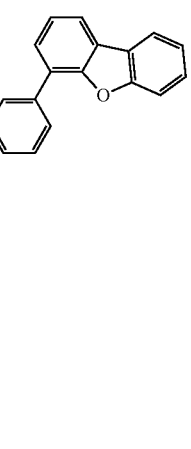

-continued
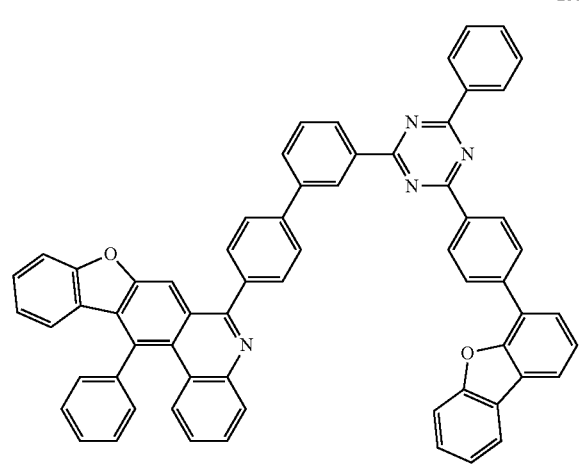
253
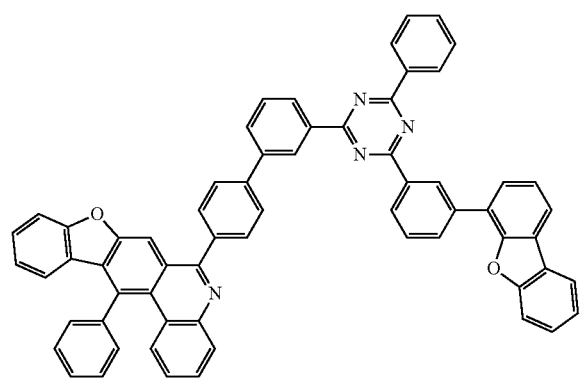
254
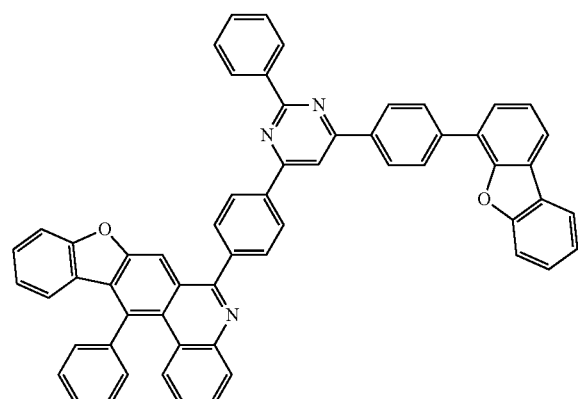
255
-continued
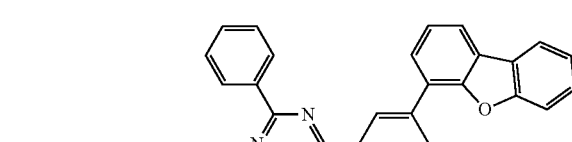
256
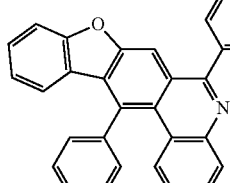
257
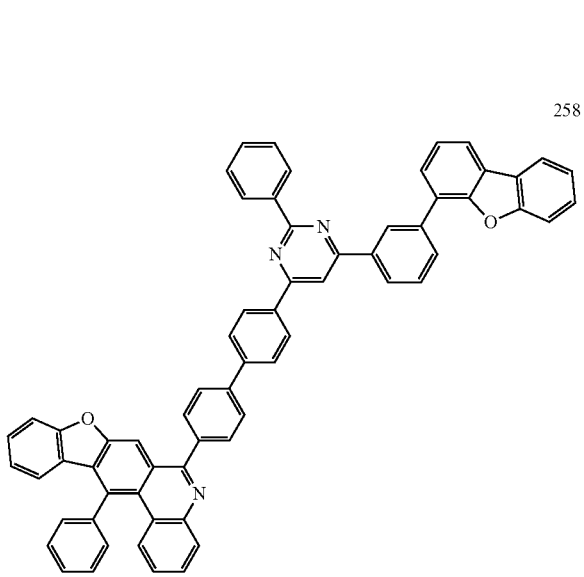
258

259
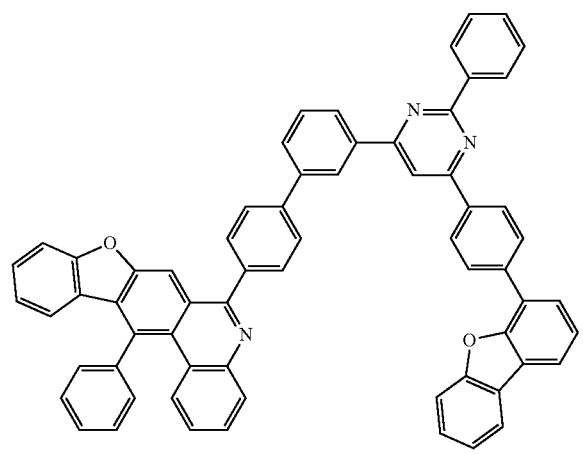
260
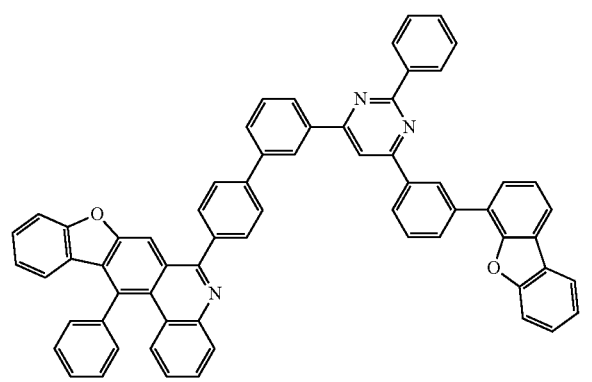
261
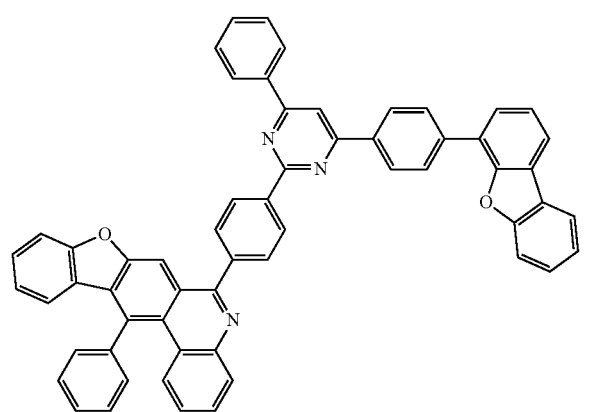
262
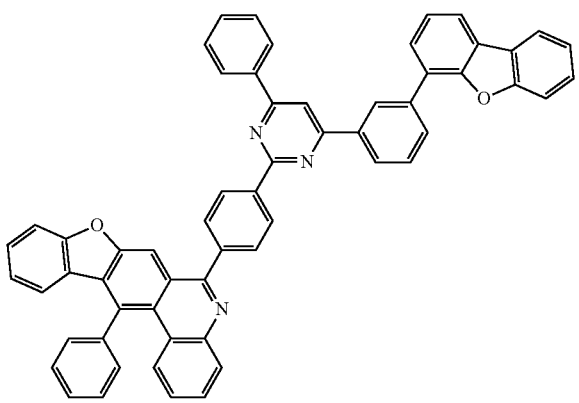
263
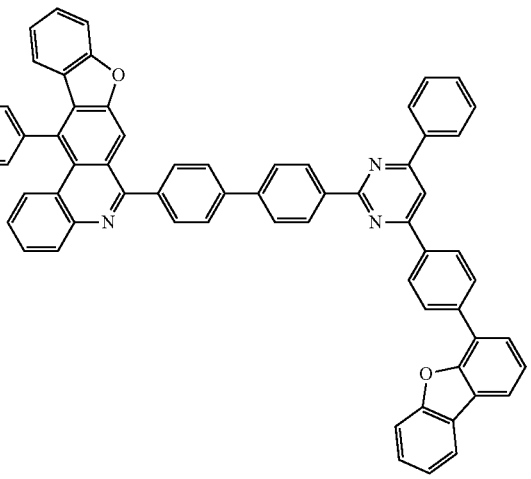
264
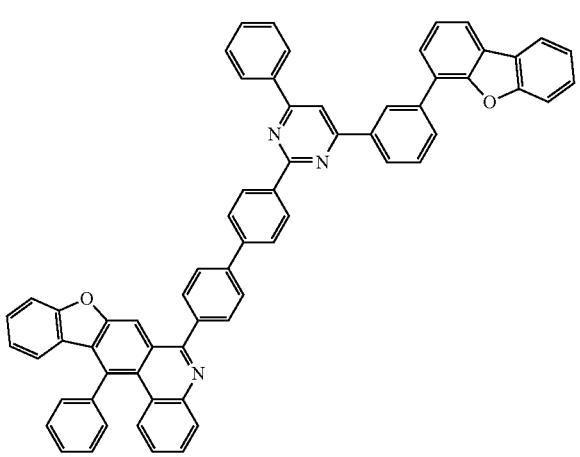

827
-continued
265
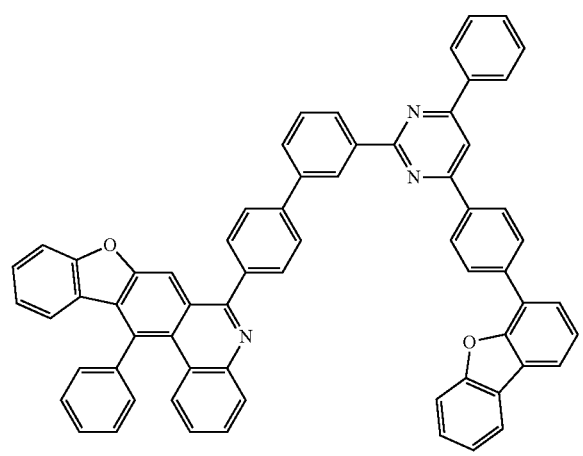
266
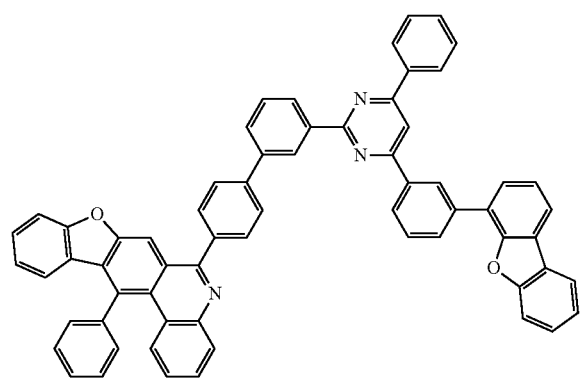
267
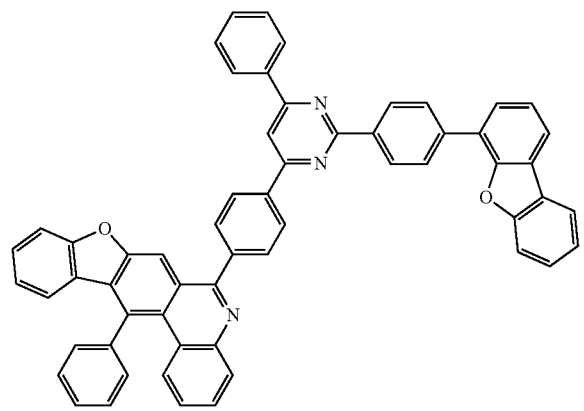
828
-continued
268
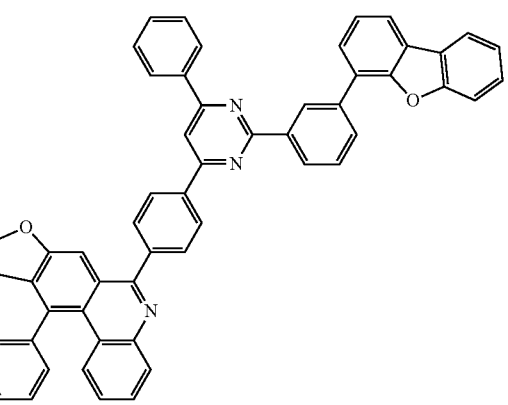
269
270
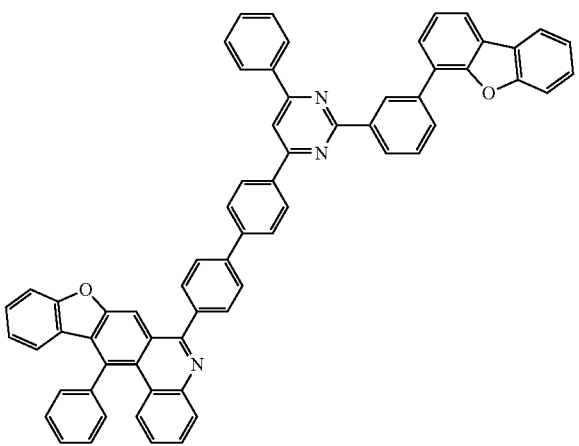

271
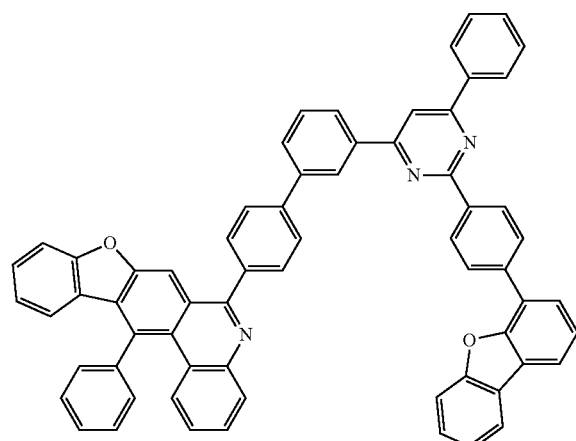
272
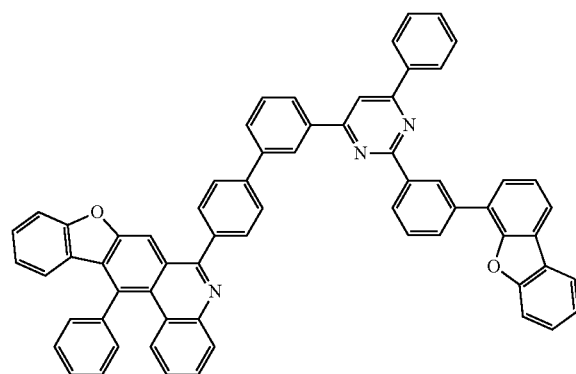
273
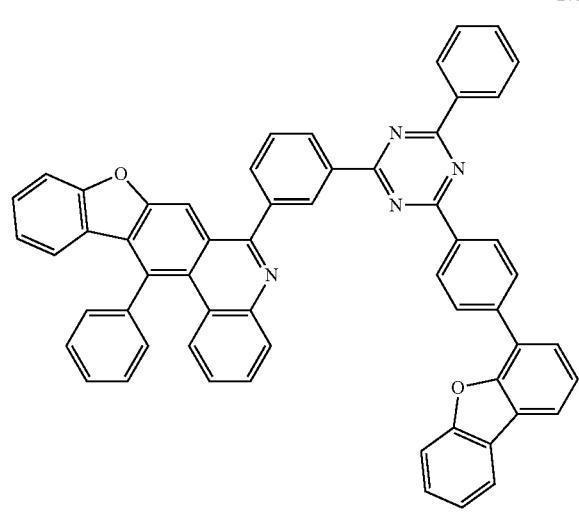
274
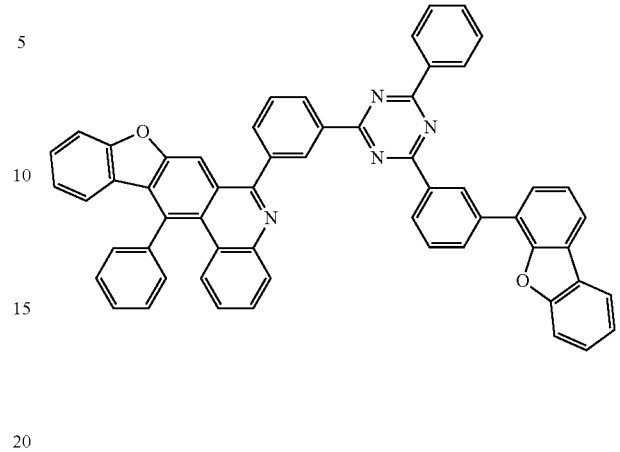
275
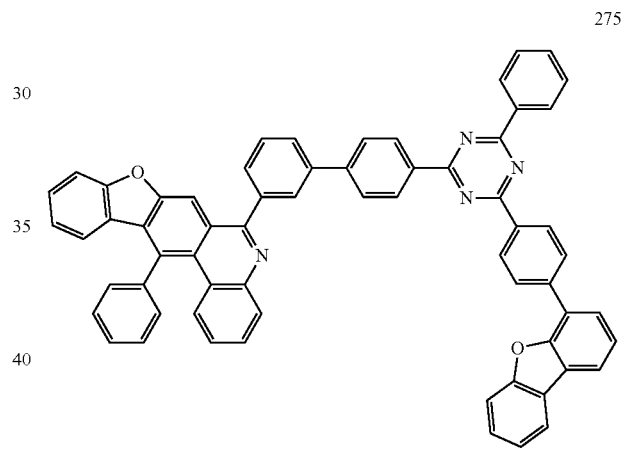
276
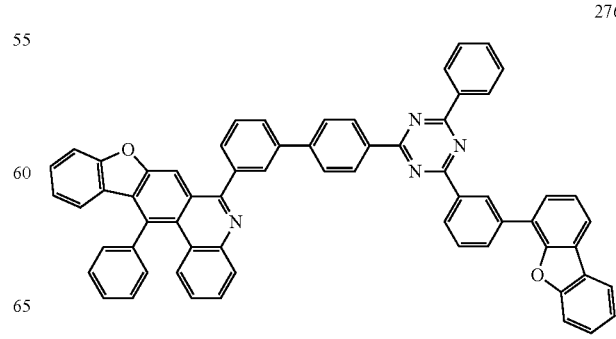

277
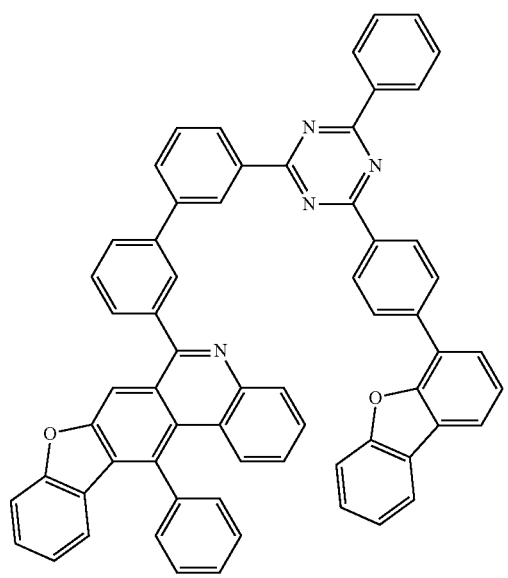
278
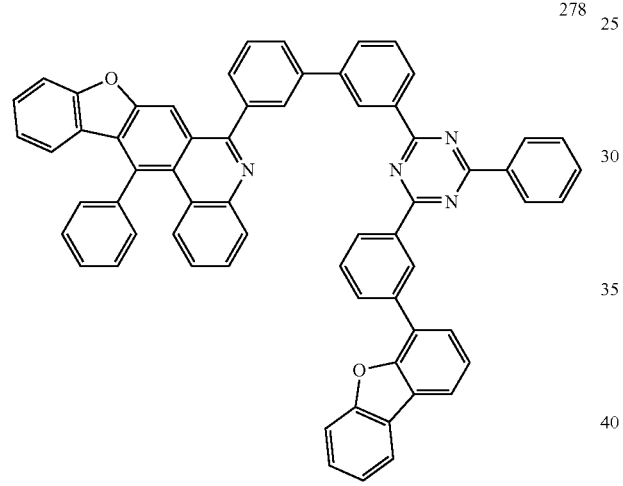
279
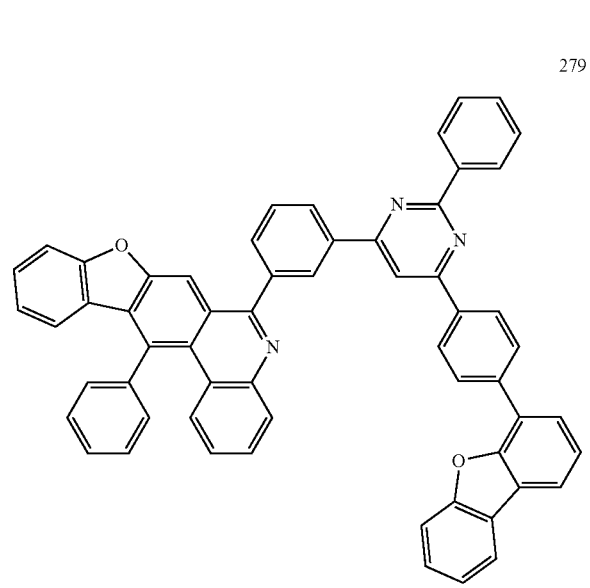
280
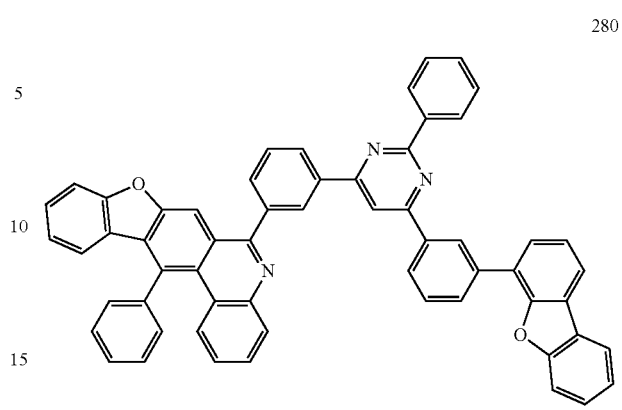
281
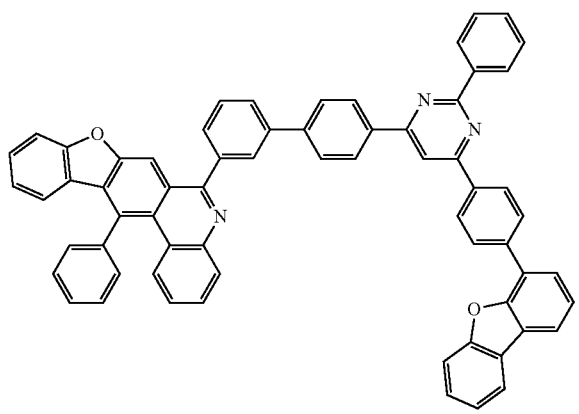
282
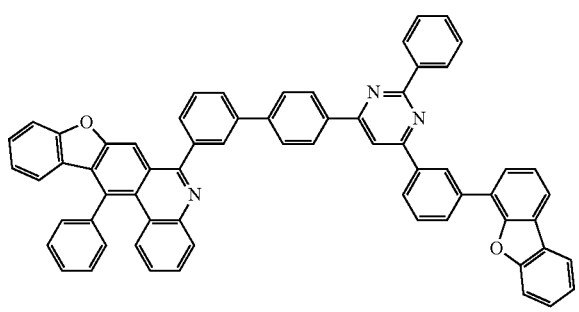

283
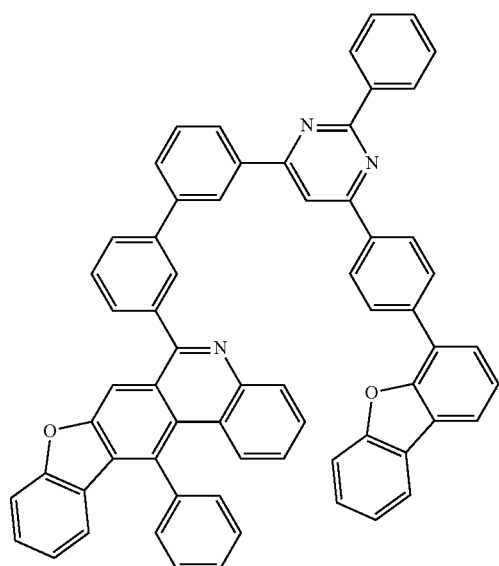
284
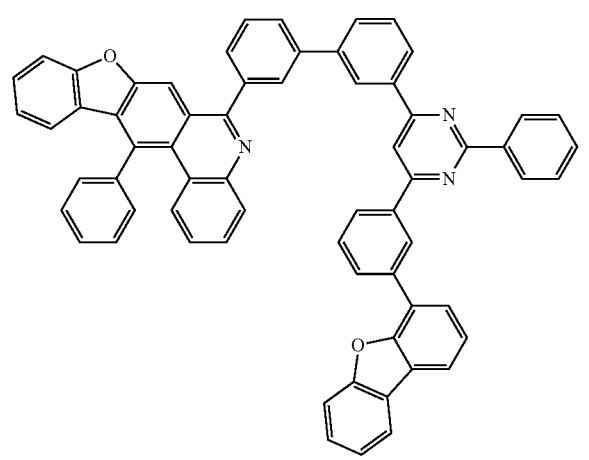
285
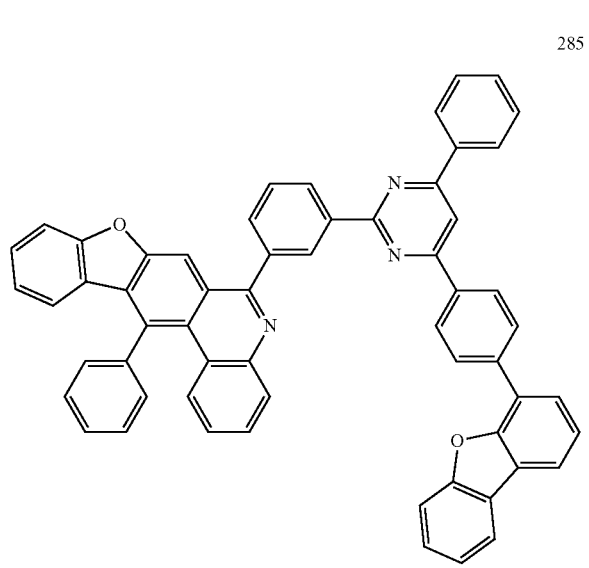
286
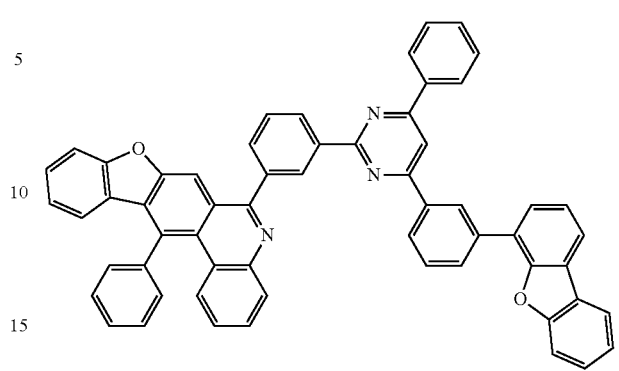
287
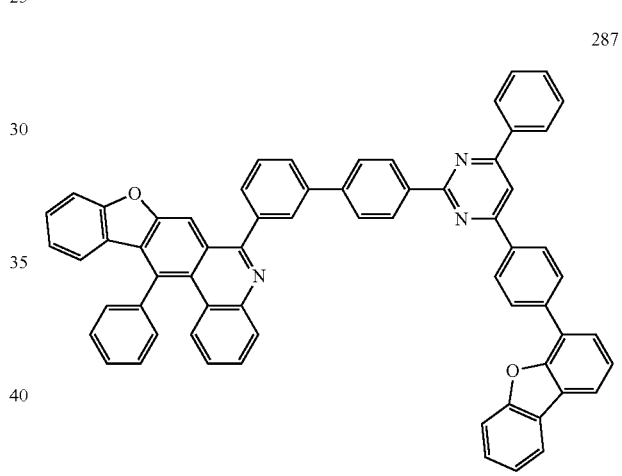
288
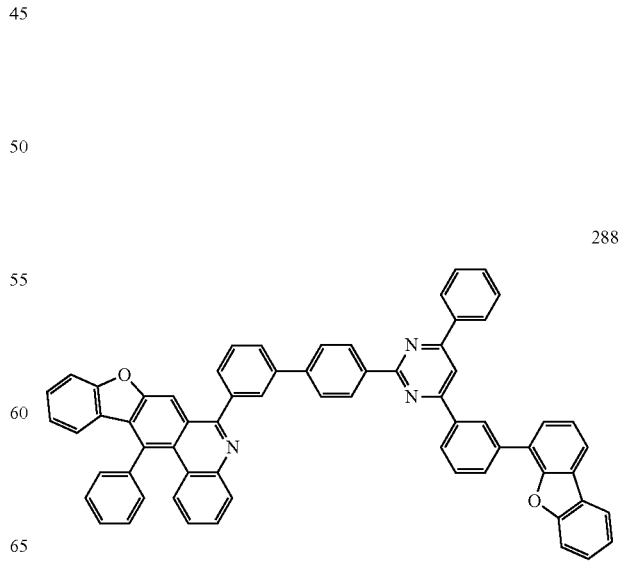

835
-continued
289
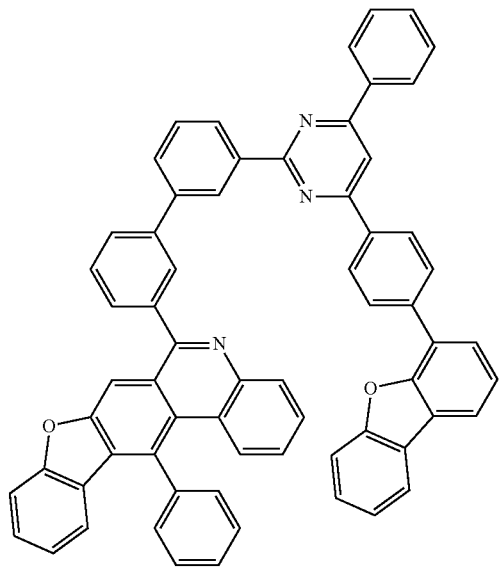
290
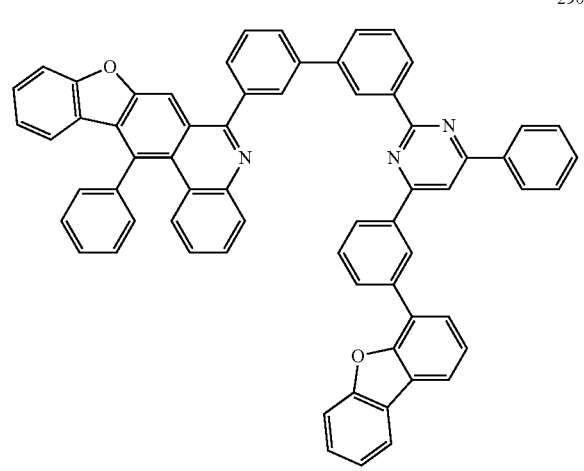
836
-continued
291
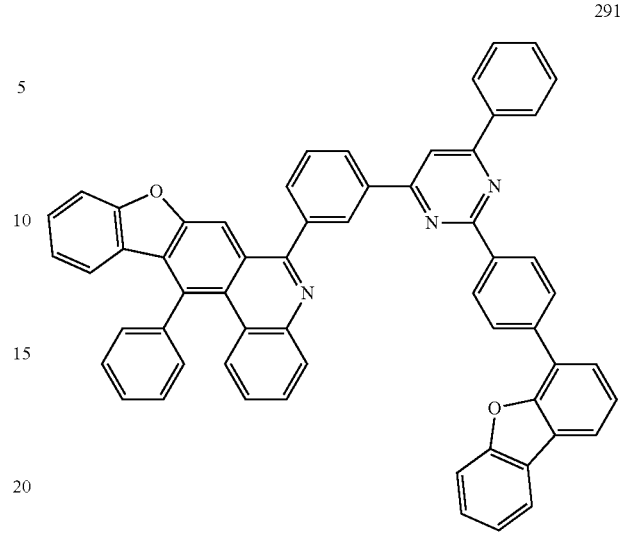
292
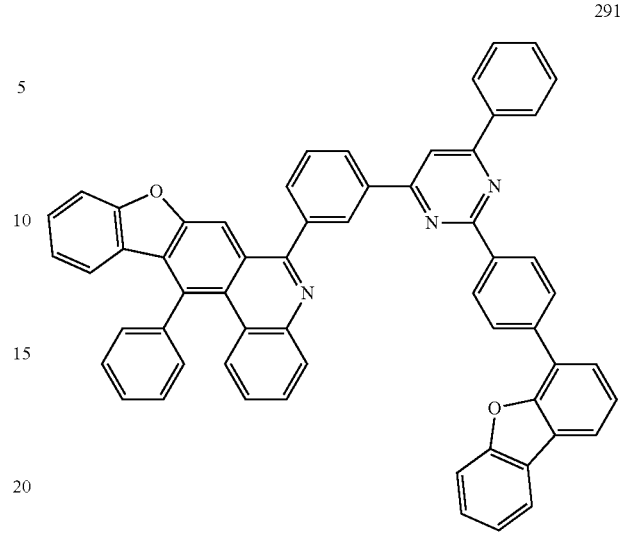
293

294
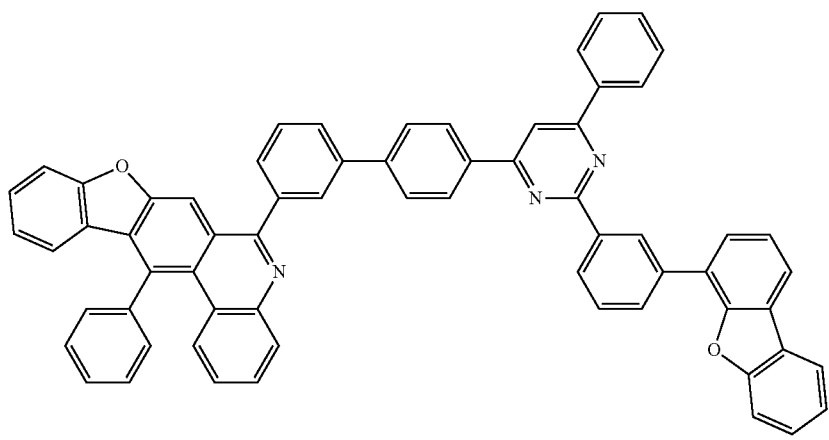
295
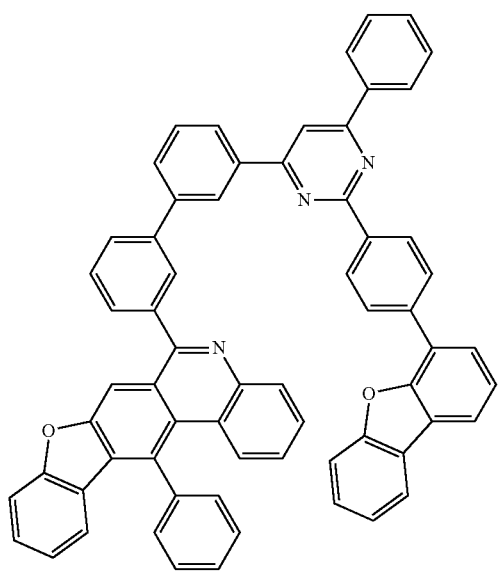
296
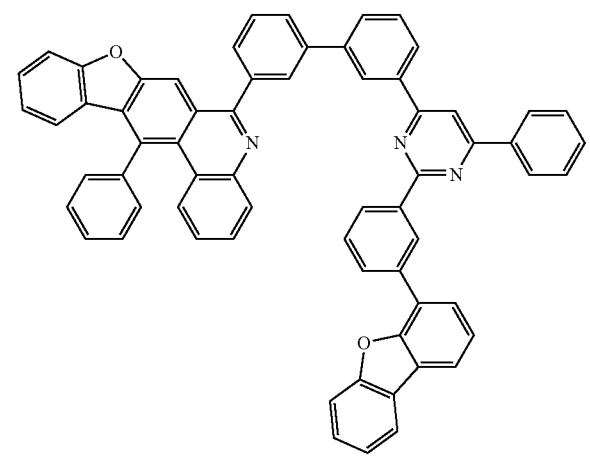
297
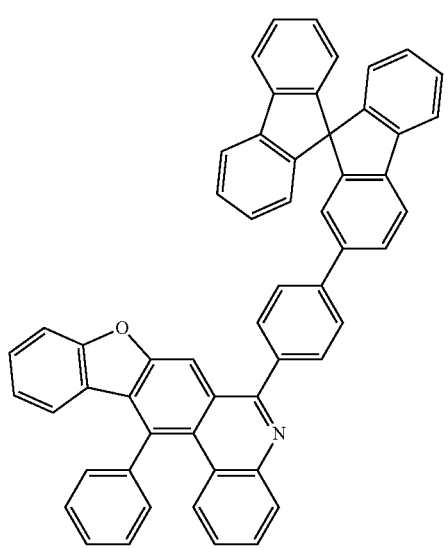
298
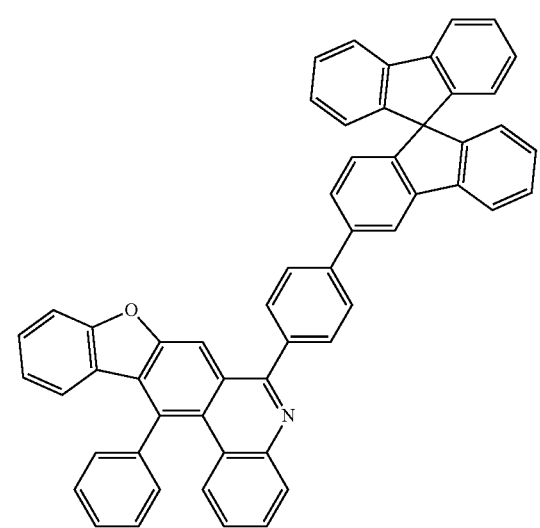

| 299 | 300 |
|---|---|
| 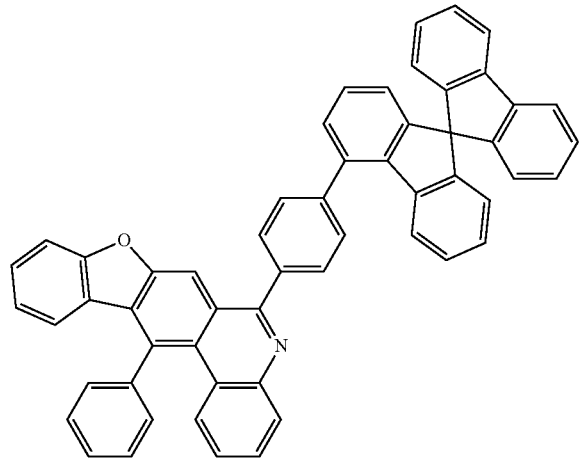 | 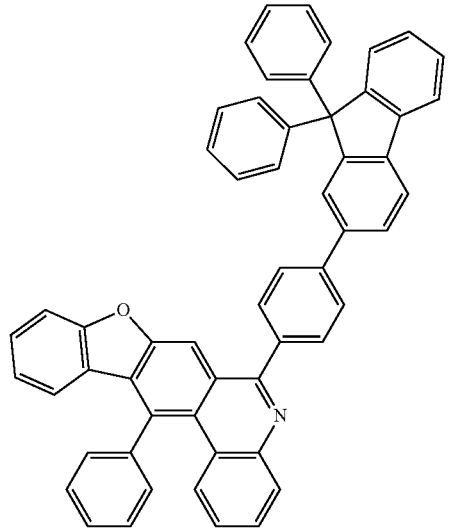 |
| 301 | 302 |
|---|---|
| 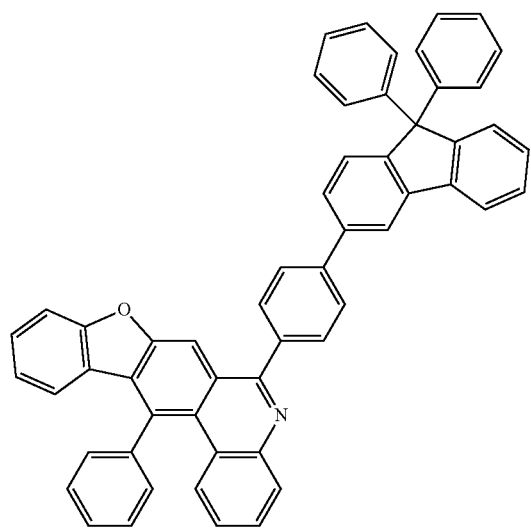 | 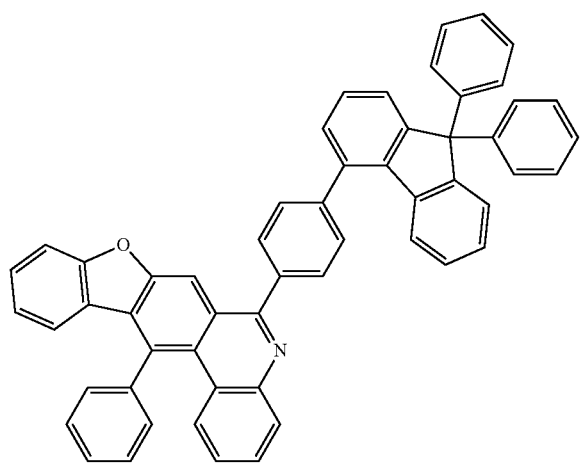 |

-continued
841
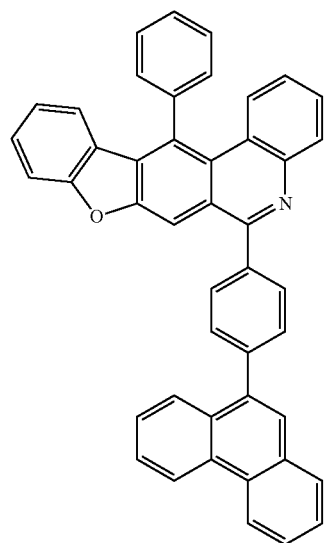
303
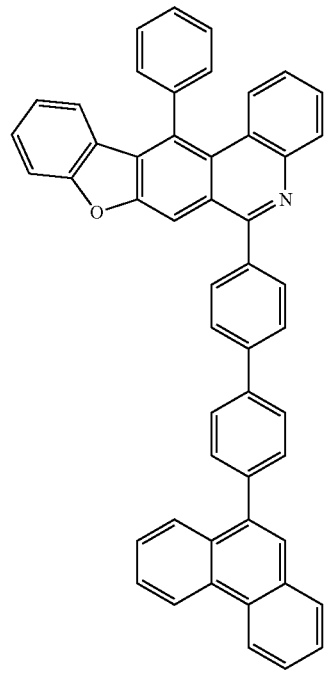
842
305
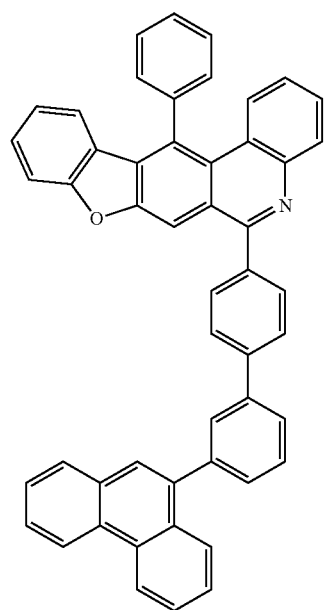
304
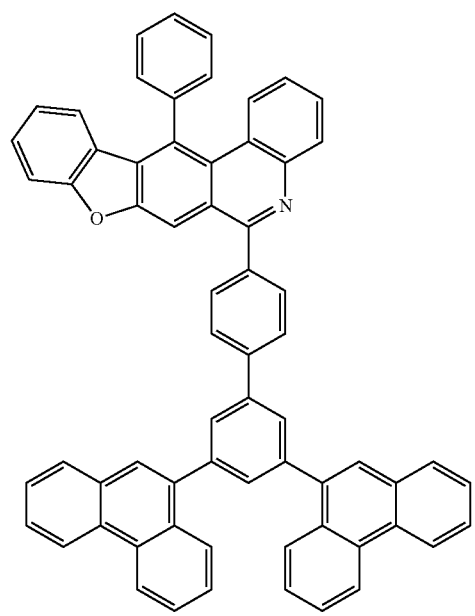
306

-continued
843
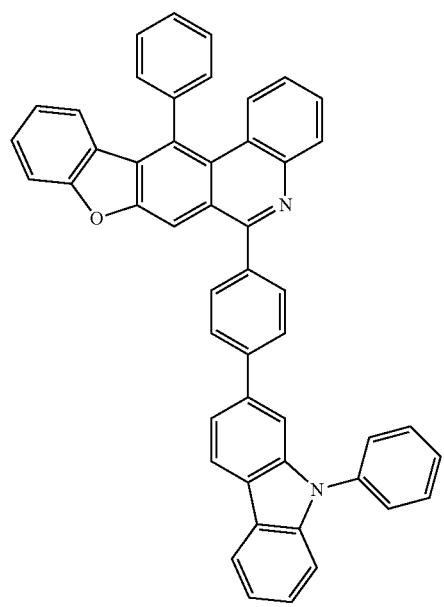
307
844
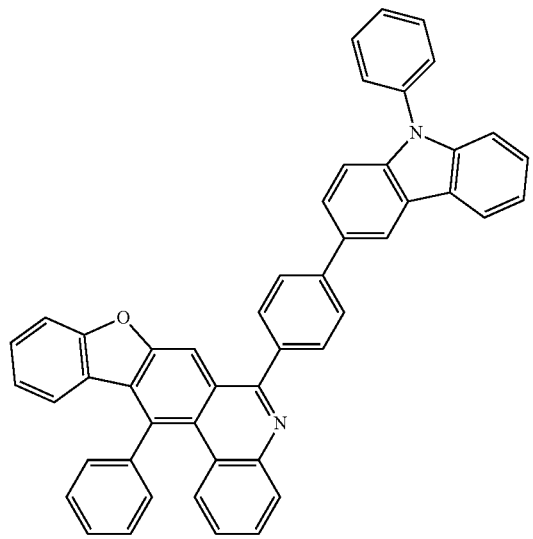
308
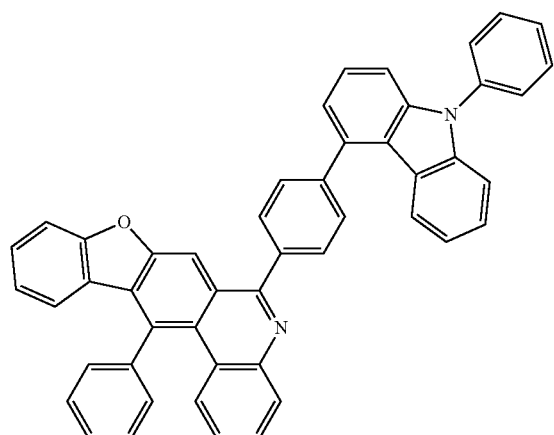 [SMILES: c1ccc(-c2c3c(cc4c(-c5ccc(-c6cccc7c6c6ccccc6n7-c6ccccc6)cc5)nc5ccccc5c24)oc2ccccc23)cc1]
309
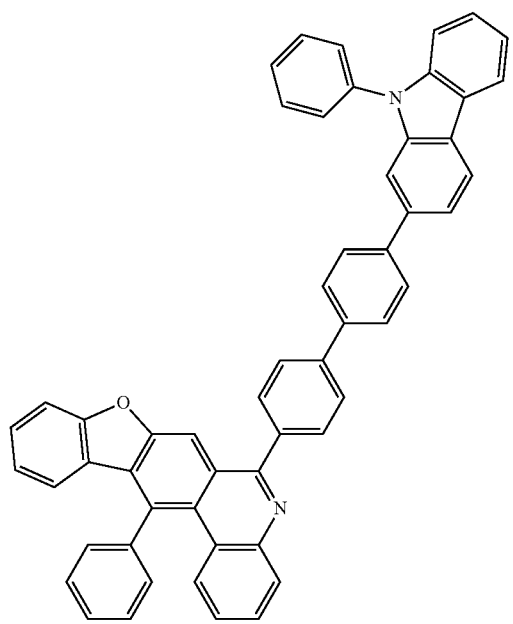
310

-continued
311
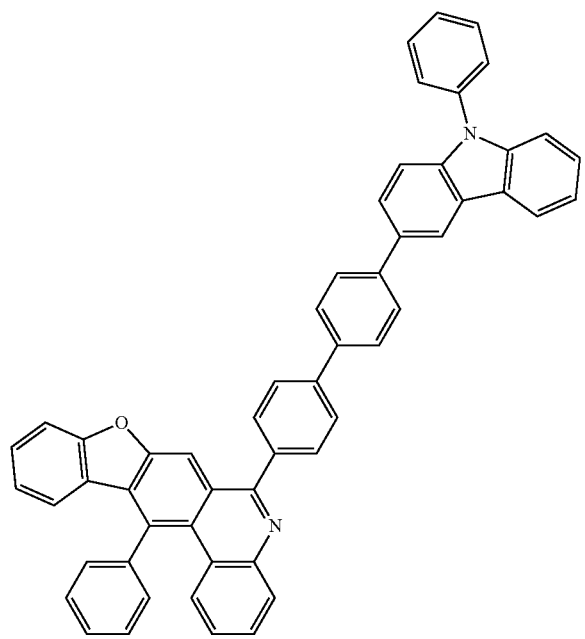
312
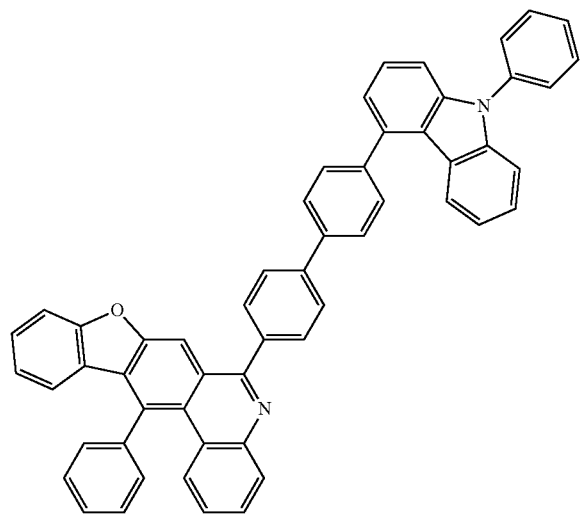
313
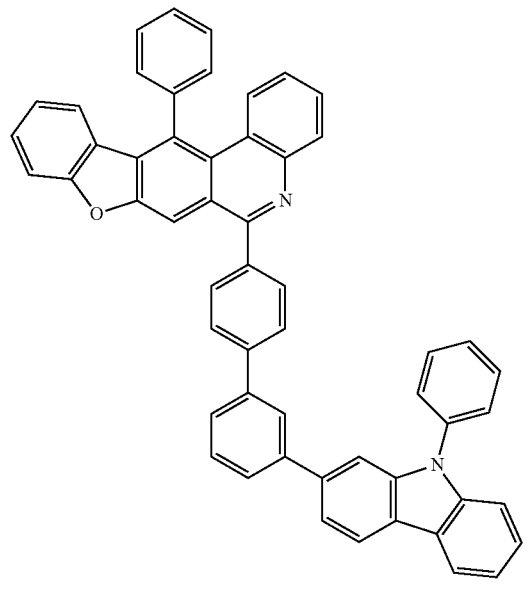
314
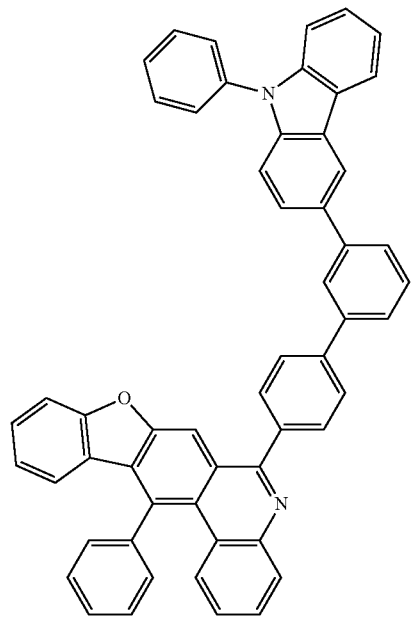

315
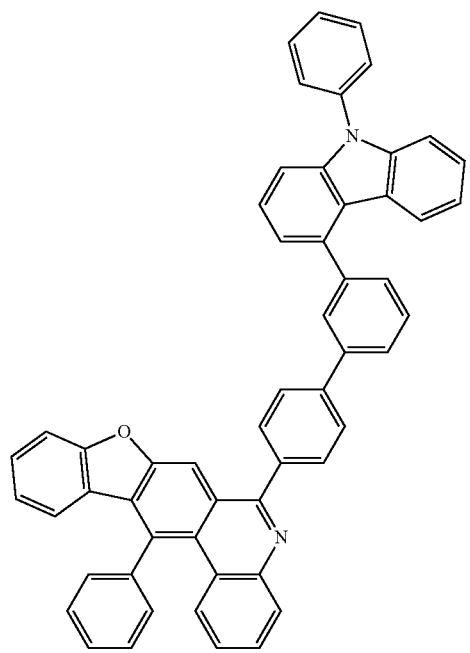
316
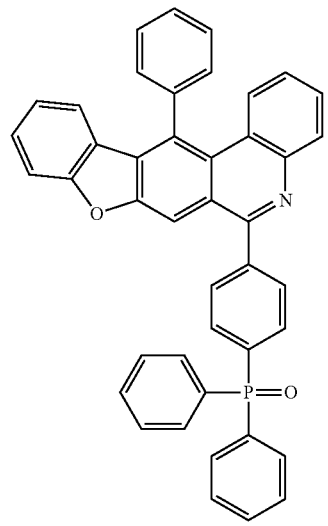
317
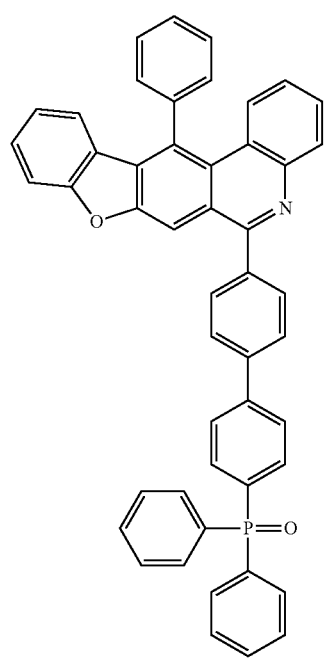
318
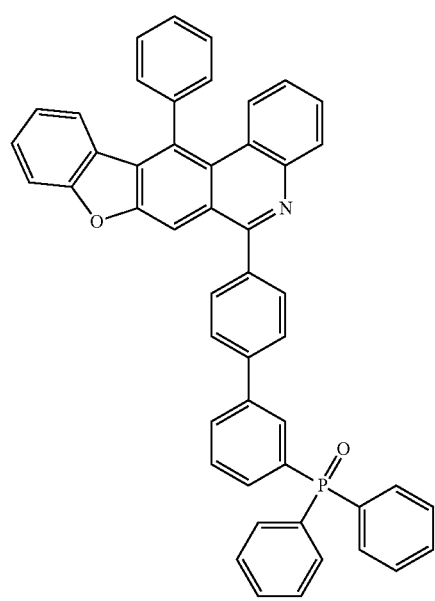

849 850
-continued
| 319 | 320 |
|---|---|
| 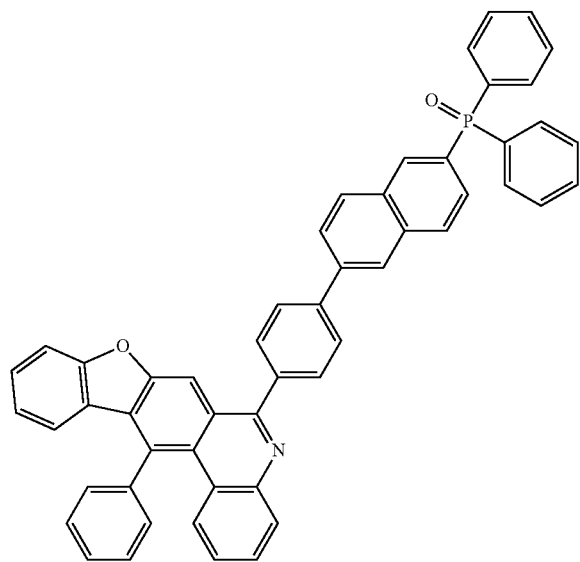 | 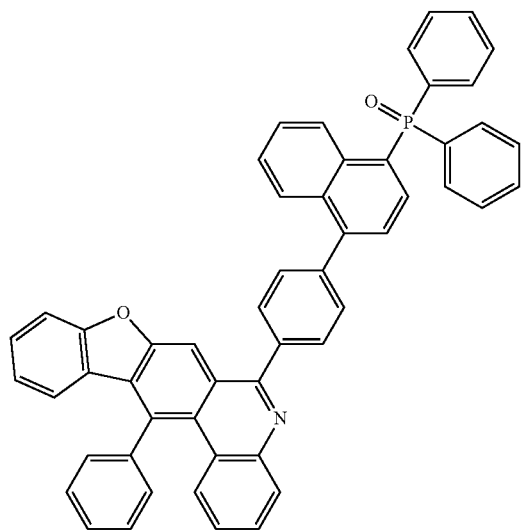 |
| 321 | 322 |
|---|---|
| 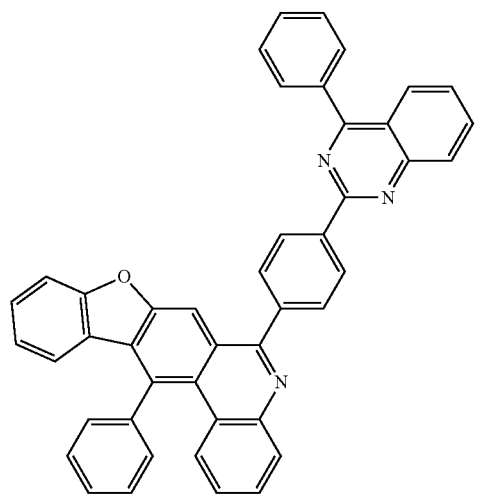 | 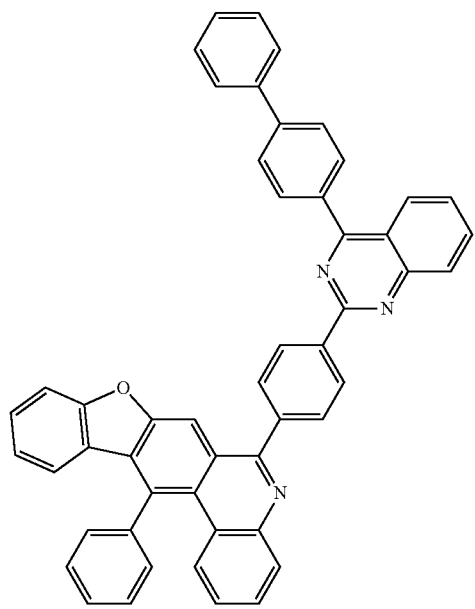 |

323
324
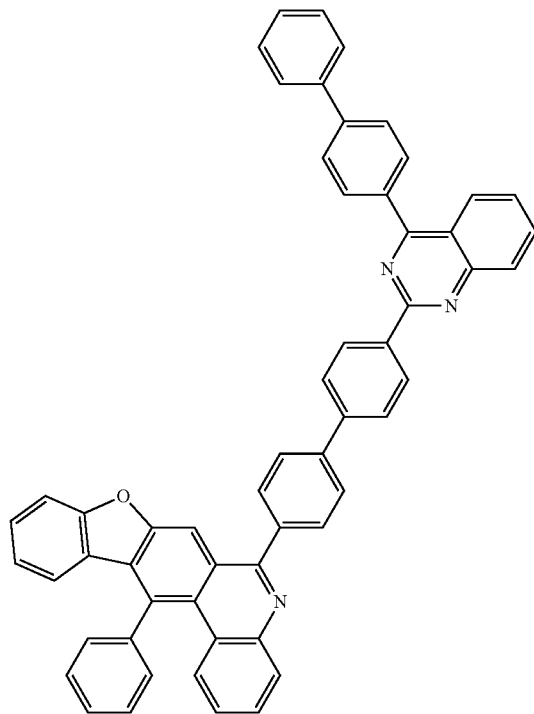
325
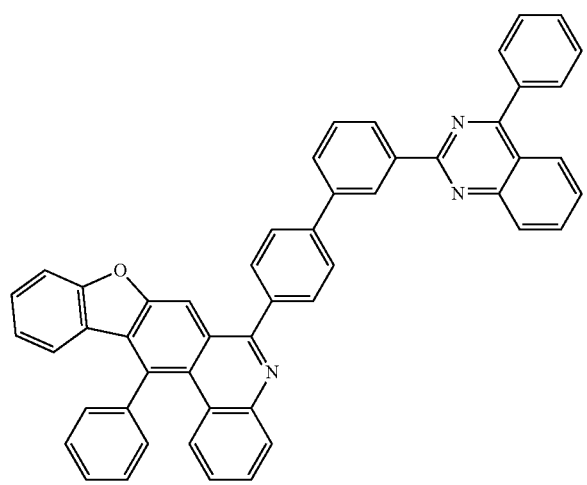
326
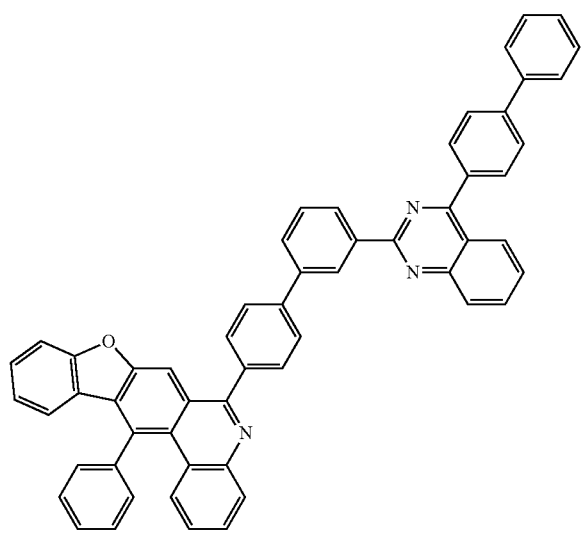

327
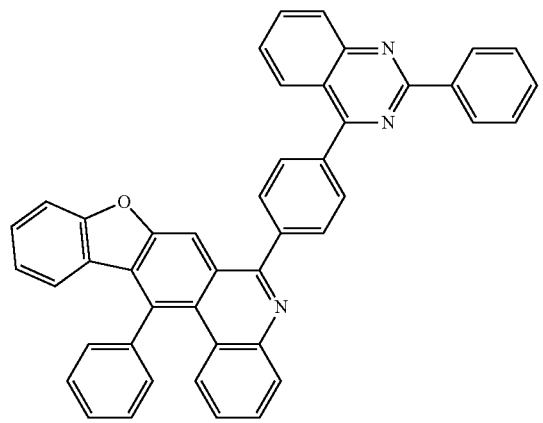
328
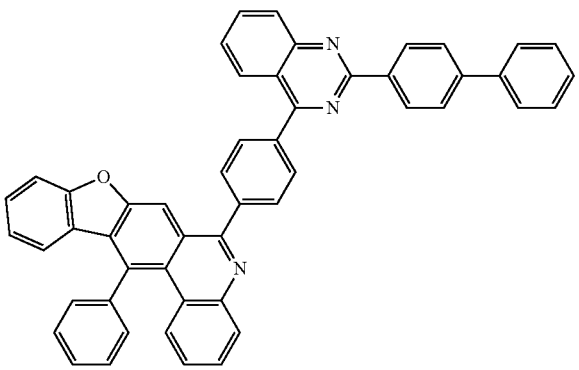
329
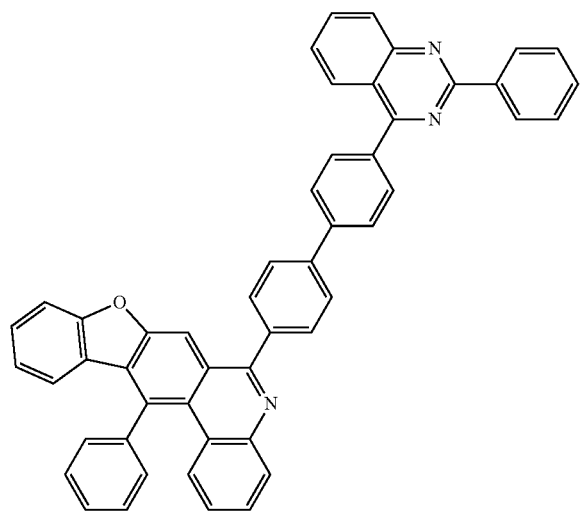
330
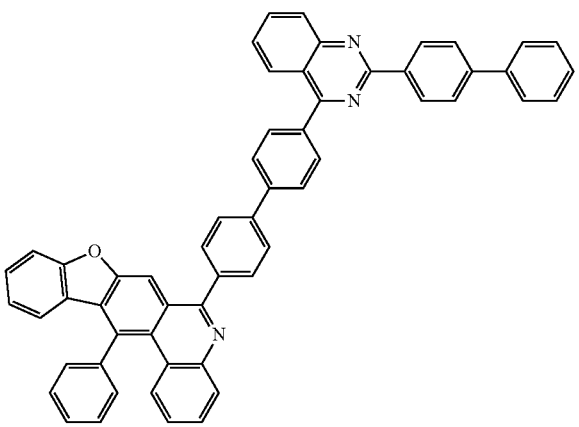

-continued
855
331
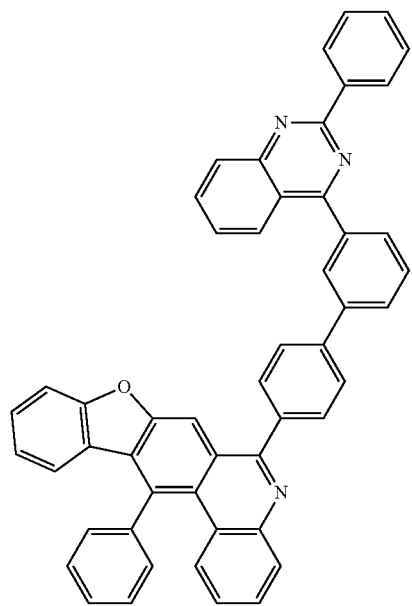
856
332
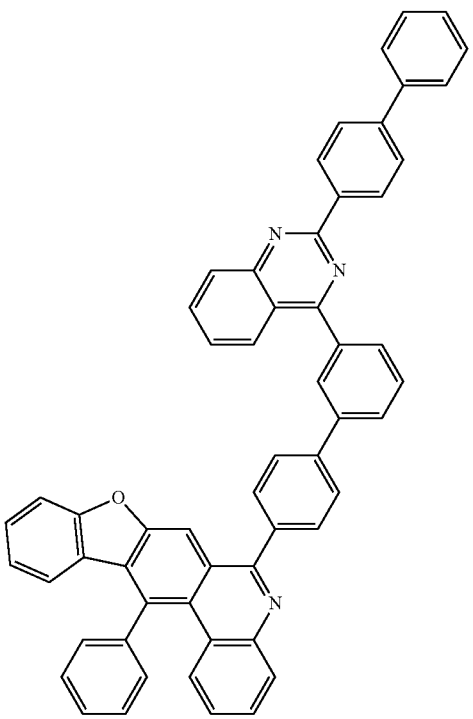
333
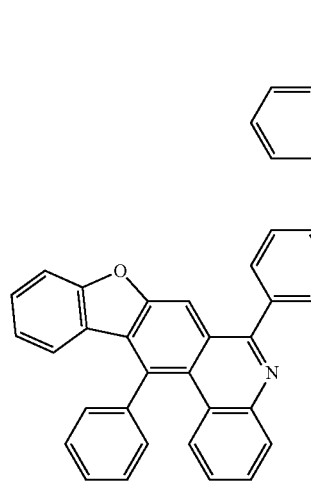
334
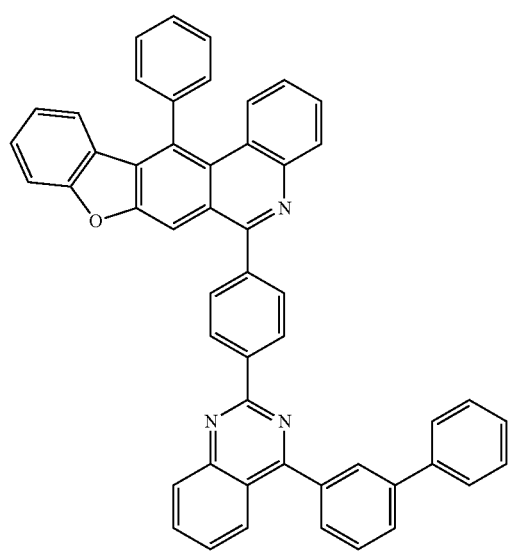

-continued
335
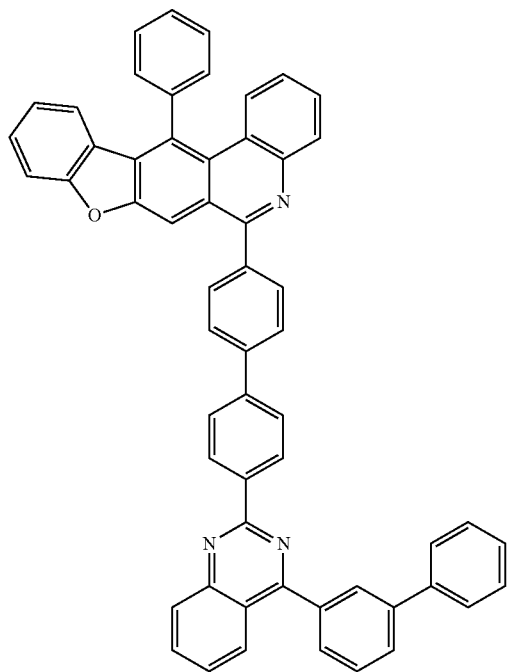
336
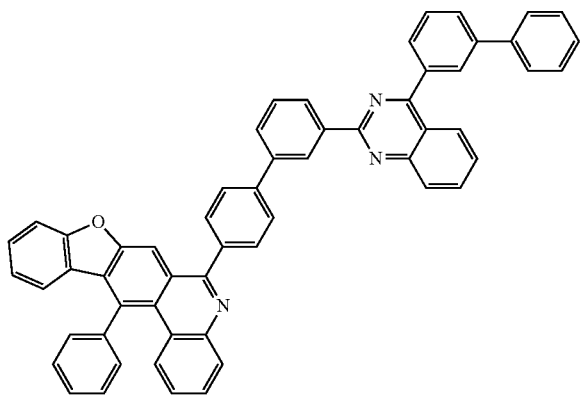
337
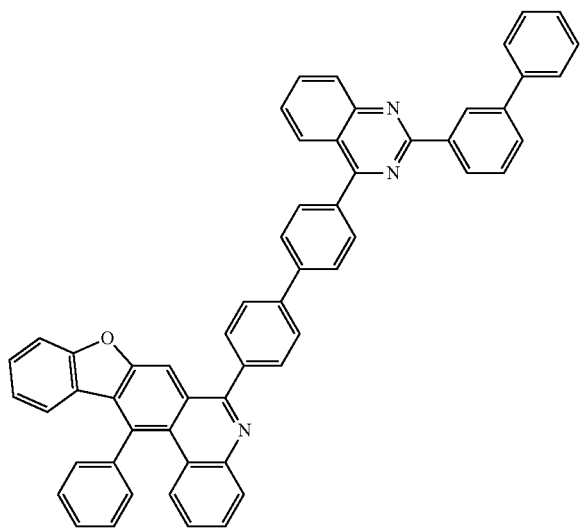
338
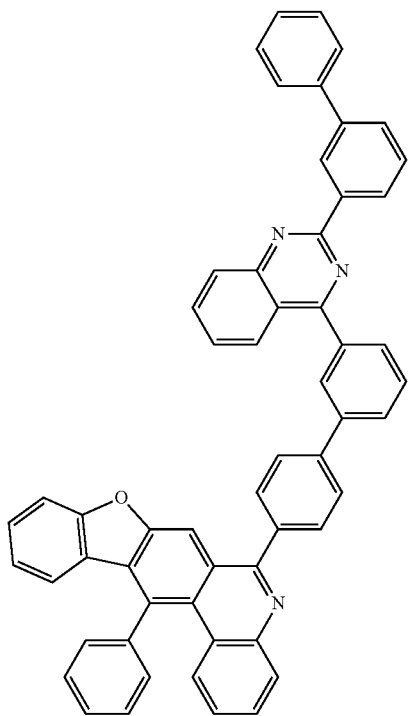

-continued
339
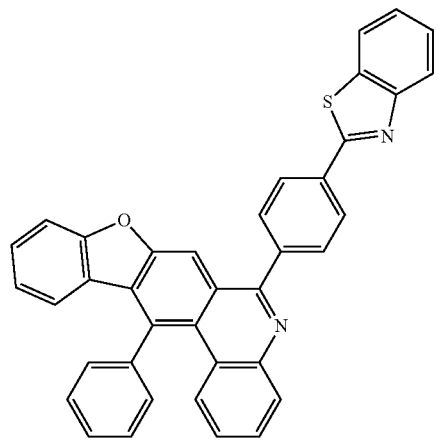
340
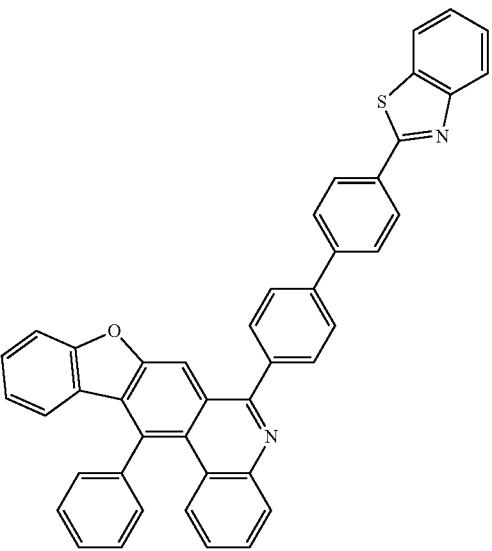
341
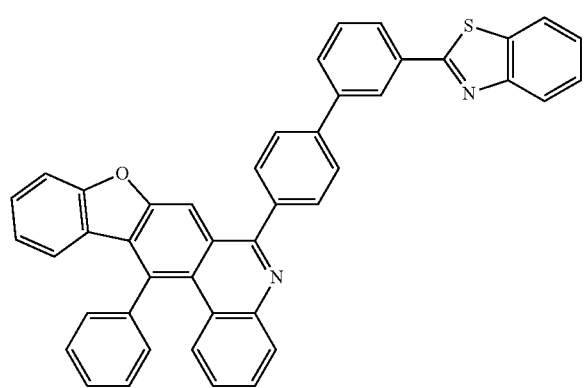
342
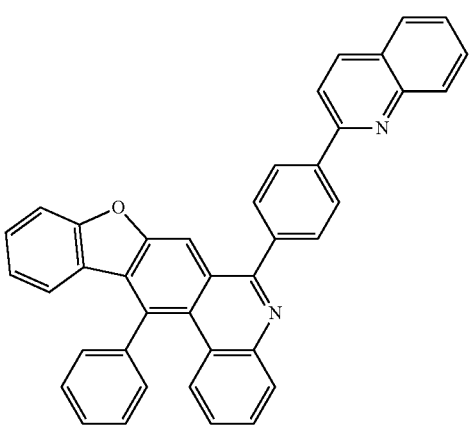
343
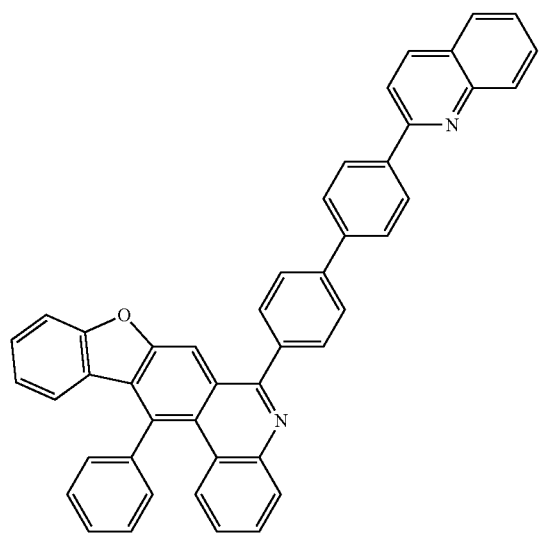
344
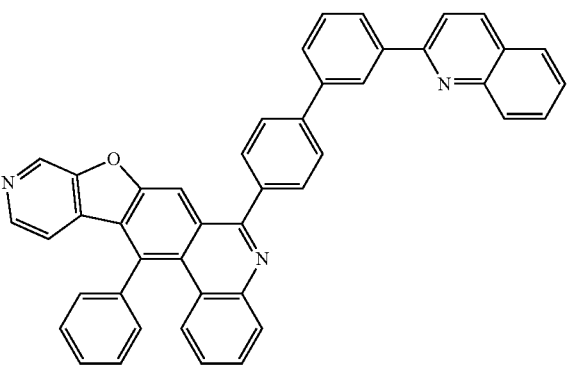

345
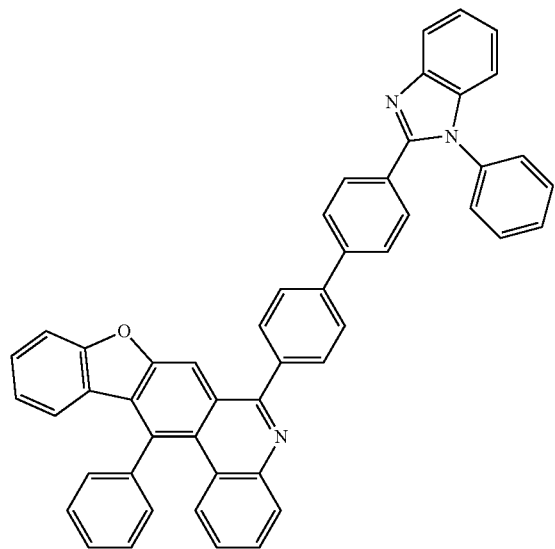
346
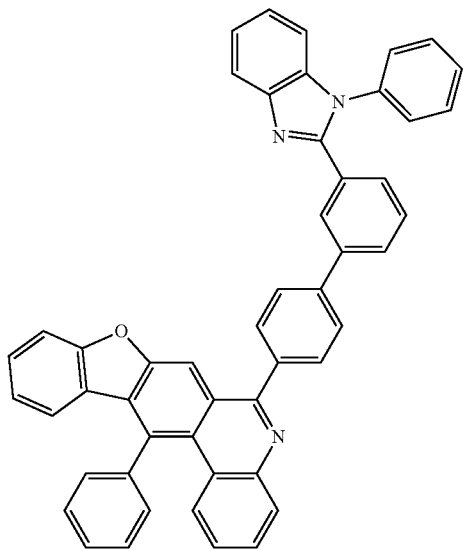
347
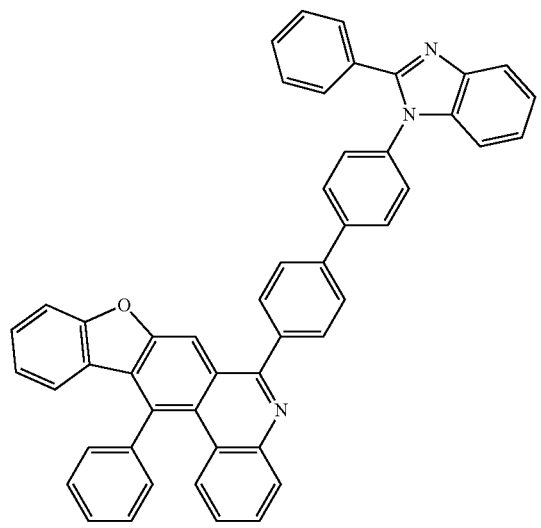
348
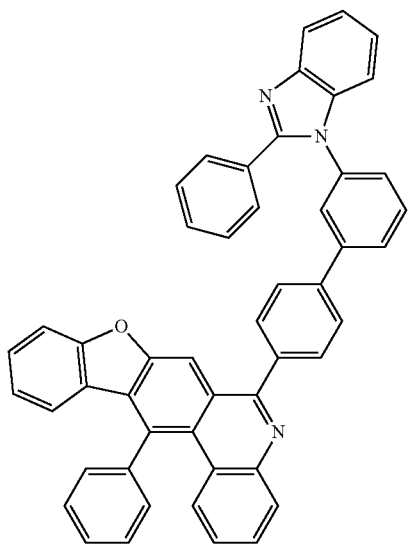

-continued
349
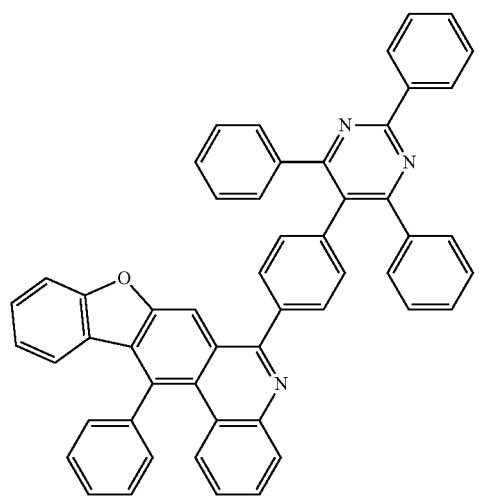
350
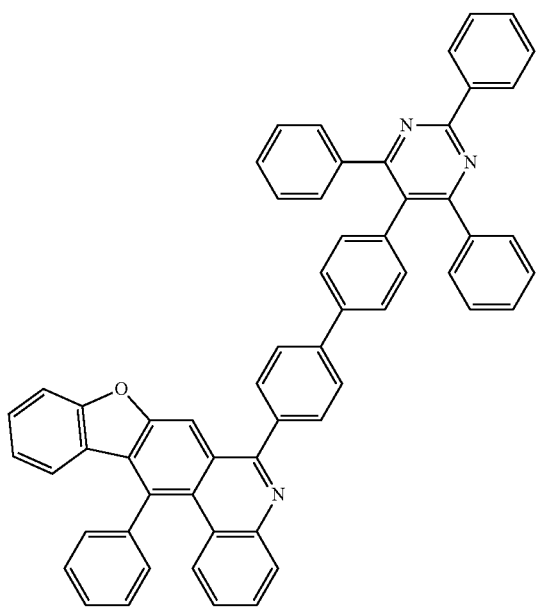
351
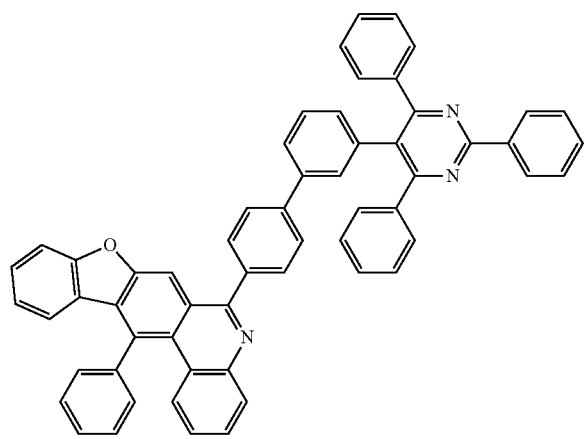
352
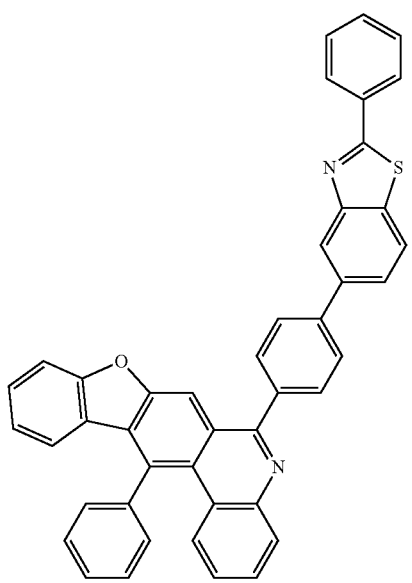

-continued
353
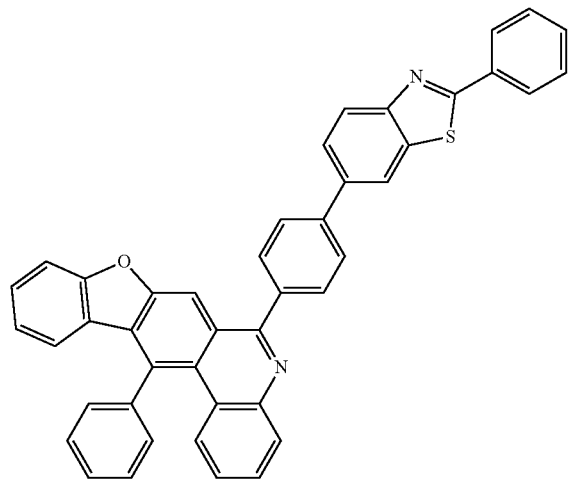
354
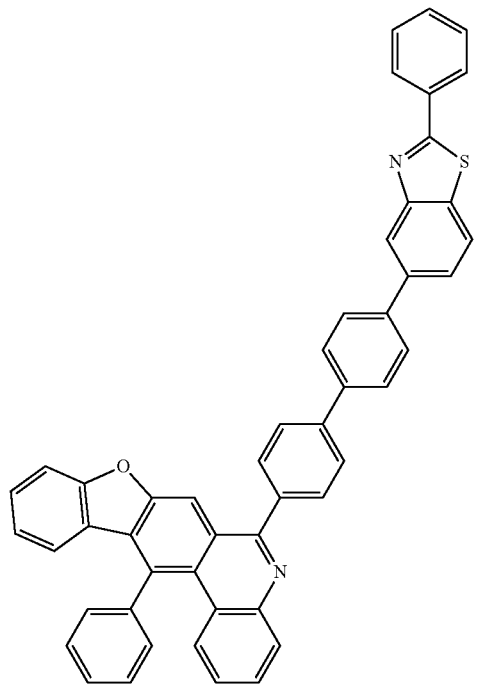
355
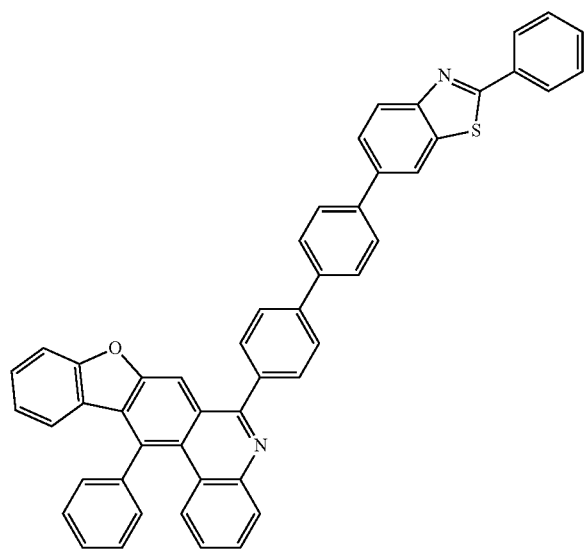
356
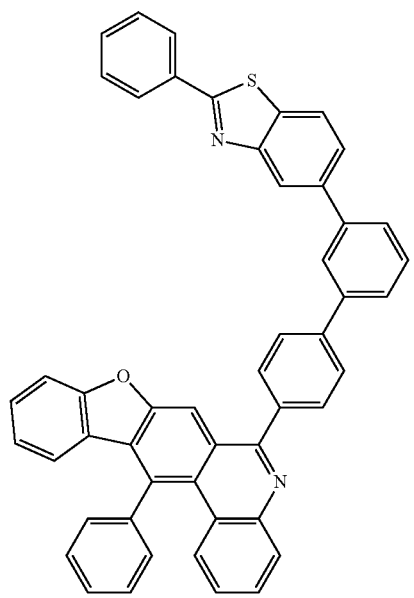

867 868
-continued
357 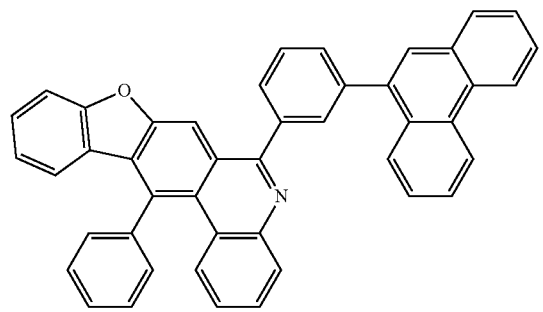 358
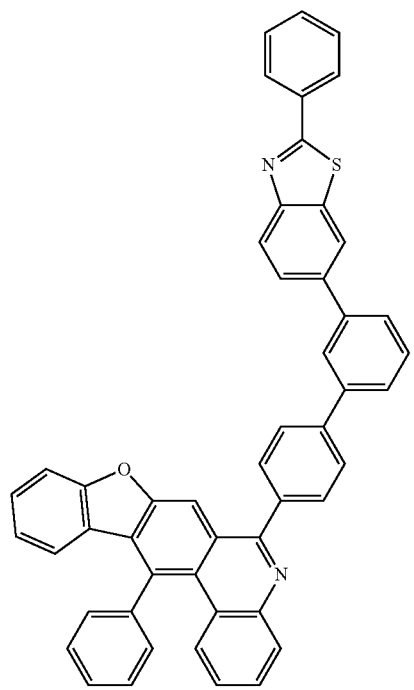
359 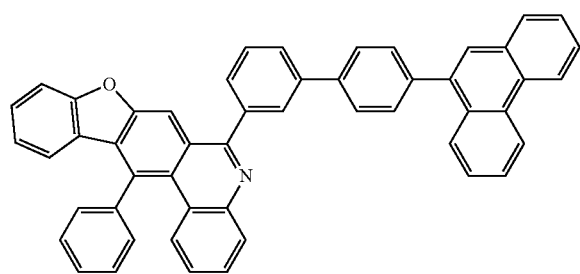 360 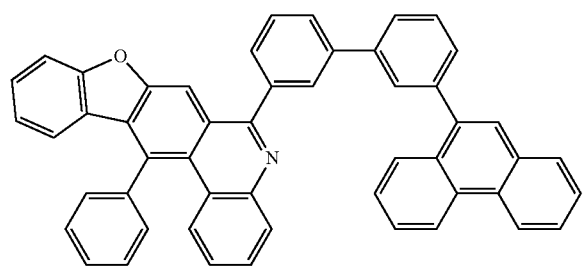
361 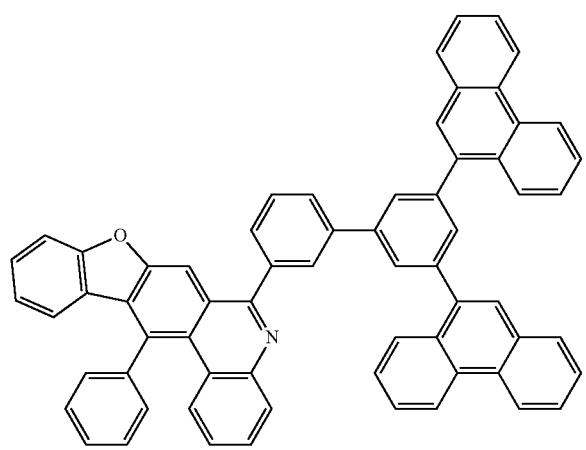 362 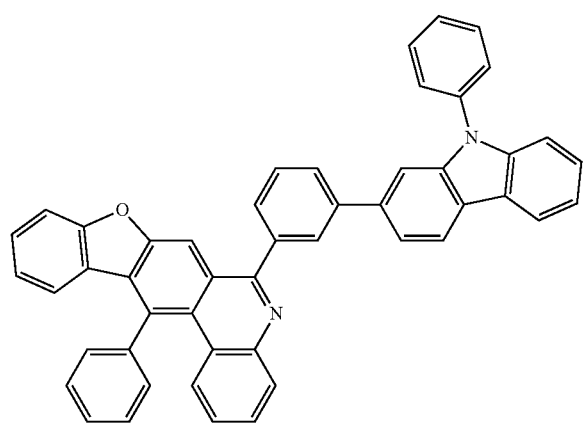

-continued
363
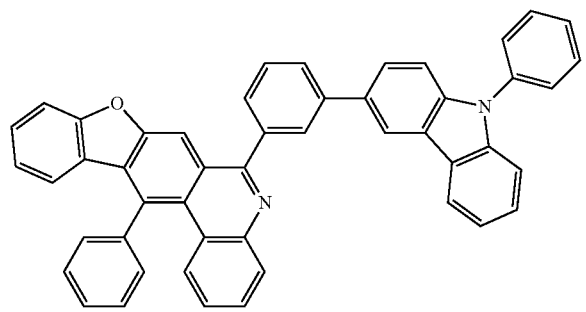
364
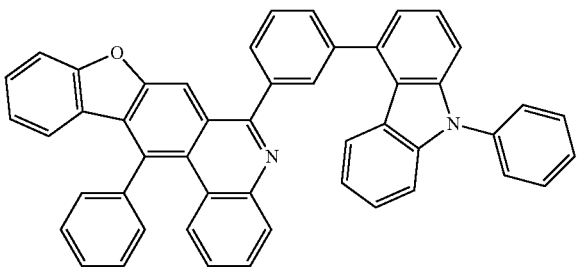
365
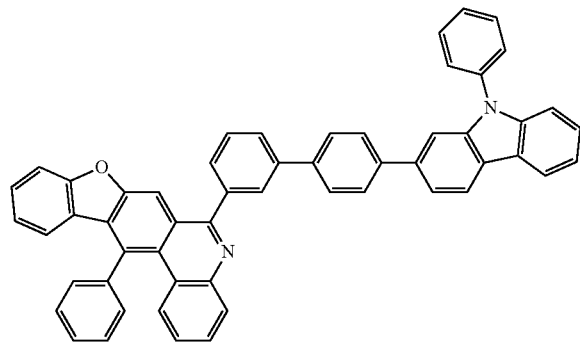
366
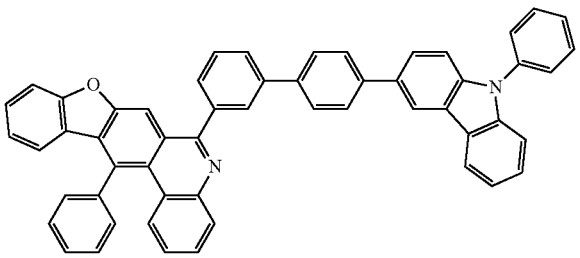
367
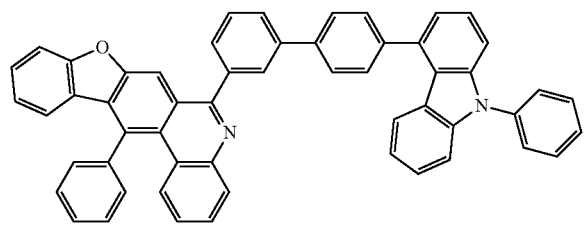
368
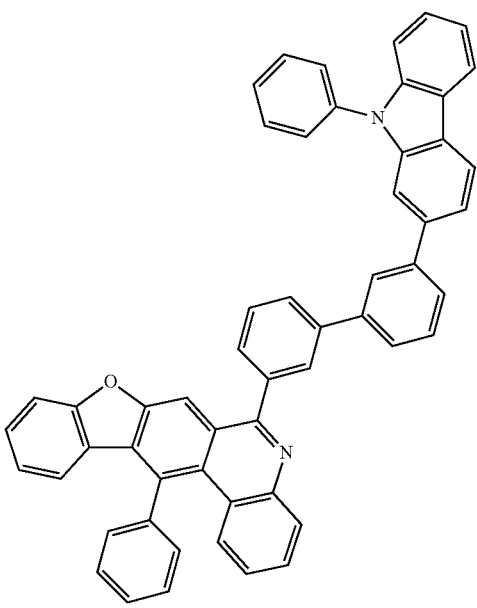

369
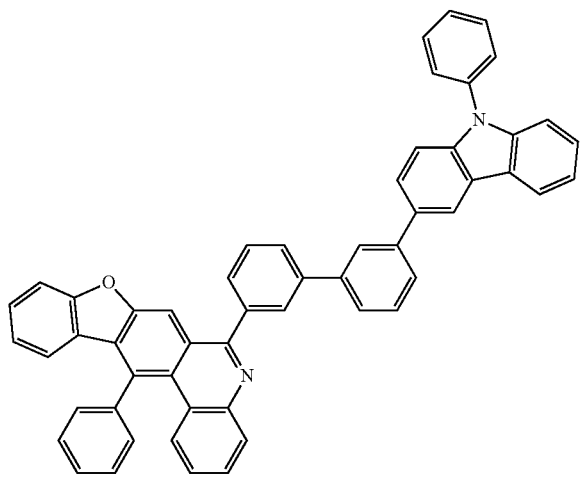
370
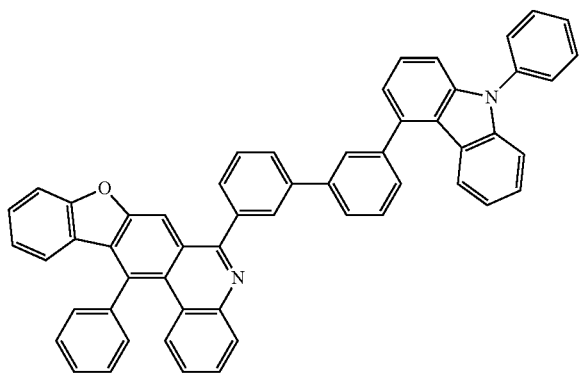
371
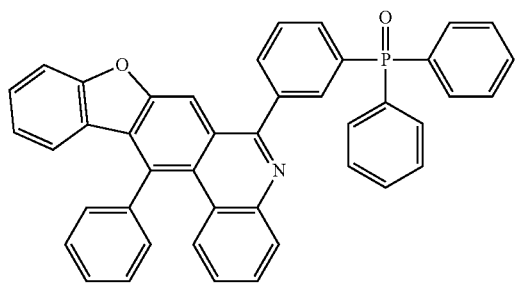
372
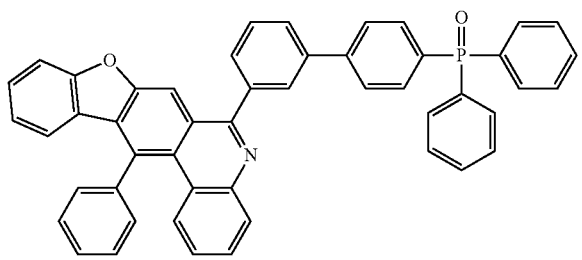
373
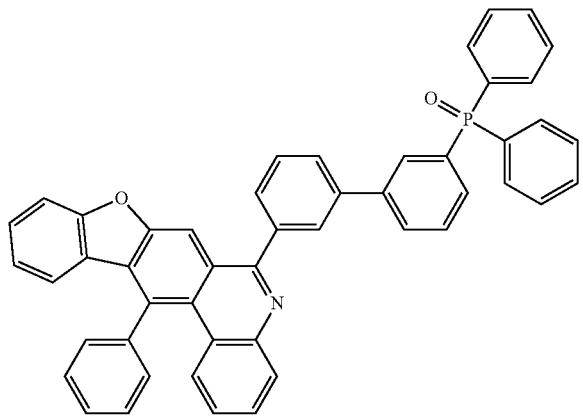
374
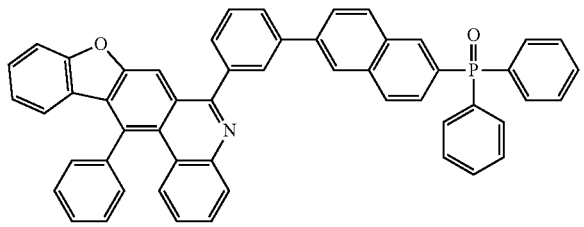
375
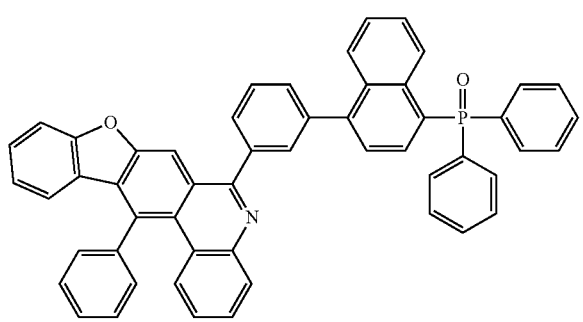
376
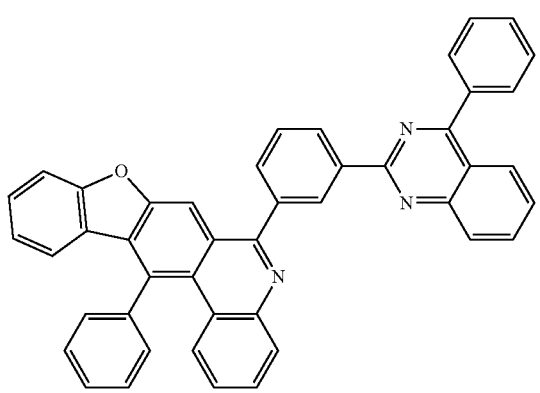

-continued
377
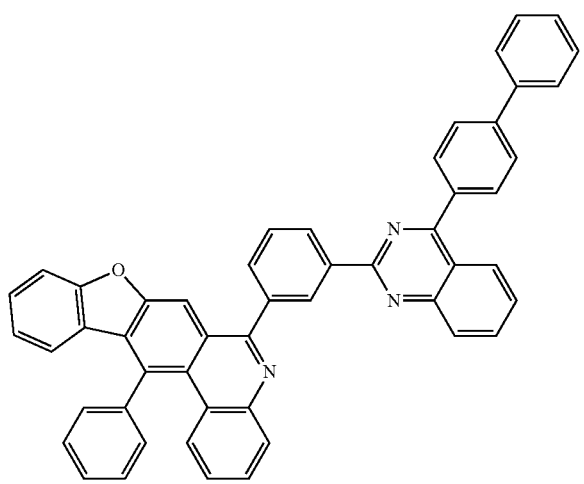
378
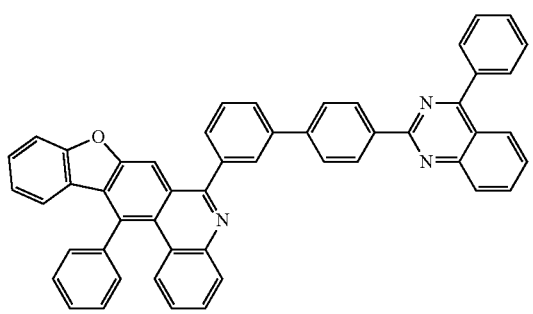
379
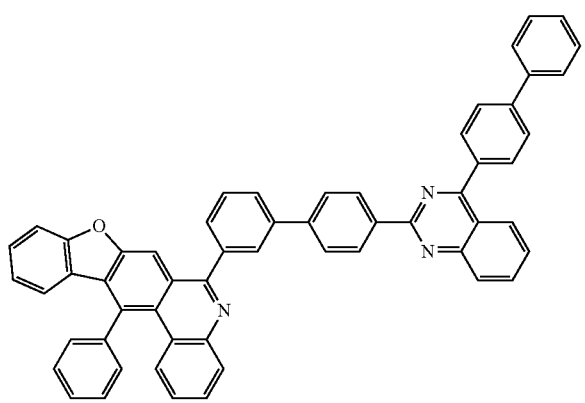
380
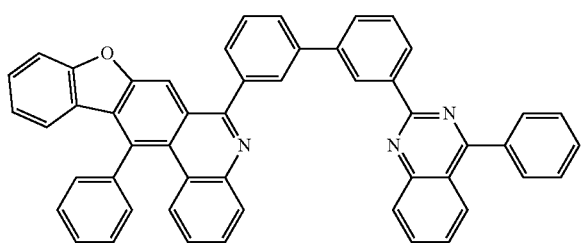
381
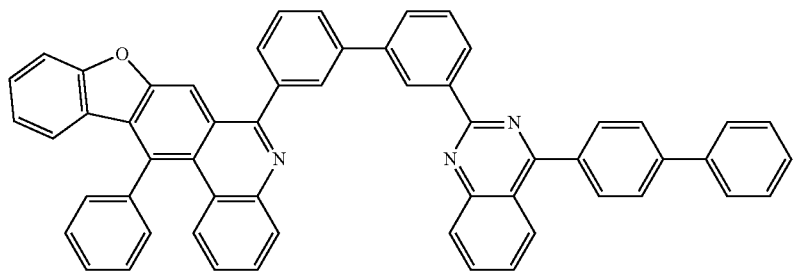
382
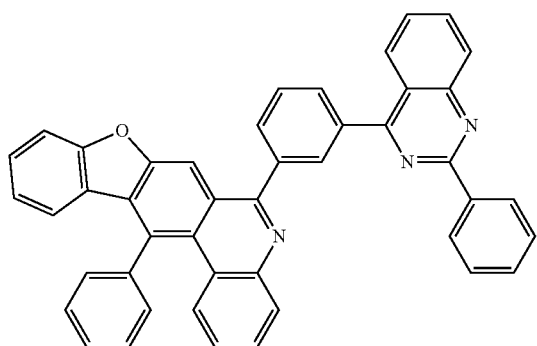
383
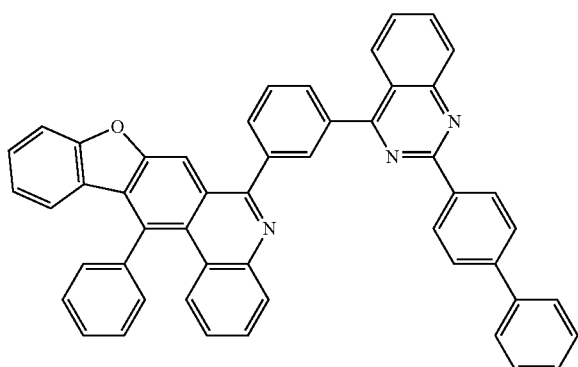

384
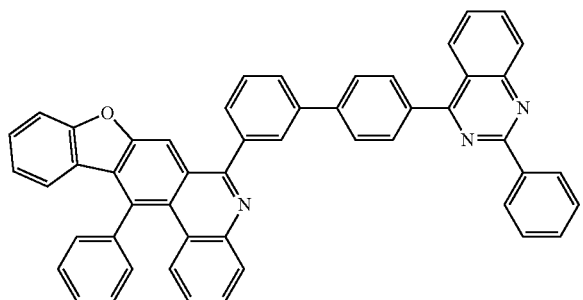
385
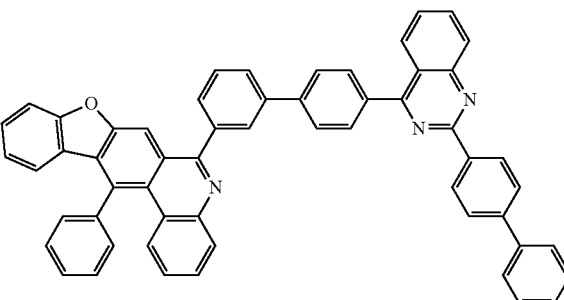
386
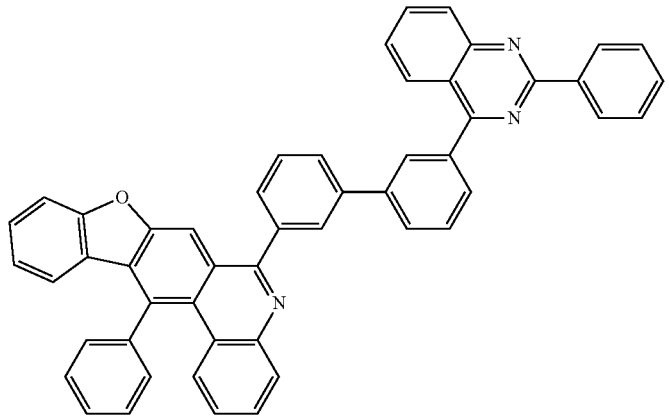
387
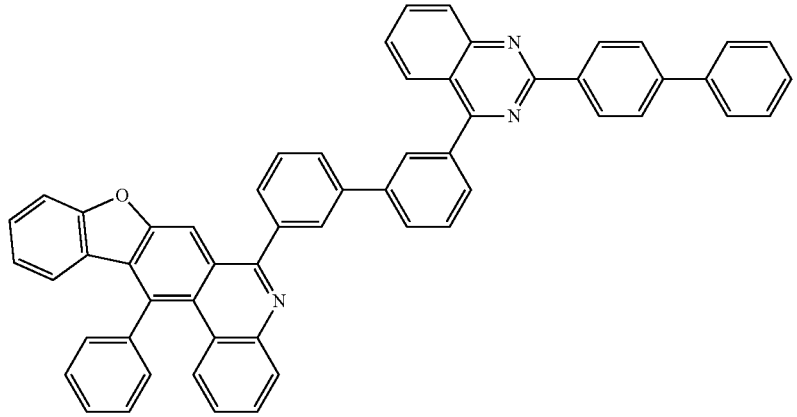
388
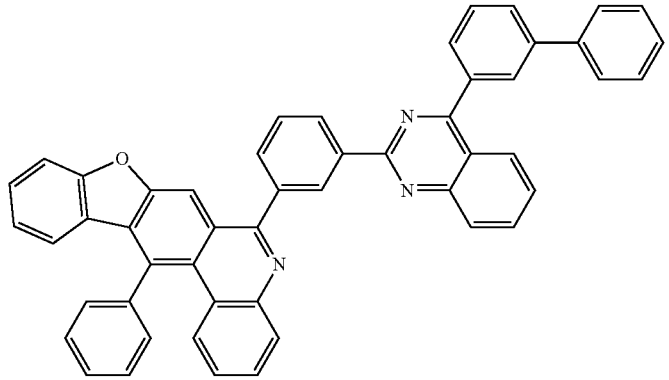

-continued
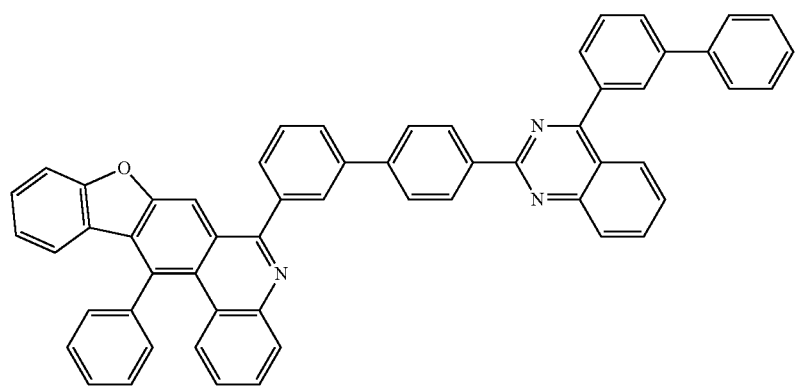
389
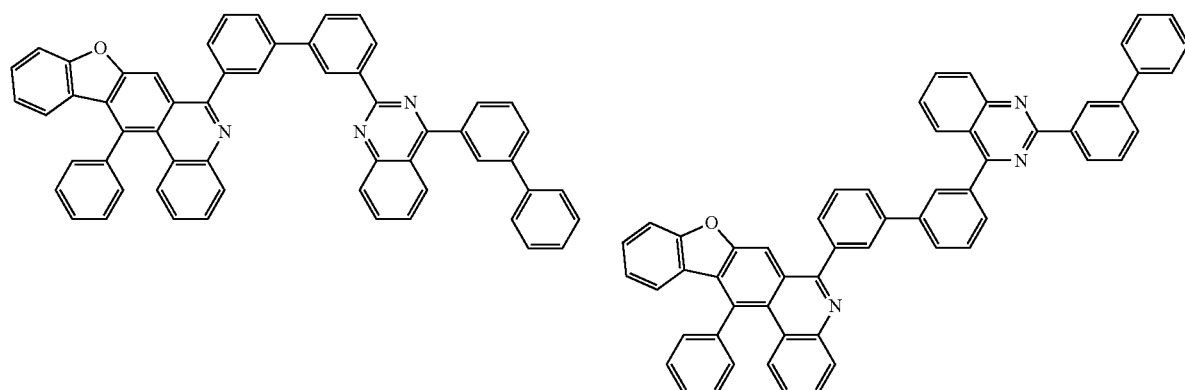
390
391
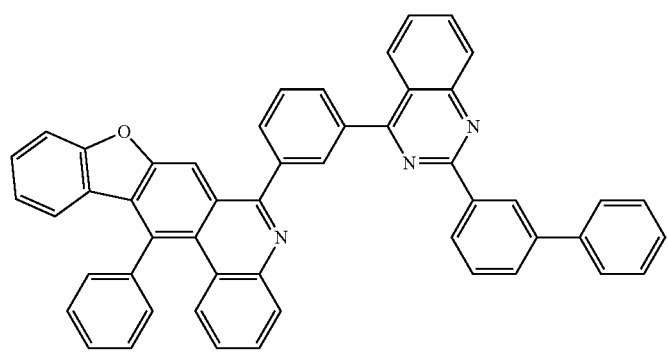
392
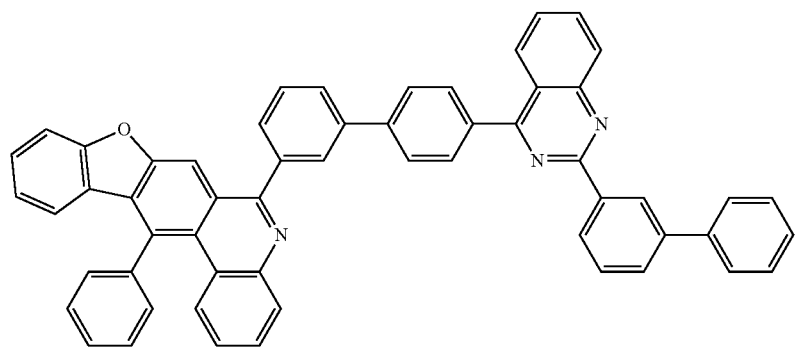
393

-continued
394
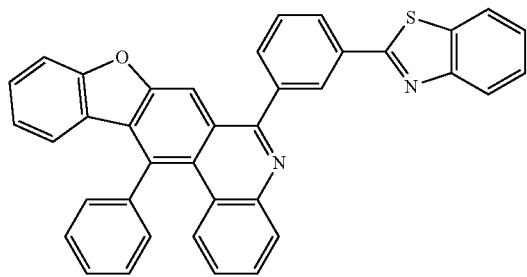
395
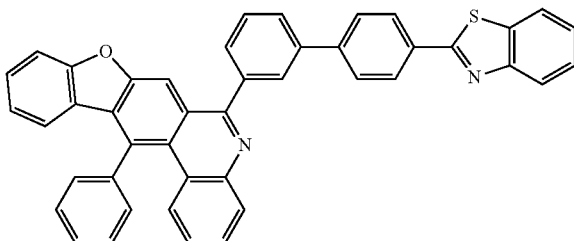
396
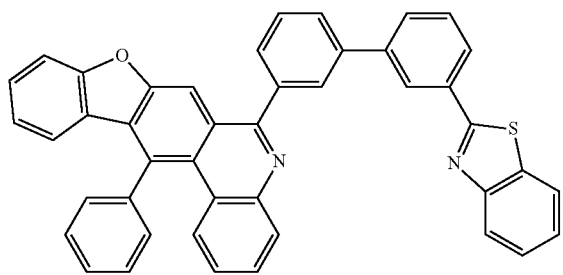
397
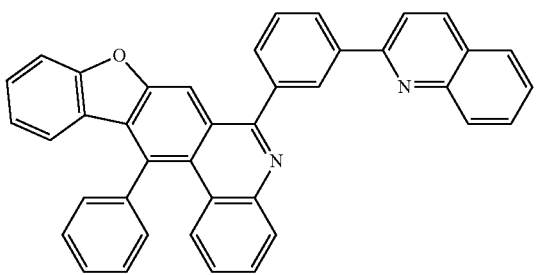
398
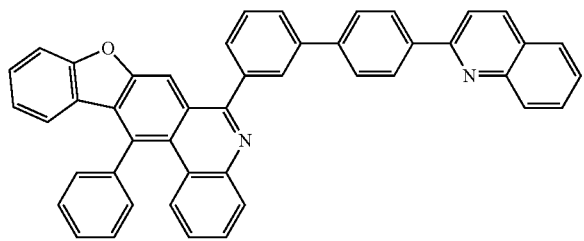
399
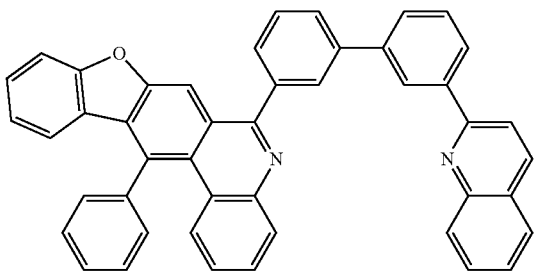
400
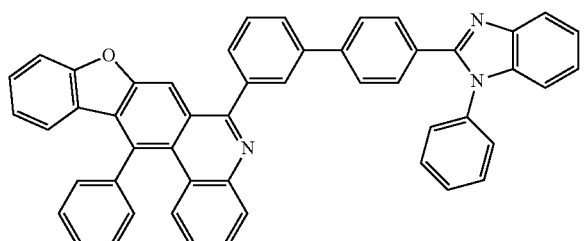
401
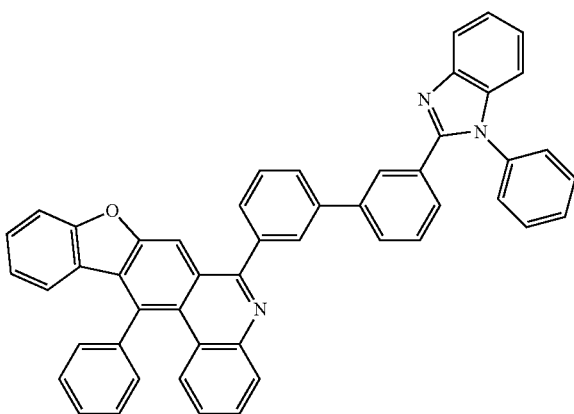

-continued
402
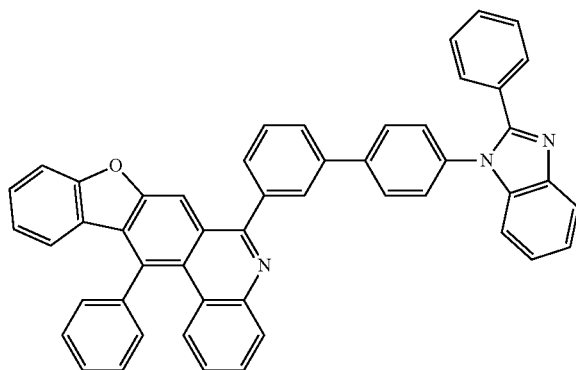
403
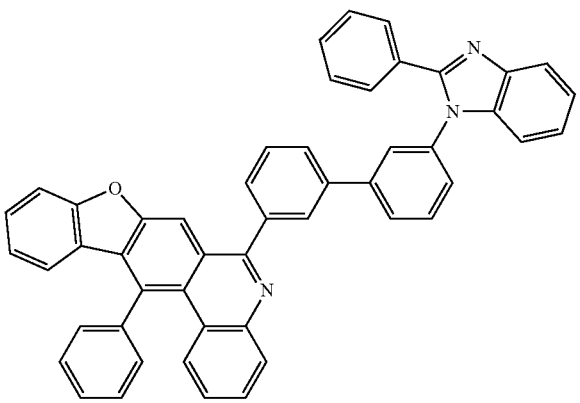
404
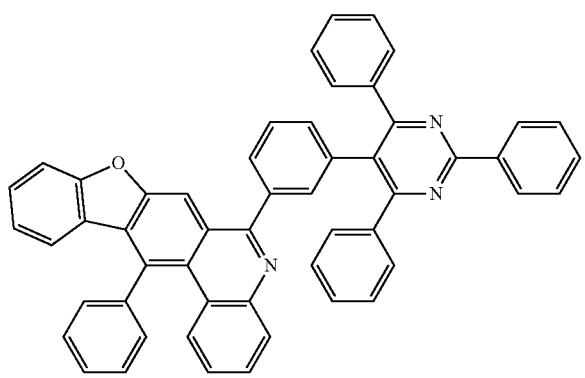
405
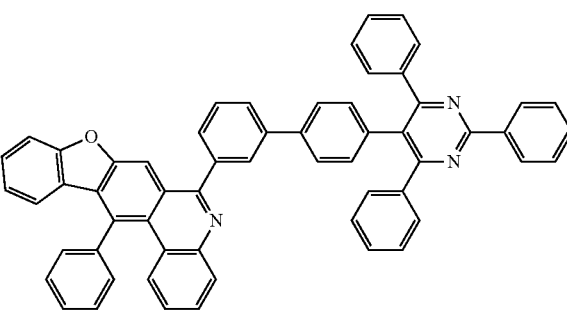
406
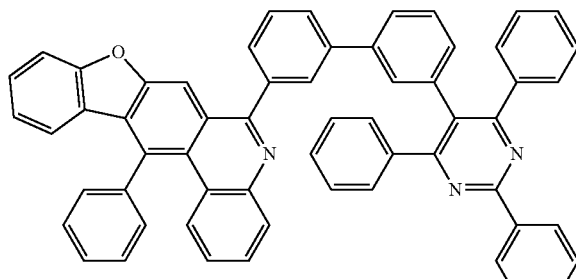
407
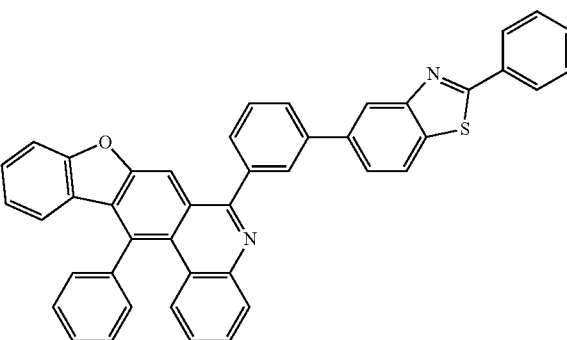
408
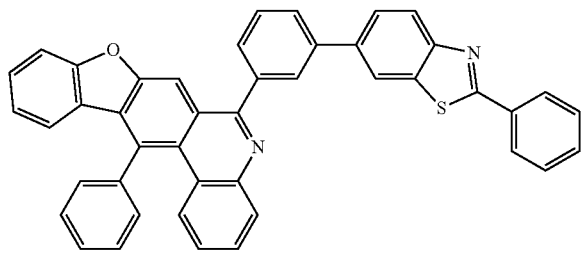
409
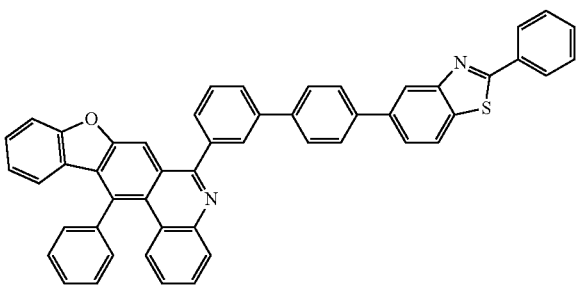

-continued
410
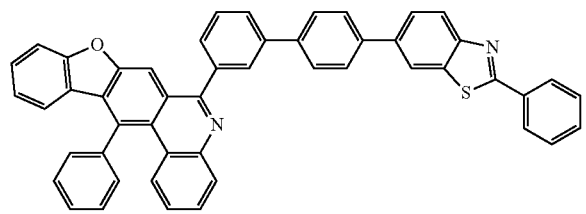
411
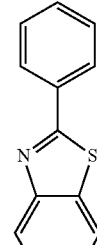
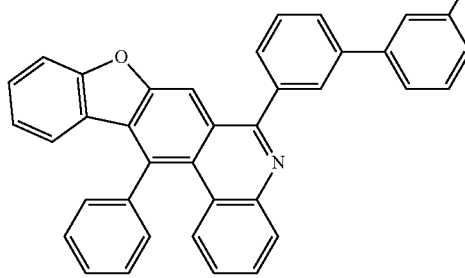
412
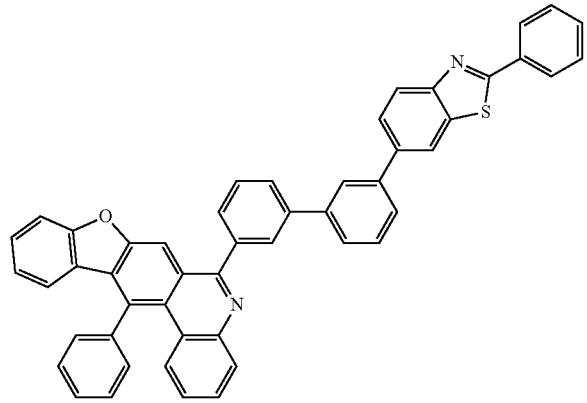
413
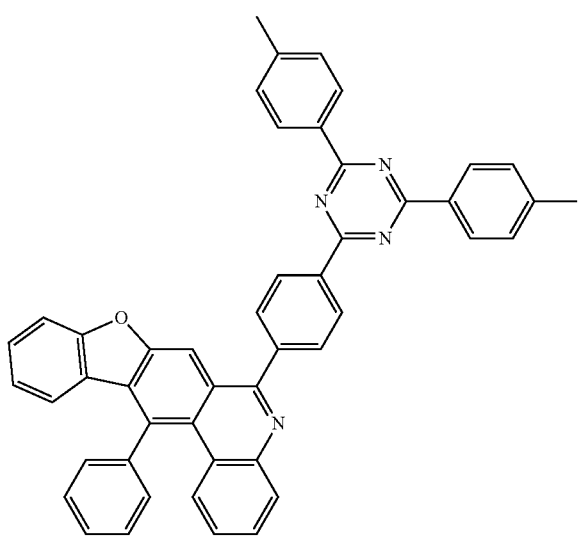

-continued
414
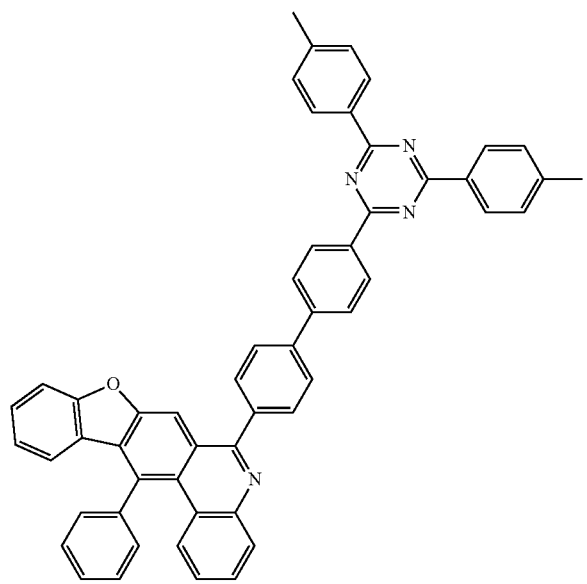
415
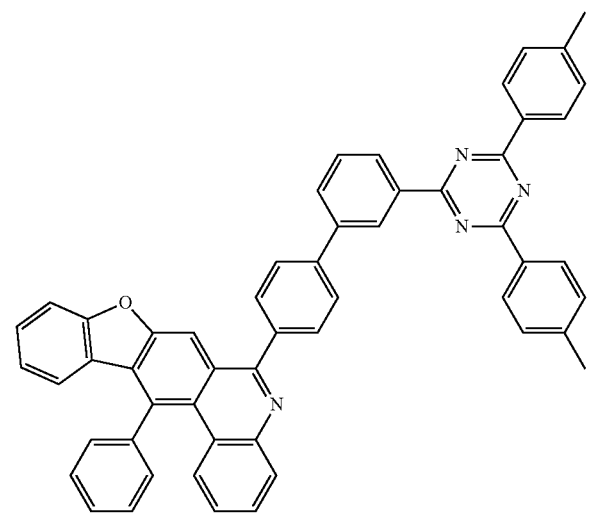
416
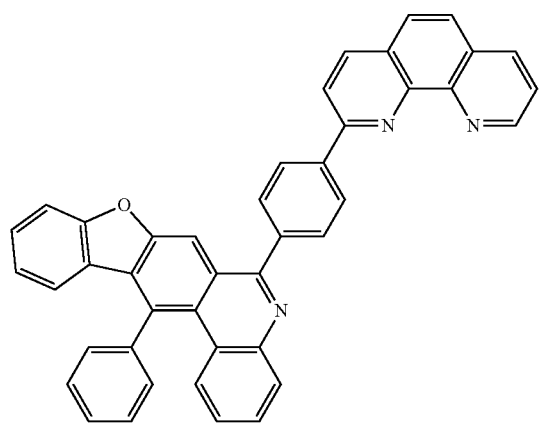
417
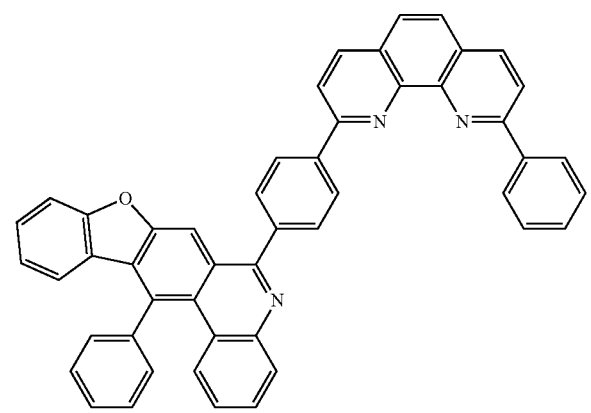
418
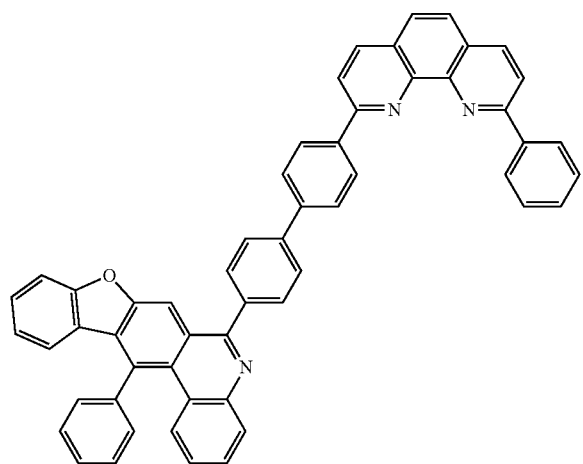
419
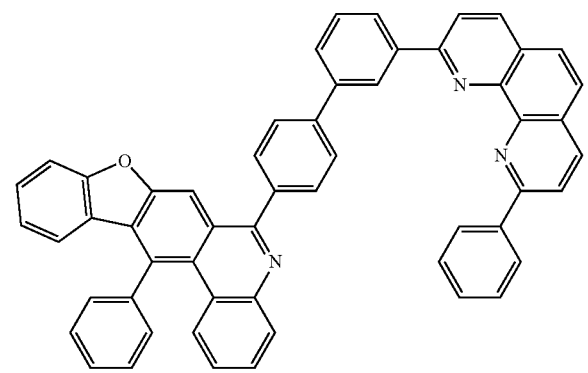

-continued
887  888
420
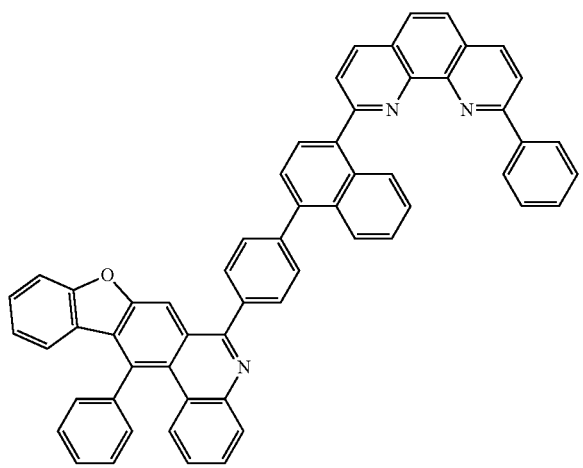
421
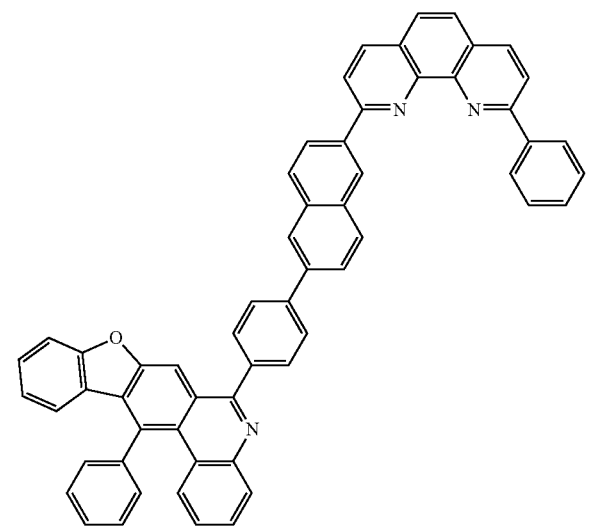
422
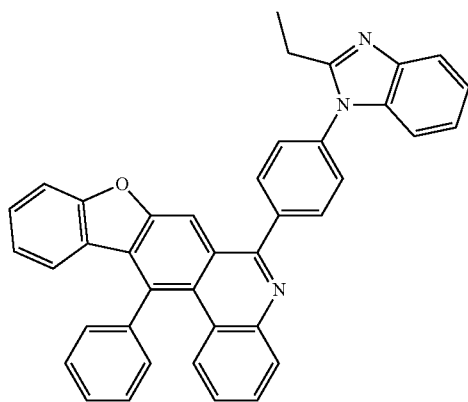
423
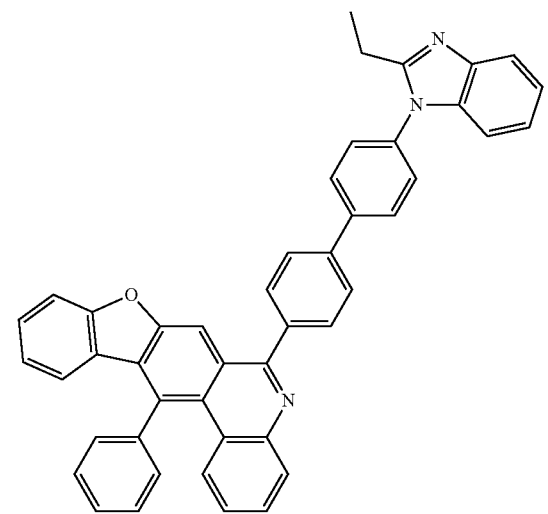
424
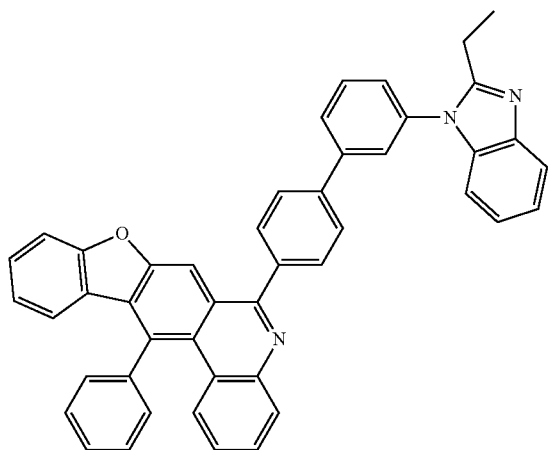
425
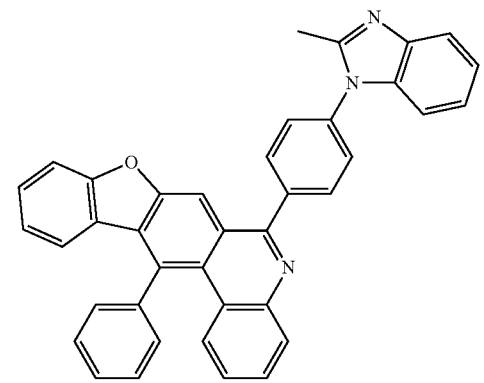

-continued
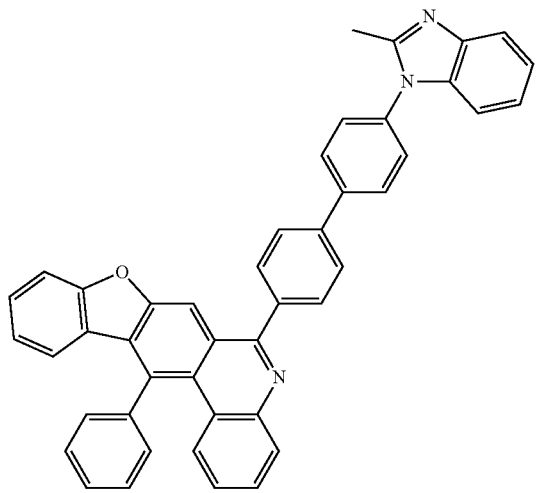
426
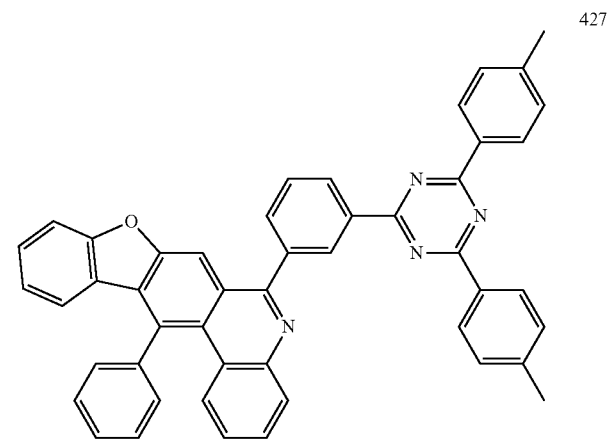
427
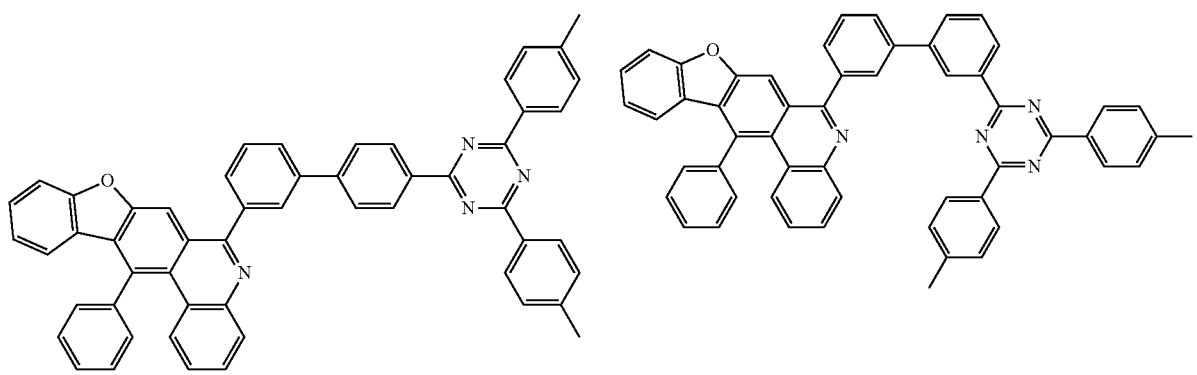
428 429
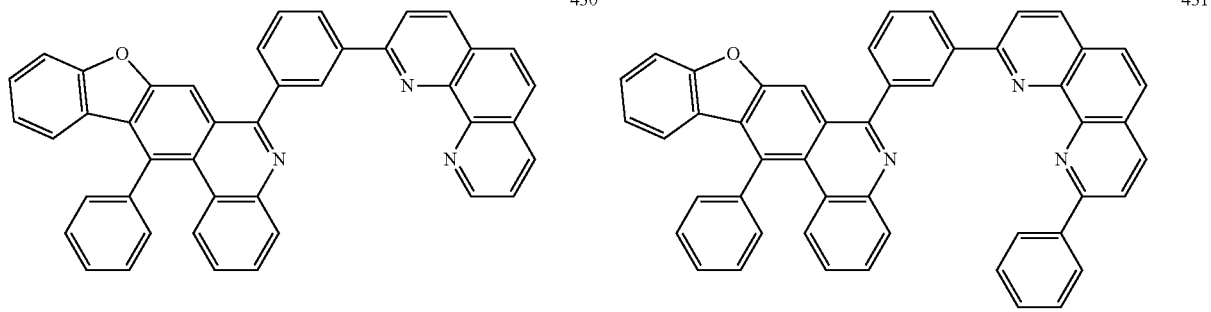
430 431
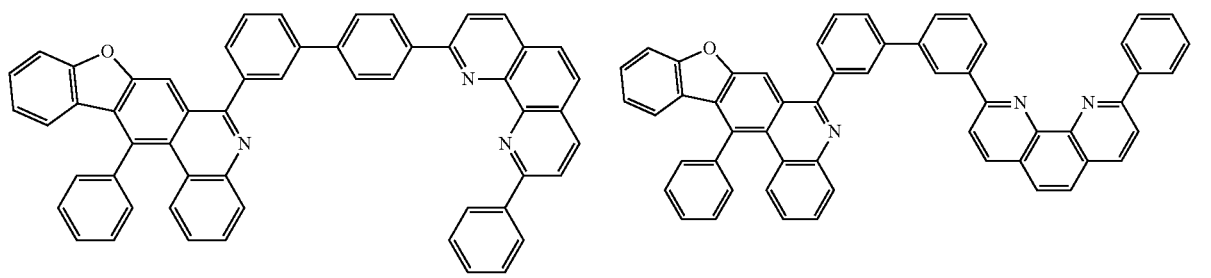
432 433

-continued
891
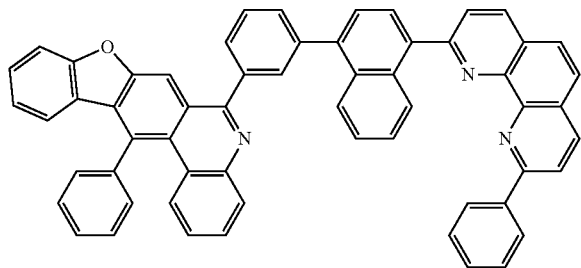
434
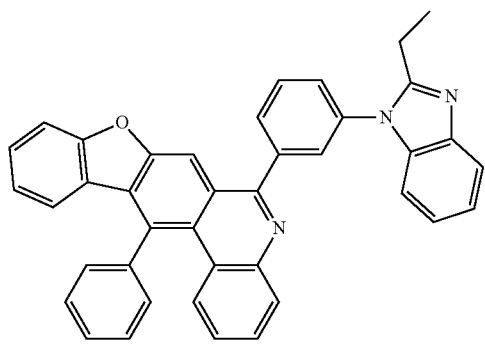
436
892
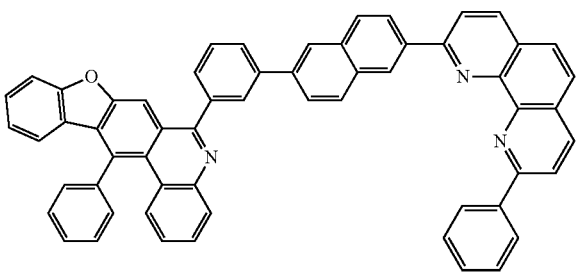
435
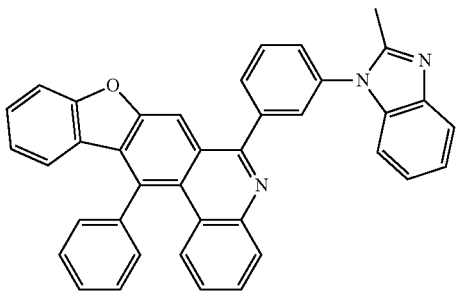
437
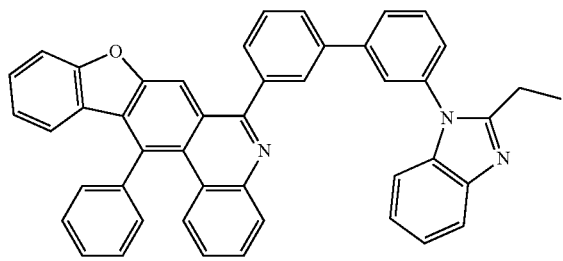
438
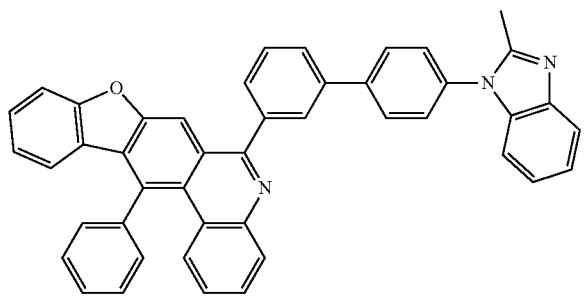
440
439
441
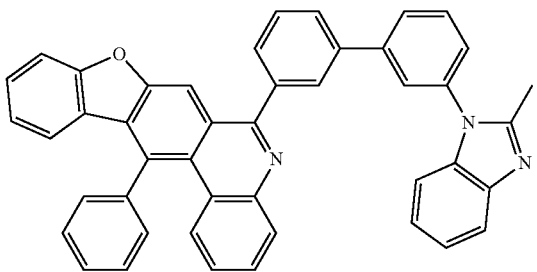

893 894
-continued
442
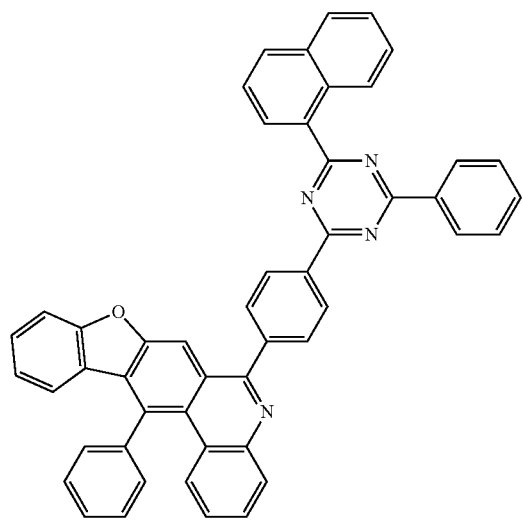
443
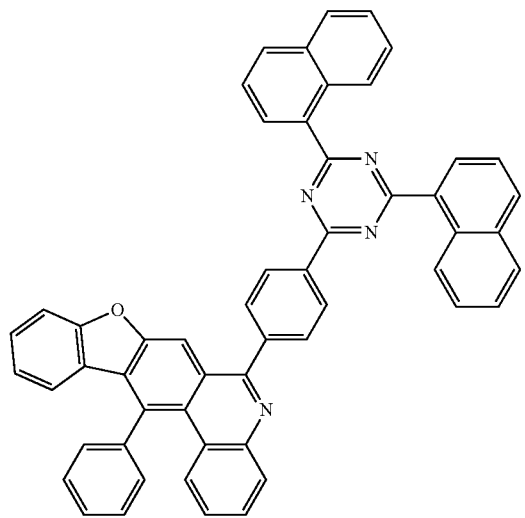
444
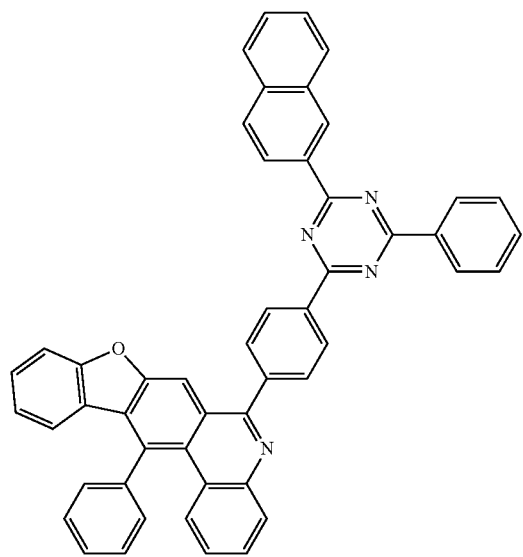
445
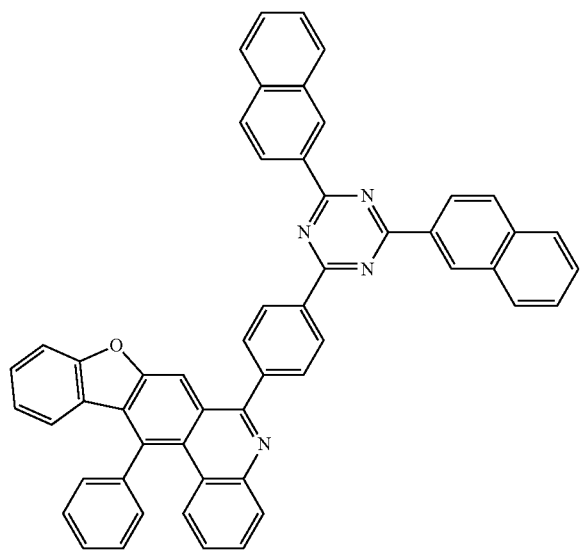

-continued
446
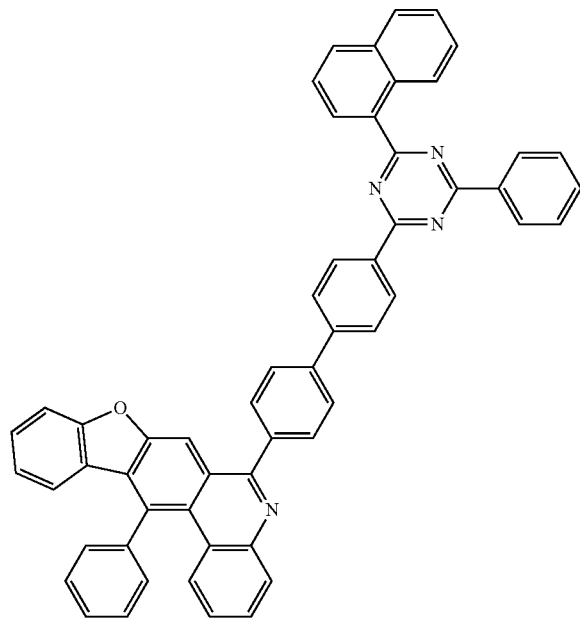
447
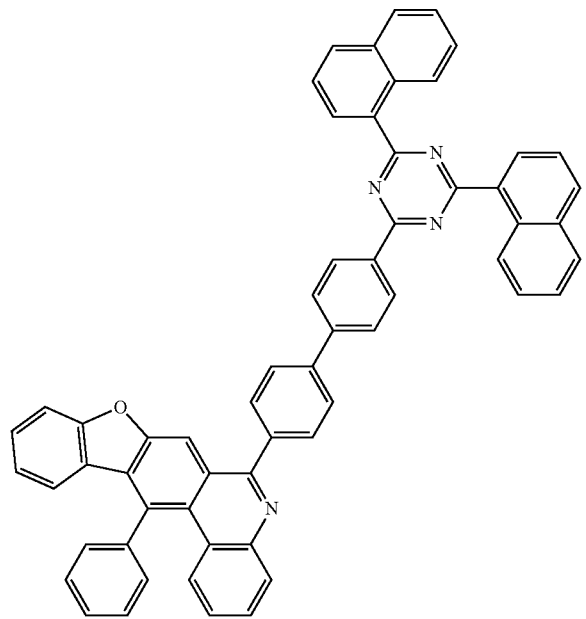
448
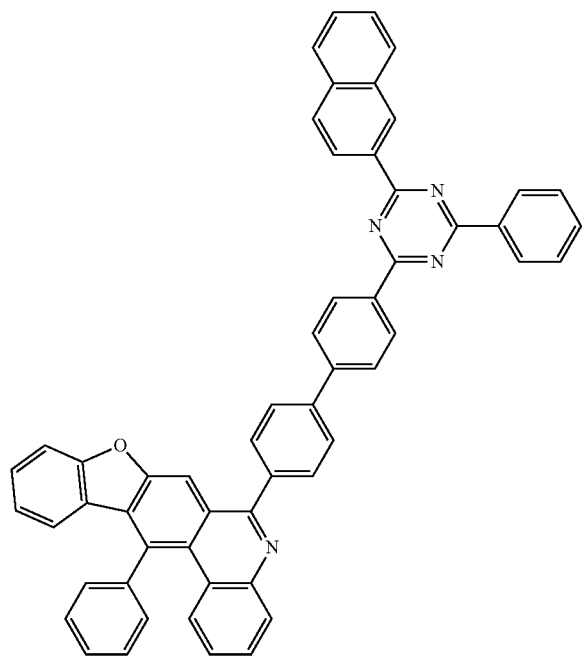
449
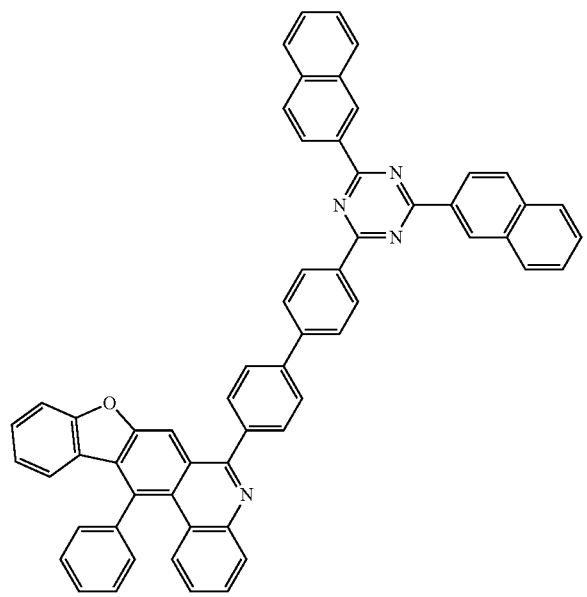

-continued
450
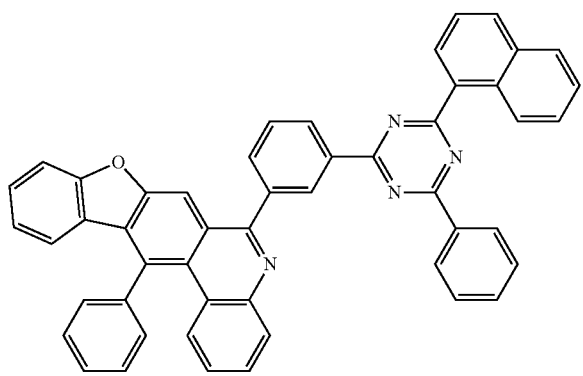
451
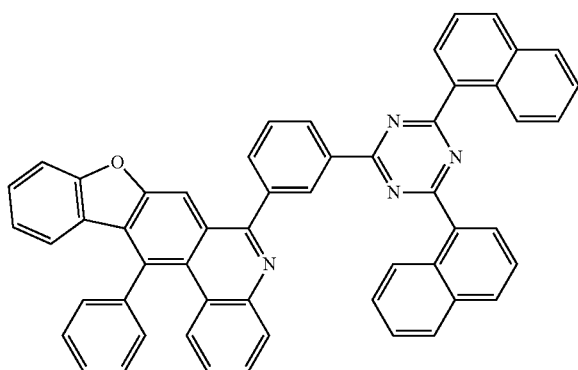
452
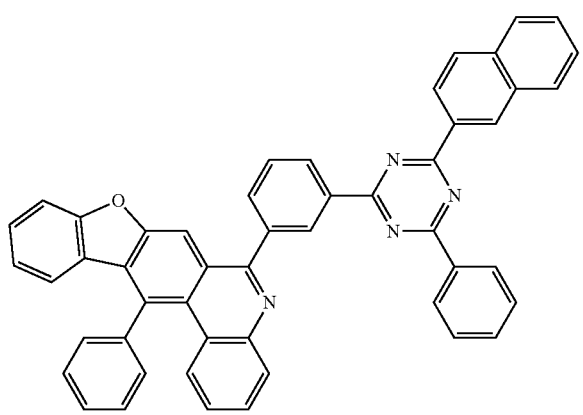
453
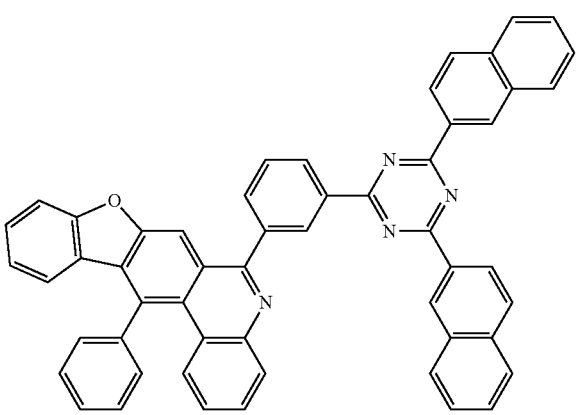
454
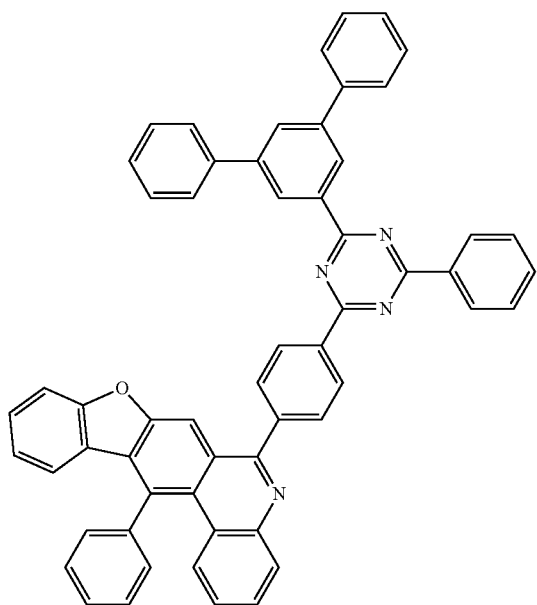
455
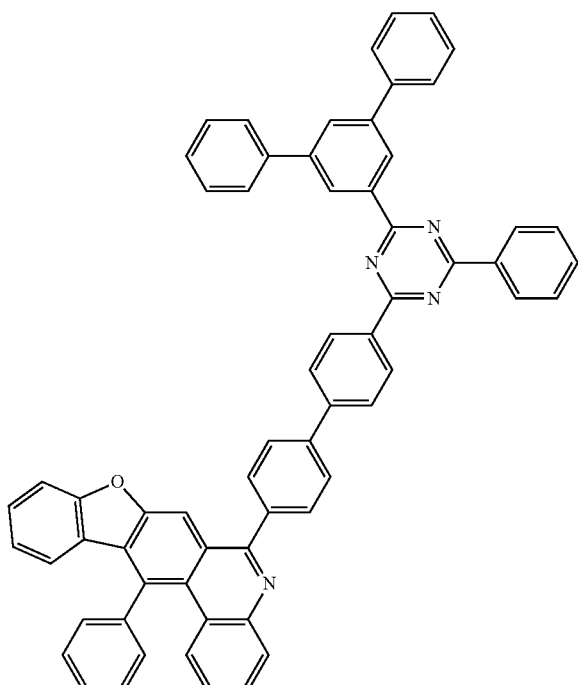

456
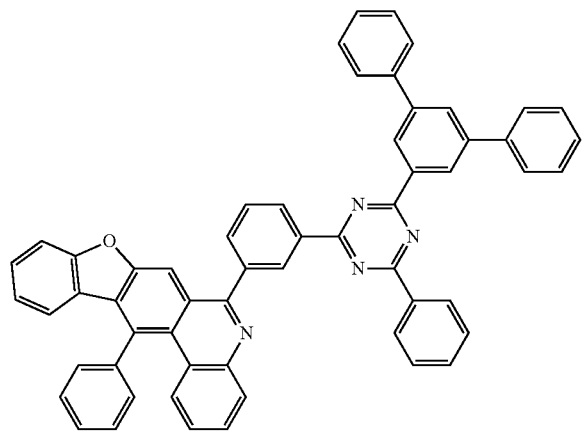
457
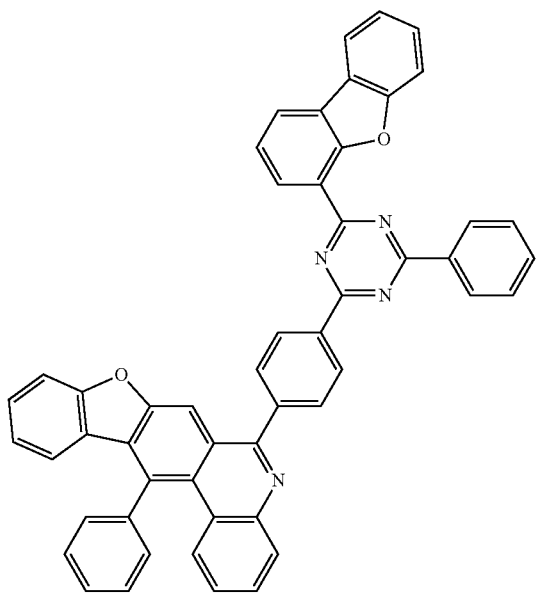
458
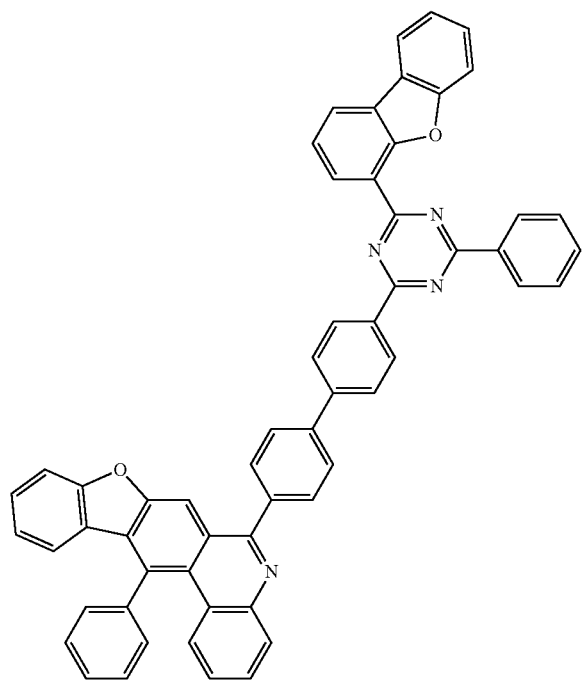
459
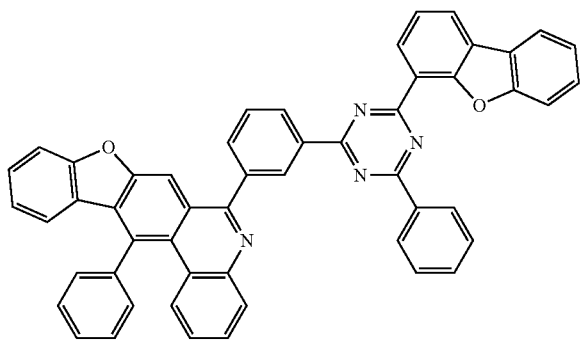

-continued
901
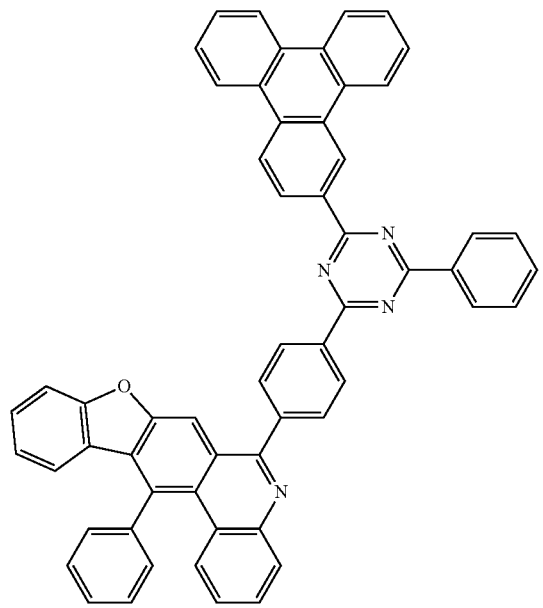
460
902
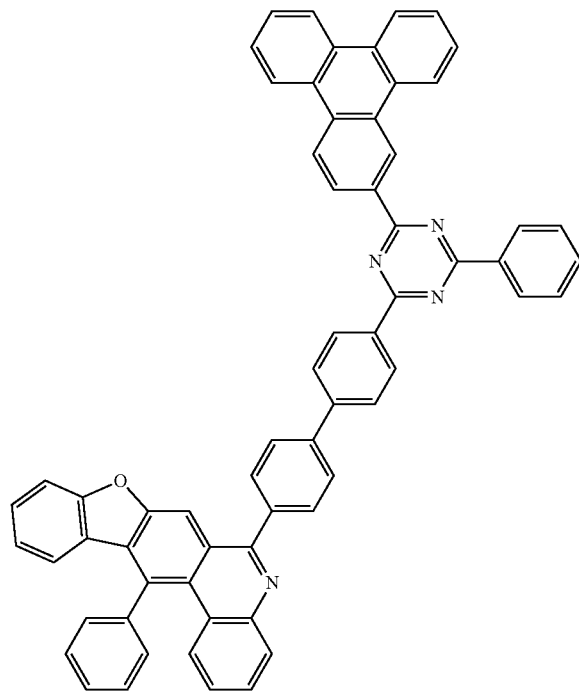
461
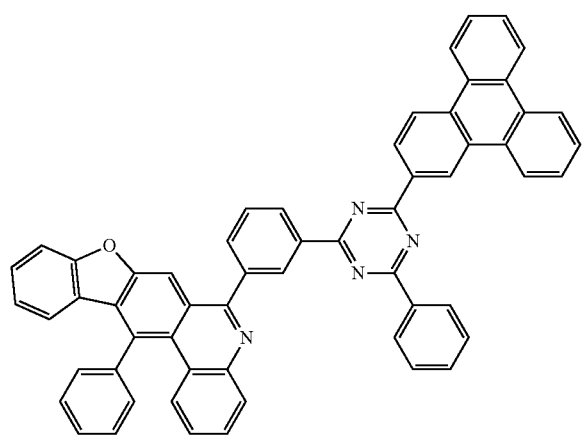
462
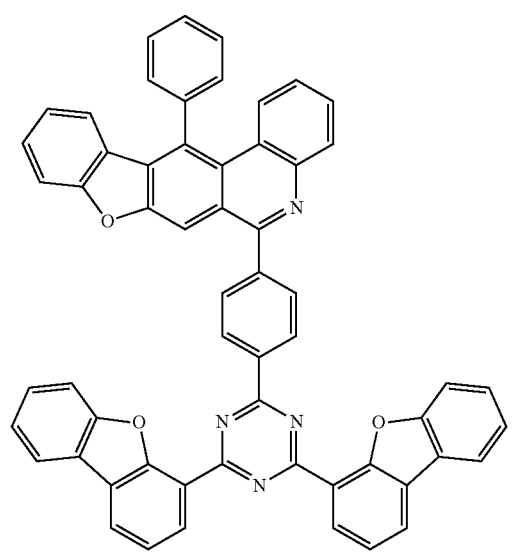
463

-continued
903
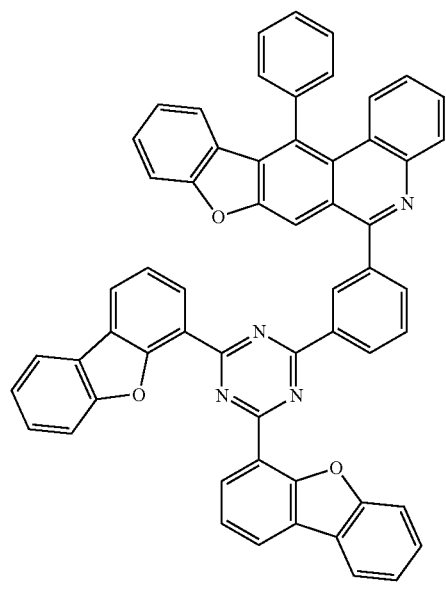
464
904
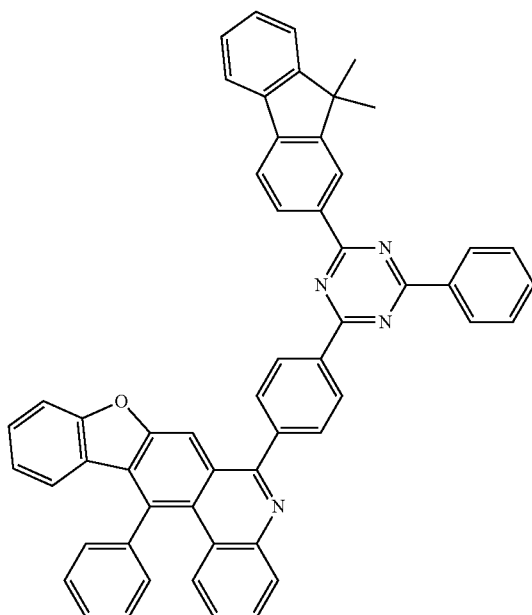
465
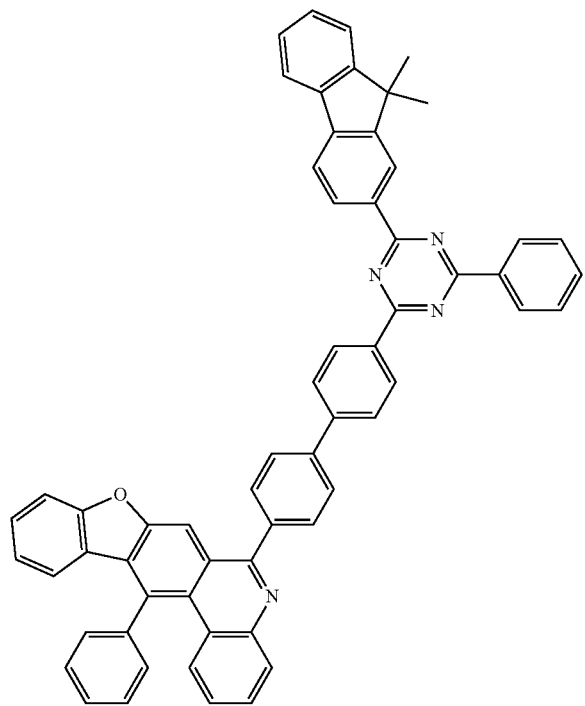
466
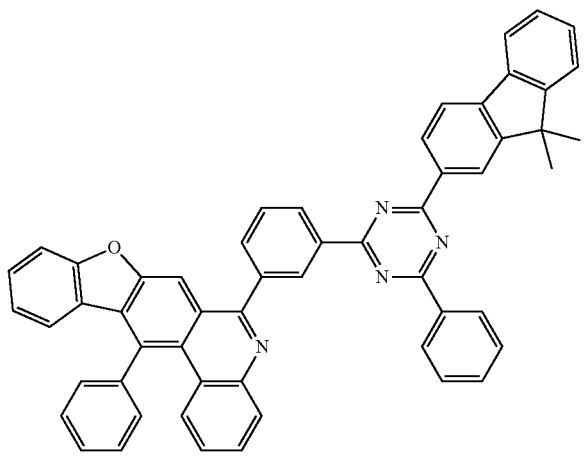
467

905 906
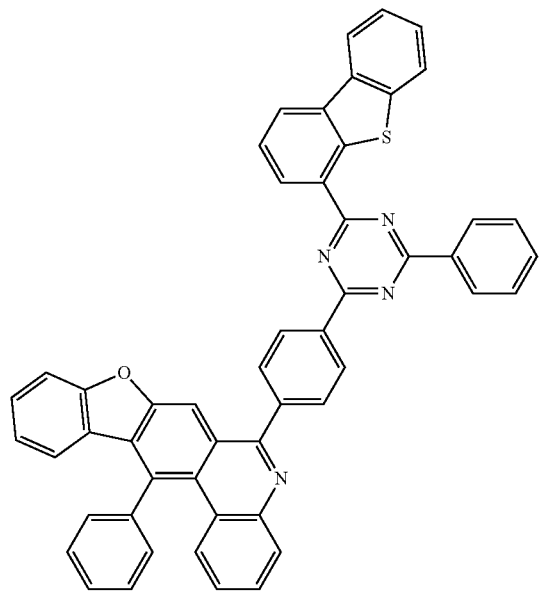
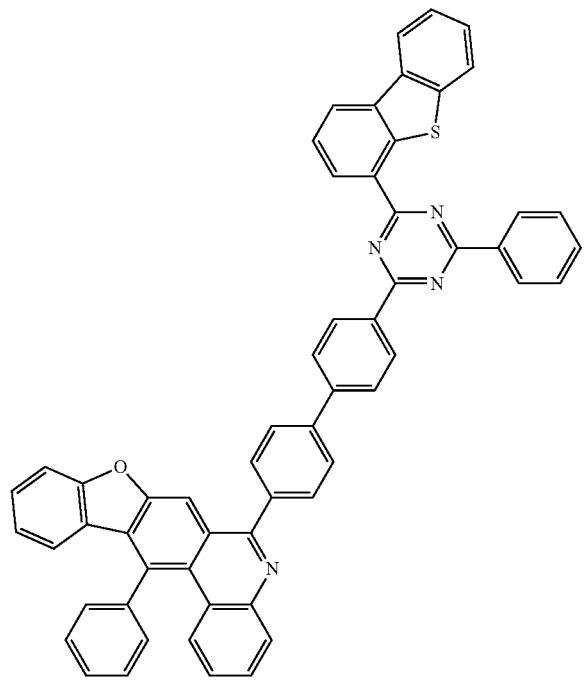
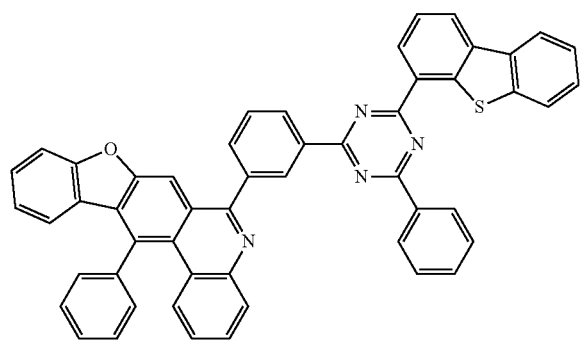
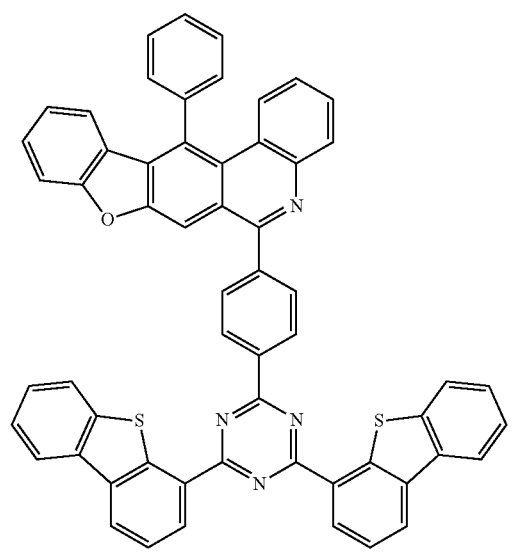

907
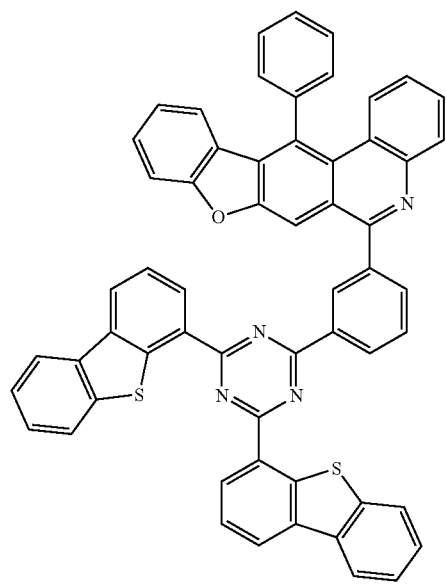
908
-continued
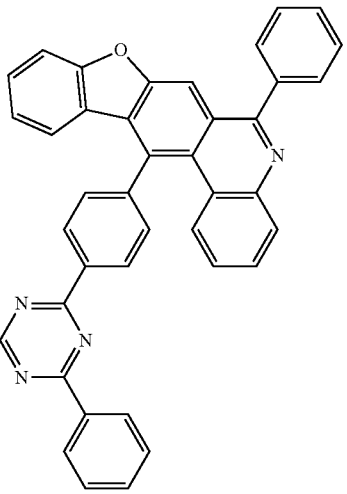
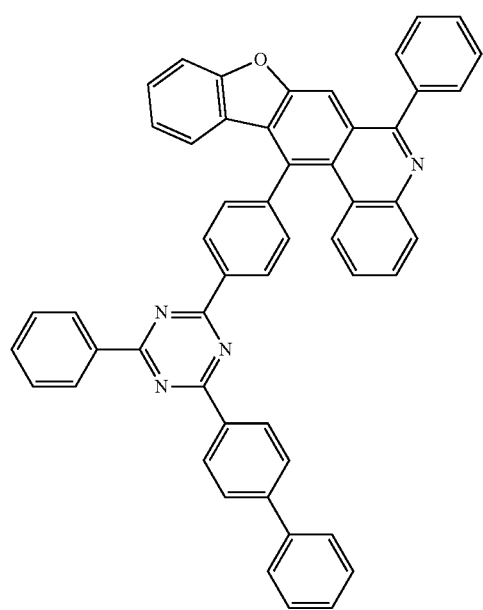
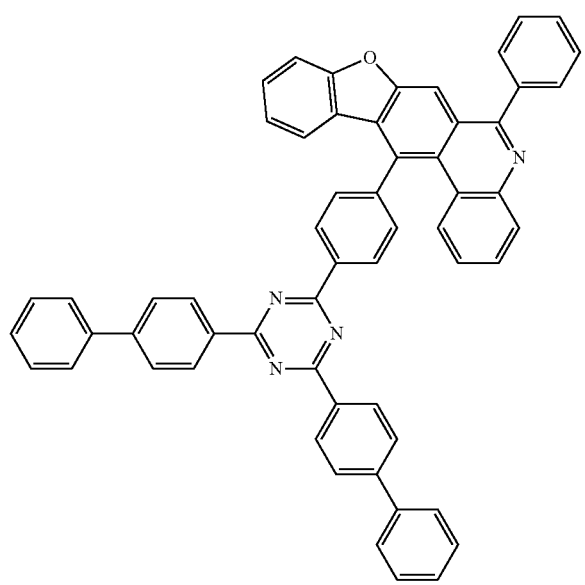

-continued
909
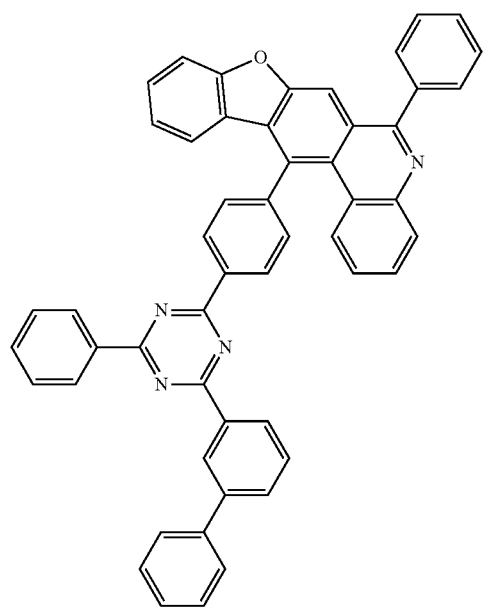
476
910
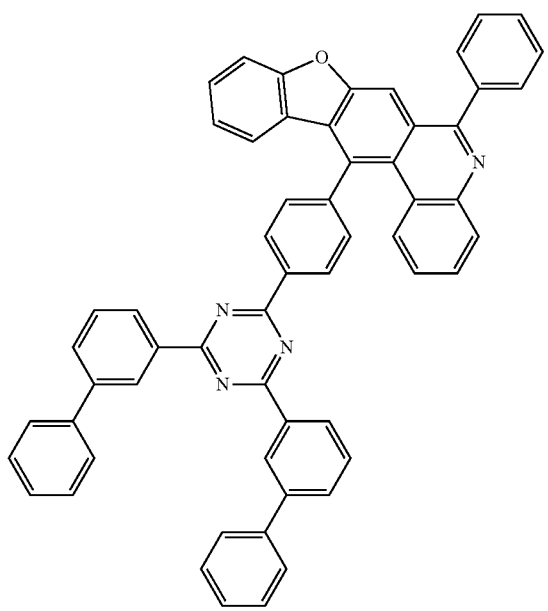
477
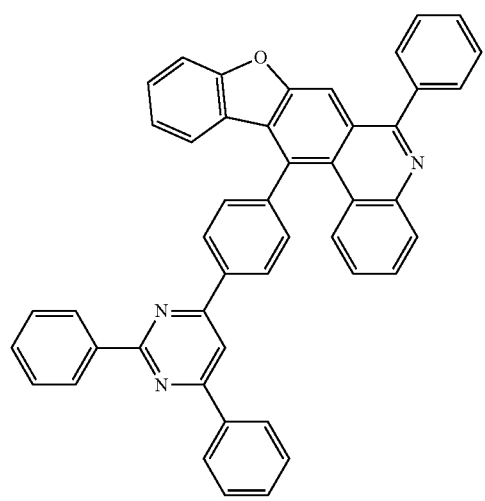
478
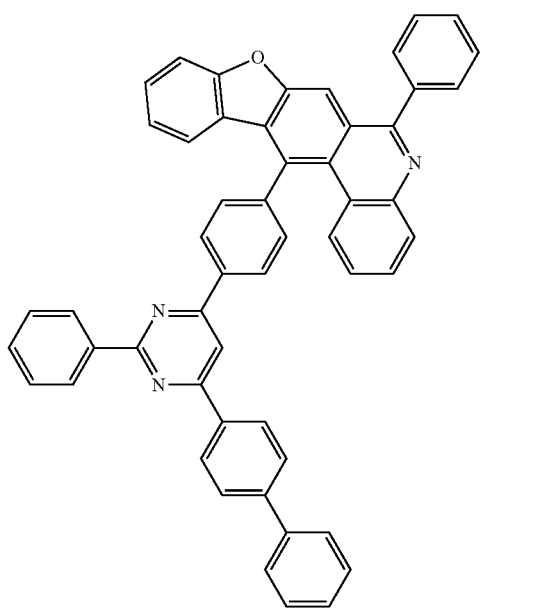
479

-continued
911
480
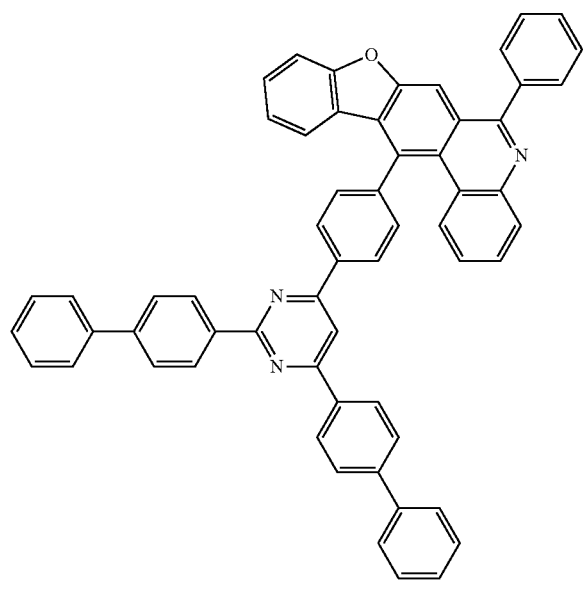
912
481
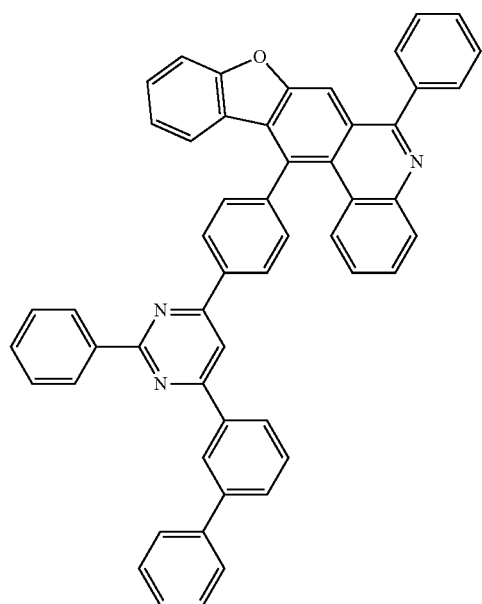
482
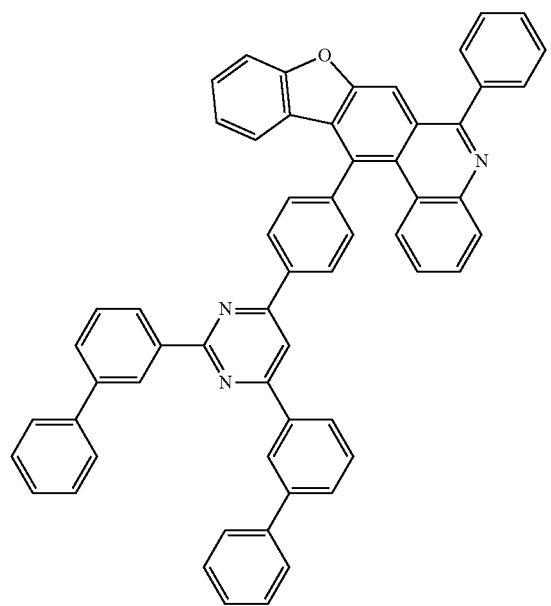
483
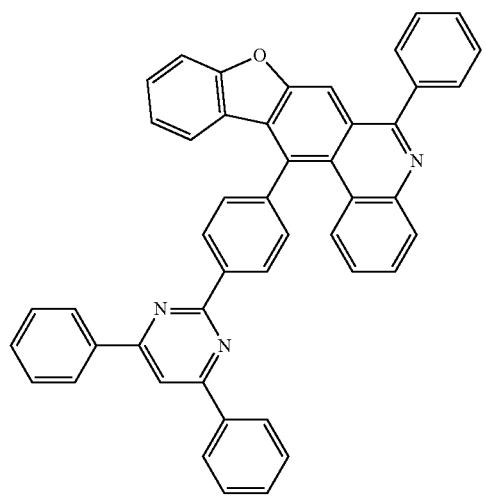

913
914
-continued
484
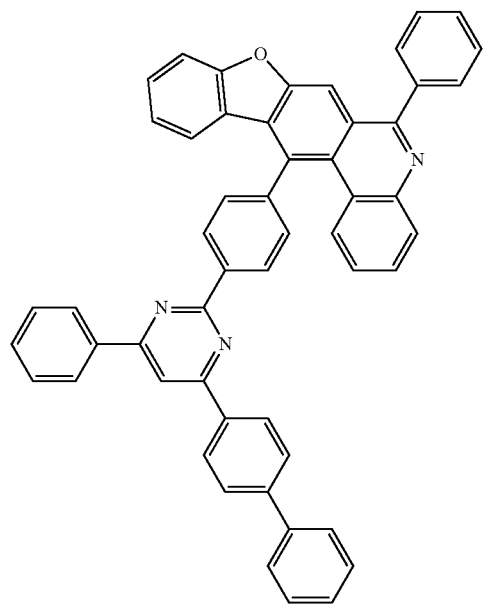
485
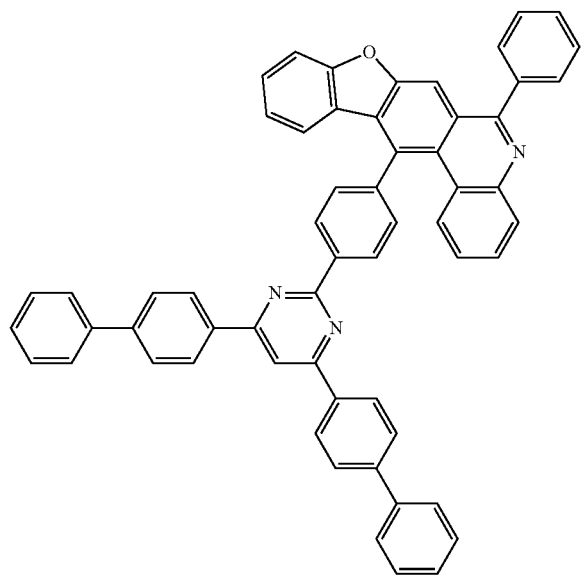
486
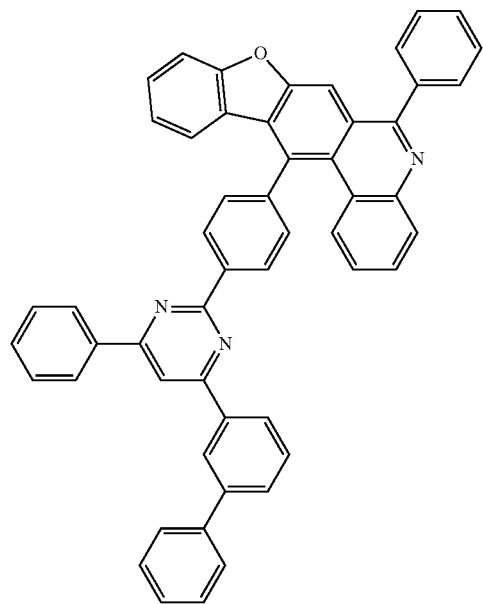
487
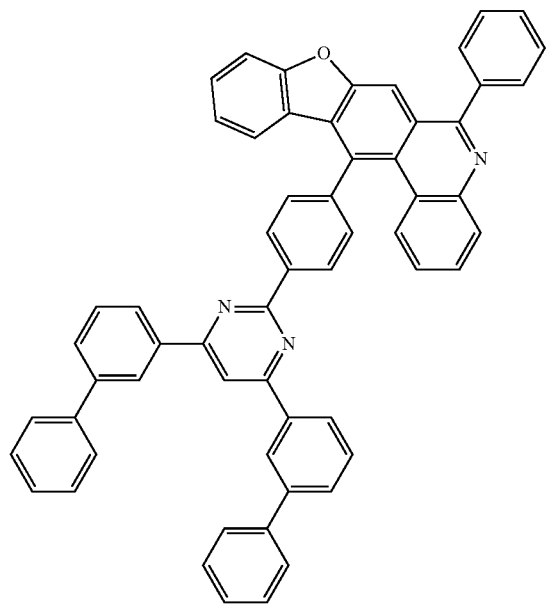

915 916
-continued
488 489
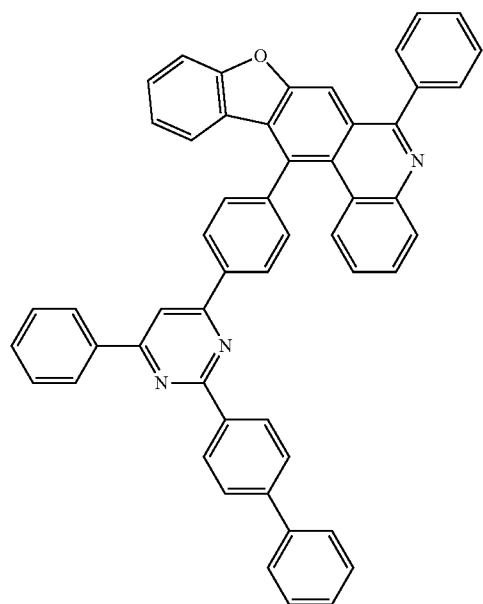
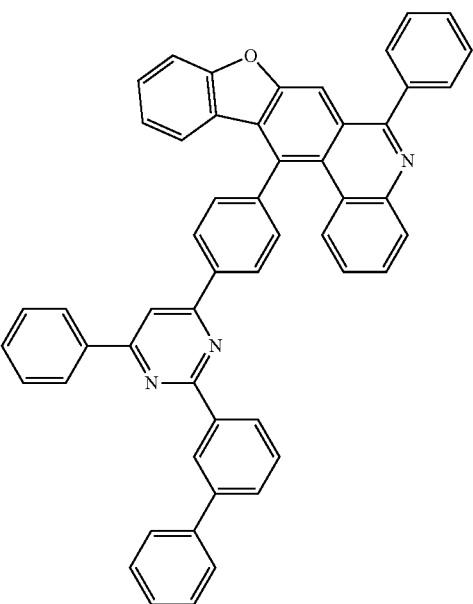
490 491
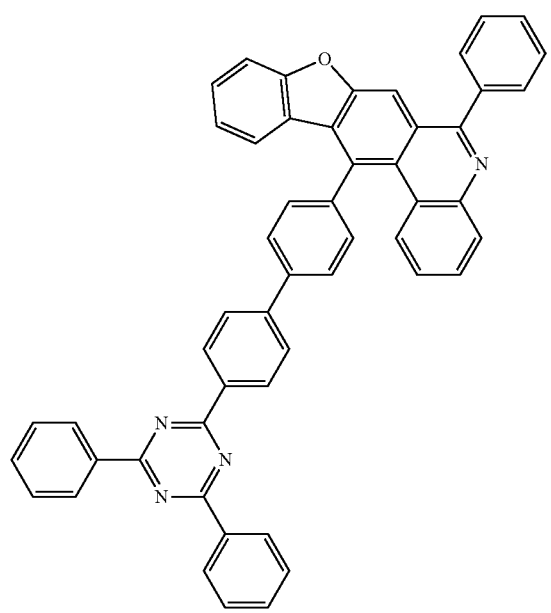
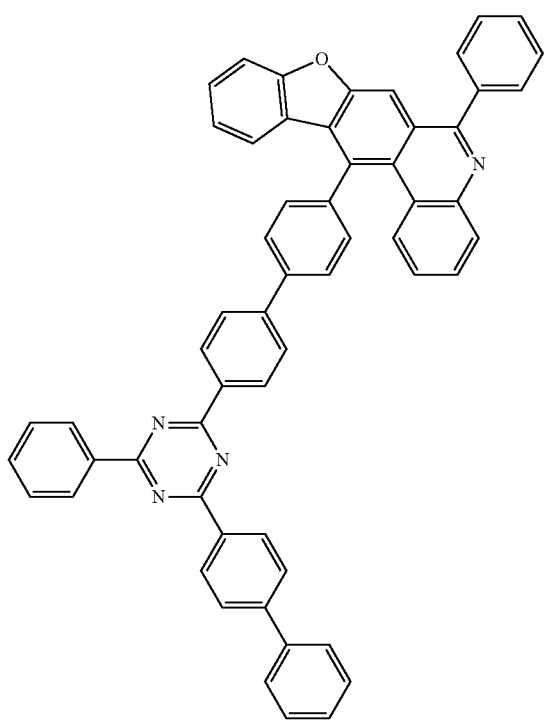

-continued
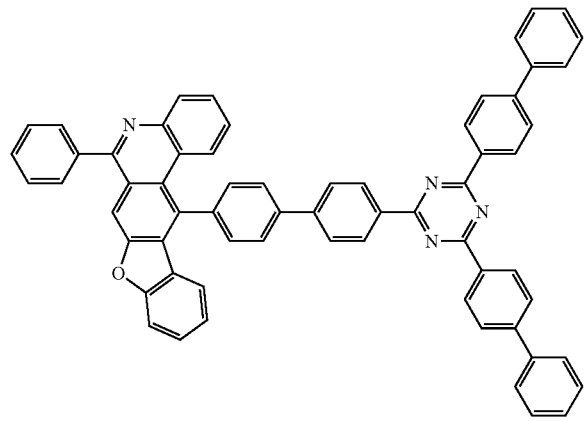
492
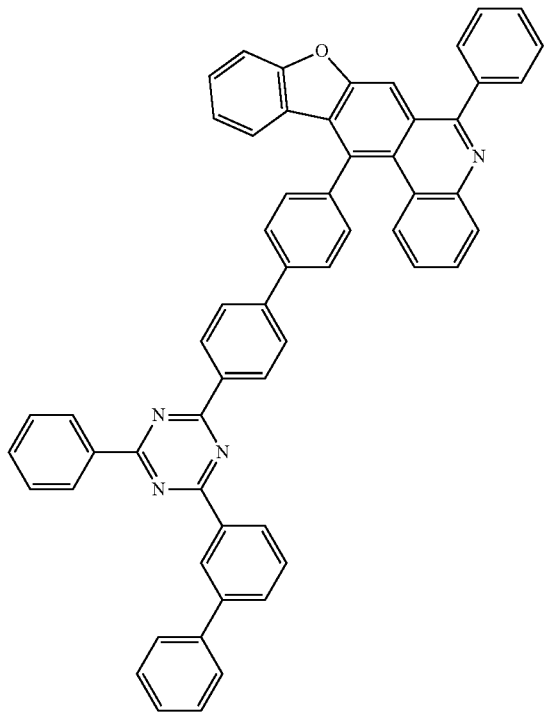
493
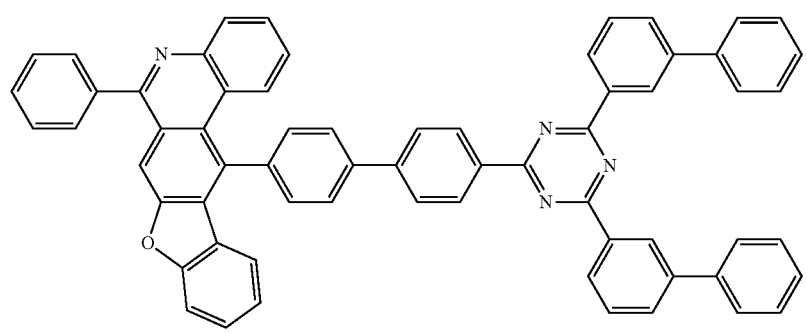
494

-continued
919
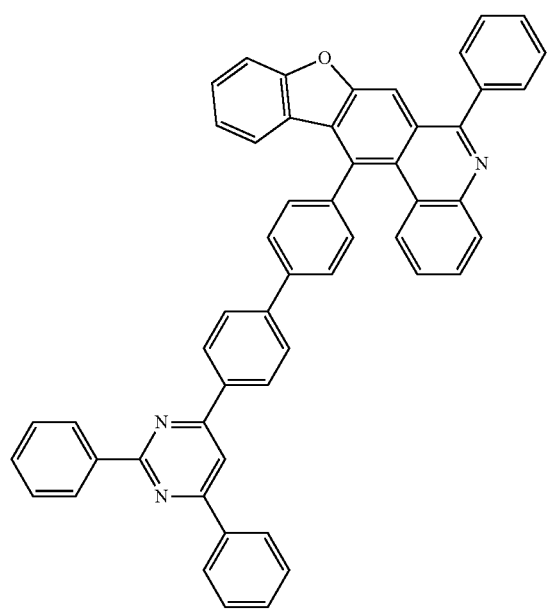
495
920
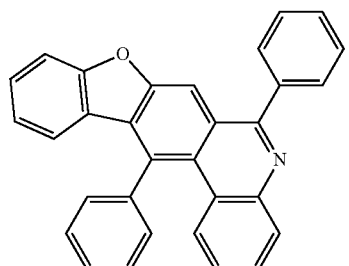
496
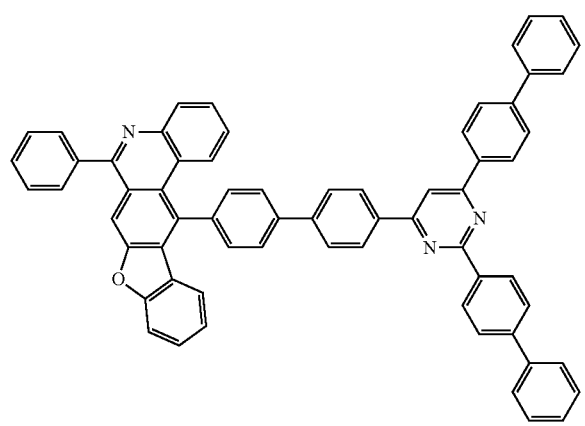
497
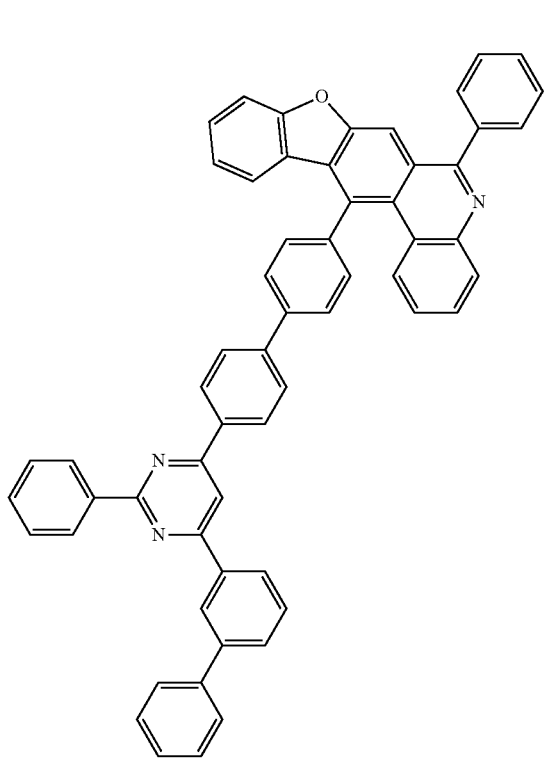
498

921 922
-continued
499
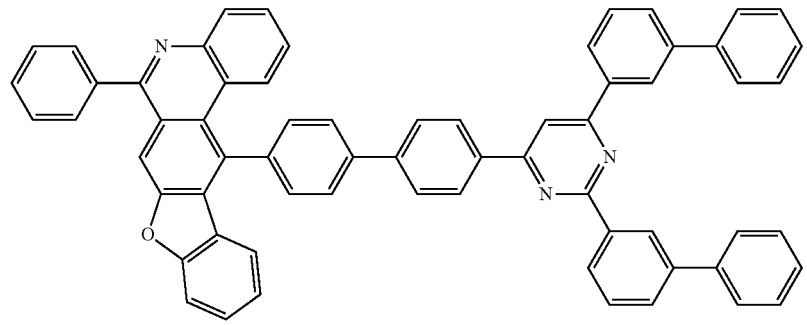
500
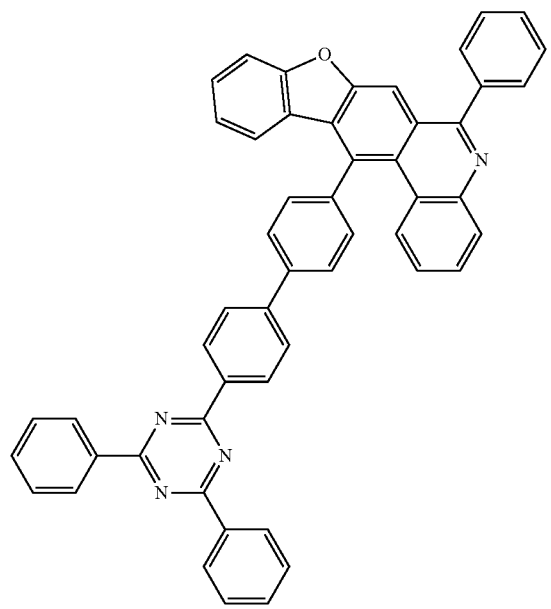
501
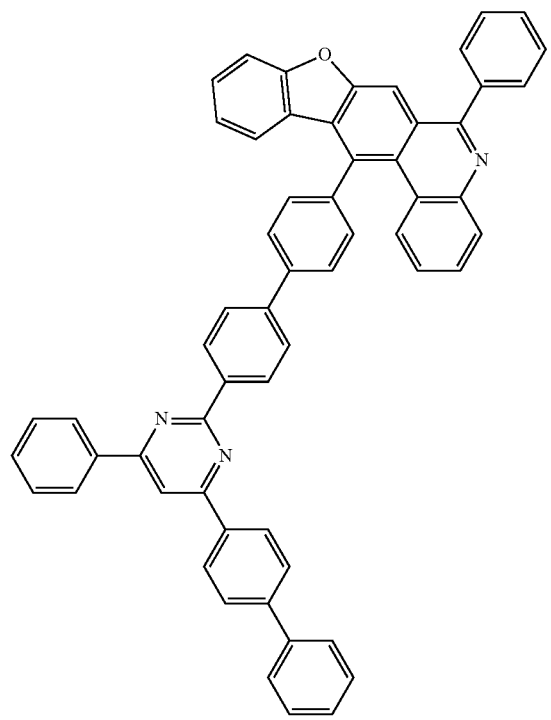

923
-continued
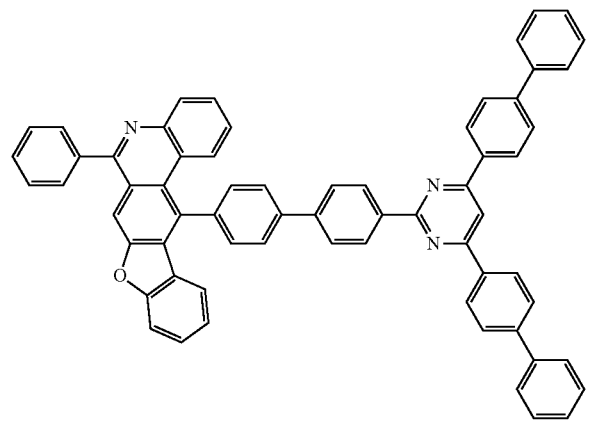
502
924
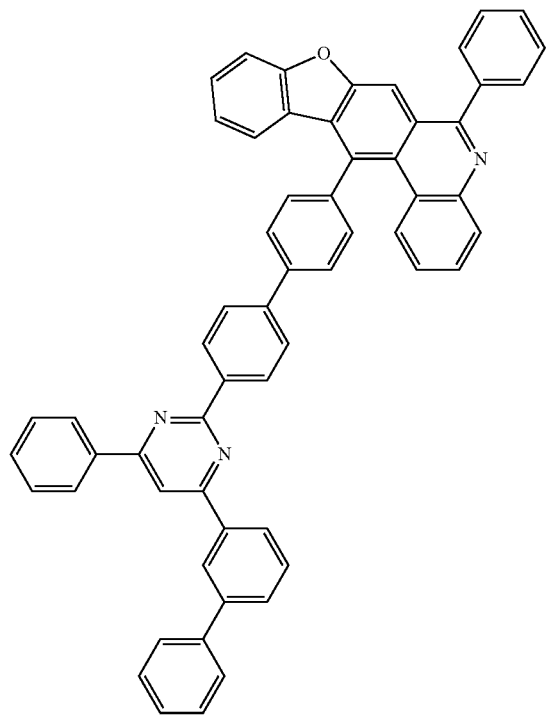
503
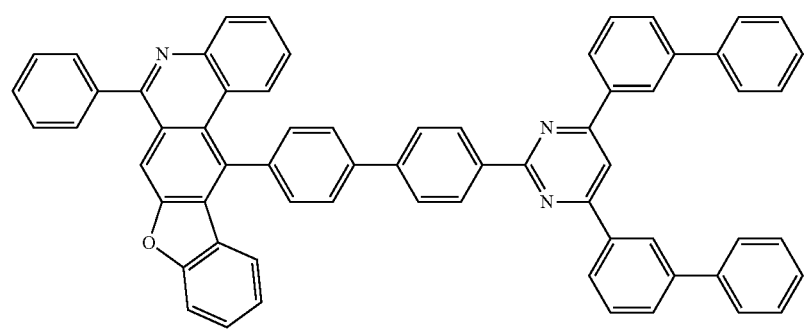
504

-continued
925
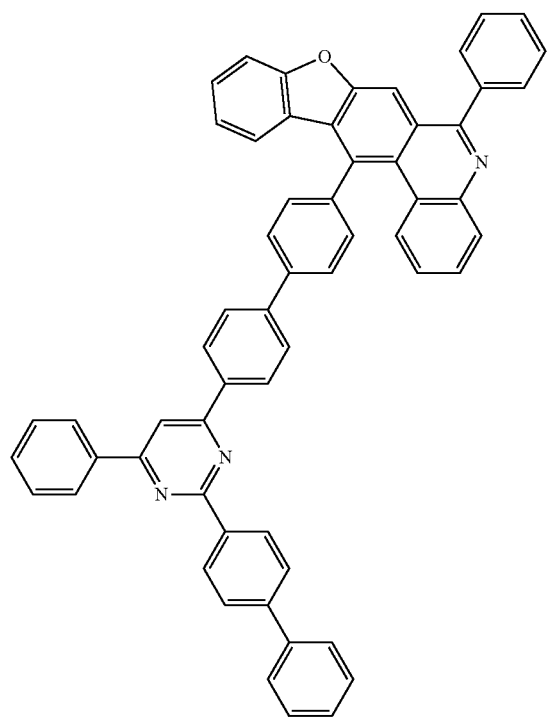
505
926
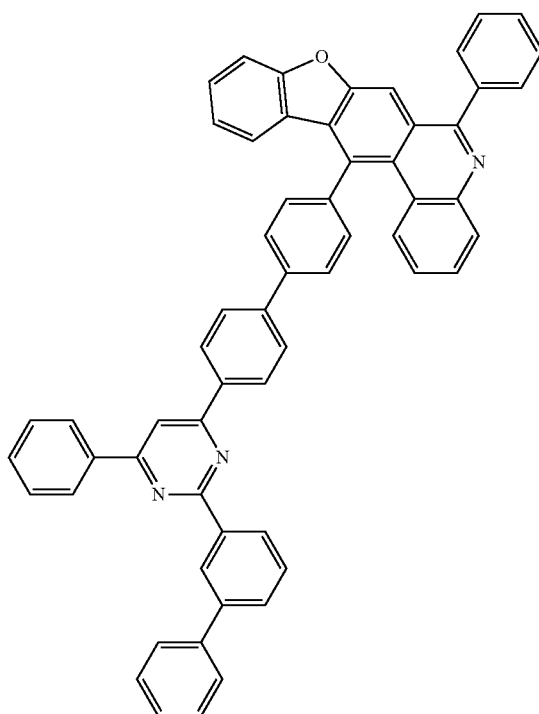
506
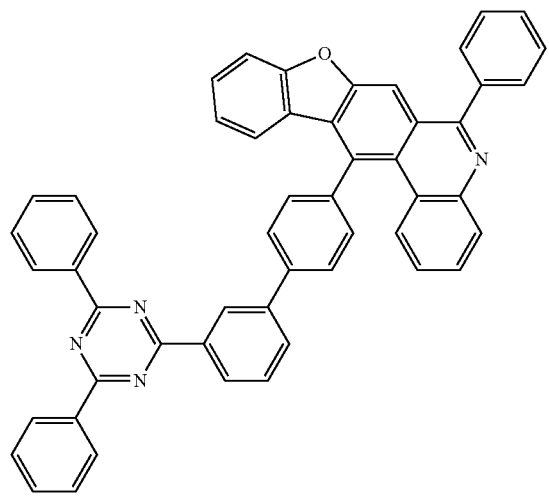
507
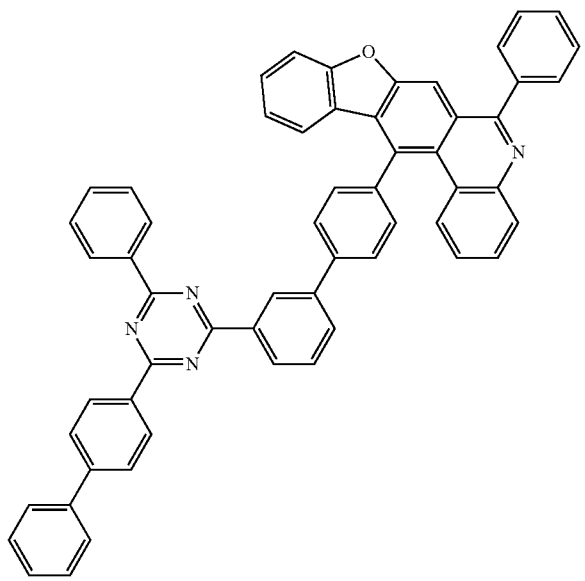
508

| 509 | 510 |
|---|---|
| 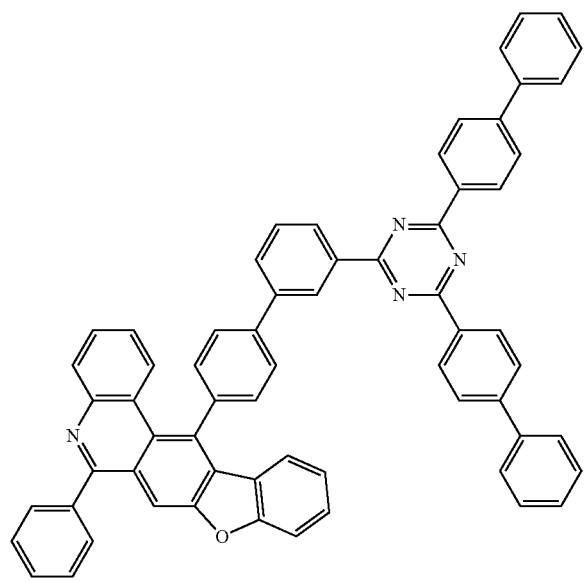 | 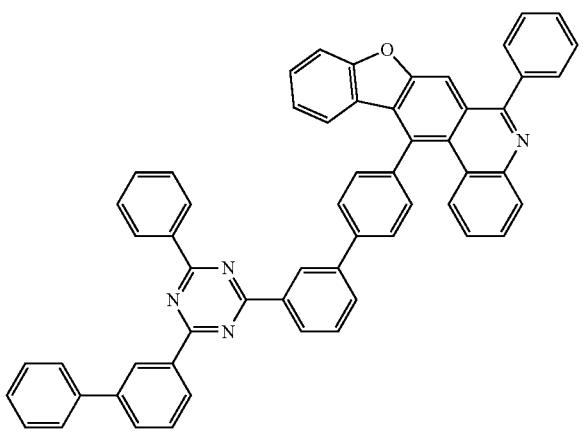 |
| 511 | 512 |
|---|---|
| 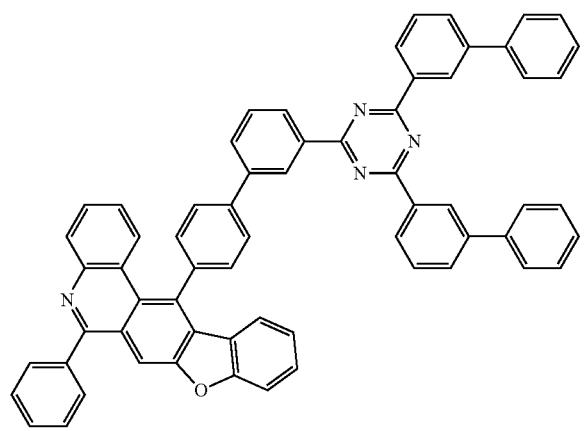 | 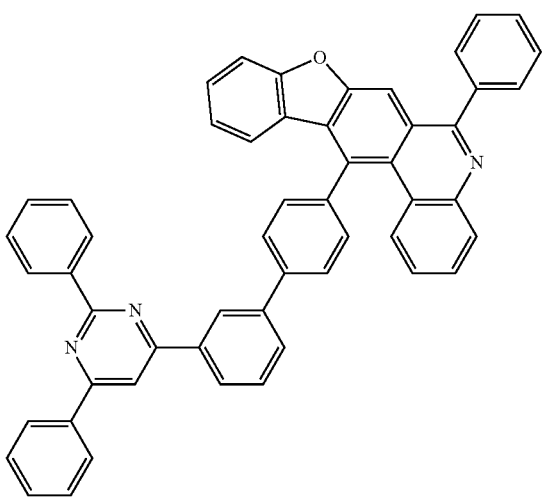 |

-continued
513
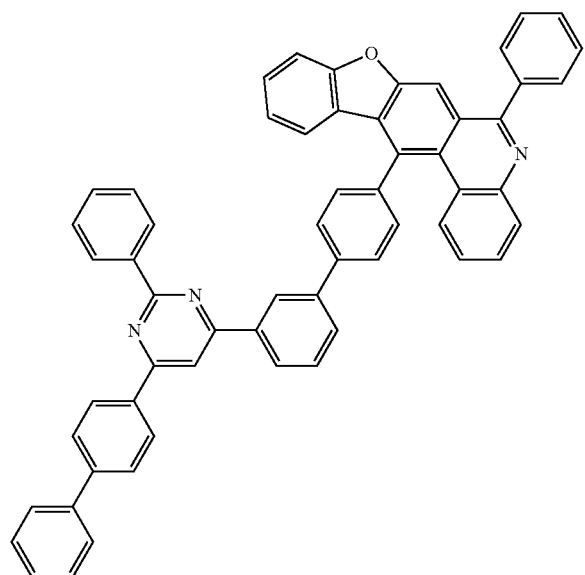
514
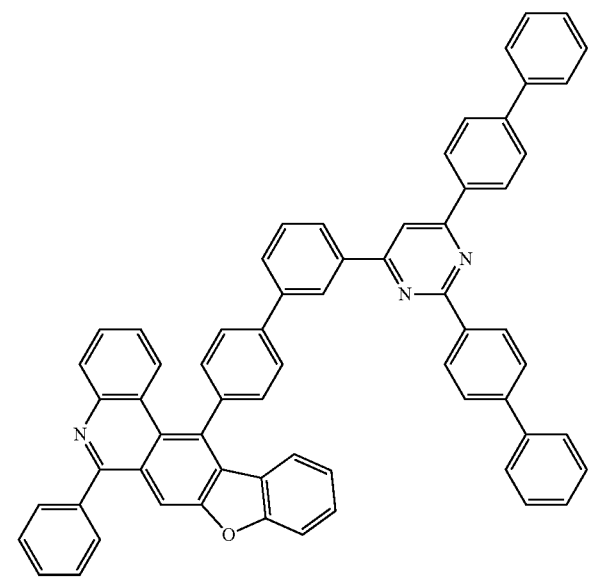
515
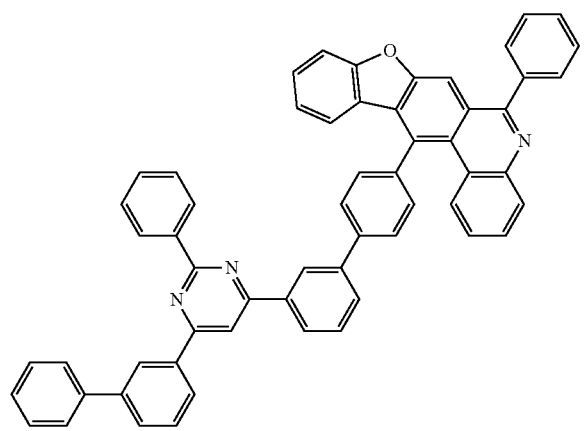
516
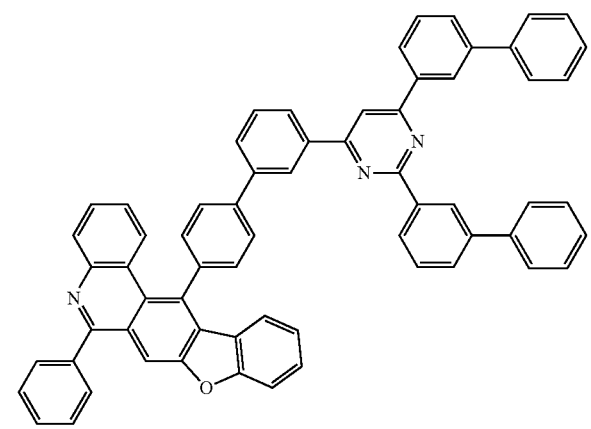
517
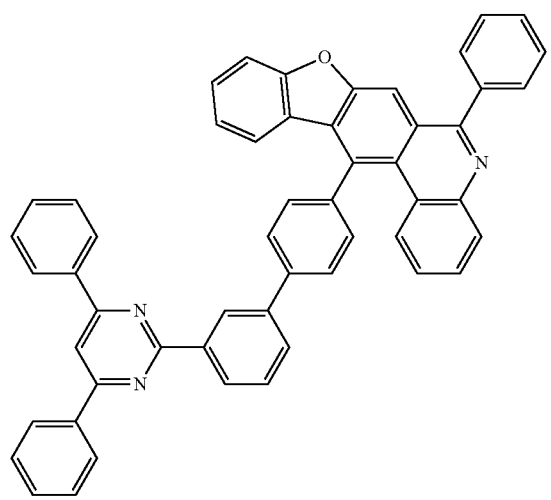
518
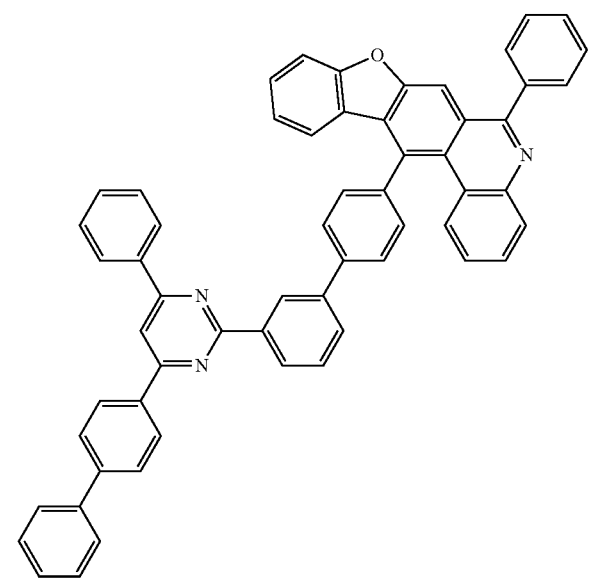

-continued
931
519
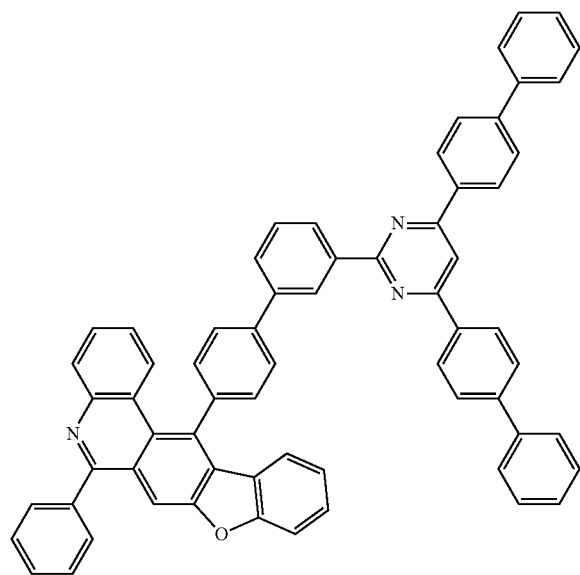
932
520
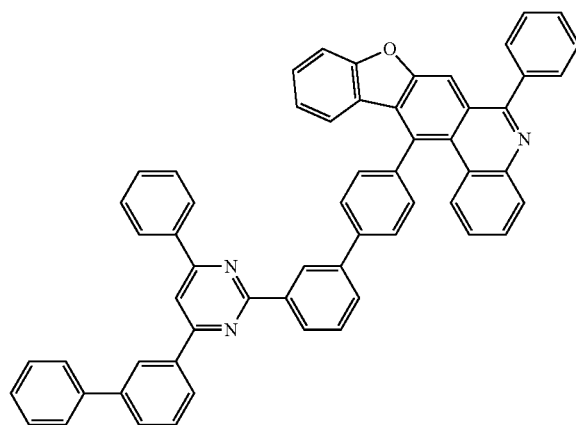
521
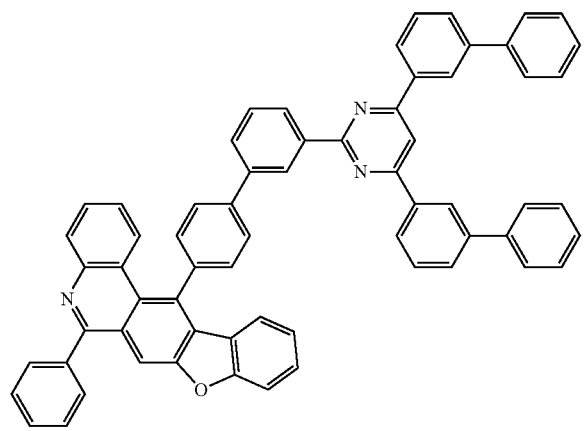
522
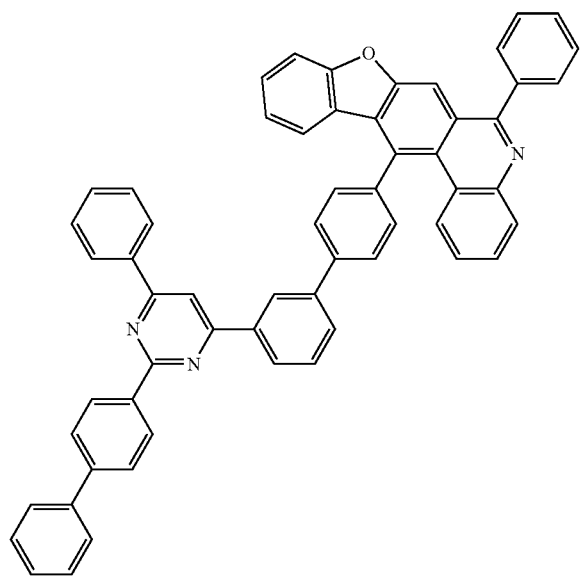

523
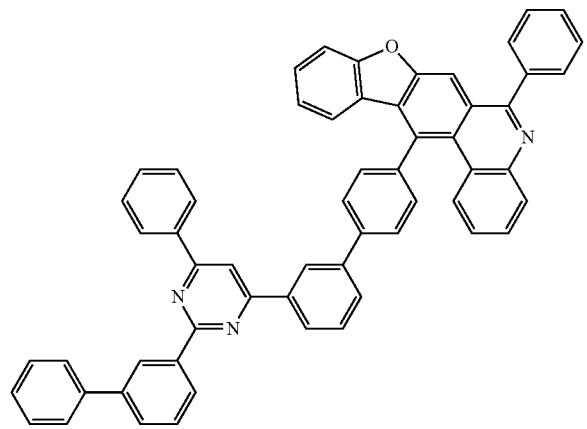
524
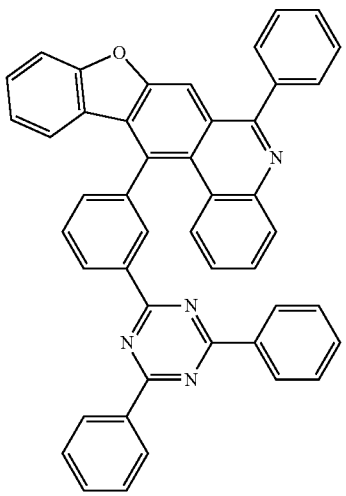
525
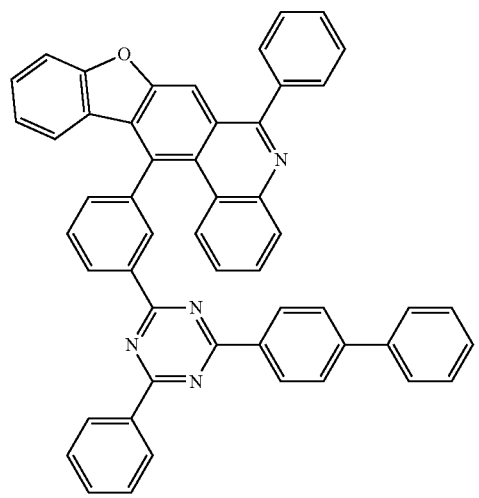
526
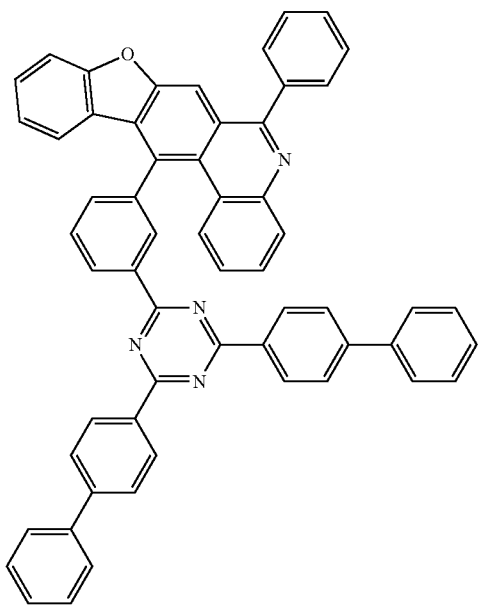

-continued
935 527 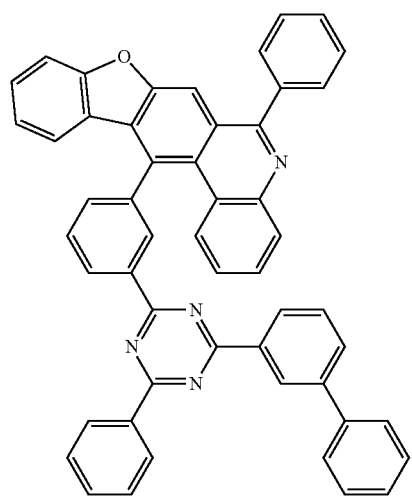
936 528 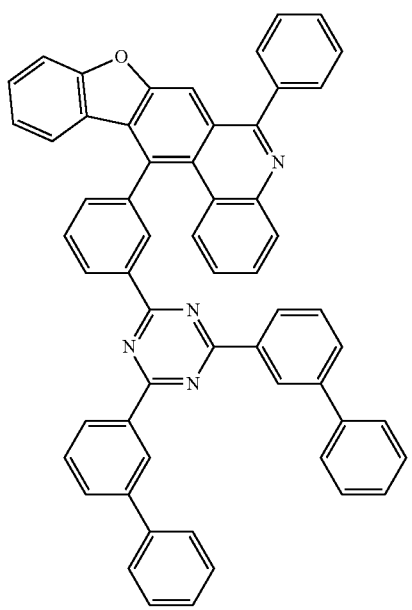
529 530 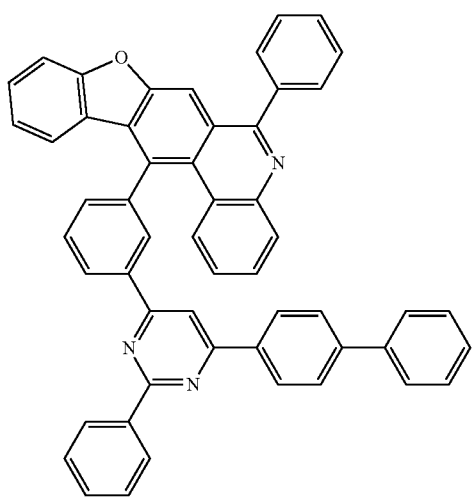

-continued
937
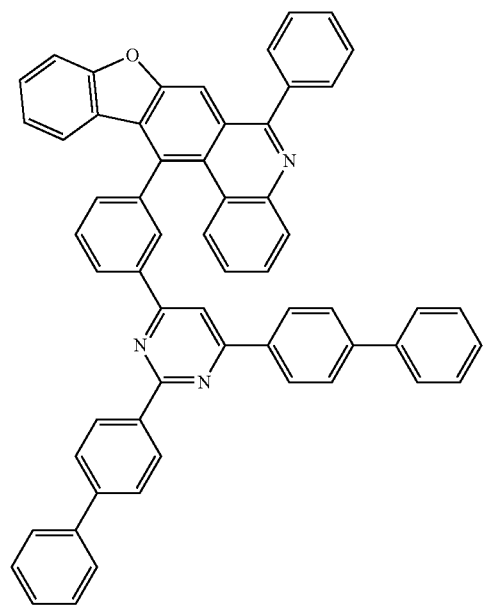
531
938
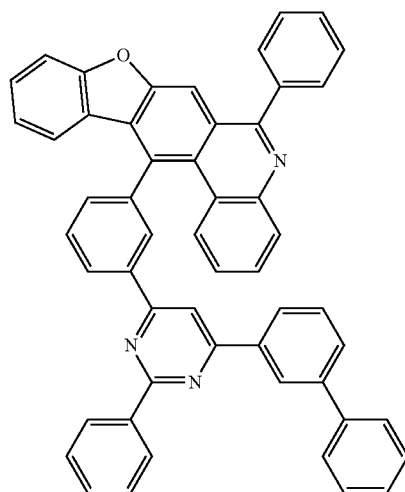
532
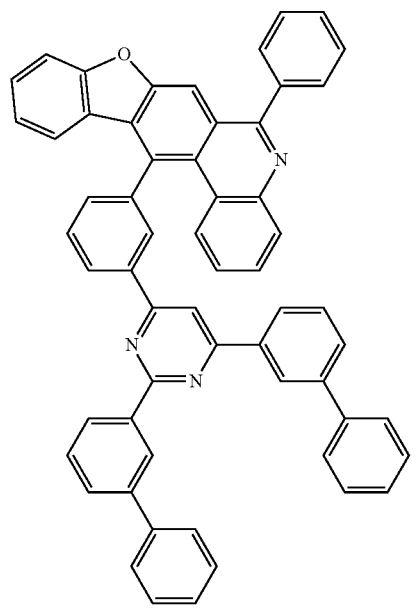
533
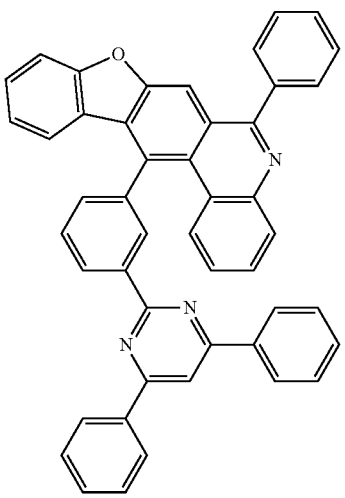
534

-continued
535
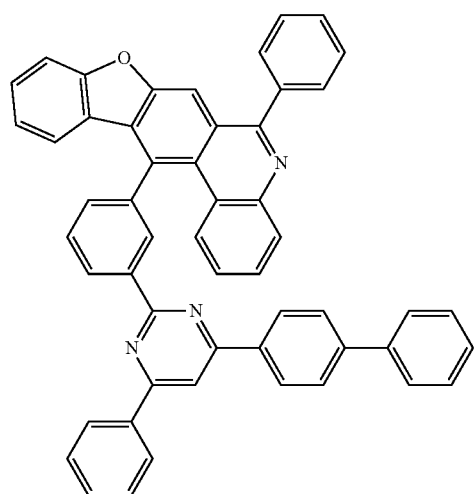
536
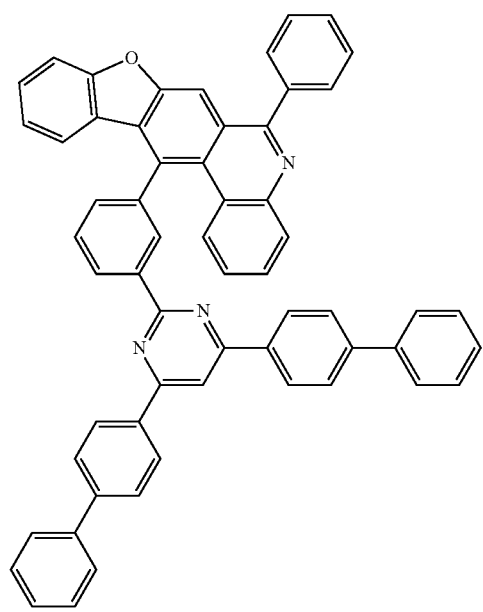
537
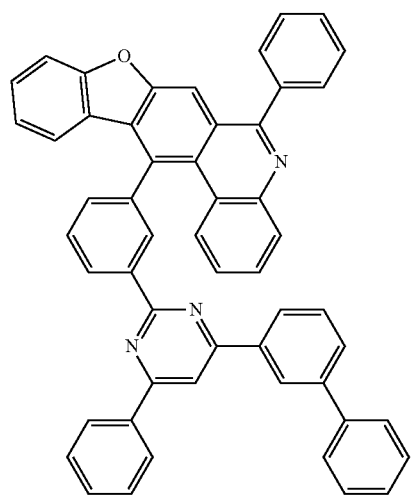
538
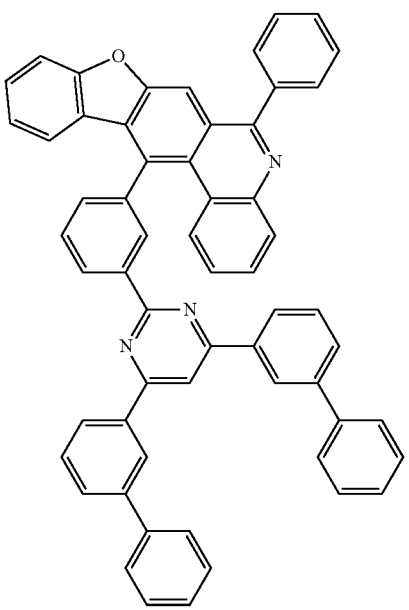

941 942
-continued
539 540
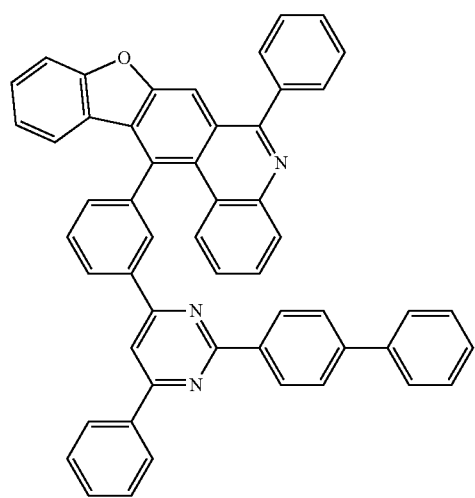 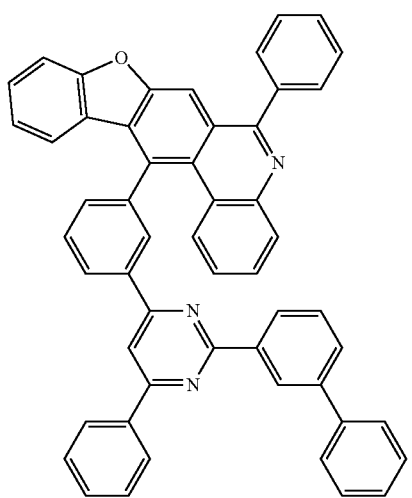
541 542
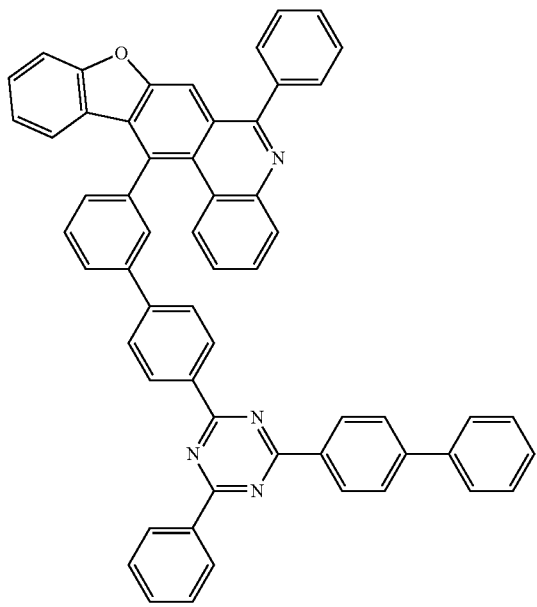

543
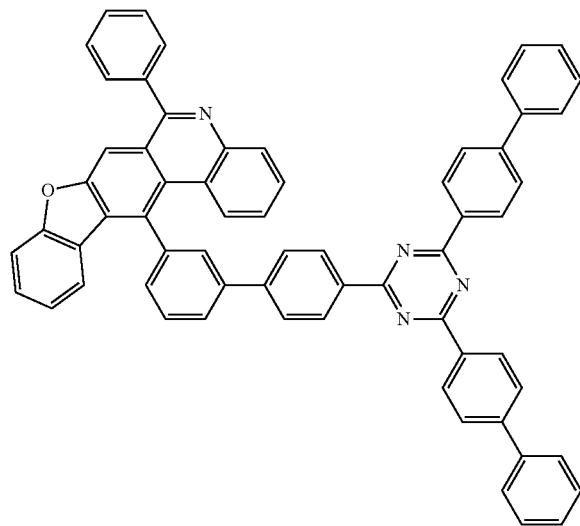
544
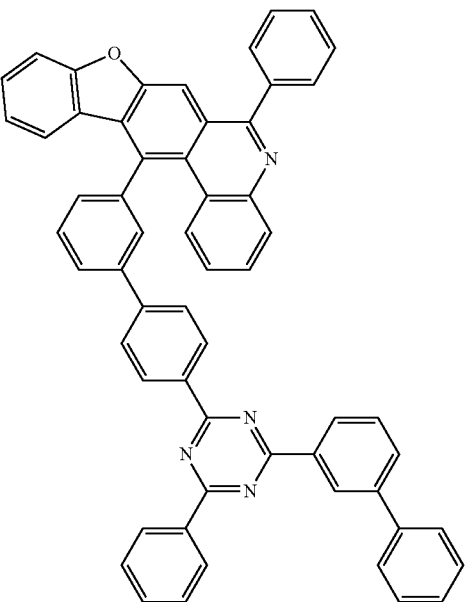
545
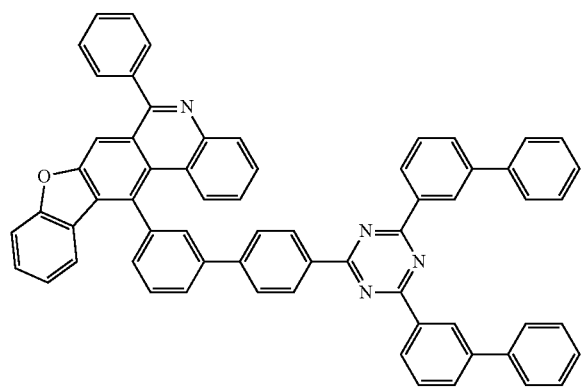
546
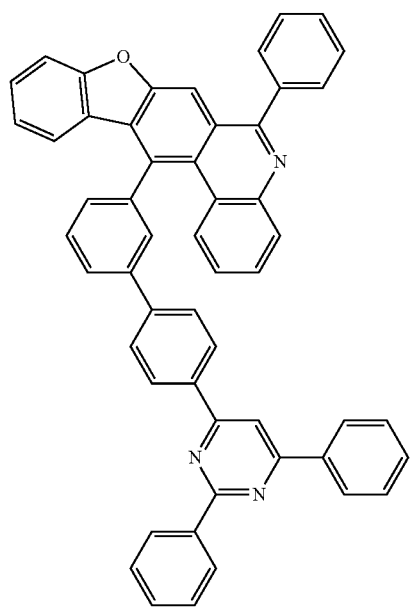

-continued
547
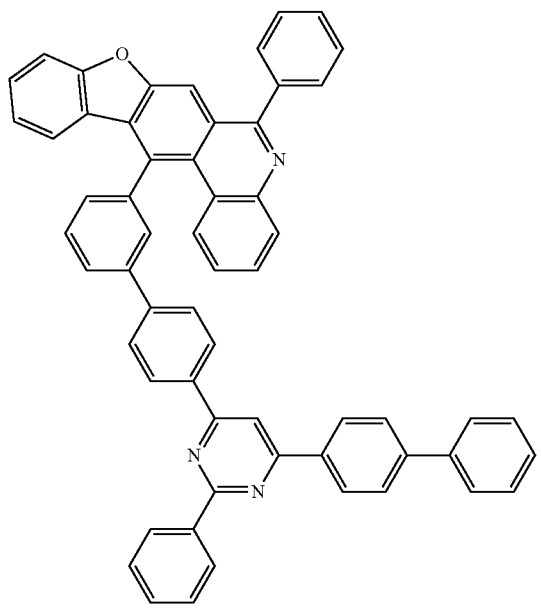
548
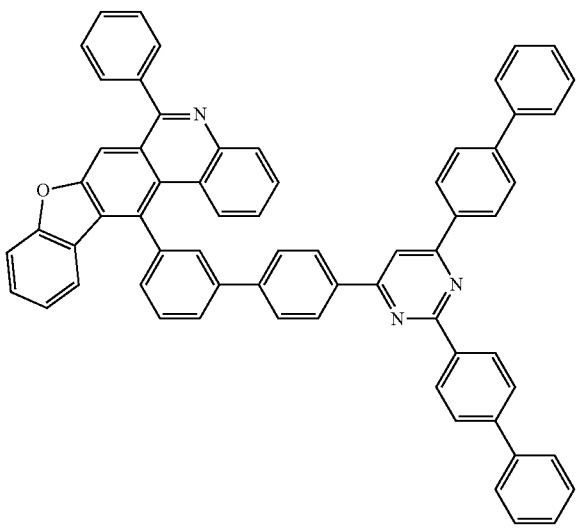
549
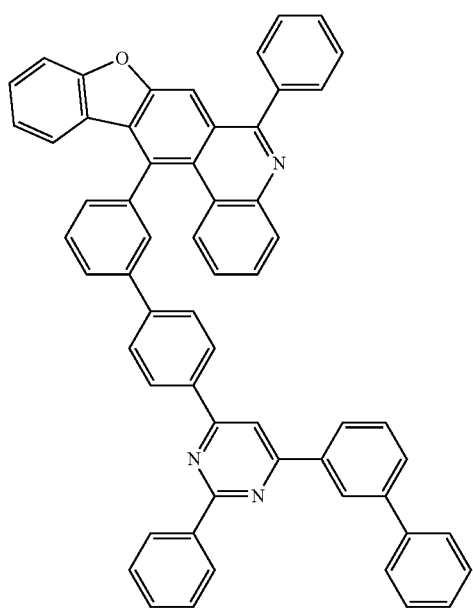
550
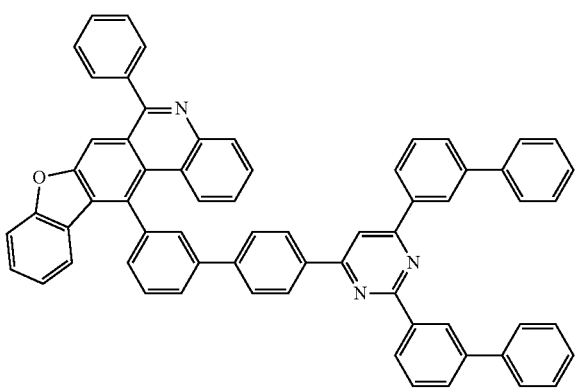

-continued
947 551
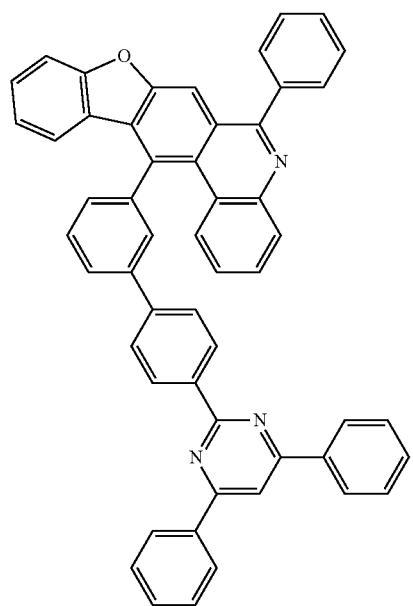
948 552
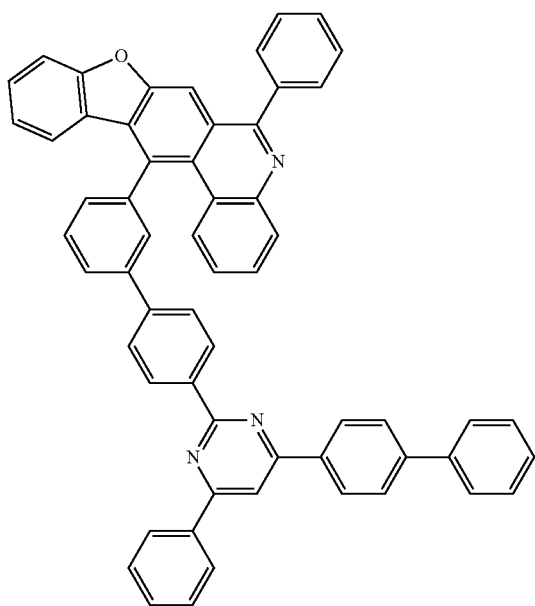
553
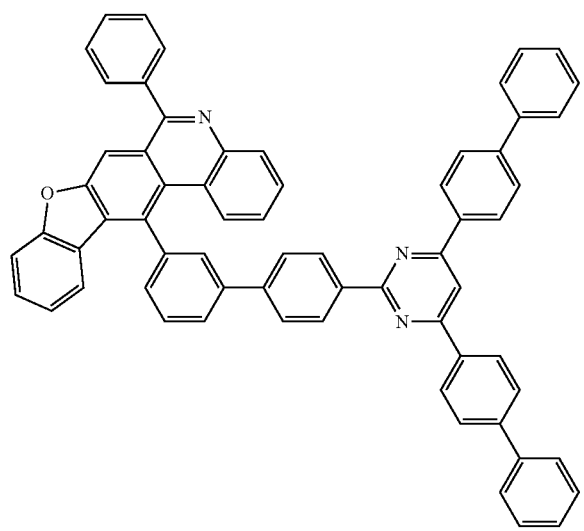
554
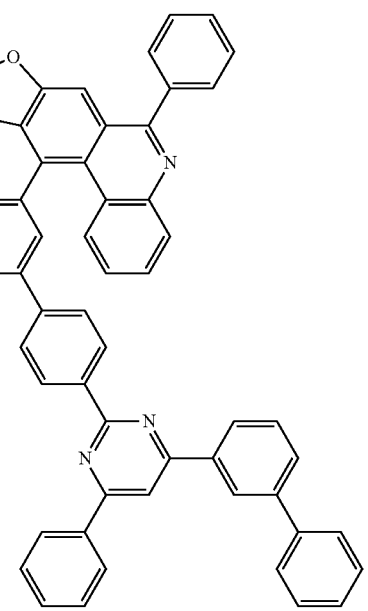

555
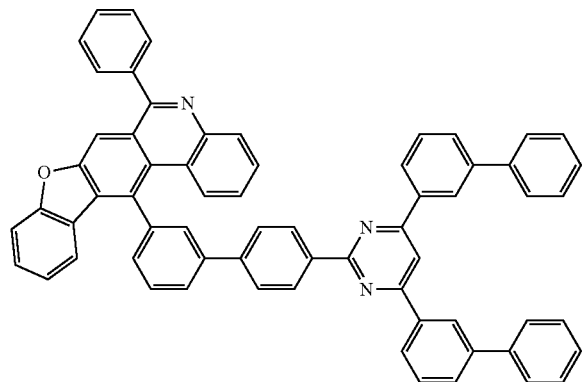
556
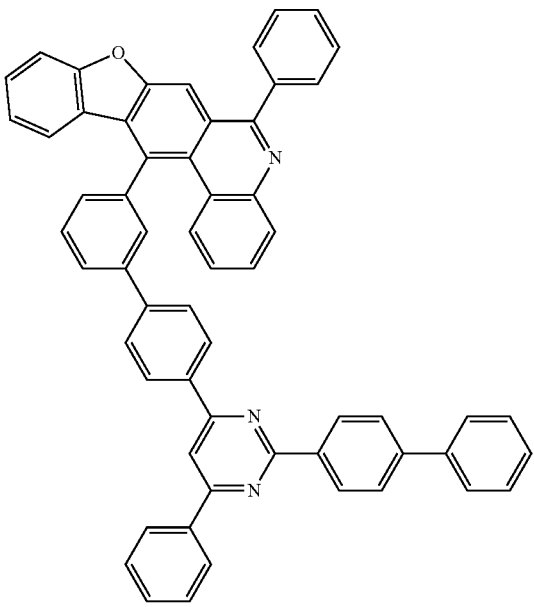
557
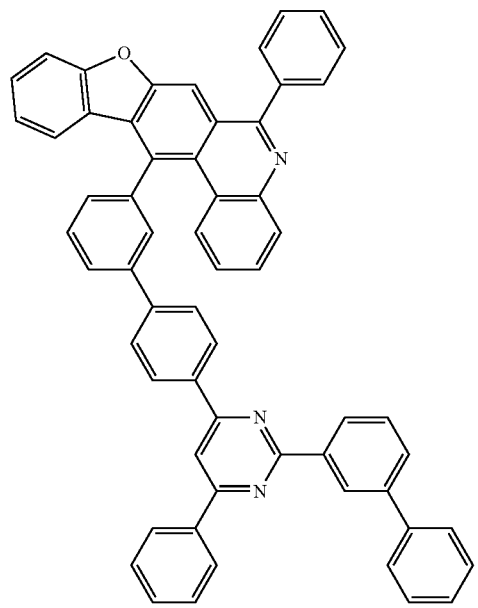
558
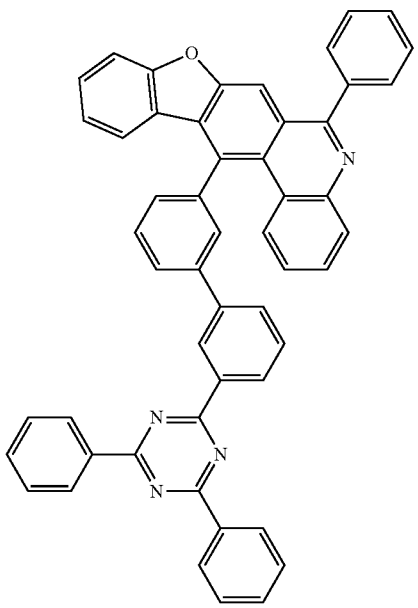

-continued
951
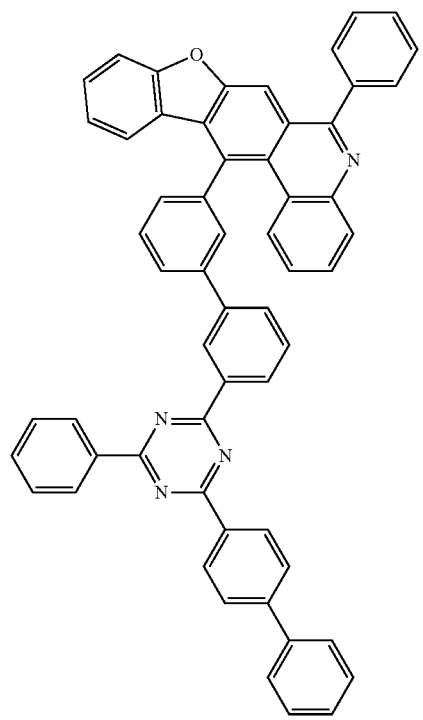
952
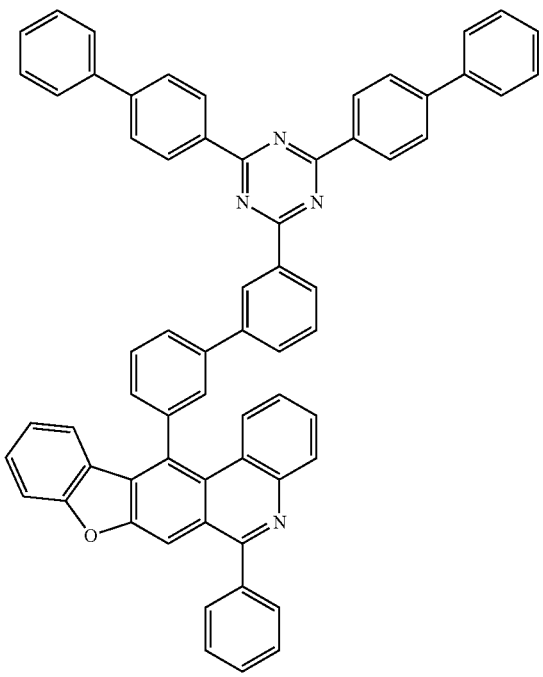
561
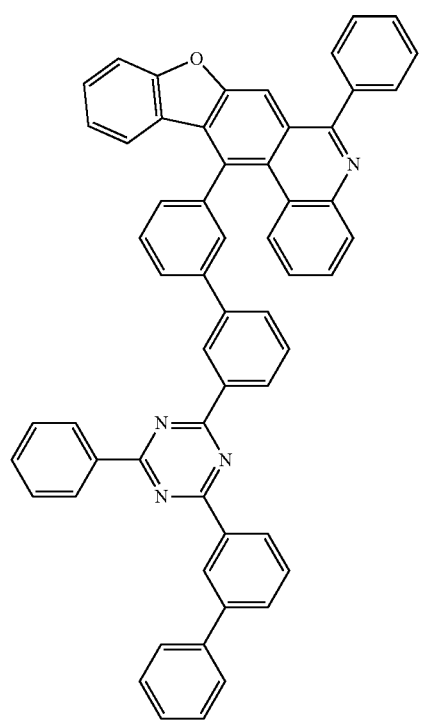
562

953
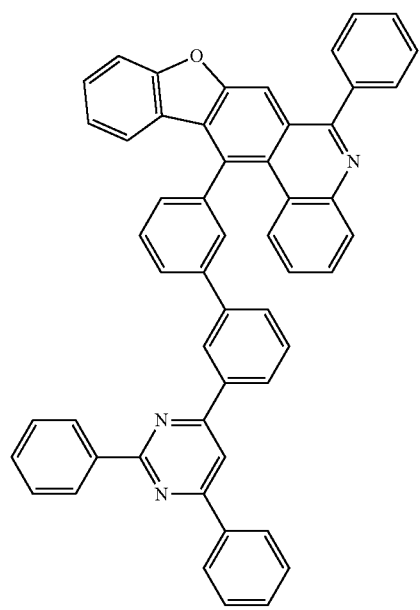
954
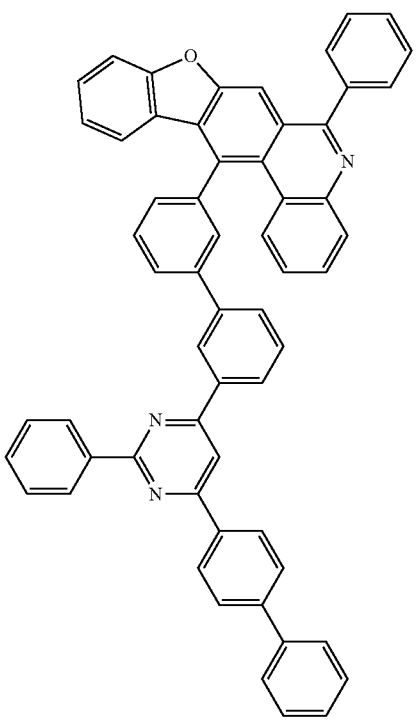
-continued
565
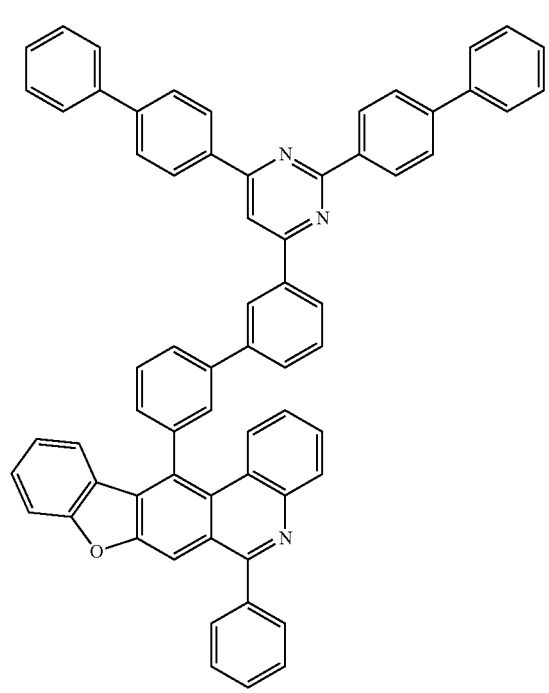
566
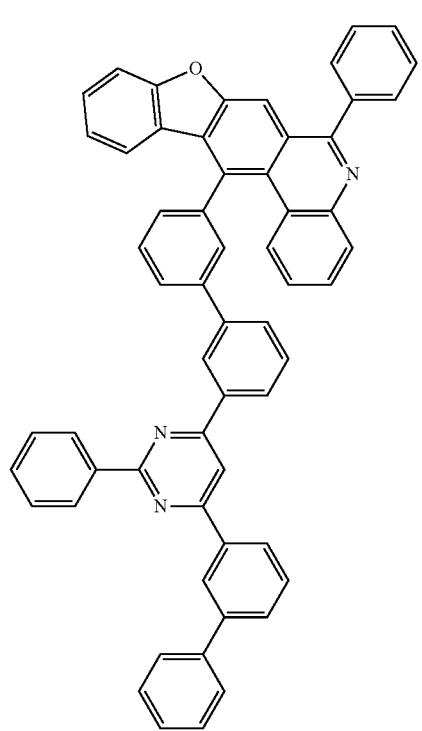

-continued
567
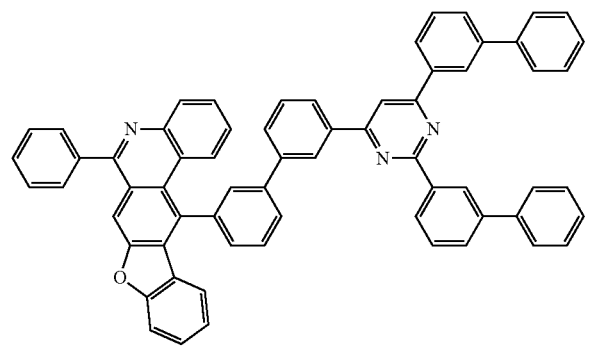
568
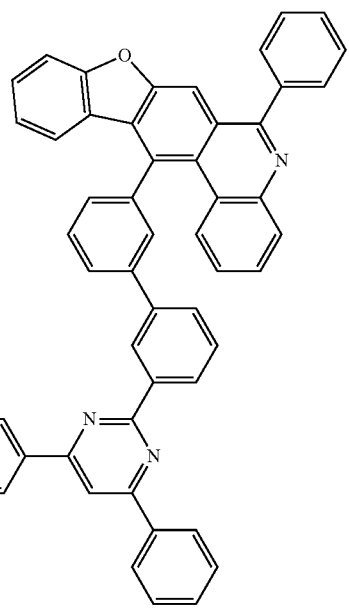
569
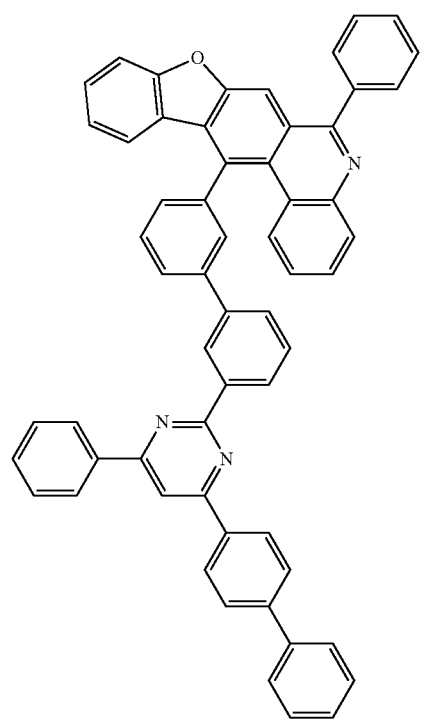
570
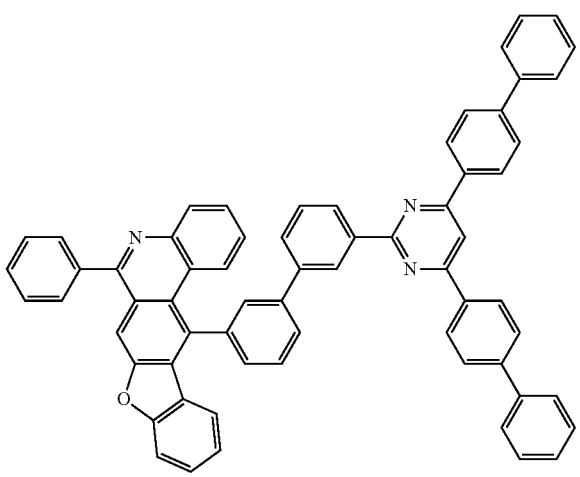

-continued
571
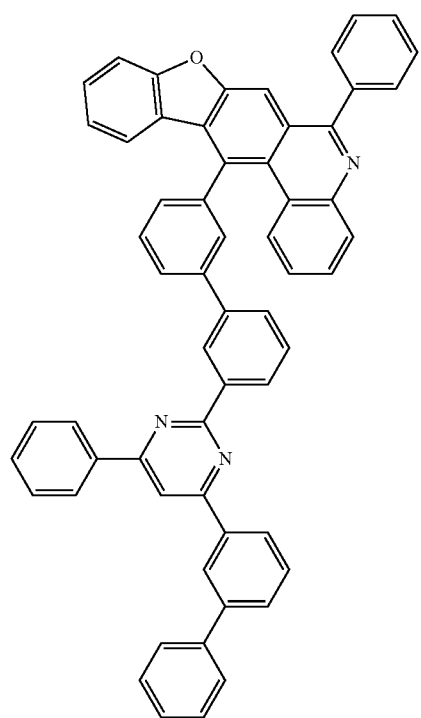
572
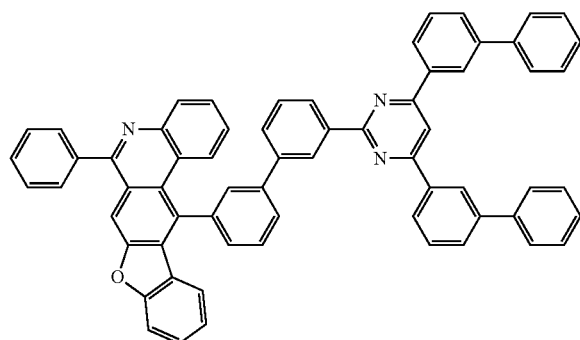
573
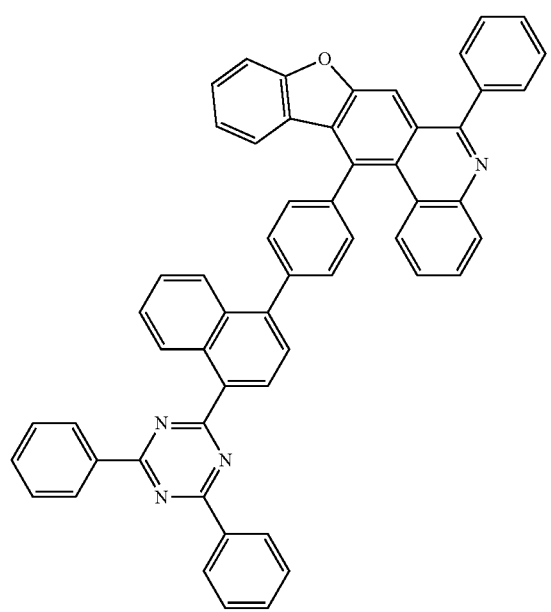
574
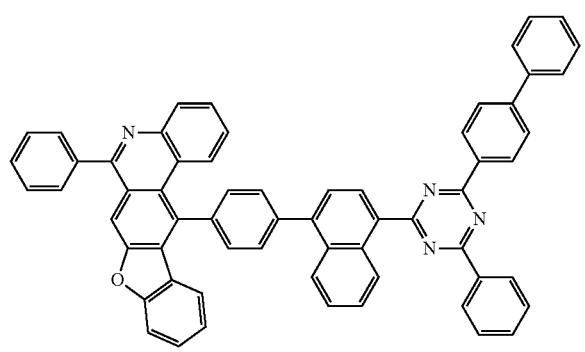

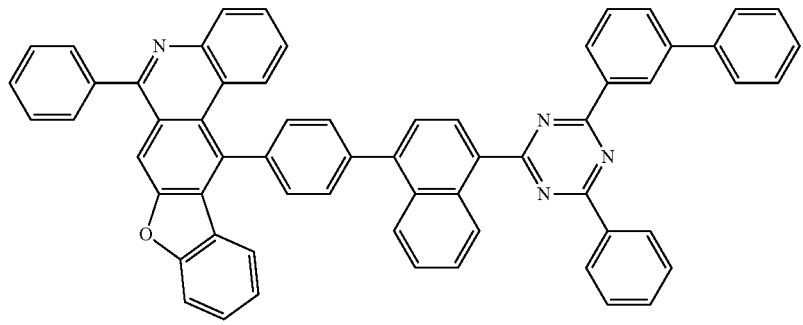
575
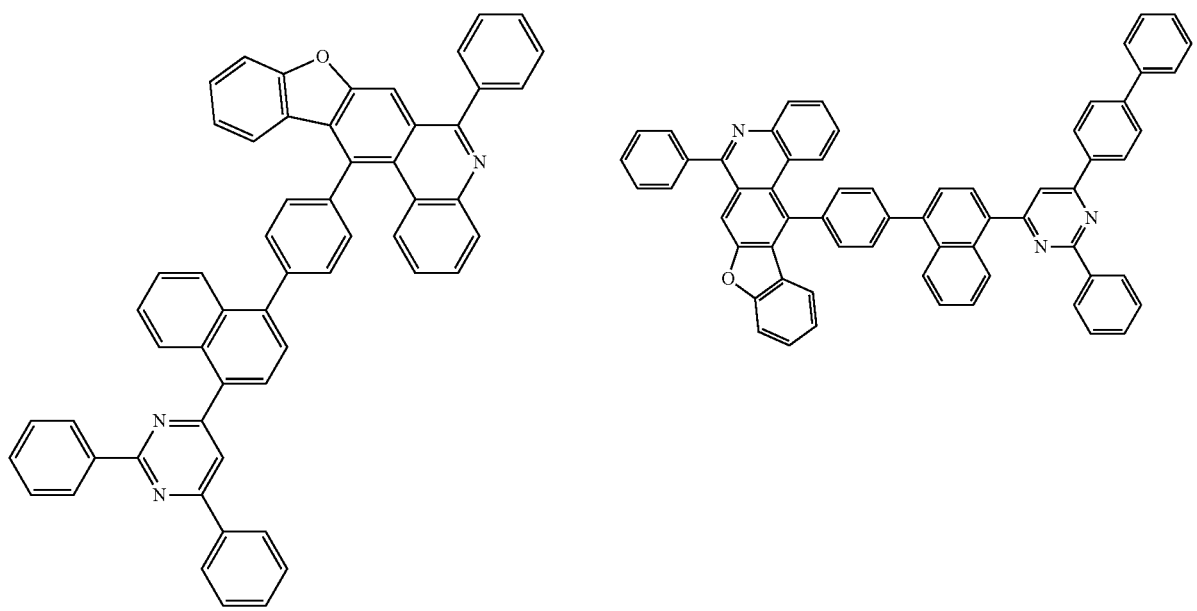
576
577
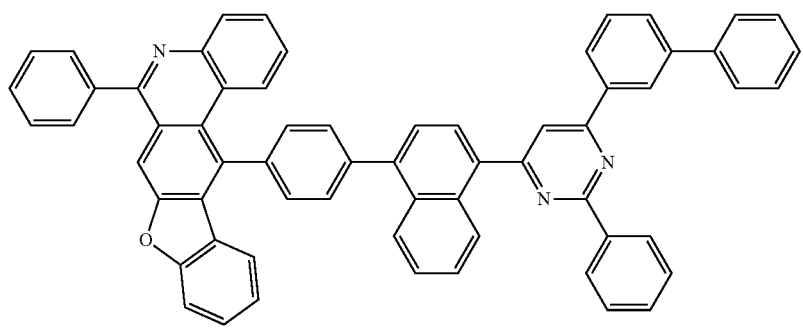
578

-continued
579
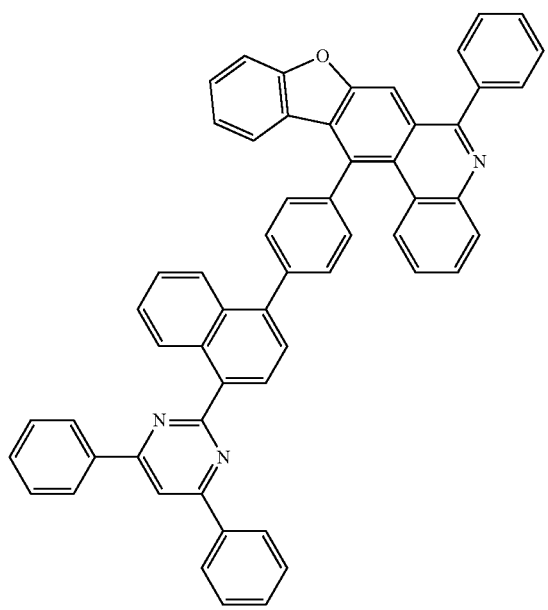
580
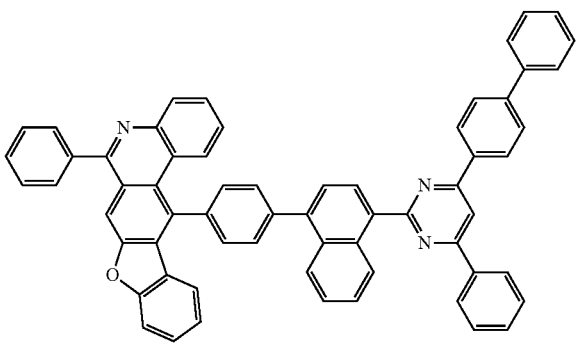
581
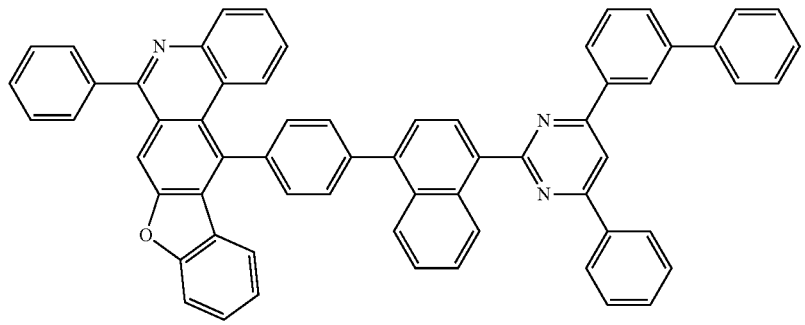
582
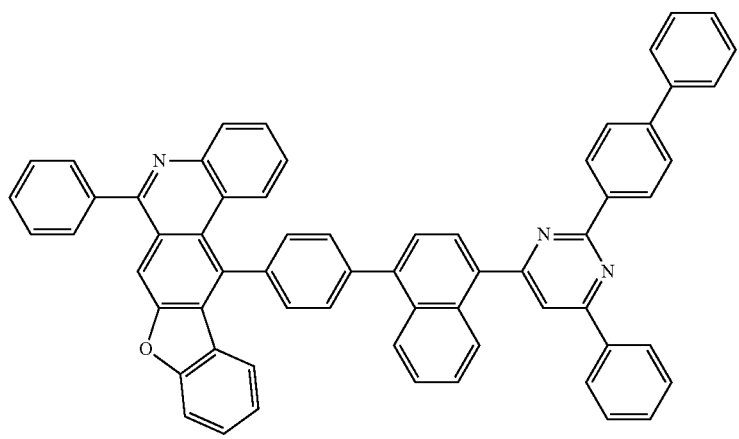

963 964
-continued
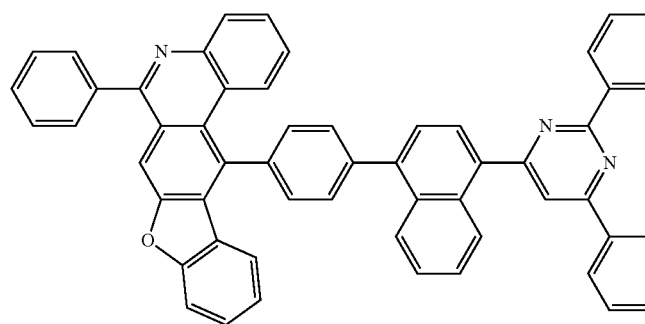
583
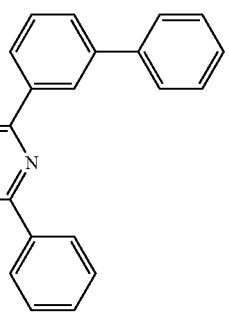
584
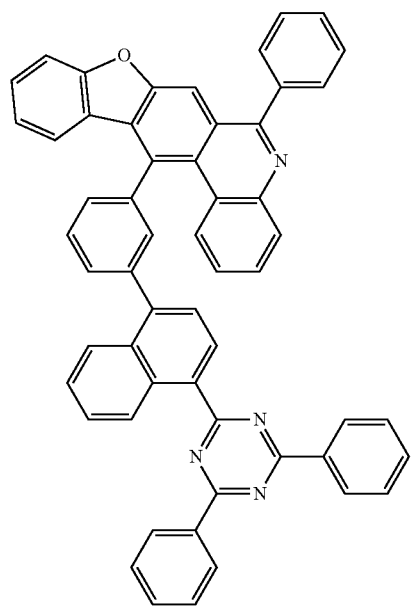
585
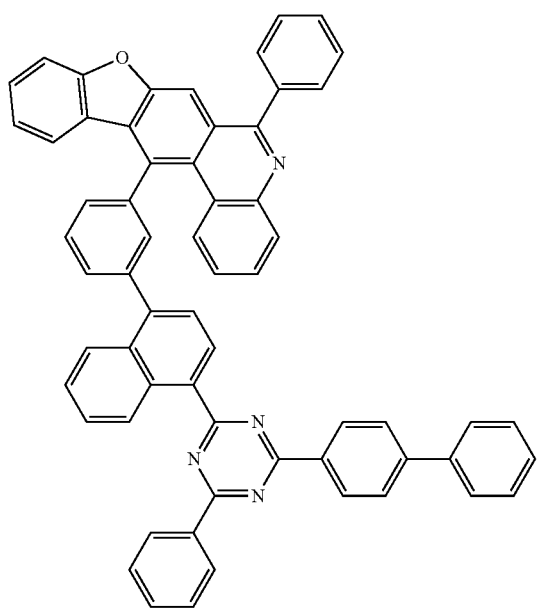
-continued
586
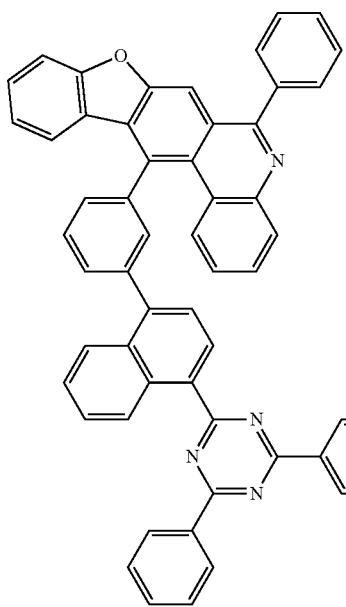

965
-continued
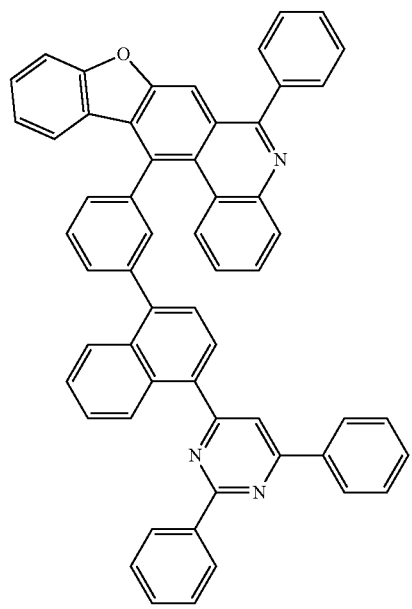
587
966
-continued
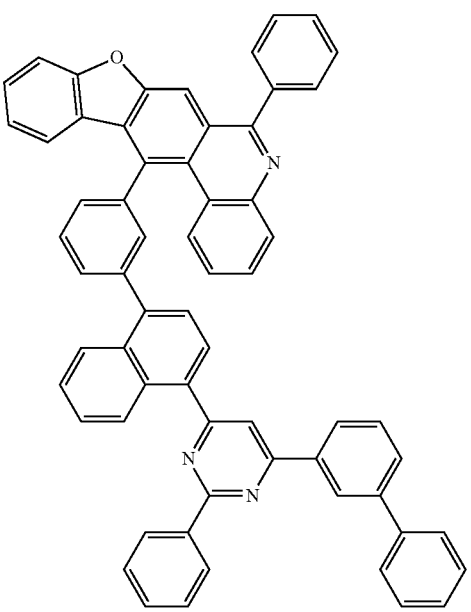
589
588
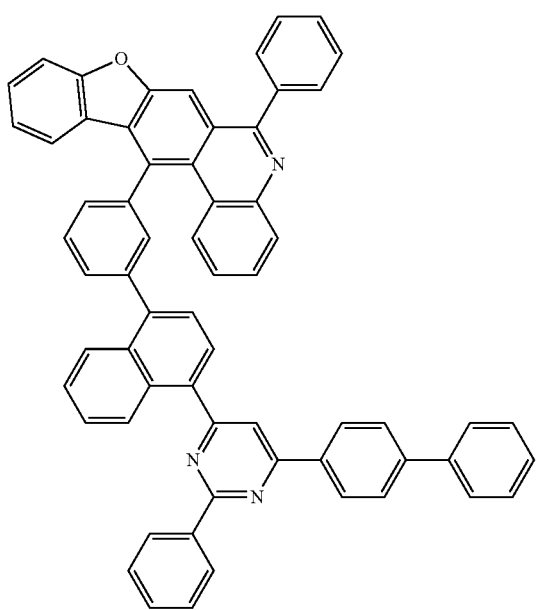
590
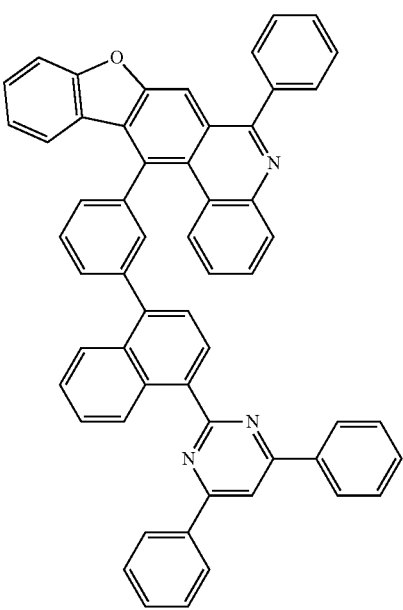

967
-continued
968
-continued
591
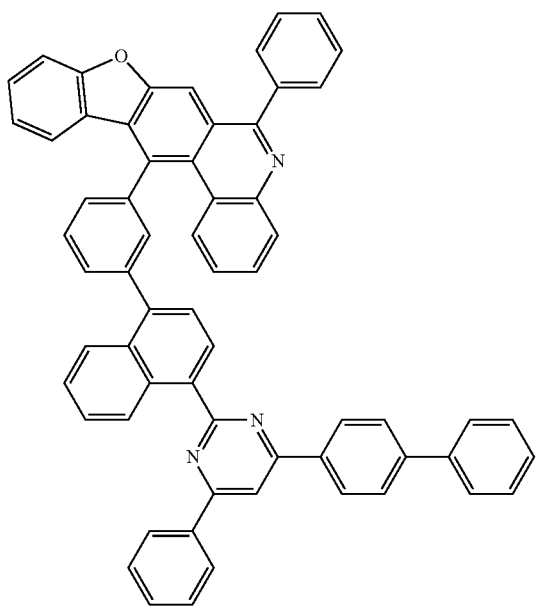
593
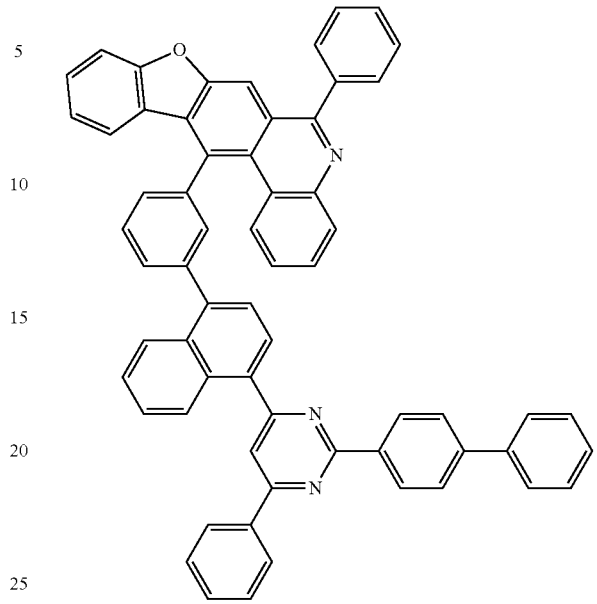
594
592
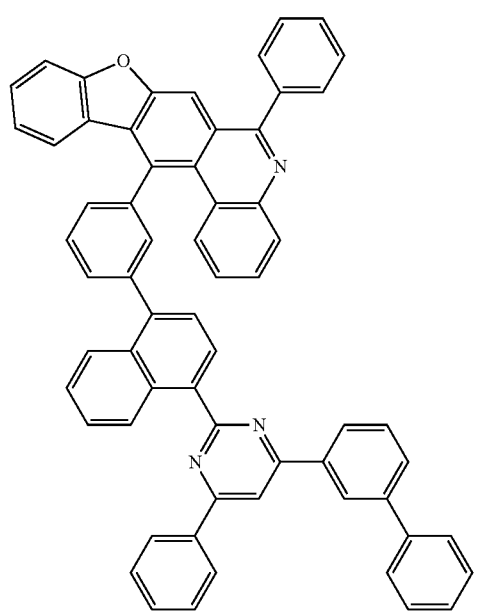
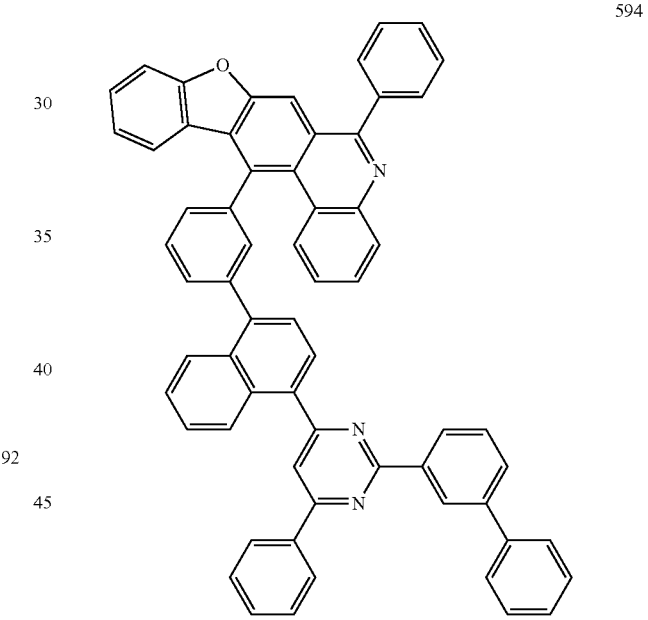
595

969
-continued
596
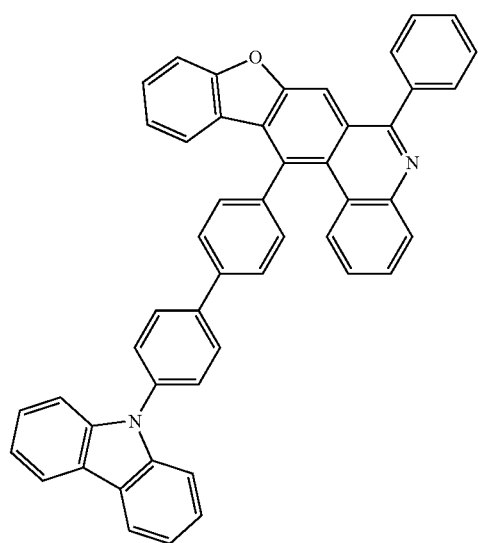
597
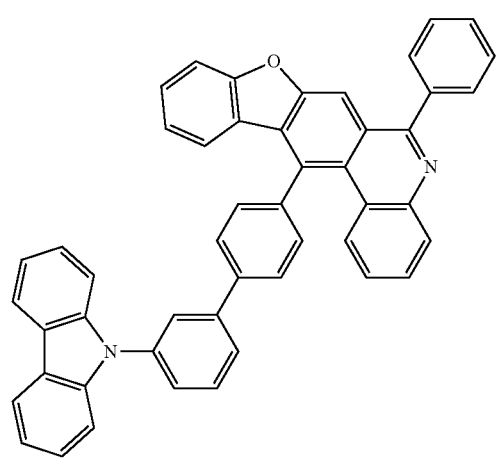
598
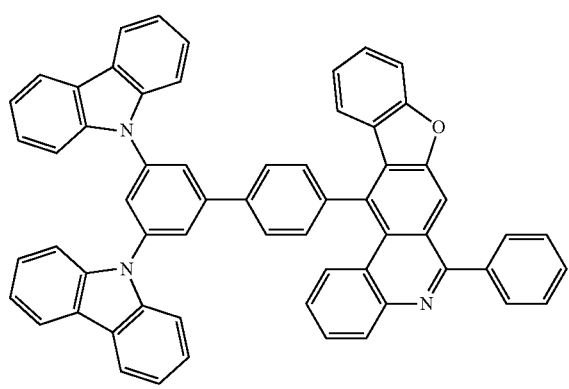
970
-continued
599
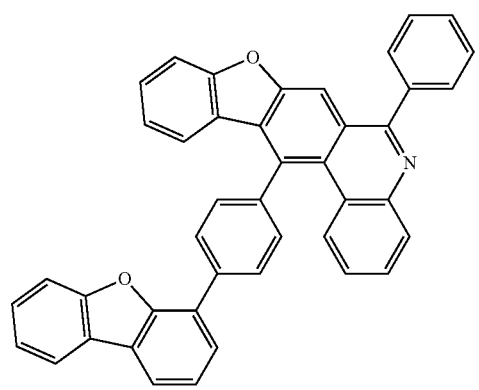
600
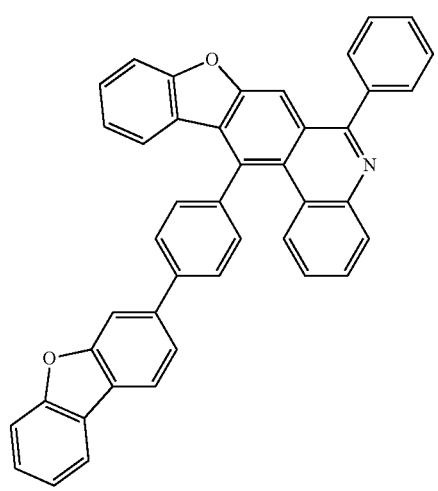
601
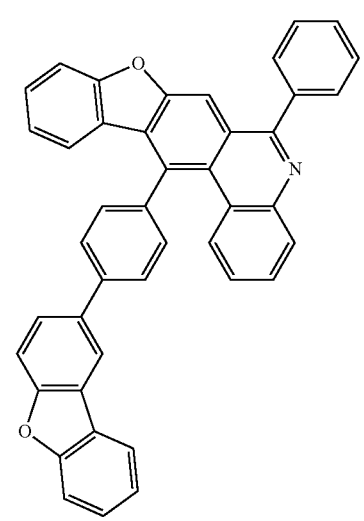

971
-continued
972
-continued
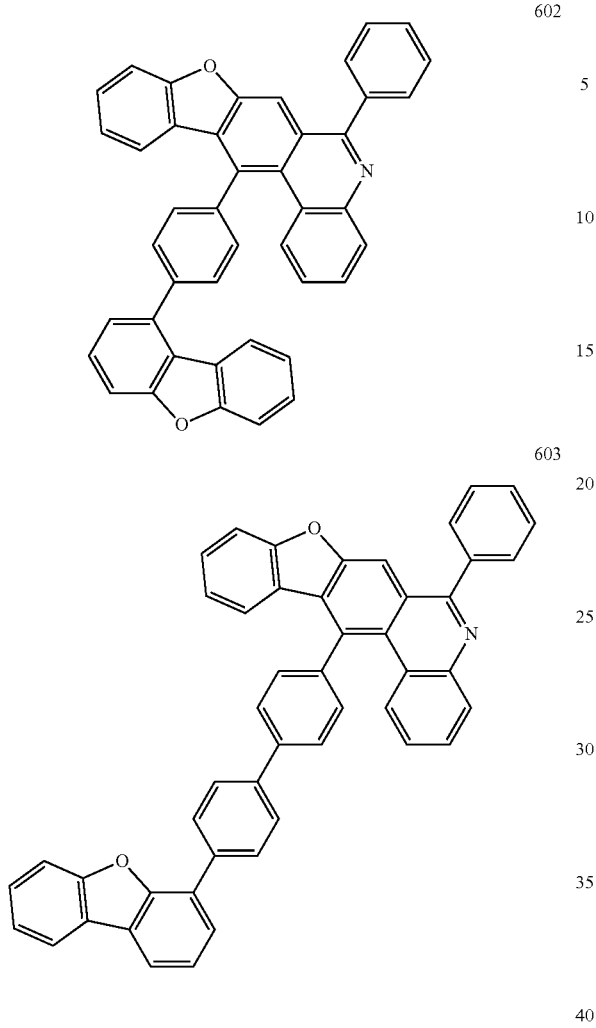
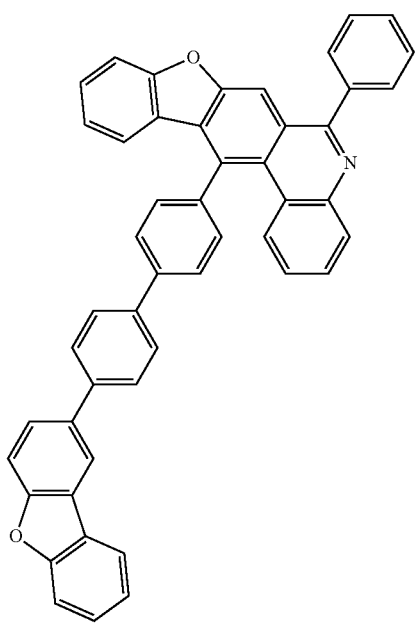
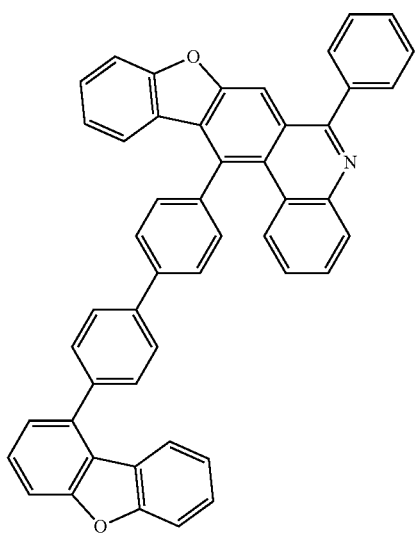

-continued
607
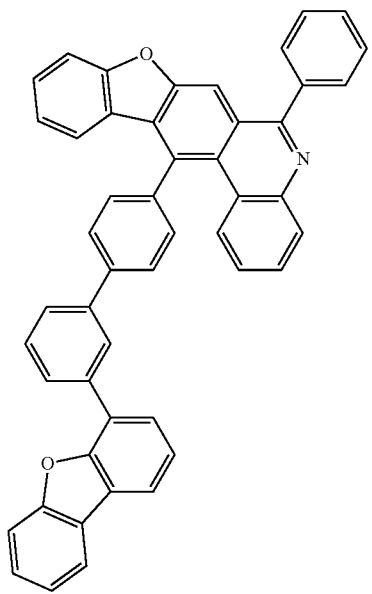
608
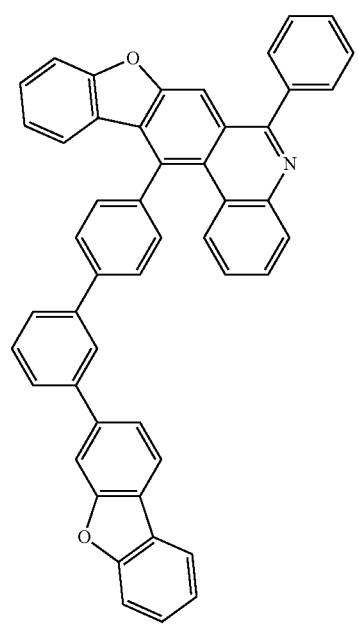
-continued
609
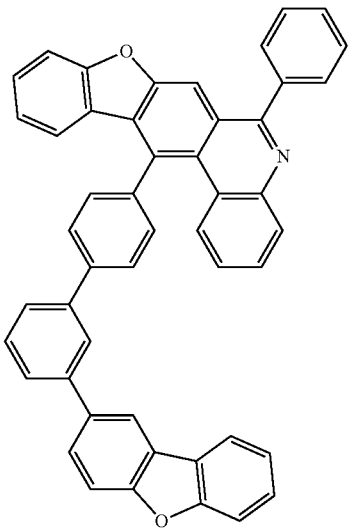
610
611
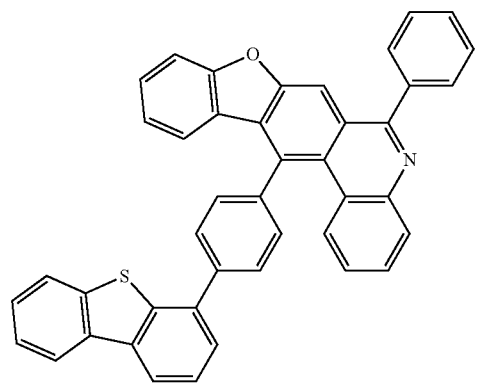

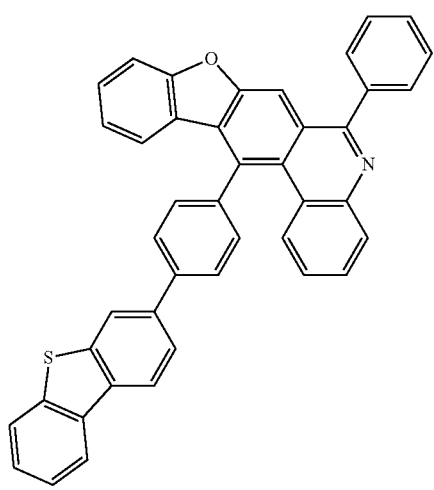
612
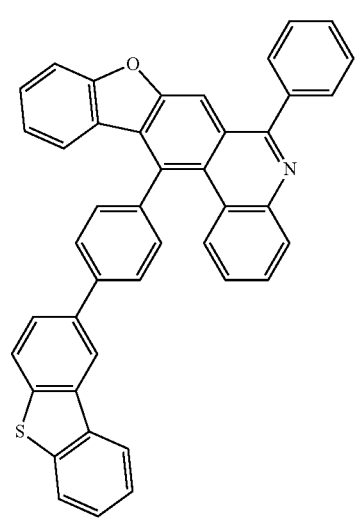
613
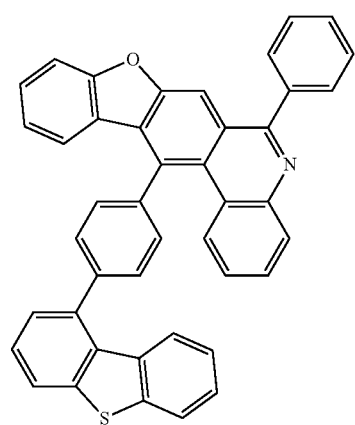
614
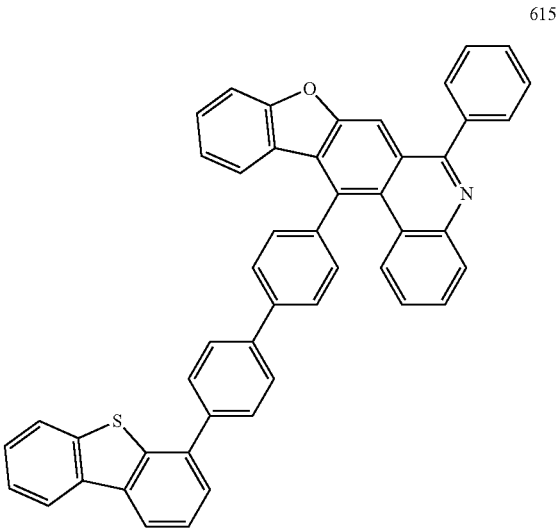
615
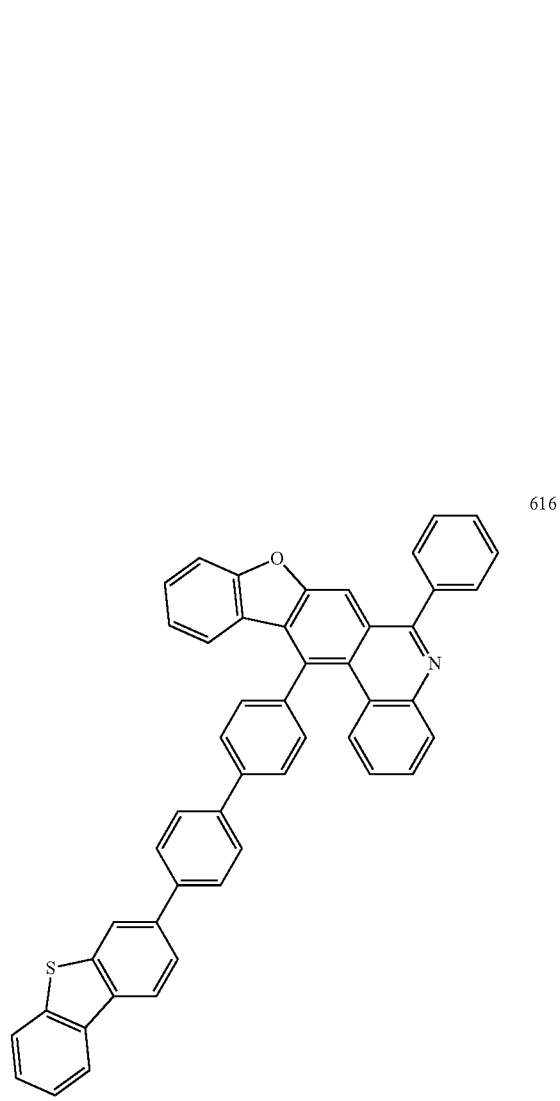
616

977
-continued
617
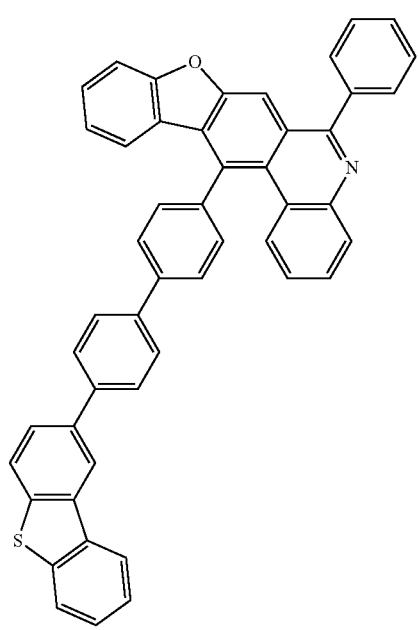
619
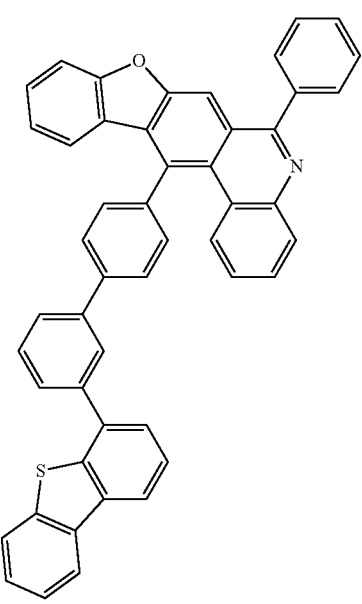
618
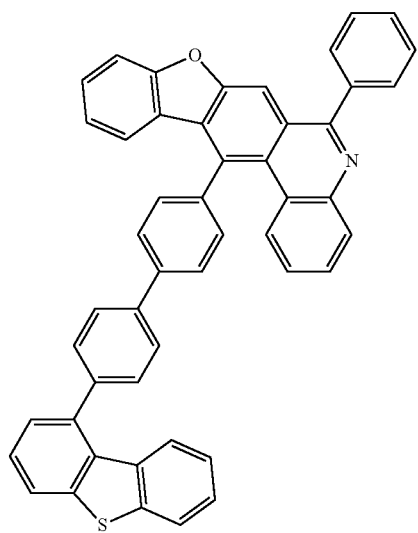
978
-continued
620
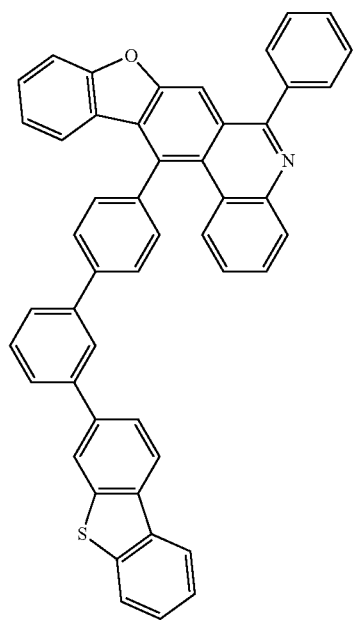

979
-continued
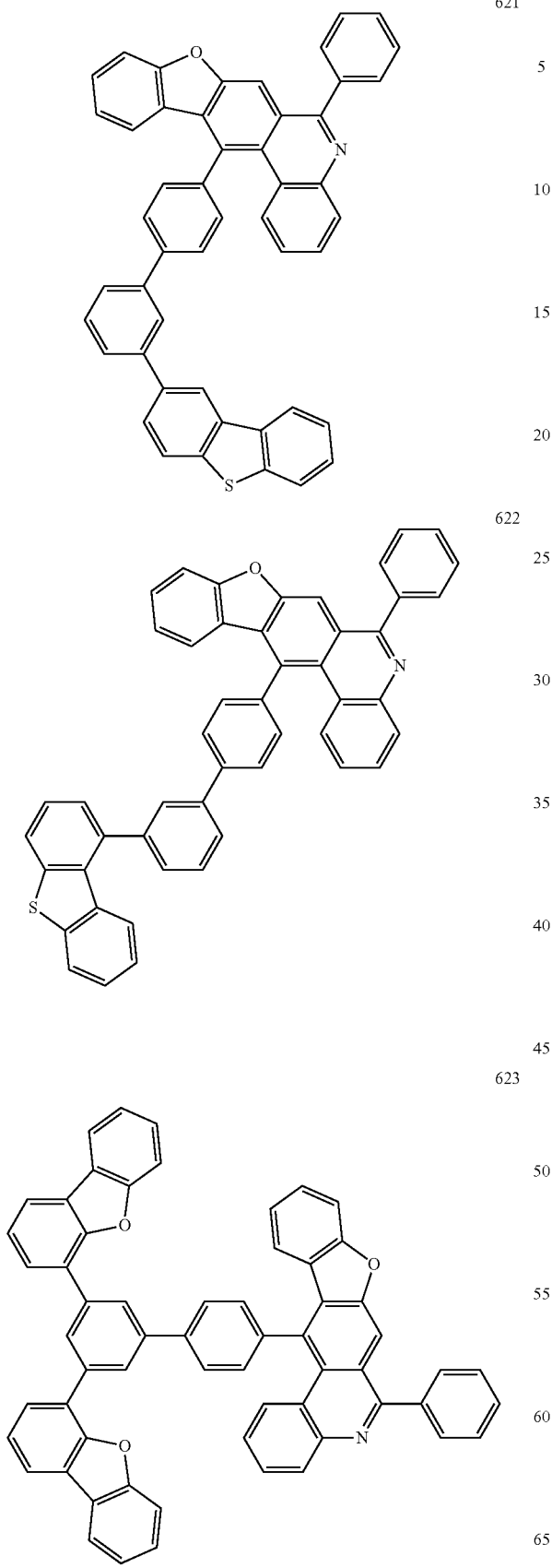
980
-continued
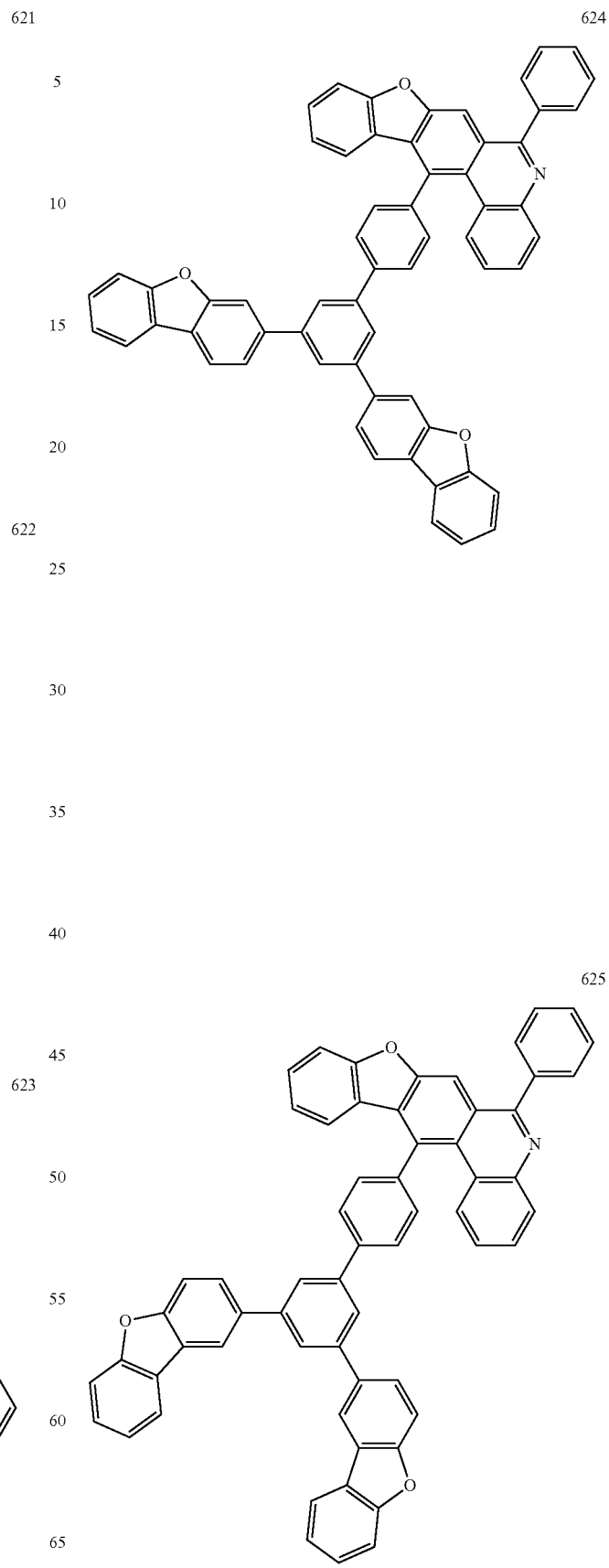

981
-continued
982
-continued
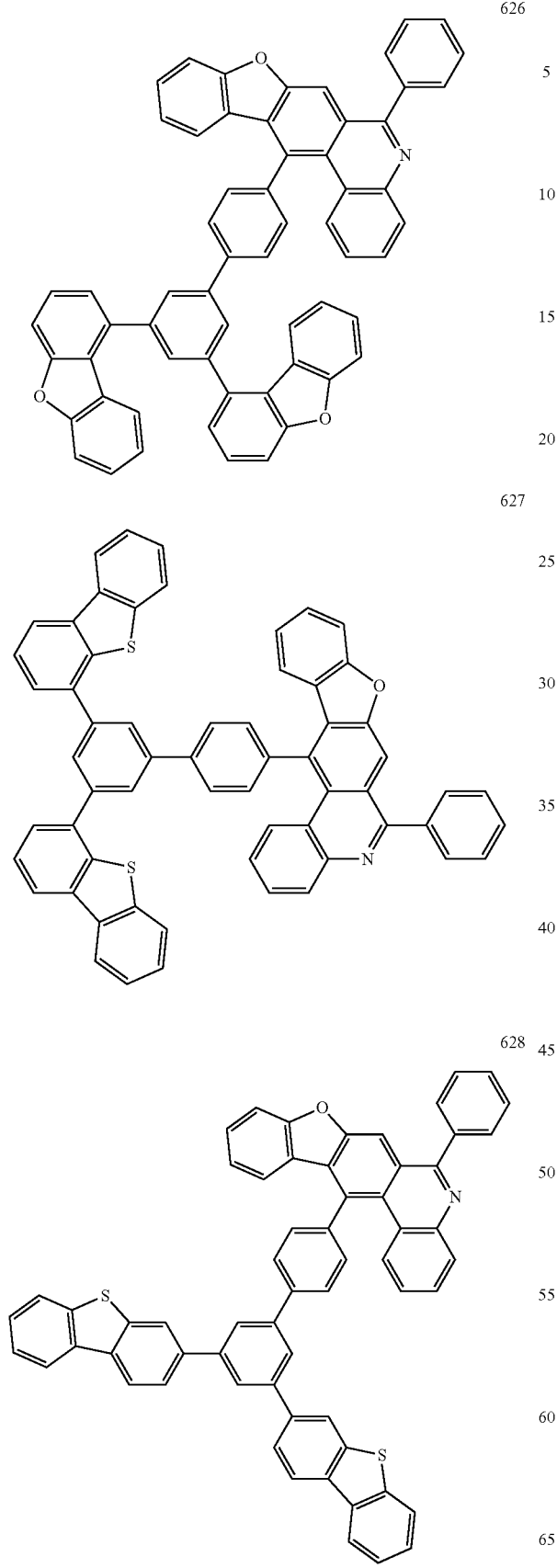
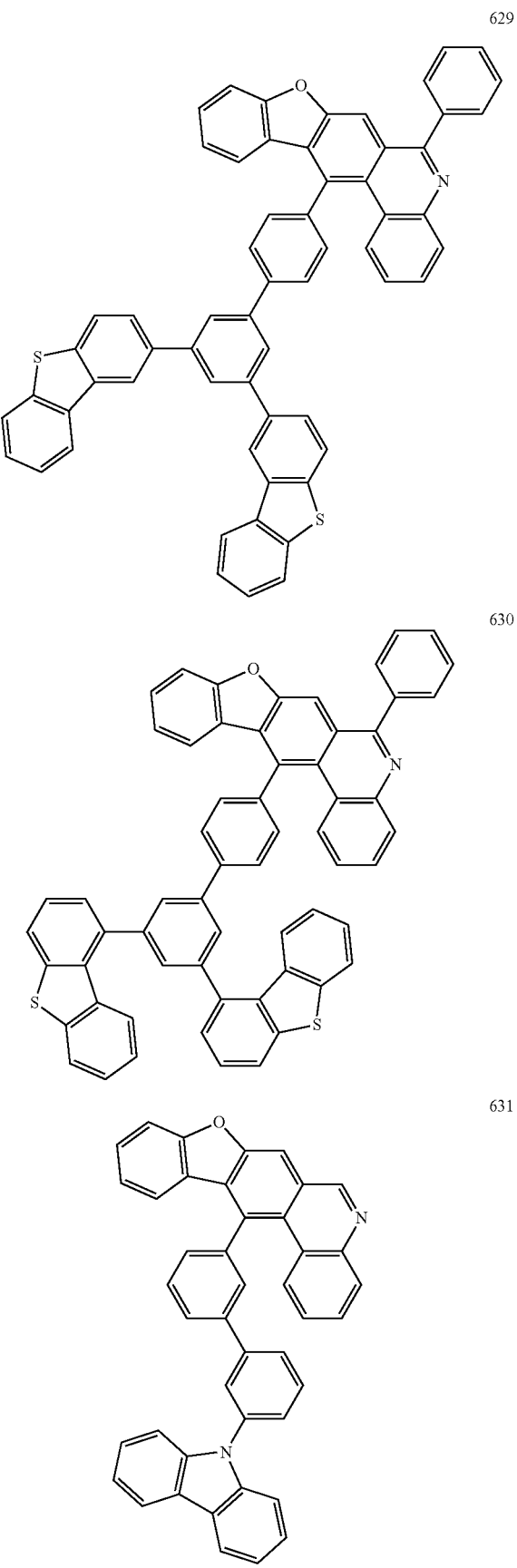

983
-continued
632
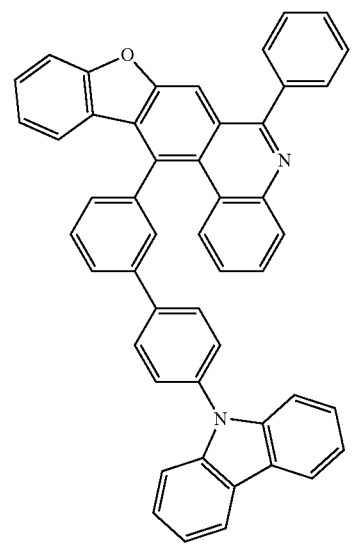
633
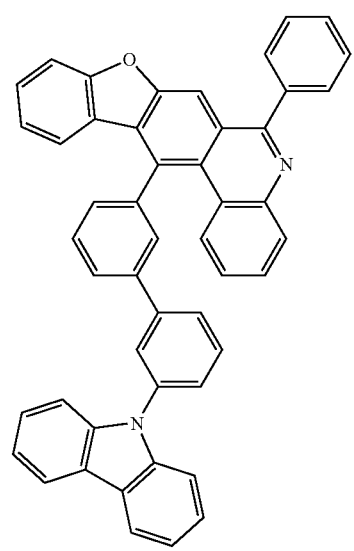
634
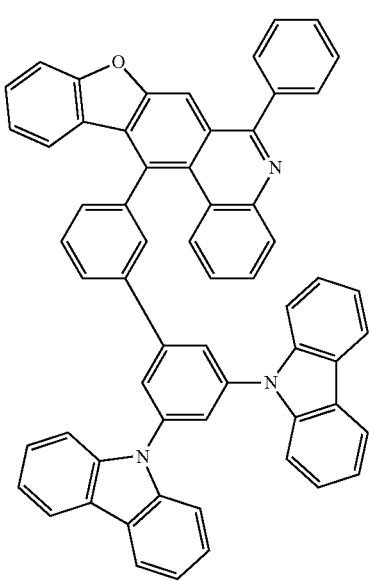
984
-continued
635
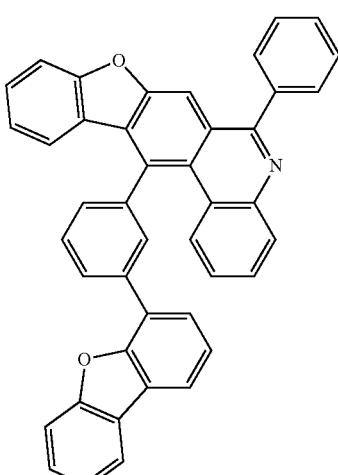
636
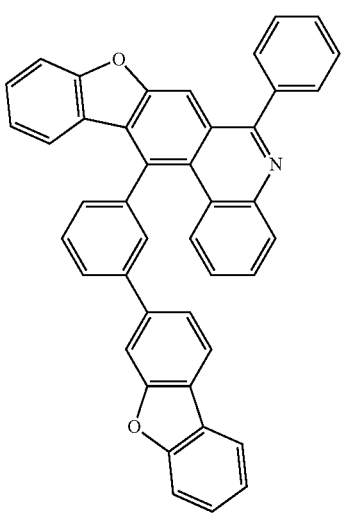
637
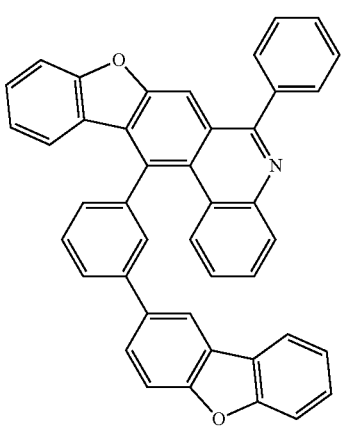

638
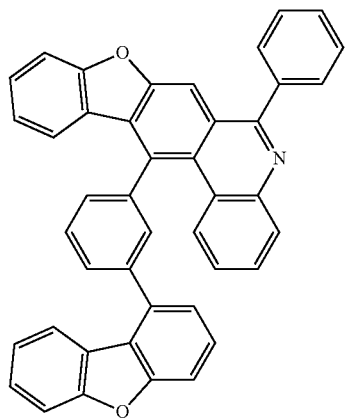
639
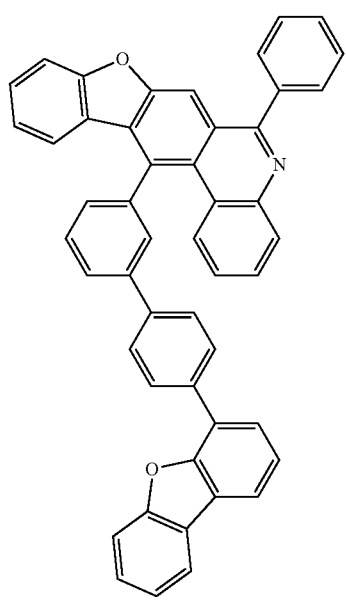
640
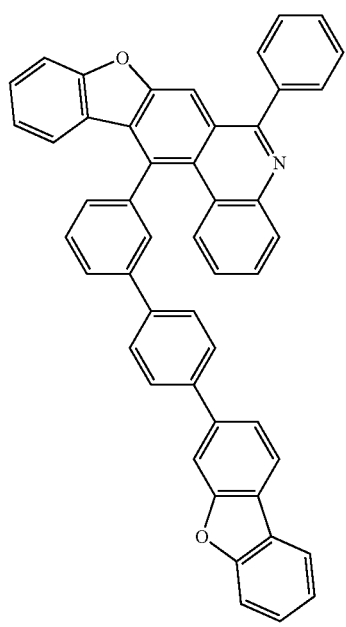
641
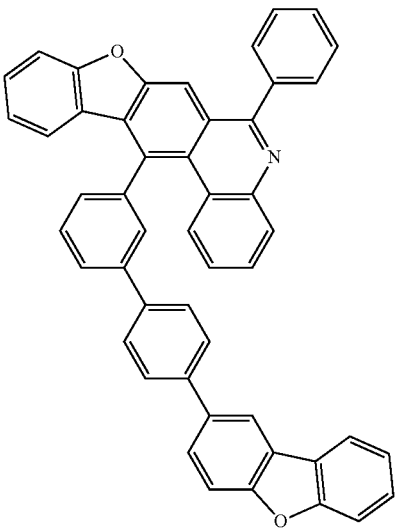
642
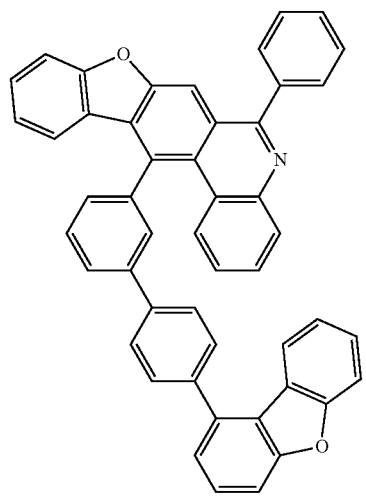
643
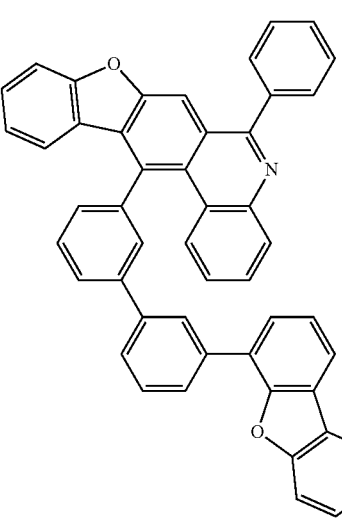

| 644 | 647 |
|---|---|
| 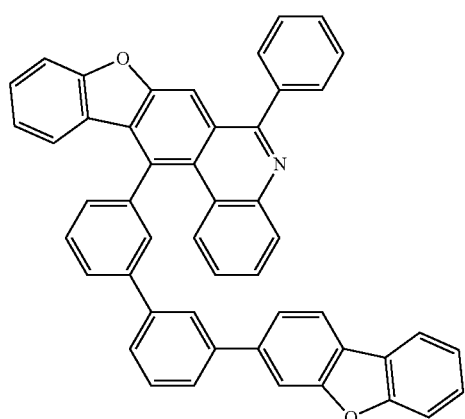 | 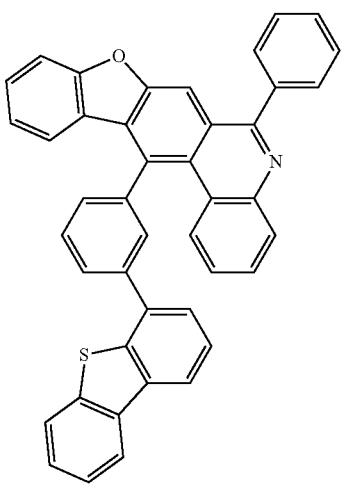 |
| 645 | 648 |
| 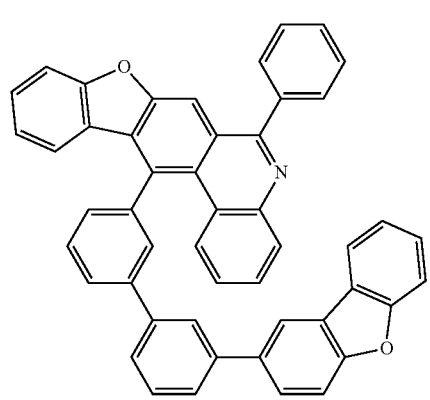 | 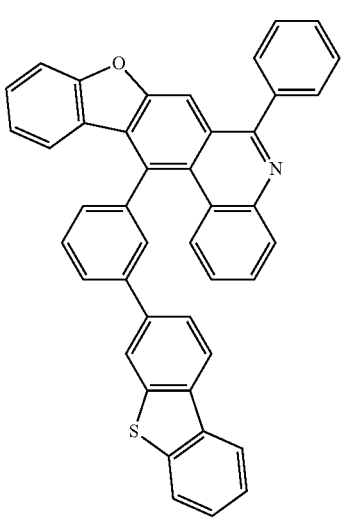 |
| 646 | 649 |
| 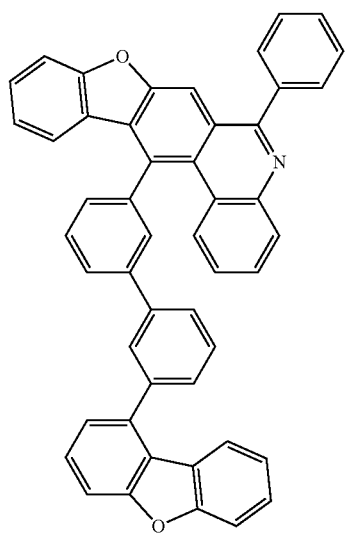 | 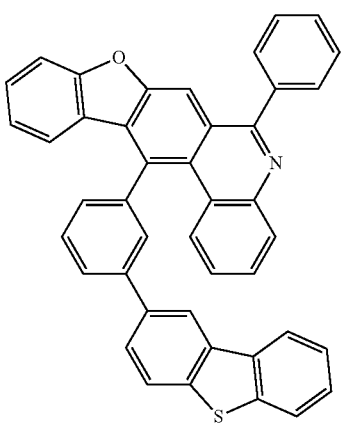 |

989
-continued
650
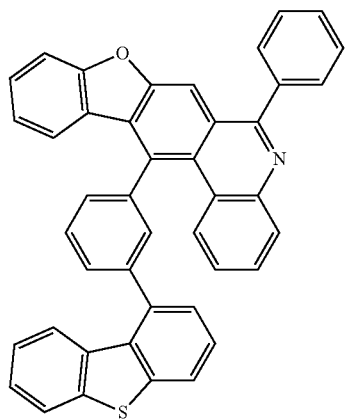
651
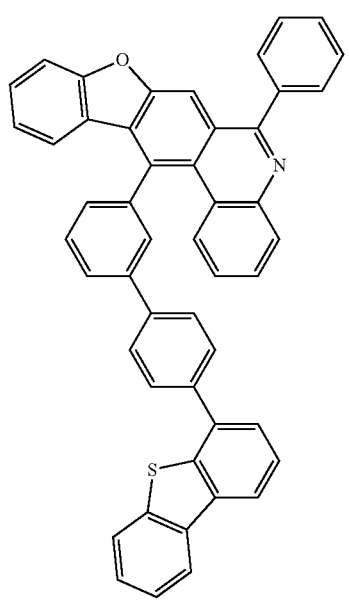
652
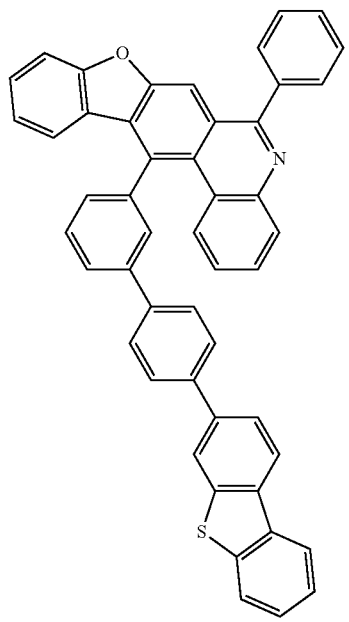
990
-continued
653
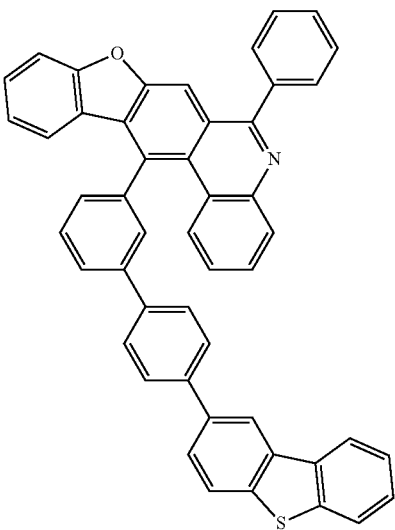
654
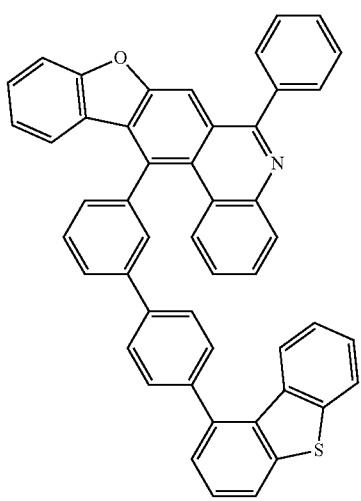
655
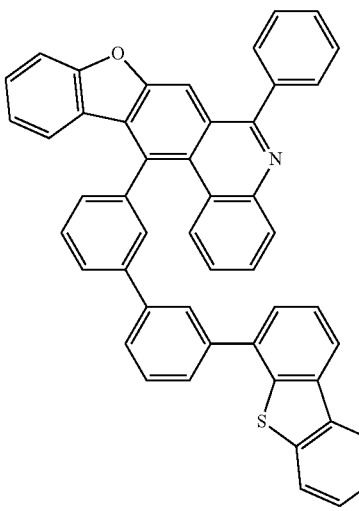

991
-continued
992
-continued
656
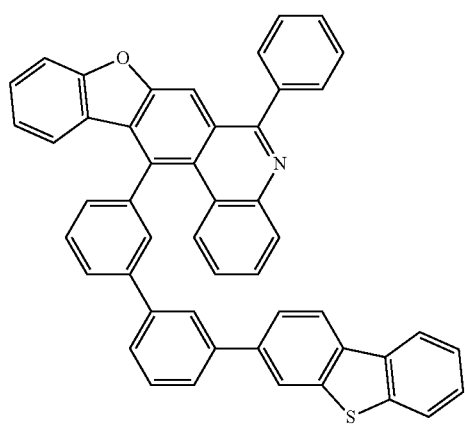
659
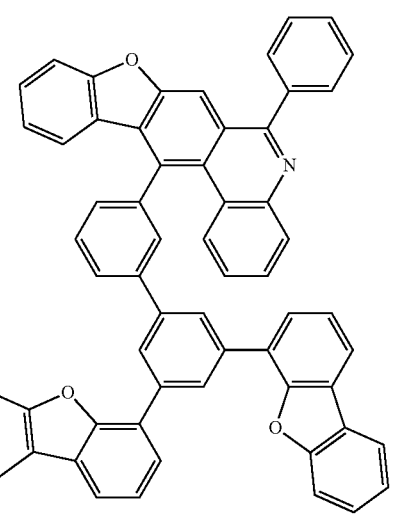
657
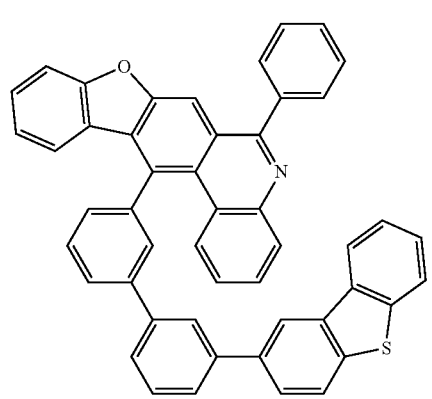
658
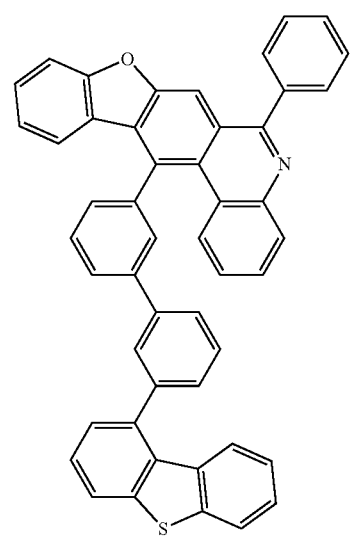
660
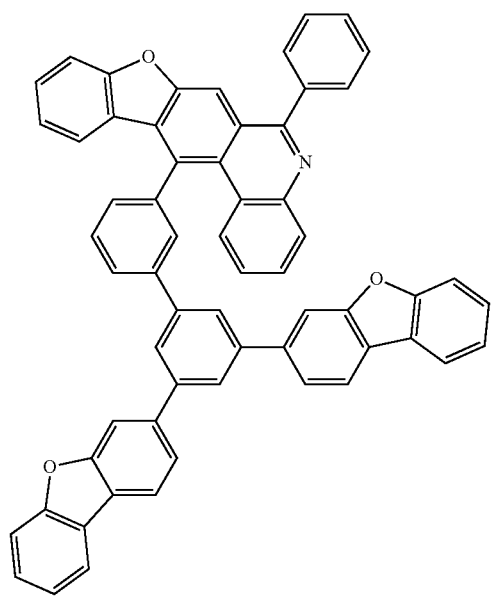

993
-continued
994
-continued
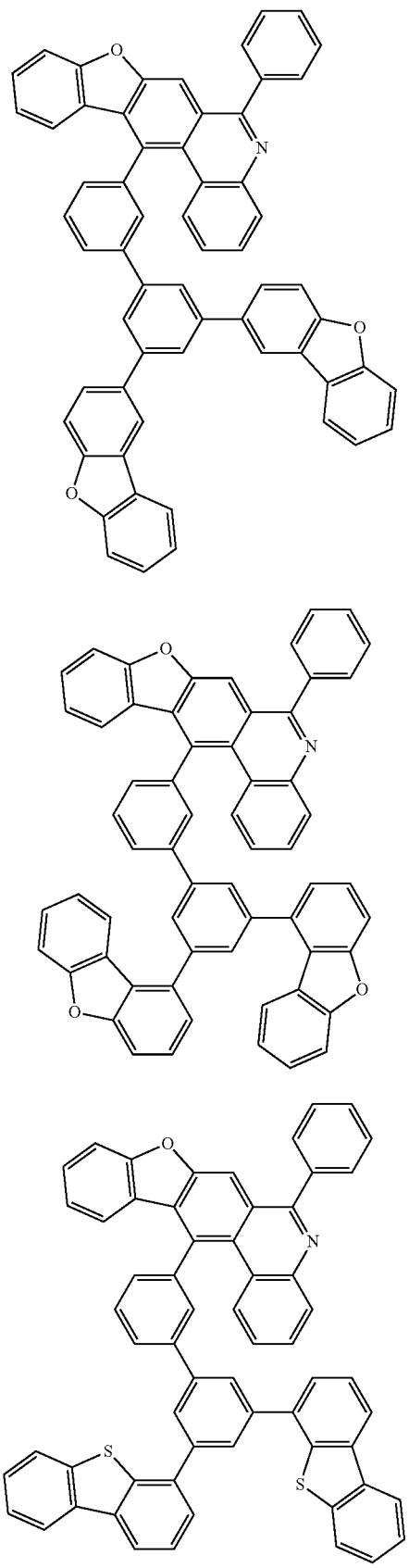
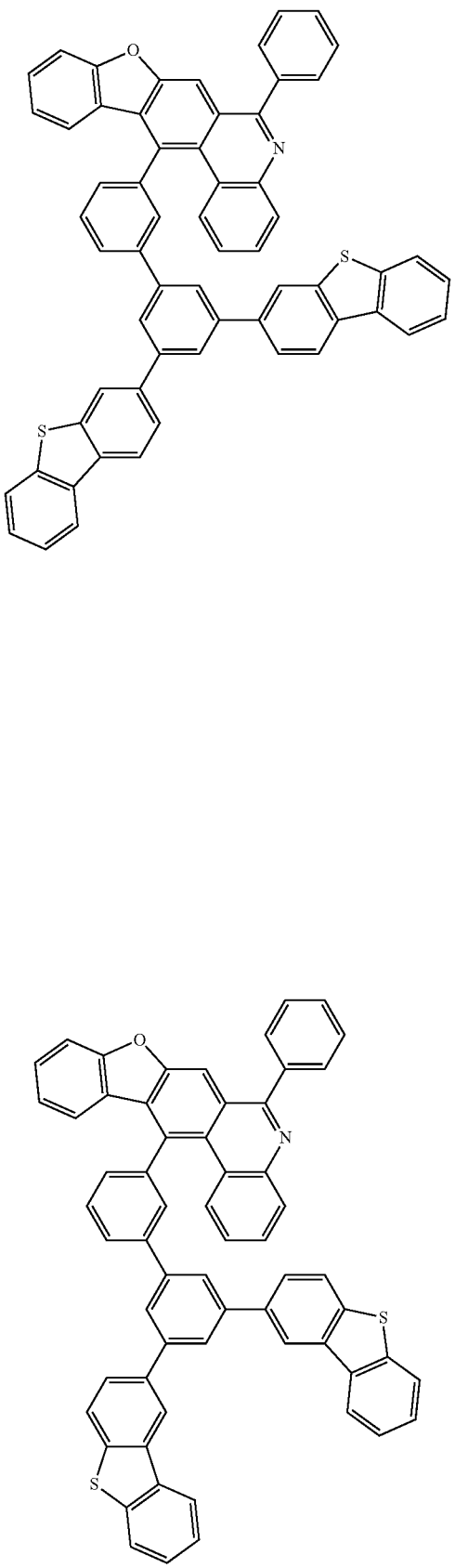

995
-continued
996
-continued
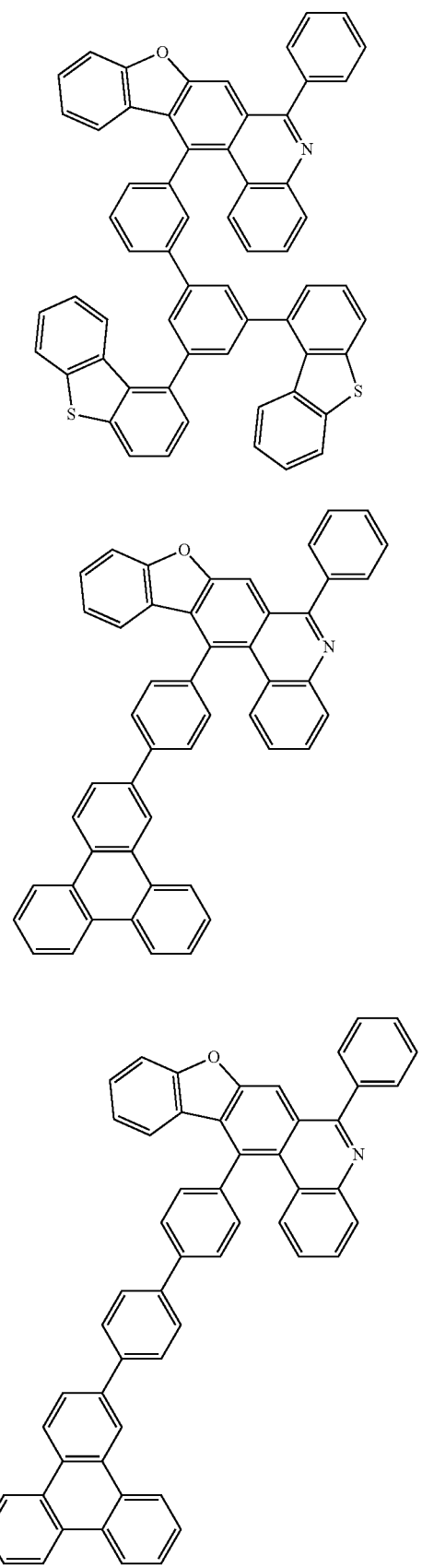
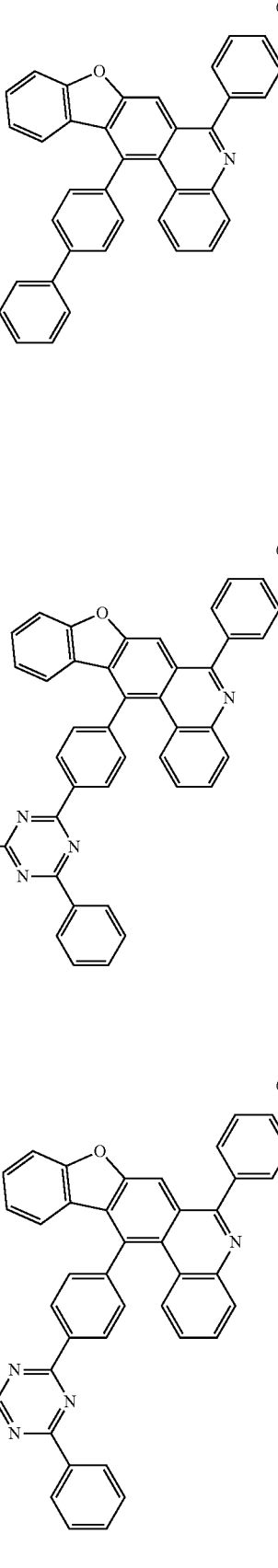

997
-continued
672
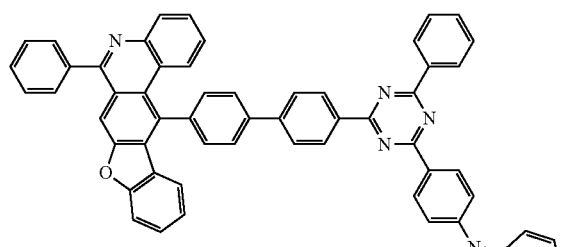
673
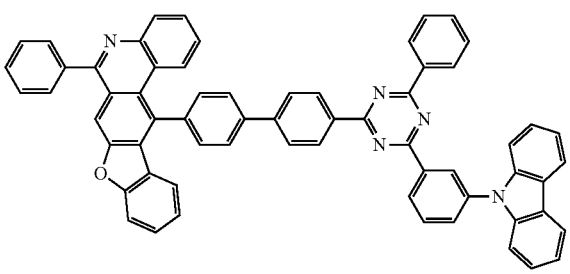
674
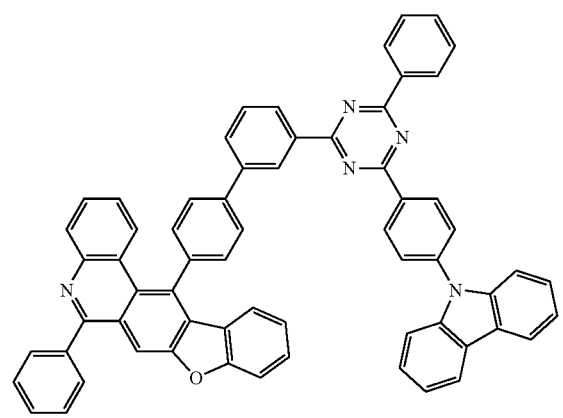
675
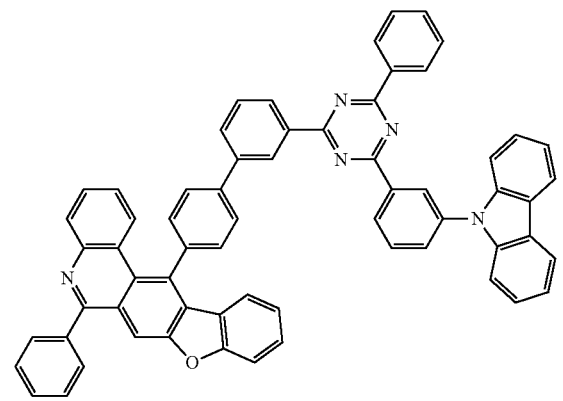
998
-continued
676
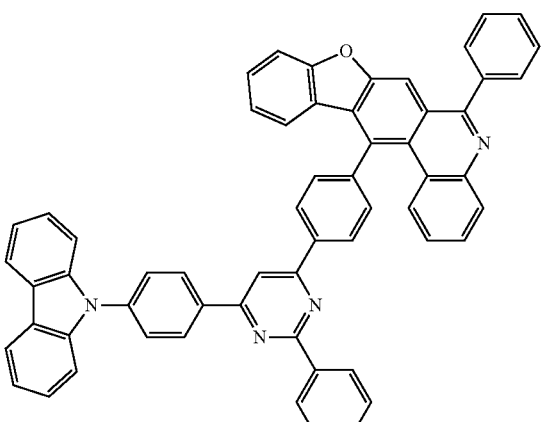
677
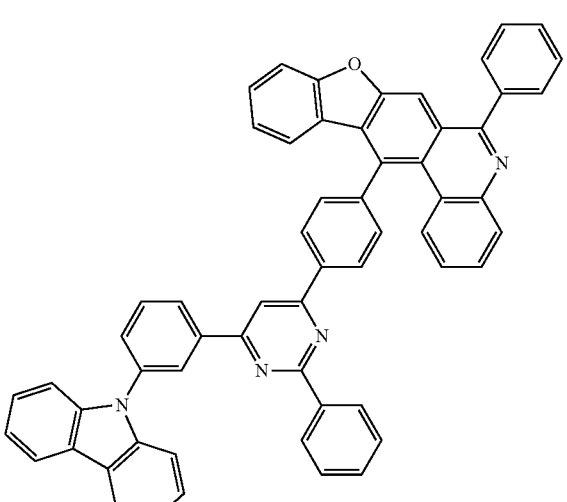
678
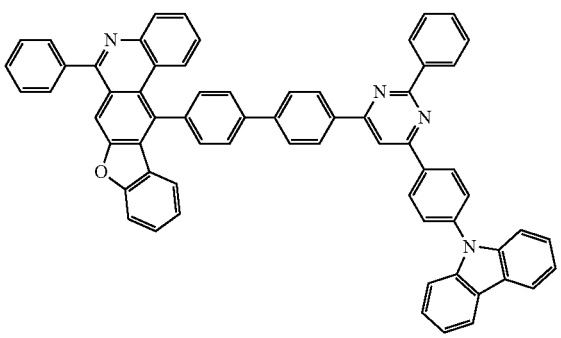
679
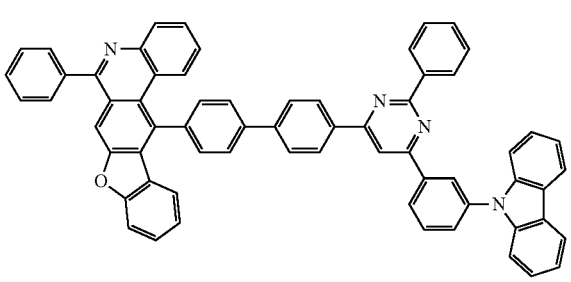

-continued
680
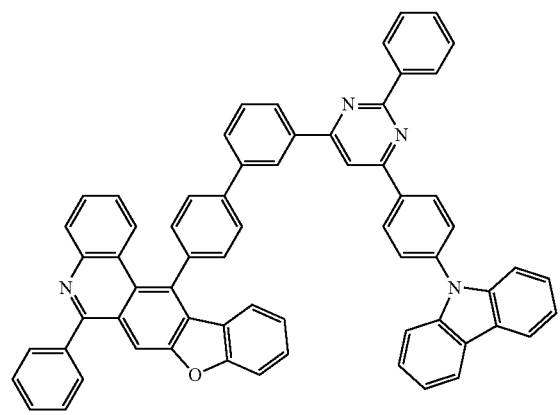
681
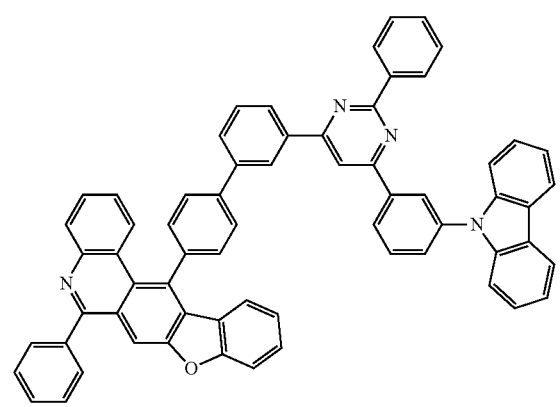
682
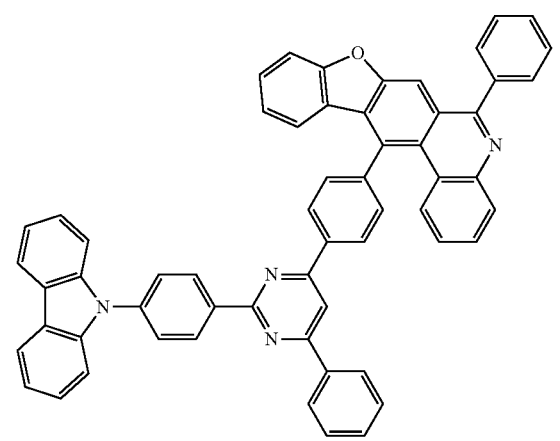
-continued
683
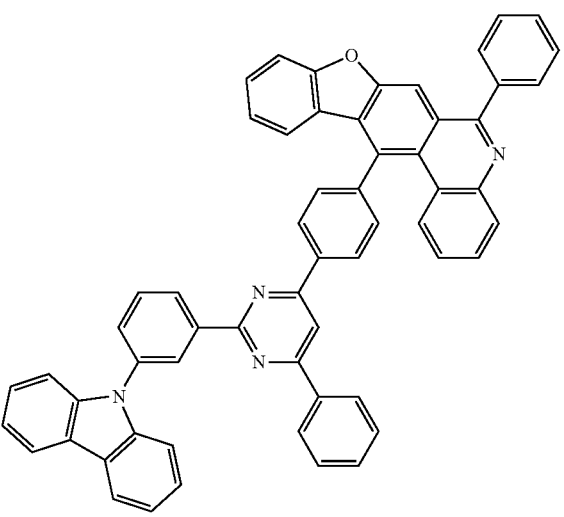
684
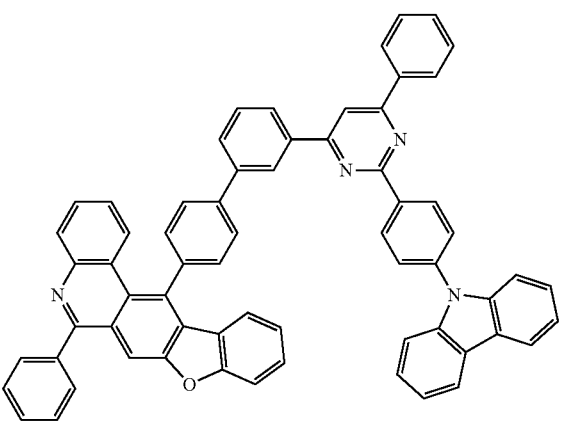
685

1001
-continued
686
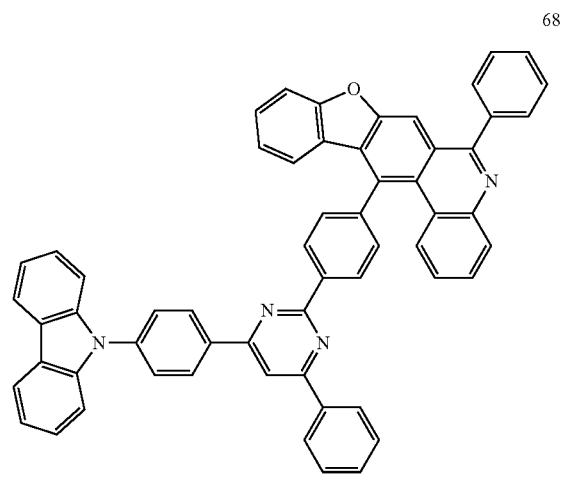
687
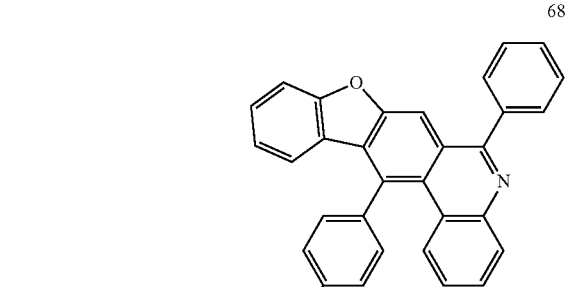
688
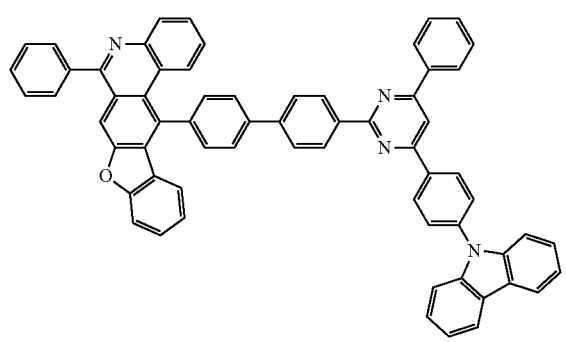
1002
-continued
689
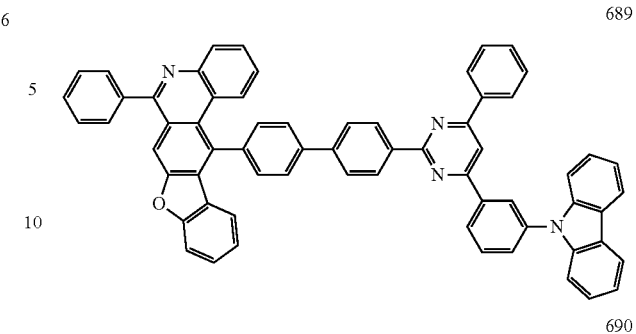
690
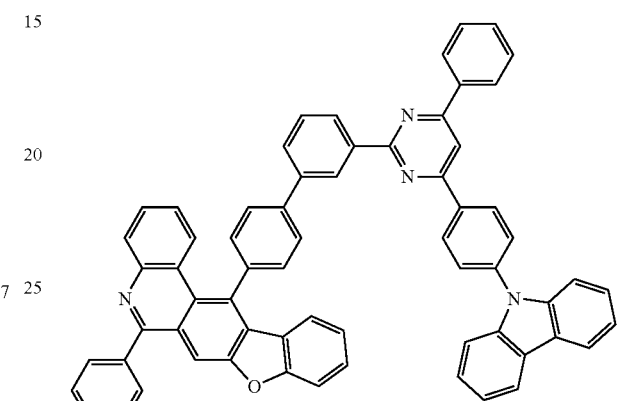
691
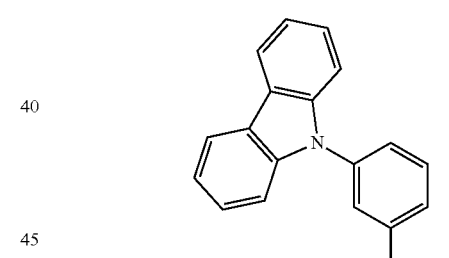
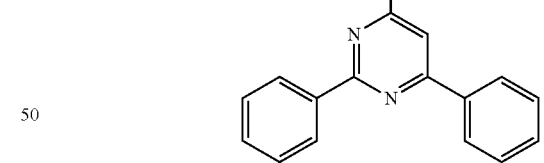
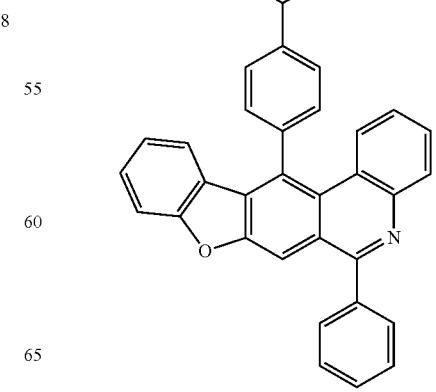

1003
-continued
692
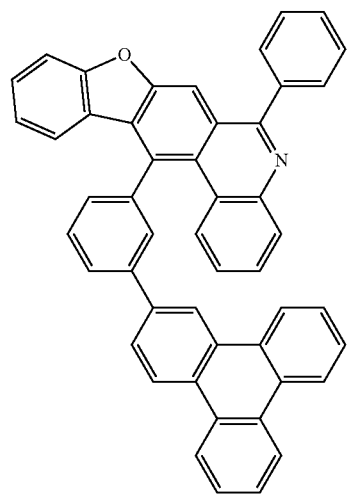
1004
-continued
694
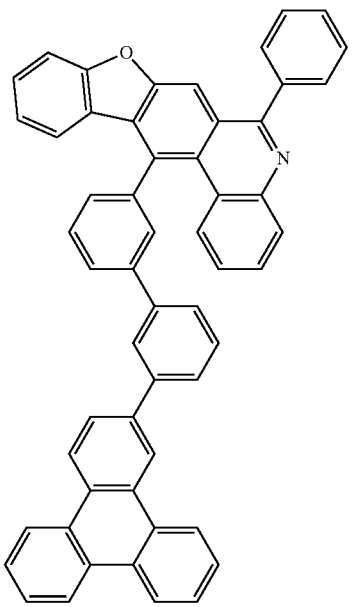
693
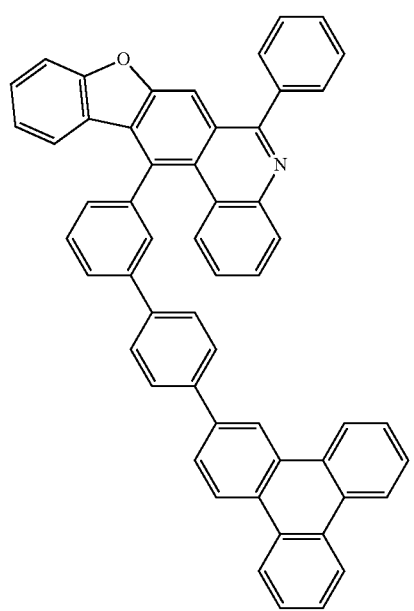
695
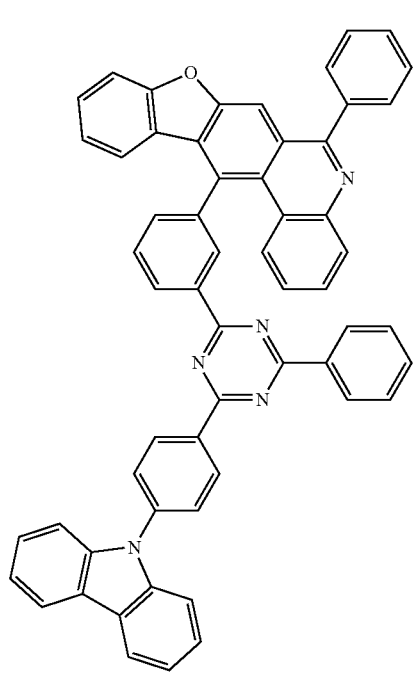

1005
-continued
1006
-continued
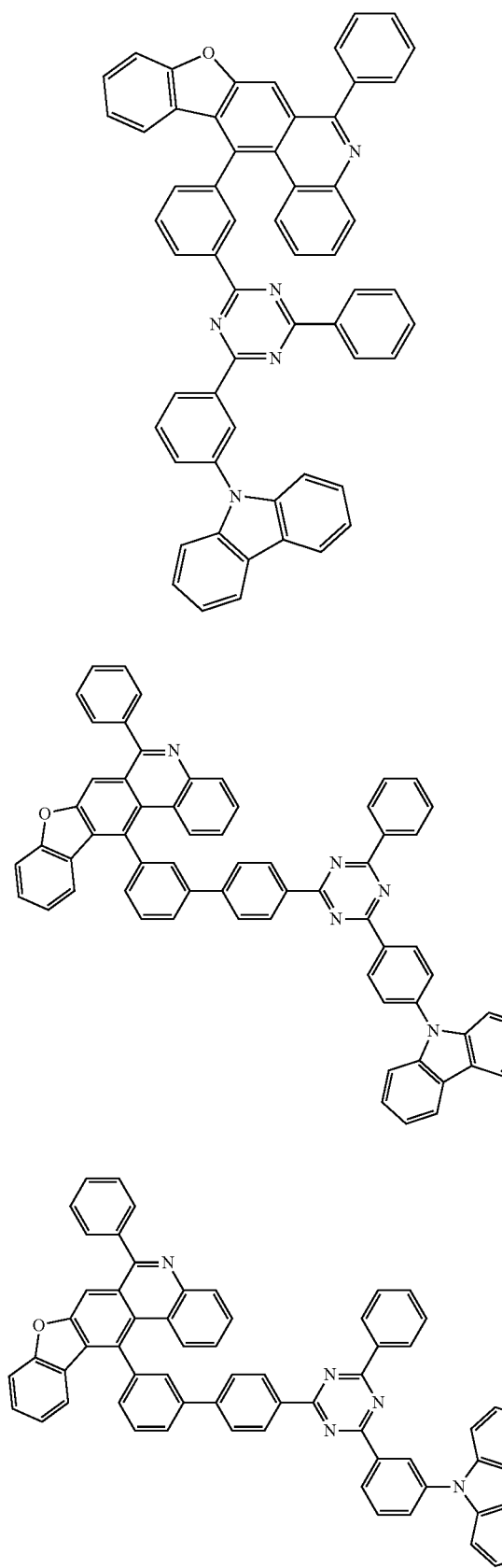
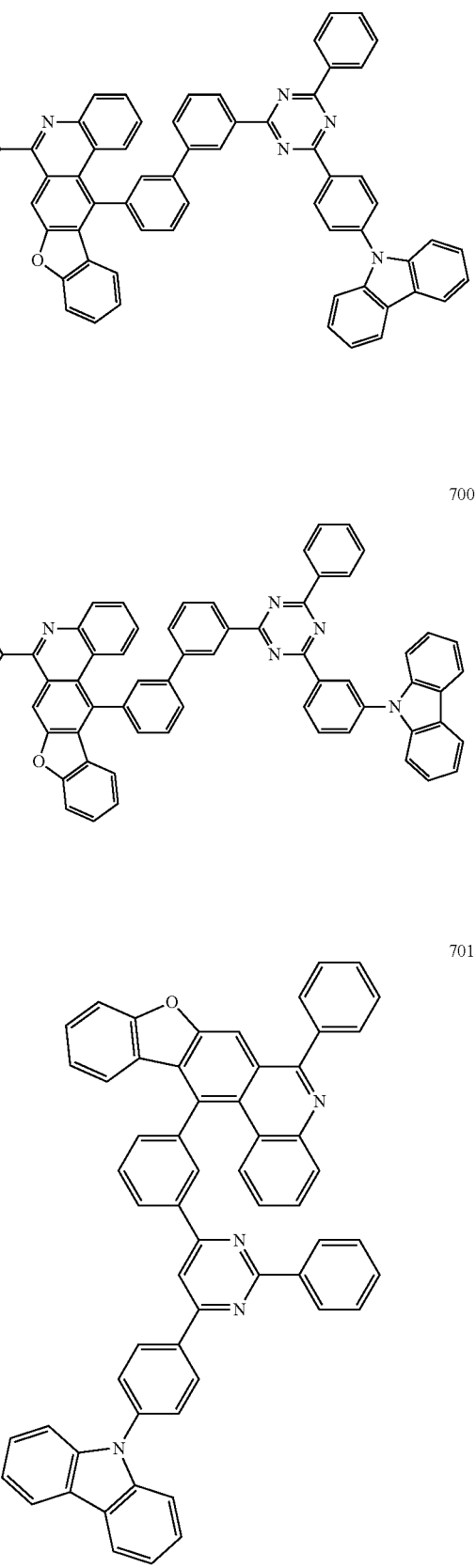

1007
-continued
1008
-continued
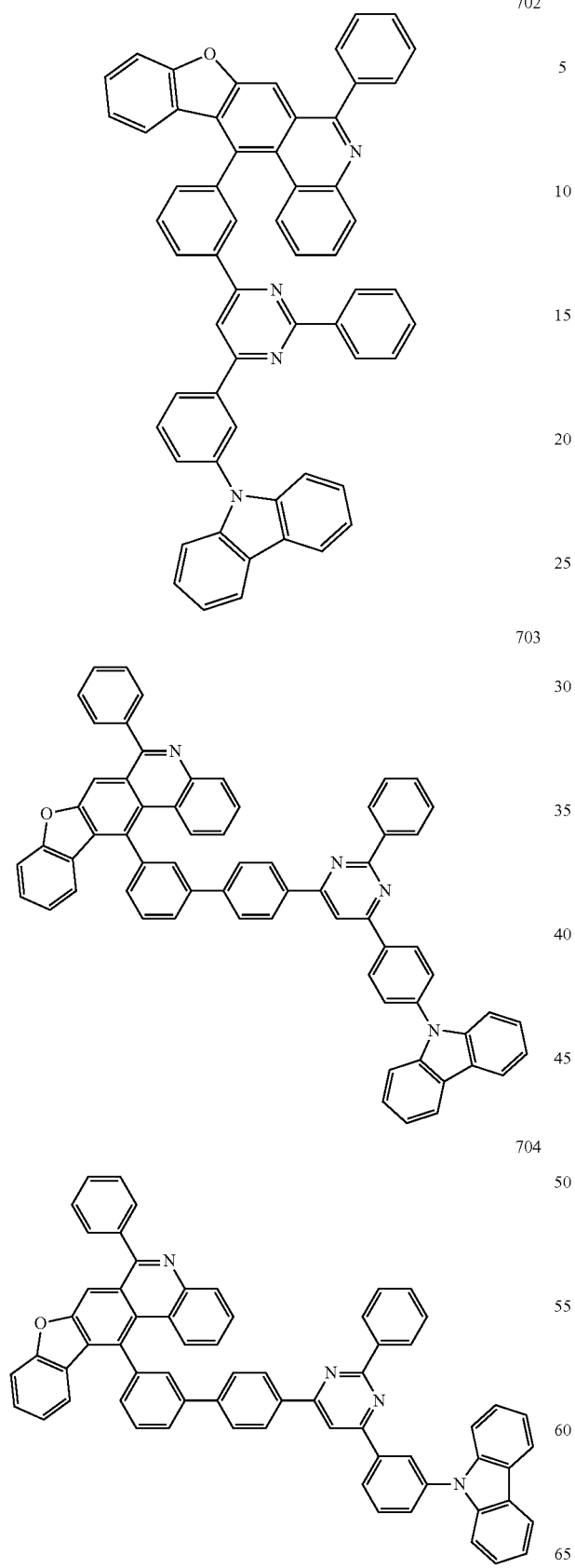
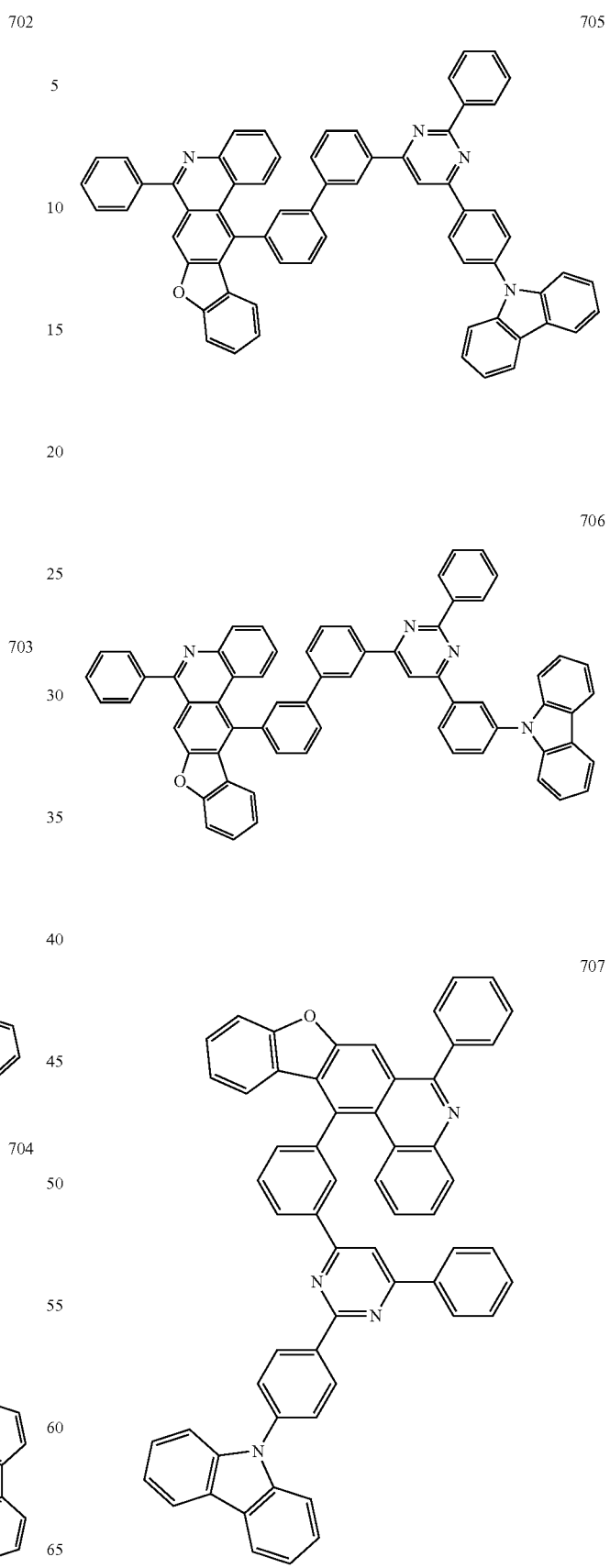

1009
-continued
1010
-continued
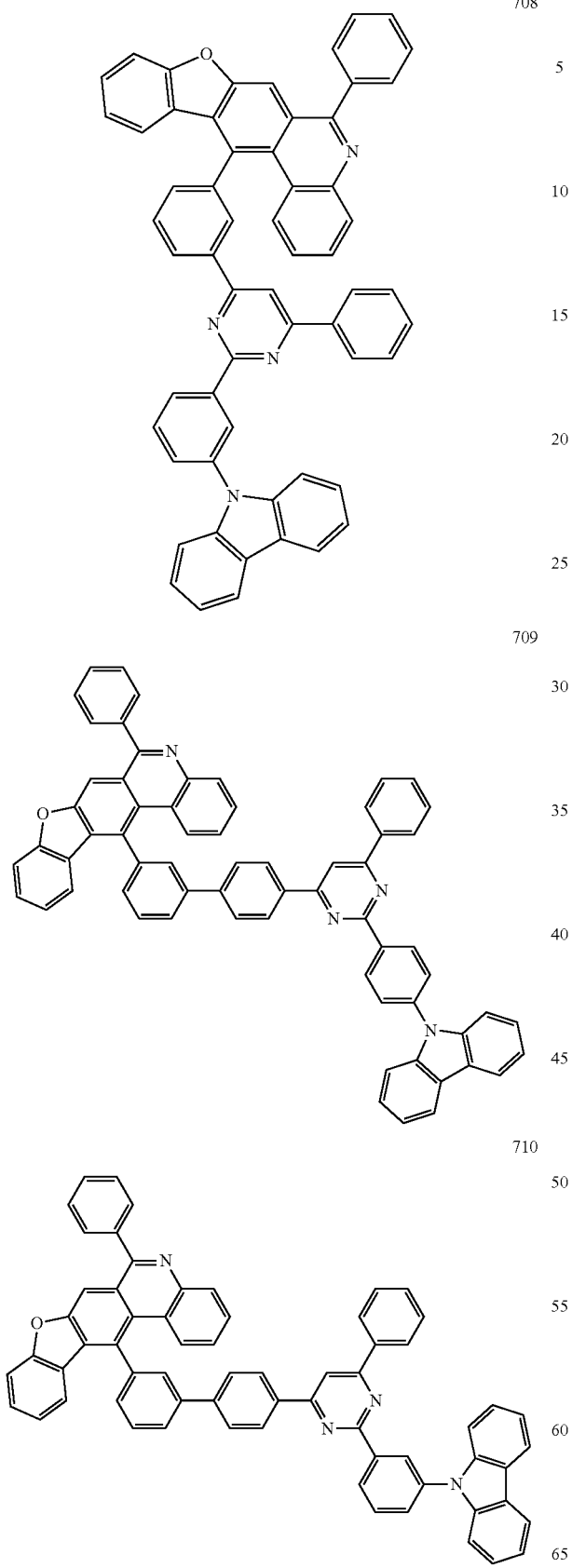
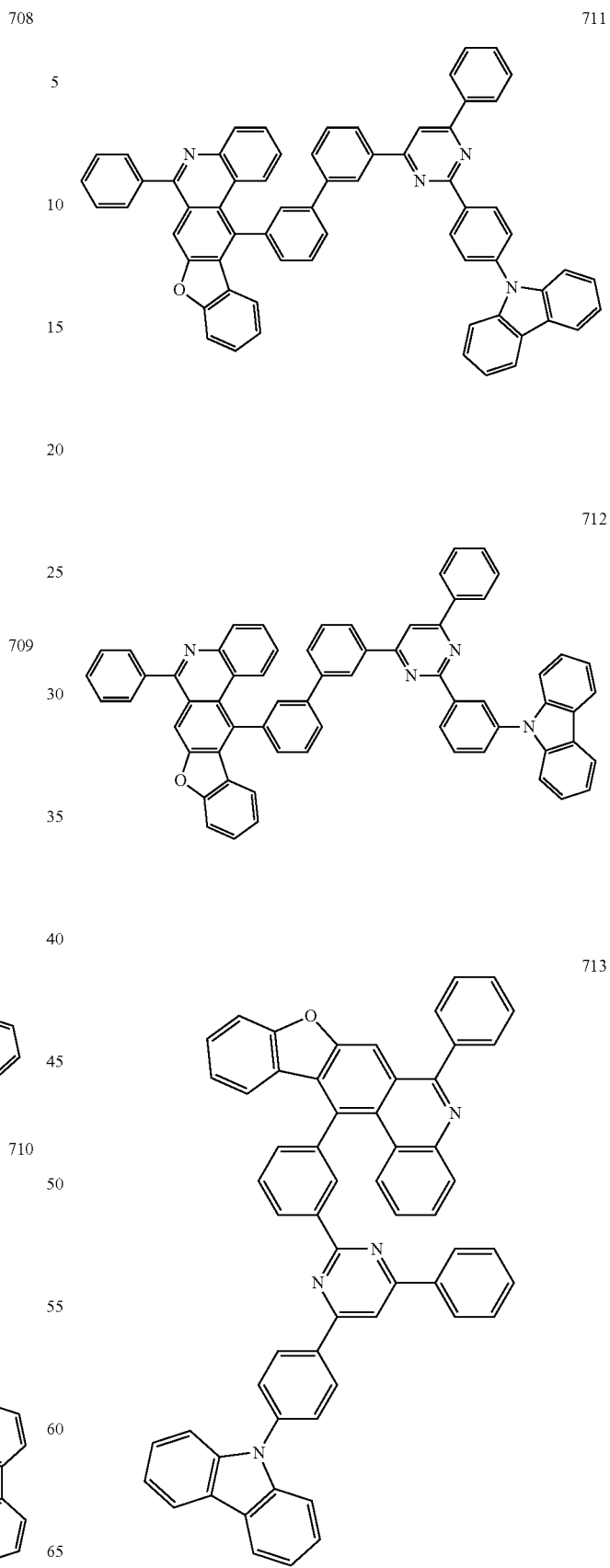

1011
-continued
714
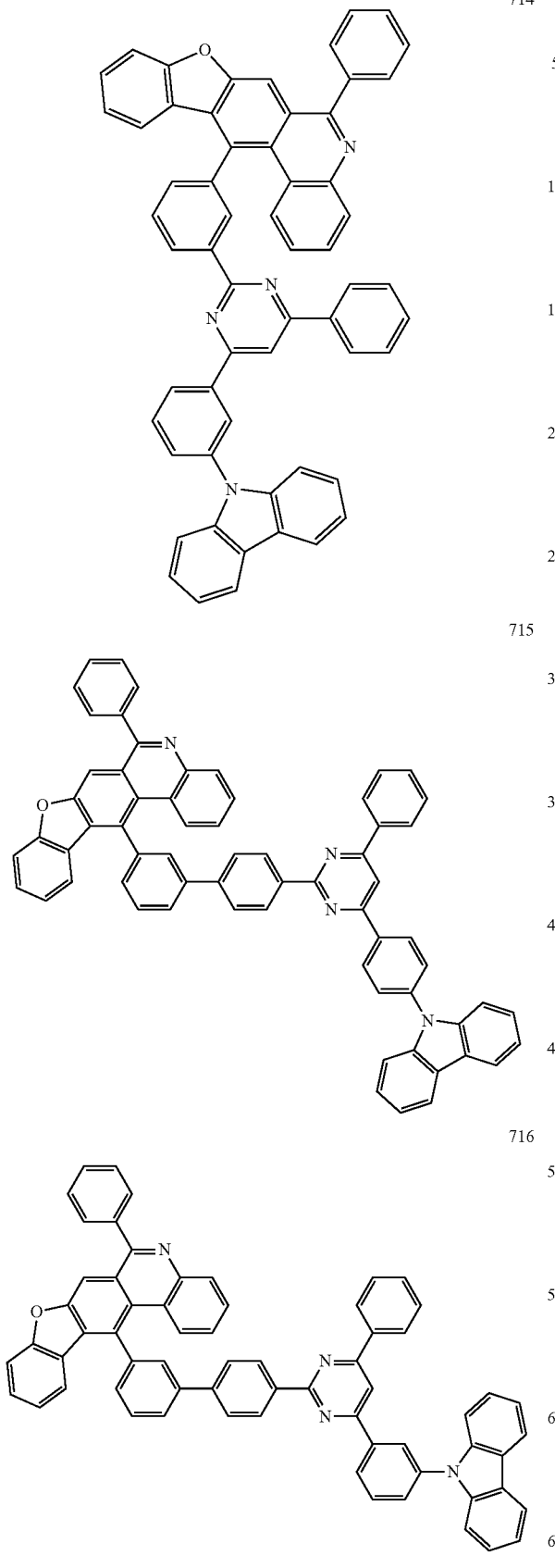
715
716
1012
-continued
717
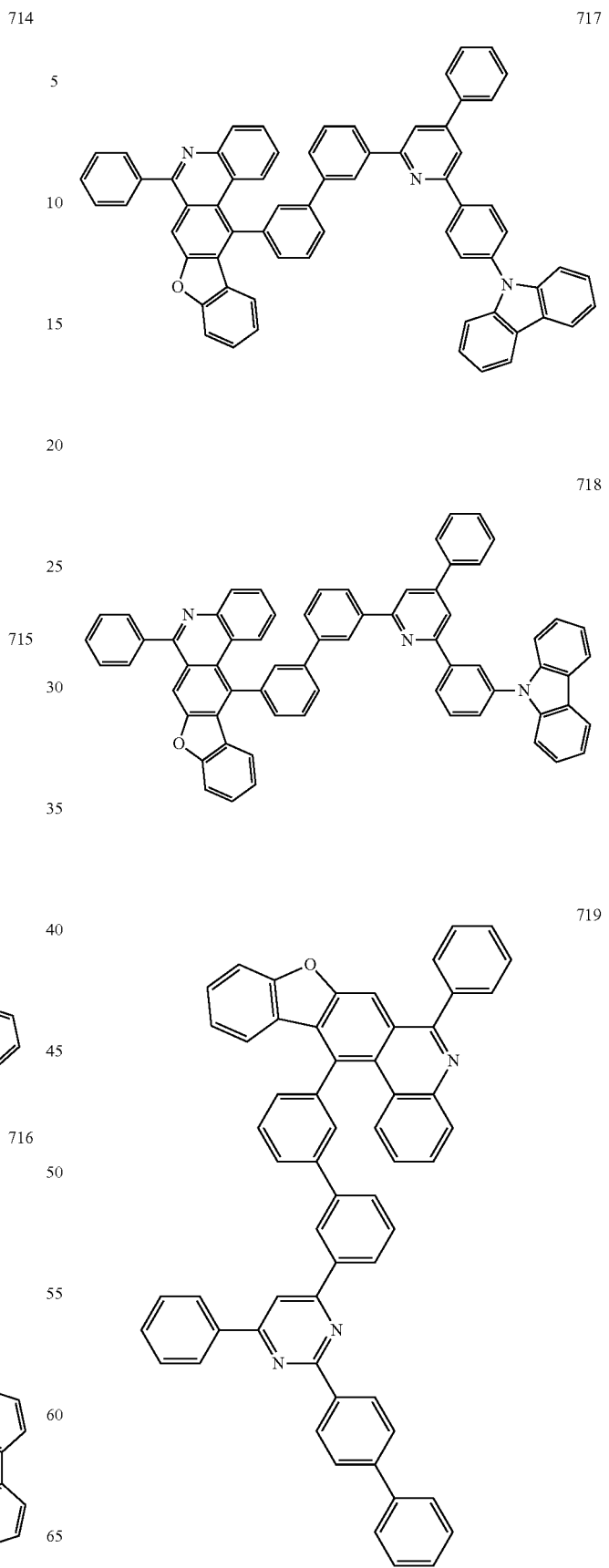
718
719

1013
-continued
720
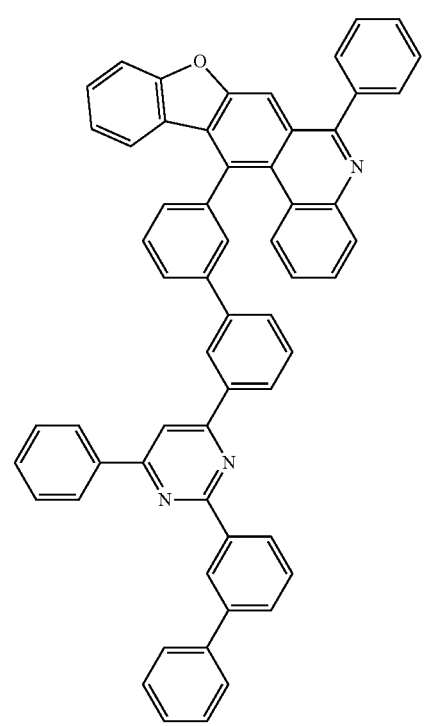
721
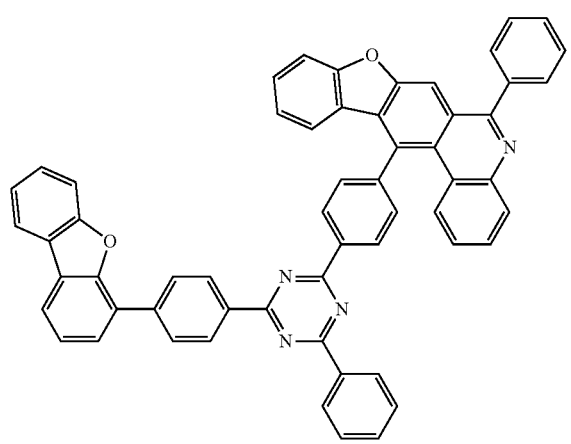
722
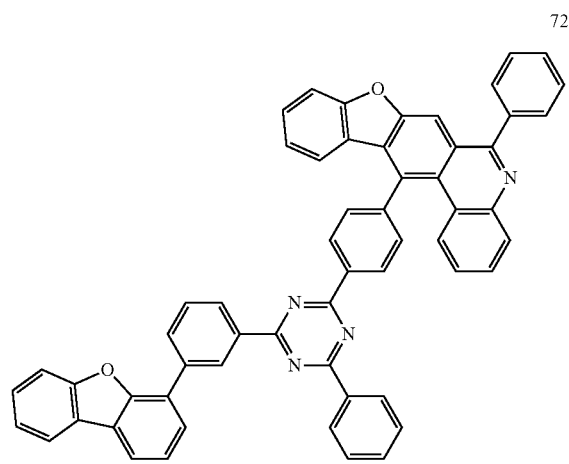
1014
-continued
723
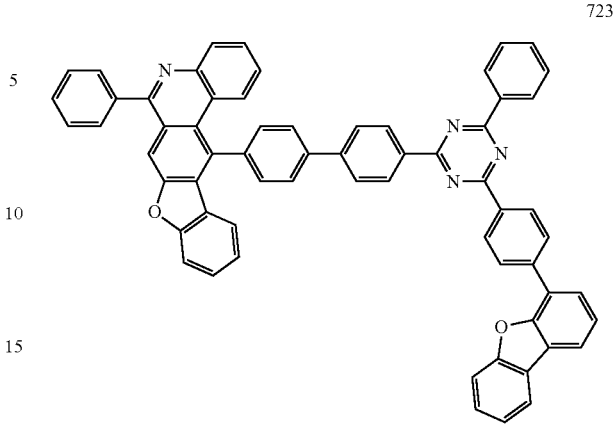
724
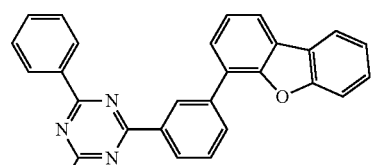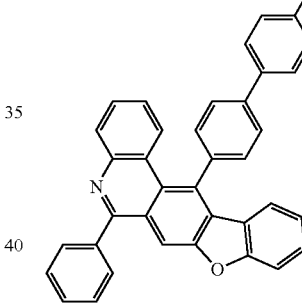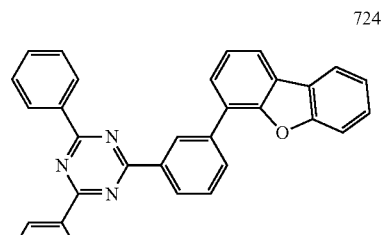
725
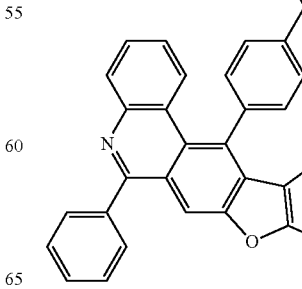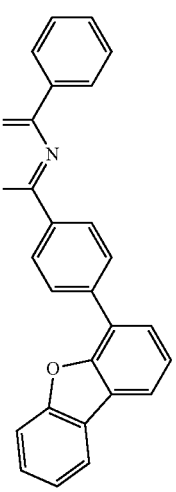

726
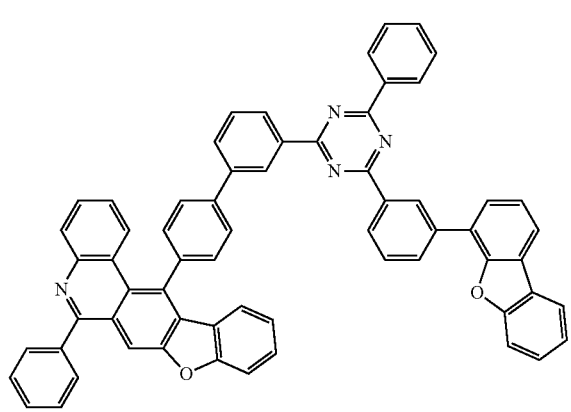
727
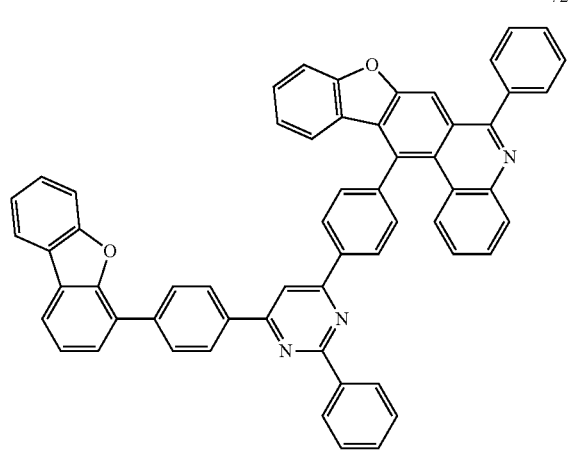
728
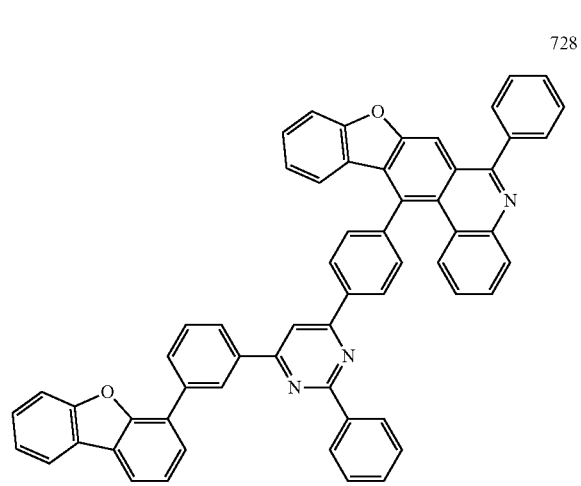
729
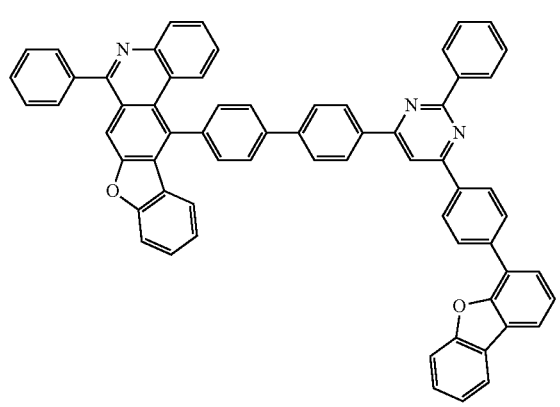
730
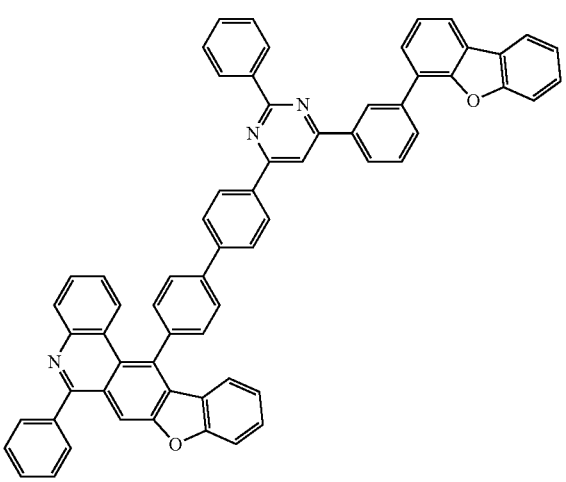
731
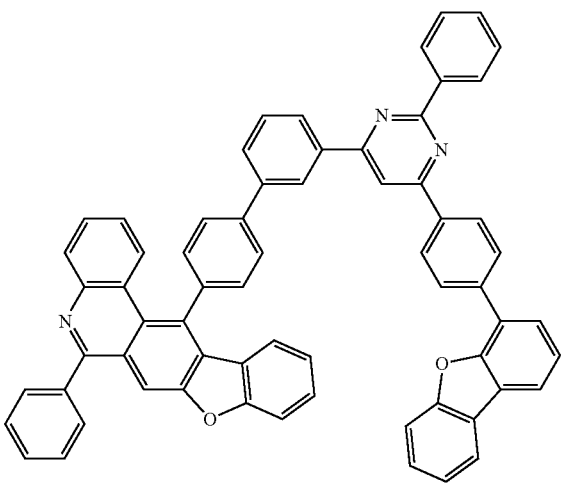

1017
-continued
732
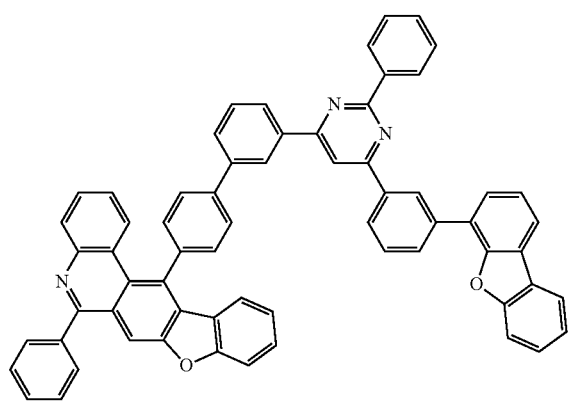
733
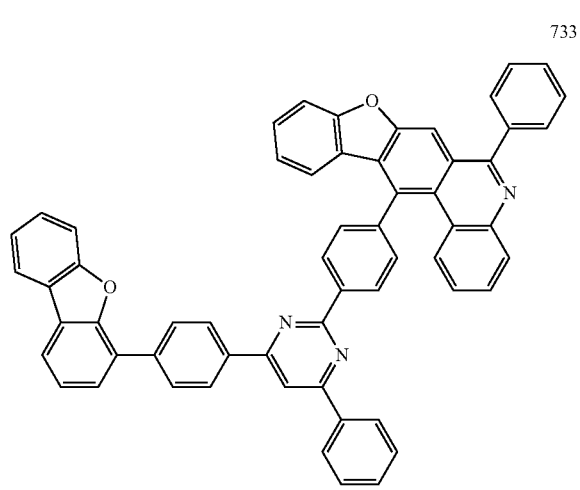
734
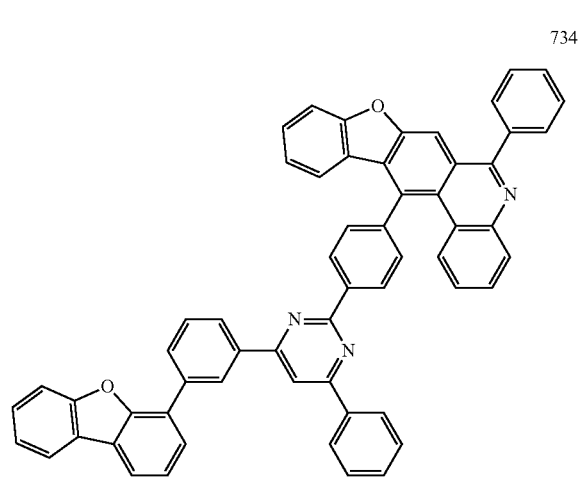
1018
-continued
735
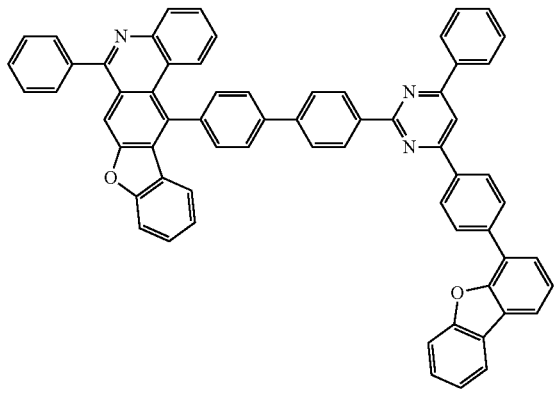
736
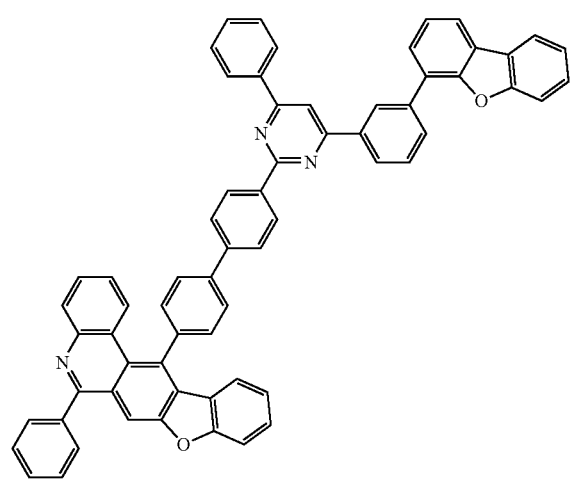
737
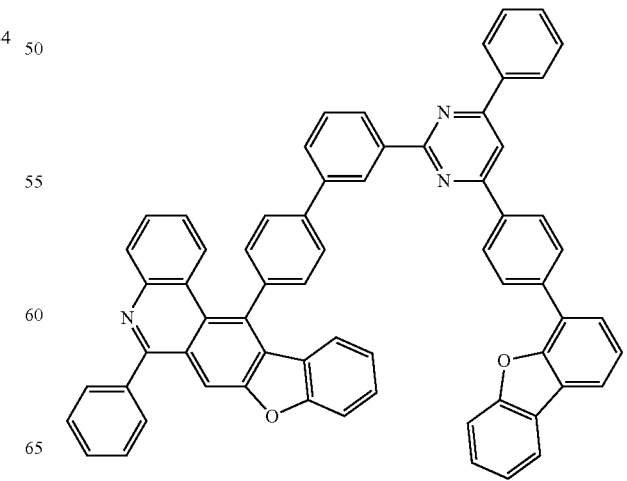

738
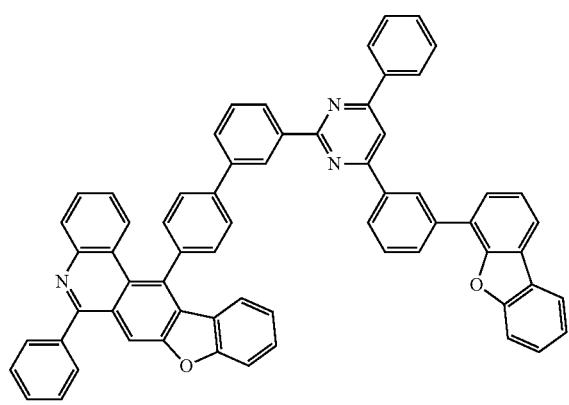
739
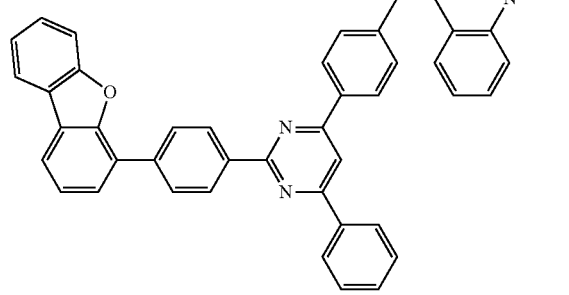
740
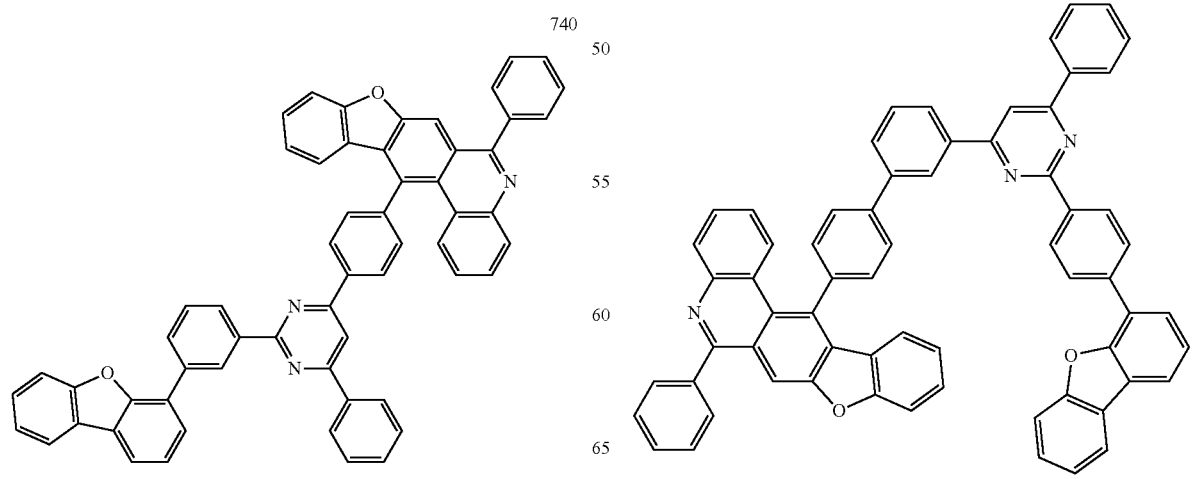
741
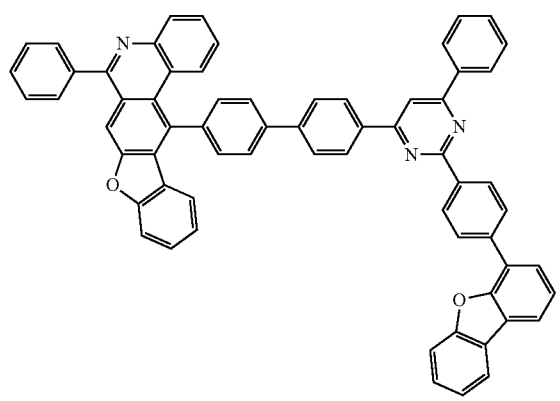
742
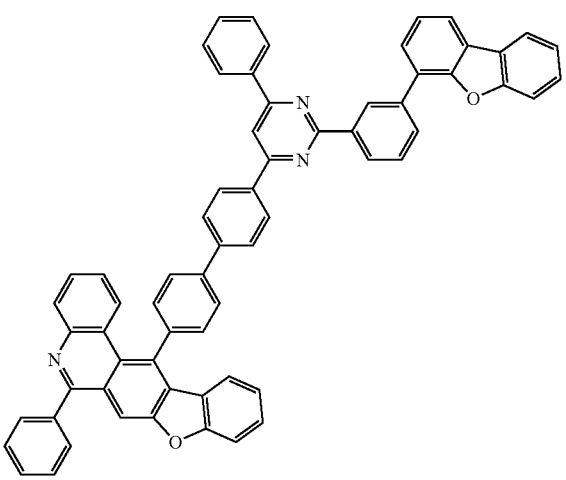
743

1021
-continued
744
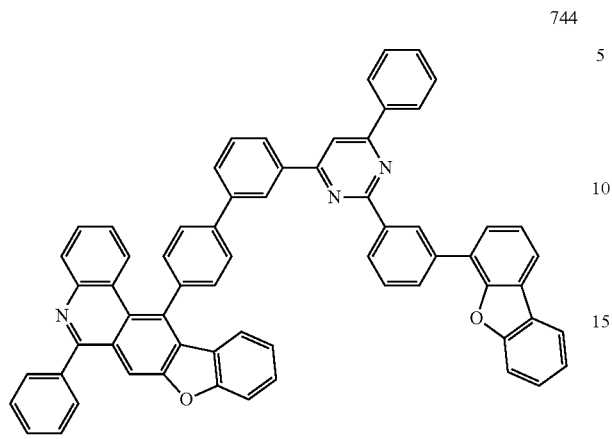
1022
-continued
746
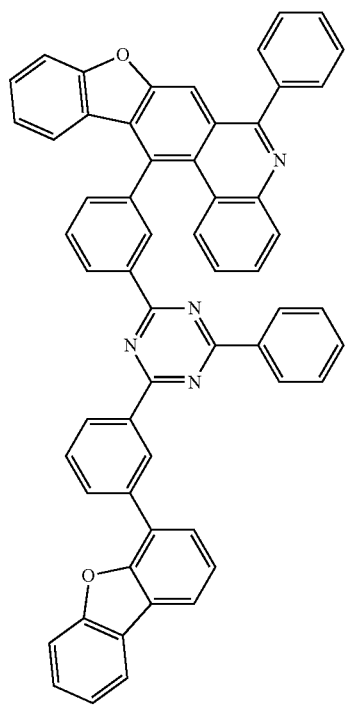
745
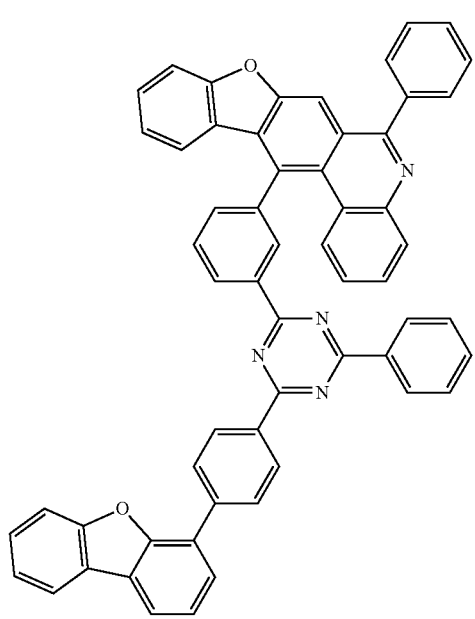
747
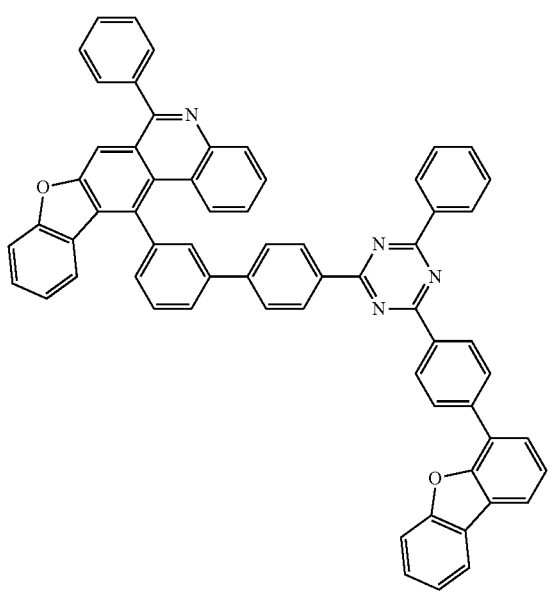

1023
-continued
1024
-continued
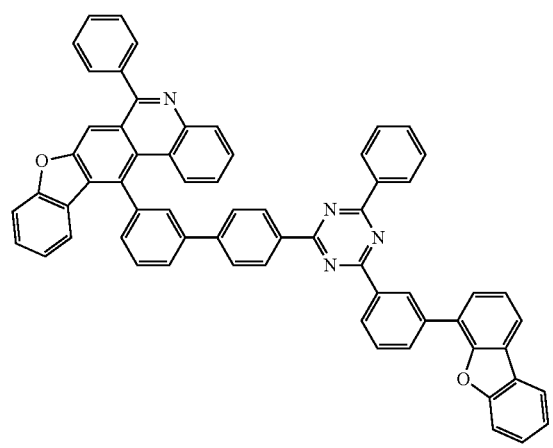
748
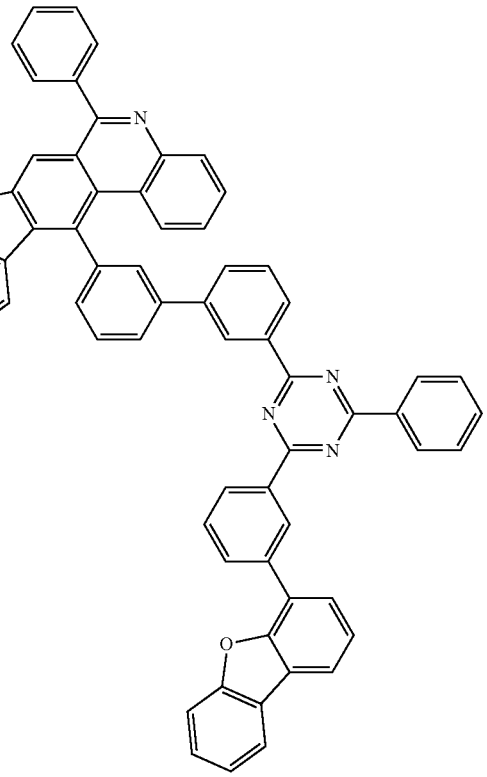
750
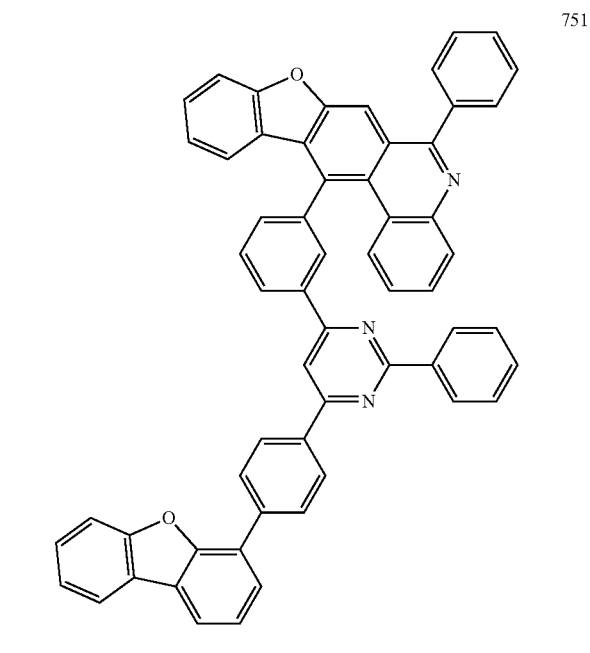
751
749

1025
-continued
752
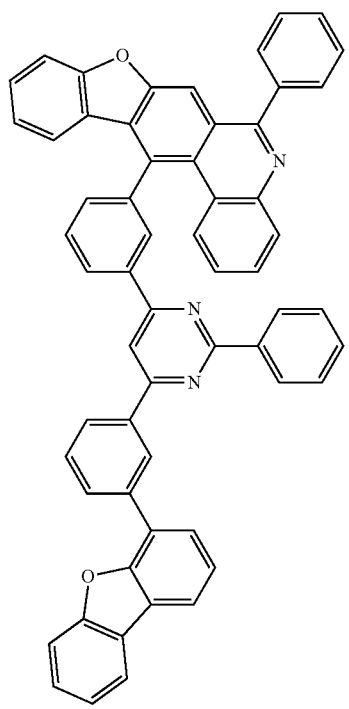
1026
-continued
754
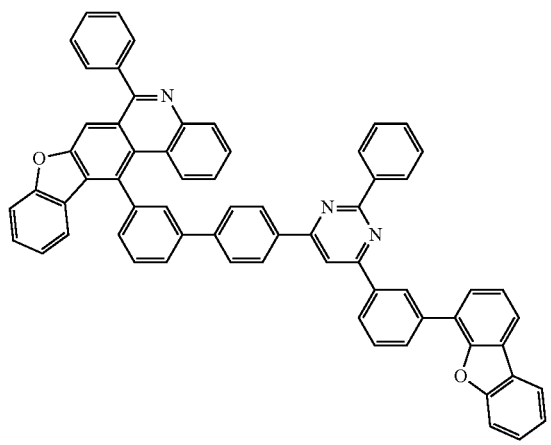
753
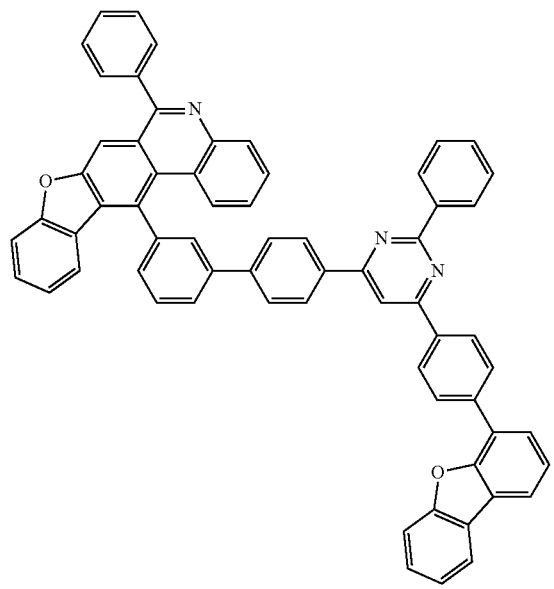
755
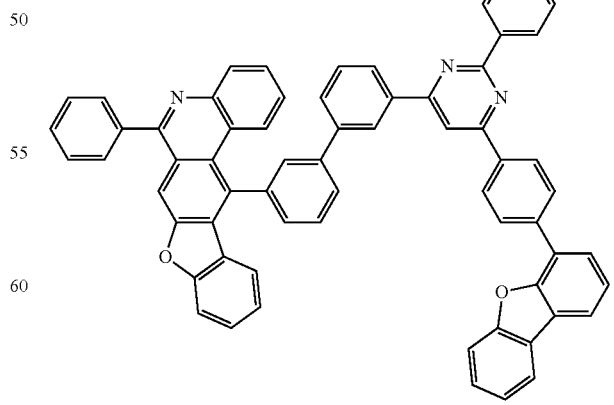

1027
-continued
756
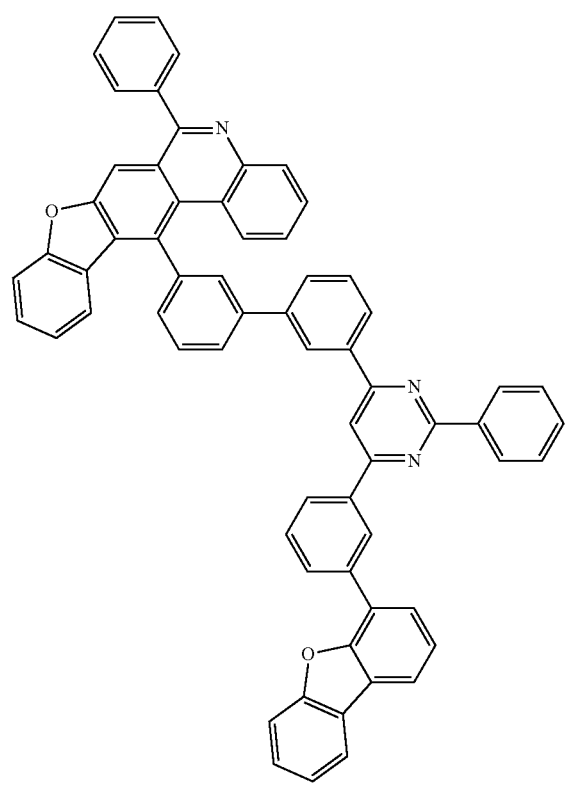
1028
-continued
758
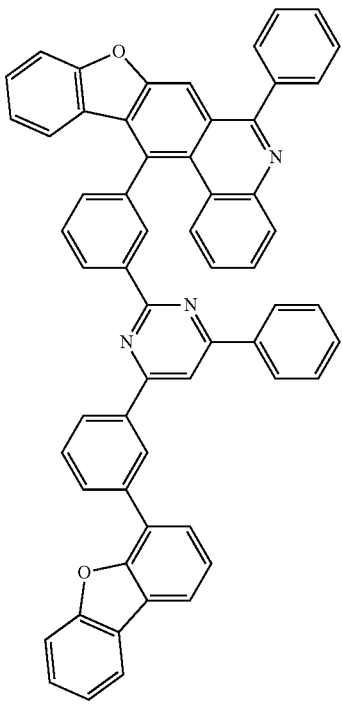
757
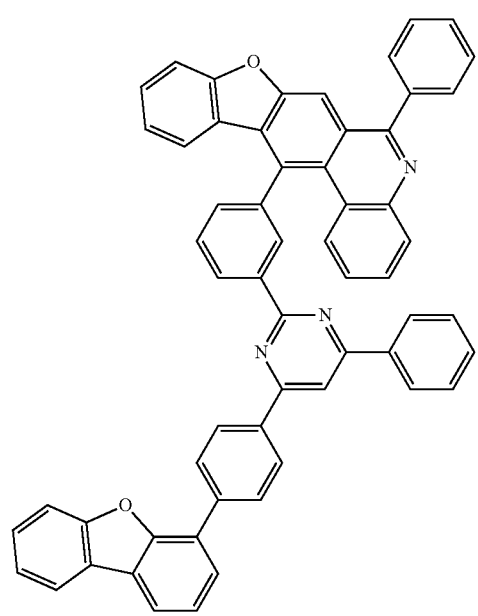
759
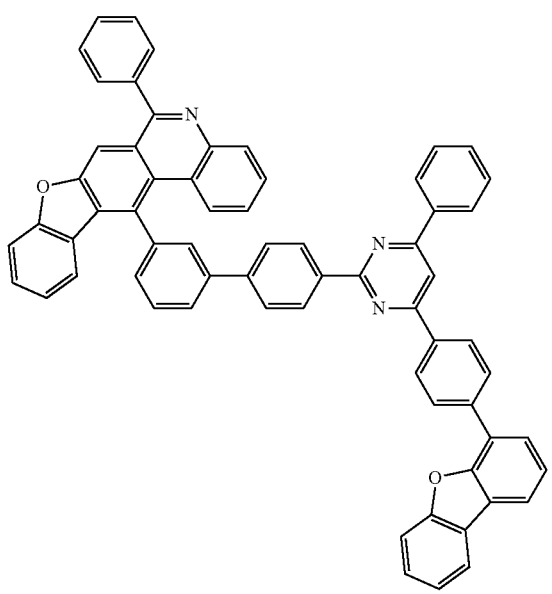

1029
-continued
1030
-continued
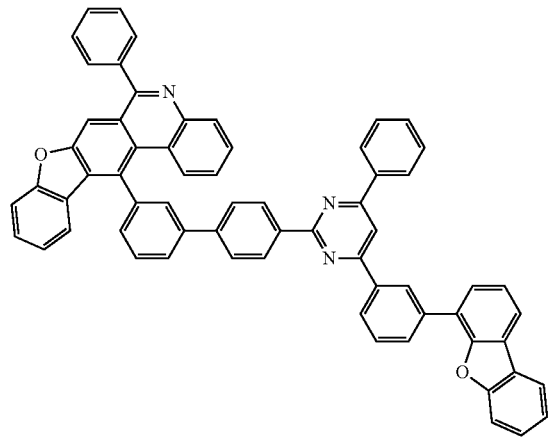
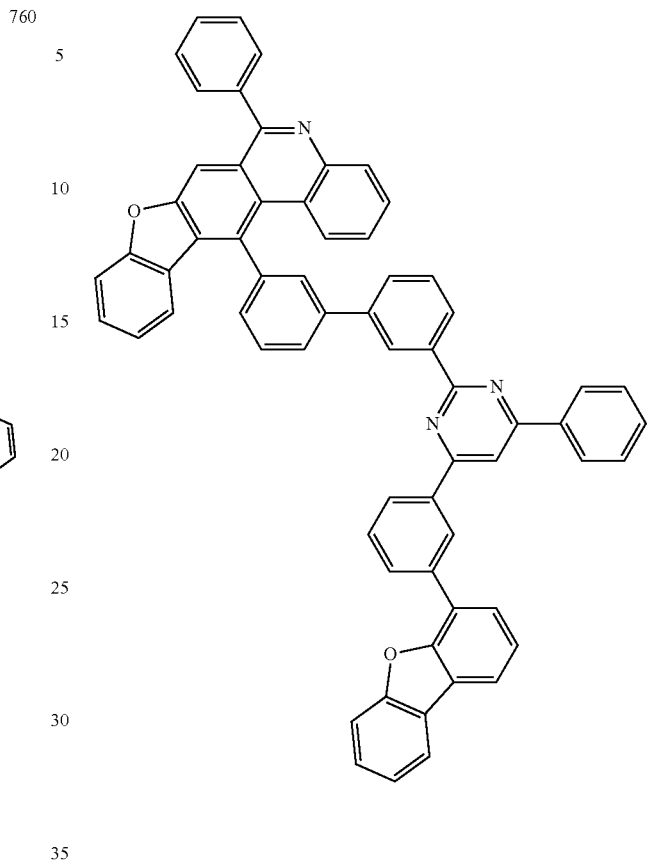

1031
-continued
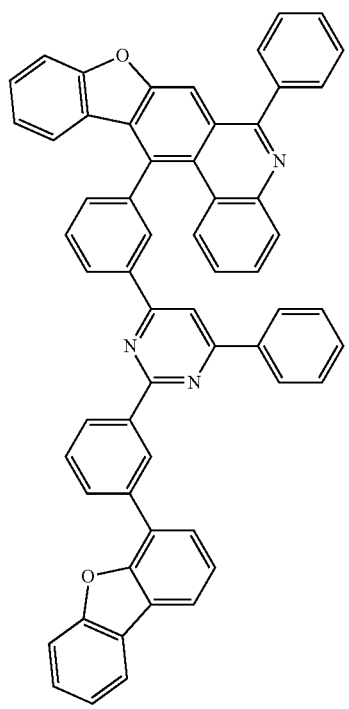
764
1032
-continued
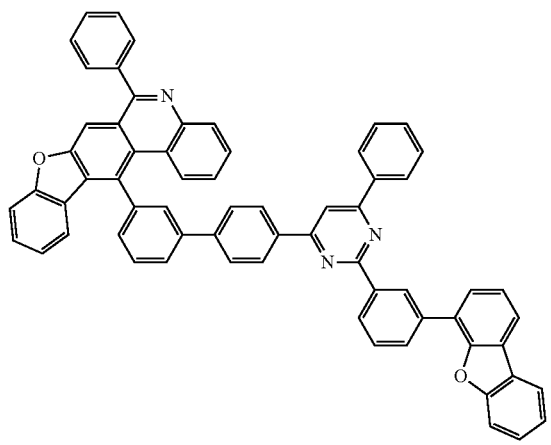
766
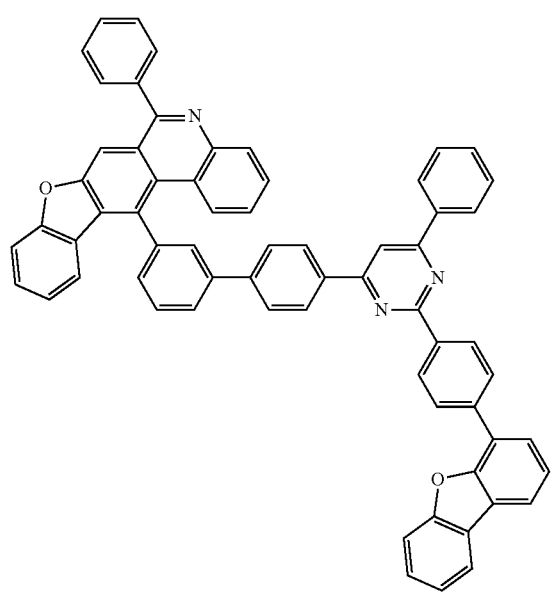
765
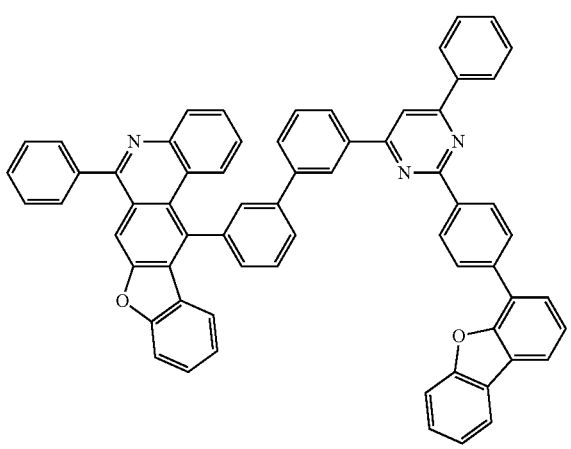
767

1033
-continued
1034
-continued
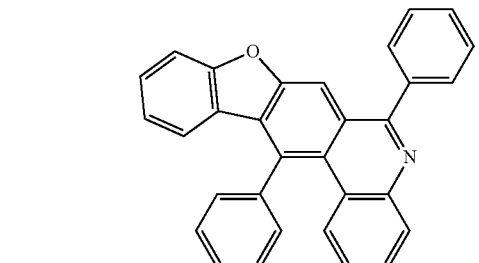
770
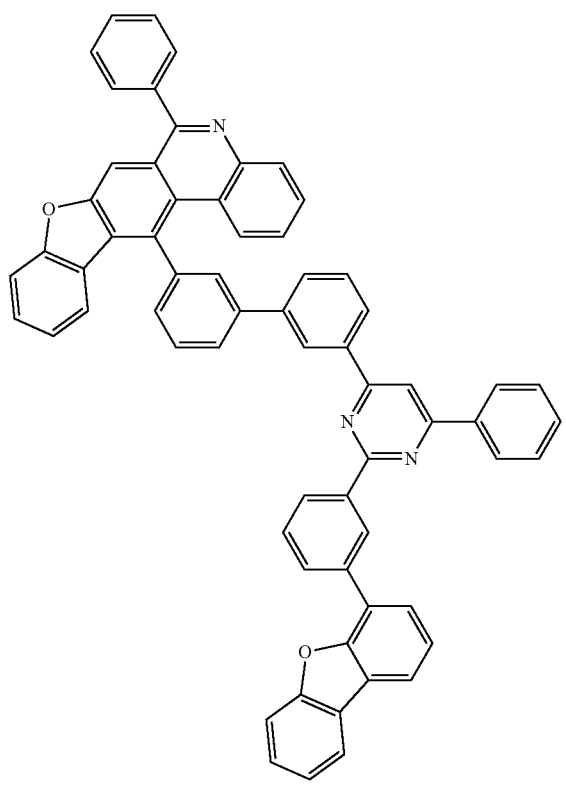
768
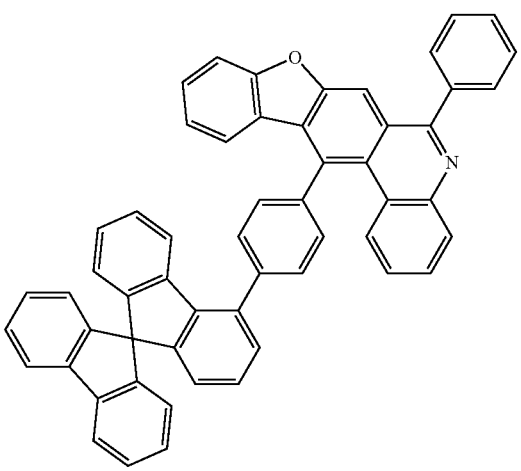
771
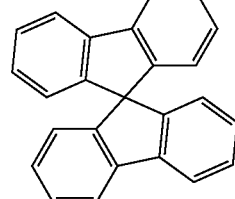
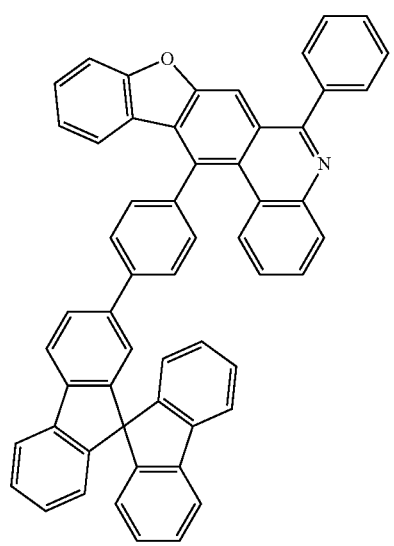
769
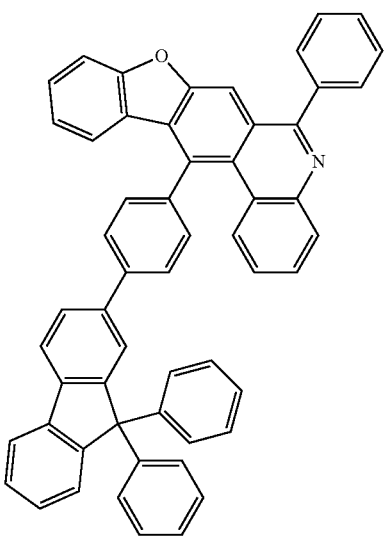
772

1035
-continued
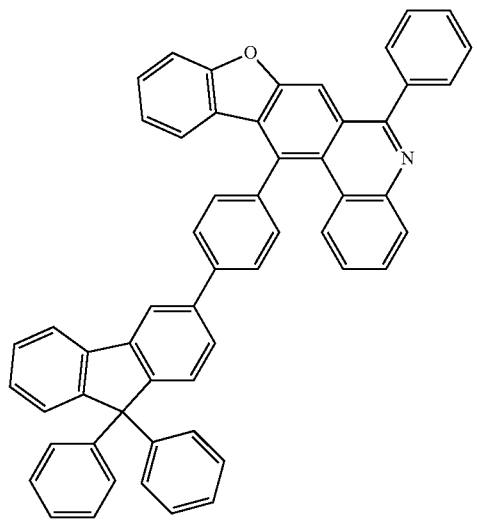
773
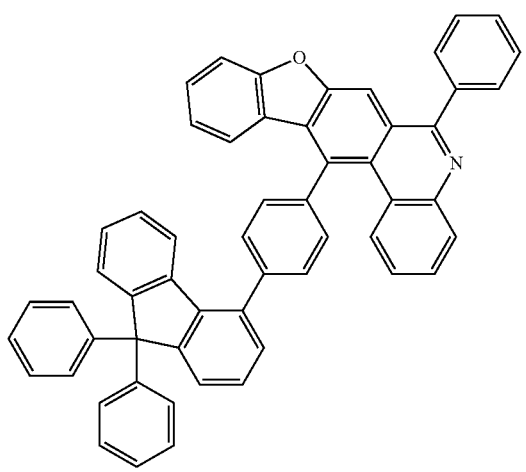
774
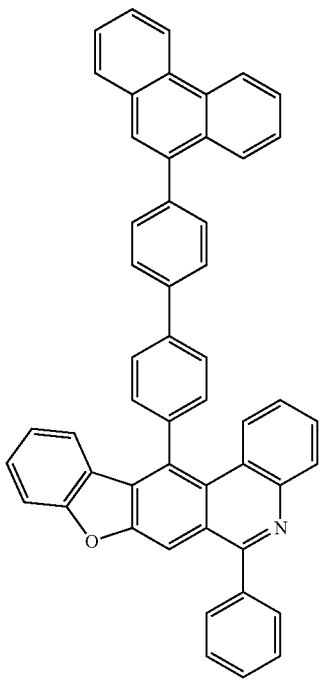
775
1036
-continued
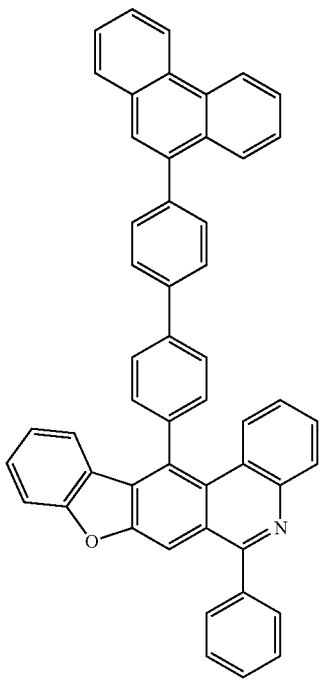
776
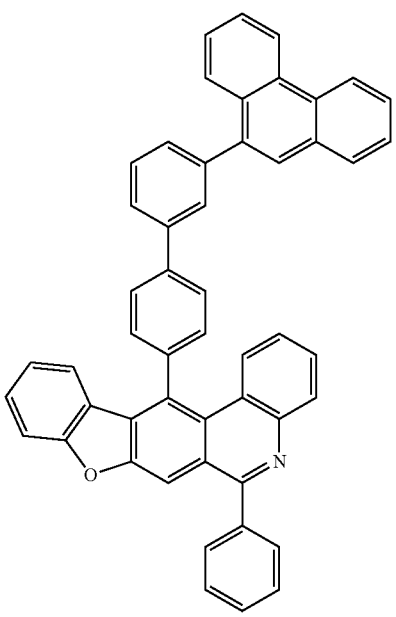
777

1037
-continued
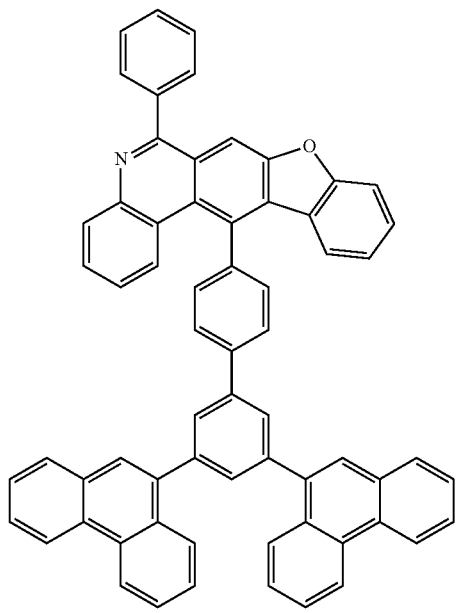
778
1038
-continued
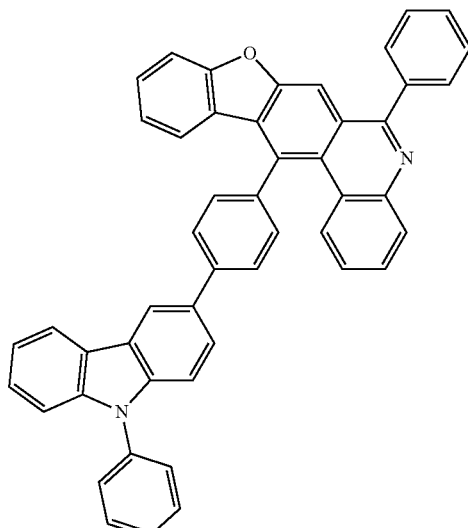
780
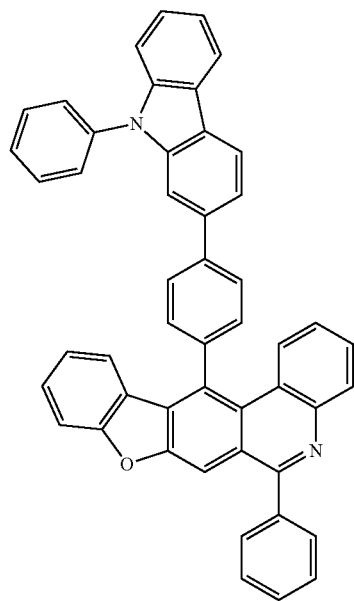
779
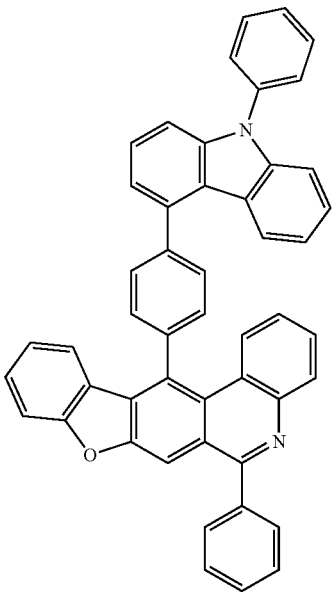
781

1039
-continued
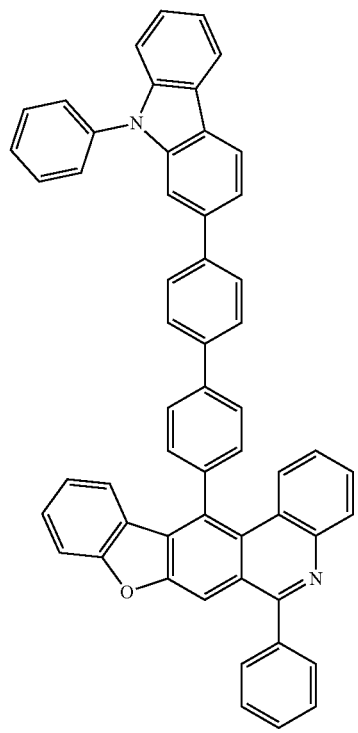
782
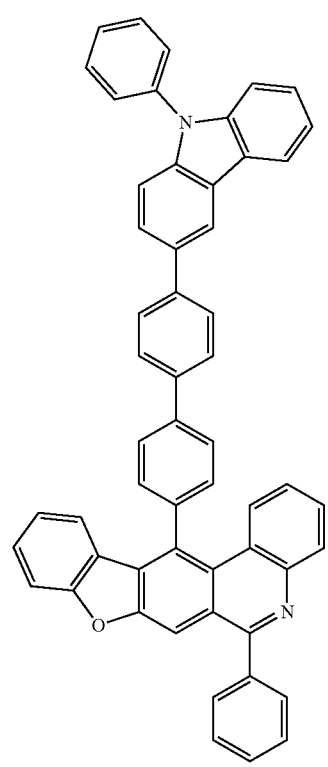
783
1040
-continued
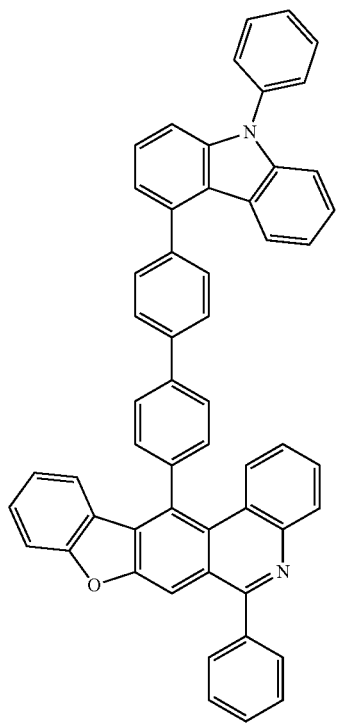
784
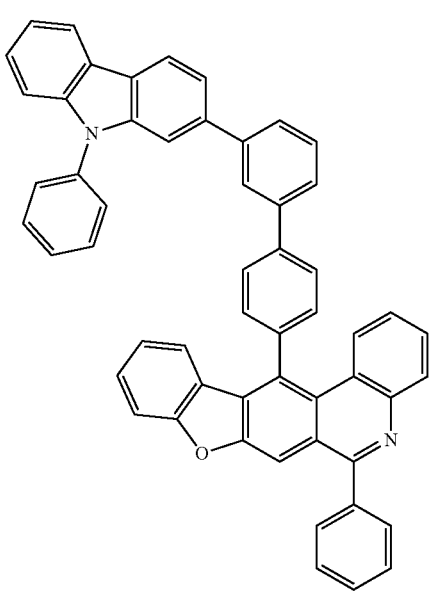
785

1041
-continued
786
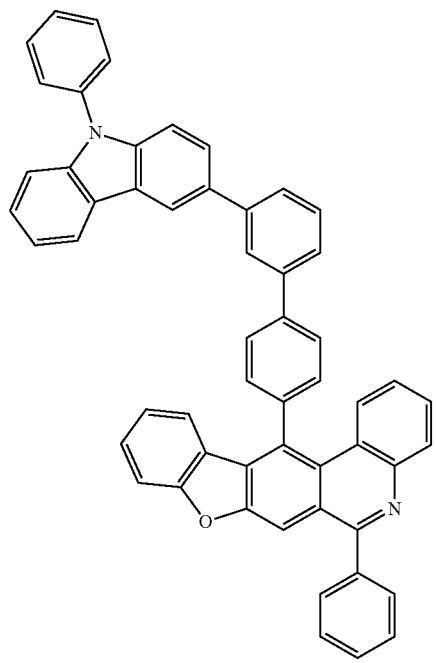
787
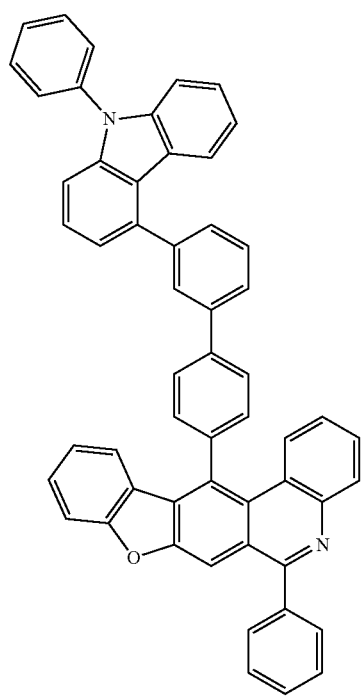
1042
-continued
788
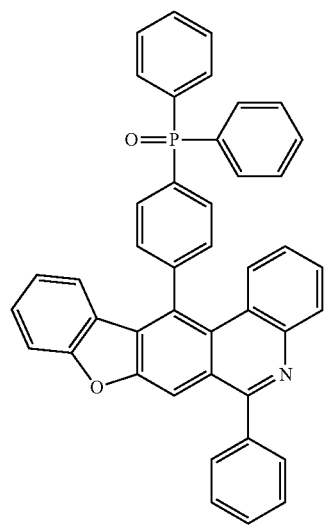
789
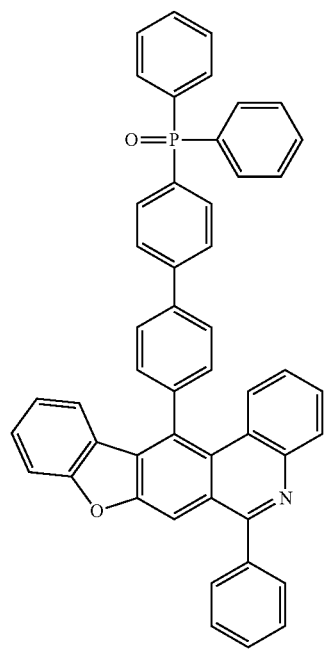

790
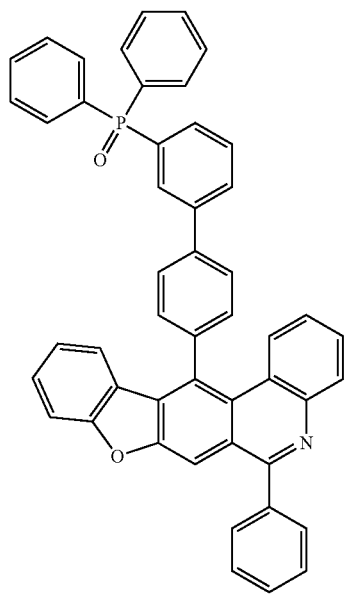
791
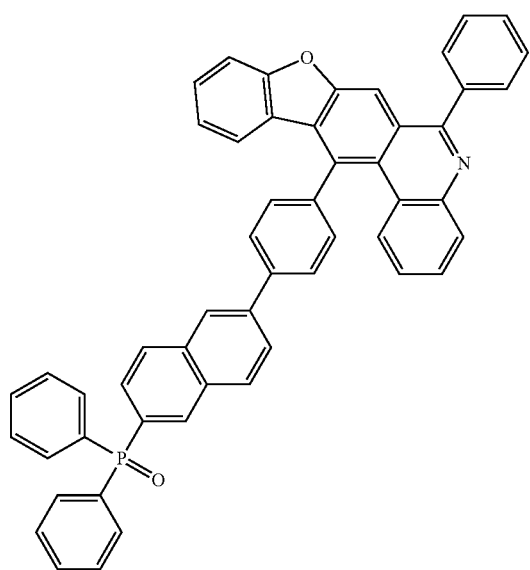
792
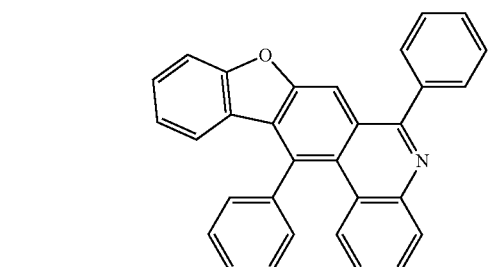
793
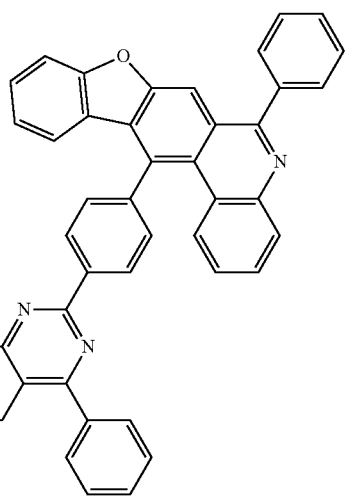
794
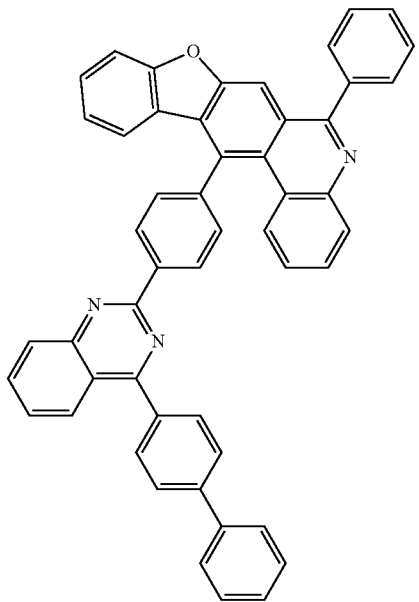

1045
-continued
795
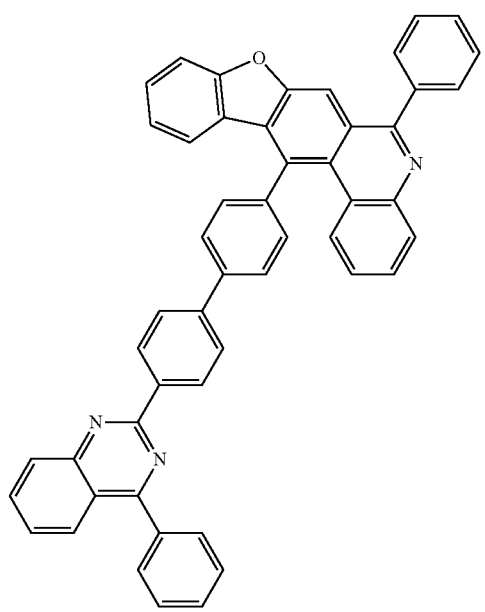
796
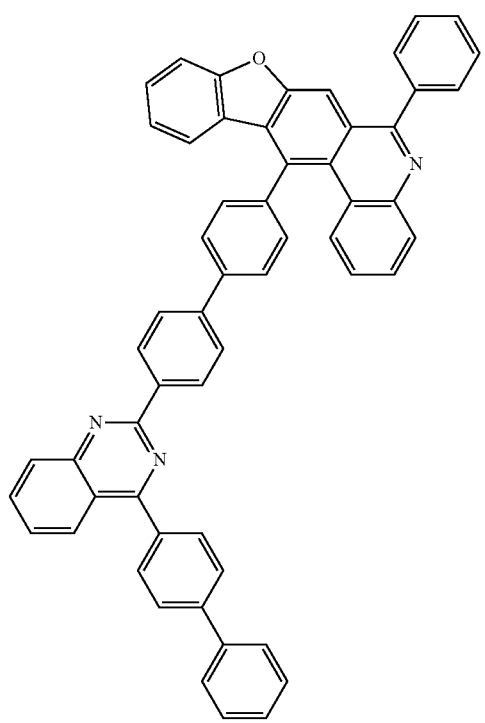
1046
-continued
797
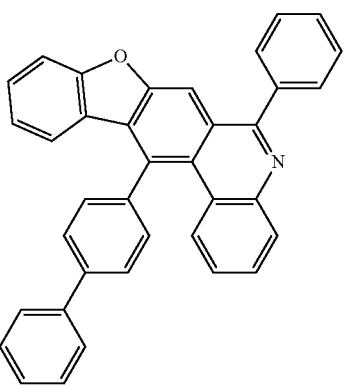
798
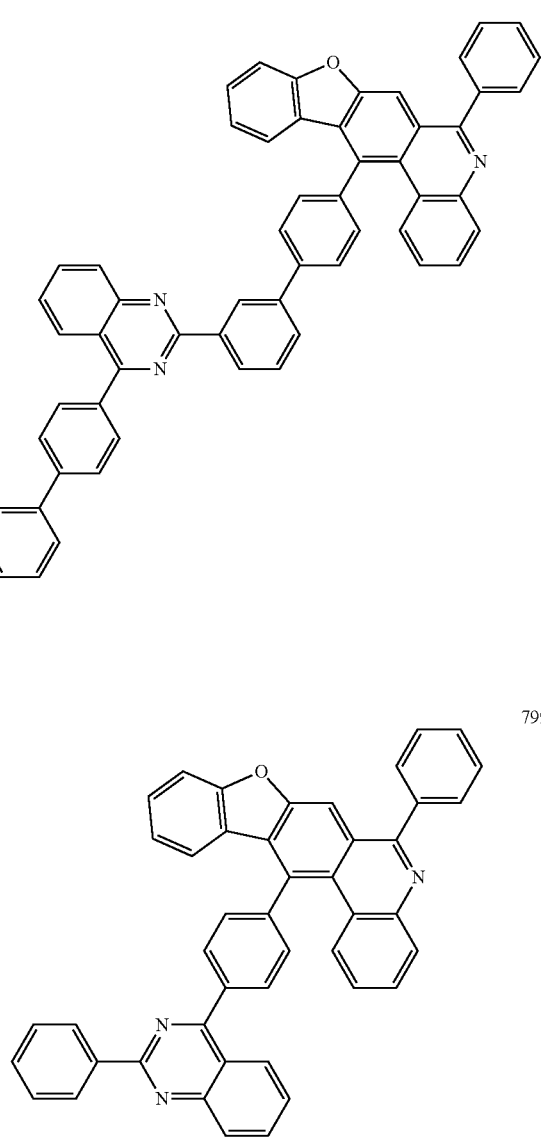
799

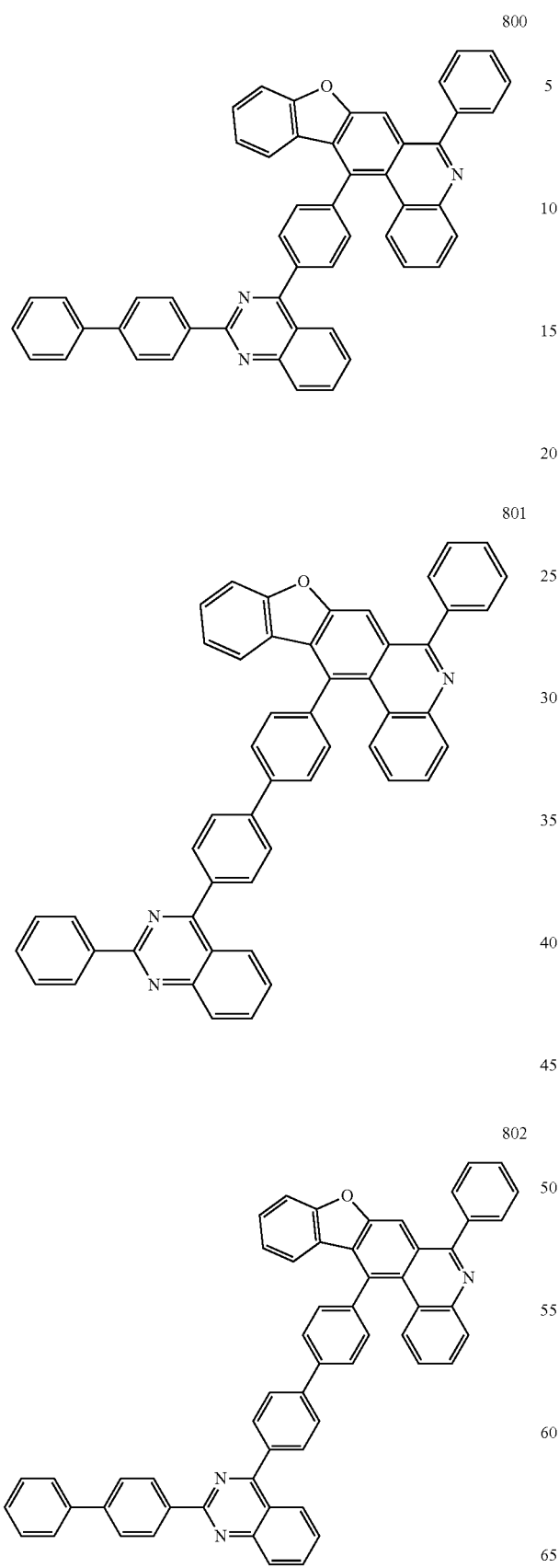
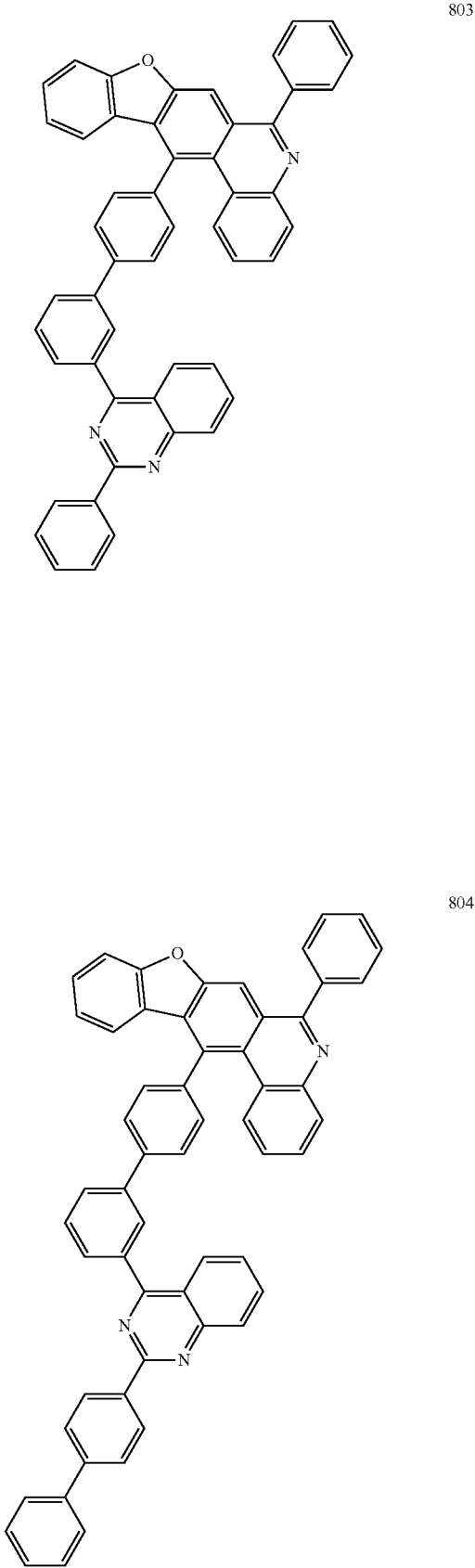

1049
-continued
1050
-continued
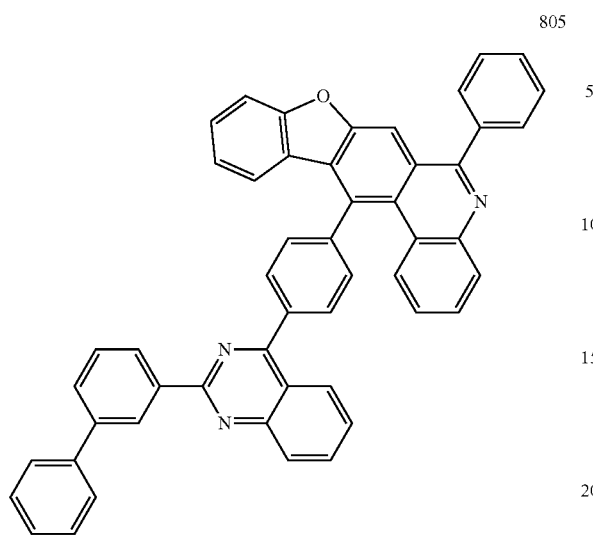
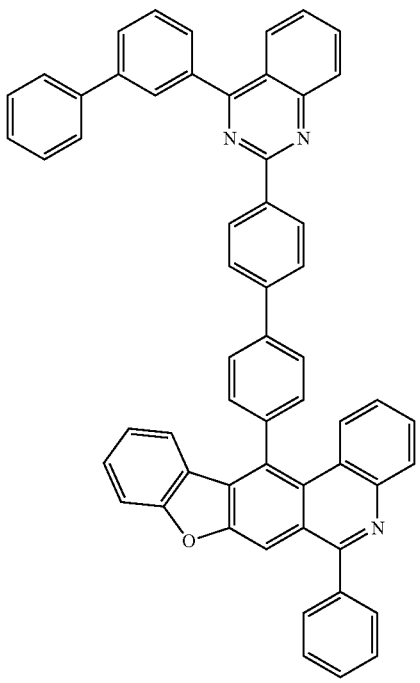
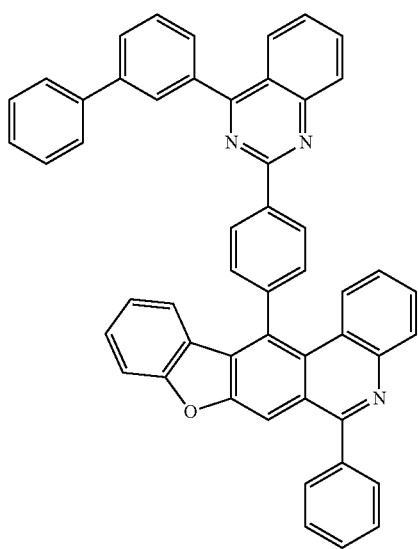
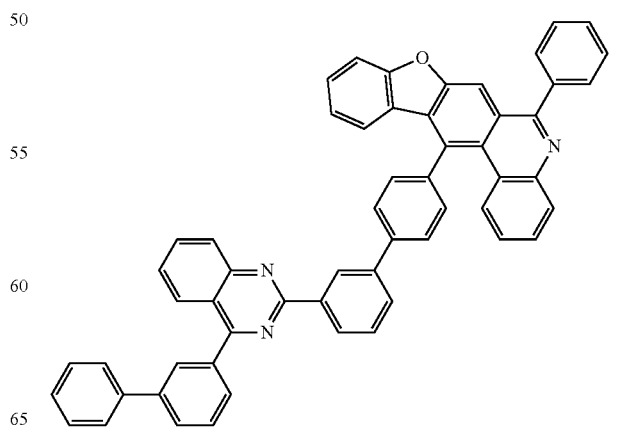

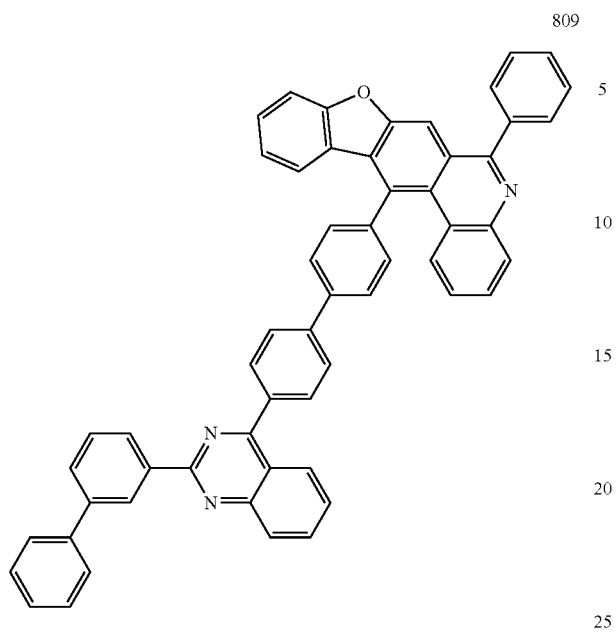
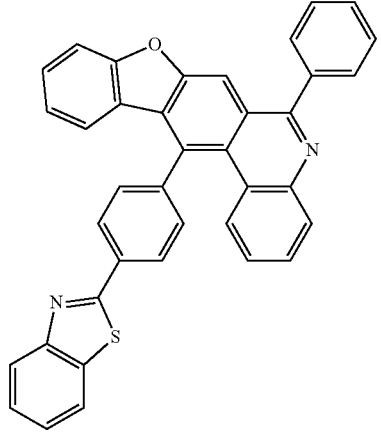
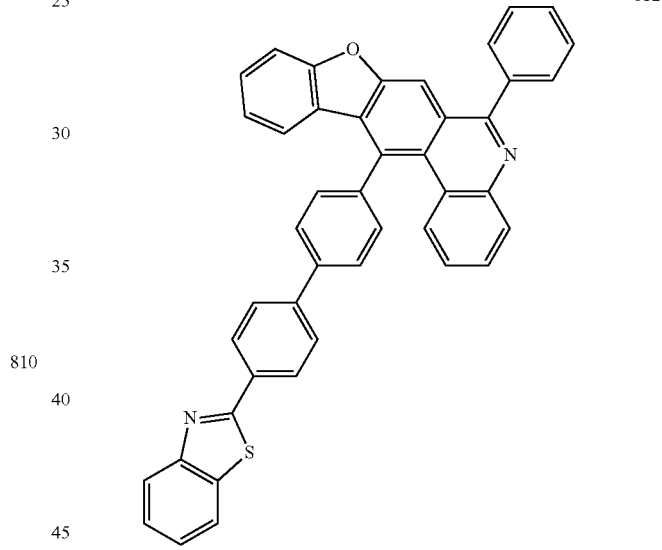
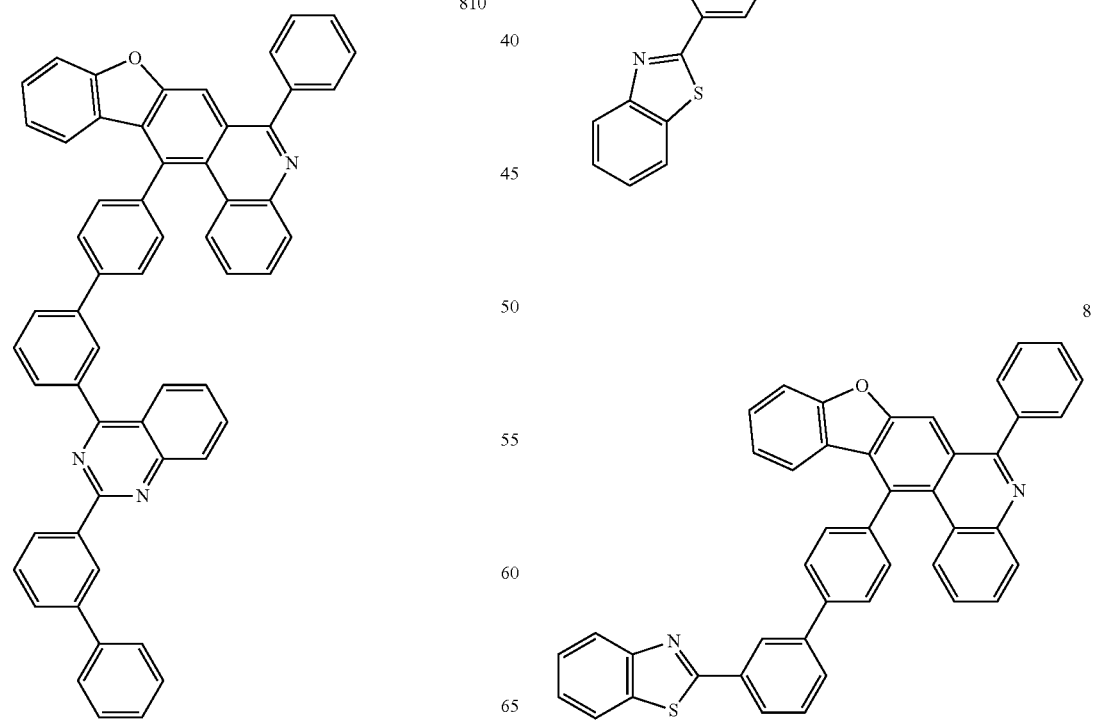

1053
-continued
814
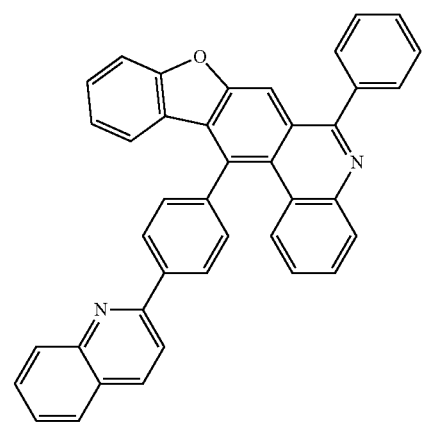
815
816
1054
-continued
817
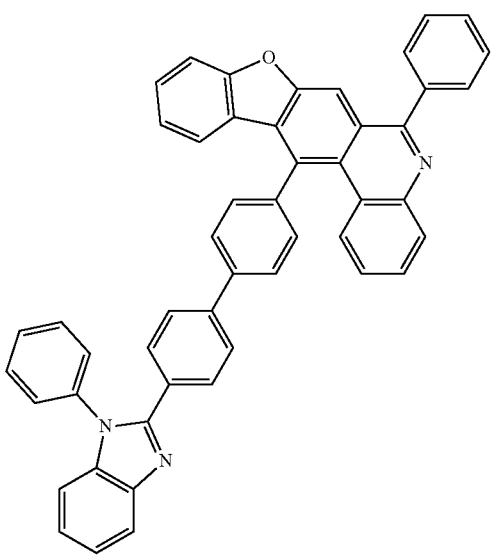
818
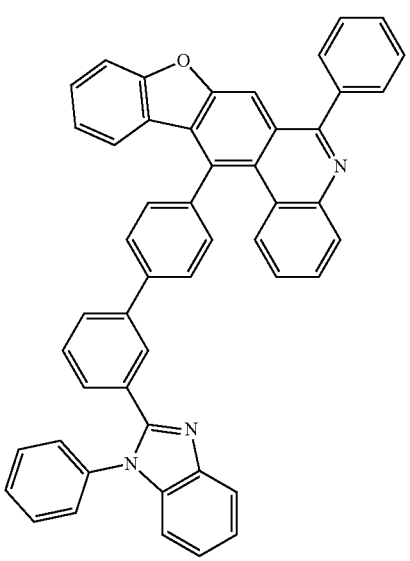
819
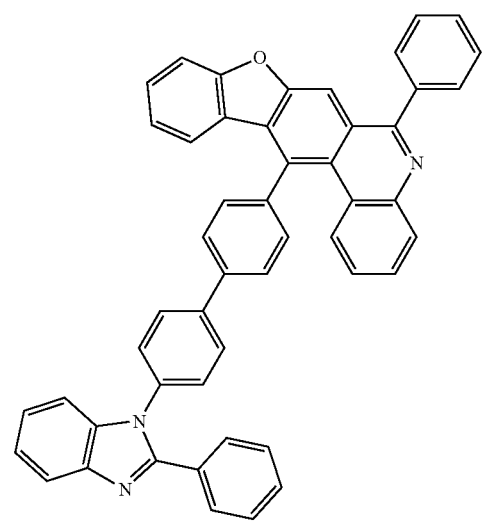

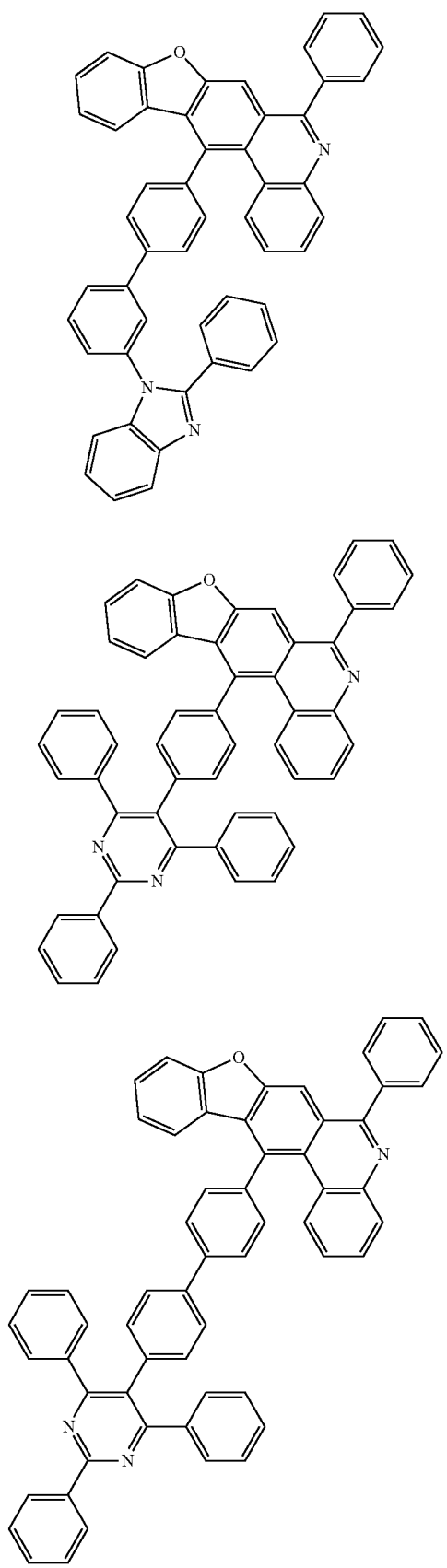
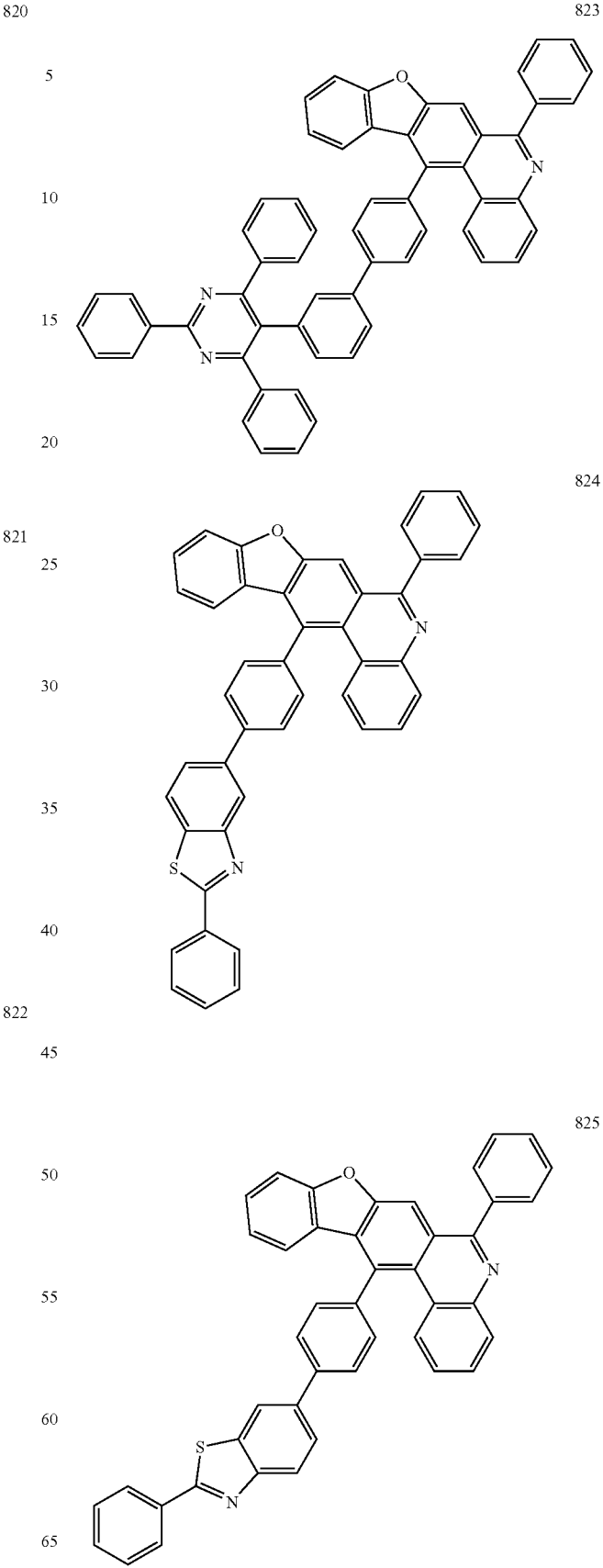

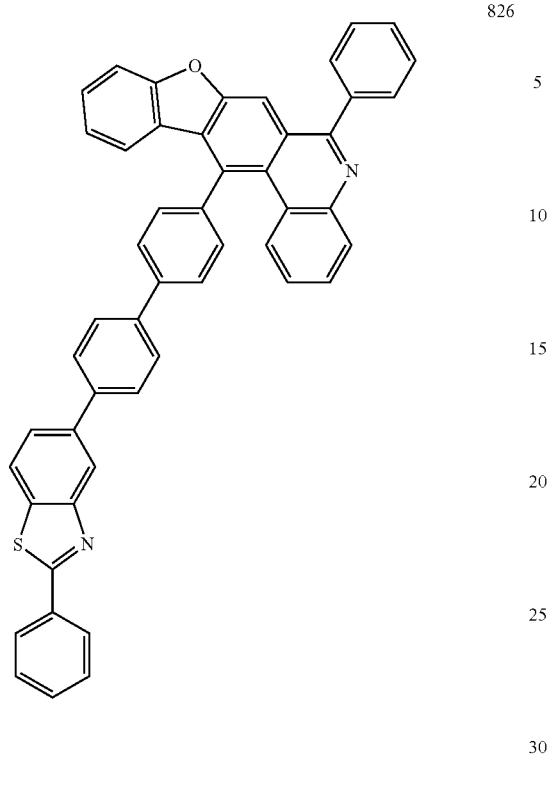
826
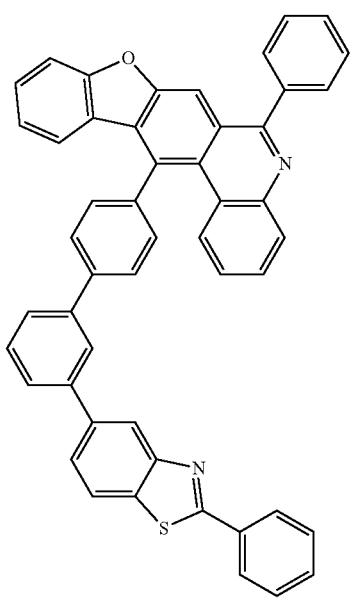
828
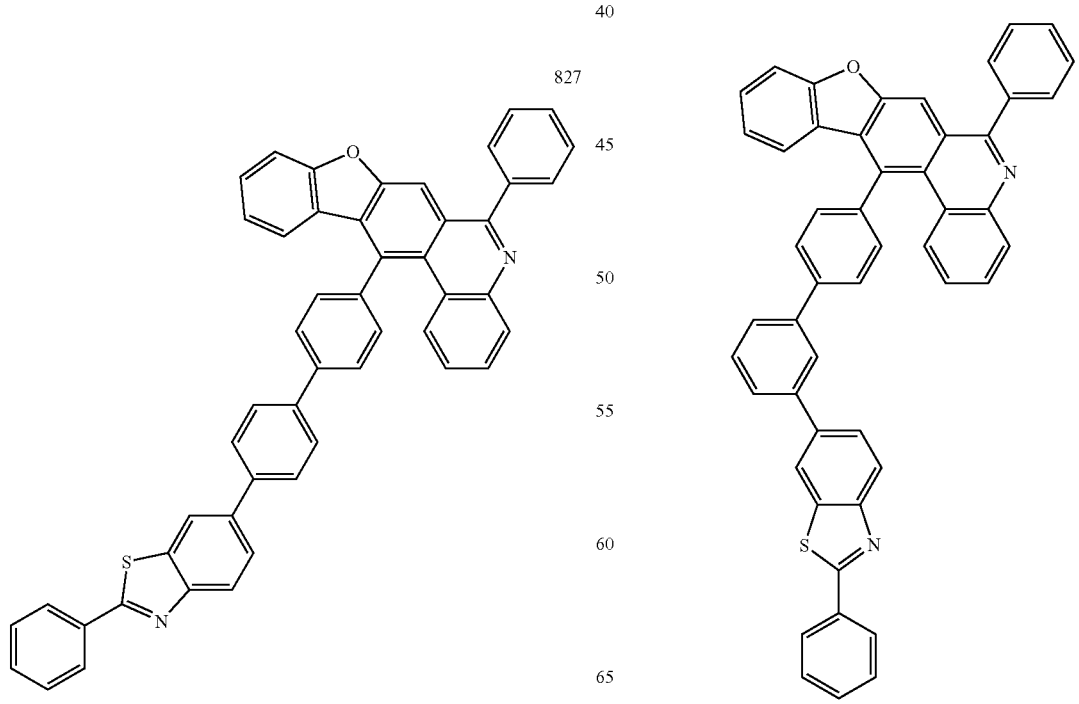
827
829

1059
-continued
830
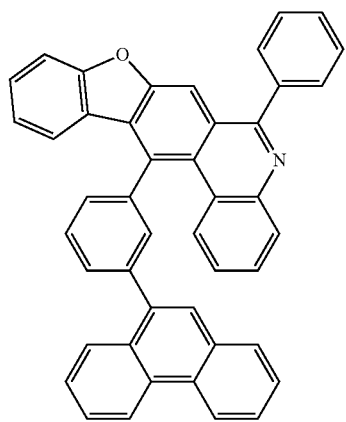
831
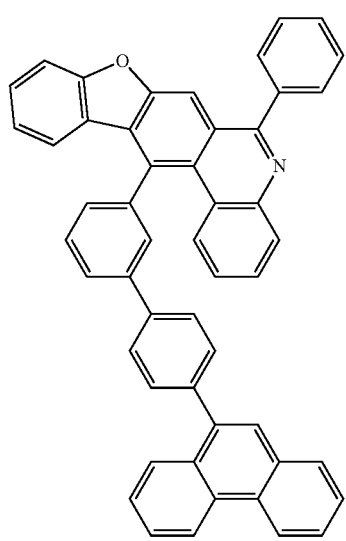
832
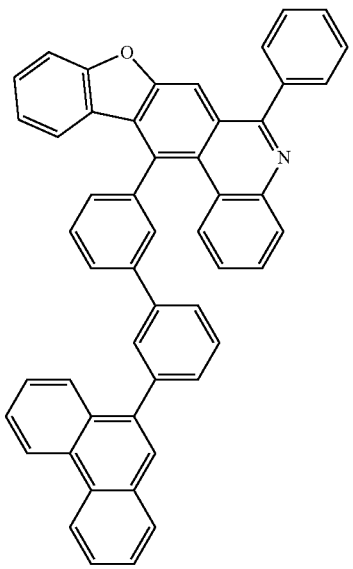
1060
-continued
833
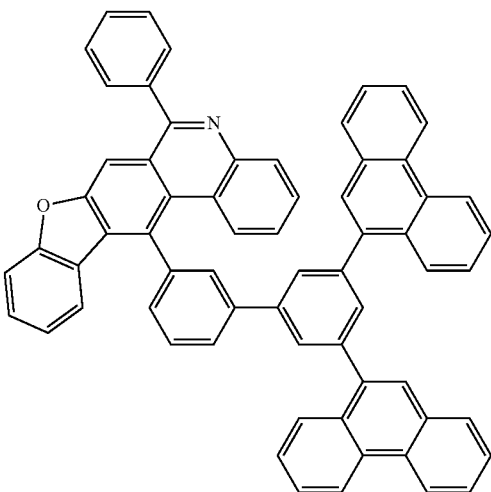
834
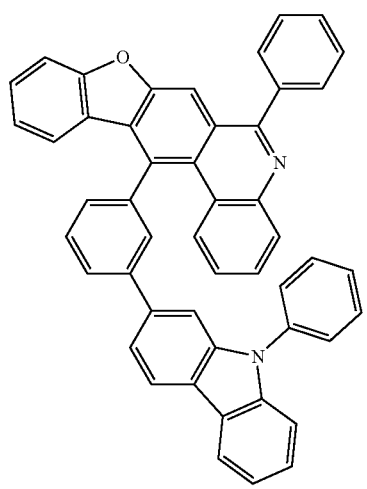
835
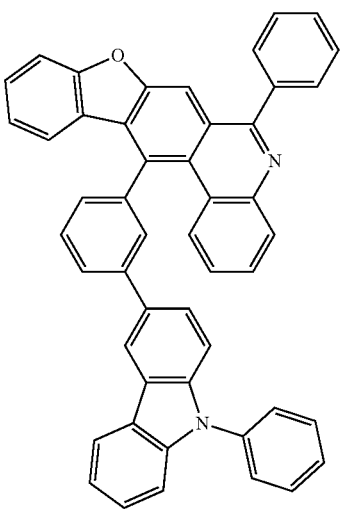

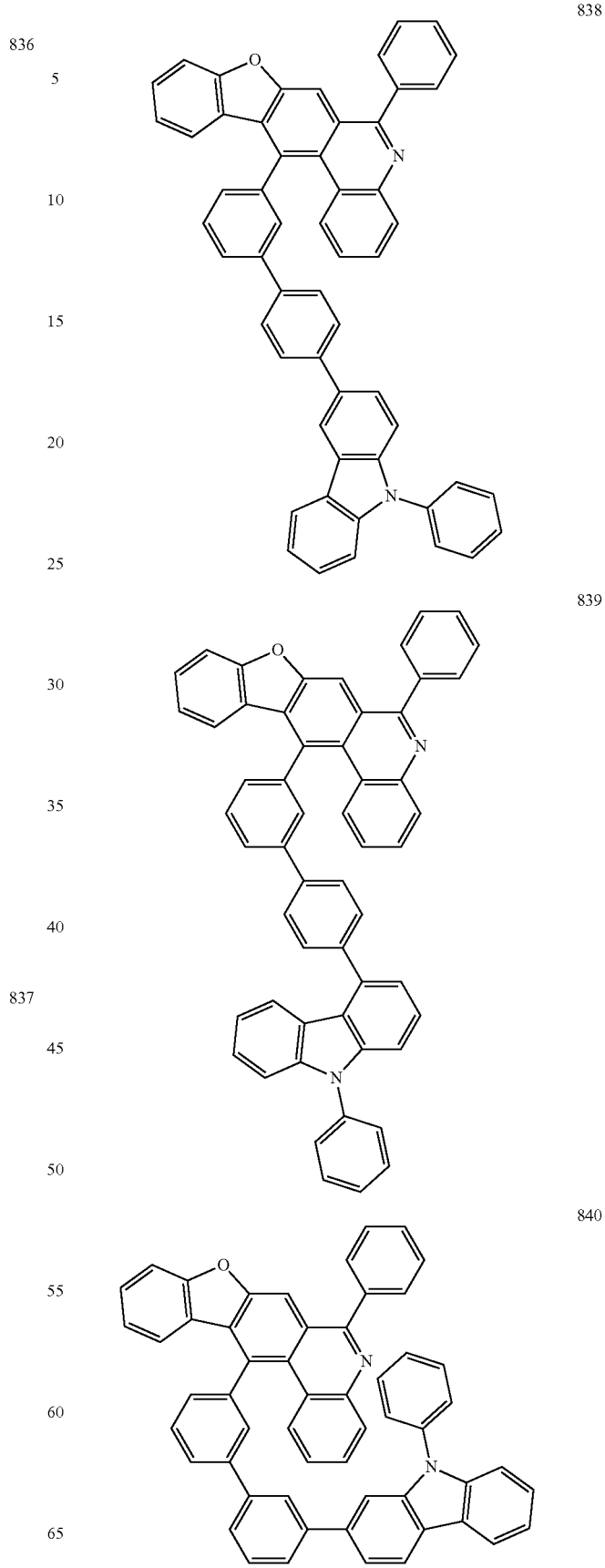

841
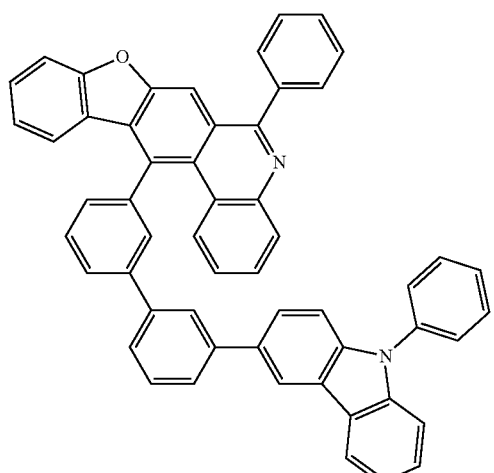
842
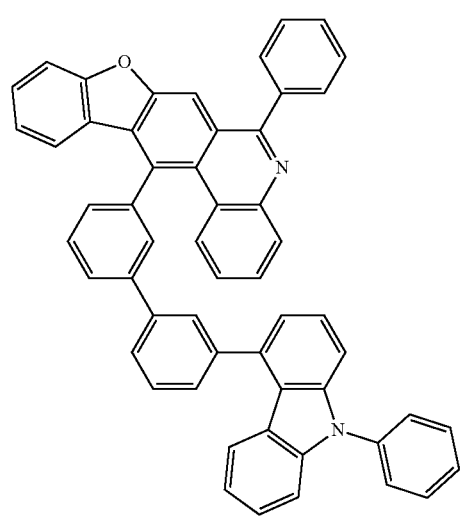
843
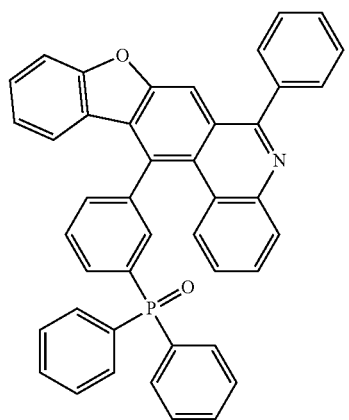
844
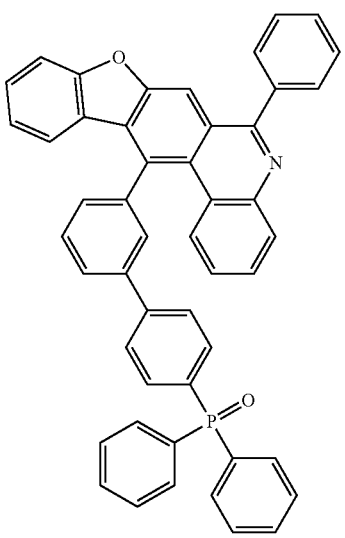
845
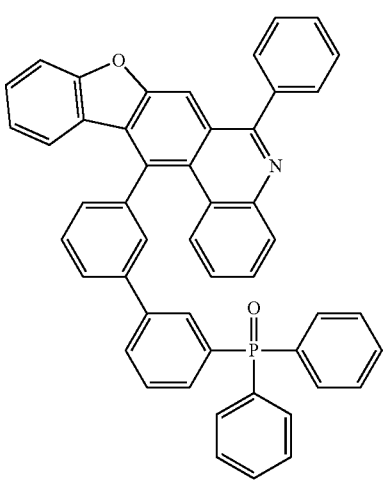
846
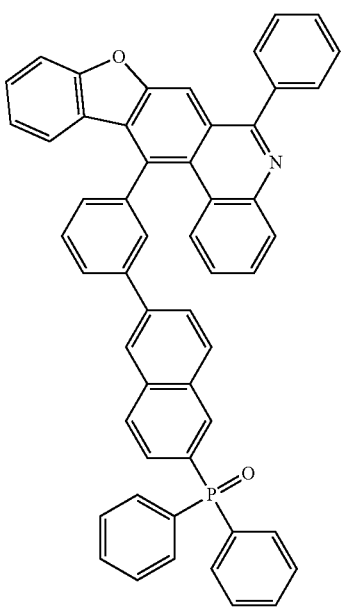

1065
-continued
847
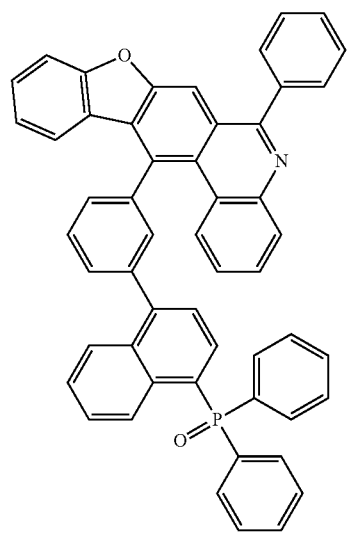
848
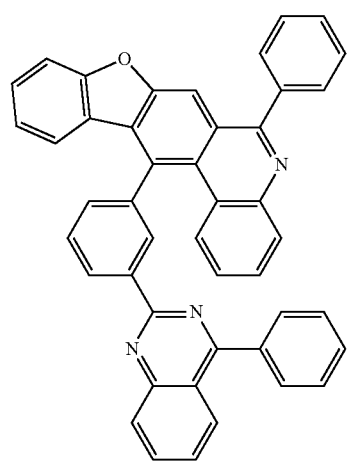
849
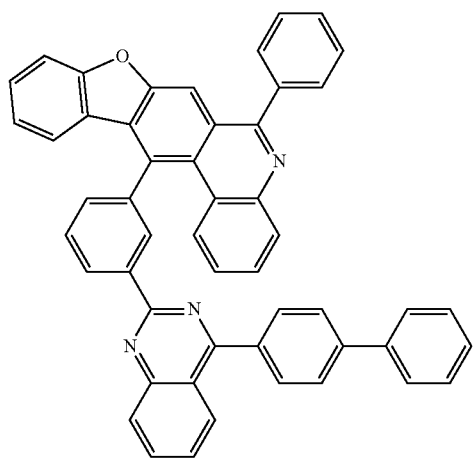
1066
-continued
850
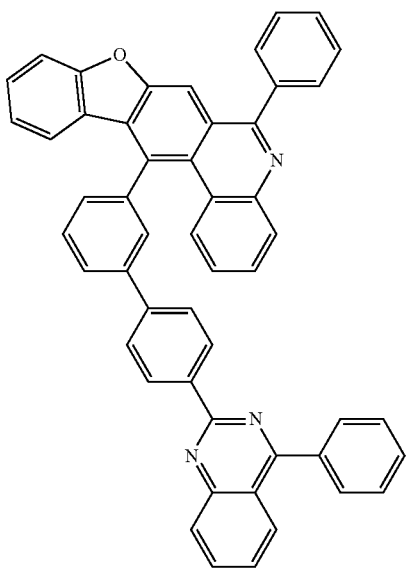
851
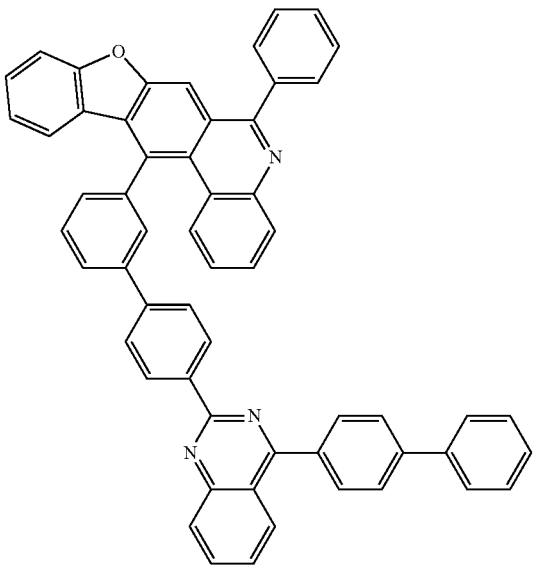

1067
-continued
852
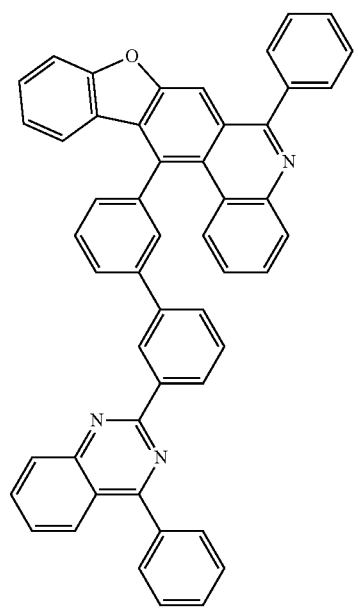
853
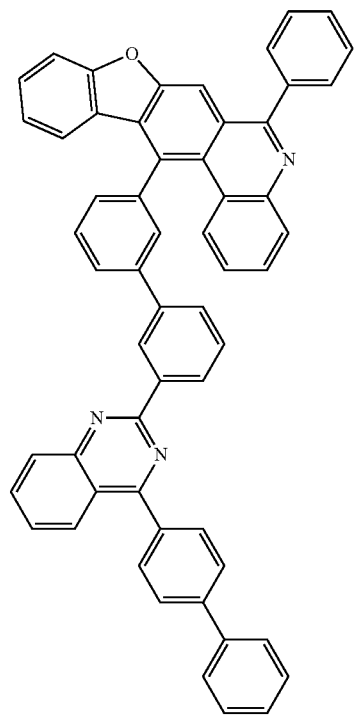
1068
-continued
854
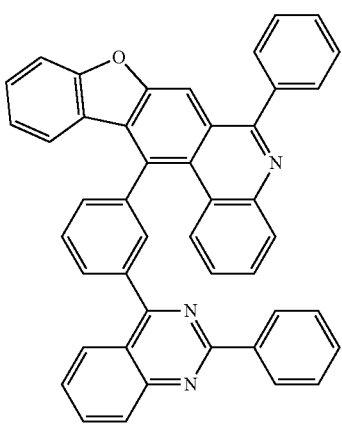
855
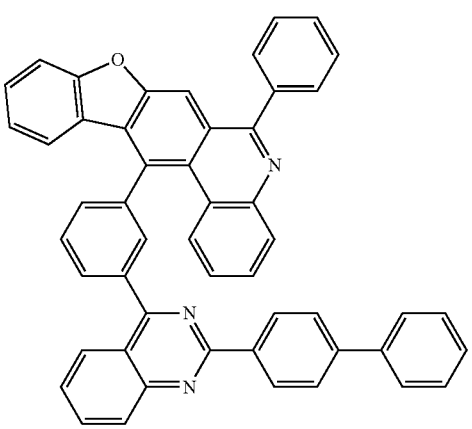
856
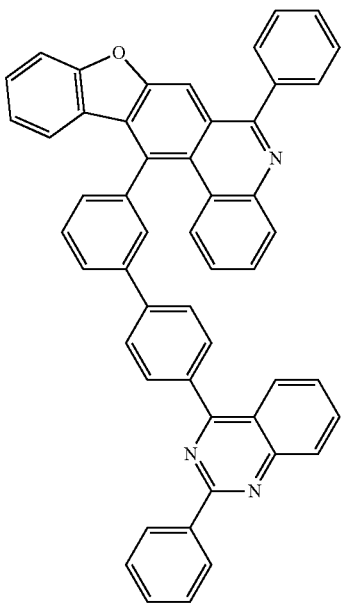

1069
-continued
1070
-continued
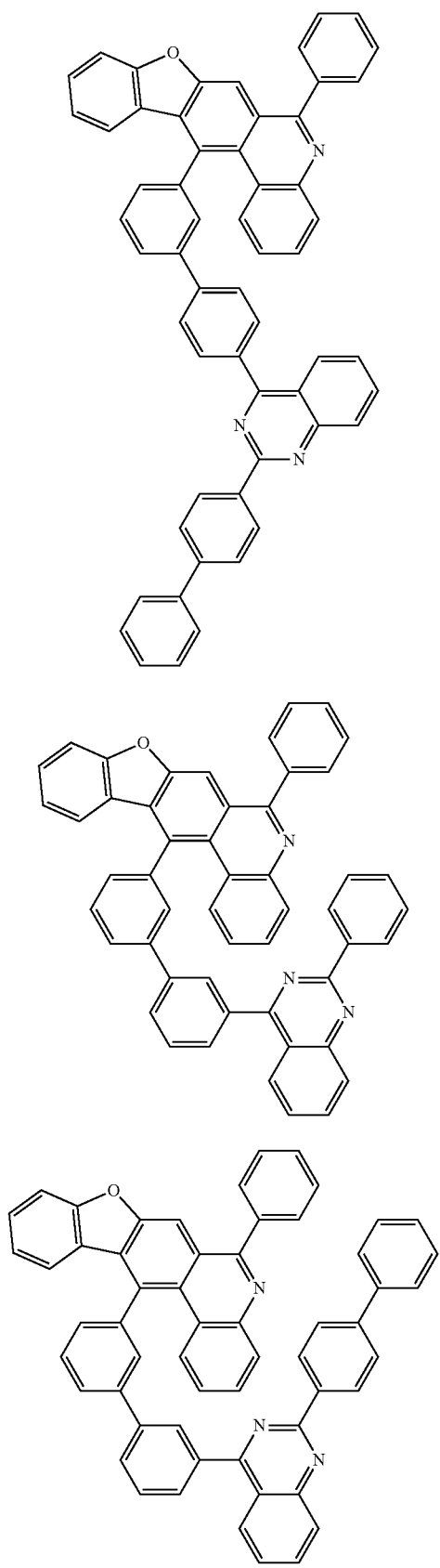
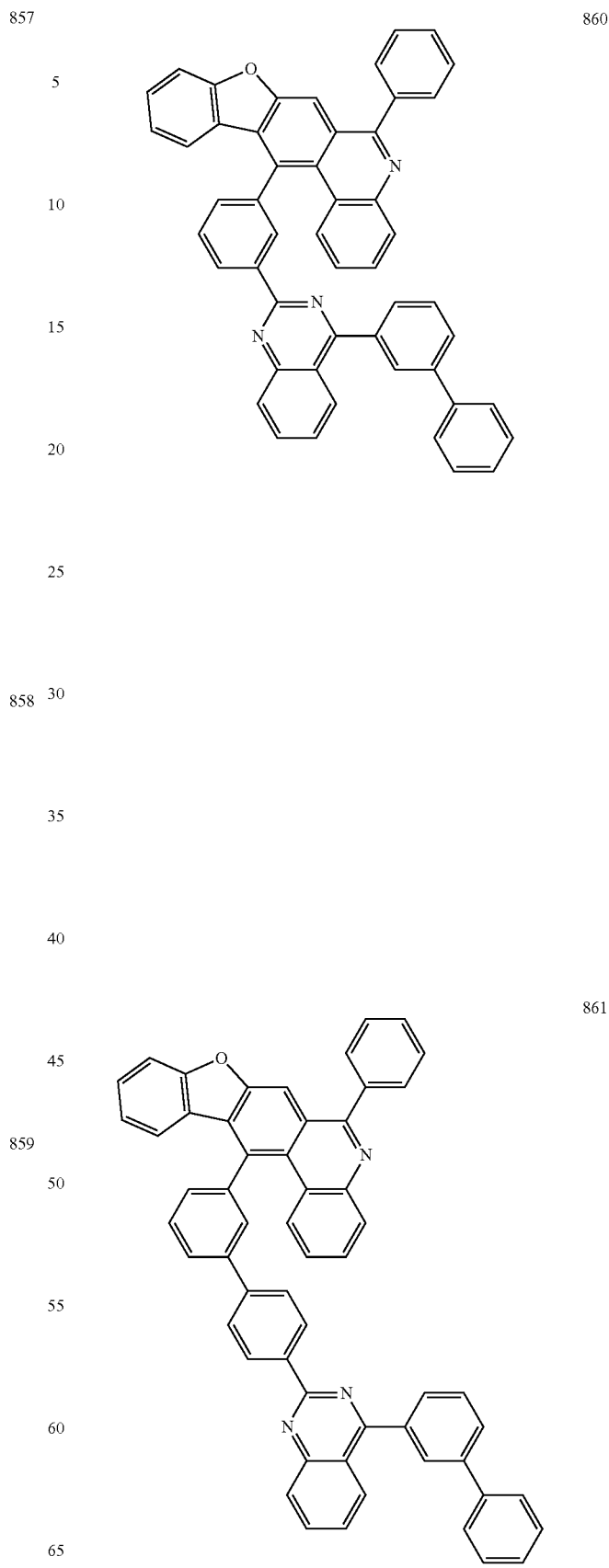

1071
-continued
1072
-continued
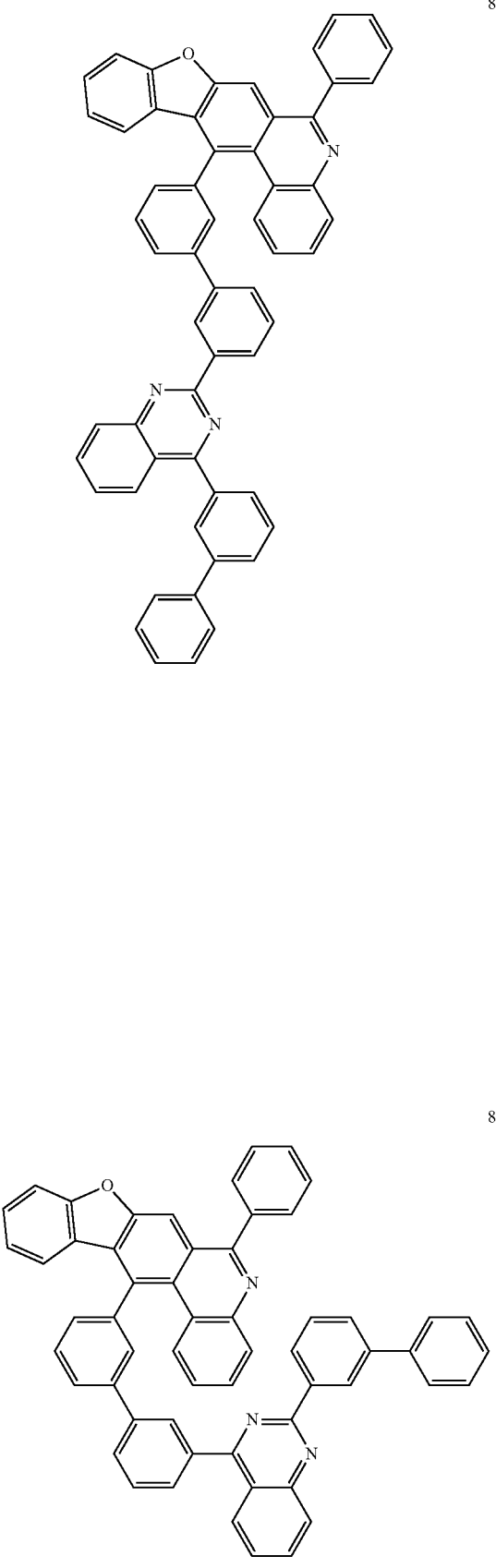
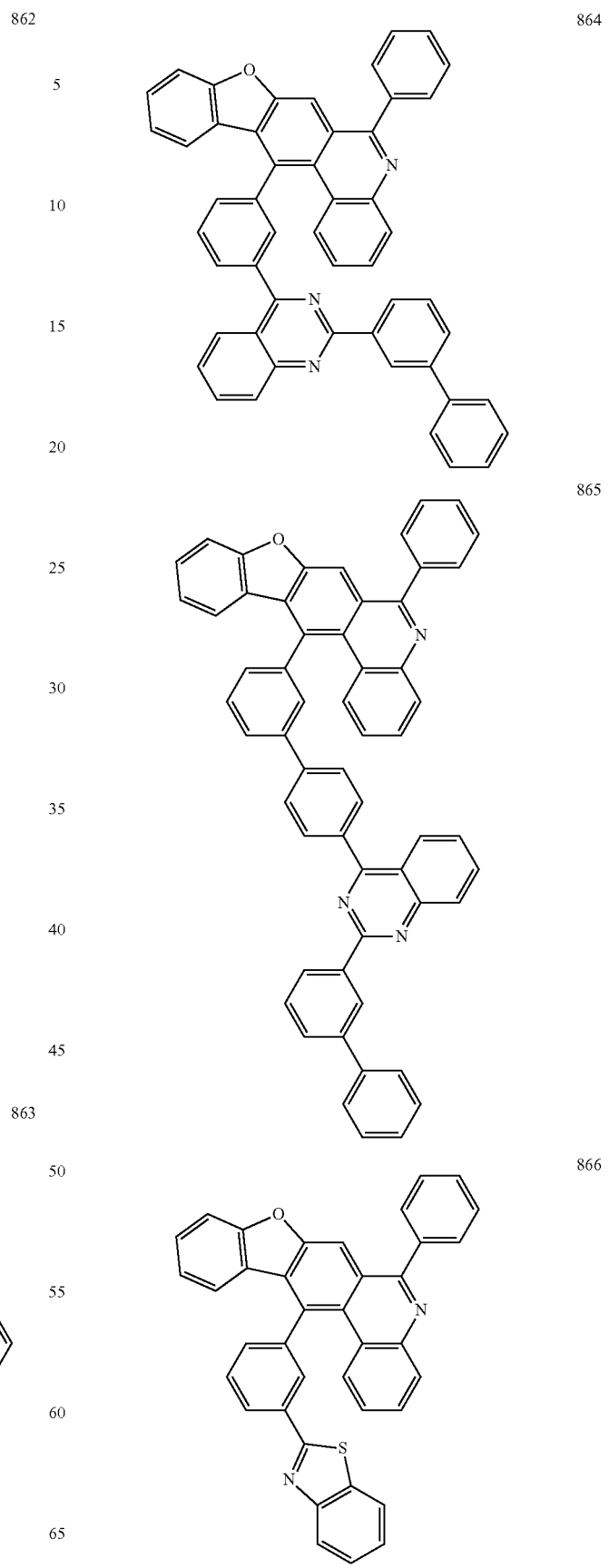

1073
-continued
867
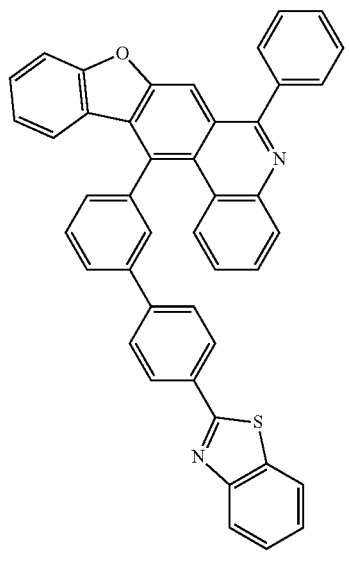
868
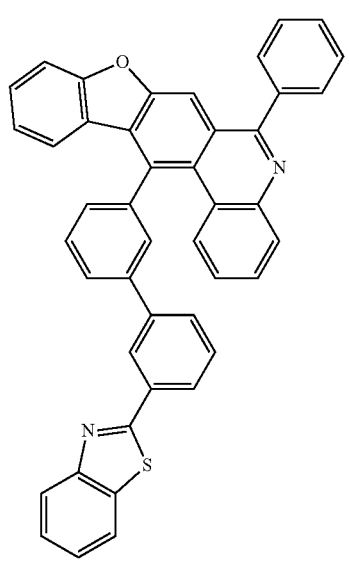
869
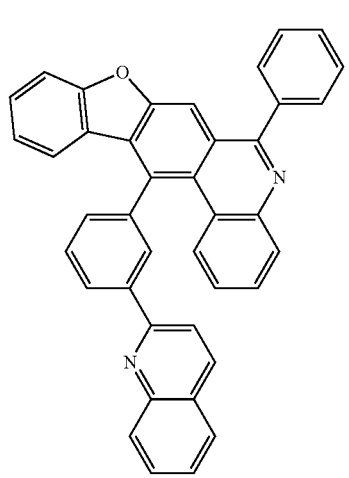
1074
-continued
870
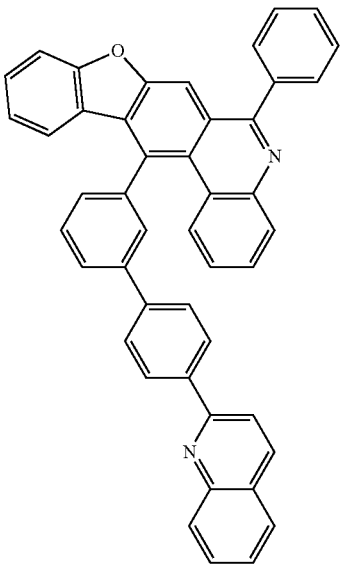
871
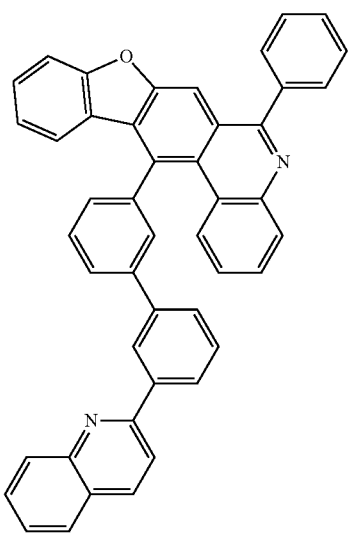
872
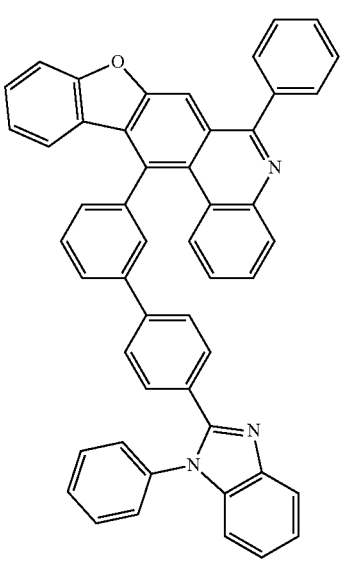

1075
-continued
873
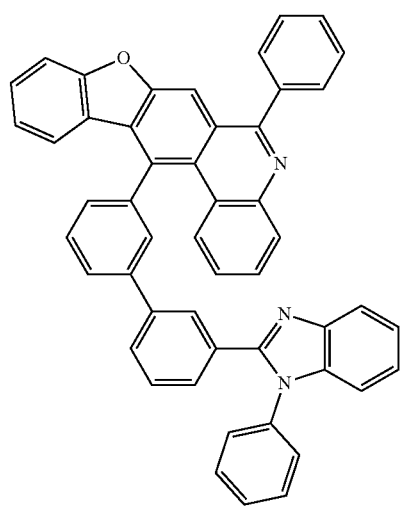
874
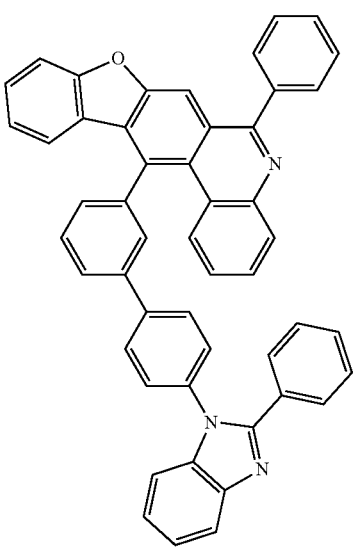
875
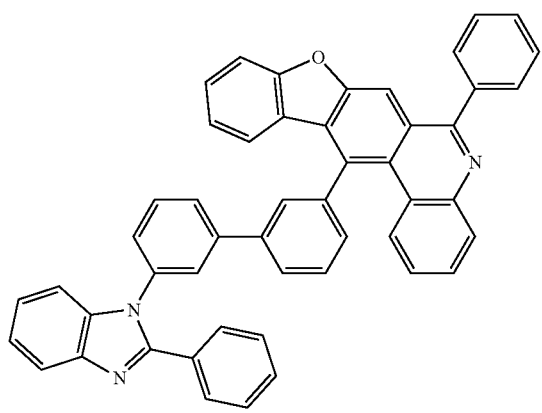
1076
-continued
876
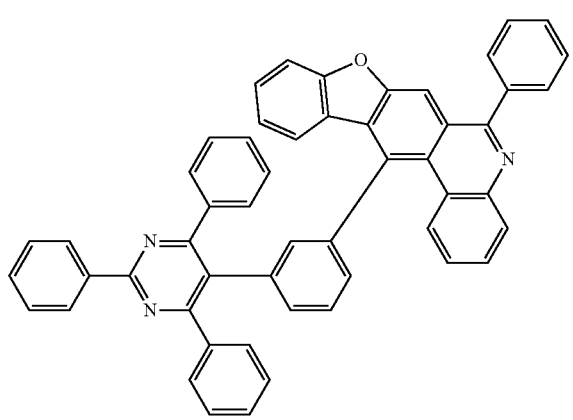
877
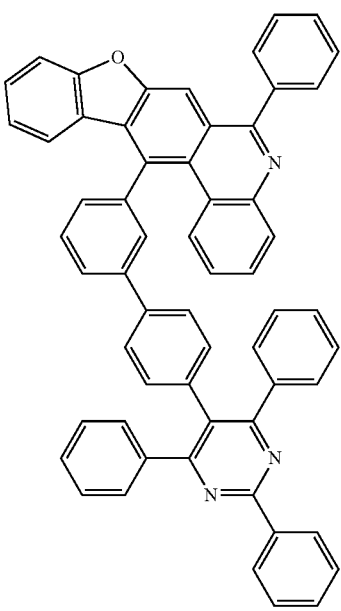

1077
-continued
878
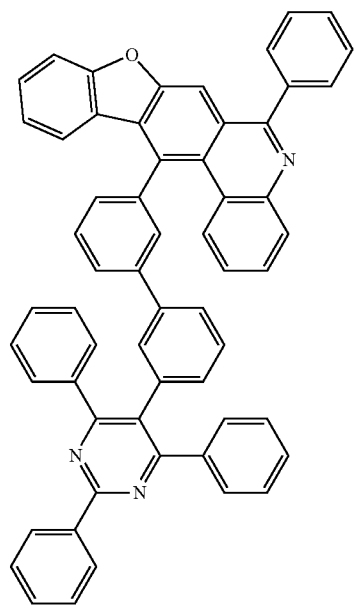
879
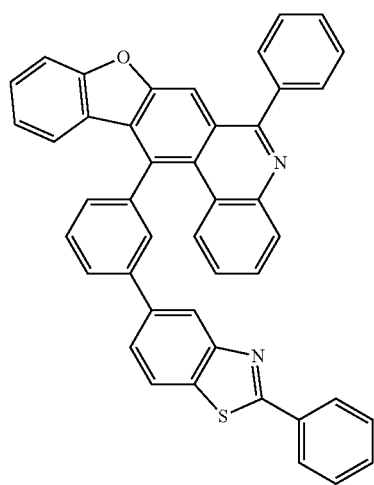
880
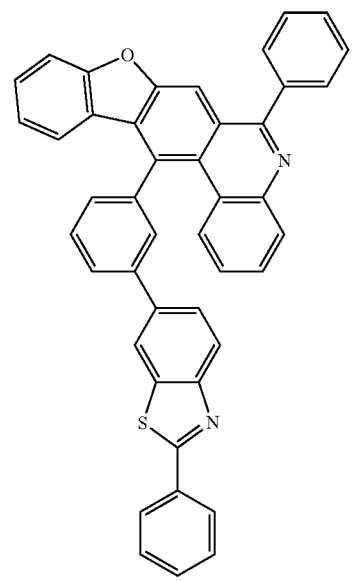
1078
-continued
881
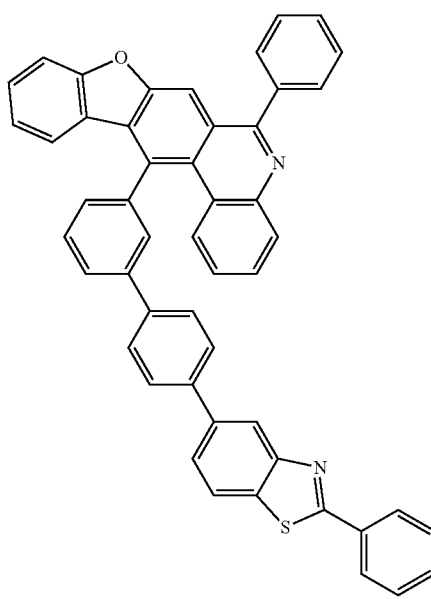
882
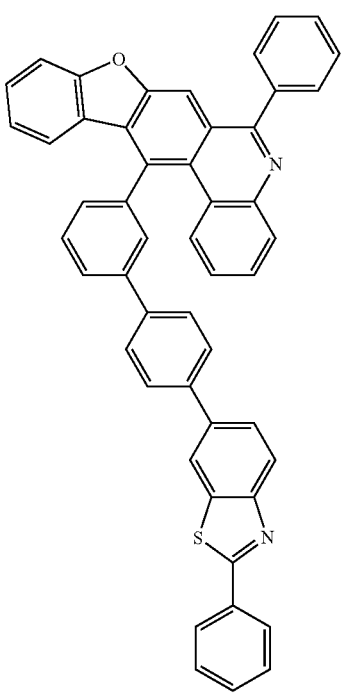
883
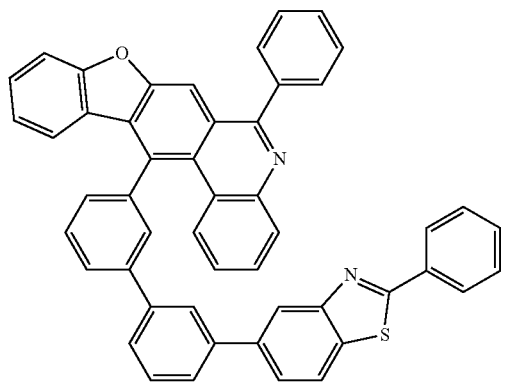

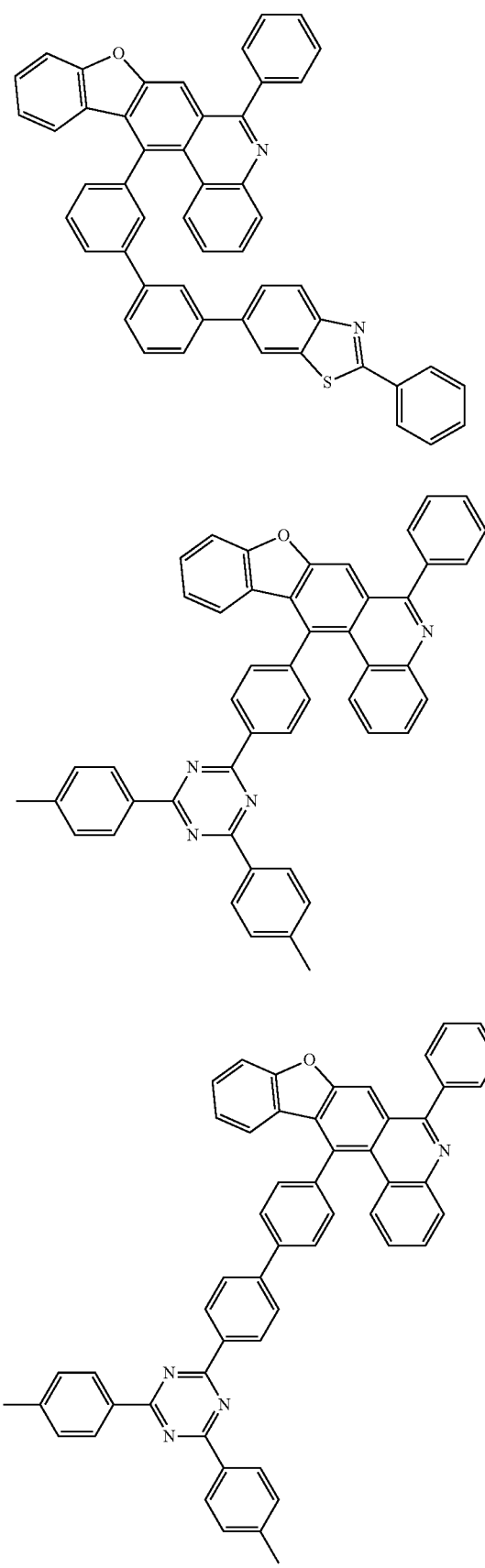
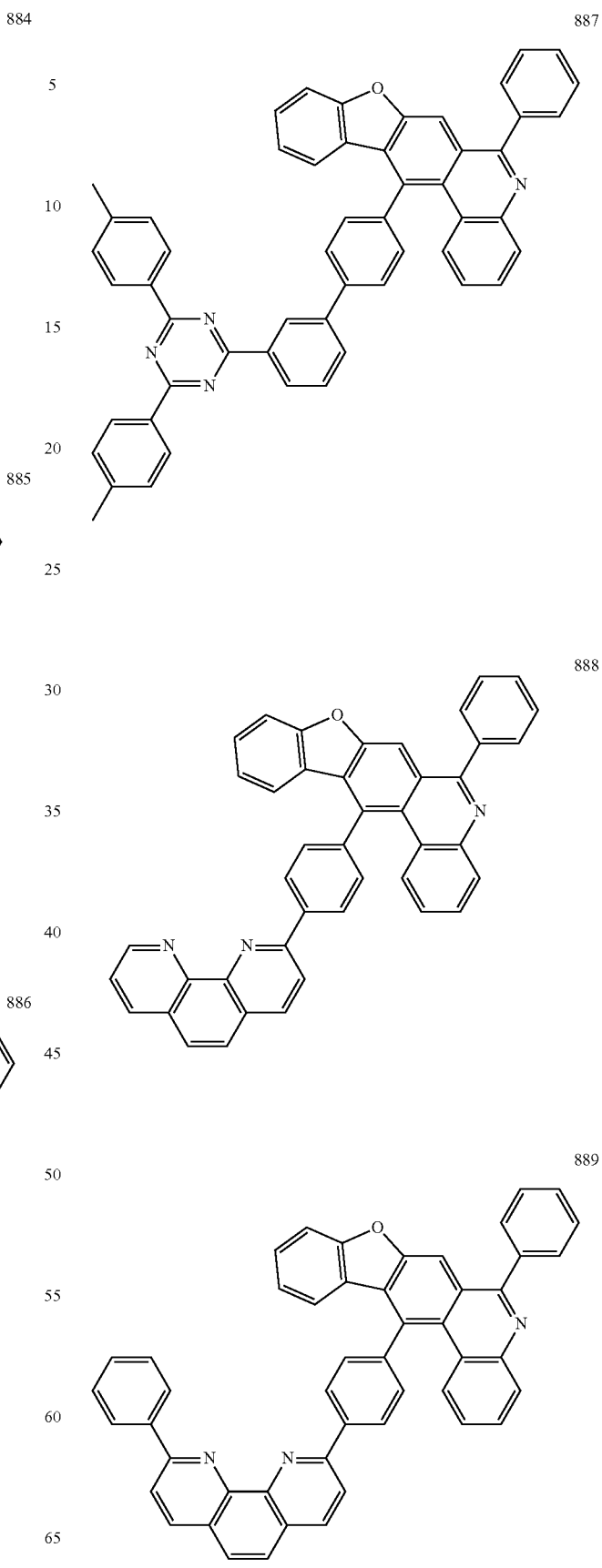

890
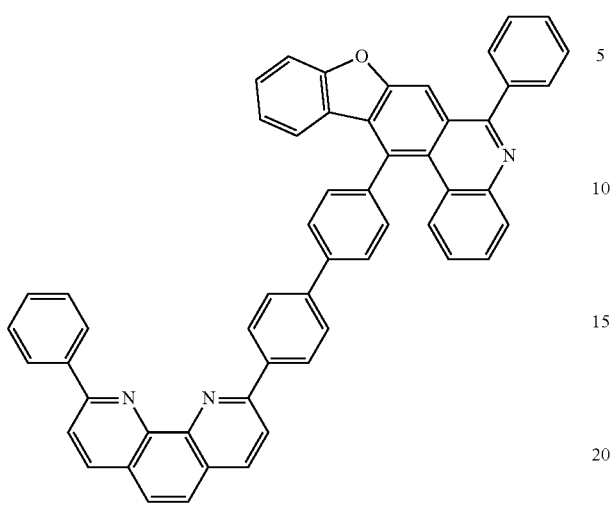
891
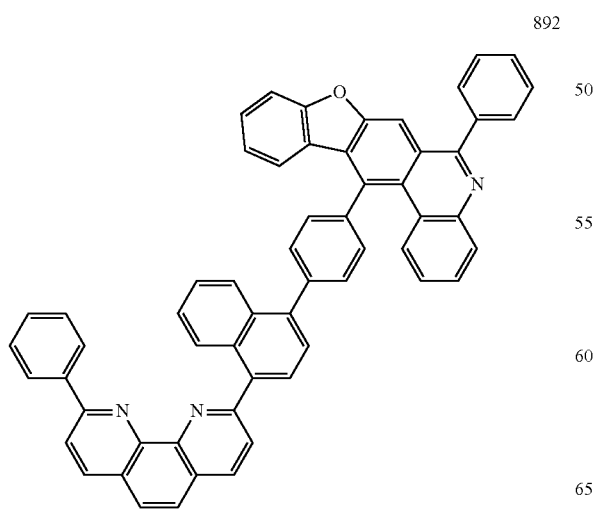
892
893
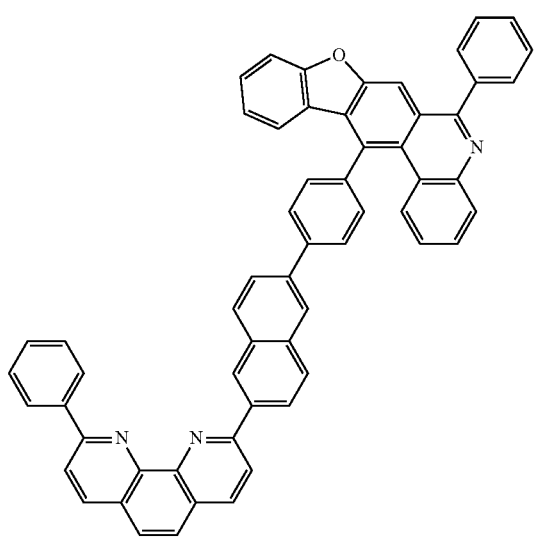
894
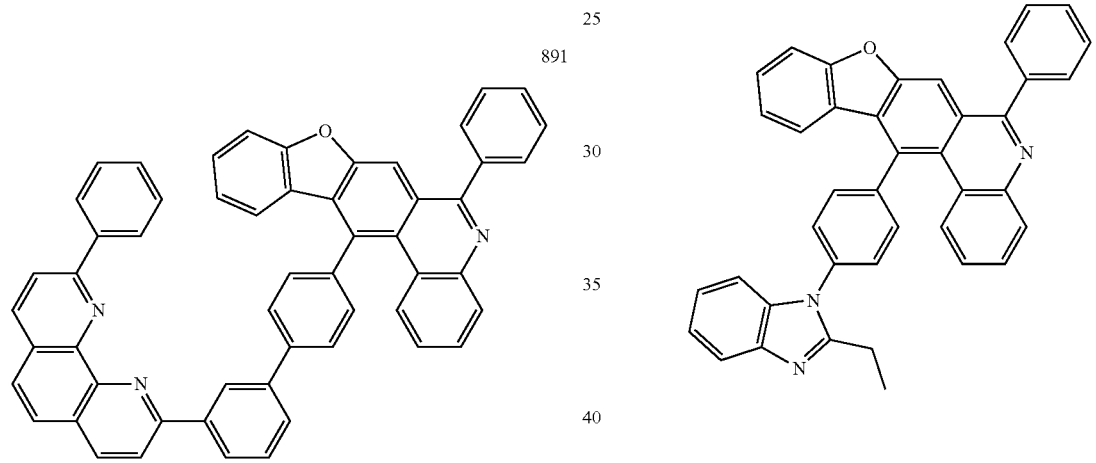
895
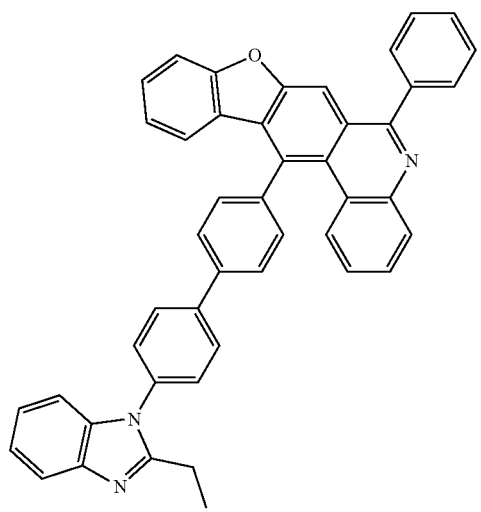

1083
-continued
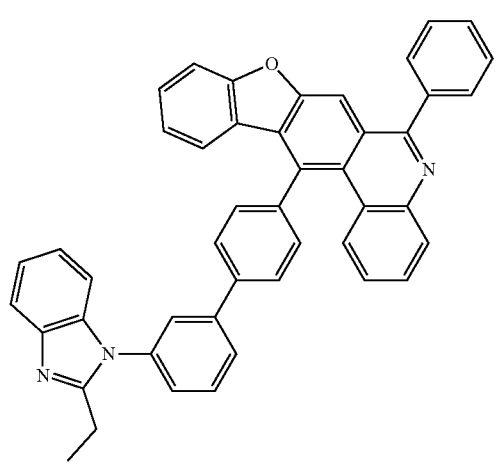
896
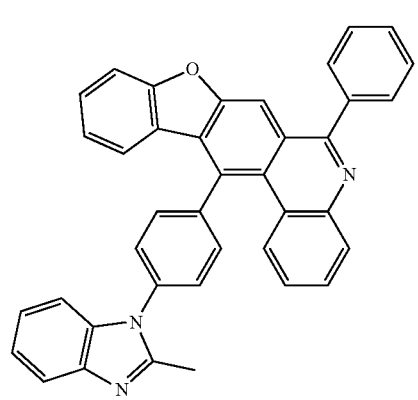
897
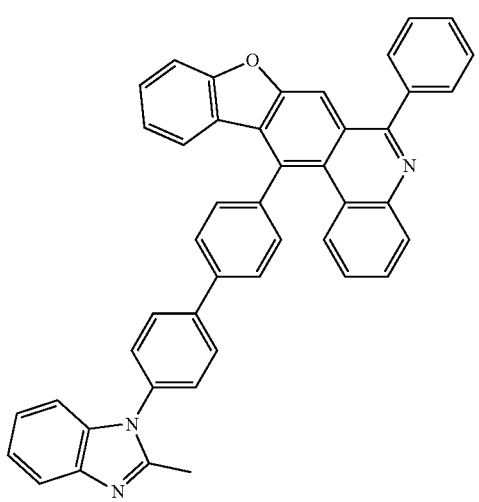
898
1084
-continued
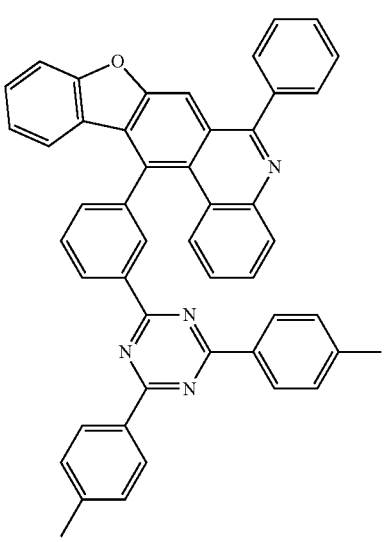
899
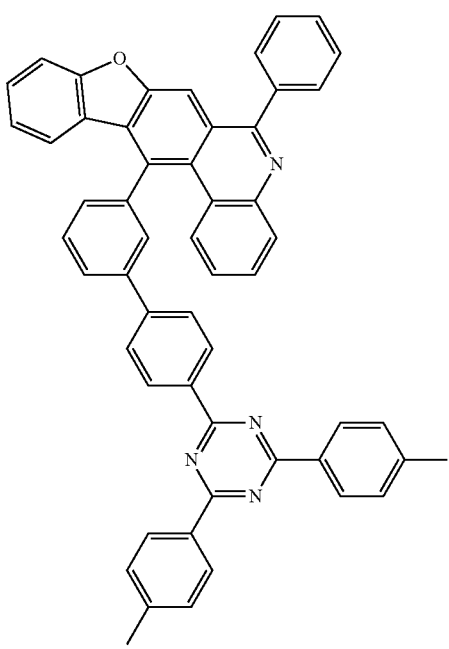
900

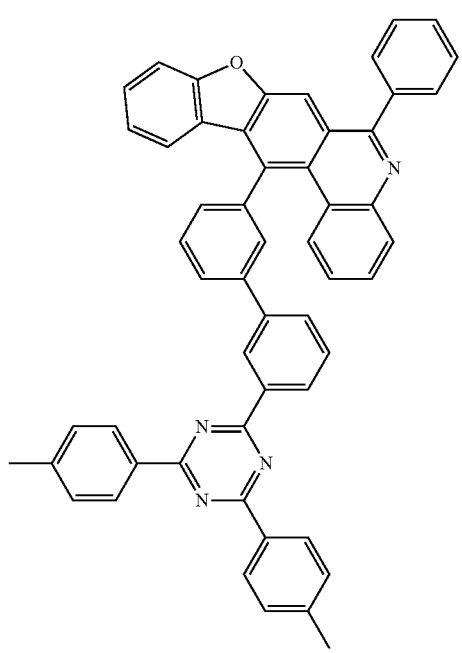
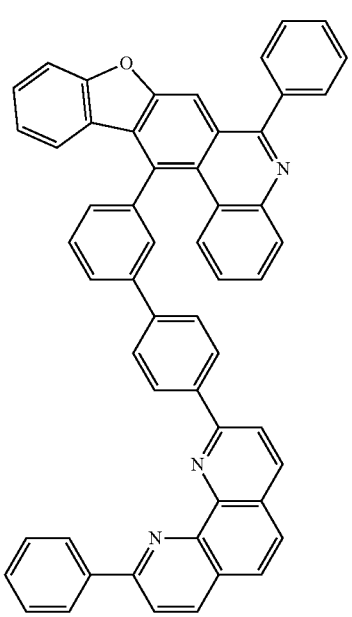
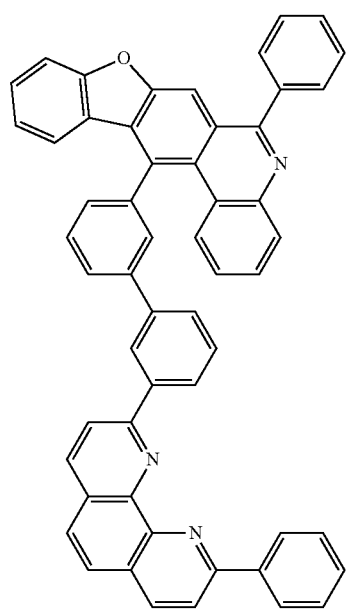

906
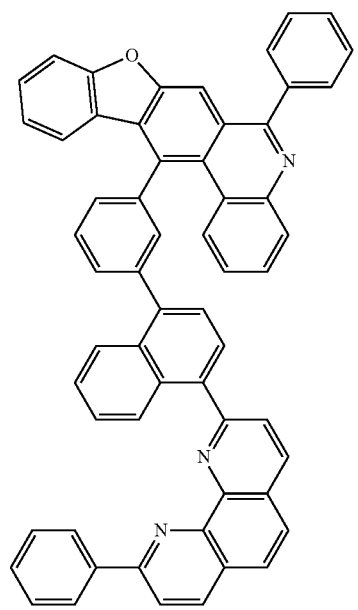
907
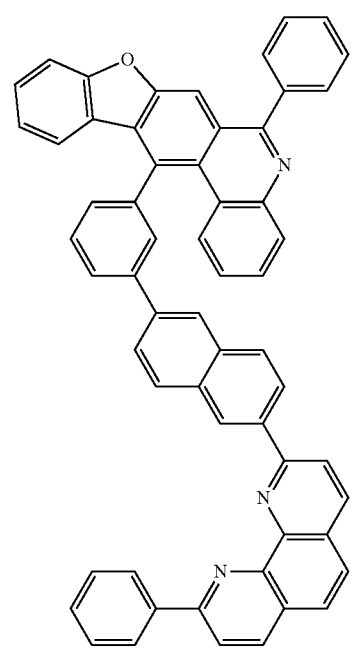
908
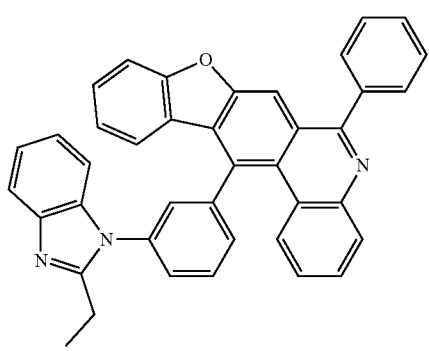
909
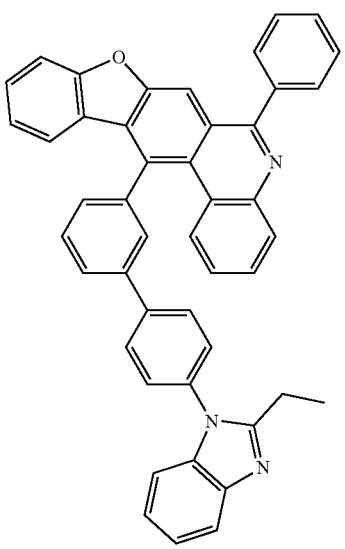
910
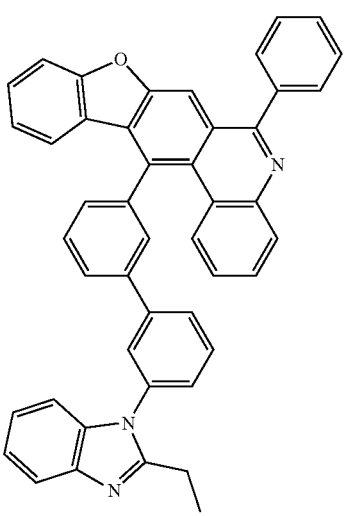
911
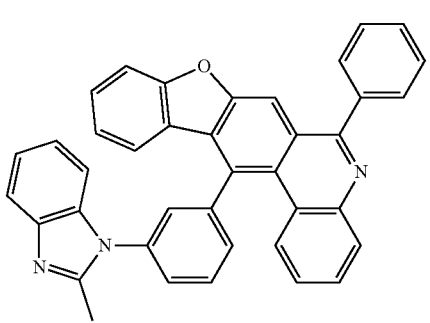

1089
-continued
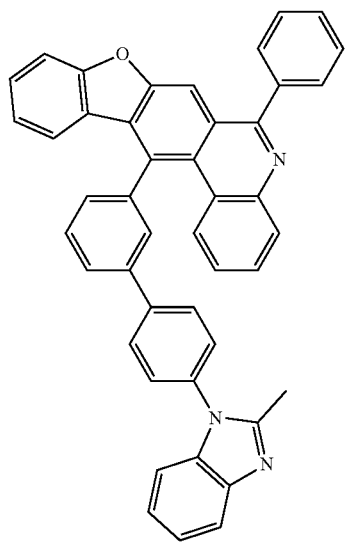
912
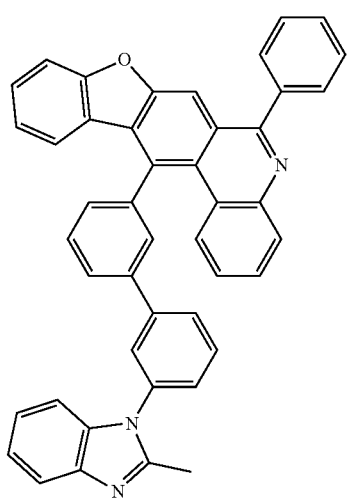
913
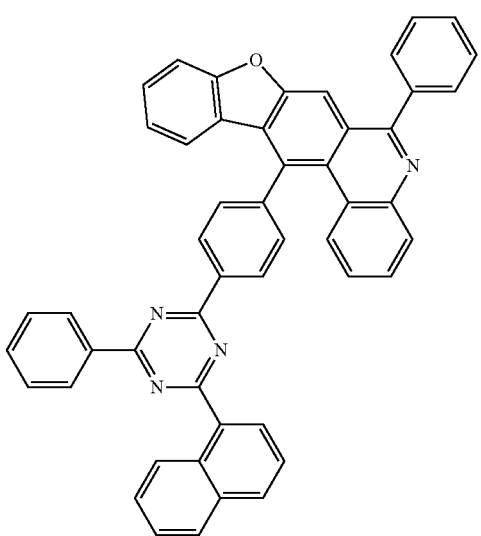
914
1090
-continued
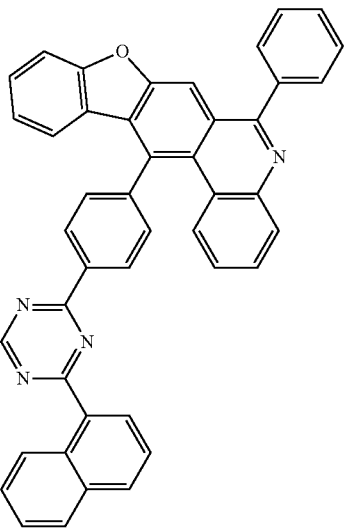
915
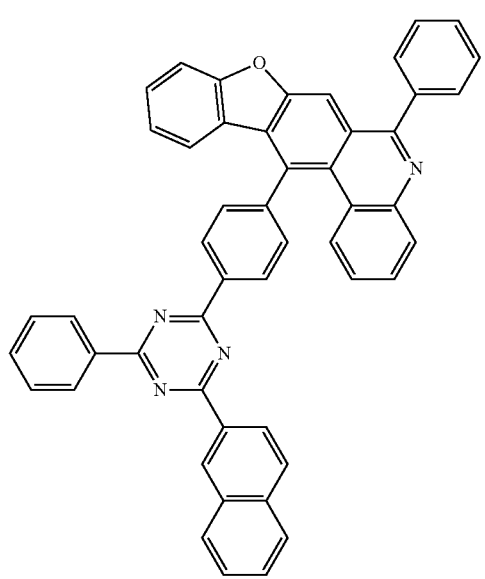
916

917
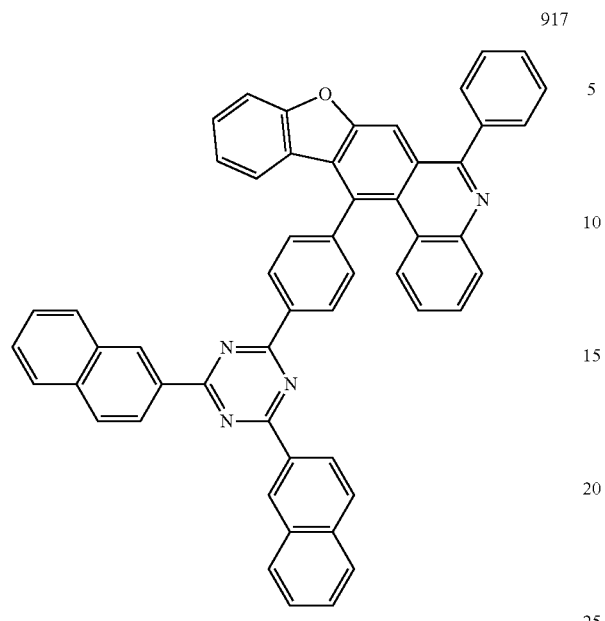
918
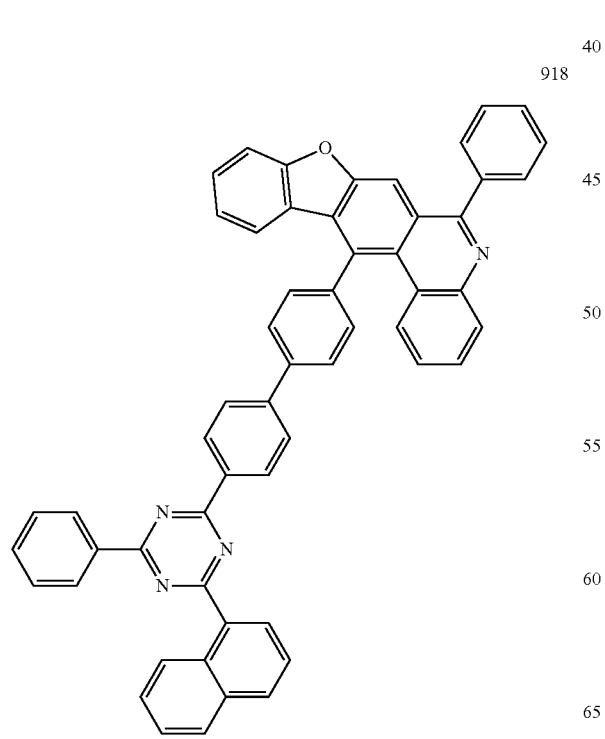
919
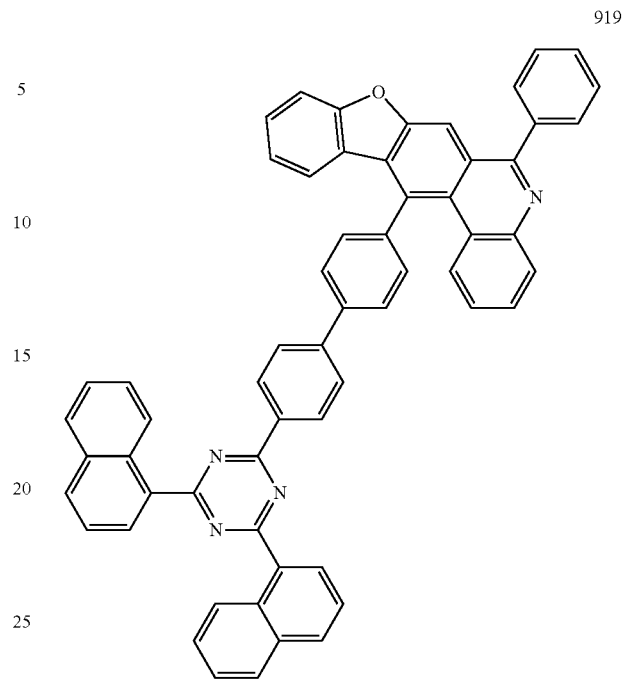
920
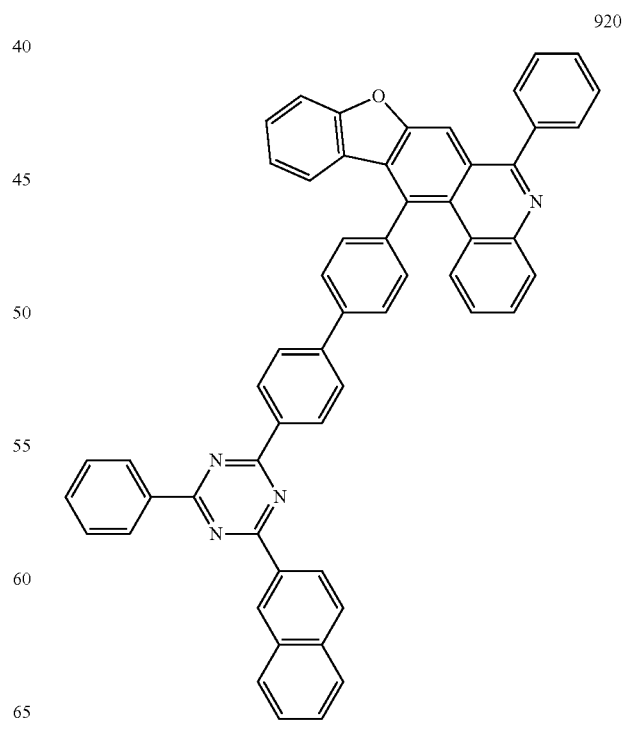

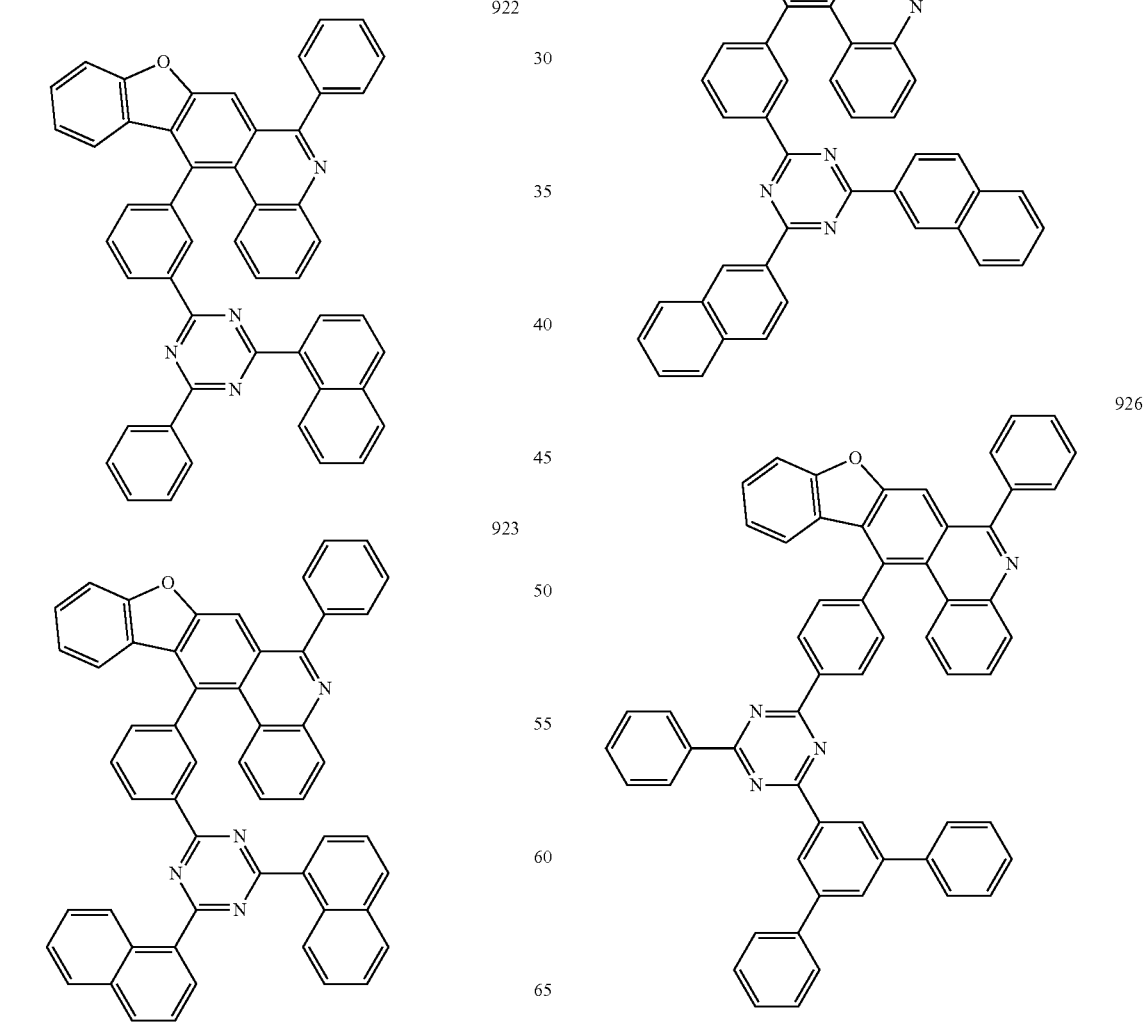

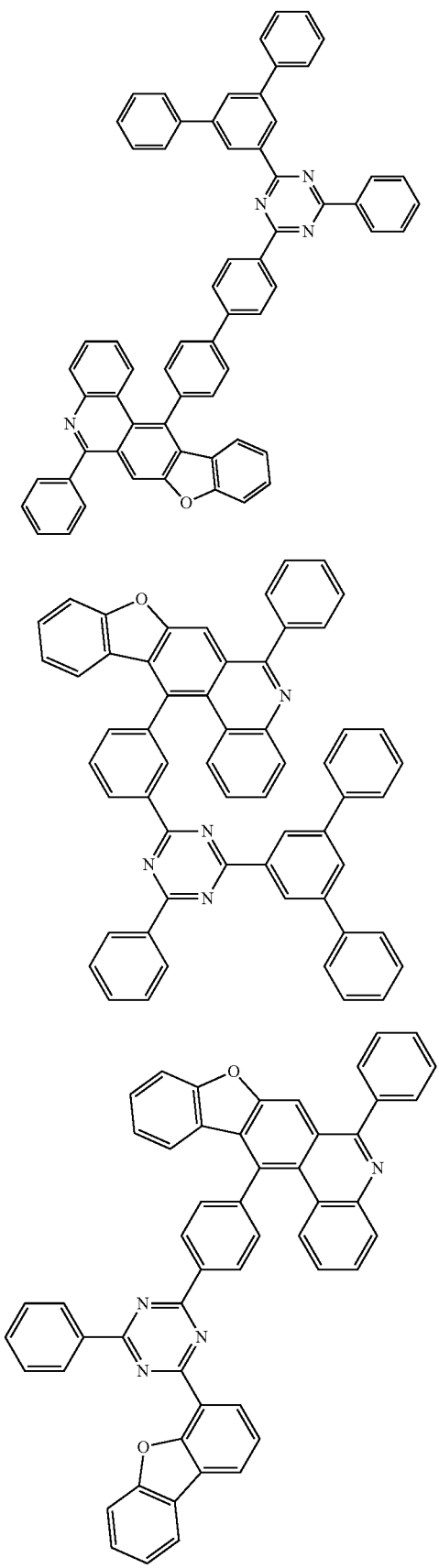
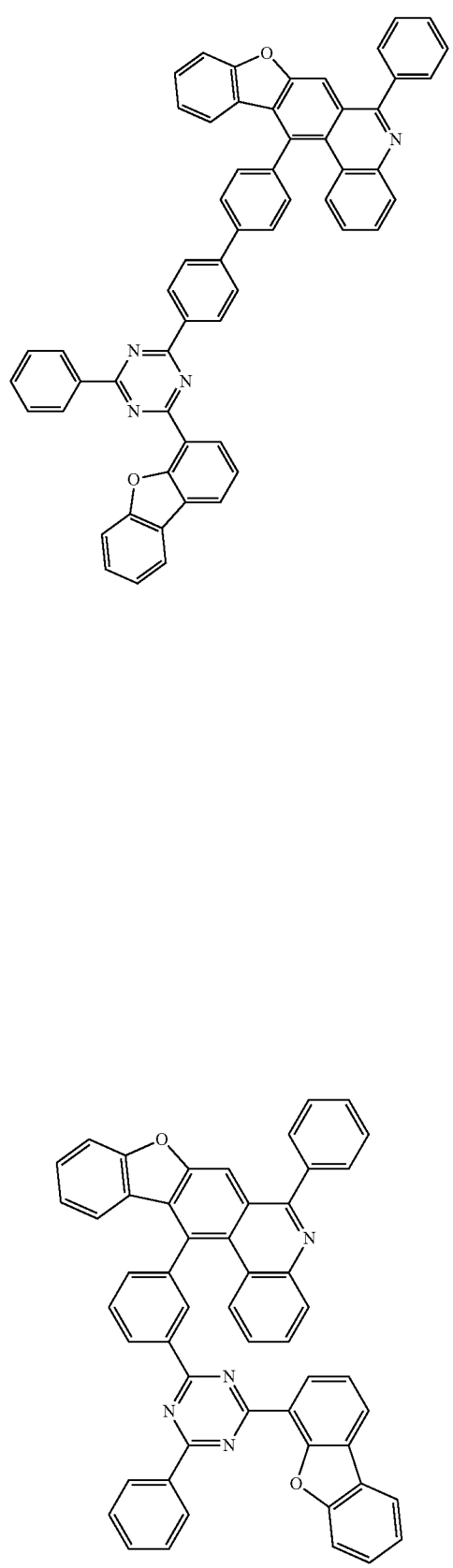

1097
-continued
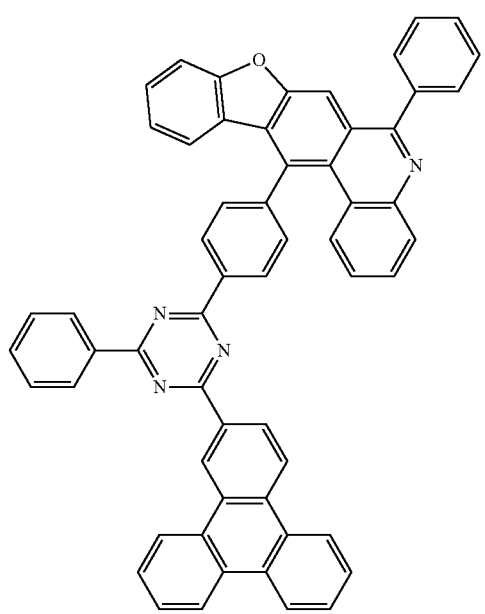
932
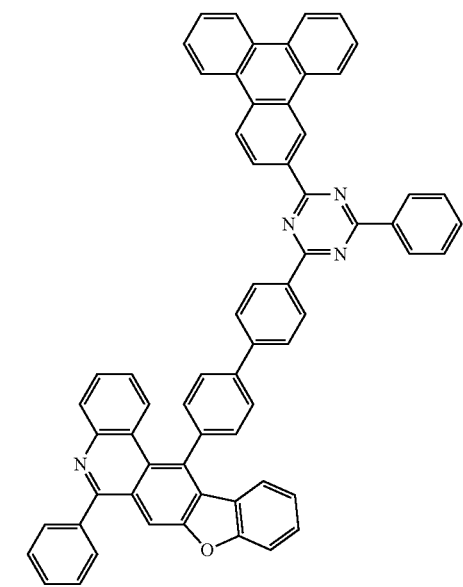
933
1098
-continued
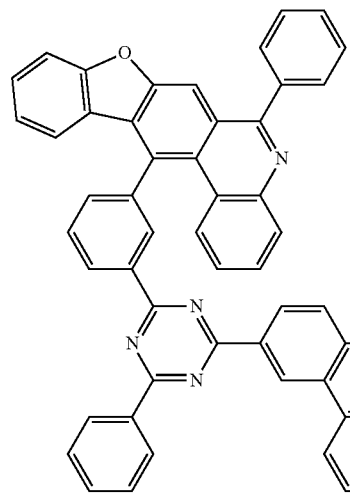
934
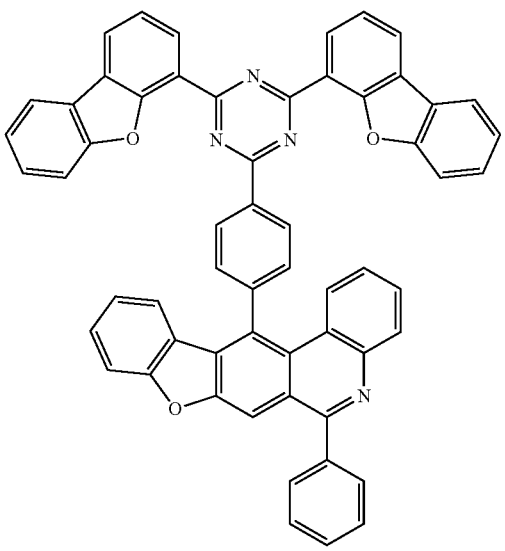
935
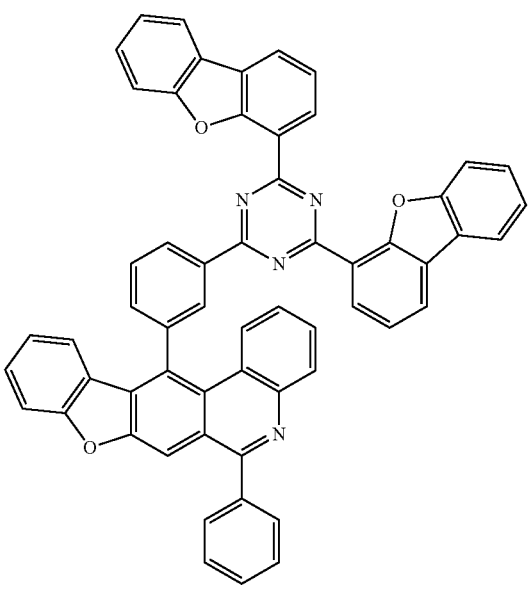
936

1099
-continued
1100
-continued
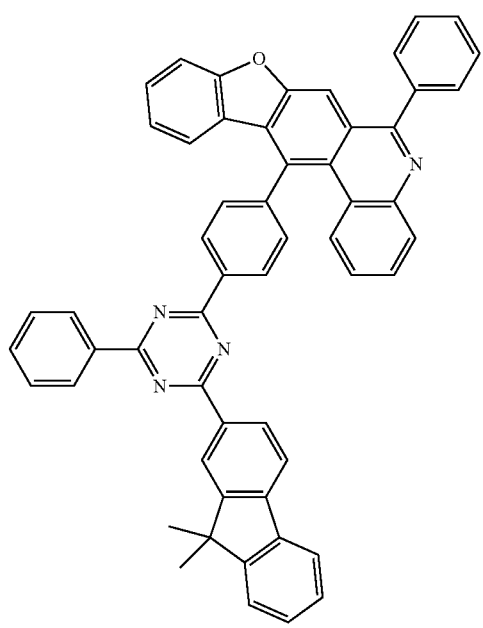
937
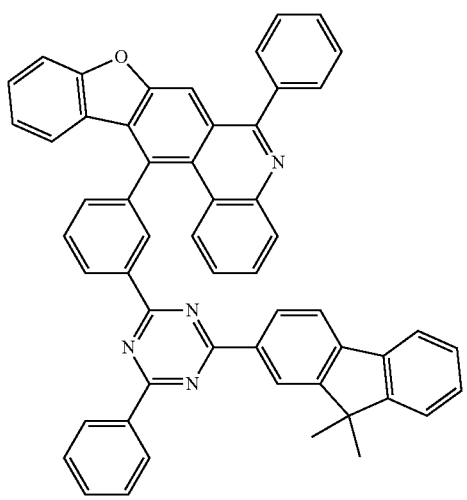
939
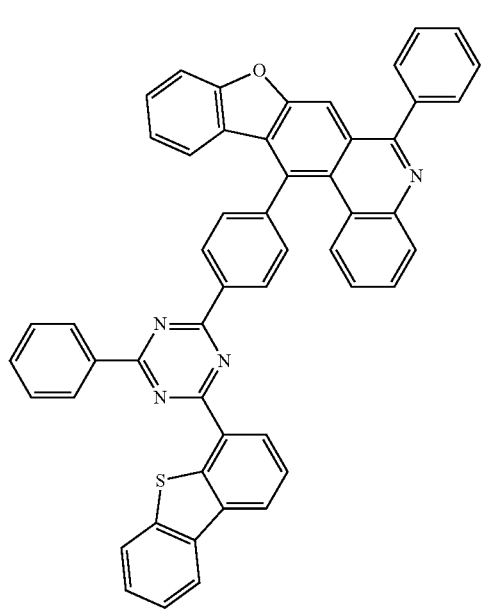
940
938

1101-continued
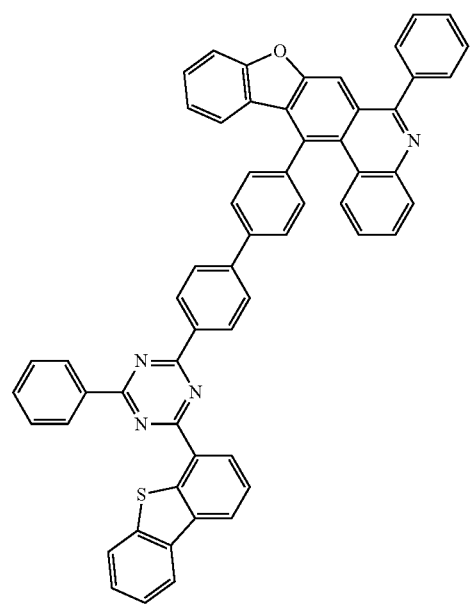
941
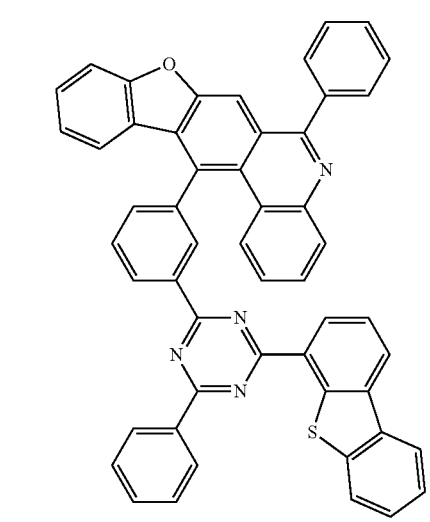
942
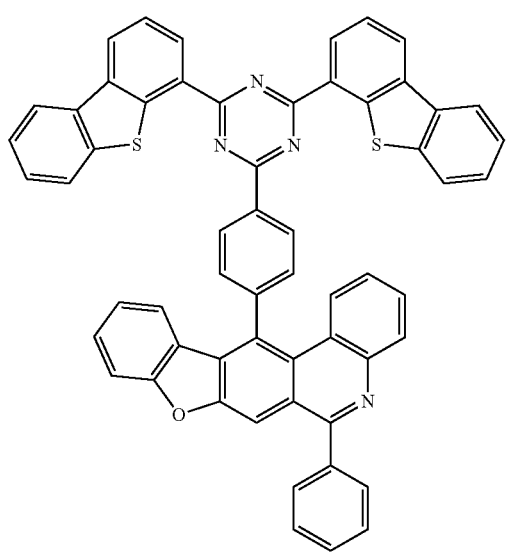
943
1102-continued
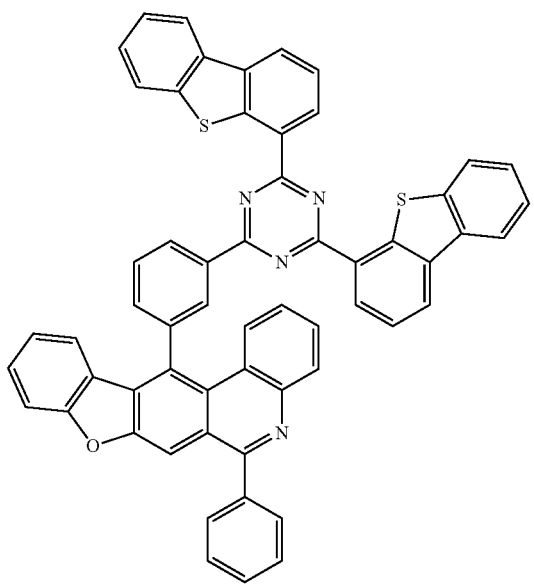
944
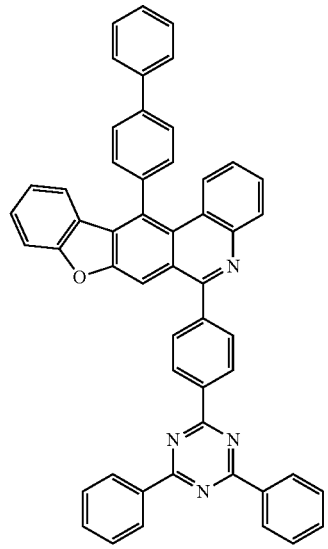
945

1103-continued
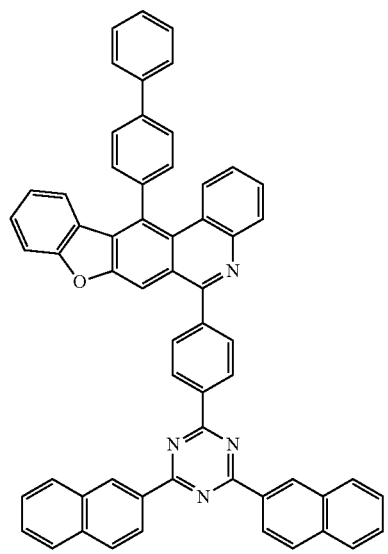
946
1104-continued
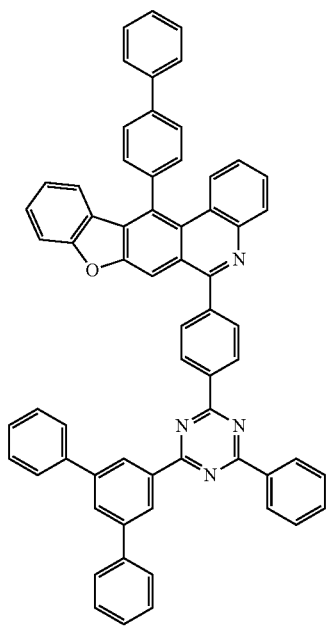
948
947
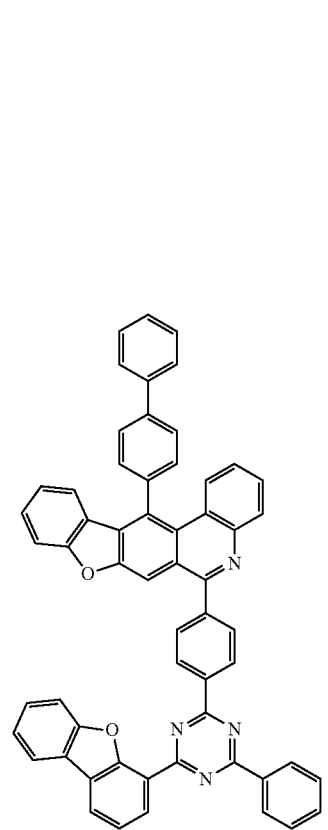
949

1105
-continued
950
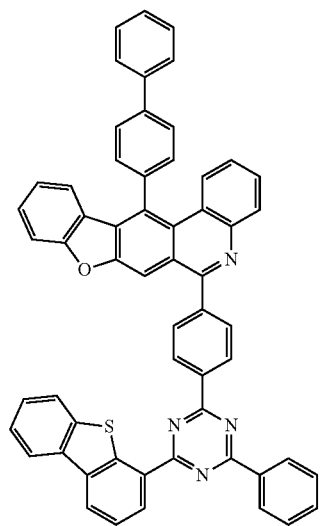
951
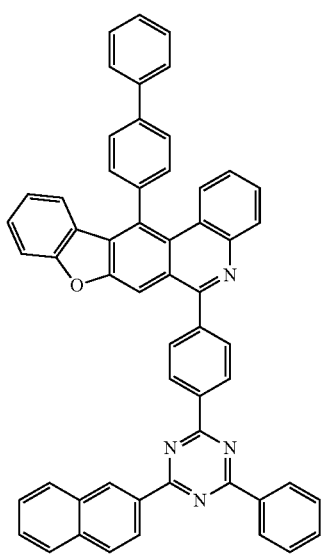
1106
-continued
952
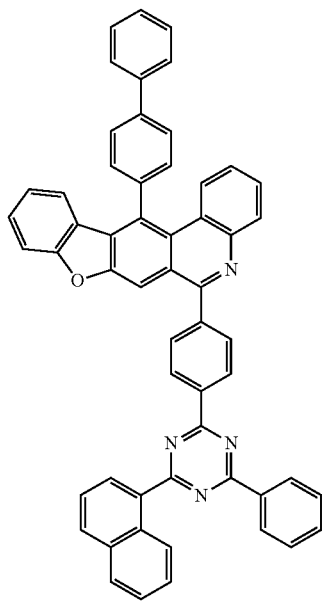
953
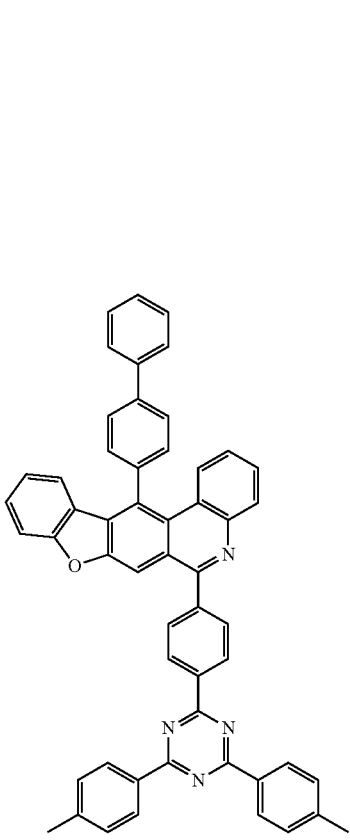

1107
-continued
954
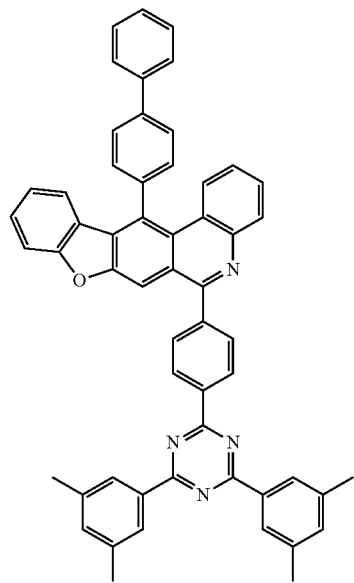
1108
-continued
956
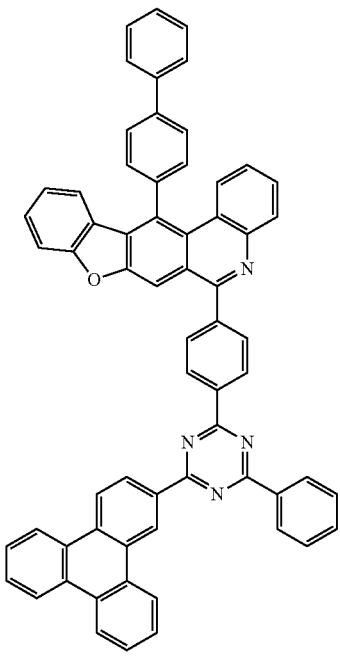
955
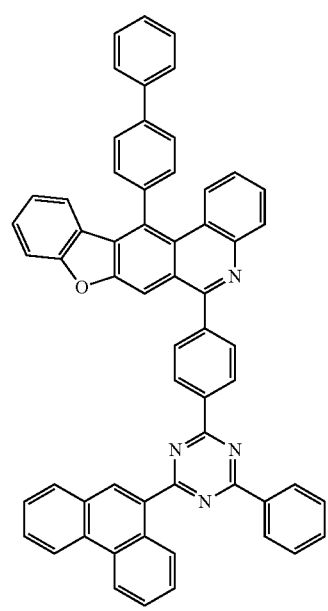
957
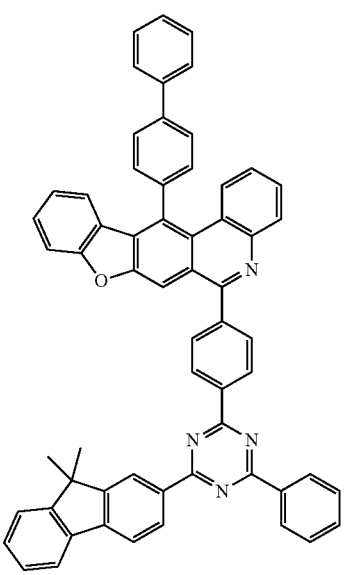

1109
-continued
958
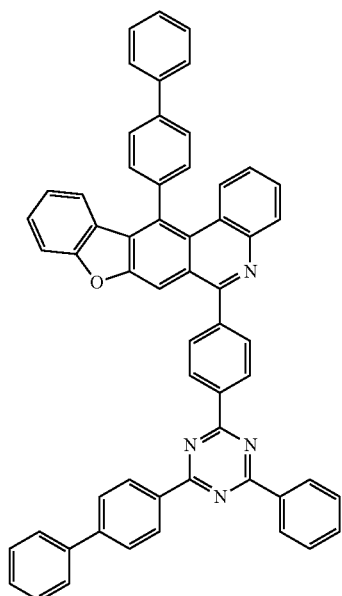
959
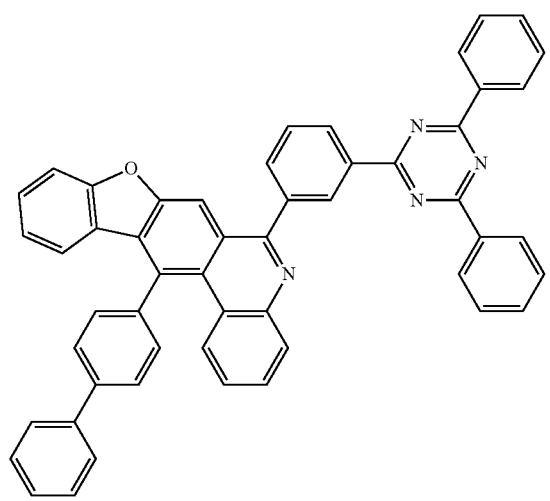
960
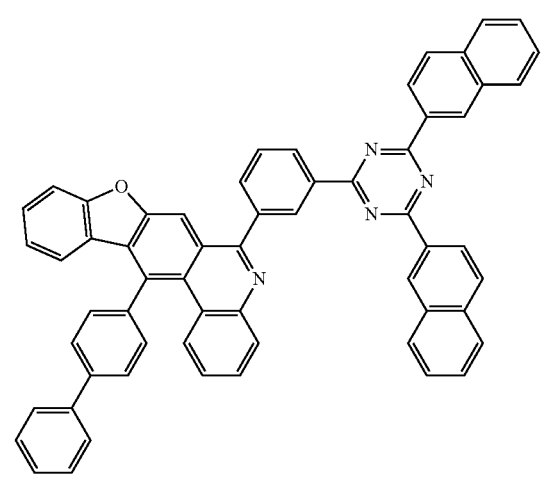
1110
-continued
961
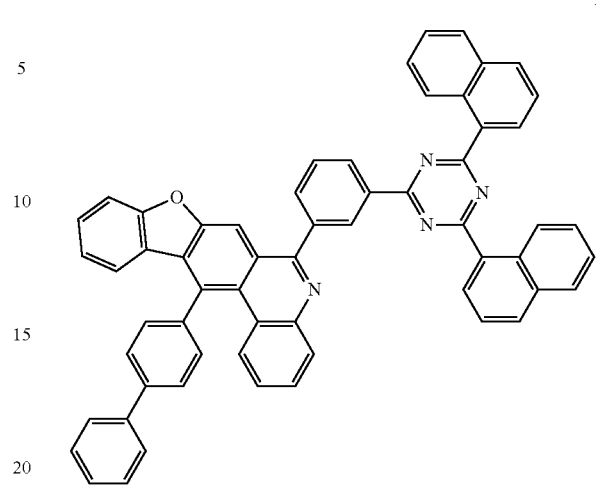
962
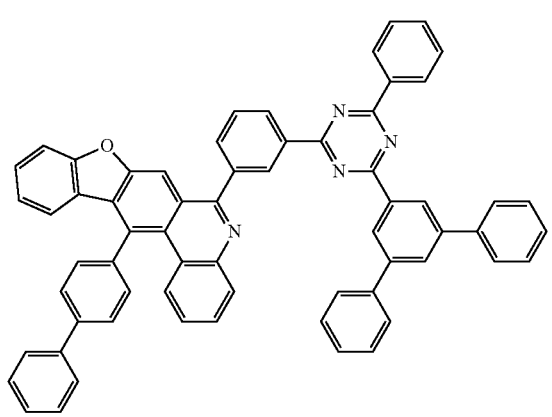
963
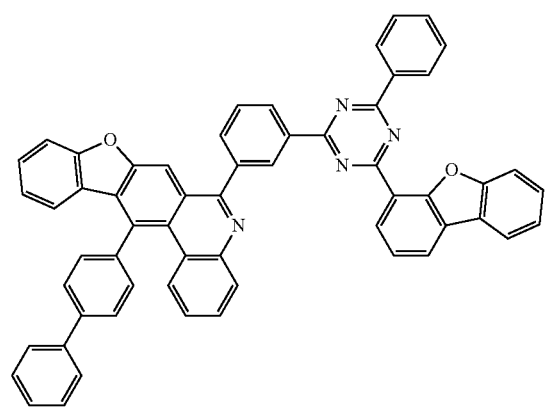

| 1111 -continued | 1112 -continued |
|---|---|
| 964 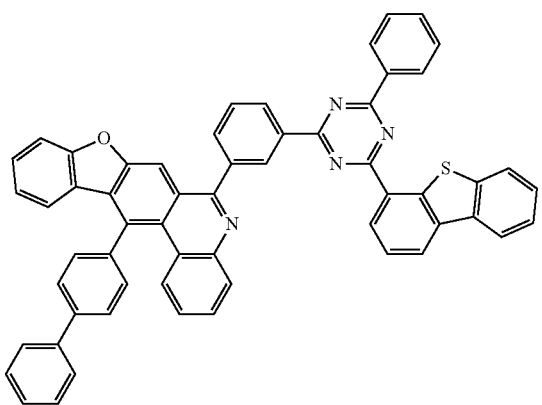 | 967 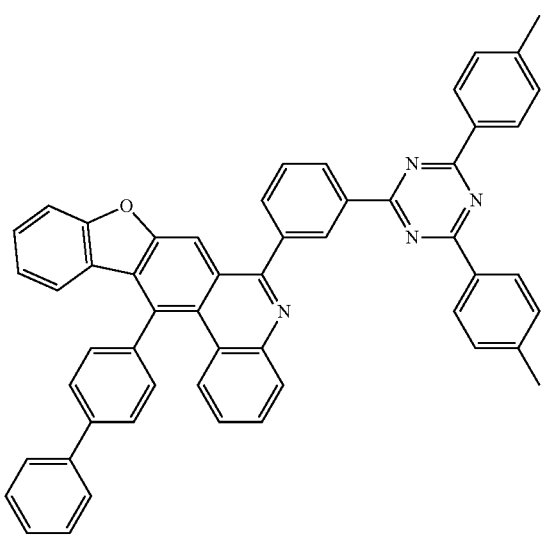 |
| 965 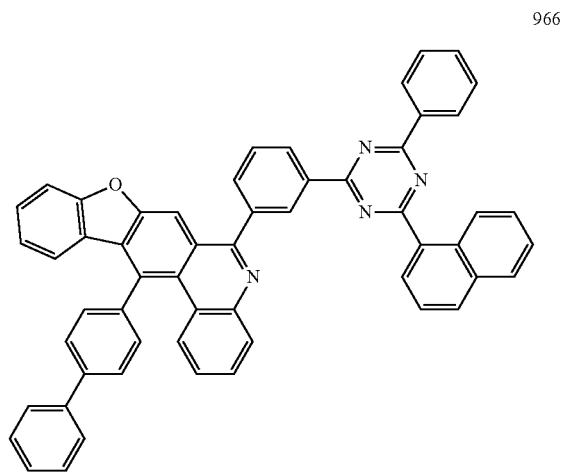 | 968 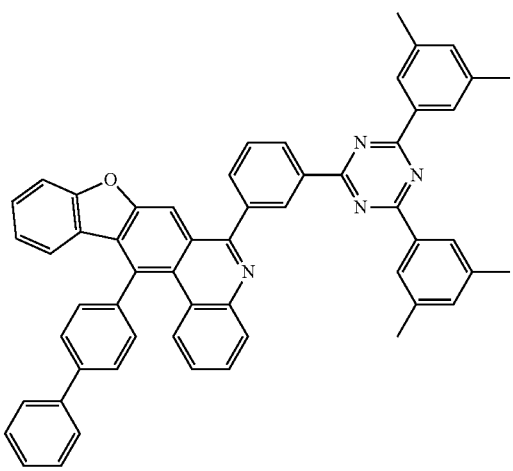 |
| 966 | 969 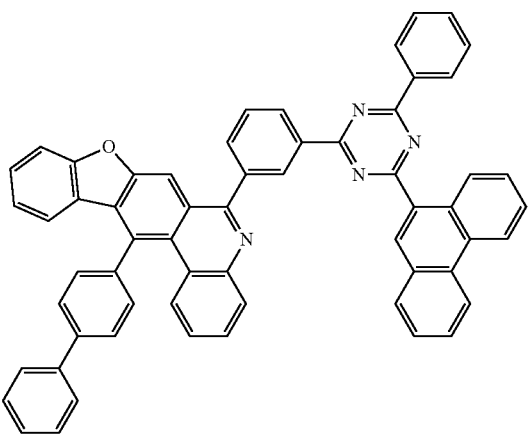 |

1113
-continued
970
971
972
1114
-continued
973
974
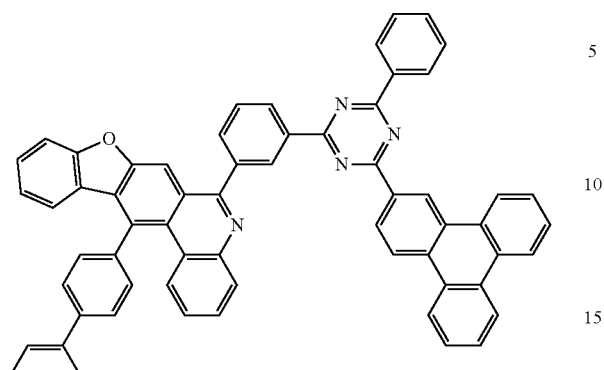
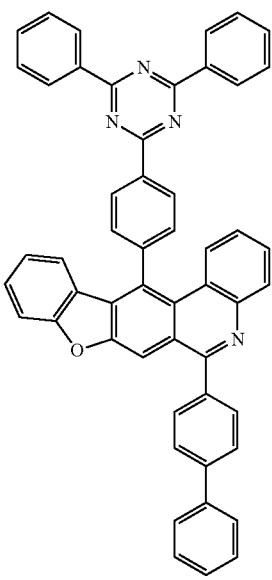
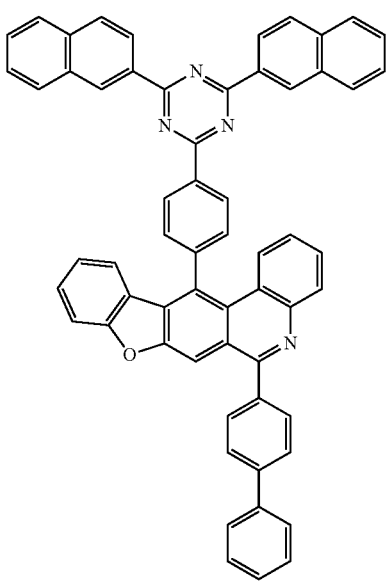

1115
-continued
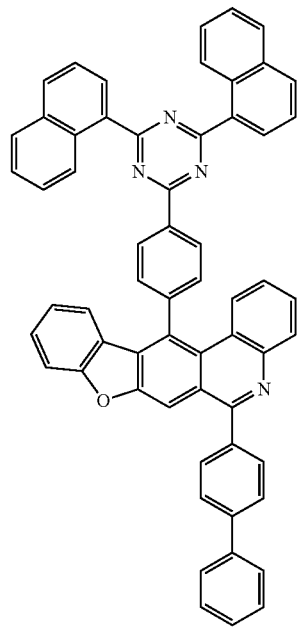
975
1116
-continued
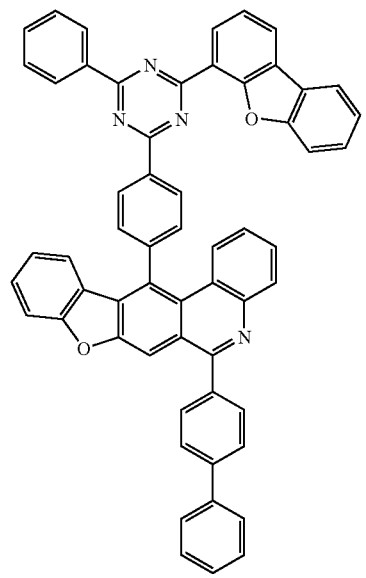
977
976
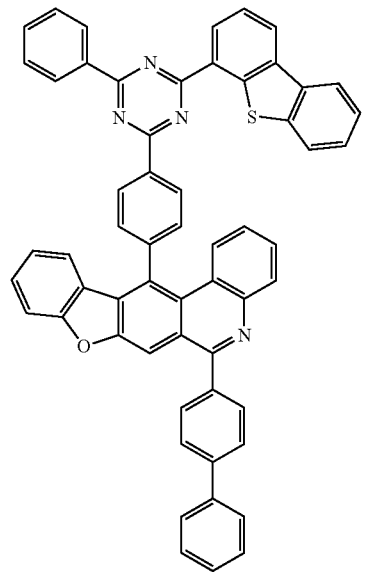
978

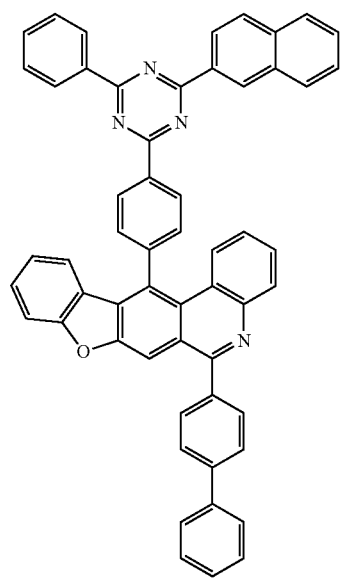
979
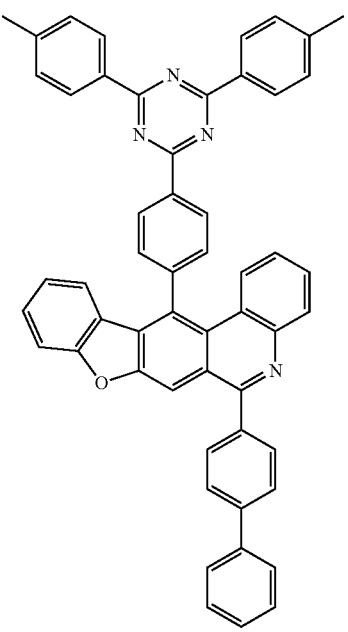
981
980
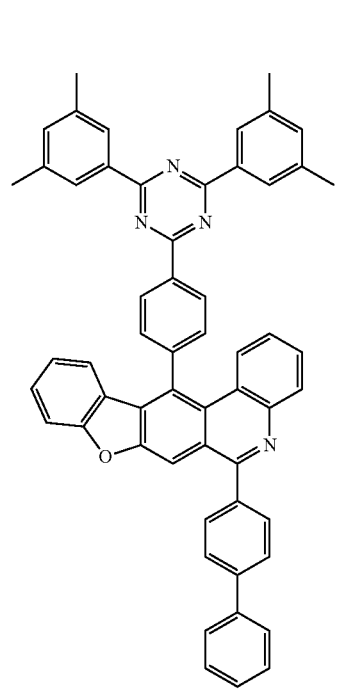
982

1119
-continued
983
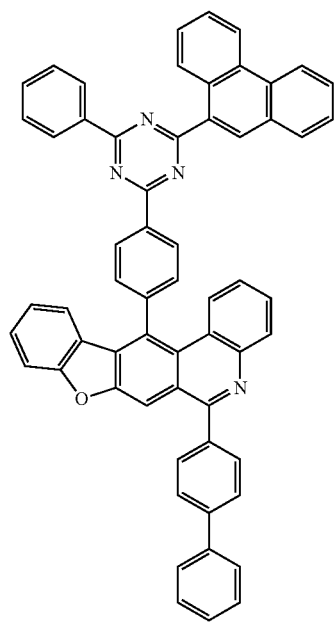
984
1120
-continued
985
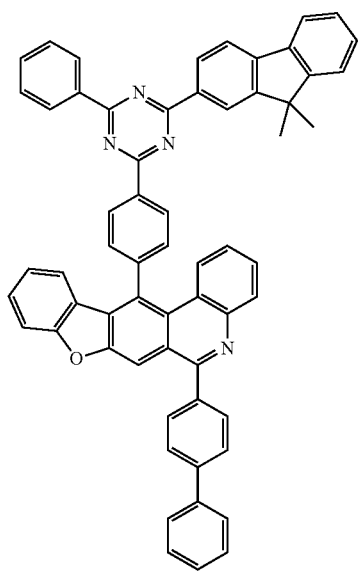
986
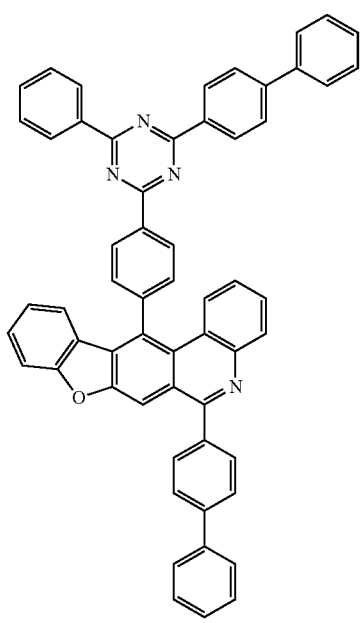

1121
-continued
1122
-continued
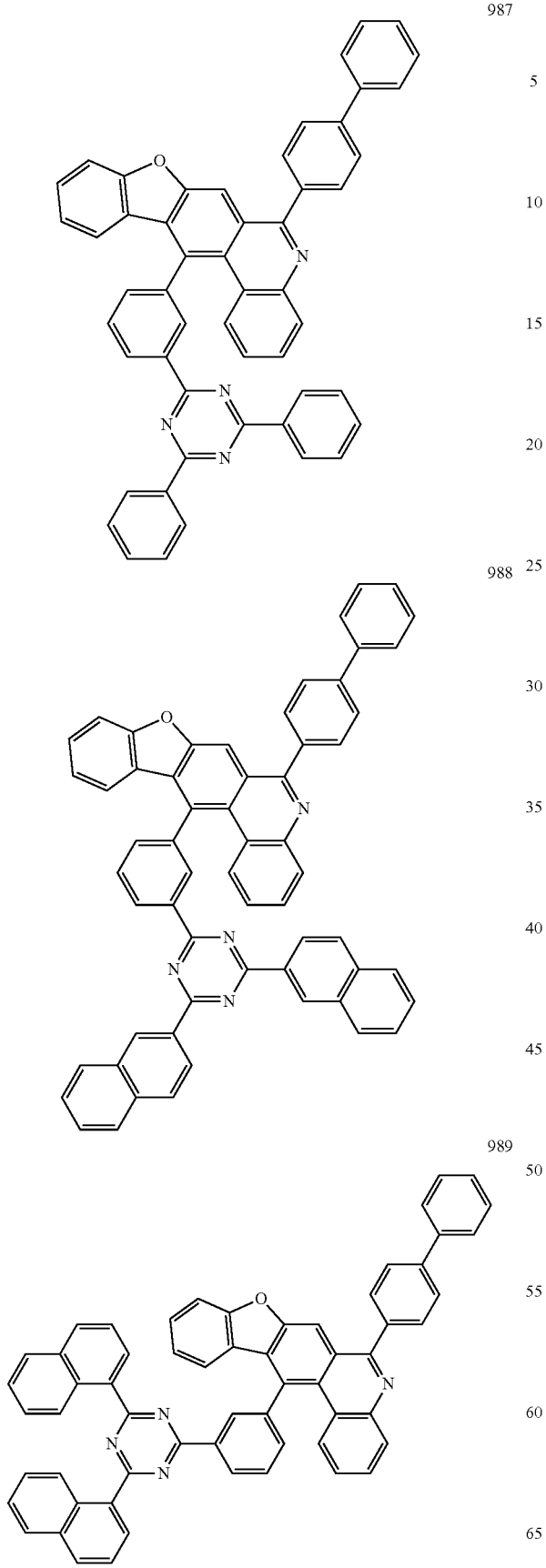
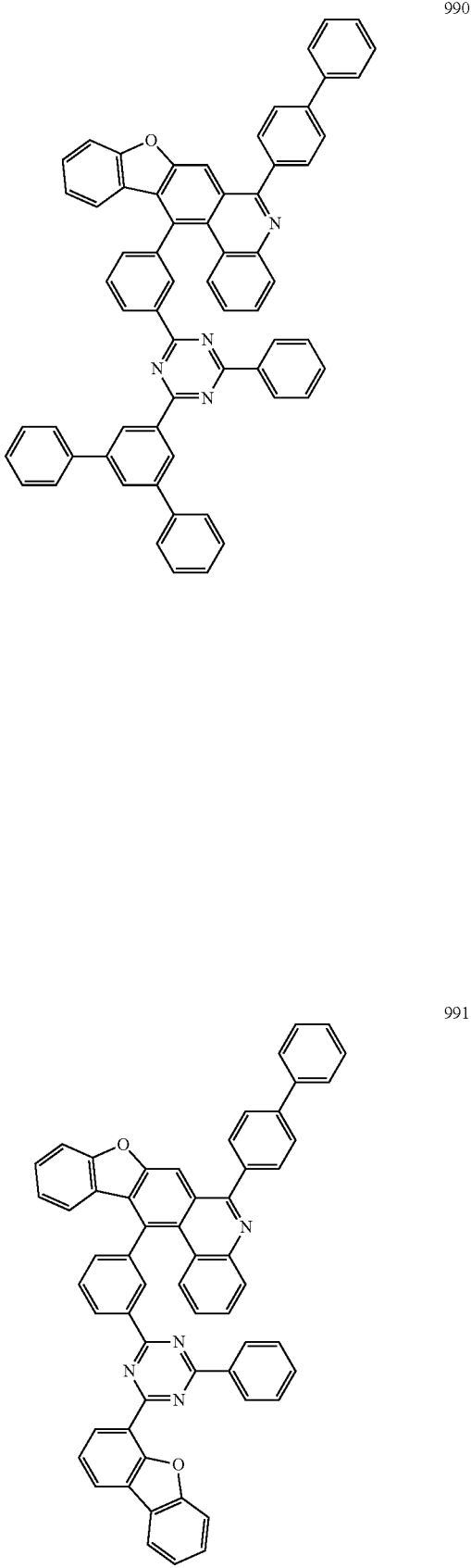

992
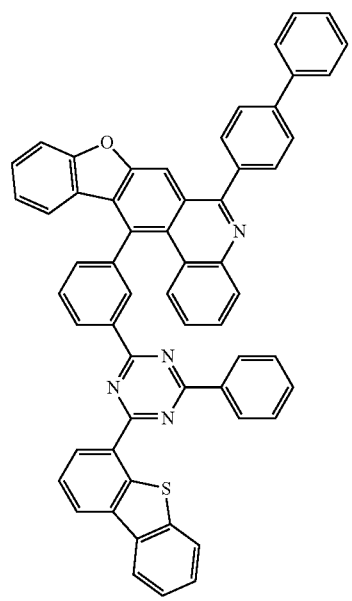
993
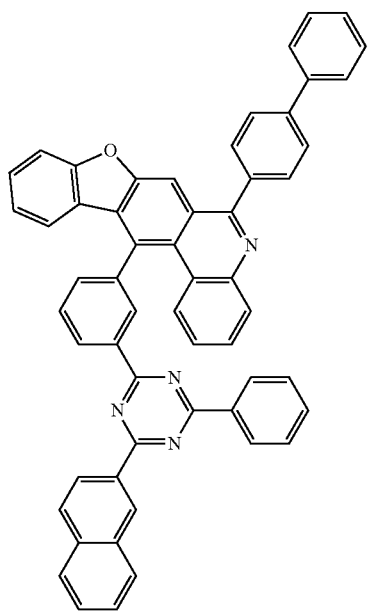
994
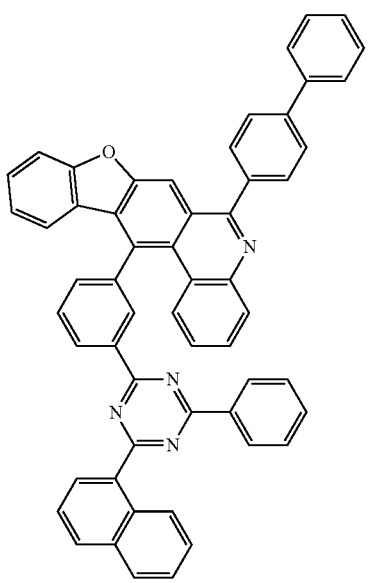
995
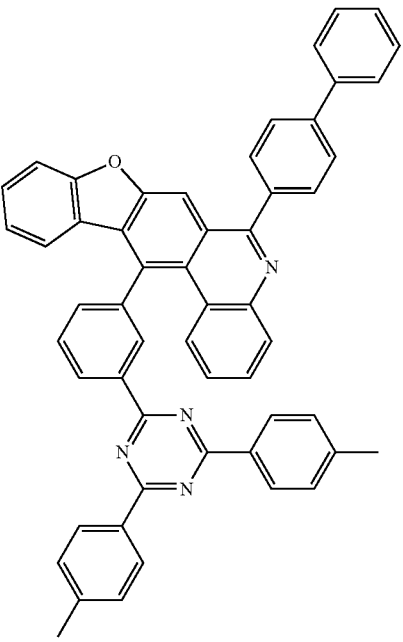

1125
-continued
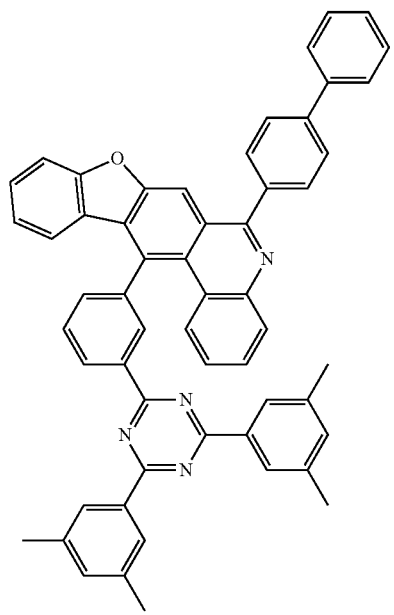
996
1126
-continued
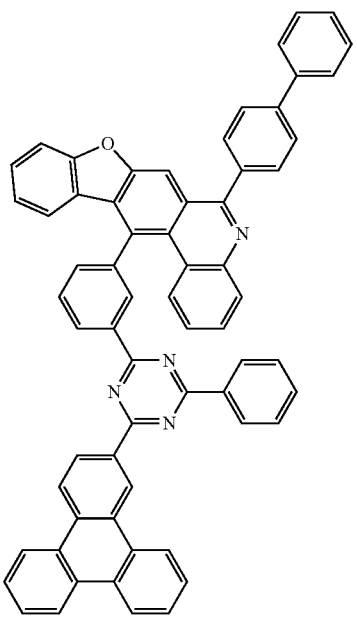
998
997
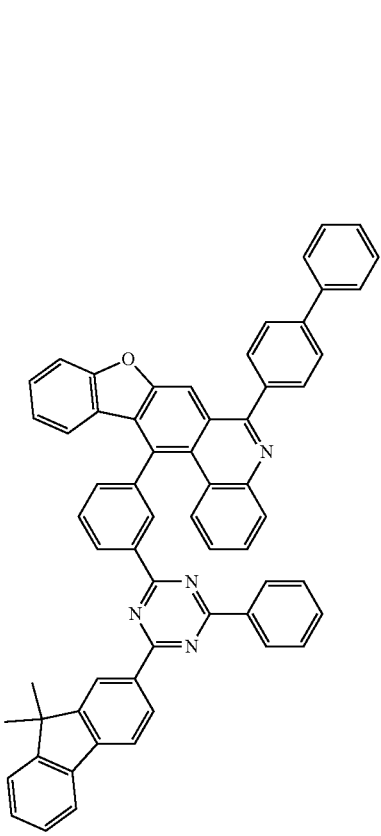
999

1127
-continued
1128
-continued
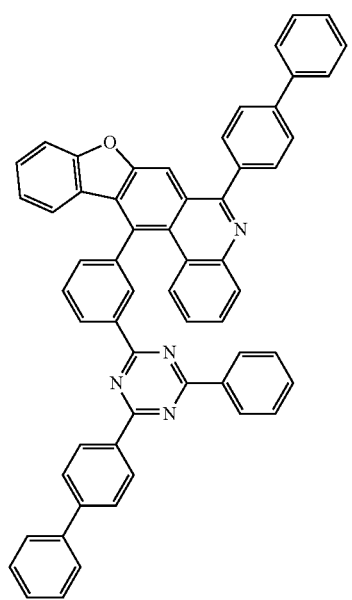
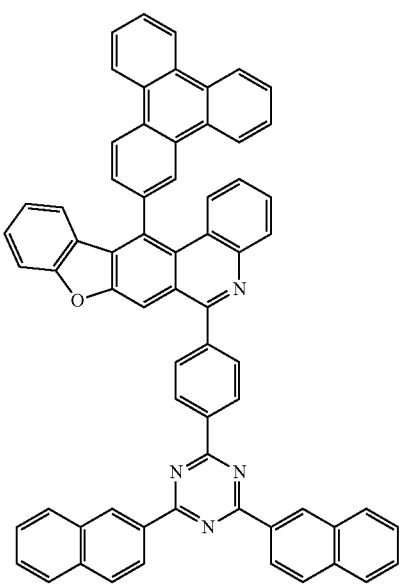

1129
-continued
1130
-continued
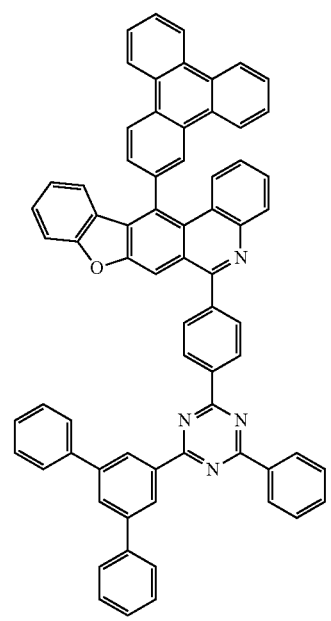
1004
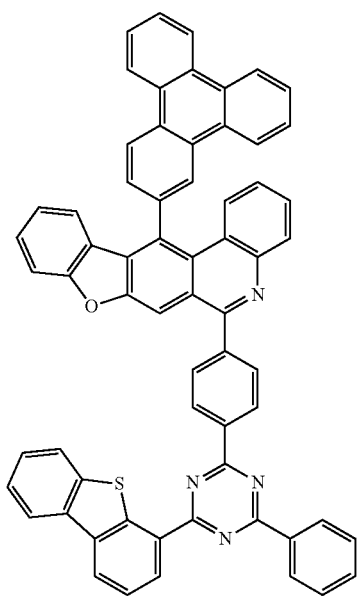
1006
1005
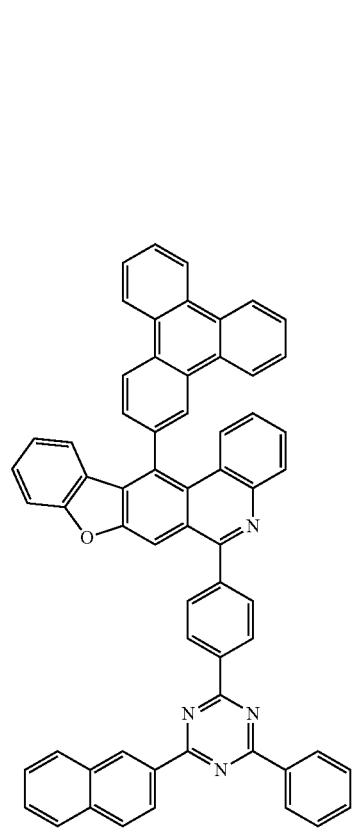
1007

1131
-continued
1132
-continued
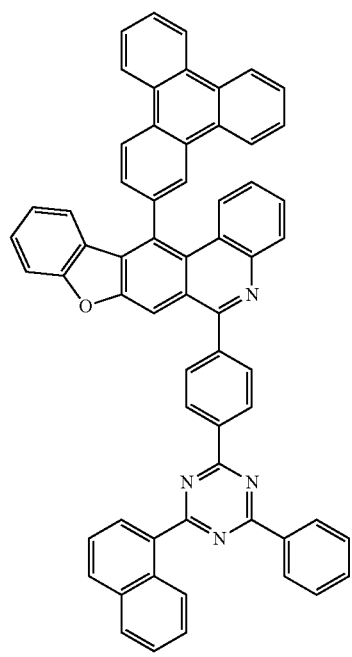
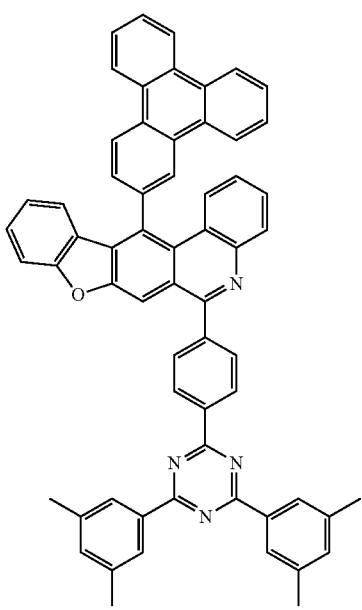
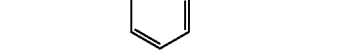

1133
-continued
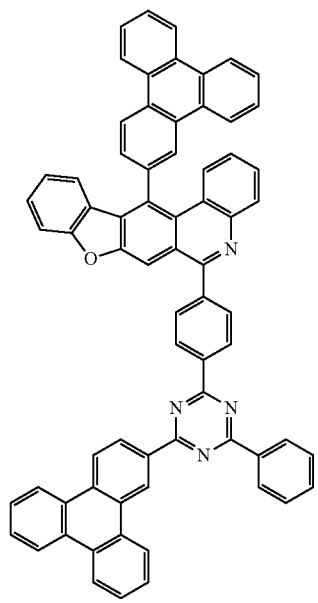
1134
-continued
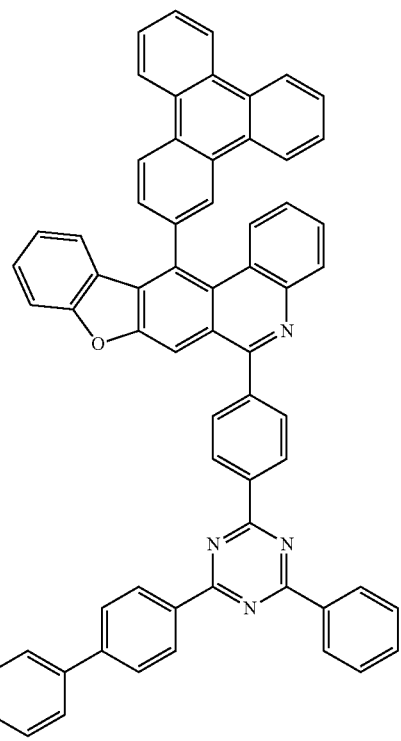
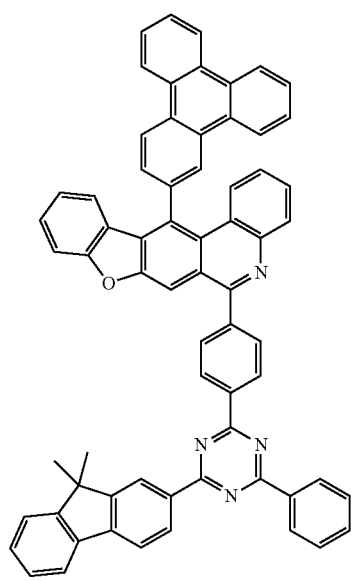
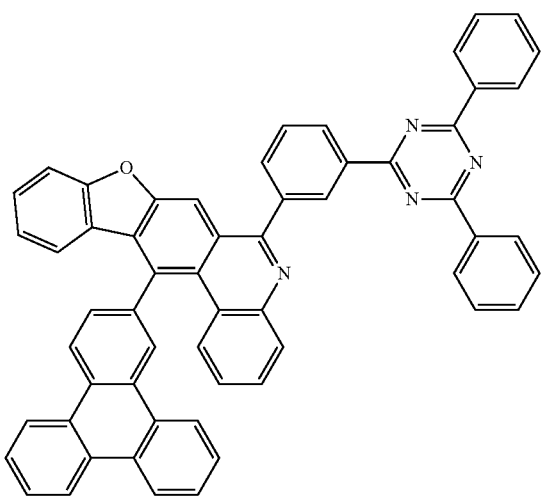

1135
-continued
1016
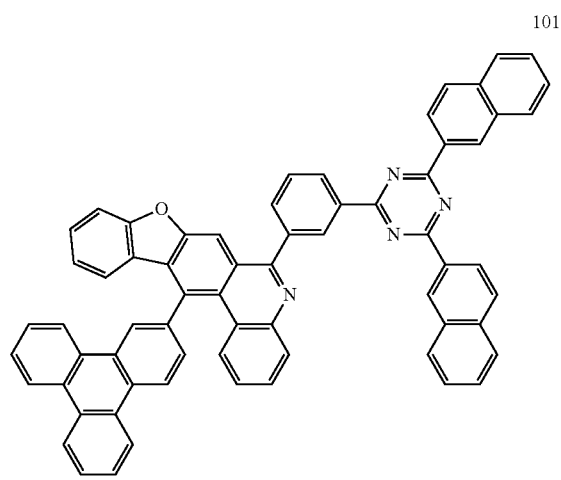
1017
1018
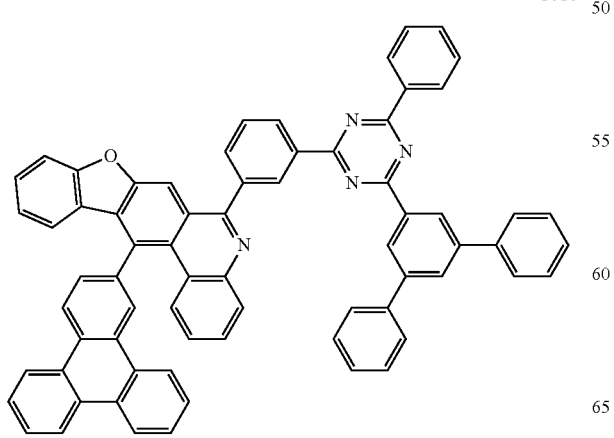
1136
-continued
1019
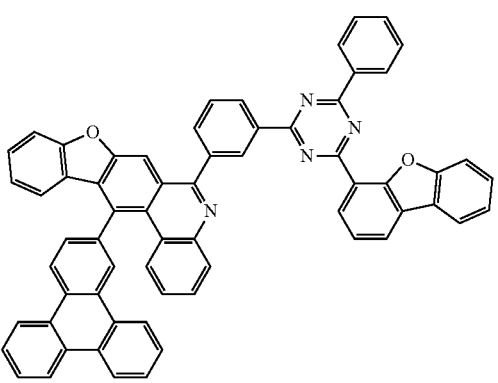
1020
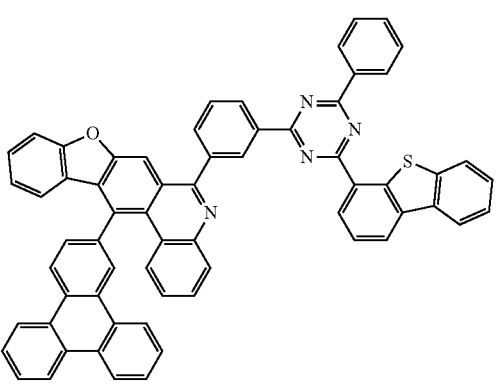
1021
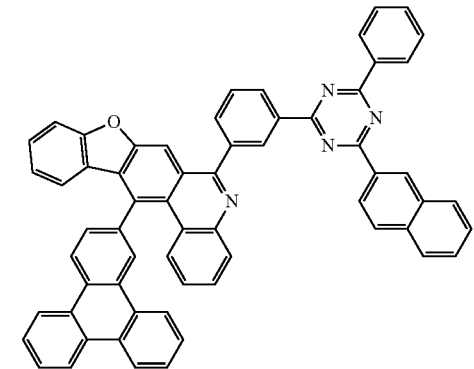
1022
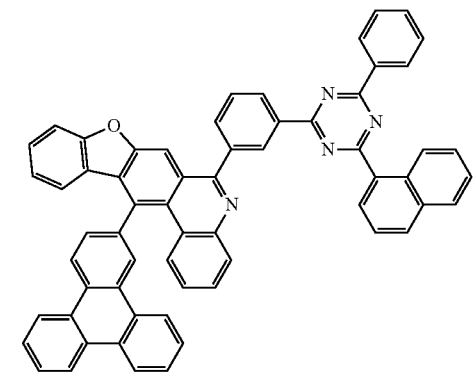

1137
-continued
1138
-continued
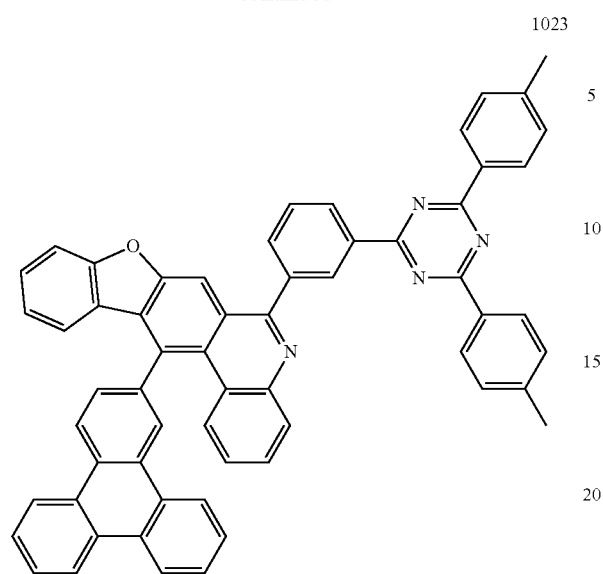
1023
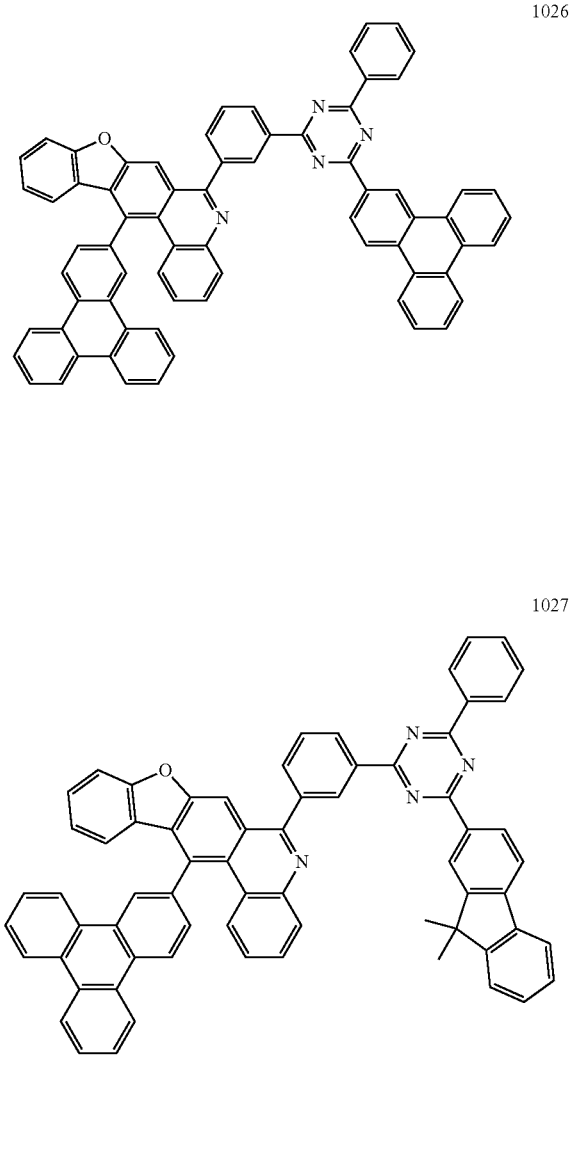
1026
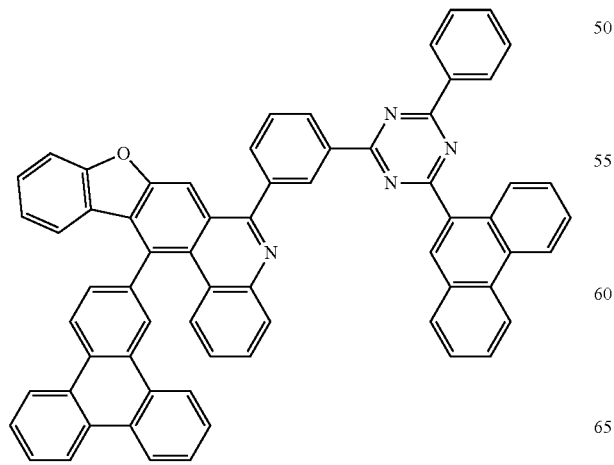
1024
1025
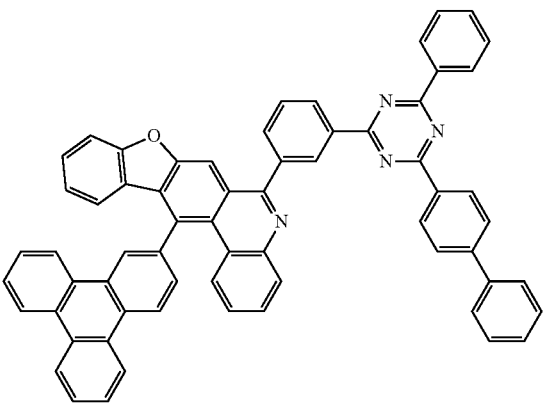
1027
1028

1139
-continued
1140
-continued
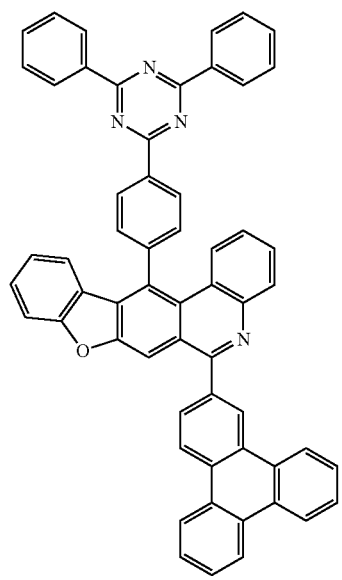
1029
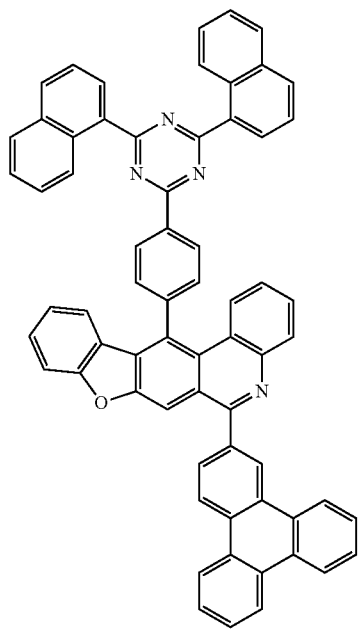
1031
1030
1032
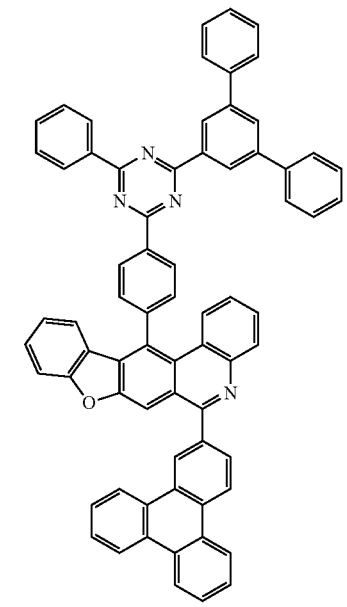

1141
-continued
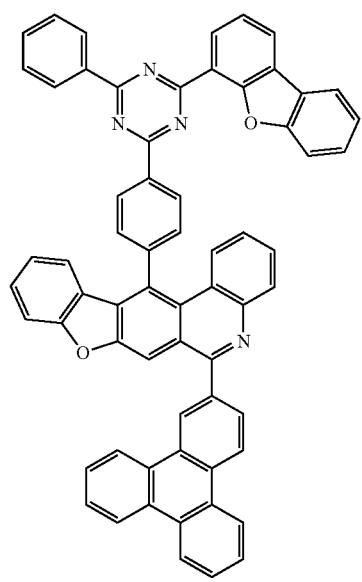
1033
1142
-continued
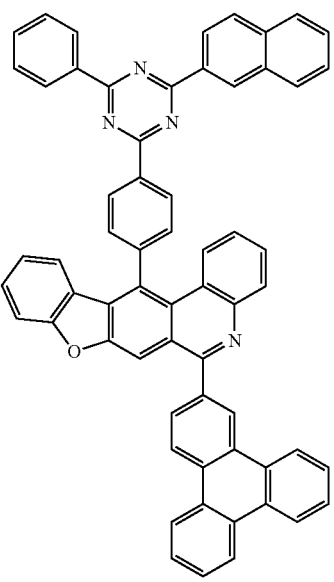
1035
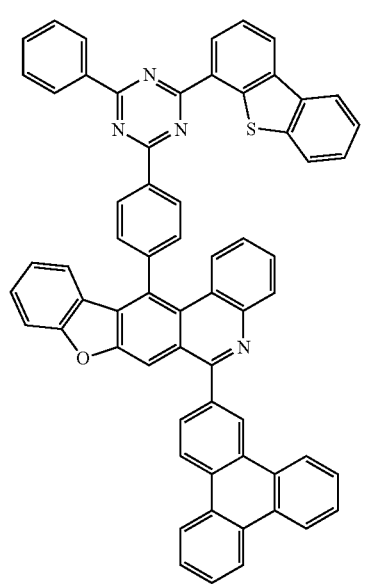
1034
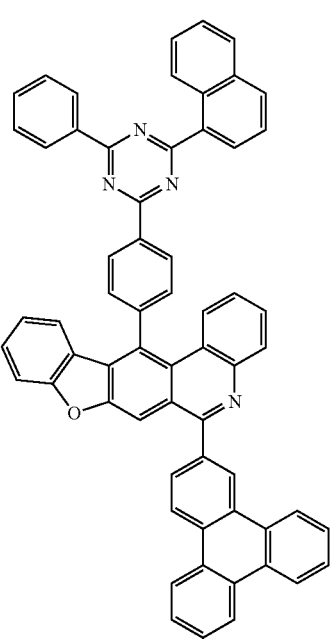
1036

1143
-continued
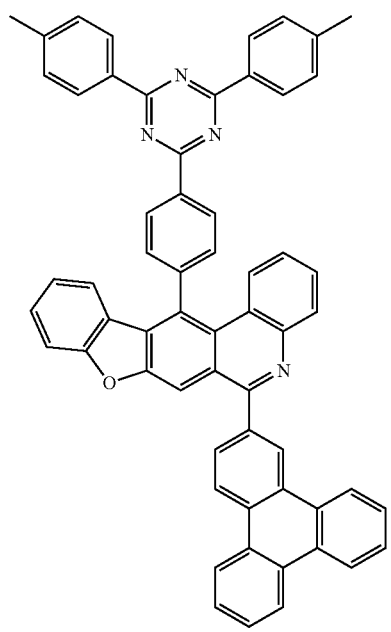
1037
1144
-continued
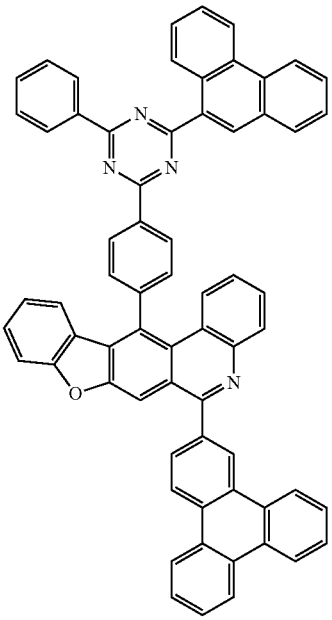
1039
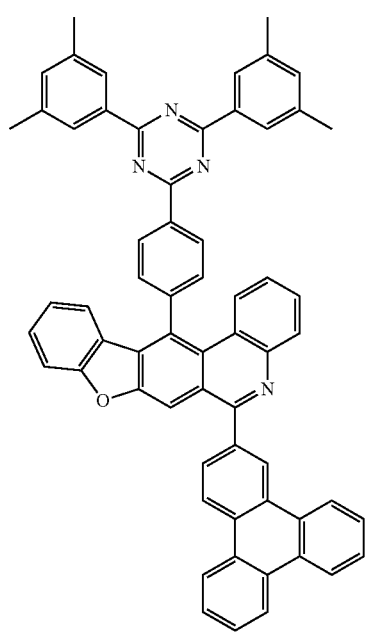
1038
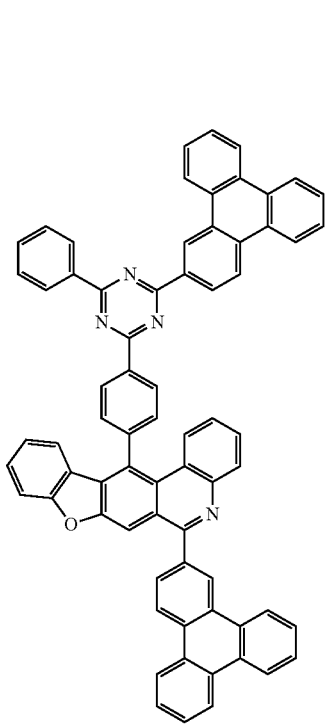
1040

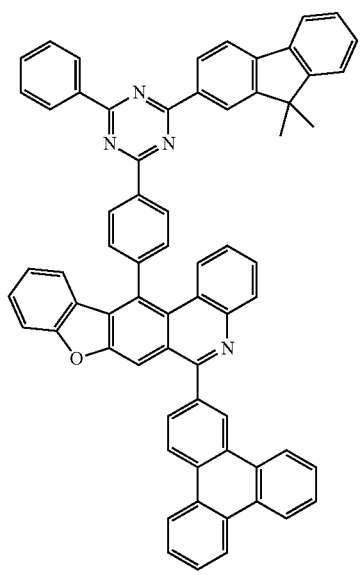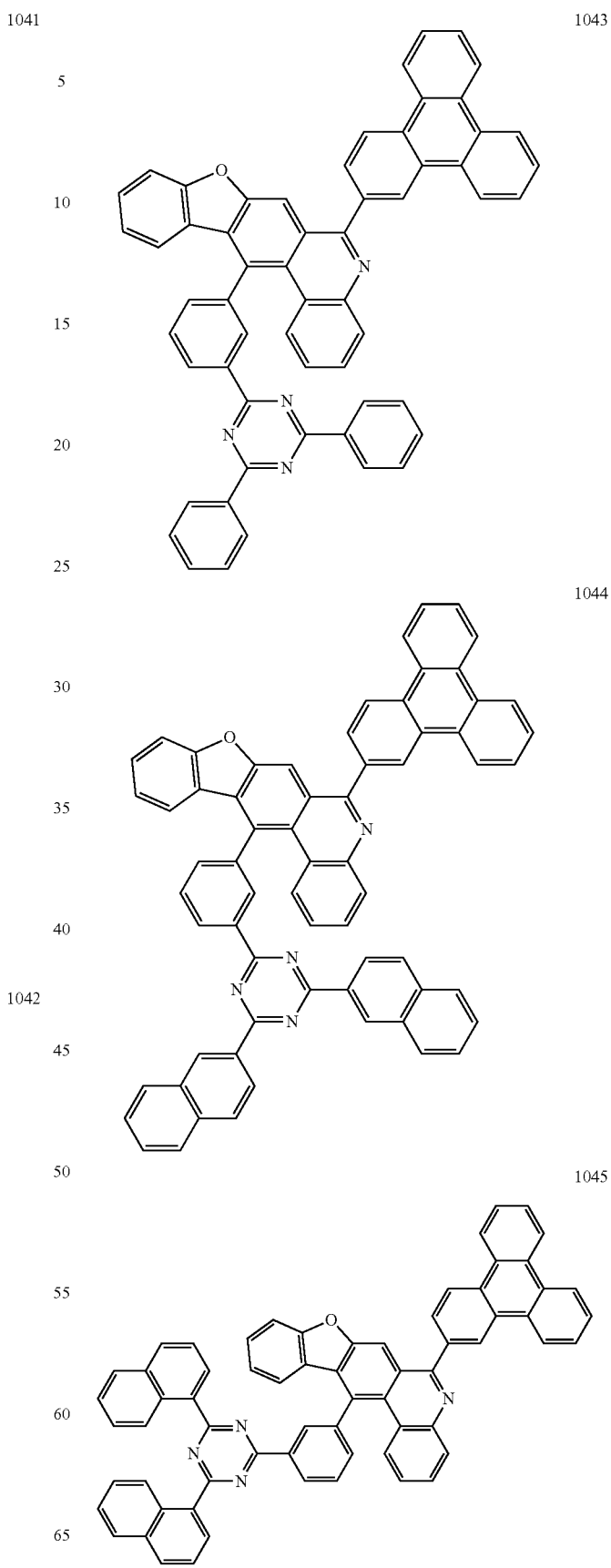

1147
-continued
1148
-continued
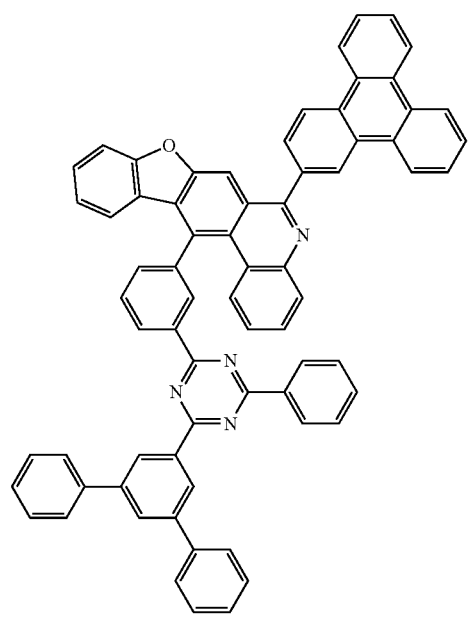 [SMILES: c1ccc(-c2cc(-c3ccccc3)cc(-c3nc(-c4ccccc4)nc(-c4cccc(-c5c6c(cc7c(-c8ccc9c%10ccccc%10c%10ccccc%10c9c8)nc8ccccc8c57)oc5ccccc56)c4)n3)c2)cc1]
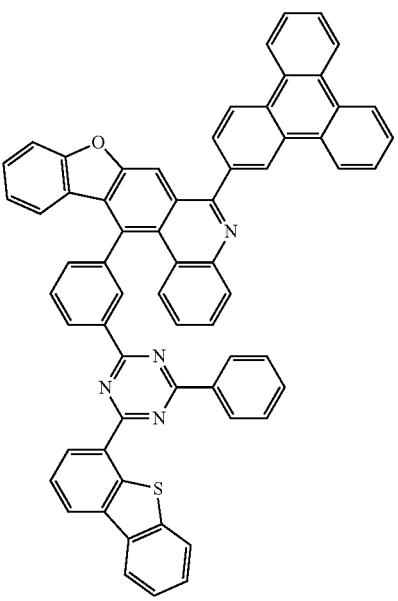

1149
-continued
1050
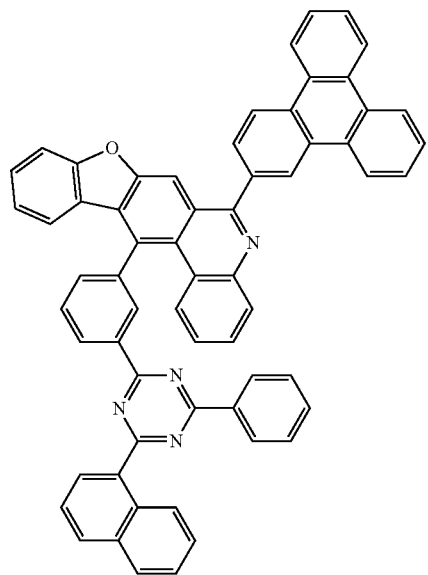
1051
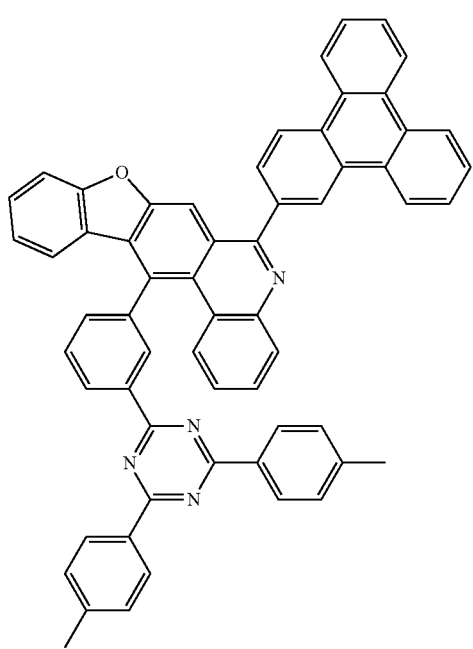 [SMILES: Cc1ccc(-c2nc(-c3ccc(C)cc3)nc(-c3cccc(-c4c5c(cc6c(-c7ccc8c9ccccc9c9ccccc9c8c7)nc7ccccc7c46)oc4ccccc45)c3)n2)cc1]
1150
-continued
1052
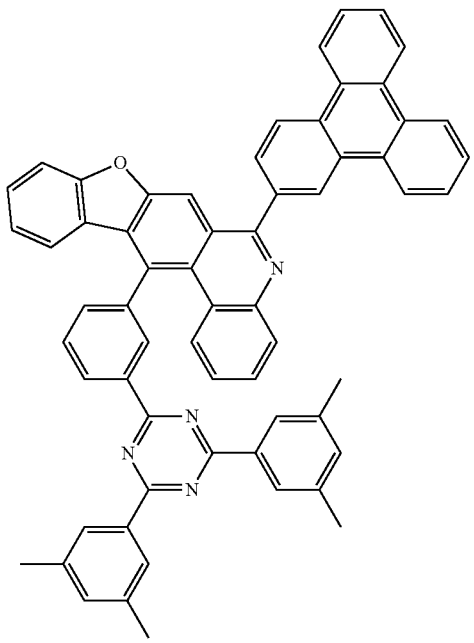
1053
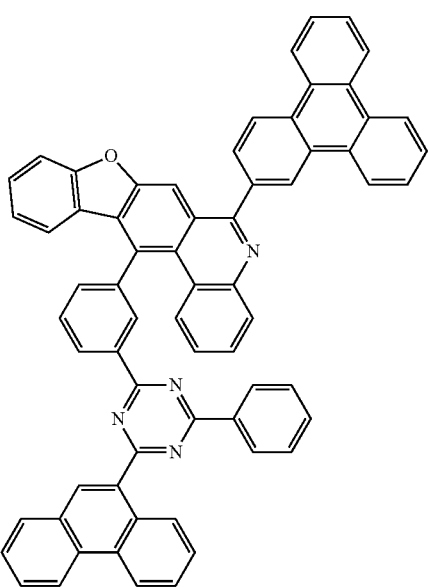

1151
-continued
1054
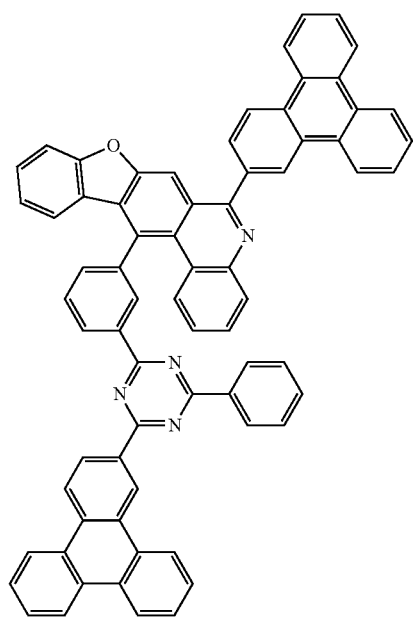 [SMILES: c1ccc(-c2nc(-c3cccc(-c4c5c(cc6c(-c7ccc8c9ccccc9c9ccccc9c8c7)nc7ccccc7c46)oc4ccccc45)c3)nc(-c3ccc4c5ccccc5c5ccccc5c4c3)n2)cc1]
1055
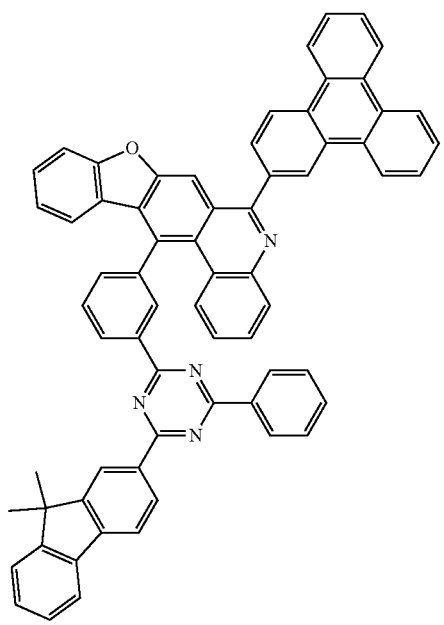 [SMILES: CC1(C)c2ccccc2-c2ccc(-c3nc(-c4ccccc4)nc(-c4cccc(-c5c6c(cc7c(-c8ccc9c%10ccccc%10c%10ccccc%10c9c8)nc8ccccc8c57)oc5ccccc56)c4)n3)cc21]
1152
-continued
1056
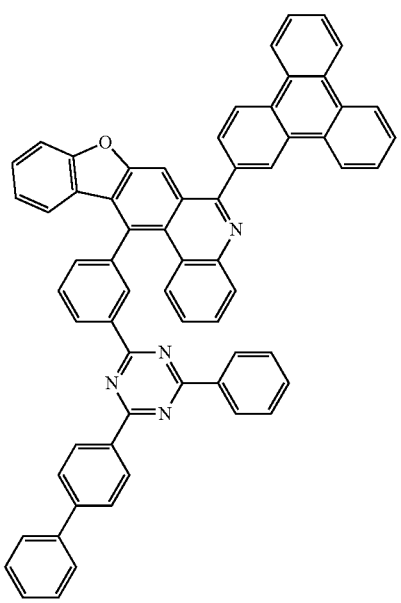 [SMILES: c1ccc(-c2ccc(-c3nc(-c4ccccc4)nc(-c4cccc(-c5c6c(cc7c(-c8ccc9c%10ccccc%10c%10ccccc%10c9c8)nc8ccccc8c57)oc5ccccc56)c4)n3)cc2)cc1]
1057
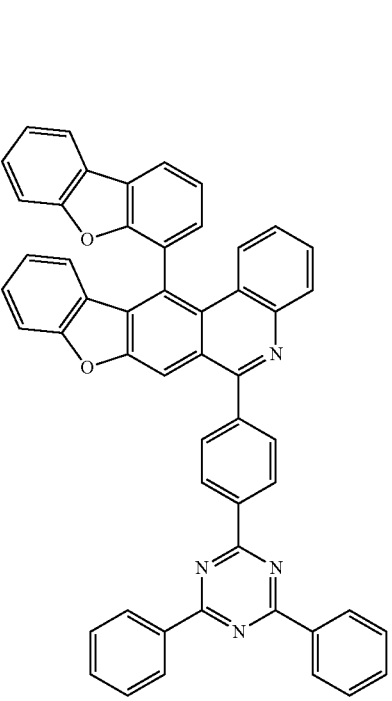 [SMILES: c1ccc(-c2nc(-c3ccccc3)nc(-c3ccc(-c4nc5ccccc5c5c(-c6cccc7c6oc6ccccc67)c6c(cc45)oc4ccccc46)cc3)n2)cc1]

1153
-continued
1058
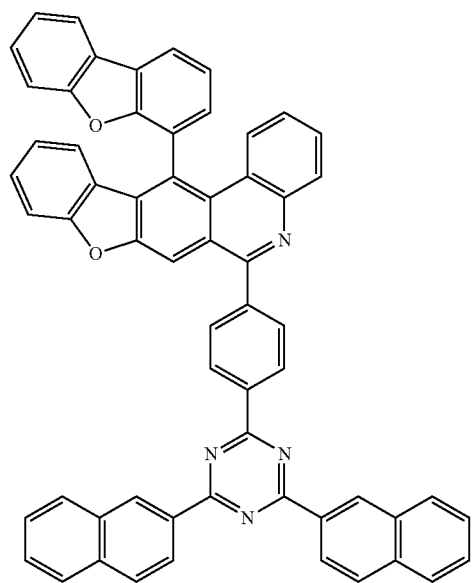 [SMILES: c1ccc2cc(-c3nc(-c4ccc(-c5nc6ccccc6c6c(-c7cccc8c7oc7ccccc78)c7c(cc56)oc5ccccc57)cc4)nc(-c4ccc5ccccc5c4)n3)ccc2c1]
1059
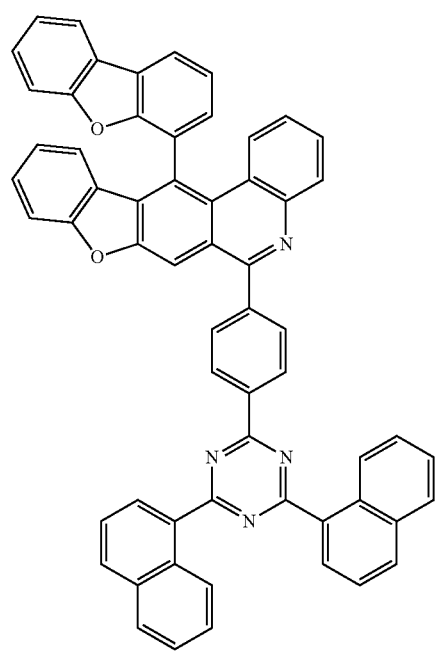
1154
-continued
1060
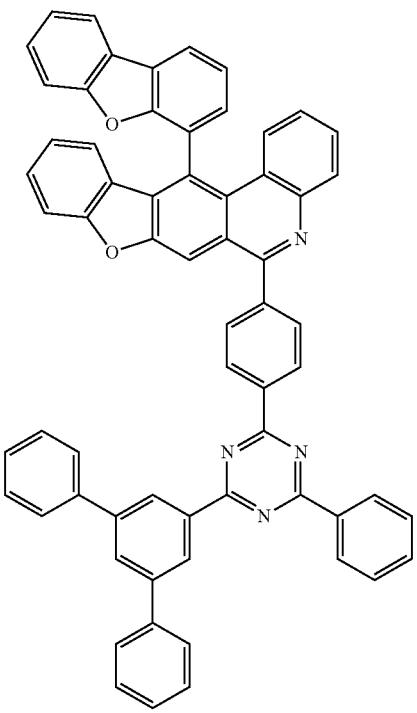 [SMILES: c1ccc(-c2cc(-c3ccccc3)cc(-c3nc(-c4ccccc4)nc(-c4ccc(-c5nc6ccccc6c6c(-c7cccc8c7oc7ccccc78)c7c(cc56)oc5ccccc57)cc4)n3)c2)cc1]
1061
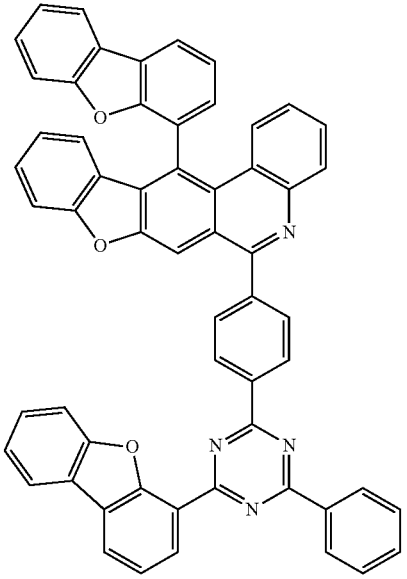

1155
-continued
1156
-continued
1062
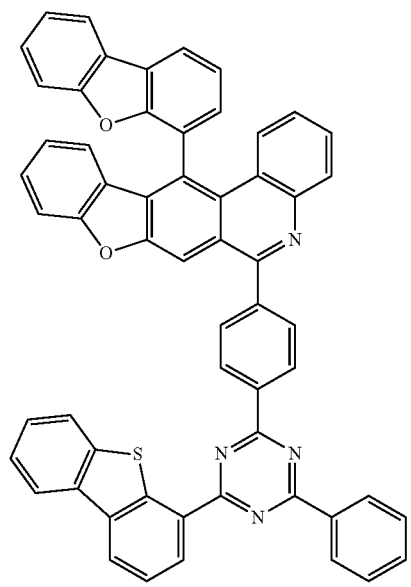
1064
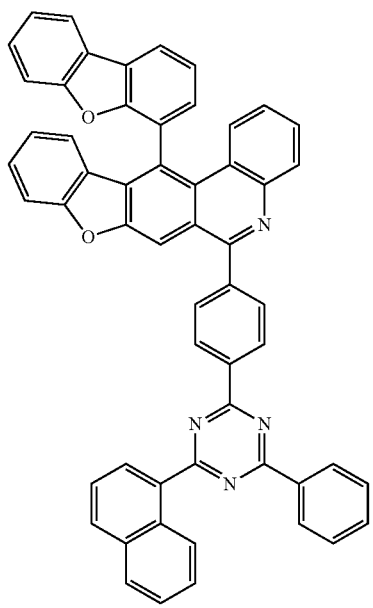
1063
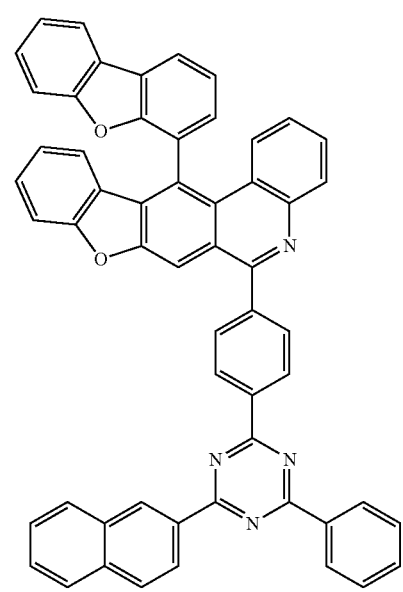
1065
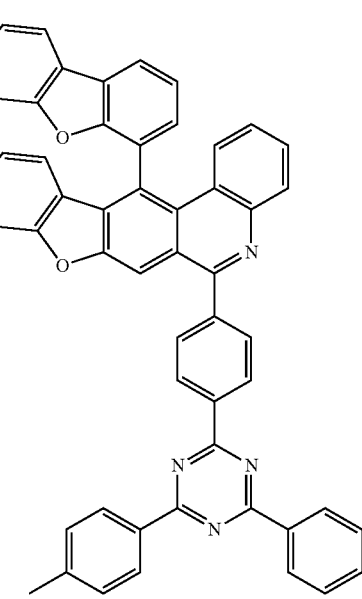

1157
-continued
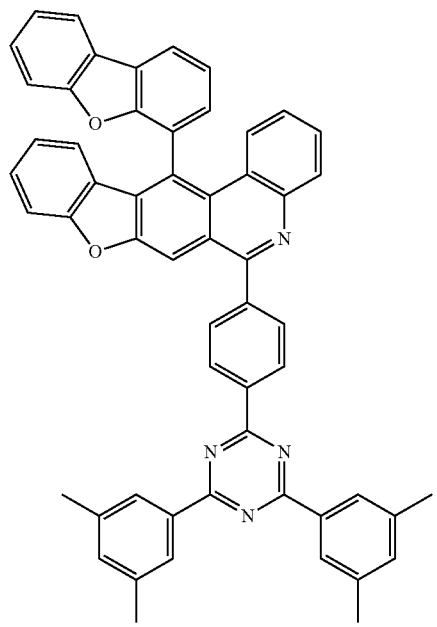
1066
1158
-continued
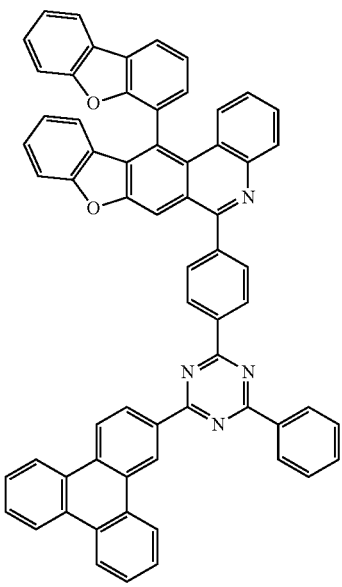 [SMILES: c1ccc(-c2nc(-c3ccc(-c4nc5ccccc5c5c(-c6cccc7c6oc6ccccc67)c6c(cc45)oc4ccccc46)cc3)nc(-c3ccc4c5ccccc5c5ccccc5c4c3)n2)cc1]
1068
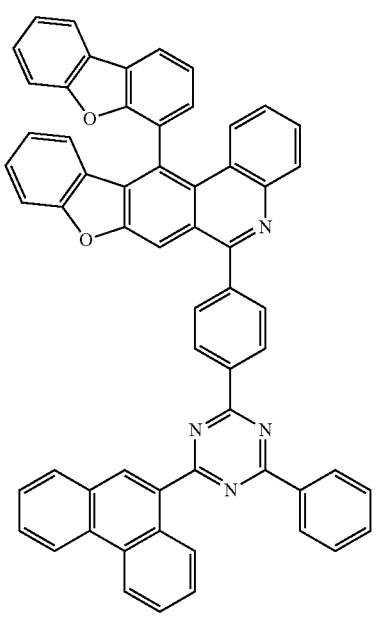
1067
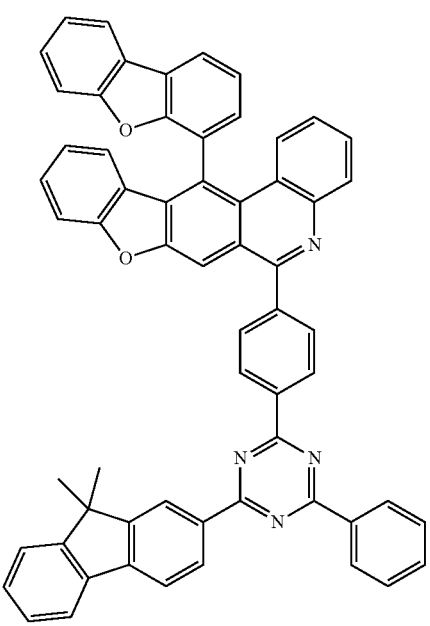
1069

1159
-continued
1160
-continued
1070
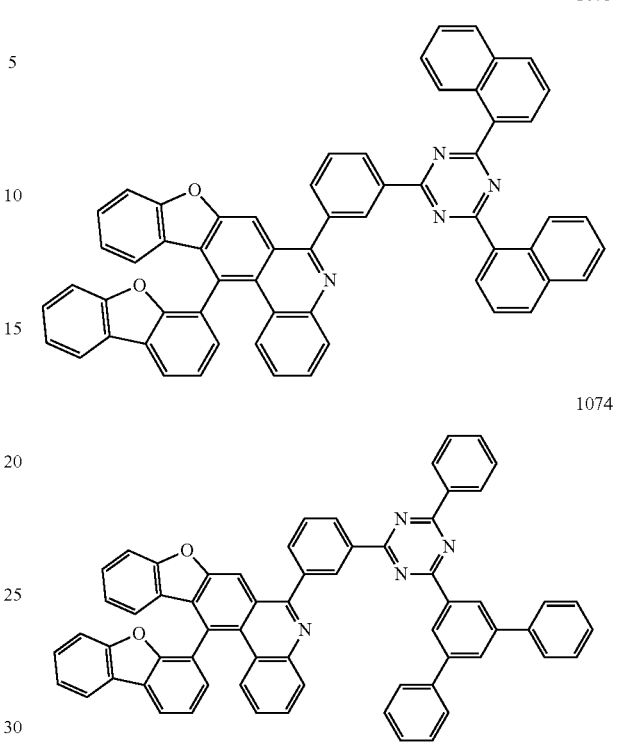
1073
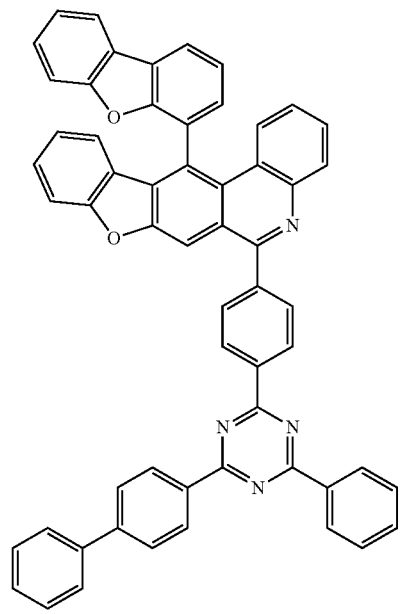
1074
1071
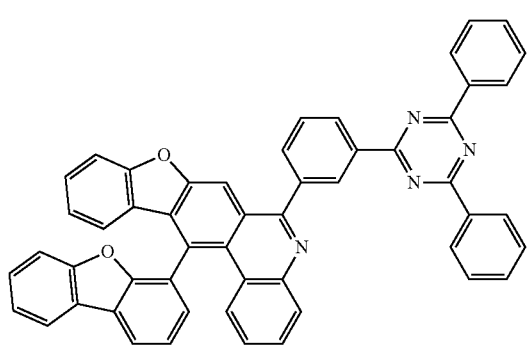
1075
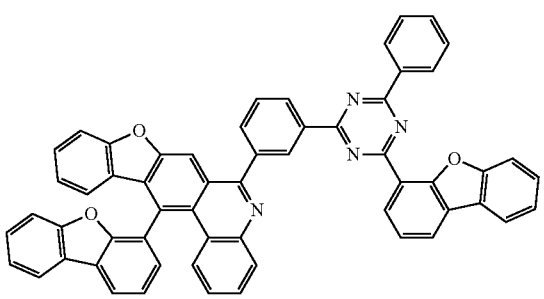
1072
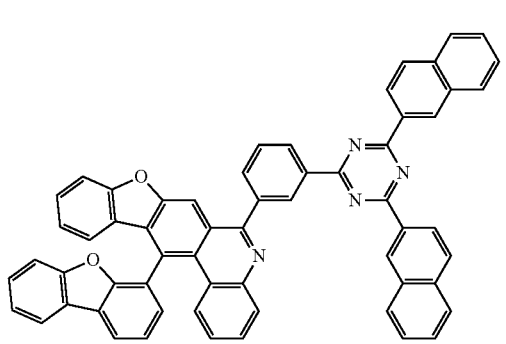
1076
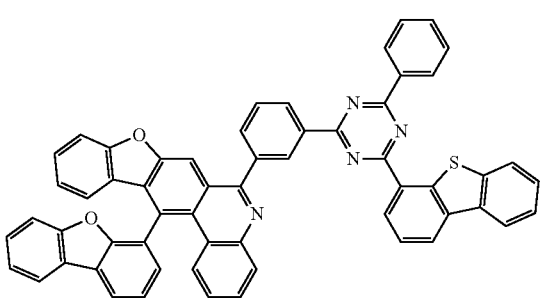 [SMILES: c1ccc(-c2nc(-c3cccc(-c4nc5ccccc5c5c(-c6cccc7c6oc6ccccc67)c6c(cc45)oc4ccccc46)c3)nc(-c3cccc4c3oc3ccccc34)n2)cc1]

1077
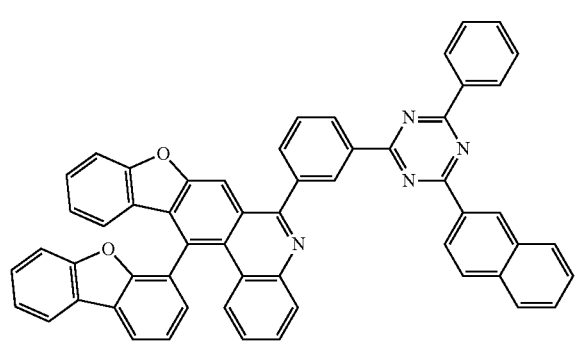
1078
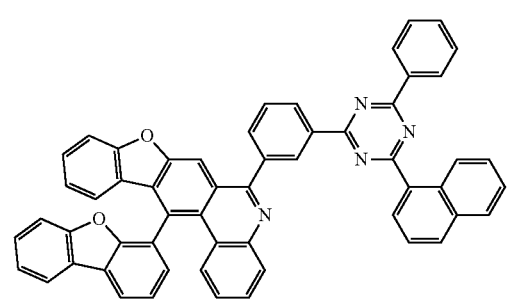
1079
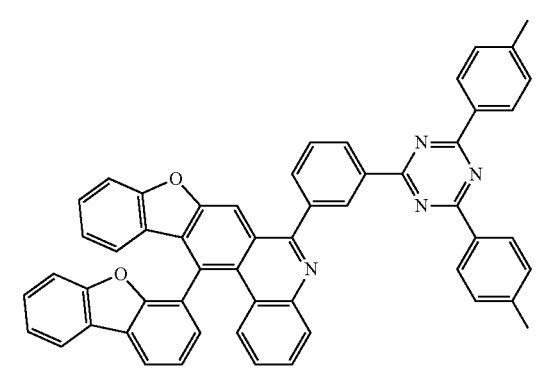 [SMILES: Cc1ccc(-c2nc(-c3ccc(C)cc3)nc(-c3cccc(-c4nc5ccccc5c5c(-c6cccc7c6oc6ccccc67)c6c(cc45)oc4ccccc46)c3)n2)cc1]
1080
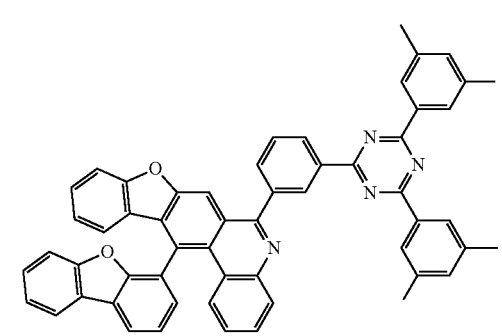
1081
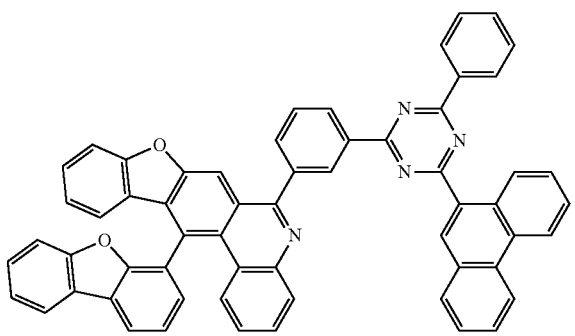
1082
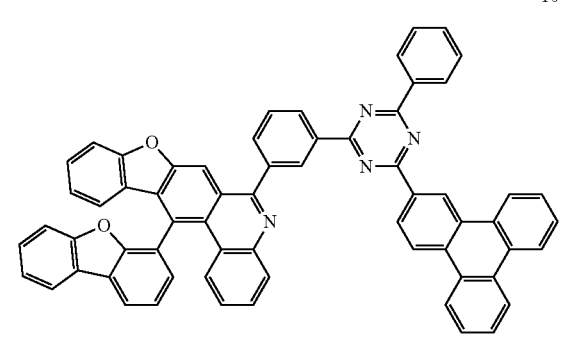
1083
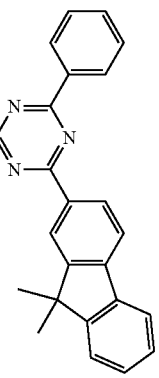
1084
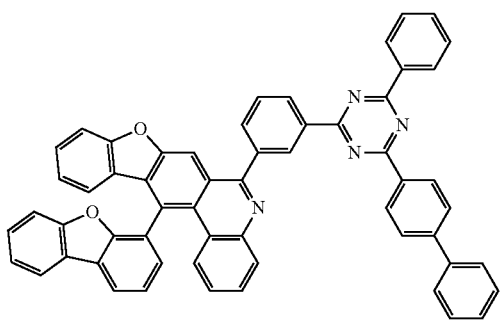

1163
-continued
1085
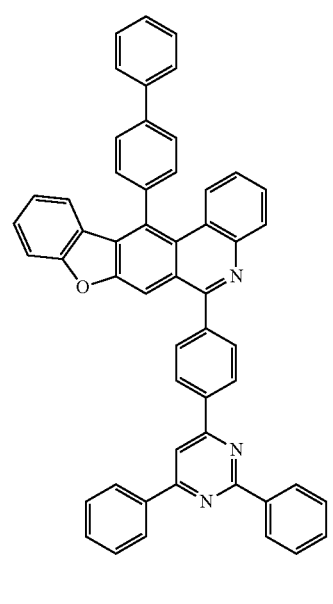
1086
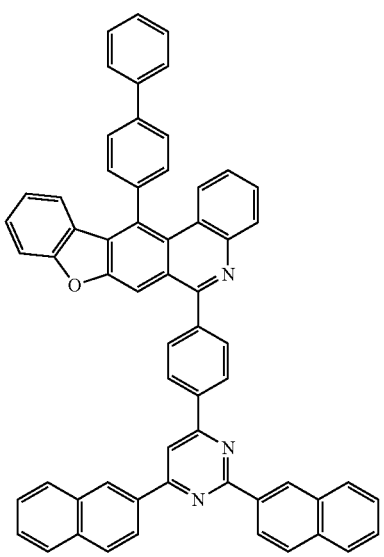 [SMILES: c1ccc(-c2ccc(-c3c4c(cc5c(-c6ccc(-c7cc(-c8ccc9ccccc9c8)nc(-c8ccc9ccccc9c8)n7)cc6)nc6ccccc6c35)oc3ccccc34)cc2)cc1]
1164
-continued
1087
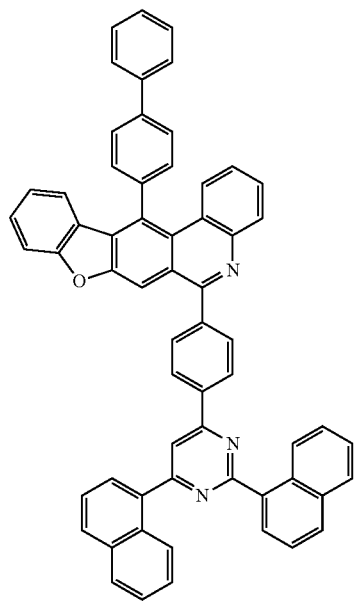
1088
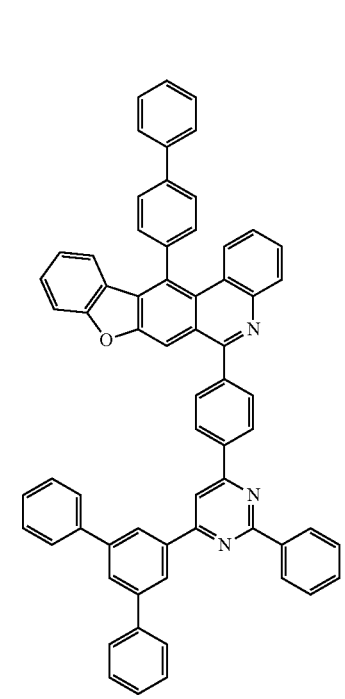 [SMILES: c1ccc(-c2ccc(-c3c4c(cc5c(-c6ccc(-c7cc(-c8cc(-c9ccccc9)cc(-c9ccccc9)c8)nc(-c8ccccc8)n7)cc6)nc6ccccc6c35)oc3ccccc34)cc2)cc1]

1165
-continued
1089
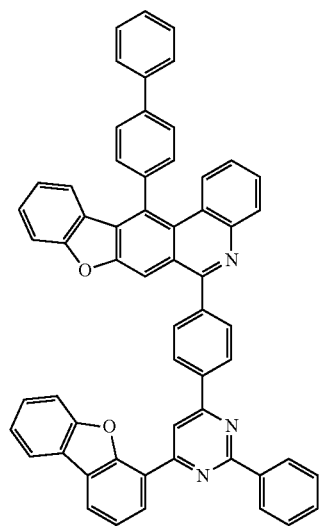
1090
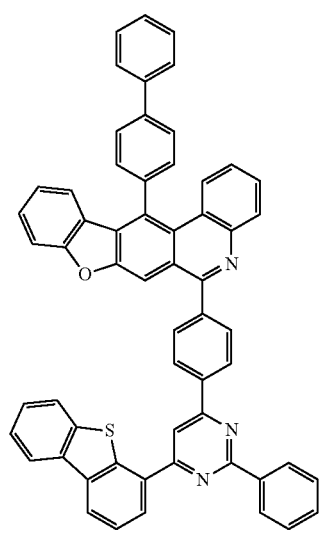
1091
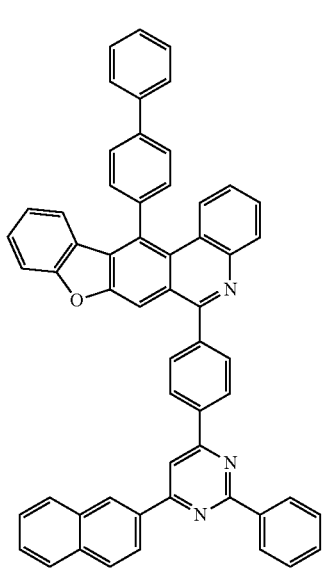
1166
-continued
1092
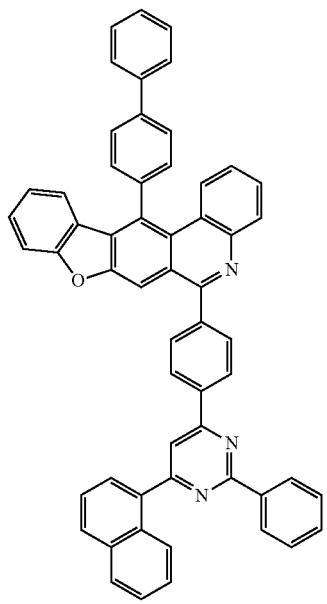
1093
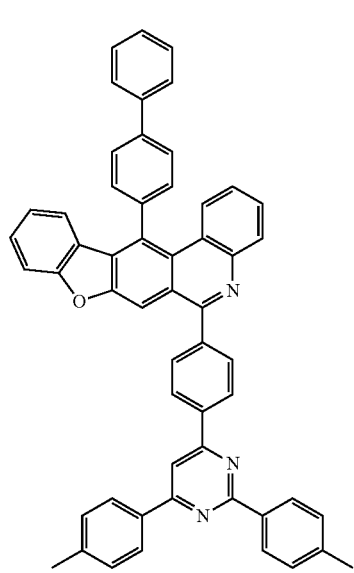

1167-continued
1094
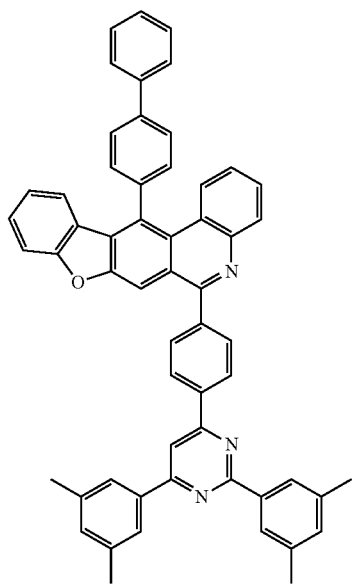
1168-continued
1096
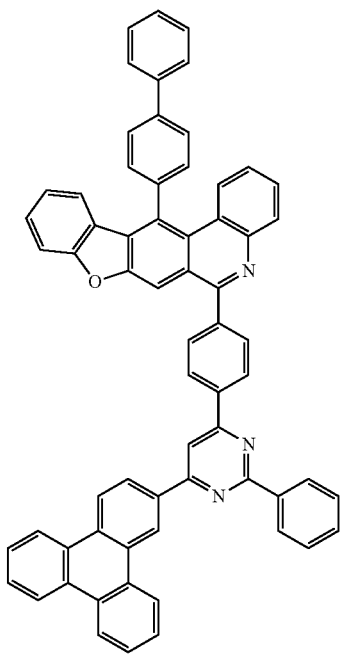 [SMILES: c1ccc(-c2ccc(-c3c4c(cc5c(-c6ccc(-c7cc(-c8ccc9c%10ccccc%10c%10ccccc%10c9c8)nc(-c8ccccc8)n7)cc6)nc6ccccc6c35)oc3ccccc34)cc2)cc1]
1095
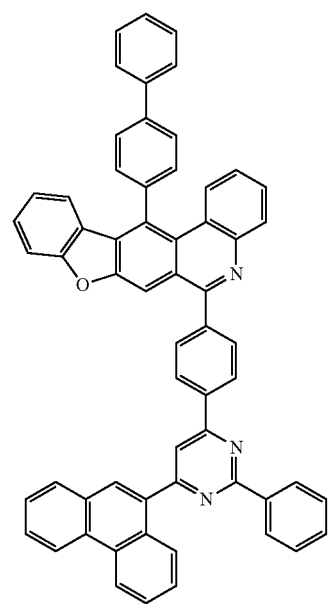
1097
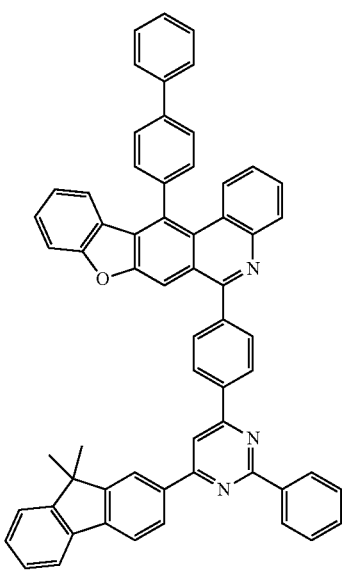

1098
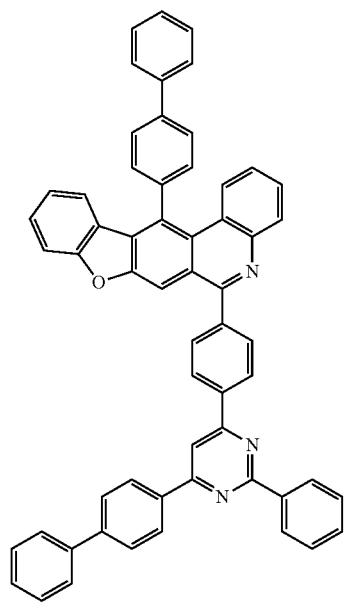
1099
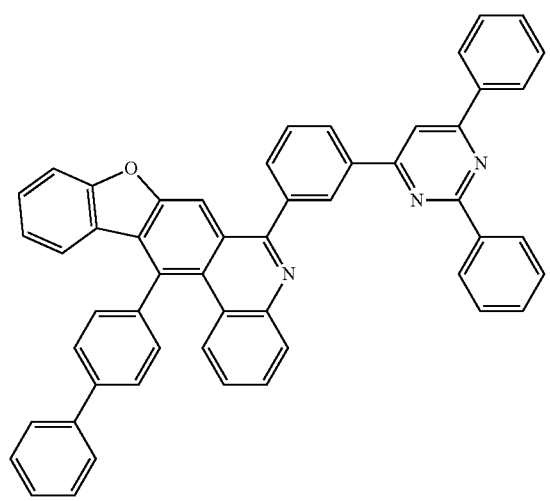 [SMILES: c1ccc(-c2ccc(-c3c4c(cc5c(-c6cccc(-c7cc(-c8ccccc8)nc(-c8ccccc8)n7)c6)nc6ccccc6c35)oc3ccccc34)cc2)cc1]
1100
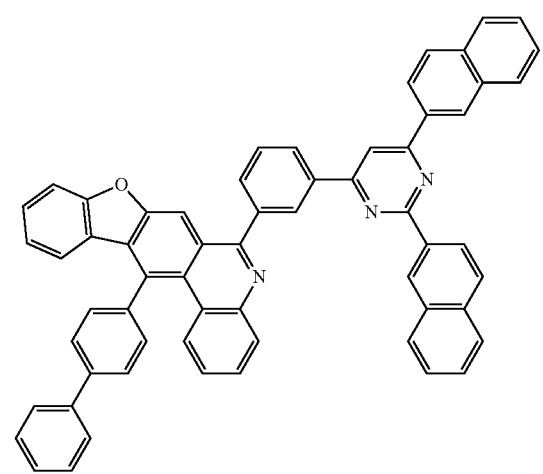
1101
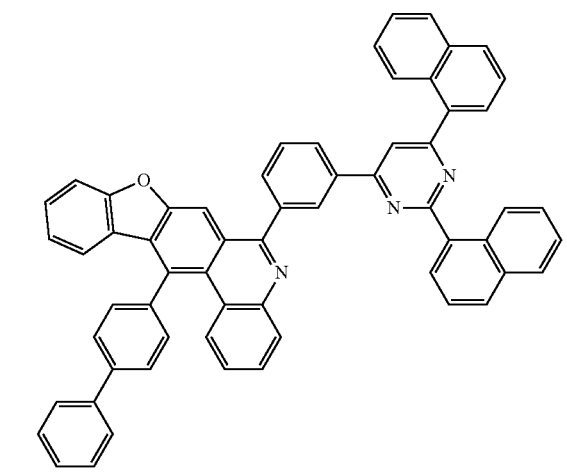
1102
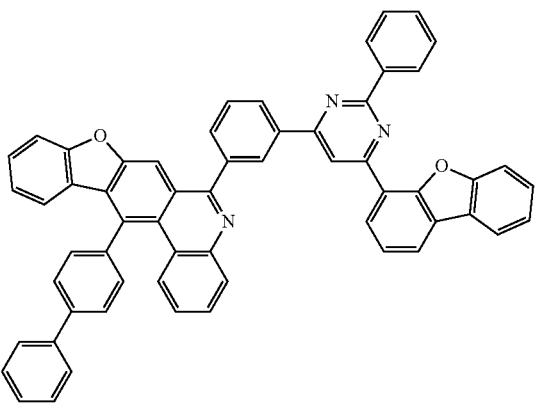
1103

1171
-continued
1104
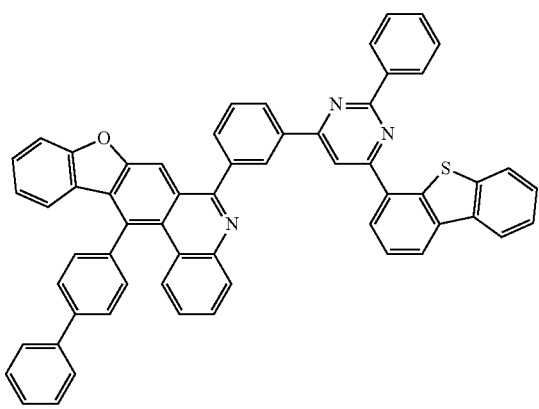 [SMILES: c1ccc(-c2ccc(-c3c4c(cc5c(-c6cccc(-c7cc(-c8cccc9c8oc8ccccc89)nc(-c8ccccc8)n7)c6)nc6ccccc6c35)oc3ccccc34)cc2)cc1]
1105
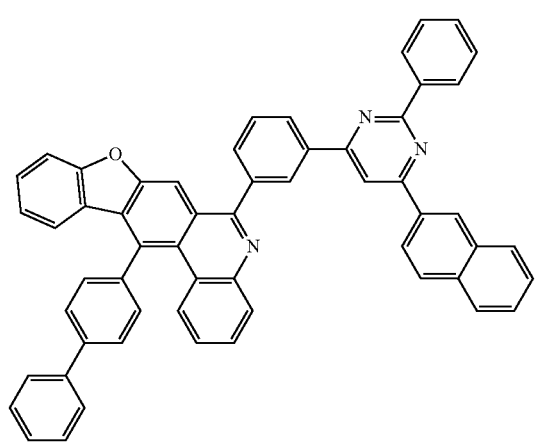
1106
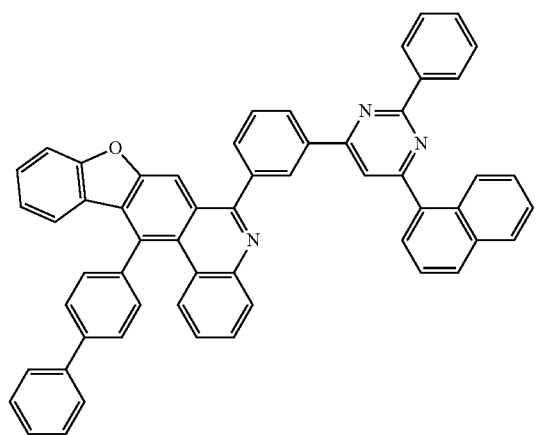
1172
-continued
1107
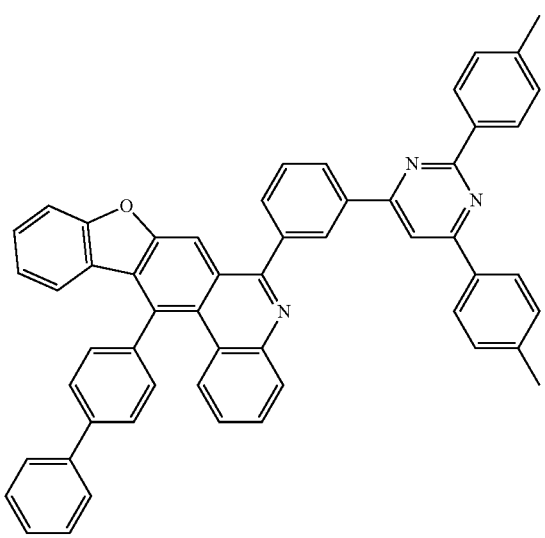
1108
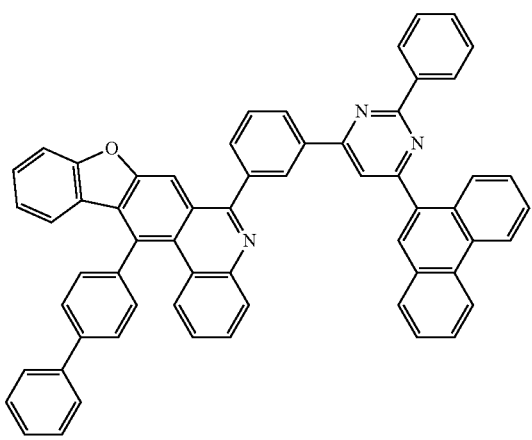
1109

1173
-continued
1110
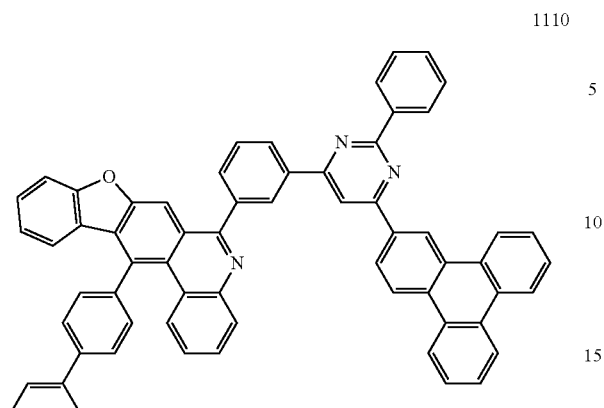
1111
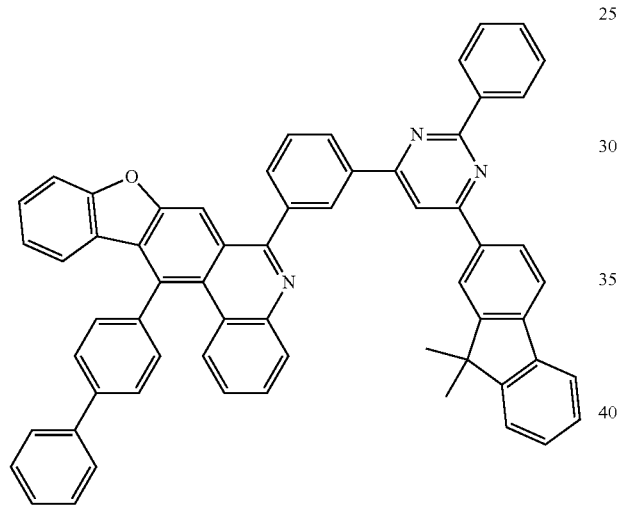
1112
1174
-continued
1113
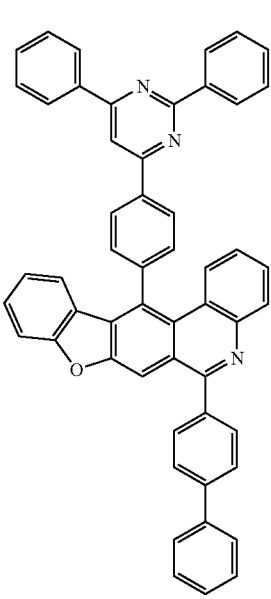
1114
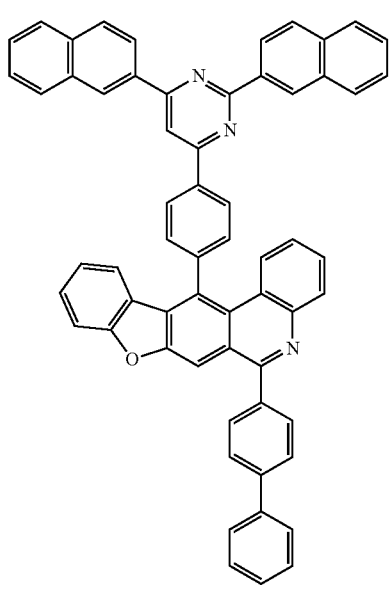

1175
-continued
1115
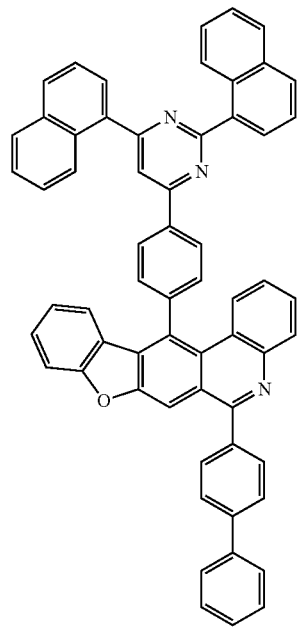
1116
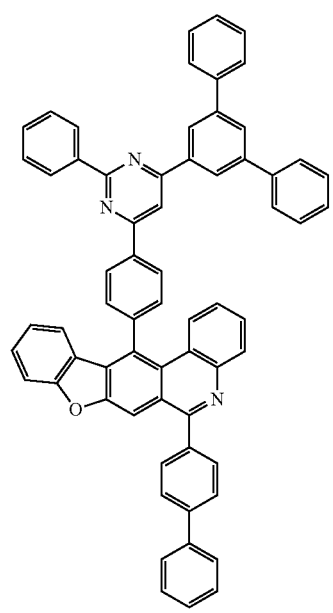
1176
-continued
1117
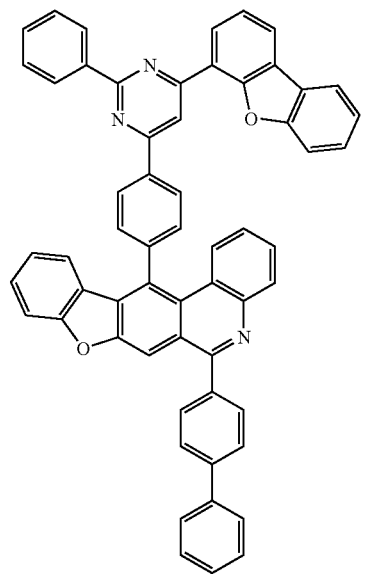
1118
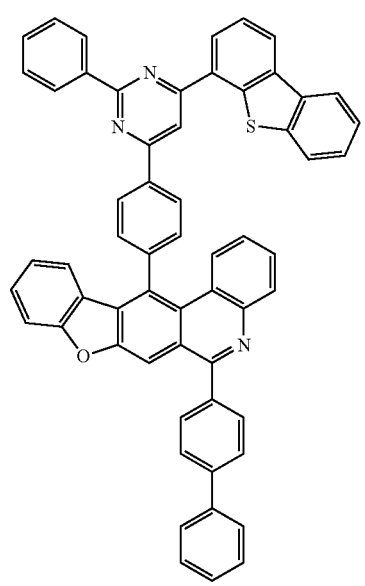

1177
-continued
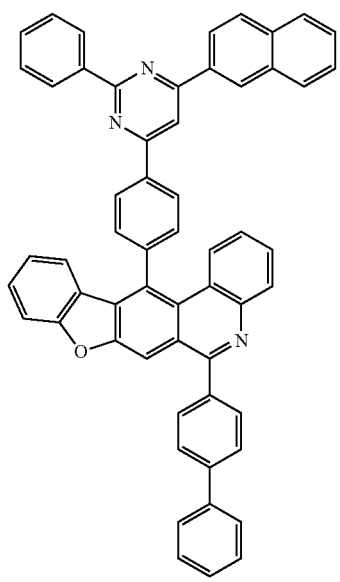
1119
1178
-continued
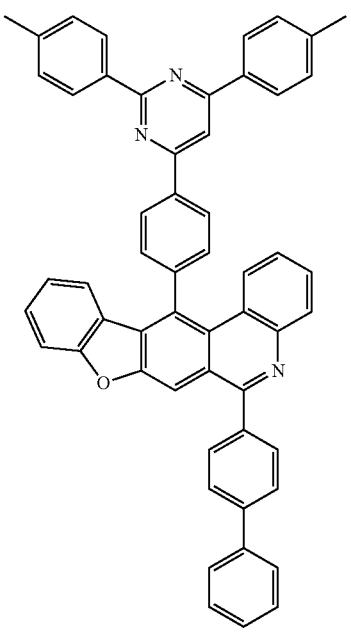
1121
1120
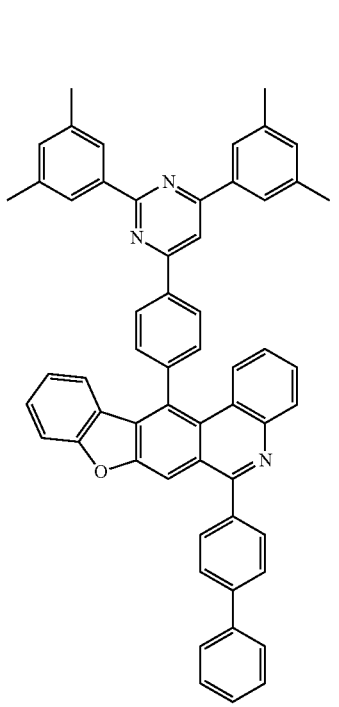
1122

1179
-continued
1123
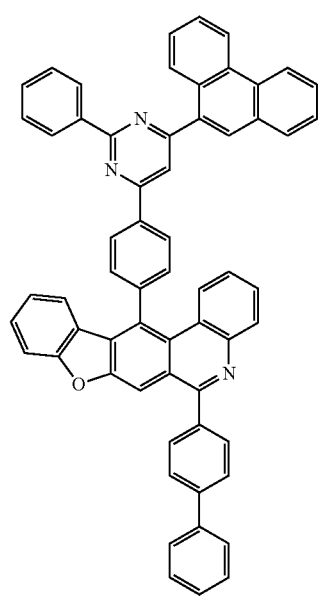
1124
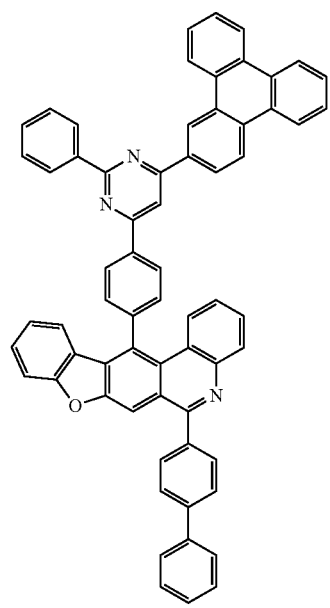
1180
1125
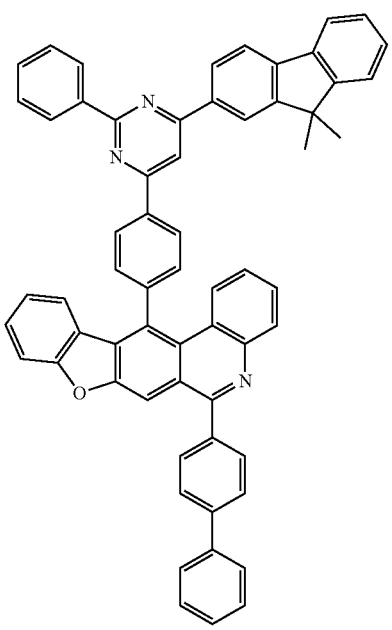
1126
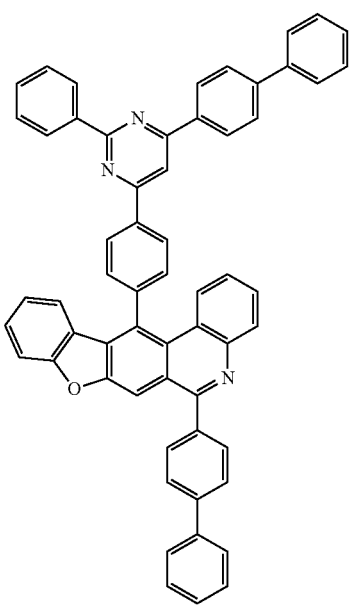

1181
-continued
1127
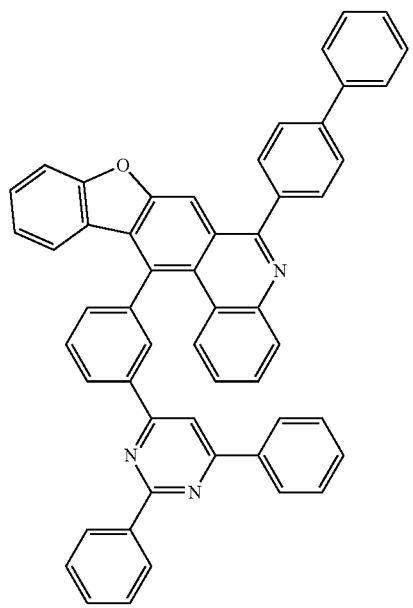
1128
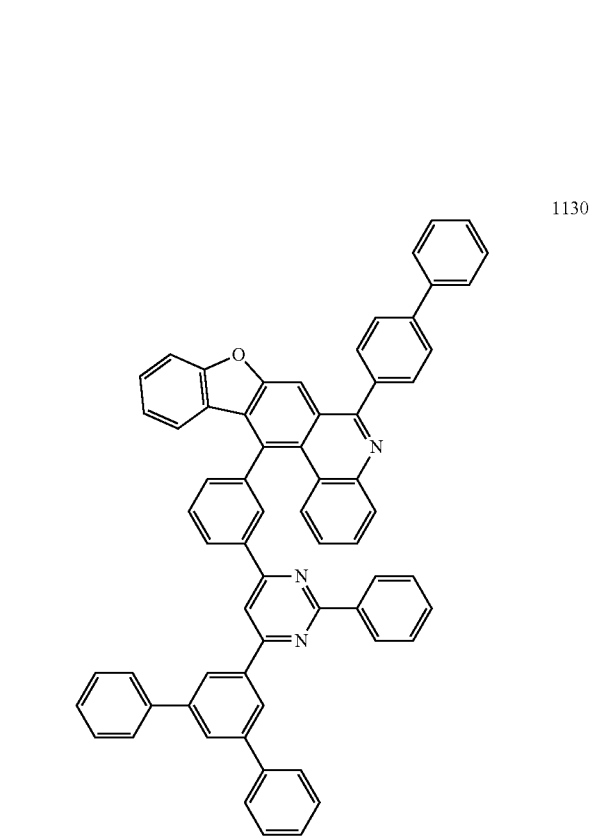
1182
-continued
1129
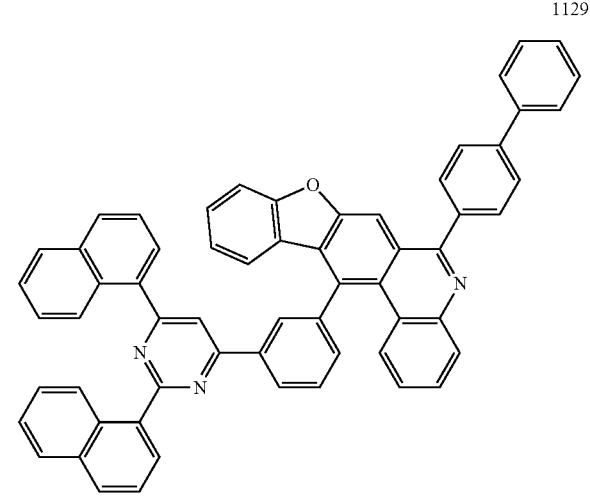
1130

1183
-continued
1131
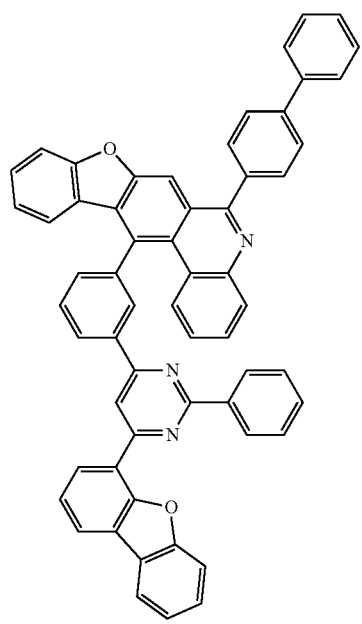
1132
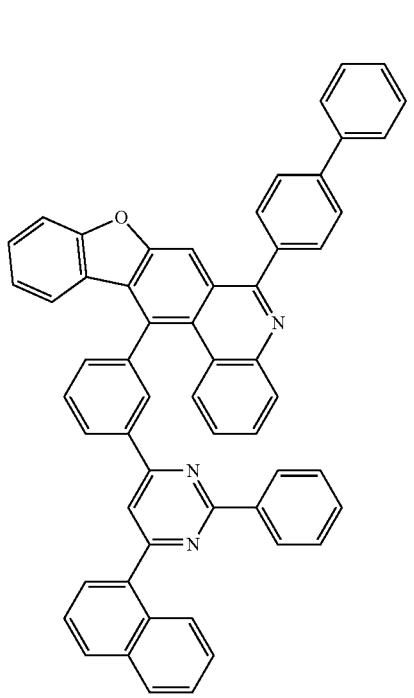
1184
-continued
1133
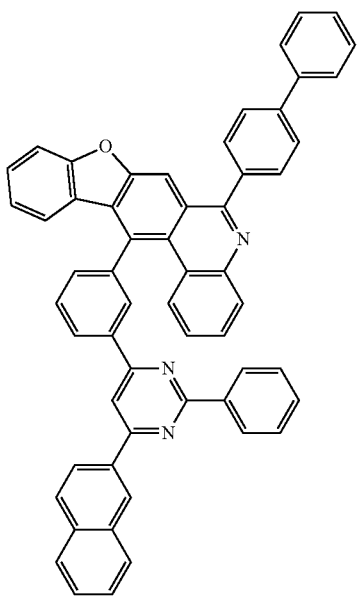
1134

1185
-continued
1186
-continued
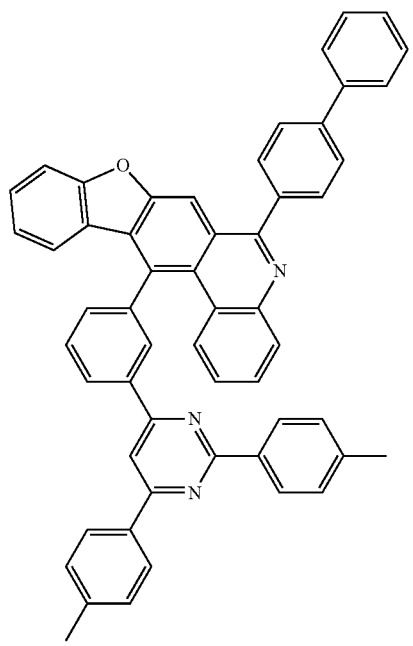
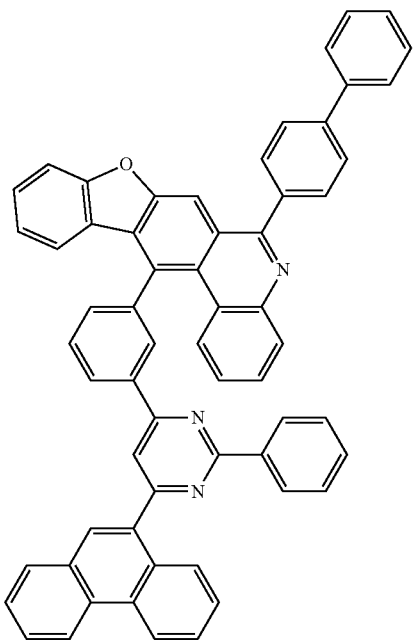

8. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

9. The organic light emitting device of claim 8, wherein the organic material layer comprises a light emitting layer, and the light emitting layer comprises the heterocyclic compound.

10. The organic light emitting device of claim 8, wherein the organic material layer comprises an electron injection layer or an electron transfer layer, and the electron injection layer or the electron transfer layer comprises the heterocyclic compound.

11. The organic light emitting device of claim 8, wherein the organic material layer comprises an electron blocking layer or a hole blocking layer, and the electron blocking layer or the hole blocking layer comprises the heterocyclic compound.

12. The organic light emitting device of claim 8, further comprising one, two or more layers selected from the group consisting of a light emitting layer, a hole injection layer, a hole transfer layer, an electron injection layer, an electron transfer layer, an electron blocking layer and a hole blocking layer.

13. The organic light emitting device of claim 8, comprising:
a first electrode;
a first stack provided on the first electrode and comprising a first light emitting layer;
a charge generation layer provided on the first stack;
a second stack provided on the charge generation layer and comprising a second light emitting layer; and
a second electrode provided on the second stack.

14. The organic light emitting device of claim 13, wherein the charge generation layer comprises the heterocyclic compound.

15. The organic light emitting device of claim 13, wherein the charge generation layer is an N-type charge generation layer, and the charge generation layer comprises the heterocyclic compound.

* * * * *